(12) United States Patent
Yamagishi et al.

(10) Patent No.: US 9,302,991 B2
(45) Date of Patent: Apr. 5, 2016

(54) ARYLAMIDE DERIVATIVES AS TTX-S BLOCKERS

(75) Inventors: Tatsuya Yamagishi, Aichi (JP); Kiyoshi Kawamura, Aichi (JP); Yoshimasa Arano, Aichi (JP); Mikio Morita, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 316 days.

(21) Appl. No.: 13/879,673

(22) PCT Filed: Oct. 18, 2011

(86) PCT No.: PCT/JP2011/005802
§ 371 (c)(1),
(2), (4) Date: May 9, 2013

(87) PCT Pub. No.: WO2012/053186
PCT Pub. Date: Apr. 26, 2012

(65) Prior Publication Data
US 2014/0336377 A1 Nov. 13, 2014

Related U.S. Application Data

(60) Provisional application No. 61/522,792, filed on Aug. 12, 2011, provisional application No. 61/394,017, filed on Oct. 18, 2010, provisional application No. 61/418,002, filed on Nov. 30, 2010.

(51) Int. Cl.
| | |
|---|---|
| C07D 213/64 | (2006.01) |
| A61K 31/44 | (2006.01) |
| A61K 31/4427 | (2006.01) |
| A61K 31/444 | (2006.01) |
| A61K 31/506 | (2006.01) |
| C07D 213/75 | (2006.01) |
| C07D 213/81 | (2006.01) |
| C07D 239/42 | (2006.01) |
| C07D 401/12 | (2006.01) |
| C07D 401/14 | (2006.01) |
| C07D 413/12 | (2006.01) |
| C07D 413/14 | (2006.01) |
| C07D 417/12 | (2006.01) |
| C07D 417/14 | (2006.01) |
| C07D 471/04 | (2006.01) |

(52) U.S. Cl.
CPC .............. *C07D 213/64* (2013.01); *A61K 31/44* (2013.01); *A61K 31/444* (2013.01); *A61K 31/4427* (2013.01); *A61K 31/506* (2013.01); *C07D 213/75* (2013.01); *C07D 213/81* (2013.01); *C07D 239/42* (2013.01); *C07D 401/12* (2013.01); *C07D 401/14* (2013.01); *C07D 413/12* (2013.01); *C07D 413/14* (2013.01); *C07D 417/12* (2013.01); *C07D 417/14* (2013.01); *C07D 471/04* (2013.01)

(58) Field of Classification Search
CPC .. C07D 213/64; C07D 213/75; C07D 213/81; C07D 239/42; C07D 401/12; C07D 401/14; C07D 413/12; C07D 413/14; C07D 417/12; C07D 417/14; C07D 471/04; A61K 31/44; A61K 31/444; A61K 31/506; A61K 31/4427
See application file for complete search history.

(56) References Cited

U.S. PATENT DOCUMENTS

| | | |
|---|---|---|
| 6,630,495 B1 | 10/2003 | Cooke et al. |
| 2004/0044040 A1 | 3/2004 | Neubert et al. |
| 2005/0009889 A1 | 1/2005 | Foor et al. |
| 2005/0020643 A1 | 1/2005 | Foor et al. |
| 2008/0293674 A1 | 11/2008 | Schwarz et al. |
| 2009/0143358 A1 | 6/2009 | Marron et al. |
| 2011/0105530 A1 | 5/2011 | Dales et al. |

FOREIGN PATENT DOCUMENTS

| | | |
|---|---|---|
| JP | 7-25853 | 1/1995 |
| JP | 2003-506466 | 2/2003 |
| JP | 2004-518629 | 6/2004 |
| JP | 2005-520838 | 7/2005 |
| JP | 2005-521697 | 7/2005 |

(Continued)

OTHER PUBLICATIONS

Extended European Search Report issued Apr. 1, 2014 in corresponding European Application No. 11834032.2.
International Search Report issued Dec. 6, 2011 in corresponding International (PCT) Application No. PCT/JP2011/005802.
T. Kayano et al., "Primary structure of rat brain sodium channel III deduced from the cDNA sequence", FEBS Letters, vol. 228, No. 1, pp. 187-194, Feb. 1988.

(Continued)

*Primary Examiner* — Alexander R Pagano
(74) *Attorney, Agent, or Firm* — Wenderoth, Lind & Ponack, L.L.P.

(57) ABSTRACT

The present invention relates to arylamide derivatives which have blocking activities of voltage gated sodium channels as the TTX-S channels, and which are useful in the treatment or prevention of disorders and diseases in which voltage gated sodium channels are involved. The invention also relates to pharmaceutical compositions comprising these compounds and the use of these compounds and compositions in the prevention or treatment of such diseases in which voltage gated sodium channels are involved.

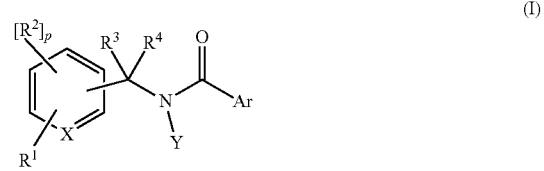

(I)

6 Claims, No Drawings

(56) References Cited

FOREIGN PATENT DOCUMENTS

| | | |
|---|---|---|
| JP | 2005-526100 | 9/2005 |
| JP | 2007-536307 | 12/2007 |
| JP | 2010-522242 | 7/2010 |
| WO | 03/037274 | 5/2003 |
| WO | 03/080596 | 10/2003 |
| WO | 2005/068430 | 7/2005 |
| WO | 2009/058299 | 5/2009 |
| WO | 2009/117269 | 9/2009 |
| WO | 2009/156484 | 12/2009 |
| WO | WO 2009156484 A2 * | 12/2009 |
| WO | 2010/035166 | 4/2010 |
| WO | 2010/051188 | 5/2010 |
| WO | 2010/137351 | 12/2010 |

OTHER PUBLICATIONS

C. Lu et al., "Isolation of a Human-Brain Sodium-Channel Gene Encoding Two Isoforms of the Subtype III α-Subunit", Journal of Molecular Neuroscience, vol. 10, No. 1, pp. 67-70, 1998.

Y. Chen et al., "Cloning, distribution and functional analysis of the type III sodium channel from human brain", European Journal of Neuroscience, vol. 12, No. 12, pp. 4281-4289, 2000.

J. Black et al., "Upregulation of a Silent Sodium Channel After Peripheral, but not Central, Nerve Injury in DRG Neurons", Journal of Neurophysiology, vol. 82, pp. 2776-2785, 1999.

M. Craner et al., "Changes of Sodium Channel Expression in Experimental Painful Diabetic Neuropathy", Annuals of Neurology, vol. 52, No. 6, pp. 786-792, 2002.

S. Dib-Hajj et al., "Plasticity of sodium channel expression in DRG neurons in the chronic constriction injury model of neuropathic pain", Pain, vol. 83, pp. 591-600, 1999.

S. Hong et al., "Early Painful Diabetic Neuropathy is Associated with Differential Changes in Tetrodotoxin-sensitive and -resistant Sodium Channels in Dorsal Root Ganglion Neurons in the Rat", The Journal of Biochemistry, vol. 279, No. 28, Issue of Jul. 9, 2004, pp. 29341-29350.

C. Kim et al., "The changes in expression of three subtypes of TTX sensitive sodium channels in sensory neurons after spinal nerve ligation", Molecular Brain Research, vol. 95, pp. 153-161, 2001.

B. Haim et al., "Altered Sodium Channel Expression in Second-Order Spinal Sensory Neurons Contributes to Pain after Peripheral Nerve Injury", The Journal of Neuroscience, vol. 24, No. 20, pp. 4832-4839, 2004.

J. Cox et al., "An SCN9A channelopathy causes congenital inability to experience pain", Nature, vol. 444, pp. 894-898, Dec. 14, 2006.

M. Baker et al., "Involvement of $Na^+$ channels in pain pathways", Trends in Pharmacological Sciences, vol. 22, No. 1, pp. 27-31, Jan. 2001.

Y. Lyu et al., "Low dose of tetrodotoxin reduces neuropathic pain behaviors in an animal model", Brain Research, vol. 871, pp. 98-103, 2000.

* cited by examiner

ARYLAMIDE DERIVATIVES AS TTX-S BLOCKERS

This application claims the benefit of U.S. Provisional Application No. 61/394,017, filed Oct. 18, 2010, U.S. Provisional Application No. 61/418,002, filed Nov. 30, 2010, and U.S. Provisional Application No. 61/522,792, filed Aug. 12, 2011.

TECHNICAL FIELD

The present invention relates to the arylamide derivatives which are sodium channel blockers and have a number of therapeutic applications, particularly in the treatment of pain.

BACKGROUND ART

The arylamide derivatives of the present invention are sodium channel blockers and have a number of therapeutic applications, particularly in the treatment of pain.

More particularly, the arylamide derivatives of the invention are selective tetrodotoxin-sensitive (TTX-S) blockers. In the discussion that follows, the invention is exemplified by reference to the inhibition of $Na_{v1.3}$ or $Na_{v1.7}$ channel as the TTX-S channels. They show the affinity for $Na_{v1.3}$ or $Na_{v1.7}$ channel which is significantly greater than their affinity for $Na_{v1.5}$ channel as the tetrodotoxin-resistant (TTX-R) sodium channels. Arylamide derivatives of the invention show good selectivity for the $Na_{v1.3}$ or $Na_{v1.7}$ channel as compared with $Na_{v1.5}$ channel.

The rat $Na_{v1.3}$ channel and the human $Na_{v1.3}$ channel have been cloned in 1988, 1998, 2000 respectively (NPL 1, NPL 2). The $Na_{v1.3}$ channel was formerly known as brain type III sodium channel. $Na_{v1.3}$ is present at relatively high levels in the nervous system of rat embryos but is barely detectable in adult rats. $Na_{v1.3}$ is up-regulated following axotomy in the Spinal Nerve Ligation (SNL), Chronic Constriction Injury (CCI), and diabetic neuropathy models (NPL 3, NPL 4, NPL 6, NPL 7) The up-regulation of $Na_{v1.3}$ channel contributes to rapidly repriming sodium current in small dorsal root ganglion (DRG) neurons (NPL 8). These observations suggest that $Na_{v1.3}$ may make a key contribution to neuronal hyperexcitability.

In order to validate the contribution of $Na_{v1.3}$ sodium channel in the pain states, specific antisense oligonucleotides (ASO) were used in animal pain models. $Na_{v1.3}$ sodium channel ASO treatment significantly attenuated pain-related behaviors after CCI operation (NPL 9). These findings suggest that $Na_{v1.3}$ sodium channel antagonist is useful to treat neuropathic pain conditions.

The $Na_{v1.7}$ channel appears to be the best 'validated' pain target. The most exciting findings with respect to $Na_{v1.7}$ have come from human genetic studies. Cox et al. (NPL 10) discovered SCN9A mutations that cause a loss of $Na_{v1.7}$ function in three families from Pakistan. Their observations link loss of $Na_{v1.7}$ function with a congenital inability to experience pain, adding to the evidence indicating $Na_{v1.7}$ channel as an essential participant in human nociception.

By contrast, Gain-of-function mutations have also been described that lead to enhanced pain, for example, Primary Erythermalgia in one case and Paroxysmal Extreme Pain Disorder in another. These gain-of-function mutations in patients led to different types of gating changes in $Na_{v1.7}$ sodium currents and, interestingly, different degrees of effectiveness of specific sodium channel blocking drugs. The implication from these findings is that a selective $Na_{v1.7}$ blocker may be an effective treatment for pain in man.

A local anaesthetic lidocaine and a volatile anaesthetic halothane are known to act on both TTX-R and TTX-S sodium channels with poor selectivity and low potency ($IC_{50}$ values range from 50 microM to 10 mM). These anaesthetics at high systemic concentrations could cause devastating side effects, e.g., paralysis and cardiac arrest. However, systemic administration of lidocaine at low concentrations is effective to treat chronic pain (NPL 11). In rats, application of a very low dose of TTX to the DRG of the injured segment of the L5 spinal nerve significantly reduces mechanical allodynic behavior (NPL 12). This suggests that TTX-S subtypes of sodium channels play an important role in maintaining allodynic behaviors in an animal model of neuropathic pain.

The $Na_{v1.5}$ channel is also a member of TTX-resistant sodium channels. The $Na_{v1.5}$ channel is almost exclusively expressed in cardiac tissue and has been shown to underlie a variety of cardiac arrhythmias and conduction disorders.

CITATION LIST

Non Patent Literature

{NPL 1} FEBS Lett. 228 (1), 187-194, 1988; J. Mol. Neurosci., 10 (1), 67-70, 1998
{NPL 2} Eur. J. Neurosci. 12 (12), 4281-4289, 2000
{NPL 3} J Neurophysiol 82, 2776-2785, 1999. J. A. Black et al.
{NPL 4} Ann Neurol 52, 786-792, 2002. M. J. Cranner et al.
{NPL 5} Pain 83, 591-600, 1999. S. Dib-Hajj et al.
{NPL 6} J Biol Chem 279, 29341-29350, 2004. S. Hong et al.
{NPL 7} Mol Brain Res 95, 153-161, 2001. C. H. Kim et al.
{NPL 8} J Neurophysiol 82, 2776-2785, 1999. J. A. Black et al.
{NPL 9} J. Neurosci. 24, 4832-4839, 2004, Hains, B. C. et al.
{NPL 10} Nature 444, 894-898, 2006
{NPL 11} Trends in Pharm. Sci 22, 27-31, 2001, Baker, M. D. et al.
{NPL 12} Brain Res 871, 98-103, 2000, Lyu, Y. S. et al.

SUMMARY OF INVENTION

Technical Problem

It is an objective of the invention to provide new TTX-S blockers that are good drug candidates. Preferred compounds should bind potently to the TTX-S ($Na_{v1.3}$ and/or $Na_{v1.7}$) channels whilst showing little affinity for other sodium channels, particularly the $Na_{v1.5}$ channel. They should be well absorbed from the gastrointestinal tract, be metabolically stable and possess favorable pharmacokinetic properties. They should be non-toxic and demonstrate few side-effects. Furthermore, the ideal drug candidate will exist in a physical form that is stable, non-hygroscopic and easily formulated.

In particular, the arylamide derivatives of the present invention are selective for the TTX-S channels over the $Na_{v1.5}$ channel, leading to improvements in the side-effect profile.

The arylamide derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Other conditions that may be treated with the arylamide derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

The compounds showed activities against $Na_{v1.3}$ or $Na_{v1.7}$ channel. In addition they showed selectivity for the $Na_{v1.3}$ or $Na_{v1.7}$ channel as compared with $Na_{v1.5}$ channel.

Certain amide derivatives are disclosed in WO 2005/070889, and JP2007186435, which are not for sodium channel blockers of this invention but for quite different biological targets.

WO 2003037274 discloses pyrazole derivatives as sodium channel blockers. The PCT application PCT/JP2010/003649, which has not been laid open, discloses a use of a related compound.

Solution to Problem

With respect to other compounds disclosed in the art, the compounds of the present invention may show less toxicity, good absorption and distribution, good solubility, less plasma protein binding, less drug-drug interaction, good metabolic stability, reduced inhibitory activity at HERG channel, and/or reduced QT prolongation.

[1] This invention provides a use of a compound of the following formula (I) or a pharmaceutically acceptable salt, prodrug, solvate or composition thereof for the manufacture of a medicament for the treatment of a condition or disorder in which TTX-S channel blockers are involved:

[Chem. 1]

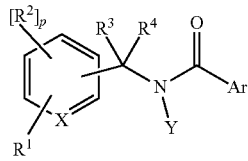

(I)

wherein:

$R^1$ is independently selected from the group consisting of —$CF_3$, —$CHF_2$, —$OCF_3$, —$OCHF_2$, —$OCH_2CHF_2$, —$OCH_2CF_3$, —$OCF_2CHF_2$, —$OCF_2CF_3$, —$OCH_2CH_2CF_3$, —$OCH(CH_3)CF_3$, —$OCH_2C(CH_3)F_2$, —$OCH_2CF_2CHF_2$, —$OCH_2CF_2CF_3$, —$OCH_2CH_2OCH_2CF_3$, —$NHCH_2CF_3$, —$SCF_3$, —$SCH_2CF_3$, —$CH_2CF_3$, —$CH_2CH_2CF_3$, —$CH_2OCH_2CF_3$, and —$OCH_2CH_2OCF_3$;

$R^2$ is independently selected from the group consisting of:
(1) hydrogen, (2) halogen, (3) hydroxyl, (4) —$O_n$—$C_{1-6}$ alkyl, where the alkyl is unsubstituted or substituted with one or more substituents independently selected from $R^5$, (5) —$O_n$—$C_{3-6}$ cycloalkyl, where the cycloalkyl is unsubstituted or substituted with one or more substituents independently selected from $R^5$, (6) —$O_n$—$C_{2-4}$ alkenyl, where the alkenyl is unsubstituted or substituted with one or more substituents independently selected from $R^5$, (7) —$O_n$-phenyl or —$O_n$-naphthyl, where the phenyl or naphthyl is unsubstituted or substituted with one or more substituents independently selected from $R^5$, (8) —$O_n$-heterocyclic group, where the heterocyclic group is unsubstituted or substituted with one or more substituents independently selected from $R^5$, (9) —(C=O)—$NR^7R^8$, (10) —$NR^7R^8$, (11) —$S(O)_2$—$NR^7R^8$, (12) —$NR^7$—$S(O)_2R^8$, (13) —$S(O)_t$—$R^7$, where t is 0, 1 or 2, (14) —$NR^7$(C=O)$R^8$, (15) —CN, and (16) —$NO_2$;

wherein n is 0 or 1, when n is 0, a chemical bond is present in the place of —$O_n$—;

p is 1, 2, 3, or 4; when p is two or more than two, $R^2$ may be same or different;

$R^3$ and $R^4$ are independently hydrogen or $C_{1-6}$ alkyl which is unsubstituted or substituted with one or more substituents independently selected from halogen, hydroxyl, and —O—$C_{1-6}$ alkyl; or $R^3$ form a 3 to 7 membered ring with $R^4$ which may contain nitrogen atom, oxygen atom, sulfur atom or double bond, wherein the 3 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

$R^5$ is selected from the group consisting of:
(1) hydrogen, (2) halogen, (3) hydroxyl, (4) —(C=O)$_m$—$O_l$—$C_{1-6}$ alkyl, where the alkyl is unsubstituted or substituted with one or more substituents independently selected from $R^6$, (5) —$O_l$—($C_{1-3}$)perfluoroalkyl, (6) —(C=O)$_m$—$O_l$—$C_{3-6}$ cycloalkyl, where the cycloalkyl is unsubstituted or substituted with one or more substituents independently selected from $R^6$, (7) —(C=O)$_m$—$O_l$—$C_{2-4}$ alkenyl, where the alkenyl is unsubstituted or substituted with one or more substituents independently selected from $R^6$, (8) —(C=O)$_m$—$O_l$-phenyl or —(C=O)$_m$—$O_l$-naphthyl, where the phenyl or naphthyl is unsubstituted or substituted with one or more substituents independently selected from $R^6$, (9) —(C=O)$_m$—$O_l$-heterocyclic group, where the heterocyclic group is unsubstituted or substituted with one or more substituents independently selected from $R^6$, (10) —(C=O)—$NR^7R^8$, (11) —$NR^7R^8$, (12) —$S(O)_2$—$NR^7R^8$, (13) —$S(O)_t$—$R^7$, where t is 0, 1 or 2, (14) —$CO_2H$, (15) —CN, and (16) —$NO_2$;

wherein l is 0 or 1 and m is 0 or 1; when l is 0 or m is 0, a chemical bond is present in the place of —$O_F$ or —(C=O)$_m$—, and when l is 0 and m is 0, a chemical bond is present in the place of —(C=O)$_m$—$O_l$—;

$R^6$ is independently selected from the group consisting of:
(1) hydrogen, (2) hydroxyl, (3) halogen, (4) —$C_{1-6}$ alkyl, (5) —$C_{3-6}$ cycloalkyl, (6) —O—$C_{1-6}$ alkyl, (7) —O(C=O)—$C_{1-6}$ alkyl, (8) —NH—$C_{1-6}$ alkyl, (9) phenyl, (10) heterocyclic group, and (11) —CN;

$R^7$ and $R^8$ are independently hydrogen, $C_{1-6}$ alkyl, $C_{2-6}$ alkenyl, $C_{3-7}$ cycloalkyl, or aryl, which is unsubstituted or substituted with one or more substituents independently selected from halogen, hydroxyl, $C_{1-6}$ alkyl, —O—$C_{1-6}$ alkyl, $C_{3-7}$ cycloalkyl, and —O—$C_{3-7}$ cycloalkyl; or $R^7$ form a 4 to 7 membered ring with $R^8$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

X is carbon atom, or nitrogen atom;

Y is hydrogen, or $C_{1-6}$ alkyl;

Ar is aryl which is optionally substituted with 1 to 5 substituents independently selected from the group consisting of:

(1) halogen, (2) hydroxyl, (3) —$O_n$-phenyl or —$O_n$-naphthyl, where the phenyl or naphthyl is unsubstituted or substituted with one or more substituents independently selected from $R^5$, (4) —$O_n$-heterocyclic group, where the heterocyclic group is unsubstituted or substituted with one or more substituents independently selected from $R^5$, (5) —$O_n$—$C_{1-6}$ alkyl, where the alkyl is unsubstituted or substituted with one or more substituents independently selected from $R^5$, (6) —$O_n$—$C_{3-6}$ cycloalkyl, where the cycloalkyl is unsubstituted or substituted with one or more substituents independently selected from $R^5$, (7) —$O_n$—$C_{2-4}$ alkenyl, where the alkenyl is unsubstituted or substituted with one or more substituents independently selected from $R^5$, (8) —(C=O)—$NR^7R^8$, (9) —$NR^7R^8$, (10) —S(O)$_2$—$NR^7R^8$, (11) —$NR^7$—S(O)$_2R^8$, (12) —S(O)$_t$—$R^7$, where t is 0, 1 or 2, (13) —$NR^7$(C=O)$_{1-2}{}^8$, (14) —CN, and (15) —$NO_2$;

wherein n is 0 or 1; when n is 0, a chemical bond is present in the place of —$O_n$—.

[2] This invention provides a compound represented by above formula (I) wherein $R^1$ is independently selected from the group consisting of —$CF_3$, —$CHF_2$, —$OCF_3$, —$OCHF_2$, —$OCH_2CHF_2$, —$OCH_2CF_3$, —$OCF_2CHF_2$, —$OCF_2CF_3$, —$OCH_2CH_2CF_3$, —$OCH(CH_3)CF_3$, —$OCH_2C(CH_3)F_2$, —$OCH_2CF_2CHF_2$, —$OCH_2CF_2CF_3$, —$OCH_2CH_2OCH_2CF_3$, —$NHCH_2CF_3$, —$SCF_3$, —$SCH_2CF_3$, —$CH_2CF_3$, —$CH_2CH_2CF_3$, —$CH_2OCH_2CF_3$, and —$OCH_2CH_2OCF_3$;

$R^2$ is independently selected from the group consisting of:

(1) hydrogen, (2) halogen, (3) hydroxyl, (4) —$O_n$—$C_{1-6}$ alkyl, where the alkyl is unsubstituted or substituted with one or more substituents independently selected from $R^5$, (5) —$O_n$—$C_{3-6}$ cycloalkyl, where the cycloalkyl is unsubstituted or substituted with one or more substituents independently selected from $R^5$, (6) —$O_n$—$C_{2-4}$ alkenyl, where the alkenyl is unsubstituted or substituted with one or more substituents independently selected from $R^5$, (7) —$O_n$-phenyl or —$O_n$-naphthyl, where the phenyl or naphthyl is unsubstituted or substituted with one or more substituents independently selected from $R^5$, (8) —$O_n$-heterocyclic group, where the heterocyclic group is unsubstituted or substituted with one or more substituents independently selected from $R^5$, (9) —(C=O)—$NR^7R^8$, (10) —$NR^7R^8$, (11) —S(O)$_2$—$NR^7R^8$, (12) —$NR^7$—S(O)$_2R^8$, (13) —S(O)$_t$—$R^7$, where t is 0, 1 or 2, (14) —$NR^7$(C=O)$R^8$, (15) —CN, and (16) —$NO_2$;

wherein n is 0 or 1, when n is 0, a chemical bond is present in the place of —$O_n$—;

p is 1, 2, 3, or 4; when p is two or more than two, $R^2$ may be same or different;

$R^3$ and $R^4$ are independently hydrogen or $C_{1-6}$ alkyl which is unsubstituted or substituted with one substituents independently selected from halogen, hydroxyl, and —O—$C_{1-6}$ alkyl; or $R^3$ form a 3 to 7 membered ring with $R^4$ which may contain nitrogen atom, oxygen atom, sulfur atom or double bond, wherein the 3 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

$R^5$ is selected from the group consisting of:

(1) hydrogen, (2) halogen, (3) hydroxyl, (4) —(C=O)$_m$—$O_l$—$C_{1-6}$ alkyl, where the alkyl is unsubstituted or substituted with one or more substituents independently selected from $R^6$, (5) —$O_l$—($C_{1-3}$)perfluoroalkyl, (6) —(C=O)$_m$—$O_l$—$C_{3-6}$ cycloalkyl, where the cycloalkyl is unsubstituted or substituted with one or more substituents independently selected from $R^6$, (7) —(C=O)$_m$—$O_l$—$C_{2-4}$ alkenyl, where the alkenyl is unsubstituted or substituted with one or more substituents independently selected from $R^6$, (8) —(C=O)$_m$—$O_l$-phenyl or —(C=O)$_m$—$O_l$-naphthyl, where the phenyl or naphthyl is unsubstituted or substituted with one or more substituents independently selected from $R^6$, (9) —(C=O)$_m$—$O_l$-heterocyclic group, where the heterocyclic group is unsubstituted or substituted with one or more substituents independently selected from $R^6$, (10) —(C=O)—$NR^7R^8$, (11) —$NR^7R^8$, (12) —S(O)$_2$—$NR^7R^8$, (13) —S(O)$_t$—$R^7$, where t is 0, 1 or 2, (14) —$CO_2H$, (15) —CN, and (16) —$NO_2$;

wherein l is 0 or 1 and m is 0 or 1; when l is 0 or m is 0, a chemical bond is present in the place of —$O_l$— or —(C=O)$_m$—, and when l is 0 and m is 0, a chemical bond is present in the place of —(C=O)$_m$—$O_l$—;

$R^6$ is independently selected from the group consisting of:

(1) hydrogen, (2) hydroxyl, (3) halogen, (4) —$C_{1-6}$ alkyl, (5) —$C_{3-6}$ cycloalkyl, (6) —O—$C_{1-6}$ alkyl, (7) —O(C=O)—$C_{1-6}$ alkyl, (8) —NH—$C_{1-6}$ alkyl, (9) phenyl, (10) heterocyclic group, and (11) —CN;

$R^7$ and $R^8$ are independently hydrogen, $C_{1-6}$ alkyl, $C_{2-6}$ alkenyl, $C_{3-7}$ cycloalkyl, or aryl, which is unsubstituted or substituted with one or more substituents independently selected from halogen, hydroxyl, $C_{1-6}$ alkyl, —O—$C_{1-6}$ alkyl, $C_{3-7}$ cycloalkyl, and —O—$C_{3-7}$ cycloalkyl; or $R^7$ form a 4 to 7 membered ring with $R^8$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

X is nitrogen atom;

Y is hydrogen or $C_{1-6}$ alkyl;

Ar is selected from the group consisting of:

pyridyl, pyrimidyl, benzimidazolonyl, indazolyl, isoquinolyl, imidazopyridyl, naphthyridinyl, 3- to 8-quinolyl, quinoxalinyl, benzoisoxazolyl, pyrazolopyridyl, triazolyl, thiazolyl, and benzimidazolyl;

wherein said pyridyl, pyrimidyl benzimidazolonyl, indazolyl, isoquinolyl, imidazopyridyl, naphthyridinyl, 3- to 8-quinolyl, quinoxalinyl, benzoisoxazolyl, pyrazolopyridyl, triazolyl, thiazolyl, and benzimidazolyl may be optionally substituted with 1 to 5 substituents independently selected from the group consisting of:

(1) halogen, (2) hydroxyl, (3) —$O_n$-phenyl or —$O_n$-naphthyl, where the phenyl or naphthyl is unsubstituted or substituted with one or more substituents independently selected from $R^5$, (4) —$O_n$-heterocyclic group, where the heterocyclic group is unsubstituted or substituted with one or more substituents independently selected from $R^5$, (5) —$O_n$—$C_{1-6}$ alkyl, where the alkyl is unsubstituted or substituted with one or more substituents independently selected from $R^5$, (6) —$O_n$—$C_{3-6}$ cycloalkyl, where the cycloalkyl is unsubstituted or substituted with one or more substituents independently selected from $R^5$, (7) —$O_n$—$C_{2-4}$ alkenyl, where the alkenyl is unsubstituted or substituted with one or more substituents independently selected from $R^5$, (8) —(C=O)—$NR^7R^8$, (9) —$NR^7R^8$, (10) —$S(O)_2$—$NR^7R^8$, (11) —$NR^7$—$S(O)_2R^8$, (12) —$S(O)_t$—$R^7$, where t is 0, 1 or 2, (13) —$NR^7(C=O)R^8$, (14) —CN, and (15) —$NO_2$;

wherein n is 0 or 1; when n is 0, a chemical bond is present in the place of —$O_n$—;

or a prodrug thereof or a pharmaceutically acceptable salt thereof.

[3] Preferable compounds of this invention are represented by above formula (I) wherein Ar is pyridyl or pyrimidyl;

wherein said pyridyl or pyrimidyl may be optionally substituted with 1 to 5 substituents independently selected from the group consisting of:

(1) halogen, (2) hydroxyl, (3) —$O_n$-phenyl or —$O_n$-naphthyl, where the phenyl or naphthyl is unsubstituted or substituted with one or more substituents independently selected from $R^5$, (4) —$O_n$-heterocyclic group, where the heterocyclic group is unsubstituted or substituted with one or more substituents independently selected from $R^5$, (5) —$O_n$—$C_{1-6}$ alkyl, where the alkyl is unsubstituted or substituted with one or more substituents independently selected from $R^5$, (6) —$O_n$—$C_{3-6}$ cycloalkyl, where the cycloalkyl is unsubstituted or substituted with one or more substituents independently selected from $R^5$, (7) —$O_n$—$C_{2-4}$ alkenyl, where the alkenyl is unsubstituted or substituted with one or more substituents independently selected from $R^5$, (8) —(C=O)—$NR^7R^8$, (9) —$NR^7R^8$, (10) —$S(O)_2$—$NR^7R^8$, (11) —$NR^7$—$S(O)_2R^8$, (12) —$S(O)_t$—$R^7$, where t is 0, 1 or 2, (13) —$NR^7(C=O)R^8$, (14) —CN, and (15) —$NO_2$;

wherein n is 0 or 1; when n is 0, a chemical bond is present in the place of —$O_n$—; and the descriptors are the same as in the definition described in [2]; or a prodrug thereof or a pharmaceutically acceptable salt thereof.

[4] Preferable compounds of this invention are represented by above formula (I) wherein $R^1$ is independently selected from the group consisting of —$CF_3$, —$CHF_2$, —$OCF_3$, —$OCHF_2$, —$OCH_2CHF_2$, —$OCH_2CF_3$, —$OCF_2CHF_2$, —$OCF_2CF_3$, —$OCH_2CH_2CF_3$, —$OCH(CH_3)CF_3$, —$OCH_2C(CH_3)_2F_2$, —$OCH_2CF_2CHF_2$, —$OCH_2CF_2CF_3$, —$OCH_2CH_2OCH_2CF_3$, —$NHCH_2CF_3$, —$SCF_3$, —$SCH_2CF_3$, —$CH_2CF_3$, —$CH_2CH_2CF_3$, —$CH_2OCH_2CF_3$, and —$OCH_2CH_2OCF_3$;

$R^2$ is independently selected from the group consisting of:
(1) hydrogen, (2) halogen, (3) hydroxyl, (4) —$O_n$—$C_{1-6}$ alkyl, where the alkyl is unsubstituted or substituted with one or more substituents independently selected from $R^5$, (5) —$O_n$—$C_{3-6}$ cycloalkyl, where the cycloalkyl is unsubstituted or substituted with one or more substituents independently selected from $R^5$, (6) —$O_n$—$C_{2-4}$ alkenyl, where the alkenyl is unsubstituted or substituted with one or more substituents independently selected from $R^5$, (7) —$O_n$-phenyl or —$O_n$-naphthyl, where the phenyl or naphthyl is unsubstituted or substituted with one or more substituents independently selected from $R^5$, (8) —$O_n$-heterocyclic group, where the heterocyclic group is unsubstituted or substituted with one or more substituents independently selected from $R^5$, (9) —(C=O)—$NR^7R^8$, (10) —$NR^7R^8$, (11) —$S(O)_2$—$NR^7R^8$, (12) —$NR^7$—$S(O)_2R^8$, (13) —$S(O)_t$—$R^7$, where t is 0, 1 or 2, (14) —$NR^7(C=O)R^8$, (15) —CN, and (16) —$NO_2$;

wherein n is 0 or 1, when n is 0, a chemical bond is present in the place of —$O_n$—;

p is 1, 2, 3, or 4; when p is two or more than two, $R^2$ may be same or different;

$R^3$ and $R^4$ are independently hydrogen or $C_{1-6}$ alkyl which is unsubstituted or substituted with one or more substituents independently selected from halogen, hydroxyl, and —O—$C_{1-6}$ alkyl; or $R^3$ form a 3 to 7 membered ring with $R^4$ which may contain nitrogen atom, oxygen atom, sulfur atom or double bond, wherein the 3 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

$R^5$ is selected from the group consisting of:
(1) hydrogen, (2) halogen, (3) hydroxyl, (4) —(C=O)$_m$—$O_l$—$C_{1-6}$ alkyl, where the alkyl is unsubstituted or substituted with one or more substituents independently selected from $R^6$, (5) —$O_l$—(C$_{1-3}$)perfluoroalkyl, (6) —(C=O)$_m$—$O_l$—$C_{3-6}$ cycloalkyl, where the cycloalkyl is unsubstituted or substituted with one or more substituents independently selected from $R^6$, (7) —(C=O)$_m$—$O_l$—$C_{2-4}$alkenyl, where the alkenyl is unsubstituted or substituted with one or more substituents independently selected from $R^6$, (8) —(C=O)$_m$—$O_l$-phenyl or —(C=O)$_m$—$O_l$-naphthyl, where the phenyl or naphthyl is unsubstituted or substituted with one or more substituents independently selected from $R^6$, (9) —(C=O)$_m$—$O_l$-heterocyclic group, where the heterocyclic group is unsubstituted or substituted with one or more substituents independently selected from $R^6$, (10) —(C=O)—$NR^7R^8$, (11) —$NR^7R^8$, (12) —$S(O)_2$—$NR^7R^8$, (13) —$S(O)_t$—$R^7$, where t is 0, 1 or 2, (14) —$CO_2H$, (15) —CN, and (16) —$NO_2$;

wherein l is 0 or 1 and m is 0 or 1; when l is 0 or m is 0, a chemical bond is present in the place of —$O_l$— or —(C=O)$_m$—, and when l is 0 and m is 0, a chemical bond is present in the place of —(C=O)$_m$—$O_l$—;

$R^6$ is independently selected from the group consisting of:
(1) hydrogen, (2) hydroxyl, (3) halogen, (4) —$C_{1-6}$ alkyl, (5) —$C_{3-6}$ cycloalkyl, (6) —O—$C_{1-6}$ alkyl, (7) —O(C=O)—$C_{1-6}$ alkyl, (8) —NH—$C_{1-6}$ alkyl, (9) phenyl, (10) heterocyclic group, and (11) —CN;

$R^7$ and $R^8$ are independently hydrogen, $C_{1-6}$ alkyl, $C_{2-6}$ alkenyl, $C_{3-7}$ cycloalkyl, or aryl, which is unsubstituted or substituted with one or more substituents independently selected from halogen, hydroxyl, $C_{1-6}$ alkyl, —O—$C_{1-6}$ alkyl, $C_{3-7}$ cycloalkyl, and —O—$C_{3-7}$ cycloalkyl; or $R^7$ form a 4 to 7 membered ring with $R^8$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

X is carbon atom;

Y is hydrogen or $C_{1-6}$ alkyl;

Ar is 4-pyridyl, 4-pyrimidyl or 6-pyrimidyl which is substituted at the 2-position with a substituent independently selected from (1) —(C=O)—$NR^7R^8$, (2) —$NR^7$—$S(O)_2R^8$, (3) —$NR^7$(C=O)$R^8$; and which is optionally substituted with 1 to 3 substituents independently selected from the group consisting of:

(1) halogen, (2) hydroxyl, (3) —$O_n$-phenyl or —$O_n$-naphthyl, where the phenyl or naphthyl is unsubstituted or substituted with one or more substituents independently selected from $R^5$, (4) —$O_n$-heterocyclic group, where the heterocyclic group is unsubstituted or substituted with one or more substituents independently selected from $R^5$, (5) —$O_n$—$C_{1-6}$ alkyl, where the alkyl is unsubstituted or substituted with one or more substituents independently selected from $R^5$, (6) —$O_n$—$C_{3-6}$ cycloalkyl, where the cycloalkyl is unsubstituted or substituted with one or more substituents independently selected from $R^5$, (7) —$O_n$—$C_{2-4}$ alkenyl, where the alkenyl is unsubstituted or substituted with one or more substituents independently selected from $R^5$, (8) —(C=O)—$NR^7R^8$, (9) —$NR^7R^8$, (10) —$S(O)_2$—$NR^7R^8$, (11) —$NR^7$—$S(O)_2R^8$, (12) —$S(O)_t$—$R^7$, where t is 0, 1 or 2, (13) —$NR^7$(C=O)$R^8$, (14) —CN, and (15) —$NO_2$;

wherein n is 0 or 1; when n is 0, a chemical bond is present in the place of —$O_n$—; or a prodrug thereof or a pharmaceutically acceptable salt thereof.

[5] Preferable compounds of this invention are represented by formula (II)

{Chem. 2}

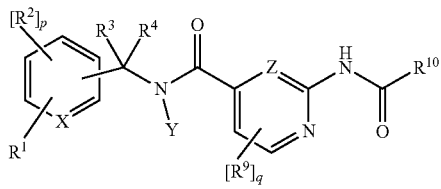

(II)

wherein $R^1$ is independently selected from the group consisting of —$CF_3$, —$CHF_2$, —$OCF_3$, —$OCHF_2$, —$OCH_2CHF_2$, —$OCH_2CF_3$, —$OCF_2CHF_2$, —$OCF_2CF_3$, —$OCH_2CH_2CF_3$, —$OCH(CH_3)CF_3$, —$OCH_2C(CH_3)F_2$, —$OCH_2CF_2CHF_2$, —$OCH_2CF_2CF_3$, —$OCH_2CH_2OCH_2CF_3$, —$NHCH_2CF_3$, —$SCF_3$, —$SCH_2CF_3$, —$CH_2CF_3$, —$CH_2CH_2CF_3$, —$CH_2OCH_2CF_3$, and —$OCH_2CH_2OCF_3$;

$R^2$ is independently selected from the group consisting of: (1) hydrogen, (2) halogen, (3) hydroxyl, (4) —$O_n$—$C_{1-6}$ alkyl, where the alkyl is unsubstituted or substituted with one or more substituents independently selected from $R^5$, (5) —$O_n$—$C_{3-6}$ cycloalkyl, where the cycloalkyl is unsubstituted or substituted with one or more substituents independently selected from $R^5$, (6) —$O_n$—$C_{2-4}$ alkenyl, where the alkenyl is unsubstituted or substituted with one or more substituents independently selected from $R^5$, (7) —$O_n$-phenyl or —$O_n$-naphthyl, where the phenyl or naphthyl is unsubstituted or substituted with one or more substituents independently selected from $R^5$, (8) —$O_n$-heterocyclic group, where the heterocyclic group is unsubstituted or substituted with one or more substituents independently selected from $R^5$, (9) —(C=O)—$NR^7R^8$, (10) —$NR^7R^8$, (11) —$S(O)_2$—$NR^7R^8$, (12) —$NR^7$—$S(O)_2R^8$, (13) —$S(O)_t$—$R^7$, where t is 0, 1 or 2, (14) —$NR^7$(C=O)$R^8$, (15) —CN, and (16) —$NO_2$;

wherein n is 0 or 1, when n is 0, a chemical bond is present in the place of —$O_n$—;

p is 1, 2, 3, or 4; when p is two or more than two, $R^2$ may be same or different;

$R^3$ and $R^4$ are independently hydrogen or $C_{1-6}$ alkyl which is unsubstituted or substituted with one or more substituents independently selected from halogen, hydroxyl, and —O—$C_{1-6}$ alkyl, both $R^3$ and $R^4$ are not $C_{1-6}$ alkyl at the same time.

$R^5$ is selected from the group consisting of:

(1) hydrogen, (2) halogen, (3) hydroxyl, (4) —(C=O)$_m$—$O_l$—$C_{1-6}$ alkyl, where the alkyl is unsubstituted or substituted with one or more substituents independently selected from $R^6$, (5) —$O_l$—($C_{1-3}$)perfluoroalkyl, (6) —(C=O)$_m$—$O_l$—$C_{3-6}$ cycloalkyl, where the cycloalkyl is unsubstituted or substituted with one or more substituents independently selected from $R^6$, (7) —(C=O)$_m$—$O_l$—$C_{2-4}$ alkenyl, where the alkenyl is unsubstituted or substituted with one or more substituents independently selected from $R^6$, (8) —(C=O)$_m$—$O_l$-phenyl or —(C=O)$_m$—$O_l$-naphthyl, where the phenyl or naphthyl is unsubstituted or substituted with one or more substituents independently selected from $R^6$, (9) —(C=O)$_m$—$O_l$-heterocyclic group, where the heterocyclic group is unsubstituted or substituted with one or more substituents independently selected from $R^6$, (10) —(C=O)—$NR^7R^8$, (11) —$NR^7R^8$, (12) —$S(O)_2$—$NR^7R^8$, (13) —$S(O)_t$—$R^7$, where t is 0, 1 or 2, (14) —$CO_2H$, (15) —CN, and (16) —$NO_2$;

wherein l is 0 or 1 and m is 0 or 1; when l is 0 or m is 0, a chemical bond is present in the place of —$O_l$— or —(C=O)$_m$—, and when l is 0 and m is 0, a chemical bond is present in the place of —(C=O)$_m$—$O_l$—;

$R^6$ is independently selected from the group consisting of: (1) hydrogen, (2) hydroxyl, (3) halogen, (4) —$C_{1-6}$ alkyl, (5) —$C_{3-6}$ cycloalkyl, (6) —O—$C_{1-6}$ alkyl, (7) —O(C=O)—$C_{1-6}$ alkyl, (8) —NH—$C_{1-6}$ alkyl, (9) phenyl, (10) heterocyclic group, and (11) —CN; $R^7$ and $R^8$ are independently hydrogen, $C_{1-6}$ alkyl, $C_{2-6}$ alkenyl, $C_{3-7}$ cycloalkyl, or aryl, which is unsubstituted or substituted with one or more substituents independently selected from halogen, hydroxyl, $C_{1-6}$ alkyl, and —O—$C_{1-6}$ alkyl; or $R^7$ form a 4 to 7 membered ring with $R^8$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

X is nitrogen atom or carbon atom;

Z is nitrogen atom or carbon atom;

Y is hydrogen, or $C_{1-6}$ alkyl;

$R^9$ is independently selected from the group consisting of:
(1) hydrogen, (2) halogen, (3) —$O_n$—$C_{1-6}$ alkyl, where the alkyl is unsubstituted or substituted with one or more substituents independently selected from $R^5$, (4) —$O_n$—$C_{3-6}$ cycloalkyl, where the cycloalkyl is unsubstituted or substituted with one or more substituents independently selected from $R^5$, and (5) —$O_n$—$C_{2-4}$ alkenyl, where the alkenyl is unsubstituted or substituted with one or more substituents independently selected from $R^5$;

wherein n is 0 or 1, when n is 0, a chemical bond is present in the place of —$O_n$—;

q is 1, 2 or 3; when q is two or more than two, $R^9$ may be same or different;

$R^{10}$ is independently hydrogen, $C_{1-6}$ alkyl, $C_{2-6}$ alkenyl, $C_{3-7}$ cycloalkyl, or aryl, which is unsubstituted or substituted with one or more substituents independently selected from halogen, hydroxyl, $C_{1-6}$ alkyl, —O—$C_{1-6}$ alkyl, —$C_{3-7}$ cycloalkyl, and —O—$C_{3-7}$ cycloalkyl;

or a prodrug thereof or a pharmaceutically acceptable salt thereof.

[6] Compounds of formula (II) are further preferred wherein:

$R^1$ is selected from the group consisting of —$CF_3$, —$OCF_3$, —$OCH_2CHF_2$, —$OCF_2CHF_2$, —$OCF_2CF_3$, —$OCH_2CF_2CF_3$, —$OCH_2CF_2CHF_2$ and —$OCH_2CF_3$;

$R^2$ is independently selected from the group consisting of:
(1) hydrogen, (2) halogen, (3) methyl, and (4) methoxy;

p is 1;

$R^3$ is hydrogen;

$R^4$ is hydrogen or methyl;

Y is hydrogen;

[Chem. 3]

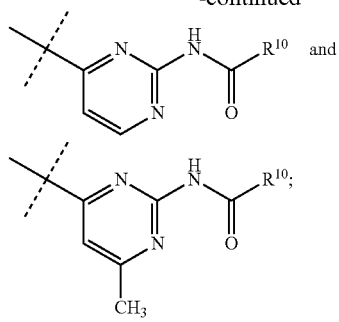

is selected from the group consisting of:

[Chem. 4]

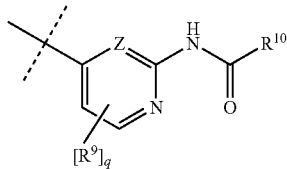

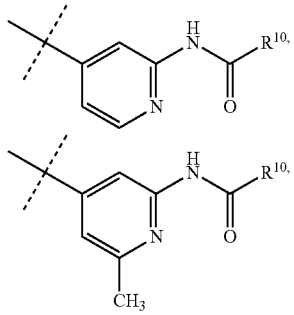

and $R^{10}$ is selected from the group consisting of methyl, ethyl, isopropyl, and cyclopropyl; or a pharmaceutically acceptable salt thereof.

[7] Compounds of formula (II) are further especially preferred wherein:

$R^1$ is selected from the group consisting of —$CF_3$, —$OCF_3$, —$OCH_2CHF_2$, —$OCF_2CHF_2$, —$OCF_2CF_3$, —$OCH_2CF_2CF_3$, —$OCH_2CF_2CHF_2$ and —$OCH_2CF_3$;

$R^2$ is independently selected from the group consisting of:
(1) hydrogen, (2) halogen, (3) methyl, and (4) methoxy;

p is 1;

$R^3$ is hydrogen;

$R^4$ is methyl;

Y is hydrogen;

[Chem. 5]

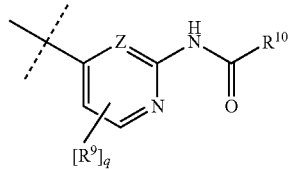

is selected from the group consisting of:

[Chem. 6]

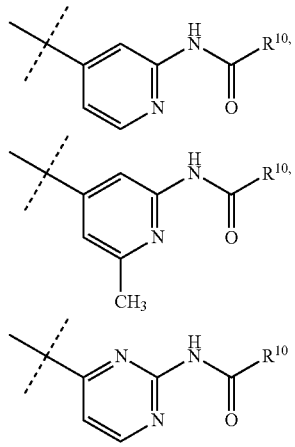

and

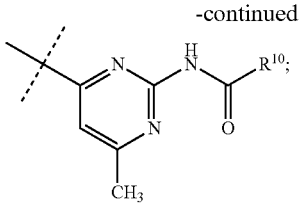

and

R[10] is selected from the group consisting of methyl, ethyl, isopropyl, and cyclopropyl;

or a pharmaceutically acceptable salt thereof.

[8] In addition, compounds of formula (II) are further especially preferred wherein:

R[1] is selected from the group consisting of —CF$_3$, —OCF$_3$, —OCH$_2$CHF$_2$, —OCF$_2$CHF$_2$, —OCF$_2$CF$_3$, —OCH$_2$CF$_2$CF$_3$, —OCH$_2$CF$_2$CHF$_2$ and —OCH$_2$CF$_3$;

R[2] is independently selected from the group consisting of: (1) hydrogen, (2) halogen, (3) methyl, and (4) methoxy;

p is 1;

R[3] and R[4] are both hydrogen;

X is nitrogen atom;

Y is hydrogen;

[Chem. 7]

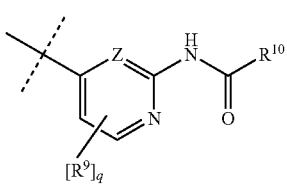

is selected from the group consisting of:

[Chem. 8]

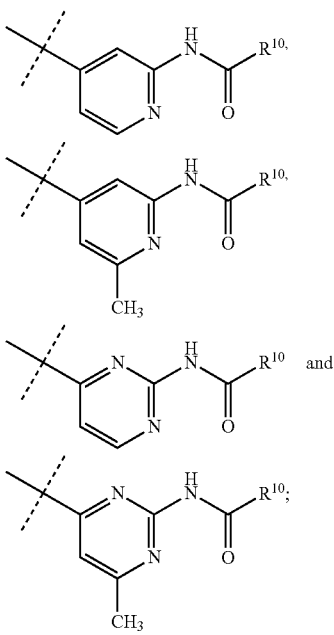

and

R[10] is selected from the group consisting of methyl, ethyl, isopropyl, and cyclopropyl;

or a pharmaceutically acceptable salt thereof.

[9] Suitable individual compounds of the invention are:
2-acetamido-N-(1-(6-(2,2,2-trifluoroethoxy)pyridin-3-yl)ethyl)isonicotinamide;
2-acetamido-N-((4-(2,2,2-trifluoroethoxy)pyridin-2-yl)methyl)isonicotinamide;
N-((5-acetamido-6-(2,2,2-trifluoroethoxy)pyridin-3-yl)methyl)-3-(trifluoromethoxy)benzamide;
2-oxo-N-(1-(6-(2,2,2-trifluoroethoxy)pyridin-3-yl)ethyl)-2,3-dihydro-1H-benzo[d]imidazole-4-carboxamide;
2-methyl-N-(1-(6-(2,2,2-trifluoroethoxy)pyridin-3-yl)ethyl)-2H-indazole-3-carboxamide;
(R)-2-acetamido-N-(1-(4-(trifluoromethyl)phenyl)ethyl)isonicotinamide;
(R)-2-acetamido-N-(1-(3-(trifluoromethyl)phenyl)ethyl)isonicotinamide;
2-isobutyramido-N-(1-(6-(2,2,2-trifluoroethoxy)pyridin-3-yl)ethyl)isonicotinamide;
2-(cyclopropanecarboxamido)-N-(1-(6-(2,2,2-trifluoroethoxy)pyridin-3-yl)ethyl)isonicotinamide;
2-benzamido-N-(1-(6-(2,2,2-trifluoroethoxy)pyridin-3-yl)ethyl)isonicotinamide;
2-propionamido-N-(1-(6-(2,2,2-trifluoroethoxy)pyridin-3-yl)ethyl)isonicotinamide;
2-(methylsulfonamido)-N-(1-(6-(2,2,2-trifluoroethoxy)pyridin-3-yl)ethyl)benzamide;
3-(1H-imidazol-1-yl)-N-(1-(6-(2,2,2-trifluoroethoxy)pyridin-3-yl)ethyl)benzamide;
2-acetamido-N-((6-(2,2,2-trifluoroethoxy)pyridin-3-yl)methyl)isonicotinamide;
N-(1-(6-(2,2,2-trifluoroethoxy)pyridin-3-yl)ethyl)quinoline-8-carboxamide;
N-(1-(6-(2,2,2-trifluoroethoxy)pyridin-3-yl)ethyl)quinoline-2-carboxamide;
2-acetamido-N-((2-(2,2,2-trifluoroethoxy)pyridin-4-yl)methyl)isonicotinamide;
2-acetamido-N-(4-(trifluoromethoxy)benzyl)isonicotinamide;
3-acetamido-N-(1-(6-(2,2,2-trifluoroethoxy)pyridin-3-yl)ethyl)picolinamide;
2-(1H-imidazol-1-yl)-N-(1-(6-(2,2,2-trifluoroethoxy)pyridin-3-yl)ethyl)isonicotinamide;
2-acetamido-N-methyl-N-(1-(6-(2,2,2-trifluoroethoxy)pyridin-3-yl)ethyl)isonicotinamide;
2-acetamido-N-((6-(2,2,2-trifluoroethoxy)pyridin-2-yl)methyl)isonicotinamide;
6-acetamido-N-((6-(2,2,2-trifluoroethoxy)pyridin-2-yl)methyl)picolinamide;
2-acetamido-N-(3-(trifluoromethoxy)benzyl)isonicotinamide;
N-(1-(6-(2,2,2-trifluoroethoxy)pyridin-3-yl)ethyl)-1,6-naphthyridine-2-carboxamide;
N-(1-(6-(2,2,2-trifluoroethoxy)pyridin-3-yl)ethyl)quinoline-3-carboxamide;
N-(1-(6-(2,2,2-trifluoroethoxy)pyridin-3-yl)ethyl)isoquinoline-3-carboxamide;
N-(1-(6-(2,2,2-trifluoroethoxy)pyridin-3-yl)ethyl)quinoxaline-2-carboxamide;
N-(1-(6-(2,2,2-trifluoroethoxy)pyridin-3-yl)ethyl)isoquinoline-6-carboxamide;
6-(tert-butyl)-N-(1-(6-(2,2,2-trifluoroethoxy)pyridin-3-yl)ethyl)nicotinamide;
1-methyl-N-(1-(6-(2,2,2-trifluoroethoxy)pyridin-3-yl)ethyl)-1H-indazole-3-carboxamide;

N-(1-(6-(2,2,2-trifluoroethoxy)pyridin-3-yl)ethyl)benzo[c]isoxazole-3-carboxamide;
1-methyl-N-(1-(6-(2,2,2-trifluoroethoxy)pyridin-3-yl)ethyl)-1H-pyrazolo[3,4-b]pyridine-3-carboxamide;
N-(1-(6-(2,2,2-trifluoroethoxy)pyridin-3-yl)ethyl)imidazo[1,2-a]pyridine-2-carboxamide;
1-methyl-N-(1-(6-(2,2,2-trifluoroethoxy)pyridin-3-yl)ethyl)-3-(trifluoromethyl)-1H-pyrazole-5-carboxamide;
5-methyl-1-phenyl-N-(1-(6-(2,2,2-trifluoroethoxy)pyridin-3-yl)ethyl)-1H-1,2,3-triazole-4-carboxamide;
4-methyl-2-phenyl-N-(1-(6-(2,2,2-trifluoroethoxy)pyridin-3-yl)ethyl)thiazole-5-carboxamide;
1-methyl-5-phenyl-N-(1-(6-(2,2,2-trifluoroethoxy)pyridin-3-yl)ethyl)-1H-pyrazole-3-carboxamide;
2-acetamido-N-(2-fluoro-5-(trifluoromethyl)benzyl)isonicotinamide;
2-butyramido-N-(1-(6-(2,2,2-trifluoroethoxy)pyridin-3-yl)ethyl)isonicotinamide;
2-(2-methoxyacetamido)-N-(1-(6-(2,2,2-trifluoroethoxy)pyridin-3-yl)ethyl)isonicotinamide;
2-(cyclobutanecarboxamido)-N-(1-(6-(2,2,2-trifluoroethoxy)pyridin-3-yl)ethyl)isonicotinamide;
2-acetamido-N-(3-(difluoromethoxy)benzyl)isonicotinamide;
4-methoxy-N-(1-(6-(2,2,2-trifluoroethoxy)pyridin-3-yl)ethyl)quinoline-2-carboxamide;
8-hydroxy-N-(1-(6-(2,2,2-trifluoroethoxy)pyridin-3-yl)ethyl)quinoline-2-carboxamide;
3-isopropyl-N-(1-(6-(2,2,2-trifluoroethoxy)pyridin-3-yl)ethyl)-1H-pyrazole-5-carboxamide;
3-(tert-butyl)-1-methyl-N-(1-(6-(2,2,2-trifluoroethoxy)pyridin-3-yl)ethyl)-1H-pyrazole-5-carboxamide;
6-(piperidin-1-yl)-N-(1-(6-(2,2,2-trifluoroethoxy)pyridin-3-yl)ethyl)nicotinamide;
N-(1-(6-(2,2,2-trifluoroethoxy)pyridin-3-yl)ethyl)-1H-benzo[d]imidazole-2-carboxamide;
N-(1-(6-(2,2,2-trifluoroethoxy)pyridin-3-yl)ethyl)pyrazolo[1,5-a]pyridine-2-carboxamide;
N-(1-(6-(2,2,2-trifluoroethoxy)pyridin-3-yl)ethyl)benzo[d]isoxazole-3-carboxamide;
2-acetamido-N-(1-(5-chloro-6-(2,2,2-trifluoroethoxy)pyridin-3-yl)ethyl)isonicotinamide;
2-acetamido-N-(3-(trifluoromethyl)benzyl)isonicotinamide;
N-((6-(2,2,2-trifluoroethoxy)pyridin-2-yl)methyl)quinoline-8-carboxamide;
2-methyl-N-((6-(2,2,2-trifluoroethoxy)pyridin-2-yl)methyl)-2H-indazole-3-carboxamide;
6-(tert-butyl)-N-((6-(2,2,2-trifluoroethoxy)pyridin-2-yl)methyl)nicotinamide;
2-oxo-N-((6-(2,2,2-trifluoroethoxy)pyridin-2-yl)methyl)-2,3-dihydro-1H-benzo[d]imidazole-4-carboxamide;
2-acetamido-N-(1-(6-(2,2,2-trifluoroethoxy)pyridin-3-yl)propyl)isonicotinamide;
2-acetamido-6-methyl-N-(1-(6-(2,2,2-trifluoroethoxy)pyridin-3-yl)ethyl)isonicotinamide;
2-methyl-6-propionamido-N-(1-(6-(2,2,2-trifluoroethoxy)pyridin-3-yl)ethyl)isonicotinamide;
2-(cyclopropanecarboxamido)-6-methyl-N-(1-(6-(2,2,2-trifluoroethoxy)pyridin-3-yl)ethyl)isonicotinamide;
2-isobutyramido-6-methyl-N-(1-(6-(2,2,2-trifluoroethoxy)pyridin-3-yl)ethyl)isonicotinamide;
2-acetamido-N-(1-(6-(2,2,2-trifluoroethoxy)pyridin-2-yl)ethyl)isonicotinamide;
N-(1-(6-(2,2,2-trifluoroethoxy)pyridin-2-yl)ethyl)benzo[c]isoxazole-3-carboxamide;
1-methyl-N-(1-(6-(2,2,2-trifluoroethoxy)pyridin-2-yl)ethyl)-1H-indazole-3-carboxamide;
2-acetamido-N-(1-(4-(2,2,2-trifluoroethoxy)pyridin-2-yl)ethyl)isonicotinamide;
2-acetamido-N-(1-(3-(trifluoromethoxy)phenyl)ethyl)isonicotinamide;
2-acetamido-N-(1-(4-(trifluoromethoxy)phenyl)ethyl)isonicotinamide;
N-(1-(5-chloro-6-(2,2,2-trifluoroethoxy)pyridin-3-yl)ethyl)-2-propionamidoisonicotinamide;
2-propionamido-N-(1-(6-(2,2,2-trifluoroethoxy)pyridin-2-yl)ethyl)isonicotinamide;
2-propionamido-N-(1-(2-(2,2,2-trifluoroethoxy)pyridin-4-yl)ethyl)isonicotinamide;
2-acetamido-N-(1-(5-fluoro-6-(2,2,2-trifluoroethoxy)pyridin-3-yl)ethyl)isonicotinamide;
2-acetamido-N-(1-(2-methyl-6-(2,2,2-trifluoroethoxy)pyridin-4-yl)ethyl)isonicotinamide;
N-(1-(5-fluoro-6-(2,2,2-trifluoroethoxy)pyridin-3-yl)ethyl)-2-propionamidoisonicotinamide;
N-(1-(2-methyl-6-(2,2,2-trifluoroethoxy)pyridin-4-yl)ethyl)-2-propionamidoisonicotinamide;
2-(cyclopropanecarboxamido)-N-(1-(6-(2,2,2-trifluoroethoxy)pyridin-2-yl)ethyl)isonicotinamide;
2-(cyclopropanecarboxamido)-N-(1-(6-(2,2,2-trifluoroethoxy)pyridin-3-yl)propyl)isonicotinamide;
2-(cyclopropanecarboxamido)-N-(1-(3-(trifluoromethoxy)phenyl)ethyl)isonicotinamide;
N-(1-(5-chloro-6-(2,2,2-trifluoroethoxy)pyridin-3-yl)ethyl)-2-(cyclopropanecarboxamido)isonicotinamide;
2-(cyclopropanecarboxamido)-N-(1-(5-fluoro-6-(2,2,2-trifluoroethoxy)pyridin-3-yl)ethyl)isonicotinamide;
2-methoxy-6-propionamido-N-(1-(6-(2,2,2-trifluoroethoxy)pyridin-3-yl)ethyl)isonicotinamide;
2-(cyclopropanecarboxamido)-6-methoxy-N-(1-(6-(2,2,2-trifluoroethoxy)pyridin-3-yl)ethyl)isonicotinamide;
2-isobutyramido-6-methoxy-N-(1-(6-(2,2,2-trifluoroethoxy)pyridin-3-yl)ethyl)isonicotinamide;
2-acetamido-N-(1-(3-(2,2,2-trifluoroethoxy)phenyl)ethyl)isonicotinamide;
2-acetamido-N-(1-(5-methyl-6-(2,2,2-trifluoroethoxy)pyridin-3-yl)ethyl)isonicotinamide;
2-propionamido-N-(1-(3-(2,2,2-trifluoroethoxy)phenyl)ethyl)isonicotinamide;
N-(1-(5-methyl-6-(2,2,2-trifluoroethoxy)pyridin-3-yl)ethyl)-2-propionamidoisonicotinamide;
2-(cyclopropanecarboxamido)-N-(1-(3-(2,2,2-trifluoroethoxy)phenyl)ethyl)isonicotinamide;
2-(cyclopropanecarboxamido)-N-(1-(5-methyl-6-(2,2,2-trifluoroethoxy)pyridin-3-yl)ethyl)isonicotinamide;
2-acetamido-N-(1-(4-(2,2,2-trifluoroethoxy)phenyl)ethyl)isonicotinamide;
2-propionamido-N-(1-(4-(2,2,2-trifluoroethoxy)phenyl)ethyl)isonicotinamide;
2-(cyclopropanecarboxamido)-N-(1-(4-(2,2,2-trifluoroethoxy)phenyl)ethyl)isonicotinamide;
2-acetamido-N-((5-chloro-6-(2,2,2-trifluoroethoxy)pyridin-3-yl)methyl)isonicotinamide;
N-((5-chloro-6-(2,2,2-trifluoroethoxy)pyridin-3-yl)methyl)-2-propionamidoisonicotinamide;
N-((5-chloro-6-(2,2,2-trifluoroethoxy)pyridin-3-yl)methyl)-2-(cyclopropanecarboxamido)isonicotinamide;
2-(cyclopropanecarboxamido)-N-(1-(6-(2,2,2-trifluoroethoxy)pyridin-3-yl)ethyl)pyrimidine-4-carboxamide;
2-propionamido-N-(1-(6-(2,2,2-trifluoroethoxy)pyridin-3-yl)ethyl)pyrimidine-4-carboxamide;
2-acetamido-N-(1-(4-fluoro-3-(2,2,2-trifluoroethoxy)phenyl)ethyl)isonicotinamide;

N-(1-(4-fluoro-3-(2,2,2-trifluoroethoxy)phenyl)ethyl)-2-propionamidoisonicotinamide;
2-acetamido-N-(3-fluoro-5-(trifluoromethyl)benzyl)isonicotinamide;
2-(cyclopropanecarboxamido)-N-(3-fluoro-5-(trifluoromethyl)benzyl)isonicotinamide;
2-(cyclopropanecarboxamido)-5-fluoro-N-(1-(6-(2,2,2-trifluoroethoxy)pyridin-3-yl)ethyl)isonicotinamide;
2-(cyclopropanecarboxamido)-N-(3-(trifluoromethyl)benzyl)isonicotinamide;
(R)-2-(cyclopropanecarboxamido)-N-(1-(3-(trifluoromethyl)phenyl)ethyl)isonicotinamide;
2-(cyclopropanecarboxamido)-N-(1-(4-(trifluoromethoxy)phenyl)ethyl)isonicotinamide;
2-propionamido-N-(3-(trifluoromethyl)benzyl)isonicotinamide;
(R)-2-propionamido-N-(1-(3-(trifluoromethyl)phenyl)ethyl)isonicotinamide;
2-propionamido-N-(1-(3-(trifluoromethoxy)phenyl)ethyl)isonicotinamide;
2-propionamido-N-(1-(4-(trifluoromethoxy)phenyl)ethyl)isonicotinamide;
2-methyl-N-(1-(6-(2,2,2-trifluoroethoxy)pyridin-3-yl)ethyl)-1H-benzo[d]imidazole-4-carboxamide;
N-(1-(5-chloro-6-(2,2,2-trifluoroethoxy)pyridin-3-yl)ethyl)-2-methyl-1H-benzo[d]imidazole-4-carboxamide;
N-(1-(5-chloro-6-(2,2,2-trifluoroethoxy)pyridin-3-yl)ethyl)-2-(cyclopropanecarboxamido)oxazole-5-carboxamide;
N-(1-(5-chloro-6-(2,2,2-trifluoroethoxy)pyridin-3-yl)ethyl)-2-(cyclopropanecarboxamido)-4-methyloxazole-5-carboxamide;
2-acetamido-N-(1-(6-(3,3,3-trifluoropropoxy)pyridin-3-yl)ethyl)isonicotinamide;
2-propionamido-N-(1-(6-(3,3,3-trifluoropropoxy)pyridin-3-yl)ethyl)isonicotinamide;
2-(cyclopropanecarboxamido)-N-(1-(6-(3,3,3-trifluoropropoxy)pyridin-3-yl)ethyl)isonicotinamide;
6-propionamido-N-(1-(6-(2,2,2-trifluoroethoxy)pyridin-3-yl)ethyl)pyrimidine-4-carboxamide;
6-(cyclopropanecarboxamido)-N-(1-(6-(2,2,2-trifluoroethoxy)pyridin-3-yl)ethyl)pyrimidine-4-carboxamide;
N-(1-(5-chloro-6-(2,2,2-trifluoroethoxy)pyridin-3-yl)ethyl)-6-propionamidopyrimidine-4-carboxamide;
6-methyl-2-propionamido-N-(1-(6-(2,2,2-trifluoroethoxy)pyridin-3-yl)ethyl)pyrimidine-4-carboxamide;
2-(cyclopropanecarboxamido)-6-methyl-N-(1-(6-(2,2,2-trifluoroethoxy)pyridin-3-yl)ethyl)pyrimidine-4-carboxamide;
2-acetamido-N-(4-((trifluoromethyl)thio)benzyl)isonicotinamide;
2-propionamido-N-(4-((trifluoromethyl)thio)benzyl)isonicotinamide;
2-(cyclopropanecarboxamido)-N-(4-((trifluoromethyl)thio)benzyl)isonicotinamide;
2-methyl-6-propionamido-N-(4-((trifluoromethyl)thio)benzyl)isonicotinamide;
(R)-2-methyl-6-propionamido-N-(1-(3-(trifluoromethyl)phenyl)ethyl)isonicotinamide;
2-methyl-6-propionamido-N-(3-(trifluoromethyl)benzyl)isonicotinamide;
N-(2-fluoro-5-(trifluoromethyl)benzyl)-2-methyl-6-propionamidoisonicotinamide;
N-(3-(difluoromethoxy)benzyl)-2-methyl-6-propionamidoisonicotinamide;
N-(1-(5-chloro-6-(2,2,2-trifluoroethoxy)pyridin-3-yl)ethyl)-2-methyl-6-propionamidoisonicotinamide;
N-(1-(5-fluoro-6-(2,2,2-trifluoroethoxy)pyridin-3-yl)ethyl)-2-methyl-6-propionamidoisonicotinamide;
2-methyl-N-(1-(5-methyl-6-(2,2,2-trifluoroethoxy)pyridin-3-yl)ethyl)-6-propionamidoisonicotinamide;
2-methyl-6-propionamido-N-(1-(6-(2,2,2-trifluoroethoxy)pyridin-3-yl)propyl)isonicotinamide;
2-methyl-6-propionamido-N-(1-(3-(trifluoromethoxy)phenyl)ethyl)isonicotinamide;
2-methyl-6-propionamido-N-(1-(4-(trifluoromethyl)phenyl)ethyl)isonicotinamide;
2-methyl-6-propionamido-N-(1-(4-(2,2,2-trifluoroethoxy)phenyl)ethyl)isonicotinamide
2-methyl-6-propionamido-N-((2-(2,2,2-trifluoroethoxy)pyridin-4-yl)methyl)isonicotinamide;
N,2-dimethyl-6-propionamido-N-(1-(6-(2,2,2-trifluoroethoxy)pyridin-3-yl)ethyl)isonicotinamide;
2-methyl-6-propionamido-N-(1-(6-(2,2,2-trifluoroethoxy)pyridin-2-yl)ethyl)isonicotinamide;
2-methyl-6-propionamido-N-(1-(6-(3,3,3-trifluoropropoxy)pyridin-3-yl)ethyl)isonicotinamide;
2-acetamido-N-(1-(5-methoxy-6-(2,2,2-trifluoroethoxy)pyridin-3-yl)ethyl)isonicotinamide;
N-(1-(5-methoxy-6-(2,2,2-trifluoroethoxy)pyridin-3-yl)ethyl)-2-propionamidoisonicotinamide;
2-(cyclopropanecarboxamido)-N-(1-(5-methoxy-6-(2,2,2-trifluoroethoxy)pyridin-3-yl)ethyl)isonicotinamide;
N-(1-(5-methoxy-6-(2,2,2-trifluoroethoxy)pyridin-3-yl)ethyl)-2-methyl-6-propionamidoisonicotinamide;
2-propionamido-N-(1-(6-((2,2,2-trifluoroethyl)thio)pyridin-3-yl)ethyl)isonicotinamide;
2-methyl-6-propionamido-N-(1-(6-((2,2,2-trifluoroethyl)thio)pyridin-3-yl)ethyl)isonicotinamide;
2-(cyclopropanecarboxamido)-N-((2-methoxy-6-(2,2,2-trifluoroethoxy)pyridin-3-yl)methyl)isonicotinamide;
2-acetamido-N-((2-methoxy-6-(2,2,2-trifluoroethoxy)pyridin-3-yl)methyl)isonicotinamide;
N-((2-methoxy-6-(2,2,2-trifluoroethoxy)pyridin-3-yl)methyl)-2-propionamidoisonicotinamide;
N-((2-methoxy-6-(2,2,2-trifluoroethoxy)pyridin-3-yl)methyl)-2-methyl-6-propionamidoisonicotinamide;
2-propionamido-N-((6-(2,2,2-trifluoroethoxy)pyridin-3-yl)methyl)isonicotinamide;
2-(cyclopropanecarboxamido)-N-((6-(2,2,2-trifluoroethoxy)pyridin-3-yl)methyl)isonicotinamide;
2-methyl-6-propionamido-N-((6-(2,2,2-trifluoroethoxy)pyridin-3-yl)methyl)isonicotinamide;
2-ethyl-6-propionamido-N-(1-(6-(2,2,2-trifluoroethoxy)pyridin-3-yl)ethyl)isonicotinamide;
2-(cyclopropanecarboxamido)-N-methyl-N-(1-(6-(2,2,2-trifluoroethoxy)pyridin-3-yl)ethyl)isonicotinamide;
(R)-2-methyl-6-propionamido-N-(1-(5-(2,2,2-trifluoroethoxy)pyridin-2-yl)ethyl)isonicotinamide;
2-(cyclopropanecarboxamido)-N-(1-(6-((2,2,2-trifluoroethyl)amino)pyridin-3-yl)ethyl)isonicotinamide;
2-methyl-6-propionamido-N-(1-(6-((2,2,2-trifluoroethyl)amino)pyridin-3-yl)ethyl)isonicotinamide;
N-ethyl-2-methyl-6-propionamido-N-(1-(6-(2,2,2-trifluoroethoxy)pyridin-3-yl)ethyl)isonicotinamide;
N4-(1-(5-chloro-6-(2,2,2-trifluoroethoxy)pyridin-3-yl)ethyl)-N2-ethylpyridine-2,4-dicarboxamide;
2-propionamido-N-((2-(2,2,2-trifluoroethoxy)pyridin-4-yl)methyl)isonicotinamide;
2-(cyclopropanecarboxamido)-N-((2-(2,2,2-trifluoroethoxy)pyridin-4-yl)methyl)isonicotinamide;
2-methyl-6-propionamido-N-(1-(2-(2,2,2-trifluoroethoxy)pyridin-4-yl)ethyl)isonicotinamide;

2-methyl-6-propionamido-N-((4-(2,2,2-trifluoroethoxy)pyridin-2-yl)methyl)isonicotinamide;
2-acetamido-N-((2-methyl-6-(2,2,2-trifluoroethoxy)pyridin-3-yl)methyl)isonicotinamide;
N-((2-methyl-6-(2,2,2-trifluoroethoxy)pyridin-3-yl)methyl)-2-propionamidoisonicotinamide;
2-(cyclopropanecarboxamido)-N-((2-methyl-6-(2,2,2-trifluoroethoxy)pyridin-3-yl)methyl)isonicotinamide;
2-methyl-N-((2-methyl-6-(2,2,2-trifluoroethoxy)pyridin-3-yl)methyl)-6-propionamidoisonicotinamide;
2-isobutyramido-N-((6-(2,2,2-trifluoroethoxy)pyridin-3-yl)methyl)isonicotinamide;
2-isobutyramido-N-((2-(2,2,2-trifluoroethoxy)pyridin-4-yl)methyl)isonicotinamide;
2-isobutyramido-N-((2-methoxy-6-(2,2,2-trifluoroethoxy)pyridin-3-yl)methyl)isonicotinamide;
N-((5-fluoro-6-(2,2,2-trifluoroethoxy)pyridin-3-yl)methyl)-2-propionamidoisonicotinamide;
2-(cyclopropanecarboxamido)-N-((5-fluoro-6-(2,2,2-trifluoroethoxy)pyridin-3-yl)methyl)isonicotinamide;
N-((5-fluoro-6-(2,2,2-trifluoroethoxy)pyridin-3-yl)methyl)-2-isobutyramidoisonicotinamide;
N-((5-fluoro-6-(2,2,2-trifluoroethoxy)pyridin-3-yl)methyl)-2-methyl-6-propionamidoisonicotinamide;
N-((4-methyl-6-(2,2,2-trifluoroethoxy)pyridin-3-yl)methyl)-2-propionamidoisonicotinamide;
2-(cyclopropanecarboxamido)-N-((4-methyl-6-(2,2,2-trifluoroethoxy)pyridin-3-yl)methyl)isonicotinamide;
2-isobutyramido-N-((4-methyl-6-(2,2,2-trifluoroethoxy)pyridin-3-yl)methyl)isonicotinamide;
2-methyl-N-((4-methyl-6-(2,2,2-trifluoroethoxy)pyridin-3-yl)methyl)-6-propionamidoisonicotinamide;
N-((2-methoxy-6-(2,2,2-trifluoroethoxy)pyridin-3-yl)methyl)-6-methyl-2-propionamidopyrimidine-4-carboxamide;
2-(cyclopropanecarboxamido)-N-((2-methoxy-6-(2,2,2-trifluoroethoxy)pyridin-3-yl)methyl)-6-methylpyrimidine-4-carboxamide;
2-(cyclopropanecarboxamido)-6-methyl-N-(1-(6-(3,3,3-trifluoropropoxy)pyridin-3-yl)ethyl)pyrimidine-4-carboxamide;
2-propionamido-N-(1-(6-(3,3,3-trifluoropropoxy)pyridin-3-yl)ethyl)pyrimidine-4-carboxamide;
2-(cyclopropanecarboxamido)-N-(1-(6-(3,3,3-trifluoropropoxy)pyridin-3-yl)ethyl)pyrimidine-4-carboxamide;
2-propionamido-N-(1-(6-(2,2,2-trifluoroethoxy)pyridin-3-yl)propyl)isonicotinamide;
2-isobutyramido-N-(1-(6-(3,3,3-trifluoropropoxy)pyridin-3-yl)ethyl)isonicotinamide;
2-isobutyramido-N-((2-methyl-6-(2,2,2-trifluoroethoxy)pyridin-3-yl)methyl)isonicotinamide;
2-isobutyramido-N-(1-(2-(2,2,2-trifluoroethoxy)pyridin-4-yl)ethyl)isonicotinamide;
2-isobutyramido-N-(1-(6-(2,2,2-trifluoroethoxy)pyridin-2-yl)ethyl)isonicotinamide;
2-propionamido-N-((6-(3,3,3-trifluoropropoxy)pyridin-3-yl)methyl)isonicotinamide;
2-(cyclopropanecarboxamido)-N-((6-(3,3,3-trifluoropropoxy)pyridin-3-yl)methyl)isonicotinamide;
2-methyl-6-propionamido-N-((6-(3,3,3-trifluoropropoxy)pyridin-3-yl)methyl)isonicotinamide;
N-(1-(5-methoxy-6-(2,2,2-trifluoroethoxy)pyridin-3-yl)ethyl)-6-methyl-2-propionamidopyrimidine-4-carboxamide;
2-(cyclopropanecarboxamido)-N-(1-(5-methoxy-6-(2,2,2-trifluoroethoxy)pyridin-3-yl)ethyl)-6-methylpyrimidine-4-carboxamide;
2-(cyclopropanecarboxamido)-N-(1-(6-(2-(2,2,2-trifluoroethoxy)ethoxy)pyridin-3-yl)ethyl)isonicotinamide;
2-isobutyramido-N-(1-(6-(2-(2,2,2-trifluoroethoxy)ethoxy)pyridin-3-yl)ethyl)isonicotinamide;
2-acetamido-N-((4-methyl-6-(2,2,2-trifluoroethoxy)pyridin-3-yl)methyl)isonicotinamide;
2-acetamido-6-methyl-N-(1-(6-(3,3,3-trifluoropropoxy)pyridin-3-yl)ethyl)pyrimidine-4-carboxamide;
2-isobutyramido-N-(1-(6-(3,3,3-trifluoropropoxy)pyridin-3-yl)ethyl)pyrimidine-4-carboxamide;
2-(cyclopropanecarboxamido)-N-(1-(6-(2,2-difluoroethoxy)pyridin-3-yl)ethyl)isonicotinamide;
N-(1-(6-(2,2-difluoroethoxy)pyridin-3-yl)ethyl)-2-methyl-6-propionamidoisonicotinamide;
2-acetamido-N-((6-(3,3,3-trifluoropropoxy)pyridin-3-yl)methyl)isonicotinamide;
N-((5-fluoro-6-(2,2,2-trifluoroethoxy)pyridin-3-yl)methyl)-6-methyl-2-propionamidopyrimidine-4-carboxamide;
2-(cyclopropanecarboxamido)-N-((5-fluoro-6-(2,2,2-trifluoroethoxy)pyridin-3-yl)methyl)-6-methylpyrimidine-4-carboxamide;
2-isobutyramido-6-methyl-N-(1-(6-(2,2,2-trifluoroethoxy)pyridin-3-yl)ethyl)pyrimidine-4-carboxamide;
2-(cyclopropanecarboxamido)-N-(1-(5-fluoro-6-(2,2,2-trifluoroethoxy)pyridin-3-yl)ethyl)pyrimidine-4-carboxamide;
2-(cyclopropanecarboxamido)-N-(1-(5-fluoro-6-(2,2,2-trifluoroethoxy)pyridin-3-yl)ethyl)-6-methylpyrimidine-4-carboxamide;
2-(cyclobutanecarboxamido)-N-(1-(5-fluoro-6-(2,2,2-trifluoroethoxy)pyridin-3-yl)ethyl)-6-methylpyrimidine-4-carboxamide;
N-(1-(5-fluoro-6-(2,2,2-trifluoroethoxy)pyridin-3-yl)ethyl)-2-isobutyramidopyrimidine-4-carboxamide;
N-(1-(5-chloro-6-(2,2,2-trifluoroethoxy)pyridin-3-yl)ethyl)-2-propionamidopyrimidine-4-carboxamide;
N-(1-(5-chloro-6-(2,2,2-trifluoroethoxy)pyridin-3-yl)ethyl)-2-(cyclopropanecarboxamido)pyrimidine-4-carboxamide;
N-(1-(5-chloro-6-(2,2,2-trifluoroethoxy)pyridin-3-yl)ethyl)-2-isobutyramidopyrimidine-4-carboxamide;
N-(1-(5-chloro-6-(2,2,2-trifluoroethoxy)pyridin-3-yl)ethyl)-2-(cyclobutanecarboxamido)pyrimidine-4-carboxamide;
N-(1-(5-chloro-6-(2,2,2-trifluoroethoxy)pyridin-3-yl)ethyl)-6-methyl-2-propionamidopyrimidine-4-carboxamide;
N-(1-(5-chloro-6-(2,2,2-trifluoroethoxy)pyridin-3-yl)ethyl)-2-(cyclopropanecarboxamido)-6-methylpyrimidine-4-carboxamide;
N-(1-(5-chloro-6-(2,2,2-trifluoroethoxy)pyridin-3-yl)ethyl)-2-isobutyramido-6-methylpyrimidine-4-carboxamide;
N-(1-(5-chloro-6-(2,2,2-trifluoroethoxy)pyridin-3-yl)ethyl)-2-(cyclobutanecarboxamido)-6-methylpyrimidine-4-carboxamide;
2-isobutyramido-N-(1-(5-methoxy-6-(2,2,2-trifluoroethoxy)pyridin-3-yl)ethyl)-6-methylpyrimidine-4-carboxamide;
2-isobutyramido-N-(1-(6-(2,2,2-trifluoroethoxy)pyridin-3-yl)propyl)isonicotinamide;
N-(1-(5-fluoro-6-(2,2,2-trifluoroethoxy)pyridin-3-yl)ethyl)-2-isobutyramidoisonicotinamide;
2-isobutyramido-N-(1-(5-methoxy-6-(2,2,2-trifluoroethoxy)pyridin-3-yl)ethyl)isonicotinamide;
2-isobutyramido-N-((6-(3,3,3-trifluoropropoxy)pyridin-3-yl)methyl)isonicotinamide;
N-(1-(5-methyl-6-(2,2,2-trifluoroethoxy)pyridin-3-yl)ethyl)-2-propionamidopyrimidine-4-carboxamide;

2-(cyclopropanecarboxamido)-N-(1-(5-methyl-6-(2,2,2-trifluoroethoxy)pyridin-3-yl)ethyl)pyrimidine-4-carboxamide;
2-isobutyramido-N-(1-(5-methyl-6-(2,2,2-trifluoroethoxy)pyridin-3-yl)ethyl)pyrimidine-4-carboxamide;
2-(cyclobutanecarboxamido)-N-(1-(5-methyl-6-(2,2,2-trifluoroethoxy)pyridin-3-yl)ethyl)pyrimidine-4-carboxamide;
6-methyl-N-(1-(5-methyl-6-(2,2,2-trifluoroethoxy)pyridin-3-yl)ethyl)-2-propionamidopyrimidine-4-carboxamide;
2-(cyclopropanecarboxamido)-6-methyl-N-(1-(5-methyl-6-(2,2,2-trifluoroethoxy)pyridin-3-yl)ethyl)pyrimidine-4-carboxamide;
2-isobutyramido-6-methyl-N-(1-(5-methyl-6-(2,2,2-trifluoroethoxy)pyridin-3-yl)ethyl)pyrimidine-4-carboxamide;
2-(cyclobutanecarboxamido)-6-methyl-N-(1-(5-methyl-6-(2,2,2-trifluoroethoxy)pyridin-3-yl)ethyl)pyrimidine-4-carboxamide;
3-isobutyramido-N-(1-(6-(2,2,2-trifluoroethoxy)pyridin-3-yl)ethyl)picolinamide;
2-acetamido-N-(1-(5-chloro-6-(2,2,2-trifluoroethoxy)pyridin-3-yl)ethyl)pyrimidine-4-carboxamide;
2-acetamido-N-(1-(5-chloro-6-(2,2,2-trifluoroethoxy)pyridin-3-yl)ethyl)-6-methylpyrimidine-4-carboxamide;
2-acetamido-N-(1-(5-methyl-6-(2,2,2-trifluoroethoxy)pyridin-3-yl)ethyl)pyrimidine-4-carboxamide;
2-acetamido-6-methyl-N-(1-(5-methyl-6-(2,2,2-trifluoroethoxy)pyridin-3-yl)ethyl)pyrimidine-4-carboxamide;
2-acetamido-6-methyl-N-(1-(6-(2,2,2-trifluoroethoxy)pyridin-3-yl)propyl)isonicotinamide;
2-acetamido-6-methyl-N-((6-(2,2,2-trifluoroethoxy)pyridin-3-yl)methyl)isonicotinamide;
2-acetamido-N,6-dimethyl-N-((6-(2,2,2-trifluoroethoxy)pyridin-3-yl)methyl)isonicotinamide;
2-acetamido-N-(1-(5-fluoro-6-(2,2,2-trifluoroethoxy)pyridin-3-yl)ethyl)-6-methylisonicotinamide;
2-acetamido-N-((5-fluoro-6-(2,2,2-trifluoroethoxy)pyridin-3-yl)methyl)-6-methylisonicotinamide;
2-acetamido-N-((2-methoxy-6-(2,2,2-trifluoroethoxy)pyridin-3-yl)methyl)-6-methylisonicotinamide;
2-acetamido-6-methyl-N-((2-methyl-6-(2,2,2-trifluoroethoxy)pyridin-3-yl)methyl)isonicotinamide;
2-acetamido-6-methyl-N-((4-methyl-6-(2,2,2-trifluoroethoxy)pyridin-3-yl)methyl)isonicotinamide;
2-acetamido-6-methyl-N-(1-(6-(3,3,3-trifluoropropoxy)pyridin-3-yl)ethyl)isonicotinamide;
2-acetamido-6-methyl-N-((6-(3,3,3-trifluoropropoxy)pyridin-3-yl)methyl)isonicotinamide;
2-acetamido-6-methyl-N-((2-(2,2,2-trifluoroethoxy)pyridin-4-yl)methyl)isonicotinamide;
2-acetamido-6-methyl-N-(1-(6-(2,2,2-trifluoroethoxy)pyridin-2-yl)ethyl)isonicotinamide;
6-methyl-2-propionamido-N-((6-(2,2,2-trifluoroethoxy)pyridin-3-yl)methyl)pyrimidine-4-carboxamide;
2-(cyclopropanecarboxamido)-6-methyl-N-((6-(2,2,2-trifluoroethoxy)pyridin-3-yl)methyl)pyrimidine-4-carboxamide;
2-isobutyramido-N-(1-(6-(2,2,2-trifluoroethoxy)pyridin-3-yl)ethyl)pyrimidine-4-carboxamide;
2-acetamido-N-(1-(5-fluoro-6-(2,2,2-trifluoroethoxy)pyridin-3-yl)ethyl)-N,6-dimethylisonicotinamide;
N-(1-(5-fluoro-6-(2,2,2-trifluoroethoxy)pyridin-3-yl)ethyl)-N,2-dimethyl-6-propionamidoisonicotinamide;
6-propionamido-N-(1-(6-(2,2,2-trifluoroethoxy)pyridin-3-yl)ethyl)picolinamide;
6-(cyclopropanecarboxamido)-N-(1-(6-(2,2,2-trifluoroethoxy)pyridin-3-yl)ethyl)picolinamide;
6-isobutyramido-N-(1-(6-(2,2,2-trifluoroethoxy)pyridin-3-yl)ethyl)picolinamide;
N-(2-methoxy-1-(6-(2,2,2-trifluoroethoxy)pyridin-3-yl)ethyl)-2-propionamidoisonicotinamide;
2-(cyclopropanecarboxamido)-N-(2-methoxy-1-(6-(2,2,2-trifluoroethoxy)pyridin-3-yl)ethyl)isonicotinamide;
2-acetamido-N-(2-methoxy-1-(6-(2,2,2-trifluoroethoxy)pyridin-3-yl)ethyl)-6-methylisonicotinamide;
2-acetamido-N-((5-ethoxy-6-(2,2,2-trifluoroethoxy)pyridin-3-yl)methyl)isonicotinamide;
N-((5-ethoxy-6-(2,2,2-trifluoroethoxy)pyridin-3-yl)methyl)-2-propionamidoisonicotinamide;
2-(cyclopropanecarboxamido)-N-((5-ethoxy-6-(2,2,2-trifluoroethoxy)pyridin-3-yl)methyl)isonicotinamide;
N-((5-ethoxy-6-(2,2,2-trifluoroethoxy)pyridin-3-yl)methyl)-2-methyl-6-propionamidoisonicotinamide;
N-((5-ethoxy-6-(2,2,2-trifluoroethoxy)pyridin-3-yl)methyl)-2-isobutyramidoisonicotinamide;
2-acetamido-N-((5-ethoxy-6-(2,2,2-trifluoroethoxy)pyridin-3-yl)methyl)-6-methylisonicotinamide;
2-butyramido-N-((6-(2,2,2-trifluoroethoxy)pyridin-3-yl)methyl)isonicotinamide;
2-butyramido-N-(1-(5-fluoro-6-(2,2,2-trifluoroethoxy)pyridin-3-yl)ethyl)isonicotinamide;
2-butyramido-N-((5-fluoro-6-(2,2,2-trifluoroethoxy)pyridin-3-yl)methyl)isonicotinamide;
2-butyramido-N-(1-(6-(3,3,3-trifluoropropoxy)pyridin-3-yl)ethyl)isonicotinamide;
2-acetamido-N-((5-methoxy-6-(2,2,2-trifluoroethoxy)pyridin-3-yl)methyl)isonicotinamide;
N-((5-methoxy-6-(2,2,2-trifluoroethoxy)pyridin-3-yl)methyl)-2-methyl-6-propionamidoisonicotinamide;
2-isobutyramido-N-((5-methoxy-6-(2,2,2-trifluoroethoxy)pyridin-3-yl)methyl)isonicotinamide;
2-acetamido-N-((5-methoxy-6-(2,2,2-trifluoroethoxy)pyridin-3-yl)methyl)-6-methylisonicotinamide;
2-butyramido-N-((5-methoxy-6-(2,2,2-trifluoroethoxy)pyridin-3-yl)methyl)isonicotinamide;
(R)-2-propionamido-N-(1-(3-(trifluoromethyl)phenyl)ethyl)pyrimidine-4-carboxamide;
(R)-2-isobutyramido-N-(1-(3-(trifluoromethyl)phenyl)ethyl)pyrimidine-4-carboxamide;
(R)-2-(cyclobutanecarboxamido)-N-(1-(3-(trifluoromethyl)phenyl)ethyl)pyrimidine-4-carboxamide;
2-acetamido-N-(3-(trifluoromethoxy)benzyl)pyrimidine-4-carboxamide;
2-propionamido-N-(3-(trifluoromethoxy)benzyl)pyrimidine-4-carboxamide;
2-isobutyramido-N-(3-(trifluoromethoxy)benzyl)pyrimidine-4-carboxamide;
2-(cyclobutanecarboxamido)-N-(3-(trifluoromethoxy)benzyl)pyrimidine-4-carboxamide;
2-acetamido-N-((2-morpholino-6-(2,2,2-trifluoroethoxy)pyridin-3-yl)methyl)isonicotinamide;
2-isobutyramido-N-((2-morpholino-6-(2,2,2-trifluoroethoxy)pyridin-3-yl)methyl)isonicotinamide;
2-acetamido-6-methyl-N-((2-morpholino-6-(2,2,2-trifluoroethoxy)pyridin-3-yl)methyl)isonicotinamide;
2-methyl-N-((2-morpholino-6-(2,2,2-trifluoroethoxy)pyridin-3-yl)methyl)-6-propionamidoisonicotinamide;
N-(1-(5-ethoxy-6-(2,2,2-trifluoroethoxy)pyridin-3-yl)ethyl)-2-methyl-6-propionamidoisonicotinamide;
2-acetamido-N-(1-(5-ethoxy-6-(2,2,2-trifluoroethoxy)pyridin-3-yl)ethyl)-6-methylisonicotinamide;
2-acetamido-N-((2-methoxy-6-(2,2,2-trifluoroethoxy)pyridin-3-yl)methyl)-N-methylisonicotinamide;

N-((2-methoxy-6-(2,2,2-trifluoroethoxy)pyridin-3-yl)methyl)-N-methyl-2-propionamidoisonicotinamide;
2-(cyclopropanecarboxamido)-N-((2-methoxy-6-(2,2,2-trifluoroethoxy)pyridin-3-yl)methyl)-N-methylisonicotinamide;
2-acetamido-N-((2-methoxy-6-(2,2,2-trifluoroethoxy)pyridin-3-yl)methyl)-N,6-dimethylisonicotinamide;
N-((2-methoxy-6-(2,2,2-trifluoroethoxy)pyridin-3-yl)methyl)-N,2-dimethyl-6-propionamidoisonicotinamide;
N-((2-(4-methylpiperazin-1-yl)-6-(2,2,2-trifluoroethoxy)pyridin-3-yl)methyl)-2-propionamidoisonicotinamide;
2-(cyclopropanecarboxamido)-N-((2-(4-methylpiperazin-1-yl)-6-(2,2,2-trifluoroethoxy)pyridin-3-yl)methyl)isonicotinamide;
2-isobutyramido-N-((2-(4-methylpiperazin-1-yl)-6-(2,2,2-trifluoroethoxy)pyridin-3-yl)methyl)isonicotinamide;
2-methyl-N-((2-(4-methylpiperazin-1-yl)-6-(2,2,2-trifluoroethoxy)pyridin-3-yl)methyl)-6-propionamidoisonicotinamide;
2-isobutyramido-N-((2-methoxy-6-(2,2,2-trifluoroethoxy)pyridin-3-yl)methyl)-N-methylisonicotinamide;
2-acetamido-N-(1-(3-(trifluoromethoxy)phenyl)ethyl)pyrimidine-4-carboxamide;
2-propionamido-N-(1-(3-(trifluoromethoxy)phenyl)ethyl)pyrimidine-4-carboxamide;
2-(cyclopropanecarboxamido)-N-(1-(3-(trifluoromethoxy)phenyl)ethyl)pyrimidine-4-carboxamide;
2-isobutyramido-N-(1-(3-(trifluoromethoxy)phenyl)ethyl)pyrimidine-4-carboxamide;
2-(cyclobutanecarboxamido)-N-(1-(3-(trifluoromethoxy)phenyl)ethyl)pyrimidine-4-carboxamide;
2-acetamido-N-((2-(piperidin-1-yl)-6-(2,2,2-trifluoroethoxy)pyridin-3-yl)methyl)isonicotinamide;
N-((2-(piperidin-1-yl)-6-(2,2,2-trifluoroethoxy)pyridin-3-yl)methyl)-2-propionamidoisonicotinamide;
2-(cyclopropanecarboxamido)-N-((2-(piperidin-1-yl)-6-(2,2,2-trifluoroethoxy)pyridin-3-yl)methyl)isonicotinamide;
2-isobutyramido-N-((2-(piperidin-1-yl)-6-(2,2,2-trifluoroethoxy)pyridin-3-yl)methyl)isonicotinamide;
2-methyl-N-((2-(piperidin-1-yl)-6-(2,2,2-trifluoroethoxy)pyridin-3-yl)methyl)-6-propionamidoisonicotinamide;
2-acetamido-6-methyl-N-((2-(piperidin-1-yl)-6-(2,2,2-trifluoroethoxy)pyridin-3-yl)methyl)isonicotinamide;
2-butyramido-N-((2-(piperidin-1-yl)-6-(2,2,2-trifluoroethoxy)pyridin-3-yl)methyl)isonicotinamide;
2-acetamido-N-((5-fluoro-2-methyl-6-(2,2,2-trifluoroethoxy)pyridin-3-yl)methyl)isonicotinamide;
N-((5-fluoro-2-methyl-6-(2,2,2-trifluoroethoxy)pyridin-3-yl)methyl)-2-propionamidoisonicotinamide;
2-(cyclopropanecarboxamido)-N-((5-fluoro-2-methyl-6-(2,2,2-trifluoroethoxy)pyridin-3-yl)methyl)isonicotinamide;
2-acetamido-N-((5-fluoro-2-methyl-6-(2,2,2-trifluoroethoxy)pyridin-3-yl)methyl)-6-methylisonicotinamide;
N-((5-fluoro-2-methyl-6-(2,2,2-trifluoroethoxy)pyridin-3-yl)methyl)-2-methyl-6-propionamidoisonicotinamide;
N-((5-fluoro-2-methyl-6-(2,2,2-trifluoroethoxy)pyridin-3-yl)methyl)-2-isobutyramidoisonicotinamide;
(R)-2-acetamido-N-((6-(((1,1,1-trifluoropropan-2-yl)oxy)pyridin-3-yl)methyl)isonicotinamide;
(R)-2-propionamido-N-((6-(((1,1,1-trifluoropropan-2-yl)oxy)pyridin-3-yl)methyl)isonicotinamide;
(R)-2-(cyclopropanecarboxamido)-N-((6-(((1,1,1-trifluoropropan-2-yl)oxy)pyridin-3-yl)methyl)isonicotinamide;
(R)-2-methyl-6-propionamido-N-((6-(((1,1,1-trifluoropropan-2-yl)oxy)pyridin-3-yl)methyl)isonicotinamide;
(R)-2-isobutyramido-N-((6-(((1,1,1-trifluoropropan-2-yl)oxy)pyridin-3-yl)methyl)isonicotinamide;
(R)-2-acetamido-6-methyl-N-((6-(((1,1,1-trifluoropropan-2-yl)oxy)pyridin-3-yl)methyl)isonicotinamide;
(R)-2-butyramido-N-((6-(((1,1,1-trifluoropropan-2-yl)oxy)pyridin-3-yl)methyl)isonicotinamide;
2-(2-hydroxy-2-methylpropanamido)-N-((2-methoxy-6-(2,2,2-trifluoroethoxy)pyridin-3-yl)methyl)-6-methylisonicotinamide;
2-(2-hydroxy-2-methylpropanamido)-6-methyl-N-(1-(5-methyl-6-(2,2,2-trifluoroethoxy)pyridin-3-yl)ethyl)isonicotinamide;
N-(1-(5-chloro-6-(2,2,2-trifluoroethoxy)pyridin-3-yl)ethyl)-2-(2-hydroxy-2-methylpropanamido)-6-methylisonicotinamide;
2-(2-hydroxy-2-methylpropanamido)-6-methyl-N-((2-methyl-6-(2,2,2-trifluoroethoxy)pyridin-3-yl)methyl)isonicotinamide;
2-(2-hydroxy-2-methylpropanamido)-6-methyl-N-((6-(3,3,3-trifluoropropoxy)pyridin-3-yl)methyl)isonicotinamide;
N-((5-fluoro-2-methoxy-6-(2,2,2-trifluoroethoxy)pyridin-3-yl)methyl)-2-propionamidoisonicotinamide;
N-((5-fluoro-2-methoxy-6-(2,2,2-trifluoroethoxy)pyridin-3-yl)methyl)-2-methyl-6-propionamidoisonicotinamide;
N-((5-fluoro-2-methoxy-6-(2,2,2-trifluoroethoxy)pyridin-3-yl)methyl)-2-isobutyramidoisonicotinamide;
2-acetamido-N-(1-(5-methoxy-6-(2,2,2-trifluoroethoxy)pyridin-3-yl)ethyl)-6-methylisonicotinamide;
2-butyramido-N-(1-(5-methoxy-6-(2,2,2-trifluoroethoxy)pyridin-3-yl)ethyl)isonicotinamide;
2-acetamido-N-((2-ethoxy-6-(2,2,2-trifluoroethoxy)pyridin-3-yl)methyl)isonicotinamide;
N-((2-ethoxy-6-(2,2,2-trifluoroethoxy)pyridin-3-yl)methyl)-2-propionamidoisonicotinamide;
N-((2-ethoxy-6-(2,2,2-trifluoroethoxy)pyridin-3-yl)methyl)-2-methyl-6-propionamidoisonicotinamide;
N-((2-ethoxy-6-(2,2,2-trifluoroethoxy)pyridin-3-yl)methyl)-2-isobutyramidoisonicotinamide;
2-acetamido-N-((2-ethoxy-6-(2,2,2-trifluoroethoxy)pyridin-3-yl)methyl)-6-methylisonicotinamide;
2-butyramido-N-((2-ethoxy-6-(2,2,2-trifluoroethoxy)pyridin-3-yl)methyl)isonicotinamide;
2-acetamido-N-((2-ethoxy-6-(2,2,2-trifluoroethoxy)pyridin-3-yl)methyl)-6-methylpyrimidine-4-carboxamide;
6-methyl-2-propionamido-N-(1-(6-(2,2,2-trifluoroethoxy)pyridin-3-yl)propyl)pyrimidine-4-carboxamide;
2-(cyclopropanecarboxamido)-6-methyl-N-(1-(6-(2,2,2-trifluoroethoxy)pyridin-3-yl)propyl)pyrimidine-4-carboxamide;
2-isobutyramido-6-methyl-N-((6-(2,2,2-trifluoroethoxy)pyridin-3-yl)methyl)pyrimidine-4-carboxamide;
2-acetamido-6-methyl-N-((2-methyl-6-(2,2,2-trifluoroethoxy)pyridin-3-yl)methyl)pyrimidine-4-carboxamide;
6-methyl-N-((2-methyl-6-(2,2,2-trifluoroethoxy)pyridin-3-yl)methyl)-2-propionamidopyrimidine-4-carboxamide;
2-(cyclopropanecarboxamido)-6-methyl-N-((2-methyl-6-(2,2,2-trifluoroethoxy)pyridin-3-yl)methyl)pyrimidine-4-carboxamide;
2-isobutyramido-6-methyl-N-((2-methyl-6-(2,2,2-trifluoroethoxy)pyridin-3-yl)methyl)pyrimidine-4-carboxamide;
6-methyl-2-propionamido-N-(3-(trifluoromethoxy)benzyl)pyrimidine-4-carboxamide;
2-(cyclopropanecarboxamido)-6-methyl-N-(3-(trifluoromethoxy)benzyl)pyrimidine-4-carboxamide;
2-isobutyramido-6-methyl-N-(3-(trifluoromethoxy)benzyl)pyrimidine-4-carboxamide;
(R)-2-(cyclopropanecarboxamido)-6-methyl-N-(1-(3-(trifluoromethyl)phenyl)ethyl)pyrimidine-4-carboxamide;

2-acetamido-6-methyl-N-((4-methyl-6-(2,2,2-trifluoroethoxy)pyridin-3-yl)methyl)pyrimidine-4-carboxamide;

6-methyl-N-((4-methyl-6-(2,2,2-trifluoroethoxy)pyridin-3-yl)methyl)-2-propionamido pyrimidine-4-carboxamide;

2-(cyclopropanecarboxamido)-6-methyl-N-((4-methyl-6-(2,2,2-trifluoroethoxy)pyridin-3-yl)methyl)pyrimidine-4-carboxamide;

2-isobutyramido-6-methyl-N-((4-methyl-6-(2,2,2-trifluoroethoxy)pyridin-3-yl)methyl)pyrimidine-4-carboxamide;

2-(cyclopropanecarboxamido)-6-methyl-N-(3-(trifluoromethyl)benzyl)pyrimidine-4-carboxamide;

2-isobutyramido-6-methyl-N-(3-(trifluoromethyl)benzyl)pyrimidine-4-carboxamide;

6-methyl-2-propionamido-N-(1-(4-(2,2,2-trifluoroethoxy)phenyl)ethyl)pyrimidine-4-carboxamide;

2-(cyclopropanecarboxamido)-6-methyl-N-(1-(4-(2,2,2-trifluoroethoxy)phenyl)ethyl)pyrimidine-4-carboxamide;

2-isobutyramido-6-methyl-N-(1-(4-(2,2,2-trifluoroethoxy)phenyl)ethyl)pyrimidine-4-carboxamide;

N-((2-ethoxy-6-(2,2,2-trifluoroethoxy)pyridin-3-yl)methyl)-6-methyl-2-propionamidopyrimidine-4-carboxamide;

N-((2-ethoxy-6-(2,2,2-trifluoroethoxy)pyridin-3-yl)methyl)-2-isobutyramido-6-methyl pyrimidine-4-carboxamide;

2-(cyclopropanecarboxamido)-N-((2-ethoxy-6-(2,2,2-trifluoroethoxy)pyridin-3-yl)methyl)-6-methylpyrimidine-4-carboxamide;

N-(1-(5-(hydroxymethyl)-6-(2,2,2-trifluoroethoxy)pyridin-3-yl)ethyl)-2-methyl-6-propionamidoisonicotinamide;

2-acetamido-6-methyl-N-((5-methyl-6-(2,2,2-trifluoroethoxy)pyridin-3-yl)methyl)pyrimidine-4-carboxamide;

6-methyl-N-((5-methyl-6-(2,2,2-trifluoroethoxy)pyridin-3-yl)methyl)-2-propionamido pyrimidine-4-carboxamide;

2-(cyclopropanecarboxamido)-6-methyl-N-((5-methyl-6-(2,2,2-trifluoroethoxy)pyridin-3-yl)methyl)pyrimidine-4-carboxamide;

2-isobutyramido-6-methyl-N-((5-methyl-6-(2,2,2-trifluoroethoxy)pyridin-3-yl)methyl)pyrimidine-4-carboxamide;

2-acetamido-N-((5-methyl-6-(2,2,2-trifluoroethoxy)pyridin-3-yl)methyl)isonicotinamide;

N-((5-methyl-6-(2,2,2-trifluoroethoxy)pyridin-3-yl)methyl)-2-propionamidoisonicotinamide;

2-(cyclopropanecarboxamido)-N-((5-methyl-6-(2,2,2-trifluoroethoxy)pyridin-3-yl)methyl)isonicotinamide;

2-isobutyramido-N-((5-methyl-6-(2,2,2-trifluoroethoxy)pyridin-3-yl)methyl)isonicotinamide;

2-acetamido-6-methyl-N-((5-methyl-6-(2,2,2-trifluoroethoxy)pyridin-3-yl)methyl)isonicotinamide;

2-methyl-N-((5-methyl-6-(2,2,2-trifluoroethoxy)pyridin-3-yl)methyl)-6-propionamidoisonicotinamide;

2-acetamido-N-((2-methoxy-6-(2,2,2-trifluoroethoxy)pyridin-3-yl)methyl)-6-methylpyrimidine-4-carboxamide;

2-isobutyramido-N-((2-methoxy-6-(2,2,2-trifluoroethoxy)pyridin-3-yl)methyl)-6-methylpyrimidine-4-carboxamide;

6-methyl-2-propionamido-N-(1-(3-(2,2,2-trifluoroethoxy)phenyl)ethyl)pyrimidine-4-carboxamide;

2-(cyclopropanecarboxamido)-6-methyl-N-(1-(3-(2,2,2-trifluoroethoxy)phenyl)ethyl)pyrimidine-4-carboxamide;

2-isobutyramido-6-methyl-N-(1-(3-(2,2,2-trifluoroethoxy)phenyl)ethyl)pyrimidine-4-carboxamide;

2-isobutyramido-N-(1-(5-methyl-6-(2,2,2-trifluoroethoxy)pyridin-3-yl)ethyl)isonicotinamide;

2-acetamido-6-methyl-N-(1-(5-methyl-6-(2,2,2-trifluoroethoxy)pyridin-3-yl)ethyl)isonicotinamide;

2-(cyclopropanecarboxamido)-N-(2-fluoro-5-(trifluoromethyl)benzyl)pyrimidine-4-carboxamide;

2-acetamido-N-(1-(3-(2,2,2-trifluoroethoxy)phenyl)ethyl)pyrimidine-4-carboxamide;

2-propionamido-N-(1-(3-(2,2,2-trifluoroethoxy)phenyl)ethyl)pyrimidine-4-carboxamide;

2-isobutyramido-N-(1-(3-(2,2,2-trifluoroethoxy)phenyl)ethyl)pyrimidine-4-carboxamide;

N-((5-chloro-6-(2,2,2-trifluoroethoxy)pyridin-3-yl)methyl)-6-methyl-2-propionamidopyrimidine-4-carboxamide;

N-((5-chloro-6-(2,2,2-trifluoroethoxy)pyridin-3-yl)methyl)-2-isobutyramido-6-methylpyrimidine-4-carboxamide;

N-((5-fluoro-2-methyl-6-(2,2,2-trifluoroethoxy)pyridin-3-yl)methyl)-2-isobutyramido-6-methylpyrimidine-4-carboxamide;

2-(cyclopropanecarboxamido)-6-methyl-N-(1-(6-(2,2,2-trifluoroethoxy)pyridin-2-yl)ethyl)pyrimidine-4-carboxamide;

2-isobutyramido-6-methyl-N-(1-(6-(2,2,2-trifluoroethoxy)pyridin-2-yl)ethyl)pyrimidine-4-carboxamide;

N-((5-fluoro-2-methyl-6-(2,2,2-trifluoroethoxy)pyridin-3-yl)methyl)-2-(2-hydroxy-2-methylpropanamido)-6-methylisonicotinamide;

2-(cyclopropanecarboxamido)-N-((5-fluoro-2-methyl-6-(2,2,2-trifluoroethoxy)pyridin-3-yl)methyl)-6-methylpyrimidine-4-carboxamide;

2-acetamido-N,6-dimethyl-N-(1-(5-methyl-6-(2,2,2-trifluoroethoxy)pyridin-3-yl)ethyl)isonicotinamide;

2-acetamido-N-methyl-N-(1-(5-methyl-6-(2,2,2-trifluoroethoxy)pyridin-3-yl)ethyl)isonicotinamide;

N-methyl-N-(1-(5-methyl-6-(2,2,2-trifluoroethoxy)pyridin-3-yl)ethyl)-2-propionamidoisonicotinamide;

2-acetamido-N,6-dimethyl-N-((5-methyl-6-(2,2,2-trifluoroethoxy)pyridin-3-yl)methyl)isonicotinamide;

2-acetamido-N-methyl-N-((5-methyl-6-(2,2,2-trifluoroethoxy)pyridin-3-yl)methyl)isonicotinamide;

N-methyl-N-((5-methyl-6-(2,2,2-trifluoroethoxy)pyridin-3-yl)methyl)-2-propionamidoisonicotinamide;

2-(cyclopropanecarboxamido)-N-((6-(2,2,2-trifluoroethoxy)pyridin-3-yl)methyl)pyrimidine-4-carboxamide;

2-isobutyramido-N-((6-(2,2,2-trifluoroethoxy)pyridin-3-yl)methyl)pyrimidine-4-carboxamide;

2-acetamido-N-(1-(5-methoxy-6-(2,2,2-trifluoroethoxy)pyridin-3-yl)ethyl)pyrimidine-4-carboxamide;

2-(cyclopropanecarboxamido)-N-(1-(5-methoxy-6-(2,2,2-trifluoroethoxy)pyridin-3-yl)ethyl)pyrimidine-4-carboxamide;

2-isobutyramido-N-(1-(5-methoxy-6-(2,2,2-trifluoroethoxy)pyridin-3-yl)ethyl)pyrimidine-4-carboxamide;

2-(cyclopropanecarboxamido)-N-((5-fluoro-6-(2,2,2-trifluoroethoxy)pyridin-3-yl)methyl)pyrimidine-4-carboxamide;

2-(cyclopropanecarboxamido)-N-((4-methyl-6-(2,2,2-trifluoroethoxy)pyridin-3-yl)methyl)pyrimidine-4-carboxamide;

2-(cyclopropanecarboxamido)-N-(3-(trifluoromethyl)benzyl)pyrimidine-4-carboxamide;

2-(cyclopropanecarboxamido)-N-(1-(4-(2,2,2-trifluoroethoxy)phenyl)ethyl)pyrimidine-4-carboxamide;

2-isobutyramido-N-(1-(4-(2,2,2-trifluoroethoxy)phenyl)ethyl)pyrimidine-4-carboxamide;

2-(cyclopropanecarboxamido)-N-((2-methyl-6-(2,2,2-trifluoroethoxy)pyridin-3-yl)methyl)pyrimidine-4-carboxamide;

N-((5-chloro-6-(2,2,2-trifluoroethoxy)pyridin-3-yl)methyl)-2-(2-hydroxy-2-methylpropanamido)-6-methylisonicotinamide;

2-acetamido-N-((5-chloro-6-(2,2,2-trifluoroethoxy)pyridin-3-yl)methyl)pyrimidine-4-carboxamide;
N-((5-chloro-6-(2,2,2-trifluoroethoxy)pyridin-3-yl)methyl)-2-propionamidopyrimidine-4-carboxamide;
N-((5-chloro-6-(2,2,2-trifluoroethoxy)pyridin-3-yl)methyl)-2-(cyclopropanecarboxamido)pyrimidine-4-carboxamide;
N-((5-chloro-6-(2,2,2-trifluoroethoxy)pyridin-3-yl)methyl)-2-isobutyramidopyrimidine-4-carboxamide;
2-(cyclopropanecarboxamido)-N-(1-(6-(2,2,2-trifluoroethoxy)pyridin-3-yl)propyl)pyrimidine-4-carboxamide;
N-((4-methyl-6-(2,2,2-trifluoroethoxy)pyridin-3-yl)methyl)-2-pivalamidoisonicotinamide;
6-methyl-2-propionamido-N-(1-(3-(trifluoromethoxy)phenyl)ethyl)pyrimidine-4-carboxamide;
2-(cyclopropanecarboxamido)-6-methyl-N-(1-(3-(trifluoromethoxy)phenyl)ethyl)pyrimidine-4-carboxamide;
2-isobutyramido-6-methyl-N-(1-(3-(trifluoromethoxy)phenyl)ethyl)pyrimidine-4-carboxamide;
2-isobutyramido-N-(1-(3-(trifluoromethoxy)phenyl)ethyl)isonicotinamide;
2-butyramido-N-(1-(3-(trifluoromethoxy)phenyl)ethyl)isonicotinamide;
2-acetamido-6-methyl-N-(1-(3-(trifluoromethoxy)phenyl)ethyl)isonicotinamide;
2-(2-hydroxy-2-methylpropanamido)-6-methyl-N-(1-(3-(trifluoromethoxy)phenyl)ethyl)isonicotinamide;
N-((2-ethoxy-6-(2,2,2-trifluoroethoxy)pyridin-3-yl)methyl)-2-(2-hydroxy-2-methylpropanamido)-6-methylisonicotinamide;
2-(cyclopropanecarboxamido)-6-methyl-N-((6-(3,3,3-trifluoropropoxy)pyridin-3-yl)methyl)pyrimidine-4-carboxamide;
2-isobutyramido-6-methyl-N-((6-(3,3,3-trifluoropropoxy)pyridin-3-yl)methyl)pyrimidine-4-carboxamide;
2-acetamido-6-methyl-N-(1-(3-(trifluoromethoxy)phenyl)ethyl)pyrimidine-4-carboxamide;
N-(1-(5-methyl-6-(2,2,2-trifluoroethoxy)pyridin-3-yl)ethyl)-2-(methylamino)isonicotinamide;
2-methoxy-N-(1-(5-methyl-6-(2,2,2-trifluoroethoxy)pyridin-3-yl)ethyl)isonicotinamide;
6-acetamido-N-(1-(5-methyl-6-(2,2,2-trifluoroethoxy)pyridin-3-yl)ethyl)picolinamide;
N-(1-(5-methyl-6-(2,2,2-trifluoroethoxy)pyridin-3-yl)ethyl)-3-(2-oxopyrrolidin-1-yl)benzamide;
N-(1-(5-methyl-6-(2,2,2-trifluoroethoxy)pyridin-3-yl)ethyl)quinoline-6-carboxamide;
N-(1-(5-methyl-6-(2,2,2-trifluoroethoxy)pyridin-3-yl)ethyl)quinoline-8-carboxamide;
N-(1-(5-methyl-6-(2,2,2-trifluoroethoxy)pyridin-3-yl)ethyl)quinoxaline-2-carboxamide;
N-(1-(5-methyl-6-(2,2,2-trifluoroethoxy)pyridin-3-yl)ethyl)quinoline-3-carboxamide;
N-(1-(5-methyl-6-(2,2,2-trifluoroethoxy)pyridin-3-yl)ethyl)imidazo[1,2-a]pyridine-2-carboxamide;
1-methyl-N-(1-(5-methyl-6-(2,2,2-trifluoroethoxy)pyridin-3-yl)ethyl)-1H-pyrazolo[3,4-b]pyridine-3-carboxamide;
N-(1-(5-methyl-6-(2,2,2-trifluoroethoxy)pyridin-3-yl)ethyl)-1H-benzo[d]imidazole-4-carboxamide;
(R)-6-methyl-2-propionamido-N-((6-(((1,1,1-trifluoropropan-2-yl)oxy)pyridin-3-yl)methyl)pyrimidine-4-carboxamide;
(R)-2-(cyclopropanecarboxamido)-6-methyl-N-((6-(((1,1,1-trifluoropropan-2-yl)oxy)pyridin-3-yl)methyl)pyrimidine-4-carboxamide;
(R)-2-isobutyramido-6-methyl-N-((6-(((1,1,1-trifluoropropan-2-yl)oxy)pyridin-3-yl)methyl)pyrimidine-4-carboxamide;
(R)-2-(cyclopropanecarboxamido)-N-((6-(((1,1,1-trifluoropropan-2-yl)oxy)pyridin-3-yl)methyl)pyrimidine-4-carboxamide;
2-acetamido-N-((5-methoxy-6-(2,2,2-trifluoroethoxy)pyridin-3-yl)methyl)-6-methylpyrimidine-4-carboxamide;
2-(cyclopropanecarboxamido)-N-((5-methoxy-6-(2,2,2-trifluoroethoxy)pyridin-3-yl)methyl)-6-methylpyrimidine-4-carboxamide;
2-isobutyramido-N-((5-methoxy-6-(2,2,2-trifluoroethoxy)pyridin-3-yl)methyl)-6-methylpyrimidine-4-carboxamide;
2-(cyclopropanecarboxamido)-N-((5-methoxy-6-(2,2,2-trifluoroethoxy)pyridin-3-yl)methyl)pyrimidine-4-carboxamide;
2-(hydroxymethyl)-N-(1-(5-methyl-6-(2,2,2-trifluoroethoxy)pyridin-3-yl)ethyl)-6-propionamidoisonicotinamide;
2-(cyclopropanecarboxamido)-6-(hydroxymethyl)-N-(1-(5-methyl-6-(2,2,2-trifluoroethoxy)pyridin-3-yl)ethyl)isonicotinamide;
2-(hydroxymethyl)-6-isobutyramido-N-(1-(5-methyl-6-(2,2,2-trifluoroethoxy)pyridin-3-yl)ethyl)isonicotinamide;
N-(1-(4-(2,2-difluoroethoxy)-2-methylphenyl)ethyl)-2-isobutyramidoisonicotinamide;
2-(cyclopropanecarboxamido)-N-methyl-N-(1-(5-methyl-6-(2,2,2-trifluoroethoxy)pyridin-3-yl)ethyl)pyrimidine-4-carboxamide;
2-(cyclopropanecarboxamido)-N-methyl-N-((5-methyl-6-(2,2,2-trifluoroethoxy)pyridin-3-yl)methyl)pyrimidine-4-carboxamide;
2-(cyclopropanecarboxamido)-N,6-dimethyl-N-((5-methyl-6-(2,2,2-trifluoroethoxy)pyridin-3-yl)methyl)pyrimidine-4-carboxamide;
2-(cyclobutanecarboxamido)-6-methyl-N-(1-(6-(2,2,2-trifluoroethoxy)pyridin-3-yl)ethyl)isonicotinamide;
2-(cyclopropanecarboxamido)-N-(3-(trifluoromethoxy)benzyl)pyrimidine-4-carboxamide;
2-(cyclopropanecarboxamido)-N-(1-(5-ethoxy-6-(2,2,2-trifluoroethoxy)pyridin-3-yl)ethyl)pyrimidine-4-carboxamide;
2-(cyclopropanecarboxamido)-N-((6-(3,3,3-trifluoropropoxy)pyridin-3-yl)methyl)pyrimidine-4-carboxamide;
6-methyl-N-(1-(5-methyl-6-(2,2,2-trifluoroethoxy)pyridin-3-yl)ethyl)-2-(oxazol-2-ylamino)pyrimidine-4-carboxamide;
N-(1-(5-chloro-6-(2,2,2-trifluoroethoxy)pyridin-3-yl)ethyl)-2-methyl-6-(oxazol-2-ylamino)isonicotinamide;
2-ethoxy-6-methyl-N-(1-(5-methyl-6-(2,2,2-trifluoroethoxy)pyridin-3-yl)ethyl)pyrimidine-4-carboxamide;
2-(cyclopentanecarboxamido)-6-methyl-N-(1-(6-(2,2,2-trifluoroethoxy)pyridin-3-yl)ethyl)isonicotinamide;
2-propionamido-N-((6-(trifluoromethyl)pyridin-2-yl)methyl)isonicotinamide;
2-methyl-6-propionamido-N-((6-(trifluoromethyl)pyridin-2-yl)methyl)isonicotinamide;
2-isobutyramido-N-((6-(trifluoromethyl)pyridin-2-yl)methyl)isonicotinamide;
2-amino-6-methyl-N-((5-methyl-6-(2,2,2-trifluoroethoxy)pyridin-3-yl)methyl)pyrimidine-4-carboxamide;
2-propionamido-N-((6-(2,2,2-trifluoroethoxy)pyridin-2-yl)methyl)isonicotinamide;
2-(cyclopropanecarboxamido)-N-((6-(2,2,2-trifluoroethoxy)pyridin-2-yl)methyl)isonicotinamide;

2-acetamido-6-methyl-N-((6-(2,2,2-trifluoroethoxy)pyridin-2-yl)methyl)isonicotinamide;
2-methyl-6-propionamido-N-((6-(2,2,2-trifluoroethoxy)pyridin-2-yl)methyl)isonicotinamide;
2-isobutyramido-N-((6-(2,2,2-trifluoroethoxy)pyridin-2-yl)methyl)isonicotinamide;
2-butyramido-N-((6-(2,2,2-trifluoroethoxy)pyridin-2-yl)methyl)isonicotinamide;
2-(cyclopropanecarboxamido)-6-methyl-N-((6-(2,2,2-trifluoroethoxy)pyridin-2-yl)methyl)pyrimidine-4-carboxamide;
2-pivalamido-N-((6-(2,2,2-trifluoroethoxy)pyridin-2-yl)methyl)isonicotinamide;
6-methyl-N-(1-(5-methyl-6-(2,2,2-trifluoroethoxy)pyridin-3-yl)ethyl)-2-(methylamino)pyrimidine-4-carboxamide;
2-(dimethylamino)-6-methyl-N-(1-(5-methyl-6-(2,2,2-trifluoroethoxy)pyridin-3-yl)ethyl)pyrimidine-4-carboxamide;
6-methyl-N-(1-(5-methyl-6-(2,2,2-trifluoroethoxy)pyridin-3-yl)ethyl)-2-(pyrrolidin-1-yl)pyrimidine-4-carboxamide;
2-((2-methoxyethyl)amino)-6-methyl-N-(1-(5-methyl-6-(2,2,2-trifluoroethoxy)pyridin-3-yl)ethyl)pyrimidine-4-carboxamide;
N4-(1-(5-chloro-6-(2,2,2-trifluoroethoxy)pyridin-3-yl)ethyl)-N2-ethyl-6-methylpyridine-2,4-dicarboxamide;
N2,6-dimethyl-N4-(1-(5-methyl-6-(2,2,2-trifluoroethoxy)pyridin-3-yl)ethyl)pyridine-2,4-dicarboxamide;
N2-ethyl-6-methyl-N4-(1-(5-methyl-6-(2,2,2-trifluoroethoxy)pyridin-3-yl)ethyl)pyridine-2,4-dicarboxamide;
2,6-dimethoxy-N-(1-(5-methyl-6-(2,2,2-trifluoroethoxy)pyridin-3-yl)ethyl)isonicotinamide;
2-methyl-6-pivalamido-N-((6-(2,2,2-trifluoroethoxy)pyridin-3-yl)methyl)isonicotinamide;
N2-ethyl-N4-((2-methoxy-6-(2,2,2-trifluoroethoxy)pyridin-3-yl)methyl)pyridine-2,4-dicarboxamide;
2-acrylamido-6-methyl-N-(1-(6-(2,2,2-trifluoroethoxy)pyridin-3-yl)ethyl)isonicotinamide;
2-isobutyramido-6-methyl-N-((6-(2,2,2-trifluoroethoxy)pyridin-3-yl)methyl)isonicotinamide;
2-isobutyramido-6-methyl-N-(1-(6-(2,2,2-trifluoroethoxy)pyridin-3-yl)propyl)isonicotinamide;
N-(1-(6-(2,2-difluoroethoxy)pyridin-3-yl)ethyl)-2-isobutyramido-6-methylisonicotinamide;
N-(1-(5-fluoro-6-(2,2,2-trifluoroethoxy)pyridin-3-yl)ethyl)-2-isobutyramido-6-methylisonicotinamide;
2-isobutyramido-N-(1-(5-methoxy-6-(2,2,2-trifluoroethoxy)pyridin-3-yl)ethyl)-6-methylisonicotinamide;
2-isobutyramido-6-methyl-N-(1-(6-(2-(2,2,2-trifluoroethoxy)ethoxy)pyridin-3-yl)ethyl)isonicotinamide;
2-isobutyramido-6-methyl-N-(1-(6-(3,3,3-trifluoropropoxy)pyridin-3-yl)ethyl)isonicotinamide;
2-isobutyramido-6-methyl-N-((6-(3,3,3-trifluoropropoxy)pyridin-3-yl)methyl)isonicotinamide;
N-((5-fluoro-6-(2,2,2-trifluoroethoxy)pyridin-3-yl)methyl)-2-isobutyramido-6-methylisonicotinamide;
2-isobutyramido-N-((5-methoxy-6-(2,2,2-trifluoroethoxy)pyridin-3-yl)methyl)-6-methylisonicotinamide;
2-isobutyramido-6-methyl-N-((2-methyl-6-(2,2,2-trifluoroethoxy)pyridin-3-yl)methyl)isonicotinamide;
2-isobutyramido-N-((2-methoxy-6-(2,2,2-trifluoroethoxy)pyridin-3-yl)methyl)-6-methylisonicotinamide;
(R)-2-isobutyramido-6-methyl-N-((6-((1,1,1-trifluoropropan-2-yl)oxy)pyridin-3-yl)methyl)isonicotinamide;
2-isobutyramido-6-methyl-N-((6-(2,2,2-trifluoroethoxy)pyridin-2-yl)methyl)isonicotinamide;
2-isobutyramido-6-methyl-N-(1-(2-(2,2,2-trifluoroethoxy)pyridin-4-yl)ethyl)isonicotinamide;
2-isobutyramido-6-methyl-N-((2-(2,2,2-trifluoroethoxy)pyridin-4-yl)methyl)isonicotinamide;
2-isobutyramido-6-methyl-N-(1-(3-(trifluoromethoxy)phenyl)ethyl)isonicotinamide;
2-isobutyramido-6-methyl-N-((6-(trifluoromethyl)pyridin-2-yl)methyl)isonicotinamide;
N4-ethyl-N2-(1-(5-methyl-6-(2,2,2-trifluoroethoxy)pyridin-3-yl)ethyl)pyridine-2,4-dicarboxamide;
N2-(1-(5-chloro-6-(2,2,2-trifluoroethoxy)pyridin-3-yl)ethyl)-N4-ethylpyridine-2,4-dicarboxamide;
2-(2-hydroxy-2-methylpropanamido)-6-methyl-N-((5-methyl-6-(2,2,2-trifluoroethoxy)pyridin-3-yl)methyl)isonicotinamide;
2-methoxy-6-methyl-N-(1-(5-methyl-6-(2,2,2-trifluoroethoxy)pyridin-3-yl)ethyl)pyrimidine-4-carboxamide;
N2-ethyl-6-methyl-N4-(1-(5-methyl-6-(2,2,2-trifluoroethoxy)pyridin-3-yl)ethyl)pyrimidine-2,4-dicarboxamide;
N2-isopropyl-6-methyl-N4-(1-(5-methyl-6-(2,2,2-trifluoroethoxy)pyridin-3-yl)ethyl)pyrimidine-2,4-dicarboxamide;
6-methyl-2-(oxazol-2-ylamino)-N-((6-(2,2,2-trifluoroethoxy)pyridin-3-yl)methyl)pyrimidine-4-carboxamide;
N2-ethyl-N4-((2-methoxy-6-(2,2,2-trifluoroethoxy)pyridin-3-yl)methyl)-6-methylpyridine-2,4-dicarboxamide;
N2-cyclopropyl-N4-((2-methoxy-6-(2,2,2-trifluoroethoxy)pyridin-3-yl)methyl)-6-methylpyridine-2,4-dicarboxamide;
N2-isopropyl-N4-((2-methoxy-6-(2,2,2-trifluoroethoxy)pyridin-3-yl)methyl)-6-methylpyridine-2,4-dicarboxamide;
N2,6-dimethyl-N4-(1-(3-(trifluoromethoxy)phenyl)ethyl)pyridine-2,4-dicarboxamide;
N2-ethyl-6-methyl-N4-(1-(3-(trifluoromethoxy)phenyl)ethyl)pyridine-2,4-dicarboxamide;
N2-isopropyl-6-methyl-N4-(1-(3-(trifluoromethoxy)phenyl)ethyl)pyridine-2,4-dicarboxamide;
6-methyl-N4-(1-(3-(trifluoromethoxy)phenyl)ethyl)pyridine-2,4-dicarboxamide;
N-(1-(5-ethoxy-6-(2,2,2-trifluoroethoxy)pyridin-3-yl)ethyl)-2-isobutyramido-6-methylisonicotinamide;
2-isobutyramido-6-methyl-N-((4-methyl-6-(2,2,2-trifluoroethoxy)pyridin-3-yl)methyl)isonicotinamide;
2-isobutyramido-6-methyl-N-(1-(6-((2,2,2-trifluoroethyl)amino)pyridin-3-yl)ethyl)isonicotinamide;
3-acetamido-4-fluoro-N-(1-(5-methyl-6-(2,2,2-trifluoroethoxy)pyridin-3-yl)ethyl)benzamide;
N2-ethyl-N-4-((4-methyl-6-(2,2,2-trifluoroethoxy)pyridin-3-yl)methyl)pyridine-2,4-dicarboxamide;
2-isobutyramido-6-methyl-N-(1-(5-methyl-6-(2,2,2-trifluoroethoxy)pyridin-3-yl)ethyl)isonicotinamide;
N-(1-(5-chloro-6-(2,2,2-trifluoroethoxy)pyridin-3-yl)ethyl)-2-isobutyramido-6-methylisonicotinamide;
N-(1-(5-chloro-6-(2,2,2-trifluoroethoxy)pyridin-3-yl)ethyl)-2-isobutyramidoisonicotinamide;
2-propionamido-N-(3-(trifluoromethoxy)benzyl)isonicotinamide;
2-(cyclopropanecarboxamido)-N-(3-(trifluoromethoxy)benzyl)isonicotinamide;
2-acetamido-6-methyl-N-(3-(trifluoromethoxy)benzyl)isonicotinamide;
2-methyl-6-propionamido-N-(3-(trifluoromethoxy)benzyl)isonicotinamide;
2-isobutyramido-N-(3-(trifluoromethoxy)benzyl)isonicotinamide;
2-isobutyramido-6-methyl-N-(3-(trifluoromethoxy)benzyl)isonicotinamide;

(R)-2-acetamido-6-methyl-N-(1-(3-(trifluoromethyl)phenyl)ethyl)isonicotinamide;
(R)-2-isobutyramido-N-(1-(3-(trifluoromethyl)phenyl)ethyl)isonicotinamide;
(R)-2-isobutyramido-6-methyl-N-(1-(3-(trifluoromethyl)phenyl)ethyl)isonicotinamide;
2-acetamido-6-methyl-N-(3-(trifluoromethyl)benzyl)isonicotinamide;
2-isobutyramido-N-(3-(trifluoromethyl)benzyl)isonicotinamide;
2-isobutyramido-6-methyl-N-(3-(trifluoromethyl)benzyl)isonicotinamide;
8-hydroxy-N-(1-(5-methyl-6-(2,2,2-trifluoroethoxy)pyridin-3-yl)ethyl)quinoline-2-carboxamide;
2-((3,4-dimethylisoxazol-5-yl)amino)-6-methyl-N-(1-(6-(2,2,2-trifluoroethoxy)pyridin-3-yl)ethyl)pyrimidine-4-carboxamide;
6-methyl-2-((1-methyl-1H-pyrazol-3-yl)amino)-N-(1-(6-(2,2,2-trifluoroethoxy)pyridin-3-yl)ethyl)pyrimidine-4-carboxamide;
2-((1,3-dimethyl-1H-pyrazol-5-yl)amino)-6-methyl-N-(1-(6-(2,2,2-trifluoroethoxy)pyridin-3-yl)ethyl)pyrimidine-4-carboxamide;
6-methyl-N-(1-(6-(2,2,2-trifluoroethoxy)pyridin-3-yl)ethyl)-2-((5-(trifluoromethyl)-4H-1,2,4-triazol-3-yl)amino)pyrimidine-4-carboxamide;
6-methyl-2-((3-methylisothiazol-5-yl)amino)-N-(1-(6-(2,2,2-trifluoroethoxy)pyridin-3-yl)ethyl)pyrimidine-4-carboxamide;
6-methyl-N-(1-(6-(2,2,2-trifluoroethoxy)pyridin-3-yl)ethyl)-2-((4-(trifluoromethyl)oxazol-2-yl)amino)pyrimidine-4-carboxamide;
N-(4-fluoro-3-(trifluoromethyl)benzyl)-2-isobutyramidoisonicotinamide;
N-(3,5-bis(trifluoromethyl)benzyl)-2-isobutyramidoisonicotinamide;
N-(3-fluoro-4-(trifluoromethyl)benzyl)-2-isobutyramidoisonicotinamide;
N-(3-fluoro-5-(trifluoromethyl)benzyl)-2-isobutyramidoisonicotinamide;
N-(2-chloro-5-(trifluoromethyl)benzyl)-2-isobutyramidoisonicotinamide;
N-(4-chloro-3-(trifluoromethyl)benzyl)-2-isobutyramidoisonicotinamide;
(R)—N-(1-(3,5-bis(trifluoromethyl)phenyl)ethyl)-2-isobutyramidoisonicotinamide;
2-(2-hydroxy-2-methylpropanamido)-6-methyl-N-((6-(2,2,2-trifluoroethoxy)pyridin-2-yl)methyl)isonicotinamide;
2-(2-hydroxy-2-methylpropanamido)-6-methyl-N-(1-(3-(2,2,2-trifluoroethoxy)phenyl)ethyl)isonicotinamide;
2-acetamido-N-(1-(6-(2,2-difluoroethoxy)-5-methylpyridin-3-yl)ethyl)isonicotinamide;
N-(1-(6-(2,2-difluoroethoxy)-5-methylpyridin-3-yl)ethyl)-2-propionamidoisonicotinamide;
2-(cyclopropanecarboxamido)-N-(1-(6-(2,2-difluoroethoxy)-5-methylpyridin-3-yl)ethyl)isonicotinamide;
N-(1-(6-(2,2-difluoroethoxy)-5-methylpyridin-3-yl)ethyl)-2-methyl-6-propionamidoisonicotinamide;
N-(1-(6-(2,2-difluoroethoxy)-5-methylpyridin-3-yl)ethyl)-2-isobutyramidoisonicotinamide;
2-acetamido-N-(1-(6-(2,2-difluoroethoxy)-5-methylpyridin-3-yl)ethyl)-6-methylisonicotinamide;
N-(1-(6-(2,2-difluoroethoxy)-5-methylpyridin-3-yl)ethyl)-2-isobutyramido-6-methylisonicotinamide;
2-(cyclopropanecarboxamido)-N-(1-(6-(2,2-difluoroethoxy)-5-methylpyridin-3-yl)ethyl)pyrimidine-4-carboxamide;
2-(cyclopropanecarboxamido)-N-(1-(6-(2,2-difluoroethoxy)-5-methylpyridin-3-yl)ethyl)-6-methylpyrimidine-4-carboxamide;
N-(2-fluoro-5-(trifluoromethyl)benzyl)-2-isobutyramidoisonicotinamide;
2-isobutyramido-N-(1-(3-(2,2,2-trifluoroethoxy)phenyl)ethyl)isonicotinamide;
2-isobutyramido-N-(1-(4-(2,2,2-trifluoroethoxy)phenyl)ethyl)isonicotinamide;
2-(cyclopropanecarboxamido)-N-((2-methoxy-6-(2,2,2-trifluoroethoxy)pyridin-3-yl)methyl)pyrimidine-4-carboxamide;
2-(cyclopropanecarboxamido)-N-((5-methyl-6-(2,2,2-trifluoroethoxy)pyridin-3-yl)methyl)pyrimidine-4-carboxamide;
2-acetamido-N-(1-(4-(2,2-difluoroethoxy)-2-methylphenyl)ethyl)-6-methylisonicotinamide;
2-isobutyramido-N-((3-methyl-6-(2,2,2-trifluoroethoxy)pyridin-2-yl)methyl)isonicotinamide;
2-isobutyramido-6-methyl-N-((3-methyl-6-(2,2,2-trifluoroethoxy)pyridin-2-yl)methyl)isonicotinamide;
2-(cyclopropanecarboxamido)-N-((3-methyl-6-(2,2,2-trifluoroethoxy)pyridin-2-yl)methyl)isonicotinamide;
2-methyl-6-(thiazol-2-yl)-N-(1-(6-(2,2,2-trifluoroethoxy)pyridin-3-yl)ethyl)isonicotinamide;
N-(1-(5-methyl-6-(2,2,2-trifluoroethoxy)pyridin-3-yl)ethyl)-3-(1H-pyrazol-1-yl)benzamide;
2-methacrylamido-6-methyl-N-(1-(6-(2,2,2-trifluoroethoxy)pyridin-3-yl)ethyl)isonicotinamide;
N-(2-fluoro-5-(trifluoromethyl)benzyl)-2-propionamidoisonicotinamide;
2-(cyclopropanecarboxamido)-N-(2-fluoro-5-(trifluoromethyl)benzyl)isonicotinamide;
2-acetamido-N-(2-fluoro-5-(trifluoromethyl)benzyl)-6-methylisonicotinamide;
N-(2-fluoro-5-(trifluoromethyl)benzyl)-2-isobutyramido-6-methylisonicotinamide;
2-isobutyramido-N-((4-methyl-6-(2,2,2-trifluoroethoxy)pyridin-2-yl)methyl)isonicotinamide;
2-isobutyramido-6-methyl-N-((4-methyl-6-(2,2,2-trifluoroethoxy)pyridin-2-yl)methyl)isonicotinamide;
2-(cyclopropanecarboxamido)-N-((4-methyl-6-(2,2,2-trifluoroethoxy)pyridin-2-yl)methyl)isonicotinamide;
N-(1-(5-chloro-6-(2,2,2-trifluoroethoxy)pyridin-3-yl)ethyl)-2,5-dimethylbenzo[d]oxazole-7-carboxamide;
2,5-dimethyl-N-((4-methyl-6-(2,2,2-trifluoroethoxy)pyridin-3-yl)methyl)benzo[d]oxazole-7-carboxamide;
N-(1-(6-(2,2-difluoroethoxy)-5-methylpyridin-3-yl)ethyl)-2,5-dimethylbenzo[d]oxazole-7-carboxamide;
2,5-dimethyl-N-((2-(2,2,2-trifluoroethoxy)pyridin-4-yl)methyl)benzo[d]oxazole-7-carboxamide;
2,5-dimethyl-N-(1-(2-(2,2,2-trifluoroethoxy)pyridin-4-yl)ethyl)benzo[d]oxazole-7-carboxamide;
2,5-dimethyl-N-((6-(2,2,2-trifluoroethoxy)pyridin-3-yl)methyl)benzo[d]oxazole-7-carboxamide;
2,5-dimethyl-N-(1-(6-(2,2,2-trifluoroethoxy)pyridin-3-yl)ethyl)benzo[d]oxazole-7-carboxamide;
6-methyl-N-(1-(6-(2,2,2-trifluoroethoxy)pyridin-3-yl)ethyl)-2-((2,2,2-trifluoroethyl)amino)pyrimidine-4-carboxamide;
2-isobutyramido-6-methyl-N-(1-(4-(2,2,2-trifluoroethoxy)phenyl)ethyl)isonicotinamide;
2-acetamido-N-(4-fluoro-3-(trifluoromethoxy)benzyl)isonicotinamide;
N-(4-fluoro-3-(trifluoromethoxy)benzyl)-2-propionamidoisonicotinamide;

2-(cyclopropanecarboxamido)-N-(4-fluoro-3-(trifluoromethoxy)benzyl)isonicotinamide;
N-(4-fluoro-3-(trifluoromethoxy)benzyl)-2-methyl-6-propionamidoisonicotinamide;
N-(4-fluoro-3-(trifluoromethoxy)benzyl)-2-isobutyramidoisonicotinamide;
2-acetamido-N-(4-fluoro-3-(trifluoromethoxy)benzyl)-6-methylisonicotinamide;
N-(4-fluoro-3-(trifluoromethoxy)benzyl)-2-isobutyramido-6-methylisonicotinamide;
2-(cyclopropanecarboxamido)-N-(4-fluoro-3-(trifluoromethoxy)benzyl)pyrimidine-4-carboxamide;
2-(cyclopropanecarboxamido)-N-(4-fluoro-3-(trifluoromethoxy)benzyl)-6-methylpyrimidine-4-carboxamide;
2-acetamido-N-(3-methyl-5-(trifluoromethoxy)benzyl)isonicotinamide;
N-(3-methyl-5-(trifluoromethoxy)benzyl)-2-propionamidoisonicotinamide;
2-(cyclopropanecarboxamido)-N-(3-methyl-5-(trifluoromethoxy)benzyl)isonicotinamide;
2-methyl-N-(3-methyl-5-(trifluoromethoxy)benzyl)-6-propionamidoisonicotinamide;
2-isobutyramido-N-(3-methyl-5-(trifluoromethoxy)benzyl)isonicotinamide;
2-acetamido-6-methyl-N-(3-methyl-5-(trifluoromethoxy)benzyl)isonicotinamide;
2-isobutyramido-6-methyl-N-(3-methyl-5-(trifluoromethoxy)benzyl)isonicotinamide;
2-(cyclopropanecarboxamido)-N-(3-methyl-5-(trifluoromethoxy)benzyl)pyrimidine-4-carboxamide;
2-(cyclopropanecarboxamido)-6-methyl-N-(3-methyl-5-(trifluoromethoxy)benzyl)pyrimidine-4-carboxamide;
2-acetamido-N-(2-fluoro-5-(trifluoromethoxy)benzyl)isonicotinamide;
N-(2-fluoro-5-(trifluoromethoxy)benzyl)-2-propionamidoisonicotinamide;
2-(cyclopropanecarboxamido)-N-(2-fluoro-5-(trifluoromethoxy)benzyl)isonicotinamide;
N-(2-fluoro-5-(trifluoromethoxy)benzyl)-2-methyl-6-propionamidoisonicotinamide;
N-(2-fluoro-5-(trifluoromethoxy)benzyl)-2-isobutyramidoisonicotinamide;
2-acetamido-N-(2-fluoro-5-(trifluoromethoxy)benzyl)-6-methylisonicotinamide;
N-(2-fluoro-5-(trifluoromethoxy)benzyl)-2-isobutyramido-6-methylisonicotinamide;
2-(cyclopropanecarboxamido)-N-(2-fluoro-5-(trifluoromethoxy)benzyl)pyrimidine-4-carboxamide;
2-(cyclopropanecarboxamido)-N-(2-fluoro-5-(trifluoromethoxy)benzyl)-6-methylpyrimidine-4-carboxamide;
N-(3-(difluoromethoxy)benzyl)-2-isobutyramidoisonicotinamide;
N-(3-(difluoromethoxy)benzyl)-2-isobutyramido-6-methylisonicotinamide;
N-((5-chloro-6-(2,2-difluoroethoxy)pyridin-3-yl)methyl)-2-propionamidoisonicotinamide;
N-((5-chloro-6-(2,2-difluoroethoxy)pyridin-3-yl)methyl)-2-methyl-6-propionamidoisonicotinamide;
N-((5-chloro-6-(2,2-difluoroethoxy)pyridin-3-yl)methyl)-2-isobutyramidoisonicotinamide;
N-((5-chloro-6-(2,2-difluoroethoxy)pyridin-3-yl)methyl)-2-isobutyramido-6-methylisonicotinamide;
2-butyramido-N-((5-chloro-6-(2,2-difluoroethoxy)pyridin-3-yl)methyl)isonicotinamide;
N-((5-chloro-6-(2,2-difluoroethoxy)pyridin-3-yl)methyl)-2-(cyclopropanecarboxamido)-6-methylpyrimidine-4-carboxamide;
N-((5-chloro-6-(2,2-difluoroethoxy)pyridin-3-yl)methyl)-2-(2-hydroxy-2-methylpropanamido)-6-methylisonicotinamide;
2-acetamido-N-(1-(5-chloro-6-(2,2-difluoroethoxy)pyridin-3-yl)ethyl)isonicotinamide;
N-(1-(5-chloro-6-(2,2-difluoroethoxy)pyridin-3-yl)ethyl)-2-propionamidoisonicotinamide;
N-(1-(5-chloro-6-(2,2-difluoroethoxy)pyridin-3-yl)ethyl)-2-(cyclopropanecarboxamido)isonicotinamide;
2-acetamido-N-(1-(5-chloro-6-(2,2-difluoroethoxy)pyridin-3-yl)ethyl)-6-methylisonicotinamide;
N-(1-(5-chloro-6-(2,2-difluoroethoxy)pyridin-3-yl)ethyl)-2-methyl-6-propionamidoisonicotinamide;
N-(1-(5-chloro-6-(2,2-difluoroethoxy)pyridin-3-yl)ethyl)-2-isobutyramidoisonicotinamide;
N-(1-(5-chloro-6-(2,2-difluoroethoxy)pyridin-3-yl)ethyl)-2-isobutyramido-6-methylisonicotinamide;
2-butyramido-N-(1-(5-chloro-6-(2,2-difluoroethoxy)pyridin-3-yl)ethyl)isonicotinamide;
N-(1-(5-chloro-6-(2,2-difluoroethoxy)pyridin-3-yl)ethyl)-2-(cyclopropanecarboxamido)pyrimidine-4-carboxamide;
2-butyramido-N-(1-(6-(2,2-difluoroethoxy)-5-methylpyridin-3-yl)ethyl)isonicotinamide;
2-propionamido-N-((6-(2,2,3,3-tetrafluoropropoxy)pyridin-3-yl)methyl)isonicotinamide;
2-(cyclopropanecarboxamido)-N-((6-(2,2,3,3-tetrafluoropropoxy)pyridin-3-yl)methyl)isonicotinamide;
2-isobutyramido-N-((6-(2,2,3,3-tetrafluoropropoxy)pyridin-3-yl)methyl)isonicotinamide;
2-isobutyramido-N-((4-methyl-5-(2,2,2-trifluoroethoxy)pyridin-2-yl)methyl)isonicotinamide;
2-isobutyramido-6-methyl-N-((4-methyl-5-(2,2,2-trifluoroethoxy)pyridin-2-yl)methyl)isonicotinamide;
N-((6-(2,2,3,3,3-pentafluoropropoxy)pyridin-3-yl)methyl)-2-propionamidoisonicotinamide;
2-(cyclopropanecarboxamido)-N-((6-(2,2,3,3,3-pentafluoropropoxy)pyridin-3-yl)methyl)isonicotinamide;
2-isobutyramido-N-((6-(2,2,3,3,3-pentafluoropropoxy)pyridin-3-yl)methyl)isonicotinamide;
2-acetamido-6-methyl-N-((6-(2,2,3,3,3-pentafluoropropoxy)pyridin-3-yl)methyl)isonicotinamide;
2-methyl-N-((6-(2,2,3,3,3-pentafluoropropoxy)pyridin-3-yl)methyl)-6-propionamidoisonicotinamide;
2-isobutyramido-6-methyl-N-((6-(2,2,3,3,3-pentafluoropropoxy)pyridin-3-yl)methyl)isonicotinamide;
2-acetamido-6-methyl-N-((6-(2,2,3,3-tetrafluoropropoxy)pyridin-3-yl)methyl)isonicotinamide;
2-methyl-6-propionamido-N-((6-(2,2,3,3-tetrafluoropropoxy)pyridin-3-yl)methyl)isonicotinamide;
2-isobutyramido-6-methyl-N-((6-(2,2,3,3-tetrafluoropropoxy)pyridin-3-yl)methyl)isonicotinamide;
N-((6-(2,2,3,3,3-pentafluoropropoxy)pyridin-3-yl)methyl)-2-pivalamidoisonicotinamide;
2-(cyclopropanecarboxamido)-N-((6-(2,2,3,3,3-pentafluoropropoxy)pyridin-3-yl)methyl)pyrimidine-4-carboxamide;
2-(cyclopropanecarboxamido)-6-methyl-N-((6-(2,2,3,3,3-pentafluoropropoxy)pyridin-3-yl)methyl)pyrimidine-4-carboxamide;
2-(cyclopropanecarboxamido)-N-((6-(2,2,3,3-tetrafluoropropoxy)pyridin-3-yl)methyl)pyrimidine-4-carboxamide;
2-(cyclopropanecarboxamido)-6-methyl-N-((6-(2,2,3,3-tetrafluoropropoxy)pyridin-3-yl)methyl)pyrimidine-4-carboxamide;
2-propionamido-N-(1-(6-(2,2,3,3-tetrafluoropropoxy)pyridin-3-yl)ethyl)isonicotinamide;

2-isobutyramido-N-(1-(6-(2,2,3,3-tetrafluoropropoxy)pyridin-3-yl)ethyl)isonicotinamide;
2-acetamido-6-methyl-N-(1-(6-(2,2,3,3-tetrafluoropropoxy)pyridin-3-yl)ethyl)isonicotinamide;
2-methyl-6-propionamido-N-(1-(6-(2,2,3,3-tetrafluoropropoxy)pyridin-3-yl)ethyl)isonicotinamide;
2-isobutyramido-6-methyl-N-(1-(6-(2,2,3,3-tetrafluoropropoxy)pyridin-3-yl)ethyl)isonicotinamide;
2-(cyclopropanecarboxamido)-N-(1-(6-(2,2,3,3-tetrafluoropropoxy)pyridin-3-yl)ethyl)pyrimidine-4-carboxamide;
5-(4-chlorophenyl)-N-((5-methyl-6-(2,2,2-trifluoroethoxy)pyridin-3-yl)methyl)furan-2-carboxamide;
5-(4-chlorophenyl)-N-((6-(2,2,2-trifluoroethoxy)pyridin-3-yl)methyl)furan-2-carboxamide;
5-(4-chlorophenyl)-N-(1-(6-(2,2,2-trifluoroethoxy)pyridin-3-yl)ethyl)furan-2-carboxamide;
2-(3-methylbutanamido)-N-(1-(6-(2,2,2-trifluoroethoxy)pyridin-3-yl)ethyl)isonicotinamide;
2-(3-methylbutanamido)-N-((6-(2,2,2-trifluoroethoxy)pyridin-3-yl)methyl)isonicotinamide;
2-propionamido-N-(4-((2,2,2-trifluoroethoxy)methyl)benzyl)isonicotinamide;
2-(cyclopropanecarboxamido)-N-(4-((2,2,2-trifluoroethoxy)methyl)benzyl)isonicotinamide;
2-methyl-6-propionamido-N-(4-((2,2,2-trifluoroethoxy)methyl)benzyl)isonicotinamide;
2-isobutyramido-N-(4-((2,2,2-trifluoroethoxy)methyl)benzyl)isonicotinamide;
2-acetamido-6-methyl-N-(4-((2,2,2-trifluoroethoxy)methyl)benzyl)isonicotinamide;
2-isobutyramido-6-methyl-N-(4-((2,2,2-trifluoroethoxy)methyl)benzyl)isonicotinamide;
2-(cyclopropanecarboxamido)-N-(4-((2,2,2-trifluoroethoxy)methyl)benzyl)pyrimidine-4-carboxamide;
2-(cyclopropanecarboxamido)-6-methyl-N-(4-((2,2,2-trifluoroethoxy)methyl)benzyl)pyrimidine-4-carboxamide;
2-acetamido-N-(1-(3-chloro-4-(2,2,2-trifluoroethoxy)phenyl)ethyl)isonicotinamide;
N-(1-(3-chloro-4-(2,2,2-trifluoroethoxy)phenyl)ethyl)-2-propionamidoisonicotinamide;
N-(1-(3-chloro-4-(2,2,2-trifluoroethoxy)phenyl)ethyl)-2-isobutyramidoisonicotinamide;
N-(1-(3-chloro-4-(2,2,2-trifluoroethoxy)phenyl)ethyl)-2-(cyclopropanecarboxamido)isonicotinamide;
2-acetamido-N-(1-(3-chloro-4-(2,2,2-trifluoroethoxy)phenyl)ethyl)-6-methylisonicotinamide;
N-(1-(3-chloro-4-(2,2,2-trifluoroethoxy)phenyl)ethyl)-2-methyl-6-propionamidoisonicotinamide;
N-(1-(3-chloro-4-(2,2,2-trifluoroethoxy)phenyl)ethyl)-2-isobutyramido-6-methylisonicotinamide;
N-(1-(3-chloro-4-(2,2,2-trifluoroethoxy)phenyl)ethyl)-2-(cyclopropanecarboxamido)-6-methylpyrimidine-4-carboxamide;
N-(1-(3-chloro-4-(2,2,2-trifluoroethoxy)phenyl)ethyl)-2-(cyclopropanecarboxamido)pyrimidine-4-carboxamide;
2-acetamido-N-(4-fluoro-3-(trifluoromethyl)benzyl)isonicotinamide;
2-acetamido-N-(4-chloro-3-(trifluoromethyl)benzyl)isonicotinamide;
2-acetamido-N-(3,5-bis(trifluoromethyl)benzyl)isonicotinamide;
(R)-2-(cyclopropanecarboxamido)-N-(1-(3-(trifluoromethyl)phenyl)ethyl)pyrimidine-4-carboxamide;
2-(cyclopropanecarboxamido)-N-((6-(3,3,3-trifluoropropyl)pyridin-3-yl)methyl)isonicotinamide;
2-methyl-6-propionamido-N-((6-(3,3,3-trifluoropropyl)pyridin-3-yl)methyl)isonicotinamide;
2-isobutyramido-N-((6-(3,3,3-trifluoropropyl)pyridin-3-yl)methyl)isonicotinamide;
2-isobutyramido-6-methyl-N-((6-(3,3,3-trifluoropropyl)pyridin-3-yl)methyl)isonicotinamide;
2-(cyclopropanecarboxamido)-N-(1-(6-(2,2,3,3,3-pentafluoropropoxy)pyridin-3-yl)ethyl)isonicotinamide;
2-isobutyramido-N-(1-(6-(2,2,3,3,3-pentafluoropropoxy)pyridin-3-yl)ethyl)isonicotinamide;
2-acetamido-6-methyl-N-(1-(6-(2,2,3,3,3-pentafluoropropoxy)pyridin-3-yl)ethyl)isonicotinamide;
2-methyl-N-(1-(6-(2,2,3,3,3-pentafluoropropoxy)pyridin-3-yl)ethyl)-6-propionamidoisonicotinamide;
2-isobutyramido-6-methyl-N-(1-(6-(2,2,3,3,3-pentafluoropropoxy)pyridin-3-yl)ethyl)isonicotinamide;
2-(cyclopropanecarboxamido)-N-(1-(6-(2,2,3,3,3-pentafluoropropoxy)pyridin-3-yl)ethyl)pyrimidine-4-carboxamide;
2-(cyclopropanecarboxamido)-6-methyl-N-(1-(6-(2,2,3,3,3-pentafluoropropoxy)pyridin-3-yl)ethyl)pyrimidine-4-carboxamide;
2-acetamido-N-(4-chloro-3-(trifluoromethyl)benzyl)-6-methylisonicotinamide;
2-acetamido-N-(3,5-bis(trifluoromethyl)benzyl)-6-methylisonicotinamide;
2-isobutyramido-6-methyl-N-(4-((2,2,2-trifluoroethoxy)benzyl)isonicotinamide;
N-(1-(3-chloro-4-(2,2-difluoroethoxy)phenyl)ethyl)-2-(cyclopropanecarboxamido)-6-methylisonicotinamide;
N-(2-chloro-4-(2,2-difluoroethoxy)benzyl)-2-(cyclopropanecarboxamido)pyrimidine-4-carboxamide;
N-(3-(difluoromethoxy)benzyl)-2-propionamidoisonicotinamide;
2-(cyclopropanecarboxamido)-N-(3-(difluoromethoxy)benzyl)isonicotinamide;
2-acetamido-N-(3-(difluoromethoxy)benzyl)-6-methylisonicotinamide;
2-acetamido-N-((5-chloro-6-(2,2-difluoroethoxy)pyridin-3-yl)methyl)isonicotinamide;
N-((5-chloro-6-(2,2-difluoroethoxy)pyridin-3-yl)methyl)-2-(cyclopropanecarboxamido)isonicotinamide;
2-acetamido-N-((5-chloro-6-(2,2-difluoroethoxy)pyridin-3-yl)methyl)-6-methylisonicotinamide;
N-((5-chloro-6-(2,2-difluoroethoxy)pyridin-3-yl)methyl)-2-(cyclopropanecarboxamido)pyrimidine-4-carboxamide;
2-acetamido-N-(2-chloro-5-(trifluoromethyl)benzyl)-6-methylisonicotinamide;
2-acetamido-N-((5-ethyl-6-(2,2,2-trifluoroethoxy)pyridin-3-yl)methyl)isonicotinamide;
N-((5-ethyl-6-(2,2,2-trifluoroethoxy)pyridin-3-yl)methyl)-2-propionamidoisonicotinamide;
2-(cyclopropanecarboxamido)-N-((5-ethyl-6-(2,2,2-trifluoroethoxy)pyridin-3-yl)methyl)isonicotinamide;
N-((5-ethyl-6-(2,2,2-trifluoroethoxy)pyridin-3-yl)methyl)-2-isobutyramidoisonicotinamide;
2-acetamido-N-((5-ethyl-6-(2,2,2-trifluoroethoxy)pyridin-3-yl)methyl)-6-methylisonicotinamide;
N-((5-ethyl-6-(2,2,2-trifluoroethoxy)pyridin-3-yl)methyl)-2-methyl-6-propionamidoisonicotinamide;
N-((5-ethyl-6-(2,2,2-trifluoroethoxy)pyridin-3-yl)methyl)-2-isobutyramido-6-methylisonicotinamide;
N-((5-ethyl-6-(2,2,2-trifluoroethoxy)pyridin-3-yl)methyl)-2-(2-hydroxy-2-methylpropanamido)-6-methylisonicotinamide;
2-(cyclopropanecarboxamido)-N-((5-ethyl-6-(2,2,2-trifluoroethoxy)pyridin-3-yl)methyl)pyrimidine-4-carboxamide;

2-(cyclopropanecarboxamido)-N-((5-ethyl-6-(2,2,2-trifluoroethoxy)pyridin-3-yl)methyl)-6-methylpyrimidine-4-carboxamide;
N-((6-(2,2-difluoropropoxy)pyridin-3-yl)methyl)-2-propionamidoisonicotinamide;
2-acetamido-N-((6-(2,2-difluoropropoxy)pyridin-3-yl)methyl)-6-methylisonicotinamide;
N-((6-(2,2-difluoropropoxy)pyridin-3-yl)methyl)-2-methyl-6-propionamidoisonicotinamide;
N-((6-(2,2-difluoropropoxy)pyridin-3-yl)methyl)-2-isobutyramidoisonicotinamide;
N-((6-(2,2-difluoropropoxy)pyridin-3-yl)methyl)-2-isobutyramido-6-methylisonicotinamide;
2-butyramido-N-((6-(2,2-difluoropropoxy)pyridin-3-yl)methyl)isonicotinamide;
2-acetamido-N-((6-(2,2,2-trifluoroethoxy)-5-(trifluoromethyl)pyridin-3-yl)methyl)isonicotinamide;
2-propionamido-N-((6-(2,2,2-trifluoroethoxy)-5-(trifluoromethyl)pyridin-3-yl)methyl)isonicotinamide;
2-acetamido-6-methyl-N-((6-(2,2,2-trifluoroethoxy)-5-(trifluoromethyl)pyridin-3-yl)methyl)isonicotinamide;
2-acetamido-N-(2-fluoro-3-(trifluoromethyl)benzyl)isonicotinamide;
2-acetamido-N-(2-fluoro-3-(trifluoromethyl)benzyl)-6-methylisonicotinamide;
N-(2-fluoro-3-(trifluoromethyl)benzyl)-2-isobutyramidoisonicotinamide;
2-(cyclopropanecarboxamido)-N-(2-fluoro-3-(trifluoromethyl)benzyl)pyrimidine-4-carboxamide;
2-(cyclopropanecarboxamido)-N-(4-fluoro-3-(trifluoromethyl)benzyl)pyrimidine-4-carboxamide;
2-(cyclopropanecarboxamido)-N-(3-fluoro-5-(trifluoromethyl)benzyl)pyrimidine-4-carboxamide;
N-(4-chloro-3-(trifluoromethyl)benzyl)-2-(cyclopropanecarboxamido)pyrimidine-4-carboxamide;
N-(2-chloro-5-(trifluoromethyl)benzyl)-2-(cyclopropanecarboxamido)pyrimidine-4-carboxamide;
N-(3,5-bis(trifluoromethyl)benzyl)-2-(cyclopropanecarboxamido)pyrimidine-4-carboxamide;
2-acetamido-N-((6-(2,2-difluoroethoxy)-5-methylpyridin-3-yl)methyl)isonicotinamide;
N-((6-(2,2-difluoroethoxy)-5-methylpyridin-3-yl)methyl)-2-propionamidoisonicotinamide;
2-(cyclopropanecarboxamido)-N-((6-(2,2-difluoroethoxy)-5-methylpyridin-3-yl)methyl)isonicotinamide;
N-((6-(2,2-difluoroethoxy)-5-methylpyridin-3-yl)methyl)-2-methyl-6-propionamidoisonicotinamide;
N-((6-(2,2-difluoroethoxy)-5-methylpyridin-3-yl)methyl)-2-isobutyramidoisonicotinamide;
2-acetamido-N-((6-(2,2-difluoroethoxy)-5-methylpyridin-3-yl)methyl)-6-methylisonicotinamide;
N-((6-(2,2-difluoroethoxy)-5-methylpyridin-3-yl)methyl)-2-isobutyramido-6-methylisonicotinamide;
2-(cyclopropanecarboxamido)-N-((6-(2,2-difluoroethoxy)-5-methylpyridin-3-yl)methyl)pyrimidine-4-carboxamide;
2-(cyclopropanecarboxamido)-N-((6-(2,2-difluoroethoxy)-5-methylpyridin-3-yl)methyl)-6-methylpyrimidine-4-carboxamide;
2-acetamido-N-(2-fluoro-3-(trifluoromethoxy)benzyl)isonicotinamide;
N-(2-fluoro-3-(trifluoromethoxy)benzyl)-2-propionamidoisonicotinamide;
2-(cyclopropanecarboxamido)-N-(2-fluoro-3-(trifluoromethoxy)benzyl)isonicotinamide;
N-(2-fluoro-3-(trifluoromethoxy)benzyl)-2-methyl-6-propionamidoisonicotinamide;
N-(2-fluoro-3-(trifluoromethoxy)benzyl)-2-isobutyramidoisonicotinamide;
2-acetamido-N-(2-fluoro-3-(trifluoromethoxy)benzyl)-6-methylisonicotinamide;
N-(2-fluoro-3-(trifluoromethoxy)benzyl)-2-isobutyramido-6-methylisonicotinamide;
2-(cyclopropanecarboxamido)-N-(2-fluoro-3-(trifluoromethoxy)benzyl)pyrimidine-4-carboxamide;
2-(cyclopropanecarboxamido)-N-(2-fluoro-3-(trifluoromethoxy)benzyl)-6-methylpyrimidine-4-carboxamide;
N-(2-fluoro-3-(trifluoromethoxy)benzyl)-2-(2-hydroxy-2-methylpropanamido)-6-methylisonicotinamide;
2-acetamido-N-(4-methoxy-3-(trifluoromethoxy)benzyl)-6-methylisonicotinamide;
2-butyramido-N-((6-(2,2-difluoroethoxy)-5-methylpyridin-3-yl)methyl)isonicotinamide;
2-acetamido-N-(2-chloro-3-(trifluoromethyl)benzyl)isonicotinamide;
2-acetamido-N-(2-chloro-3-(trifluoromethyl)benzyl)-6-methylisonicotinamide;
N-(2-chloro-3-(trifluoromethyl)benzyl)-2-isobutyramidoisonicotinamide;
2-acetamido-N-(4-methyl-3-(trifluoromethyl)benzyl)isonicotinamide;
2-acetamido-N-((5-bromo-6-(2,2,2-trifluoroethoxy)pyridin-3-yl)methyl)isonicotinamide;
2-acetamido-N-((5-phenyl-6-(2,2,2-trifluoroethoxy)pyridin-3-yl)methyl)isonicotinamide;
2-acetamido-N-((5-(2-fluorophenyl)-6-(2,2,2-trifluoroethoxy)pyridin-3-yl)methyl)isonicotinamide;
2-acetamido-N-((5-(o-tolyl)-6-(2,2,2-trifluoroethoxy)pyridin-3-yl)methyl)isonicotinamide;
2-acetamido-N-((5-(3-fluorophenyl)-6-(2,2,2-trifluoroethoxy)pyridin-3-yl)methyl)isonicotinamide;
2-acetamido-N-((5-(m-tolyl)-6-(2,2,2-trifluoroethoxy)pyridin-3-yl)methyl)isonicotinamide;
2-acetamido-N-((5-(4-fluorophenyl)-6-(2,2,2-trifluoroethoxy)pyridin-3-yl)methyl)isonicotinamide;
2-acetamido-N-((5-(thiophen-3-yl)-6-(2,2,2-trifluoroethoxy)pyridin-3-yl)methyl)isonicotinamide;
2-acetamido-N-((5-(furan-2-yl)-6-(2,2,2-trifluoroethoxy)pyridin-3-yl)methyl)isonicotinamide;
2-isobutyramido-N-(4-((2,2,2-trifluoroethyl)benzyl)isonicotinamide;
2-propionamido-N-(4-(trifluoromethoxy)benzyl)isonicotinamide;
2-isobutyramido-N-(4-(trifluoromethoxy)benzyl)isonicotinamide;
2-isobutyramido-6-methyl-N-(4-(trifluoromethoxy)benzyl)isonicotinamide;
2-(cyclopropanecarboxamido)-6-methyl-N-(4-(trifluoromethoxy)benzyl)pyrimidine-4-carboxamide;
2-isobutyramido-6-methyl-N-(1-(4-(trifluoromethoxy)phenyl)ethyl)isonicotinamide;
N-((6-(2,2-difluoroethoxy)-4-methylpyridin-3-yl)methyl)-2-propionamidoisonicotinamide;
2-acetamido-N-((6-(2,2-difluoroethoxy)-4-methylpyridin-3-yl)methyl)-6-methylisonicotinamide;
2-(cyclopropanecarboxamido)-N-(3-methyl-4-(2,2,2-trifluoroethoxy)benzyl)pyrimidine-4-carboxamide;
2-(cyclopropanecarboxamido)-6-methyl-N-(3-methyl-4-(2,2,2-trifluoroethoxy)benzyl)pyrimidine-4-carboxamide;
N-(1-(6-(2,2-difluoropropoxy)pyridin-3-yl)ethyl)-2-propionamidoisonicotinamide;
2-(cyclopropanecarboxamido)-N-(1-(6-(2,2-difluoropropoxy)pyridin-3-yl)ethyl)isonicotinamide;

2-acetamido-N-(1-(6-(2,2-difluoropropoxy)pyridin-3-yl)
ethyl)-6-methylisonicotinamide;
N-(1-(6-(2,2-difluoropropoxy)pyridin-3-yl)ethyl)-2-methyl-
6-propionamidoisonicotinamide;
N-(1-(6-(2,2-difluoropropoxy)pyridin-3-yl)ethyl)-2-isobu-
tyramidoisonicotinamide;
N-(1-(6-(2,2-difluoropropoxy)pyridin-3-yl)ethyl)-2-isobu-
tyramido-6-methylisonicotinamide;
2-butyramido-N-(1-(6-(2,2-difluoropropoxy)pyridin-3-yl)
ethyl)isonicotinamide;
2-acetamido-N-(3-methyl-4-(2,2,2-trifluoroethoxy)benzyl)
isonicotinamide;
N-(3-methyl-4-(2,2,2-trifluoroethoxy)benzyl)-2-propiona-
midoisonicotinamide;
2-(cyclopropanecarboxamido)-N-(3-methyl-4-(2,2,2-trif-
luoroethoxy)benzyl)isonicotinamide;
2-isobutyramido-N-(3-methyl-4-(2,2,2-trifluoroethoxy)ben-
zyl)isonicotinamide;
2-acetamido-6-methyl-N-(3-methyl-4-(2,2,2-trifluoroet-
hoxy)benzyl)isonicotinamide;
2-methyl-N-(3-methyl-4-(2,2,2-trifluoroethoxy)benzyl)-6-
propionamidoisonicotinamide;
2-isobutyramido-6-methyl-N-(3-methyl-4-(2,2,2-trifluoro-
ethoxy)benzyl)isonicotinamide;
2-(2-hydroxy-2-methylpropanamido)-6-methyl-N-(3-me-
thyl-4-(2,2,2-trifluoroethoxy)benzyl)isonicotinamide;
2-acetamido-N-(1-(2-chloro-4-(2,2,2-trifluoroethoxy)phe-
nyl)ethyl)isonicotinamide;
N-(1-(2-chloro-4-(2,2,2-trifluoroethoxy)phenyl)ethyl)-2-
propionamidoisonicotinamide;
N-(1-(2-chloro-4-(2,2,2-trifluoroethoxy)phenyl)ethyl)-2-
(cyclopropanecarboxamido)isonicotinamide;
N-(1-(2-chloro-4-(2,2,2-trifluoroethoxy)phenyl)ethyl)-2-
isobutyramidoisonicotinamide
2-acetamido-N-(1-(2-chloro-4-(2,2,2-trifluoroethoxy)phe-
nyl)ethyl)-6-methylisonicotinamide;
N-(1-(2-chloro-4-(2,2,2-trifluoroethoxy)phenyl)ethyl)-2-
isobutyramido-6-methylisonicotinamide;
N-(1-(2-chloro-4-(2,2,2-trifluoroethoxy)phenyl)ethyl)-2-
(cyclopropanecarboxamido)pyrimidine-4-carboxamide;
N-(1-(2-chloro-4-(2,2,2-trifluoroethoxy)phenyl)ethyl)-2-
(cyclopropanecarboxamido)-6-methylpyrimidine-4-car-
boxamide;
2-acetamido-N-(3-methyl-4-(trifluoromethoxy)benzyl)
isonicotinamide;
N-(3-methyl-4-(trifluoromethoxy)benzyl)-2-propionami-
doisonicotinamide;
2-(cyclopropanecarboxamido)-N-(3-methyl-4-(trifluo-
romethoxy)benzyl)isonicotinamide;
2-isobutyramido-N-(3-methyl-4-(trifluoromethoxy)benzyl)
isonicotinamide;
2-acetamido-6-methyl-N-(3-methyl-4-(trifluoromethoxy)
benzyl)isonicotinamide;
2-isobutyramido-6-methyl-N-(3-methyl-4-(trifluo-
romethoxy)benzyl)isonicotinamide;
2-(cyclopropanecarboxamido)-N-(3-methyl-4-(trifluo-
romethoxy)benzyl)pyrimidine-4-carboxamide;
2-(cyclopropanecarboxamido)-6-methyl-N-(3-methyl-4-
(trifluoromethoxy)benzyl)pyrimidine-4-carboxamide;
2-(2-hydroxy-2-methylpropanamido)-6-methyl-N-(3-me-
thyl-4-(trifluoromethoxy)benzyl)isonicotinamide;
2-acetamido-N-(4-methoxy-3-(trifluoromethyl)benzyl)-6-
methylisonicotinamide;
2-acetamido-N-(2-methyl-3-(trifluoromethyl)benzyl)isoni-
cotinamide;
2-acetamido-6-methyl-N-(2-methyl-3-(trifluoromethyl)ben-
zyl)isonicotinamide;
2-isobutyramido-N-(2-methyl-3-(trifluoromethyl)benzyl)
isonicotinamide;
2-(cyclopropanecarboxamido)-N-(2-methyl-3-(trifluorom-
ethyl)benzyl)pyrimidine-4-carboxamide;
2-acetamido-N-(2-methoxy-3-(trifluoromethyl)benzyl)
isonicotinamide;
2-acetamido-N-(2-methoxy-3-(trifluoromethyl)benzyl)-6-
methylisonicotinamide;
2-isobutyramido-N-(2-methoxy-3-(trifluoromethyl)benzyl)
isonicotinamide;
2-(cyclopropanecarboxamido)-N-(2-methoxy-3-(trifluo-
romethyl)benzyl)pyrimidine-4-carboxamide;
2-(cyclopropanecarboxamido)-6-methyl-N-((6-(2,2,2-trif-
luoroethoxy)pyridin-3-yl)methyl)isonicotinamide;
2-(cyclopropanecarboxamido)-6-methyl-N-(1-(5-methyl-6-
(2,2,2-trifluoroethoxy)pyridin-3-yl)ethyl)isonicotina-
mide;
2-(cyclopropanecarboxamido)-6-methyl-N-((5-methyl-6-(2,
2,2-trifluoroethoxy)pyridin-3-yl)methyl)isonicotinamide;
2-(cyclopropanecarboxamido)-N-((5-ethyl-6-(2,2,2-trifluo-
roethoxy)pyridin-3-yl)methyl)-6-methylisonicotinamide;
N-((5-chloro-6-(2,2-difluoroethoxy)pyridin-3-yl)methyl)-2-
(cyclopropanecarboxamido)-6-methylisonicotinamide;
2-(cyclopropanecarboxamido)-6-methyl-N-((6-(2,2,3,3,3-
pentafluoropropoxy)pyridin-3-yl)methyl)isonicotina-
mide;
2-(cyclopropanecarboxamido)-6-methyl-N-(1-(6-(2,2,3,3-
tetrafluoropropoxy)pyridin-3-yl)ethyl)isonicotinamide;
2-(cyclopropanecarboxamido)-N-((6-(2,2-difluoropropoxy)
pyridin-3-yl)methyl)-6-methylisonicotinamide;
2-(cyclopropanecarboxamido)-6-methyl-N-((6-(2,2,3,3-tet-
rafluoropropoxy)pyridin-3-yl)methyl)isonicotinamide;
2-(cyclopropanecarboxamido)-6-methyl-N-(3-methyl-4-(2,
2,2-trifluoroethoxy)benzyl)isonicotinamide;
N-(1-(5-chloro-6-(2,2,2-trifluoroethoxy)pyridin-3-yl)ethyl)-
2-(cyclopropanecarboxamido)-6-methylisonicotinamide;
2-(cyclopropanecarboxamido)-N-(1-(5-fluoro-6-(2,2,2-trif-
luoroethoxy)pyridin-3-yl)ethyl)-6-methylisonicotina-
mide;
2-(cyclopropanecarboxamido)-N-(1-(5-methoxy-6-(2,2,2-
trifluoroethoxy)pyridin-3-yl)ethyl)-6-methylisonicotina-
mide;
2-(cyclopropanecarboxamido)-6-methyl-N-((2-methyl-6-(2,
2,2-trifluoroethoxy)pyridin-3-yl)methyl)isonicotinamide;
2-(cyclopropanecarboxamido)-6-methyl-N-(3-(trifluo-
romethoxy)benzyl)isonicotinamide;
2-(cyclopropanecarboxamido)-6-methyl-N-(1-(6-(2,2,3,3,3-
pentafluoropropoxy)pyridin-3-yl)ethyl)isonicotinamide;
(R)-2-(cyclopropanecarboxamido)-6-methyl-N-(1-(3-(trif-
luoromethyl)phenyl)ethyl)isonicotinamide;
2-(cyclopropanecarboxamido)-6-methyl-N-(1-(3-(trifluo-
romethoxy)phenyl)ethyl)isonicotinamide;
N-(1-(5-ethoxy-6-(2,2,2-trifluoroethoxy)pyridin-3-yl)
ethyl)-2-propionamidoisonicotinamide;
N-(1-(5-ethoxy-6-(2,2,2-trifluoroethoxy)pyridin-3-yl)
ethyl)-2-isobutyramidoisonicotinamide;
2-acetamido-6-methyl-N-((6-(2,2,2-trifluoroethoxy)pyri-
din-3-yl)methyl)pyrimidine-4-carboxamide;
N-(2-fluoro-5-(trifluoromethyl)benzyl)-6-methyl-2-propi-
onamidopyrimidine-4-carboxamide;
2-acetamido-6-methyl-N-(3-(trifluoromethoxy)benzyl)pyri-
midine-4-carboxamide;
2-acetamido-6-methyl-N-(3-(trifluoromethyl)benzyl)pyri-
midine-4-carboxamide;
2-acetamido-6-methyl-N-(1-(4-(2,2,2-trifluoroethoxy)phe-
nyl)ethyl)pyrimidine-4-carboxamide;

N-(1-(5-(hydroxymethyl)-6-(2,2,2-trifluoroethoxy)pyridin-3-yl)ethyl)-2-isobutyramidoisonicotinamide;
2-acetamido-6-methyl-N-(1-(3-(2,2,2-trifluoroethoxy)phenyl)ethyl)pyrimidine-4-carboxamide;
2-(cyclopropanecarboxamido)-N-(1-(6-(2,2-difluoroethoxy)pyridin-3-yl)ethyl)pyrimidine-4-carboxamide;
2-(cyclopropanecarboxamido)-N-((5-fluoro-2-methoxy-6-(2,2,2-trifluoroethoxy)pyridin-3-yl)methyl)pyrimidine-4-carboxamide;
2-(cyclopropanecarboxamido)-N-((6-(2,2-difluoroethoxy)-5-methylpyridin-3-yl)methyl)-6-methylisonicotinamide;
2-(cyclopropanecarboxamido)-6-methyl-N-(3-(trifluoromethyl)benzyl)isonicotinamide;
2-(1-methylcyclopropanecarboxamido)-N-((6-(2,2,2-trifluoroethoxy)pyridin-3-yl)methyl)isonicotinamide;
N-(1-(5-methyl-6-(2,2,2-trifluoroethoxy)pyridin-3-yl)ethyl)-2-(1-methylcyclopropanecarboxamido)isonicotinamide;
N-((5-methyl-6-(2,2,2-trifluoroethoxy)pyridin-3-yl)methyl)-2-(1-methylcyclopropanecarboxamido)isonicotinamide;
N-(1-(5-chloro-6-(2,2,2-trifluoroethoxy)pyridin-3-yl)ethyl)-2-(1-methylcyclopropanecarboxamido)isonicotinamide;
N-((5-chloro-6-(2,2,2-trifluoroethoxy)pyridin-3-yl)methyl)-2-(1-methylcyclopropanecarboxamido)isonicotinamide;
2-(1-methylcyclopropanecarboxamido)-N-(3-(trifluoromethoxy)benzyl)isonicotinamide;
2-acetamido-N-(1-(4-(2,2-difluoroethoxy)-3-methylphenyl)ethyl)isonicotinamide;
N-(1-(4-(2,2-difluoroethoxy)-3-methylphenyl)ethyl)-2-propionamidoisonicotinamide;
2-(cyclopropanecarboxamido)-N-(1-(4-(2,2-difluoroethoxy)-3-methylphenyl)ethyl)isonicotinamide;
N-(1-(4-(2,2-difluoroethoxy)-3-methylphenyl)ethyl)-2-isobutyramidoisonicotinamide;
2-(cyclopropanecarboxamido)-N-(1-(4-(2,2-difluoroethoxy)-3-methylphenyl)ethyl)pyrimidine-4-carboxamide;
2-acetamido-N-(1-(4-(2,2-difluoroethoxy)-3-methylphenyl)ethyl)-6-methylisonicotinamide;
N-(1-(4-(2,2-difluoroethoxy)-3-methylphenyl)ethyl)-2-isobutyramido-6-methylisonicotinamide;
2-(cyclopropanecarboxamido)-N-(1-(4-(2,2-difluoroethoxy)-3-methylphenyl)ethyl)-6-methylisonicotinamide;
N-(2-methoxy-4-(trifluoromethoxy)benzyl)-2-propionamidoisonicotinamide;
2-(cyclopropanecarboxamido)-N-(2-methoxy-4-(trifluoromethoxy)benzyl)isonicotinamide;
2-isobutyramido-N-(2-methoxy-4-(trifluoromethoxy)benzyl)isonicotinamide;
2-acetamido-N-(2-methoxy-4-(trifluoromethoxy)benzyl)-6-methylisonicotinamide;
2-isobutyramido-N-(2-methoxy-4-(trifluoromethoxy)benzyl)-6-methylisonicotinamide;
2-(cyclopropanecarboxamido)-N-(2-methoxy-4-(trifluoromethoxy)benzyl)pyrimidine-4-carboxamide;
2-(cyclopropanecarboxamido)-N-(2-methoxy-4-(trifluoromethoxy)benzyl)-6-methylpyrimidine-4-carboxamide;
N-(4-fluoro-3-(trifluoromethyl)benzyl)-2-isobutyramido-6-methylisonicotinamide;
N-(3-fluoro-5-(trifluoromethyl)benzyl)-2-isobutyramido-6-methylisonicotinamide;
N-(2-fluoro-3-(trifluoromethyl)benzyl)-2-isobutyramido-6-methylisonicotinamide;
N-(4-chloro-3-(trifluoromethyl)benzyl)-2-isobutyramido-6-methylisonicotinamide;
N-(2-chloro-3-(trifluoromethyl)benzyl)-2-isobutyramido-6-methylisonicotinamide;
2-isobutyramido-6-methyl-N-(2-methyl-3-(trifluoromethyl)benzyl)isonicotinamide;
2-isobutyramido-N-(2-methoxy-3-(trifluoromethyl)benzyl)-6-methylisonicotinamide;
2-isobutyramido-6-methyl-N-(1-(3-(2,2,2-trifluoroethoxy)phenyl)ethyl)isonicotinamide;
N-(3-methoxy-4-(2,2,2-trifluoroethoxy)benzyl)-2-propionamidoisonicotinamide;
2-isobutyramido-N-(3-methoxy-4-(2,2,2-trifluoroethoxy)benzyl)isonicotinamide;
2-acetamido-N-(3-methoxy-4-(2,2,2-trifluoroethoxy)benzyl)-6-methylisonicotinamide;
2-isobutyramido-N-(3-methoxy-4-(2,2,2-trifluoroethoxy)benzyl)-6-methylisonicotinamide;
2-(cyclopropanecarboxamido)-N-(3-methoxy-4-(2,2,2-trifluoroethoxy)benzyl)-6-methylpyrimidine-4-carboxamide;
N-(1-(6-(2,2-difluoroethoxy)-5-ethylpyridin-3-yl)ethyl)-2-propionamidoisonicotinamide;
2-(cyclopropanecarboxamido)-N-(1-(6-(2,2-difluoroethoxy)-5-ethylpyridin-3-yl)ethyl)isonicotinamide;
N-(1-(6-(2,2-difluoroethoxy)-5-ethylpyridin-3-yl)ethyl)-2-isobutyramidoisonicotinamide;
2-(cyclopropanecarboxamido)-N-(1-(6-(2,2-difluoroethoxy)-5-ethylpyridin-3-yl)ethyl)pyrimidine-4-carboxamide;
2-acetamido-N-(1-(6-(2,2-difluoroethoxy)-5-ethylpyridin-3-yl)ethyl)-6-methylisonicotinamide;
2-(cyclopropanecarboxamido)-N-(1-(6-(2,2-difluoroethoxy)-5-ethylpyridin-3-yl)ethyl)-6-methylisonicotinamide;
N-(1-(6-(2,2-difluoroethoxy)-5-ethylpyridin-3-yl)ethyl)-2-isobutyramido-6-methylisonicotinamide;
2-(cyclopropanecarboxamido)-N-(1-(6-(2,2-difluoroethoxy)-5-ethylpyridin-3-yl)ethyl)-6-methylpyrimidine-4-carboxamide;
N-((5-bromo-6-(2,2,2-trifluoroethoxy)pyridin-3-yl)methyl)-2-propionamidoisonicotinamide;
N-((5-bromo-6-(2,2,2-trifluoroethoxy)pyridin-3-yl)methyl)-2-(cyclopropanecarboxamido)isonicotinamide;
N-((5-bromo-6-(2,2,2-trifluoroethoxy)pyridin-3-yl)methyl)-2-isobutyramidoisonicotinamide;
N-((5-bromo-6-(2,2,2-trifluoroethoxy)pyridin-3-yl)methyl)-2-(cyclopropanecarboxamido)pyrimidine-4-carboxamide;
2-acetamido-N-((5-bromo-6-(2,2,2-trifluoroethoxy)pyridin-3-yl)methyl)-6-methylisonicotinamide;
N-((5-bromo-6-(2,2,2-trifluoroethoxy)pyridin-3-yl)methyl)-2-(cyclopropanecarboxamido)-6-methylisonicotinamide;
N-((5-bromo-6-(2,2,2-trifluoroethoxy)pyridin-3-yl)methyl)-2-isobutyramido-6-methylisonicotinamide;
N-((5-bromo-6-(2,2,2-trifluoroethoxy)pyridin-3-yl)methyl)-2-(cyclopropanecarboxamido)-6-methylpyrimidine-4-carboxamide;
2-acetamido-N-(1-(5-methyl-6-(2,2,3,3-tetrafluoropropoxy)pyridin-3-yl)ethyl)isonicotinamide;
2-isobutyramido-N-(1-(5-methyl-6-(2,2,3,3-tetrafluoropropoxy)pyridin-3-yl)ethyl)isonicotinamide;
2-isobutyramido-6-methyl-N-(1-(5-methyl-6-(2,2,3,3-tetrafluoropropoxy)pyridin-3-yl)ethyl)isonicotinamide;
2-(cyclopropanecarboxamido)-N-(1-(5-methyl-6-(2,2,3,3-tetrafluoropropoxy)pyridin-3-yl)ethyl)pyrimidine-4-carboxamide;
2-(cyclopropanecarboxamido)-6-methyl-N-(1-(5-methyl-6-(2,2,3,3-tetrafluoropropoxy)pyridin-3-yl)ethyl)pyrimidine-4-carboxamide;

2-(2-hydroxy-2-methylpropanamido)-6-methyl-N-(1-(5-methyl-6-(2,2,3,3-tetrafluoropropoxy)pyridin-3-yl)ethyl)isonicotinamide;

2-acetamido-N-((6-(2,2-difluoroethoxy)-5-ethylpyridin-3-yl)methyl)isonicotinamide;

N-((6-(2,2-difluoroethoxy)-5-ethylpyridin-3-yl)methyl)-2-isobutyramidoisonicotinamide;

N-((6-(2,2-difluoroethoxy)-5-ethylpyridin-3-yl)methyl)-2-isobutyramido-6-methylisonicotinamide;

2-(cyclopropanecarboxamido)-N-((6-(2,2-difluoroethoxy)-5-ethylpyridin-3-yl)methyl)pyrimidine-4-carboxamide;

2-(cyclopropanecarboxamido)-N-((6-(2,2-difluoroethoxy)-5-ethylpyridin-3-yl)methyl)-6-methylpyrimidine-4-carboxamide;

N-((6-(2,2-difluoroethoxy)-5-ethylpyridin-3-yl)methyl)-2-(2-hydroxy-2-methylpropan amido)-6-methylisonicotinamide;

2-acetamido-N-((5-cyclopropyl-6-(2,2-difluoroethoxy)pyridin-3-yl)methyl)isonicotinamide;

N-((5-cyclopropyl-6-(2,2-difluoroethoxy)pyridin-3-yl)methyl)-2-isobutyramidoisonicotinamide;

N-((5-cyclopropyl-6-(2,2-difluoroethoxy)pyridin-3-yl)methyl)-2-isobutyramido-6-methylisonicotinamide;

2-(cyclopropanecarboxamido)-N-((5-cyclopropyl-6-(2,2-difluoroethoxy)pyridin-3-yl)methyl)pyrimidine-4-carboxamide;

5-chloro-2-propionamido-N-(1-(6-(2,2,2-trifluoroethoxy)pyridin-3-yl)ethyl)isonicotinamide;

5-chloro-2-(cyclopropanecarboxamido)-N-(1-(6-(2,2,2-trifluoroethoxy)pyridin-3-yl)ethyl)isonicotinamide;

2-acetamido-N-((6-(2,2,3,3,3-pentafluoropropoxy)pyridin-3-yl)methyl)isonicotinamide;

2-(cyclopropanecarboxamido)-N-(1-(6-(2,2,3,3-tetrafluoropropoxy)pyridin-3-yl)ethyl)isonicotinamide;

2-propionamido-N-((6-(3,3,3-trifluoropropyl)pyridin-3-yl)methyl)isonicotinamide;

2-acetamido-N-(1-(6-(2,2,3,3,3-pentafluoropropoxy)pyridin-3-yl)ethyl)isonicotinamide N-(1-(5-methyl-6-(2,2,3,3-tetrafluoropropoxy)pyridin-3-yl)ethyl)-2-propionamidoisonicotinamide;

2-(cyclopropanecarboxamido)-N-(1-(5-methyl-6-(2,2,3,3-tetrafluoropropoxy)pyridin-3-yl)ethyl)isonicotinamide;

2-acetamido-6-methyl-N-(1-(5-methyl-6-(2,2,3,3-tetrafluoropropoxy)pyridin-3-yl)ethyl)isonicotinamide;

2-butyramido-N-(1-(5-methyl-6-(2,2,3,3-tetrafluoropropoxy)pyridin-3-yl)ethyl)isonicotinamide;

N-(1-(5-methyl-6-(2,2,3,3-tetrafluoropropoxy)pyridin-3-yl)ethyl)-2-pivalamidoisonicotinamide;

N-((6-(2,2-difluoroethoxy)-5-ethylpyridin-3-yl)methyl)-2-propionamidoisonicotinamide;

2-(cyclopropanecarboxamido)-N-((6-(2,2-difluoroethoxy)-5-ethylpyridin-3-yl)methyl)isonicotinamide;

2-acetamido-N-((6-(2,2-difluoroethoxy)-5-ethylpyridin-3-yl)methyl)-6-methylisonicotinamide;

2-butyramido-N-((6-(2,2-difluoroethoxy)-5-ethylpyridin-3-yl)methyl)isonicotinamide;

N-(1-(5-cyclopropyl-6-(2,2-difluoroethoxy)pyridin-3-yl)ethyl)-2-isobutyramido-6-methylisonicotinamide;

2-(cyclopropanecarboxamido)-N-(1-(5-cyclopropyl-6-(2,2-difluoroethoxy)pyridin-3-yl)ethyl)pyrimidine-4-carboxamide;

2-acetamido-N-(1-(6-(2,2-difluoroethoxy)-5-methylpyridin-3-yl)ethyl)-N,6-dimethylisonicotinamide;

N-(1-(6-(2,2-difluoroethoxy)-5-methylpyridin-3-yl)ethyl)-2-isobutyramido-N,6-dimethylisonicotinamide;

2-(cyclopropanecarboxamido)-N-(1-(6-(2,2-difluoroethoxy)-5-methylpyridin-3-yl)ethyl)-6-methylisonicotinamide;

2-acetamido-N-((5-methyl-6-(2,2,3,3-tetrafluoropropoxy)pyridin-3-yl)methyl)isonicotinamide;

N-((5-methyl-6-(2,2,3,3-tetrafluoropropoxy)pyridin-3-yl)methyl)-2-propionamidoisonicotinamide;

2-isobutyramido-N-((5-methyl-6-(2,2,3,3-tetrafluoropropoxy)pyridin-3-yl)methyl)isonicotinamide;

2-(cyclopropanecarboxamido)-N-((5-methyl-6-(2,2,3,3-tetrafluoropropoxy)pyridin-3-yl)methyl)isonicotinamide;

2-(cyclopropanecarboxamido)-N-((5-methyl-6-(2,2,3,3-tetrafluoropropoxy)pyridin-3-yl)methyl)pyrimidine-4-carboxamide;

2-acetamido-6-methyl-N-((5-methyl-6-(2,2,3,3-tetrafluoropropoxy)pyridin-3-yl)methyl)isonicotinamide;

2-isobutyramido-6-methyl-N-((5-methyl-6-(2,2,3,3-tetrafluoropropoxy)pyridin-3-yl)methyl)isonicotinamide;

2-(cyclopropanecarboxamido)-6-methyl-N-((5-methyl-6-(2,2,3,3-tetrafluoropropoxy)pyridin-3-yl)methyl)isonicotinamide;

2-(cyclopropanecarboxamido)-6-methyl-N-((5-methyl-6-(2,2,3,3-tetrafluoropropoxy)pyridin-3-yl)methyl)pyrimidine-4-carboxamide;

2-(2-cyclopropylacetamido)-6-methyl-N-(1-(6-(2,2,2-trifluoroethoxy)pyridin-3-yl)ethyl)isonicotinamide;

2-(2-cyclopropylacetamido)-6-methyl-N-((6-(2,2,2-trifluoroethoxy)pyridin-3-yl)methyl)isonicotinamide;

2-(2-cyclopropylacetamido)-N-(1-(6-(2,2-difluoroethoxy)-5-methylpyridin-3-yl)ethyl)-6-methylisonicotinamide;

2-(2-cyclopropylacetamido)-N-((6-(2,2-difluoroethoxy)-5-methylpyridin-3-yl)methyl)-6-methylisonicotinamide;

N-(1-(5-chloro-6-(2,2-difluoroethoxy)pyridin-3-yl)ethyl)-2-(2-cyclopropylacetamido)-6-methylisonicotinamide;

2-(2-cyclopropylacetamido)-6-methyl-N-(1-(5-methyl-6-(2,2,2-trifluoroethoxy)pyridin-3-yl)ethyl)isonicotinamide;

2-(2-cyclopropylacetamido)-6-methyl-N-((5-methyl-6-(2,2,2-trifluoroethoxy)pyridin-3-yl)methyl)isonicotinamide;

N-(1-(5-chloro-6-(2,2,2-trifluoroethoxy)pyridin-3-yl)ethyl)-2-(2-cyclopropylacetamido)-6-methylisonicotinamide;

N-((5-chloro-6-(2,2,2-trifluoroethoxy)pyridin-3-yl)methyl)-2-(2-cyclopropylacetamido)-6-methylisonicotinamide;

2-(2-cyclopropylacetamido)-N-(1-(5-fluoro-6-(2,2,2-trifluoroethoxy)pyridin-3-yl)ethyl)-6-methylisonicotinamide;

2-(2-cyclopropylacetamido)-6-methyl-N-((4-methyl-6-(2,2,2-trifluoroethoxy)pyridin-3-yl)methyl)isonicotinamide;

2-(2-cyclopropylacetamido)-6-methyl-N-(1-(6-(3,3,3-trifluoropropoxy)pyridin-3-yl)ethyl)isonicotinamide;

2-(2-cyclopropylacetamido)-N-((2-methoxy-6-(2,2,2-trifluoroethoxy)pyridin-3-yl)methyl)-6-methylisonicotinamide;

2-(2-cyclopropylacetamido)-6-methyl-N-(3-(trifluoromethyl)benzyl)isonicotinamide;

2-(2-cyclopropylacetamido)-6-methyl-N-(3-(trifluoromethoxy)benzyl)isonicotinamide;

N-(3-fluoro-4-(trifluoromethoxy)benzyl)-2-propionamidoisonicotinamide;

N-(3-fluoro-4-(trifluoromethoxy)benzyl)-2-isobutyramidoisonicotinamide;

N-(3-fluoro-4-(trifluoromethoxy)benzyl)-2-isobutyramido-6-methylisonicotinamide;

2-(cyclopropanecarboxamido)-N-(3-fluoro-4-(trifluoromethoxy)benzyl)pyrimidine-4-carboxamide;

2-acetamido-N-(3-chloro-4-(trifluoromethoxy)benzyl)isonicotinamide;

N-(3-chloro-4-(trifluoromethoxy)benzyl)-2-propionamidoisonicotinamide;
N-(3-chloro-4-(trifluoromethoxy)benzyl)-2-(cyclopropanecarboxamido)isonicotinamide;
N-(3-chloro-4-(trifluoromethoxy)benzyl)-2-isobutyramidoisonicotinamide;
2-acetamido-N-(3-chloro-4-(trifluoromethoxy)benzyl)-6-methylisonicotinamide;
N-(3-chloro-4-(trifluoromethoxy)benzyl)-2-isobutyramido-6-methylisonicotinamide;
N-(3-chloro-4-(trifluoromethoxy)benzyl)-2-(cyclopropanecarboxamido)pyrimidine-4-carboxamide;
N-(3-chloro-4-(trifluoromethoxy)benzyl)-2-(cyclopropanecarboxamido)-6-methylpyrimidine-4-carboxamide;
2-(cyclopropanecarboxamido)-N-(2-fluoro-5-(trifluoromethyl)benzyl)-6-methylisonicotinamide;
2-(cyclopropanecarboxamido)-N-(3-fluoro-5-(trifluoromethyl)benzyl)-6-methylisonicotinamide;
2-(cyclopropanecarboxamido)-N-(2-fluoro-3-(trifluoromethyl)benzyl)-6-methylisonicotinamide;
2-(cyclopropanecarboxamido)-N-(4-fluoro-3-(trifluoromethyl)benzyl)isonicotinamide;
2-(cyclopropanecarboxamido)-N-(2-fluoro-3-(trifluoromethyl)benzyl)isonicotinamide;
N-(1-(2-fluoro-5-(trifluoromethyl)phenyl)ethyl)-2-isobutyramido-6-methylisonicotinamide;
2-acetamido-N-(1-(2-fluoro-5-(trifluoromethyl)phenyl)ethyl)-6-methylisonicotinamide;
N-(1-(3-chloro-4-(2,2-difluoroethoxy)phenyl)ethyl)-2-propionamidoisonicotinamide;
N-(1-(3-chloro-4-(2,2-difluoroethoxy)phenyl)ethyl)-2-(cyclopropanecarboxamido)pyrimidine-4-carboxamide;
N-(1-(3-chloro-4-(2,2-difluoroethoxy)phenyl)ethyl)-2-(cyclopropanecarboxamido)-6-methylpyrimidine-4-carboxamide;
(R)-2-(2-cyclopropylacetamido)-6-methyl-N-(1-(3-(trifluoromethyl)phenyl)ethyl)isonicotinamide;
N-(2-chloro-3-(trifluoromethyl)benzyl)-2-(cyclopropanecarboxamido)pyrimidine-4-carboxamide;
2-acetamido-6-methyl-N-(4-methyl-3-(trifluoromethyl)benzyl)isonicotinamide;
2-acetamido-N-(4-(2,2-difluoroethoxy)-3-methylbenzyl)isonicotinamide;
N-(4-(2,2-difluoroethoxy)-3-methylbenzyl)-2-propionamidoisonicotinamide;
2-(cyclopropanecarboxamido)-N-(4-(2,2-difluoroethoxy)-3-methylbenzyl)isonicotinamide;
N-(4-(2,2-difluoroethoxy)-3-methylbenzyl)-2-isobutyramidoisonicotinamide;
2-(cyclopropanecarboxamido)-N-(4-(2,2-difluoroethoxy)-3-methylbenzyl)pyrimidine-4-carboxamide;
2-acetamido-N-(4-(2,2-difluoroethoxy)-3-methylbenzyl)-6-methylisonicotinamide;
N-(4-(2,2-difluoroethoxy)-3-methylbenzyl)-2-isobutyramido-6-methylisonicotinamide;
N-(4-(2,2-difluoroethoxy)-3-methylbenzyl)-2-(2-hydroxy-2-methylpropanamido)-6-methylisonicotinamide;
2-(cyclopropanecarboxamido)-N-(4-(2,2-difluoroethoxy)-3-methylbenzyl)-6-methylpyrimidine-4-carboxamide;
2-acetamido-N-(3-chloro-4-(2,2-difluoroethoxy)benzyl)isonicotinamide;
N-(3-chloro-4-(2,2-difluoroethoxy)benzyl)-2-propionamidoisonicotinamide;
N-(3-chloro-4-(2,2-difluoroethoxy)benzyl)-2-(cyclopropanecarboxamido)isonicotinamide;
N-(3-chloro-4-(2,2-difluoroethoxy)benzyl)-2-isobutyramidoisonicotinamide;
N-(3-chloro-4-(2,2-difluoroethoxy)benzyl)-2-(cyclopropanecarboxamido)pyrimidine-4-carboxamide;
2-acetamido-N-(3-chloro-4-(2,2-difluoroethoxy)benzyl)-6-methylisonicotinamide;
N-(3-chloro-4-(2,2-difluoroethoxy)benzyl)-2-isobutyramido-6-methylisonicotinamide;
N-(3-chloro-4-(2,2-difluoroethoxy)benzyl)-2-(cyclopropanecarboxamido)-6-methylpyrimidine-4-carboxamide;
2-(cyclopropanecarboxamido)-N-(4-(2,2-difluoroethoxy)-2-methylbenzyl)isonicotinamide;
N-(4-(2,2-difluoroethoxy)-2-methylbenzyl)-2-isobutyramidoisonicotinamide;
2-acetamido-N-(4-(2,2-difluoroethoxy)-2-methylbenzyl)-6-methylisonicotinamide;
N-(4-(2,2-difluoroethoxy)-2-methylbenzyl)-2-isobutyramido-6-methylisonicotinamide;
2-acetamido-6-methyl-N-(1-(3-(2,2,2-trifluoroethoxy)phenyl)ethyl)isonicotinamide;
N-(4-fluoro-3-(trifluoromethyl)benzyl)-2-propionamidoisonicotinamide;
N-(3-fluoro-5-(trifluoromethyl)benzyl)-2-propionamidoisonicotinamide;
N-(2-fluoro-3-(trifluoromethyl)benzyl)-2-propionamidoisonicotinamide;
N-(4-chloro-3-(trifluoromethyl)benzyl)-2-propionamidoisonicotinamide;
N-(2-chloro-3-(trifluoromethyl)benzyl)-2-propionamidoisonicotinamide;
N-(3,5-bis(trifluoromethyl)benzyl)-2-propionamidoisonicotinamide;
N-(2-methyl-3-(trifluoromethyl)benzyl)-2-propionamidoisonicotinamide;
N-(2-methoxy-3-(trifluoromethyl)benzyl)-2-propionamidoisonicotinamide;
N-(4-methyl-3-(trifluoromethyl)benzyl)-2-propionamidoisonicotinamide;
2-(cyclopropanecarboxamido)-N-(4-fluoro-3-(trifluoromethyl)benzyl)-6-methylpyrimidine-4-carboxamide;
2-(cyclopropanecarboxamido)-N-(3-fluoro-5-(trifluoromethyl)benzyl)-6-methylpyrimidine-4-carboxamide;
2-(cyclopropanecarboxamido)-N-(2-fluoro-3-(trifluoromethyl)benzyl)-6-methylpyrimidine-4-carboxamide;
N-(4-chloro-3-(trifluoromethyl)benzyl)-2-(cyclopropanecarboxamido)-6-methylpyrimidine-4-carboxamide;
N-(2-chloro-3-(trifluoromethyl)benzyl)-2-(cyclopropanecarboxamido)-6-methylpyrimidine-4-carboxamide;
N-(3,5-bis(trifluoromethyl)benzyl)-2-(cyclopropanecarboxamido)-6-methylpyrimidine-4-carboxamide;
2-(cyclopropanecarboxamido)-6-methyl-N-(2-methyl-3-(trifluoromethyl)benzyl)pyrimidine-4-carboxamide;
2-(cyclopropanecarboxamido)-N-(2-methoxy-3-(trifluoromethyl)benzyl)-6-methylpyrimidine-4-carboxamide;
2-(cyclopropanecarboxamido)-6-methyl-N-(4-methyl-3-(trifluoromethyl)benzyl)pyrimidine-4-carboxamide;
2-(cyclopropanecarboxamido)-N-(4-methoxy-3-(trifluoromethyl)benzyl)-6-methylpyrimidine-4-carboxamide;
2-acetamido-N-(1-(3-((trifluoromethyl)thio)phenyl)ethyl)isonicotinamide;
2-isobutyramido-N-(1-(3-((trifluoromethyl)thio)phenyl)ethyl)isonicotinamide;
2-acetamido-6-methyl-N-(1-(3-((trifluoromethyl)thio)phenyl)ethyl)isonicotinamide;
2-isobutyramido-6-methyl-N-(1-(3-((trifluoromethyl)thio)phenyl)ethyl)isonicotinamide;
2-(cyclopropanecarboxamido)-N-(1-(3-((trifluoromethyl)thio)phenyl)ethyl)pyrimidine-4-carboxamide;

N-(4-(2,2-difluoroethoxy)-3-fluorobenzyl)-2-propionamidoisonicotinamide;
2-(cyclopropanecarboxamido)-N-(4-(2,2-difluoroethoxy)-3-fluorobenzyl)isonicotinamide;
N-(4-(2,2-difluoroethoxy)-3-fluorobenzyl)-2-isobutyramido-6-methylisonicotinamide;
2-butyramido-N-(4-(2,2-difluoroethoxy)-3-fluorobenzyl)isonicotinamide;
2-(cyclopropanecarboxamido)-N-(4-(2,2-difluoroethoxy)-3-fluorobenzyl)-6-methylpyrimidine-4-carboxamide;
2-acetamido-N-(1-(3-chloro-5-(trifluoromethoxy)phenyl)ethyl)isonicotinamide;
N-(1-(3-chloro-5-(trifluoromethoxy)phenyl)ethyl)-2-isobutyramidoisonicotinamide;
N-(1-(3-chloro-5-(trifluoromethoxy)phenyl)ethyl)-2-isobutyramido-6-methylisonicotinamide;
2-acetamido-N-(1-(3-chloro-5-(trifluoromethoxy)phenyl)ethyl)-6-methylisonicotinamide;
N-(1-(3-chloro-5-(trifluoromethoxy)phenyl)ethyl)-2-(cyclopropanecarboxamido)pyrimidine-4-carboxamide;
2-(cyclopropanecarboxamido)-N-(1-(4-fluoro-3-(2,2,2-trifluoroethoxy)phenyl)ethyl)-6-methylpyrimidine-4-carboxamide;
N-(2-chloro-4-(2,2-difluoroethoxy)benzyl)-2-propionamidoisonicotinamide;
N-(2-chloro-4-(2,2-difluoroethoxy)benzyl)-2-(cyclopropanecarboxamido)isonicotinamide;
N-(2-chloro-4-(2,2-difluoroethoxy)benzyl)-2-isobutyramidoisonicotinamide;
2-acetamido-N-(2-chloro-4-(2,2-difluoroethoxy)benzyl)-6-methylisonicotinamide;
N-(2-chloro-4-(2,2-difluoroethoxy)benzyl)-2-isobutyramido-6-methylisonicotinamide;
N-(2-chloro-4-(2,2-difluoroethoxy)benzyl)-2-(cyclopropanecarboxamido)-6-methylpyrimidine-4-carboxamide;
N-(1-(4-(2,2-difluoroethoxy)-3-fluorophenyl)ethyl)-2-isobutyramido-6-methylisonicotinamide;
N-(1-(2-fluoro-3-(trifluoromethyl)phenyl)ethyl)-2-isobutyramido-6-methylisonicotinamide;
2-(cyclopropanecarboxamido)-N-(4-(trifluoromethoxy)benzyl)isonicotinamide;
2-methyl-6-propionamido-N-(4-(trifluoromethoxy)benzyl)isonicotinamide;
2-acetamido-6-methyl-N-(4-(trifluoromethoxy)benzyl)isonicotinamide;
(R)-2-acetamido-6-methyl-N-(1-(4-(trifluoromethoxy)phenyl)ethyl)isonicotinamide;
(R)-2-(cyclopropanecarboxamido)-N-(1-(4-(trifluoromethoxy)phenyl)ethyl)pyrimidine-4-carboxamide;
(R)-2-(cyclopropanecarboxamido)-6-methyl-N-(1-(4-(trifluoromethoxy)phenyl)ethyl)pyrimidine-4-carboxamide;
(R)-2-isobutyramido-N-(1-(4-(trifluoromethoxy)phenyl)ethyl)isonicotinamide;
N-((6-(2,2-difluoroethoxy)-4-methylpyridin-3-yl)methyl)-2-isobutyramidoisonicotinamide;
2-(cyclopropanecarboxamido)-N-(1-(6-(2,2-difluoropropoxy)pyridin-3-yl)ethyl)pyrimidine-4-carboxamide;
2-(cyclopropanecarboxamido)-N-(4-methoxy-3-(trifluoromethyl)benzyl)pyrimidine-4-carboxamide;
N-(1-(5-chloro-6-(2,2-difluoroethoxy)pyridin-3-yl)ethyl)-2-(cyclopropanecarboxamido)-6-methylisonicotinamide;
2-(cyclopropanecarboxamido)-N-(1-(6-(2,2-difluoropropoxy)pyridin-3-yl)ethyl)-6-methylisonicotinamide;
2-(cyclopropanecarboxamido)-N-((5-fluoro-6-(2,2,2-trifluoroethoxy)pyridin-3-yl)methyl)-6-methylisonicotinamide;
2-(cyclopropanecarboxamido)-6-methyl-N-((6-(3,3,3-trifluoropropyl)pyridin-3-yl)methyl)isonicotinamide;
2-(cyclopropanecarboxamido)-6-methyl-N-(1-(6-(3,3,3-trifluoropropoxy)pyridin-3-yl)ethyl)isonicotinamide;
2-(1-methylcyclopropanecarboxamido)-N-(1-(6-(2,2,2-trifluoroethoxy)pyridin-3-yl)ethyl)isonicotinamide;
N-((6-(2,2-difluoroethoxy)-5-methylpyridin-3-yl)methyl)-2-(1-methylcyclopropanecarboxamido)isonicotinamide;
2-(1-methylcyclopropanecarboxamido)-N-(1-(6-(3,3,3-trifluoropropoxy)pyridin-3-yl)ethyl)isonicotinamide;
2-(1-methylcyclopropanecarboxamido)-N-((6-(3,3,3-trifluoropropoxy)pyridin-3-yl)methyl)isonicotinamide;
N-((4-methyl-6-(2,2,2-trifluoroethoxy)pyridin-3-yl)methyl)-2-(1-methylcyclopropanecarboxamido)isonicotinamide;
N-((2-methoxy-6-(2,2,2-trifluoroethoxy)pyridin-3-yl)methyl)-2-(1-methylcyclopropanecarboxamido)isonicotinamide;
2-(1-methylcyclopropanecarboxamido)-N-(3-(trifluoromethyl)benzyl)isonicotinamide;
2-(cyclopropanecarboxamido)-N-(1-(4-(2,2-difluoroethoxy)-3-methylphenyl)ethyl)-6-methylpyrimidine-4-carboxamide;
2-acetamido-N-(2-methoxy-4-(trifluoromethoxy)benzyl)isonicotinamide;
N-(2-chloro-5-(trifluoromethyl)benzyl)-2-isobutyramido-6-methylisonicotinamide;
2-acetamido-N-(3-methoxy-4-(2,2,2-trifluoroethoxy)benzyl)isonicotinamide;
2-(cyclopropanecarboxamido)-N-((5-cyclopropyl-6-(2,2-difluoroethoxy)pyridin-3-yl)methyl)-6-methylpyrimidine-4-carboxamide;
N-((5-cyclopropyl-6-(2,2-difluoroethoxy)pyridin-3-yl)methyl)-2-(2-hydroxy-2-methyl propanamido)-6-methylisonicotinamide;
N-((5-cyclopropyl-6-(2,2-difluoroethoxy)pyridin-3-yl)methyl)-2-propionamidoisonicotinamide;
2-acetamido-N-((5-cyclopropyl-6-(2,2-difluoroethoxy)pyridin-3-yl)methyl)-6-methylisonicotinamide;
2-acetamido-N-(1-(5-cyclopropyl-6-(2,2-difluoroethoxy)pyridin-3-yl)ethyl)-6-methylisonicotinamide;
N-(1-(5-cyclopropyl-6-(2,2-difluoroethoxy)pyridin-3-yl)ethyl)-2-isobutyramidoisonicotinamide;
2-(cyclopropanecarboxamido)-N-(1-(5-cyclopropyl-6-(2,2-difluoroethoxy)pyridin-3-yl)ethyl)-6-methylpyrimidine-4-carboxamide;
N-((6-(2,2-difluoroethoxy)-5-isopropylpyridin-3-yl)methyl)-2-isobutyramidoisonicotinamide;
N-((6-(2,2-difluoroethoxy)-5-isopropylpyridin-3-yl)methyl)-2-isobutyramido-6-methylisonicotinamide;
2-(cyclopropanecarboxamido)-N-((6-(2,2-difluoroethoxy)-5-isopropylpyridin-3-yl)methyl)pyrimidine-4-carboxamide;
2-(cyclopropanecarboxamido)-N-((6-(2,2-difluoroethoxy)-5-isopropylpyridin-3-yl)methyl)-6-methylpyrimidine-4-carboxamide;
2-(cyclopropanecarboxamido)-N-(1-(6-(2,2-difluoroethoxy)-5-methylpyridin-3-yl)ethyl)-N,6-dimethylpyrimidine-4-carboxamide;
N-((5-chloro-6-(2,2-difluoroethoxy)pyridin-3-yl)methyl)-2-(2-cyclopropylacetamido)-6-methylisonicotinamide;
2-(2-cyclopropylacetamido)-6-methyl-N-((6-(3,3,3-trifluoropropoxy)pyridin-3-yl)methyl)isonicotinamide;
2-(cyclopropanecarboxamido)-N-(3-fluoro-4-(trifluoromethoxy)benzyl)isonicotinamide;
2-acetamido-N-(3-fluoro-4-(trifluoromethoxy)benzyl)-6-methylisonicotinamide;

2-(cyclopropanecarboxamido)-N-(3-fluoro-4-(trifluoromethoxy)benzyl)-6-methylpyrimidine-4-carboxamide;
2-acetamido-N-(1-(2-fluoro-5-(trifluoromethyl)phenyl)ethyl)isonicotinamide;
N-(1-(2-fluoro-5-(trifluoromethyl)phenyl)ethyl)-2-isobutyramidoisonicotinamide;
2-acetamido-N-(1-(3-chloro-4-(2,2-difluoroethoxy)phenyl)ethyl)isonicotinamide;
N-(1-(3-chloro-4-(2,2-difluoroethoxy)phenyl)ethyl)-2-isobutyramidoisonicotinamide;
2-acetamido-N-(1-(3-chloro-4-(2,2-difluoroethoxy)phenyl)ethyl)-6-methylisonicotinamide;
N-(1-(3-chloro-4-(2,2-difluoroethoxy)phenyl)ethyl)-2-isobutyramido-6-methylisonicotinamide;
2-(cyclopropanecarboxamido)-N-(3-methoxy-4-(2,2,2-trifluoroethoxy)benzyl)isonicotinamide;
2-(cyclopropanecarboxamido)-N-(1-(4-(2,2-difluoroethoxy)-2-methylphenyl)ethyl)pyrimidine-4-carboxamide;
N-(1-(4-(2,2-difluoroethoxy)-2-methylphenyl)ethyl)-2-isobutyramido-6-methylisonicotinamide;
2-isobutyramido-N,6-dimethyl-N-(1-(6-(2,2,2-trifluoroethoxy)pyridin-3-yl)ethyl)isonicotinamide;
N-(4-(2,2-difluoroethoxy)-3-methoxybenzyl)-2-propionamidoisonicotinamide;
N-(4-(2,2-difluoroethoxy)-3-methoxybenzyl)-2-isobutyramido-6-methylisonicotinamide;
2-(cyclopropanecarboxamido)-N-(1-(6-(2,2-difluoroethoxy)-5-methoxypyridin-3-yl)ethyl)isonicotinamide;
2-acetamido-N-(1-(6-(2,2-difluoroethoxy)-5-methoxypyridin-3-yl)ethyl)-6-methylisonicotinamide;
N-(1-(6-(2,2-difluoroethoxy)-5-methoxypyridin-3-yl)ethyl)-2-isobutyramido-6-methylisonicotinamide;
2-acetamido-N-(1-(4-(2,2-difluoroethoxy)-3-methoxyphenyl)ethyl)-6-methylisonicotinamide;
N-(1-(4-(2,2-difluoroethoxy)-3-methoxyphenyl)ethyl)-2-isobutyramidoisonicotinamide;
N-(1-(4-(2,2-difluoroethoxy)-3-methoxyphenyl)ethyl)-2-isobutyramido-6-methylisonicotinamide;
2-(cyclopropanecarboxamido)-N-(1-(2-fluoro-4-(trifluoromethyl)phenyl)ethyl)pyrimidine-4-carboxamide;
2-acetamido-N-(1-(2-chloro-4-(2,2-difluoroethoxy)phenyl)ethyl)isonicotinamide;
N-(1-(2-chloro-4-(2,2-difluoroethoxy)phenyl)ethyl)-2-propionamidoisonicotinamide;
N-(1-(2-chloro-4-(2,2-difluoroethoxy)phenyl)ethyl)-2-(cyclopropanecarboxamido)isonicotinamide;
N-(1-(2-chloro-4-(2,2-difluoroethoxy)phenyl)ethyl)-2-isobutyramidoisonicotinamide;
N-(1-(2-chloro-4-(2,2-difluoroethoxy)phenyl)ethyl)-2-(cyclopropanecarboxamido)pyrimidine-4-carboxamide;
N-(1-(2-chloro-4-(2,2-difluoroethoxy)phenyl)ethyl)-2-isobutyramido-6-methylisonicotinamide;
N-(1-(2-chloro-4-(2,2-difluoroethoxy)phenyl)ethyl)-2-(cyclopropanecarboxamido)-6-methylpyrimidine-4-carboxamide;
N-(1-(4-(2,2-difluoroethoxy)-3,5-difluorophenyl)ethyl)-2-propionamidoisonicotinamide;
2-(cyclopropanecarboxamido)-N-(1-(4-(2,2-difluoroethoxy)-3,5-difluorophenyl)ethyl)isonicotinamide;
N-(1-(4-(2,2-difluoroethoxy)-3,5-difluorophenyl)ethyl)-2-isobutyramido-6-methylisonicotinamide;
2-acetamido-N-(3-(2,2-difluoroethoxy)-2-methylbenzyl)isonicotinamide;
N-(3-(2,2-difluoroethoxy)-2-methylbenzyl)-2-propionamidoisonicotinamide;
2-(cyclopropanecarboxamido)-N-(3-(2,2-difluoroethoxy)-2-methylbenzyl)isonicotinamide;
N-(3-(2,2-difluoroethoxy)-2-methylbenzyl)-2-isobutyramidoisonicotinamide;
2-(cyclopropanecarboxamido)-N-(3-(2,2-difluoroethoxy)-2-methylbenzyl)pyrimidine-4-carboxamide;
2-acetamido-N-(3-(2,2-difluoroethoxy)-2-methylbenzyl)-6-methylisonicotinamide;
N-(3-(2,2-difluoroethoxy)-2-methylbenzyl)-2-isobutyramido-6-methylisonicotinamide;
N-(3-(2,2-difluoroethoxy)-2-methylbenzyl)-2-(2-hydroxy-2-methylpropanamido)-6-methylisonicotinamide;
2-(cyclopropanecarboxamido)-N-(3-(2,2-difluoroethoxy)-2-methylbenzyl)-6-methylpyrimidine-4-carboxamide;
N-((6-(2,2-difluoroethoxy)-2-methylpyridin-3-yl)methyl)-2-propionamidoisonicotinamide;
2-(cyclopropanecarboxamido)-N-((6-(2,2-difluoroethoxy)-2-methylpyridin-3-yl)methyl)isonicotinamide;
N-((6-(2,2-difluoroethoxy)-2-methylpyridin-3-yl)methyl)-2-isobutyramidoisonicotinamide;
2-acetamido-N-((6-(2,2-difluoroethoxy)-2-methylpyridin-3-yl)methyl)-6-methylisonicotinamide;
2-(cyclopropanecarboxamido)-N-((6-(2,2-difluoroethoxy)-2-methylpyridin-3-yl)methyl)-6-methylisonicotinamide;
N-((6-(2,2-difluoroethoxy)-2-methylpyridin-3-yl)methyl)-2-isobutyramido-6-methylisonicotinamide;
2-(cyclopropanecarboxamido)-N-((6-(2,2-difluoroethoxy)-2-methylpyridin-3-yl)methyl)-6-methylpyrimidine-4-carboxamide;
2-acetamido-N-(1-(5-(2,2-difluoroethoxy)-2-methylphenyl)ethyl)isonicotinamide;
2-acetamido-N-(1-(5-(2,2-difluoroethoxy)-2-methylphenyl)ethyl)-6-methylisonicotinamide;
2-(cyclopropanecarboxamido)-N-(1-(5-(2,2-difluoroethoxy)-2-methylphenyl)ethyl)pyrimidine-4-carboxamide;
2-(cyclopropanecarboxamido)-N-(1-(5-(2,2-difluoroethoxy)-2-methylphenyl)ethyl)-6-methylpyrimidine-4-carboxamide;
2-(cyclopropanecarboxamido)-N-(1-(3-(2,2-difluoroethoxy)-4-methylphenyl)ethyl)pyrimidine-4-carboxamide;
2-(cyclopropanecarboxamido)-N-(4-(2,2-difluoroethoxy)-3-methoxybenzyl)isonicotinamide;
N-((5-chloro-6-(2,2,2-trifluoroethoxy)pyridin-3-yl)methyl)-2-(cyclopropanecarboxamido)-6-methylpyrimidine-4-carboxamide;
2-(2-hydroxy-2-methylpropanamido)-N-(2-methoxy-3-(trifluoromethyl)benzyl)-6-methylisonicotinamide;
2-(2-hydroxy-2-methylpropanamido)-6-methyl-N-((5-methyl-6-(2,2,3,3-tetrafluoropropoxy)pyridin-3-yl)methyl)isonicotinamide;
2-(cyclopropanecarboxamido)-N,6-dimethyl-N-((6-(2,2,2-trifluoroethoxy)pyridin-3-yl)methyl)isonicotinamide;
2-acetamido-N-((6-(2,2-difluoroethoxy)-2-methoxypyridin-3-yl)methyl)isonicotinamide;
N-((6-(2,2-difluoroethoxy)-2-methoxypyridin-3-yl)methyl)-2-propionamidoisonicotinamide;
2-(cyclopropanecarboxamido)-N-((6-(2,2-difluoroethoxy)-2-methoxypyridin-3-yl)methyl)isonicotinamide;
N-((6-(2,2-difluoroethoxy)-2-methoxypyridin-3-yl)methyl)-2-isobutyramidoisonicotinamide;
2-(cyclopropanecarboxamido)-N-((6-(2,2-difluoroethoxy)-2-methoxypyridin-3-yl)methyl)pyrimidine-4-carboxamide;
2-acetamido-N-((6-(2,2-difluoroethoxy)-2-methoxypyridin-3-yl)methyl)-6-methylisonicotinamide;
N-((6-(2,2-difluoroethoxy)-2-methoxypyridin-3-yl)methyl)-2-isobutyramido-6-methylisonicotinamide;

N-((6-(2,2-difluoroethoxy)-2-methoxypyridin-3-yl)methyl)-2-(2-hydroxy-2-methylpropanamido)-6-methylisonicotinamide;

2-(cyclopropanecarboxamido)-N-((6-(2,2-difluoroethoxy)-2-methoxypyridin-3-yl)methyl)-6-methylpyrimidine-4-carboxamide;

2-acetamido-N-(1-(6-(2,2-difluoroethoxy)-2-methoxypyridin-3-yl)ethyl)isonicotinamide;

N-(1-(6-(2,2-difluoroethoxy)-2-methoxypyridin-3-yl)ethyl)-2-propionamidoisonicotinamide;

2-(cyclopropanecarboxamido)-N-(1-(6-(2,2-difluoroethoxy)-2-methoxypyridin-3-yl)ethyl)isonicotinamide;

N-(1-(6-(2,2-difluoroethoxy)-2-methoxypyridin-3-yl)ethyl)-2-isobutyramidoisonicotinamide;

2-(cyclopropanecarboxamido)-N-(1-(6-(2,2-difluoroethoxy)-2-methoxypyridin-3-yl)ethyl)pyrimidine-4-carboxamide;

2-acetamido-N-(1-(6-(2,2-difluoroethoxy)-2-methoxypyridin-3-yl)ethyl)-6-methylisonicotinamide;

N-(1-(6-(2,2-difluoroethoxy)-2-methoxypyridin-3-yl)ethyl)-2-isobutyramido-6-methylisonicotinamide;

N-(1-(6-(2,2-difluoroethoxy)-2-methoxypyridin-3-yl)ethyl)-2-(2-hydroxy-2-methylpropanamido)-6-methylisonicotinamide;

2-(cyclopropanecarboxamido)-N-(1-(6-(2,2-difluoroethoxy)-2-methoxypyridin-3-yl)ethyl)-6-methylpyrimidine-4-carboxamide;

N-(1-(6-(2,2,3,3,3-pentafluoropropoxy)pyridin-3-yl)ethyl)-2-propionamidoisonicotinamide;

2-(cyclopropanecarboxamido)-N-((6-(2,2-difluoropropoxy)pyridin-3-yl)methyl)isonicotinamide;

2-(cyclopropanecarboxamido)-N-((6-(2,2-difluoropropoxy)pyridin-3-yl)methyl)pyrimidine-4-carboxamide;

N-((6-(2,2-difluoroethoxy)-5-ethylpyridin-3-yl)methyl)-2-pivalamidoisonicotinamide;

N-(1-(5-cyclopropyl-6-(2,2-difluoroethoxy)pyridin-3-yl)ethyl)-2-propionamidoisonicotinamide;

2-(cyclopropanecarboxamido)-N-(1-(5-cyclopropyl-6-(2,2-difluoroethoxy)pyridin-3-yl)ethyl)isonicotinamide;

N-(1-(3-chloro-4-(2,2-difluoroethoxy)phenyl)ethyl)-2-(cyclopropanecarboxamido)isonicotinamide;

N-(1-(4-(2,2-difluoroethoxy)-2-methylphenyl)ethyl)-2-propionamidoisonicotinamide;

2-(cyclopropanecarboxamido)-N-(1-(4-(2,2-difluoroethoxy)-2-methylphenyl)ethyl)isonicotinamide;

2-(cyclopropanecarboxamido)-N-(4-(2,2-difluoroethoxy)-2-methylbenzyl)-6-methylpyrimidine-4-carboxamide;

2-acetamido-6-methyl-N-(1-(4-(2,2,2-trifluoroethoxy)phenyl)ethyl)isonicotinamide;

N-(4-methoxy-3-(trifluoromethyl)benzyl)-2-propionamidoisonicotinamide;

2-acetamido-N-((6-(2-(trifluoromethoxy)ethoxy)pyridin-3-yl)methyl)isonicotinamide;

2-propionamido-N-((6-(2-(trifluoromethoxy)ethoxy)pyridin-3-yl)methyl)isonicotinamide;

2-(cyclopropanecarboxamido)-N-((6-(2-(trifluoromethoxy)ethoxy)pyridin-3-yl)methyl)isonicotinamide;

2-isobutyramido-N-((6-(2-(trifluoromethoxy)ethoxy)pyridin-3-yl)methyl)isonicotinamide;

2-acetamido-6-methyl-N-((6-(2-(trifluoromethoxy)ethoxy)pyridin-3-yl)methyl)isonicotinamide;

2-isobutyramido-6-methyl-N-((6-(2-(trifluoromethoxy)ethoxy)pyridin-3-yl)methyl)isonicotinamide;

2-(2-hydroxy-2-methylpropanamido)-6-methyl-N-((6-(2-(trifluoromethoxy)ethoxy)pyridin-3-yl)methyl)isonicotinamide;

2-(cyclopropanecarboxamido)-N-((6-(2-(trifluoromethoxy)ethoxy)pyridin-3-yl)methyl)pyrimidine-4-carboxamide;

2-acetamido-N-(1-(3-(2,2-difluoroethoxy)-5-methylphenyl)ethyl)isonicotinamide;

N-(1-(3-(2,2-difluoroethoxy)-5-methylphenyl)ethyl)-2-propionamidoisonicotinamide;

2-(cyclopropanecarboxamido)-N-(1-(3-(2,2-difluoroethoxy)-5-methylphenyl)ethyl)isonicotinamide;

N-(1-(3-(2,2-difluoroethoxy)-5-methylphenyl)ethyl)-2-isobutyramidoisonicotinamide;

2-acetamido-N-(1-(3-(2,2-difluoroethoxy)-5-methylphenyl)ethyl)-6-methylisonicotinamide;

N-(1-(3-(2,2-difluoroethoxy)-5-methylphenyl)ethyl)-2-isobutyramido-6-methylisonicotinamide;

N-(1-(3-(2,2-difluoroethoxy)-5-methylphenyl)ethyl)-2-(2-hydroxy-2-methylpropanamido)-6-methylisonicotinamide;

2-(cyclopropanecarboxamido)-N-(1-(3-(2,2-difluoroethoxy)-5-methylphenyl)ethyl)pyrimidine-4-carboxamide;

2-(cyclopropanecarboxamido)-N-(1-(3-(2,2-difluoroethoxy)-5-methylphenyl)ethyl)-6-methylpyrimidine-4-carboxamide;

2-acetamido-N-(3-(2,2-difluoroethoxy)-5-methylbenzyl)isonicotinamide;

N-(3-(2,2-difluoroethoxy)-5-methylbenzyl)-2-propionamidoisonicotinamide;

2-(cyclopropanecarboxamido)-N-(3-(2,2-difluoroethoxy)-5-methylbenzyl)isonicotinamide;

N-(3-(2,2-difluoroethoxy)-5-methylbenzyl)-2-isobutyramidoisonicotinamide;

2-acetamido-N-(3-(2,2-difluoroethoxy)-5-methylbenzyl)-6-methylisonicotinamide;

N-(3-(2,2-difluoroethoxy)-5-methylbenzyl)-2-isobutyramido-6-methylisonicotinamide;

N-(3-(2,2-difluoroethoxy)-5-methylbenzyl)-2-(2-hydroxy-2-methylpropanamido)-6-methylisonicotinamide;

2-(cyclopropanecarboxamido)-N-(3-(2,2-difluoroethoxy)-5-methylbenzyl)pyrimidine-4-carboxamide;

2-(cyclopropanecarboxamido)-N-(3-(2,2-difluoroethoxy)-5-methylbenzyl)-6-methylpyrimidine-4-carboxamide;

2-acetamido-N-(1-(3-chloro-4-(2,2-difluoroethoxy)-5-methylphenyl)ethyl)isonicotinamide;

N-(1-(3-chloro-4-(2,2-difluoroethoxy)-5-methylphenyl)ethyl)-2-propionamidoisonicotinamide;

N-(1-(3-chloro-4-(2,2-difluoroethoxy)-5-methylphenyl)ethyl)-2-(cyclopropanecarboxamido)isonicotinamide;

N-(1-(3-chloro-4-(2,2-difluoroethoxy)-5-methylphenyl)ethyl)-2-isobutyramidoisonicotinamide;

2-acetamido-N-(1-(3-chloro-4-(2,2-difluoroethoxy)-5-methylphenyl)ethyl)-6-methylisonicotinamide;

N-(1-(3-chloro-4-(2,2-difluoroethoxy)-5-methylphenyl)ethyl)-2-isobutyramido-6-methylisonicotinamide;

N-(1-(3-chloro-4-(2,2-difluoroethoxy)-5-methylphenyl)ethyl)-2-(2-hydroxy-2-methylpropanamido)-6-methylisonicotinamide;

N-(1-(3-chloro-4-(2,2-difluoroethoxy)-5-methylphenyl)ethyl)-2-(cyclopropanecarboxamido)pyrimidine-4-carboxamide;

N-(1-(3-chloro-4-(2,2-difluoroethoxy)-5-methylphenyl)ethyl)-2-(cyclopropanecarboxamido)-6-methylpyrimidine-4-carboxamide;

2-acetamido-N-(1-(4-(2,2-difluoroethoxy)-3,5-dimethylphenyl)ethyl)isonicotinamide;

N-(1-(4-(2,2-difluoroethoxy)-3,5-dimethylphenyl)ethyl)-2-propionamidoisonicotinamide;

2-(cyclopropanecarboxamido)-N-(1-(4-(2,2-difluoroethoxy)-3,5-dimethylphenyl)ethyl)isonicotinamide;

N-(1-(4-(2,2-difluoroethoxy)-3,5-dimethylphenyl)ethyl)-2-isobutyramidoisonicotinamide;
2-acetamido-N-(1-(4-(2,2-difluoroethoxy)-3,5-dimethylphenyl)ethyl)-6-methylisonicotinamide;
N-(1-(4-(2,2-difluoroethoxy)-3,5-dimethylphenyl)ethyl)-2-isobutyramido-6-methylisonicotinamide;
N-(1-(4-(2,2-difluoroethoxy)-3,5-dimethylphenyl)ethyl)-2-(2-hydroxy-2-methylpropan amido)-6-methylisonicotinamide;
2-(cyclopropanecarboxamido)-N-(1-(4-(2,2-difluoroethoxy)-3,5-dimethylphenyl)ethyl)pyrimidine-4-carboxamide;
2-(cyclopropanecarboxamido)-N-(1-(4-(2,2-difluoroethoxy)-3,5-dimethylphenyl)ethyl)-6-methylpyrimidine-4-carboxamide;
2-acetamido-N-(4-(2,2-difluoroethoxy)-3,5-dimethylbenzyl)isonicotinamide;
N-(4-(2,2-difluoroethoxy)-3,5-dimethylbenzyl)-2-propionamidoisonicotinamide;
2-(cyclopropanecarboxamido)-N-(4-(2,2-difluoroethoxy)-3,5-dimethylbenzyl)isonicotinamide;
N-(4-(2,2-difluoroethoxy)-3,5-dimethylbenzyl)-2-isobutyramidoisonicotinamide;
2-acetamido-N-(4-(2,2-difluoroethoxy)-3,5-dimethylbenzyl)-6-methylisonicotinamide;
N-(4-(2,2-difluoroethoxy)-3,5-dimethylbenzyl)-2-isobutyramido-6-methylisonicotinamide;
N-(4-(2,2-difluoroethoxy)-3,5-dimethylbenzyl)-2-(2-hydroxy-2-methylpropanamido)-6-methylisonicotinamide;
2-(cyclopropanecarboxamido)-N-(4-(2,2-difluoroethoxy)-3,5-dimethylbenzyl)pyrimidine-4-carboxamide;
2-(cyclopropanecarboxamido)-N-(4-(2,2-difluoroethoxy)-3,5-dimethylbenzyl)-6-methylpyrimidine-4-carboxamide;
2-acetamido-N-(1-(4-(1,1,2,2-tetrafluoroethoxy)phenyl)ethyl)isonicotinamide;
2-propionamido-N-(1-(4-(1,1,2,2-tetrafluoroethoxy)phenyl)ethyl)isonicotinamide;
2-(cyclopropanecarboxamido)-N-(1-(4-(1,1,2,2-tetrafluoroethoxy)phenyl)ethyl)isonicotinamide;
2-isobutyramido-N-(1-(4-(1,1,2,2-tetrafluoroethoxy)phenyl)ethyl)isonicotinamide;
2-acetamido-6-methyl-N-(1-(4-(1,1,2,2-tetrafluoroethoxy)phenyl)ethyl)isonicotinamide;
2-isobutyramido-6-methyl-N-(1-(4-(1,1,2,2-tetrafluoroethoxy)phenyl)ethyl)isonicotinamide;
2-(2-hydroxy-2-methylpropanamido)-6-methyl-N-(1-(4-(1,1,2,2-tetrafluoroethoxy)phenyl)ethyl)isonicotinamide;
2-(cyclopropanecarboxamido)-N-(1-(4-(1,1,2,2-tetrafluoroethoxy)phenyl)ethyl)pyrimidine-4-carboxamide;
2-(cyclopropanecarboxamido)-6-methyl-N-(1-(4-(1,1,2,2-tetrafluoroethoxy)phenyl)ethyl)pyrimidine-4-carboxamide;
2-acetamido-N-(1-(3-(1,1,2,2-tetrafluoroethoxy)phenyl)ethyl)isonicotinamide;
2-propionamido-N-(1-(3-(1,1,2,2-tetrafluoroethoxy)phenyl)ethyl)isonicotinamide;
2-(cyclopropanecarboxamido)-N-(1-(3-(1,1,2,2-tetrafluoroethoxy)phenyl)ethyl)isonicotinamide;
2-isobutyramido-N-(1-(3-(1,1,2,2-tetrafluoroethoxy)phenyl)ethyl)isonicotinamide;
2-acetamido-6-methyl-N-(1-(3-(1,1,2,2-tetrafluoroethoxy)phenyl)ethyl)isonicotinamide;
2-isobutyramido-6-methyl-N-(1-(3-(1,1,2,2-tetrafluoroethoxy)phenyl)ethyl)isonicotinamide;
2-(2-hydroxy-2-methylpropanamido)-6-methyl-N-(1-(3-(1,1,2,2-tetrafluoroethoxy)phenyl)ethyl)isonicotinamide;
2-(cyclopropanecarboxamido)-N-(1-(3-(1,1,2,2-tetrafluoroethoxy)phenyl)ethyl)pyrimidine-4-carboxamide;
2-(cyclopropanecarboxamido)-6-methyl-N-(1-(3-(1,1,2,2-tetrafluoroethoxy)phenyl)ethyl)pyrimidine-4-carboxamide;
2-acetamido-N-(1-(3-(difluoromethyl)phenyl)ethyl)isonicotinamide;
N-(1-(3-(difluoromethyl)phenyl)ethyl)-2-propionamidoisonicotinamide;
2-(cyclopropanecarboxamido)-N-(1-(3-(difluoromethyl)phenyl)ethyl)isonicotinamide;
N-(1-(3-(difluoromethyl)phenyl)ethyl)-2-isobutyramidoisonicotinamide;
2-acetamido-N-(1-(3-(difluoromethyl)phenyl)ethyl)-6-methylisonicotinamide;
N-(1-(3-(difluoromethyl)phenyl)ethyl)-2-isobutyramido-6-methylisonicotinamide;
N-(1-(3-(difluoromethyl)phenyl)ethyl)-2-(2-hydroxy-2-methylpropanamido)-6-methylisonicotinamide;
2-(cyclopropanecarboxamido)-N-(1-(3-(difluoromethyl)phenyl)ethyl)pyrimidine-4-carboxamide;
2-(cyclopropanecarboxamido)-N-(1-(3-(difluoromethyl)phenyl)ethyl)-6-methylpyrimidine-4-carboxamide;
2-acetamido-N-(1-(4-(perfluoroethoxy)phenyl)ethyl)isonicotinamide;
N-(1-(4-(perfluoroethoxy)phenyl)ethyl)-2-propionamidoisonicotinamide;
2-(cyclopropanecarboxamido)-N-(1-(4-(perfluoroethoxy)phenyl)ethyl)isonicotinamide;
2-isobutyramido-N-(1-(4-(perfluoroethoxy)phenyl)ethyl)isonicotinamide;
2-acetamido-6-methyl-N-(1-(4-(perfluoroethoxy)phenyl)ethyl)isonicotinamide;
2-isobutyramido-6-methyl-N-(1-(4-(perfluoroethoxy)phenyl)ethyl)isonicotinamide;
2-(2-hydroxy-2-methylpropanamido)-6-methyl-N-(1-(4-(perfluoroethoxy)phenyl)ethyl)isonicotinamide;
2-(cyclopropanecarboxamido)-N-(1-(4-(perfluoroethoxy)phenyl)ethyl)pyrimidine-4-carboxamide;
2-(cyclopropanecarboxamido)-6-methyl-N-(1-(4-(perfluoroethoxy)phenyl)ethyl)pyrimidine-4-carboxamide;
(R)-2-acetamido-N-(1-(3-(perfluoroethoxy)phenyl)ethyl)isonicotinamide;
(R)—N-(1-(3-(perfluoroethoxy)phenyl)ethyl)-2-propionamidoisonicotinamide;
(R)-2-(cyclopropanecarboxamido)-N-(1-(3-(perfluoroethoxy)phenyl)ethyl)isonicotinamide;
(R)-2-isobutyramido-N-(1-(3-(perfluoroethoxy)phenyl)ethyl)isonicotinamide;
(R)-2-acetamido-6-methyl-N-(1-(3-(perfluoroethoxy)phenyl)ethyl)isonicotinamide;
(R)-2-isobutyramido-6-methyl-N-(1-(3-(perfluoroethoxy)phenyl)ethyl)isonicotinamide;
(R)-2-(2-hydroxy-2-methylpropanamido)-6-methyl-N-(1-(3-(perfluoroethoxy)phenyl)ethyl)isonicotinamide;
(R)-2-(cyclopropanecarboxamido)-N-(1-(3-(perfluoroethoxy)phenyl)ethyl)pyrimidine-4-carboxamide;
(R)-2-(cyclopropanecarboxamido)-6-methyl-N-(1-(3-(perfluoroethoxy)phenyl)ethyl)pyrimidine-4-carboxamide;
2-butyramido-N-((5-cyclopropyl-6-(2,2-difluoroethoxy)pyridin-3-yl)methyl)isonicotinamide;
2-acetamido-N-(3-fluoro-4-(trifluoromethoxy)benzyl)isonicotinamide;
and
2-(cyclopropanecarboxamido)-N-(4-fluoro-3-(trifluoromethyl)benzyl)-6-methylisonicotinamide;

or a prodrug thereof or a pharmaceutically acceptable salt thereof.

[10] More suitable individual compounds of the invention are:

2-acetamido-N-(1-(6-(2,2,2-trifluoroethoxy)pyridin-3-yl) ethyl)isonicotinamide;
2-isobutyramido-N-(1-(6-(2,2,2-trifluoroethoxy)pyridin-3-yl)ethyl)isonicotinamide;
2-(cyclopropanecarboxamido)-N-(1-(6-(2,2,2-trifluoroethoxy)pyridin-3-yl)ethyl)isonicotinamide;
2-propionamido-N-(1-(6-(2,2,2-trifluoroethoxy)pyridin-3-yl)ethyl)isonicotinamide;
2-acetamido-6-methyl-N-(1-(6-(2,2,2-trifluoroethoxy)pyridin-3-yl)ethyl)isonicotinamide;
2-methyl-6-propionamido-N-(1-(6-(2,2,2-trifluoroethoxy)pyridin-3-yl)ethyl)isonicotinamide;
2-isobutyramido-6-methyl-N-(1-(6-(2,2,2-trifluoroethoxy)pyridin-3-yl)ethyl)isonicotinamide;
2-acetamido-N-(1-(3-(trifluoromethoxy)phenyl)ethyl)isonicotinamide;
N-(1-(5-fluoro-6-(2,2,2-trifluoroethoxy)pyridin-3-yl)ethyl)-2-methyl-6-propionamidoisonicotinamide;
2-methyl-6-propionamido-N-(1-(6-(3,3,3-trifluoropropoxy)pyridin-3-yl)ethyl)isonicotinamide;
2-isobutyramido-N-((6-(2,2,2-trifluoroethoxy)pyridin-3-yl)methyl)isonicotinamide;
2-isobutyramido-N-((4-methyl-6-(2,2,2-trifluoroethoxy)pyridin-3-yl)methyl)isonicotinamide;
2-isobutyramido-N-(1-(6-(3,3,3-trifluoropropoxy)pyridin-3-yl)ethyl)isonicotinamide;
N-(1-(5-fluoro-6-(2,2,2-trifluoroethoxy)pyridin-3-yl)ethyl)-2-isobutyramidoisonicotinamide;
2-acetamido-6-methyl-N-((4-methyl-6-(2,2,2-trifluoroethoxy)pyridin-3-yl)methyl)isonicotinamide;
2-acetamido-N-methyl-N-(1-(5-methyl-6-(2,2,2-trifluoroethoxy)pyridin-3-yl)ethyl)isonicotinamide;
2-isobutyramido-N-(1-(3-(trifluoromethoxy)phenyl)ethyl)isonicotinamide;
2-isobutyramido-6-methyl-N-((6-(2,2,2-trifluoroethoxy)pyridin-3-yl)methyl)isonicotinamide;
N-(1-(5-fluoro-6-(2,2,2-trifluoroethoxy)pyridin-3-yl)ethyl)-2-isobutyramido-6-methylisonicotinamide;
2-isobutyramido-6-methyl-N-(1-(6-(3,3,3-trifluoropropoxy)pyridin-3-yl)ethyl)isonicotinamide;
2-isobutyramido-6-methyl-N-(1-(3-(trifluoromethoxy)phenyl)ethyl)isonicotinamide;
2-isobutyramido-6-methyl-N-((4-methyl-6-(2,2,2-trifluoroethoxy)pyridin-3-yl)methyl)isonicotinamide;
(R)-2-isobutyramido-N-(1-(3-(trifluoromethyl)phenyl) ethyl)isonicotinamide;
(R)-2-isobutyramido-6-methyl-N-(1-(3-(trifluoromethyl) phenyl)ethyl)isonicotinamide;
2-acetamido-N-(1-(6-(2,2-difluoroethoxy)-5-methylpyridin-3-yl)ethyl)isonicotinamide;
N-(1-(6-(2,2-difluoroethoxy)-5-methylpyridin-3-yl)ethyl)-2-isobutyramidoisonicotinamide;
2-acetamido-N-(1-(6-(2,2-difluoroethoxy)-5-methylpyridin-3-yl)ethyl)-6-methylisonicotinamide;
N-(1-(6-(2,2-difluoroethoxy)-5-methylpyridin-3-yl)ethyl)-2-isobutyramido-6-methylisonicotinamide;
2-(cyclopropanecarboxamido)-N-(1-(6-(2,2-difluoroethoxy)-5-methylpyridin-3-yl)ethyl)pyrimidine-4-carboxamide;
2-(cyclopropanecarboxamido)-N-(1-(6-(2,2-difluoroethoxy)-5-methylpyridin-3-yl)ethyl)-6-methylpyrimidine-4-carboxamide;
2-isobutyramido-N-(1-(3-(2,2,2-trifluoroethoxy)phenyl) ethyl)isonicotinamide;
2-isobutyramido-N-(1-(4-(2,2,2-trifluoroethoxy)phenyl) ethyl)isonicotinamide;
2-isobutyramido-6-methyl-N-(1-(4-(2,2,2-trifluoroethoxy) phenyl)ethyl)isonicotinamide;
2-isobutyramido-6-methyl-N-(1-(6-(2,2,3,3,3-pentafluoropropoxy)pyridin-3-yl)ethyl)isonicotinamide;
N-((5-chloro-6-(2,2-difluoroethoxy)pyridin-3-yl)methyl)-2-(cyclopropanecarboxamido)pyrimidine-4-carboxamide;
N-((6-(2,2-difluoroethoxy)-5-methylpyridin-3-yl)methyl)-2-isobutyramidoisonicotinamide;
2-acetamido-N-((6-(2,2-difluoroethoxy)-4-methylpyridin-3-yl)methyl)-6-methylisonicotinamide;
N-(1-(6-(2,2-difluoropropoxy)pyridin-3-yl)ethyl)-2-isobutyramido-6-methylisonicotinamide;
2-acetamido-N-(3-methyl-4-(trifluoromethoxy)benzyl) isonicotinamide;
2-isobutyramido-N-(2-methoxy-3-(trifluoromethyl)benzyl) isonicotinamide;
2-isobutyramido-N-(2-methoxy-4-(trifluoromethoxy)benzyl)isonicotinamide;
2-acetamido-N-(2-methoxy-4-(trifluoromethoxy)benzyl)-6-methylisonicotinamide;
2-isobutyramido-6-methyl-N-(1-(3-(2,2,2-trifluoroethoxy) phenyl)ethyl)isonicotinamide;
2-acetamido-N-(1-(5-methyl-6-(2,2,3,3-tetrafluoropropoxy) pyridin-3-yl)ethyl)isonicotinamide;
2-isobutyramido-N-(1-(5-methyl-6-(2,2,3,3-tetrafluoropropoxy)pyridin-3-yl)ethyl)isonicotinamide;
2-isobutyramido-6-methyl-N-(1-(5-methyl-6-(2,2,3,3-tetrafluoropropoxy)pyridin-3-yl)ethyl)isonicotinamide;
2-(cyclopropanecarboxamido)-N-(1-(5-methyl-6-(2,2,3,3-tetrafluoropropoxy)pyridin-3-yl)ethyl)pyrimidine-4-carboxamide;
2-(cyclopropanecarboxamido)-6-methyl-N-(1-(5-methyl-6-(2,2,3,3-tetrafluoropropoxy)pyridin-3-yl)ethyl)pyrimidine-4-carboxamide;
2-acetamido-6-methyl-N-(1-(5-methyl-6-(2,2,3,3-tetrafluoropropoxy)pyridin-3-yl)ethyl)isonicotinamide;
2-acetamido-N-((5-methyl-6-(2,2,3,3-tetrafluoropropoxy) pyridin-3-yl)methyl)isonicotinamide;
2-isobutyramido-N-((5-methyl-6-(2,2,3,3-tetrafluoropropoxy)pyridin-3-yl)methyl)isonicotinamide;
2-(cyclopropanecarboxamido)-N-((5-methyl-6-(2,2,3,3-tetrafluoropropoxy)pyridin-3-yl)methyl)pyrimidine-4-carboxamide;
2-acetamido-6-methyl-N-(1-(3-(2,2,2-trifluoroethoxy)phenyl)ethyl)isonicotinamide;
N-((6-(2,2-difluoroethoxy)-2-methoxypyridin-3-yl)methyl)-2-isobutyramidoisonicotinamide;
2-(cyclopropanecarboxamido)-N-(1-(6-(2,2-difluoroethoxy)-2-methoxypyridin-3-yl)ethyl)isonicotinamide; and
N-(1-(6-(2,2-difluoroethoxy)-2-methoxypyridin-3-yl) ethyl)-2-isobutyramidoisonicotinamide;

or a prodrug thereof or a pharmaceutically acceptable salt thereof.

[11] The present invention provides a pharmaceutical composition comprising a compound or a prodrug thereof or a pharmaceutically acceptable salt thereof, as described in any one of [2] to [10], and a pharmaceutically acceptable carrier.

[12] The present invention provides the pharmaceutical composition as described in [11], further comprising another pharmacologically active agent.

[13] The present invention provides a method for the treatment of a condition or disorder in which TTX-S channel blockers are involved, in an animal, including a human, which comprises administering to the animal in need of such treatment a therapeutically effective amount of a compound or a prodrug thereof or a pharmaceutically acceptable salt thereof, as described in any one of [2] to [10].

[14] The present invention provides the method as described in [13], wherein said condition or disorder is selected from the group consisting of: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia; and combinations thereof.

[15] The present invention provides the use as described in [1], wherein said condition or disorder is selected from the group consisting of: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia; and combinations thereof.

[16] The present invention provides a process for preparing a pharmaceutical composition comprising mixing a compound described in any one of [2] to [10] or a pharmaceutically acceptable salt thereof or a prodrug thereof and a pharmaceutically acceptable carrier or excipient.

[17] The present invention provides an intermediate in a process for preparing a compound of formula (I) described in any one of [2] to [10] or a prodrug thereof or a pharmaceutically acceptable salt thereof.

DESCRIPTION OF EMBODIMENTS

Examples of conditions or disorders mediated by TTX-S channels blocking activity include, but are not limited to, TTX-S channels related diseases. The compounds of the present invention show the TTX-S channels blocking activity. The compounds of the present invention may show less toxicity, good absorption and distribution, good solubility, less protein binding affinity other than TTX-S channels, less drug-drug interaction, good metabolic stability, reduced inhibitory activity at HERG channel, and/or reduced QT prolongation.

As appreciated by those of skill in the art, "halogen" or "halo" as used herein is intended to include fluoro, chloro, bromo and iodo. Similarly, $C_{1-6}$, as in $C_{1-6}$ alkyl is defined to identify the group as having 1, 2, 3, 4, 5 or 6 carbons in a linear or branched arrangement, such that $C_{1-6}$ alkyl specifically includes methyl, ethyl, n-propyl, isopropyl, n-butyl, iso-butyl, tert-butyl, pentyl, and hexyl. Similarly, $C_{2-6}$ alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents.

The term "alkenyl", as used herein, means a hydrocarbon radical having at least one double bond including, but not limited to, ethenyl, propenyl, 1-butenyl, 2-butenyl and the like.

The term "cycloalkyl", as used herein, means a mono- or bicyclic ring, but not limited to, cyclopropyl, cyclobutyl, cyclopentyl, cyclohexyl, cycloheptyl, norboranyl, and adamantyl groups and the like.

The term "aryl", as used herein, means mono- or bi-carbocyclic or mono- or bi-heterocyclic ring which may contain 0-4 heteroatoms selected from O, N and S, but not limited to, phenyl, naphthyl, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, frazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, phthalazyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof.

The term "heterocyclic group" as used herein includes both unsaturated and saturated heterocyclic moieties, wherein the unsaturated heterocyclic moieties (i.e. "heteroaryl") include benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, frazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, triazolopyrimidyl, tetrahydrothienyl, 3,4-dihydro-2H-pyrido[3,2-b][1,4]oxazinyl, 2-oxo-2,5,6,7-tetrahydro-1H-cyclopentapyridyl, 4,5,6,7-tetrahydro-indazolyl, 5,6,7,8-tetrahydro-1,6-naphthyridyl, and N-oxides thereof and S-oxides thereof.

The term "$C_0$", as used herein, means direct bond.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 2007).

The terms "treating" or "treatment", as used herein, includes prohibiting, restraining, slowing, stopping, or reversing the progression or severity of an existing symptom or disorder. As used herein, the term "preventing" or "to prevent" includes prohibiting, restraining, or inhibiting the incidence or occurrence of a symptom or disorder".

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

Compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl.

(ii) where the compound of the formula (I) contains an amino group, an amide derivative prepared by reacting with a suitable acid halide or a suitable acid anhydride is exemplified as a prodrug. A particularly preferred amide derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

Compounds of formula (I) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

Compounds of formula (I) may have polymorphs in crystalline form, which are within the scope of the present invention.

Additionally, compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be one or more chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2$H, $^3$H, $^{11}$C, $^{13}$C, $^{14}$C, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{123}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

With respect to other compounds disclosed in the art, certain compounds exhibit unexpected properties, such as with respect to duration of action and/or metabolism, such as increased metabolic stability, enhanced oral bioavailability or absorption, and/or decreased drug-drug interactions.

The compounds of formula (I), being $Na_{v1.3}$ and/or $Na_{v1.7}$ channel blockers, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central poststroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

(i) pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

(ii) heart and vascular pain, including pain caused by angina, myocardical infarction, mitral stenosis, pericarditis, Raynaud's phenomenon, scleredoma and skeletal muscle ischemia;

(iii) head pain, such as migraine (including migraine with aura and migraine without aura), cluster headache, tension-type headache mixed headache and headache associated with vascular disorders; and (vi) orofacial pain, including dental pain, otic pain, burning mouth syndrome and temporomandibular myofascial pain.

Compounds of formula (I) are also expected to be useful in the treatment of multiple sclerosis.

The invention also relates to therapeutic use of compounds of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

TTX-S sodium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with TTX-S sodium channels, including one or more of the following conditions or diseases: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A TTX-S sodium channels blocker may be usefully combined with another pharmacologically active compound, or with two or more other pharmacologically active compounds, particularly in the treatment of inflammatory, pain and urological diseases or disorders. For example, a TTX-S sodium channels blocker, particularly a compound of formula (I), or a prodrug thereof or a pharmaceutically acceptable salt or solvate thereof, as defined above, may be administered simultaneously, sequentially or separately in combination with one or more agents selected from

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an H1 antagonist having a sedative action, e.g. diphenhydramine, pyrilamine, promethazine, chlorpheniramine or chlorcyclizine;
- a sedative such as glutethimide, meprobamate, methaqualone or dichloralphenazone;
  - a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or
- (−)-(R)-6-{2-[4-(3-fluorophenyl)-4-hydroxy-1-piperidinyl]-1-hydroxyethyl-3,4-dihydro-2(1H)-quinolinone;
  - an alpha-adrenergic, e.g. doxazosin, tamsulosin, clonidine, guanfacine, dexmetatomidine, modafinil, or
- 4-amino-6,7-dimethoxy-2-(5-methane-sulfonamido-1,2,3,4-tetrahydroisoquinol-2-yl)-5-(2-pyridyl)quinazoline;
  - a tricyclic antidepressant, e.g. desipramine, imipramine, amitriptyline or nortriptyline;
  - an anticonvulsant, e.g. carbamazepine, lamotrigine, topiratmate or valproate;
  - a tachykinin (NK) antagonist, particularly an NK-3, NK-2 or NK-1 antagonist, e.g. alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or
- 3-[[2-methoxy-5-(trifluoromethoxy)phenyl]-methylamino]-2-phenylpiperidine (2S,3S);
  - a muscarinic antagonist, e.g. oxybutynin, tolterodine, propiverine, tropsiumchloride, darifenacin, solifenacin, temiverine and ipratropium;
  - a COX-2 selective inhibitor, e.g. celecoxib, rofecoxib, parecoxib, valdecoxib, deracoxib, etoricoxib, or lumiracoxib;
  - a coal-tar analgesic, in particular paracetamol;
  - a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(registered trademark) or sarizotan;
  - a vanilloid receptor agonist (e.g. resinferatoxin) or antagonist (e.g. capsazepine);
  - a transient receptor potential cation channel subtype (V1, V2, V3, V4, M8, A1) agonist or antagonist;
  - a beta-adrenergic such as propranolol;
  - a local anaesthetic such as mexiletine;
  - a corticosteroid such as dexamethasone;
  - a 5-HT receptor agonist or antagonist, particularly a 5-HT1B/1D agonist such as eletriptan, sumatriptan, naratriptan, zolmitriptan or rizatriptan;
  - a 5-HT2A receptor antagonist such as
- R(+)-alpha-(2,3-dimethoxy-phenyl)-1-[2-(4-fluorophenylethyl)]-4-piperidinemethanol (MDL-100907);
  - a cholinergic (nicotinic) analgesic, such as ispronicline (TC-1734),
- (E)-N-methyl-4-(3-pyridinyl)-3-buten-1-amine (RJR-2403),
- (R)-5-(2-azetidinylmethoxy)-2-chloropyridine (ABT-594) or nicotine;
  Tramadol(registered trademark);
  a PDEV inhibitor, such as
- 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil),
- (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil),
- 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil),
- 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one,
- 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one,
- 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one,
- 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide,
- 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;
  - an alpha-2-delta ligand such as gabapentin, pregabalin, 3-methylgabapentin, (1alpha,3 alpha,5alpha)(3-aminomethyl-bicyclo[3.2.0]hept-3-yl)-acetic acid, (3S,5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy) proline, (2S,4S)-4-(3-fluorobenzyl)-proline, [R1R,5R,6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4- dimethyl-cyclopentyl)-acetic acid, (3S,5R)-3aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

a metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as
1-(3-biphenyl-4-ylmethyl-4-hydroxy-chroman-7-yl)-cyclopentanecarboxylic acid (CP-105696),
5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton,
6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a calcium channel blocker, such as ziconotide, zonisamide, mibefrazil;

a 5-HT3 antagonist, such as ondansetron;

a chemotherapy drug such as oxaliplatin, 5-fluorouracil, leukovolin, paclitaxel;

a calcitonin gene related peptide (CGRP) antagonist;

a bradykinin (BK1 and BK2) antagonist;

a voltage-gated sodium-dependent channel blocker ($Na_{v1.3}$, $Na_{v1.7}$, $Na_{v1.8}$);

a voltage dependent calcium channel blocker (N-type, T-type);

a P2X (ion channel type ATP receptor) antagonist;

an acid-sensing ion channel (ASIC1a, ASIC3) antagonist; and the pharmaceutically acceptable salts and solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

Compounds of formula (I) or pharmaceutically acceptable salts thereof may also be formulated in rectal compositions such as suppositories or retention enemas, e.g. containing conventional suppository bases such as cocoa butter or other glycerides.

Compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:

DCM Dichloromethane
DMF N,N-Dimethylformamide
DMA N,N-Dimethylacetamide
DME 1,2-Dimethoxyethane
DMSO Dimethyl sulfoxide
EDC 1-Ethyl-3-(3-dimethylaminopropyl)carbodiimide Hydrochloride
ESI Electrospray ionization
EtOAc Ethyl acetate
EtOH Ethanol
HOBT 1-Hydroxybenztriazole
HBTU O-(Benzotriazol-1-yl)-N,N,N',N'-tetramethyluronium Hexafluorophosphate
HPLC High-Performance Liquid Chromatography
LC Liquid Chromatography
LG Leaving Group
tR Retention Time
MeCN Acetonitrile
MeOH Methanol
MHz Megahertz
MS Mass Spectrometry
NMR Nuclear Magnetic Resonance
PG Protecting Group
TFA Trifluoroacetic acid
THF Tetrahydrofuran
TLC Thin Layer Chromatography
UV Ultraviolet The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0] non-5-ene (DBN), 1,4-diazabicyclo[2,2,2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, N,N-dimethylacetamide (DMA), and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, dichloromethane, dichloroethane and chloroform are preferred.

EXAMPLES

The invention is illustrated in the following non-limiting examples in which, unless stated otherwise: all reagents are commercially available, all operations are carried out at room or ambient temperature, that is, in the range of about 18-25° C.; evaporation of solvent is carried out using a rotary evaporator under reduced pressure with a bath temperature of up to about 60° C.; reactions are monitored by thin layer chromatography (TLC) and reaction times are given for illustration only; the structure and purity of all isolated compounds are assured by at least one of the following techniques: TLC (Merck silica gel 60 $F_{254}$ precoated TLC plates or Merck $NH_2$ $F_{254}$ precoated HPTLC plates), mass spectrometry or NMR. Yields are given for illustrative purposes only. Flash column chromatography is carried out using Merck silica gel 60 (230-400 mesh ASTM), Fuji Silysia Chromatorex (registered trade mark) DU3050 (Amino Type), Wako Wakogel C300-HG, Biotage silica KP-Sil, Yamazen Hi-FLASH column, YMC DispoPack-SIL, or Biotage amino bounded silica KP-NH. The purification of compounds using HPLC (preparative LC-MS) is performed by the following apparatus and conditions.

Apparatus; Waters MS-trigger AutoPurification(trademark) system

Column; Waters XTerra C18, 19×50 mm, 5 micrometer particle

Condition A: Methanol or acetonitrile/0.01% (v/v) ammonia aqueous solution

Condition B: Methanol or acetonitrile/0.05% (v/v) formic acid aqueous solution

Low-resolution mass spectral data (ESI) are obtained by the following apparatus and conditions: Apparatus; Waters Alliance HPLC system on ZQ or ZMD mass spectrometer and UV detector. NMR data are determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L (liter(s)), mL (milliliter(s)), g (gram(s)), mg (milligram(s)), mol (moles), mmol (millimoles).

Each prepared compound is generally named by ChemBioDraw (Ultra, version 12.0, CambridgeSoft).

Conditions for Determining HPLC Retention Time:
Method:
Apparatus: Waters ACQUITY Ultra Parformance LC with TUV Detector and ZQ mass spectrometer
Column: Waters ACQUITY C18, 2.1×100 mm, 1.7 micrometer particle size
Column Temperature: 60° C.
Flow rate: 0.7 mL/min
Run time: 3 min
UV detection: 210 nm
MS detection: ESI positive/negative mode
Mobile phases:
A1: 10 mM Ammonium acetate
B1: acetonitrile
Gradient program: (QC_neutral_full_3 min)

| Time (min) | A1 (%) | B1 (%) |
|---|---|---|
| 0 | 95 | 5 |
| 0.1 | 95 | 5 |
| 1.8 | 5 | 95 |
| 2.3 | 95 | 5 |

All of the arylamide derivatives of the formula (I) can be prepared by the procedures described in the general methods presented below or by the specific methods described in the Example synthesis part and Intermediate synthesis part, or by routine modifications thereof. The present invention also encompasses any one or more of these processes for preparing the arylamide derivatives of formula (I), in addition to any novel intermediates used therein.

In the following general methods, descriptors are as previously defined for the arylamide derivatives of the formula (I) unless otherwise stated.

<Scheme A>

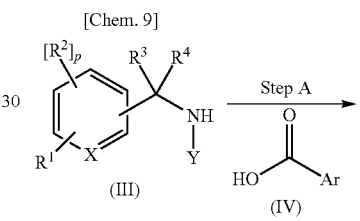

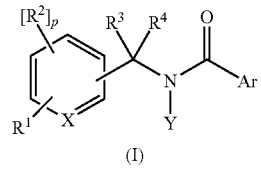

In Step A, a compound of formula (I) can be prepared from a compound of formula (IV) by amidation with a compound of formula (III) using a suitable condensation agent such as HBTU and EDC-HOBT, preferably under the presence of a base such as triethylamine and N,N-diisopropylethylamine in a suitable solvent such as DMF, DMA and dichloromethane at a temperature of from about 5 to 60° C. for about 1-24 hours. In addition, a compound of formula (I) can be also prepared from a compound of formula (III) by amidation with an acid halide prepared from a compound of formula (IV) using thionyl chloride or oxalyl chloride, preferably under the presence of a base such as triethylamine, pyridine, and N,N-diisopropylethylamine in a suitable solvent such as dichloromethane at a temperature of from about 5 to 40° C. for about 1-24 hours.

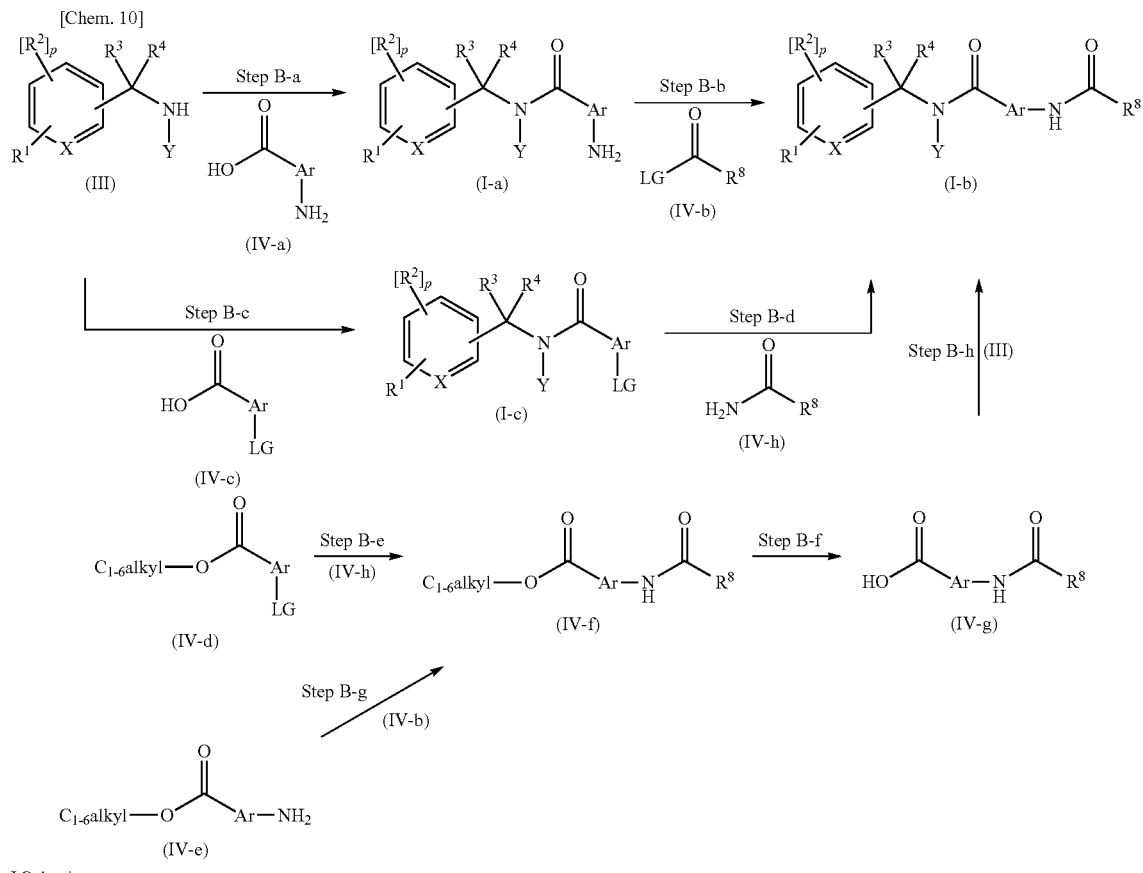

<Scheme B>

LG: leaving group

When Ar-acid of formula (IV-a) has a NH₂ group, in Step B-a, a compound of formula (I-a) can be prepared as described in the preparation of a compound of formula (I) in Step A.

Then, a compound of formula (I-b) can be prepared, in Step B-b, by acylation with a suitable acid halide of formula (IV-b) using a suitable base such as pyridine and a suitable solvent such as DMA at a temperature of from about 5 to 120° C. for about 1-24 hours. Examples of suitable acid halide include, but not limited to, acid halides such as acetyl chloride, propionyl chloride, isobutyryl chloride, and cyclopropanecarbonyl chloride.

In Step B-c, a compound of formula of (1-c) can be prepared as described in the preparation of a compound of formula (I) in Step A.

When a leaving group of formula (I-c), in Step B-d, is such as O-trifluoromethanesulfonate, O-tosylate, O-mesylate, iodide, bromide, and chloride, a compound of formula (I-b) can be prepared by coupling of a compound of formula (I-c) with a suitable carboxamide of formula (IV-h) under coupling conditions in suitable organic solvents in the presence of a suitable transition metal catalyst and in the presence or absence of a base. Examples of suitable transition metal catalysts include: tetrakis(triphenylphosphine)palladium(0), bis(triphenylphosphine)palladium(11) chloride, copper(0), copper(1) acetate, copper(1) bromide, copper(1) chloride, copper(1) iodide, copper(1) oxide, copper(11) trifluoromethanesulfonate, copper(11) acetate, copper(11) bromide, copper(11) chloride, copper(11) iodide, copper(11) oxide, copper(11) trifluoromethanesulfonate, palladium(11) acetate, palladium(11) chloride, bis(acetonitrile)dichloropalladium(II), bis(dibenzylideneacetone)palladium(0), tris(dibenzylideneacetone)dipalladium(0) and [1,1'-bis(diphenylphosphino)ferrocene] palladium(11) dichloride. Preferred catalysts are tetrakis(triphenylphosphine)palladium(0), bis(triphenylphosphine)palladium(11) chloride, palladium(11) acetate, palladium(11) chloride, bis(acetonitrile)dichloropalladium(0), bis(dibenzylideneacetone)palladium(0), tris(dibenzylideneacetone)dipalladium(0) and [1,1-bis(diphenylphosphino)ferrocene]palladium(11) dichloride. Examples of suitable carboxamide include, but not limited to, carboximides such as acetamide, propionamide, isobutyramide and cyclopropanecarboxamide. Examples of suitable organic solvent include: THF; 1,4-dioxane; DMF; MeCN; alcohols, such as methanol or ethanol; halogenated hydrocarbons, such as DCM, 1,2-dichloroethane, chloroform or carbon tetrachloride; and diethylether; in the presence or absence of base such as tripotassium phosphate, sodium bicarbonate, sodium cabonate or potassium carbonate. This reaction can be carried out in the presence of a suitable additive agent. Examples of such additive agents include: 4,5-Bis(diphenylphosphino)-9,9-dimethylxanthene, triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine. The reaction can be carried out at a temperature of from about 50 to 200° C., more preferably from about 80 to 150° C. Reaction times are, in general, from about 5 minutes to 48 hrs, more preferably from about 30 minutes to 24 hrs. In an alternative case, the reaction can be carried out with microwave system. The reaction can be carried out at a temperature in the range from about 100 to 200° C., preferably in the range from about 120 to 160° C. Reaction times are, in general, from about 10 minutes to 3 hrs, preferably from about 15 minutes to 1 hr.

In Step B-e and Step B-g, a compound of formula (IV-f), can be prepared as descried in the Step B-d and Step B-b, respectively.

In Step B-f, a compound of formula (IV-g) can be prepared by hydrolysis of the ester compound of formula (IV-f). The hydrolysis can be carried out by the conventional procedures. In a typical procedure, the hydrolysis is carried out under basic conditions, e.g. in the presence of sodium hydroxide, potassium hydroxide or lithium hydroxide. Suitable solvents include, for example: alcohols such as water, methanol, ethanol, propanol, butanol, 2-methoxyethanol, and ethylene gylcol; ethers such as THF, DME, and 1,4-dioxane; amides such as DMF and hexamethylphospholictriamide; and sulfoxides such as DMSO. Preferred solvents are water, methanol, ethanol, propanol, THF, DME, 1,4-dioxane, DMF, and DMSO. This reaction can be carried out at a temperature in the range of from about 20 to 100° C. for from about 30 minutes to 24 hrs.

The key intermediate amines of formula (X), (V-f), (X-a), (X-b) and (XVI-b) can be prepared by the following general synthetic route Scheme C, D, E, and F.

<Scheme C>

[Chem. 11]

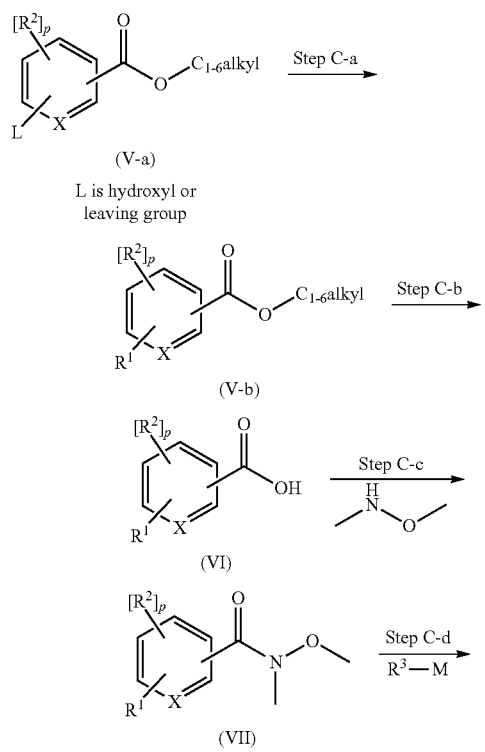

(V-a)

L is hydroxyl or leaving group

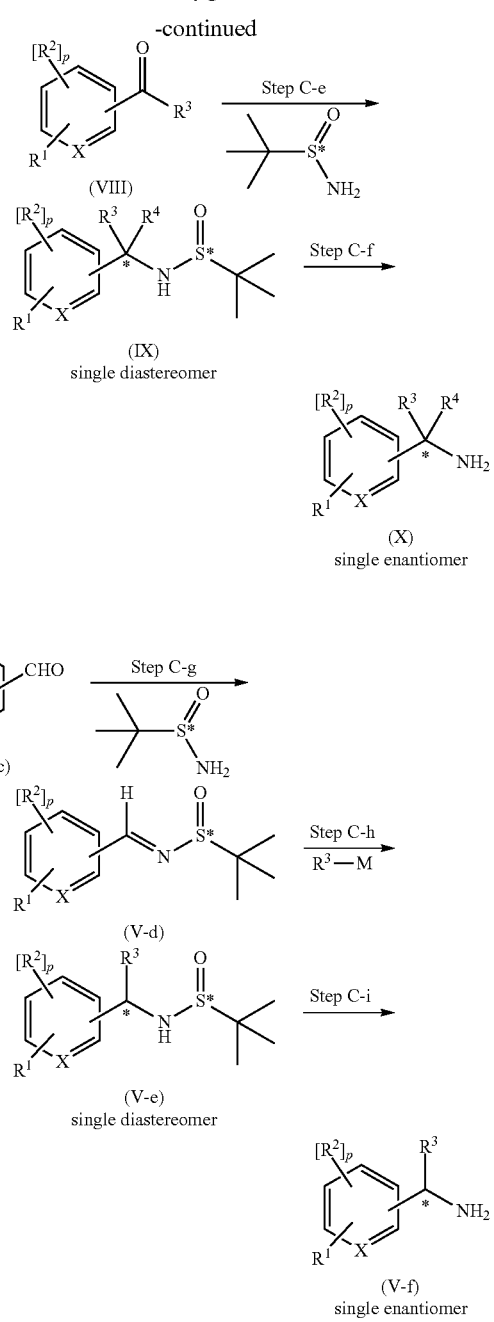

When L in a compound of formula (V-a) is a hydroxyl or a leaving group, In Step C-a, a compound of formula (V-b) can be prepared by alkylation or $S_N$—Ar reaction using suitable conditions.

In the case of alkylation of a hydroxyl group, suitable alkyl halide or alkyl sulfonate can be used as an alkylating reagent in organic solvent in the presence of suitable base include, but not limited to, such as sodium hydride, potassium carbonate, cesium carbonate, and potassium tert-butoxide. Examples of suitable alkyl halides include such as alkyl-chloride, alkyl-bromide and alkyl-iodide. Examples of suitable alkyl sulfonates include, but not limited to, such as alkyl mesylate, alkytriflate and alkyl tosylate. Mitsunobu reaction can also be applied for the alkylation step by using corresponding alcohol in organic solvent in the presence of azo-dicarboxylate include, but not limited to, such as diethyl azodicarboxylate, diisopropyl azodicarboxylate, and diter-butyl azodicarboxylate as a coupling reagent. Examples of suitable organic solvent include such as THF, 1,4-dioxane, DMF, MeCN, and toluene. The reaction can be carried out at a temperature of from about −20 to 180° C., more preferably from about 0 to 150° C. Reaction times are, in general, from about 30 minutes to 48 hrs, more preferably from about 30 minutes to 24 hrs.

In the case of $S_N$—Ar reaction (O-arylation) for the formation of a compound of formula (V-b), a leaving group can be replaced with a corresponding alcohol in the presence of a base in an inert solvent. Examples of suitable base include, but not limited to, such as sodium hydroxide, potassium hydroxide, potassium carbonate, sodium carbonate and cesium carbonate, potassium tert-butoxide, sodium hydride. Examples of suitable solvents include, but not limited to, such as water, THF, 1,4-dioxane, MeCN, DCM, 1,2-dichloroethane, DMSO, DMA and DMF. Examples of suitable leaving group include, but not limited to, such as O-trifluoromethanesulfonate, O-tosylate, O-mesylate, iodide, bromide, chloride and fluoride.

In Step C-b, a compound of formula (VI) can be prepared by the method described in Step B-f.

In Step C-c, a compound of formula (VII) can be prepared from acid of the formula (VI) and N,O-dimethylhydroxylamine (Weinreb amide formation) by the method described in Step-A.

In Step C-d, a compound of formula (VIII) can be prepared from compound of formula (VII) by the treatment with a suitable alkyl-metal reagent in an inert solvent. Examples of suitable alkyl-metal reagent include, but not limited to, such as methyllithium, ethyllithium, methylmagnesium chloride, methylmagnesium bromide, methylmagnesium iodide. Examples of inert solvent include, but not limited to, such as THF, DME, and 1,4-dioxane. The reaction can be carried out at a temperature of from about −40 to 100° C., more preferably from about 0 to 50° C. Reaction times are, in general, from about 5 minutes to 48 hrs, more preferably from about 30 minutes to 24 hrs.

In Step C-e, a compound of formula (IX) can be prepared as a single diastereomer from carbonyl compound of formula (VIII) and a chiral tert-butanesulfinamide by the conventional methods known to those skilled in the art (Pure Appl. Chem., 75, 39-46, 2003; Tetrahedron Lett., 45, 6641-6643, 2004). In the following intermediate and example section, a compound name of formula (IX) is described as an (R) or (S) isomer, which represents the configuration of a sulfur atom.

In Step C-f, a compound of formula (X) can be prepared as a single enantiomer from a compound of formula (IX) by the treatment with acidic condition by the conventional methods known to those skilled in the art (Pure Appl. Chem., 75, 39-46, 2003; Tetrahedron Lett., 45, 6641-6643, 2004).

In Step C-g, a compound of formula (V-d) can be prepared from aldehyde of formula (V-c) and chiral tert-butanesulfinamide by the conventional methods known to those skilled in the art (Pure Appl. Chem., 75, 39-46, 2003; Tetrahedron Lett., 45, 6641-6643, 2004).

In Step C-h, a compound of (V-e) can be prepared as a single diastereomer from chiral sulfinyl imine of formula (V-d) and alkyl-metal reagent by the conventional methods known to those skilled in the art (Pure Appl. Chem., 75, 39-46, 2003; Tetrahedron Lett., 45, 6641-6643, 2004).

In Step C-i, a compound of formula (V-f) can be prepared as a single enantiomer from a compound of formula (V-e) by the treatment with acidic condition by the conventional methods known to those skilled in the art (Pure Appl. Chem., 75, 39-46, 2003; Tetrahedron Lett., 45, 6641-6643, 2004).

<Scheme D>

[Chem. 12]

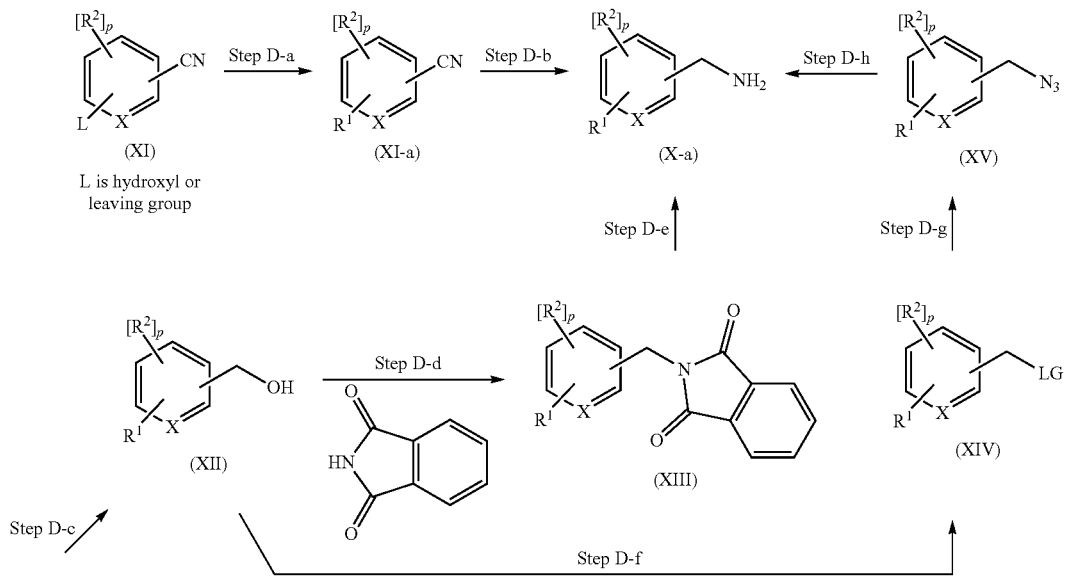

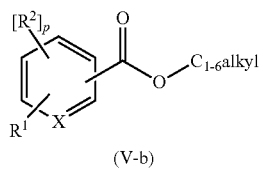

(V-b)

In Step D-a, a compound of formula (XI-a) can be prepared by the method described in Step C-a.

In Step D-b, a compound of formula (X-a) can be prepared by hydrogenation of a compound of formula (XI-a) under known hydrogenolysis conditions, for example, in the presence of a suitable metal catalyst under a hydrogen atmosphere, or in the presence of hydrogen sources such as formic acid or ammonium formate, in an inert solvent. If desired, the reaction is carried out under acidic conditions, for example, in the presence of hydrochloric acid or acetic acid. A preferred metal catalyst is selected from, for example, nickel catalysts such as Raney nickel, Pd—C, palladiumhydroxide-carbon, platinumoxide, platinum-carbon, ruthenium-carbon, Fe, Zn, Sn, and $SnCl_2$. Examples of suitable inert aqueous or non-aqueous organic solvents include, but not limited to, alcohols, such as methanol, ethanol or ammonic methanol; ethers, such as THF or 1,4-dioxane; acetone; DMF; halogenated hydrocarbons, such as DCM, 1,2-dichloroethane or chloroform; and acetic acid; or mixtures thereof. The reaction can be carried out at a temperature in the range of from about 20 to 150° C., preferably in the range of from about 20 to 80° C. Reaction times are, in general, from about 10 minutes to 4 days, preferably from about 30 minutes to 24 hrs. This reaction can be carried out under a hydrogen atmosphere at a pressure ranging from about 1 to 100 atms, preferably from about 1 to 5 atms.

In Step D-c, a compound of formula (XII) can be prepared by reduction of a compound of formula (V-b). The reduction may be carried out in the presence of a suitable reducing reagent in an inert solvent or without solvent. A preferred reducing agent is selected from, for example, but not limited to, such as sodium borohydride, lithium aluminum hydride, lithium borohydride, boran-complex, and diisobutylaluminium hydride. Reaction temperatures are generally in the range of from about −78 to 100° C., preferably in the range of from about −70 to 60° C. Reaction times are, in general, from about 30 minute to a day. Examples of suitable solvents include: THF; 1,4-dioxane; DMF; MeCN; alcohols, such as methanol or ethanol, and halogenated hydrocarbons, such as DCM, 1,2-dichloroethane, chloroform or carbon tetrachloride.

In Step D-d, a compound of formula (XIII) can be prepared by the method described in Step C-a (Mitsunobu reaction).

In Step D-e, a compound of formula (X-a) can be prepared by de-protection with such as hydrazine in an inert solvent. Example of suitable solvents include such as water, methanol or ethanol. The reaction can be carried out at a temperature in the range of from about 0 to 150° C., preferably in the range of from about 50 to 100° C. Reaction times are, in general, from about 10 minutes to 96 hrs, preferably from about 30 minutes to 24 hr.

When LG is such as O-trifluoromethanesulfonate, O-tosylate, O-mesylate, iodide, bromide, and chloride, in Step D-f, a compound of formula (XIV) can be prepared by sulfonylation or substitution with halogen of a compound of formula (XII) under, for example, known sulfonylation condition or known halogenation conditions in an inert solvent.

LG is leaving group

In case of sulfonylation, the reaction can be carried out in the presence of a base in an inert solvent. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as TEA, tributylamine, diisopropylethylamine, 2,6-lutidine, pyridine or dimethylaminopyridine. Examples of suitable inert aqueous or non-aqueous organic solvents include: alcohols, such as methanol or ethanol; ethers, such as THF or 1,4-dioxane; acetone; dimethylformamide; halogenated hydrocarbons, such as dichloromethane, 1,2-dichloroethane or chloroform; and pyridine; or mixtures thereof. The reaction can be carried out at a temperature in the range of from about −10° C. to 200° C., preferably in the range of from about 20 to 100° C. Reaction times are, in general, from about 10 minutes to 4 days, preferably from about 10 minutes to 24 hrs.

In case of halogenation, example of halogen source is such as thionyl chloride, N-bromosuccinimide, N-chlorosuccinimide, iodine, bromine, phosphorous trichloride, phosphorous tribromide, carbontetrachloride, or carbontetrabromide. In the halogenation reaction, the reaction can be carried out in the presence of reducing agent such as triphenylphosphine. Examples of suitable organic solvent include such as THF, 1,4-dioxane, DCM, 1,2-dichloroethane, carbontetrachloride, toluene, or DMF.

In Step D-g, a compound of formula (XV) can be prepared by substitution reaction with azide group of a compound of formula (XIV). The reaction can be carried out with a suitable reagent in an inert solvent. A preferred reagent is selected from, for example, lithium azide, sodium azide, potassium azide, or cesium azide. Reaction temperatures are generally in the range of from about 20 to 150° C., preferably in the range of from about 50 to 120° C. Reaction times are, in general, from about 30 minutes to 96 hrs, preferably from about 1 hrs to 24 hrs. Examples of suitable solvents include such as THF, 1,4-dioxane, DMF, acetonitrile or DMSO.

In Step D-h, a compound of formula (X-a) can be prepared from a compound of formula of (XV) by hydrogenation reaction by the method described in Step D-b above.

<Scheme E>

[Chem. 13]

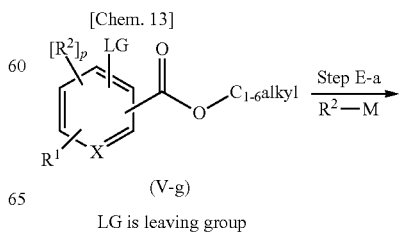

(V-g)

LG is leaving group

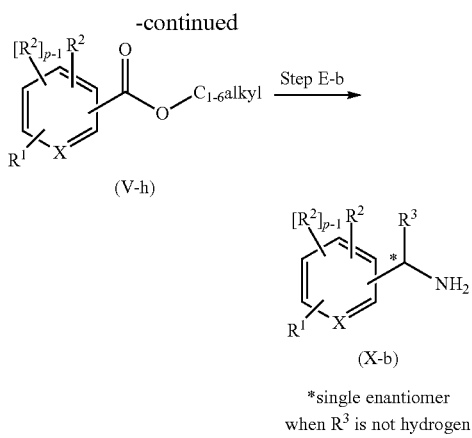

When LG of a compound (V-g) is a suitable group such as O-trifluoromethanesulfonate, O-tosylate, O-mesylate, iodide, bromide, or chloride, in Step E-a, additional substituent can be introduced to give a compound of formula (V-h) by the reaction with a suitable alkyl-metal reagent in the presence of a suitable transition metal catalyst and base in an inert solvent as described in the method Step B-d. Examples of suitable alkyl-metal reagents include, but not limited to, trimethylboroxine, cyclopropylboronic acid, dimethylzinc, diethylzinc, methylmagnesium chloride, methylmagnesium bromide, methylmagnesium iodide or arylboronic acids and heteroarylboronic acids.

In Step E-b, multi-substituted amine of formula (X-b) can be prepared from a compound (V-h) through multiple steps by the method described in Scheme C and Scheme D above.

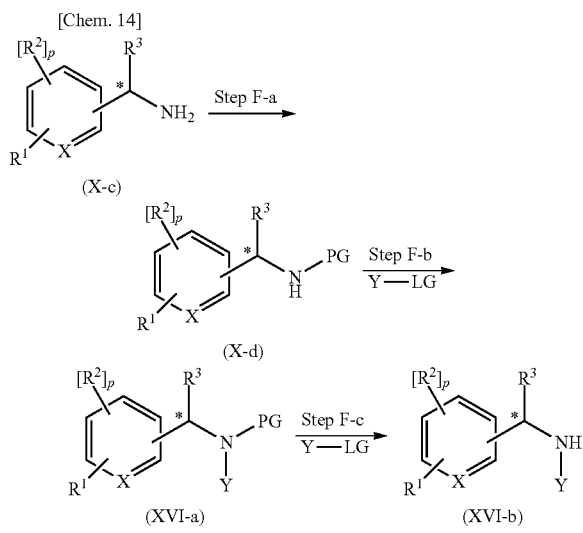

Y is not hydrogen
PG is protecting group
LG is leaving group
*single enantiomer
when R³ is not hydrogen In Step F-a, a protecting group can be introduced by the conventional methods known to those skilled in the art (typical amino protecting groups described in "Protective Groups in Organic Synthesis Forth Edition" edited by T. W. Greene et al. (John Wiley & Sons, 2007)).

When LG is a suitable group such as O-trifluoromethanesulfonate, O-tosylate, O-mesylate, iodide, bromide, or chloride, in Step F-b, a compound of formula (XVI-a) can be prepared by N-alkylation with an alkylating reagent in the presence of a suitable base in an inert solvent. Examples of a suitable base include, but not limited to, such as sodium hydride, potassium carbonate, cesium carbonate, potassium tert-butoxide. Examples of suitable organic solvent include such as THF, 1,4-dioxane, DMF, MeCN, DMA, toluene. The reaction can be carried out at a temperature of from about −20 to 150° C., more preferably from about 0 to 100° C. Reaction times are, in general, from about 30 minutes to 48 hrs, more preferably from about 30 minutes to 24 hrs.

In Step F-c, a compound of formula (XVI-b) can be prepared by de-protection of a compound of formula (XVI-a) by the conventional methods known to those skilled in the art (typical amino protecting groups described in "Protective Groups in Organic Synthesis Forth Edition" edited by T. W. Greene et al. (John Wiley & Sons, 2007)).

All starting materials in the following general syntheses may be commercially available or obtained by the conventional methods known to those skilled in the art, otherwise noted in the intermediate synthesis part.

Intermediate Synthesis Part
<Amine Synthesis Part>

Amine-1:(−)-1-(6-(2,2,2-trifluoroethoxy)pyridin-3-yl)ethanamine hydrochloride (single enantiomer)

<Step-1>:6-(2,2,2-trifluoroethoxy)nicotinic acid

A mixture of 6-chloronicotinic acid (7.0 g, 44.4 mmol), 2,2,2-trifluoroethanol (6.40 mL, 89.0 mmol) and sodium hydride (5.33 g, 133.0 mmol, 60% in oil) in N,N-dimethylacetamide (400 mL) is stirred at 90° C. for 21 hours. After cooling to room temperature, the reaction mixture is poured slowly into 2M hydrochloric acid (300 mL) and extracted with n-hexane/ethyl acetate (1:10, 500 mL). The organic layer is washed with 2M hydrochloric acid (300 mL×2) and dried over sodium sulfate. The organic solvent is concentrated under reduced pressure to give 7.64 g (78% yield) of the title compound as colorless oil. This material is used for the next reaction (Step-2) without further purification.

MS (ESI) m/z: 222 (M+H)⁺.

<Step-2>:N-methoxy-N-methyl-6-(2,2,2-trifluoroethoxy)nicotinamide

A mixture of 6-(2,2,2-trifluoroethoxy)nicotinic acid (10.4 g, 47.3 mmol, Step-1), N,O-dimethylhydroxylamine hydrochloride (5.08 g, 52.1 mmol), HOBT (9.59 g, 71.0 mmol), EDC (13.6 g, 71.0 mmol) and triethylamine (26.4 mL, 189 mmol) in N,N-dimethylacetamide (237 mL) is stirred at 60° C. for 16 hours. The reaction mixture is poured into saturated aqueous sodium hydrogen carbonate (300 mL) and extracted with ethyl acetate (500 mL). The organic layer is washed with saturated aqueous sodium hydrogen carbonate (300 mL×2) and dried over sodium sulfate, and concentrated in vacuo. The residue is purified by column chromatography on silica gel eluting with n-hexane/ethyl acetate (4:1) to give 6.54 g (52% yield) of the title compound as colorless oil.

¹H-NMR (300 MHz, CDCl₃) δ 8.60 (1H, d, J=2.2 Hz), 8.05 (1H, dd, J=8.8, 2.2 Hz), 6.88 (1H, d, J=8.8 Hz), 4.80 (2H, q, J=8.4 Hz), 3.57 (3H, s), 3.38 (3H, s), MS (ESI) m/z: 265 (M+H)⁺. Hereafter, in the NMR data results, "delta" is used in place of "δ".

<Step-3>:1-(6-(2,2,2-trifluoroethoxy)pyridin-3-yl)ethanone

To a stirred solution of N-methoxy-N-methyl-6-(2,2,2-trifluoroethoxy)nicotinamide (6.54 g, 24.8 mmol, Step-2) in tetrahydrofuran (80 mL) is added dropwise 1.06M methylmagnesium bromide (46.7 mL, 49.5 mmol) at 0° C. The reaction mixture is stirred at room temperature for 1.5 hours. The reaction mixture is poured into saturated aqueous sodium hydrogen carbonate (100 mL) and extracted with ethyl acetate (300 mL). The organic layer is washed with water (100 mL×2) and dried over sodium sulfate and concentrated in vacuo. The residue is purified by column chromatography on silica gel eluting with n-hexane/ethyl acetate (1:1) to give 4.51 g (83% yield) of the title compound as colorless oil.
$^1$H-NMR (300 MHz, CDCl$_3$) delta 8.75 (1H, dd, J=2.6, 0.7 Hz), 8.23 (1H, dd, J=8.4, 2.6 Hz), 6.93 (1H, dd, J=8.4, 0.7 Hz), 4.85 (2H, q, J=8.4 Hz), 2.59 (3H, s), MS (ESI) m/z: 220 (M+H)$^+$.

<Step-4>:(R)-2-methyl-N-(1-(6-(2,2,2-trifluoroethoxy)pyridin-3-yl)ethyl)propane-2-sulfinamide (single diastereomer)

A mixture of 1-(6-(2,2,2-trifluoroethoxy)pyridin-3-yl)ethanone (4.51 g, 20.58 mmol, Step-3), (R)-2-methylpropane-2-sulfinamide (3.74 g, 30.9 mmol) and tetraethyl orthotitanate (6.47 mL, 30.9 mmol) in tetrahydrofuran (23 mL) is stirred at 70° C. for 17 hours. The reaction mixture is cooled to 0° C., sodium borohydride (2.72 g, 72.0 mmol) is added there, and the mixture is stirred at same temperature for 1 hour. Saturated aqueous sodium hydrogen carbonate (50 mL) is added to the reaction mixture, and the mixture is stirred for 10 minutes. After filtration through a pad of celite (registered trademark), the filtrate is extracted with ethyl acetate (300 mL). The organic layer is washed with water (100 mL×2) and dried over sodium sulfate and concentrated in vacuo. The residue is purified by column chromatography on silica gel eluting with n-hexane/ethyl acetate (4:1 to 1:1) to give 6.25 g (94% yield) of the title compound as colorless oil.
$^1$H-NMR (300 MHz, CDCl$_3$) delta 8.11 (1H, d, J=2.2 Hz), 7.67 (1H, dd, J=8.4, 2.2 Hz), 6.87 (1H, d, J=8.4 Hz), 4.76 (2H, q, J=8.4 Hz), 4.61-4.50 (1H, m), 3.37 (1H, br s), 1.53 (3H, d, J=7.0 Hz), 1.31 (9H, s), MS (ESI) m/z: 325 (M+H)$^+$.

<Step-5>:(−)-1-(6-(2,2,2-trifluoroethoxy)pyridin-3-yl)ethanamine hydrochloride (single enantiomer)

(R)-2-methyl-N-(1-(6-(2,2,2-trifluoroethoxy)pyridin-3-yl)ethyl)propane-2-sulfinamide (single diastereomer) (6.15 g, 18.9 mmol, Step-4) is dissolved in 8M hydrochloric acid in methanol (20 mL). The mixture is stirred at room temperature for 2 hours. The reaction mixture is concentrated under reduced pressure. The residue is crystallized from n-hexane/ethyl acetate to give 4.40 g (90% yield) of the title compound as a white solid.
$^1$H-NMR (300 MHz, DMSO-d$_6$) delta 8.63 (2H, br s), 8.34 (1H, d, J=2.6 Hz), 8.03 (1H, dd, J=8.8, 2.6 Hz), 7.07 (1H, d, J=8.8 Hz), 5.02 (2H, q, J=9.2 Hz), 4.53-4.42 (1H, m), 1.54 (3H, d, J=7.0 Hz), MS (ESI) m/z: 221 (M+H)$^+$.
$[\alpha]_D^{23}$=−0.96 (c=1.05, methanol)

Amine-2:(4-(2,2,2-trifluoroethoxy)pyridin-2-yl)methanamine hydrochloride

<Step-1>:4-(2,2,2-trifluoroethoxy)picolinonitrile

To a solution of potassium tert-butoxide (0.45 g, 4.02 mmol) in tetrahydrofuran (8 mL) is added 2,2,2-trifluoroethanol (0.27 mL, 3.69 mmol), and the mixture is stirred at room temperature for 20 minutes. A solution of 4-nitropicolinonitrile (0.50 g, 3.35 mmol) in tetrahydrofuran (8 mL) is added dropwise the mixture, and the resulting mixture is stirred at room temperature for 20 minutes. The reaction mixture is poured into saturated aqueous ammonium chloride solution (20 mL) and extracted with ethyl acetate (30 mL). The organic layer is dried over sodium sulfate and concentrated in vacuo to give 0.71 g (>99% yield) of the title compound as yellow oil. This material is used for the next reaction (Step-2) without further purification.
MS (ESI) m/z: 203 (M+H)$^+$.

<Step-2>:(4-(2,2,2-trifluoroethoxy)pyridin-2-yl)methanamine hydrochloride

A mixture of 4-(2,2,2-trifluoroethoxy)picolinonitrile (0.71 g, 3.51 mmol, Step-1), hydrochloric acid (0.21 mL, 7.03 mmol) and palladium 10% on carbon (0.15 g) in methanol (35 mL) is vigorously stirred at room temperature under hydrogen atmosphere (0.3 MPa) for 4 hours. After filtration through a pad of celite, the filtrate is concentrated in vacuo. The residue is crystallized from ethyl acetate to give 0.43 g (44% yield) of the title compound as a white solid.
$^1$H-NMR (300 MHz, DMSO-d$_6$) delta 8.61-8.40 (2H, br s), 8.49 (1H, d, J=5.9 Hz), 7.28 (1H, d, J=2.2 Hz), 7.14 (1H, dd, J=5.9, 2.6 Hz), 4.94 (2H, q, J=8.8 Hz), 4.11 (2H, s), MS (ESI) m/z: 207 (M+H)$^+$.

Amine-3:(+)—N-methyl-1-(6-(2,2,2-trifluoroethoxy)pyridin-3-yl)ethanamine hydrochloride (single enantiomer)

<Step-1>:tert-butyl (1-(6-(2,2,2-trifluoroethoxy)pyridin-3-yl)ethyl)carbamate (single enantiomer A mixture of (−)-1-(6-(2,2,2-trifluoroethoxy)pyridin-3-yl)ethanamine hydrochloride (200 mg, 0.78 mmol, Amine-1, single enantiomer), di-tert-butyldicarbonate (0.18 mL, 0.78 mmol), and triethylamine (0.22 mL, 1.56 mmol) in dichloromethane (5 mL) is stirred at room temperature for 1 hour. After removal of the solvent, the residue is purified by column chromatography on silica gel eluting with n-hexane/ethyl acetate (4:1) to give 221 mg (89% yield) of the title compound as a white solid.
$^1$H-NMR (300 MHz, CDCl$_3$) delta 8.06 (1H, d, J=2.6 Hz), 7.57 (1H, dd, J=8.6, 2.6 Hz), 6.81 (1H, d, J=8.6 Hz), 4.72 (2H, q, J=8.6 Hz), 4.81-4.66 (1H, m), 1.50 (3H, s), 1.39 (9H, s), MS (ESI) m/z: 321 (M+H)$^+$.

<Step-2>:tert-butyl methyl(1-(6-(2,2,2-trifluoroethoxy)pyridin-3-yl)ethyl)carbamate (single enantiomer)

To a stirred solution of tert-butyl(1-(6-(2,2,2-trifluoroethoxy)pyridin-3-yl)ethyl)carbamate (221 mg, 0.69 mmol, Step-1, single enantiomer) and sodium hydride (61 mg, 1.52 mmol, 60% in oil) in N,N-dimethylformamide (7 mL) is added dropwise iodomethane (0.065 mL, 1.04 mL) at room temperature. After stirring at room temperature for 3.5 hours, the reaction mixture is slowly poured into water (30 mL) and extracted with ethyl acetate (30 mL). The organic layer is washed with water (30 mL) and dried over sodium sulfate. After concentration in vacuo, the residue is purified by column chromatography on silica gel eluting with n-hexane/ethyl acetate (9:1) to give 198 mg (86% yield) of the title compound as colorless oil.

¹H-NMR (300 MHz, CDCl₃) delta 8.05 (1H, d, J=2.6 Hz), 7.56 (1H, dd, J=8.4, 2.6 Hz), 6.84 (1H, d, J=8.4 Hz), 5.54-5.34 (1H, m), 4.75 (2H, q, J=8.4 Hz), 2.59 (3H, s), 1.51 (3H, s), 1.47 (9H, s), MS (ESI) m/z: 335 (M+H)⁺.

<Step-3>:(+)-N-methyl-1-(6-(2,2,2-trifluoroethoxy)pyridin-3-yl)ethanamine hydrochloride (single enantiomer)

tert-butyl methyl(1-(6-(2,2,2-trifluoroethoxy)pyridin-3-yl)ethyl)carbamate (198 mg, 0.59 mmol, Step-2, single enantiomer) is dissolved in 4M hydrochloric acid ethyl acetate solution (3 mL). The mixture is stirred at room temperature for 1.5 hours. After concentration under reduced pressure, the residue is crystallized from n-hexane to give 68 mg (42% yield) of the title compound as a white solid.

¹H-NMR (300 MHz, DMSO-d₆) delta 9.51 (1H, br s), 9.21 (1H, br s), 8.34 (1H, d, J=2.6 Hz), 8.03 (1H, dd, J=8.8, 2.6 Hz), 7.11 (1H, d, J=8.8 Hz), 5.02 (2H, q, J=9.2 Hz), 4.42-4.35 (1H, m), 2.40 (3H, t, J=5.5 Hz), 1.57 (3H, d, J=6.6 Hz), MS (ESI) m/z: 235 (M+H)⁺.

$[\alpha]_D^{23}$=+8.30 (c=1.79, methanol)

Amine-4:(6-(2,2,2-trifluoroethoxy)pyridin-2-yl)methanamine

<Step-1>:6-(2,2,2-trifluoroethoxy)picolinic acid

The title compound is prepared in >99% yield (2.40 g, colorless oil) from 6-chloropicolinic acid (1.18 g, 7.49 mmol) by the similar manner in Step-1 of Amine-1.

MS (ESI) m/z: 222 (M+H)⁺.

<Step-2>:Methyl 6-(2,2,2-trifluoroethoxy)picolinate

A mixture of 6-(2,2,2-trifluoroethoxy)picolinic acid (2.40 g, 10.9 mmol, Step-1), methyl iodide (3.39 mL, 54.3 mmol) and potassium carbonate (4.50 g, 32.6 mmol) in N,N-dimethylacetamide (54 mL) is stirred at room temperature for 4 hours. The reaction mixture is poured into water (100 mL) and extracted with n-hexane/ethyl acetate (1:10, 100 mL). The organic layer is washed with water (100 mL), dried over sodium sulfate, and concentrated in vacuo. The residue is purified by column chromatography on silica gel eluting with n-hexane/ethyl acetate (5:1) to give 1.14 g (45% yield) of the title compound as colorless oil.

¹H-NMR (270 MHz, CDCl₃) delta 7.82-7.74 (2H, m), 7.06 (1H, dd, J=7.3, 2.0 Hz), 4.86 (2H, q, J=8.6 Hz), 3.96 (3H, s), MS (ESI) m/z: 236 (M+H)⁺.

<Step-3>:(6-(2,2,2-trifluoroethoxy)pyridin-2-yl)methanol

To a stirred solution of methyl 6-(2,2,2-trifluoroethoxy)picolinate (0.40 g, 1.69 mmol, Step-2) in tetrahydrofuran (17 mL) is added slowly lithium aluminum hydride (0.096 g, 2.53 mmol) at 0° C. The resulting mixture is stirred at room temperature for 1 hour. The reaction mixture is carefully quenched with 25% aqueous ammonia solution at 0° C. Then the mixture is diluted with dichloromethane (50 mL) and celite is added to the mixture. After stirring at room temperature for 1 hour, the mixture is filtrated through a pad of celite, and the filtrate is concentrated in vacuo to give 0.32 g (92% yield) of the title compound as a white solid. This material is used for the next reaction (Step-4) without further purification.

MS (ESI) m/z: 208 (M+H)⁺.

<Step-4>:2-(chloromethyl)-6-(2,2,2-trifluoroethoxy)pyridine

A mixture of (6-(2,2,2-trifluoroethoxy)pyridin-2-yl)methanol (0.32 g, 1.55 mmol, Step-3), thionyl chloride (0.23 mL, 3.10 mmol) in dichloromethane (16 mL) is stirred at room temperature for 1 hour. The organic solvent is concentrated under reduced pressure and dried to give 0.35 g (>99% yield) of the title compound as yellow oil. This material is used for the next reaction (Step-5) without further purification.

MS (ESI) m/z: 226 (M+H)⁺.

<Step-5>:2-(azidomethyl)-6-(2,2,2-trifluoroethoxy)pyridine

A mixture of 2-(chloromethyl)-6-(2,2,2-trifluoroethoxy)pyridine (0.35 g, 1.55 mmol, Step-4) and sodium azide (0.20 g, 3.10 mmol) in N,N-dimethylacetamide (8 mL) is stirred 90° C. for 1 hour. The reaction mixture is poured into water (50 mL), and extracted with n-hexane/ethyl acetate (1:10, 50 mL). The organic layer is washed with water (50 mL) and dried over sodium sulfate. The organic fraction is concentrated in vacuo to give 0.44 g (>99% yield) of the title compound as colorless oil. This material is used for the next reaction (Step-6) without further purification.

MS (ESI) m/z: 233 (M+H)⁺.

<Step-6>:(6-(2,2,2-trifluoroethoxy)pyridin-2-yl)methanamine

A mixture of 2-(azidomethyl)-6-(2,2,2-trifluoroethoxy)pyridine (Step-5, 0.44 g, 1.90 mmol) and palladium 10% on carbon (0.070 g) in methanol (12 mL) is vigorously stirred at room temperature under hydrogen atmosphere (0.3 MPa) for 3 hours. After filtration through a pad of celite, the filtrate is concentrated in vacuo. The residue is diluted with methanol (4 mL) and applied onto a strong cation exchange cartridge (BondElute(registered trademark) SCX, 1 g/6 mL, Varian Inc.), and the solid phase matrix is rinsed with methanol (5 mL). The crude mixture is eluted with 1M ammonia in methanol (5 mL) and concentrated under reduced pressure to give 0.27 g (68% yield) of the title compound as dark brown oil.

MS (ESI) m/z: 207 (M+H)⁺.

Amine-5:(+)-1-(5-chloro-6-(2,2,2-trifluoroethoxy)pyridin-3-yl)ethanamine hydrochloride (single enantiomer)

<Step-1>:5-chloro-6-(2,2,2-trifluoroethoxy)nicotinic acid

The title compound is prepared in 54% yield (2.88 g, a white solid) from 5,6-dichloronicotinic acid (4.0 g, 20.8 mmol) by the similar manner in Step-1 of Amine-1.

MS (ESI) m/z: 256 (M+H)⁺.

<Step-2>:5-chloro-N-methoxy-N-methyl-6-(2,2,2-trifluoroethoxy)nicotinamide

A mixture of 5-chloro-6-(2,2,2-trifluoroethoxy)nicotinic acid (2.0 g, 7.8 mmol, Step-1), N,O-dimethylhydroxylamine hydrochloride (0.916 g, 9.39 mmol), HBTU (3.56 g, 9.39 mmol) and triethylamine (5.45 mL, 39.1 mmol) in dichloromethane (39 mL) is stirred at room temperature for 3 hours.

The reaction mixture is poured into water (100 mL) and extracted with dichloromethane (200 mL). The organic layer is washed with water (100 mL) and dried over sodium sulfate and concentrated in vacuo. The residue is purified by column chromatography on silica gel eluting with n-hexane/ethyl acetate (4:1) to give 2.2 g (94% yield) of the title compound as a white solid.

$^1$H-NMR (300 MHz, CDCl$_3$) delta 8.50 (1H, d, J=1.8 Hz), 8.13 (1H, d, J=1.8 Hz), 4.86 (2H, q, J=8.4 Hz), 3.59 (3H, s), 3.38 (3H, s), MS (ESI) m/z: 299 (M+H)$^+$.

<Step-3>:1-(5-chloro-6-(2,2,2-trifluoroethoxy)pyridin-3-yl)ethanone

The title compound is prepared in >99% yield (1.71 g, a white solid) from 5-chloro-N-methoxy-N-methyl-6-(2,2,2-trifluoroethoxy)nicotinamide (1.91 g, 6.40 mmol, Step-2) by the similar manner in Step-3 of Amine-1.

$^1$H-NMR (300 MHz, CDCl$_3$) delta 8.63 (1H, d, J=2.2 Hz), 8.27 (1H, d, J=2.2 Hz), 4.90 (2H, q, J=8.4 Hz), 2.60 (3H, s), MS (ESI) m/z: 254 (M+H)$^+$.

<Step-4>:(R)—N-(1-(5-chloro-6-(2,2,2-trifluoroethoxy)pyridin-3-yl)ethyl)-2-methylpropane-2-sulfinamide (single diastereomer)

The title compound is prepared in 57% yield (0.65 g, a white solid) from 1-(5-chloro-6-(2,2,2-trifluoroethoxy)pyridin-3-yl)ethanone (0.8 g, 3.15 mmol, Step-3) and (R)-2-methylpropane-2-sulfinamide by the similar manner in Step-4 of Amine-1.

$^1$H-NMR (300 MHz, CDCl$_3$) delta 8.02 (1H, d, J=2.2 Hz), 7.71 (1H, d, J=2.2 Hz), 4.82 (2H, q, J=8.4 Hz), 4.59-4.49 (1H, m), 3.36 (1H, d, J=2.9 Hz), 1.53 (3H, d, J=6.6 Hz), 1.24 (9H, s), MS (ESI) m/z: 359 (M+H)$^+$.

<Step-5>:(+)-1-(5-chloro-6-(2,2,2-trifluoroethoxy)pyridin-3-yl)ethanamine hydrochloride (single enantiomer)

The title compound is prepared in 85% yield (0.45 g, a white solid) from (R)—N-(1-(5-chloro-6-(2,2,2-trifluoroethoxy)pyridin-3-yl)ethyl)-2-methylpropane-2-sulfinamide (single diastereomer) (0.65 g, 1.81 mmol, Step-4) by the similar manner in Step-5 of Amine-1.

$^1$H-NMR (300 MHz, DMSO-d$_6$) delta 8.49 (2H, br s), 8.28 (1H, d, J=2.2 Hz), 8.23 (1H, d, J=2.2 Hz), 5.10 (2H, q, J=9.1 Hz), 4.54-4.43 (1H, m), 1.52 (3H, d, J=6.6 Hz), MS (ESI) m/z: 255 (M+H)$^+$.

$[\alpha]_D^{23}$=+5.26 (c=1.28, methanol)

Amine-6:(−)-1-(6-(2,2,2-trifluoroethoxy)pyridin-3-yl)propan-1-amine hydrochloride (single enantiomer)

<Step-1>:1-(6-(2,2,2-trifluoroethoxy)pyridin-3-yl)propan-1-one

The title compound is prepared in 87% yield (0.53 g, colorless oil) from N-methoxy-N-methyl-6-(2,2,2-trifluoroethoxy)nicotinamide (0.70 g, 2.65 mmol, Step-2 of Amine-1) and ethyl magnesium bromide instead of methyl magnesium bromide by the similar manner in Step-3 of Amine-1.

$^1$H-NMR (270 MHz, CDCl$_3$) delta 8.76 (1H, d, J=2.0 Hz), 8.22 (1H, dd, J=8.6, 2.3 Hz), 6.92 (1H, d, J=8.6 Hz), 4.83 (2H, q, J=8.6 Hz), 2.96 (2H, q, J=7.3 Hz), 1.23 (3H, t, J=7.3 Hz), MS (ESI) m/z: 234 (M+H)$^+$.

<Step-2>:(R)-2-methyl-N-(1-(6-(2,2,2-trifluoroethoxy)pyridin-3-yl)propyl)propane-2-sulfinamide (single diastereomer)

The title compound is prepared in 50% yield (0.39 g, colorless oil) from 1-(6-(2,2,2-trifluoroethoxy)pyridin-3-yl)propan-1-one (0.54 g, 2.29 mmol, Step-1) and (R)-2-methylpropane-2-sulfinamide by the similar manner in Step-4 of Amine-1.

$^1$H-NMR (300 MHz, CDCl$_3$) delta 8.07 (1H, d, J=2.6 Hz), 7.62 (1H, dd, J=8.4, 2.6 Hz), 6.86 (1H, d, J=8.4 Hz), 4.74 (2H, q, J=8.4 Hz), 4.26 (1H, m), 2.07 (1H, m), 1.72 (1H, m), 1.22 (9H, s), 0.82 (3H, t, J=7.3 Hz), MS (ESI) m/z: 339 (M+H)$^+$.

<Step-3>:(−)-1-(6-(2,2,2-trifluoroethoxy)pyridin-3-yl)propan-1-amine hydrochloride (single enantiomer)

The title compound is prepared in >99% yield (0.34 g, colorless oil) from (R)-2-methyl-N-(1-(6-(2,2,2-trifluoroethoxy)pyridin-3-yl)propyl)propane-2-sulfinamide (single diastereomer) (0.37 g, 1.81 mmol, Step-2) by the similar manner in Step-5 of Amine-1.

$^1$H-NMR (300 MHz, DMSO-d$_6$) delta 8.62 (2H, br s), 8.30 (1H, d, J=2.2 Hz), 7.99 (1H, dd, J=8.8, 2.6 Hz), 7.07 (1H, d, J=8.8 Hz), 5.00 (2H, q, J=8.8 Hz), 4.17 (1H, m), 1.99 (1H, m), 1.85 (1H, m), 0.74 (3H, t, J=7.3 Hz), MS (ESI) m/z: 235 (M+H)$^+$.

$[\alpha]_D^{23}$=−9.86 (c=1.18, methanol)

Amine-7:(+)-1-(6-(2,2,2-trifluoroethoxy)pyridin-2-yl)ethanamine hydrochloride (single enantiomer)

<Step-1>:6-(2,2,2-trifluoroethoxy)picolinic acid

The title compound is prepared in >99% yield (2.11 g, colorless oil) from 6-chloropicolinic acid (1.5 g, 9.52 mmol) by the similar manner in Step-1 of Amine-1. MS (ESI) m/z: 222 (M+H)$^+$.

<Step-2>:N-methoxy-N-methyl-6-(2,2,2-trifluoroethoxy)picolinamide

The title compound is prepared in 75% yield (1.88 g, colorless oil) from 6-(2,2,2-trifluoroethoxy)picolinic acid (2.11 g, 9.52 mmol, Step-1) by the similar manner in Step-2 of Amine-1.

$^1$H-NMR (300 MHz, CDCl$_3$) delta 7.74 (1H, m), 7.33 (1H, m), 6.95 (1H, d, J=8.4 Hz), 4.79 (2H, q, J=8.4 Hz), 3.74 (3H, s), 3.39 (3H, s), MS (ESI) m/z: 265 (M+H)$^+$.

<Step-3>:1-(6-(2,2,2-trifluoroethoxy)pyridin-2-yl)ethanone

The title compound is prepared in >99% yield (0.57 g, a white solid) from N-methoxy-N-methyl-6-(2,2,2-trifluoroethoxy)picolinamide (0.7 g, 2.65 mmol, Step-2) by the similar manner in Step-3 of Amine-1.

$^1$H-NMR (300 MHz, DMSO-d$_6$) delta 7.99 (1H, m), 7.66 (1H, d, J=7.0 Hz), 7.27 (1H, d, J=8.4 Hz), 5.10 (2H, q, J=9.2 Hz), 2.61 (3H, s), MS (ESI) m/z: 220 (M+H)$^+$.

<Step-4>:(R)-2-methyl-N-(1-(6-(2,2,2-trifluoroethoxy)pyridin-2-yl)ethyl)propane-2-sulfinamide (single diastereomer)

The title compound is prepared in 50% yield (0.35 g, colorless oil) from 1-(6-(2,2,2-trifluoroethoxy)pyridin-2-yl)

ethanone (0.48 g, 2.17 mmol, Step-3) and (R)-2-methylpropane-2-sulfinamide by the similar manner in Step-4 of Amine-1.

$^1$H-NMR (300 MHz, DMSO-d$_6$) delta 7.62 (1H, m), 6.98 (1H, d, J=7.3 Hz), 6.75 (1H, d, J=8.1 Hz), 4.88-4.63 (2H, m), 4.51 (1H, m), 1.49 (3H, d, J=6.6 Hz), 1.25 (9H, s), MS (ESI) m/z: 325 (M+H)$^+$.

<Step-5>:(+)-1-(6-(2,2,2-trifluoroethoxy)pyridin-2-yl)ethanamine hydrochloride (single enantiomer)

The title compound is prepared in >99% yield (0.30 g, a white solid) from (R)-2-methyl-N-(1-(6-(2,2,2-trifluoroethoxy)pyridin-2-yl)ethyl)propane-2-sulfinamide (single diastereomer) (0.35 g, 1.08 mmol, Step-4) by the similar manner in Step-5 of Amine-1.

$^1$H-NMR (300 MHz, DMSO-d$_6$) delta 8.45 (2H, br s), 7.86 (1H, m), 7.19 (1H, d, J=7.3 Hz), 6.96 (1H, d, J=8.1 Hz), 5.17 (2H, dq, J=9.2, 1.1 Hz), 4.46 (1H, q, J=6.6 Hz), 1.48 (3H, d, J=6.6 Hz), MS (ESI) m/z: 221 (M+H)$^+$.

$[\alpha]_D^{23}$=+7.02 (c=1.20, methanol)

Amine-8:(+)-1-(4-(2,2,2-trifluoroethoxy)pyridin-2-yl)ethanamine hydrochloride (single enantiomer)

<Step-1>:4-(2,2,2-trifluoroethoxy)picolinic acid

The title compound is prepared in >99% yield (2.11 g, colorless oil) from 4-chloropicolinic acid (1.5 g, 9.52 mmol) by the similar manner in Step-1 of Amine-1. MS (ESI) m/z: 222 (M+H)$^+$.

<Step-2>:N-methoxy-N-methyl-4-(2,2,2-trifluoroethoxy)picolinamide

The title compound is prepared in 26% yield (0.66 g, colorless oil) from 4-(2,2,2-trifluoroethoxy)picolinic acid (2.1 g, 9.52 mmol, Step-1) by the similar manner in Step-2 of Amine-5.

MS (ESI) m/z: 265 (M+H)$^+$.

<Step-3>:1-(4-(2,2,2-trifluoroethoxy)pyridin-2-yl)ethanone

The title compound is prepared in 21% yield (0.12 g, a white solid) from N-methoxy-N-methyl-4-(2,2,2-trifluoroethoxy)picolinamide (0.66 g, 2.51 mmol, Step-2) by the similar manner in Step-3 of Amine-1.

$^1$H-NMR (300 MHz, CDCl$_3$) delta 8.57 (1H, d, J=5.5 Hz), 7.59 (1H, d, J=2.9 Hz), 7.07 (1H, dd, J=5.5, 2.9 Hz), 4.48 (2H, q, J=7.7 Hz), 2.73 (3H, s), MS (ESI) m/z: 220 (M+H)$^+$.

<Step-4>:(R)-2-methyl-N-(1-(4-(2,2,2-trifluoroethoxy)pyridin-2-yl)ethyl)propane-2-sulfinamide (single diastereomer)

The title compound is prepared in 35% yield (60 mg, colorless oil) from 1-(4-(2,2,2-trifluoroethoxy)pyridin-2-yl)ethanone (120 mg, 0.53 mmol, Step-3) and (R)-2-methylpropane-2-sulfinamide by the similar manner in Step-4 of Amine-1.

$^1$H-NMR (300 MHz, CDCl$_3$) delta 8.44 (1H, d, J=5.9 Hz), 6.89 (1H, d, J=2.6 Hz), 6.75 (1H, dd, J=5.9, 2.6 Hz), 4.68 (1H, d, J=6.2 Hz), 4.53 (1H, t, J=6.2 Hz), 4.40 (2H, q, J=7.7 Hz), 1.51 (3H, d, J=6.6 Hz), 1.26 (9H, s), MS (ESI) m/z: 325 (M+H)$^+$.

<Step-5>:(+)-1-(4-(2,2,2-trifluoroethoxy)pyridin-2-yl)ethanamine hydrochloride (single enantiomer)

The title compound is prepared in 77% yield (40 mg, a white solid) from (R)-2-methyl-N-(1-(4-(2,2,2-trifluoroethoxy)pyridin-2-yl)ethyl)propane-2-sulfinamide (single diastereomer) (60 mg, 0.19 mmol, Step-4) by the similar manner in Step-5 of Amine-1.

$^1$H-NMR (300 MHz, DMSO-d$_6$) delta 8.54 (1H, d, J=5.8 Hz), 8.51 (2H, br s), 7.37 (1H, d, J=2.6 Hz), 7.20 (1H, dd, J=5.8, 2.6 Hz), 4.98 (2H, q, J=8.8 Hz), 4.54-4.42 (1H, m), 1.51 (3H, d, J=7.0 Hz), MS (ESI) m/z: 221 (M+H)$^+$.

$[\alpha]_\alpha^{23}$=+11.37 (c=1.33, methanol)

Amine-9:(+)-1-(3-(trifluoromethoxy)phenyl)ethanamine hydrochloride (single enantiomer)

<Step-1>:(R)-2-methyl-N-(1-(3-(trifluoromethoxy)phenyl)ethyl)propane-2-sulfinamide (single diastereomer)

The title compound is prepared in 83% yield (0.38 g, a white solid) from 1-(3-(trifluoromethoxy)phenyl)ethanone (0.30 g, 1.47 mmol) and (R)-2-methylpropane-2-sulfinamide by the similar manner in Step-4 of Amine-1.

$^1$H-NMR (300 MHz, CDCl$_3$) delta 7.38 (1H, t, J=7.7 Hz), 7.33-7.27 (1H, m), 7.24-7.19 (1H, m), 7.17-7.15 (1H, m), 4.62-4.53 (1H, m), 3.43 (1H, br s), 1.52 (3H, d, J=7.0 Hz), 1.25 (9H, s), MS (ESI) m/z: 310 (M+H)$^+$.

<Step-2>:(+)-1-(3-(trifluoromethoxy)phenyl)ethanamine hydrochloride (single enantiomer The title compound is prepared in 94% yield (0.28 g, a white solid) from (R)-2-methyl-N-(1-(3-(trifluoromethoxy)phenyl)ethyl)propane-2-sulfinamide (single diastereomer) (0.38 g, 1.22 mmol, Step-1) by the similar manner in Step-5 of Amine-1.

$^1$H-NMR (300 MHz, DMSO-d$_6$) delta 8.57 (2H, br s), 7.63-7.55 (3H, m), 7.47-7.34 (1H, m), 4.55-4.41 (1H, m), 1.52 (3H, d, J=7.0 Hz), MS (ESI) m/z: 206 (M+H)$^+$.

$[\alpha]_D^{23}$=+3.02 (c=1.21, methanol)

Amine-10:(+)-1-(4-(trifluoromethoxy)phenyl)ethanamine hydrochloride (single enantiomer)

<Step-1>: (R)-2-methyl-N-(1-(4-(trifluoromethoxy)phenyl)ethyl)propane-2-sulfinamide (single diastereomer)

The title compound is prepared in 77% yield (0.35 g, colorless oil) from 1-(4-(trifluoromethoxy)phenyl)ethanone (0.30 g, 1.47 mmol) and (R)-2-methylpropane-2-sulfinamide by the similar manner in Step-4 of Amine-1.

$^1$H-NMR (300 MHz, CDCl$_3$) delta 7.42-7.35 (2H, m), 7.24-7.16 (2H, m), 4.64-4.52 (1H, m), 3.40 (1H, br s), 1.51 (3H, d, J=7.0 Hz), 1.24 (9H, s), MS (ESI) m/z: 310 (M+H)$^+$.

<Step-2>:(+)-1-(4-(trifluoromethoxy)phenyl)ethanamine hydrochloride (single enantiomer The title compound is prepared in 86% yield (0.24 g, a white solid) from (R)-2-methyl-N-(1-(4-(trifluoromethoxy)phenyl)ethyl)propane-2-sulfinamide (single diastereomer) (0.35 g, 1.14 mmol, Step-1) by the similar manner in Step-5 of Amine-1.

¹H-NMR (300 MHz, DMSO-d₆) delta 8.38 (2H, br s), 7.67-7.61 (2H, m), 7.49-7.43 (2H, m), 4.52-4.42 (1H, m), 1.51 (3H, d, J=7.0 Hz), MS (ESI) m/z: 206 (M+H)⁺.
$[\alpha]_D^{24}$=+2.79 (c=1.18, methanol)

Amine-11: (+)-1-(2-(2,2,2-trifluoroethoxy)pyridin-4-yl)ethanamine hydrochloride (single enantiomer)

<Step-1>:2-(2,2,2-trifluoroethoxy)isonicotinic acid

The title compound is prepared in >99% yield (2.08 g, colorless oil) from 2-chloroisonicotinic acid (1.50 g, 9.52 mmol) by the similar manner in Step-1 of Amine-1.
MS (ESI) m/z: 222 (M+H)⁺.

<Step-2>:N-methoxy-N-methyl-2-(2,2,2-trifluoroethoxy)isonicotinamide

The title compound is prepared in 52% yield (1.30 g, colorless oil) from 2-(2,2,2-trifluoroethoxy)isonicotinic acid (2.08 g, 9.42 mmol, Step-1) by the similar manner in Step-2 of Amine-5.
¹H-NMR (300 MHz, CDCl₃) delta 8.19 (1H, d, J=5.1 Hz), 7.16 (1H, m), 7.07 (1H, s), 4.77 (2H, q, J=8.4 Hz), 3.55 (3H, s), 3.35 (3H, s), MS (ESI) m/z: 265 (M+H)⁺.

<Step-3>:1-(2-(2,2,2-trifluoroethoxy)pyridin-4-yl)ethanone

The title compound is prepared in 63% yield (0.68 g, a white solid) from N-methoxy-N-methyl-2-(2,2,2-trifluoroethoxy)isonicotinamide (1.3 g, 4.92 mmol, Step-2) by the similar manner in Step-3 of Amine-1.
¹H-NMR (300 MHz, DMSO-d₆) delta 8.38 (1H, d, J=5.5 Hz), 7.48 (1H, dd, J=5.1, 1.5 Hz), 7.43 (1H, s), 5.05 (2H, q, J=9.2 Hz), 2.61 (3H, s), MS (ESI) m/z: 220 (M+H)⁺.

<Step-4>:(R)-2-methyl-N-(1-(2-(2,2,2-trifluoroethoxy)pyridin-4-yl)ethyl)propane-2-sulfinamide (single diastereomer)

The title compound is prepared in 75% yield (0.52 g, a white solid) from 1-(2-(2,2,2-trifluoroethoxy)pyridin-4-yl)ethanone (0.47 g, 2.14 mmol, Step-3) and (R)-2-methylpropane-2-sulfinamide by the similar manner in Step-4 of Amine-1.
¹H-NMR (300 MHz, DMSO-d₆) delta 8.11 (1H, d, J=5.5 Hz), 7.13 (1H, d, J=5.1 Hz), 7.02 (1H, s), 5.87 (1H, d, J=8.1 Hz), 4.97 (2H, q, J=9.2 Hz), 4.37 (1H, m), 1.36 (3H, d, J=7.0 Hz), 1.11 (9H, s), MS (ESI) m/z: 325 (M+H)⁺.

<Step-5>:(+)-1-(2-(2,2,2-trifluoroethoxy)pyridin-4-yl)ethanamine hydrochloride (single enantiomer)

The title compound is prepared in >99% yield (0.44 g, a white solid) from (R)-2-methyl-N-(1-(2-(2,2,2-trifluoroethoxy)pyridin-4-yl)ethyl)propane-2-sulfinamide (single diastereomer) (0.52 g, 1.60 mmol, Step-4) by the similar manner in Step-5 of Amine-1.
¹H-NMR (300 MHz, DMSO-d₆) delta 8.75 (2H, br s), 8.23 (1H, d, J=5.1 Hz), 7.27 (1H, d, J=5.5 Hz), 7.14 (1H, s), 5.00 (2H, q, J=9.2 Hz), 4.42 (1H, m), 1.48 (3H, d, J=6.6 Hz), MS (ESI) m/z: 221 (M+H)⁺.
$[\alpha]_D^{22}$=+4.56 (c=1.24, methanol)

Amine-12: (−)-1-(5-fluoro-6-(2,2,2-trifluoroethoxy)pyridin-3-yl)ethanamine hydrochloride (single enantiomer)

<Step-1>:2-chloro-5-fluoro-6-(2,2,2-trifluoroethoxy)nicotinic acid

A mixture of 2,6-dichloro-5-fluoronicotinic acid (1.0 g, 4.8 mmol), 2,2,2-trifluoroethanol (0.69 mL, 9.5 mmol) and sodium hydroxide (0.57 g, 14.3 mmol) in water (24 mL) is stirred at 80° C. for 40 hours. After cooling to 0° C., the mixture is acidified with conc. hydrochloric acid (pH 2). The resulting white precipitate is collected by filtration and dried to give 1.05 g (80% yield) of the title compound as a white solid.
MS (ESI) m/z: 274 (M+H)⁺.

<Step-2>:2-chloro-5-fluoro-N-methoxy-N-methyl-6-(2,2,2-trifluoroethoxy)nicotinamide The title compound is prepared in 30% yield (0.36 g, colorless oil) from 2-chloro-5-fluoro-6-(2,2,2-trifluoroethoxy)nicotinic acid (1.05 g, 3.83 mmol, Step-1) by the similar manner in Step-2 of Amine-5.
¹H-NMR (300 MHz, CDCl₃) delta 7.46 (1H, d, J=8.4 Hz), 4.82 (2H, q, J=8.1 Hz), 3.53 (3H, s), 3.36 (3H, s), MS (ESI) m/z: 317 (M+H)⁺.

<Step-3>:1-(2-chloro-5-fluoro-6-(2,2,2-trifluoroethoxy)pyridin-3-yl)ethanone

The title compound is prepared in 75% yield (0.23 g, colorless oil) from 2-chloro-5-fluoro-N-methoxy-N-methyl-6-(2,2,2-trifluoroethoxy)nicotinamide (0.36 g, 1.14 mmol, Step-2) by the similar manner in Step-3 of Amine-1.
¹H-NMR (300 MHz, CDCl₃) delta 7.84 (1H, d, J=9.2 Hz), 4.86 (2H, q, J=8.1 Hz), 2.70 (3H, s).

<Step-4>:1-(5-fluoro-6-(2,2,2-trifluoroethoxy)pyridin-3-yl)ethanone

A mixture of 1-(2-chloro-5-fluoro-6-(2,2,2-trifluoroethoxy)pyridin-3-yl)ethanone (0.23 g, 0.86 mmol, Step-3) and triethylamine (0.17 mL, 1.20 mmol) in ethanol (9 mL) is stirred at room temperature for 1 hour. Then 10% palladium on carbon (0.03 g, 0.28 mmol) is added to the mixture. The mixture is stirred at room temperature under a balloon of hydrogen gas for 5 hours. After filtration through a pad of celite, the filtrate is concentrated under reduced pressure. The residue is purified by column chromatography on silica gel eluting with n-hexane/ethyl acetate (5:1) to give 0.15 g (76% yield) of the title compound as colorless oil.
¹H-NMR (300 MHz, CDCl₃) delta 8.51 (1H, d, J=1.8 Hz), 7.94 (1H, dd, J=10.3, 1.8 Hz), 4.89 (2H, q, J=8.4 Hz), 2.59 (3H, s).

<Step-5>:(R)—N-(1-(5-fluoro-6-(2,2,2-trifluoroethoxy)pyridin-3-yl)ethyl)-2-methylpropane-2-sulfinamide (single diastereomer)

The title compound is prepared in 78% yield (0.17 g, a white solid) from 1-(5-fluoro-6-(2,2,2-trifluoroethoxy)pyridin-3-yl)ethanone (0.15 g, 0.65 mmol, Step-4) and (R)-2-methylpropane-2-sulfinamide by the similar manner in Step-4 of Amine-1.

¹H-NMR (300 MHz, CDCl₃) delta 7.89 (1H, d, J=2.2 Hz), 7.44 (1H, dd, J=10.7, 2.2 Hz), 4.82 (2H, q, J=8.4 Hz), 4.55 (1H, m), 1.52 (3H, d, J=6.2 Hz), 1.23 (9H, s), MS (ESI) m/z: 343 (M+H)⁺.

<Step-6>:(−)-1-(5-fluoro-6-(2,2,2-trifluoroethoxy) pyridin-3-yl)ethanamine hydrochloride (single enantiomer)

The title compound is prepared in 94% yield (0.13 g, a white solid) from (R)—N-(1-(5-fluoro-6-(2,2,2-trifluoroethoxy)pyridin-3-yl)ethyl)-2-methylpropane-2-sulfinamide (single diastereomer) (0.17 g, 0.50 mmol, Step-5) by the similar manner in Step-5 of Amine-1.

¹H-NMR (300 MHz, DMSO-d₆) delta 8.52 (2H, br s), 8.15 (1H, d, J=1.8 Hz), 8.05 (1H, dd, J=11.4, 1.8 Hz), 5.11 (2H, q, J=8.8 Hz), 4.48 (1H, m), 1.51 (3H, d, J=7.0 Hz), MS (ESI) m/z: 239 (M+H)⁺.

$[\alpha]_D^{22}$=−1.11 (c=1.25, methanol)

Amine-13:(+)-1-(2-methyl-6-(2,2,2-trifluoroethoxy) pyridin-4-yl)ethanamine hydrochloride (single enantiomer)

<Step-1>:2-hydroxy-N-methoxy-N,6-dimethylisonicotinamide

The title compound is prepared in 43% yield (0.27 g, a white solid) from 2-hydroxy-6-methylisonicotinic acid (0.50 g, 3.27 mmol) by the similar manner in Step-2 of Amine-5.

¹H-NMR (300 MHz, CDCl₃) delta 12.96 (1H, br s), 6.57 (1H, s), 6.20 (1H, s), 3.62 (3H, s), 3.33 (3H, s), 2.39 (3H, s), MS (ESI) m/z: 197 (M+H)⁺.

<Step-2>:1-(2-hydroxy-6-methylpyridin-4-yl)ethanone

The title compound is prepared in 39% yield (82 mg, a white solid) from 2-hydroxy-N-methoxy-N,6-dimethylisonicotinamide (270 mg, 1.39 mmol, Step-1) by the similar manner in Step-3 of Amine-1.

¹H-NMR (300 MHz, CDCl₃) delta 12.80 (1H, br s), 6.91-6.89 (1H, m), 6.53-6.51 (1H, m), 2.54 (3H, s), 2.41 (3H, s), MS (ESI) m/z: 152 (M+H)⁺.

<Step-3>:1-(2-methyl-6-(2,2,2-trifluoroethoxy)pyridin-4-yl)ethanone

A mixture of 1-(2-hydroxy-6-methylpyridin-4-yl)ethanone (82 mg, 0.542 mmol, Step-2), 2,2,2-trifluoroethyl trifluoromethanesulfonate (86 microL, 0.60 mmol) and cesium carbonate (350 mg, 1.09 mmol) in DMF (5 mL) is stirred at room temperature for 1.5 hours. The reaction mixture is poured into saturated aqueous sodium hydrogen carbonate (10 mL) and extracted with ethyl acetate (30 mL). The organic layer is washed with saturated aqueous sodium hydrogen carbonate (10 mL×2) and dried over sodium sulfate, and concentrated in vacuo. The residue is purified by column chromatography on silica gel eluting with n-hexane/ethyl acetate (1:1) to give 44 mg (35% yield) of the title compound as a white solid.

¹H-NMR (300 MHz, CDCl₃) delta 7.26 (1H, s), 7.10 (1H, s), 4.79 (2H, q, J=8.4 Hz), 2.58 (3H, s), 2.51 (3H, s), MS (ESI) m/z: 234 (M+H)⁺.

<Step-4>:(R)-2-methyl-N-(1-(2-methyl-6-(2,2,2-trifluoroethoxy)pyridin-4-yl)ethyl)propane-2-sulfinamide (single diastereomer)

The title compound is prepared in 78% yield (50 mg, colorless oil) from 1-(2-methyl-6-(2,2,2-trifluoroethoxy)pyridin-4-yl)ethanone (44 mg, 0.19 mmol, Step-3) and (R)-2-methylpropane-2-sulfinamide by the similar manner in Step-4 of Amine-1.

¹H-NMR (300 MHz, CDCl₃) delta 6.78 (1H, s), 6.63 (1H, s), 4.75 (2H, q, J=8.8 Hz), 4.50-4.41 (1H, m), 3.41 (1H, d, J=2.9 Hz), 2.43 (3H, s), 1.48 (3H, d, J=6.6 Hz), 1.25 (9H, s), MS (ESI) m/z: 339 (M+H)⁺.

<Step-5>:(+)-1-(2-methyl-6-(2,2,2-trifluoroethoxy) pyridin-4-yl)ethanamine hydrochloride (single enantiomer)

The title compound is prepared in 75% yield (34 mg, a white solid) from (R)-2-methyl-N-(1-(2-methyl-6-(2,2,2-trifluoroethoxy)pyridin-4-yl)ethyl)propane-2-sulfinamide (single diastereomer) (50 mg, 0.15 mmol, Step-4) by the similar manner in Step-5 of Amine-1.

¹H-NMR (300 MHz, DMSO-d₆) delta 8.33 (2H, br s), 7.07 (1H, s), 6.88 (1H, s), 5.00 (2H, q, J=9.1 Hz), 4.51-4.32 (1H, m), 2.43 (3H, s), 1.46 (3H, d, J=6.6 Hz), MS (ESI) m/z: 235 (M+H)⁺.

$[\alpha]_D^{23}$=+7.76 (c=1.17, methanol)

Amine-14:(+)-1-(6-(2,2-difluoroethoxy)-5-methylpyridin-3-yl)ethanamine hydrochloride (single enantiomer)

<Step-1>:6-(2,2-difluoroethoxy)-5-methylnicotinic acid

The title compound is prepared in 73% yield (1.02 g, an off-white solid) from 6-fluoro-5-methylnicotinic acid (1.00 g, 6.45 mmol) and 2,2-difluoroethanol (1.06 g, 12.9 mmol) by the similar manner in Step-1 of Amine-1.

¹H-NMR (300 MHz, DMSO-d₆) delta 13.09 (1H, br s), 8.56 (1H, d, J=2.2 Hz), 8.07 (1H, d, J=2.2 Hz), 6.42 (1H, tt, J=54.3, 3.7 Hz), 4.66 (2H, td, J=14.7, 3.7 Hz), 2.21 (3H, s), MS (ESI) m/z: 218 (M+H)⁺.

<Step-2>:6-(2,2-difluoroethoxy)-N-methoxy-N,5-dimethylnicotinamide

The title compound is prepared in 98% yield (1.20 g, a white solid) from 6-(2,2-difluoroethoxy)-5-methylnicotinic acid (1.02 g, 4.70 mmol, Step-1) by the similar manner in Step-2 of Amine-1.

¹H-NMR (300 MHz, CDCl₃) delta 8.43 (1H, d, J=2.2 Hz), 7.84 (1H, br s), 6.16 (1H, tt, J=55.8, 4.4 Hz), 4.60 (2H, td, J=13.2, 4.4 Hz), 3.58 (3H, s), 3.37 (3H, s), 2.25 (3H, s), MS (ESI) m/z: 261 (M+H)⁺.

<Step-3>:1-(6-(2,2-difluoroethoxy)-5-methylpyridin-3-yl)ethanone

The title compound is prepared in >99% yield (0.99 g, a white solid) from 6-(2,2-difluoroethoxy)-N-methoxy-N,5-dimethylnicotinamide (1.20 g, 4.61 mmol, Step-2) by the similar manner in Step-3 of Amine-1.

¹H-NMR (270 MHz, CDCl₃) delta 8.58 (1H, d, J=2.0 Hz), 8.01-8.00 (1H, m), 6.16 (1H, tt, J=55.4, 4.0 Hz), 4.63 (2H, td, J=13.2, 4.0 Hz), 2.57 (3H, s), 2.26 (3H, s), MS (ESI) m/z: 216 (M+H)⁺.

<Step-4>:(R)—N-(1-(6-(2,2-difluoroethoxy)-5-methylpyridin-3-yl)ethyl)-2-methylpropane-2-sulfinamide (single diastereomer)

The title compound is prepared in 82% yield (1.22 g, colorless oil) from 1-(6-(2,2-difluoroethoxy)-5-methylpyridin-3-yl)ethanone (0.99 g, 4.61 mmol, Step-3) and (R)-2-methylpropane-2-sulfinamide by the similar manner in Step-4 of Amine-1.
¹H-NMR (300 MHz, CDCl₃) delta 7.97 (1H, d, J=2.2 Hz), 7.43 (1H, br s), 6.14 (1H, tt, J=55.8, 4.4 Hz), 4.59-4.46 (3H, m), 3.32 (1H, br s), 2.22 (3H, s), 1.50 (3H, d, J=6.6 Hz), 1.23 (9H, s), MS (ESI) m/z: 321 (M+H)⁺.

<Step-5>:(+)-1-(6-(2,2-difluoroethoxy)-5-methylpyridin-3-yl)ethanamine hydrochloride (single enantiomer)

The title compound is prepared in 94% yield (0.91 g, a white solid) from (R)—N-(1-(6-(2,2-difluoroethoxy)-5-methylpyridin-3-yl)ethyl)-2-methylpropane-2-sulfinamide (single diastereomer) (1.22 g, 3.80 mmol, Step-4) by the similar manner in Step-5 of Amine-1.
¹H-NMR (270 MHz, DMSO-d₆) delta 8.58 (2H, br s), 8.13 (1H, d, J=2.0 Hz), 7.82 (1H, br s), 6.40 (1H, tt, J=54.7, 3.3 Hz), 4.60 (2H, td, J=15.2, 3.3 Hz), 4.42-4.36 (1H, m), 2.19 (3H, s), 1.52 (3H, d, J=6.6 Hz), MS (ESI) m/z: 217 (M+H)⁺.
$[\alpha]_D^{26}$=+3.09 (c=1.18, methanol)

Amine-15:N-(5-(aminomethyl)-2-(2,2,2-trifluoroethoxy)pyridin-3-yl)acetamide hydrochloride <Step-1>:methyl 5-chloro-6-(2,2,2-trifluoroethoxy)nicotinate A mixture of 5-chloro-6-(2,2,2-trifluoroethoxy)nicotinic acid (5.6 g, 21.9 mmol, Step-1 of Amine-5) and sulfuric acid (0.12 mL, 2.25 mmol) in methanol (40 mL) is refluxed with stirring for 2 days. After removal of the solvent, the residue is poured into 2M sodium hydroxide (100 mL) and extracted with ethyl acetate and dried over sodium sulfate and concentrated in vacuo to give 3.28 g (56% yield) of the title compound as a white solid.
¹H-NMR (300 MHz, CDCl₃) delta 8.68 (1H, d, J=2.2 Hz), 8.30 (1H, d, J=2.2 Hz), 4.88 (2H, q, J=8.4 Hz), 3.94 (3H, s), MS (ESI) m/z: 270 (M+H)⁺.

<Step-2>:methyl 5-acetamido-6-(2,2,2-trifluoroethoxy)nicotinate

A mixture of methyl 5-chloro-6-(2,2,2-trifluoroethoxy) nicotinate (3.08 g, 11.4 mmol, Step-1), acetamide (0.70 mL, 13.7 mmol), tris(dibenzylideneacetone)dipalladium(0) (0.73 g, 0.80 mmol), potassium phosphate (7.27 g, 34.3 mmol) and 2-di-tert-butylphosphino-2',4',6'-triisopropylbiphenyl (0.34 g, 0.800 mmol) in tert-butyl alcohol (114 mL) is stirred for 3 hours at 110° C. The reaction mixture is poured into water and extricated with ethyl acetate and dried over sodium sulfate and concentrated in vacuo. The residue is purified by column chromatography on silica gel eluting with n-hexane/ethyl acetate (3:1 to 1:1) to give 0.59 g (18% yield) of the title compound as a white solid.
MS (ESI) m/z: 293 (M+H)⁺.

<Step-3>:N-(5-(hydroxymethyl)-2-(2,2,2-trifluoroethoxy)pyridin-3-yl)acetamide

The title compound is prepared in 39% yield (0.21 g, a white solid) from methyl 5-acetamido-6-(2,2,2-trifluoroethoxy)nicotinate (0.59 g, 2.00 mmol, Step-2) by the similar manner in Step-3 of Amine-4.
¹H-NMR (300 MHz, DMSO-d₆) delta 9.37 (1H, s), 8.24 (1H, s), 7.82 (1H, s), 5.25 (1H, t, J=5.9 Hz), 5.04 (2H, q, J=9.2 Hz), 4.43 (2H, d, J=5.5 Hz), 2.10 (3H, s), MS (ESI) m/z: 265 (M+H)⁺.

<Step-4>:N-(5-(chloromethyl)-2-(2,2,2-trifluoroethoxy)pyridin-3-yl)acetamide

The title compound is prepared in >99% yield (0.22 g, a white solid) from N-(5-(hydroxymethyl)-2-(2,2,2-trifluoroethoxy)pyridin-3-yl)acetamide (0.21 g, 0.78 mmol, Step-3) by the similar manner in Step-4 of Amine-4.
MS (ESI) m/z: 283 (M+H)⁺.

<Step-5>:N-(5-(azidomethyl)-2-(2,2,2-trifluoroethoxy)pyridin-3-yl)acetamide

The title compound is prepared in >99% yield (0.22 g, a white solid) from N-(5-(chloromethyl)-2-(2,2,2-trifluoroethoxy)pyridin-3-yl)acetamide (0.22 g, 0.78 mmol, Step-4) by the similar manner in Step-5 of Amine-4.
MS (ESI) m/z: 290 (M+H)⁺.

<Step-6>:N-(5-(aminomethyl)-2-(2,2,2-trifluoroethoxy)pyridin-3-yl)acetamide hydrochloride The title compound is prepared in 82% yield (0.22 g, a white solid) from N-(5-(azidomethyl)-2-(2,2,2-trifluoroethoxy)pyridin-3-yl)acetamide (0.22 g, 0.78 mmol, Step-5) by the similar manner in Step-6 of Amine-4.
¹H-NMR (300 MHz, DMSO-d₆) delta 9.52 (1H, s), 8.41 (1H, d, J=1.8 Hz), 8.38 (2H, br s), 8.03 (1H, d, J=1.8 Hz), 5.08 (2H, q, J=9.2 Hz), 3.99 (2H, s), 2.12 (3H, s).

Amine-16:1-(3-(2,2,2-trifluoroethoxy)phenyl)ethanamine hydrochloride (single enantiomer)

<Step-1>:1-(3-(2,2,2-trifluoroethoxy)phenyl)ethanone

The title compound is prepared in 84% yield (0.67 g, a white solid) from 1-(3-hydroxyphenyl)ethanone (0.5 g, 3.67 mmol) by the similar manner in Step-3 of Amine-13.
¹H-NMR (300 MHz, CDCl₃) delta 7.64 (1H, dd, J=7.7, 1.1 Hz), 7.53-7.46 (1H, m), 7.43 (1H, t, J=7.7 Hz), 7.18 (1H, ddd, J=7.7, 2.9, 1.1 Hz), 4.41 (2H, q, J=8.1 Hz), 2.61 (3H, s), MS (ESI) m/z: 219 (M+H)⁺.

<Step-2>:(R)-2-methyl-N-(1-(3-(2,2,2-trifluoroethoxy)phenyl)ethyl)propane-2-sulfinamide (single diastereomer)

The title compound is prepared in 72% yield (0.71 g, colorless oil) from 1-(3-(2,2,2-trifluoroethoxy)phenyl)ethanone (0.67 g, 3.08 mmol, Step-1) and (R)-2-methylpropane-2-sulfinamide by the similar manner in Step-4 of Amine-1.
¹H-NMR (300 MHz, CDCl₃) delta 7.30 (1H, t, J=8.1 Hz), 7.08-7.03 (1H, m), 7.01-6.96 (1H, m), 6.86 (1H, ddd, J=8.1, 2.6, 1.1 Hz), 4.57-4.48 (1H, m), 4.36 (2H, q, J=8.1 Hz), 3.42 (1H, br s), 1.51 (3H, d, J=7.0 Hz), 1.24 (9H, s), MS (ESI) m/z: 324 (M+H)$^+$.

<Step-3>:1-(3-(2,2,2-trifluoroethoxy)phenyl)ethanamine hydrochloride (single enantiomer)

The title compound is prepared in 84% yield (0.473 g, a pale-yellow solid) from (R)-2-methyl-N-(1-(3-(2,2,2-trifluoroethoxy)phenyl)ethyl)propane-2-sulfinamide (single diastereomer) (0.71 g, 2.21 mmol, Step-2) by the similar manner in Step-5 of Amine-1.

$^1$H-NMR (300 MHz, DMSO-d$_6$) delta 8.35 (2H, br s), 7.40 (1H, t, J=7.9 Hz), 7.24-7.21 (1H, m), 7.18-7.13 (1H, m), 7.08 (1H, dd, J=8.9, 2.6 Hz), 4.73 (2H, q, J=8.9 Hz), 4.44-4.31 (1H, m), 1.48 (3H, d, J=6.6 Hz), MS (ESI) m/z: 220 (M+H)$^+$.

Amine-17:1-(5-methyl-6-(2,2,2-trifluoroethoxy)pyridin-3-yl)ethanamine hydrochloride (single enantiomer)

<Step-1>:5-methyl-6-(2,2,2-trifluoroethoxy)nicotinic acid

The title compound is prepared in >99% yield (2.27 g, yellow oil) from 6-fluoro-5-methylnicotinic acid (1.5 g, 9.67 mmol) by the similar manner in Step-1 of Amine-1.

MS (ESI) m/z: 234 (M–H)$^-$.

<Step-2>:N-methoxy-N,5-dimethyl-6-(2,2,2-trifluoroethoxy)nicotinamide

The title compound is prepared in 76% yield (2.03 g, colorless oil) from 5-methyl-6-(2,2,2-trifluoroethoxy)nicotinic acid (2.27 g, 9.67 mmol, Step-1) by the similar manner in Step-2 of Amine-5.

$^1$H-NMR (300 MHz, CDCl$_3$) delta 8.43 (1H, d, J=2.2 Hz), 7.86 (1H, m), 4.82 (2H, q, J=8.4 Hz), 3.60 (3H, s), 3.38 (3H, s), 2.26 (3H, s), MS (ESI) m/z: 279 (M+H)$^+$.

<Step-3>:1-(5-methyl-6-(2,2,2-trifluoroethoxy)pyridin-3-yl)ethanone

The title compound is prepared in 86% yield (1.47 g, a white solid) from N-methoxy-N,5-dimethyl-6-(2,2,2-trifluoroethoxy)nicotinamide (2.03 g, 7.31 mmol, Step-2) by the similar manner in Step-3 of Amine-1.

$^1$H-NMR (300 MHz, CDCl$_3$) delta 8.59 (1H, d, J=2.0 Hz), 8.03 (1H, d, J=2.2 Hz), 4.84 (2H, q, J=8.4 Hz), 2.57 (3H, s), 2.27 (3H, s), MS (ESI) m/z: 234 (M+H)$^+$.

<Step-4>:(R)-2-methyl-N-(1-(5-methyl-6-(2,2,2-trifluoroethoxy)pyridin-3-yl)ethyl)propane-2-sulfinamide (single diastereomer)

The title compound is prepared in 79% yield (1.70 g, colorless oil) from 1-(5-methyl-6-(2,2,2-trifluoroethoxy)pyridin-3-yl)ethanone (1.47 g, 6.32 mmol, Step-3) and (R)-2-methylpropane-2-sulfinamide by the similar manner in Step-4 of Amine-1.

$^1$H-NMR (300 MHz, CDCl$_3$) delta 7.94 (1H, d, J=2.2 Hz), 7.45 (1H, d, J=2.2 Hz), 4.76 (2H, q, J=8.8 Hz), 4.56-4.43 (1H, m), 3.32 (1H, d, J=2.6 Hz), 2.24 (3H, s), 1.51 (3H, d, J=6.6 Hz), 1.23 (9H, s), MS (ESI) m/z: 339 (M+H)$^+$.

<Step-5>:1-(5-methyl-6-(2,2,2-trifluoroethoxy)pyridin-3-yl)ethanamine hydrochloride (single enantiomer)

The title compound is prepared in 94% yield (1.27 g, a white solid) from (R)-2-methyl-N-(1-(5-methyl-6-(2,2,2-trifluoroethoxy)pyridin-3-yl)ethyl)propane-2-sulfinamide (single diastereomer) (1.70 g, 5.01 mmol, Step-4) by the similar manner in Step-5 of Amine-1.

$^1$H-NMR (300 MHz, DMSO-d$_6$) delta 8.56 (2H, br s), 8.16 (1H, d, J=2.0 Hz), 7.87 (1H, d, J=2.0 Hz), 5.03 (2H, q, J=9.2 Hz), 4.50-4.28 (1H, m), 2.20 (3H, s), 1.50 (3H, d, J=7.0 Hz), MS (ESI) m/z: 235 (M+H)$^+$.

Amine-18:1-(4-(2,2,2-trifluoroethoxy)phenyl)ethanamine hydrochloride (single enantiomer

<Step-1>:1-(4-(2,2,2-trifluoroethoxy)phenyl)ethanone

The title compound is prepared in 81% yield (0.65 g, a white solid) from 1-(4-hydroxyphenyl)ethanone (0.5 g, 3.67 mmol) by the similar manner in Step-3 of Amine-13.

$^1$H-NMR (300 MHz, CDCl$_3$) delta 7.97 (2H, d, J=8.8 Hz), 6.99 (2H, d, J=8.8 Hz), 4.42 (2H, q, J=7.7 Hz), 2.58 (3H, s), MS (ESI) m/z: 219 (M+H)$^+$.

<Step-2>:(R)-2-methyl-N-(1-(4-(2,2,2-trifluoroethoxy)phenyl)ethyl)propane-2-sulfinamide (single diastereomer)

The title compound is prepared in 76% yield (0.73 g, colorless oil) from 1-(4-(2,2,2-trifluoroethoxy)phenyl)ethanone (0.65 g, 2.99 mmol, Step-1) and (R)-2-methylpropane-2-sulfinamide by the similar manner in Step-4 of Amine-1.

$^1$H-NMR (300 MHz, CDCl$_3$) delta 7.35-7.28 (2H, m), 6.96-6.88 (2H, m), 4.57-4.46 (1H, m), 4.35 (2H, q, J=8.0 Hz), 3.32 (1H, br s), 1.49 (3H, d, J=6.6 Hz), 1.23 (9H, s), MS (ESI) m/z: 324 (M+H)$^+$.

<Step-3>:1-(4-(2,2,2-trifluoroethoxy)phenyl)ethanamine hydrochloride (single enantiomer)

The title compound is prepared in 86% yield (0.50 g, a white solid) from (R)-2-methyl-N-(1-(4-(2,2,2-trifluoroethoxy)phenyl)ethyl)propane-2-sulfinamide (single diastereomer) (0.73 g, 2.26 mmol, Step-2) by the similar manner in Step-5 of Amine-1.

$^1$H-NMR (300 MHz, DMSO-d$_6$) delta 8.43 (2H, br s), 7.48 (2H, d, J=8.6 Hz), 7.11 (2H, d, J=8.6 Hz), 4.79 (2H, q, J=8.8 Hz), 4.48-4.31 (1H, m), 1.49 (3H, d, J=7.0 Hz), MS (ESI) m/z: 220 (M+H)$^+$.

Amine-19: (5-chloro-6-(2,2,2-trifluoroethoxy)pyridin-3-yl)methanamine

<Step-1>:methyl 5-chloro-6-(2,2,2-trifluoroethoxy)nicotinate

The title compound is prepared in 95% yield (350 mg, a white solid) from 5-chloro-6-(2,2,2-trifluoroethoxy)nicotinic acid (350 mg, 1.4 mmol, Step-1 of Amine-5) by the similar manner in Step-2 of Amine-27.

¹H-NMR (300 MHz, CDCl₃) delta 8.68 (1H, d, J=1.5 Hz), 8.29 (1H d, J=1.5 Hz), 4.88 (q, J=8.1 Hz), 3.94 (3H, s).

<Step-2>: (5-chloro-6-(2,2,2-trifluoroethoxy)pyridin-3-yl)methanol

The title compound is prepared in 78% yield (210 mg, a white solid) from methyl 5-chloro-6-(2,2,2-trifluoroethoxy)nicotinate (300 mg, 1.1 mmol, Step-1) and diisobutylalminium hydride (1.0 M in hexane, 2.4 mL, 2.4 mmol) by the similar manner in Step-3 of Amine-4.
¹H-NMR (300 MHz, CDCl₃) delta 8.00 (1H, d, J=2.2 Hz), 7.76 (1H, d, J=2.2 Hz), 4.82 (2H, q, J=8.8 Hz), 4.66 (2H, s), MS (ESI) m/z: 242 (M+H)⁺.

<Step-3>:2-((5-chloro-6-(2,2,2-trifluoroethoxy)pyridin-3-yl)methyl)isoindoline-1,3-dione The title compound is prepared in 64% yield (210 mg, a white solid) from (5-chloro-6-(2,2,2-trifluoroethoxy)pyridin-3-yl)methanol (211 mg, 0.87 mmol, Step-2) by the similar manner in Step-3 of Amine-24.
¹H-NMR (300 MHz, CDCl₃) delta 8.15 (1H, s), 7.90-7.80 (3H, m), 7.75-7.70 (2H, m), 4.79 (2H, q, J=8.1 Hz), 4.78 (2H, s), MS (ESI) m/z: 371 (M+H)⁺.

<Step-4>:(5-chloro-6-(2,2,2-trifluoroethoxy)pyridin-3-yl)methanamine

The title compound is prepared in >99% yield (150 mg, clear colorless oil) from 2-((5-chloro-6-(2,2,2-trifluoroethoxy)pyridin-3-yl)methyl)isoindoline-1,3-dione (210 mg, 0.56 mmol, Step-3) by the similar manner in Step-4 of Amine-24.
¹H-NMR (300 MHz, CDCl₃) delta 7.96 (1H, s), 7.75 (1H, s), 4.81 (2H, q, J=8.8 Hz), 3.84 (2H, s), 1.38 (2H, br s), MS (ESI) m/z: 241 (M+H)⁺.

Amine-20:1-(4-fluoro-3-(2,2,2-trifluoroethoxy)phenyl)ethanamine hydrochloride (single enantiomer)

<Step-1>:4-fluoro-3-hydroxy-N-methoxy-N-methylbenzamide

The title compound is prepared in 55% yield (0.70 g, colorless oil) from 4-fluoro-3-hydroxybenzoic acid (1.0 g, 6.41 mmol) by the similar manner in Step-2 of Amine-5.
MS (ESI) m/z: 200 (M+H)⁺.

<Step-2>:1-(4-fluoro-3-hydroxyphenyl)ethanone

The title compound is prepared in 26% yield (0.14 g, a white solid) from 4-fluoro-3-hydroxy-N-methoxy-N-methylbenzamide (0.70 g, 3.50 mmol, Step-1) by the similar manner in Step-3 of Amine-1.
¹H-NMR (300 MHz, CDCl₃) delta 7.63 (1H, dd, J=8.0, 2.2 Hz), 7.55-7.49 (1H, m), 7.16 (1H, dd, J=9.9, 8.4 Hz), 5.33 (1H, d, J=3.3 Hz), 2.57 (3H, s), MS (ESI) m/z: 153 (M–H)⁻.

<Step-3>:1-(4-fluoro-3-(2,2,2-trifluoroethoxy)phenyl)ethanone

The title compound is prepared in 83% yield (0.18 g, a white solid) from 1-(4-fluoro-3-hydroxyphenyl)ethanone (0.14 g, 0.92 mmol, Step-2) by the similar manner in Step-3 of Amine-13.

¹H-NMR (300 MHz, CDCl₃) delta 7.70-7.55 (2H, m), 7.21 (1H, dd, J=10.3, 8.8 Hz), 4.48 (2H, q, J=8.1 Hz), 2.60 (3H, s), MS (ESI) m/z: 237 (M+H)⁺.

<Step-4>:(R)—N-(1-(4-fluoro-3-(2,2,2-trifluoroethoxy)phenyl)ethyl)-2-methylpropane-2-sulfinamide (single diastereomer)

The title compound is prepared in 83% yield (0.21 g, colorless oil) from 1-(4-fluoro-3-(2,2,2-trifluoroethoxy)phenyl)ethanone (0.18 g, 0.76 mmol, Step-3) and (R)-2-methylpropane-2-sulfinamide by the similar manner in Step-4 of Amine-1.
¹H-NMR (300 MHz, CDCl₃) delta 7.15-6.98 (3H, m), 4.56-4.45 (1H, m), 4.43 (2H, q, J=8.0 Hz), 3.39 (1H, br s), 1.54 (3H, d, J=6.6 Hz), 1.24 (9H, s), MS (ESI) m/z: 342 (M+H)⁺.

<Step-5>:1-(4-fluoro-3-(2,2,2-trifluoroethoxy)phenyl)ethanamine hydrochloride (single enantiomer)

The title compound is prepared in 90% yield (0.16 g, a white solid) from (R)—N-(1-(4-fluoro-3-(2,2,2-trifluoroethoxy)phenyl)ethyl)-2-methylpropane-2-sulfinamide (single diastereomer) (0.21 g, 0.63 mmol, Step-4) by the similar manner in Step-5 of Amine-1.
¹H-NMR (300 MHz, DMSO-d₆) delta 8.40 (2H, br s), 7.56 (1H, dd, J=8.4, 2.2 Hz), 7.37 (1H, dd, J=11.4, 8.4 Hz), 7.23-7.16 (1H, m), 4.95-4.78 (2H, m), 4.43-4.31 (1H, m), 1.50 (3H, d, J=6.6 Hz), MS (ESI) m/z: 238 (M+H)⁺.

Amine-21:1-(6-(3,3,3-trifluoropropoxy)pyridin-3-yl)ethanamine hydrochloride (single enantiomer)

<Step-1>:methyl 6-(3,3,3-trifluoropropoxy)nicotinate

The title compound is prepared in 47% yield (1.37 g, colorless oil) from methyl 6-chloronicotinate (2.0 g, 11.7 mmol) and 3,3,3-trifluoropropan-1-ol instead of 2,2,2-trifluoroethanol by the similar manner in Step-1 of Amine-2.
MS (ESI) m/z: 250 (M+H)⁺.

<Step-2>:6-(3,3,3-trifluoropropoxy)nicotinic acid 2M sodium hydroxide (5 mL) is added to a solution of methyl 6-(3,3,3-trifluoropropoxy)nicotinate (1.37 g, 5.50 mmol, Step-1) in methanol (30 mL) is stirred for 2 hours at 60° C. After removal of the solvent, the residue is dissolved in water (30 mL) and acidified with conc. hydrochloric acid (pH 2). The resulting white precipitate is collected by filtration and dried to give 1.15 g (86% yield) of the title compound as a white solid.
MS (ESI) m/z: 236 (M+H)⁺.

<Step-3>:N-methoxy-N-methyl-6-(3,3,3-trifluoropropoxy)nicotinamide

The title compound is prepared in 74% yield (0.97 g, colorless oil) from 6-(3,3,3-trifluoropropoxy)nicotinic acid (1.11 g, 4.72 mmol, Step-2) by the similar manner in Step-2 of Amine-5.
¹H-NMR (300 MHz, CDCl₃) delta 8.61 (1H, d, J=2.2 Hz), 8.00 (1H, dd, J=8.8, 2.6 Hz), 6.77 (1H, d, J=8.4 Hz), 4.59 (2H, t, J=6.6 Hz), 3.57 (3H, s), 3.37 (3H, s), 2.70-2.55 (2H, m), MS (ESI) m/z: 279 (M+H)⁺.

<Step-4>:1-(6-(3,3,3-trifluoropropoxy)pyridin-3-yl) ethanone

The title compound is prepared in >99% yield (0.82 g, a white solid) from N-methoxy-N-methyl-6-(3,3,3-trifluoropropoxy)nicotinamide (0.97 g, 3.50 mmol, Step-3) by the similar manner in Step-3 of Amine-1.

$^1$H-NMR (300 MHz, CDCl$_3$) delta 8.76 (1H, d, J=2.6 Hz), 8.16 (1H, dd, J=8.8, 2.6 Hz), 6.81 (1H, d, J=8.8 Hz), 4.62 (2H, t, J=6.2 Hz), 2.70-2.55 (2H, m), 2.57 (3H, s), MS (ESI) m/z: 234 (M+H)$^+$.

<Step-5>:(R)-2-methyl-N-(1-(6-(3,3,3-trifluoropropoxy)pyridin-3-yl)ethyl)propane-2-sulfinamide (single diastereomer)

The title compound is prepared in 80% yield (0.95 g, a white solid) from 1-(6-(3,3,3-trifluoropropoxy)pyridin-3-yl) ethanone (0.82 g, 3.51 mmol, Step-4) and (R)-2-methylpropane-2-sulfinamide by the similar manner in Step-4 of Amine-1.

$^1$H-NMR (300 MHz, CDCl$_3$) delta 8.10 (1H, d, J=2.2 Hz), 7.60 (1H, dd, J=8.8, 2.6 Hz), 6.75 (1H, d, J=8.4 Hz), 4.53 (2H, t, J=6.2 Hz), 4.6-4.45 (1H, m), 3.33 (1H, br s), 2.70-2.55 (2H, m), 1.51 (3H, d, J=6.6 Hz), 1.22 (9H, s), MS (ESI) m/z: 339 (M+H)$^+$.

<Step-6>:1-(6-(3,3,3-trifluoropropoxy)pyridin-3-yl) ethanamine hydrochloride (single enantiomer)

The title compound is prepared in >99% yield (0.76 g, colorless gum) from (R)-2-methyl-N-(1-(6-(3,3,3-trifluoropropoxy)pyridin-3-yl)ethyl)propane-2-sulfinamide (single diastereomer) (0.94 g, 2.79 mmol, Step-5) by the similar manner in Step-5 of Amine-1.

$^1$H-NMR (300 MHz, DMSO-d$_6$) delta 8.54 (2H, br s), 8.28 (1H, d, J=2.2 Hz), 7.92 (1H, dd, J=8.8, 2.2 Hz), 6.89 (1H, d, J=8.8 Hz), 4.48 (2H, t, J=5.7 Hz), 4.40 (1H, m), 2.78 (2H, m), 1.50 (3H, d, J=7.0 Hz), MS (ESI) m/z: 235 (M+H)$^+$.

Amine-22:1-(5-methoxy-6-(2,2,2-trifluoroethoxy)pyridin-3-yl)ethanamine hydrochloride (single enantiomer)

<Step-1>:6-chloro-N,5-dimethoxy-N-methylnicotinamide

The title compound is prepared in >99% yield (0.41 g, a white solid) from 6-chloro-5-methoxynicotinic acid (0.35 g, 1.79 mmol) by the similar manner in Step-2 of Amine-5.

$^1$H-NMR (300 MHz, CDCl$_3$) delta 8.40 (1H, d, J=1.8 Hz), 7.58 (1H, d, J=1.8 Hz), 3.96 (3H, s), 3.59 (3H, s), 3.40 (3H, s), MS (ESI) m/z: 231 (M+H)$^+$.

<Step-2>1-(6-chloro-5-methoxypyridin-3-yl)ethanone

The title compound is prepared in 76% yield (0.38 g, a white solid) from 6-chloro-N,5-dimethoxy-N-methylnicotinamide (0.41 g, 1.79 mmol, Step-1) by the similar manner in Step-3 of Amine-1.

$^1$H-NMR (300 MHz, CDCl$_3$) delta 8.54 (1H, d, J=1.8 Hz), 7.74 (1H, d, J=1.8 Hz), 3.99 (3H, s), 2.65 (3H, s), MS (ESI) m/z: 186 (M+H)$^+$.

<Step-3>:1-(5-methoxy-6-(2,2,2-trifluoroethoxy)pyridin-3-yl)ethanone

The title compound is prepared in >99% yield (0.25 g, a white solid) from 1-(6-chloro-5-methoxypyridin-3-yl)ethanone (0.18 g, 0.99 mmol, Step-2) by the similar manner in Step-1 of Amine-2.

$^1$H-NMR (300 MHz, CDCl$_3$) delta 8.32 (1H, d, J=2.0 Hz), 7.67 (1H, d, J=2.0 Hz), 4.90 (2H, q, J=8.4 Hz), 3.94 (3H, s), 2.60 (3H, s), MS (ESI) m/z: 250 (M+H)$^+$.

<Step-4>:(R)—N-(1-(5-methoxy-6-(2,2,2-trifluoroethoxy)pyridin-3-yl)ethyl)-2-methyl propane-2-sulfinamide (single diastereomer)

The title compound is prepared in 83% yield (0.29 g, a white solid) from 1-(5-methoxy-6-(2,2,2-trifluoroethoxy)pyridin-3-yl)ethanone (0.25 g, 0.99 mmol, Step-3) and (R)-2-methylpropane-2-sulfinamide by the similar manner in Step-4 of Amine-1.

$^1$H-NMR (300 MHz, CDCl$_3$) delta 7.68 (1H, d, J=1.8 Hz), 7.16 (1H, d, J=1.8 Hz), 4.83 (2H, q, J=8.4 Hz), 4.62-4.46 (1H, m), 3.90 (3H, s), 3.37 (1H, d, J=2.9 Hz), 1.54 (3H, d, J=6.6 Hz), 1.24 (9H, s), MS (ESI) m/z: 355 (M+H)$^+$.

<Step-5>:1-(5-methoxy-6-(2,2,2-trifluoroethoxy)pyridin-3-yl)ethanamine hydrochloride (single enantiomer)

The title compound is prepared in 97% yield (0.23 g, a white solid) from (R)—N-(1-(5-methoxy-6-(2,2,2-trifluoroethoxy)pyridin-3-yl)ethyl)-2-methylpropane-2-sulfinamide (single diastereomer) (0.29 g, 0.82 mmol, Step-4) by the similar manner in Step-5 of Amine-1.

$^1$H-NMR (300 MHz, DMSO-d$_6$) delta 8.41 (2H, br s), 7.81 (1H, d, J=1.8 Hz), 7.69 (1H, d, J=1.8 Hz), 5.01 (2H, q, J=9.1 Hz), 4.51-4.38 (1H, m), 3.86 (3H, s), 1.53 (3H, d, J=6.6 Hz), MS (ESI) m/z: 251 (M+H)$^+$.

Amine-23:1-(6-((2,2,2-trifluoroethyl)thio)pyridin-3-yl)ethanamine hydrochloride (single enantiomer)

<Step-1>:1-(6-((2,2,2-trifluoroethyl)thio)pyridin-3-yl)ethanone

The title compound is prepared in 64% yield (0.39 g, an orange solid) from 1-(6-chloropyridin-3-yl)ethanone (0.40 g, 2.54 mmol) and 2,2,2-trifluoroethanethiol instead of 2,2,2-trifluoroethanol by the similar manner in Step-1 of Amine-1.

$^1$H-NMR (300 MHz, CDCl$_3$) delta 8.98 (1H, dd, J=2.2, 0.9 Hz), 8.08 (1H, dd, J=8.4, 2.2 Hz), 7.32 (1H, dd, J=8.4, 0.9 Hz), 4.11 (2H, q, J=9.9 Hz), 2.61 (3H, s), MS (ESI) m/z: 236 (M+H)$^+$.

<Step-2>:(R)-2-methyl-N-(1-(6-((2,2,2-trifluoroethyl)thio)pyridin-3-yl)ethyl)propane-2-sulfinamide (single diastereomer)

The title compound is prepared in 64% yield (0.56 g, orange oil) from 1-(6-((2,2,2-trifluoroethyl)thio)pyridin-3-yl)ethanone (0.39 g, 1.64 mmol, Step-1) and (R)-2-methylpropane-2-sulfinamide by the similar manner in Step-4 of Amine-1.

$^1$H-NMR (300 MHz, CDCl$_3$) delta 8.44 (1H, d, J=2.2 Hz), 7.56 (1H, dd, J=8.2, 2.2 Hz), 7.23 (1H, d, J=8.2 Hz), 4.65-4.48

(1H, m), 4.04 (1H, q, J=9.9 Hz), 4.03 (1H, q, J=9.9 Hz), 3.38 (1H, d, J=2.9 Hz), 1.54 (3H, d, J=6.6 Hz), 1.24 (9H, s), MS (ESI) m/z: 341 (M+H)+.

<Step-3>:1-(6-((2,2,2-trifluoroethyl)thio)pyridin-3-yl)ethanamine hydrochloride (single enantiomer)

The title compound is prepared in 89% yield (0.26 g, a white solid) from (R)-2-methyl-N-(1-(6-((2,2,2-trifluoroethyl)thio)pyridin-3-yl)ethyl)propane-2-sulfinamide (single diastereomer) (0.36 g, 1.05 mmol, Step-2) by the similar manner in Step-5 of Amine-1.

$^1$H-NMR (300 MHz, DMSO-d$_6$) delta 8.61 (2H, br s), 8.59 (1H, d, J=2.2 Hz), 7.91 (1H, dd, J=8.4, 2.0 Hz), 7.54 (1H, d, J=8.4 Hz), 4.55-4.36 (1H, m), 4.28 (2H, q, J=10.4 Hz), 1.52 (3H, d, J=7.0 Hz), MS (ESI) m/z: 237 (M+H)+.

Amine-24:(2-methoxy-6-(2,2,2-trifluoroethoxy)pyridin-3-yl)methanamine

<Step-1>:methyl 2-methoxy-6-(2,2,2-trifluoroethoxy)nicotinate

The title compound is prepared in 54% yield (1.79 g, colorless oil) from methyl 6-chloro-2-methoxynicotinate (2.5 g, 12.4 mmol) by the similar manner in Step-1 of Amine-2.

$^1$H-NMR (300 MHz, CDCl$_3$) delta 8.21 (1H, d, J=8.0 Hz), 6.47 (1H, d, J=8.0 Hz), 4.79 (2H, q, J=8.8 Hz), 4.07 (3H, s), 3.87 (3H, s), MS (ESI) m/z: 266 (M+H)+.

<Step-2>:(2-methoxy-6-(2,2,2-trifluoroethoxy)pyridin-3-yl)methanol

The title compound is prepared in 74% yield (1.19 g, a white solid) from methyl 2-methoxy-6-(2,2,2-trifluoroethoxy)nicotinate (1.79 g, 5.02 mmol, Step-1) by the similar manner in Step-3 of Amine-4.

$^1$H-NMR (300 MHz, CDCl$_3$) delta 7.54 (1H, d, J=8.0 Hz), 6.41 (1H, d, J=8.0 Hz), 4.72 (2H, q, J=8.8 Hz), 4.59 (2H, s), 3.97 (3H, s), 2.10 (1H, br s), MS (ESI) m/z: 238 (M+H)+.

<Step-3>:2-((2-methoxy-6-(2,2,2-trifluoroethoxy)pyridin-3-yl)methyl)isoindoline-1,3-dione A mixture of (2-methoxy-6-(2,2,2-trifluoroethoxy)pyridin-3-yl)methanol (1.19 g, 5.02 mmol, Step-2), phthalimide (0.74 g, 5.02 mmol), di-tert-butyl azodicarboxylate (1.05 g, 6.02 mmol) and triphenylphosphine (1.97 g, 7.53 mmol) in tetrahydrofuran (50 mL) is stirred at room temperature for 20 hours. The reaction mixture is concentrated in vacuo. The residue is purified by column chromatography on silica gel eluting with n-hexane/ethyl acetate (6:1) to give 0.67 g (37% yield) of the title compound as a white solid.

$^1$H-NMR (300 MHz, CDCl$_3$) delta 7.87-7.84 (2H, m), 7.74-7.72 (2H, m), 7.53 (1H, d, J=8.0 Hz), 6.37 (1H, d, J=8.1 Hz), 4.80 (2H, s), 4.71 (2H, q, J=8.8 Hz), 3.94 (3H, s), MS (ESI) m/z: 367 (M+H)+.

<Step-4>:(2-methoxy-6-(2,2,2-trifluoroethoxy)pyridin-3-yl)methanamine

Hydrazine hydrate (0.13 mL) is added to a solution of 2-((2-methoxy-6-(2,2,2-trifluoroethoxy)pyridin-3-yl)methyl)isoindoline-1,3-dione (0.67 g, 1.83 mmol) in methanol (20 mL) and stirred for 20 hours at 50° C. After removal of the solvent, the residue is poured into 2N sodium hydroxide (10 mL) and extracted with dichloromethane (30 mL×3) and dried over sodium sulfate, and concentrated in vacuo to give 0.41 g (95% yield) of the title compound as a white solid.

$^1$H-NMR (300 MHz, CDCl$_3$) delta 7.48 (1H, d, J=7.4 Hz), 6.38 (1H, d, J=7.4 Hz), 4.74 (q, J=8.8 Hz), 3.95 (3H, s), 3.73 (2H, s), 1.46 (2H, br s).

Amine-25:5-(1-aminoethyl)-N-(2,2,2-trifluoroethyl)pyridin-2-amine hydrochloride (single enantiomer)

<Step-1>:1-(6-((2,2,2-trifluoroethyl)amino)pyridin-3-yl)ethanone

A mixture of 1-(6-chloropyridin-3-yl)ethanone (1.0 g, 6.43 mmol) and 2,2,2-trifluoroethanamine hydrochloride (1.57 g, 11.8 mmol) in 1-methylpyrrolidin-2-one (10 mL) is stirred at 230° C. for 45 minutes under microwave irradiation. The reaction mixture is poured into water, extracted with ethyl acetate and dried over sodium sulfate and concentrated in vacuo. The residue is purified by column chromatography on silica gel eluting with n-hexane/ethyl acetate (4:1 to 1:1) to give 490 mg (35% yield) of the title compound as a yellow solid.

$^1$H-NMR (300 MHz, CDCl$_3$) delta 8.75 (1H, d, J=2.2 Hz), 8.05 (1H, dd, J=8.4, 2.2 Hz), 6.53 (1H, d, J=8.4 Hz), 5.07 (1H, br s), 4.23 (1H, q, J=9.0 Hz), 4.21 (1H, q, J=9.0 Hz), 2.53 (3H, s), MS (ESI) m/z: 219 (M+H)+.

<Step-2>:(R)-2-methyl-N-(1-(6-((2,2,2-trifluoroethyl)amino)pyridin-3-yl)ethyl)propane-2-sulfinamide (single diastereomer)

The title compound is prepared in 28% yield (180 mg, colorless oil) from 1-(6-((2,2,2-trifluoroethyl)amino)pyridin-3-yl)ethanone (441 mg, 2.02 mmol, Step-1) and (R)-2-methylpropane-2-sulfinamide by the similar manner in Step-4 of Amine-1.

$^1$H-NMR (300 MHz, CDCl$_3$) delta 8.10 (1H, d, J=2.6 Hz), 7.47 (1H, dd, J=8.8, 2.6 Hz), 6.49 (1H, d, J=8.8 Hz), 4.72-4.58 (1H, m), 4.52-4.38 (1H, m), 4.13 (2H, q, J=7.0 Hz), 3.38 (1H, br s), 1.50 (3H, d, J=6.6 Hz), 1.23 (9H, s), MS (ESI) m/z: 324 (M+H)+.

<Step-3>:5-(1-aminoethyl)-N-(2,2,2-trifluoroethyl)pyridin-2-amine hydrochloride (single enantiomer)

The title compound is prepared in >99% yield (142 mg, a white solid) from (R)-2-methyl-N-(1-(6-((2,2,2-trifluoroethyl)amino)pyridin-3-yl)ethyl)propane-2-sulfinamide (single diastereomer) (180 mg, 0.56 mmol, Step-2) by the similar manner in Step-5 of Amine-1.

$^1$H-NMR (300 MHz, DMSO-d$_6$) delta 8.31 (2H, br s), 8.13 (1H, s), 7.78 (1H, d, J=8.4 Hz), 6.84 (1H, d, J=8.4 Hz), 4.42-4.18 (3H, m), 1.47 (3H, d, J=6.6 Hz), MS (ESI) m/z: 220 (M+H)+.

Amine-26:N-ethyl-1-(6-(2,2,2-trifluoroethoxy)pyridin-3-yl)ethanamine hydrochloride (single enantiomer)

<Step-1>:tert-butyl ethyl(1-(6-(2,2,2-trifluoroethoxy)pyridin-3-yl)ethyl)carbamate (single enantiomer)

The title compound is prepared in >99% yield (0.24 g, colorless oil) from tert-butyl (1-(6-(2,2,2-trifluoroethoxy)pyridin-3-yl)ethyl)carbamate (0.22 g, 0.69 mmol, Step-1 of Amine-3) and iodoethane instead of iodomethane by the similar manner in Step-2 of Amine-3.

$^1$H-NMR (300 MHz, CDCl$_3$) delta 8.06 (1H, d, J=2.2 Hz), 7.58 (1H, dd, J=8.8, 2.2 Hz), 6.83 (1H, d, J=8.8 Hz), 4.75 (2H, q, J=8.0 Hz), 3.20-2.80 (2H, m), 1.54 (3H, d, J=7.3 Hz), 1.47 (9H, s), 1.01 (3H, t, J=6.6 Hz), MS (ESI) m/z: 349 (M+H)$^+$.

<Step-2>:N-ethyl-1-(6-(2,2,2-trifluoroethoxy)pyridin-3-yl)ethanamine hydrochloride (single enantiomer)

The title compound is prepared in 98% yield (0.19 g, a white solid) from tert-butyl ethyl(1-(6-(2,2,2-trifluoroethoxy)pyridin-3-yl)ethyl)carbamate (0.23 g, 0.66 mmol, Step-1) by the similar manner in Step-3 of Amine-3.

$^1$H-NMR (300 MHz, DMSO-d$_6$) delta 9.78 (1H, br s), 9.38 (1H, br s), 8.38 (1H, d, J=2.2 Hz), 8.12 (1H, dd, J=8.8, 2.2 Hz), 7.10 (1H, d, J=8.8 Hz), 5.02 (2H, q, J=8.8 Hz), 4.44-4.36 (1H, m), 2.89-2.62 (2H, m), 1.59 (3H, d, J=6.6 Hz), 1.19 (3H, t, J=7.3 Hz).

Amine-27:(2-methyl-6-(2,2,2-trifluoroethoxy)pyridin-3-yl)methanamine hydrochloride <Step-1>:2-chloro-6-(2,2,2-trifluoroethoxy)nicotinic acid A mixture of 2,6-dichloronicotinic acid (3.0 g, 15.6 mmol) and potassium tert-butoxide (5.26 g, 46.9 mmol) in 2,2,2-trifluoroethanol (52 mL) is refluxed with stirring for 5 days. After removal of solvent, the residue is dissolved in water (40 mL) then 2M hydrochloric acid (10 mL) is added. White precipitate is filtrated and dried to give 4.08 g of the title compound including 6-chloro-2-(2,2,2-trifluoroethoxy)nicotinic acid and 2,6-bis(2,2,2-trifluoroethoxy)nicotinic acid as a white solid. This material is used for the next reaction (Step-2) without further purification.

MS (ESI) m/z: 254 (M−H)$^-$.

<Step-2>:methyl 2-chloro-6-(2,2,2-trifluoroethoxy)nicotinate

Thionyl chloride (4.7 mL, 63.9 mmol) is added dropwise a solution of 2-chloro-6-(2,2,2-trifluoroethoxy)nicotinic acid including 6-chloro-2-(2,2,2-trifluoroethoxy)nicotinic acid and 2,6-bis(2,2,2-trifluoroethoxy)nicotinic acid (4.08 g, Step-1) in methanol (50 mL) and refluxed with stirring for 3 hours. After removal of solvent, the residue is purified by column chromatography on silica gel eluting with n-hexane/ethyl acetate (20:1) to give 2.90 g (67% yield) of the title compound including methyl 6-chloro-2-(2,2,2-trifluoroethoxy)nicotinate as a white solid. This material is used for the next reaction (Step-3) without further purification.

MS (ESI) m/z: 270 (M+H)$^+$.

<Step-3>:methyl 2-methyl-6-(2,2,2-trifluoroethoxy)nicotinate

Dimethylzinc (40.0 mL, 40.0 mmol) is added dropwise a solution of methyl 2-chloro-6-(2,2,2-trifluoroethoxy)nicotinate (2.70 g, 10.0 mmol, Step-2) including methyl 6-chloro-2-(2,2,2-trifluoroethoxy)nicotinate and 1,1'-bis(diphenylphosphino)ferrocene-palladium(II)dichloride dichloromethane complex (0.816 g, 1.00 mmol) and stirred at 75° C. for 1 hour. After cooling room temperature, the resulting mixture is quenched by carefully added water. The reaction mixture is extracted with ethyl acetate and dried over sodium sulfate and concentrated in vacuo. The residue is purified by column chromatography on silica gel eluting with n-Hexane/ethyl acetate (20:1) to give 0.89 g (36% yield) of the title compound as a white solid.

$^1$H-NMR (300 MHz, CDCl$_3$) delta 8.19 (1H, d, J=8.6 Hz), 6.72 (1H, d, J=8.6 Hz), 4.82 (2H, q, J=8.4 Hz), 3.88 (3H, s), 2.76 (3H, s), MS (ESI) m/z: 250 (M+H)$^+$.

<Step-4>:(2-methyl-6-(2,2,2-trifluoroethoxy)pyridin-3-yl)methanol

The title compound is prepared in >99% yield (0.70 g, colorless oil) from methyl 2-methyl-6-(2,2,2-trifluoroethoxy)nicotinate (0.79 g, 3.17 mmol, Step-3) by the similar manner in Step-3 of Amine-4.

MS (ESI) m/z: 222 (M+H)$^+$.

<Step-5>:3-(chloromethyl)-2-methyl-6-(2,2,2-trifluoroethoxy)pyridine

The title compound is prepared in 98% yield (0.74 g, colorless oil) from (2-methyl-6-(2,2,2-trifluoroethoxy)pyridin-3-yl)methanol (0.70 g, 3.17 mmol, Step-4) by the similar manner in Step-4 of Amine-4.

MS (ESI) m/z: 240 (M+H)$^+$.

<Step-6>:3-(azidomethyl)-2-methyl-6-(2,2,2-trifluoroethoxy)pyridine

The title compound is prepared in 80% yield (0.61 g, colorless oil) from 3-(chloromethyl)-2-methyl-6-(2,2,2-trifluoroethoxy)pyridine (0.74 g, 3.10 mmol, Step-5) by the similar manner in Step-5 of Amine-4.

$^1$H-NMR (300 MHz, CDCl$_3$) delta 7.52 (1H, d, J=8.2 Hz), 6.70 (1H, d, J=8.2 Hz), 4.77 (2H, q, J=8.8 Hz), 4.32 (2H, s), 2.48 (3H, s), MS (ESI) m/z: 247 (M+H)$^+$.

<Step-7>:(2-methyl-6-(2,2,2-trifluoroethoxy)pyridin-3-yl)methanamine hydrochloride The title compound is prepared in 94% yield (0.60 g, a white solid) from 3-(azidomethyl)-2-methyl-6-(2,2,2-trifluoroethoxy)pyridine (0.61 g, 2.49 mmol, Step-6) by the similar manner in Step-6 of Amine-4.

$^1$H-NMR (300 MHz, DMSO-d$_6$) delta 8.38 (2H, br s), 7.82 (1H, d, J=8.4 Hz), 6.87 (1H, d, J=8.4 Hz), 4.98 (2H, q, J=9.2 Hz), 4.05-3.93 (2H, m), 2.50 (3H, s), MS (ESI) m/z: 221 (M+H)$^+$.

Amine-28:(5-fluoro-6-(2,2,2-trifluoroethoxy)pyridin-3-yl)methanamine hydrochloride <Step-1>:5-fluoro-6-(2,2,2-trifluoroethoxy)nicotinic acid The title compound is prepared in 75% yield (21.0 g, a white solid) from 2-chloro-5-fluoro-6-(2,2,2-trifluoroethoxy)nicotinic acid (32.2 g, 118 mmol, Step-1 of Amine-12) by the similar manner in Step-4 of Amine-12.

$^1$H-NMR (300 MHz, DMSO-d$_6$) delta 13.40 (1H, br s), 8.55 (1H, d, J=1.8 Hz), 8.13 (1H, dd, J=10.3, 1.8 Hz), 5.16 (2H, q, J=9.2 Hz), MS (ESI) m/z: 238 (M−H)$^-$.

<Step-2>:methyl 5-fluoro-6-(2,2,2-trifluoroethoxy)nicotinate

The title compound is prepared in 55% yield (1.74 g, a white solid) from 5-fluoro-6-(2,2,2-trifluoroethoxy)nicotinic acid (3.0 g, 12.6 mmol, Step-1) by the similar manner in Step-2 of Amine-27.

¹H-NMR (300 MHz, DMSO-d₆) delta 8.58 (1H, d, J=1.8 Hz), 8.20 (1H, dd, J=10.3, 1.8 Hz), 5.16 (2H, q, J=8.8 Hz), 3.87 (3H, s).

<Step-3>:(5-fluoro-6-(2,2,2-trifluoroethoxy)pyridin-3-yl)methanol

The title compound is prepared in 93% yield (1.43 g, colorless oil) from methyl 5-fluoro-6-(2,2,2-trifluoroethoxy) nicotinate (1.74 g, 6.89 mmol, Step-2) by the similar manner in Step-3 of Amine-4.
MS (ESI) m/z: 226 (M+H)⁺.

<Step-4>:2-((5-fluoro-6-(2,2,2-trifluoroethoxy)pyridin-3-yl)methyl)isoindoline-1,3-dione The title compound is prepared in 99% yield (2.24 g, a white solid) from (5-fluoro-6-(2,2,2-trifluoroethoxy)pyridin-3-yl)methanol (1.44 g, 6.39 mmol, Step-3) by the similar manner in Step-3 of Amine-24.
¹H-NMR (300 MHz, DMSO-d₆) delta 8.03 (1H, d, J=1.8 Hz), 7.90-7.82 (4H, m), 7.76 (1H, dd, J=11.0, 1.8 Hz), 5.06 (2H, q, J=9.2 Hz), 4.77 (2H, s), MS (ESI) m/z: 355 (M+H)⁺.

<Step-5>:(5-fluoro-6-(2,2,2-trifluoroethoxy)pyridin-3-yl)methanamine hydrochloride The title compound is prepared in 41% yield (0.67 g, a white solid) from 2-((5-fluoro-6-(2,2,2-trifluoroethoxy)pyridin-3-yl)methyl)isoindoline-1,3-dione (2.24 g, 6.33 mmol, Step-4) by the similar manner in Step-4 of Amine-24.
¹H-NMR (300 MHz, DMSO-d₆) delta 8.56 (2H, br s), 8.14 (1H, d, J=1.8 Hz), 8.04 (1H, dd, J=11.3, 1.8 Hz), 5.11 (2H, q, J=9.2 Hz), 4.04 (2H, d, J=5.5 Hz), MS (ESI) m/z: 225 (M+H)⁺.

Amine-29:(4-methyl-6-(2,2,2-trifluoroethoxy)pyridin-3-yl)methanamine hydrochloride <Step-1>:4-methyl-6-(2,2,2-trifluoroethoxy)nicotinic acid The title compound is prepared in 52% yield (1.17 g, a white solid) from 6-fluoro-4-methylnicotinic acid (1.5 g, 9.67 mmol) by the similar manner in Step-1 of Amine-2.
¹H-NMR (300 MHz, DMSO-d₆) delta 13.06 (1H, br s), 8.63 (1H, s), 6.95 (1H, s), 5.04 (2H, q, J=9.2 Hz), 2.53 (3H, s), MS (ESI) m/z: 236 (M+H)⁺.

<Step-2>:methyl 4-methyl-6-(2,2,2-trifluoroethoxy)nicotinate

The title compound is prepared in 99% yield (1.09 g, a white solid) from 4-methyl-6-(2,2,2-trifluoroethoxy)nicotinic acid (1.04 g, 4.42 mmol, Step-1) by the similar manner in Step-2 of Amine-27.
¹H-NMR (300 MHz, CDCl₃) delta 8.72 (1H, s), 6.73 (1H, s), 4.80 (2H, q, J=8.4 Hz), 3.90 (3H, s), 2.59 (3H, s), MS (ESI) m/z: 250 (M+H)⁺.

<Step-3>:(4-methyl-6-(2,2,2-trifluoroethoxy)pyridin-3-yl)methanol

The title compound is prepared in 68% yield (0.66 g, a white solid) from methyl 4-methyl-6-(2,2,2-trifluoroethoxy) nicotinate (1.09 g, 4.38 mmol, Step-2) by the similar manner in Step-3 of Amine-4.

¹H-NMR (300 MHz, CDCl₃) delta 8.00 (1H, s), 6.71 (1H, s), 4.75 (2H, q, J=8.4 Hz), 4.66 (2H, d, J=4.0 Hz), 2.39 (3H, s), MS (ESI) m/z: 222 (M+H)⁺.

<Step-4>:5-(chloromethyl)-4-methyl-2-(2,2,2-trifluoroethoxy)pyridine

The title compound is prepared in >99% yield (0.71 g, colorless oil) from (4-methyl-6-(2,2,2-trifluoroethoxy)pyridin-3-yl)methanol (0.66 g, 2.98 mmol, Step-3) by the similar manner in Step-4 of Amine-4.
MS (ESI) m/z: 240 (M+H)⁺.

<Step-5>:5-(azidomethyl)-4-methyl-2-(2,2,2-trifluoroethoxy)pyridine

The title compound is prepared in >99% yield (0.72 g, colorless oil) from 5-(chloromethyl)-4-methyl-2-(2,2,2-trifluoroethoxy)pyridine (0.71 g, 2.95 mmol, Step-4) by the similar manner in Step-5 of Amine-4.
¹H-NMR (300 MHz, CDCl₃) delta 7.98 (1H, s), 6.75 (1H, s), 4.75 (2H, q, J=8.4 Hz), 4.30 (2H, s), 2.36 (3H, s), MS (ESI) m/z: 247 (M+H)⁺.

<Step-6>:(4-methyl-6-(2,2,2-trifluoroethoxy)pyridin-3-yl)methanamine hydrochloride The title compound is prepared in >99% yield (0.75 g, a white solid) from 5-(azidomethyl)-4-methyl-2-(2,2,2-trifluoroethoxy)pyridine (0.72 g, 2.92 mmol, Step-5) by the similar manner in Step-6 of Amine-4.
¹H-NMR (300 MHz, DMSO-d₆) delta 8.43 (2H, br s), 8.19 (1H, s), 6.89 (1H, s), 4.99 (2H, q, J=9.5 Hz), 3.99 (2H, d, J=5.9 Hz), 2.38 (3H, s), MS (ESI) m/z: 221 (M+H)⁺.

Amine-30:(6-(3,3,3-trifluoropropoxy)pyridin-3-yl)methanamine

<Step-1>: (6-(3,3,3-trifluoropropoxy)pyridin-3-yl)methanol

The title compound is prepared in 91% yield (860 mg, brown oil) from 6-(3,3,3-trifluoropropoxy)nicotinic acid (1.0 g, 4.3 mmol) by the similar manner in Step-3 of Amine-4.
¹H-NMR (300 MHz, CDCl₃) delta 8.11 (1H, d, J=2.2 Hz), 7.64 (1H, dd, J=8.0 & 2.2 Hz), 6.76 (1H, d, J=8.1 Hz), 4.64 (2H, s), 4.55 (2H, t, J=6.6 Hz), 2.70-2.53 (2H, m), MS (ESI) m/z: 222 (M+H)⁺.

<Step-2>:2-((6-(3,3,3-trifluoropropoxy)pyridin-3-yl)methyl)isoindoline-1,3-dione The title compound is prepared in 89% yield (310 mg, brown oil) from (6-(3,3,3-trifluoropropoxy)pyridin-3-yl) methanol (220 mg, 1.0 mmol, Step-1) by the similar manner in Step-3 of Amine-24.
¹H-NMR (300 MHz, CDCl₃) delta 8.26 (1H, d, J=4.4 Hz), 7.8-7.75 (2H, m), 7.75-7.60 (3H, m), 6.70 (1H, d, J=8.0 Hz), 4.78 (2H, s), 4.52 (2H, t, J=6.6 Hz), 2.66-2.50 (2H, m), MS (ESI) m/z: 351 (M+H)⁺.

<Step-3>:(6-(3,3,3-trifluoropropoxy)pyridin-3-yl)methanamine

The title compound is prepared in 86% yield (168 mg, pale brown oil) from 2-((6-(3,3,3-trifluoropropoxy)pyridin-3-yl)

methyl)isoindoline-1,3-dione (310 mg, 0.89 mmol, Step-2) by the similar manner in Step-4 of Amine-24.

$^1$H-NMR (300 MHz, CDCl$_3$) delta 8.06 (1H, d, J=2.9 Hz), 7.60 (1H, dd, J=5.9, 2.9 Hz), 6.74 (1H, d, J=8.0 Hz), 4.54 (2H, t, J=6.6 Hz), 3.82 (2H, s), 2.70-2.52 (2H, m), 1.59 (2H, br s), MS (ESI) m/z: 221 (M+H)$^+$.

Amine-31:1-(6-(2-(2,2,2-trifluoroethoxy)ethoxy) pyridin-3-yl)ethanamine hydrochloride (single enantiomer)

<Step-1>:1-(6-(2-(2,2,2-trifluoroethoxy)ethoxy)pyridin-3-yl)ethanone

The title compound is prepared in 50% yield (1.67 g, colorless oil) from 1-(6-chloropyridin-3-yl)ethanone (2.0 g, 12.9 mmol) and 2-(2,2,2-trifluoroethoxy)ethanol instead of 2,2,2-trifluoroethanol by the similar manner in Step-1 of Amine-2.

$^1$H-NMR (300 MHz, CDCl$_3$) delta 8.75 (1H, d, J=2.2 Hz), 8.16 (1H, dd, J=8.8, 2.2 Hz), 6.84 (1H, dd, J=8.4, 0.7 Hz), 4.60-4.57 (2H, m), 4.02-3.90 (4H, m), 2.58 (3H, s),
MS (ESI) m/z: 264 (M+H)$^+$.

<Step-2>:(R)-2-methyl N (1 (6 (2 (2,2,2-trifluoroethoxy)ethoxy)pyridin-3-yl)ethyl)propane-2-sulfinamide (single diastereomer)

The title compound is prepared in 24% yield (0.33 g, yellow oil) from 1-(6-(2-(2,2,2-trifluoroethoxy)ethoxy)pyridin-3-yl)ethanone (1.0 g, 3.80 mmol, Step-1) and (R)-2-methylpropane-2-sulfinamide by the similar manner in Step-4 of Amine-1.

$^1$H-NMR (300 MHz, CDCl$_3$) delta 8.10 (1H, d, J=2.2 Hz), 7.60 (1H, dd, J=8.4, 2.2 Hz), 6.79 (1H, d, J=8.4 Hz), 4.56-4.47 (3H, m), 4.00-3.90 (4H, m), 3.33 (1H, br s), 1.51 (3H, d, J=6.6 Hz), 1.23 (9H, s), MS (ESI) m/z: 369 (M+H)$^+$.

<Step-3>:1-(6-(2-(2,2,2-trifluoroethoxy)ethoxy)pyridin-3-yl)ethanamine hydrochloride (single enantiomer)

The title compound is prepared in >99% yield (0.27 g, a white solid) from (R)-2-methyl-N-(1-(6-(2-(2,2,2-trifluoroethoxy)ethoxy)pyridin-3-yl)ethyl)propane-2-sulfinamide (single diastereomer) (0.33 g, 0.90 mmol, Step-2) by the similar manner in Step-5 of Amine-1.

$^1$H-NMR (300 MHz, DMSO-d$_6$) delta 8.51 (2H, br s), 8.26 (1H, d, J=2.6 Hz), 7.91 (1H, dd, J=8.8, 2.6 Hz), 6.91 (1H, d, J=8.8 Hz), 4.43-4.36 (3H, m), 4.12 (2H, q, J=9.5 Hz), 3.94-3.87 (2H, m), 1.50 (3H, d, J=7.0 Hz), MS (ESI) m/z: 265 (M+H)$^+$.

Amine-32:1-(6-(2,2-difluoroethoxy)pyridin-3-yl) ethanamine hydrochloride (single enantiomer)

<Step-1>:1-(6-(2,2-difluoroethoxy)pyridin-3-yl) ethanone

The title compound is prepared in 71% yield (1.34 g, a white solid) from 1-(6-chloropyridin-3-yl)ethanone (1.5 g, 9.64 mmol) and 2,2-difluoroethanol instead of 2,2,2-trifluoroethanol by the similar manner in Step-1 of Amine-2.

$^1$H-NMR (300 MHz, CDCl$_3$) delta 8.75 (1H, d, J=2.2 Hz), 8.19 (1H, dd, J=8.2, 2.2 Hz), 6.88 (1H, d, J=8.2 Hz), 6.14 (1H, tt, J=55.3, 4.0 Hz), 4.61 (2H, td, J=13.5, 4.4 Hz), 2.59 (3H, s), MS (ESI) m/z: 202 (M+H)$^+$.

<Step-2>:(R)—N-(1-(6-(2,2-difluoroethoxy)pyridin-3-yl)ethyl)-2-methylpropane-2-sulfinamide (single diastereomer)

The title compound is prepared in 81% yield (1.24 g, colorless oil) from 1-(6-(2,2-difluoroethoxy)pyridin-3-yl)ethanone (1.0 g, 4.97 mmol, Step-1) and (R)-2-methylpropane-2-sulfinamide by the similar manner in Step-4 of Amine-1.

$^1$H-NMR (300 MHz, CDCl$_3$) delta 8.11 (1H, d, J=2.4 Hz), 7.64 (1H, dd, J=8.6, 2.4 Hz), 6.82 (1H, d, J=8.6 Hz), 6.13 (1H, tt, J=55.7, 4.2 Hz), 4.54 (2H, td, J=13.6, 4.0 Hz), 4.68-4.45 (1H, m), 3.34 (1H, br s), 1.52 (3H, d, J=6.2 Hz), 1.24 (9H, s), MS (ESI) m/z: 307 (M+H)$^+$.

<Step-3>:1-(6-(2,2-difluoroethoxy)pyridin-3-yl) ethanamine hydrochloride (single enantiomer)

The title compound is prepared in 93% yield (0.90 g, a white solid) from (R)—N-(1-(6-(2,2-difluoroethoxy)pyridin-3-yl)ethyl)-2-methylpropane-2-sulfinamide (single diastereomer) (1.24 g, 4.03 mmol, Step-2) by the similar manner in Step-5 of Amine-1.

$^1$H-NMR (300 MHz, DMSO-d$_6$) delta 8.52 (2H, br s), 8.28 (1H, d, J=2.2 Hz), 7.96 (1H, dd, J=8.6, 2.2 Hz), 6.99 (1H, d, J=8.6 Hz), 6.38 (1H, tt, J=54.5, 3.7 Hz), 4.57 (2H, td, J=15.0, 3.3 Hz), 4.48-4.35 (1H, m), 1.51 (3H, d, J=6.6 Hz), MS (ESI) m/z: 203 (M+H)$^+$.

Amine-33:1-(5-fluoro-6-(2,2,2-trifluoroethoxy)pyridin-3-yl)-N-methylethanamine hydrochloride (single enantiomer)

<Step-1>:tert-butyl(1-(5-fluoro-6-(2,2,2-trifluoroethoxy)pyridin-3-yl)ethyl)carbamate (single enantiomer)

The title compound is prepared in 23% yield (220 mg, a white solid) from (−)-1-(5-fluoro-6-(2,2,2-trifluoroethoxy) pyridin-3-yl)ethanamine hydrochloride (700 mg, 2.6 mmol, Step-6 of Amine-12, single enantiomer) by the similar manner in Step-1 of Amine-3.

$^1$H-NMR (300 MHz, CDCl$_3$) delta 7.87 (1H, s), 7.36 (1H, d, J=10.3 Hz), 4.86-4.70 (2H, m), 4.82 (2H, q, J=8.8 Hz), 1.44 (3H, d, J=6.6 Hz), 1.42 (9H, s), MS (ESI) m/z: 339 (M+H)$^+$.

<Step-2>:tert-butyl(1-(5-fluoro-6-(2,2,2-trifluoroethoxy)pyridin-3-yl)ethyl)(methyl)carbamate (single enantiomer)

The title compound is prepared in 94% yield (220 mg, clear colorless oil) from tert-butyl (1-(5-fluoro-6-(2,2,2-trifluoroethoxy)pyridin-3-yl)ethyl)carbamate (220 mg, 0.65 mmol, Step-1, single enantiomer) by the similar manner in Step-2 of Amine-3.

$^1$H-NMR (300 MHz, CDCl$_3$) delta 7.83 (1H, s), 7.33 (1H, d, J=11.0 Hz), 5.45 (1H, br s), 4.82 (2H, q, J=8.0 Hz), 2.61 (3H, s), 1.50 (3H, d, J=7.3 Hz), 1.49 (9H, s), MS (ESI) m/z: 353 (M+H)$^+$.

<Step-3>:1-(5-fluoro-6-(2,2,2-trifluoroethoxy)pyridin-3-yl)-N-methylethanamine hydrochloride (single enantiomer)

The title compound is prepared in 95% yield (170 mg, a white solid) from tert-butyl (1-(5-fluoro-6-(2,2,2-trifluoroethoxy)pyridin-3-yl)ethyl)(methyl)carbamate (220 mg, 0.61 mmol, Step-2, single enantiomer) by the similar manner in Step-3 of Amine-3.

$^1$H-NMR (300 MHz, DMSO-d$_6$) delta 8.17 (1H, d, J=2.2 Hz), 8.07 (1H, dd, J=11.0, 2.2 Hz), 5.13 (2H, q, J=8.8 Hz), 4.40 (1H, q, J=6.6 Hz), 2.42 (3H, s), 1.57 (3H, d, J=6.6 Hz), 1.61 (3H, d, J=6.6 Hz), MS (ESI) m/z: 253 (M+H)$^+$.

Amine-34:2-methoxy-1-(6-(2,2,2-trifluoroethoxy) pyridin-3-yl)ethanamine (single enantiomer)

<Step-1>:6-(2,2,2-trifluoroethoxy)nicotinaldehyde

The title compound is prepared in 28% yield (2.11 g, a white solid) from 6-chloronicotinaldehyde (5.25 g, 37.1 mmol) by the similar manner in Step-1 of Amine-2.

$^1$H-NMR (300 MHz, DMSO-d$_6$) delta 10.0 (1H, s), 8.79 (1H, d, J=2.2 Hz), 8.21 (1H, dd, J=8.8, 2.2 Hz), 7.17 (1H, d, J=8.8 Hz), 5.12 (2H, q, J=9.2 Hz).

<Step-2>:2-(2,2,2-trifluoroethoxy)-5-vinylpyridine n-Butyllithium (5.14 mL, 13.4 mmol) is added to a suspension of methyltriphenylphosphonium bromide (4.41 g, 12.34 mmol) in tetrahydrofuran (51 mL) at −78° C. under nitrogen atmosphere. The reaction mixture is warmed to room temperature to yield deep red ylide solution. To ylide solution, cooling in ice, is introduced 6-(2,2,2-trifluoroethoxy)nicotinaldehyde (2.11 g, 10.3 mmol, Step-1) in tetrahydrofuran (10 mL) and stirred at room temperature for 3 hours. The reaction mixture is poured into water, extracted with ethyl acetate and dried over sodium sulfate and concentrated in vacuo. The residue is purified by column chromatography on silica gel eluting with n-hexane/ethyl acetate (10:1) to give 1.56 g (75% yield) of the title compound as colorless oil.

$^1$H-NMR (300 MHz, CDCl$_3$) delta 8.10 (1H, d, J=2.6 Hz), 7.75 (1H, dd, J=8.4, 2.6 Hz), 6.84 (1H, d, J=8.4 Hz), 6.65 (1H, dd, J=17.6, 11.0 Hz), 5.68 (1H, d, J=17.6 Hz), 5.27 (1H, d, J=11.0 Hz), 4.76 (2H, q, J=8.4 Hz), MS (ESI) m/z: 204 (M+H)$^+$.

<Step-3>:1-(6-(2,2,2-trifluoroethoxy)pyridin-3-yl) ethane-1,2-diol (single enantiomer)

A 200 mL flask is charged with tert-butanol (30 mL), water (30 mL) and AD-mix-beta (10 g, 4.92 mmol). Stirring room temperature producted two clear phased. The lower aquerous phase bright yellow. The mixture is cooled to 0° C. Whereupon some of the dissolved salts precipitate. 2-(2,2,2-trifluoroethoxy)-5-vinylpyridine (1.00 g, 4.92 mmol, Step-2) is added at once, and the heterogeneous slurry is stirred vigorously at 0° C. for 15 hours. White precipitate is filtrated and filtrate is removed under reduced pressure. The residue is extracted with ethyl acetate and dried over sodium sulfate and concentrated in vacuo. The residue is purified by column chromatography on silica gel eluting with n-hexane/ethyl acetate (1:3) to give 1.01 g (86% yield) of the title compound as colorless oil.

$^1$H-NMR (300 MHz, CDCl$_3$) delta 8.11 (1H, d, J=2.2 Hz), 7.66 (1H, dd, J=8.4, 2.2 Hz), 6.86 (1H, d, J=8.4 Hz), 4.79 (1H, br s), 4.75 (2H, q, J=8.4 Hz), 3.76-3.60 (2H, m), 3.07 (1H, br s), 2.55 (1H, br s), MS (ESI) m/z: 238 (M+H)$^+$.

<Step-4>:2-hydroxy-2-(6-(2,2,2-trifluoroethoxy) pyridin-3-yl)ethyl 4-methylbenzenesulfonate (single enantiomer)

A mixture of 1-(6-(2,2,2-trifluoroethoxy)pyridin-3-yl) ethane-1,2-diol (1.01 g, 4.24 mmol, Step-3, single enantiomer), p-toluenesulfonyl chloride (0.97 g, 5.09 mmol) and pyridine (3.43 mL, 42.4 mmol) in dichloromethane (21 mL) is stirred at room temperature for 20 hours. Then p-toluenesulfonyl chloride (0.97 g, 5.09 mmol) is added to the reaction mixture and stirred for 24 hours. The reaction mixture is poured into water and extracted with ethyl acetate and dried over sodium sulfate and concentrated in vacuo. The residue is purified by column chromatography on silica gel eluting with n-hexane/ethyl acetate (2:1 to 1:1) to give 1.64 g (99% yield) of the title compound as colorless oil.

MS (ESI) m/z: 392 (M+H)$^+$.

<Step-5>:5-(oxiran-2-yl)-2-(2,2,2-trifluoroethoxy) pyridine (single enantiomer)

A mixture of 2-hydroxy-2-(6-(2,2,2-trifluoroethoxy)pyridin-3-yl)ethyl 4-methylbenzenesulfonate (1.66 g, 4.25 mmol, Step-4, single enantiomer) and potassium carbonate (1.76 g, 12.8 mmol) in methanol (43 mL) is stirred at room temperature for 2 hours. White precipitate is filtrated and filtrate is concentrated in vacuo. The residue is poured into water, extracted with ethyl acetate and dried over sodium sulfate and concentrated in vacuo to give 0.89 g (95% yield) of the title compound as colorless oil. This material is used for the next reaction (Step-6) without further purification.

$^1$H-NMR (300 MHz, CDCl$_3$) delta 8.12 (1H, d, J=2.2 Hz), 7.48 (1H, dd, J=8.8, 2.2 Hz), 6.86 (1H, d, J=8.8 Hz), 4.76 (2H, q, J=8.4 Hz), 3.86 (1H, dd, J=4.0, 2.6 Hz), 3.18 (1H, dd, J=5.1, 4.0 Hz), 2.82 (1H, dd, J=5.1, 2.6 Hz).

<Step-6>:2-azido-2-(6-(2,2,2-trifluoroethoxy)pyridin-3-yl)ethanol (single enantiomer)

Sodium azide (1.05 g, 16.2 mmol) and lithium perchlorate (6.45 g, 60.7 mmol) are added to a solution of 5-(oxiran-2-yl)-2-(2,2,2-trifluoroethoxy)pyridine (0.89 g, 4.04 mmol, Step-5, single enantiomer) in acetonitrile (100 mL) is refluxed with stirring for 5 hours. White precipitate is filtrated and filtrate is concentrated in vacuo. The residue is poured into water, extracted with ethyl acetate and dried over sodium sulfate and concentrated in vacuo. The residue is purified by column chromatography on silica gel eluting with n-hexane/ ethyl acetate (1:1) to give 0.39 g (37% yield) of the title compound as colorless oil.

$^1$H-NMR (300 MHz, CDCl$_3$) delta 8.12 (1H, d, J=2.3 Hz), 7.65 (1H, dd, J=8.6, 2.3 Hz), 6.91 (1H, d, J=8.6 Hz), 4.77 (2H, q, J=8.6 Hz), 4.66 (1H, t, J=6.3 Hz), 3.76 (2H, t, J=6.3 Hz).

<Step-7>:2-amino-2-(6-(2,2,2-trifluoroethoxy)pyridin-3-yl)ethanol hydrochloride (single enantiomer)

The title compound is prepared in 54% yield (0.22 g, a white solid) from 2-azido-2-(6-(2,2,2-trifluoroethoxy)pyridin-3-yl)ethanol (0.39 g, 1.49 mmol, Step-6, single enantiomer) by the similar manner in Step-6 of Amine-4.

$^1$H-NMR (300 MHz, DMSO-d$_6$) delta 8.54 (2H, br s), 8.30 (1H, d, J=2.2 Hz), 7.96 (1H, dd, J=8.4, 2.2 Hz), 7.06 (1H, d, J=8.4 Hz), 5.01 (2H, q, J=9.2 Hz), 4.32 (1H, m), 3.72 (2H, d, J=5.6 Hz).

<Step-8>:tert-butyl(2-hydroxy-1-(6-(2,2,2-trifluoroethoxy)pyridin-3-yl)ethyl)carbamate (single enantiomer)

The title compound is prepared in 99% yield (0.049 g, a white solid) from 2-amino-2-(6-(2,2,2-trifluoroethoxy)pyridin-3-yl)ethanol hydrochloride (0.040 g, 0.147 mmol, Step-7, single enantiomer) by the similar manner in Step-1 of Amine-3.

$^1$H-NMR (300 MHz, CDCl$_3$) delta 8.10 (1H, d, J=2.2 Hz), 7.61 (1H, dd, J=8.8, 2.2 Hz), 6.85 (1H, d, J=8.8 Hz), 5.31 (1H, br s), 4.79-4.70 (3H, m), 3.92-3.74 (2H, m), 2.46 (1H, br s), 1.42 (9H, s), MS (ESI) m/z: 337 (M+H)$^+$.

<Step-9>:tert-butyl(2-methoxy-1-(6-(2,2,2-trifluoro-ethoxy)pyridin-3-yl)ethyl)carbamate (single enantiomer A mixture of tert-butyl (2-hydroxy-1-(6-(2,2,2-trifluoroethoxy)pyridin-3-yl)ethyl)carbamate (0.049 g, 0.146 mmol, Step-8, single enantiomer), silver oxide (0.68 g, 2.91 mmol), Iodomethane (0.36 mL, 5.83 mmol), and acetonitrile (1 mL) is stirred at room temperature under nitrogen atmosphere in the dark for 2 days. The mixture is purified by column chromatography on silica gel (NH-gel) eluting with ethyl acetate to give 0.046 g (90% yield) of the title compound as colorless syrup.

$^1$H-NMR (300 MHz, CDCl$_3$) delta 8.10 (1H, s), 7.63 (1H, dd, J=8.1, 2.2 Hz), 6.83 (1H, d, J=8.1 Hz), 5.33 (1H, br s), 4.78-4.70 (3H, m), 3.65-3.51 (2H, m), 3.35 (3H, s), 1.42 (9H, s), MS (ESI) m/z: 351 (M+H)$^+$.

<Step-10>:2-methoxy-1-(6-(2,2,2-trifluoroethoxy)pyridin-3-yl)ethanamine (single enantiomer A mixture of tert-butyl (2-methoxy-1-(6-(2,2,2-trifluoroethoxy)pyridin-3-yl)ethyl)carbamate (0.046 g, 0.131 mmol, Step-9, single enantiomer) and 4M hydrochloric acid ethyl acetate solution (4 mL) is stirred at room temperature for 2 hours. After removal of the solvent, the residue is diluted with methanol (4 mL) and applied onto a strong cation exchange cartridge (BondElute (registered trademark) SCX, 1 g/6 mL, Varian Inc.), and the solid phase matrix is rinsed with methanol (5 mL). The crude mixture is eluted with 1M ammonia in methanol (5 mL) and concentrated under reduced pressure to give 0.030 g (91% yield) of the title compound as colorless syrup.

$^1$H-NMR (270 MHz, CDCl$_3$) delta 8.12 (1H, d, J=2.6 Hz), 7.71 (1H, dd, J=8.6, 2.6 Hz), 6.84 (1H, d, J=8.6 Hz), 4.75 (2H, q, J=8.6 Hz), 4.20-4.15 (1H, m), 3.49-3.33 (2H, m), 3.39 (3H, s), MS (ESI) m/z: 251 (M+H)$^+$.

Amine-35:(5-ethoxy-6-(2,2,2-trifluoroethoxy)pyridin-3-yl)methanamine hydrochloride <Step-1>:methyl 6-chloro-5-ethoxynicotinate The title compound is prepared in 43% yield (0.68 g, a white solid) from methyl 6-chloro-5-hydroxynicotinate (1.37 g, 7.28 mmol) and iodoethane instead of iodomethane by the similar manner in Step-2 of Amine-4.

$^1$H-NMR (300 MHz, CDCl$_3$) delta 8.58 (1H, d, J=1.8 Hz), 7.75 (1H, d, J=1.8 Hz), 4.19 (2H, q, J=7.0 Hz), 3.96 (3H, s), 1.52 (3H, t, J=7.0 Hz), MS (ESI) m/z: 216 (M+H)$^+$.

<Step-2>:methyl 5-ethoxy-6-(2,2,2-trifluoroethoxy)nicotinate

The title compound is prepared in 44% yield (0.33 g, a white solid) from methyl 6-chloro-5-ethoxynicotinate (0.58 g, 2.69 mmol, Step-1) by the similar manner in Step-1 of Amine-2.

$^1$H-NMR (270 MHz, CDCl$_3$) delta 8.37 (1H, d, J=1.8 Hz), 7.66 (1H, d, J=1.8 Hz), 4.88 (2H, q, J=8.6 Hz), 4.15 (2H, q, J=7.0 Hz), 3.92 (3H, s), 1.48 (3H, t, J=7.0 Hz), MS (ESI) m/z: 280 (M+H)$^+$.

<Step-3>:(5-ethoxy-6-(2,2,2-trifluoroethoxy)pyridin-3-yl)methanol

The title compound is prepared in >99% yield (0.30 g, a white solid) from methyl 5-ethoxy-6-(2,2,2-trifluoroethoxy)nicotinate (0.33 g, 1.19 mmol, Step-2) by the similar manner in Step-3 of Amine-4.

$^1$H-NMR (300 MHz, CDCl$_3$) delta 7.65 (1H, d, J=1.4 Hz), 7.19 (1H, d, J=1.4 Hz), 4.83 (2H, q, J=8.8 Hz), 4.64 (2H, d, J=4.7 Hz), 4.11 (2H, q, J=7.0 Hz), 1.47 (3H, t, J=7.0 Hz), MS (ESI) m/z: 252 (M+H)$^+$.

<Step-4>:5-(chloromethyl)-3-ethoxy-2-(2,2,2-trifluoroethoxy)pyridine

The title compound is prepared in >99% yield (0.27 g, a white solid) from (5-ethoxy-6-(2,2,2-trifluoroethoxy)pyridin-3-yl)methanol (0.25 g, 1.19 mmol, Step-3) by the similar manner in Step-4 of Amine-4.

MS (ESI) m/z: 270 (M+H).

<Step-5>:5-(azidomethyl)-3-ethoxy-2-(2,2,2-trifluoroethoxy)pyridine

The title compound is prepared in 87% yield (0.28 g, yellow oil) from 5-(chloromethyl)-3-ethoxy-2-(2,2,2-trifluoroethoxy)pyridine (0.32 g, 1.18 mmol, Step-4) by the similar manner in Step-5 of Amine-4.

$^1$H-NMR (270 MHz, CDCl$_3$) delta 7.63 (1H, d, J=2.0 Hz), 7.08 (1H, d, J=2.0 Hz), 4.83 (2H, q, J=8.6 Hz), 4.29 (2H, s), 4.11 (2H, q, J=6.9 Hz), 1.47 (3H, t, J=6.9 Hz), MS (ESI) m/z: 277 (M+H)$^+$.

<Step-6>:(5-ethoxy-6-(2,2,2-trifluoroethoxy)pyridin-3-yl)methanamine hydrochloride The title compound is prepared in 49% yield (0.14 g, a white solid) from 5-(azidomethyl)-3-ethoxy-2-(2,2,2-trifluoroethoxy)pyridine (0.28 g, 1.03 mmol, Step-5) by the similar manner in Step-6 of Amine-4.

$^1$H-NMR (300 MHz, DMSO-d$_6$) delta 8.25 (2H, br s), 7.77 (1H, d, J=1.8 Hz), 7.60 (1H, d, J=1.8 Hz), 5.02 (2H, q, J=9.2 Hz), 4.09 (2H, q, J=6.9 Hz), 3.99 (2H, s), 1.36 (3H, t, J=6.9 Hz), MS (ESI) m/z: 251 (M+H)$^+$.

Amine-36:(5-methoxy-6-(2,2,2-trifluoroethoxy)pyridin-3-yl)methanamine hydrochloride <Step-1>:methyl 5-methoxy-6-(2,2,2-trifluoroethoxy)nicotinate The title compound is prepared in 65% yield (0.94 g, a white solid) from methyl 6-chloro-5-methoxynicotinate (1.10 g, 5.43 mmol) by the similar manner in Step-1 of Amine-2.

$^1$H-NMR (300 MHz, CDCl$_3$) delta 8.38 (1H, d, J=1.8 Hz), 7.67 (1H, d, J=1.8 Hz), 4.89 (2H, q, J=8.4 Hz), 3.93 (3H, s), 3.92 (3H, s), MS (ESI) m/z: 266 (M+H)$^+$.

<Step-2>:(5-methoxy-6-(2,2,2-trifluoroethoxy)pyridin-3-yl)methanol

The title compound is prepared in >99% yield (0.45 g, a white solid) from methyl 5-methoxy-6-(2,2,2-trifluoroethoxy)nicotinate (0.50 g, 1.89 mmol, Step-1) by the similar manner in Step-3 of Amine-4.
$^1$H-NMR (300 MHz, CDCl$_3$) delta 7.65 (1H, d, J=1.6 Hz), 7.20 (1H, d, J=1.6 Hz), 4.83 (2H, q, J=8.4 Hz), 4.66 (2H, d, J=5.9 Hz), 3.90 (3H, s), 1.67 (1H, t, J=5.9 Hz),
MS (ESI) m/z: 238 (M+H)$^+$.

<Step-3>:5-(chloromethyl)-3-methoxy-2-(2,2,2-trifluoroethoxy)pyridine

The title compound is prepared in >99% yield (0.43 g, a white solid) from (5-methoxy-6-(2,2,2-trifluoroethoxy)pyridin-3-yl)methanol (0.40 g, 1.67 mmol, Step-2) by the similar manner in Step-4 of Amine-4.
MS (ESI) m/z: 256 (M+H)$^+$.

<Step-4>:5-(azidomethyl)-3-methoxy-2-(2,2,2-trifluoroethoxy)pyridine

The title compound is prepared in 91% yield (0.45 g, colorless oil) from 5-(chloromethyl)-3-methoxy-2-(2,2,2-trifluoroethoxy)pyridine (0.48 g, 1.89 mmol, Step-3) by the similar manner in Step-5 of Amine-4.
$^1$H-NMR (300 MHz, CDCl$_3$) delta 7.64 (1H, d, J=1.8 Hz), 7.09 (1H, d, J=1.8 Hz), 4.85 (2H, q, J=8.4 Hz), 4.31 (2H, s), 3.91 (3H, s), MS (ESI) m/z: 263 (M+H)$^+$.

<Step-5>:(5-methoxy-6-(2,2,2-trifluoroethoxy)pyridin-3-yl)methanamine hydrochloride The title compound is prepared in 61% yield (0.29 g, a white solid) from 5-(azidomethyl)-3-methoxy-2-(2,2,2-trifluoroethoxy)pyridine (0.45 g, 1.72 mmol, Step-4) by the similar manner in Step-6 of Amine-4.
$^1$H-NMR (300 MHz, DMSO-d$_6$) delta 8.44 (2H, br s), 7.78 (1H, d, J=1.8 Hz), 7.70 (1H, d, J=1.8 Hz), 4.98 (2H, q, J=9.2 Hz), 4.15-3.88 (2H, m), 3.83 (3H,s), MS (ESI) m/z: 237 (M+H)$^+$.

Amine-37:(2-morpholino-6-(2,2,2-trifluoroethoxy)pyridin-3-yl)methanamine hydrochloride <Step-1>:2,2,2-trifluoroethyl 2-chloro-6-(2,2,2-trifluoroethoxy)nicotinate The title compound is prepared in 84% yield (1.64 g, a white solid) from 2-chloro-6-hydroxynicotinic acid (1.00 g, 5.76 mmol) by the similar manner in Step-3 of Amine-13.
$^1$H-NMR (300 MHz, CDCl$_3$) delta 8.26 (1H, d, J=8.4 Hz), 6.89 (1H, d, J=8.4 Hz), 4.81 (2H, q, J=8.4 Hz), 4.69 (2H, q, J=8.4 Hz).

<Step-2>:2,2,2-trifluoroethyl 2-morpholino-6-(2,2,2-trifluoroethoxy)nicotinate

A mixture of 2,2,2-trifluoroethyl 2-chloro-6-(2,2,2-trifluoroethoxy)nicotinate (0.30 g, 0.89 mmol, Step-1), morpholine (0.77 mL, 8.89 mmol) and triethylamine (0.62 mL, 4.44 mmol) in tetrahydrofuran (2 mL) is stirred at 140° C. for 10 minutes under microwave irradiation. The reaction mixture is poured into water and extracted with ethyl acetate and dried over sodium sulfate and concentrated in vacuo to give 0.35 g (>99% yield) of the title compound as a yellow solid. This material is used for the next reaction (Step-3) without further purification.
$^1$H-NMR (300 MHz, CDCl$_3$) delta 8.16 (1H, d, J=8.4 Hz), 6.33 (1H, d, J=8.4 Hz), 4.72 (2H, q, J=8.4 Hz), 4.63 (2H, q, J=8.4 Hz), 3.82 (4H, t, J=4.8 Hz), 3.44 (4H, t, J=4.8 Hz) MS (ESI) m/z: 389 (M+H)$^+$.

<Step-3>:(2-morpholino-6-(2,2,2-trifluoroethoxy)pyridin-3-yl)methanol

The title compound is prepared in >99% yield (0.26 g, colorless oil) from 2,2,2-trifluoroethyl 2-morpholino-6-(2,2,2-trifluoroethoxy)nicotinate (0.35 g, 0.90 mmol, Step-2) by the similar manner in Step-3 of Amine-4.
MS (ESI) m/z: 293 (M+H)$^+$.

<Step-4>:2-((2-morpholino-6-(2,2,2-trifluoroethoxy)pyridin-3-yl)methyl)isoindoline-1,3-dione The title compound is prepared in 11% yield (0.04 g, a white solid) from (2-morpholino-6-(2,2,2-trifluoroethoxy)pyridin-3-yl)methanol (0.27 g, 0.92 mmol, Step-3) by the similar manner in Step-3 of Amine-24.
$^1$H-NMR (300 MHz, CDCl$_3$) delta 7.87-7.84 (2H, m), 7.78-7.73 (2H, m), 7.43 (1H, d, J=8.1 Hz), 6.48 (1H, d, J=8.1 Hz), 4.86 (2H, s), 4.72 (2H, q, J=8.4 Hz), 3.38 (4H, t, J=4.8 Hz), 3.15 (4H, J=4.8 Hz), MS (ESI) m/z: 422 (M+H)$^+$.

<Step-5>:(2-morpholino-6-(2,2,2-trifluoroethoxy)pyridin-3-yl)methanamine hydrochloride The title compound is prepared in >99% yield (0.03 g, a white solid) from 2-((2-morpholino-6-(2,2,2-trifluoroethoxy)pyridin-3-yl)methyl)isoindoline-1,3-dione (0.04 g, 0.10 mmol, Step-4) by the similar manner in Step-4 of Amine-24.
MS (ESI) m/z: 292 (M+H)$^+$.

Amine-38:1-(5-ethoxy-6-(2,2,2-trifluoroethoxy)pyridin-3-yl)ethanamine hydrochloride (single enantiomer)

<Step-1>:6-chloro-5-ethoxynicotinic acid

The title compound is prepared in 98% yield (0.68 g, a white solid) from methyl 6-chloro-5-ethoxynicotinate (0.74 g, 3.42 mmol, Step-1 of Amine-35) by the similar manner in Step-2 of Amine-21.
$^1$H-NMR (270 MHz, DMSO-d$_6$) delta 8.45 (1H, d, J=1.5 Hz), 7.84 (1H, d, J=1.5 Hz), 4.24 (2H, q, J=7.7 Hz), 1.38 (3H, t, J=7.7 Hz), MS (ESI) m/z: 202 (M+H)$^+$.

<Step-2>:6-chloro-5-ethoxy-N-methoxy-N-methylnicotinamide

The title compound is prepared in 94% yield (0.77 g, yellow oil) from 6-chloro-5-ethoxynicotinic acid (0.68 g, 3.35 mmol, Step-1) by the similar manner in Step-2 of Amine-5.
$^1$H-NMR (300 MHz, CDCl$_3$) delta 8.37 (1H, d, J=2.0 Hz), 7.56 (1H, d, J=2.0 Hz), 4.16 (2H, q, J=7.0 Hz), 3.57 (3H, s), 3.40 (3H, s), 1.51 (3H, t, J=7.0 Hz), MS (ESI) m/z: 245 (M+H)$^+$.

<Step-3>:1-(6-chloro-5-ethoxypyridin-3-yl)ethanone

The title compound is prepared in 85% yield (0.54 g, a white solid) from 6-chloro-5-ethoxy-N-methoxy-N-methylnicotinamide (0.77 g, 3.16 mmol, Step-2) by the similar manner in Step-3 of Amine-1.

¹H-NMR (270 MHz, CDCl₃) delta 8.51 (1H, d, J=2.0 Hz), 7.70 (1H, d, J=2.0 Hz), 4.19 (2H, q, J=7.8 Hz), 2.64 (3H, s), 1.51 (3H, t, J=7.8 Hz), MS (ESI) m/z: 200 (M+H)⁺.

<Step-4>:1-(5-ethoxy-6-(2,2,2-trifluoroethoxy)pyridin-3-yl)ethanone

The title compound is prepared in 81% yield (0.58 g, a white solid) from 1-(6-chloro-5-ethoxypyridin-3-yl)ethanone (0.54 g, 2.69 mmol, Step-3) by the similar manner in Step-1 of Amine-2.
¹H-NMR (270 MHz, CDCl₃) delta 8.31 (1H, d, J=1.8 Hz), 7.65 (1H, d, J=1.8 Hz), 4.89 (2H, q, J=9.5 Hz), 4.15 (2H, q, J=7.7 Hz), 2.59 (3H, s), 1.48 (3H, t, J=7.7 Hz), MS (ESI) m/z: 264 (M+H)⁺.

<Step-5>:(R)—N-(1-(5-ethoxy-6-(2,2,2-trifluoroethoxy)pyridin-3-yl)ethyl)-2-methylpropane-2-sulfinamide (single diastereomer)

The title compound is prepared in 93% yield (0.75 g, colorless oil) from 1-(5-ethoxy-6-(2,2,2-trifluoroethoxy)pyridin-3-yl)ethanone (0.58 g, 2.19 mmol, Step-4) and (R)-2-methylpropane-2-sulfinamide by the similar manner in Step-4 of Amine-1.
¹H-NMR (300 MHz, CDCl₃) delta 7.67 (1H, d, J=1.8 Hz), 7.15 (1H, d, J=1.8 Hz), 4.82 (2H, q, J=8.4 Hz), 4.67-4.43 (1H, m), 4.10 (2H, q, J=7.0 Hz), 3.36 (1H, br s), 1.53 (3H, d, J=6.6 Hz), 1.46 (3H, t, J=7.0 Hz), 1.26 (9H, s), MS (ESI) m/z: 369 (M+H)⁺.

<Step-6>:1-(5-ethoxy-6-(2,2,2-trifluoroethoxy)pyridin-3-yl)ethanamine hydrochloride (single enantiomer)

The title compound is prepared in 81% yield (0.50 g, a white solid) from (R)—N-(1-(5-ethoxy-6-(2,2,2-trifluoroethoxy)pyridin-3-yl)ethyl)-2-methylpropane-2-sulfinamide (single diastereomer) (0.75 g, 2.04 mmol, Step-5) by the similar manner in Step-5 of Amine-1.
¹H-NMR (270 MHz, DMSO-d₆) delta 8.39 (2H, br s), 7.80 (1H, d, J=1.8 Hz), 7.66 (1H, d, J=1.8 Hz), 5.02 (2H, q, J=10.3 Hz), 4.48-4.37 (1H, m), 4.13 (2H, q, J=7.7 Hz), 1.52 (3H, d, J=7.3 Hz), 1.37 (3H, t, J=7.7 Hz), MS (ESI) m/z: 265 (M+H)⁺.

Amine-39:1-(2-methoxy-6-(2,2,2-trifluoroethoxy)pyridin-3-yl)-N-methylmethanamine hydrochloride <Step-1>:tert-butyl((2-methoxy-6-(2,2,2-trifluoroethoxy)pyridin-3-yl)methyl)carbamate The title compound is prepared in 90% yield (130 mg, a white solid) from (2-methoxy-6-(2,2,2-trifluoroethoxy)pyridin-3-yl)methanamine (100 mg, 0.42 mmol, Step-4 of Amine-24) by the similar manner in Step-1 of Amine-3.
¹H-NMR (300 MHz, CDCl₃) delta 7.53 (1H, d, J=8.1 Hz), 6.38 (1H, d, J=8.0 Hz), 4.95 (1H, br s), 4.73 (2H, q, J=8.8 Hz), 4.18 (2H, d, J=5.1 Hz), 3.94 (3H, s), 1.44 (9H, s), MS (ESI) m/z: 337 (M+H)⁺.

<Step-2>:tert-butyl((2-methoxy-6-(2,2,2-trifluoroethoxy)pyridin-3-yl)methyl)(methyl)carbamate The title compound is prepared in 80% yield (100 mg, clear colorless oil) from tert-butyl ((2-methoxy-6-(2,2,2-trifluoroethoxy)pyridin-3-yl)methyl)carbamate (120 mg, 0.36 mmol, Step-1) by the similar manner in Step-2 of Amine-3.
¹H-NMR (300 MHz, CDCl₃) delta 7.43 (1H, br s), 6.40 (1H, d, J=8.0 Hz), 4.74 (2H, q, J=8.8 Hz), 4.32 (2H, br s), 3.93 (3H, s), 2.85 (3H, s), 1.46 (9H, s), MS (ESI) m/z: 351 (M+H)⁺.

<Step-3>:1-(2-methoxy-6-(2,2,2-trifluoroethoxy)pyridin-3-yl)-N-methylmethanamine hydrochloride The title compound is prepared in >99% yield (74 mg, a white solid) from tert-butyl ((2-methoxy-6-(2,2,2-trifluoroethoxy)pyridin-3-yl)methyl)(methyl)carbamate (90 mg, 0.26 mmol, Step-2) by the similar manner in Step-3 of Amine-3.
¹H-NMR (300 MHz, DMSO-d₆) delta 8.75 (2H, br s), 7.84 (1H, d, J=8.0 Hz), 6.62 (1H, d, J=8.0 Hz), 5.05 (2H, q, J=8.8 Hz), 4.02 (2H, s), 3.95 (3H, s), 3.33 (3H, s), MS (ESI) m/z: 251 (M+H)⁺.

Amine-40: (2-(4-methylpiperazin-1-yl)-6-(2,2,2-trifluoroethoxy)pyridin-3-yl)methanamine hydrochloride <Step-1>:2,2,2-trifluoroethyl 2-(4-methylpiperazin-1-yl)-6-(2,2,2-trifluoroethoxy)nicotinate The title compound is prepared in >99% yield (0.71 g, yellow oil) from 2,2,2-trifluoroethyl 2-chloro-6-(2,2,2-trifluoroethoxy)nicotinate (0.75 g, 2.04 mmol, Step-1 of Amine-37) and 1-methylpiperazine instead of morpholine by the similar manner in Step-2 of Amine-37.
¹H-NMR (300 MHz, CDCl₃) delta 8.11 (1H, d, J=8.4 Hz), 6.27 (1H, d, J=8.4 Hz), 4.71 (2H, q, J=8.4 Hz), 4.63 (2H, q, J=8.4 Hz), 3.47 (4H, t, J=5.1 Hz)), 2.51 (4H, t, J=5.1 Hz), 2.33 (3H, s), MS (ESI) m/z: 402 (M+H)⁺.

<Step-2>:(2-(4-methylpiperazin-1-yl)-6-(2,2,2-trifluoroethoxy)pyridin-3-yl)methanol The title compound is prepared in >99% yield (0.76 g, colorless oil) from 2,2,2-trifluoroethyl 2-(4-methylpiperazin-1-yl)-6-(2,2,2-trifluoroethoxy)nicotinate (0.99 g, 2.48 mmol, Step-1) by the similar manner in Step-3 of Amine-4.
MS (ESI) m/z: 306 (M+H)⁺.

<Step-3>:2-((2-(4-methylpiperazin-1-yl)-6-(2,2,2-trifluoroethoxy)pyridin-3-yl)methy1)isoindoline-1,3-dione The title compound is prepared in 83% yield (0.90 g, a white solid) from (2-(4-methylpiperazin-1-yl)-6-(2,2,2-trifluoroethoxy)pyridin-3-yl)methanol (0.76 g, 2.45 mmol, Step-2) by the similar manner in Step-3 of Amine-24.
¹H-NMR (300 MHz, DMSO-d₆) delta 7.91-7.83 (4H, m), 7.42 (1H, d, J=8.4 Hz), 6.48 (1H, d, J=8.4 Hz), 4.94 (2H, q, J=9.2 Hz), 4.70 (2H, s), 3.12 (4H, m), 2.45 (4H, m), 2.21 (3H, s), MS (ESI) m/z: 435 (M+H)⁺.

<Step-4>:(2-(4-methylpiperazin-1-yl)-6-(2,2,2-trifluoroethoxy)pyridin-3-yl)methanamine hydrochloride The title compound is prepared in >99% yield (0.78 g, a yellow solid) from 2-((2-(4-methylpiperazin-1-yl)-6-(2,2,2-trifluoroethoxy)pyridin-3-yl)methyl)isoindoline-1,3-dione (0.90 g, 2.06 mmol, Step-3) by the similar manner in Step-4 of Amine-24. MS (ESI) m/z: 305 (M+H)⁺.

Amine-41:(2-(piperidin-1-yl)-6-(2,2,2-trifluoroethoxy)pyridin-3-yl)methanamine

<Step-1>:2,2,2-trifluoroethyl 2-(piperidin-1-yl)-6-(2,2,2-trifluoroethoxy)nicotinate The title compound is prepared in >99% yield (0.70 g, colorless oil) from 2,2,2-trifluoroethyl 2-chloro-6-(2,2,2-trifluoroethoxy)nicotinate (0.75 g, 2.04 mmol, Step-1 of Amine-37) and 1-methylpiperazine instead of morpholine by the similar manner in Step-2 of Amine-37.
¹H-NMR (270 MHz, CDCl₃) delta 8.07 (1H, d, J=8.6 Hz), 6.21 (1H, d, J=8.6 Hz), 4.72 (2H, q, J=8.6 Hz), 4.62 (2H, q, J=8.6 Hz), 3.40 (4H, br s), 1.66 (4H, br s), 1.55 (2H, br s), MS (ESI) m/z: 387 (M+H)⁺.

<Step-2>:(2-(piperidin-1-yl)-6-(2,2,2-trifluoroethoxy)pyridin-3-yl)methanol

The title compound is prepared in >99% yield (0.53 g, colorless oil) from 2,2,2-trifluoroethyl 2-(piperidin-1-yl)-6-(2,2,2-trifluoroethoxy)nicotinate (0.70 g, 1.81 mmol, Step-1) by the similar manner in Step-3 of Amine-4.
MS (ESI) m/z: 291 (M+H)⁺.

<Step-3>:2-((2-(piperidin-1-yl)-6-(2,2,2-trifluoroethoxy)pyridin-3-yl)methyl)isoindoline-1,3-dione The title compound is prepared in 75% yield (0.58 g, a white solid) from (2-(piperidin-1-yl)-6-(2,2,2-trifluoroethoxy)pyridin-3-yl)methanol (0.53 g, 1.83 mmol, Step-2) by the similar manner in Step-3 of Amine-24.
¹H-NMR (300 MHz, DMSO-d₆) delta 7.32-7.25 (4H, m), 6.82 (1H, d, J=8.4 Hz), 5.85 (1H, d, J=8.4 Hz), 4.35 (2H, q, J=9.2 Hz), 4.11 (2H, s), 1.91 (4H, m), 1.06 (4H, m), 0.99 (2H, m), MS (ESI) m/z: 420 (M+H)⁺.

<Step-4>:(2-(piperidin-1-yl)-6-(2,2,2-trifluoroethoxy)pyridin-3-yl)methanamine

The title compound is prepared in >99% yield (0.40 g, colorless oil) from 2-((2-(piperidin-1-yl)-6-(2,2,2-trifluoroethoxy)pyridin-3-yl)methyl)isoindoline-1,3-dione (0.58 g, 1.38 mmol, Step-3) by the similar manner in Step-4 of Amine-24.
¹H-NMR (300 MHz, DMSO-d₆) delta 8.42 (2H, br s), 7.91 (1H, d, J=8.1 Hz), 6.65 (1H, d, J=8.1 Hz), 4.98 (2H, q, J=9.2 Hz), 3.95 (2H, d, J=5.5 Hz), 3.01 (4H, m), 1.64 (4H, m), 1.56 (2H, m).

Amine-42: (5-fluoro-2-methyl-6-(2,2,2-trifluoroethoxy)pyridin-3-yl)methanamine

<Step-1>:methyl 2-chloro-5-fluoro-6-(2,2,2-trifluoroethoxy)nicotinate

The title compound is prepared in 55% yield (1.7 g, a white solid) from 2-chloro-5-fluoro-6-(2,2,2-trifluoroethoxy)nicotinic acid (3.0 g, 11.0 mmol, Step-1 of Amine-12) by the similar manner in Step-2 of Amine-4.
MS (ESI) m/z: 288 (M+H)⁺.

<Step-2>:methyl 5-fluoro-2-methyl-6-(2,2,2-trifluoroethoxy)nicotinate

The title compound is prepared in 75% yield (280 mg, clear colorless oil) from methyl 2-chloro-5-fluoro-6-(2,2,2-trifluoroethoxy)nicotinate (400 mg, 1.4 mmol, Step-1) by the similar manner in Step-3 of Amine-27.
¹H-NMR (300 MHz, CDCl₃) delta 7.95 (1H, d, J=10.2 Hz), 4.88 (2H, q, J=8.0 Hz), 3.90 (3H, s), 2.72 (3H, s).

<Step-3>:(5-fluoro-2-methyl-6-(2,2,2-trifluoroethoxy)pyridin-3-yl)methanol

The title compound is prepared in 94% yield (240 mg, clear colorless oil) from methyl 5-fluoro-2-methyl-6-(2,2,2-trifluoroethoxy)nicotinate (280 mg, 1.0 mmol, Step-2) by the similar manner in Step-3 of Amine-4.
¹H-NMR (300 MHz, CDCl₃) delta 7.46 (1H, d, J=10.3 Hz), 4.82 (2H, q, J=8.8 Hz), 4.65 (2H, s), 2.39 (3H, s), MS (ESI) m/z: 240 (M+H)⁺.

<Step-4>:2-((5-fluoro-2-methyl-6-(2,2,2-trifluoroethoxy)pyridin-3-yl)methyl)isoindoline-1,3-dione The title compound is prepared in 81% yield (290 mg, a white solid) from (5-fluoro-2-methyl-6-(2,2,2-trifluoroethoxy)pyridin-3-yl)methanol (230 mg, 1.0 mmol, Step-3) by the similar manner in Step-3 of Amine-24.
¹H-NMR (300 MHz, CDCl₃) delta 7.90-7.82 (2H, m), 7.80-7.70 (2H, m), 7.44 (1H, d, J=10.3 Hz), 4.85-4.75 (4H, m), 2.59 (3H, s), MS (ESI) m/z: 369 (M+H)⁺.

<Step-5>:(5-fluoro-2-methyl-6-(2,2,2-trifluoroethoxy)pyridin-3-yl)methanamine

The title compound is prepared in 94% yield (170 mg, a white solid) from 2-((5-fluoro-2-methyl-6-(2,2,2-trifluoroethoxy)pyridin-3-yl)methyl)isoindoline-1,3-dione (280 mg, 0.77 mmol, Step-4) by the similar manner in Step-4 of Amine-24.
¹H-NMR (300 MHz, CDCl₃) delta 7.43 (1H, d, J=10.3 Hz), 4.82 (2H, q, J=8.8 Hz), 3.81 (2H, s), 2.39 (3H, s), 1.31 (2H, br s).

Amine-43: (R)-(6-((1,1,1-trifluoropropan-2-yl)oxy)pyridin-3-yl)methanamine hydrochloride <Step-1>: (R)-6-((1,1,1-trifluoropropan-2-yl)oxy)nicotinonitrile The title compound is prepared in 76% yield (592 mg, colorless oil) from 6-chloronicotinonitrile (500 mg, 3.61 mmol) and (R)-1,1,1-trifluoropropan-2-ol instead of 2,2,2-trifluoroethanol by the similar manner in Step-1 of Amine-1.
¹H-NMR (300 MHz, CDCl₃) delta 8.48 (1H, d, J=2.6 Hz), 7.86 (1H, dd, J=8.8, 2.6 Hz), 6.92 (1H, d, J=8.8 Hz), 5.81 (1H, septet, J=6.6 Hz), 1.52 (3H, d, J=6.6 Hz).

<Step-2>:(R)-(6-((1,1,1-trifluoropropan-2-yl)oxy)pyridin-3-yl)methanamine hydrochloride The title compound is prepared in 83% yield (98 mg, an orange solid) from (R)-6-((1,1,1-trifluoropropan-2-yl)oxy)nicotinonitrile (100 mg, 0.46 mmol) by the similar manner in Step-2 of Amine-2.
¹H-NMR (300 MHz, DMSO-d₆) delta 8.43 (2H, br s), 8.29 (1H, d, J=2.5 Hz), 7.95 (1H, dd, J=8.4, 2.5 Hz), 6.99 (1H, d, J=8.4 Hz), 5.90 (1H, septet, J=6.6 Hz), 4.03-3.96 (2H, m), 1.43 (3H, d, J=6.6 Hz), MS (ESI) m/z: 221 (M+H)⁺.

Amine-44: (5-fluoro-2-methyl-6-(2,2,2-trifluoroethoxy)pyridin-3-yl)methanamine

<Step-1>:methyl 5-fluoro-2-methoxy-6-(2,2,2-trifluoroethoxy)nicotinate

To a stirred solution of methyl 2-chloro-5-fluoro-6-(2,2,2-trifluoroethoxy)nicotinate (1.1 g, 3.9 mmol, Step-1 of Amine-42) in THF (35 mL) is added sodium methanolate (0.32 g, 5.8 mmol) at 0° C. The mixture is stirred at 60° C. for 2 hours and cooled to room temperature. The mixture is poured into water and extracted with dichloromethane (10 mL×3). The combined organic layer is washed with water, brine, and dried over sodium sulfate. The organic solvent is removed under reduced pressure. The residue is purified by column chromatography on silica gel eluting with n-hexane/ethyl acetate (9:1) to give 310 mg (28% yield) of the title compound as a white solid.
¹H-NMR (300 MHz, CDCl₃) delta 8.02 (1H, d, J=9.5 Hz), 4.83 (2H, q, J=8.1 Hz), 4.01 (3H, s), 3.88 (3H, s), MS (ESI) m/z: 284 (M+H)⁺.

<Step-2>:(5-fluoro-2-methoxy-6-(2,2,2-trifluoroethoxy)pyridin-3-yl)methanol

The title compound is prepared in 97% yield (370 mg, clear colorless oil) from methyl 5-fluoro-2-methoxy-6-(2,2,2-trifluoroethoxy)nicotinate (430 mg, 1.5 mmol, Step-1) by the similar manner in Step-3 of Amine-4.
¹H-NMR (300 MHz, CDCl₃) delta 7.47 (1H, d, J=9.5 Hz), 4.75 (2H, q, J=8.8 Hz), 4.65-4.60 (2H, m), 3.99 (3H, s), 1.92 (1H, br s), MS (ESI) m/z: 256 (M+H)⁺.

<Step-3>:2-((5-fluoro-2-methoxy-6-(2,2,2-trifluoroethoxy)pyridin-3-yl)methyl)isoindoline-1,3-dione The title compound is prepared in 41% yield (230 mg, a white solid) from (5-fluoro-2-methoxy-6-(2,2,2-trifluoroethoxy)pyridin-3-yl)methanol (370 mg, 1.4 mmol, Step-2) by the similar manner in Step-3 of Amine-24.
¹H-NMR (300 MHz, CDCl₃) delta 7.90-7.80 (2H, m), 7.75-7.70 (2H, m), 7.40 (1H, d, J=10.3 Hz), 4.81 (2H, s), 4.73 (2H, q, J=8.8 Hz), 3.97 (3H, s), MS (ESI) m/z: 385 (M+H)⁺.

<Step-4>:(5-fluoro-2-methoxy-6-(2,2,2-trifluoroethoxy)pyridin-3-yl)methanamine

The title compound is prepared in 95% yield (170 mg, a white solid) from 2-((5-fluoro-2-methoxy-6-(2,2,2-trifluoroethoxy)pyridin-3-yl)methyl)isoindoline-1,3-dione (270 mg, 0.70 mmol, Step-3) by the similar manner in Step-4 of Amine-24.
¹H-NMR (300 MHz, CDCl₃) delta 7.40 (1H, d, J=9.5 Hz), 4.75 (2H, q, J=8.8 Hz), 3.98 (3H, s), 3.77 (2H, s), 1.55 (2H, br s).

Amine-45:(2-ethoxy-6-(2,2,2-trifluoroethoxy)pyridin-3-yl)methanamine hydrochloride <Step-1>:ethyl 2-ethoxy-6-(2,2,2-trifluoroethoxy)nicotinate Sodium ethoxide (1.4 mL, 3.55 mmol, 20% in ethanol) is added to a solution of 2,2,2-trifluoroethyl 2-chloro-6-(2,2,2-trifluoroethoxy)nicotinate (400 mg, 1.19 mmol, Step-1 of Amine-37) in tetrahydrofuran (15 mL) and stirred at room temperature for 1 hour. The reaction mixture is poured into water and extracted with ethyl acetate and dried over sodium sulfate and concentrated in vacuo. The residue is purified by column chromatography on silica gel eluting with n-Hexane/ethyl acetate (7:1) to give 305 mg (88% yield) of title compound as a white solid.
¹H-NMR (300 MHz, CDCl₃) delta 8.20 (1H, d, J=8.2 Hz), 7.26 (1H, d, J=8.2 Hz), 4.75 (2H, q, J=8.4 Hz), 4.45 (2H, q, J=7.0 Hz), 4.32 (2H, q, J=7.0 Hz), 1.45 (3H, t, J=7.0 Hz), 1.37 (3H, t, J=7.0 Hz), MS (ESI) m/z: 294 (M+H)⁺.

<Step-2>:(2-ethoxy-6-(2,2,2-trifluoroethoxy)pyridin-3-yl)methanol

The title compound is prepared in >99% yield (267 mg, a white solid) from ethyl 2-ethoxy-6-(2,2,2-trifluoroethoxy)nicotinate (305 mg, 1.04 mmol, Step-1) by the similar manner in Step-3 of Amine-4.
¹H-NMR (300 MHz, CDCl₃) delta 7.53 (1H, d, J=7.8 Hz), 6.40 (1H, d, J=7.8 Hz), 4.72 (2H, q, J=8.8 Hz), 4.59 (2H, d, J=6.6 Hz), 4.40 (2H, q, J=7.0 Hz), 2.13 (1H, t, J=6.6 Hz), 1.41 (3H, t, J=7.0 Hz), MS (ESI) m/z: 252 (M+H)⁺.

<Step-3>:2-((2-ethoxy-6-(2,2,2-trifluoroethoxy)pyridin-3-yl)methyl)isoindoline-1,3-dione The title compound is prepared in 79% yield (321 mg, a white solid) from (2-ethoxy-6-(2,2,2-trifluoroethoxy)pyridin-3-yl)methanol (267 mg, 1.06 mmol, Step-2) by the similar manner in Step-3 of Amine-24.
¹H-NMR (300 MHz, CDCl₃) delta 7.91-7.80 (2H, m), 7.75-7.63 (2H, m), 7.53 (1H, d, J=7.9 Hz), 6.35 (1H, d, J=7.9 Hz), 4.80 (2H, s), 4.68 (2H, q, J=8.4 Hz), 4.33 (2H, q, J=7.3 Hz), 1.35 (3H, t, J=7.3 Hz), MS (ESI) m/z: 381 (M+H)⁺.

<Step-4>:(2-ethoxy-6-(2,2,2-trifluoroethoxy)pyridin-3-yl)methanamine hydrochloride The title compound is prepared in 76% yield (184 mg, a white solid) from 2-((2-ethoxy-6-(2,2,2-trifluoroethoxy)pyridin-3-yl)methyl)isoindoline-1,3-dione (321 mg, 0.84 mmol, Step-3) by the similar manner in Step-4 of Amine-24.
¹H-NMR (300 MHz, DMSO-d₆) delta 8.11 (2H, br s), 7.79 (1H, d, J=7.9 Hz), 6.57 (1H, d, J=7.9 Hz), 5.01 (2H, q, J=9.2 Hz), 4.38 (2H, q, J=7.0 Hz), 3.93-3.79 (2H, m), 1.35 (3H, t, J=7.0 Hz), MS (ESI) m/z: 251 (M+H)⁺.

Amine-46: (5-(1-aminoethyl)-2-(2,2,2-trifluoroethoxy)pyridin-3-yl)methanol hydrochloride (single enantiomer)

<Step-1>:methyl 5-methyl-6-(2,2,2-trifluoroethoxy)nicotinate

The title compound is prepared in 88% yield (2.87 g, a white solid) from 5-methyl-6-(2,2,2-trifluoroethoxy)nicotinic acid (3.08 g, 13.1 mmol, Step-1 of Amine-17) by the similar manner in Step-2 of Amine-4.
MS (ESI) m/z: 250 (M+H)⁺.

<Step-2>:methyl 5-(bromomethyl)-6-(2,2,2-trifluoroethoxy)nicotinate

A mixture of N-bromosuccinimide (464 mg, 2.61 mmol), 2,2'-azobis(2-methylpropionitrile) (16 mg, 0.10 mmol) and methyl 5-methyl-6-(2,2,2-trifluoroethoxy)nicotinate (500 mg, 2.01 mmol, Step-1) in dichloroethane (10 mL) is stirred at 85° C. for 4 hours. After cooling to room temperature, the reaction mixture is poured into water extracted with dichloroethane and dried over sodium sulfate and concentrated in vacuo. The residue is purified by column chromatography on silica gel eluting with n-Hexane/ethyl acetate (10:1) to give 658 mg (>99% yield) of the title compound as colorless oil.

MS (ESI) m/z: 329 (M+H)+.

<Step-3>:methyl 5-(acetoxymethyl)-6-(2,2,2-trifluoroethoxy)nicotinate

A mixture of methyl 5-(bromomethyl)-6-(2,2,2-trifluoroethoxy)nicotinate (0.68 g, 2.07 mmol, Step-2) and sodium acetate (0.51 g, 6.20 mmol) in DMA (10 mL) is stirred at 130° C. for 2 hours. After cooling to room temperature, the reaction mixture is poured into water, extracted with ethyl acetate and dried over sodium sulfate and concentrated in vacuo. The residue is purified by column chromatography on silica gel eluting with n-Hexane/ethyl acetate (6:1) to give 0.35 g (56% yield) of the title compound as colorless oil.

MS (ESI) m/z: 308 (M+H)+.

<Step-4>:5-(hydroxymethyl)-6-(2,2,2-trifluoroethoxy)nicotinic acid

The title compound is prepared in >99% yield (0.29 g, a white solid) from methyl 5-(acetoxymethyl)-6-(2,2,2-trifluoroethoxy)nicotinate (0.35 g, 1.15 mmol, Step-3) by the similar manner in Step-2 of Amine-21.

MS (ESI) m/z: 252 (M+H)+.

<Step-5>:5-(hydroxymethyl)-N-methoxy-N-methyl-6-(2,2,2-trifluoroethoxy)nicotinamide The title compound is prepared in 41% yield (0.14 g, colorless oil) from 5-(hydroxymethyl)-6-(2,2,2-trifluoroethoxy)nicotinic acid (0.29 g, 1.15 mmol, Step-4) by the similar manner in Step-2 of Amine-5.

MS (ESI) m/z: 295 (M+H)+.

<Step-6>:1-(5-(hydroxymethyl)-6-(2,2,2-trifluoroethoxy)pyridin-3-yl)ethanone

The title compound is prepared in 97% yield (0.12 g, colorless oil) from 5-(hydroxymethyl)-N-methoxy-N-methyl-6-(2,2,2-trifluoroethoxy)nicotinamide (0.14 g, 0.48 mmol, Step-5) by the similar manner in Step-3 of Amine-1.

MS (ESI) m/z: 250 (M+H)+.

<Step-7>:(5-acetyl-2-(2,2,2-trifluoroethoxy)pyridin-3-yl)methyl acetate

A mixture of 1-(5-(hydroxymethyl)-6-(2,2,2-trifluoroethoxy)pyridin-3-yl)ethanone (0.16 g, 0.64 mmol, Step-6), acetic anhydride (0.18 mL, 1.91 mmol) and triethylamine (0.44 mL, 3.19) in dichloromethane (4 mL) is stirred at room temperature for 3 days. The reaction mixture is poured into water, extracted with ethyl acetate and dried over sodium sulfate and concentrated in vacuo to give 0.16 g (86% yield) of the title compound as colorless oil. This material is used for the next reaction (Step-8) without further purification.

MS (ESI) m/z: 292 (M+H)+.

<Step-8>:(R)—N-(1-(5-(hydroxymethyl)-6-(2,2,2-trifluoroethoxy)pyridin-3-yl)ethyl)-2-methylpropane-2-sulfinamide (single diastereomer)

The title compound is prepared in 57% yield (0.11 g, colorless oil) from (5-acetyl-2-(2,2,2-trifluoroethoxy)pyridin-3-yl)methyl acetate (0.16 g, 0.55 mmol, Step-7) and (R)-2-methylpropane-2-sulfinamide by the similar manner in Step-4 of Amine-1.

MS (ESI) m/z: 355 (M+H)+.

<Step-9>:(5-(1-aminoethyl)-2-(2,2,2-trifluoroethoxy)pyridin-3-yl)methanol hydrochloride (single enantiomer)

The title compound is prepared in >99% yield (0.09 g, a white solid) from (R)—N-(1-(5-(hydroxymethyl)-6-(2,2,2-trifluoroethoxy)pyridin-3-yl)ethyl)-2-methylpropane-2-sulfinamide (single diastereomer) (0.11 g, 0.32 mmol, Step-8) by the similar manner in Step-5 of Amine-1.

MS (ESI) m/z: 251 (M+H)+.

Amine-47: (5-methyl-6-(2,2,2-trifluoroethoxy)pyridin-3-yl)methanamine hydrochloride <Step-1>: (5-methyl-6-(2,2,2-trifluoroethoxy)pyridin-3-yl)methanol The title compound is prepared in 99% yield (0.70 g, colorless oil) from methyl 5-methyl-6-(2,2,2-trifluoroethoxy)nicotinate (0.80 g, 3.21 mmol, Step-1 of Amine-46) by the similar manner in Step-3 of Amine-4.

MS (ESI) m/z: 222 (M+H)+.

<Step-2>:5-(chloromethyl)-3-methyl-2-(2,2,2-trifluoroethoxy)pyridine

The title compound is prepared in 99% yield (0.75 g, a white solid) from (5-methyl-6-(2,2,2-trifluoroethoxy)pyridin-3-yl)methanol (0.70 g, 3.18 mmol, Step-1) by the similar manner in Step-4 of Amine-4.

<Step-3>:5-(azidomethyl)-3-methyl-2-(2,2,2-trifluoroethoxy)pyridine

The title compound is prepared in 99% yield (0.77 g, colorless oil) from 5-(chloromethyl)-3-methyl-2-(2,2,2-trifluoroethoxy)pyridine (0.75 g, 3.15 mmol, Step-2) by the similar manner in Step-5 of Amine-4.

<Step-4>:(5-methyl-6-(2,2,2-trifluoroethoxy)pyridin-3-yl)methanamine hydrochloride The title compound is prepared in 46% yield (0.37 g, a white solid) from 5-(azidomethyl)-3-methyl-2-(2,2,2-trifluoroethoxy)pyridine (0.77 g, 3.12 mmol, Step-3) by the similar manner in Step-6 of Amine-4.

$^1$H-NMR (300 MHz, DMSO-$d_6$) delta 8.41 (2H, br s), 8.12 (1H, d, J=2.2 Hz), 7.80 (1H, d, J=1.5 Hz), 5.02 (2H, q, J=9.2 Hz), 3.96 (2H, s), 2.18 (3H, s), MS (ESI) m/z: 221 (M+H)+.

Amine-48: N-methyl-1-(5-methyl-6-(2,2,2-trifluoro-ethoxy)pyridin-3-yl)ethanamine hydrochloride (single enantiomer)

<Step-1>:tert-butyl(1-(5-methyl-6-(2,2,2-trifluoroethoxy)pyridin-3-yl)ethyl)carbamate (single enantiomer)

The title compound is prepared in 95% yield (71 mg, a white solid) from 1-(5-methyl-6-(2,2,2-trifluoroethoxy)pyridin-3-yl)ethanamine hydrochloride (single enantiomer) (60 mg, 0.22 mmol, Amine-17) by the similar manner in Step-1 of Amine-3.
$^1$H-NMR (300 MHz, CDCl$_3$) delta 7.91 (1H, br s), 7.39 (1H, br s), 4.87-4.63 (4H, m), 2.23 (3H, s), 1.45-1.42 (3H, m), 1.42 (9H, s), MS (ESI) m/z: 335 (M+H)$^+$.

<Step-2>:tert-butyl methyl(1-(5-methyl-6-(2,2,2-trifluoroethoxy)pyridin-3-yl)ethyl)carbamate (single enantiomer The title compound is prepared in 92% yield (68 mg, colorless oil) from tert-butyl (1-(5-methyl-6-(2,2,2-trifluoroethoxy)pyridin-3-yl)ethyl)carbamate (single enantiomer) (71 mg, 0.21 mmol, Step-1) by the similar manner in Step-2 of Amine-3.
$^1$H-NMR (300 MHz, CDCl$_3$) delta 7.87 (1H, d, J=2.2 Hz), 7.36 (1H, d, J=2.2 Hz), 5.51-5.32 (1H, m), 4.75 (2H, q, J=8.8 Hz), 2.58 (3H, s), 2.22 (3H, s), 1.49 (9H, s), 1.49-1.47 (3H, m), MS (ESI) m/z: 349 (M+H)$^+$.

<Step-3>:N-methyl-1-(5-methyl-6-(2,2,2-trifluoroethoxy)pyridin-3-yl)ethanamine hydrochloride (single enantiomer)

The title compound is prepared in 68% yield (38 mg, a white solid) from tert-butyl methyl(1-(5-methyl-6-(2,2,2-trifluoroethoxy)pyridin-3-yl)ethyl)carbamate (single enantiomer) (68 mg, 0.19 mmol, Step-2) by the similar manner in Step-3 of Amine-3.
$^1$H-NMR (300 MHz, DMSO-d$_6$) delta 8.13 (1H, d, J=2.2 Hz), 7.83 (1H, d, J=2.2 Hz), 5.02 (2H, q, J=9.2 Hz), 4.34-4.24 (1H, m), 2.39 (3H, s), 2.20 (3H, s), 1.53 (3H, d, J=7.0 Hz), MS (ESI) m/z: 249 (M+H)$^+$.

Amine-49: N-methyl-1-(5-methyl-6-(2,2,2-trifluoroethoxy)pyridin-3-yl)methanamine hydrochloride <Step-1>:tert-butyl ((5-methyl-6-(2,2,2-trifluoroethoxy)pyridin-3-yl)methyl)carbamate The title compound is prepared in 87% yield (65 mg, a white solid) from (5-methyl-6-(2,2,2-trifluoroethoxy)pyridin-3-yl)methanamine hydrochloride (60 mg, 0.23 mmol, Amine-47) by the similar manner in Step-1 of Amine-3.
$^1$H-NMR (300 MHz, CDCl$_3$) delta 7.86 (1H, br s), 7.41 (1H, br s), 4.84-4.68 (3H, m), 4.26-4.18 (2H, m), 2.22 (3H, s), 1.46 (9H, s), MS (ESI) m/z: 321 (M+H)$^+$.

<Step-2>:tert-butyl methyl((5-methyl-6-(2,2,2-trifluoroethoxy)pyridin-3-yl)methyl)carbamate The title compound is prepared in >99% yield (68 mg, colorless oil) from tert-butyl ((5-methyl-6-(2,2,2-trifluoroethoxy)pyridin-3-yl)methyl)carbamate (65 mg, 0.20 mmol, Step-1) by the similar manner in Step-2 of Amine-3.
$^1$H-NMR (300 MHz, CDCl$_3$) delta 7.84-7.81 (1H, m), 7.41-7.34 (1H, m), 4.75 (2H, q, J=8.4 Hz), 4.32 (2H, br s), 2.79 (3H, br s), 2.23 (3H, s), 1.49 (9H, s), MS (ESI) m/z: 335 (M+H)$^+$.

<Step-3>:N-methyl-1-(5-methyl-6-(2,2,2-trifluoroethoxy)pyridin-3-yl)methanamine hydrochloride The title compound is prepared in 84% yield (47 mg, a white solid) from tert-butyl methyl((5-methyl-6-(2,2,2-trifluoroethoxy)pyridin-3-yl)methyl)carbamate (68 mg, 0.20 mmol, Step-2) by the similar manner in Step-3 of Amine-3.
$^1$H-NMR (300 MHz, DMSO-d$_6$) delta 8.96 (1H, m), 8.12 (1H, d, J=2.6 Hz), 7.79 (1H, d, J=2.6 Hz), 5.02 (2H, q, J=9.2 Hz), 4.06 (2H, t, J=5.9 Hz), 2.54-2.48 (3H, m), 2.19 (3H, s), MS (ESI) m/z: 235 (M+H)$^+$.

Amine-50: (3-methyl-6-(2,2,2-trifluoroethoxy)pyridin-2-yl)methanamine hydrochloride <Step-1>:5-methyl-2-(2,2,2-trifluoroethoxy)pyridine The title compound is prepared in 12% yield (0.55 g, colorless oil) from 2-chloro-5-methylpyridine (3.00 g, 23.5 mmol) by the similar manner in Step-1 of Amine-1.
$^1$H-NMR (300 MHz, CDCl$_3$) delta 7.93 (1H, s), 7.45 (1H, dd, J=8.4, 2.6 Hz), 6.76 (1H, d, J=8.4 Hz), 4.72 (2H, q, J=8.8 Hz), 2.26 (3H, s).

<Step-2>:5-methyl-2-(2,2,2-trifluoroethoxy)pyridine 1-oxide

A mixture of 5-methyl-2-(2,2,2-trifluoroethoxy)pyridine (0.55 g, 2.88 mmol, Step-1) and m-chloroperoxybenzoic acid (1.66 g, 5.77 mmol) in dichloromethane (50 mL) is stirred at room temperature for 20 hours. The reaction mixture is poured into 2M sodium hydroxide and extracted with ethyl acetate and dried over sodium sulfate and concentrated in vacuo. The residue is purified by column chromatography on silica gel eluting with ethyl acetate/methanol (10:1) to give 0.14 g (24% yield) of the title compound as a white solid.
$^1$H-NMR (300 MHz, CDCl$_3$) delta 8.08 (1H, s), 7.10 (1H, dd, J=8.4, 1.5 Hz), 7.03 (1H, d, J=8.4 Hz), 4.84 (2H, q, J=8.4 Hz), 2.28 (3H, s), MS (ESI) m/z: 208 (M+H)$^+$.

<Step-3>:3-methyl-6-(2,2,2-trifluoroethoxy)picolinonitrile

Trimethylsilyl cyanide (0.19 mL, 1.40 mmol) is added dropwise a solution of 5-methyl-2-(2,2,2-trifluoroethoxy)pyridine 1-oxide (0.14 g, 0.70 mmol, Step-2) and dimethylcarbamoyl chloride (0.1 mL, 1.05 mmol) in acetonitrile (10 mL) is stirred at room temperature for 2 days. Then trimethylsilyl cyanide (0.19 mL, 1.40 mmol) and dimethylcarbamoyl chloride (0.1 mL, 1.05 mmol) is added to the reaction mixture and refluxed with stirring for 20 hours. After cooling to room temperature, the reaction mixture is poured into water, extracted with ethyl acetate and dried over sodium sulfate and concentrated in vacuo. The residue is purified by column chromatography on silica gel eluting with n-hexane/ethyl acetate (2:1 to 1:1) to give 44 mg (29% yield) of the title compound as colorless oil.
$^1$H-NMR (300 MHz, CDCl$_3$) delta 7.61 (1H, d, J=8.4 Hz), 7.02 (1H, d, J=8.4 Hz), 4.74 (2H, q, J=8.4 Hz), 2.50 (3H, s).

<Step-4>:(3-methyl-6-(2,2,2-trifluoroethoxy)pyridin-2-yl)methanamine hydrochloride The title compound is prepared in 69% yield (36 mg, a white solid) from 3-methyl-6-(2,2,2-trifluoroethoxy)picolinonitrile (44 mg, 0.20 mmol, Step-3) by the similar manner in Step-2 of Amine-2.
MS (ESI) m/z: 221 (M+H)+.

Amine-51: (4-methyl-6-(2,2,2-trifluoroethoxy)pyridin-2-yl)methanamine hydrochloride <Step-1>:2-chloro-4-methylpyridine 1-oxide The title compound is prepared in 28% yield (0.94 g, yellow oil) from 2-chloro-4-methylpyridine (3.00 g, 23.5 mmol) by the similar manner in Step-2 of Amine-50.
$^1$H-NMR (300 MHz, CDCl$_3$) delta 8.25 (1H, d, J=6.6 Hz), 7.32 (1H, d, J=2.2 Hz), 7.02 (1H, dd, J=6.6, 2.2 Hz), 2.36 (3H, s), MS (ESI) m/z: 144 (M+H)+.

<Step-2>:4-methyl-2-(2,2,2-trifluoroethoxy)pyridine 1-oxide

The title compound is prepared in 12% yield (166 mg, a white solid) from 2-chloro-4-methylpyridine 1-oxide (0.94 g, 6.51 mmol, Step-1) by the similar manner in Step-1 of Amine-1.
$^1$H-NMR (300 MHz, CDCl$_3$) delta 8.09 (1H, d, J=6.6 Hz), 7.27-6.90 (2H, m), 4.90 (2H, q, J=8.4 Hz), 2.36 (3H, s), MS (ESI) m/z: 208 (M+H)+.

<Step-3>:4-methyl-6-(2,2,2-trifluoroethoxy)picolinonitrile

The title compound is prepared in 21% yield (36 mg, colorless oil) from 4-methyl-2-(2,2,2-trifluoroethoxy)pyridine 1-oxide (166 mg, 0.80 mmol, Step-2) by the similar manner in Step-3 of Amine-50.
$^1$H-NMR (270 MHz, CDCl$_3$) delta 7.22 (1H, s), 6.89 (1H, s), 4.74 (2H, q, J=8.6 Hz), 2.37 (3H, s), MS (ESI) m/z: 217 (M+H)+.

<Step-4>:(4-methyl-6-(2,2,2-trifluoroethoxy)pyridin-2-yl)methanamine hydrochloride The title compound is prepared in 69% yield (43 mg, a white solid) from 3-methyl-6-(2,2,2-trifluoroethoxy)picolinonitrile (36 mg, 0.20 mmol, Step-3) by the similar manner in Step-2 of Amine-2.
$^1$H-NMR (300 MHz, DMSO-d$_6$) delta 8.21 (2H, br s), 7.00 (1H, s), 6.81 (1H, s), 5.13 (2H, q, J=9.2 Hz), 4.08 (2H, s), 2.31 (3H, s), MS (ESI) m/z: 221 (M+H)+.

Amine-52: (5-chloro-6-(2,2-difluoroethoxy)pyridin-3-yl)methanamine hydrochloride <Step-1>:5-chloro-6-(2,2-difluoroethoxy)nicotinic acid The title compound is prepared in 83% yield (4.12 g, a white solid) from 5,6-dichloronicotinic acid (4.00 g, 20.8 mmol) and 2,2-difluoroethanol instead of 2,2,2-trifluoroethanol by the similar manner in Step-1 of Amine-1.
$^1$H-NMR (300 MHz, DMSO-d$_6$) delta 13.4 (1H, br s), 8.65 (1H, d, J=1.8 Hz), 8.28 (1H, d, J=1.8 Hz), 6.44 (1H, tt, J=54.3, 3.3 Hz), 4.73 (2H, td, J=15.0, 3.3 Hz), MS (ESI) m/z: 236 (M–H)−.

<Step-2>:methyl 5-chloro-6-(2,2-difluoroethoxy)nicotinate

The title compound is prepared in 99% yield (1.57 g, a white solid) from 5-chloro-6-(2,2-difluoroethoxy)nicotinic acid (1.5 g, 6.31 mmol, Step-1) by the similar manner in Step-2 of Amine-27.
$^1$H-NMR (300 MHz, DMSO-d$_6$) delta 8.68 (1H, d, J=2.2 Hz), 8.33 (1H, d, J=2.2 Hz), 6.44 (1H, tt, J=54.3, 3.3 Hz), 4.74 (2H, td, J=14.7, 3.3 Hz), 3.86 (3H, s), MS (ESI) m/z: 252 (M+H)+.

<Step-3>:(5-chloro-6-(2,2-difluoroethoxy)pyridin-3-yl)methanol

The title compound is prepared in 62% yield (0.87 g, colorless oil) from methyl 5-chloro-6-(2,2-difluoroethoxy)nicotinate (1.57 g, 6.25 mmol, Step-2) by the similar manner in Step-3 of Amine-4.
$^1$H-NMR (300 MHz, CDCl$_3$) delta 7.99 (1H, d, J=2.2 Hz), 7.74 (1H, d, J=2.2 Hz), 6.16 (1H, tt, J=55.4, 4.4 Hz), 4.65 (2H, d, J=5.5 Hz), 4.60 (2H, td, J=13.2, 4.0 Hz),
MS (ESI) m/z: 224 (M+H)+.

<Step-4>:2-((5-chloro-6-(2,2-difluoroethoxy)pyridin-3-yl)methyl)isoindoline-1,3-dione The title compound is prepared in 93% yield (1.27 g, a white solid) from (5-chloro-6-(2,2-difluoroethoxy)pyridin-3-yl)methanol (0.87 g, 3.88 mmol, Step-3) by the similar manner in Step-3 of Amine-24.
$^1$H-NMR (300 MHz, DMSO-d$_6$) delta 8.14-7.81 (6H, m), 6.38 (1H, tt, J=54.7, 3.3 Hz), 4.75 (2H, s), 4.62 (2H, td, J=15.0, 3.3 Hz), MS (ESI) m/z: 353 (M+H)+.

<Step-5>:(5-chloro-6-(2,2-difluoroethoxy)pyridin-3-yl)methanamine hydrochloride

The title compound is prepared in 91% yield (0.85 g, a white solid) from 2-((5-chloro-6-(2,2-difluoroethoxy)pyridin-3-yl)methyl)isoindoline-1,3-dione (1.27 g, 3.60 mmol, Step-4) by the similar manner in Step-4 of Amine-24.
$^1$H-NMR (300 MHz, DMSO-d$_6$) delta 8.43 (2H, br s), 8.24 (1H, d, J=2.2 Hz), 8.16 (1H, d, J=2.2 Hz), 6.14 (1H, tt, J=54.3, 3.3 Hz), 4.67 (2H, td, J=15.0, 3.3 Hz), 4.03 (2H, m), MS (ESI) m/z: 223 (M+H)+.

Amine-53: 1-(5-chloro-6-(2,2-difluoroethoxy)pyridin-3-yl)ethanamine hydrochloride (Single enantiomer)

<Step-1>:5-chloro-6-(2,2-difluoroethoxy)-N-methoxy-N-methylnicotinamide

The title compound is prepared in 70% yield (3.38 g, colorless oil) from 5-chloro-6-(2,2-difluoroethoxy)nicotinic acid (4.07 g, 3.60 mmol, Step-1 of Amine-52) by the similar manner in Step-2 of Amine-5.
$^1$H-NMR (300 MHz, DMSO-d$_6$) delta 8.50 (1H, d, J=1.8 Hz), 8.11 (1H, d, J=1.8 Hz), 6.17 (1H, tt, J=55.4, 4.0 Hz), 4.64 (2H, td, J=13.2, 4.0 Hz), 4.68 (3H, s), 3.37 (3H, s), MS (ESI) m/z: 281 (M+H)+.

<Step-2>:1-(5-chloro-6-(2,2-difluoroethoxy)pyridin-3-yl)ethanone

The title compound is prepared in >99% yield (2.84 g, a white solid) from 5-chloro-6-(2,2-difluoroethoxy)-N-methoxy-N-methylnicotinamide (3.38 g, 3.60 mmol, Step-1) by the similar manner in Step-3 of Amine-1.
$^1$H-NMR (300 MHz, DMSO-$d_6$) delta 8.74 (1H, d, J=2.3 Hz), 8.34 (1H, d, J=2.3 Hz), 6.43 (1H, tt, J=54.4, 3.3 Hz), 4.75 (2H, td, J=14.8, 3.3 Hz), 2.57 (3H, s), MS (ESI) m/z: 236 (M+H)$^+$.

<Step-3>:(R)—N-(1-(5-chloro-6-(2,2-difluoroethoxy)pyridin-3-yl)ethyl)-2-methylpropane-2-sulfinamide (single diastereomer)

The title compound is prepared in 85% yield (3.56 g, a white solid) from 1-(5-chloro-6-(2,2-difluoroethoxy)pyridin-3-yl)ethanone (2.88 g, 12.2 mmol, Step-2) and (R)-2-methylpropane-2-sulfinamide by the similar manner in Step-4 of Amine-1.
$^1$H-NMR (300 MHz, CDCl$_3$) delta 8.00 (1H, d, J=2.2 Hz), 7.68 (1H, d, J=2.2 Hz), 6.15 (1H, tt, J=55.8, 4.4 Hz), 4.58 (2H, td, J=13.2, 4.4 Hz), 4.52 (1H, m), 3.37 (1H, br s), 1.51 (3H, d, J=6.6 Hz), 1.22 (9H, s), MS (ESI) m/z: 341 (M+H)$^+$.

<Step-4>:1-(5-chloro-6-(2,2-difluoroethoxy)pyridin-3-yl)ethanamine hydrochloride (single enantiomer)

The title compound is prepared in 87% yield (2.49 g, a white solid) from (R)—N-(1-(5-chloro-6-(2,2-difluoroethoxy)pyridin-3-yl)ethyl)-2-methylpropane-2-sulfinamide (single diastereomer) (3.56 g, 10.5 mmol, Step-3) by the similar manner in Step-5 of Amine-1.
$^1$H-NMR (300 MHz, DMSO-$d_6$) delta 8.57 (2H, br s), 8.27 (1H, d, J=2.2 Hz), 8.20 (1H, d, J=2.2 Hz), 6.41 (1H, tt, J=54.3, 3.3 Hz), 4.67 (2H, td, J=15.0, 3.7 Hz), 4.46 (1H, q, J=6.6 Hz), 1.52 (3H, d, J=6.6 Hz), MS (ESI) m/z: 237 (M+H)$^+$.

Amine-54: (6-(2,2,3,3-tetrafluoropropoxy)pyridin-3-yl)methanamine hydrochloride

<Step-1>:5-(chloromethyl)-2-(2,2,3,3-tetrafluoropropoxy)pyridine

The title compound is prepared in >99% yield (550 mg, brown oil) from (6-(2,2,3,3-tetrafluoropropoxy)pyridin-3-yl)methanol (500 mg, 2.1 mmol) by the similar manner in Step-4 of Amine-4.
MS (ESI) m/z: 258 (M+H)$^+$.

<Step-2>:5-(azidomethyl)-2-(2,2,3,3-tetrafluoropropoxy)pyridine

The title compound is prepared in 50% yield (280 mg, clear colorless oil) from 5-(chloromethyl)-2-(2,2,3,3-tetrafluoropropoxy)pyridine (540 mg, 2.1 mmol, Step-1) by the similar manner in Step-5 of Amine-4.
$^1$H-NMR (300 MHz, CDCl$_3$) delta 8.10 (1H, d, J=2.9 Hz), 7.62 (1H, dd, J=8.8, 2.9 Hz), 8.87 (1H, d, J=8.0 Hz), 6.01 (1H, tt, J=53.5, 5.1 Hz), 4.75 (2H, tt, J=12.5, 1.5 Hz), 4.32 (2H, s), MS (ESI) m/z: 265 (M+H)$^+$.

<Step-3>:(6-(2,2,3,3-tetrafluoropropoxy)pyridin-3-yl)methanamine hydrochloride

To a stirred solution of 5-(azidomethyl)-2-(2,2,3,3-tetrafluoropropoxy)pyridine (110 mg, 2.1 mmol, Step-2) in methanol (3.5 mL) and 2M hydrochloric acid (0.2 mL) is added palladium 10% on carbon (10 mg). The mixture is stirred at room temperature under hydrogen atmosphere (1 atm) for 4 hours. The mixture is filtered through a pad of celite and washed with methanol. The filtrate is concentrated in vacuo to give 110 mg (93% yield) of the title compound as a white solid.
$^1$H-NMR (300 MHz, DMSO-$d_6$) delta 8.39 (3H, br s), 8.31 (1H, d, J=2.2 Hz), 7.96 (1H, dd, J=8.8, 2.2 Hz), 7.02 (1H, d, J=8.8 Hz), 6.68 (1H, tt, J=52.0, 5.9 Hz), 4.88 (2H, t, J=14.6 Hz), 4.01 (2H, s).

Amine-55: (4-methyl-5-(2,2,2-trifluoroethoxy)pyridin-2-yl)methanamine hydrochloride <Step-1>:4-methyl-5-(2,2,2-trifluoroethoxy)picolinonitrile A mixture of 5-bromo-4-methylpicolinonitrile (0.30 g, 1.52 mmol), 2,2,2-trifluoroethanol (0.55 mL, 7.61 mmol), copper(I) iodide (0.029 g, 0.152 mmol), 1,10-phenanthroline (0.03 g, ° C.
° C. for 3 hours under microwave irradiation. The reaction mixture is poured into water, extracted with ethyl acetate and dried over sodium sulfate and concentrated in vacuo. The residue is purified by column chromatography on silica gel eluting with n-hexane/ethyl acetate (4:1) to give 26.5 mg (8% yield) of the title compound as colorless oil.
$^1$H-NMR (300 MHz, CDCl$_3$) delta 8.22 (1H, s), 7.55 (1H, s), 4.53 (2H, q, J=7.7 Hz), 2.34 (3H, s), MS (ESI) m/z: 217 (M+H)$^+$.

<Step-2>:(4-methyl-5-(2,2,2-trifluoroethoxy)pyridin-2-yl)methanamine hydrochloride The title compound is prepared in 58% yield (18 mg, a white solid) from 4-methyl-5-(2,2,2-trifluoroethoxy)picolinonitrile (27 mg, 0.12 mmol, Step-1) by the similar manner in Step-2 of Amine-2.
MS (ESI) m/z: 221 (M+H)$^+$.

Amine-56: (6-(2,2,3,3,3-pentafluoropropoxy)pyridin-3-yl)methanamine hydrochloride <Step-1>:methyl 6-(2,2,3,3,3-pentafluoropropoxy)nicotinate To a stirred suspension of sodium hydride (3.9 g, 96 mmol, 60% in oil) in N,N-dimethylacetamide (160 mL) is added dropwise 2,2,3,3,3-pentafluoropropan-1-ol (6.4 mL, 64 mmol) at 0° C. After stirring for 10 minutes, a solution of methyl 6-chloronicotinate (5.5 g, 32 mmol) in N,N-dimethylacetamide (10 mL) is added dropwise at 0° C., and the mixture is stirred for 30 minutes at room temperature. Then, the mixture is stirred at 90° C. for 2 hours. After cooled to room temperature, 2M aqueous sodium hydroxide is added (pH is around 6). The mixture is extracted with n-hexane/ethyl acetate (1:2, 200 mL). The organic layer is washed with water, brine, and dried over sodium sulfate. The organic solvent is concentrated under reduced pressure, and the residue is purified by column chromatography on amine gel eluting with n-hexane/ethyl acetate (30:1) to give 3.1 g (34% yield) of the title compound as brown oil. MS (ESI) m/z: 286 (M+H)$^+$.

<Step-2>:(6-(2,2,3,3,3-pentafluoropropoxy)pyridin-3-yl)methanol

The title compound is prepared in 83% yield (2.3 g, a white solid) from methyl 6-(2,2,3,3,3-pentafluoropropoxy)nicotinate (3.1 g, 10.8 mmol, Step-1) by the similar manner in Step-3 of Amine-4.

$^1$H-NMR (300 MHz, CDCl$_3$) delta 8.12 (1H, d, J=2.2 Hz), 7.69 (1H, dd, J=8.0, 2.2 Hz), 6.86 (1H, d, J=8.0 Hz), 4.84 (2H, t, J=13.2 Hz), 4.66 (2H, s), 1.76 (1H, br s),
MS (ESI) m/z: 258 (M+H)$^+$.

<Step-3>:5-(chloromethyl)-2-(2,2,3,3,3-pentafluoropropoxy)pyridine

The title compound is prepared in >99% yield (2.5 g, brown oil) from (6-(2,2,3,3,3-pentafluoropropoxy)pyridin-3-yl)methanol (2.3 g, 8.9 mmol, Step-2) by the similar manner in Step-4 of Amine-4.
MS (ESI) m/z: 240 (M−Cl)$^+$.

<Step-4>:5-(azidomethyl)-2-(2,2,3,3,3-pentafluoropropoxy)pyridine

The title compound is prepared in 69% yield (1.7 g, a white solid) from 5-(chloromethyl)-2-(2,2,3,3,3-pentafluoropropoxy)pyridine (2.5 g, 8.9 mmol, Step-3) by the similar manner in Step-5 of Amine-4.

$^1$H-NMR (300 MHz, CDCl$_3$) delta 8.10 (1H, d, J=2.2 Hz), 7.63 (1H, dd, J=8.8, 2.2 Hz), 6.90 (1H, d, J=8.1 Hz), 4.85 (2H, t, J=13.9 Hz), 4.32 (2H, s).

<Step-4>:(6-(2,2,3,3,3-pentafluoropropoxy)pyridin-3-yl)methanamine hydrochloride The title compound is prepared in 90% yield (1.8 g, a white solid) from 5-(azidomethyl)-2-(2,2,3,3,3-pentafluoropropoxy)pyridine (1.7 g, 6.1 mmol, Step-3) by the similar manner in Step-3 of Amine-54.

$^1$H-NMR (300 MHz, DMSO-d$_6$) delta 8.36 (3H, br s), 8.31 (1H, s), 7.96 (1H, d, J=8.0 Hz), 7.05 (1H, d, J=8.1 Hz), 5.13 (2H, t, J=12.5 Hz), 4.06-3.98 (2H, m).

Amine-57: 1-(6-(2,2,3,3-tetrafluoropropoxy)pyridin-3-yl)ethanamine hydrochloride (single enantiomer)

<Step-1>:N-methoxy-N-methyl-6-(2,2,3,3-tetrafluoropropoxy)nicotinamide

The title compound is prepared in 87% yield (7.0 g, pale brown oil) from 6-(2,2,3,3-tetrafluoropropoxy)nicotinic acid (6.9 g, 27.0 mmol) and by the similar manner in Step-2 of Amine-5.

$^1$H-NMR (300 MHz, CDCl$_3$) delta 8.62 (1H, d, J=2.2 Hz), 8.06 (1H, dd, J=8.8, 2.2 Hz), 6.86 (1H, d, J=8.1 Hz), 6.01 (1H, tt, J=52.7, 4.4 Hz), 4.79 (2H, tt, J=12.5, 1.5 Hz), 3.58 (3H, s), 3.38 (3H, s), MS (ESI) m/z: 297 (M+H)$^+$.

<Step-2>:1-(6-(2,2,3,3-tetrafluoropropoxy)pyridin-3-yl)ethanone

The title compound is prepared in 94% yield (5.6 g, brown oil) from N-methoxy-N-methyl-6-(2,2,3,3-tetrafluoropropoxy)nicotinamide (7.0 g, 24.0 mmol) by the similar manner in Step-3 of Amine-1.

$^1$H-NMR (300 MHz, CDCl$_3$) delta 8.76 (1H, d, J=2.2 Hz), 8.21 (1H, dd, J=8.8, 2.9 Hz), 6.91 (1H, d, J=8.8 Hz), 6.00 (1H, tt, J=52.7, 4.4 Hz), 4.83 (2H, t, J=13.2 Hz), 2.60 (3H, s), MS (ESI) m/z: 252 (M+H)$^+$.

<Step-3>:(R)-2-methyl-N-(1-(6-(2,2,3,3-tetrafluoropropoxy)pyridin-3-yl)ethyl)propane-2-sulfinamide (single diastereomer)

The title compound is prepared in 76% yield (6.0 g, pale brown oil) from 1-(6-(2,2,3,3-tetrafluoropropoxy)pyridin-3-yl)ethanone (5.6 g, 22.2 mmol) and (R)-2-methylpropane-2-sulfinamide by the similar manner in Step-4 of Amine-1.

$^1$H-NMR (300 MHz, CDCl$_3$) delta 8.13 (1H, d, J=2.2 Hz), 7.66 (1H, dd, J=8.8, 2.2 Hz), 6.83 (1H, d, J=8.8 Hz), 6.01 (1H, tt, J=53.5, 5.1 Hz), 4.74 (2H, t, J=13.2 Hz), 4.60-4.50 (1H, m), 3.36 (1H, br s), 1.52 (3H, d, J=6.6 Hz), 1.23 (9H, s), MS (ESI) m/z: 357 (M+H)$^+$, 355 (M−H)$^−$.

<Step-4>:1-(6-(2,2,3,3-tetrafluoropropoxy)pyridin-3-yl)ethanamine hydrochloride (single enantiomer)

The title compound is prepared in 93% yield (5.1 g, a white solid) from (R)-2-methyl-N-(1-(6-(2,2,3,3-tetrafluoropropoxy)pyridin-3-yl)ethyl)propane-2-sulfinamide (5.1 g, 16.8 mmol, single diastereomer) by the similar manner in Step-5 of Amine-1.

$^1$H-NMR (300 MHz, DMSO-d$_6$) delta 8.62 (3H, br s), 8.33 (1H, d, J=2.2 Hz), 8.01 (1H, dd, J=8.6, 2.2 Hz), 7.03 (1H, d, J=8.1 Hz), 6.68 (1H, tt, J=51.3, 5.9 Hz), 4.88 (2H, t, J=14.6 Hz), 4.50-4.30 (1H, m), 1.53 (3H, d, J=6.6 Hz).

Amine-58: 1-(3-chloro-4-(2,2,2-trifluoroethoxy)phenyl)ethanamine hydrochloride (single enantiomer)

<Step-1>:3-chloro-N-methoxy-N-methyl-4-(2,2,2-trifluoroethoxy)benzamide

The title compound is prepared in 98% yield (1.2 g, a white solid) from 3-chloro-4-(2,2,2-trifluoroethoxy)benzoic acid (1.0 g, 3.9 mmol) by the similar manner in Step-2 of Amine-5.

$^1$H-NMR (300 MHz, CDCl$_3$) delta 7.85 (1H, d, J=2.2 Hz), 7.67 (1H, dd, J=8.8, 2.2 Hz), 6.96 (1H, d, J=8.1 Hz), 4.47 (2H, q, J=7.3 Hz), 3.56 (3H, s), 3.36 (3H, s), MS (ESI) m/z: 298 (M+H)$^+$.

<Step-2>:1-(3-chloro-4-(2,2,2-trifluoroethoxy)phenyl)ethanone

The title compound is prepared in >99% yield (1.2 g, a pale yellow solid) from 3-chloro-N-methoxy-N-methyl-4-(2,2,2-trifluoroethoxy)benzamide (1.2 g, 3.9 mmol, Step-1) by the similar manner in Step-3 of Amine-1.

$^1$H-NMR (300 MHz, CDCl$_3$) delta 8.03 (1H, d, J=2.2 Hz), 7.87 (1H, dd, J=8.8, 2.2 Hz), 6.99 (1H, d, J=8.0 Hz), 4.49 (2H, q, J=8.1 Hz), 2.58 (3H, s).

<Step-3>:(R)—N-(1-(3-chloro-4-(2,2,2-trifluoroethoxy)phenyl)ethyl)-2-methylpropane-2-sulfinamide (single diastereomer)

The title compound is prepared in 58% yield (940 mg, clear colorless oil) from 1-(3-chloro-4-(2,2,2-trifluoroethoxy)phenyl)ethanone (390 mg, 1.6 mmol, Step-2) and (R)-2-methylpropane-2-sulfinamide by the similar manner in Step-4 of Amine-1.

¹H-NMR (300 MHz, CDCl₃) delta 7.39 (1H, d, J=2.2 Hz), 7.22 (1H, dd, J=8.8, 2.2 Hz), 6.94 (1H, d, J=8.8 Hz), 4.53-4.45 (1H, m), 4.39 (2H, q, J=8.0 Hz), 3.35 (1H, br s), 1.49 (3H, d, J=6.6 Hz), 1.24 (9H, s), MS (ESI) m/z: 358 (M+H)⁺.

<Step-4>:1-(3-chloro-4-(2,2,2-trifluoroethoxy)phenyl)ethanamine hydrochloride (single enantiomer)

The title compound is prepared in 62% yield (470 mg, a white solid) from (R)—N-(1-(3-chloro-4-(2,2,2-trifluoroethoxy)phenyl)ethyl)-2-methylpropane-2-sulfinamide (single diastereomer) (940 mg, 2.6 mmol, Step-3) by the similar manner in Step-5 of Amine-1.
¹H-NMR (300 MHz, DMSO-d₆) delta 8.31 (3H, br s), 7.65 (1H, s), 7.46 (1H, d, J=8.1 Hz), 7.34 (1H, d, J=8.1 Hz), 4.90 (2H, q, J=8.8 Hz), 4.45-4.30 (1H, m), 1.47 (3H, d, J=6.6 Hz)

Amine-59:
(6-(3,3,3-trifluoropropyl)pyridin-3-yl)methanamine hydrochloride

<Step-1>:(3,3,3-trifluoropropyl)magnesium bromide

Magnesium (0.30 g, 12.4 mmol) is added to flame dried flask.
3-bromo-1,1,1-trifluoropropane (1.2 mL, 11.3 mmol) and tetrahydrofuran (11 mL) is added to the flask and refluxed with stirring for 2 hours. This material is used for the next reaction (Step-2).

<Step-2>:methyl 6-(3,3,3-trifluoropropyl)nicotinate (3,3,3-trifluoropropyl)magnesium bromide (8.16 mL, 8.16 mmol, Step-1) is added to a solution of methyl 6-chloronicotinate (0.70 g, 4.08 mmol), iron(III) acetylacetonate (0.14 g, 0.41 mmol) and 1-methyl-2-pyrrolidinone (0.23 mL, 2.39 mmol) in tetrahydrofuran (23 mL) and stirred at room temperature for 30 minutes. The reaction mixture is poured into water, extracted with ethyl acetate and dried over sodium sulfate and concentrated in vacuo. The residue is purified by column chromatography on silica gel eluting with n-hexane/ethyl acetate (3:1) to give 0.95 g (99% yield) of the title compound as a white solid.
¹H-NMR (300 MHz, CDCl₃) delta 9.14 (1H, d, J=2.2 Hz), 8.22 (1H, dd, J=8.1, 2.2 Hz), 7.27 (1H, d, J=8.1 Hz), 3.95 (3H, s), 3.13-3.08 (2H, m), 2.71-2.55 (2H, m), MS (ESI) m/z: 234 (M+H)⁺.

<Step-3>:(6-(3,3,3-trifluoropropyl)pyridin-3-yl)methanol

The title compound is prepared in >99% yield (0.35 g, colorless oil) from methyl 6-(3,3,3-trifluoropropyl)nicotinate (0.4 g, 1.72 mmol, Step-2) by the similar manner in Step-3 of Amine-4.
¹H-NMR (300 MHz, CDCl₃) delta 8.50 (1H, d, J=2.2 Hz), 7.66 (1H, dd, J=8.1, 2.2 Hz), 7.18 (1H, d, J=8.1 Hz), 4.71 (2H, s), 3.06-3.00 (2H, m), 2.66-2.50 (2H, m), 2.17 (1H, br s) MS (ESI) m/z: 206 (M+H)⁺.

<Step-4>:5-(chloromethyl)-2-(3,3,3-trifluoropropyl)pyridine

The title compound is prepared in >99% yield (0.38 g, colorless oil) from (6-(3,3,3-trifluoropropyl)pyridin-3-yl)methanol (0.35 g, 1.72 mmol, Step-3) by the similar manner in Step-4 of Amine-4.
MS (ESI) m/z: 224 (M+H)⁺.

<Step-5>:5-(azidomethyl)-2-(3,3,3-trifluoropropyl)pyridine

The title compound is prepared in >99% yield (0.39 g, colorless oil) from 5-(chloromethyl)-2-(3,3,3-trifluoropropyl)pyridine (0.38 g, 1.70 mmol, Step-4) by the similar manner in Step-5 of Amine-4.
MS (ESI) m/z: 231 (M+H)⁺.

<Step-6>:(6-(3,3,3-trifluoropropyl)pyridin-3-yl)methanamine hydrochloride

The title compound is prepared in 48% yield (0.22 g, a white solid) from 5-(azidomethyl)-2-(3,3,3-trifluoropropyl)pyridine (0.39 g, 1.69 mmol, Step-5) by the similar manner in Step-6 of Amine-4.
MS (ESI) m/z: 205 (M+H)⁺.

Amine-60:1-(6-(2,2,3,3,3-pentafluoropropoxy)pyridin-3-yl)ethanamine hydrochloride (single enantiomer)

<Step-1>:methyl 6-(2,2,3,3,3-pentafluoropropoxy)nicotinate

To a stirred suspension of sodium hydride (4.9 g, 120 mmol, 60% in oil) in N,N-dimethylacetamide (100 mL) is added dropwise 2,2,3,3,3-pentafluoropropan-1-ol (8.1 mL, 82 mmol) at 0° C. After stirring for 10 minutes, a solution of methyl 6-chloronicotinate (7.0 g, 41 mmol) in N,N-dimethylacetamide (120 mL) is added dropwise at 0° C., and the mixture is stirred for 30 minutes at room temperature. Then, the mixture is stirred at 90° C. for 2 hours. After cooled to room temperature, 2M aqueous sodium hydroxide is added (pH is around 6). The mixture is extracted with n-hexane/ethyl acetate (1:2, 200 mL). The organic layer is washed with water, brine, and dried over sodium sulfate. The organic solvent is concentrated under reduced pressure to give 8.4 g of the title compound as a crude product (include 2,2,3,3,3-pentafluoropropyl 6-(2,2,3,3,3-pentafluoropropoxy)nicotinate as a byproduct). The residue is used for the next reaction (Step-2) without further purification.
MS (ESI) m/z: 286 (M+H)⁺.

<Step-2>:6-(2,2,3,3,3-pentafluoropropoxy)nicotinic acid

The title compound is prepared in 62% yield (6.8 g, an off-white solid, yield is based on methyl 6-chloronicotinate) from methyl 6-(2,2,3,3,3-pentafluoropropoxy)nicotinate (8.4 g, crude from Step-1) by the similar manner in Step-2 of Amine-21.
¹H-NMR (300 MHz, CDCl₃) delta 8.90 (1H, d, J=2.2 Hz), 8.29 (1H, dd, J=8.8, 2.2 Hz), 6.94 (1H, d, J=8.8 Hz), 4.93 (2H, t, J=11.7 Hz), MS (ESI) m/z: 270 (M−H)⁻.

<Step-3>:N-methoxy-N-methyl-6-(2,2,3,3,3-pentafluoropropoxy)nicotinamide

The title compound is prepared in 51% yield (3.6 g, brown oil) from 6-(2,2,3,3,3-pentafluoropropoxy)nicotinic acid (6.0 g, 22.1 mmol, Step-2) by the similar manner in Step-2 of Amine-5.

¹H-NMR (300 MHz, CDCl₃) delta 8.61 (1H, d, J=2.2 Hz), 8.06 (1H, dd, J=8.8, 2.2 Hz), 6.89 (1H, d, J=8.8 Hz), 4.89 (2H, t, J=11.7 Hz), 3.57 (3H, s), 3.39 (3H, s), MS (ESI) m/z: 315 (M+H)⁺.

<Step-4>:1-(6-(2,2,3,3,3-pentafluoropropoxy)pyridin-3-yl)ethanone

The title compound is prepared in 97% yield (3.0 g, brown oil) from N-methoxy-N-methyl-6-(2,2,3,3,3-pentafluoropropoxy)nicotinamide (3.6 g, 11.3 mmol, Step-3) by the similar manner in Step-3 of Amine-1.
¹H-NMR (300 MHz, CDCl₃) delta 8.76 (1H, d, J=2.2 Hz), 8.22 (1H, dd, J=8.8, 2.2 Hz), 6.93 (1H, d, J=8.8 Hz), 4.92 (2H, t, J=13.9 Hz), 2.60 (3H, s), MS (ESI) m/z: 270 (M+H)⁺.

<Step-5>:(R)-2-methyl-N-(1-(6-(2,2,3,3,3-pentafluoropropoxy)pyridin-3-yl)ethyl)propane-2-sulfinamide (single diastereomer)

The title compound is prepared in 78% yield (3.2 g, an off-white solid) from 1-(6-(2,2,3,3,3-pentafluoropropoxy)pyridin-3-yl)ethanone (3.0 g, 11.0 mmol, Step-4) and (R)-2-methylpropane-2-sulfinamide by the similar manner in Step-4 of Amine-1.
¹H-NMR (300 MHz, CDCl₃) delta 8.12 (1H, d, J=2.2 Hz), 7.66 (1H, dd, J=8.8, 2.2 Hz), 6.85 (1H, d, J=8.8 Hz), 4.83 (2H, t, J=13.2 Hz), 4.58-4.50 (1H, m), 3.36 (1H, br s), 1.52 (3H, d, J=6.6 Hz), 1.23 (9H, s), MS (ESI) m/z: 375 (M+H)⁺.

<Step-6>:1-(6-(2,2,3,3,3-pentafluoropropoxy)pyridin-3-yl)ethanamine hydrochloride (single enantiomer)

The title compound is prepared in 84% yield (2.2 g, a white solid) from (R)-2-methyl-N-(1-(6-(2,2,3,3,3-pentafluoropropoxy)pyridin-3-yl)ethyl)propane-2-sulfinamide (3.2 g, 8.6 mmol, Step-5, single diastereomer) by the similar manner in Step-5 of Amine-1.
¹H-NMR (300 MHz, DMSO-d₆) delta 8.71 (2H, br s), 8.36 (1H, d, J=2.2 Hz), 8.05 (1H, dd, J=8.8, 2.2 Hz), 7.06 (1H, d, J=8.0 Hz), 5.13 (2H, t, J=13.2 Hz), 4.50-4.40 (1H, m), 1.54 (3H, d, J=6.6 Hz).

Amine-61: (5-ethyl-6-(2,2,2-trifluoroethoxy)pyridin-3-yl)methanamine hydrochloride <Step-1>:methyl 5-bromo-6-(2,2,2-trifluoroethoxy)nicotinate The title compound is prepared in 89% yield (2.2 g, a white solid) from 5-bromo-6-(2,2,2-trifluoroethoxy)nicotinic acid (2.4 g, 7.9 mmol) by the similar manner in Step-2 of Amine-27.
¹H-NMR (300 MHz, CDCl₃) delta 8.72 (1H, d, J=2.2 Hz), 8.47 (1H, d, J=2.2 Hz), 4.87 (2H, q, J=8.1 Hz), 3.94 (3H, s), MS (ESI) m/z: 314 (M+H)⁺.

<Step-2>:methyl 5-ethyl-6-(2,2,2-trifluoroethoxy)nicotinate

The title compound is prepared in 73% yield (610 mg, a white solid) from methyl 5-bromo-6-(2,2,2-trifluoroethoxy)nicotinate (1.0 g, 3.2 mmol, Step-1) and diethylzinc (6.4 mL, 6.4 mmol, 1M solution in n-hexane) instead of dimethylzinc by the similar manner in Step-3 of Amine-27.

¹H-NMR (300 MHz, CDCl₃) delta 8.64 (1H, d, J=2.2 Hz), 8.06 (1H, d, J=2.2 Hz), 4.82 (2H, q, J=8.8 Hz), 3.92 (3H, s), 2.67 (2H, q, J=7.3 Hz), 1.24 (3H, t, J=7.3 Hz),
MS (ESI) m/z: 264 (M+H)⁺.

<Step-3>:(5-ethyl-6-(2,2,2-trifluoroethoxy)pyridin-3-yl)methanol

The title compound is prepared in >99% yield (550 mg, clear colorless oil) from methyl 5-ethyl-6-(2,2,2-trifluoroethoxy)nicotinate (610 mg, 2.3 mmol, Step-2) by the similar manner in Step-3 of Amine-4.
¹H-NMR (300 MHz, CDCl₃) delta 8.04 (1H, s), 7.53 (1H, s), 4.76 (2H, q, J=8.8 Hz), 4.65 (1H, s), 2.64 (2H, q, J=7.3 Hz), 1.22 (3H, t, J=8.0 Hz), MS (ESI) m/z: 236 (M+H)⁺.

<Step-4>:5-(chloromethyl)-3-ethyl-2-(2,2,2-trifluoroethoxy)pyridine

The title compound is prepared in >99% yield (590 mg, clear colorless oil) from (5-ethyl-6-(2,2,2-trifluoroethoxy)pyridin-3-yl)methanol (550 mg, 2.3 mmol, Step-3) by the similar manner in Step-4 of Amine-4.

<Step-5>:5-(azidomethyl)-3-ethyl-2-(2,2,2-trifluoroethoxy)pyridine

The title compound is prepared in 87% yield (530 mg, clear colorless oil) from 5-(chloromethyl)-3-ethyl-2-(2,2,2-trifluoroethoxy)pyridine (590 mg, 2.3 mmol, Step-4) by the similar manner in Step-5 of Amine-4.
¹H-NMR (270 MHz, CDCl₃) delta 7.92 (1H, d, J=2.0 Hz), 7.44 (1H, d, J=2.0 Hz), 4.78 (2H, q, J=8.6 Hz), 4.29 (2H, s), 2.65 (2H, q, J=7.3 Hz), 1.23 (3H, t, J=7.9 Hz),
MS (ESI) m/z: 261 (M+H)⁺.

<Step-6>:(5-ethyl-6-(2,2,2-trifluoroethoxy)pyridin-3-yl)methanamine hydrochloride The title compound is prepared in >99% yield (600 mg, a white solid) from 5-(azidomethyl)-3-ethyl-2-(2,2,2-trifluoroethoxy)pyridine (530 mg, 2.0 mmol, Step-5) by the similar manner in Step-3 of Amine-54.
¹H-NMR (270 MHz, DMSO-d₆) delta 8.37 (3H, br s), 8.13 (1H, s), 7.84 (1H, s), 5.04 (2H, q, J=9.2 Hz), 4.05-3.95 (2H, m), 2.58 (2H, q, J=7.9 Hz), 1.18 (3H, t, J=7.2 Hz).

Amine-62: (6-(2,2-difluoropropoxy)pyridin-3-yl)methanamine hydrochloride

<Step-1>:6-(2,2-difluoropropoxy)nicotinic acid

The title compound is prepared in >99% yield (1.79 g, orange oil) from 6-chloronicotinic acid (1.3 g, 8.25 mmol) and 2,2-difluoropropan-1-ol instead of 2,2,2-trifluoroethanol by the similar manner in Step-1 of Amine-1.
MS (ESI) m/z: 216 (M−H)⁻.

<Step-2>:methyl 6-(2,2-difluoropropoxy)nicotinate

The title compound is prepared in 55% yield (1.04 g, a white solid) from 6-(2,2-difluoropropoxy)nicotinic acid (1.79 g, 8.25 mmol, Step-1) by the similar manner in Step-2 of Amine-4.

¹H-NMR (300 MHz, CDCl₃) delta 8.81 (1H, d, J=2.0 Hz), 8.21 (1H, dd, J=8.4, 2.0 Hz), 6.87 (1H, d, J=8.4 Hz), 4.57 (2H, t, J=12.1 Hz), 3.92 (3H, s), 1.74 (3H, t, J=18.7 Hz), MS (ESI) m/z: 232 (M+H)⁺.

<Step-3>:(6-(2,2-difluoropropoxy)pyridin-3-yl)methanol

The title compound is prepared in >99% yield (0.83 g, colorless oil) from methyl 6-(2,2-difluoropropoxy)nicotinate (0.94 g, 4.08 mmol, Step-2) by the similar manner in Step-3 of Amine-4.

¹H-NMR (300 MHz, CDCl₃) delta 8.11 (1H, d, J=2.2 Hz), 7.67 (1H, dd, J=8.4, 2.2 Hz), 6.84 (1H, d, J=8.4 Hz), 4.65 (2H, d, J=5.5 Hz), 4.51 (2H, t, J=12.1 Hz), 1.73 (3H, t, J=18.7 Hz), MS (ESI) m/z: 204 (M+H)⁺.

<Step-4>:2-((6-(2,2-difluoropropoxy)pyridin-3-yl)methyl)isoindoline-1,3-dione

The title compound is prepared in 68% yield (0.97 g, a white solid) from (6-(2,2-difluoropropoxy)pyridin-3-yl)methanol (0.87 g, 4.29 mmol, Step-3) by the similar manner in Step-3 of Amine-24.

¹H-NMR (270 MHz, CDCl₃) delta 8.25 (1H, d, J=2.3 Hz), 7.86-7.82 (2H, m), 7.75-7.70 (3H, m), 6.78 (1H, d, J=8.6 Hz), 4.79 (2H, s), 4.48 (2H, t, J=12.0 Hz), 1.70 (3H, t, J=18.8 Hz), MS (ESI) m/z: 333 (M+H)⁺.

<Step-5>:(6-(2,2-difluoropropoxy)pyridin-3-yl)methanamine hydrochloride

The title compound is prepared in >99% yield (0.70 g, a white solid) from 2-((6-(2,2-difluoropropoxy)pyridin-3-yl)methyl)isoindoline-1,3-dione (0.97 g, 2.93 mmol, Step-4) by the similar manner in Step-4 of Amine-24.

¹H-NMR (300 MHz, DMSO-d₆) delta 8.57 (2H, br s), 8.29 (1H, d, J=2.5 Hz), 7.97 (1H, dd, J=8.8, 2.5 Hz), 6.99 (1H, d, J=8.8 Hz), 4.58 (2H, q, J=13.2 Hz), 4.02-3.97 (2H, m), 1.72 (3H, t, J=19.1 Hz), MS (ESI) m/z: 203 (M+H)⁺.

Amine-63: (6-(2,2,2-trifluoroethoxy)-5-(trifluoromethyl)pyridin-3-yl)methanamine <Step-1>:ethyl 6-(2,2,2-trifluoroethoxy)-5-4-difluoromethyl)nicotinate A mixture of 5-bromo-2-(2,2,2-trifluoroethoxy)-3-(trifluoromethyl)pyridine (540 mg, 1.67 mmol), palladium acetate (94 mg, 0.42 mmol), 1,1'-bis(diphenylphosphino)ferrocene (462 mg, 0.83 mmol), and diisopropylethylamine (0.58 mL, 3.33 mmol) in ethanol-DMF (1:1, 10 mL) is stirred at 90° C. for 4 hours under carbon monoxide atmosphere (1 atm). After cooling to room temperature, the mixture is poured into water (100 mL) and extracted with EtOAc (100 mL). The combined organic layer is dried over sodium sulfate and concentrated in vacuo. The residue is purified by column chromatography on silica gel eluting with n-hexane/EtOAc (5:1) to give 257 mg (49% yield) of the title compound as green oil.

¹H-NMR (300 MHz, CDCl₃) delta 8.96 (1H, s), 8.52 (1H, s), 4.49 (2H, q, J=8.1 Hz), 4.43 (2H, q, J=7.3 Hz), 1.42 (3H, t, J=6.6 Hz).

<Step-2>:(6-(2,2,2-trifluoroethoxy)-5-(trifluoromethyl)pyridin-3-yl)methanol

To a mixture of ethyl 6-(2,2,2-trifluoroethoxy)-5-(trifluoromethyl)nicotinate (250 mg, 0.79 mmol), sodium borohydride (158 mg, 3.94 mmol), and lithium chloride (167 mg, 3.94 mmol) in THF (3 mL) is added ethanol (3 mL), and the mixture is stirred at room temperature for 4 hours. After cooling to 0° C., the reaction is quenched with water (100 mL) and extracted with EtOAc (100 mL). The separated organic layer is dried over sodium sulfate and concentrated in vacuo. The residue is purified by column chromatography on silica gel eluting with n-hexane/EtOAc (5:1) to give 62 mg (29% yield) of the title compound as green oil.

¹H-NMR (300 MHz, CDCl₃) delta 8.28 (1H, s), 7.99 (1H, s), 4.88 (2H, q, J=8.0 Hz), 4.73 (2H, d, J=5.1 Hz), 1.94 (1H, br s).

<Step-3>:2-((6-(2,2,2-trifluoroethoxy)-5-(trifluoromethyl)pyridin-3-yl)methyl)isoindoline-1,3-dione The title compound is prepared in >99% yield (137 mg, a white solid, containing triphenylphosphine oxide) from (6-(2,2,2-trifluoroethoxy)-5-(trifluoromethyl)pyridin-3-yl)methanol (62 mg, 0.23 mmol, Step-2) by the similar manner in Step-3 of Amine-24.

¹H-NMR (300 MHz, CDCl₃) delta 8.43 (1H, s), 8.03 (1H, s), 7.89-7.86 (2H, m), 7.78-7.73 (2H, m), 4.85 (2H, q, J=8.8 Hz), 4.85 (2H, s), MS (ESI) m/z: 405 (M+H)⁺.

<Step-4>:(6-(2,2,2-trifluoroethoxy)-5-(trifluoromethyl)pyridin-3-yl)methanamine

The title compound is prepared in 51% yield (47 mg, pale yellow oil) from 2-(6-(2,2,2-trifluoroethoxy)-5-(trifluoromethyl)pyridin-3-yl)methyl)isoindoline-1,3-dione (135 mg, 0.33 mmol, Step-3) by the similar manner in Step-4 of Amine-24.

¹H-NMR (300 MHz, CDCl₃) delta 8.24 (1H, s), 7.96 (1H, s), 4.86 (2H, q, J=8.0 Hz), 3.92 (2H, s), MS (ESI) m/z: 258 (M−NH₂)⁺.

Amine-64: (6-(2,2-difluoroethoxy)-5-methylpyridin-3-yl)methanamine hydrochloride <Step-1>:methyl 6-(2,2-difluoroethoxy)-5-methylnicotinate The title compound is prepared in 88% yield (2.99 g, a white solid) from 6-(2,2-difluoroethoxy)-5-methylnicotinic acid (3.19 g, 14.7 mmol, Step-1 of Amine-14) by the similar manner in Step-2 of Amine-4.

¹H-NMR (300 MHz, CDCl₃) delta 8.64 (1H, d, J=1.8 Hz), 8.03 (1H, d, J=1.8 Hz), 6.15 (1H, tt, J=55.8, 4.4 Hz), 4.61 (2H, td, J=13.2, 4.4 Hz), 3.91 (3H, s), 2.25 (3H, s), MS (ESI) m/z: 232 (M+H)⁺.

<Step-2>:(6-(2,2-difluoroethoxy)-5-methylpyridin-3-yl)methanol

The title compound is prepared in >99% yield (2.62 g, colorless oil) from methyl 6-(2,2-difluoroethoxy)-5-methylnicotinate (2.99 g, 12.9 mmol, Step-1) by the similar manner in Step-3 of Amine-4.

¹H-NMR (300 MHz, CDCl₃) delta 7.92 (1H, d, J=1.8 Hz), 7.48 (1H, d, J=1.8 Hz), 6.14 (1H, tt, J=55.8, 4.0 Hz), 4.62-4.49 (4H, m), 2.22 (3H, s), 1.80 (1H, t, J=5.9 Hz), MS (ESI) m/z: 204 (M+H)⁺.

<Step-3>:5-(chloromethyl)-2-(2,2-difluoroethoxy)-3-methylpyridine

The title compound is prepared in >99% yield (2.89 g, colorless oil) from (6-(2,2-difluoroethoxy)-5-methylpyridin-3-yl)methanol (2.62 g, 12.9 mmol, Step-2) by the similar manner in Step-4 of Amine-4.
MS (ESI) m/z: 222 (M+H)$^+$.

<Step-4>:5-(azidomethyl)-2-(2,2-difluoroethoxy)-3-methylpyridine

The title compound is prepared in 86% yield (2.56 g, colorless oil) from 5-(chloromethyl)-2-(2,2-difluoroethoxy)-3-methylpyridine (2.89 g, 12.9 mmol, Step-3) by the similar manner in Step-5 of Amine-4.
$^1$H-NMR (300 MHz, CDCl$_3$) delta 7.91 (1H, d, J=1.8 Hz), 7.42 (1H, br s), 6.15 (1H, tt, J=55.8, 4.4 Hz), 4.56 (2H, td, J=13.6, 4.4 Hz), 4.26 (2H, s), 2.24 (3H, s), MS (ESI) m/z: 229 (M+H)$^+$.

<Step-5>:(6-(2,2-difluoroethoxy)-5-methylpyridin-3-yl)methanamine hydrochloride

The title compound is prepared in 66% yield (1.77 g, a white solid) from 5-(azidomethyl)-2-(2,2-difluoroethoxy)-3-methylpyridine (2.56 g, 11.2 mmol, Step-4) by the similar manner in Step-3 of Amine-54.
$^1$H-NMR (300 MHz, DMSO-d$_6$) delta 8.40 (2H, br s), 8.11 (1H, d, J=2.2 Hz), 7.77 (1H, d, J=2.2 Hz), 6.40 (1H, tt, J=54.7, 3.7 Hz), 4.60 (2H, td, J=15.0, 3.7 Hz), 3.96 (2H, s), 2.18 (3H, s), MS (ESI) m/z: 203 (M+H)$^+$.

Amine-65: (2-fluoro-3-(trifluoromethoxy)phenyl)methanamine hydrochloride

<Step-1>: (2-fluoro-3-(trifluoromethoxy)phenyl)methanol

To a stirred solution of 2-fluoro-3-(trifluoromethoxy)benzaldehyde (1.00 g, 4.81 mmol) in methanol (20 mL) is added Sodium borohydride (0.36 g, 9.61 mmol) at 0° C. After stirring at room temperature for 16 hours, the reaction mixture is quenched with water. The mixture is diluted with ethyl acetate (100 mL) and washed with water. The organic layer is dried over sodium sulfate, and concentrated under reduced pressure to give 0.97 g (96% yield) of the title compound as colorless syrup. This material is used for the next reaction (Step-2) without further purification.
$^1$H-NMR (300 MHz, CDCl$_3$) delta 7.43-7.38 (1H, m), 7.28-7.14 (2H, m), 4.81 (2H, d, J=5.9 Hz), 1.86 (1H, t, J=5.9 Hz).

<Step-2>:1-(chloromethyl)-2-fluoro-3-(trifluoromethoxy)benzene

The title compound is prepared in >99% yield (1.06 g, colorless oil) from (2-fluoro-3-(trifluoromethoxy)phenyl)methanol (0.97 g, 4.63 mmol, Step-1) by the similar manner in Step-4 of Amine-4.

<Step-3>:1-(azidomethyl)-2-fluoro-3-(trifluoromethoxy)benzene

The title compound is prepared in 75% yield (0.81 g, colorless oil) from 1-(chloromethyl)-2-fluoro-3-(trifluoromethoxy)benzene (1.06 g, 4.63 mmol, Step-2) by the similar manner in Step-5 of Amine-4.
$^1$H-NMR (270 MHz, CDCl$_3$) delta 7.35-7.16 (3H, m), 4.47 (2H, s).

<Step-4>:(2-fluoro-3-(trifluoromethoxy)phenyl)methanamine hydrochloride

A mixture of 1-(azidomethyl)-2-fluoro-3-(trifluoromethoxy)benzene (0.81 g, 3.46 mmol, Step-3), palladium 10% on carbon (0.20 g), 4M hydrochloric acid ethyl acetate solution (4 mL), and methanol (20 mL) is stirred at room temperature under hydrogen atmosphere (1 atm). After filtration through a pad of celite, the filtrate is concentrated under reduced pressure. The residue is crystallized from ether and diisopropyl ether to give 0.85 g (>99% yield) of the title compound as a white solid.
$^1$H-NMR (270 MHz, DMSO-d$_6$) delta 7.73-7.59 (2H, m), 7.42-7.36 (1H, m), 4.13 (2H, s), MS (ESI) m/z: 251 (M+MeCN+H)$^+$.

Amine-66:(4-methoxy-3-(trifluoromethoxy)phenyl)methanamine hydrochloride

<Step-1>: (4-methoxy-3-(trifluoromethoxy)phenyl)methanol

The title compound is prepared in >99% yield (1.31 g, colorless syrup) from 4-methoxy-3-(trifluoromethoxy)benzaldehyde (1.30 g, 5.90 mmol) by the similar manner in Step-1 of Amine-65.
$^1$H-NMR (300 MHz, CDCl$_3$) delta 7.27-7.24 (2H, m), 6.98 (1H, d, J=9.5 Hz), 4.64 (2H, d, J=5.9 Hz), 3.89 (3H, s), 1.68 (1H, t, J=5.9 Hz).

<Step-2>:4-(chloromethyl)-1-methoxy-2-(trifluoromethoxy)benzene

The title compound is prepared in >99% yield (1.42 g, colorless oil) from (4-methoxy-3-(trifluoromethoxy)phenyl)methanol (1.31 g, 5.90 mmol, Step-1) by the similar manner in Step-4 of Amine-4.

<Step-3>:4-(azidomethyl)-1-methoxy-2-(trifluoromethoxy)benzene

The title compound is prepared in 96% yield (1.40 g, colorless oil) from 4-(chloromethyl)-1-methoxy-2-(trifluoromethoxy)benzene (1.42 g, 5.90 mmol, Step-2) by the similar manner in Step-5 of Amine-4.
$^1$H-NMR (270 MHz, CDCl$_3$) delta 7.26-7.21 (2H, m), 7.00 (1H, d, J=8.6 Hz), 4.30 (2H, s), 3.90 (3H, s).

<Step-4>:(4-methoxy-3-(trifluoromethoxy)phenyl)methanamine hydrochloride

The title compound is prepared in 91% yield (1.32 g, a white solid) from 4-(azidomethyl)-1-methoxy-2-(trifluoromethoxy)benzene (1.40 g, 5.65 mmol, Step-3) by the similar manner in Step-3 of Amine-54.
$^1$H-NMR (270 MHz, DMSO-d$_6$) delta 7.56-7.49 (2H, m), 7.29 (1H, d, J=8.6 Hz), 4.00 (2H, br s), 3.87 (3H, s), MS (ESI) m/z: 263 (M+MeCN+H)$^+$.

Amine-67: (5-bromo-6-(2,2,2-trifluoroethoxy)pyridin-3-yl)methanamine hydrochloride <Step-1>: (5-bromo-6-(2,2,2-trifluoroethoxy)pyridin-3-yl)methanol The title compound is prepared in 84% yield (610 mg, a white solid) from methyl 5-bromo-6-(2,2,2-trifluoroethoxy)nicotinate (800 mg, 2.6 mmol, Step-1 of Amine-61) by the similar manner in Step-2 of Amine-63.
$^1$H-NMR (300 MHz, CDCl$_3$) delta 8.04 (1H, s), 7.94 (1H, s), 4.81 (2H, q, J=8.1 Hz), 4.66 (2H, d, J=5.1 Hz), 1.73 (1H, t, J=5.9 Hz), MS (ESI) m/z: 286 (M+H)$^+$.

<Step-2>:2-((5-bromo-6-(2,2,2-trifluoroethoxy)pyridin-3-yl)methyl)isoindoline-1,3-dione The title compound is prepared in 88% yield (770 mg, a white solid) from (5-bromo-6-(2,2,2-trifluoroethoxy)pyridin-3-yl)methanol (600 mg, 2.1 mmol, Step-1) by the similar manner in Step-3 of Amine-24.
$^1$H-NMR (300 MHz, CDCl$_3$) delta 8.19 (1H, d, J=2.2 Hz), 7.99 (1H, d, J=2.2 Hz), 7.89-7.81 (2H, m), 7.78-7.70 (2H, m), 4.78 (2H, s), 4.77 (2H, q, J=8.8 Hz), MS (ESI) m/z: 417 (M+H)$^+$.

<Step-3>:(5-bromo-6-(2,2,2-trifluoroethoxy)pyridin-3-yl)methanamine hydrochloride Free base of the title compound is prepared in 97% yield (510 mg, clear colorless oil) from 2-((5-bromo-6-(2,2,2-trifluoroethoxy)pyridin-3-yl)methyl)isoindoline-1,3-dione (770 mg, 1.8 mmol, Step-2) by the similar manner in Step-4 of Amine-24. The obtained amine is suspended in 4M hydrochloric acid in dioxane (3 mL), and the mixture is stirred for 30 minutes at room temperature to give a white precipitate. The precipitate is collected by filtration, washed with dichloromethane, dried in vacuo to give 540 mg (94% yield) of the title compound as a white solid.
$^1$H-NMR (300 MHz, DMSO-d$_6$) delta 8.40 (2H, br s), 8.33 (1H, d, J=2.2 Hz), 8.30 (1H, d, J=1.5 Hz), 5.09 (2H, q, J=8.8 Hz), 4.08-4.00 (2H, m).

Amine-68: 1-(4-(2,2-difluoroethoxy)-3-methylphenyl)ethanamine hydrochloride (single enantiomer)

<Step-1>:methyl 4-(2,2-difluoroethoxy)-3-methylbenzoate

To a stirred solution of methyl 4-hydroxy-3-methylbenzoate (1.5 g, 9.0 mmol), 2,2-difluoroethanol (0.90 g, 10.8 mmol), triphenylphosphine (3.6 g, 13.5 mmol) in THF (40 mL) is added dropwise diethyl azodicarboxylate (4.9 mL, 10.8 mmol, 40% solution in toluene) at 0° C. The mixture is stirred at room temperature for 30 minutes, and then at 60° C. for 2 hours. After cooled to room temperature, the mixture is concentrated under reduced pressure. The residue is purified by column chromatography on silica gel eluting with n-hexane/ethyl acetate (18:1) to give 1.9 g (90% yield) of the title compound as a white solid.
$^1$H-NMR (300 MHz, CDCl$_3$) delta 7.90-7.85 (2H, m), 6.79 (1H, d, J=8.8 Hz), 6.13 (1H, tt, J=54.9, 4.4 Hz), 4.24 (2H, td, J=12.5, 3.7 Hz), 3.89 (3H, s), 2.27 (3H, s).

<Step-2>:4-(2,2-difluoroethoxy)-3-methylbenzoic acid

The title compound is prepared in >99% yield (1.1 g, a white solid) from methyl 4-(2,2-difluoroethoxy)-3-methylbenzoate (1.0 g, 4.3 mmol, Step-1) by the similar manner in Step-2 of Amine-21.
$^1$H-NMR (300 MHz, CDCl$_3$) delta 7.97-7.90 (2H, m), 6.83 (1H, d, J=8.1 Hz), 6.14 (tt, J=54.9, 4.4 Hz), 4.26 (2H, td, J=12.5, 4.4 Hz), 2.28 (3H, s), MS (ESI) m/z: 215 (M−H)$^−$.

<Step-3>:4-(2,2-difluoroethoxy)-N-methoxy-N,3-dimethylbenzamide

The title compound is prepared in 94% yield (900 mg, clear colorless oil) from 4-(2,2-difluoroethoxy)-3-methylbenzoic acid (800 mg, 3.7 mmol, Step-2) by the similar manner in Step-2 of Amine-5.
$^1$H-NMR (300 MHz, CDCl$_3$) delta 7.60-7.50 (2H, m), 6.78 (1H, d, J=8.0 Hz), 6.13 (1H, tt, J=54.9, 4.4 Hz), 4.23 (2H, td, J=12.4, 3.7 Hz), 3.56 (3H, s), 3.35 (3H, s), 2.26 (3H, s), MS (ESI) m/z: 260 (M+H)$^+$.

<Step-4>:1-(4-(2,2-difluoroethoxy)-3-methylphenyl)ethanone

The title compound is prepared in 98% yield (730 mg, pale yellow oil) from 4-(2,2-difluoroethoxy)-N-methoxy-N,3-dimethylbenzamide (900 mg, 3.4 mmol, Step-3) by the similar manner in Step-3 of Amine-1.
$^1$H-NMR (300 MHz, CDCl$_3$) delta 7.84-7.80 (2H, m), 6.81 (1H, d, J=8.0 Hz), 6.14 (1H, tt, J=54.9, 3.7 Hz), 4.25 (2H, td, J=12.5, 3.7 Hz), 2.82 (3H, s), 2.28 (3H, s), MS (ESI) m/z: 215 (M+H)$^+$.

<Step-5>:(R)—N-(1-(4-(2,2-difluoroethoxy)-3-methylphenyl)ethyl)-2-methylpropane-2-sulfinamide (single diastereomer)

The title compound is prepared in 47% yield (520 mg, clear colorless oil) from 1-(4-(2,2-difluoroethoxy)-3-methylphenyl)ethanone (750 mg, 3.5 mmol, Step-4) and (R)-2-methylpropane-2-sulfinamide by the similar manner in Step-4 of Amine-1.
$^1$H-NMR (300 MHz, CDCl$_3$) delta 7.14 (2H, br s), 6.75 (1H, d, J=8.8 Hz), 6.10 (tt, J=54.9, 4.4 Hz), 4.50-4.40 (1H, m), 4.17 (2H, td, J=13.2, 4.4 Hz), 3.33 (1H, br s), 2.24 (3H, s), 1.47 (3H, d, J=6.6 Hz), 1.23 (9H, s).

<Step-6>:1-(4-(2,2-difluoroethoxy)-3-methylphenyl)ethanamine hydrochloride (single enantiomer)

The title compound is prepared in 96% yield (390 mg, a white solid) from (R)—N-(1-(4-(2,2-difluoroethoxy)-3-methylphenyl)ethyl)-2-methylpropane-2-sulfinamide (single diastereomer) (750 mg, 3.5 mmol, Step-4) by the similar manner in Step-5 of Amine-1.
$^1$H-NMR (300 MHz, DMSO-d$_6$) delta 8.23 (2H, br s), 7.31-7.25 (2H, m), 7.06 (1H, d, J=8.8 Hz), 6.40 (1H, tt, J=54.2, 2.9 Hz), 4.33 (2H, td, J=14.7, 3.7 Hz), 2.18 (3H, s), 1.47 (3H, d, J=6.6 Hz).

Amine-69: (6-(2,2-difluoroethoxy)-4-methylpyridin-3-yl)methanamine

<Step-1>:6-(2,2-difluoroethoxy)-4-methylnicotinic acid

The title compound is prepared in 87% yield (849 mg, a pale yellow solid) from 6-fluoro-4-methylnicotinic acid (700 mg, 4.51 mmol) and 2,2-difluoroethanol (555 mg, 6.77 mmol) instead of 2,2,2-trifluoroethanol by the similar manner in Step-1 of Amine-1.

$^1$H-NMR (300 MHz, DMSO-d$_6$) delta 8.64 (1H, s), 6.88 (1H, s), 6.39 (1H, tt, J=54.2, 3.7 Hz), 4.62 (2H, td, J=15.4, 3.7 Hz), 2.60 (3H, s), MS (ESI) m/z: 216 (M−H)$^−$.

<Step-2>:methyl 6-(2,2-difluoroethoxy)-4-methylnicotinate

The title compound is prepared in 36% yield (579 mg, a colorless oil, ca 55% purity) from 6-(2,2-difluoroethoxy)-4-methylnicotinic acid (840 mg, 3.87 mmol, Step-1) by the similar manner in Step-2 of Amine-27.

$^1$H-NMR (300 MHz, CDCl$_3$) delta 8.72 (1H, s), 6.68 (1H, s), 6.12 (1H, tt, J=55.7, 4.4 Hz), 4.57 (2H, td, J=13.9, 4.4 Hz), 3.40 (3H, s), 2.59 (3H, s), MS (ESI) m/z: 232 (M+H)$^+$.

<Step-3>:(6-(2,2-difluoroethoxy)-4-methylpyridin-3-yl)methanol

The title compound is prepared in 65% yield (334 mg, a white solid) from methyl 6-(2,2-difluoroethoxy)-4-methylnicotinate (579 mg, 2.51 mmol, Step-2) by the similar manner in Step-2 of Amine-63.

$^1$H-NMR (300 MHz, CDCl$_3$) delta 8.00 (1H, s), 6.66 (1H, s), 6.11 (1H, tt, J=55.7, 4.4 Hz), 4.66 (2H, d, J=5.1 Hz), 4.52 (2H, td, J=13.9, 4.4 Hz), 2.38 (3H, s), MS (ESI) m/z: 204 (M+H)$^+$.

<Step-4>:2-((6-(2,2-difluoroethoxy)-4-methylpyridin-3-yl)methyl)isoindoline-1,3-dione The title compound is prepared in >99% yield (769 mg, a white solid, containing triphenylphosphine oxide) from (6-(2,2-difluoroethoxy)-4-methylpyridin-3-yl)methanol (330 mg, 1.62 mmol, Step-3) by the similar manner in Step-3 of Amine-24.

$^1$H-NMR (300 MHz, CDCl$_3$) delta 8.15 (1H, s), 7.87-7.84 (2H, m), 7.74-7.71 (2H, m), 6.62 (1H, s), 6.21 (1H, tt, J=36.6, 4.4 Hz), 4.81 (2H, s), 4.48 (2H, td, J=15.4, 4.4 Hz), 2.44 (3H, s), MS (ESI) m/z: 333 (M+H)$^+$.

<Step-5>:(6-(2,2-difluoroethoxy)-4-methylpyridin-3-yl)methanamine

The title compound is prepared in 43% yield (115 mg, pale yellow oil) from 2-((6-(2,2-difluoroethoxy)-4-methylpyridin-3-yl)methyl)isoindoline-1,3-dione (440 mg, 1.32 mmol, Step-4) by the similar manner in Step-4 of Amine-24.

$^1$H-NMR (300 MHz, CDCl$_3$) delta 7.97 (1H, s), 6.64 (1H, s), 6.11 (1H, tt, J=55.7, 4.4 Hz), 4.51 (2H, td, J=13.9, 4.4 Hz), 2.83 (2H, s), 2.34 (3H, s), MS (ESI) m/z: 203 (M+H)$^+$.

Amine-70:1-(2-chloro-4-(2,2,2-trifluoroethoxy)phenyl)ethanamine hydrochloride (single enantiomer)

<Step-1>:2-chloro-N-methoxy-N-methyl-4-(2,2,2-trifluoroethoxy)benzamide

The title compound is prepared in 68% yield (480 mg, a pale brown solid) from 2-chloro-4-(2,2,2-trifluoroethoxy)benzoic acid (600 mg, 2.4 mmol) by the similar manner in Step-2 of Amine-5.

$^1$H-NMR (300 MHz, CDCl$_3$) delta 7.32 (1H, d, J=8.1 Hz), 7.01 (1H, d, J=2.2 Hz), 6.89 (1H, dd, J=8.1, 2.2 Hz), 4.37 (2H, q, J=8.1 Hz), 3.48 (3H, br s), 3.34 (3H, br s), MS (ESI) m/z: 298 (M+H)$^+$.

<Step-2>:1-(2-chloro-4-(2,2,2-trifluoroethoxy)phenyl)ethanone

The title compound is prepared in >99% yield (400 mg, pale yellow oil) from 2-chloro-N-methoxy-N-methyl-4-(2,2,2-trifluoroethoxy)benzamide (470 mg, 1.6 mmol, Step-1) by the similar manner in Step-3 of Amine-1.

$^1$H-NMR (270 MHz, CDCl$_3$) delta 7.68 (1H, d, J=8.6 Hz), 7.01 (1H, d, J=2.6 Hz), 6.89 (1H, dd, J=8.6, 2.6 Hz), 4.38 (2H, q, J=7.9 Hz), 2.65 (3H, s).

<Step-3>:(R)—N-(1-(2-chloro-4-(2,2,2-trifluoroethoxy)phenyl)ethyl)-2-methylpropane-2-sulfinamide (single diastereomer)

The title compound is prepared in 72% yield (390 mg, clear colorless oil) from 1-(2-chloro-4-(2,2,2-trifluoroethoxy)phenyl)ethanone (390 mg, 1.6 mmol, Step-2) and (R)-2-methylpropane-2-sulfinamide by the similar manner in Step-4 of Amine-1.

$^1$H-NMR (300 MHz, CDCl$_3$) delta 7.40 (1H, d, J=8.8 Hz), 6.97 (1H, s), 6.90-6.83 (1H, m), 5.00-4.90 (1H, m), 4.33 (2H, q, J=8.0 Hz), 3.52 (1H, br s), 1.50 (3H, d, J=6.6 Hz), 1.23 (9H, s), MS (ESI) m/z: 358 (M+H)$^+$.

<Step-4>:1-(2-chloro-4-(2,2,2-trifluoroethoxy)phenyl)ethanamine hydrochloride (single enantiomer)

The title compound is prepared in 71% yield (220 mg, a white solid) from (R)—N-(1-(2-chloro-4-(2,2,2-trifluoroethoxy)phenyl)ethyl)-2-methylpropane-2-sulfinamide (single diastereomer) (380 mg, 1.0 mmol, Step-3) by the similar manner in Step-5 of Amine-1.

$^1$H-NMR (300 MHz, DMSO-d$_6$) delta 8.57 (2H, br s), 7.69 (1H, d, J=8.0 Hz), 7.30 (1H, d, J=2.9 Hz), 7.20 (1H, dd, J=8.8, 2.9 Hz), 4.83 (2H, q, J=8.8 Hz), 4.70-4.60 (1H, m), 1.47 (3H, d, J=6.6 Hz).

Amine-71: 1-(6-(2,2-difluoropropoxy)pyridin-3-yl)ethanamine hydrochloride (single enantiomer <Step-1>:6-(2,2-difluoropropoxy)-N-methoxy-N-methylnicotinamide The title compound is prepared in 45% yield (0.96 g, colorless oil) from 6-(2,2-difluoropropoxy)nicotinic acid (1.79 g, 8.25 mmol, Step-1 of Amine-62) by the similar manner in Step-2 of Amine-5.

$^1$H-NMR (300 MHz, CDCl$_3$) delta 8.61 (1H, d, J=2.2 Hz), 8.04 (1H, dd, J=8.4, 2.2 Hz), 6.85 (1H, d, J=8.4 Hz), 4.56 (2H, t, J=12.1 Hz), 3.58 (3H, s), 3.38 (3H, s), 1.75 (3H, t, J=18.7 Hz), MS (ESI) m/z: 261 (M+H)$^+$.

<Step-2>:1-(6-(2,2-difluoropropoxy)pyridin-3-yl)ethanone

The title compound is prepared in 95% yield (0.75 g, a white solid) from 6-(2,2-difluoropropoxy)-N-methoxy-N-methylnicotinamide (0.96 g, 3.67 mmol, Step-1) by the similar manner in Step-3 of Amine-1.

¹H-NMR (300 MHz, CDCl₃) delta 8.76 (1H, d, J=2.6 Hz), 8.20 (1H, dd, J=8.8, 2.6 Hz), 6.90 (1H, d, J=8.8 Hz), 4.59 (2H, t, J=12.1 Hz), 2.59 (3H, s), 1.75 (3H, t, J=18.7 Hz), MS (ESI) m/z: 216 (M+H)⁺.

<Step-3>:(R)—N-(1-(6-(2,2-difluoropropoxy)pyridin-3-yl)ethyl)-2-methylpropane-2-sulfinamide (single diastereomer)

The title compound is prepared in 85% yield (0.95 g, colorless oil) from 1-(6-(2,2-difluoropropoxy)pyridin-3-yl)ethanone (0.75 g, 3.49 mmol, Step-2) and (R)-2-methylpropane-2-sulfinamide by the similar manner in Step-4 of Amine-1.

¹H-NMR (300 MHz, CDCl₃) delta 8.11 (1H, d, J=2.6 Hz), 7.64 (1H, dd, J=8.8, 2.6 Hz), 6.83 (1H, d, J=8.8 Hz), 4.60-4.51 (1H, m), 4.50 (2H, t, J=12.1 Hz), 3.36-3.33 (1H, m), 1.73 (3H, t, J=18.7 Hz), 1.52 (3H, d, J=6.6 Hz), 1.23 (9H, s), MS (ESI) m/z: 321 (M+H)⁺.

<Step-4>:1-(6-(2,2-difluoropropoxy)pyridin-3-yl)ethanamine hydrochloride (single enantiomer)

The title compound is prepared in 89% yield (0.66 g, a white solid) from (R)—N-(1-(6-(2,2-difluoropropoxy)pyridin-3-yl)ethyl)-2-methylpropane-2-sulfinamide (single diastereomer) (0.95 g, 2.96 mmol, Step-3) by the similar manner in Step-5 of Amine-1.

¹H-NMR (300 MHz, DMSO-d₆) delta 8.40 (2H, br s), 8.28 (1H, d, J=2.2 Hz), 7.94 (1H, dd, J=8.8, 2.2 Hz), 7.02 (1H, d, J=8.8 Hz), 4.58 (2H, q, J=13.6 Hz), 4.48-4.41 (1H, m), 1.72 (3H, t, J=19.4 Hz), 1.51 (3H, d, J=6.6 Hz), MS (ESI) m/z: 217 (M+H)⁺.

Amine-72: 1-(2-chloro-4-(2,2-trifluoroethoxy)phenyl)ethanamine hydrochloride (single enantiomer)

<Step-1>:2-chloro-N-methoxy-N-methyl-4-(2,2,2-trifluoroethoxy)benzamide

The title compound is prepared in 68% yield (480 mg, a pale brown solid) from 2-chloro-4-(2,2,2-trifluoroethoxy)benzoic acid (600 mg, 2.4 mmol) by the similar manner in Step-2 of Amine-5.

¹H-NMR (300 MHz, CDCl₃) delta 7.32 (1H, d, J=8.1 Hz), 7.01 (1H, d, J=2.2 Hz), 6.89 (1H, dd, J=8.1, 2.2 Hz), 4.37 (2H, q, J=8.1 Hz), 3.48 (3H, br s), 3.34 (3H, br s), MS (ESI) m/z: 298 (M+H)⁺.

<Step-2>:1-(2-chloro-4-(2,2,2-trifluoroethoxy)phenyl)ethanone

The title compound is prepared in >99% yield (400 mg, pale yellow oil) from 2-chloro-N-methoxy-N-methyl-4-(2,2,2-trifluoroethoxy)benzamide (470 mg, 1.6 mmol, Step-1) by the similar manner in Step-3 of Amine-1.

¹H-NMR (270 MHz, CDCl₃) delta 7.68 (1H, d, J=8.6 Hz), 7.01 (1H, d, J=2.6 Hz), 6.89 (1H, dd, J=8.6, 2.6 Hz), 4.38 (2H, q, J=7.9 Hz), 2.65 (3H, s).

<Step-3>:(R)—N-(1-(2-chloro-4-(2,2,2-trifluoroethoxy)phenyl)ethyl)-2-methylpropane-2-sulfinamide (single diastereomer)

The title compound is prepared in 72% yield (390 mg, clear colorless oil) from 1-(2-chloro-4-(2,2,2-trifluoroethoxy)phenyl)ethanone (390 mg, 1.6 mmol, Step-2) and (R)-2-methylpropane-2-sulfinamide by the similar manner in Step-4 of Amine-1.

¹H-NMR (300 MHz, CDCl₃) delta 7.40 (1H, d, J=8.8 Hz), 6.97 (1H, s), 6.90-6.83 (1H, m), 5.00-4.90 (1H, m), 4.33 (2H, q, J=8.0 Hz), 3.52 (1H, br s), 1.50 (3H, d, J=6.6 Hz), 1.23 (9H, s), MS (ESI) m/z: 358 (M+H)⁺.

<Step-4>:1-(2-chloro-4-(2,2,2-trifluoroethoxy)phenyl)ethanamine hydrochloride (single enantiomer)

The title compound is prepared in 71% yield (220 mg, a white solid) from (R)—N-(1-(2-chloro-4-(2,2,2-trifluoroethoxy)phenyl)ethyl)-2-methylpropane-2-sulfinamide (single diastereomer) (380 mg, 1.0 mmol, Step-3) by the similar manner in Step-5 of Amine-1.

¹H-NMR (300 MHz, DMSO-d₆) delta 8.57 (2H, br s), 7.69 (1H, d, J=8.0 Hz), 7.30 (1H, d, J=2.9 Hz), 7.20 (1H, dd, J=8.8, 2.9 Hz), 4.83 (2H, q, J=8.8 Hz), 4.70-4.60 (1H, m), 1.47 (3H, d, J=6.6 Hz).

Amine-73: (3-methyl-4-(trifluoromethoxylphenyl)methanamine

<Step-1>:3-methyl-4-(trifluoromethoxy)benzonitrile

The title compound is prepared in >99% yield (0.79 g, colorless syrup) from 4-bromo-2-methyl-1-(trifluoromethoxy)benzene (1.00 g, 3.92 mmol) by the similar manner of Example I-16 in WO2009/145721.

¹H-NMR (300 MHz, CDCl₃) delta 7.58-7.53 (2H, m), 7.36-7.28 (1H, m), 2.36 (3H, s).

<Step-2>:(3-methyl-4-(trifluoromethoxy)phenyl)methanamine

The title compound is prepared in 50% yield (0.40 g, pale red oil) from 3-methyl-4-(trifluoromethoxy)benzonitrile (0.79 g, 3.92 mmol, Step-1) by the similar manner of Example I-17 in WO2009/145721.

¹H-NMR (300 MHz, CDCl₃) delta 7.25 (1H, s), 7.21-7.15 (2H, m), 3.84 (2H, s), 2.31 (3H, s).

Amine-74: 1-(6-(2,2-difluoroethoxy)-5-ethylpyridin-3-yl)ethanamine hydrochloride (single enantiomer)

<Step-1>:5-bromo-6-(2,2-difluoroethoxy)nicotinic acid

The title compound is prepared in >99% yield (4.7 g, a pale orange solid) from 5-bromo-6-chloronicotinic acid (3.0 g, 12.7 mmol) and 2,2-difluoroethanol (2.1 g, 25.4 mmol) instead of 2,2,2-trifluoroethanol by the similar manner in Step-1 of Amine-1.

¹H-NMR (300 MHz, CDCl₃) delta 8.78 (1H, d, J=2.2 Hz), 8.48 (1H, d, J=2.2 Hz), 6.18 (1H, tt, J=54.9, 3.7 Hz), 4.67 (2H, td, J=13.2, 4.4 Hz).

<Step-2>:methyl 5-bromo-6-(2,2-difluoroethoxy)nicotinate

The title compound is prepared in 63% yield (3.1 g, an off-white solid) from 5-bromo-6-(2,2-difluoroethoxy)nicotinic acid (4.7 g, 16.5 mmol, Step-1) by the similar manner in Step-2 of Amine-27.

¹H-NMR (300 MHz, CDCl₃) delta 8.72 (1H, d, J=2.2 Hz), 8.44 (1H, d, J=2.2 Hz), 6.17 (1H, tt, J=13.2, 4.4 Hz), 4.65 (2H, td, J=13.2, 4.4 Hz), 3.93 (3H, s), MS (ESI) m/z: 296 (M+H)⁺.

<Step-3>:methyl 6-(2,2-difluoroethoxy)-5-ethylnicotinate

The title compound is prepared in 88% yield (660 mg, clear colorless oil) from methyl 5-bromo-6-(2,2-difluoroethoxy) nicotinate (900 mg, 3.0 mmol, Step-2) and diethylzinc instead of dimethylzinc by the similar manner in Step-3 of Amine-27.
¹H-NMR (300 MHz, CDCl₃) delta 8.64 (1H, d, J=2.2 Hz), 8.04 (1H, d, J=2.2 Hz), 6.15 (1H, tt, J=55.7, 4.4 Hz), 4.62 (2H, td, J=13.2, 3.7 Hz), 3.92 (3H, s), 2.64 (2H, q, J=7.4 Hz), 1.22 (3H, t, J=7.4 Hz), MS (ESI) m/z: 246 (M+H)⁺.

<Step-4>:6-(2,2-difluoroethoxy)-5-ethylnicotinic acid

The title compound is prepared in 92% yield (330 mg, a white solid) from methyl 6-(2,2-difluoroethoxy)-5-ethylnicotinate (380 mg, 1.6 mmol, Step-3) by the similar manner in Step-2 of Amine-21.
¹H-NMR (300 MHz, CDCl₃) delta 8.73 (1H, d, J=2.2 Hz), 8.08 (1H, J=2.2 Hz), 6.16 (1H, tt, J=54.9, 3.7 Hz), 4.64 (2H, td, J=13.2, 3.7 Hz), 2.67 (2H, q, J=7.3 Hz), 1.24 (3H, t, J=7.3 Hz), MS (ESI) m/z: 232 (M+H)⁺, 230 (M−H)⁻.

<Step-5>:6-(2,2-difluoroethoxy)-5-ethyl-N-methoxy-N-methylnicotinamide

The title compound is prepared in 83% yield (270 mg, clear colorless oil) from 6-(2,2-difluoroethoxy)-5-ethylnicotinic acid (270 mg, 1.2 mmol, Step-4) by the similar manner in Step-2 of Amine-5.
¹H-NMR (300 MHz, CDCl₃) delta 8.44 (1H, d, J=2.2 Hz), 7.86 (1H, d, J=2.2 Hz), 6.16 (1H, tt, J=54.9, 3.7 Hz), 4.60 (2H, td, J=13.2, 3.7 Hz), 3.59, (3H, s), 3.38 (3H, s), 2.65 (2H, q, J=7.3 Hz), 1.22 (3H, t, J=7.3 Hz), MS (ESI) m/z: 275 (M+H)⁺.

<Step-6>:1-(6-(2,2-difluoroethoxy)-5-ethylpyridin-3-yl)ethanone

The title compound is prepared in >99% yield (220 mg, clear colorless oil) from 6-(2,2-difluoroethoxy)-5-ethyl-N-methoxy-N-methylnicotinamide (260 mg, 0.96 mmol, Step-5) by the similar manner in Step-3 of Amine-1.
¹H-NMR (300 MHz, CDCl₃) delta 8.59 (1H, d, J=2.2 Hz), 8.03 (1H, d, J=2.2 Hz), 6.15 (1H, tt, J=55.7, 4.4 Hz), 4.63 (2H, td, J=13.9, 4.4 Hz), 2.65 (2H, q, J=7.3 Hz), 2.58 (3H, s), 1.23 (3H, t, J=7.3 Hz), MS (ESI) m/z: 230 (M+H)⁺.

<Step-7>:(R)—N-(1-(6-(2,2-difluoroethoxy)-5-ethylpyridin-3-yl)ethyl)-2-methylpropane-2-sulfinamide (single diastereomer)

The title compound is prepared in 76% yield (240 mg, clear colorless oil) from 1-(6-(2,2-difluoroethoxy)-5-ethylpyridin-3-yl)ethanone (220 mg, 0.94 mmol, Step-6) and (R)-2-methylpropane-2-sulfinamide by the similar manner in Step-4 of Amine-1.
¹H-NMR (300 MHz, CDCl₃) delta 7.95 (1H, d, J=2.2 Hz), 7.43 (1H, d, J=2.2 Hz), 6.14 (1H, tt, J=55.7, 3.7 Hz), 4.60-4.48 (3H, m), 2.62 (2H, q, J=7.3 Hz), 1.51 (3H, d, J=6.6 Hz), 1.23 (9H, s), 1.20 (3H, t, J=7.3 Hz), MS (ESI) m/z: 335 (M+H)⁺.

<Step-8>:1-(6-(2,2-difluoroethoxy)-5-ethylpyridin-3-yl)ethanamine hydrochloride (single enantiomer)

The title compound is prepared in 75% yield (140 mg, a white solid) from (R)—N-(1-(6-(2,2-difluoroethoxy)-5-ethylpyridin-3-yl)ethyl)-2-methylpropane-2-sulfinamide (single diastereomer) (240 mg, 0.71 mmol, Step-7) by the similar manner in Step 5 of Amine-1.
¹H-NMR (300 MHz, DMSO-d₆) delta 8.44 (2H, br s), 8.12 (1H, d, J=2.2 Hz), 7.82 (1H, d, J=2.2 Hz), 6.40 (1H, tt, J=54.9, 3.7 Hz), 4.60 (2H, td, J=15.4, 3.7 Hz), 4.44-4.40 (1H, m), 2.57 (2H, q, J=7.3 Hz), 1.52 (3H, d, J=6.6 Hz), 1.18 (3H, t, J=7.3 Hz).

Amine-75:1-(5-methyl-6-(2,2,3,3-tetrafluoropropoxy)pyridin-3-yl)ethanamine hydrochloride (single enantiomer)

<Step-1>:5-methyl-6-(2,2,3,3-tetrafluoropropoxy) nicotinic acid

The title compound is prepared in >99% yield (3.7 g, a white solid) from 6-fluoro-5-methylnicotinic acid (2.0 g, 12.9 mmol) and 2,2,3,3-tetrafluoropropan-1-ol (3.4 g, 25.8 mmol) instead of 2,2,2-trifluoroethanol by the similar manner in Step-1 of Amine-1.
¹H-NMR (300 MHz, CDCl₃) delta 8.74 (1H, d, J=2.2 Hz), 8.09 (1H, d, J=2.2 Hz), 6.00 (1H, tt, J=52.7, 3.7 Hz), 4.84 (2H, t, J=12.5 Hz), 2.28 (3H, s), MS (ESI) m/z: 268 (M+H)⁺, 266 (M−H)⁻.

<Step-2>:N-methoxy-N,5-dimethyl-6-(2,2,3,3-tetrafluoropropoxy)nicotinamide

The title compound is prepared in 83% yield (960 mg, clear colorless oil) from 5-methyl-6-(2,2,3,3-tetrafluoropropoxy) nicotinic acid (800 mg, 3.7 mmol, Step-1) by the similar manner in Step-2 of Amine-5.
¹H-NMR (300 MHz, CDCl₃) delta 8.44 (1H, s), 7.86 (1H, s), 6.01 (1H, tt, J=53.2, 4.4 Hz), 4.79 (2H, t, J=12.5 Hz), 3.57 (3H, s), 3.37 (3H, s), 2.24 (3H, s), MS (ESI) m/z: 311 (M+H)⁺.

<Step-3>:1-(5-methyl-6-(2,2,3,3-tetrafluoropropoxy) pyridin-3-yl)ethanone

The title compound is prepared in >99% yield (820 mg, clear colorless oil) from N-methoxy-N,5-dimethyl-6-(2,2,3,3-tetrafluoropropoxy)nicotinamide (900 mg, 3.4 mmol, Step-2) by the similar manner in Step-3 of Amine-1.
¹H-NMR (300 MHz, CDCl₃) delta 8.59 (1H, d, J=1.8 Hz), 8.02 (1H, d, J=1.8 Hz), 5.99 (1H, tt, J=53.2, 4.4 Hz), 4.83 (2H, td, J=12.5, 1.5 Hz), 2.57 (3H, s), 2.26 (3H, s), MS (ESI) m/z: 266 (M+H)⁺.

<Step-4>:(R)-2-methyl-N-(1-(5-methyl-6-(2,2,3,3-tetrafluoropropoxy)pyridin-3-yl)ethyl)propane-2-sulfinamide (single diastereomer)

The title compound is prepared in 77% yield (880 mg, clear colorless oil) from 1-(5-methyl-6-(2,2,3,3-tetrafluoropropoxy)pyridin-3-yl)ethanone (820 mg, 3.1 mmol, Step-3) and (R)-2-methylpropane-2-sulfinamide by the similar manner in Step-4 of Amine-1.
¹H-NMR (300 MHz, CDCl₃) delta 7.94 (1H, d, J=2.2 Hz), 7.44 (1H, d, J=2.2 Hz), 6.00 (1H, tt, J=53.2, 4.4 Hz), 4.12 (2H, td, J=12.5, 1.5 Hz), 4.50 (1H, m), 2.21 (3H, s), 1.50 (3H, d, J=6.6 Hz), 1.22 (9H, s), MS (ESI) m/z: 371 (M+H)+.

Step-5>:1-(5-methyl-6-(2,2,3,3-tetrafluoropropoxy) pyridin-3-yl)ethanamine hydrochloride (single enantiomer)

The title compound is prepared in >99% yield (800 mg, a orange gum) from (R)-2-methyl-N-(1-(5-methyl-6-(2,2,3,3-tetrafluoropropoxy)pyridin-3-yl)ethyl)propane-2-sulfinamide (single diastereomer) (880 mg, 32.4 mmol, Step-4) by the similar manner in Step-5 of Amine-1.

$^1$H-NMR (300 MHz, DMSO-$d_6$) delta 8.60 (2H, br s), 8.13 (1H, d, J=2.2 Hz), 7.84 (1H, d, J=2.2 Hz), 6.68 (1H, tt, J=51.7, 5.5 Hz), 4.87 (2H, t, J=13.9 Hz), 4.38 (1H, m), 2.18 (3H, s), 1.50 (3H, d, J=6.6 Hz).

Amine-76: (6-(2,2-difluoroethoxy)-5-ethylpyridin-3-yl)methanamine hydrochloride

<Step-1>: (6-(2,2-difluoroethoxy)-5-ethylpyridin-3-yl)methanol

The title compound is prepared in 97% yield (230 mg, clear colorless oil) from methyl 6-(2,2-difluoroethoxy)-5-ethylnicotinate (270 mg, 1.1 mmol, Step-3 of Amine-74) by the similar manner in Step-3 of Amine-4.

$^1$H-NMR (300 MHz, CDCl$_3$) delta 7.94 (1H, d, J=2.2 Hz), 7.50 (1H, d, J=2.2 Hz), 6.14 (1H, tt, J=55.7, 4.5 Hz), 4.63 (2H, d, J=5.1 Hz), 4.55 (2H, td, 13.2, 3.7 Hz), 2.62 (2H, q, J=7.3 Hz), 1.64 (1H, t, J=5.9 Hz), 1.21 (3H, t, J=7.3 Hz), MS (ESI) m/z: 218 (M+H)+.

Step-2>:5-(chloromethyl)-2-(2,2-difluoroethoxy)-3-ethylpyridine

The title compound is prepared in 99% yield (250 mg, a white solid) from (6-(2,2-difluoroethoxy)-5-ethylpyridin-3-yl)methanol (230 mg, 1.1 mmol, Step-1) by the similar manner in Step-4 of Amine-4.

<Step-3>:5-(azidomethyl)-2-(2,2-difluoroethoxy)-3-ethylpyridine

The title compound is prepared in 99% yield (250 mg, clear colorless oil) from 5-(chloromethyl)-2-(2,2-difluoroethoxy)-3-ethylpyridine (250 mg, 1.1 mmol, Step-2) by the similar manner in Step-5 of Amine-4.

MS (ESI) m/z: 243 (M+H)+.

Step-4>:(6-(2,2-difluoroethoxy)-5-ethylpyridin-3-yl) methanamine hydrochloride

The title compound is prepared in 61% yield (160 mg, a white solid) from 5-(azidomethyl)-2-(2,2-difluoroethoxy)-3-ethylpyridine (250 mg, 1.0 mmol, Step-3) by the similar manner in Step-3 of Amine-54.

$^1$H-NMR (300 MHz, DMSO-$d_6$) delta 8.41 (2H, br s), 8.10 (1H, d, J=2.2 Hz), 7.80 (1H, d, J=2.2 Hz), 6.38 (1H, tt, J=55.0, 3.7 Hz), 4.59 (2H, td, J=15.0, 3.7 Hz), 3.96 (2H, s), 2.55 (2H, q, J=7.3 Hz), 1.16 (3H, t, J=7.3 Hz) MS (ESI) m/z: 217 (M+H)+.

Amine-77: (5-cyclopropyl-6-(2,2-difluoroethoxy) pyridin-3-yl)methanamine hydrochloride <Step-1>:methyl 5-cyclopropyl-6-(2,2-difluoroethoxy)nicotinate A mixture of methyl 5-bromo-6-(2,2-difluoroethoxy)nicotinate (900 mg, 3.0 mmol, Step-2 of Amine-74), cyclopropylboronic acid (780 mg, 9.1 mmol), palladium(II) acetate (34 mg, 0.15 mmol), tricyclohexylphosphine (0.60 mL, 0.30 mmol, 0.5M in toluene) and potassium phosphate (1.6 g, 7.6 mmol) in toluene/water (10:1, 33 mL) is stirred at reflux temperature overnight. After cooled to room temperature, the mixture is filtered through a pad of celite, washed with ethyl acetate. The filtrate is extracted with ethyl acetate and dried over sodium sulfate. The organic solvent is removed under reduced pressure and then the residue is purified by column chromatography on silica gel eluting with n-hexane/ethyl acetate (15:1) to give 630 mg (81% yield) of the title compound as a pale yellow solid.

$^1$H-NMR (300 MHz, CDCl$_3$) delta 8.58 (1H, d, J=2.2 Hz), 7.72 (1H, d, J=2.2 Hz), 6.17 (1H, tt, J=55.7, 4.4 Hz), 4.64 (2H, td, J=13.9, 4.4 Hz), 3.90 (3H, s), 2.13-2.03 (1H, m), 1.06-0.97 (2H, m), 0.75-0.70 (2H, m), MS (ESI) m/z: 258 (M+H)+.

<Step-2>:(5-cyclopropyl-6-(2,2-difluoroethoxy)pyridin-3-yl)methanol

The title compound is prepared in 96% yield (230 mg, clear colorless oil) from methyl 5-cyclopropyl-6-(2,2-difluoroethoxy)nicotinate (270 mg, 1.1 mmol, Step-1) by the similar manner in Step-3 of Amine-4.

$^1$H-NMR (300 MHz, CDCl$_3$) delta 7.87 (1H, d, J=2.2 Hz), 7.19 (1H, d, J=2.2 Hz), 6.12 (1H, tt, J=55.7, 4.4 Hz), 4.68-4.50 (2H, m), 2.11-2.00 (1H, m), 1.00-0.91 (2H, m), 0.71-0.62 (2H, m), 1.23 (1H, br s), MS (ESI) m/z: 230 (M+H)+.

<Step-3>:5-(chloromethyl)-3-cyclopropyl-2-(2,2-difluoroethoxy)pyridine

The title compound is prepared in 99% yield (280 mg, a white solid) from (5-cyclopropyl-6-(2,2-difluoroethoxy)pyridin-3-yl)methanol (230 mg, 1.1 mmol, Step-2) by the similar manner in Step-4 of Amine-4.

<Step-4>:5-(azidomethyl)-3-cyclopropyl-2-(2,2-difluoroethoxy)pyridine

The title compound is prepared in 99% yield (290 mg, clear colorless oil) from 5-(chloromethyl)-3-cyclopropyl-2-(2,2-difluoroethoxy)pyridine (280 mg, 1.1 mmol, Step-3) by the similar manner in Step-5 of Amine-4.

MS (ESI) m/z: 255 (M+H)+.

<Step-5>:(5-cyclopropyl-6-(2,2-difluoroethoxy)pyridin-3-yl)methanamine hydrochloride The title compound is prepared in 67% yield (200 mg, a white solid) from 5-(azidomethyl)-3-cyclopropyl-2-(2,2-difluoroethoxy)pyridine (250 mg, 1.0 mmol, Step-4) by the similar manner in Step-3 of Amine-54.

$^1$H-NMR (300 MHz, DMSO-$d_6$) delta 8.38 (2H, br s), 8.02 (1H, d, J=2.2 Hz), 7.54 (1H, d, J=2.2 Hz), 6.40 (1H, tt, J=55.0, 3.7 Hz), 4.60 (2H, td, J=15.0, 3.7 Hz), 3.93 (2H, s), 2.02 (1H, m), 1.00-0.94 (2H, m), 0.75-0.70 (2H, m).

Amine-78: 1-(5-cyclopropyl-6-(2,2-difluoroethoxy) pyridin-3-yl)ethanamine hydrochloride (single enantiomer)

<Step-1>:5-cyclopropyl-6-(2,2-difluoroethoxy)nicotinic acid

The title compound is prepared in 99% yield (0.33 g, a white solid) from methyl 5-cyclopropyl-6-(2,2-difluoroethoxy)nicotinate (0.35 g, 1.36 mmol, Step-1 of Amine-77) by the similar manner in Step-2 of Amine-21.
$^1$H-NMR (300 MHz, CDCl$_3$) delta 8.67 (1H, d, J=2.2 Hz), 7.77 (1H, d, J=2.2 Hz), 6.18 (1H, tt, J=55.4, 4.4 Hz), 4.66 (2H, td, J=13.6, 4.4 Hz), 2.14-2.05 (1H, m), 1.06-0.99 (2H, m), 0.80-0.72 (2H, m) MS (ESI) m/z: 242 (M−H)$^-$.

<Step-2>:5-cyclopropyl-6-(2,2-difluoroethoxy)-N-methoxy-N-methylnicotinamide

The title compound is prepared in 77% yield (0.25 g, colorless oil) from 5-cyclopropyl-6-(2,2-difluoroethoxy)nicotinic acid (0.27 g, 1.11 mmol, Step-1) by the similar manner in Step-2 of Amine-5.
$^1$H-NMR (300 MHz, CDCl$_3$) delta 8.38 (1H, d, J=2.2 Hz), 7.55 (1H, d, J=2.2 Hz), 6.18 (1H, tt, J=55.8, 4.4 Hz), 4.62 (2H, td, J=13.6, 4.0 Hz), 3.56 (3H, s), 3.36 (3H, s), 2.11-2.04 (1H, m), 1.05-0.96 (2H, m), 0.76-0.68 (2H, m), MS (ESI) m/z: 287 (M+H)$^+$.

<Step-3>:1-(5-cyclopropyl-6-(2,2-difluoroethoxy) pyridin-3-yl)ethanone

The title compound is prepared in 96% yield (0.20 g, a white solid) from 5-cyclopropyl-6-(2,2-difluoroethoxy)-N-methoxy-N-methylnicotinamide (0.25 g, 0.856 mmol, Step-2) by the similar manner in Step-3 of Amine-1.
$^1$H-NMR (300 MHz, CDCl$_3$) delta 8.53 (1H, d, J=2.2 Hz), 7.72 (1H, d, J=2.2 Hz), 6.18 (1H, tt, J=55.4, 4.0 Hz), 4.65 (2H, td, J=13.6, 4.0 Hz), 2.56 (3H, s), 2.13-2.04 (1H, m), 1.04-0.98 (2H, m), 0.76-0.71 (2H, m), MS (ESI) m/z: 242 (M+H)$^+$.

<Step-4>:(R)—N-(1-(5-cyclopropyl-6-(2,2-difluoroethoxy)pyridin-3-yl)ethyl)-2-methylpropane-2-sulfinamide (single diastereomer)

The title compound is prepared in 73% yield (0.21 g, colorless oil) from 1-(5-cyclopropyl-6-(2,2-difluoroethoxy)pyridin-3-yl)ethanone (0.20 g, 0.82 mmol, Step-3) and (R)-2-methylpropane-2-sulfinamide by the similar manner in Step-4 of Amine-1.
$^1$H-NMR (270 MHz, CDCl$_3$) delta 7.89 (1H, d, J=2.3 Hz), 7.13 (1H, d, J=2.3 Hz), 6.15 (1H, tt, J=55.7, 4.3 Hz), 4.56 (2H, td, J=13.5, 4.3 Hz), 4.46 (1H, m), 2.05 (1H, m), 1.48 (3H, d, J=6.6 Hz), 1.21 (9H, m), 1.00-0.93 (2H, m), 0.70-0.65 (2H, m), MS (ESI) m/z: 347 (M+H)$^+$.

<Step-5>:1-(5-cyclopropyl-6-(2,2-difluoroethoxy) pyridin-3-yl)ethanamine hydrochloride (single enantiomer)

The title compound is prepared in 82% yield (0.14 g, a white solid) from (R)—N-(1-(5-cyclopropyl-6-(2,2-difluoroethoxy)pyridin-3-yl)ethyl)-2-methylpropane-2-sulfinamide (single diastereomer) (0.21 g, 0.56 mmol, Step-4) by the similar manner in Step-5 of Amine-1.
$^1$H-NMR (270 MHz, DMSO-d$_6$) delta 8.53 (2H, br s), 8.03 (1H, d, J=2.2 Hz), 7.60 (1H, d, J=2.2 Hz), 6.40 (1H, tt, J=55.0, 3.3 Hz), 4.60 (2H, td, J=15.0, 3.3 Hz), 4.35 (1H, m), 2.06-1.97 (1H, m), 1.48 (3H, d, J=6.6 Hz), 0.99-0.93 (2H, m), 0.78-0.73 (2H, m), MS (ESI) m/z: 243 (M+H)$^+$.

Amine-79: 1-(6-(2,2-difluoroethoxy)-5-methylpyridin-3-yl)-N-methylethanamine hydrochloride (single enantiomer)

<Step-1>:tert-butyl (1-(6-(2,2-difluoroethoxy)-5-methylpyridin-3-yl)ethyl)carbamate (single enantiomer)

The title compound is prepared in >99% yield (380 mg, clear colorless oil) from 1-(6-(2,2-difluoroethoxy)-5-methylpyridin-3-yl)ethanamine hydrochloride (300 mg, 1.2 mmol, Amine-14) by the similar manner in Step-1 of Amine-3.
MS (ESI) m/z: 317 (M+H)$^+$.

<Step-2>:tert-butyl(1-(6-(2,2-difluoroethoxy)-5-methylpyridin-3-yl)ethyl)(methyl)carbamate (single enantiomer The title compound is prepared in 74% yield (280 mg, clear colorless oil) from tert-butyl (1-(6-(2,2-difluoroethoxy)-5-methylpyridin-3-yl)ethyl)carbamate (370 mg, 1.1 mmol, Step-1, single enantiomer) by the similar manner in Step-2 of Amine-3.
$^1$H-NMR (300 MHz, CDCl$_3$) delta 7.86 (1H, s), 7.33 (1H, s), 6.14 (tt, J=8.1, 3.7 Hz), 5.50-5.25 (1H, br s), 4.53 (2H, td, J=13.9, 4.4 Hz), 2.58 (3H, s), 2.20 (3H, s), 1.49 (9H, s), 1.47 (3H, 7.4 Hz), MS (ESI) m/z: 331 (M+H)$^+$.

<Step-3>:1-(6-(2,2-difluoroethoxy)-5-methylpyridin-3-yl)-N-methylethanamine hydrochloride The title compound is prepared in >99% yield (240 mg, a white solid) from tert-butyl (1-(6-(2,2-difluoroethoxy)-5-methylpyridin-3-yl)ethyl)(methyl)carbamate (270 mg, 0.83 mmol, Step-2) by the similar manner in Step-3 of Amine-3.
MS (ESI) m/z: 200 (M+H$_2$)$^+$.

Amine-80: (5-methyl-6-(2,2,3,3-tetrafluoropropoxy) pyridin-3-yl)methanamine hydrochloride <Step-1>: (5-methyl-6-(2,2,3,3-tetrafluoropropoxy) pyridin-3-yl)methanol The title compound is prepared in 98% yield (0.93 g) from 5-methyl-6-(2,2,3,3-tetrafluoropropoxy)nicotinic acid (1.00 g, 3.74 mmol, Step-1 of Amine-75) by the similar manner in Step-3 of Amine-4.
$^1$H-NMR (300 MHz, CDCl$_3$) delta 7.95 (1H, s), 7.51 (1H, s), 6.01 (1H, tt, J=52.7, 4.4 Hz), 4.74 (2H, t, J=12.5 Hz), 4.63 (2H, s), 2.22 (3H, s), MS (ESI) m/z: 254 (M+H)$^+$.

<Step-2>:5-(chloromethyl)-3-methyl-2-(2,2,3,3-tetrafluoropropoxy)pyridine

The title compound is prepared in >99% yield (1.02 g) from (5-methyl-6-(2,2,3,3-tetrafluoropropoxy)pyridin-3-yl)methanol (0.93 g, 3.67 mmol, Step-1) by the similar manner in Step-4 of Amine-4.
MS (ESI) m/z: 272 (M+H)$^+$.

Step-3>:5-(azidomethyl)-3-methyl-2-(2,2,3,3-tetrafluoropropoxy)pyridine

The title compound is prepared in 74% yield (770 mg, pale yellow oil) from 5-(chloromethyl)-3-methyl-2-(2,2,3,3-tetrafluoropropoxy)pyridine (1.02 g, 3.67 mmol, Step-2) by the similar manner in Step-5 of Amine-4.

$^1$H-NMR (300 MHz, CDCl$_3$) delta 7.93 (1H, s), 7.44 (1H, s), 6.00 (1H, tt, J=53.5, 4.4 Hz), 4.75 (2H, td, J=12.5, 1.4 Hz), 4.27 (2H, s), 2.24 (3H, s), MS (ESI) m/z: 279 (M+H)$^+$.

<Step-4>:(5-methyl-6-(2,2,3,3-tetrafluoropropoxy) pyridin-3-yl)methanamine hydrochloride The title compound is prepared in 62% yield (546 mg, pale yellow oil) from 5-(azidomethyl)-3-methyl-2-(2,2,3,3-tetrafluoropropoxy)pyridine (750 mg, 2.70 mmol, Step-3) by the similar manner in Step-6 of Amine-4.

$^1$H-NMR (300 MHz, DMSO-d$_6$) delta 8.51 (3H, br s), 8.13 (1H, s), 7.82 (1H, s), 6.70 (1H, tt, J=52.0, 5.1 Hz), 4.88 (2H, t, J=13.9 Hz), 3.97 (2H, d, J=5.9 Hz), 2.19 (3H, s), MS (ESI) m/z: 236.2 (M+H)$^+$.

Amine-81: 1-(2-fluoro-5-(trifluoromethyl)phenyl)ethanamine hydrochloride (single enantiomer <Step-1>: (S,E)-N-(2-fluoro-5-(trifluoromethyl)benzylidene)-2-methylpropane-2-sulfinamide (single enantiomer)

A mixture of 2-fluoro-5-(trifluoromethyl)benzaldehyde (1.00 g, 5.21 mmol), (S)-2-methylpropane-2-sulfinamide (631 mg, 5.21 mmol), and copper sulfate (1.66 g, 10.4 mmol) in dichloromethane is stirred at room temperature for 12 hours. Additional copper sulfate (1.66 g, 10.4 mmol) is added, and the mixture is stirred at room temperature for 5 hours. Then, the mixture is filtered through a pad of Celite, and the filtrate is concentrated in vacuo. The residue is purified by column chromatography on silica gel eluting with n-hexane/EtOAc (10:1) to give 314 mg (20% yield) of the title compound as colorless oil.

$^1$H-NMR (300 MHz, CDCl$_3$) delta 8.91 (1H, s), 8.30-8.26 (1H, m), 7.80-7.73 (1H, m), 7.30 (1H, t, J=9.0 Hz), 1.29 (9H, s), MS (ESI) m/z: 296 (M+H)$^+$.

<Step-2>:(S)—N-(1-(2-fluoro-5-(trifluoromethyl) phenyl)ethyl)-2-methylpropane-2-sulfinamide (single diastereomer)

To a solution of (S,E)-N-(2-fluoro-5-(trifluoromethyl)benzylidene)-2-methylpropane-2-sulfinamide (single enantiomer) (150 mg, 0.51 mmol, Step-1) in dichloromethane (5 mL) is added dropwise a solution of methylmagnesium bromide in THF (0.99 M, 2.57 mL, 2.54 mmol) at −78° C. The resulting mixture is stirred at −78° C. for 2 hours and at room temperature for 1 hour. The reaction is quenched by saturated aqueous ammonium chloride solution (50 mL), and the aqueous phase is extracted with EtOAc (50 mL×2). The combined organic layer is dried over sodium sulfate and concentrated in vacuo. The residue is purified by column chromatography on silica gel eluting with n-hexane/EtOAc (3:1-1:1) to give 63 mg (40% yield) of the title compound as a white solid.

$^1$H-NMR (300 MHz, CDCl$_3$) delta 7.67 (1H, d, J=6.6 Hz), 7.57-7.50 (1H, m), 7.16 (1H, t, J=8.8 Hz), 4.98-4.90 (1H, m), 3.36 (1H, br s), 1.58 (3H, d, J=6.6 Hz), 1.22 (9H, s), MS (ESI) m/z: 312 (M+H)$^+$.

Step-3>:1-(2-fluoro-5-(trifluoromethyl)phenyl)ethanamine hydrochloride (single enantiomer)

The title compound is prepared in 87% yield (43 mg, a white solid) from (S)—N-(1-(2-fluoro-5-(trifluoromethyl) phenyl)ethyl)-2-methylpropane-2-sulfinamide (single diastereomer) (63 mg, 0.20 mmol, Step-2) by the similar manner in Step-5 of Amine-1.

$^1$H-NMR (300 MHz, DMSO-d$_6$) delta 8.75-8.45 (3H, m), 8.10 (1H, br s), 7.87 (1H, br s), 7.55 (1H, t, J=9.5 Hz), 4.70 (1H, q, J=6.6 Hz), 1.54 (3H, d, J=6.6 Hz), MS (ESI) m/z: 208 (M+H)$^+$.

Amine-82: 1-(3-chloro-4-(2,2-difluoroethoxy)phenyl)ethanamine hydrochloride (single enantiomer)

<Step-1>:3-chloro-4-(2,2-difluoroethoxy)-N-methoxy-N-methylbenzamide

The title compound is prepared in >99% yield (1.1 g, a white solid) from 3-chloro-4-(2,2-difluoroethoxy)benzoic acid (900 mg, 3.8 mmol) by the similar manner in Step-2 of Amine-5.

$^1$H-NMR (300 MHz, CDCl$_3$) delta 7.84 (1H, d, J=2.2 Hz), 7.67 (1H, dd, J=8.8, 2.2 Hz), 6.93 (1H, d, J=8.8 Hz), 6.17 (1H, tt, J=54.2, 3.7 Hz), 4.28 (td, J=12.5, 3.7 Hz), 3.56 (3H, s), 3.36 (3H, s), MS (ESI) m/z: 280 (M+H)$^+$.

<Step-2>:1-(3-chloro-4-(2,2-difluoroethoxy)phenyl) ethanone

The title compound is prepared in 95% yield (860 mg, a white solid) from 3-chloro-4-(2,2-difluoroethoxy)-N-methoxy-N-methylbenzamide (1.1 g, 3.9 mmol, Step-1) by the similar manner in Step-3 of Amine-1.

$^1$H-NMR (300 MHz, CDCl$_3$) delta 8.02 (1H, d, J=2.2 Hz), 7.87 (1H, dd, J=8.8, 2.2 Hz), 6.97 (1H, d, J=8.8 Hz), 6.18 (1H, tt, J=54.9, 4.4 Hz), 4.31 (2H, td, J=12.5, 4.4 Hz), 2.57 (3H, s).

<Step-3>:(R)—N-(1-(3-chloro-4-(2,2-difluoroethoxy)phenyl)ethyl)-2-methylpropane-2-sulfinamide (single diastereomer)

The title compound is prepared in 62% yield (780 mg, clear colorless oil) from 1-(3-chloro-4-(2,2-difluoroethoxy)phenyl)ethanone (860 mg, 3.7 mmol, Step-2) and (R)-2-methylpropane-2-sulfinamide by the similar manner in Step-4 of Amine-1.

$^1$H-NMR (300 MHz, CDCl$_3$) delta 7.38 (1H, d, J=2.2 Hz), 7.21 (1H, dd, J=8.8, 2.2 Hz), 6.14 (1H, tt, J=54.9, 4.4 Hz), 4.53-4.43 (1H, m), 4.23 (2H, td, J=13.2, 4.4 Hz), 3.34 (1H, br s), 1.48 (3H, d, J=6.6 Hz), 1.23 (9H, s), MS (ESI) m/z: 340 (M+H)$^+$.

<Step-4>:1-(3-chloro-4-(2,2-difluoroethoxy)phenyl) ethanamine hydrochloride (single enantiomer)

The title compound is prepared in 98% yield (610 mg, a white solid) from (R)—N-(1-(3-chloro-4-(2,2-difluoroethoxy)phenyl)ethyl)-2-methylpropane-2-sulfinamide (single diastereomer) (780 mg, 2.3 mmol, Step-3) by the similar manner in Step-5 of Amine-1.

$^1$H-NMR (300 MHz, DMSO-d$_6$) delta 8.48 (2H, br s), 7.66 (1H, d, J=2.2 Hz), 7.47 (1H, dd, J=8.8, 2.2 Hz), 7.29 (1H, d, J=8.8 Hz), 6.42 (1H, tt, J=54.2, 3.7 Hz), 4.44 (2H, td, J=13.9, 2.9 Hz), 1.49 (3H, d, J=6.6 Hz).

Amine-83: 1-(4-(2,2-difluoroethoxy)-2-methylphenyl)ethanamine hydrochloride (single enantiomer)

<Step-1>:1-(4-(2,2-difluoroethoxy)-2-methylphenyl)ethanone

The title compound is prepared in 75% yield (1.6 g, a white solid) from 1-(4-hydroxy-2-methylphenyl)ethanone (900 mg, 10 mmol) by the similar manner in Step-1 of Amine-68.
$^1$H-NMR (300 MHz, CDCl$_3$) delta 7.75 (1H, d, J=8.8 Hz), 6.80-6.75 (2H, m), 6.10 (1H, tt, J=54.9, 4.4 Hz), 4.23 (2H, td, J=12.4, 3.7 Hz), 2.57 (3H, s), 2.56 (3H, s), MS (ESI) m/z: 215 (M+H)$^+$.

<Step-2>:(R)—N-(1-(4-(2,2-difluoroethoxy)-2-methylphenyl)ethyl)-2-methylpropane-2-sulfinamide (single diastereomer)

The title compound is prepared in 42% yield (1.0 g, clear colorless oil) from 1-(4-(2,2-difluoroethoxy)-2-methylphenyl)ethanone (1.6 g, 7.5 mmol, Step-1) and (R)-2-methylpropane-2-sulfinamide by the similar manner in Step-4 of Amine-1.
MS (ESI) m/z: 320 (M+H)$^+$.

<Step-3>:1-(4-(2,2-difluoroethoxy)-2-methylphenyl)ethanamine hydrochloride (single enantiomer)

The title compound is prepared in 59% yield (470 mg, a white solid) from (R)—N-(1-(4-(2,2-difluoroethoxy)-2-methylphenyl)ethyl)-2-methylpropane-2-sulfinamide (single diastereomer) (1.0 g, 3.1 mmol, Step-2) by the similar manner in Step-5 of Amine-1.
$^1$H-NMR (300 MHz, DMSO-d$_6$) delta 8.26 (2H, br s), 7.46 (1H, d, J=8.8 Hz), 6.97-6.90 (2H, m), 6.38 (1H, tt, J=54.2, 3.7 Hz), 4.48 (1H, d, J=6.6 Hz), 4.31 (2H, td, J=14.6, 3.7 Hz), 2.33 (3H, s), 1.44 (3H, d, J=7.3 Hz).

Amine-84:(4-(2,2-difluoroethoxy)-3-methylphenyl)methanamine hydrochloride

<Step-1>: (4-(2,2-difluoroethoxy)-3-methylphenyl)methanol

The title compound is prepared in >99% yield (710 mg, clear colorless oil) from methyl 4-(2,2-difluoroethoxy)-3-methylbenzoate (750 mg, 3.3 mmol, Step-1 of Amine-68) by the similar manner in Step-3 of Amine-4.
$^1$H-NMR (300 MHz, CDCl$_3$) delta 7.20-7.13 (2H, m), 6.78 (1H, d, J=8.1 Hz), 6.11 (1H, tt, J=54.9, 4.4 Hz), 4.60 (2H, d, J=5.9 Hz), 4.19 (2H, td, J=13.2, 4.4 Hz), 2.25 (3H, s).

<Step-2>:4-(chloromethyl)-1-(2,2-difluoroethoxy)-2-methylbenzene

The title compound is prepared in >99% yield (1.8 g, clear colorless oil) from (4-(2,2-difluoroethoxy)-3-methylphenyl)methanol (1.6 g, 7.9 mmol, Step-1) by the similar manner in Step-4 of Amine-4.

<Step-3>:4-(azidomethyl)-1-(2,2-difluoroethoxy)-2-methylbenzene

The title compound is prepared in 39% yield (700 mg, clear colorless oil) from 4-(chloromethyl)-1-(2,2-difluoroethoxy)-2-methylbenzene (1.8 g, 7.9 mmol, Step-2) by the similar manner in Step-5 of Amine-4.
$^1$H-NMR (300 MHz, CDCl$_3$) delta 7.14-7.08 (2H, m), 6.78 (1H, d, J=8.8 Hz), 6.11 (1H, tt, J=55.7, 4.4 Hz), 4.25 (2H, s), 4.16 (2H, td, J=13.2, 8.8 Hz), 2.25 (3H, s).

<Step-4>:(4-(2,2-difluoroethoxy)-3-methylphenyl)methanamine hydrochloride

The title compound is prepared in 95% yield (690 mg, a white solid) from 4-(azidomethyl)-1-(2,2-difluoroethoxy)-2-methylbenzene (700 mg, 3.1 mmol, Step-3) by the similar manner in Step-3 of Amine-54.
$^1$H-NMR (300 MHz, DMSO-d$_6$) delta 8.30 (2H, br s), 7.32-7.25 (2H, m), 7.04 (1H, d, J=8.8 Hz), 6.40 (1H, tt, J=54.2, 3.7 Hz), 4.33 (2H, td, J=14.7, 3.7 Hz), 3.95-3.85 (2H, m), 2.17 (3H, s), MS (ESI) m/z: positive ion of a fragment signal, 185, is observed.

Amine-85:(3-chloro-4-(2,2-difluoroethoxy)phenyl)methanamine hydrochloride

<Step-1>:methyl 3-chloro-4-(2,2-difluoroethoxy)benzoate

The title compound is prepared in 98% yield (2.0 g, a white solid) from methyl 3-chloro-4-hydroxybenzoate (1.5 g, 8.0 mmol) by the similar manner in Step-1 of Amine-68.
$^1$H-NMR (300 MHz, CDCl$_3$) delta 8.09 (1H, d, J=2.2 Hz), 7.94 (1H, dd, J=8.8, 2.2 Hz), 6.94 (1H, d, J=8.0 Hz), 6.18 (1H, tt, J=54.9, 4.4 Hz), 4.30 (2H, td, J=12.5, 4.4 Hz), 3.91 (3H, s).

Step-2>:(3-chloro-4-(2,2-difluoroethoxy)phenyl)methanol

The title compound is prepared in >99% yield (860 mg, clear colorless oil) from methyl 3-chloro-4-(2,2-difluoroethoxy)benzoate (930 mg, 3.7 mmol, Step-1) by the similar manner in Step-3 of Amine-4.
$^1$H-NMR (300 MHz, CDCl$_3$) delta 7.42 (1H, d, J=2.2 Hz), 7.22 (1H, dd, J=8.1, 2.2 Hz), 6.93 (1H, d, J=8.8 Hz), 6.15 (1H, tt, J=54.9, 4.4 Hz), 4.63 (2H, d, J=5.1 Hz), 4.24 (2H, td, J=12.8, 4.4 Hz), 1.75-1.65 (1H, m).

Step-3>:2-chloro-4-(chloromethyl)-1-(2,2-difluoroethoxy)benzene

The title compound is prepared in >99% yield (930 mg, clear colorless oil) from (3-chloro-4-(2,2-difluoroethoxy)phenyl)methanol (860 mg, 3.8 mmol, Step-2) by the similar manner in Step-4 of Amine-4.
MS (ESI) m/z: negative ion of an adduct signal (+HCO$_2$), 285, is observed.

Step-4>:4-(azidomethyl)-2-chloro-1-(2,2-difluoroethoxy)benzene

The title compound is prepared in 88% yield (840 mg, clear colorless oil) from 2-chloro-4-(chloromethyl)-1-(2,2-difluoroethoxy)benzene (930 mg, 3.8 mmol, Step-3) by the similar manner in Step-5 of Amine-4.
$^1$H-NMR (300 MHz, CDCl$_3$) delta 7.37 (1H, d, J=2.2 Hz), 7.19 (1H, dd, J=8.0, 2.2 Hz), 6.93 (1H, d, J=8.8 Hz), 6.15 (1H, tt, J=51.3, 4.4 Hz), 4.28 (2H, s), 4.24 (2H, td, J=13.2, 3.2 Hz).

Step-5>:(3-chloro-4-(2,2-difluoroethoxy)phenyl)methanamine hydrochloride

The title compound is prepared in 96% yield (780 mg, a white solid) from 4-(azidomethyl)-2-chloro-1-(2,2-difluoroethoxy)benzene (790 mg, 3.2 mmol, Step-4) by the similar manner in Step-3 of Amine-54.

$^1$H-NMR (300 MHz, DMSO-d$_6$) delta 8.26 (2H, br s), 7.63 (1H, s), 7.43 (1H, J=8.8 Hz), 7.28 (1H, d, J=8.8 Hz), 6.42 (1H, tt, J=54.2, 4.4 Hz), 4.44 (2H, td, 14.6, 3.7 Hz), 3.98 (2H, s).

MS (ESI) m/z: positive ion of a fragment signal, 205, is observed.

Amine-86:(4-(2,2-difluoroethoxy)-2-methylphenyl)methanamine hydrochloride

<Step-1>:methyl 4-(2,2-difluoroethoxy)-2-methylbenzoate

The title compound is prepared in 89% yield (970 mg, a white solid) from methyl 4-hydroxy-2-methylbenzoate (1.1 g, 4.6 mmol) by the similar manner in Step-1 of Amine-68.

$^1$H-NMR (300 MHz, CDCl$_3$) delta 7.94 (1H, d, J=7.3, 2.2 Hz), 6.77-6.73 (2H, m), 6.10 (1H, tt, J=54.9, 4.4 Hz), 4.21 (2H, td, J=13.2, 4.4 Hz), 4.17 (3H, s), 2.60 (3H, s), MS (ESI) m/z: 231 (M+H)$^+$.

Step-2>:(4-(2,2-difluoroethoxy)-2-methylphenyl)methanol

The title compound is prepared in 91% yield (1.3 g, a white solid) from methyl 4-(2,2-difluoroethoxy)-2-methylbenzoate (1.7 g, 7.3 mmol, Step-1) by the similar manner in Step-3 of Amine-4.

$^1$H-NMR (300 MHz, CDCl$_3$) delta 7.27 (1H, J=8.1 Hz), 6.78-6.71 (2H, m), 6.08 (1H, tt, J=54.9, 3.7 Hz), 4.65 (2H, d, J=5.1 Hz), 4.17 (2H, td, J=13.2, 4.4 Hz), 2.36 (3H, s), 1.45 (1H, d, J=5.1 Hz).

Step-3>:1-(chloromethyl)-4-(2,2-difluoroethoxy)-2-methylbenzene

The title compound is prepared in >99% yield (1.5 g, clear colorless oil) from (4-(2,2-difluoroethoxy)-2-methylphenyl)methanol (1.3 g, 6.6 mmol, Step-2) by the similar manner in Step-4 of Amine-4.

<Step-4>:1-(azidomethyl)-4-(2,2-difluoroethoxy)-2-methylbenzene

The title compound is prepared in 70% yield (1.1 g, clear colorless oil) from 1-(chloromethyl)-4-(2,2-difluoroethoxy)-2-methylbenzene (1.5 g, 6.6 mmol, Step-3) by the similar manner in Step-5 of Amine-4.

$^1$H-NMR (300 MHz, CDCl$_3$) delta 7.19 (1H, d, J=8.8 Hz), 6.80 (1H, d, J=2.2 Hz), 6.73 (1H, dd, J=8.8, 2.2 Hz), 6.08 (1H, tt, J=54.9, 4.4 Hz), 4.29 (2H, s), 4.18 (2H, td, J=13.2, 4.4 Hz), 3.17 (3H, s).

Step-5>:(4-(2,2-difluoroethoxy)-2-methylphenyl)methanamine hydrochloride

The title compound is prepared in 89% yield (970 mg, a white solid) from 1-(azidomethyl)-4-(2,2-difluoroethoxy)-2-methylbenzene (1.1 g, 4.6 mmol, Step-4) by the similar manner in Step-3 of Amine-54.

$^1$H-NMR (300 MHz, DMSO-d$_6$) delta 8.28 (2H, br s), 7.35 (1H, d, J=8.0 Hz), 6.92-6.86 (2H, m), 6.38 (1H, tt, J=54.1, 3.7 Hz), 4.31 (2H, td, J=14.6, 3.7 Hz), 4.00-3.90 (2H, m), 2.34 (3H, s).

Amine-87:(6-(2,2-difluoroethoxy)-5-isopropylpyridin-3-yl)methanamine hydrochloride <Step-1>:methyl 6-(2,2-difluoroethoxy)-5-(prop-1-en-2-yl)nicotinate The title compound is prepared in 71% yield (491 mg, colorless oil) from methyl 5-bromo-6-(2,2-difluoroethoxy)nicotinate (793 mg, 2.68 mmol, Step-2 of Amine-74) by the similar manner in Step-1 of Amine-77.

$^1$H-NMR (300 MHz, CDCl$_3$) delta 8.68 (1H, d, J=2.2 Hz), 8.11 (1H, d, J=2.2 Hz), 6.14 (1H, tt, J=55.4, 4.0 Hz), 5.27 (2H, br s), 4.63 (2H, td, J=13.6, 4.0 Hz), 3.92 (3H, s), 2.11 (3H, s), MS (ESI) m/z: 258 (M+H)$^+$.

Step-2>:methyl 6-(2,2-difluoroethoxy)-5-isopropylnicotinate

Palladium 10% on carbon (50 mg) is added to a solution of methyl 6-(2,2-difluoroethoxy)-5-(prop-1-en-2-yl)nicotinate (491 mg, 1.91 mmol, Step-1) in methanol (20 mL) and stirred at room temperature under hydrogen atomosphare (1 atm) for 2 hours. The reaction mixture is filtrated through a pad of Celite and filtrate is concentrated in vacuo to give 490 mg (99% yield) of the title compound as colorless oil. This material is used for the next reaction (Step-3) without further purification.

$^1$H-NMR (300 MHz, CDCl$_3$) delta 8.63 (1H, d, J=1.8 Hz), 8.08 (1H, d, J=1.8 Hz), 6.15 (1H, tt, J=55.4, 4.0 Hz), 4.62 (2H, td, J=13.6, 4.0 Hz), 3.91 (3H, s), 3.19 (1H, septet, J=7.0 Hz), 1.24 (6H, d, J=7.0 Hz), MS (ESI) m/z: 260 (M+H)$^+$.

<Step-3>:(6-(2,2-difluoroethoxy)-5-isopropylpyridin-3-yl)methanol

The title compound is prepared in >99% yield (433 mg, colorless oil) from methyl 6-(2,2-difluoroethoxy)-5-isopropylnicotinate (490 mg, 1.89 mmol, Step-2) by the similar manner in Step-3 of Amine-4.

MS (ESI) m/z: 232 (M+H)$^+$.

<Step-4>:5-(chloromethyl)-2-(2,2-difluoroethoxy)-3-isopropylpyridine

The title compound is prepared in >99% yield (463 mg, a white solid) from (6-(2,2-difluoroethoxy)-5-isopropylpyridin-3-yl)methanol (433 mg, 1.87 mmol, Step-3) by the similar manner in Step-4 of Amine-4.

<Step-5>:5-(azidomethyl)-2-(2,2-difluoroethoxy)-3-isopropylpyridine

The title compound is prepared in >99% yield (470 mg, colorless oil) from 5-(chloromethyl)-2-(2,2-difluoroethoxy)-3-isopropylpyridine (463 mg, 1.85 mmol, Step-4) by the similar manner in Step-5 of Amine-4.

MS (ESI) m/z: 257 (M+H)$^+$.

<Step-6>:(6-(2,2-difluoroethoxy)-5-isopropylpyridin-3-yl)methanamine hydrochloride The title compound is prepared in 93% yield (456 mg, a white solid) from 5-(azidomethyl)-2-(2,2-difluoroethoxy)-3-isopropylpyridine (470 mg, 1.83 mmol, Step-5) by the similar manner in Step-3 of Amine-54.

$^1$H-NMR (300 MHz, DMSO-d$_6$) delta 8.49 (2H, br s), 8.09 (1H, d, J=2.2 Hz), 7.89 (1H, d, J=2.2 Hz), 6.39 (1H, tt, J=54.7, 3.3 Hz), 4.59 (2H, td, J=15.0, 3.3 Hz), 4.00-3.94 (2H, m), 3.09 (1H, septet, J=7.0 Hz), 1.19 (6H, d, J=7.0 Hz), MS (ESI) m/z: 231 (M+H)⁺.

Amine-88:1-(3-((trifluoromethyl)thio)phenyl)ethanamine hydrochloride (single enantiomer <Step-1>:(S,E)-2-methyl-N-(3-((trifluoromethyl)thio)benzylidene)propane-2-sulfinamide To a mixture of 3-((trifluoromethyl)thio)benzaldehyde (800 mg, 3.88 mmol) and (S)-1-2-methylpropane-2-sulfinamide (470 mg, 3.88 mmol) in THF (5 mL) is added titanium (IV) ethoxide (1.33 g, 5.82 mmol), and the mixture is refluxed with stirring for 2 hours. After cooling to room temperature, the resulting mixture is poured to water (100 mL). The aqueous layer is extracted with ethyl acetate (100 mL). The organic layer is dried over sodium sulfate and concentrated in vacuo. The residue is purified by column chromatography on silica gel eluting with n-hexane/ethyl acetate (10:1) to give 1.01 g (84% yield) of the title compound as pale yellow oil.
¹H-NMR (300 MHz, CDCl₃) delta 8.60 (1H, s), 8.14 (1H, s), 7.96 (1H, d, J=7.3 Hz), 7.80 (1H, d, J=7.3 Hz), 7.56 (1H, t, J=7.3 Hz), 1.28 (9H, s), MS (ESI) m/z: 310 (M+H)⁺.

<Step-2>:(S)-2-methyl-N-(1-(3-((trifluoromethyl)thio)phenyl)ethyl)propane-2-sulfinamide (single diastereomer)

The title compound is prepared in 71% yield (522 mg, a white solid) from (S,E)-2-methyl-N-(3-((trifluoromethyl)thio)benzylidene)propane-2-sulfinamide (700 mg, 2.26 mmol, Step-1) by the similar manner in Step-2 of Amine-81.
¹H-NMR (300 MHz, CDCl₃) delta 7.64 (1H, s), 7.56 (1H, d, J=7.3 Hz), 7.45 (1H, d, J=7.3 Hz), 7.42 (1H, t, J=7.3 Hz), 4.65-4.57 (1H, m), 3.33 (1H, br s), 1.54 (3H, d, J=6.6 Hz), 1.21 (9H, s), MS (ESI) m/z: 326 (M+H)⁺.

<Step-3>:1-(3-((trifluoromethyl)thio)phenyl)ethanamine hydrochloride (single enantiomer)

The title compound is prepared in 44% yield (180 mg, a white solid) from (S)-2-methyl-N-(1-(3-((trifluoromethyl)thio)phenyl)ethyl)propane-2-sulfinamide (single diastereomer) (521 mg, 1.60 mmol, Step-2) by the similar manner in Step-5 of Amine-1.
¹H-NMR (300 MHz, DMSO-d₆) delta 8.73 (3H, br s), 7.93 (1H, s), 7.81 (1H, d, J=7.3 Hz), 7.42 (1H, d, J=8.1 Hz), 7.61 (1H, t, J=8.0 Hz), 4.49 (1H, q, J=6.6 Hz), 1.53 (3H, d, J=6.6 Hz).

Amine-89:1-(4-(2,2-difluoroethoxy)-3-fluorophenyl)ethanamine hydrochloride (single enantiomer)

<Step-1>:methyl 4-(2,2-difluoroethoxy)-3-fluorobenzoate

The title compound is prepared in 96% yield (2.73 g, a white solid) from methyl 3-fluoro-4-hydroxybenzoate (2.0 g, 11.0 mmol) by the similar manner in Step-1 of Amine-68.
¹H-NMR (300 MHz, CDCl₃) delta 7.84-7.76 (2H, m), 7.00 (1H, t, J=8.4 Hz), 6.14 (1H, tt, J=55.0, 4.0 Hz), 4.31 (2H, td, J=12.8, 4.0 Hz), 3.91 (3H, s).

<Step-2>:4-(2,2-difluoroethoxy)-3-fluorobenzoic acid

The title compound is prepared in 96% yield (1.23 g, a white solid) from methyl 4-(2,2-difluoroethoxy)-3-fluorobenzoate (1.37 g, 5.83 mmol, Step-1) by the similar manner in Step-2 of Carboxylic acid-1.
¹H-NMR (300 MHz, DMSO-d₆) delta 7.79-7.69 (2H, m), 7.36 (1H, t, J=8.4 Hz), 6.45 (1H, tt, J=54.3, 3.7 Hz), 4.51 (2H, td, J=14.7, 3.7 Hz), MS (ESI) m/z: 219 (M−H)⁻.

<Step-3>:4-(2,2-difluoroethoxy)-3-fluoro-N-methoxy-N-methylbenzamide

The title compound is prepared in 97% yield (1.43 g, a yellow solid) from 4-(2,2-difluoroethoxy)-3-fluorobenzoic acid (1.23 g, 5.58 mmol, Step-2) by the similar manner in Step-2 of Amine-5.
¹H-NMR (300 MHz, CDCl₃) delta 7.60-7.53 (2H, m), 6.99 (1H, t, J=8.4 Hz), 6.14 (1H, tt, J=54.7, 4.0 Hz), 4.30 (2H, td, J=12.8, 4.0 Hz), 3.56 (3H, s), 3.36 (3H, s), MS (ESI) m/z: 264 (M+H)⁺.

<Step-4>:1-(4-(2,2-difluoroethoxy)-3-fluorophenyl)ethanone

The title compound is prepared in 98% yield (1.16 g, orange oil) from 4-(2,2-difluoroethoxy)-3-fluoro-N-methoxy-N-methylbenzamide (1.43 g, 5.43 mmol, Step-3) by the similar manner in Step-3 of Amine-1.
¹H-NMR (300 MHz, CDCl₃) delta 7.77-7.69 (2H, m), 7.02 (1H, t, J=7.7 Hz), 6.15 (1H, tt, J=53.9, 4.0 Hz), 4.32 (2H, td, J=12.8, 4.0 Hz), 2.57 (3H, s).

<Step-5>:(R)—N-(1-(4-(2,2-difluoroethoxy)-3-fluorophenyl)ethyl)-2-methylpropane-2-sulfinamide (single diastereomer)

The title compound is prepared in 84% yield (1.44 g, colorless oil) from 1-(4-(2,2-difluoroethoxy)-3-fluorophenyl)ethanone (1.16 g, 5.31 mmol, Step-4) and (R)-2-methylpropane-2-sulfinamide by the similar manner in Step-4 of Amine-1.
¹H-NMR (300 MHz, CDCl₃) delta 7.17-6.92 (3H, m), 6.10 (1H, tt, J=55.0, 4.4 Hz), 4.54-4.45 (1H, m), 4.33-4.18 (2H, m), 3.37 (1H, br s), 1.48 (3H, d, J=6.6 Hz), 1.24 (9H, s), MS (ESI) m/z: 324 (M+H)⁺.

<Step-6>:1-(4-(2,2-difluoroethoxy)-3-fluorophenyl)ethanamine hydrochloride (single enantiomer)

The title compound is prepared in 84% yield (0.95 g, a white solid) from (R)—N-(1-(4-(2,2-difluoroethoxy)-3-fluorophenyl)ethyl)-2-methylpropane-2-sulfinamide (1.44 g, 4.46 mmol, Step-5, single diastereomer) by the similar manner in Step-5 of Amine-1.
¹H-NMR (300 MHz, DMSO-d₆) delta 8.58 (2H, br s), 7.49 (1H, d, J=13.2 Hz), 7.33-7.24 (2H, m), 6.40 (1H, tt, J=54.3, 3.3 Hz), 4.46-4.30 (3H, m), 1.48 (3H, d, J=7.0 Hz).

Amine-90:1-(3-chloro-5-(trifluoromethoxy)phenyl)ethanamine hydrochloride (single enantiomer <Step-1>:3-chloro-N-methoxy-N-methyl-5-(trifluoromethoxy)benzamide The title compound is prepared in 97% yield (800 mg, colorless oil) from 3-chloro-5-(trifluoromethoxy)benzoic acid (700 mg, 2.91 mmol) by the similar manner in Step-2 of Amine-5.

¹H-NMR (300 MHz, CDCl₃) delta 7.65 (1H, s), 7.48 (1H, s), 7.33 (1H, s), 3.56 (3H, s), 3.74 (3H, s), MS (ESI) m/z: 284 (M+H)⁺.

<Step-2>:1-(3-chloro-5-(trifluoromethoxy)phenyl) ethanone

The title compound is prepared in 90% yield (608 mg, colorless oil) from 3-chloro-N-methoxy-N-methyl-5-(trifluoromethoxy)benzamide (800 mg, 2.82 mmol, Step-1) by the similar manner in Step-3 of Amine-1.

¹H-NMR (300 MHz, CDCl₃) delta 7.86 (1H, s), 7.69 (1H, s), 7.44 (1H, s), 2.61 (3H, s).

<Step-3>:(R)—N-(1-(3-chloro-5-(trifluoromethoxy) phenyl)ethyl)-2-methylpropane-2-sulfinamide (single diastereomer)

The title compound is prepared in 48% yield (416 mg, a white solid) from 1-(3-chloro-5-(trifluoromethoxy)phenyl) ethanone (600 mg, 2.51 mmol, Step-2) and (R)-2-methylpropane-2-sulfinamide (457 mg, 3.77 mmol) by the similar manner in Step-4 of Amine-1.

¹H-NMR (300 MHz, CDCl₃) delta 7.29 (1H, s), 7.17 (1H, s), 7.11 (1H, s), 4.57-4.47 (1H, m), 3.42 (1H, br s), 1.52 (3H, d, J=6.6 Hz), 1.24 (9H, s), MS (ESI) m/z: 344 (M+H)⁺.

<Step-4>:1-(3-chloro-5-(trifluoromethoxy)phenyl) ethanamine hydrochloride (single enantiomer)

The title compound is prepared in 84% yield (281 mg, a white solid) from (R)—N-(1-(3-chloro-5-(trifluoromethoxy) phenyl)ethyl)-2-methylpropane-2-sulfinamide (single diastereomer) (415 mg, 1.21 mmol, Step-3) by the similar manner in Step-5 of Amine-1.

¹H-NMR (300 MHz, DMSO-d₆) delta 8.54 (3H, br s), 7.72 (1H, s), 7.61 (1H, s), 7.58 (1H, s), 4.51 (1H, q, J=6.6 Hz), 1.50 (3H, d, J=7.3 Hz).

Amine-91: (2-chloro-4-(2,2-difluoroethoxy)phenyl)methanamine

<Step-1>:methyl 2-chloro-4-(2,2-difluoroethoxy)benzoate

The title compound is prepared in 94% yield (3.5 g, clear colorless oil) from methyl 2-chloro-4-hydroxybenzoate (2.8 g, 15 mmol) by the similar manner in Step-1 of Amine-68.

¹H-NMR (300 MHz, CDCl₃) delta 7.90 (1H, d, J=8.8 Hz), 7.00 (1H, d, J=2.9 Hz), 6.85 (1H, dd, J=8.8, 2.9 Hz), 6.10 (1H, tt, J=54.9, 4.4 Hz), 4.22 (2H, td, J=12.5, 3.7 Hz), 4.17 (3H, s), MS (ESI) m/z: 251 (M+H)⁺

<Step-2>:(2-chloro-4-(2,2-difluoroethoxy)phenyl) methanol

The title compound is prepared in 95% yield (1.4 g, clear colorless oil) from methyl 2-chloro-4-(2,2-difluoroethoxy) benzoate (1.6 g, 6.4 mmol, Step-1) by the similar manner in Step-3 of Amine-4.

¹H-NMR (300 MHz, CDCl₃) delta 7.40 (1H, d, J=8.0 Hz), 6.96 (1H, d, J=2.2 Hz), 6.84 (1H, dd, J=8.0, 2.2 Hz), 6.08 (1H, tt, J=54.9, 4.4 Hz), 4.72 (2H, d, J=5.9 Hz), 4.16 (2H, td, J=12.5, 3.7 Hz), 1.93 (1H, t, J=5.9 Hz).

<Step-3>:2-(2-chloro-4-(2,2-difluoroethoxy)benzyl) isoindoline-1,3-dione

The title compound is prepared in 79% yield (1.7 g, a white solid) from (2-chloro-4-(2,2-difluoroethoxy)phenyl)methanol (1.4 g, 6.1 mmol, Step-2) by the similar manner in Step-3 of Amine-24.

¹H-NMR (300 MHz, CDCl₃) delta 7.89-7.85 (2H, m), 7.76-7.72 (2H, m), 7.24 (1H, d, J=8.8 Hz), 6.87 (1H, d, J=2.9 Hz), 6.77 (1H, dd, J=8.8, 2.9 Hz), 6.05 (1H, tt, J=54.9, 4.4 Hz), 4.94 (2H, s), 4.14 (2H, td, J=13.2, 4.4 Hz), MS (ESI) m/z: 352 (M+H)⁺.

<Step-4>:(2-chloro-4-(2,2-difluoroethoxy)phenyl) methanamine

The title compound is prepared in 86% yield (920 mg, clear colorless oil) from 2-(2-chloro-4-(2,2-difluoroethoxy)benzyl)isoindoline-1,3-dione (1.7 g, 4.8 mmol, Step-3) by the similar manner in Step-4 of Amine-24.

¹H-NMR (300 MHz, CDCl₃) delta 7.30 (1H, d, J=8.8 Hz), 6.95 (1H, d, J=2.2 Hz), 6.81 (1H, dd, J=8.8, 2.2 Hz), 6.08 (1H, tt, J=54.9, 4.4 Hz), 4.16 (2H, td, J=12.5, 3.7 Hz), 3.87 (2H, s), 1.56 (2H, br s).

MS (ESI) m/z: positive ion of a fragment signal, 205, is observed.

Amine-92:(4-(2,2-difluoroethoxy)-3-fluorophenyl) methanamine hydrochloride

<Step-1>: (4-(2,2-difluoroethoxy)-3-fluorophenyl)methanol

The title compound is prepared in >99% yield (1.28 g, colorless oil) from methyl 4-(2,2-difluoroethoxy)-3-fluorobenzoate (1.37 g, 5.83 mmol, Step-1 of Amine-89) by the similar manner in Step-3 of Amine-4.

¹H-NMR (300 MHz, CDCl₃) delta 7.17-6.94 (3H, m), 6.11 (1H, tt, J=55.0, 4.0 Hz), 4.64 (2H, d, J=5.9 Hz), 4.25 (2H, td, J=13.2, 4.0 Hz), 1.78 (1H, t, J=5.9 Hz), MS (ESI) m/z: 205 (M−H)⁻.

<Step-2>:4-(chloromethyl)-1-(2,2-difluoroethoxy)-2-fluorobenzene

The title compound is prepared in 93% yield (1.29 g, colorless oil) from (4-(2,2-difluoroethoxy)-3-fluorophenyl) methanol (1.28 g, 6.21 mmol, Step-1) by the similar manner in Step-4 of Amine-4.

<Step-3>:4-(azidomethyl)-1-(2,2-difluoroethoxy)-2-fluorobenzene

The title compound is prepared in 88% yield (1.17 g, colorless oil) from 4-(chloromethyl)-1-(2,2-difluoroethoxy)-2-fluorobenzene (1.29 g, 5.75 mmol, Step-2) by the similar manner in Step-5 of Amine-4.

¹H-NMR (300 MHz, CDCl₃) delta 7.12-6.96 (3H, m), 6.12 (1H, tt, J=55.0 Hz, 4.0 Hz), 4.31-4.21 (4H, m).

<Step-4>:(4-(2,2-difluoroethoxy)-3-fluorophenyl) methanamine hydrochloride

The title compound is prepared in 79% yield (0.96 g, a white solid) from 4-(azidomethyl)-1-(2,2-difluoroethoxy)-2- fluorobenzene (1.17 g, 5.04 mmol, Step-3) by the similar manner in Step-3 of Amine-54.

$^1$H-NMR (300 MHz, DMSO-d$_6$) delta 7.47 (1H, d, J=12.5 Hz), 7.36-7.25 (2H, m), 6.42 (1H, tt, J=54.3, 3.3 Hz), 4.42 (2H, td, J=14.7, 3.3 Hz), 3.96 (2H, s).

Amine-93:1-(2-fluoro-3-(trifluoromethyl)phenyl) ethanamine hydrochloride (single enantiomer)

<Step-1>:2-fluoro-N-methoxy-N-methyl-3-(trifluoromethyl)benzamide

The title compound is prepared in >99% yield (1.40 g, yellow oil) from 2-fluoro-3-(trifluoromethyl)benzoic acid (1.00 g, 4.81 mmol) by the similar manner in Step-2 of Amine-5.

$^1$H-NMR (300 MHz, CDCl$_3$) delta 7.73-7.60 (2H, m), 7.32 (1H, t, J=7.3 Hz), 3.54 (3H, br s), 3.38 (3H, br s), MS (ESI) m/z: 252 (M+H)$^+$.

<Step-2>:1-(2-fluoro-3-(trifluoromethyl)phenyl) ethanone

The title compound is prepared in 73% yield (600 mg, a white solid) from 2-fluoro-N-methoxy-N-methyl-3-(trifluoromethyl)benzamide (1.00 g, 3.98 mmol, Step-1) by the similar manner in Step-3 of Amine-1.

$^1$H-NMR (300 MHz, CDCl$_3$) delta 8.12-8.03 (1H, m), 7.81 (1H, t, J=6.6 Hz), 7.35 (1H, t, J=7.3 Hz), 2.69 (3H, d, J=5.1 Hz).

<Step-3>:(R)—N-(1-(2-fluoro-3-(trifluoromethyl) phenyl)ethyl)-2-methylpropane-2-sulfinamide (single diastereomer)

The title compound is prepared in 56% yield (511 mg, a white solid) from 1-(2-fluoro-3-(trifluoromethyl)phenyl) ethanone (600 mg, 2.91 mmol, Step-2) and (R)-2-methylpropane-2-sulfinamide (529 mg, 4.37 mmol) by the similar manner in Step-4 of Amine-1.

$^1$H-NMR (300 MHz, CDCl$_3$) delta 7.62 (1H, t, J=6.6 Hz), 7.54 (1H, t, J=7.3 Hz), 7.25 (1H, t, J=8.0 Hz), 4.86 (1H, quintet, J=6.6 Hz), 3.56 (1H, d, J=5.1 Hz), 1.56 (3H, d, J=6.6 Hz), 1.23 (9H, s), MS (ESI) m/z: 312 (M+H)$^+$.

<Step-4>:1-(2-fluoro-3-(trifluoromethyl)phenyl) ethanamine hydrochloride (single enantiomer The title compound is prepared in 91% yield (357 mg, a white solid) from (R)—N-(1-(2-fluoro-3-(trifluoromethyl) phenyl)ethyl)-2-methylpropane-2-sulfinamide (single diastereomer) (500 mg, 1.61 mmol, Step-3) by the similar manner in Step-5 of Amine-1.

$^1$H-NMR (300 MHz, DMSO-d$_6$) delta 8.86 (3H, br s), 8.2-8.0 (1H, m), 7.90-7.75 (1H, m), 7.53 (1H, t, J=8.0 Hz), 4.75-4.62 (1H, m), 1.56 (3H, t, J=6.6 Hz).

Amine-94:1-(6-(2,2-difluoroethoxy)-5-methoxypyridin-3-yl)ethanamine hydrochloride (single enantiomer)

<Step-1>:1-(6-(2,2-difluoroethoxy)-5-methoxypyridin-3-yl)ethanone

The title compound is prepared in 72% yield (0.94 g, a white solid) from 1-(6-chloro-5-methoxypyridin-3-yl)ethanone (1.04 g, 5.60 mmol, Step-2 of Amine-22) and 2,2-difluoroethanol instead of 2,2,2-trifluoroethanol by the similar manner in Step-1 of Amine-2.

$^1$H-NMR (300 MHz, DMSO-d$_6$) delta 8.41 (1H, d, J=1.8 Hz), 7.64 (1H, d, J=1.8 Hz), 6.42 (1H, tt, J=54.7, 3.7 Hz), 4.66 (2H, td, J=15.0, 3.7 Hz), 3.87 (3H, s), 2.57 (3H, s), MS (ESI) m/z: 232 (M+H)$^+$.

<Step-2>:(R)—N-(1-(6-(2,2-difluoroethoxy)-5-methoxypyridin-3-yl)ethyl)-2-methylpropane-2-sulfinamide (single diastereomer)

The title compound is prepared in 77% yield (1.05 g, a white solid) from 1-(6-(2,2-difluoroethoxy)-5-methoxypyridin-3-yl)ethanone (0.94 g, 4.04 mmol, Step-1) and (R)-2-methylpropane-2-sulfinamide by the similar manner in Step-4 of Amine-1.

$^1$H-NMR (300 MHz, DMSO-d$_6$) delta 7.66 (1H, d, J=1.8 Hz), 7.42 (1H, d, J=1.8 Hz), 6.38 (1H, tt, J=55.0, 3.7 Hz), 5.64 (1H, d, J=7.0 Hz), 4.53 (2H, td, J=14.7, 3.7 Hz), 4.35 (1H, quintet, J=7.0 Hz), 3.79 (3H, s), 1.40 (3H, d, J=7.0 Hz), 1.10 (9H, s), MS (ESI) m/z: 337 (M+H)$^+$.

<Step-3>:1-(6-(2,2-difluoroethoxy)-5-methoxypyridin-3-yl)ethanamine hydrochloride (single enantiomer)

The title compound is prepared in 90% yield (0.76 g, a white solid) from (R)—N-(1-(6-(2,2-difluoroethoxy)-5-methoxypyridin-3-yl)ethyl)-2-methylpropane-2-sulfinamide (single diastereomer) (1.05 g, 3.12 mmol, Step-2) by the similar manner in Step-5 of Amine-1.

$^1$H-NMR (300 MHz, DMSO-d$_6$) delta 8.59 (2H, br s), 7.88 (1H, d, J=1.8 Hz), 7.74 (1H, d, J=1.8 Hz), 6.39 (1H, tt, J=54.7, 3.7 Hz), 4.56 (2H, td, J=15.0, 3.7 Hz), 4.40 (1H, m), 3.83 (3H, s), 1.53 (3H, d, J=6.6 Hz), MS (ESI) m/z: 233 (M+H)$^+$.

Amine-95:1-(2-chloro-4-(2,2-difluoroethoxy)phenyl) ethanamine hydrochloride (single enantiomer)

<Step-1>:methyl 2-chloro-4-(2,2-difluoroethoxy)benzoate

The title compound is prepared in 94% yield (3.5 g, clear colorless oil) from methyl 2-chloro-4-hydroxybenzoate (1.3 g, 16 mmol) by the similar manner in Step-1 of Amine-68.

$^1$H-NMR (300 MHz, CDCl$_3$) delta 7.90 (1H, d, J=8.8 Hz), 7.00 (1H, d, J=2.9 Hz), 6.85 (1H, dd, J=8.8, 2.9 Hz), 6.10 (1H, tt, J=54.9, 4.4 Hz), 4.22 (2H, td, J=12.5, 3.7 Hz), 3.91 (3H, s), MS (ESI) m/z: 251 (M+H)$^+$.

<Step-2>:2-chloro-4-(2,2-difluoroethoxy)benzoic acid

The title compound is prepared in >99% yield (1.8 g, a white solid) from methyl 2-chloro-4-(2,2-difluoroethoxy) benzoate (1.9 g, 7.5 mmol, Step-1) by the similar manner in Step-2 of Carboxylic acid-1.

$^1$H-NMR (300 MHz, CDCl$_3$) delta 8.06 (1H, d, J=8.8 Hz), 7.04 (1H, d, J=2.8 Hz), 6.89 (1H, dd, J=8.8, 2.2 Hz), 6.11 (1H, tt, J=54.9, 3.7 Hz), 4.24 (2H, td, J=13.2, 4.4 Hz), MS (ESI) m/z: 235 (M−H)$^−$.

<Step-3>:2-chloro-4-(2,2-difluoroethoxy)-N-methoxy-N-methylbenzamide

The title compound is prepared in 81% yield (1.5 g, clear colorless oil) from 2-chloro-4-(2,2-difluoroethoxy)benzoic acid (1.6 g, 6.8 mmol, Step-2) by the similar manner in Step-2 of Amine-5.
$^1$H-NMR (300 MHz, CDCl$_3$) delta 7.31 (1H, d, J=8.8 Hz), 6.98 (1H, d, J=3.0 Hz), 6.87 (1H, dd, J=8.8, 2.9 Hz), 6.10 (1H, tt, J=54.9, 4.4 Hz), 4.20 (2H, td, J=12.5, 3.7 Hz), 3.51 (3H, br s), 3.35 (3H, br s), MS (ESI) m/z: 280 (M+H)$^+$.

<Step-4>:1-(2-chloro-4-(2,2-difluoroethoxy)phenyl) ethanone

The title compound is prepared in 95% yield (1.2 g, pale brown oil) from 2-chloro-4-(2,2-difluoroethoxy)-N-methoxy-N-methylbenzamide (1.6 g, 6.8 mmol, Step-3) by the similar manner in Step-3 of Amine-1.
$^1$H-NMR (300 MHz, CDCl$_3$) delta 7.68 (1H, d, J=8.8 Hz), 6.97 (1H, d, J=2.2 Hz), 6.87 (1H, dd, J=8.8, 2.2 Hz), 6.10 (1H, tt, J=54.9, 3.7 Hz), 4.22 (2H, td, J=12.5, 3.7 Hz), 2.65 (3H, s), MS (ESI) m/z: 235 (M+H)$^+$.

<Step-5>:(R)—N-(1-(2-chloro-4-(2,2-difluoroethoxy)phenyl)ethyl)-2-methylpropane-2-sulfinamide (single diastereomer)

The title compound is prepared in 55% yield (990 mg, clear colorless oil) from 1-(2-chloro-4-(2,2-difluoroethoxy)phenyl)ethanone (1.2 g, 5.2 mmol, Step-4) and (R)-2-methylpropane-2-sulfinamide by the similar manner in Step-4 of Amine-1.
$^1$H-NMR (300 MHz, CDCl$_3$) delta 7.38 (1H, J=8.8 Hz), 6.94 (1H, d, J=2.2 Hz), 6.85 (1H, dd, J=8.8, 2.2 Hz), 6.07 (1H, tt, J=54.9, 3.7 Hz), 5.00-4.88 (1H, m), 4.16 (2H, td, J=12.5, 3.7 Hz), 3.51 (1H, d, J=3.7 Hz), 1.49 (3H, d, J=6.6 Hz), 1.23 (9H, s), MS (ESI) m/z: 340 (M+H)$^+$.

<Step-6>:1-(2-chloro-4-(2,2-difluoroethoxy)phenyl) ethanamine hydrochloride (single enantiomer)

The title compound is prepared in 88% yield (690 mg, an off-white solid) from (R)—N-(1-(2-chloro-4-(2,2-difluoroethoxy)phenyl)ethyl)-2-methylpropane-2-sulfinamide (990 mg, 2.2 mmol, Step-5, single diastereomer) by the similar manner in Step-5 of Amine-1.
$^1$H-NMR (300 MHz, DMSO-d$_6$) delta 8.70 (2H, br s), 7.72 (1H, d, J=8.8 Hz), 7.22 (1H, d, J=2.9 Hz), 7.14 (1H, dd, J=8.8, 2.9 Hz), 6.40 (1H, tt, J=54.2, 2.9 Hz), 4.62 (1H, t, J=5.9 Hz), 4.39 (2H, td, J=14.7, 2.9 Hz), 1.48 (3H, d, J=6.6 Hz).
MS (ESI) m/z: positive ion of a fragment signal, 219, is observed.

Amine-96:1-(4-(2,2-difluoroethoxy)-3,5-difluorophenyl)ethanamine hydrochloride (single enantiomer)

<Step-1>:1-(4-(2,2-difluoroethoxy)-3,5-difluorophenyl)ethanone

The title compound is prepared in 87% yield (600 mg, pale brown oil) from 1-(3,5-difluoro-4-hydroxyphenyl)ethanone (500 mg, 2.9 mmol) by the similar manner in Step-1 of Amine-68.
$^1$H-NMR (300 MHz, CDCl$_3$) delta 7.59-7.50 (2H, m), 6.09 (1H, tt, J=54.9, 4.4 Hz), 4.41 (2H, td, J=12.5, 3.7 Hz), 2.57 (3H, s).

<Step-2>:(R)—N-(1-(4-(2,2-difluoroethoxy)-3,5-difluorophenyl)ethyl)-2-methylpropane-2-sulfinamide (single diastereomer)

The title compound is prepared in 88% yield (750 mg, a white solid) from 1-(4-(2,2-difluoroethoxy)-3,5-difluorophenyl)ethanone (590 mg, 2.5 mmol, Step-1) and (R)-2-methylpropane-2-sulfinamide by the similar manner in Step-4 of Amine-1.
$^1$H-NMR (300 MHz, CDCl$_3$) delta 6.96-6.90 (2H, m), 6.07 (1H, tt, J=54.9, 4.4 Hz), 4.50-4.40 (1H, m), 4.29 (2H, td, J=13.2, 3.7 Hz), 3.39 (1H, br s), 1.47 (3H, d, J=6.6 Hz), 1.24 (9H, s), MS (ESI) m/z: 342 (M+H)$^+$.

<Step-3>:1-(4-(2,2-difluoroethoxy)-3,5-difluorophenyl)ethanamine hydrochloride (single enantiomer)

The title compound is prepared in 80% yield (480 mg, a white solid) from (R)—N-(1-(4-(2,2-difluoroethoxy)-3,5-difluorophenyl)ethyl)-2-methylpropane-2-sulfinamide (750 mg, 2.2 mmol, Step-2, single diastereomer) by the similar manner in Step-5 of Amine-1.
$^1$H-NMR (300 MHz, DMSO-d$_6$) delta 8.64 (2H, br s), 7.48-7.39 (2H, m), 6.34 (1H, tt, J=53.5, 2.9 Hz), 4.42 (2H, td, J=15.4, 2.9 Hz), 4.40 (1H, br s), 1.49 (3H, d, J=6.6 Hz).
MS (ESI) m/z: positive ion of a fragment signal, 221, is observed.

Amine-97: 1-(6-(2,2-difluoroethoxy)-2-methoxypyridin-3-yl)ethanamine hydrochloride (single enantiomer)

<Step-1>:2,2-difluoroethyl 2-chloro-6-(2,2-difluoroethoxy)nicotinate

The title compound is prepared in 92% yield (2.9 g, clear colorless oil) from 2-chloro-6-hydroxynicotinic acid (1.8 g, 11 mmol) and 2,2-difluoroethyl trifluoromethanesulfonate instead of 2,2,2-trifluoroethyl trifluoromethanesulfonate by the similar manner in Step-3 of Amine-13.
$^1$H-NMR (300 MHz, CDCl$_3$) delta 8.23 (1H, d, J=8.0 Hz), 6.84 (1H, d, J=8.8 Hz), 6.32-5.88 (2H, m), 4.66-4.46 (4H, m). MS (ESI) m/z: 302 (M+H)$^+$.

Step-2>:methyl 6-(2,2-difluoroethoxy)-2-methoxynicotinate

The title compound is prepared in 26% yield (620 mg, a white solid) from 2,2-difluoroethyl 2-chloro-6-(2,2-difluoroethoxy)nicotinate (2.9 g, 9.8 mmol, Step-1) by the similar manner in Step-1 of Amine-44.
$^1$H-NMR (300 MHz, CDCl$_3$) delta 8.19 (1H, d, J=8.0 Hz), 6.42 (1H, d, J=8.1 Hz), 6.12 (1H, tt, J=54.9, 3.7 Hz), 4.58 (2H, td, J=13.2, 4.4 Hz), 4.04 (3H, s), 3.87 (3H, s), MS (ESI) m/z: 248 (M+H)$^+$.

Step-3>:6-(2,2-difluoroethoxy)-2-methoxynicotinic acid

The title compound is prepared in 91% yield (270 mg, a white solid) from methyl 6-(2,2-difluoroethoxy)-2-methoxynicotinate (320 mg, 1.3 mmol, Step-2) by the similar manner in Step-2 of Carboxylic acid-1.

¹H-NMR (300 MHz, CDCl₃) delta 8.39 (1H, d, J=8.8 Hz), 6.59 (1H, d, J=8.0 Hz), 6.12 (1H, tt, J=54.9, 3.7 Hz), 4.60 (2H, td, J=13.2, 4.4 Hz), 4.17 (3H, s), MS (ESI) m/z: 234 (M+H)⁺.

<Step-4>:6-(2,2-difluoroethoxy)-N,2-dimethoxy-N-methylnicotinamide

The title compound is prepared in >99% yield (990 mg, clear colorless oil) from 6-(2,2-difluoroethoxy)-2-methoxynicotinic acid (910 mg, 4.5 mmol, Step-3) by the similar manner in Step-2 of Amine-5.
MS (ESI) m/z: 277 (M+H)⁺.

<Step-5>:1-(6-(2,2-difluoroethoxy)-2-methoxypyridin-3-yl)ethanone

The title compound is prepared in 69% yield (650 mg, pale yellow oil) from 6-(2,2-difluoroethoxy)-N,2-dimethoxy-N-methylnicotinamide (980 mg, 3.6 mmol, Step-4) by the similar manner in Step-3 of Amine-1.
¹H-NMR (270 MHz, CDCl₃) delta 8.18 (1H, d, J=8.6 Hz), 6.54 (1H, d, J=8.6 Hz), 6.12 (1H, tt, J=55.4, 4.0 Hz), 4.59 (2H, td, J=13.8, 4.6 Hz), 4.04 (3H, s), 2.59 (3H, s), MS (ESI) m/z: 232 (M+H)⁺.

<Step-6>:(R)—N-(1-(6-(2,2-difluoroethoxy)-2-methoxypyridin-3-yl)ethyl)-2-methylpropane-2-sulfinamide (single diastereomer)

The title compound is prepared in 73% yield (400 mg, clear colorless oil) from 1-(6-(2,2-difluoroethoxy)-2-methoxypyridin-3-yl)ethanone (380 mg, 1.6 mmol, Step-5) and (R)-2-methylpropane-2-sulfinamide by the similar manner in Step-4 of Amine-1.
¹H-NMR (300 MHz, CDCl₃) delta 7.52 (1H, d, J=8.1 Hz), 6.37 (1H, d, J=8.1 Hz), 6.12 (1H, tt, J=55.7, 4.4 Hz), 4.63 (1H, quintet, J=6.6 Hz), 4.51 (2H, td, J=13.9, 4.4 Hz), 3.92 (3H, s), 3.74 (1H, d, J=5.9 Hz), 1.46 (3H, d, J=7.3 Hz), 1.21 (9H, s), MS (ESI) m/z: 337 (M+H)⁺.

<Step-7>:1-(6-(2,2-difluoroethoxy)-2-methoxypyridin-3-yl)ethanaminehydrochloride (single enantiomer)

The title compound is prepared in 96% yield (350 mg, a white solid) from (R)—N-(1-(6-(2,2-difluoroethoxy)-2-methoxypyridin-3-yl)ethyl)-2-methylpropane-2-sulfinamide (450 mg, 1.3 mmol, Step-6, single diastereomer) by the similar manner in Step-5 of Amine-1.
¹H-NMR (300 MHz, DMSO-d₆) delta 8.36 (2H, br s), 7.86 (1H, d, J=8.1 Hz), 6.57 (1H, d, J=8.1 Hz), 6.42 (1H, tt, J=54.9, 3.7 Hz), 4.59 (2H, td, J=14.6, 2.9 Hz), 4.52-4.40 (1H, br s), 3.93 (3H, s), 1.46 (3H, d, J=6.6 Hz).
MS (ESI) m/z: positive ion of a fragment signal, 216, is observed.

Amine-98:(3-(2,2-difluoroethoxy)-2-methylphenyl)methanamine

<Step-1>:methyl 3-(2,2-difluoroethoxy)-2-methylbenzoate

The title compound is prepared in 85% yield (2.1 g, clear colorless oil) from methyl 3-hydroxy-2-methylbenzoate (1.8 g, 11 mmol) by the similar manner in Step-1 of Amine-68.
¹H-NMR (300 MHz, CDCl₃) delta 7.48 (1H, d, J=8.0 Hz), 7.21 (1H, t, J=8.1 Hz), 6.95 (1H, d, J=8.1 Hz), 6.12 (1H, tt, J=54.9, 4.4 Hz), 4.19 (2H, td, J=12.5, 3.7 Hz), 3.90 (3H, s), 2.45 (3H, s), MS (ESI) m/z: 231 (M+H)⁺.

<Step-2>:(3-(2,2-difluoroethoxy)-2-methylphenyl)methanol

The title compound is prepared in >99% yield (810 mg, a white solid) from methyl 3-(2,2-difluoroethoxy)-2-methylbenzoate (890 mg, 3.9 mmol, Step-1) by the similar manner in Step-3 of Amine-4.
¹H-NMR (300 MHz, CDCl₃) delta 7.18 (1H, t, J=7.3 Hz), 7.06 (1H, d, J=7.3 Hz), 6.79 (1H, d, J=7.3 Hz), 6.11 (1H, tt, J=54.9, 4.4 Hz), 4.71 (2H, d, J=5.1 Hz), 4.18 (2H, td, J=13.2, 4.4 Hz), 2.24 (3H, s).

<Step-3>:2-(3-(2,2-difluoroethoxy)-2-methylbenzyl)isoindoline-1,3-dione

The title compound is prepared in 78% yield (1.0 g, a white solid) from (3-(2,2-difluoroethoxy)-2-methylphenyl)methanol (810 mg, 4.0 mmol, Step-2) by the similar manner in Step-3 of Amine-24.
¹H-NMR (300 MHz, CDCl₃) delta 7.90-7.85 (2H, m), 7.77-7.73 (2H, m), 7.10 (1H, t, J=8.0 Hz), 6.95 (1H, d, J=7.3 Hz), 6.74 (1H, d, J=8.1 Hz), 6.10 (1H, tt, J=54.9, 3.7 Hz), 4.89 (2H, s), 4.16 (2H, td, J=13.2, 4.4 Hz), 2.36 (3H, s), MS (ESI) m/z: 332 (M+H)⁺.

<Step-4>:(3-(2,2-difluoroethoxy)-2-methylphenyl)methanamine

The title compound is prepared in 77% yield (490 mg, a white solid) from 2-(3-(2,2-difluoroethoxy)-2-methylbenzyl)isoindoline-1,3-dione (1.0 g, 3.1 mmol, Step-3) by the similar manner in Step-4 of Amine-24.
¹H-NMR (270 MHz, DMSO-d₆) delta 7.12 (1H, t, J=7.3 Hz), 7.02 (1H, d, J=7.3 Hz), 6.88 (1H, d, J=7.9 Hz), 6.38 (1H, tt, J=54.7, 3.9 Hz), 4.25 (2H, td, J=14.5, 3.3 Hz), 3.68 (2H, s), 3.28 (2H, br s), 2.12 (3H, s)
MS (ESI) m/z: positive ion of a fragment signal, 185, is observed.

Amine-99: (6-(2,2-difluoroethoxy)-2-methoxypyridin-3-yl)methanamine

<Step-1>: (6-(2,2-difluoroethoxy)-2-methoxypyridin-3-yl)methanol

The title compound is prepared in 90% yield (240 mg, a white solid) from methyl 6-(2,2-difluoroethoxy)-2-methoxynicotinate (300 mg, 1.2 mmol, Step-2 of Amine-97) by the similar manner in Step-3 of Amine-4.
¹H-NMR (300 MHz, CDCl₃) delta 7.52 (1H, d, J=7.3 Hz), 6.37 (1H, d, J=8.1 Hz), 6.12 (1H, tt, J=55.7, 4.4 Hz), 4.59 (2H, d, J=6.6 Hz), 4.52 (2H, td, J=13.2, 4.4 Hz), 3.96 (3H, s), 2.08 (1H, t, J=6.6 Hz).

<Step-2>:2-((6-(2,2-difluoroethoxy)-2-methoxypyridin-3-yl)methyl)isoindoline-1,3-dione The title compound is prepared in 89% yield (330 mg, a white solid) from (6-(2,2-difluoroethoxy)-2-methoxypyridin-3-yl)methanol (240 mg, 1.1 mmol, Step-1) by the similar manner in Step-3 of Amine-24.
MS (ESI) m/z: 349 (M+H)⁺.

<Step-3>:(6-(2,2-difluoroethoxy)-2-methoxypyridin-3-yl)methanamine

The title compound is prepared in >99% yield (210 mg, clear colorless oil) from 2-((6-(2,2-difluoroethoxy)-2-methoxypyridin-3-yl)methyl)isoindoline-1,3-dione (330 mg, 0.95 mmol, Step-2) by the similar manner in Step-4 of Amine-24.
$^1$H-NMR (300 MHz, CDCl$_3$) delta 7.45 (1H, d, J=7.3 Hz), 6.34 (1H, d, J=8.0 Hz), 6.13 (1H, tt, J=55.7, 3.7 Hz), 4.51 (2H, td, J=13.9, 4.4 Hz), 3.95 (3H, s), 3.72 (2H, s), 1.66 (2H, br s).
MS (ESI) m/z: positive ion of a fragment signal, 202, is observed.

Amine-100: 1-(5-(2,2-difluoroethoxy)-2-methylphenyl)ethanamine hydrochloride (single enantiomer)

<Step-1>:methyl 5-(2,2-difluoroethoxy)-2-methylbenzoate

The title compound is prepared in 76% yield (1.3 g, clear colorless oil) from methyl 5-hydroxy-2-methylbenzoate (750 mg, 9.1 mmol) by the similar manner in Step-1 of Amine-68.
$^1$H-NMR (300 MHz, CDCl$_3$) delta 7.45 (1H, d, J=2.9 Hz), 7.18 (1H, d, J=8.8 Hz), 6.99 (1H, dd, J=8.8, 2.9 Hz), 6.09 (1H, tt, J=54.9, 4.4 Hz), 4.19 (2H, td, J=13.2, 4.4 Hz), 3.90 (3H, s), 2.53 (3H, s), MS (ESI) m/z: 231 (M+H)$^+$.

<Step-2>:5-(2,2-difluoroethoxy)-2-methylbenzoic acid

The title compound is prepared in 97% yield (680 mg, a white solid) from methyl 5-(2,2-difluoroethoxy)-2-methylbenzoate (750 mg, 3.3 mmol, Step-1) by the similar manner in Step-2 of Carboxylic acid-1.
$^1$H-NMR (300 MHz, CDCl$_3$) delta 7.60 (1H, d, J=2.9 Hz), 7.22 (1H, d, J=8.0 Hz), 7.05 (1H, dd, J=8.8, 2.9 Hz), 6.10 (1H, tt, J=54.9, 3.7 Hz), 4.22 (2H, td, J=12.5, 3.7 Hz), 2.59 (3H, s).

<Step-3>:5-(2,2-difluoroethoxy)-N-methoxy-N,2-dimethylbenzamide

The title compound is prepared in 85% yield (580 mg, clear colorless oil) from 5-(2,2-difluoroethoxy)-2-methylbenzoic acid (570 mg, 2.6 mmol, Step-2) by the similar manner in Step-2 of Amine-5.
$^1$H-NMR (300 MHz, CDCl$_3$) delta 7.14 (1H, d, J=8.1 Hz), 6.89-6.83 (2H, m), 6.07 (1H, tt, J=54.9, 4.4 Hz), 4.16 (2H, td, J=13.2, 4.4 Hz), 3.53 (3H, br s), 3.31 (3H, br s), 2.27 (3H, s), MS (ESI) m/z: 260 (M+H)$^+$.

<Step-4>:1-(5-(2,2-difluoroethoxy)-2-methylphenyl)ethanone

The title compound is prepared in 94% yield (450 mg, pale brown oil) from 5-(2,2-difluoroethoxy)-N-methoxy-N,2-dimethylbenzamide (580 mg, 2.2 mmol, Step-3) by the similar manner in Step-3 of Amine-1.
$^1$H-NMR (300 MHz, CDCl$_3$) delta 7.23 (1H, d, J=2.2 Hz), 7.18 (1H, d, J=8.1 Hz), 6.94 (1H, dd, J=8.8, 2.9 Hz), 6.10 (1H, tt, J=54.9, 3.7 Hz), 4.20 (2H, td, J=12.5, 3.7 Hz), 2.57 (3H, s), 2.45 (3H, s).

<Step-5>: (R)—N-(1-(5-(2,2-difluoroethoxy)-2-methylphenyl)ethyl)-2-methylpropane-2-sulfinamide (single diastereomer)

The title compound is prepared in 61% yield (400 mg, clear colorless oil) from 1-(5-(2,2-difluoroethoxy)-2-methylphenyl)ethanone (440 mg, 2.1 mmol, Step-4) and (R)-2-methylpropane-2-sulfinamide by the similar manner in Step-4 of Amine-1.
$^1$H-NMR (300 MHz, CDCl$_3$) delta 7.10 (1H, d, J=8.1 Hz), 6.99 (1H, d, J=2.9 Hz), 6.73 (1H, dd, J=8.8, 2.9 Hz), 6.09 (1H, tt, J=54.9, 4.4 Hz), 4.78-4.70 (1H, m), 4.17 (2H, td, J=13.2, 3.7 Hz), 3.34 (1H, br s), 2.31 (3H, s), 1.46 (3H, d, J=6.6 Hz), 1.25 (9H, s), MS (ESI) m/z: 320 (M+H)$^+$.

<Step-6>:1-(5-(2,2-difluoroethoxy)-2-methylphenyl)ethanamine hydrochloride (single enantiomer)

The title compound is prepared in 88% yield (280 mg, a white solid) from (R)—N-(1-(5-(2,2-difluoroethoxy)-2-methylphenyl)ethyl)-2-methylpropane-2-sulfinamide (400 mg, 1.2 mmol, Step-5, single diastereomer) by the similar manner in Step-5 of Amine-1.
$^1$H-NMR (300 MHz, DMSO-d$_6$) delta 8.53 (2H, br s), 7.31 (1H, d, J=2.2 Hz), 7.16 (1H, d, J=8.8 Hz), 6.90 (1H, dd, J=8.8, 2.9 Hz), 6.41 (1H, tt, J=54.2, 3.7 Hz), 4.51-4.40 (1H, m), 4.30 (2H, td, J=14.6, 3.7 Hz), 2.27 (3H, s), 1.46 (3H, d, J=6.6 Hz).
MS (ESI) m/z: positive ion of a fragment signal, 199, is observed.

Amine-101: (6-(2,2-difluoroethoxy)-2-methylpyridin-3-yl)methanamine

<Step-1>:3-bromo-6-(2,2-difluoroethoxy)-2-methylpyridine

To a mixture of 3,6-dibromo-2-methylpyridine (2.00 g, 7.97 mmol) and 2,2-difluoroethanol (981 mg, 12.0 mmol) in THF (100 mL) is added potassium tert-butoxide (1.34 g, 12.0 mmol), and the mixture is stirred at 70° C. for 12 hours. After cooling to room temperature, the resulting mixture is poured to water (200 mL). The aqueous layer is extracted with ethyl acetate (200 mL×2). The organic layer is dried over sodium sulfate and concentrated in vacuo. The residue is purified by column chromatography on silica gel eluting with n-hexane/ethyl acetate (8:1) to give 1.94 g (97% yield) of the title compound as colorless oil.
$^1$H-NMR (300 MHz, CDCl$_3$) delta 7.67 (1H, d, J=8.8 Hz), 6.54 (1H, d, J=8.1 Hz), 6.11 (1H, tt, J=55.7, 4.4 Hz), 4.50 (2H, td, J=13.2, 4.4 Hz), 2.54 (3H, s), MS (ESI) m/z: 252 (M+H)$^+$.

<Step-2>:ethyl 6-(2,2-difluoroethoxy)-2-methylnicotinate

The title compound is prepared in 77% yield (1.74 g, yellow oil) from 3-bromo-6-(2,2-difluoroethoxy)-2-methylpyridine (2.32 g, 9.20 mmol, Step-1) by the similar manner in Step-1 of Amine-63.
$^1$H-NMR (300 MHz, CDCl$_3$) delta 8.17 (1H, d, J=8.1 Hz), 6.67 (1H, d, J=8.1 Hz), 6.14 (1H, tt, J=55.8, 4.4 Hz), 4.59 (2H, td, J=13.6, 4.2 Hz), 4.34 (2H, q, J=7.1 Hz), 2.75 (3H, s), 1.39 (3H, t, J=7.3 Hz), MS (ESI) m/z: 246 (M+H)$^+$.

<Step-3>:(6-(2,2-difluoroethoxy)-2-methylpyridin-3-yl)methanol

The title compound is prepared in >99% yield (619 mg, yellow oil) from ethyl 6-(2,2-difluoroethoxy)-2-methylnicotinate (700 mg, 2.85 mmol, Step-2) by the similar manner in Step-3 of Amine-4.
$^1$H-NMR (300 MHz, CDCl$_3$) delta 7.58 (1H, d, J=9.5 Hz), 6.64 (1H, d, J=8.8 Hz), 6.13 (1H, tt, J=62.2, 5.1 Hz), 4.65 (2H, d, J=5.9 Hz), 4.53 (2H, td, J=15.4, 5.1 Hz), 3.74 (1H, br s), 2.47 (3H, s), MS (ESI) m/z: 204 (M+H)⁺.

<Step-4>:2-((6-(2,2-difluoroethoxy)-2-methylpyridin-3-yl)methyl)isoindoline-1,3-dione The title compound is prepared in 65% yield (619 mg, a white solid) from (6-(2,2-difluoroethoxy)-2-methylpyridin-3-yl)methanol (580 mg, 2.85 mmol, Step-3) by the similar manner in Step-3 of Amine-24.

¹H-NMR (270 MHz, CDCl₃) delta 7.88-7.82 (2H, m), 7.76-7.70 (2H, m), 7.63 (1H, d, J=7.9 Hz), 6.59 (1H, d, J=7.9 Hz), 6.11 (1H, tt, J=56.0, 4.0 Hz), 4.81 (2H, s), 4.50 (2H, td, J=13.8, 4.6 Hz), 2.62 (3H, s), MS (ESI) m/z: 333 (M+H)⁺.

<Step-5>:(6-(2,2-difluoroethoxy)-2-methylpyridin-3-yl)methanamine

The title compound is prepared in >99% yield (380 mg, yellow oil) from 2-((6-(2,2-difluoroethoxy)-2-methylpyridin-3-yl)methyl)isoindoline-1,3-dione (610 mg, 1.84 mmol, Step-4) by the similar manner in Step-4 of Amine-24.

¹H-NMR (300 MHz, CDCl₃) delta 7.54 (1H, d, J=8.1 Hz), 6.63 (1H, d, J=8.1 Hz), 6.14 (1H, tt, J=55.7, 4.4 Hz), 4.53 (2H, td, J=13.9, 3.7 Hz), 3.82 (2H, s), 2.45 (3H, s).

Amine-102: 1-(4-(2,2-difluoroethoxy)-3-methoxyphenyl)ethanamine hydrochloride (single enantiomer)

<Step-1>:methyl 4-(2,2-difluoroethoxy)-3-methoxybenzoate

The title compound is prepared in 80% yield (2.17 g, a white solid) from methyl 4-hydroxy-3-methoxybenzoate (2.0 g, 11.0 mmol) by the similar manner in Step-1 of Amine-68.

¹H-NMR (300 MHz, CDCl₃) delta 7.66 (1H, dd, J=8.4, 2.2 Hz), 7.58 (1H, d, J=2.2 Hz), 6.91 (1H, d, J=8.4 Hz), 6.16 (1H, tt, J=55.0, 4.4 Hz), 4.28 (2H, td, J=13.2, 4.4 Hz), 3.93 (3H, s), 3.91 (3H, s).

<Step-2>:4-(2,2-difluoroethoxy)-3-methoxybenzoic acid

The title compound is prepared in 95% yield (1.05 g, a white solid) from methyl 4-(2,2-difluoroethoxy)-3-methoxybenzoate (1.17 g, 4.74 mmol, Step-1) by the similar manner in Step-2 of Carboxylic acid-1.

¹H-NMR (300 MHz, DMSO-d₆) delta 7.53 (1H, dd, J=8.4, 1.8 Hz), 7.46 (1H, d, J=1.8 Hz), 7.11 (1H, d, J=8.4 Hz), 6.39 (1H, tt, J=54.3, 3.7 Hz), 4.35 (2H, td, J=14.7, 3.7 Hz), 3.80 (3H, s), MS (ESI) m/z: 231 (M−H)⁻.

<Step-3>:4-(2,2-difluoroethoxy)-N,3-dimethoxy-N-methylbenzamide

The title compound is prepared in 86% yield (0.97 g, clear colorless oil) from 4-(2,2-difluoroethoxy)-3-methoxybenzoic acid (0.95 g, 4.09 mmol, Step-2) by the similar manner in Step-2 of Amine-5.

¹H-NMR (300 MHz, CDCl₃) delta 7.37-7.33 (2H, m), 6.90 (1H, d, J=8.1 Hz), 6.15 (1H, tt, J=55.0, 4.0 Hz), 4.27 (2H, td, J=13.2, 4.0 Hz), 3.90 (3H, s), 3.57 (3H, s), 3.37 (3H, s), MS (ESI) m/z: 276 (M+H)⁺.

<Step-4>:1-(4-(2,2-difluoroethoxy)-3-methoxyphenyl)ethanone

The title compound is prepared in 95% yield (0.77 g, pale yellow oil) from 4-(2,2-difluoroethoxy)-N,3-dimethoxy-N-methylbenzamide (0.97 g, 3.51 mmol, Step-3) by the similar manner in Step-3 of Amine-1.

¹H-NMR (300 MHz, CDCl₃) delta 7.58-7.51 (2H, m), 6.94-6.90 (1H, m), 6.16 (1H, tt, J=55.4, 4.0 Hz), 4.29 (2H, td, J=12.8, 4.0 Hz), 3.93 (3H, s), 2.58 (3H, s), MS (ESI) m/z: 231 (M+H)⁺.

<Step-5>:(R)—N-(1-(4-(2,2-difluoroethoxy)-3-methoxyphenyl)ethyl)-2-methylpropane-2-sulfinamide (single diastereomer)

The title compound is prepared in 97% yield (1.09 g, yellow oil) from 1-(4-(2,2-difluoroethoxy)-3-methoxyphenyl)ethanone (0.77 g, 3.35 mmol, Step-4) and (R)-2-methylpropane-2-sulfinamide by the similar manner in Step-4 of Amine-1.

¹H-NMR (300 MHz, CDCl₃) delta 6.94-6.86 (3H, m), 6.12 (tt, J=55.1, 4.4 Hz), 4.55-4.46 (1H, m), 4.21 (2H, td, J=13.2, 4.4 Hz), 3.88 (3H, s), 3.38 (1H, br s), 1.50 (3H, d, J=6.6 Hz), 1.24 (9H, s), MS (ESI) m/z: 336 (M+H)⁺.

<Step-6>:1-(4-(2,2-difluoroethoxy)-3-methoxyphenyl)ethanamine hydrochloride (single enantiomer)

The title compound is prepared in 78% yield (0.68 g, a white solid) from (R)—N-(1-(4-(2,2-difluoroethoxy)-3-methoxyphenyl)ethyl)-2-methylpropane-2-sulfinamide (1.09 g, 3.25 mmol, Step-5, single diastereomer) by the similar manner in Step-5 of Amine-1.

¹H-NMR (300 MHz, DMSO-d₆) delta 8.53 (2H, br s), 7.29 (1H, br s), 7.05-6.97 (2H, m), 6.35 (1H, tt, J=55.0, 3.7 Hz), 4.36-4.18 (3H, m), 3.46 (3H, s), 1.49 (3H, d, J=6.6 Hz), MS (ESI) m/z: 232 (M+H)⁺.

Amine-103: 1-(3-(2,2-difluoroethoxy)-4-methylphenyl)ethanamine hydrochloride (single enantiomer)

<Step-1>:methyl 3-(2,2-difluoroethoxy)-4-methylbenzoate

The title compound is prepared in 78% yield (2.2 g, a white solid) from methyl 3-hydroxy-4-methylbenzoate (750 mg, 9.1 mmol) by the similar manner in Step-1 of Amine-68.

¹H-NMR (300 MHz, CDCl₃) delta 7.62 (1H, dd, J=8.1, 1.5 Hz), 7.45 (1H, s), 7.22 (1H, d, J=7.3 Hz), 6.13 (1H, tt, J=54.9, 3.7 Hz), 4.25 (2H, td, J=12.5, 3.7 Hz), 4.20 (3H, s), 2.29 (3H, s), MS (ESI) m/z: 231 (M+H)⁺.

<Step-2>:3-(2,2-difluoroethoxy)-4-methylbenzoic acid

The title compound is prepared in 94% yield (1.1 g, a white solid) from methyl 3-(2,2-difluoroethoxy)-4-methylbenzoate (1.2 g, 5.2 mmol, Step-1) by the similar manner in Step-2 of Carboxylic acid-1.

¹H-NMR (300 MHz, DMSO-d₆) delta 12.9 (1H, s), 7.52 (1H, d, J=7.3 Hz), 7.48 (1H, s), 7.30 (1H, d, J=8.0 Hz), 6.41

(1H, tt, J=54.1, 3.7 Hz), 4.40 (2H, td, J=14.7, 2.9 Hz), 2.23 (3H, s), MS (ESI) m/z: 215 (M−H)⁻.

<Step-3>:3-(2,2-difluoroethoxy)-N-methoxy-N,4-dimethylbenzamide

The title compound is prepared in 86% yield (1.1 g, a white solid) from 3-(2,2-difluoroethoxy)-4-methylbenzoic acid (970 mg, 4.5 mmol, Step-2) by the similar manner in Step-2 of Amine-5.
¹H-NMR (300 MHz, CDCl₃) delta 7.29 (1H, dd, J=8.1, 1.5 Hz), 7.18 (1H, d, J=8.1 Hz), 7.16 (1H, s), 6.12 (1H, tt, J=54.9, 3.7 Hz), 4.22 (2H, td, J=13.2, 4.4 Hz), 3.57 (3H, s), 3.36 (3H, s), 2.28 (3H, s), MS (ESI) m/z: 260 (M+H)⁺.

<Step-4>:1-(3-(2,2-difluoroethoxy)-4-methylphenyl)ethanone

The title compound is prepared in >99% yield (880 mg, pale yellow oil) from 3-(2,2-difluoroethoxy)-N-methoxy-N,4-dimethylbenzamide (1.1 g, 4.1 mmol, Step-3) by the similar manner in Step-3 of Amine-1.
¹H-NMR (300 MHz, CDCl₃) delta 7.51 (1H, dd, J=8.1, 1.5 Hz), 7.41 (1H, d, J=1.5 Hz), 7.24 (1H, d, J=8.1 Hz), 6.13 (1H, tt, J=54.9, 3.7 Hz), 4.26 (2H, td, J=13.2, 3.7 Hz), 2.59 (3H, s), 2.30 (3H, s).

<Step-5>:(R)—N-(1-(3-(2,2-difluoroethoxy)-4-methylphenyl)ethyl)-2-methylpropane-2-sulfinamide (single diastereomer)

The title compound is prepared in 66% yield (860 mg, clear colorless oil) from 1-(3-(2,2-difluoroethoxy)-4-methylphenyl)ethanone (880 mg, 4.1 mmol, Step-4) and (R)-2-methylpropane-2-sulfinamide by the similar manner in Step-4 of Amine-1.
¹H-NMR (300 MHz, CDCl₃) delta 7.14 (1H, d, J=8.1 Hz), 6.91 (1H, dd, J=8.0, 1.5 Hz), 6.81 (1H, d, J=1.5 Hz), 6.11 (1H, tt, J=54.9, 4.4 Hz), 4.53-4.46 (1H, m), 4.20 (2H, td, J=13.2, 4.4 Hz), 3.38 (1H, d, J=2.2 Hz), 2.22 (3H, s), 1.50 (3H, d, J=5.9 Hz), 1.24 (9H, s), MS (ESI) m/z: 320 (M+H)⁺.

<Step-6>:1-(3-(2,2-difluoroethoxy)-4-methylphenyl)ethanamine hydrochloride (single enantiomer)

The title compound is prepared in 83% yield (560 mg, a white solid) from (R)—N-(1-(3-(2,2-difluoroethoxy)-4-methylphenyl)ethyl)-2-methylpropane-2-sulfinamide (860 mg, 2.7 mmol, Step-5, single diastereomer) by the similar manner in Step-5 of Amine-1.
¹H-NMR (300 MHz, DMSO-d₆) delta 8.43 (2H, br s), 7.26 (1H, s), 7.21 (1H, d, J=8.0 Hz), 7.01 (1H, d, J=6.6 Hz), 6.44 (1H, tt, J=54.2, 2.9 Hz), 4.38-4.27 (3H, m), 2.16 (3H, s), 1.50 (3H, d, J=7.3 Hz).
MS (ESI) m/z: positive ion of a fragment signal, 199, is observed.

Amine-104:1-(2-fluoro-4-(trifluoromethyl)phenyl)ethanamine hydrochloride (single enantiomer)

<Step-1>: (S,E)-N-(2-fluoro-4-(trifluoromethyl)benzylidene)-2-methylpropane-2-sulfinamide The title compound is prepared in 95% yield (1.17 g, a pale yellow solid) from 2-fluoro-4-(trifluoromethyl)benzaldehyde (800 mg, 4.16 mmol) and (S)-2-methylpropane-2-sulfinamide (606 mg, 5.00 mmol) by the similar manner in Step-1 of Amine-88.
¹H-NMR (300 MHz, CDCl₃) delta 8.91 (1H, s), 8.14 (1H, t, J=7.3 Hz), 7.51 (1H, d, J=8.8 Hz), 7.45 (1H, d, J=10.2 Hz), 1.29 (9H, s), MS (ESI) m/z: 296 (M+H)⁺.

<Step-2>:(S)—N-(1-(2-fluoro-4-(trifluoromethyl)phenyl)ethyl)-2-methylpropane-2-sulfinamide (single diastereomer)

The title compound is prepared in 68% yield (838 mg, colorless oil) from (S,E)-N-(2-fluoro-4-(trifluoromethyl)benzylidene)-2-methylpropane-2-sulfinamide (1.17 g, 3.97 mmol, Step-1) by the similar manner in Step-2 of Amine-81.
¹H-NMR (300 MHz, CDCl₃) delta 7.52 (1H, t, J=7.3 Hz), 7.42 (1H, d, J=8.0 Hz), 7.32 (1H, d, J=10.3 Hz), 4.82 (1H, quintet, J=5.9 Hz), 3.58 (1H, d, J=5.1 Hz), 1.55 (3H, d, J=6.6 Hz), 1.24 (9H, s), MS (ESI) m/z: 312 (M+H)⁺.

<Step-3>:1-(2-fluoro-4-(trifluoromethyl)phenyl)ethanamine hydrochloride (single enantiomer)

The title compound is prepared in 94% yield (596 mg, a white solid) from (S)—N-(1-(2-fluoro-4-(trifluoromethyl)phenyl)ethyl)-2-methylpropane-2-sulfinamide (single diastereomer) (810 mg, 2.60 mmol, Step-2) by the similar manner in Step-5 of Amine-1.
¹H-NMR (300 MHz, DMSO-d₆) delta 8.90 (3H, br s), 8.01-7.93 (1H, m), 7.82-7.70 (2H, m), 4.66 (1H, q, J=6.6 Hz), 1.55 (3H, d, J=6.6 Hz).

Amine-105: (6-(2-(trifluoromethoxy)ethoxy)pyridin-3-yl)methanamine

<Step-1>:6-(2-(trifluoromethoxy)ethoxy)nicotinonitrile

The title compound is prepared in 95% yield (509 mg, colorless oil) from 6-bromonicotinonitrile (422 mg, 2.31 mmol) and 2-(trifluoromethoxy)ethanol (300 mg, 2.31 mmol) by the similar manner in Step-1 of Amine-101.
¹H-NMR (300 MHz, CDCl₃) delta 8.47 (1H, d, J=2.2 Hz), 7.83 (1H, dd, J=8.8, 2.2 Hz), 6.90 (1H, d, J=8.8 Hz), 4.65-4.60 (2H, m), 4.33-4.29 (2H, m).

<Step-2>:(6-(2-(trifluoromethoxy)ethoxy)pyridin-3-yl)methanamine

The title compound is prepared in 64% yield (291 mg, a brown solid) from 6-(2-(trifluoromethoxy)ethoxy)nicotinonitrile (450 mg, 1.94 mmol) by the similar manner in Step-2 of Amine-2.
¹H-NMR (300 MHz, CDCl₃) delta 8.04 (1H, s), 7.60 (1H, d, J=6.6 Hz), 6.78 (1H, d, J=8.8 Hz), 4.55 (2H, t, J=4.4 Hz), 4.30 (2H, t, J=4.4 Hz), 3.82 (2H, s), MS (ESI) m/z: 237 (M+H)⁺.

Amine-106: (4-(2,2-difluoroethoxy)-3-methoxyphenyl)methanamine hydrochloride

<Step-1>: (4-(2,2-difluoroethoxy)-3-methoxyphenyl)methanol

The title compound is prepared in >99% yield (0.89 g, a white solid) from methyl 4-(2,2-difluoroethoxy)-3-methoxybenzoate (1.00 g, 4.06 mmol, Step-1 of Amine-102) by the similar manner in Step-3 of Amine-4.

¹H-NMR (300 MHz, CDCl₃) delta 6.97-6.86 (3H, m), 6.12 (1H, tt, J=55.0, 4.4 Hz), 4.64 (2H, d, J=5.9 Hz), 4.22 (2H, td, J=13.2, 4.4 Hz), 3.89 (3H, s), 1.67 (1H, t, J=5.9 Hz).

<Step-2>:4-(chloromethyl)-1-(2,2-difluoroethoxy)-2-methoxybenzene

The title compound is prepared in >99% yield (0.96 g, a white solid) from (4-(2,2-difluoroethoxy)-3-methoxyphenyl) methanol (0.89 g, 4.06 mmol, Step-1) by the similar manner in Step-4 of Amine-4.

<Step-3>:4-(azidomethyl)-1-(2,2-difluoroethoxy)-2-methoxybenzene

The title compound is prepared in 94% yield (0.93 g, colorless oil) from 4-(chloromethyl)-1-(2,2-difluoroethoxy)-2-methoxybenzene (0.96 g, 4.06 mmol, Step-2) by the similar manner in Step-5 of Amine-4.

¹H-NMR (300 MHz, CDCl₃) delta 6.89-6.83 (3H, m), 6.13 (1H, tt, J=55.0 Hz, 4.4 Hz), 4.29-4.18 (4H, m), 3.89 (3H, s).

<Step-4>:(4-(2,2-difluoroethoxy)-3-methoxyphenyl) methanamine hydrochloride

The title compound is prepared in 80% yield (0.77 g, a white solid) from 4-(azidomethyl)-1-(2,2-difluoroethoxy)-2-methoxybenzene (0.93 g, 3.81 mmol, Step-3) by the similar manner in Step-3 of Amine-54.

¹H-NMR (300 MHz, DMSO-d₆) delta 8.36 (2H, br s), 7.25 (1H, s), 7.07-6.97 (2H, m), 6.38 (1H, tt, J=54.3, 3.7 Hz), 4.28 (2H, td, J=13.9, 3.7 Hz), 4.00-3.90 (2H, m), 3.80 (3H, s).

Amine-107: (R)-1-(3-(2,2-difluoroethoxy)-5-methylphenyl)ethanamine hydrochloride (single enantiomer)

<Step-1>:3-(2,2-difluoroethoxy)-5-methylbenzoic acid

The title compound is prepared in >96% yield (975 mg, a white solid) from methyl 3-(2,2-difluoroethoxy)-5-methylbenzoate (0.85 g, 3.9 mmol, Step-1 of Amine-108) by the similar manner in Step-2 of Carboxylic acid-1.

¹H-NMR (300 MHz, CDCl₃) delta 7.60 (1H, s), 7.42 (1H, s), 7.02 (1H, s), 6.11 (1H, tt, J=54.9, 4.4 Hz), 4.23 (2H, td, J=12.5, 3.7 Hz), 2.40 (3H, s), MS (ESI) m/z: 215 (M+H)⁺.

<Step-2>:3-(2,2-difluoroethoxy)-N-methoxy-N,5-dimethylbenzamide

The title compound is prepared in >99% yield (1.07 g, colorless oil) from 3-(2,2-difluoroethoxy)-5-methylbenzoic acid (0.85 g, 3.9 mmol, Step-1) by the similar manner in Step-2 of Amine-5.

¹H-NMR (300 MHz, CDCl₃) delta 7.13 (1H, s), 7.00 (1H, s), 6.84 (1H, s), 6.08 (1H, tt, J=54.9, 4.4 Hz), 4.19 (2H, td, J=13.2, 4.4 Hz), 3.57 (3H, s), 3.34 (3H, s), 2.36 (3H, s), MS (ESI) m/z: 260 (M+H)⁺.

<Step-3>:1-(3-(2,2-difluoroethoxy)-5-methylphenyl) ethanone

The title compound is prepared in 97% yield (0.85 g, colorless oil) from 3-(2,2-difluoroethoxy)-N-methoxy-N,5-dimethylbenzamide (1.06 g, 4.1 mmol, Step-2) by the similar manner in Step-3 of Amine-1.

¹H-NMR (300 MHz, CDCl₃) delta 7.42 (1H, s), 7.30 (1H, s), 6.97 (1H, s), 6.10 (1H, tt, J=54.9, 4.4 Hz), 4.22 (2H, td, J=13.2, 4.4 Hz), 2.59 (3H, s), 2.40 (3H, s), MS (ESI) m/z: 215 (M+H)⁺.

<Step-4>:(R)—N-(1-(3-(2,2-difluoroethoxy)-5-methylphenyl)ethyl)-2-methylpropane-2-sulfinamide (single diastereomer)

The title compound is prepared in 77% yield (0.97 g, colorless oil) from 1-(3-(2,2-difluoroethoxy)-5-methylphenyl) ethanone (0.85 g, 3.9 mmol, Step-3) and (R)-2-methylpropane-2-sulfinamide by the similar manner in Step-4 of Amine-1.

¹H-NMR (300 MHz, CDCl₃) delta 6.81 (1H, s), 6.73 (1H, s), 6.66 (1H, s), 6.08 (1H, tt, J=59.3, 3.7 Hz), 4.50-4.43 (1H, m), 4.17 (2H, td, J=13.2, 4.4 Hz), 3.38 (1H, br s), 2.33 (3H, s), 1.49 (3H, d, J=6.6 Hz), 1.24 (9H, s), MS (ESI) m/z: 320 (M+H)⁺, 318 (M−H)⁻.

<Step-5>:1-(3-(2,2-difluoroethoxy)-5-methylphenyl) ethanamine hydrochloride (single enantiomer)

The title compound is prepared in 88% yield (0.67 g, a white solid) from (R)—N-(1-(3-(2,2-difluoroethoxy)-5-methylphenyl)ethyl)-2-methylpropane-2-sulfinamide (0.97 g, 3.0 mmol, Step-4, single diastereomer) by the similar manner in Step-5 of Amine-1.

¹H-NMR (300 MHz, DMSO-d₆) delta 8.37 (2H, br s), 7.00 (1H, s), 6.93 (1H, s), 6.86 (1H, s), 6.40 (1H, tt, J=54.2, 3.7 Hz), 4.36-4.25 (3H, m), 2.30 (3H, s), 1.47 (3H, d, J=6.6 Hz), MS (ESI) m/z: 214 (M−H)⁻.

Amine-108: (3-(2,2-difluoroethoxy)-5-methylphenyl)methanamine

<Step-1>:methyl 3-(2,2-difluoroethoxy)-5-methylbenzoate

The title compound is prepared in 75% yield (1.9 g, pale yellow oil) from methyl 3-hydroxy-5-methylbenzoate (1.8 g, 10.8 mmol) by the similar manner in Step-1 of Amine-68.

¹H-NMR (300 MHz, CDCl₃) delta 7.53 (1H, s), 7.36 (1H, s), 6.96 (1H, s), 6.09 (1H, tt, J=54.9, 3.7 Hz), 4.21 (2H, td, J=12.5, 3.7 Hz), 3.91 (3H, s), 2.38 (3H, s).

<Step-2>: (3-(2,2-difluoroethoxy)-5-methylphenyl)methanol

The title compound is prepared in 98% yield (0.69 g, colorless oil) from methyl 3-(2,2-difluoroethoxy)-5-methylbenzoate (0.80 g, 3.5 mmol, Step-1) by the similar manner in Step-3 of Amine-4.

¹H-NMR (300 MHz, CDCl₃) delta 6.83 (1H, s), 6.75 (1H, s), 6.68 (1H, s), 6.08 (1H, tt, J=54.9, 4.4 Hz), 4.65 (2H, br s), 4.18 (2H, td, J=13.2, 3.7 Hz), 2.34 (3H, s), 1.71 (1H, br s).

<Step-3>:2-(3-(2,2-difluoroethoxy)-5-methylbenzyl) isoindoline-1,3-dione

The title compound is prepared in 92% yield (1.03 g, a white solid) from (3-(2,2-difluoroethoxy)-5-methylphenyl) methanol (0.68 g, 3.4 mmol, Step-2) by the similar manner in Step-3 of Amine-24.

¹H-NMR (300 MHz, CDCl₃) delta 7.87-7.84 (2H, m), 7.73-7.70 (2H, m), 6.89 (1H, s), 6.79 (1H, s), 6.64 (1H, s), 6.05 (1H, tt, J=55.7, 4.4 Hz), 4.77 (2H, s), 4.14 (2H, td, J=12.5, 3.7 Hz), 2.30 (3H, s), MS (ESI) m/z: 332 (M+H)+.

<Step-4>: (3-(2,2-difluoroethoxy)-5-methylphenyl)methanamine

The title compound is prepared in 93% yield (0.58 g, colorless oil) from 2-(3-(2,2-difluoroethoxy)-5-methylbenzyl)isoindoline-1,3-dione (1.03 g, 3.1 mmol, Step-3) by the similar manner in Step-4 of Amine-24.
$^1$H-NMR (300 MHz, CDCl$_3$) delta 6.79 (1H, s), 6.70 (1H, s), 6.63 (1H, s), 6.08 (1H, tt, J=54.9, 3.7 Hz), 4.18 (2H, td, J=13.2, 4.4 Hz), 3.81 (2H, s), 2.33 (3H, s), 1.58 (2H, br s), MS (ESI) m/z: 202 (M+H)+.

Amine-109: 1-(3-chloro-4-(2,2-difluoroethoxy)-5-methylphenyl)ethanamine hydrochloride (single enantiomer)

<Step-1>:1-(3-chloro-4-(2,2-difluoroethoxy)-5-methylphenyl)ethanone

The title compound is prepared in 96% yield (0.65 g, a white solid) from 1-(3-chloro-4-hydroxy-5-methylphenyl)ethanone (0.50 g, 2.71 mmol) by the similar manner in Step-1 of Amine-68.
$^1$H-NMR (300 MHz, CDCl$_3$) delta 7.83 (1H, d, J=2.0 Hz), 7.71 (1H, d, J=2.0 Hz), 6.13 (1H, tt, J=54.6, 4.0 Hz), 4.23 (2H, td, J=13.4, 4.0 Hz), 2.57 (3H, s), 2.38 (3H, s), MS (ESI) m/z: 249 (M+H)+.

<Step-2>:(R)—N-(1-(3-chloro-4-(2,2-difluoroethoxy)-5-methylphenyl)ethyl)-2-methyl propane-2-sulfinamide (single diastereomer)

The title compound is prepared in 93% yield (0.85 g, yellow oil) from 1-(3-chloro-4-(2,2-difluoroethoxy)-5-methylphenyl)ethanone (0.65 g, 2.61 mmol, Step-1) and (R)-2-methylpropane-2-sulfinamide by the similar manner in Step-4 of Amine-1.
$^1$H-NMR (300 MHz, CDCl$_3$) delta 7.20 (1H, d, J=2.2 Hz), 7.07 (1H, d, J=2.2 Hz), 6.12 (1H, tt, J=54.9, 4.0 Hz), 4.51-4.38 (1H, m), 4.15 (2H, m), 3.35 (1H, br s), 2.32 (3H, s), 1.47 (3H, d, J=6.6 Hz), 1.24 (9H, s), MS (ESI) m/z: 354 (M+H)+.

<Step-3>:1-(3-chloro-4-(2,2-difluoroethoxy)-5-methylphenyl)ethanamine hydrochloride (single enantiomer)

The title compound is prepared in 69% yield (0.48 g, a white solid) from (R)—N-(1-(3-chloro-4-(2,2-difluoroethoxy)-5-methylphenyl)ethyl)-2-methylpropane-2-sulfinamide (0.85 g, 2.41 mmol, Step-2, single diastereomer) by the similar manner in Step-5 of Amine-1.
$^1$H-NMR (300 MHz, DMSO-d$_6$) delta 8.42 (2H, br s), 7.50 (1H, d, J=1.8 Hz), 7.34 (1H, d, J=1.8 Hz), 6.36 (1H, tt, J=54.0, 3.3 Hz), 4.41-4.27 (1H, m), 4.20 (2H, td, J=15.0, 3.3 Hz), 2.28 (3H, s), 1.46 (3H, d, J=7.0 Hz), MS (ESI) m/z: positive ion of a fragment signal, 233, is observed.

Amine-110:1-(4-(2,2-difluoroethoxy)-3,5-dimethylphenyl)ethanamine hydrochloride (single enantiomer)

<Step-1>:1-(4-(2,2-difluoroethoxy)-3,5-dimethylphenyl)ethanone

The title compound is prepared in 98% yield (0.68 g, a white solid) from 1-(4-hydroxy-3,5-dimethylphenyl)ethanone (0.50 g, 3.05 mmol) by the similar manner in Step-1 of Amine-68.
$^1$H-NMR (300 MHz, CDCl$_3$) delta 7.65 (2H, s), 6.10 (1H, tt, J=54.5, 4.0 Hz), 4.05 (2H, td, J=13.5, 4.0 Hz), 2.55 (3H, s), 2.50 (6H, s), MS (ESI) m/z: 229 (M+H)+.

<Step-2>:(R)—N-(1-(4-(2,2-difluoroethoxy)-3,5-dimethylphenyl)ethyl)-2-methylpropane-2-sulfinamide (single diastereomer)

The title compound is prepared in 89% yield (0.89 g, yellow oil) from 1-(4-(2,2-difluoroethoxy)-3,5-dimethylphenyl)ethanone (0.68 g, 2.98 mmol, Step-1) and (R)-2-methylpropane-2-sulfinamide by the similar manner in Step-4 of Amine-1.
$^1$H-NMR (300 MHz, CDCl$_3$) delta 6.99 (2H, s), 6.08 (1H, tt, J=55.0, 4.0 Hz), 4.48-4.38 (1H, m), 3.99 (2H, td, J=13.6, 4.0 Hz), 3.33 (1H, br s), 2.28 (6H, s), 1.46 (3H, d, J=6.6 Hz), 1.25 (9H, s), MS (ESI) m/z: 334 (M+H)+.

<Step-3>:1-(4-(2,2-difluoroethoxy)-3,5-dimethylphenyl)ethanamine hydrochloride (single enantiomer)

The title compound is prepared in 83% yield (0.59 g, a white solid) from (R)—N-(1-(4-(2,2-difluoroethoxy)-3,5-dimethylphenyl)ethyl)-2-methylpropane-2-sulfinamide (0.89 g, 2.66 mmol, Step-2, single diastereomer) by the similar manner in Step-5 of Amine-1.
$^1$H-NMR (300 MHz, DMSO-d$_6$) delta 8.28 (2H, br s), 7.15 (2H, s), 6.34 (1H, tt, J=54.2 3.3 Hz), 4.36-4.18 (1H, m), 4.05 (2H, td, J=15.2, 3.3 Hz), 2.23 (6H, s), 1.44 (3H, d, J=7.0 Hz).
MS (ESI) m/z: positive ion of a fragment signal, 213, is observed.

Amine-111: (4-(2,2-difluoroethoxy)-3,5-dimethylphenyl)methanamine hydrochloride

<Step-1>:methyl 4-(2,2-difluoroethoxy)-3,5-dimethylbenzoate

The title compound is prepared in 92% yield (0.67 g, colorless oil) from methyl 4-hydroxy-3,5-dimethylbenzoate (0.54 g, 2.98 mmol) by the similar manner in Step-1 of Amine-68.
$^1$H-NMR (300 MHz, CDCl$_3$) delta 7.73 (2H, s), 6.10 (1H, tt, J=54.7, 4.0 Hz), 4.04 (2H, td, J=13.5, 4.0 Hz), 3.89 (3H, s), 2.31 (6H, s), MS (ESI) m/z: 245 (M+H)+.

<Step-2>: (4-(2,2-difluoroethoxy)-3,5-dimethylphenyl)methanol

The title compound is prepared in 99% yield (0.59 g, colorless oil) from methyl 4-(2,2-difluoroethoxy)-3,5-dimethylbenzoate (0.67 g, 2.73 mmol, Step-1) by the similar manner in Step-3 of Amine-4.
$^1$H-NMR (300 MHz, CDCl$_3$) delta 7.03 (2H, s), 6.09 (1H, tt, J=54.9, 4.0 Hz), 4.59 (2H, d, J=5.1 Hz), 4.00 (2H, td, J=13.5, 4.0 Hz), 2.29 (6H, s).

<Step-3>:5-(chloromethyl)-2-(2,2-difluoroethoxy)-1,3-dimethylbenzene

The title compound is prepared in 98% yield (0.62 g, a white solid) from (4-(2,2-difluoroethoxy)-3,5-dimethylphenyl)methanol (0.59 g, 2.71 mmol, Step-2) by the similar manner in Step-4 of Amine-4.

<Step-4>:5-(azidomethyl)-2-(2,2-difluoroethoxy)-1,3-dimethylbenzene

The title compound is prepared in 93% yield (0.60 g, yellow oil) from 5-(chloromethyl)-2-(2,2-difluoroethoxy)-1,3-dimethylbenzene (0.62 g, 2.65 mmol, Step-3) by the similar manner in Step-5 of Amine-4.
$^1$H-NMR (300 MHz, CDCl$_3$) delta 6.98 (2H, s), 6.09 (1H, tt, J=55.1, 4.0 Hz), 4.23 (2H, s), 4.00 (2H, td, J=13.7, 4.0 Hz), 2.30 (6H, s).

<Step-5>:(4-(2,2-difluoroethoxy)-3,5-dimethylphenyl)methanamine hydrochloride

The title compound is prepared in 91% yield (0.56 g, a white solid) from 5-(azidomethyl)-2-(2,2-difluoroethoxy)-1,3-dimethylbenzene (0.60 g, 2.47 mmol, Step-4) by the similar manner in Step-3 of Amine-54.
$^1$H-NMR (300 MHz, DMSO-d$_6$) delta 8.27 (2H, br s), 7.14 (2H, s), 6.34 (1H, tt, J=54.2 3.3 Hz), 4.05 (2H, td, J=15.2, 3.3 Hz), 3.87 (2H, s), 2.22 (6H, s), MS (ESI) m/z: positive ion of a fragment signal, 199, is observed.

Amine-112:
1-(4-(1,1,2,2-tetrafluoroethoxy)phenyl)ethanamine hydrochloride (single enantiomer <Step-1>:N-methoxy-N-methyl-4-(1,1,2,2-tetrafluoroethoxy)benzamide The title compound is prepared in >99% yield (1.18 g, colorless oil) from 4-(1,1,2,2-tetrafluoroethoxy)benzoic acid (1.00 g, 4.20 mmol) by the similar manner in Step-2 of Amine-5.
$^1$H-NMR (300 MHz, CDCl$_3$) delta 7.77-7.73 (2H, m), 7.26-7.24 (2H, m), 5.92 (1H, tt, J=52.8, 2.9 Hz), 3.55 (3H, s), 3.37 (3H, s), MS (ESI) m/z: 282 (M+H)$^+$.

<Step-2>:1-(4-(1,1,2,2-tetrafluoroethoxy)phenyl)ethanone

The title compound is prepared in 83% yield (0.82 g, yellow oil) from N-methoxy-N-methyl-4-(1,1,2,2-tetrafluoroethoxy)benzamide (1.18 g, 4.20 mmol, Step-1) by the similar manner in Step-3 of Amine-1.
$^1$H-NMR (300 MHz, CDCl$_3$) delta 8.03-7.99 (2H, m), 7.32-7.29 (2H, m), 5.94 (1H, tt, J=52.8, 2.9 Hz), 2.61 (3H, s), MS (ESI) m/z: 237 (M+H)$^+$.

<Step-3>:(R)-2-methyl-N-(1-(4-(1,1,2,2-tetrafluoroethoxy)phenyl)ethyl)propane-2-sulfinamide (single diastereomer)

The title compound is prepared in 80% yield (0.95 g, a white solid) from 1-(4-(1,1,2,2-tetrafluoroethoxy)phenyl)ethanone (0.82 g, 3.46 mmol, Step-2) and (R)-2-methylpropane-2-sulfinamide by the similar manner in Step-4 of Amine-1.
$^1$H-NMR (300 MHz, CDCl$_3$) delta 7.39-7.35 (2H, m), 7.21-7.17 (2H, m), 5.91 (1H, tt, J=52.8, 2.9 Hz), 4.60-4.52 (1H, m), 3.39 (1H, br s), 1.51 (3H, d, J=6.6 Hz), 1.24 (9H, s), MS (ESI) m/z: 342 (M+H)$^+$.

<Step-4>:1-(4-(1,1,2,2-tetrafluoroethoxy)phenyl)ethanamine hydrochloride (single enantiomer The title compound is prepared in 83% yield (0.63 g, a white solid) from (R)-2-methyl-N-(1-(4-(1,1,2,2-tetrafluoroethoxy)phenyl)ethyl)propane-2-sulfinamide (0.95 g, 2.77 mmol, Step-3, single diastereomer) by the similar manner in Step-5 of Amine-1.
$^1$H-NMR (300 MHz, DMSO-d$_6$) delta 8.55 (2H, br s), 7.64 (2H, d, J=8.8 Hz), 7.36 (2H, d, J=8.8 Hz), 6.83 (1H, tt, J=52.1, 2.9 Hz), 4.49-4.41 (1H, m), 1.52 (3H, d, J=6.6 Hz), MS (ESI) m/z: positive ion of a fragment signal, 221, is observed.

Amine-113:
1-(3-(1,1,2,2-tetrafluoroethoxy)phenyl)ethanamine hydrochloride (single enantiomer)

<Step-1>: N-methoxy-N-methyl-3-(1,1,2,2-tetrafluoroethoxy)benzamide

The title compound is prepared in >99% yield (0.95 g, colorless oil) from 3-(1,1,2,2-tetrafluoroethoxy)benzoic acid (0.80 g, 3.36 mmol) by the similar manner in Step-2 of Amine-5.
$^1$H-NMR (300 MHz, CDCl$_3$) delta 7.64-7.57 (2H, m), 7.44 (1H, t, J=8.1 Hz), 7.35-7.28 (1H, m), 5.92 (1H, tt, J=52.8, 2.9 Hz), 3.56 (3H, s), 3.37 (3H, s), MS (ESI) m/z: 282 (M+H)$^+$.

<Step-2>:
1-(3-(1,1,2,2-tetrafluoroethoxy)phenyl)ethanone

The title compound is prepared in >99% yield (0.79 g, colorless oil) from N-methoxy-N-methyl-3-(1,1,2,2-tetrafluoroethoxy)benzamide (0.95 g, 3.36 mmol, Step-1) by the similar manner in Step-3 of Amine-1.
$^1$H-NMR (300 MHz, CDCl$_3$) delta 7.88 (1H, d, J=8.1 Hz), 7.79 (1H, s), 7.54-7.40 (2H, m), 5.94 (1H, tt, J=52.8, 2.9 Hz), 2.62 (3H, s), MS (ESI) m/z: 237 (M+H)$^+$.

<Step-3>:(R)-2-methyl-N-(1-(3-(1,1,2,2-tetrafluoroethoxy)phenyl)ethyl)propane-2-sulfinamide (single diastereomer)

The title compound is prepared in 81% yield (0.92 g, colorless oil) from 1-(3-(1,1,2,2-tetrafluoroethoxy)phenyl)ethanone (0.79 g, 3.36 mmol, Step-2) and (R)-2-methylpropane-2-sulfinamide by the similar manner in Step-4 of Amine-1.
$^1$H-NMR (300 MHz, CDCl$_3$) delta 7.39-7.14 (4H, m), 5.91 (1H, tt, J=52.8, 2.9 Hz), 4.60-4.51 (1H, m), 3.43 (1H, br s), 1.52 (3H, d, J=6.6 Hz), 1.24 (9H, s), MS (ESI) m/z: 342 (M+H)$^+$.

<Step-4>:1-(3-(1,1,2,2-tetrafluoroethoxy)phenyl)ethanamine hydrochloride (single enantiomer)

The title compound is prepared in 91% yield (0.67 g, a white solid) from (R)-2-methyl-N-(1-(3-(1,1,2,2-tetrafluoroethoxy)phenyl)ethyl)propane-2-sulfinamide (0.92 g, 2.71 mmol, Step-3, single diastereomer) by the similar manner in Step-5 of Amine-1.
$^1$H-NMR (300 MHz, DMSO-d$_6$) delta 8.62 (2H, br s), 7.56-7.47 (3H, m), 7.30 (1H, br s), 6.85 (1H, tt, J=52.1, 2.9 Hz), 4.53-4.42 (1H, m), 1.52 (3H, d, J=6.6 Hz), MS (ESI) m/z: positive ion of a fragment signal, 221, is observed.

Amine-114: 1-(3-(difluoromethyl)phenyl)ethanamine hydrochloride (single enantiomer)

<Step-1>:1-(3-(difluoromethyl)phenyl)ethanone

A mixture of 1-bromo-3-(difluoromethyl)benzene (0.72 g, 3.48 mmol), tributyl(1-ethoxyvinyl)tin (1.38 g, 3.83 mmol), dichlorobis(triphenylphosphine)-palladium(II) (0.24 g, 0.35 mmol) in toluene (12 mL) is heated at 100° C. under nitrogen atmosphere for 16 hours. After cooling to room temperature, 2M hydrochloric acid (12 mL) is added to the mixture. Then the resulting mixture is stirred at room temperature for 1 hour. The mixture is diluted with ethyl acetate (100 mL) and washed with water (100 mL). The organic layer is dried over sodium sulfate, and concentrated under reduced pressure. The residue is purified by column chromatography on silica-gel eluting with n-hexane/ethyl acetate (30:1) to give 0.58 g (98% yield) of the title compound as colorless oil.

$^1$H-NMR (300 MHz, CDCl$_3$) delta 8.10-8.06 (2H, m), 7.73 (1H, d, J=7.3 Hz), 7.58 (1H, t, J=7.3 Hz), 6.71 (1H, t, J=56.5 Hz), 2.65 (3H, s), MS (ESI) m/z: 171 (M+H)$^+$.

<Step-2>:(R)—N-(1-(3-(difluoromethyl)phenyl)ethyl)-2-methylpropane-2-sulfinamide (single diastereomer)

The title compound is prepared in 56% yield (0.53 g, colorless oil) from 1-(3-(difluoromethyl)phenyl)ethanone (0.58 g, 3.41 mmol, Step-1) and (R)-2-methylpropane-2-sulfinamide by the similar manner in Step-4 of Amine-1.

$^1$H-NMR (300 MHz, CDCl$_3$) delta 7.49-7.43 (4H, m), 6.65 (1H, t, J=56.5 Hz), 4.64-4.56 (1H, m), 3.41 (1H, br s), 1.53 (3H, d, J=6.6 Hz), 1.24 (9H, s), MS (ESI) m/z: 276 (M+H)$^+$.

<Step-3>:1-(3-(difluoromethyl)phenyl)ethanamine hydrochloride (single enantiomer)

The title compound is prepared in 88% yield (0.35 g, a white solid) from (R)—N-(1-(3-(difluoromethyl)phenyl)ethyl)-2-methylpropane-2-sulfinamide (0.53 g, 1.91 mmol, Step-2, single diastereomer) by the similar manner in Step-5 of Amine-1.

$^1$H-NMR (300 MHz, DMSO-d$_6$) delta 8.52 (2H, br s), 7.75-7.51 (4H, m), 7.04 (1H, t, J=55.4 Hz), 4.61-4.41 (1H, m), 1.50 (3H, d, J=7.0 Hz), MS (ESI) m/z: 172 (M+H)$^+$.

Amine-115:
1-(4-(perfluoroethoxy)phenyl)ethanamine hydrochloride (single enantiomer)

<Step-1>:
N-methoxy-N-methyl-4-(perfluoroethoxy)benzamide

The title compound is prepared in 51% yield (894 mg, a colorless oil) from 4-(perfluoroethoxy)benzoic acid (1.50 g, 5.86 mmol) by the similar manner in Step-2 of Amine-5.
MS (ESI) m/z: 300 (M+H)$^+$.

<Step-2>: 1-(4-(perfluoroethoxy)phenyl)ethanone

The title compound is prepared in 97% yield (737 mg, a colorless oil) from N-methoxy-N-methyl-4-(perfluoroethoxy)benzamide (894 mg, 2.99 mmol, Step-1) by the similar manner in Step-3 of Amine-1.
MS (ESI) m/z: 255 (M+H)$^+$.

<Step-3>:(R)-2-methyl-N-(1-(4-(perfluoroethoxy)phenyl)ethyl)propane-2-sulfinamide (single diastereomer)

The title compound is prepared in 78% yield (812 mg, a yellow oil) from 1-(4-(perfluoroethoxy)phenyl)ethanone (737 mg, 2.90 mmol, Step-2) and (R)-2-methylpropane-2-sulfinamide by the similar manner in Step-4 of Amine-1.
MS (ESI) m/z: 360 (M+H)$^+$.

<Step-4>:1-(4-(perfluoroethoxy)phenyl)ethanamine hydrochloride (single enantiomer)

The title compound is prepared in 84% yield (554 mg, a white solid) from (R)-2-methyl-N-(1-(4-(perfluoroethoxy)phenyl)ethyl)propane-2-sulfinamide (812 mg, 2.26 mmol, Step-3, single diastereomer) by the similar manner in Step-5 of Amine-1.
MS (ESI) m/z: 256 (M+H)$^+$.

<Carboxylic Acid Part>

Carboxylic acid-1: 2-propionamidoisonicotinic acid

<Step-1>: Methyl 2-propionamidoisonicotinate

To a stirred solution of methyl 2-aminoisonicotinate (1.00 g, 6.57 mmol) in pyridine (22 mL) is added propionyl chloride (0.69 mL, 7.89 mmol) at 0° C. After stirring at 0° C. for 2 hours, the reaction mixture is poured into 2M hydrochloric acid (100 mL) and extracted with ethyl acetate (100 mL). The organic layer is dried over sodium sulfate, and concentrated under reduced pressure to give 1.07 g (78% yield) of the title compound as a yellow solid. This material is used for the next reaction (Step-2) without further purification.

$^1$H-NMR (300 MHz, DMSO-d$_6$) delta 10.71 (1H, s), 8.60 (1H, s), 8.47 (1H, d, J=5.1 Hz), 7.50 (1H, dd, J=5.1, 1.1 Hz), 3.88 (3H, s), 2.40 (2H, q, J=7.7 Hz), 1.06 (3H, t, J=7.7 Hz), MS (ESI) m/z: 209 (M+H)$^+$.

<Step-2>: 2-propionamidoisonicotinic acid

A mixture of methyl 2-propionamidoisonicotinate (1.07 g, 5.15 mmol), 2M aqueous sodium hydroxide solution (5 mL) and methanol (25 mL) is stirred at 50° C. for 2 hours. After removal of the methanol by evaporation, the solution is acidified by 2M hydrochloric acid and extracted with ethyl acetate. The organic layer is dried over sodium sulfate and concentrated in vacuo. The residue is crystallized from tetrahydrofuran and n-hexane to give 0.76 g (76% yield) of the title compound as a white solid.

$^1$H-NMR (300 MHz, DMSO-d$_6$) delta 10.65 (1H, s), 8.57 (1H, s), 8.44 (1H, d, J=5.1 Hz), 7.48 (1H, d, J=5.1 Hz), 2.40 (2H, q, J=7.3 Hz), 1.06 (3H, t, J=7.3 Hz), MS (ESI) m/z: 195 (M+H)$^+$.

Carboxylic acid-2:
2-(cyclopropanecarboxamido)isonicotinic acid

<Step-1>: methyl 2-(cyclopropanecarboxamido)isonicotinate

The title compound is prepared in 92% yield (1.60 g, a yellow solid) from methyl 2-aminoisonicotinate (1.20 g, 7.89 mmol) and cyclopropanecarbonyl chloride by the similar manner in Step-1 of Carboxylic acid-1.

$^1$H-NMR (300 MHz, DMSO-d$_6$) delta 8.73 (1H, s), 8.39 (1H, d, J=4.4 Hz), 8.28 (1H, br s), 7.59 (1H, dd, J=5.1, 1.4 Hz), 3.93 (3H, s), 1.59-1.50 (1H, m), 1.17-1.12 (2H, m), 0.96-0.89 (2H, m), MS (ESI) m/z: 221 (M+H)$^+$, 219 (M−H)$^−$.

<Step-2>: 2-(cyclopropanecarboxamido)isonicotinic acid

The title compound is prepared in 94% yield (1.41 g, a white solid) from methyl 2-(cyclopropanecarboxamido)

isonicotinate (1.60 g, 7.27 mmol, Step-1) by the similar manner in Step-2 of Carboxylic acid-1.

$^1$H-NMR (300 MHz, DMSO-d$_6$) delta 11.02 (1H, s), 8.57 (1H, s), 8.47 (1H, d, J=5.1 Hz), 7.49 (1H, dd, J=5.1, 1.5 Hz), 2.07-1.98 (1H, m), 0.85-0.79 (4H, m), MS (ESI) m/z: 207 (M+H)$^+$, 205 (M−H)$^−$.

Carboxylic acid-3: 2-isobutyramidoisonicotinic acid

<Step-1>: methyl 2-isobutyramidoisonicotinate

The title compound is prepared in 93% yield (2.20 g, a yellow solid) from methyl 2-aminoisonicotinate hydrochloride (2.00 g, 10.6 mmol) and isobutyryl chloride by the similar manner in Step-1 of Carboxylic acid-1.

$^1$H-NMR (270 MHz, CDCl$_3$) delta 8.78 (1H, s), 8.39 (1H, d, J=5.3 Hz), 7.99 (1H, br s), 7.60 (1H, dd, J=5.3, 1.3 Hz), 3.94 (3H, s), 2.58 (1H, septet, J=7.3 Hz), 1.28 (6H, d, J=7.3 Hz), MS (ESI) m/z: 223 (M+H)$^+$.

<Step-2>: 2-isobutyramidoisonicotinic acid

The title compound is prepared in 87% yield (1.79 g, a white solid) from methyl 2-isobutyramidoisonicotinate (2.20 g, 7.27 mmol, Step-1) by the similar manner in Step-2 of Carboxylic acid-1.

$^1$H-NMR (270 MHz, DMSO-d$_6$) delta 10.65 (1H, s), 8.60 (1H, s), 8.47 (1H, d, J=5.3 Hz), 7.50 (1H, dd, J=5.3, 1.3 Hz), 2.77 (1H, septet, J=6.6 Hz), 1.10 (6H, d, J=6.6 Hz), MS (ESI) m/z: 207 (M−H)$^−$.

Carboxylic acid-4: 2-acetamido-6-methylisonicotinic acid

<Step-1>: methyl 2-acetamido-6-methylisonicotinate

A mixture of methyl 2-chloro-6-methylisonicotinate (2.00 g, 10.8 mmol), acetamide (1.27 g, 21.6 mmol), tris(dibenzylideneacetone)dipalladium(0) (0.20 g, 0.22 mmol), 4,5-bis(diphenylphosphino)-9,9-dimethylxanthene (0.37 g, 0.65 mmol), tripotassium phosphate (2.74 g, 12.9 mmol) and 1,4-dioxane (26 mL) is heated by microwave irradiation at 150° C. for 1 hr. After cooling to room temperature, the mixture is filtered through a pad of celite. The filtrate is concentrated under reduced pressure and the residue is purified by column chromatography on silica gel eluting with n-hexane/ethyl acetate (4:11:3) to give 1.99 g (89% yield) of the title compound as a yellow solid.

$^1$H-NMR (270 MHz, CDCl$_3$) delta 8.50 (1H, br s), 8.17 (1H, br s), 7.47 (1H, br s), 3.94 (3H, s), 2.50 (3H, s), 2.22 (3H, s), MS (ESI) m/z: 209 (M+H)$^+$.

<Step-2>: 2-acetamido-6-methylisonicotinic acid

A mixture of methyl 2-acetamido-6-methylisonicotinate (1.99 g, 9.56 mmol, Step-1), 0.5M aqueous sodium hydroxide solution (20 mL, 10.0 mmol) and tetrahydrofuran (64 mL) is stirred at room temperature for 2.5 hours. The mixture is acidified by 2M hydrochloric acid and the organic solvent is removed by evaporation. The precipitate is collected by filtration and washed with diisopropyl ether to give 0.81 g (44% yield) of the title compound as a slight yellow solid.

$^1$H-NMR (270 MHz, DMSO-d$_6$) delta 10.60 (1H, s), 8.34 (1H, s), 7.36 (1H, s), 2.45 (3H, s), 2.08 (3H, s), MS (ESI) m/z: 195 (M+H)$^+$.

Carboxylic acid-5: 2-isobutyramido-6-methylisonicotinic acid

<Step-1>: methyl 2-isobutyramido-6-methylisonicotinate

The title compound is prepared in quantitative yield (1.27 g, yellow syrup) from methyl 2-chloro-6-methylisonicotinate (1.00 g, 5.39 mmol) and isobutyramide by the similar manner in Step-1 of Carboxylic acid-4.

$^1$H-NMR (300 MHz, CDCl$_3$) delta 8.57 (1H, s), 7.89 (1H, br s), 7.47 (1H, s), 3.93 (3H, s), 2.54 (1H, septet, J=6.6 Hz), 2.51 (3H, s), 1.27 (6H, d, J=6.6 Hz), MS (ESI) m/z: 237 (M+H)$^+$.

<Step-2>: 2-isobutyramido-6-methylisonicotinic acid

The title compound is prepared in 88% yield (1.05 g, a pale pink solid) from methyl 2-isobutyramido-6-methylisonicotinate (1.00 g, 5.39 mmol, Step-1) by the similar manner in Step-2 of Carboxylic acid-1.

$^1$H-NMR (300 MHz, DMSO-d$_6$) delta 10.58 (1H, s), 8.39 (1H, s), 7.37 (1H, s), 2.74 (1H, septet, J=6.6 Hz), 2.46 (3H, s), 1.06 (6H, d, J=6.6 Hz), MS (ESI) m/z: 223 (M+H)$^+$.

Carboxylic acid-6: 2-(cyclopropanecarboxamido)-6-methylpyrimidine-4-carboxylic acid <Step-1>: methyl 2-(cyclopropanecarboxamido)-6-methylpyrimidine-4-carboxylate The title compound is prepared in 71% yield (2.70 g, brown oil) from methyl 2-chloro-6-methylpyrimidine-4-carboxylate (3.00 g, 16.1 mmol) and cyclopropanecarboxamide by the similar manner in Step-1 of Carboxylic acid-4.

MS (ESI) m/z: 236 (M+H)$^+$, 234 (M−H)$^−$.

<Step-2>: 2-(cyclopropanecarboxamido)-6-methylpyrimidine-4-carboxylic acid

The title compound is prepared in 73% yield (1.85 g, a pale yellow solid) from methyl 2-(cyclopropanecarboxamido)-6-methylpyrimidine-4-carboxylate (2.70 g, 11.5 mmol, Step-1) by the similar manner in Step-2 of Carboxylic acid-4.

$^1$H-NMR (300 MHz, DMSO-d$_6$) delta 11.16 (1H, s), 2.48 (3H, s), 2.18-2.09 (1H, m), 0.86-0.82 (4H, m), MS (ESI) m/z: 222 (M+H)$^+$.

Carboxylic acid-7: 2-(cyclopropanecarboxamido)pyrimidine-4-carboxylic acid

<Step-1>: methyl 2-(cyclopropanecarboxamido) pyrimidine-4-carboxylate

The title compound is prepared in quantitative yield (1.93 g, a pale yellow solid) from methyl 2-chloropyrimidine-4-carboxylate (1.50 g, 8.69 mmol) and cyclopropanecarboxamide by the similar manner in Step-1 of Carboxylic acid-4.

$^1$H-NMR (300 MHz, CDCl$_3$) delta 8.86 (1H, d, J=5.1 Hz), 8.38 (1H, br s), 7.67 (1H, d, J=5.1 Hz), 4.03 (3H, s), 2.20-2.08 (1H, m), 1.23-1.18 (2H, m), 0.99-0.93 (2H, m), MS (ESI) m/z: 222 (M+H)$^+$.

<Step-2>:
2-(cyclopropanecarboxamido)pyrimidine-4-carboxylic acid

The title compound is prepared in 66% yield (1.19 g, an off-white solid) from methyl 2-(cyclopropanecarboxamido)pyrimidine-4-carboxylate (1.93 g, 8.72 mmol, Step-1) by the similar manner in Step-2 of Carboxylic acid-4.
$^1$H-NMR (300 MHz, DMSO-$d_6$) delta 11.20 (1H, s), 8.89 (1H, d, J=4.4 Hz), 7.63 (1H, d, J=4.4 Hz), 2.20-2.10 (1H, m), 0.83 (4H, d, J=6.6 Hz), MS (ESI) m/z: 206 (M−H)$^-$.

Carboxylic acid-8: 2-butyramidoisonicotinic acid

<Step-1>: methyl 2-butyramidoisonicotinate

The title compound is prepared in 82% yield (1.94 g, a white solid) from methyl 2-aminoisonicotinate hydrochloride (2.00 g, 10.6 mmol) and butyryl chloride by the similar manner in Step-1 of Carboxylic acid-1.
$^1$H-NMR (300 MHz, CDCl$_3$) delta 8.76 (1H, s), 8.39 (1H, d, J=5.1 Hz), 8.08 (1H, br s), 7.60 (1H, dd, J=5.1, 1.5 Hz), 3.95 (3H, s), 2.41 (2H, t, J=7.3 Hz), 1.80 (2H, sextet, J=7.3 Hz), 1.02 (3H, t, J=7.3 Hz), MS (ESI) m/z: 223 (M+H)$^+$.

<Step-2>: 2-butyramidoisonicotinic acid

The title compound is prepared in 76% yield (1.28 g, a white solid) from methyl 2-butyramidoisonicotinate (1.94 g, 8.71 mmol, Step-1) by the similar manner in Step-2 of Carboxylic acid-1.
$^1$H-NMR (300 MHz, DMSO-$d_6$) delta 10.66 (1H, s), 8.58 (1H, s), 8.45 (1H, d, J=5.1 Hz), 7.48 (1H, dd, J=5.1, 1.5 Hz), 2.37 (2H, t, J=7.3 Hz), 1.59 (2H, sextet, J=7.3 Hz), 0.89 (3H, t, J=7.3 Hz), MS (ESI) m/z: 209 (M+H)$^+$, 207 (M−H)$^-$.

Carboxylic acid-9: 2-pivalamidoisonicotinic acid

<Step-1>: methyl 2-pivalamidoisonicotinate

The title compound is prepared in quantitative yield (1.25 g, colorless syrup) from methyl 2-aminoisonicotinate hydrochloride (1.00 g, 5.30 mmol) and pivaloyl chloride by the similar manner in Step-1 of Carboxylic acid-1.
$^1$H-NMR (270 MHz, CDCl$_3$) delta 8.81 (1H, s), 8.39 (1H, d, J=5.3 Hz), 8.24 (1H, br s), 7.61 (1H, dd, J=5.3, 1.3 Hz), 3.94 (3H, s), 1.35 (9H, s).

<Step-2>: 2-pivalamidoisonicotinic acid

The title compound is prepared in 61% yield (0.72 g, a white solid) from methyl 2-pivalamidoisonicotinate (1.25 g, 5.30 mmol, Step-1) by the similar manner in Step-2 of Carboxylic acid-1.
$^1$H-NMR (270 MHz, DMSO-$d_6$) delta 10.07 (1H, s), 8.55 (1H, s), 8.49 (1H, d, J=5.3 Hz), 7.53 (1H, d, J=5.3 Hz), 1.25 (9H, s), MS (ESI) m/z: 223 (M+H)$^+$.

Carboxylic acid-10: 2-methyl-6-propionamidoisonicotinic acid

<Step-1>: methyl 2-methyl-6-propionamidoisonicotinate

The title compound is prepared in 60% yield (2.16 g, a pale yellow solid) from methyl 2-chloro-6-methylisonicotinate (3.00 g, 16.2 mmol) and propionamide by the similar manner in Step-1 of Carboxylic acid-4.
$^1$H-NMR (300 MHz, CDCl$_3$) delta 8.55 (1H, s), 7.93 (1H, br s), 7.47 (1H, s), 3.93 (3H, s), 2.51 (3H, s), 2.44 (2H, q, J=7.3 Hz), 1.26 (3H, t, J=7.3 Hz), MS (ESI) m/z: 223 (M+H)$^+$.

<Step-2>: 2-methyl-6-propionamidoisonicotinic acid

The title compound is prepared in 96% yield (1.95 g, a white solid) from methyl 2-methyl-6-propionamidoisonicotinate (2.16 g, 9.72 mmol, Step-1) by the similar manner in Step-2 of Carboxylic acid-1.
$^1$H-NMR (300 MHz, DMSO-$d_6$) delta 10.60 (1H, s), 8.40 (1H, s), 7.38 (1H, s), 2.47 (3H, s), 2.40 (2H, q, J=7.3 Hz), 1.06 (3H, t, J=7.3 Hz), MS (ESI) m/z: 209 (M+H)$^+$.

Carboxylic acid-11: 2-(cyclopropanecarboxamido)-6-methylisonicotinic acid

<Step-1>: methyl 2-(cyclopropanecarboxamido)-6-methylisonicotinate

The title compound is prepared in 66% yield (1.3 g, a pale yellow solid) from methyl 2-chloro-6-methylisonicotinate (1.5 g, 8.1 mmol) and cyclopropanecarboxamide by the similar manner in Step-1 of Carboxylic acid-4.
$^1$H-NMR (300 MHz, CDCl$_3$) delta 8.52 (1H, s), 8.17 (1H, br s), 7.46 (1H, s), 3.92 (3H, s), 2.52 (3H, s), 1.60-1.50 (1H, m), 1.15-1.10 (2H, m), 0.93-0.88 (2H, m), MS (ESI) m/z: 235 (M+H)$^+$, 233 (M−H)$^-$.

<Step-2>: 2-(cyclopropanecarboxamido)-6-methylisonicotinic acid

The title compound is prepared in 89% yield (1.1 g, a white solid) from methyl 2-(cyclopropanecarboxamido)-6-methylisonicotinate (1.3 g, 5.3 mmol, Step-1) by the similar manner in Step-2 of Carboxylic acid-1.
$^1$H-NMR (300 MHz, DMSO-$d_6$) delta 10.96 (1H, s), 8.38 (1H, s), 7.37 (1H, s), 2.48 (3H, s), 2.04-1.90 (1H, m), 0.83-0.70 (4H, m), MS (ESI) m/z: 221 (M+H)$^+$, 219 (M−H)$^+$.

Carboxylic acid-12: 2-acetamido-6-methylpyrimidine-4-carboxylic acid

<Step-1>: methyl 2-acetamido-6-methylpyrimidine-4-carboxylate

The title compound is prepared in 68% yield (0.76 g, a yellow solid) from methyl 2-chloro-6-methylpyrimidine-4-carboxylate (1.0 g, 5.4 mmol) and acetamide by the similar manner in Step-1 of Carboxylic acid-4.
$^1$H-NMR (300 MHz, CDCl$_3$) delta 8.01 (1H, br s), 7.54 (1H, s), 4.00 (3H, s), 2.59 (3H, s), 2.53 (3H, s), MS (ESI) m/z: 210 (M+H)$^+$.

<Step-2>: 2-acetamido-6-methylpyrimidine-4-carboxylic acid

The title compound is prepared in 30% yield (0.21 g, a yellow solid) from methyl 2-acetamido-6-methylpyrimidine-4-carboxylate (1.3 g, 5.3 mmol, Step-1) by the similar manner in Step-2 of Carboxylic acid-4.

$^1$H-NMR (300 MHz, DMSO-d$_6$) delta 10.76 (1H, s), 7.55 (1H, s), 2.49 (3H, s), 2.20 (3H, s), MS (ESI) m/z: 196 (M+H)$^+$.

Carboxylic acid-13:
6-methyl-2-propionamidopyrimidine-4-carboxylic acid

<Step-1>: methyl 6-methyl-2-propionamidopyrimidine-4-carboxylate

The title compound is prepared in 61% yield (0.73 g, a yellow solid) from methyl 2-chloro-6-methylpyrimidine-4-carboxylate (1.0 g, 5.4 mmol) and propionamide by the similar manner in Step-1 of Carboxylic acid-4.
$^1$H-NMR (300 MHz, CDCl$_3$) delta 8.05 (1H, br s), 7.54 (1H, s), 4.00 (3H, s), 2.77 (2H, q, J=7.3 Hz), 2.59 (3H, s), 1.24 (3H, t, J=7.3 Hz), MS (ESI) m/z: 224 (M+H)$^+$.

<Step-2>: 6-methyl-2-propionamidopyrimidine-4-carboxylic acid

The title compound is prepared in 19% yield (0.13 g, a yellow solid) from methyl 6-methyl-2-propionamidopyrimidine-4-carboxylate (0.73 g, 3.3 mmol, Step-1) by the similar manner in Step-2 of Carboxylic acid-4.
$^1$H-NMR (300 MHz, CDCl$_3$) delta 8.10 (1H, br s), 7.68 (1H, s), 2.66 (2H, q, J=7.3 Hz), 2.60 (3H, s), 1.26 (3H, t, J=7.3 Hz), MS (ESI) m/z: 210 (M+H)$^+$.

Carboxylic acid-14:
2-isobutyramido-6-methylpyrimidine-4-carboxylic acid

<Step-1>: methyl 2-isobutyramido-6-methylpyrimidine-4-carboxylate

The title compound is prepared in 88% yield (1.1 g, a yellow solid) from methyl 2-chloro-6-methylpyrimidine-4-carboxylate (1.0 g, 5.4 mmol) and isobutyramide by the similar manner in Step-1 of Carboxylic acid-4.
$^1$H-NMR (300 MHz, CDCl$_3$) delta 8.22 (1H, br s), 7.56 (1H, s), 4.01 (3H, s), 2.90 (1H, sep, J=7.3 Hz), 2.61 (3H, s), 1.26 (6H, d, J=7.3 Hz), MS (ESI) m/z: 238 (M+H)$^+$, 236 (M−H)$^-$.

<Step-2>: 2-isobutyramido-6-methylpyrimidine-4-carboxylic acid

The title compound is prepared in 46% yield (0.49 g, a yellow solid) from methyl 2-isobutyramido-6-methylpyrimidine-4-carboxylate (1.1 g, 4.7 mmol, Step-1) by the similar manner in Step-2 of Carboxylic acid-4.
$^1$H-NMR (270 MHz, DMSO-d$_6$) delta 10.89 (1H, br s), 7.55 (1H, s), 2.84 (1H, septet, J=7.3 Hz), 2.47 (3H, s), 1.10 (6H, d, J=7.3 Hz), MS (ESI) m/z: 224 (M+H)$^+$.

Carboxylic acid-15: 2-(2-hydroxy-2-methylpropanamido)-6-methylisonicotinic acid

<Step-1>: methyl 2-(2-acetoxy-2-methylpropanamido)-6-methylisonicotinate

The title compound is prepared in 80% yield (0.89 g, a yellow solid) from methyl 2-chloro-6-methylisonicotinate (0.70 g, 3.8 mmol) and 1-amino-2-methyl-1-oxopropan-2-yl acetate by the similar manner in Step-1 of Carboxylic acid-4.
$^1$H-NMR (300 MHz, CDCl$_3$) delta 8.58 (1H, s), 8.34 (1H, br s), 7.50 (1H, s), 3.93 (3H s), 2.52 (3H, s), 2.16 (3H, s), 1.73 (6H, s), MS (ESI) m/z: 295 (M+H)$^+$.

<Step-2>: 2-(2-hydroxy-2-methylpropanamido)-6-methylisonicotinic acid

The title compound is prepared in 80% yield (0.54 g, a white solid) from methyl 2-(2-acetoxy-2-methylpropanamido)-6-methylisonicotinate (0.83 g, 2.8 mmol, Step-1) by the similar manner in Step-2 of Carboxylic acid-4.
$^1$H-NMR (300 MHz, DMSO-d$_6$) delta 9.50 (1H, br s), 8.39 (1H, s), 7.45 (1H, s), 6.07 (1H, br s), 2.48 (3H, s), 1.37 (6H, s), MS (ESI) m/z: 239 (M+H)$^+$.

Carboxylic acid-16: 2-(ethylcarbamoyl)isonicotinic acid

<Step-1>: methyl 2-(ethylcarbamoyl)isonicotinate

A mixture of 4-(methoxycarbonyl)picolinic acid (1.00 g, 5.12 mmol) and magnesium chloride (312 mg, 3.28 mmol) in dichloromethane (10 mL) is stirred at room temperature for 0.5 hour. Then, ethylamine hydrochloride (627 mg, 7.69 mmol) and triethylamine (1.07 mL, 7.69 mmol) are added. After stirring at room temperature for 20 hours, the mixture is poured onto water (50 mL). The aqueous phase is extracted with EtOAc (50 mL×2). The combined organic layer is dried over sodium sulfate and concentrated in vacuo. The residue is purified by column chromatography on silica gel eluting with n-hexane/ethyl acetate (3:1 1:1) to give 525 mg (49% yield) of the title compound as a white solid.
$^1$H-NMR (270 MHz, CDCl$_3$) delta 8.74-8.68 (2H, m), 8.01-7.97 (2H, m), 3.99 (3H, s), 3.60-3.49 (2H, m),1.29 (3H, t, J=7.3 Hz), MS (ESI) m/z: 209 (M+H)$^+$.

<Step-2>: 2-(ethylcarbamoyl)isonicotinic acid

A mixture of methyl 2-(ethylcarbamoyl)isonicotinate (520 mg, 2.50 mmol, Step-1), 2M aqueous sodium hydroxide solution (2.5 mL), and methanol (6 mL) is stirred at room temperature for 3 hours. After addition of 2M hydrochloric acid (2.5 mL), the solvent is removed by evaporation. The residue is suspended in THF (20 mL), and the mixture is filtered through a pad of Celite. The filtrate is concentrated in vacuo to give 491 mg (quantitative yield) of the title compound as a white solid.
$^1$H-NMR (270 MHz, DMSO-d$_6$) delta 13.9 (1H, br s), 8.93 (1H, t, J=5.9 Hz), 8.82 (1H, d, J=5.3 Hz), 8.40 (1H, s), 8.00 (1H, d, J=5.3 Hz), 3.34 (2H, quintet, J=6.6 Hz), 1.13 (3H, t, J=7.3 Hz), MS (ESI) m/z: 195 (M+H)$^+$.

Carboxylic acid-17: 4-(ethylcarbamoyl)picolinic acid

<Step-1>: methyl 4-(ethylcarbamoyl)picolinate

To a mixture of 2-(methoxycarbonyl)isonicotinic acid (150 mg, 0.83 mmol), ethylamine hydrochloride salt (203 mg, 2.48 mmol), and diisopropylethylamine (0.72 mL, 4.14 mmol) in DMF is added HBTU (377 mg, 0.99 mmol) at 0° C. After stirring at room temperature for 1 hour, the mixture is poured onto water (30 mL). The aqueous phase is extracted with dichloromethane (30 mL×2). The combined organic layer is dried over sodium sulfate and concentrated in vacuo. The residue is purified by column chromatography on silica gel eluting with n-hexane/ethyl acetate (2:1~1:1) to give 83 mg (48% yield) of the title compound as a white solid.

$^1$H-NMR (300 MHz, CDCl$_3$) delta 8.72 (1H, s), 8.70 (1H, d, J=5.1 Hz), 8.10-7.85 (2H, m), 3.99 (3H, s), 3.55 (2H, quintet, J=7.3 Hz), 1.29 (3H, t, J=7.3 Hz), MS (ESI) m/z: 209 (M+H)$^+$.

<Step-2>: 4-(ethylcarbamoyl)picolinic acid

The title compound is prepared in quantitative yield (78 mg, a white solid) from methyl 4-(ethylcarbamoyl)picolinate (83 mg, 0.40 mmol) by the similar manner in Step-1 of Carboxylic acid-16.

$^1$H-NMR (270 MHz, DMSO-d$_6$) delta 8.93 (1H, br s), 8.82 (1H, d, J=4.6 Hz), 8.40 (1H, s), 7.99 (1H, d, J=4.6 Hz), 1.32 (3H, t, J=7.3 Hz), MS (ESI) m/z: 195 (M+H)$^+$.

Carboxylic acid-18:
2-(1-methylcyclopropanecarboxamido)isonicotinic acid

<Step-1>: methyl 2-(1-methylcyclopropanecarboxamido)isonicotinate

The title compound is prepared in 86% yield (0.30 g, a white solid) from methyl 2-chloroisonicotinate (0.25 g, 1.46 mmol) and 1-methylcyclopropanecarboxamide by the similar manner in Step-1 of Carboxylic acid-4.

$^1$H-NMR (300 MHz, CDCl$_3$) delta 8.76 (1H, s), 8.40 (1H, d, J=5.1 Hz), 8.26 (1H, br s), 7.60 (1H, d, J=5.1 Hz), 3.93 (3H, s), 1.51 (3H, s), 1.38-1.34 (2H, m), 0.77-0.74 (2H, m), MS (ESI) m/z: 235 (M+H)$^+$.

<Step-2>: 2-(1-methylcyclopropanecarboxamido)isonicotinic acid

The title compound is prepared in 90% yield (0.25 g, a white solid) from methyl 2-(1-methylcyclopropanecarboxamido)isonicotinate (0.30 g, 1.26 mmol, Step-1) by the similar manner in Step-2 of Carboxylic acid-1.

$^1$H-NMR (300 MHz, DMSO-d$_6$) delta 9.78 (1H, s), 8.50-8.48 (2H, m), 7.53 (1H, d, J=4.4 Hz), 1.43 (3H, s), 1.15-1.13 (2H, m), 0.70-0.66 (2H, m), MS (ESI) m/z: 221 (M+H)$^+$.

Carboxylic acid-19:
2-(2-cyclopropylacetamido)-6-methylisonicotinic acid

<Step-1>: methyl 2-(2-cyclopropylacetamido)-6-methylisonicotinate

The title compound is prepared in 67% yield (316 mg) from methyl 2-chloro-6-methylisonicotinate (350 mg, 1.89 mmol) and 2-cyclopropylacetamide (243 mg, 2.45 mmol) by the similar manner in Step-1 of Carboxylic acid-4.

$^1$H-NMR (300 MHz, CDCl$_3$) delta 8.56 (1H, br s), 8.22 (1H, s), 7.47 (1H, s), 3.93 (3H, s), 2.51 (3H, s), 2.36 (2H, d, J=7.3 Hz), 1.11 (1H, quintet, 4.4 Hz), 0.72 (2H, q, J=5.5 Hz), 0.30 (2H, q, J=5.1 Hz), MS (ESI) m/z: 249.3 (M+H)$^+$.

<Step-2>: 2-(2-cyclopropylacetamido)-6-methylisonicotinic acid

The title compound is prepared in 76% yield (216 mg) from methyl 2-(2-cyclopropylacetamido)-6-methylisonicotinate (300 mg, 1.21 mmol, Step-1) by the similar manner in Step-2 of Carboxylic acid-1.

$^1$H-NMR (300 MHz, DMSO-d$_6$) delta 10.55 (1H, s), 8.42 (1H, s), 7.39 (1H, s), 2.47 (3H, s), 2.28 (2H, d, J=6.6 Hz), 1.05 (1H, quintet, J=4.4 Hz), 0.46 (2H, d, J=7.3 Hz), 0.19 (2H, d, J=4.4 Hz), MS (ESI) m/z: 233 (M–H)$^-$.

EXAMPLE SYNTHESIS PART

Example 1

(−)-2-acetamido-N-(1-(6-(2,2,2-trifluoroethoxy)pyridin-3-yl)ethyl)isonicotinamide (single enantiomer)

A mixture of (−)-1-(6-(2,2,2-trifluoroethoxy)pyridin-3-yl)ethanamine hydrochloride (1.50 g, 5.12 mmol, Amine-1, single enantiomer), 2-acetamidoisonicotinic acid (1.01 g, 5.63 mmol), HBTU (2.33 g, 6.14 mmol) and triethylamine (3.57 mL, 25.6 mmol) in dichloromethane (51 mL) is stirred at room temperature for 15 hours. The reaction mixture is poured into water (50 mL) and extracted with dichloromethane (50 mL). The organic layer is dried over sodium sulfate and concentrated under reduced pressure. The residue is recrystallized from ethyl acetate to give 1.30 g (66% yield) of the title compound as a white solid.

$^1$H-NMR (300 MHz, DMSO-d$_6$) delta 10.6 (1H, s), 9.08 (1H, d, J=8.1 Hz), 8.41-8.38 (2H, m), 8.18 (1H, d, J=2.2 Hz), 7.82 (1H, dd, J=8.4, 2.2 Hz), 7.43 (1H, d, J=5.1 Hz), 6.96 (1H, d, J=8.8 Hz), 5.14 (1H, m), 4.96 (2H, q, J=9.2 Hz), 2.09 (3H, s), 1.47 (3H, d, J=7.0 Hz), MS (ESI) m/z: 383 (M+H)$^+$
[α]$^{26}$; =−0.49 (c=1.25, methanol)

Example 2

2-acetamido-N-((4-(2,2,2-trifluoroethoxy)pyridin-2-yl)methyl)isonicotinamide

To a mixture of (4-(2,2,2-trifluoroethoxy)pyridin-2-yl)methanamine dihydrochloride (20 mg, 0.070 mmol, Amine-2), 2-acetamidoisonicotinic acid (15 mg, 0.084 mmol) and N,N-diisopropylethylamine (0.049 mL, 0.28 mmol) in N,N-dimethylformamide (0.5 mL) is added a solution of HBTU (40 mg, 0.11 mmol) in N,N-dimethylformamide (0.5 mL) at room temperature. After stirring at room temperature for 2 hours, the mixture is poured into water (2 mL) and extracted with ethyl acetate (3 mL). The organic layer is dried over sodium sulfate and concentrated under reduced pressure. The residue is purified by column chromatography on NH-silica gel eluting with ethyl acetate and then by preparative LC-MS to give 9.8 mg (38% yield) of the title compound.

Examples except for the alternative routes descried below are prepared according to the procedure similar to that described in Example 2, using the appropriate amine and the carboxylic acid (see Table 1). The reactants are commercially available materials or obtained by conventional methods known to those skilled in the art, otherwise noted in the intermediate synthesis part.

The procedures for the alternative route are described below.

Example 8

2-isobutyramido-N-(1-(6-(2,2,2-trifluoroethoxy)pyridin-3-yl)ethyl)isonicotinamide (single enantiomer)

<Step-1>: 2-amino-N-(1-(6-(2,2,2-trifluoroethoxy)pyridin-3-yl)ethyl)isonicotinamide (single enantiomer)

To a mixture of (−)-1-(6-(2,2,2-trifluoroethoxy)pyridin-3-yl)ethanamine hydrochloride (300 mg, 1.17 mmol, Amine-1, single enantiomer), 2-aminoisonicotinic acid (161 mg, 1.17 mmol), and N,N-diisopropylethylamine (0.82 mL, 4.68 mmol) in N,N-dimethylformamide (12 mL) is added HBTU (665 mg, 1.75 mmol) at room temperature. After stirring at room temperature for 1 hour, the mixture is poured onto water (20 mL), and the mixture is extracted with ethyl acetate (20 mL). The organic layer is dried over sodium sulfate and concentrated under reduced pressure. The residue is purified by column chromatography on silica gel eluting with dichloromethane/methanol (10:1) to give 252 mg (63% yield) of the title compound as a slight brown solid.

$^1$H-NMR (300 MHz, CDCl$_3$) delta 8.17-8.13 (2H, m), 7.65 (1H, dd, J=8.8, 2.2 Hz), 6.87-6.81 (3H, m), 6.33 (1H, d, J=7.3 Hz), 5.28 (1H, quintet, J=6.6 Hz), 4.75 (2H, q, J=8.8 Hz), 4.62 (2H, br s), 1.60 (3H, d, J=6.6 Hz), MS (ESI) m/z: 341 (M+H)$^+$.

<Step-2>: 2-isobutyramido-N-(1-(6-(2,2,2-trifluoroethoxy)pyridin-3-yl)ethyl)isonicotinamide (Example 8, single enantiomer)

To a mixture of 2-amino-N-(1-(6-(2,2,2-trifluoroethoxy)pyridin-3-yl)ethyl)isonicotinamide (25 mg, 0.073 mmol, Step-1, single enantiomer) and pyridine (0.024 mL, 0.29 mmol) in N,N-dimethylacetamide (1 mL) is added isobutyryl chloride (16 mg, 0.15 mmol) at room temperature. After stirring at room temperature for 2 hours, the mixture is poured onto water (2 mL), and the mixture is extracted with ethyl acetate (3 mL). The organic layer is dried over sodium sulfate and concentrated under reduced pressure. The residue is purified by column chromatography on NH-silica gel eluting with ethyl acetate and then by preparative LC-MS to give 12.9 mg (43% yield) of the title compound.

The following examples, Examples 10, 41, 42, 662 (single enantiomer) are prepared according to the procedure similar to that described in Example 8, using the appropriate acid chloride such as benzoyl chloride, 2-methoxyacetyl chloride, cyclobutanecarbonyl chloride, and isovaleryl chloride instead of isobutyryl chloride, respectively.

Example 51

N-(1-(6-(2,2,2-trifluoroethoxy)pyridin-3-yl)ethyl)benzo[d]isoxazole-3-carboxamide (single enantiomer)

To a solution of (−)-1-(6-(2,2,2-trifluoroethoxy)pyridin-3-yl)ethanamine hydrochloride (20 mg, 0.078 mmol, Amine-1, single enantiomer) and N,N-diisopropylethylamine (0.054 mL, 0.31 mmol) in dichloromethane (0.5 mL) is added dropwise a solution of benzo[d]isoxazole-3-carbonyl chloride (17 mg, 0.094 mmol) in dichloromethane (0.5 mL) at room temperature. The reaction mixture is stirred at room temperature for 1 hour. The mixture is diluted with ethyl acetate (3 mL) and washed with water (1.5 mL). The organic layer is dried over sodium sulfate, and concentrated under reduced pressure. The residue is purified by column chromatography on NH-silica gel eluting with ethyl acetate and then preparative LC-MS to give 9.1 mg (32% yield) of the title compound.

Example 81

2-methoxy-6-propionamido-N-(1-(6-(2,2,2-trifluoroethoxy)pyridin-3-yl)ethyl)isonicotinamide (single enantiomer)

<Step-1>: 2-amino-6-methoxy-N-(1-(6-(2,2,2-trifluoroethoxy)pyridin-3-yl)ethyl)isonicotinamide (single enantiomer)

The title compound is prepared in 65% yield (187 mg, a white solid) from (−)-1-(6-(2,2,2-trifluoroethoxy)pyridin-3-yl)ethanamine hydrochloride (200 mg, 0.78 mmol, Amine-1, single enantiomer) and 2-amino-6-methoxyisonicotinic acid (131 mg, 0.78 mmol) by the similar manner in Step-1 of Example-8.

$^1$H-NMR (270 MHz, CDCl$_3$) delta 8.14 (1H, d, J=2.0 Hz), 7.63 (1H, dd, J=8.6, 2.6 Hz), 6.83 (1H, d, J=8.6 Hz), 6.41 (1H, d, J=7.3 Hz), 6.35 (1H, d, J=1.3 Hz), 6.27 (1H, s), 5.23 (1H, quintet, J=6.6 Hz), 4.74 (2H, q, J=8.6 Hz), 4.50 (2H, br s), 3.84 (3H, s), 1.56 (3H, d, J=6.6 Hz), MS (ESI) m/z: 371 (M+H)$^+$, 369 (M−H)$^−$.

<Step-2>: 2-methoxy-6-propionamido-N-(1-(6-(2,2,2-trifluoroethoxy)pyridin-3-yl)ethyl)isonicotinamide (Example-81, single enantiomer)

The title compound is prepared in 39% yield (11.2 mg) from 2-amino-6-methoxy-N-(1-(6-(2,2,2-trifluoroethoxy)pyridin-3-yl)ethyl)isonicotinamide (25 mg, 0.068 mmol, single enantiomer, Step-1) and propionyl chloride (19 mg, 0.20 mmol) by the similar manner in Step-2 of Example-8.

The following examples, Examples 82 and 83 (single enantiomer) are prepared according to the procedure similar to that described in Example 81, using the appropriate acid chloride such as cyclopropanecarbonyl chloride and isobutyryl chloride instead of propionyl chloride, respectively.

Example 97

2-propionamido-N-(1-(6-(2,2,2-trifluoroethoxy)pyridin-3-yl)ethyl)pyrimidine-4-carboxamide (single enantiomer)

<Step-1>: 2-amino-N-(1-(6-(2,2,2-trifluoroethoxy)pyridin-3-yl)ethyl)pyrimidine-4-carboxamide (single enantiomer)

The title compound is prepared in 80% yield (98 mg, a white solid) from (−)-1-(6-(2,2,2-trifluoroethoxy)pyridin-3-yl)ethanamine hydrochloride (92 mg, 0.36 mmol, Amine-1, single enantiomer) and 2-aminopyrimidine-4-carboxylic acid (50 mg, 0.36 mmol) by the similar manner in Step-1 of Example 8.

$^1$H-NMR (270 MHz, CDCl$_3$) delta 8.50 (1H, d, J=5.1 Hz), 8.18 (1H, d, J=2.2 Hz), 7.99 (1H, br s), 7.67 (1H, dd, J=8.8, 2.9 Hz), 7.40 (1H, d, J=5.1 Hz), 6.85 (1H, d, J=8.1 Hz), 5.30-5.20 (1H, m), 5.09 (2H, br s), 4.75 (2H, q, J=8.8 Hz), 1.62 (3H, d, J=7.3 Hz), MS (ESI) m/z: 342 (M+H)$^+$, 340 (M−H)$^−$.

<Step-2>: 2-propionamido-N-(1-(6-(2,2,2-trifluoroethoxy)pyridin-3-yl)ethyl)pyrimidine-4-carboxamide (Example-97, single enantiomer)

The title compound is prepared from 2-amino-N-(1-(6-(2,2,2-trifluoroethoxy)pyridin-3-yl)ethyl)pyrimidine-4-carboxamide (20 mg, 0.06 mmol, Step-1, single enantiomer) and propionyl chloride (8 mg, 0.09 mmol) according to the procedure similar to that described in Step-2 of Example 8.

Example 102

2-(cyclopropanecarboxamido)-5-fluoro-N-(1-(6-(2,2,2-trifluoroethoxy)pyridin-3-yl)ethyl)isonicotinamide (single enantiomer)

<Step-1>: 2-amino-5-fluoro-N-(1-(6-(2,2,2-trifluoroethoxy)pyridin-3-yl)ethyl)isonicotinamide (single enantiomer)

The title compound is prepared in 24% yield (102 mg, a white solid) from (−)-1-(6-(2,2,2-trifluoroethoxy)pyridin-3- yl)ethanamine hydrochloride (300 mg, 1.17 mmol, Amine-1, single enantiomer) and 2-amino-5-fluoroisonicotinic acid (182 mg, 1.17 mmol) by the similar manner in Step-1 of Example-8.

$^{1}$H-NMR (300 MHz, CDCl$_{3}$) delta 8.17 (1H, d, J=2.2 Hz), 8.02 (1H, d, J=2.9 Hz), 7.65 (1H, dd, J=8.8, 2.2 Hz), 7.07 (1H, d, J=5.1 Hz), 6.96-6.85 (1H, m), 6.86 (1H, d, J=8.8 Hz), 5.33-5.23 (1H, m), 4.75 (2H, q, J=8.8 Hz), 4.54 (2H, br s), 1.61 (3H, d, J=7.3 Hz), MS (ESI) m/z: 359 (M+H)$^{+}$, 357 (M–H)$^{-}$.

<Step-2>: 2-(cyclopropanecarboxamido)-5-fluoro-N-(1-(6-(2,2,2-trifluoroethoxy)pyridin-3-yl)ethyl) isonicotinamide (Example-102, single enantiomer)

The title compound is prepared in 11% yield (4.4 mg) from 2-amino-5-fluoro-N-(1-(6-(2,2,2-trifluoroethoxy)pyridin-3-yl)ethyl)isonicotinamide (34 mg, 0.095 mmol, Step-1, single enantiomer) and cyclopropanecarbonyl chloride (20 mg, 0.19 mmol) by the similar manner in Step-2 of Example-8.

Example 112

N-(1-(5-chloro-6-(2,2,2-trifluoroethoxy)pyridin-3-yl) ethyl)-2-(cyclopropanecarboxamido)oxazole-5-carboxamide (single enantiomer)

<Step-1>: 2-amino-N-(1-(5-chloro-6-(2,2,2-trifluoroethoxy)pyridin-3-yl)ethyl)oxazole-5-carboxamide (single enantiomer)

The title compound is prepared in 47% yield (106 mg, clear colorless oil) from (+)-1-(5-chloro-6-(2,2,2-trifluoroethoxy) pyridin-3-yl)ethanamine hydrochloride (182 mg, 0.63 mmol, Amine-5, single enantiomer) and 2-aminooxazole-5-carboxylic acid (80 mg, 0.63 mmol) by the similar manner in Step-1 of Example 8.

$^{1}$H-NMR (270 MHz, CDCl$_{3}$) delta 8.06 (1H, s), 7.70 (1H, s), 7.41 (1H, s), 6.05 (1H, d, J=7.3 Hz), 5.30-5.20 (1H, m), 5.08 (2H, br s), 4.80-4.69 (2H, m), 2.88 (3H, s), 1.58 (3H, d, J=7.3 Hz), MS (ESI) m/z: 365 (M+H)$^{+}$, 363 (M–H)$^{-}$.

<Step-2>: N-(1-(5-chloro-6-(2,2,2-trifluoroethoxy) pyridin-3-yl)ethyl)-2-(cyclopropanecarboxamido) oxazole-5-carboxamide (Example-112, single enantiomer)

The title compound is prepared from 2-amino-N-(1-(5-chloro-6-(2,2,2-trifluoroethoxy)pyridin-3-yl)ethyl)oxazole-5-carboxamide (30 mg, 0.08 mmol, Step-1, single enantiomer) and cyclopropanecarbonyl chloride (13 mg, 0.12 mmol) according to the procedure similar to that described in Step-2 of Example 8.

Example 113

N-(1-(5-chloro-6-(2,2,2-trifluoroethoxy)pyridin-3-yl) ethyl)-2-(cyclopropanecarboxamido)-4-methyloxazole-5-carboxamide (single enantiomer)

<Step-1>: 2-amino-N-(1-(5-chloro-6-(2,2,2-trifluoroethoxy)pyridin-3-yl)ethyl)-4-methyloxazole-5-carboxamide (single enantiomer)

The title compound is prepared in 41% yield (92 mg, a white solid) from (+)-1-(5-chloro-6-(2,2,2-trifluoroethoxy) pyridin-3-yl)ethanamine hydrochloride (171 mg, 0.59 mmol, Amine-5, single enantiomer) and 2-amino-4-methyloxazole-5-carboxylic acid (100 mg, 0.70 mmol) by the similar manner in Step-1 of Example 8.

$^{1}$H-NMR (300 MHz, CDCl$_{3}$) delta 8.05 (1H, d, J=2.2 Hz), 7.69 (1H, d, J=2.2 Hz), 6.03 (1H, d, J=7.3 Hz), 5.20 (1H, quintet, J=7.3 Hz), 5.16 (2H, br s), 4.80 (2H, q, J=8.1 Hz), 2.37 (3H, s), 1.56 (3H, d, J=6.6 Hz), MS (ESI) m/z: 377 (M–H)$^{-}$.

<Step-2>: N-(1-(5-chloro-6-(2,2,2-trifluoroethoxy) pyridin-3-yl)ethyl)-2-(cyclopropanecarboxamido-4-methyloxazole-5-carboxamide (Example-113, single enantiomer)

The title compound is prepared in 23% yield (6.8 mg) from 2-amino-N-(1-(5-chloro-6-(2,2,2-trifluoroethoxy)pyridin-3-yl)ethyl)-4-methyloxazole-5-carboxamide (25 mg, 0.07 mmol, Step-1, single enantiomer) and cyclopropanecarbonyl chloride (10 mg, 0.1 mmol) according to the procedure similar to that described in Step-2 of Example 8.

Example 117

6-propionamido-N-(1-(6-(2,2,2-trifluoroethoxy)pyridin-3-yl)ethyl)pyrimidine-4-carboxamide (single enantiomer)

<Step-1>: 6-amino-N-(1-(6-(2,2,2-trifluoroethoxy) pyridin-3-yl)ethyl)pyrimidine-4-carboxamide (single enantiomer)

The title compound is prepared in 89% yield (175 mg, a white solid) from (–)-1-(6-(2,2,2-trifluoroethoxy)pyridin-3-yl)ethanamine hydrochloride (148 mg, 0.58 mmol, Amine-1, single enantiomer) and 6-aminopyrimidine-4-carboxylic acid (80 mg, 0.58 mmol) by the similar manner in Step-1 of Example 8.

$^{1}$H-NMR (300 MHz, CDCl$_{3}$) delta 8.53 (1H, s), 8.23-8.12 (2H, m), 7.66 (1H, d, J=8.8 Hz), 7.23 (1H, s), 6.85 (1H, d, J=8.8 Hz), 5.24 (1H, quintet, J=7.3 Hz), 5.17 (2H, br s), 4.74 (2H, q, J=8.8 Hz), 1.61 (3H, d, J=6.6 Hz), MS (ESI) m/z: 340 (M–H)$^{-}$.

<Step-2>: 6-propionamido-N-(1-(6-(2,2,2-trifluoroethoxy)pyridin-3-yl)ethyl)pyrimidine-4-carboxamide (Example-117, single enantiomer)

The title compound is prepared from 6-amino-N-(1-(6-(2,2,2-trifluoroethoxy)pyridin-3-yl)ethyl)pyrimidine-4-carboxamide (30 mg, 0.09 mmol, Step-1, single enantiomer) and propionyl chloride (12 mg, 0.13 mmol) according to the procedure similar to that described in Step-2 of Example 8.

Example 118

6-(cyclopropanecarboxamido)-N-(1-(6-(2,2,2-trifluoroethoxy)pyridin-3-yl)ethyl)pyrimidine-4-carboxamide (single enantiomer)

The title compound is prepared from 6-amino-N-(1-(6-(2,2,2-trifluoroethoxy)pyridin-3-yl)ethyl)pyrimidine-4-carboxamide (30 mg, 0.09 mmol, Step-1 of Example 117, single enantiomer) and cyclopropanecarbonyl chloride (14 mg, 0.13 mmol) according to the procedure similar to that described in Step-2 of Example 8.

Example 119

N-(1-(5-chloro-6-(2,2,2-trifluoroethoxy)pyridin-3-yl)ethyl)-6-propionamidopyrimidine-4-carboxamide (single enantiomer)

<Step-1>: 6-amino-N-(1-(5-chloro-6-(2,2,2-trifluoroethoxy)pyridin-3-yl)ethyl)pyrimidine-4-carb oxamide (single enantiomer)

The title compound is prepared in 90% yield (195 mg, clear colorless oil) from (+)-1-(5-chloro-6-(2,2,2-trifluoroethoxy)pyridin-3-yl)ethanamine hydrochloride (167 mg, 0.58 mmol, Amine-5, single enantiomer) and 6-aminopyrimidine-4-carboxylic acid (80 mg, 0.58 mmol) by the similar manner in Step-1 of Example 8.
$^1$H-NMR (300 MHz, CDCl$_3$) delta 8.54 (1H, d, J=1.5 Hz), 8.21 (1H, d, J=7.3 Hz), 8.07 (1H, d, J=2.2 Hz), 7.71 (1H, d, J=2.2 Hz), 7.21 (1H, d, J=1.5 Hz), 5.21 (1H, quintet, J=7.3 Hz), 5.17 (2H, br s), 4.80 (2H, q, J=8.1 Hz), 1.62 (3H, d, J=7.3 Hz), MS (ESI) m/z: 374 (M−H)$^-$.

<Step-2>: N-(1-(5-chloro-6-(2,2,2-trifluoroethoxy)pyridin-3-yl)ethyl)-6-propionamidopyrimidine-4-carboxamide (Example-119, single enantiomer)

The title compound is prepared from 6-amino-N-(1-(5-chloro-6-(2,2,2-trifluoroethoxy)pyridin-3-yl)ethyl)pyrimidine-4-carb oxamide (30 mg, 0.08 mmol, Step-1, single enantiomer) and propionyl chloride (11 mg, 0.12 mmol) according to the procedure similar to that described in Step-2 of Example 8.

Example 183

2-propionamido-N-(1-(6-(3,3,3-trifluoropropoxy)pyridin-3-yl)ethyl)pyrimidine-4-carb oxamide (single enantiomer)

<Step-1>: 2-amino-N-(1-(6-(3,3,3-trifluoropropoxy)pyridin-3-yl)ethyl)pyrimidine-4-carboxamide (single enantiomer)

The title compound is prepared in 64% yield (100 mg, a white solid) from 1-(6-(3,3,3-trifluoropropoxy)pyridin-3-yl)ethanamine hydrochloride (120 mg, 0.4 mmol, Amine-21, single enantiomer) and 2-aminopyrimidine-4-carboxylic acid (62 mg, 0.4 mmol) by the similar manner in Step-1 of Example 8.
$^1$H-NMR (300 MHz, CDCl$_3$) delta 8.50 (1H, d, J=4.4 Hz), 8.18 (1H, d, J=2.9 Hz), 8.00 (1H, d, J=8.1 Hz), 7.61 (1H, dd, J=8.1, 2.2 Hz), 7.40 (1H, d, J=5.1 Hz), 6.75 (1H, d, J=8.8 Hz), 5.30-5.20 (1H, m), 5.09 (2H, br s), 4.54 (2H, t, J=6.6 Hz), 2.70-2.50 (2H, m), 1.61 (3H, d, J=6.6 Hz), MS (ESI) m/z: 356 (M+H)$^+$, 354 (M−H)$^-$.

<Step-2>: 2-propionamido-N-(1-(6-(3,3,3-trifluoropropoxy)pyridin-3-yl)ethyl)pyrimidine-4-carb oxamide (Example-183, single enantiomer)

The title compound is prepared from 2-amino-N-(1-(6-(3,3,3-trifluoropropoxy)pyridin-3-yl)ethyl)pyrimidine-4-carboxamide (Step-1, single enantiomer) and propionyl chloride according to the procedure similar to that described in Step-2 of Example 8.

The following example, Example 199 (single enantiomer) is prepared according to the procedure similar to that described in Example 183, using isobutyryl chloride instead of propionyl chloride.

Example 208

2-(cyclobutanecarboxamido)-N-(1-(5-fluoro-6-(2,2,2-trifluoroethoxy)pyridin-3-yl)ethyl)-6-methylpyrimidine-4-carboxamide (single enantiomer)

<Step-1>: 2-amino-N-(1-(5-fluoro-6-(2,2,2-trifluoroethoxy)pyridin-3-yl)ethyl)-6-methylpyrimidine-4-carboxamide (single enantiomer)

The title compound is prepared in 70% yield (170 mg, clear colorless oil) from (−)-1-(5-fluoro-6-(2,2,2-trifluoroethoxy)pyridin-3-yl)ethanamine hydrochloride (179 mg, 0.65 mmol, Amine-12, single enantiomer) and 2-amino-6-methylpyrimidine-4-carboxylic acid (100 mg, 0.65 mmol) by the similar manner in Step-1 of Example 8.
$^1$H-NMR (270 MHz, CDCl$_3$) delta 8.02 (1H, br s), 7.43 (1H, dd, J=10.2, 2.2 Hz), 7.28 (1H, s), 5.30-5.15 (1H, m), 5.03 (2H, br s), 4.81 (2H, q, J=6.6 Hz), 2.43 (3H, s), 1.61 (3H, d, J=7.4 Hz), MS (ESI) m/z: 374 (M+H)$^+$, 372 (M−H)$^-$.

<Step-2>: 2-(cyclobutanecarboxamido)-N-(1-(5-fluoro-6-(2,2,2-trifluoroethoxy)pyridin-3-yl)ethyl)-6-methylpyrimidine-4-carboxamide (Example-208, single enantiomer)

The title compound is prepared from 2-amino-N-(1-(5-fluoro-6-(2,2,2-trifluoroethoxy)pyridin-3-yl)ethyl)-6-methylpyrimidine-4-carboxamide (20 mg, 0.05 mmol, Step-1, single enantiomer) and cyclobutanecarbonyl chloride (13 mg, 0.1 mmol) according to the procedure similar to that described in Step-2 of Example 8.

Example 209

N-(1-(5-fluoro-6-(2,2,2-trifluoroethoxy)pyridin-3-yl)ethyl)-2-isobutyramidopyrimidine-4-carboxamide (single enantiomer)

<Step-1>: 2-amino-N-(1-(5-fluoro-6-(2,2,2-trifluoroethoxy)pyridin-3-yl)ethyl)pyrimidine-4-carboxamide (single enantiomer)

The title compound is prepared in 55% yield (142 mg, a white solid) from (−)-1-(5-fluoro-6-(2,2,2-trifluoroethoxy)pyridin-3-yl)ethanamine hydrochloride (197 mg, 0.72 mmol, Amine-12, single enantiomer) and 2-aminopyrimidine-4-carboxylic acid (100 mg, 0.72 mmol) by the similar manner in Step-1 of Example 8.
$^1$H-NMR (270 MHz, CDCl$_3$) delta 8.52 (1H, d, J=4.4 Hz), 8.01 (1H, d, J=5.9 Hz), 7.96 (1H, d, J=2.2 Hz), 7.44 (1H, dd, J=11.0, 2.2 Hz), 7.38 (1H, s), 5.30-5.19 (1H, m), 5.12 (2H, br s), 4.88-4.76 (2H, m), 1.62 (3H, d, J=7.3 Hz), MS (ESI) m/z: 360 (M+H)$^+$, 358 (M−H)$^-$.

<Step-2>: N-(1-(5-fluoro-6-(2,2,2-trifluoroethoxy)pyridin-3-yl)ethyl)-2-isobutyramidopyrimidine-4-carboxamide (Example-209, single enantiomer)

The title compound is prepared from 2-amino-N-(1-(5-fluoro-6-(2,2,2-trifluoroethoxy)pyridin-3-yl)ethyl)pyrimidine-4-carboxamide (20 mg, 0.06 mmol, Step-1, single enantiomer) and isobutyryl chloride (120 mg, 1.1 mmol) according to the procedure similar to that described in Step-2 of Example 8.

Example 210

N-(1-(5-chloro-6-(2,2,2-trifluoroethoxy)pyridin-3-yl)ethyl)-2-propionamidopyrimidine-4-carboxamide (single enantiomer)

<Step-1>: 2-amino-N-(1-(5-chloro-6-(2,2,2-trifluoroethoxy)pyridin-3-yl)ethyl)pyrimidine-4-carb oxamide (single enantiomer)

The title compound is prepared in 50% yield (135 mg, a white solid) from (+)-1-(5-chloro-6-(2,2,2-trifluoroethoxy)pyridin-3-yl)ethanamine hydrochloride (210 mg, 0.72 mmol, Amine-5, single enantiomer) and 2-aminopyrimidine-4-carboxylic acid (100 mg, 0.72 mmol) by the similar manner in Step-1 of Example 8.
$^1$H-NMR (300 MHz, CDCl$_3$) delta 8.52 (1H, d, J=4.4 Hz), 8.08 (1H, d, J=2.2 Hz), 8.01 (1H, d, J=7.3 Hz), 7.72 (1H, d, J=2.2 Hz), 7.39 (1H, d, J=5.1 Hz), 5.22 (1H, quintet, J=7.3 Hz), 5.12 (2H, br s), 4.81 (2H, q, J=8.8 Hz), 1.62 (3H, d, J=7.3 Hz),
MS (ESI) m/z: 376 (M+H)$^+$, 374 (M−H)$^−$.

<Step-2>: N-(1-(5-chloro-6-(2,2,2-trifluoroethoxy)pyridin-3-yl)ethyl)-2-propionamidopyrimidine-4-carboxamide (Example-210, single enantiomer)

The title compound is prepared from 2-amino-N-(1-(5-chloro-6-(2,2,2-trifluoroethoxy)pyridin-3-yl)ethyl)pyrimidine-4-carb oxamide (20 mg, 0.05 mmol, Step-1, single enantiomer) and propionyl chloride (25 mg, 0.27 mmol) according to the procedure similar to that described in Step-2 of Example 8.

Example 212

N-(1-(5-chloro-6-(2,2,2-trifluoroethoxy)pyridin-3-yl)ethyl)-2-isobutyramidopyrimidine-4-carboxamide (single enantiomer)

The title compound is prepared from 2-amino-N-(1-(5-chloro-6-(2,2,2-trifluoroethoxy)pyridin-3-yl)ethyl)pyrimidine-4-carb oxamide (20 mg, 0.05 mmol, Step-1 of Example 210, single enantiomer) and isobutyryl chloride (28 mg, 0.27 mmol) according to the procedure similar to that described in Step-2 of Example 8.

Example 213

N-(1-(5-chloro-6-(2,2,2-trifluoroethoxy)pyridin-3-yl)ethyl)-2-(cyclobutanecarboxamido)pyrimidine-4-carboxamide (single enantiomer)

The title compound is prepared from 2-amino-N-(1-(5-chloro-6-(2,2,2-trifluoroethoxy)pyridin-3-yl)ethyl)pyrimidine-4-carb oxamide (20 mg, 0.05 mmol, Step-1 of Example 210, single enantiomer) and cyclobutanecarbonyl chloride (32 mg, 0.27 mmol) according to the procedure similar to that described in Step-2 of Example 8.

Example 217

N-(1-(5-chloro-6-(2,2,2-trifluoroethoxy)pyridin-3-yl)ethyl)-2-(cyclobutanecarboxamido)-6-methylpyrimidine-4-carboxamide (single enantiomer)

<Step-1>: 2-amino-N-(1-(5-chloro-6-(2,2,2-trifluoroethoxy)pyridin-3-yl)ethyl)-6-methylpyrimidine-4-carboxamide (single enantiomer)

The title compound is prepared in 52% yield (146 mg, clear pale yellow oil) from (+)-1-(5-chloro-6-(2,2,2-trifluoroethoxy)pyridin-3-yl)ethanamine hydrochloride (210 mg, 0.72 mmol, Amine-5, single enantiomer) and 2-amino-6-methylpyrimidine-4-carboxylic acid (110 mg, 0.72 mmol) by the similar manner in Step-1 of Example 8.
$^1$H-NMR (300 MHz, CDCl$_3$) delta 8.07 (1H, d, J=2.2 Hz), 8.05-8.00 (1H, m), 7.71 (1H, d, J=2.2 Hz), 7.28 (1H, s), 5.22 (1H, quintet, J=7.3 Hz), 5.03 (2H, br s), 4.80 (2H, q, J=7.3 Hz), 2.43 (3H, s), 1.61 (3H, d, J=6.6 Hz), MS (ESI) m/z: 390 (M+H)$^+$, 388 (M−H)$^−$.

<Step-2>: N-(1-(5-chloro-6-(2,2,2-trifluoroethoxy)pyridin-3-yl)ethyl)-2-(cyclobutanecarboxamido)-6-methylpyrimidine-4-carboxamide (Example-217, single enantiomer)

The title compound is prepared from 2-amino-N-(1-(5-chloro-6-(2,2,2-trifluoroethoxy)pyridin-3-yl)ethyl)-6-methylpyrimidine-4-carboxamide (20 mg, 0.05 mmol, Step-1, single enantiomer) and cyclobutanecarbonyl chloride (27 mg, 0.26 mmol) according to the procedure similar to that described in Step-2 of Example 8.

Example 223

N-(1-(5-methyl-6-(2,2,2-trifluoroethoxy)pyridin-3-yl)ethyl)-2-propionamidopyrimidine-4-carboxamide (single enantiomer)

<Step-1>: 2-amino-N-(1-(5-methyl-6-(2,2,2-trifluoroethoxy)pyridin-3-yl)ethyl)pyrimidine-4-carb oxamide (single enantiomer)

The title compound is prepared in 36% yield (95 mg, clear pale yellow oil) from 1-(5-methyl-6-(2,2,2-trifluoroethoxy)pyridin-3-yl)ethanamine hydrochloride (200 mg, 0.74 mmol, Amine-17, single enantiomer) and 2-aminopyrimidine-4-carboxylic acid (103 mg, 0.74 mmol) by the similar manner in Step-1 of Example 8.
$^1$H-NMR (300 MHz, CDCl$_3$) delta 8.50 (1H, d, J=5.1 Hz), 8.00 (1H, s), 7.50 (1H, s), 7.40 (1H, d, J=4.4 Hz), 5.21 (1H, quintet, J=8.0 Hz), 5.09 (2H, br s), 4.75 (2H, q, J=8.8 Hz), 2.23 (3H, s), 1.60 (3H, d, J=6.6 Hz), MS (ESI) m/z: 356 (M+H)$^+$, 354 (M−H)$^−$.

<Step-2>: N-(1-(5-methyl-6-(2,2,2-trifluoroethoxy)pyridin-3-yl)ethyl)-2-propionamidopyrimidine-4-carboxamide (Example-223, single enantiomer)

The title compound is prepared from 2-amino-N-(1-(5-methyl-6-(2,2,2-trifluoroethoxy)pyridin-3-yl)ethyl)pyrimidine-4-carb oxamide (20 mg, 0.06 mmol, Step-1, single enantiomer) and propionyl chloride (26 mg, 0.28 mmol) according to the procedure similar to that described in Step-2 of Example 8.

Example 225

2-isobutyramido-N-(1-(5-methyl-6-(2,2,2-trifluoroethoxy)pyridin-3-yl)ethyl)pyrimidine-4-carboxamide (single enantiomer)

The title compound is prepared from 2-amino-N-(1-(5-methyl-6-(2,2,2-trifluoroethoxy)pyridin-3-yl)ethyl)pyrimidine-4-carboxamide (20 mg, 0.06 mmol, Step-1 of Example 223, single enantiomer) and isobutyryl chloride (30 mg, 0.28 mmol) according to the procedure similar to that described in Step-2 of Example 8.

Example 226

2-(cyclobutanecarboxamido)-N-(1-(5-methyl-6-(2,2,2-trifluoroethoxy)pyridin-3-yl)ethyl)pyrimidine-4-carboxamide (single enantiomer)

The title compound is prepared from 2-amino-N-(1-(5-methyl-6-(2,2,2-trifluoroethoxy)pyridin-3-yl)ethyl)pyrimidine-4-carboxamide (20 mg, 0.06 mmol, Step-1 of Example 223, single enantiomer) and cyclobutanecarbonyl chloride (33 mg, 0.28 mmol) according to the procedure similar to that described in Step-2 of Example 8.

Example 230

2-(cyclobutanecarboxamido)-6-methyl-N-(1-(5-methyl-6-(2,2,2-trifluoroethoxy)pyridin-3-yl)ethyl)pyrimidine-4-carboxamide (single enantiomer)

<Step-1>: 2-amino-6-methyl-N-(1-(5-methyl-6-(2,2,2-trifluoroethoxy)pyridin-3-yl)ethyl)pyrimidine-4-carboxamide (single enantiomer)

The title compound is prepared in 54% yield (110 mg, clear pale yellow oil) from 1-(5-methyl-6-(2,2,2-trifluoroethoxy)pyridin-3-yl)ethanamine hydrochloride (150 mg, 0.56 mmol, Amine-17, single enantiomer) and 2-amino-6-methylpyrimidine-4-carboxylic acid (85 mg, 0.56 mmol) by the similar manner in Step-1 of Example 8.
$^1$H-NMR (270 MHz, CDCl$_3$) delta 8.05-7.97 (2H, m), 7.46 (1H, s), 7.29 (1H, s), 5.21 (1H, quintet, J=6.6 Hz), 5.01 (2H, br s), 4.75 (2H, q, J=8.8 Hz), 2.43 (3H, s), 2.23 (3H, s), 1.60 (3H, d, J=6.6 Hz), MS (ESI) m/z: 370 (M+H)$^+$, 368 (M−H)$^-$.

<Step-2>: 2-(cyclobutanecarboxamido)-6-methyl-N-(1-(5-methyl-6-(2,2,2-trifluoroethoxy)pyridin-3-yl)ethyl)pyrimidine-4-carboxamide (Example-230, single enantiomer)

The title compound is prepared from 2-amino-6-methyl-N-(1-(5-methyl-6-(2,2,2-trifluoroethoxy)pyridin-3-yl)ethyl)pyrimidine-4-carboxamide (20 mg, 0.05 mmol, Step-1, single enantiomer) and cyclobutanecarbonyl chloride (28 mg, 0.27 mmol) according to the procedure similar to that described in Step-2 of Example 8.

Example 231

3-isobutyramido-N-(1-(6-(2,2,2-trifluoroethoxy)pyridin-3-yl)ethyl)picolinamide (single enantiomer)

<Step-1>: 3-amino-N-(1-(6-(2,2,2-trifluoroethoxy)pyridin-3-yl)ethyl)picolinamide (single enantiomer)

The title compound is prepared in 74% yield (98 mg, a white solid) from (−)-1-(6-(2,2,2-trifluoroethoxy)pyridin-3-yl)ethanamine hydrochloride (100 mg, 0.39 mmol, Amine-1, single enantiomer) and 3-aminopicolinic acid (54 mg, 0.39 mmol) by the similar manner in Step-1 of Example-8.
$^1$H-NMR (270 MHz, CDCl$_3$) delta 8.36 (1H, d, J=7.3 Hz), 8.18 (1H, d, J=2.0 Hz), 7.85 (1H, d, J=4.0 Hz), 7.68 (1H, dd, J=8.6, 2.6 Hz), 7.16 (1H, dd, J=8.6, 4.0 Hz), 6.98 (1H, d, J=7.9 Hz), 6.84 (1H, d, J=8.6 Hz), 5.92 (2H, br s), 5.21 (1H, quintet, J=7.3 Hz), 4.74 (2H, q, J=8.6 Hz), 1.60 (3H, d, J=7.3 Hz), MS (ESI) m/z: 339 (M−H)$^-$.

<Step-2>: 3-isobutyramido-N-(1-(6-(2,2,2-trifluoroethoxy)pyridin-3-yl)ethyl)picolinamide (Example-231, single enantiomer)

The title compound is prepared in 52% yield (15 mg) from 3-amino-N-(1-(6-(2,2,2-trifluoroethoxy)pyridin-3-yl)ethyl)picolinamide (24 mg, 0.071 mmol, Step-1, single enantiomer) and isobutyryl chloride (23 mg, 0.21 mmol) by the similar manner in Step-2 of Example-8.

Example 232

2-acetamido-N-(1-(5-chloro-6-(2,2,2-trifluoroethoxy)pyridin-3-yl)ethyl)pyrimidine-4-carboxamide (single enantiomer)

The title compound is prepared from 2-amino-N-(1-(5-chloro-6-(2,2,2-trifluoroethoxy)pyridin-3-yl)ethyl)pyrimidine-4-carboxamide (20 mg, 0.05 mmol, Step-1 of Example 210, single enantiomer) and acetyl chloride (21 mg, 0.27 mmol) according to the procedure similar to that described in Step-2 of Example 8.

Example 234

2-acetamido-N-(1-(5-methyl-6-(2,2,2-trifluoroethoxy)pyridin-3-yl)ethyl)pyrimidine-4-carboxamide (single enantiomer)

The title compound is prepared from 2-amino-N-(1-(5-methyl-6-(2,2,2-trifluoroethoxy)pyridin-3-yl)ethyl)pyrimidine-4-carboxamide (20 mg, 0.06 mmol, Step-1 of Example 223, single enantiomer) and acetyl chloride (22 mg, 0.28 mmol) according to the procedure similar to that described in Step-2 of Example 8.

Example 250

2-isobutyramido-N-(1-(6-(2,2,2-trifluoroethoxy)pyridin-3-yl)ethyl)pyrimidine-4-carboxamide (single enantiomer)

The title compound is prepared from 2-amino-N-(1-(6-(2,2,2-trifluoroethoxy)pyridin-3-yl)ethyl)pyrimidine-4-carboxamide (20 mg, 0.06 mmol, Step-1 of Example 97, single enantiomer) and isobutyryl chloride (31 mg, 0.29 mmol) according to the procedure similar to that described in Step-2 of Example 8.

Example 253

6-propionamido-N-(1-(6-(2,2,2-trifluoroethoxy)pyridin-3-yl)ethyl)picolinamide (single enantiomer <Step-1>: 6-amino-N-(1-(6-(2,2,2-trifluoroethoxy)pyridin-3-yl)ethyl)picolinamide (single enantiomer)

The title compound is prepared in 28% yield (75 mg, slight brown syrup) from (−)-1-(6-(2,2,2-trifluoroethoxy)pyridin-3-yl)ethanamine hydrochloride (200 mg, 0.78 mmol, Amine-1, single enantiomer) and 6-aminopicolinic acid (108 mg, 0.78 mmol) by the similar manner in Step-1 of Example-8. MS (ESI) m/z: 341 (M+H)$^+$, 339 (M−H)$^-$.

<Step-2>: 6-propionamido-N-(1-(6-(2,2,2-trifluoroethoxy)pyridin-3-yl)ethyl)picolinamide (Example-253, single enantiomer)

The title compound is prepared in 18% yield (5.1 mg) from 6-amino-N-(1-(6-(2,2,2-trifluoroethoxy)pyridin-3-yl)ethyl)picolinamide (25 mg, 0.073 mmol, Step-1, single enantiomer) and propionyl chloride (24 mg, 0.26 mmol) by the similar manner in Step-2 of Example-8.

The following examples, Examples 254 and 255 (single enantiomer) are prepared according to the procedure similar to that described in Example 253, using the appropriate acid chloride such as cyclopropanecarbonyl chloride and isobutyryl chloride instead of propionyl chloride, respectively.

Example 274

(R)-2-propionamido-N-(1-(3-(trifluoromethyl)phenyl)ethyl)pyrimidine-4-carboxamide <Step-1>: (R)-2-amino-N-(1-(3-(trifluoromethyl)phenyl)ethyl)pyrimidine-4-carboxamide The title compound is prepared in 72% yield (161 mg, a white solid) from (R)-1-(3-(trifluoromethyl)phenyl)ethanamine (136 mg, 0.72 mmol) and 2-aminopyrimidine-4-carboxylic acid (100 mg, 0.72 mmol) by the similar manner in Step-1 of Example 8.

$^1$H-NMR (300 MHz, CDCl$_3$) delta 8.53 (1H, d, J=4.4 Hz), 8.15-8.02 (1H, m), 7.7-7.4 (4H, m), 7.42 (1H, d, J=5.1 Hz), 5.32 (1H, quintet, J=7.3 Hz), 5.12 (2H, br s), 1.64 (3H, d, J=7.3 Hz), MS (ESI) m/z: 311 (M+H)$^+$, 309 (M−H)$^-$.

<Step-2>: (R)-2-propionamido-N-(1-(3-(trifluoromethyl)phenyl)ethyl)pyrimidine-4-carboxamide (Example-274, single enantiomer)

The title compound is prepared from (R)-2-amino-N-(1-(3-(trifluoromethyl)phenyl)ethyl)pyrimidine-4-carboxamide (20 mg, 0.06 mmol, Step-1) and propionyl chloride (18 mg, 0.19 mmol) according to the procedure similar to that described in Step-2 of Example 8.

The following examples, Example 275 and 276 (single enantiomer) are prepared according to the procedure similar to that described in Example 274, using isobutyryl chloride and cyclobutanecarbonyl chloride instead of propionyl chloride, respectively.

Example 277

2-acetamido-N-(3-(trifluoromethoxy)benzyl)pyrimidine-4-carboxamide

<Step-1>: 2-amino-N-(3-(trifluoromethoxy)benzyl)pyrimidine-4-carboxamide

The title compound is prepared in 37% yield (82 mg, a white solid) from (3-(trifluoromethoxy)phenyl)methanamine (137 mg, 0.72 mmol) and 2-aminopyrimidine-4-carboxylic acid (100 mg, 0.72 mmol) by the similar manner in Step-1 of Example 8.

$^1$H-NMR (300 MHz, CDCl$_3$) delta 8.55 (1H, d, J=5.1 Hz), 8.19 (1H, br s), 7.47 (1H, d, J=4.4 Hz), 7.40 (1H, t, J=8.1 Hz), 7.35-7.10 (3H, m), 5.11 (2H, br s), 4.65 (2H, d, J=6.6 Hz), MS (ESI) m/z: 313 (M+H)$^+$, 311 (M−H)$^-$.

<Step-2>: 2-acetamido-N-(3-(trifluoromethoxy)benzyl)pyrimidine-4-carboxamide (Example-277)

The title compound is prepared from 2-amino-N-(3-(trifluoromethoxy)benzyl)pyrimidine-4-carboxamide (15 mg, 0.05 mmol, Step-1) and acetyl chloride (11 mg, 0.14 mmol) according to the procedure similar to that described in Step-2 of Example 8.

The following examples, Example 278, 279, 280 are prepared according to the procedure similar to that described in Example 277, using propionyl chloride, isobutyryl chloride, and cyclobutanecarbonyl chloride instead of acetyl chloride, respectively.

Example 297

2-acetamido-N-(1-(3-(trifluoromethoxy)phenyl)ethyl)pyrimidine-4-carboxamide (single enantiomer)

Step-1

2-amino-N-(1-(3-(trifluoromethoxy)phenyl)ethyl)pyrimidine-4-carboxamide (single enantiomer)

The title compound is prepared in 76% yield (134 mg, a white solid) from (+)-(3-(trifluoromethoxy)phenyl)methanamine hydrochloride (130 mg, 0.54 mmol, Amine-9, single enantiomer) and 2-aminopyrimidine-4-carboxylic acid (75 mg, 0.54 mmol) by the similar manner in Step-1 of Example 8.

$^1$H-NMR (300 MHz, CDCl$_3$) delta 8.51 (1H, d, J=5.1 Hz), 8.04 (1H, d, J=8.0 Hz), 7.41 (1H, d, J=5.1 Hz), 7.39-7.30 (2H, m), 7.21 (1H, s), 7.13 (1H, d, J=8.1 Hz), 5.28 (1H, quintet, J=8.1 Hz), 5.09 (2H, br s), 1.61 (3H, d, J=7.3 Hz), MS (ESI) m/z: 327 (M+H)$^+$, 325 (M−H)$^-$.

<Step-2>: 2-acetamido-N-(1-(3-(trifluoromethoxy)phenyl)ethyl)pyrimidine-4-carboxamide (Example-297, single enantiomer)

The title compound is prepared from 2-amino-N-(1-(3-(trifluoromethoxy)phenyl)ethyl)pyrimidine-4-carboxamide (15 mg, 0.05 mmol, Step-1, single enantiomer) and acetyl chloride (4 mg, 0.05 mmol) according to the procedure similar to that described in Step-2 of Example 8.

The following examples, Example 298, 300, 301 (single enantiomer) are prepared according to the procedure similar to that described in Example 297, using propionyl chloride, isobutyryl chloride, and cyclobutanecarbonyl chloride instead of acetyl chloride, respectively.

Example 381

2-acetamido-N-(1-(3-(2,2,2-trifluoroethoxy)phenyl) ethyl)pyrimidine-4-carboxamide (single enantiomer)

<Step-1>: 2-amino-N-(1-(3-(2,2,2-trifluoroethoxy) phenyl)ethyl)pyrimidine-4-carboxamide (single enantiomer)

The title compound is prepared in 42% yield (102 mg, a white solid) from 1-(3-(2,2,2-trifluoroethoxy)phenyl)ethanamine hydrochloride (139 mg, 0.72 mmol, Amine-16, single enantiomer) and 2-aminopyrimidine-4-carboxylic acid (100 mg, 0.72 mmol) by the similar manner in Step-1 of Example 8.

$^1$H-NMR (300 MHz, CDCl$_3$) delta 8.50 (1H, d, J=5.1 Hz), 8.03 (1H, d, J=7.3 Hz), 7.40 (1H, d, J=4.4 Hz), 7.31 (1H, t, J=8.0 Hz), 7.07 (1H, d, J=8.1 Hz), 6.98 (1H, d, J=2.2 Hz), 6.83 (1H, dd, J=8.1, 2.2 Hz), 5.24 (1H, quintet, J=7.3 Hz), 5.10 (2H, br s), 4.35 (2H, q, J=8.1 Hz), 1.60 (3H, d, J=7.3 Hz), MS (ESI) m/z: 341 (M+H)$^+$, 339 (M−H)$^-$.

<Step-2>: 2-acetamido-N-(1-(3-(2,2,2-trifluoroethoxy)phenyl)ethyl)pyrimidine-4-carboxamide (Example-381, single enantiomer)

The title compound is prepared from 2-amino-N-(1-(3-(2,2,2-trifluoroethoxy)phenyl)ethyl)pyrimidine-4-carboxamide (15 mg, 0.04 mmol, Step-1, single enantiomer) and acetyl chloride (10 mg, 0.13 mmol) according to the procedure similar to that described in Step-2 of Example 8.

The following examples, Example 382, 383 (single enantiomer) are prepared according to the procedure similar to that described in Example 381, using propionyl chloride and isobutyryl chloride, instead of acetyl chloride, respectively.

Example 398

2-isobutyramido-N-((6-(2,2,2-trifluoroethoxy)pyridin-3-yl)methyl)pyrimidine-4-carboxamide <Step-1>: 2-amino-N-((6-(2,2,2-trifluoroethoxy) pyridin-3-yl)methyl)pyrimidine-4-carboxamide The title compound is prepared in 22% yield (42 mg, a white solid) from (6-(2,2,2-trifluoroethoxy)pyridin-3-yl) methanamine hydrochloride (140 mg, 0.58 mmol) and 2-aminopyrimidine-4-carboxylic acid (80 mg, 0.58 mmol) by the similar manner in Step-1 of Example 8.

$^1$H-NMR (270 MHz, CDCl$_3$) delta 8.53 (1H, d, J=4.4 Hz), 8.13 (1H, d, J=2.2 Hz), 8.11 (1H, br s), 7.67 (1H, dd, J=8.1, 2.2 Hz), 7.44 (1H, d, J=5.1 Hz), 6.86 (1H, d, J=8.8 Hz), 5.08 (2H, br s), 4.76 (2H, q, J=8.8 Hz), 4.57 (2H, d, J=6.6 Hz), MS (ESI) m/z: 328 (M+H)$^+$, 326 (M−H)$^-$.

<Step-2>: 2-isobutyramido-N-((6-(2,2,2-trifluoroethoxy)pyridin-3-yl)methyl)pyrimidine-4-carboxamide (Example-398)

The title compound is prepared from 2-amino-N-((6-(2,2,2-trifluoroethoxy)pyridin-3-yl)methyl)pyrimidine-4-carboxamide (17 mg, 0.05 mmol, Step-1) and isobutyryl chloride (17 mg, 0.16 mmol) according to the procedure similar to that described in Step-2 of Example 8.

Example 399

2-acetamido-N-(1-(5-methoxy-6-(2,2,2-trifluoroethoxy)pyridin-3-yl)ethyl)pyrimidine-4-carboxamide (single enantiomer)

<Step-1>: 2-amino-N-(1-(5-methoxy-6-(2,2,2-trifluoroethoxy)pyridin-3-yl)ethyl)pyrimidine-4-carboxamide (single enantiomer)

The title compound is prepared in 51% yield (95 mg, a white solid) from 1-(5-methoxy-6-(2,2,2-trifluoroethoxy)pyridin-3-yl)ethanamine hydrochloride (144 mg, 0.50 mmol, Amine-22, single enantiomer) and 2-aminopyrimidine-4-carboxylic acid (70 mg, 0.50 mmol) by the similar manner in Step-1 of Example 8.

$^1$H-NMR (300 MHz, CDCl$_3$) delta 8.51 (1H, d, J=5.1 Hz), 8.00 (1H, d, J=8.1 Hz), 7.74 (1H, d, J=2.2 Hz), 7.40 (1H, d, J=5.1 Hz), 7.13 (1H, d, J=2.2 Hz), 5.24 (1H, quintet, J=7.3 Hz), 5.14 (2H, br s), 4.83 (2H, q, J=8.8 Hz), 3.88 (3H, s), 1.63 (3H, d, J=6.6 Hz), MS (ESI) m/z: 372 (M+H)$^+$, 370 (M−H)$^-$.

<Step-2>: 2-acetamido-N-(1-(5-methoxy-6-(2,2,2-trifluoroethoxy)pyridin-3-yl)ethyl)pyrimidine-4-carboxamide (Example-399, single enantiomer)

The title compound is prepared from 2-amino-N-(1-(5-methoxy-6-(2,2,2-trifluoroethoxy)pyridin-3-yl)ethyl)pyrimidine-4-carboxamide (15 mg, 0.04 mmol, Step-1, single enantiomer) and acetyl chloride (10 mg, 0.12 mmol) according to the procedure similar to that described in Step-2 of Example 8.

The following example, Example 401 (single enantiomer) is prepared according to the procedure similar to that described in Step-2 of Example 8, using isobutyryl chloride instead of acetyl chloride.

Example 406

2-isobutyramido-N-(1-(4-(2,2,2-trifluoroethoxy) phenyl)ethyl)pyrimidine-4-carboxamide (single enantiomer)

<Step-1>: 2-amino-N-(1-(4-(2,2,2-trifluoroethoxy) phenyl)ethyl)pyrimidine-4-carboxamide (single enantiomer)

The title compound is prepared in 32% yield (78 mg, a white solid) from 1-(4-(2,2,2-trifluoroethoxy)phenyl)ethanamine hydrochloride (184 mg, 0.72 mmol, Amine-18, single enantiomer) and 2-aminopyrimidine-4-carboxylic acid (100 mg, 0.72 mmol) by the similar manner in Step-1 of Example 8.

$^1$H-NMR (270 MHz, CDCl$_3$) delta 8.50 (1H, d, J=4.0 Hz), 8.00 (1H, d, J=7.9 Hz), 7.41 (1H, d, J=5.9 Hz), 7.35 (2H, d, J=8.6 Hz), 6.92 (2H, d, J=7.9 Hz), 5.23 (1H, quintet, J=7.2 Hz), 5.11 (2H, br s), 4.34 (2H, q, J=7.9 Hz), 1.59 (3H, d, J=6.6 Hz),
MS (ESI) m/z: 339 (M−H)$^-$.

<Step-2>: 2-isobutyramido-N-(1-(4-(2,2,2-trifluoroethoxy)phenyl)ethyl)pyrimidine-4-carboxamide (Example-406, single enantiomer)

The title compound is prepared from 2-amino-N-(1-(4-(2,2,2-trifluoroethoxy)phenyl)ethyl)pyrimidine-4-carboxamide (15 mg, 0.04 mmol, Step-1, single enantiomer) and isobutyryl chloride (14 mg, 0.13 mmol) according to the procedure similar to that described in Step-2 of Example 8.

Example 409

2-acetamido-N-((5-chloro-6-(2,2,2-trifluoroethoxy) pyridin-3-yl)methyl)pyrimidine-4-carboxamide <Step-1>: 2-amino-N-((5-chloro-6-(2,2,2-trifluoroethoxy)pyridin-3-yl)methyl)pyrimidine-4-carb oxamide The title compound is prepared in 17% yield (43 mg, pale yellow oil) from (5-chloro-6-(2,2,2-trifluoroethoxy)pyridin-3-yl)methanamine hydrochloride (199 mg, 0.72 mmol, Amine-19) and 2-aminopyrimidine-4-carboxylic acid (100 mg, 0.72 mmol) by the similar manner in Step-1 of Example 8.

$^1$H-NMR (300 MHz, CDCl$_3$) delta 8.53 (1H, d, J=5.1 Hz), 8.16 (1H, br s), 8.03 (1H, s), 7.73 (1H, s), 7.43 (1H, d, J=4.4 Hz), 5.10 (2H, br s), 4.84 (2H, q, J=10.3 Hz), 4.56 (2H, d, J=6.6 Hz), MS (ESI) m/z: 362 (M+H)$^+$, 360 (M−H)$^-$.

<Step-2>: 2-acetamido-N-((5-chloro-6-(2,2,2-trifluoroethoxy)pyridin-3-yl)methyl)pyrimidine-4-carboxamide (Example-409)

The title compound is prepared from 2-amino-N-((5-chloro-6-(2,2,2-trifluoroethoxy)pyridin-3-yl)methyl)pyrimidine-4-carboxamide (10 mg, 0.03 mmol, Step-1) and acetyl chloride (7 mg, 0.08 mmol) according to the procedure similar to that described in Step-2 of Example 8.

The following example, Example 410 and 412 are prepared according to the procedure similar to that described in Example 409, using propionyl chloride and isobutyryl chloride instead of acetyl chloride, respectively.

Example 445

2-(hydroxymethyl)-N-(1-(5-methyl-6-(2,2,2-trifluoroethoxy)pyridin-3-yl)ethyl)-6-propionamidoisonicotinamide (single enantiomer)

<Step-1>: 2-(acetoxymethyl)-6-chloroisonicotinic acid

A mixture of methyl 2-(bromomethyl)-6-chloroisonicotinate and sodium acetate in N,N-dimethylacetamide is stirred at 120° C. for 2 hours. The mixture is cooled to room temperature and diluted with water (50 mL). The mixture is washed with ethyl acetate/toluene (2:1, 80 mL×2). Water layer is acidified (to pH 4) by the addition of 2M hydrochloric acid, extracted with ethyl acetate (80 mL×2), dried over sodium sulfate. The organic solvent is removed under reduced pressure to give the title compound as a crude product (590 mg, clear brown oil, include N,N-dimethylacetamide). This is used without purification in the next step.

<Step-2>: (6-chloro-4-((1-(5-methyl-6-(2,2,2-trifluoroethoxy)pyridin-3-yl)ethyl)carbamoyl)pyridin-2-yl) methyl acetate (single enantiomer)

The title compound is prepared in 21% yield (100 mg, a yellow solid) from 1-(5-methyl-6-(2,2,2-trifluoroethoxy)pyridin-3-yl)ethanamine hydrochloride (295 mg, 1.1 mmol, Amine-17, single enantiomer) and 2-(acetoxymethyl)-6-chloroisonicotinic acid (500 mg, 1.1 mmol, Step-1) by the similar manner in Step-1 of Example 8.

$^1$H-NMR (270 MHz, CDCl$_3$) delta 8.00 (1H, s), 7.58 (1H, s), 7.52 (1H, s), 7.47 (1H, s), 6.40-6.28 (1H, m), 5.26 (1H, quintet, J=6.6 Hz), 5.20 (2H, s), 4.76 (2H, q, J=8.6 Hz), 2.25 (3H, s), 2.18 (3H, s), 1.61 (3H, d, J=7.3 Hz), MS (ESI) m/z: 446 (M+H)$^+$, 444 (M−H)$^-$.

<Step-3>: 2-chloro-6-(hydroxymethyl)-N-(1-(5-methyl-6-(2,2,2-trifluoroethoxy)pyridin-3-yl)ethyl) isonicotinamide (single enantiomer)

To a stirred solution of (6-chloro-4-((1-(5-methyl-6-(2,2,2-trifluoroethoxy)pyridin-3-yl)ethyl)carbamoyl)pyridin-2-yl)methyl acetate (95 mg, 0.21 mmol, Step-2, single enantiomer) in THF (5 mL) is added 2M aqueous sodium hydroxide solution (0.16 mL, 0.32 mmol) at room temperature, and the mixture is stirred at room temperature for 1 day. The reaction mixture is neutralized with 2M hydrochloric acid (0.16 mL, 0.32 mmol) and extracted with dichloromethane (50 mL×2). The organic layer is washed with brine, dried over sodium sulfate. The organic solvent is removed under reduced pressure to give 72 mg (84% yield) of the title compound as yellow oil.

$^1$H-NMR (300 MHz, CDCl$_3$) delta 7.99 (1H, s), 7.58 (1H, s), 7.55 (1H, s), 7.46 (1H, s), 6.66 (1H, d, J=7.3 Hz), 5.30-5.15 (1H, m), 4.80-4.70 (4H, m), 3.78-3.70 (1H, m), 2.23 (3H, s), 1.61 (3H, d, J=7.3 Hz), MS (ESI) m/z: 404 (M+H)$^+$, 402 (M−H)$^-$.

<Step-4>: 2-(hydroxymethyl)-N-(1-(5-methyl-6-(2,2,2-trifluoroethoxy)pyridin-3-yl)ethyl)-6-propionamidoisonicotinamide (Example-445, single enantiomer)

A mixture of 2-chloro-6-(hydroxymethyl)-N-(1-(5-methyl-6-(2,2,2-trifluoroethoxy)pyridin-3-yl)ethyl)isonicotinamide (17 mg, 0.04 mmol, Step-3, single enantiomer), propionamide (6 mg, 0.08 mmol), tris(dibenzylideneacetone) dipalladium(0) (1 mg, 0.8 microM), 4,5-bis (diphenylphosphino)-9,9-dimethylxanthene (1.5 mg, 2.5 microM), tripotassium phosphate (11 mg, 0.05 mmol) and 1,4-dioxane (1 mL) is heated by microwave irradiation at 150° C. for 1 hour. After cooling to room temperature, the mixture is filtered through a pad of celite. The filtrate is concentrated under reduced pressure and the residue is diluted with methanol (4 mL) and applied onto a strong cation exchange cartridge (BondElute(registered trademark) SCX, 1 g/6 mL, Varian Inc.), and the solid phase matrix is rinsed with methanol (5 mL). The crude mixture is eluted with 1M ammonia in methanol (5 mL) and concentrated under reduced pressure and then by preparative LC-MS to give 4.4 mg (24% yield) of the title compound.

The following example, Example 446 and 447 (single enantiomer) are prepared according to the procedure similar to that described in Step-4 of Example 445, using cyclopropanecarboxamide and isobutyramide instead of propionamide, respectively.

Example 452

2-(cyclobutanecarboxamido)-6-methyl-N-(1-(6-(2,2,2-trifluoroethoxy)pyridin-3-yl)ethyl)isonicotinamide (single enantiomer)

<Step-1>: 2-amino-6-methyl-N-(1-(6-(2,2,2-trifluoroethoxy)pyridin-3-yl)ethyl)isonicotinamide (single enantiomer)

The title compound is prepared in 71% yield (413 mg, a brown solid) from (−)-1-(6-(2,2,2-trifluoroethoxy)pyridin-3- yl)ethanamine hydrochloride (422 mg, 1.6 mmol, Amine-1, single enantiomer) and 2-amino-6-methylisonicotinic acid (250 mg, 1.6 mmol) by the similar manner in Step-1 of Example 8.

$^1$H-NMR (270 MHz, CDCl$_3$) delta 8.17 (1H, s), 7.65 (1H, d, J=8.6 Hz), 6.85 (1H, d, J=8.6 Hz), 6.70 (1H, s), 6.64 (1H, s), 6.26-6.18 (1H, m), 5.30-5.20 (1H, m), 4.75 (2H, q, J=8.6 Hz), 4.53 (2H, br s), 2.42 (3H, s), 1.61 (3H, d, J=7.3 Hz), MS (ESI) m/z: 355 (M+H)$^+$, 353 (M−H)$^−$.

<Step-2>: 2-(cyclobutanecarboxamido)-6-methyl-N-(1-(6-(2,2,2-trifluoroethoxy)pyridin-3-yl)ethyl)isonicotinamide (Example-452, single enantiomer)

The title compound is prepared from 2-amino-6-methyl-N-(1-(6-(2,2,2-trifluoroethoxy)pyridin-3-yl)ethyl)isonicotinamide (Step-1, single enantiomer) and cyclobutanecarbonyl chloride according to the procedure similar to that described in Step-2 of Example 8.

The following example, Example 459, 482, 571 (single enantiomer) are prepared according to the procedure similar to that described in Example 452, using cyclopentanecarbonyl chloride, acryloyl chloride, methacryloyl chloride instead of cyclobutanecarbonyl chloride.

Example 456

6-methyl-N-(1-(5-methyl-6-(2,2,2-trifluoroethoxy)pyridin-3-yl)ethyl)-2-(oxazol-2-ylamino)pyrimidine-4-carboxamide (single enantiomer)

<Step-1>: 2-chloro-6-methyl-N-(1-(5-methyl-6-(2,2,2-trifluoroethoxy)pyridin-3-yl)ethyl)pyrimidine-4-carboxamide (single enantiomer)

The title compound is prepared in 69% yield (296 mg, clear colorless oil) from 1-(5-methyl-6-(2,2,2-trifluoroethoxy)pyridin-3-yl)ethanamine hydrochloride (300 mg, 1.1 mmol, Amine-17, single enantiomer) and 2-chloro-6-methylpyrimidine-4-carboxylic acid (191 mg, 1.1 mmol) by the similar manner in Step-1 of Example 8.

$^1$H-NMR (300 MHz, CDCl$_3$) delta 8.10-7.93 (2H, m), 7.90 (1H, s), 7.47 (1H, s), 5.28-5.15 (1H, m), 4.76 (2H, q, J=8.8 Hz), 2.63 (3H, s), 2.24 (3H, s), 1.63 (3H, d, J=6.6 Hz), MS (ESI) m/z: 389 (M+H)$^+$, 387 (M−H)$^−$.

<Step-2>: 6-methyl-N-(1-(5-methyl-6-(2,2,2-trifluoroethoxy)pyridin-3-yl)ethyl)-2-(oxazol-2-ylamino)pyrimidine-4-carboxamide (Example-456, single enantiomer)

The title compound is prepared from 2-chloro-6-methyl-N-(1-(5-methyl-6-(2,2,2-trifluoroethoxy)pyridin-3-yl)ethyl)pyrimidine-4-carboxamide (25 mg, 0.06 mmol, Step-1, single enantiomer) and oxazol-2-amine (16 mg, 0.19 mmol) according to the procedure similar to that described in Step-4 of Example 445.

Example 457

N-(1-(5-chloro-6-(2,2,2-trifluoroethoxy)pyridin-3-yl)ethyl)-2-methyl-6-(oxazol-2-ylamino)isonicotinamide (single enantiomer)

<Step-1>: 2-bromo-N-(1-(5-chloro-6-(2,2,2-trifluoroethoxy)pyridin-3-yl)ethyl)-6-methylisonicotinamide (single enantiomer)

The title compound is prepared in 83% yield (387 mg, a yellow solid) from (+)-1-(5-chloro-6-(2,2,2-trifluoroethoxy)pyridin-3-yl)ethanamine hydrochloride (300 mg, 1.0 mmol, Amine-5, single enantiomer) and 2-bromo-6-methylisonicotinic acid (223 mg, 1.0 mmol) by the similar manner in Step-1 of Example 8.

$^1$H-NMR (300 MHz, CDCl$_3$) delta 8.08 (1H, d, J=2.2 Hz), 7.71 (1H, d, J=2.2 Hz), 7.56 (1H, s), 7.41 (1H, s), 6.27 (1H, d, J=7.3 Hz), 5.26 (1H, quintet, J=7.3 Hz), 4.82 (2H, q, J=7.9 Hz), 2.60 (3H, s), 1.63 (3H, d, J=6.6 Hz), MS (ESI) m/z: 452 (M+H)$^+$, 450 (M−H)$^−$.

<Step-2>: N-(1-(5-chloro-6-(2,2,2-trifluoroethoxy)pyridin-3-yl)ethyl)-2-methyl-6-(oxazol-2-ylamino)isonicotinamide (Example-457, single enantiomer)

The title compound is prepared from 2-bromo-N-(1-(5-chloro-6-(2,2,2-trifluoroethoxy)pyridin-3-yl)ethyl)-6-methylisonicotinamide (25 mg, 0.06 mmol, Step-1, single enantiomer) and oxazol-2-amine (16 mg, 0.19 mmol) according to the procedure similar to that described in Step-4 of Example 445.

Example 458

2-ethoxy-6-methyl-N-(1-(5-methyl-6-(2,2,2-trifluoroethoxy)pyridin-3-yl)ethyl)pyrimidine-4-carboxamide (single enantiomer)

A mixture of 2-chloro-6-methyl-N-(1-(5-methyl-6-(2,2,2-trifluoroethoxy)pyridin-3-yl)ethyl)pyrimidine-4-carboxamide (40 mg, 0.1 mmol, Step-1 of Example 456, single enantiomer) and cesium carbonate (50 mg, 0.15 mmol) in ethanol (2 mL) is heated by microwave irradiation at 160° C. for 1 hour. After cooled to room temperature, the mixture is concentrated under reduced pressure. The residue is suspended in ethyl acetate and filtered through a short column of amine gel eluting with ethyl acetate. The filtrate is concentrated and then by preparative LC-MS to give 17 mg (41% yield) of the title compound.

The following example, Example 472, 473, 474, 475 (single enantiomer) are prepared according to the procedure similar to that described in Example 458, using methanamine, dimethyamine, pyrrolidine, 2-methoxyethanamine, respectively in ethanol.

Example 476

N4-(1-(5-chloro-6-(2,2,2-trifluoroethoxy)pyridin-3-yl)ethyl)-N2-ethyl-6-methylpyridine-2,4-dicarboxamide (single enantiomer)

<Step-1>: methyl 4-((1-(5-chloro-6-(2,2,2-trifluoroethoxy)pyridin-3-yl)ethyl)carbamoyl)-6-methylpicolinate (single enantiomer)

The title compound is prepared from (+)-1-(5-chloro-6-(2,2,2-trifluoroethoxy)pyridin-3-yl)ethanamine hydrochloride (Amine-5, single enantiomer) and 2-(methoxycarbonyl)-6-methylisonicotinic acid by the similar manner in Step-1 of Example 8.

$^1$H-NMR (300 MHz, CDCl$_3$) delta 8.18 (1H, s), 8.09 (1H, s), 7.78-7.70 (2H, m), 6.84 (1H, d, J=7.3 Hz), 5.29 (1H, quintet, J=6.6 Hz), 4.81 (2H, q, J=8.8 Hz), 4.01 (3H, s), 2.68 (3H, s), 1.63 (3H, d, J=6.6 Hz), MS (ESI) m/z: 432 (M+H)$^+$, 430 (M−H)$^−$.

<Step-2>: 4-((1-(5-chloro-6-(2,2,2-trifluoroethoxy) pyridin-3-yl)ethyl)carbamoyl)-6-methylpicolinic acid (single enantiomer)

To a stirred solution of methyl 4-((1-(5-chloro-6-(2,2,2-trifluoroethoxy)pyridin-3-yl)ethyl)carbamoyl)-6-methylpicolinate (160 mg, 0.37 mmol, Step-1, single enantiomer) in THF (5 mL) is added 2M aqueous sodium hydroxide (0.74 mL) at room temperature. The mixture is stirred at 50° C. overnight. After cooled to room temperature, the mixture is neutralized with 2M hydrochloric acid (0.74 mL) and extracted with ethyl acetate (5 mL×5). Combined organic layers are dried over sodium sulfate and concentrated under reduced pressure to give 86 mg (56% yield) of the title compound as a yellow amorphous solid.

$^1$H-NMR (300 MHz, CDCl$_3$) delta 8.72 (1H, s), 8.32 (1H, d, J=7.3 Hz), 8.16 (1H, d, J=1.5 Hz), 8.06 (1H, s), 7.89 (1H, d, J=2.2 Hz), 7.78 (1H, br s), 5.34 (1H, quintet, J=7.3 Hz), 4.78 (2H, q, J=9.5 Hz), 2.69 (3H, s), 1.72 (3H, d, J=7.3 Hz), MS (ESI) m/z: 418 (M+H)$^+$, 416 (M−H)$^-$.

<Step-3>: N4-(1-(5-chloro-6-(2,2,2-trifluoroethoxy) pyridin-3-yl)ethyl)-N2-ethyl-6-methylpyridine-2,4-dicarboxamide (Example-476, single enantiomer)

The title compound is prepared from 4-((1-(5-chloro-6-(2,2,2-trifluoroethoxy)pyridin-3-yl)ethyl)carbamoyl)-6-methylpicolinic acid (15 mg, 0.04 mmol, Step-2, single enantiomer) and ethanamine hydrochloride by the similar manner in Example-2.

Example 477

N2,6-dimethyl-N4-(1-(5-methyl-6-(2,2,2-trifluoroethoxy)pyridin-3-yl)ethyl)pyridine-2,4-dicarboxamide (single enantiomer)

<Step-1>: methyl 6-methyl-4-((1-(5-methyl-6-(2,2,2-trifluoroethoxy)pyridin-3-yl)ethyl)carbamoyl)picolinate (single enantiomer)

The title compound is prepared in 72% yield (110 mg, clear colorless oil) from 1-(5-methyl-6-(2,2,2-trifluoroethoxy)pyridin-3-yl)ethanamine hydrochloride (97 mg, 0.36 mmol, Amine-17, single enantiomer) and 2-(methoxycarbonyl)-6-methylisonicotinic acid (70 mg, 0.36 mmol) by the similar manner in Step-1 of Example 8.

$^1$H-NMR (300 MHz, CDCl$_3$) delta 8.15 (1H, s), 8.01 (1H, d, J=2.2 Hz), 7.77 (1H, s), 7.47 (1H, d, J=2.2 Hz), 6.44 (1H, d, J=7.3 Hz), 5.40-5.20 (1H, m), 4.76 (2H, q, J=8.8 Hz), 4.03 (3H, s), 2.71 (3H, s), 2.24 (3H, s), 1.63 (3H, d, J=7.3 Hz), MS (ESI) m/z: 412 (M+H)$^+$, 410 (M−H)$^-$.

<Step-2>: 6-methyl-4-((1-(5-methyl-6-(2,2,2-trifluoroethoxy)pyridin-3-yl)ethyl)carbamoyl)picolinic acid (single enantiomer)

The title compound is prepared in 63% yield (64 mg, colorless oil) from methyl 6-methyl-4-(1-(5-methyl-6-(2,2,2-trifluoroethoxy)pyridin-3-yl)ethyl)carbamoyl)picolinate (110 mg, 0.26 mmol, Step-1, single enantiomer) by the similar manner in Step-2 of Example 476.

$^1$H-NMR (300 MHz, CDCl$_3$) delta 8.52 (1H, s), 8.06 (1H, s), 8.00 (1H, s), 7.61 (1H, d, J=7.4 Hz), 7.57 (1H, s), 6.28 (1H, br s), 5.30 (1H, quintet, J=7.3 Hz), 4.74 (2H, q, J=8.8 Hz), 2.67 (3H, s), 2.22 (3H, s), 1.67 (3H, d, J=6.6 Hz), MS (ESI) m/z: 398 (M+H)$^+$, 396 (M−H)$^-$.

<Step-3>: N2,6-dimethyl-N4-(1-(5-methyl-6-(2,2,2-trifluoroethoxy)pyridin-3-yl)ethyl)pyridine-2,4-dicarboxamide (Example-477, single enantiomer)

The title compound is prepared from 6-methyl-4-(1-(5-methyl-6-(2,2,2-trifluoroethoxy)pyridin-3-yl)ethyl)carbamoyl)picolinic acid (15 mg, 0.04 mmol, Step-2, single enantiomer) and methanamine by the similar manner in Example-2.

The following example, Example 478 (single enantiomer) is prepared according to the procedure similar to that described in Example 477 using ethanamine hydrochloride instead of methanamine.

Example 480

2-methyl-6-pivalamido-N-((6-(2,2,2-trifluoroethoxy) pyridin-3-yl)methyl)isonicotinamide

<Step-1>: 2-methyl-6-pivalamidoisonicotinic acid

To a stirred mixture of 2-amino-6-methylisonicotinic acid (150 mg, 0.99 mmol) and pyridine (310 mg, 3.9 mmol) in N,N-dimethylformamide (2.0 mL) is added pivaloyl chloride (240 mg, 2.0 mmol) at room temperature. The mixture is stirred overnight at room temperature, and diluted with saturated aqueous citric acid (10 mL). Whole is extracted with ethyl acetate/toluene (2:1, 10 mL×3). Combined organic layers are washed with water, brine, dried over sodium sulfate. The organic solvent is removed under reduced pressure to give 420 mg (quantitative yield) of the titled compound as a white solid.

MS (ESI) m/z: 237 (M+H)$^+$.

<Step-2>: 2-methyl-6-pivalamido-N-((6-(2,2,2-trifluoroethoxy)pyridin-3-yl)methyl)isonicotinamide (Example-480)

The title compound is prepared from 2-methyl-6-pivalamidoisonicotinic acid (30 mg, 0.06 mmol, Step-1) and (6-(2,2,2-trifluoroethoxy)pyridin-3-yl)methanamine hydrochloride (15 mg, 0.06 mmol) by the similar manner in Example 2.

Example 505

N2-ethyl-6-methyl-N4-(1-(5-methyl-6-(2,2,2-trifluoroethoxy)pyridin-3-yl)ethyl)pyrimidine-2,4-dicarboxamide (single enantiomer)

<Step-1>: methyl 4-methyl-6-((1-(5-methyl-6-(2,2,2-trifluoroethoxy)pyridin-3-yl)ethyl)carbamoyl)pyrimidine-2-carboxylate (single enantiomer)

The title compound is prepared in 24% yield (20 mg, clear colorless oil) from 2-chloro-6-methyl-N-(1-(5-methyl-6-(2,2,2-trifluoroethoxy)pyridin-3-yl)ethyl)pyrimidine-4-carboxamide (80 mg, 0.2 mmol, Step-1 of Example 456, single enantiomer) and methanol by the similar manner in Step-1 of Amine-63.

$^1$H-NMR (300 MHz, CDCl$_3$) delta 8.28 (1H, d, J=8.0 Hz), 8.12 (1H, s), 8.02 (1H, d, J=2.2 Hz), 5.30-5.20 (1H, m), 4.75 (2H, q, J=8.1 Hz), 4.07 (3H, s), 2.74 (3H, s), 2.23 (3H, s), 1.64 (3H, d, J=7.3 Hz), MS (ESI) m/z: 413 (M+H)$^+$, 411 (M−H)$^-$.

213

<Step-2>: 4-methyl-6-((1-(5-methyl-6-(2,2,2-trifluoroethoxy)pyridin-3-yl)ethyl)carbamoyl)pyrimidine-2-carboxylic acid (single enantiomer)

The title compound is prepared in >99% yield (50 mg, clear pale yellow oil) from methyl 4-methyl-6-(1-(5-methyl-6-(2,2,2-trifluoroethoxy)pyridin-3-yl)ethyl)carbamoyl)pyrimidine-2-carboxylate (53 mg, 0.1 mmol, Step-1, single enantiomer) by the similar manner in Step-2 of Example 476.
MS (ESI) m/z: 399 (M+H)$^+$, 397 (M−H)$^-$.

<Step-3>: N2-ethyl-6-methyl-N4-(1-(5-methyl-6-(2,2,2-trifluoroethoxy)pyridin-3-yl)ethyl)pyrimidine-2,4-dicarboxamide (Example-505, single enantiomer)

The title compound is prepared from 4-methyl-6-(1-(5-methyl-6-(2,2,2-trifluoroethoxy)pyridin-3-yl)ethyl)carbamoyl)pyrimidine-2-carboxylic acid (17 mg, 0.04 mmol, Step-2, single enantiomer) and ethanamine hydrochloride (21 mg, 0.26 mmol) by the similar manner in Example-2.

The following example, Example 506 (single enantiomer) is prepared according to the procedure similar to that described in Example 505 using propan-2-amine instead of ethanamine hydrochloride.

Example 507

6-methyl-2-(oxazol-2-ylamino)-N-((6-(2,2,2-trifluoroethoxy)pyridin-3-yl)methyl)pyrimidine-4-carboxamide <Step-1>: methyl 6-methyl-2-(oxazol-2-ylamino)pyrimidine-4-carboxylate The title compound is prepared in 22% yield (83 mg, a pale yellow solid) from methyl 2-chloro-6-methylpyrimidine-4-carboxylate (300 mg, 1.6 mmol) and oxazol-2-amine (200 mg, 2.4 mmol) by the similar manner in Step-1 of Carboxylic acid-4.
$^1$H-NMR (300 MHz, DMSO-d$_6$) delta 10.87 (1H, s), 7.85 (1H, s), 7.40 (1H, s), 7.09 (1H, s), 3.86 (3H, s), 2.44 (3H, s), MS (ESI) m/z: 235 (M+H)$^+$.

<Step-2>: 6-methyl-2-(oxazol-2-ylamino)pyrimidine-4-carboxylic acid

The title compound is prepared in quantitative yield (75 mg, a yellow solid) from methyl 6-methyl-2-(oxazol-2-ylamino)pyrimidine-4-carboxylate (80 mg, 0.3 mmol, Step-1) by the similar manner in Step-2 of Carboxylic acid-4.
MS (ESI) m/z: 221 (M+H)$^+$.

<Step-3>: 6-methyl-2-(oxazol-2-ylamino)-N-((6-(2,2,2-trifluoroethoxy)pyridin-3-yl)methyl)pyrimidine-4-carboxamide (Example-507)

The title compound is prepared from 6-methyl-2-(oxazol-2-ylamino)pyrimidine-4-carboxylic acid (25 mg, 0.11 mmol, Step-1) and (6-(2,2,2-trifluoroethoxy)pyridin-3-yl)methanamine hydrochloride (28 mg, 0.11 mmol) by the similar manner in Example-2.

214

Example 508

N2-ethyl-N4-((2-methoxy-6-(2,2,2-trifluoroethoxy)pyridin-3-yl)methyl)-6-methylpyridine-2,4-dicarboxamide <Step-1>: methyl 4-(((2-methoxy-6-(2,2,2-trifluoroethoxy)pyridin-3-yl)methyl)carbamoyl)-6-methylpicolinate The title compound is prepared from (2-methoxy-6-(2,2,2-trifluoroethoxy)pyridin-3-yl)methanamine hydrochloride (Amine-24) and 2-(methoxycarbonyl)-6-methylisonicotinic acid by the similar manner in Step-1 of Example 8.
MS (ESI) m/z: 414 (M+H)$^+$, 412 (M−H)$^-$.

<Step-2>: 4-(((2-methoxy-6-(2,2,2-trifluoroethoxy)pyridin-3-yl)methyl)carbamoyl)-6-methylpicolinic acid The title compound is prepared in 10% yield (36 mg, a brown amorphous solid) from methyl 4-(((2-methoxy-6-(2,2,2-trifluoroethoxy)pyridin-3-yl)methyl)carbamoyl)-6-methylpicolinate (360 mg, 0.87 mmol, Step-1) by the similar manner in Step-2 of Example 476.
MS (ESI) m/z: 400 (M+H)$^+$, 398 (M−H)$^-$.

<Step-3>: N2-ethyl-N-(4-(2-methoxy-6-(2,2,2-trifluoroethoxy)pyridin-3-yl)methyl)-6-methylpyridine-2,4-dicarboxamide (Example-508)

The title compound is prepared from 4-(((2-methoxy-6-(2,2,2-trifluoroethoxy)pyridin-3-yl)methyl)carbamoyl)-6-methylpicolinic acid (24 mg, 0.03 mmol, Step-2) and ethanamine hydrochloride (20 mg, 0.24 mmol) by the similar manner in Example-2.

The following examples, Example 509, 510 are prepared according to the procedure similar to that described in Example 508 using cyclopropanamine, propan-2-amine instead of ethanamine hydrochloride, respectively.

Example 511

N2,6-dimethyl-N4-(1-(3-(trifluoromethoxy)phenyl)ethyl)pyridine-2,4-dicarboxamide (single enantiomer)

<Step-1>: methyl 6-methyl-4-((1-(3-(trifluoromethoxy)phenyl)ethyl)carbamoyl)picolinate (single enantiomer The title compound is prepared from (+)-1-(3-(trifluoromethoxy)phenyl)ethanamine (Amine-9) and 2-(methoxycarbonyl)-6-methylisonicotinic acid by the similar manner in Step-1 of Example 8.
$^1$H-NMR (300 MHz, CDCl$_3$) delta 8.17 (1H, s), 7.77 (1H, s), 7.45-7.12 (4H, m), 6.45 (1H, br s), 3.53 (1H, quintet, J=7.3 Hz), 4.03 (3H, s), 2.72 (3H, s), 1.64 (3H, d, J=7.3 Hz), MS (ESI) m/z: 383 (M+H)$^+$, 381 (M−H)$^-$.

<Step-2>: 6-methyl-4-((1-(3-(trifluoromethoxy)phenyl)ethyl)carbamoyl)picolinic acid (single enantiomer)

The title compound is prepared in >99% yield (200 mg, a white solid) from methyl 6-methyl-4-((1-(3-(trifluoromethoxy)phenyl)ethyl)carbamoyl)picolinate (200 mg, 0.52 mmol, Step-1, single enantiomer) by the similar manner in Step-2 of Example 476.

$^1$H-NMR (300 MHz, DMSO-$d_6$) delta 9.22 (1H, d, J=7.3 Hz), 8.17 (1H, s), 7.54-7.35 (4H, m), 7.23 (1H, d, J=8.0 Hz), 5.20 (1H, quintet, J=7.3 Hz), 3.43 (3H, s), 1.48 (3H, d, J=6.6 Hz), MS (ESI) m/z: 369 (M+H)$^+$, 367 (M−H)$^−$.

<Step-3>: N2,6-dimethyl-N4-(1-(3-(trifluoromethoxy)phenyl)ethyl)pyridine-2,4-dicarboxamide (Example-511, single enantiomer)

The title compound is prepared from 6-methyl-4-((1-(3-(trifluoromethoxy)phenyl)ethyl)carbamoyl)picolinic acid (20 mg, 0.05 mmol, Step-2, single enantiomer) and methanamine (11 mg, 0.16 mmol) by the similar manner in Example-2.

The following examples, Example 512, 513, 514 (single enantiomer) are prepared according to the procedure similar to that described in Example 511 using ethanamine hydrochloride, propan-2-amine, ammonium chloride instead of methanamine, respectively.

Example 536

2-((3,4-dimethylisoxazol-5-yl)amino)-6-methyl-N-(1-(6-(2,2,2-trifluoroethoxy)pyridin-3-yl)ethyl)pyrimidine-4-carboxamide (single enantiomer)

<Step-1>: 2-chloro-6-methyl-N-(1-(6-(2,2,2-trifluoroethoxy)pyridin-3-yl)ethyl)pyrimidine-4-carb oxamide (single enantiomer)

The title compound is prepared in 74% yield (480 mg, clear colorless oil) from (−)-1-(6-(2,2,2-trifluoroethoxy)pyridin-3-yl)ethanamine hydrochloride (450 mg, 1.7 mmol, Amine-1, single enantiomer) and 2-chloro-6-methylpyrimidine-4-carboxylic acid (300 mg, 1.7 mmol) by the similar manner in Step-1 of Example 8.

$^1$H-NMR (300 MHz, CDCl$_3$) delta 8.18 (1H, d, J=2.2 Hz), 8.05-7.95 (1H, m), 7.90 (1H, s), 7.67 (1H, dd, J=8.8, 2.9 Hz), 6.86 (1H, d, J=8.0 Hz), 5.27 (1H, quintet, J=8.0 Hz), 4.74 (2H, q, J=8.8 Hz), 2.63 (3H, s), 1.64 (3H, d, J=7.3 Hz), MS (ESI) m/z: 375 (M+H)$^+$, 373 (M−H)$^−$.

<Step-2>: 2-((3,4-dimethylisoxazol-5-yl)amino)-6-methyl-N-(1-(6-(2,2,2-trifluoroethoxy)pyridin-3-yl)ethyl)pyrimidine-4-carboxamide (Example-536, single enantiomer)

The title compound is prepared from 2-chloro-6-methyl-N-(1-(6-(2,2,2-trifluoroethoxy)pyridin-3-yl)ethyl)pyrimidine-4-carb oxamide (20 mg, 0.05 mmol, Step-1, single enantiomer) and 3,4-dimethylisoxazol-5-amine (12 mg, 0.1 mmol) according to the procedure similar to that described in Step-4 of Example 445.

The following examples, Example 537, 538, 539, 540, 541 (single enantiomer) are prepared according to the procedure similar to that described in Example 536 using 1-methyl-1H-pyrazol-3-amine, 1,3-dimethyl-1H-pyrazol-5-amine, 5-(trifluoromethyl)-4H-1,2,4-triazol-3-amine, 3-methylisothiazol-5-amine hydrochloride, 4-(trifluoromethyl)oxazol-2-amine instead of 3,4-dimethylisoxazol-5-amine, respectively.

Example 569

2-methyl-6-(thiazol-2-yl)-N-(1-(6-(2,2,2-trifluoroethoxy)pyridin-3-yl)ethyl)isonicotinamide (single enantiomer)

<Step-1>: 2-bromo-6-methyl-N-(1-(6-(2,2,2-trifluoroethoxy)pyridin-3-yl)ethyl)isonicotinamide (single enantiomer)

The title compound is prepared in 29% yield (182 mg, a white solid) from (−)-1-(6-(2,2,2-trifluoroethoxy)pyridin-3-yl)ethanamine hydrochloride (200 mg, 0.78 mmol, Amine-1, single enantiomer) and 2-bromo-6-methylisonicotinic acid (269 mg, 1.95 mmol) by the similar manner in Step-1 of Example-8.

$^1$H-NMR (300 MHz, CDCl$_3$) delta 8.18 (1H, d, J=2.2 Hz), 7.66 (1H, dd, J=8.8, 2.2 Hz), 7.55 (1H, s), 7.41 (1H, s), 6.87 (1H, d, J=8.8 Hz), 6.28 (1H, d, J=7.3 Hz), 5.28 (1H, quintet, J=6.6 Hz), 4.76 (2H, q, J=8.8 Hz), 2.59 (3H, s), 1.63 (3H, d, J=6.6 Hz), MS (ESI) m/z: 418 (M+H)$^+$, 416 (M−H)$^−$.

<Step-2>: 2-methyl-6-(thiazol-2-yl)-N-(1-(6-(2,2,2-trifluoroethoxy)pyridin-3-yl)ethyl)isonicotinamide (Example-569, single enantiomer)

A mixture of 2-bromo-6-methyl-N-(1-(6-(2,2,2-trifluoroethoxy)pyridin-3-yl)ethyl)isonicotinamide (25 mg, 0.060 mmol, Step-1, single enantiomer), 2-tributylstannylthiazole (27 mg, 0.072 mmol), bis(triphenylphosphine)palladium(II) dichloride (8.4 mg, 0.012 mmol) and N,N-dimethylformamide (1 mL) is stirred at 120° C. under nitrogen atmosphere for 6 hours. After cooling to room temperature, the mixture is diluted with ethyl acetate (20 mL) and washed with water (20 mL). The organic layer is dried over sodium sulfate and concentrated under reduced pressure. The residue is purified by a strong cation exchange cartridge (BondElute(registered trademark) SCX, 1 g/6 mL, Varian Inc.) and then by preparative LC-MS to give 2.7 mg (11% yield) of the title compound.

Example 586

6-methyl-N-(1-(6-(2,2,2-trifluoroethoxy)pyridin-3-yl)ethyl)-2-((2,2,2-trifluoroethyl)amino)pyrimidine-4-carboxamide (single enantiomer)

A mixture of 2-chloro-6-methyl-N-(1-(6-(2,2,2-trifluoroethoxy)pyridin-3-yl)ethyl)pyrimidine-4-carb oxamide (50 mg, 0.13 mmol, Step-1 of Example 536, single enantiomer) and 2,2,2-trifluoroethanamine (3.5 mL) is heated at 100° C. for 4 days in a sealed tube. After cooled to room temperature, the mixture is concentrated and then purified by preparative LC-MS to give 7 mg (12% yield) of the title compound.

Example 663

2-(3-methylbutanamido)-N-((6-(2,2,2-trifluoroethoxy)pyridin-3-yl)methyl)isonicotinamide <Step-1>: 2-amino-N-((6-(2,2,2-trifluoroethoxy)pyridin-3-yl)methyl)isonicotinamide The title compound is prepared in 29% yield (182 mg, a white solid) from (6-(2,2,2-trifluoroethoxy)pyridin-3-yl)methanamine hydrochloride (473 mg, 1.95 mmol) and 2-aminoisonicotinic acid (269 mg, 1.95 mmol) by the similar manner in Step-1 of Example-8.

¹H-NMR (270 MHz, DMSO-d₆) delta 9.04 (1H, br s), 8.13 (1H, br s), 7.99-7.97 (1H, m), 7.76-7.72 (1H, m), 6.98-6.94 (1H, m), 6.83-6.80 (2H, m), 6.14 (2H, br s), 5.03-4.91 (2H, m), 4.40-4.38 (2H, m), MS (ESI) m/z: 327 (M+H)⁺, 325 (M−H)⁻.

<Step-2>: 2-(3-methylbutanamido)-N-((6-(2,2,2-trifluoroethoxy)pyridin-3-yl)methyl)isonicotinamide (Example-663)

The title compound is prepared from 2-amino-N-((6-(2,2,2-trifluoroethoxy)pyridin-3-yl)methyl)isonicotinamide (20 mg, 0.061 mmol, Step-1) and 3-methylbutanoyl chloride (74 mg, 0.61 mmol) by the similar manner in Step-2 of Example-8

Example 763

2-acetamido-N-((5-phenyl-6-(2,2,2-trifluoroethoxy)pyridin-3-yl)methyl)isonicotinamide <Step-1>: 2-acetamido-N-((5-bromo-6-(2,2,2-trifluoroethoxy)pyridin-3-yl)methyl)isonicotinamide The title compound is prepared in 61% yield (380 mg, a white solid) from (5-bromo-6-(2,2,2-trifluoroethoxy)pyridin-3-yl)methanamine hydrochloride (450 mg, 1.4 mmol, Amine-67) and 2-acetamidoisonicotinic acid (250 mg, 1.4 mmol) by the similar manner in Step-1 of Example 8.
¹H-NMR (300 MHz, CDCl₃) delta 8.43-8.35 (2H, m), 8.08 (1H, d, J=1.5 Hz), 8.03 (1H, br s), 7.92 (1H, d, J=2.2 Hz), 7.55 (1H, d, J=5.1 Hz), 6.91 (1H, br s), 4.80 (2H, q, J=8.8 Hz), 4.57 (2H, d, J=5.9 Hz), 2.24 (3H, s), MS (ESI) m/z: 447 (M+H)⁺.

<Step-2>: 2-acetamido-N-((5-phenyl-6-(2,2,2-trifluoroethoxy)pyridin-3-yl)methyl)isonicotinamide (Example-763)

A mixture of 2-acetamido-N-((5-bromo-6-(2,2,2-trifluoroethoxy)pyridin-3-yl)methyl)isonicotinamide (20 mg, 0.05 mmol, Step-1), phenylboronic acid (11 mg, 0.09 mmol), tetrakis(triphenylphosphine)palladium (3 mg, 2.2 microM) in dioxane (2 mL) is added saturated aqueous sodium hydrogencarbonate (0.4 mL). The mixture is heated at 100° C. for 1 hr. After cooled to room temperature, the mixture is extracted with ethyl acetate, dried over sodium sulfate. The organic solvent is removed under reduced pressure. The residue is purified by short column chromatography on amine gel eluting with ethylacetate, and then purified by preparative LC-MS to give 6 mg (30% yield) of the title compound.
The following examples, Example 764, 765, 766, 767, 768, 769, 770 are prepared according to the procedure similar to that described in Example 763 using (2-fluorophenyl)boronic acid, o-tolylboronic acid, (3-fluorophenyl)boronic acid, mtolylboronic acid, (4-fluorophenyl)boronic acid, 4,4,5,5-tetramethyl-2-(thiophen-3-yl)-1,3,2-dioxaborolane, furan-2-ylboronic acid instead of phenylboronic acid, respectively.

Example 919

5-chloro-2-propionamido-N-(1-(6-(2,2,2-trifluoroethoxy)pyridin-3-yl)ethyl)isonicotinamide (single enantiomer)

<Step-1>: 2-amino-5-chloro-N-(1-(6-(2,2,2-trifluoroethoxy)pyridin-3-yl)ethyl)isonicotinamide (single enantiomer)

The title compound is prepared in 39% yield (213 mg, a white solid) from (−)-1-(6-(2,2,2-trifluoroethoxy)pyridin-3-yl)ethanamine hydrochloride (379 mg, 1.48 mmol, Amine-1, single enantiomer) and 2-amino-5-chloroisonicotinic acid (280 mg, 1.62 mmol) by the similar manner in Step-1 of Example-8.
¹H-NMR (300 MHz, CDCl₃) delta 8.18 (1H, d, J=2.2 Hz), 8.07 (1H, s), 7.67 (1H, dd, J=8.8, 2.2 Hz), 6.87 (1H, d, J=8.8 Hz), 6.78 (1H, s), 6.61 (1H, d, J=7.3 Hz), 5.28 (1H, quintet, J=7.3 Hz), 4.76 (2H, q, J=8.8 Hz), 4.60 (2H, br s), 1.61 (3H, d, J=7.3 Hz), MS (ESI) m/z: 375 (M+H)⁺, 373 (M−H)⁻.

<Step-2>: 5-chloro-2-propionamido-N-(1-(6-(2,2,2-trifluoroethoxy)pyridin-3-yl)ethyl)isonicotinamide (Example-919, single enantiomer)

The title compound is prepared in 44% yield (10 mg) from 2-amino-5-chloro-N-(1-(6-(2,2,2-trifluoroethoxy)pyridin-3-yl)ethyl)isonicotinamide (20 mg, 0.053 mmol, single enantiomer, Step-1) and propionyl chloride (6 mg, 0.080 mmol) by the similar manner in Step-2 of Example-8.
The following examples, Examples 920 (single enantiomer) is prepared according to the procedure similar to that described in Example 919, using cyclopropanecarbonyl chloride instead of propionyl chloride.
The observed MS (positive or negative mode) and retention time by LC-MS of all examples are described in Table 1. Each chemical structure of Amine part for synthesis of Example is described as a free-base in Table 1. ¹H-NMR data of Example 8, 9, 11, 52, 60, 62, 169, 235, 483, 499, 531, 555, 557, and 558 are described in Table 2. Hydrochloride salts are prepared by treatment with 4 M HCl-EtOAc.

TABLE 1

| Example | Name | Chirality | Structure | Amine part | Carboxylic part | Observed MS | Retention time (min) |
|---|---|---|---|---|---|---|---|
| 1 | 2-acetamido-N-(1-(6-(2,2,2-trifluoroethoxy)pyridin-3-yl)ethyl)isonicotinamide | single enantiomer | 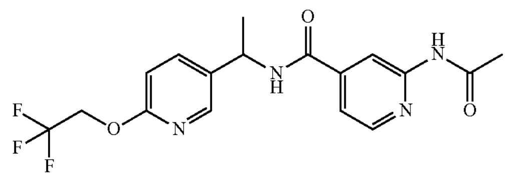 | Amine-1 | | 381.3 | 1.49 |
| 2 | 2-acetamido-N-((4-(2,2,2-trifluoroethoxy)pyridin-2-yl)methyl)isonicotinamide | | 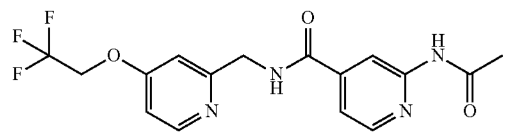 [SMILES: CC(=O)Nc1cc(C(=O)NCc2cc(OCC(F)(F)F)ccn2)ccn1] | Amine-2 | | 367.3 | 1.25 |
| 3 | N-((5-acetamido-6-(2,2,2-trifluoroethoxy)pyridin-3-yl)methyl)-3-(trifluoromethoxy)benzamide | | 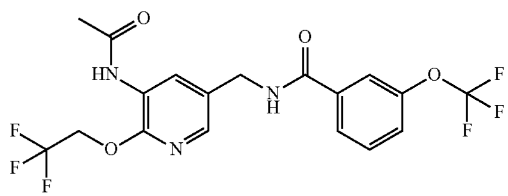 [SMILES: CC(=O)Nc1cc(CNC(=O)c2cccc(OC(F)(F)F)c2)cnc1OCC(F)(F)F] | Amine-15 | | 450.3 | 1.7 |
| 4 | 2-oxo-N-(1-(6-(2,2,2-trifluoroethoxy)pyridin-3-yl)ethyl)-2,3-dihydro-1H-benzo[d]imidazole-4-carboxamide | single enantiomer | 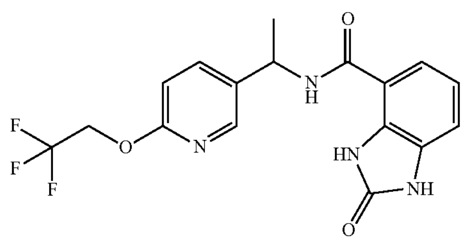 [SMILES: CC(NC(=O)c1cccc2[nH]c(=O)[nH]c12)c1ccc(OCC(F)(F)F)nc1] | Amine-1 | | 381.1 | 1.47 |

TABLE 1-continued

| Example | Chirality | Name | Structure | Amine part | Carboxylic part | Observed MS | Retention time (min) |
|---|---|---|---|---|---|---|---|
| 5 | single enantiomer | 2-methyl-N-(1-(6-(2,2,2-trifluoroethoxy)pyridin-3-yl)ethyl)-2H-indazole-3-carboxamide | 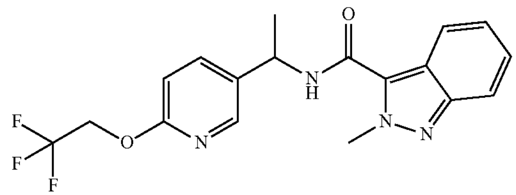 [SMILES: CC(NC(=O)c1c2ccccc2nn1C)c1ccc(OCC(F)(F)F)nc1] | Amine-1 | | 379.2 | 1.72 |
| 6 | single enantiomer | (R)-2-acetamido-N-(1-(4-(trifluoromethyl)phenyl)ethyl)isonicotinamide | 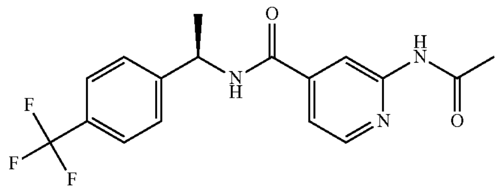 [SMILES: CC(=O)Nc1cc(C(=O)N[C@H](C)c2ccc(C(F)(F)F)cc2)ccn1] | | | 350.3 | 1.53 |
| 7 | single enantiomer | (R)-2-acetamido-N-(1-(3-(trifluoromethyl)phenyl)ethyl)isonicotinamide | 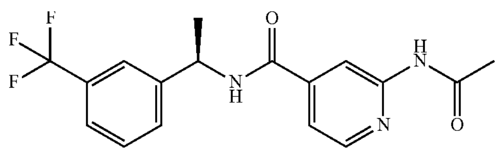 [SMILES: CC(=O)Nc1cc(C(=O)N[C@H](C)c2cccc(C(F)(F)F)c2)ccn1] | | | 352.2 | 1.52 |
| 8 | single enantiomer | 2-isobutyramido-N-(1-(6-(2,2,2-trifluoroethoxy)pyridin-3-yl)ethyl)isonicotinamide | 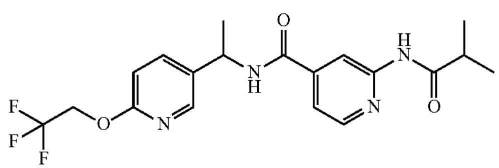 | | alternative route | 411.1 | 1.65 |
| 9 | single enantiomer | 2-(cyclopropanecarboxamido)-N-(1-(6-(2,2,2-trifluoroethoxy)pyridin-3-yl)ethyl)isonicotinamide | 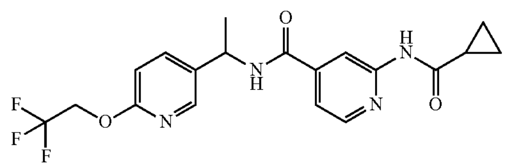 [SMILES: CC(NC(=O)c1ccnc(NC(=O)C2CC2)c1)c1ccc(OCC(F)(F)F)nc1] | Amine-1 | | 409.1 | 1.61 |

TABLE 1-continued

| Example | Name | Chirality | Structure | Amine part | Carboxylic part | Observed MS | Retention time (min) |
|---|---|---|---|---|---|---|---|
| 10 | 2-benzamido-N-(1-(6-(2,2,2-trifluoroethoxy)pyridin-3-yl)ethyl)isonicotinamide | single enantiomer | 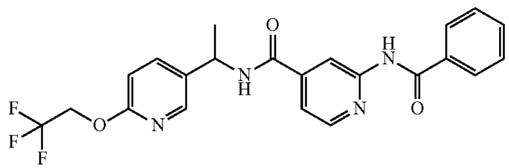 [SMILES: CC(NC(=O)c1ccnc(NC(=O)c2ccccc2)c1)c1ccc(OCC(F)(F)F)nc1] | alternative route | | 445.1 | 1.72 |
| 11 | 2-propionamido-N-(1-(6-(2,2,2-trifluoroethoxy)pyridin-3-yl)ethyl)isonicotinamide | single enantiomer | 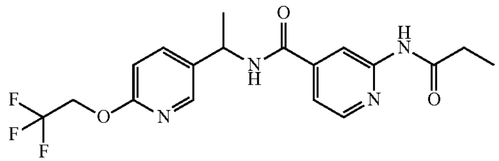 | Amine-1 | | 397.1 | 1.57 |
| 12 | 2-(methylsulfonamido)-N-(1-(6-(2,2,2-trifluoroethoxy)pyridin-3-yl)ethyl)benzamide | single enantiomer | 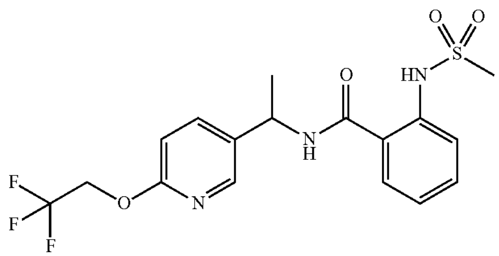 [SMILES: CC(NC(=O)c1ccccc1NS(C)(=O)=O)c1ccc(OCC(F)(F)F)nc1] | Amine-1 | | 418.1 | 1.7 |
| 13 | 3-(1H-imidazol-1-yl)-N-(1-(6-(2,2,2-trifluoroethoxy)pyridin-3-yl)ethyl)benzamide | single enantiomer | 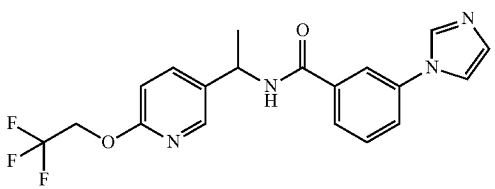 [SMILES: CC(NC(=O)c1cccc(-n2ccnc2)c1)c1ccc(OCC(F)(F)F)nc1] | Amine-1 | | 391.1 | 1.56 |

TABLE 1-continued

| Example | Name | Chirality | Structure | Amine part | Carboxylic part | Observed MS | Retention time (min) |
|---|---|---|---|---|---|---|---|
| 14 | 2-acetamido-N-((6-(2,2,2-trifluoroethoxy)pyridin-3-yl)methyl)isonicotinamide | | 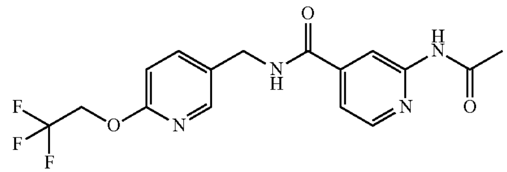 [SMILES: CC(=O)Nc1cc(C(=O)NCc2ccc(OCC(F)(F)F)nc2)ccn1] | | | 369.1 | 1.42 |
| 15 | N-(1-(6-(2,2,2-trifluoroethoxy)pyridin-3-yl)ethyl)quinoline-8-carboxamide | single enantiomer | 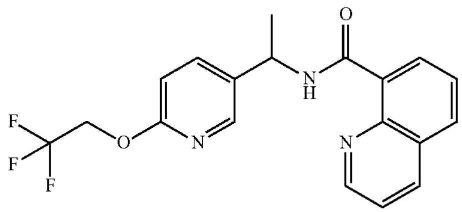 [SMILES: CC(NC(=O)c1cccc2cccnc12)c1ccc(OCC(F)(F)F)nc1] | Amine-1 | | 374.4 | 1.87 |
| 16 | N-(1-(6-(2,2,2-trifluoroethoxy)pyridin-3-yl)ethyl)quinoline-2-carboxamide | single enantiomer | 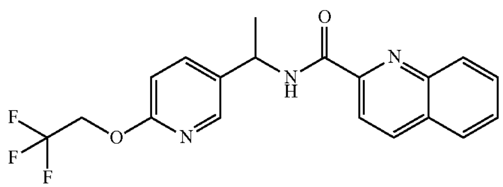 | Amine-1 | | 374.5 | 1.91 |
| 17 | 2-acetamido-N-((2-(2,2,2-trifluoroethoxy)pyridin-4-yl)methyl)isonicotinamide | | 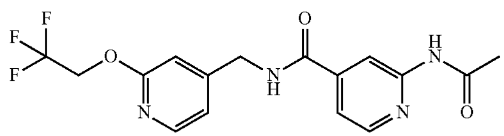 [SMILES: CC(=O)Nc1cc(C(=O)NCc2ccnc(OCC(F)(F)F)c2)ccn1] | | | 367.3 | 1.4 |
| 18 | 2-acetamido-N-(4-(trifluoromethoxy)benzyl)isonicotinamide | | 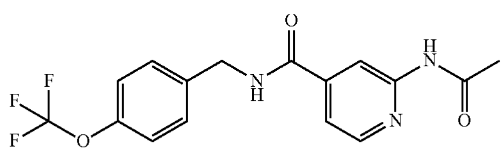 [SMILES: CC(=O)Nc1cc(C(=O)NCc2ccc(OC(F)(F)F)cc2)ccn1] | | | 352.4 | 1.5 |

TABLE 1-continued

| Example | Name | Chirality | Structure | Amine part | Carboxylic part | Observed MS | Retention time (min) |
|---|---|---|---|---|---|---|---|
| 19 | 3-acetamido-N-(1-(6-(2,2,2-trifluoroethoxy)pyridin-3-yl)ethyl)picolinamide | single enantiomer | 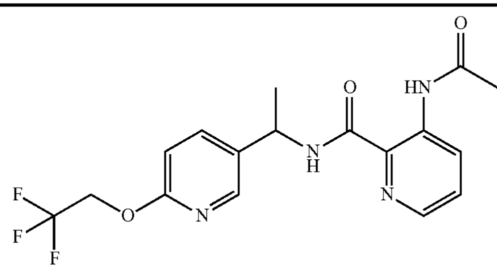 | Amine-1 | | 381.4 | 1.8 |
| 20 | 2-(1H-imidazol-1-yl)-N-(1-(6-(2,2,2-trifluoroethoxy)pyridin-3-yl)ethyl)isonicotinamide | single enantiomer | 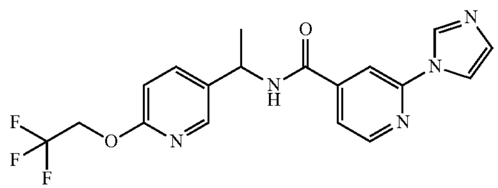 [SMILES: CC(NC(=O)c1ccnc(-n2ccnc2)c1)c1ccc(OCC(F)(F)F)nc1] | Amine-1 | | 390.4 | 1.54 |
| 21 | 2-acetamido-N-methyl-N-(1-(6-(2,2,2-trifluoroethoxy)pyridin-3-yl)ethyl)isonicotinamide | single enantiomer | 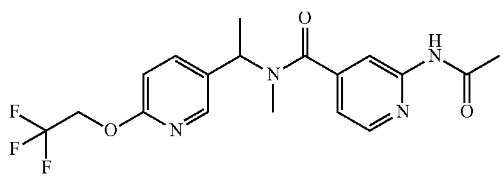 [SMILES: CC(=O)Nc1cc(C(=O)N(C)C(C)c2ccc(OCC(F)(F)F)nc2)ccn1] | Amine-3 | | 395.4 | 1.51 |
| 22 | 2-acetamido-N-((6-(2,2,2-trifluoroethoxy)pyridin-2-yl)methyl)isonicotinamide | | 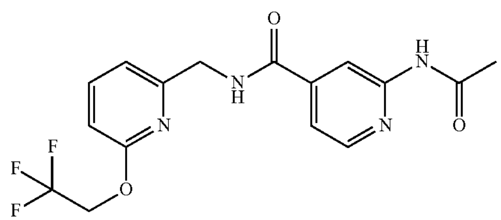 [SMILES: CC(=O)Nc1cc(C(=O)NCc2cccc(OCC(F)(F)F)n2)ccn1] | Amine-4 | | 367.4 | 1.45 |

TABLE 1-continued

| Example | Name | Chirality | Structure | Amine part | Carboxylic part | Observed MS | Retention time (min) |
|---|---|---|---|---|---|---|---|
| 23 | 6-acetamido-N-((6-(2,2,2-trifluoroethoxy)pyridin-2-yl)methyl)picolinamide | | 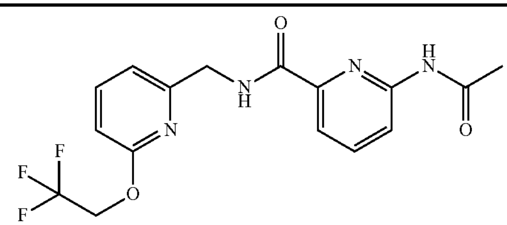 | 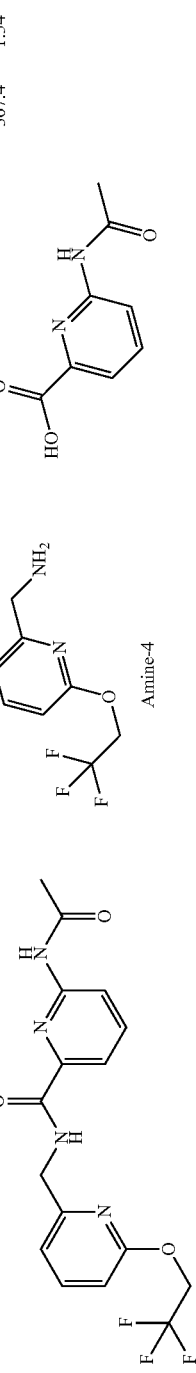<br>Amine-4 | 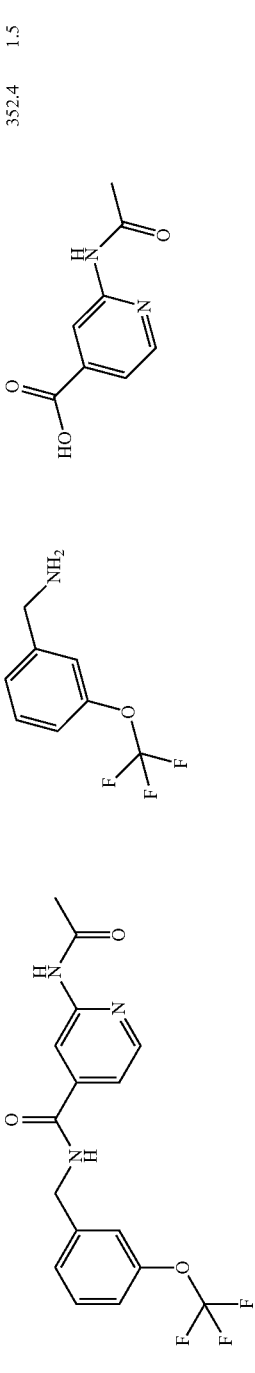 | 367.4 | 1.54 |
| 24 | 2-acetamido-N-(3-(trifluoromethoxy)benzyl)isonicotinamide | | 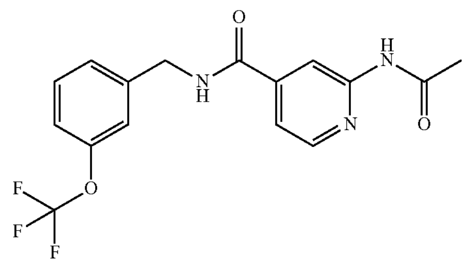 [SMILES: CC(=O)Nc1cc(C(=O)NCc2cccc(OC(F)(F)F)c2)ccn1] | 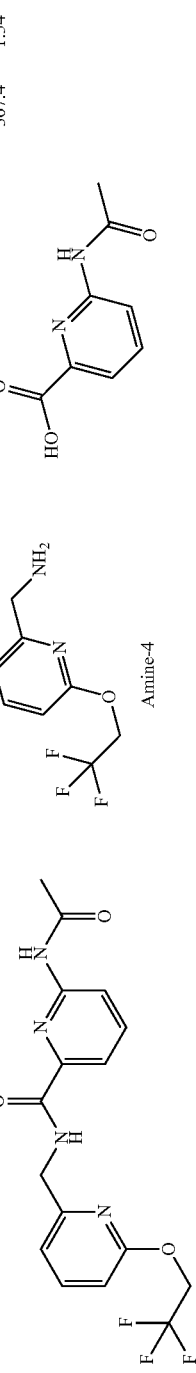 | 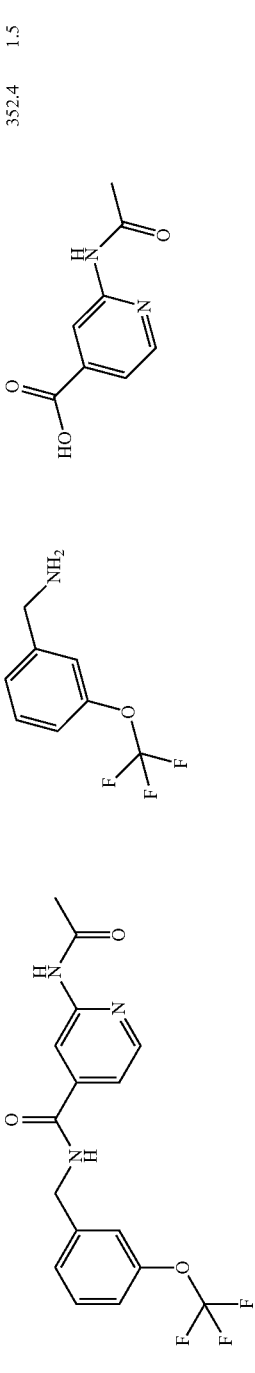 | 352.4 | 1.5 |
| 25 | N-(1-(6-(2,2,2-trifluoroethoxy)pyridin-3-yl)ethyl)-1,6-naphthyridine-2-carboxamide | single enantiomer | 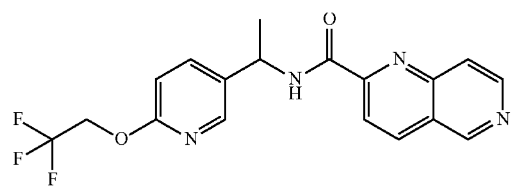 [SMILES: CC(NC(=O)c1ccc2cnccc2n1)c1ccc(OCC(F)(F)F)nc1] | 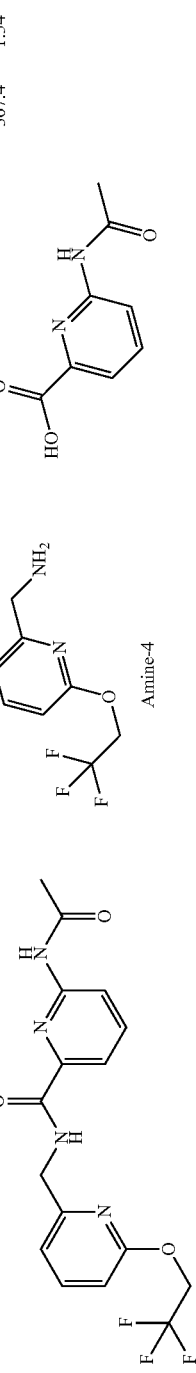<br>Amine-1 | 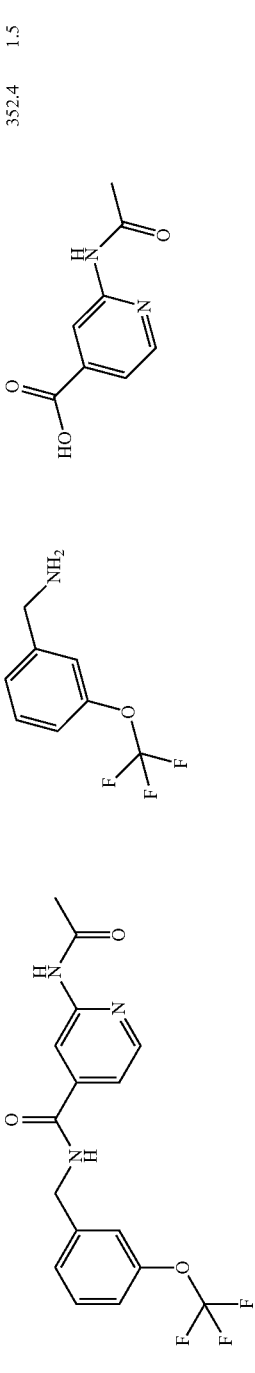 | 375.3 | 1.65 |
| 26 | N-(1-(6-(2,2,2-trifluoroethoxy)pyridin-3-yl)ethyl)quinoline-3-carboxamide | single enantiomer | 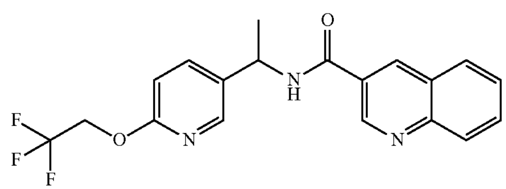 | 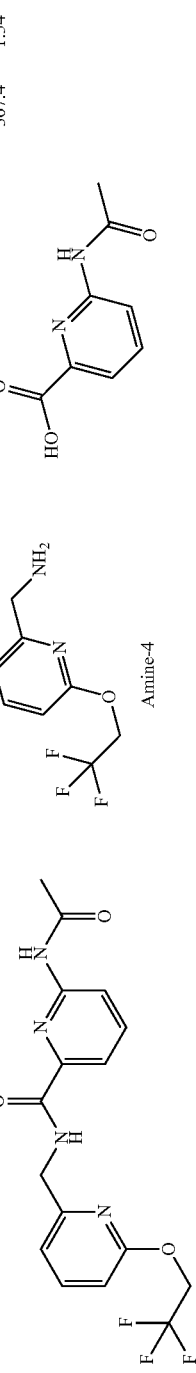<br>Amine-1 | 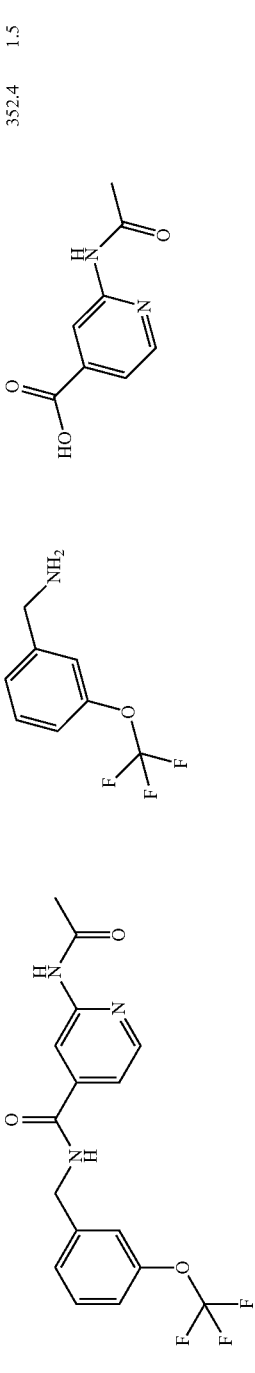 | 374.4 | 1.66 |

TABLE 1-continued

| Example | Chirality | Name | Structure | Amine part | Carboxylic part | Observed MS | Retention time (min) |
|---|---|---|---|---|---|---|---|
| 27 | single enantiomer | N-(1-(6-(2,2,2-trifluoroethoxy)pyridin-3-yl)ethyl)isoquinoline-3-carboxamide | 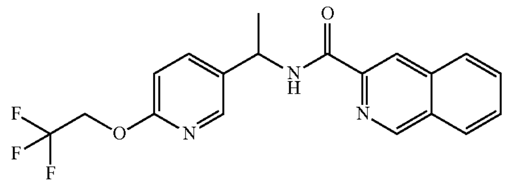 [SMILES: CC(NC(=O)c1cc2ccccc2cn1)c1ccc(OCC(F)(F)F)nc1] | Amine-1 | | 374.3 | 1.86 |
| 28 | single enantiomer | N-(1-(6-(2,2,2-trifluoroethoxy)pyridin-3-yl)ethyl)quinoxaline-2-carboxamide | 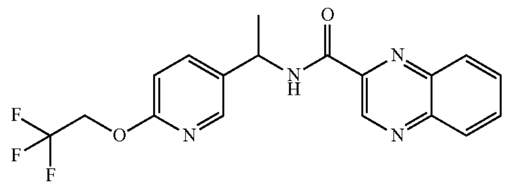 [SMILES: CC(NC(=O)c1cnc2ccccc2n1)c1ccc(OCC(F)(F)F)nc1] | Amine-1 | | 375.3 | 1.79 |
| 29 | single enantiomer | N-(1-(6-(2,2,2-trifluoroethoxy)pyridin-3-yl)ethyl)isoquinoline-6-carboxamide | 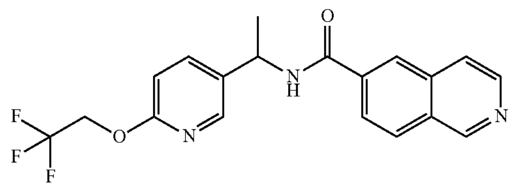 [SMILES: CC(NC(=O)c1ccc2cnccc2c1)c1ccc(OCC(F)(F)F)nc1] | Amine-1 | | 374.4 | 1.6 |
| 30 | single enantiomer | 6-(tert-butyl)-N-(1-(6-(2,2,2-trifluoroethoxy)pyridin-3-yl)ethyl)nicotinamide | 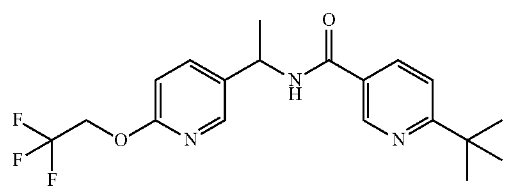 [SMILES: CC(NC(=O)c1ccc(C(C)(C)C)nc1)c1ccc(OCC(F)(F)F)nc1] | Amine-1 | | 380.4 | 1.82 |

TABLE 1-continued

| Example | Name | Chirality | Structure | Amine part | Carboxylic part | Observed MS | Retention time (min) |
|---|---|---|---|---|---|---|---|
| 31 | 1-methyl-N-(1-(6-(2,2,2-trifluoroethoxy)pyridin-3-yl)ethyl)-1H-indazole-3-carboxamide | single enantiomer | 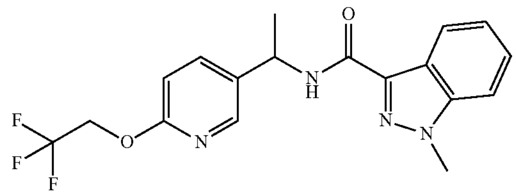 [SMILES: CC(NC(=O)c1nn(C)c2ccccc12)c1ccc(OCC(F)(F)F)nc1] | Amine-1 | | 377.4 | 1.81 |
| 32 | N-(1-(6-(2,2,2-trifluoroethoxy)pyridin-3-yl)ethyl)benzo[c]isoxazole-3-carboxamide | single enantiomer | 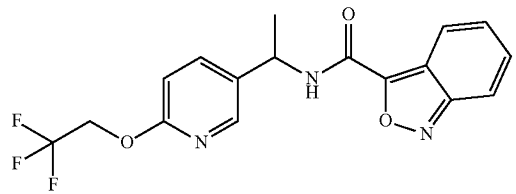 | Amine-1 | | 364.3 | 1.8 |
| 33 | 1-methyl-N-(1-(6-(2,2,2-trifluoroethoxy)pyridin-3-yl)ethyl)-1H-pyrazolo[3,4-b]pyridine-3-carboxamide | single enantiomer | 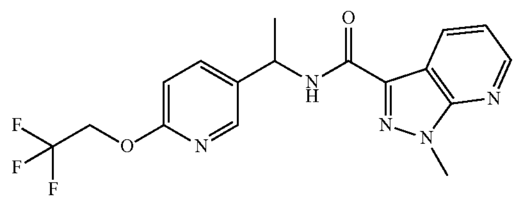 [SMILES: CC(NC(=O)c1nn(C)c2ncccc12)c1ccc(OCC(F)(F)F)nc1] | Amine-1 | | 378.4 | 1.69 |
| 34 | N-(1-(6-(2,2,2-trifluoroethoxy)pyridin-3-yl)ethyl)imidazo[1,2-a]pyridine-2-carboxamide | single enantiomer | 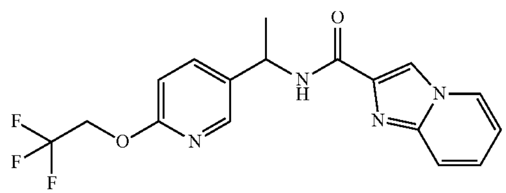 [SMILES: CC(NC(=O)c1cn2ccccc2n1)c1ccc(OCC(F)(F)F)nc1] | Amine-1 | | 363.3 | 1.58 |

TABLE 1-continued

| Example | Name | Chirality | Structure | Amine part | Carboxylic part | Observed MS | Retention time (min) |
|---|---|---|---|---|---|---|---|
| 35 | 1-methyl-N-(1-(6-(2,2,2-trifluoroethoxy)pyridin-3-yl)ethyl)-3-(trifluoromethyl)-1H-pyrazole-5-carboxamide | single enantiomer | 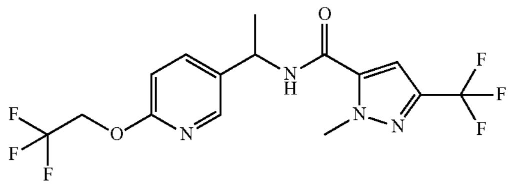 [SMILES: CC(NC(=O)c1cc(C(F)(F)F)nn1C)c1ccc(OCC(F)(F)F)nc1] | Amine-1 | | 395.3 | 1.84 |
| 36 | 5-methyl-1-phenyl-N-(1-(6-(2,2,2-trifluoroethoxy)pyridin-3-yl)ethyl)-1H-1,2,3-triazole-4-carboxamide | single enantiomer | 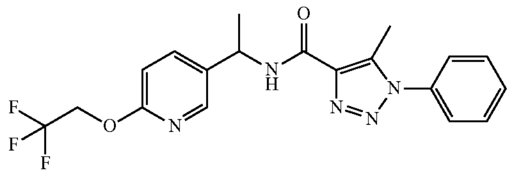 [SMILES: Cc1c(C(=O)NC(C)c2ccc(OCC(F)(F)F)nc2)nnn1-c1ccccc1] | Amine-1 | | 404.3 | 1.81 |
| 37 | 4-methyl-2-phenyl-N-(1-(6-(2,2,2-trifluoroethoxy)pyridin-3-yl)ethyl)thiazole-5-carboxamide | single enantiomer | 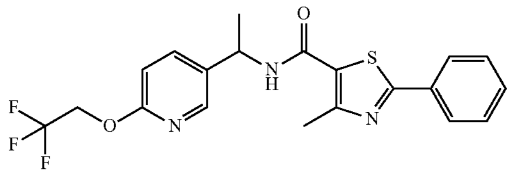 [SMILES: Cc1nc(-c2ccccc2)sc1C(=O)NC(C)c1ccc(OCC(F)(F)F)nc1] | Amine-1 | | 420.4 | 1.91 |
| 38 | 1-methyl-5-phenyl-N-(1-(6-(2,2,2-trifluoroethoxy)pyridin-3-yl)ethyl)-1H-pyrazole-3-carboxamide | single enantiomer | 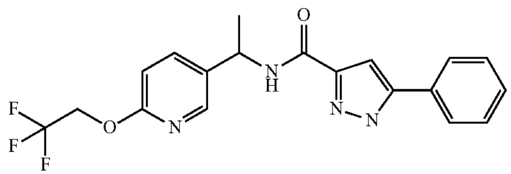 [SMILES: CC(NC(=O)c1cc(-c2ccccc2)[nH]n1)c1ccc(OCC(F)(F)F)nc1] | Amine-1 | | 403.4 | 1.81 |
| 39 | 2-acetamido-N-(2-fluoro-5-(trifluoromethyl)benzyl)isonicotinamide | | 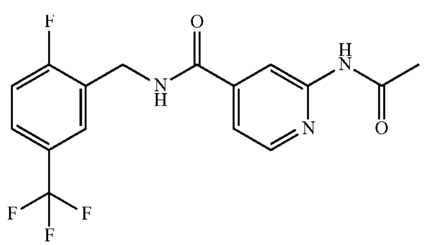 [SMILES: CC(=O)Nc1cc(C(=O)NCc2cc(C(F)(F)F)ccc2F)ccn1] | | | 354.3 | 1.46 |

TABLE 1-continued

| Example | Chirality | Name | Structure | Amine part | Carboxylic part | Observed MS | Retention time (min) |
|---|---|---|---|---|---|---|---|
| 40 | single enantiomer | 2-butyramido-N-(1-(6-(2,2,2-trifluoroethoxy)pyridin-3-yl)isonicotinamide | 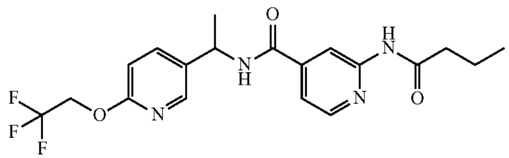 | Amine-1 | | 409.5 | 1.64 |
| 41 | single enantiomer | 2-(2-methoxyacetamido)-N-(1-(6-(2,2,2-trifluoroethoxy)pyridin-3-yl)ethyl)isonicotinamide | 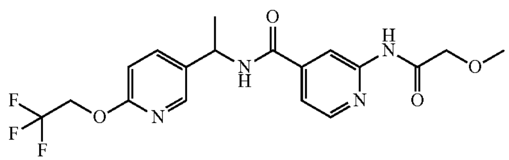 | | alternative route | 411.3 | 1.54 |
| 42 | single enantiomer | 2-(cyclobutanecarboxamido)-N-(1-(6-(2,2,2-trifluoroethoxy)pyridin-3-yl)ethyl)isonicotinamide | 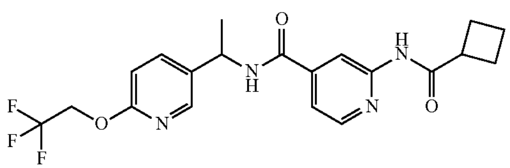 [SMILES: CC(NC(=O)c1ccnc(NC(=O)C2CCC2)c1)c1ccc(OCC(F)(F)F)nc1] | | alternative route | 421.4 | 1.68 |
| 43 | | 2-acetamido-N-(3-(difluoromethoxy)benzyl)isonicotinamide | 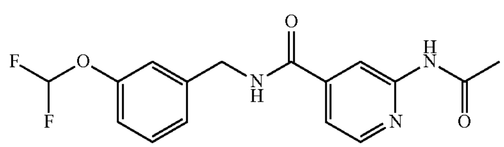 [SMILES: CC(=O)Nc1cc(C(=O)NCc2cccc(OC(F)F)c2)ccn1] | | | 334.4 | 1.37 |
| 44 | single enantiomer | 4-methoxy-N-(1-(6-(2,2,2-trifluoroethoxy)pyridin-3-yl)ethyl)quinoline-2-carboxamide | 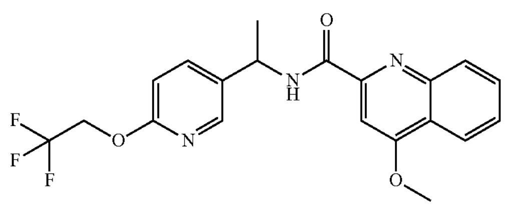 [SMILES: COc1cc(C(=O)NC(C)c2ccc(OCC(F)(F)F)nc2)nc2ccccc12] | Amine-1 | | 404.3 | 1.99 |

TABLE 1-continued

| Example | Name | Chirality | Structure | Amine part | Carboxylic part | Observed MS | Retention time (min) |
|---|---|---|---|---|---|---|---|
| 45 | 8-hydroxy-N-(1-(6-(2,2,2-trifluoroethoxy)pyridin-3-yl)ethyl)quinoline-2-carboxamide | single enantiomer | 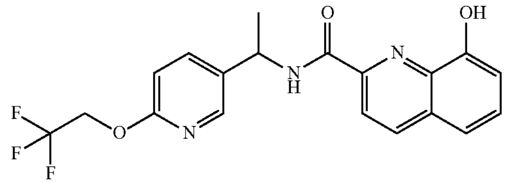 [SMILES: CC(NC(=O)c1ccc2cccc(O)c2n1)c1ccc(OCC(F)(F)F)nc1] | Amine-1 | | 390.4 | 1.8 |
| 46 | 3-isopropyl-N-(1-(6-(2,2,2-trifluoroethoxy)pyridin-3-yl)ethyl)-1H-pyrazole-5-carboxamide | single enantiomer | 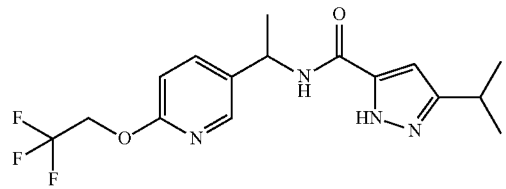 [SMILES: CC(C)c1cc(C(=O)NC(C)c2ccc(OCC(F)(F)F)nc2)[nH]n1] | Amine-1 | | 355.4 | 1.63 |
| 47 | 3-(tert-butyl)-N-methyl-N-(1-(6-(2,2,2-trifluoroethoxy)pyridin-3-yl)ethyl)-1H-pyrazole-5-carboxamide | single enantiomer | 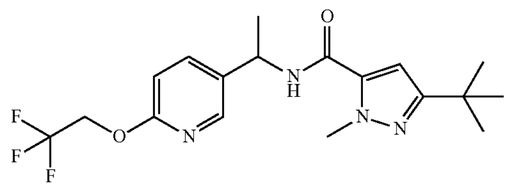 [SMILES: CC(NC(=O)c1cc(C(C)(C)C)nn1C)c1ccc(OCC(F)(F)F)nc1] | Amine-1 | | 383.4 | 1.86 |
| 48 | 6-(piperidin-1-yl)-N-(1-(6-(2,2,2-trifluoroethoxy)pyridin-3-yl)ethyl)nicotinamide | single enantiomer | 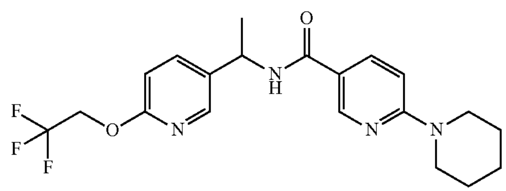 [SMILES: CC(NC(=O)c1ccc(N2CCCCC2)nc1)c1ccc(OCC(F)(F)F)nc1] | Amine-1 | | 407.4 | 1.82 |

| Example | Name | Chirality | Structure | Amine part | Carboxylic part | Observed MS | Retention time (min) |
|---|---|---|---|---|---|---|---|
| 49 | N-(1-(6-(2,2,2-trifluoroethoxy)pyridin-3-yl)ethyl)-1H-benzo[d]imidazole-2-carboxamide | single enantiomer | 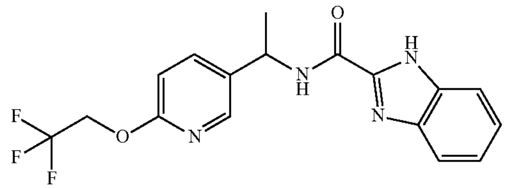 [SMILES: CC(NC(=O)c1nc2ccccc2[nH]1)c1ccc(OCC(F)(F)F)nc1] | Amine-1 | | 363.3 | 1.69 |
| 50 | N-(1-(6-(2,2,2-trifluoroethoxy)pyridin-3-yl)ethyl)pyrazolo[1,5-a]pyridine-2-carboxamide | single enantiomer | 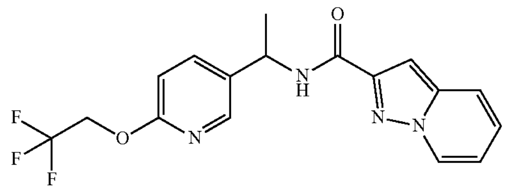 [SMILES: CC(NC(=O)c1cc2ccccn2n1)c1ccc(OCC(F)(F)F)nc1] | Amine-1 | | 363.4 | 1.68 |
| 51 | N-(1-(6-(2,2,2-trifluoroethoxy)pyridin-3-yl)ethyl)benzo[d]isoxazole-3-carboxamide | single enantiomer | 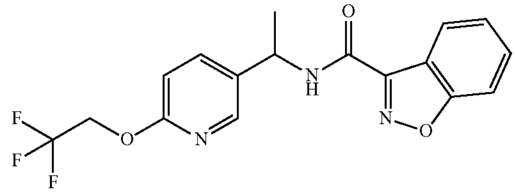 [SMILES: CC(NC(=O)c1noc2ccccc12)c1ccc(OCC(F)(F)F)nc1] | alternative route | | 363.9 | 1.87 |
| 52 | 2-acetamido-N-(1-(5-chloro-6-(2,2,2-trifluoroethoxy)pyridin-3-yl)ethyl)isonicotinamide | single enantiomer | 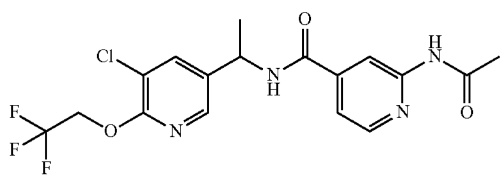 [SMILES: CC(=O)Nc1cc(C(=O)NC(C)c2cnc(OCC(F)(F)F)c(Cl)c2)ccn1] | Amine-5 | | 415.3 | 1.59 |
| 53 | 2-acetamido-N-(3-(trifluoromethyl)benzyl)isonicotinamide | | 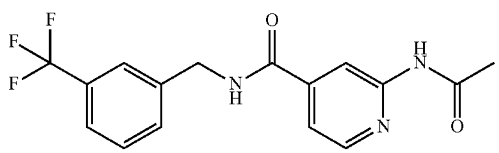 | | | 336.4 | 1.46 |

TABLE 1-continued

| Example | Name | Chirality | Structure | Amine part | Carboxylic part | Observed MS | Retention time (min) |
|---|---|---|---|---|---|---|---|
| 54 | N-((6-(2,2,2-trifluoroethoxy)pyridin-2-yl)methyl)quinoline-8-carboxamide | | 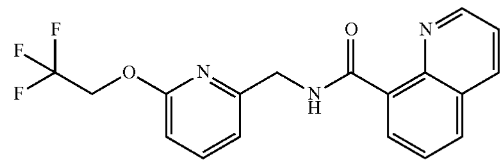 [SMILES: O=C(NCc1cccc(OCC(F)(F)F)n1)c1cccc2cccnc12] | Amine-4 | | 362.1 | 1.83 |
| 55 | 2-methyl-N-((6-(2,2,2-trifluoroethoxy)pyridin-2-yl)methyl)-2H-indazole-3-carboxamide | | 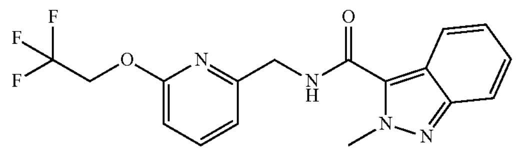 [SMILES: Cn1nc2ccccc2c1C(=O)NCc1cccc(OCC(F)(F)F)n1] | Amine-4 | | 363.4 | 1.71 |
| 56 | 6-(tert-butyl)-N-((6-(2,2,2-trifluoroethoxy)pyridin-2-yl)methyl)nicotinamide | | 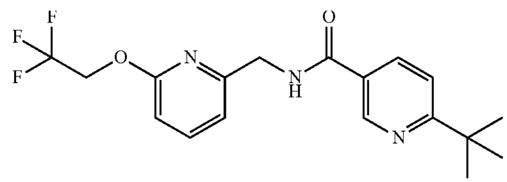 [SMILES: CC(C)(C)c1ccc(C(=O)NCc2cccc(OCC(F)(F)F)n2)cn1] | Amine-4 | | 366.4 | 1.81 |
| 57 | 2-oxo-N-((6-(2,2,2-trifluoroethoxy)pyridin-2-yl)methyl)-2,3-dihydro-1H-benzo[d]imidazole-4-carboxamide | | 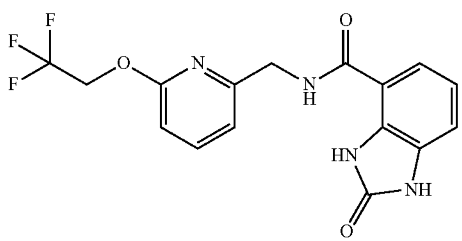 [SMILES: O=C(NCc1cccc(OCC(F)(F)F)n1)c1cccc2[nH]c(=O)[nH]c12] | Amine-4 | | 365.3 | 1.44 |

TABLE 1-continued

| Example | Name | Chirality | Structure | Amine part | Carboxylic part | Observed MS | Retention time (min) |
|---|---|---|---|---|---|---|---|
| 58 | 2-acetamido-N-(1-(6-(2,2,2-trifluoroethoxy)pyridin-3-yl)propyl)isonicotinamide | single enantiomer | 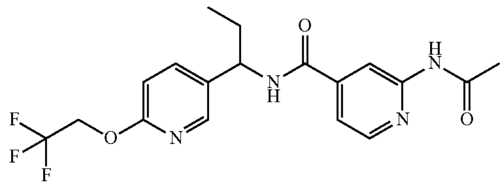 | Amine-6 | | 395.3 | 1.55 |
| 59 | 2-acetamido-6-methyl-N-(1-(6-(2,2,2-trifluoroethoxy)pyridin-3-yl)ethyl)isonicotinamide | single enantiomer | 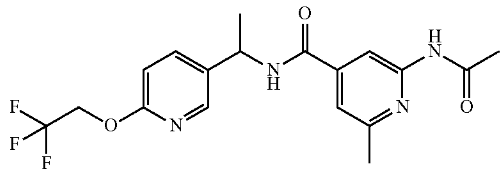 [SMILES: CC(=O)Nc1cc(C(=O)NC(C)c2ccc(OCC(F)(F)F)nc2)cc(C)n1] | Amine-1 | | 395.4 | 1.54 |
| 60 | 2-methyl-6-propionamido-N-(1-(6-(2,2,2-trifluoroethoxy)pyridin-3-yl)ethyl)isonicotinamide | single enantiomer | 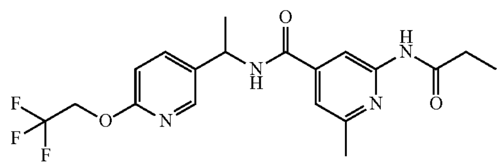 [SMILES: CCC(=O)Nc1cc(C(=O)NC(C)c2ccc(OCC(F)(F)F)nc2)cc(C)n1] | Amine-1 | | 409.4 | 1.63 |
| 61 | 2-(cyclopropanecarboxamido)-6-methyl-N-(1-(6-(2,2,2-trifluoroethoxy)pyridin-3-yl)ethyl)isonicotinamide | single enantiomer | 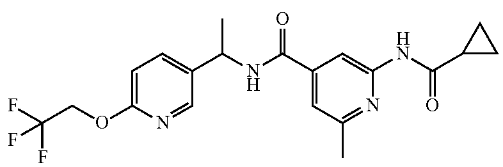 [SMILES: Cc1cc(C(=O)NC(C)c2ccc(OCC(F)(F)F)nc2)cc(NC(=O)C2CC2)n1] | Amine-1 | | 421.4 | 1.67 |

TABLE 1-continued

| Example | Chirality | Name | Structure | Amine part | Carboxylic part | Observed MS | Retention time (min) |
|---|---|---|---|---|---|---|---|
| 62 | single enantiomer | 2-isobutyramido-6-methyl-N-(1-(6-(2,2,2-trifluoroethoxy)pyridin-3-yl)ethyl)isonicotinamide | 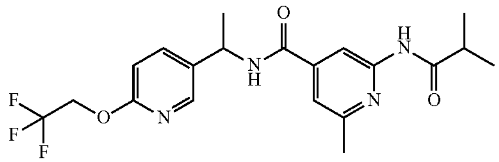 [SMILES: Cc1cc(C(=O)NC(C)c2ccc(OCC(F)(F)F)nc2)cc(NC(=O)C(C)C)n1] | Amine-1 | | 423.4 | 1.71 |
| 63 | single enantiomer | 2-acetamido-N-(1-(6-(2,2,2-trifluoroethoxy)pyridin-2-yl)ethyl)isonicotinamide | 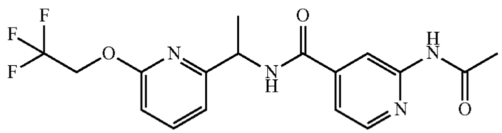 [SMILES: CC(=O)Nc1cc(C(=O)NC(C)c2cccc(OCC(F)(F)F)n2)ccn1] | Amine-7 | | 381.4 | 1.54 |
| 64 | single enantiomer | N-(1-(6-(2,2,2-trifluoroethoxy)pyridin-2-yl)ethyl)benzo[c]isoxazole-3-carboxamide | 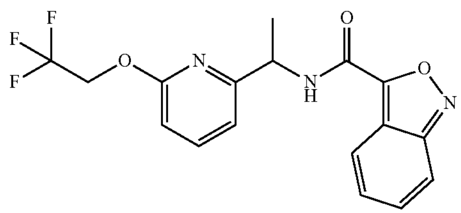 [SMILES: CC(NC(=O)c1onc2ccccc12)c1cccc(OCC(F)(F)F)n1] | Amine-7 | | 364.3 | 1.87 |
| 65 | single enantiomer | 1-methyl-N-(1-(6-(2,2,2-trifluoroethoxy)pyridin-2-yl)ethyl)-1H-indazole-3-carboxamide | 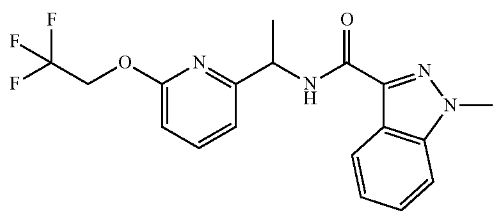 [SMILES: CC(NC(=O)c1nn(C)c2ccccc12)c1cccc(OCC(F)(F)F)n1] | Amine-7 | | 379.1 | 1.9 |

TABLE 1-continued

| Example | Name | Chirality | Structure | Amine part | Carboxylic part | Observed MS | Retention time (min) |
|---|---|---|---|---|---|---|---|
| 66 | 2-acetamido-N-(1-(4-(2,2,2-trifluoroethoxy)pyridin-2-yl)ethyl)isonicotinamide | single enantiomer | 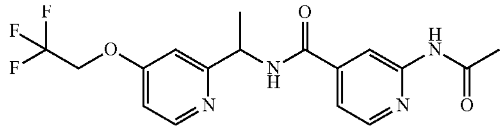 [SMILES: CC(=O)Nc1cc(C(=O)NC(C)c2cc(OCC(F)(F)F)ccn2)ccn1] | Amine-8 | | 381.3 | 1.33 |
| 67 | 2-acetamido-N-(1-(3-(trifluoromethoxy)phenyl)ethyl)isonicotinamide | single enantiomer | 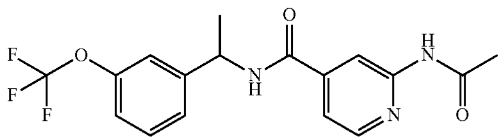 [SMILES: CC(=O)Nc1cc(C(=O)NC(C)c2cccc(OC(F)(F)F)c2)ccn1] | Amine-9 | | 366.3 | 1.56 |
| 68 | 2-acetamido-N-(1-(4-(trifluoromethoxy)phenyl)ethyl)isonicotinamide | single enantiomer | 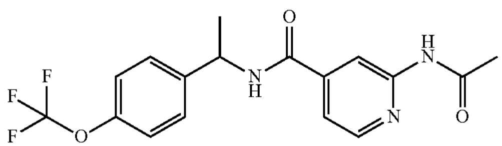 [SMILES: CC(=O)Nc1cc(C(=O)NC(C)c2ccc(OC(F)(F)F)cc2)ccn1] | Amine-10 | | 366.2 | 1.57 |
| 69 | N-(1-(5-chloro-6-(2,2,2-trifluoroethoxy)pyridin-3-yl)ethyl)-2-propionamido-isonicotinamide | single enantiomer | 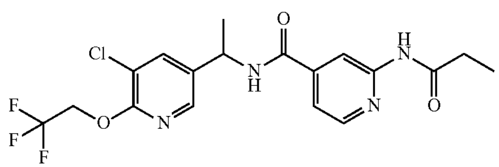 [SMILES: CCC(=O)Nc1cc(C(=O)NC(C)c2cnc(OCC(F)(F)F)c(Cl)c2)ccn1] | Amine-5 | | 429.2 | 1.68 |
| 70 | 2-propionamido-N-(1-(6-(2,2,2-trifluoroethoxy)pyridin-2-yl)ethyl)isonicotinamide | single enantiomer | 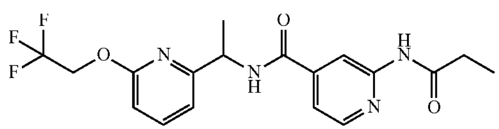 [SMILES: CCC(=O)Nc1cc(C(=O)NC(C)c2cccc(OCC(F)(F)F)n2)ccn1] | Amine-7 | | 395.2 | 1.64 |

TABLE 1-continued

| Example | Name | Chirality | Structure | Amine part | Carboxylic part | Observed MS | Retention time (min) |
|---|---|---|---|---|---|---|---|
| 71 | 2-propionamido-N-(1-(2-(2,2,2-trifluoroethoxy)pyridin-4-yl)ethyl)isonicotinamide | single enantiomer | 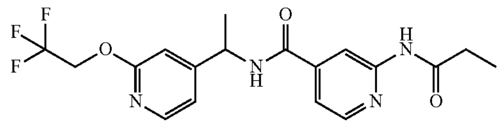 [SMILES: CCC(=O)Nc1cc(C(=O)NC(C)c2ccnc(OCC(F)(F)F)c2)ccn1] | Amine-11 | | 395.3 | 1.56 |
| 72 | 2-acetamido-N-(1-(5-fluoro-6-(2,2,2-trifluoroethoxy)pyridin-3-yl)ethyl)isonicotinamide | single enantiomer | 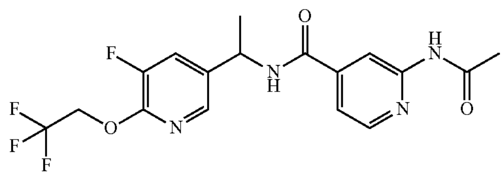 | Amine-12 | | 399.2 | 1.53 |
| 73 | 2-acetamido-N-(1-(2-methyl-6-(2,2,2-trifluoroethoxy)pyridin-4-yl)ethyl)isonicotinamide | single enantiomer | 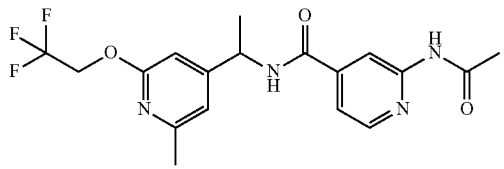 [SMILES: CC(=O)Nc1cc(C(=O)NC(C)c2cc(C)nc(OCC(F)(F)F)c2)ccn1] | Amine-13 | | 395.2 | 1.58 |
| 74 | N-(1-(5-fluoro-6-(2,2,2-trifluoroethoxy)pyridin-3-yl)ethyl)-2-propionamidoisonicotinamide | single enantiomer | 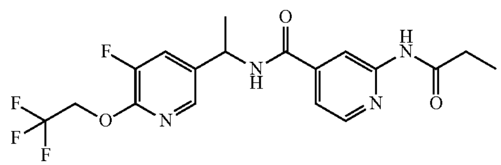 [SMILES: CCC(=O)Nc1cc(C(=O)NC(C)c2cnc(OCC(F)(F)F)c(F)c2)ccn1] | Amine-12 | | 413.2 | 1.61 |

TABLE 1-continued

| Example | Name | Chirality | Structure | Amine part | Carboxylic part | Observed MS | Retention time (min) |
|---|---|---|---|---|---|---|---|
| 75 | N-(1-(2-methyl-6-(2,2,2-trifluoroethoxy)pyridin-4-yl)ethyl)-2-propionamidoisonicotinamide | single enantiomer | 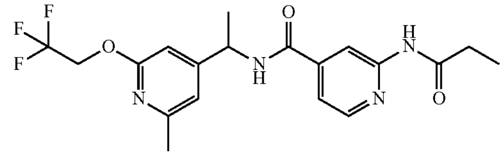 [SMILES: CCC(=O)Nc1cc(C(=O)NC(C)c2cc(C)nc(OCC(F)(F)F)c2)ccn1] | Amine-13 | | 109.3 | 1.67 |
| 76 | 2-(cyclopropanecarboxamido)-N-(1-(6-(2,2,2-trifluoroethoxy)pyridin-2-yl)ethyl)isonicotinamide | single enantiomer | 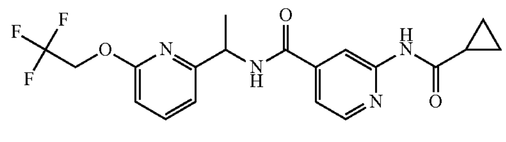 [SMILES: CC(NC(=O)c1ccnc(NC(=O)C2CC2)c1)c1cccc(OCC(F)(F)F)n1] | Amine-7 | | 407.2 | 1.68 |
| 77 | 2-(cyclopropanecarboxamido)-N-(1-(6-(2,2,2-trifluoroethoxy)pyridin-3-yl)propyl)isonicotinamide | single enantiomer | 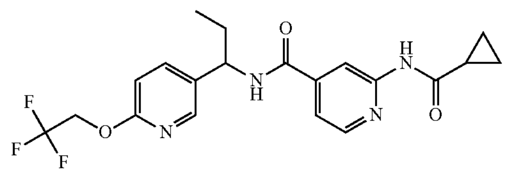 [SMILES: CCC(NC(=O)c1ccnc(NC(=O)C2CC2)c1)c1ccc(OCC(F)(F)F)nc1] | Amine-6 | | 421.2 | 1.68 |
| 78 | 2-(cyclopropanecarboxamido)-N-(1-(3-(trifluoromethoxy)phenyl)ethyl)isonicotinamide | single enantiomer | 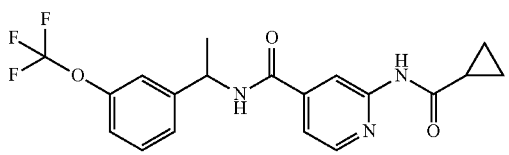 [SMILES: CC(NC(=O)c1ccnc(NC(=O)C2CC2)c1)c1cccc(OC(F)(F)F)c1] | Amine-9 | | 392.2 | 1.69 |

TABLE 1-continued

| Example | Name | Chirality | Structure | Amine part | Carboxylic part | Observed MS | Retention time (min) |
|---|---|---|---|---|---|---|---|
| 79 | N-(1-(5-chloro-6-(2,2,2-trifluoroethoxy)pyridin-3-yl)ethyl)-2-(cyclopropanecarboxamido)isonicotinamide | single enantiomer | 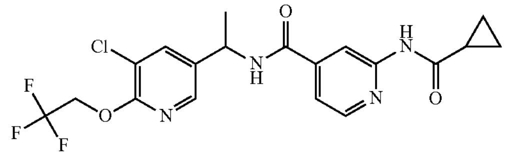 [SMILES: CC(NC(=O)c1ccnc(NC(=O)C2CC2)c1)c1cnc(OCC(F)(F)F)c(Cl)c1] | Amine-5 | | 441.2 | 1.71 |
| 80 | 2-(cyclopropanecarboxamido)-N-(1-(5-fluoro-6-(2,2,2-trifluoroethoxy)pyridin-3-yl)ethyl)isonicotinamide | single enantiomer | 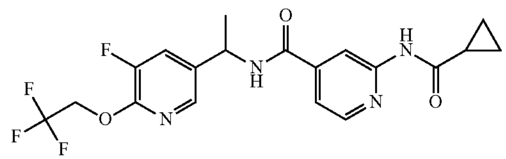 [SMILES: CC(NC(=O)c1ccnc(NC(=O)C2CC2)c1)c1cnc(OCC(F)(F)F)c(F)c1] | Amine-12 | | 425.2 | 1.65 |
| 81 | 2-methoxy-6-propionamido-N-(1-(6-(2,2,2-trifluoroethoxy)pyridin-3-yl)ethyl)isonicotinamide | single enantiomer | 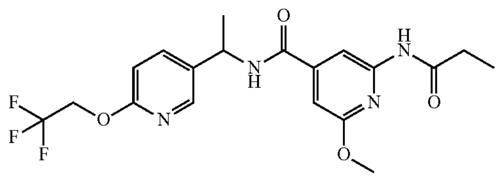 [SMILES: CCC(=O)Nc1cc(C(=O)NC(C)c2ccc(OCC(F)(F)F)nc2)cc(OC)n1] | alternative route | | 425.2 | 1.68 |
| 82 | 2-(cyclopropanecarboxamido)-6-methoxy-N-(1-(6-(2,2,2-trifluoroethoxy)pyridin-3-yl)ethyl)isonicotinamide | single enantiomer | 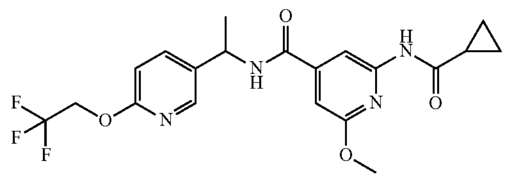 [SMILES: COc1cc(C(=O)NC(C)c2ccc(OCC(F)(F)F)nc2)cc(NC(=O)C2CC2)n1] | alternative route | | 437.2 | 1.72 |
| 83 | 2-isobutyramido-6-methoxy-N-(1-(6-(2,2,2-trifluoroethoxy)pyridin-3-yl)ethyl)isonicotinamide | single enantiomer | 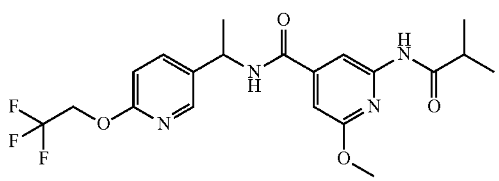 [SMILES: COc1cc(C(=O)NC(C)c2ccc(OCC(F)(F)F)nc2)cc(NC(=O)C(C)C)n1] | alternative route | | 439.3 | 1.76 |

TABLE 1-continued

| Example | Name | Chirality | Structure | Amine part | Carboxylic part | Observed MS | Retention time (min) |
|---|---|---|---|---|---|---|---|
| 84 | 2-acetamido-N-(1-(3-(2,2,2-trifluoroethoxy)phenyl)ethyl)isonicotinamide | single enantiomer | 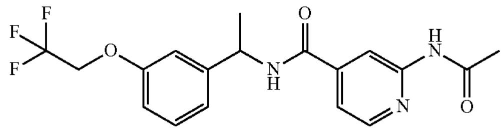 [SMILES: CC(=O)Nc1cc(C(=O)NC(C)c2cccc(OCC(F)(F)F)c2)ccn1] | Amine-16 | | 280.3 | 1.52 |
| 85 | 2-acetamido-N-(1-(5-methyl-6-(2,2,2-trifluoroethoxy)pyridin-3-yl)ethyl)isonicotinamide | single enantiomer | 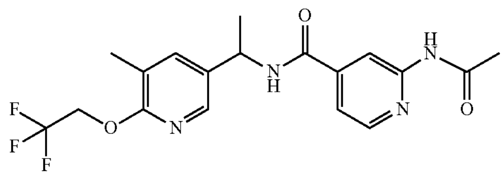 [SMILES: CC(=O)Nc1cc(C(=O)NC(C)c2cnc(OCC(F)(F)F)c(C)c2)ccn1] | Amine-17 | | 395.3 | 1.58 |
| 86 | 2-propionamido-N-(1-(3-(2,2,2-trifluoroethoxy)phenyl)ethyl)isonicotinamide | single enantiomer | 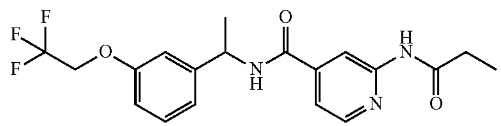 | Amine-16 | | 394.3 | 1.61 |
| 87 | N-(1-(5-methyl-6-(2,2,2-trifluoroethoxy)pyridin-3-yl)ethyl)-2-propionamidoisonicotinamide | single enantiomer | 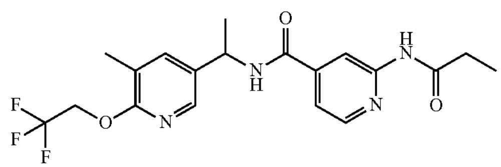 [SMILES: CCC(=O)Nc1cc(C(=O)NC(C)c2cnc(OCC(F)(F)F)c(C)c2)ccn1] | Amine-17 | | 409.3 | 1.66 |
| 88 | 2-(cyclopropanecarboxamido)-N-(1-(3-(2,2,2-trifluoroethoxy)phenyl)ethyl)isonicotinamide | single enantiomer | 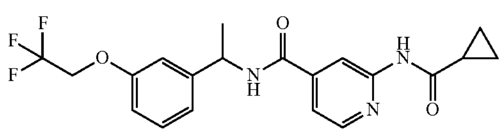 [SMILES: CC(NC(=O)c1ccnc(NC(=O)C2CC2)c1)c1cccc(OCC(F)(F)F)c1] | Amine-16 | | 406.3 | 1.64 |

TABLE 1-continued

| Example | Name | Chirality | Structure | Amine part | Carboxylic part | Observed MS | Retention time (min) |
|---|---|---|---|---|---|---|---|
| 89 | 2-(cyclopropanecarboxamido)-N-(1-(5-methyl-6-(2,2,2-trifluoroethoxy)pyridin-3-yl)isonicotinamide | single enantiomer | 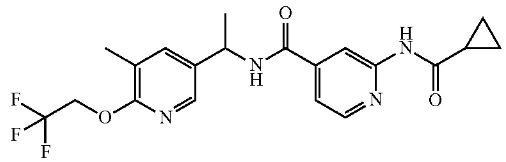 [SMILES: Cc1cc(C(C)NC(=O)c2ccnc(NC(=O)C3CC3)c2)cnc1OCC(F)(F)F] | Amine-17 | | 421.3 | 1.7 |
| 90 | 2-acetamido-N-(1-(4-(2,2,2-trifluoroethoxy)phenyl)ethyl)isonicotinamide | single enantiomer | 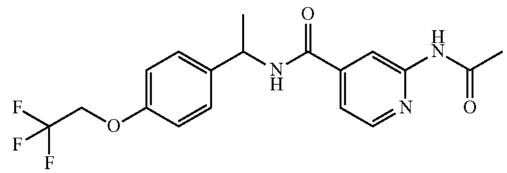 [SMILES: CC(=O)Nc1cc(C(=O)NC(C)c2ccc(OCC(F)(F)F)cc2)ccn1] | Amine-18 | | 380.3 | 1.52 |
| 91 | 2-propionamido-N-(1-(4-(2,2,2-trifluoroethoxy)phenyl)ethyl)isonicotinamide | single enantiomer | 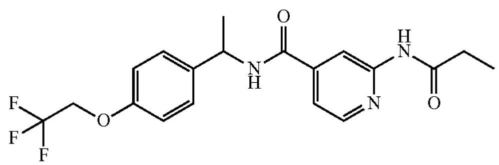 [SMILES: CCC(=O)Nc1cc(C(=O)NC(C)c2ccc(OCC(F)(F)F)cc2)ccn1] | Amine-18 | | 394.3 | 1.6 |
| 92 | 2-(cyclopropanecarboxamido)-N-(1-(4-(2,2,2-trifluoroethoxy)phenyl)ethyl)isonicotinamide | single enantiomer | 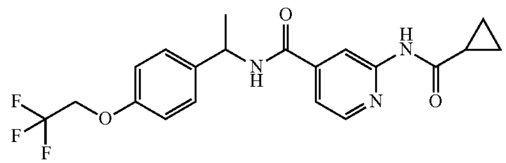 [SMILES: CC(NC(=O)c1ccnc(NC(=O)C2CC2)c1)c1ccc(OCC(F)(F)F)cc1] | Amine-18 | | 406.3 | 1.63 |
| 93 | 2-acetamido-N-((5-chloro-6-(2,2,2-trifluoroethoxy)pyridin-3-yl)methyl)isonicotinamide | | 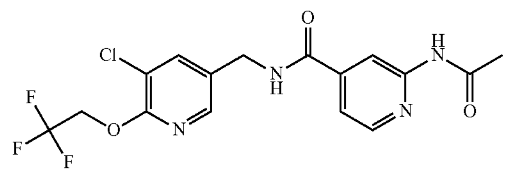 | Amine-19 | | 401.2 | 1.54 |

TABLE 1-continued

| Example | Name | Chirality | Structure | Amine part | Carboxylic part | Observed MS | Retention time (min) |
|---|---|---|---|---|---|---|---|
| 94 | N-((5-chloro-6-(2,2,2-trifluoroethoxy)pyridin-3-yl)methyl)-2-propionamidoisonicotinamide | | 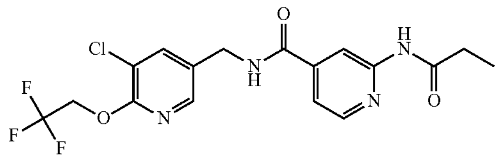 | Amine-19 | | 415.2 | 1.62 |
| 95 | N-((5-chloro-6-(2,2,2-trifluoroethoxy)pyridin-3-yl)methyl)-2-(cyclopropanecarboxamido)isonicotinamide | | 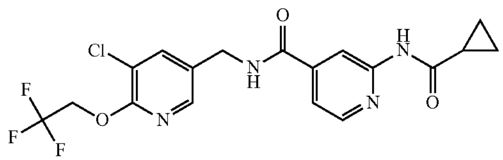 | Amine-19 | | 427.2 | 1.66 |
| 96 | 2-(cyclopropanecarboxamido)-N-(1-(6-(2,2,2-trifluoroethoxy)pyridin-3-yl)ethyl)pyrimidine-4-carboxamide | single enantiomer | 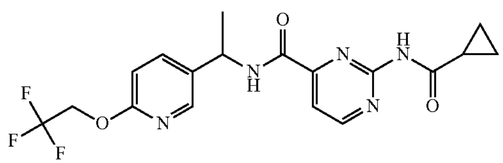 [SMILES: CC(NC(=O)c1ccnc(NC(=O)C2CC2)n1)c1ccc(OCC(F)(F)F)nc1] | Amine-1 | | 408.2 | 1.57 |
| 97 | 2-propionamido-N-(1-(6-(2,2,2-trifluoroethoxy)pyridin-3-yl)ethyl)pyrimidine-4-carboxamide | single enantiomer | 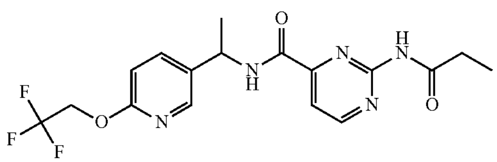 [SMILES: CCC(=O)Nc1nccc(C(=O)NC(C)c2ccc(OCC(F)(F)F)nc2)n1] | | alternative route | 396.2 | 1.55 |
| 98 | 2-acetamido-N-(1-(4-fluoro-3-(2,2,2-trifluoroethoxy)phenyl)ethyl)isonicotinamide | single enantiomer | 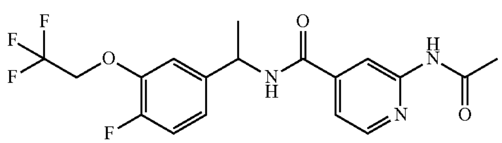 [SMILES: CC(=O)Nc1cc(C(=O)NC(C)c2ccc(F)c(OCC(F)(F)F)c2)ccn1] | Amine-20 | | 398.3 | 1.55 |

TABLE 1-continued

| Example | Name | Chirality | Structure | Amine part | Carboxylic part | Observed MS | Retention time (min) |
|---|---|---|---|---|---|---|---|
| 99 | N-(1-(4-fluoro-3-(2,2,2-trifluoroethoxy)phenyl)ethyl)-2-propionamidoisonicotinamide | single enantiomer | 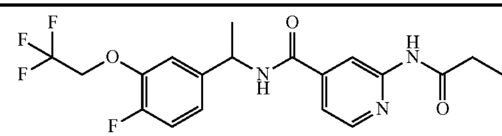 | | | 412.3 | 1.63 |
| 100 | 2-acetamido-N-(3-fluoro-5-(trifluoromethyl)benzyl)isonicotinamide | | 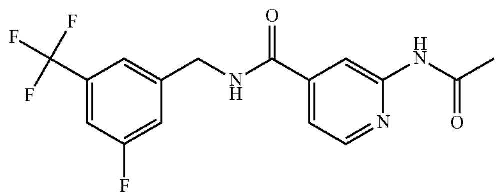 [SMILES: CC(=O)Nc1cc(C(=O)NCc2cc(F)cc(C(F)(F)F)c2)ccn1] | Amine-20 | | 354.3 | 1.51 |
| 101 | 2-(cyclopropanecarboxamido)-N-(3-fluoro-5-(trifluoromethyl)benzyl)isonicotinamide | | 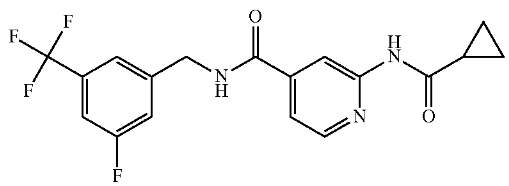 [SMILES: O=C(NCc1cc(F)cc(C(F)(F)F)c1)c1ccnc(NC(=O)C2CC2)c1] | | | 380.3 | 1.64 |
| 102 | 2-(cyclopropanecarboxamido)-5-fluoro-N-(1-(6-(2,2,2-trifluoroethoxy)pyridin-3-yl)ethyl)isonicotinamide | single enantiomer | 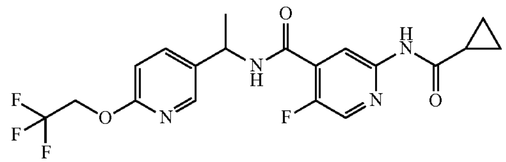 | | alternative route | 425.2 | 1.65 |
| 103 | 2-(cyclopropanecarboxamido)-N-(3-(trifluoromethyl)benzyl)isonicotinamide | | 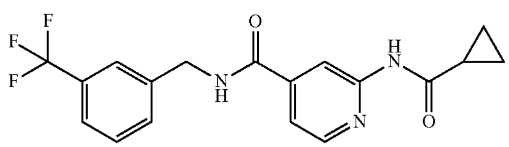 [SMILES: O=C(NCc1cccc(C(F)(F)F)c1)c1ccnc(NC(=O)C2CC2)c1] | | | 362.3 | 1.6 |

TABLE 1-continued

| Example | Name | Chirality | Structure | Amine part | Carboxylic part | Observed MS | Retention time (min) |
|---|---|---|---|---|---|---|---|
| 104 | (R)-2-(cyclopropanecarboxamido)-N-(1-(3-(trifluoromethyl)phenyl)ethyl)isonicotinamide | single enantiomer | 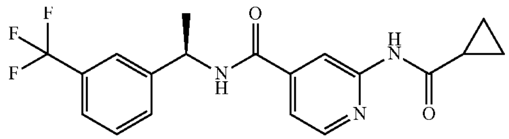 [SMILES: C[C@@H](NC(=O)c1ccnc(NC(=O)C2CC2)c1)c1cccc(C(F)(F)F)c1] | | | 376.3 | 1.66 |
| 105 | 2-(cyclopropane-carboxamido)-N-(1-(4-(trifluoromethoxy)phenyl)ethyl)isonicotinamide | single enantiomer | 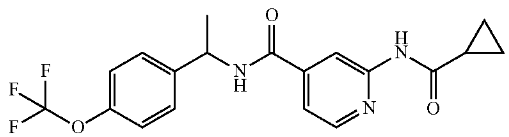 [SMILES: CC(NC(=O)c1ccnc(NC(=O)C2CC2)c1)c1ccc(OC(F)(F)F)cc1] | Amine-10 | | 392.2 | 1.7 |
| 106 | 2-propionamido-N-(3-(trifluoromethyl)benzyl)isonicotinamide | | 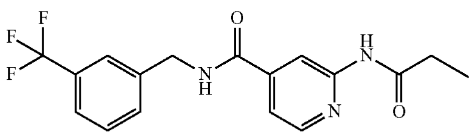 [SMILES: CCC(=O)Nc1cc(C(=O)NCc2cccc(C(F)(F)F)c2)ccn1] | | | 350.3 | 1.56 |
| 107 | (R)-2-propionamido-N-(1-(3-(trifluoromethyl)phenyl)ethyl)isonicotinamide | single enantiomer | 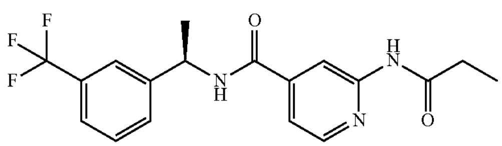 | | | 364.2 | 1.62 |
| 108 | 2-propionamido-N-(1-(3-(trifluoromethoxy)phenyl)ethyl)isonicotinamide | single enantiomer | 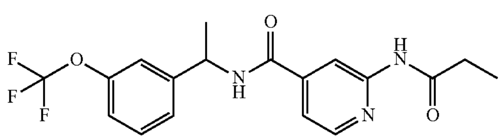 [SMILES: CCC(=O)Nc1cc(C(=O)NC(C)c2cccc(OC(F)(F)F)c2)ccn1] | Amine-9 | | 380.2 | 1.65 |

TABLE 1-continued

| Example | Name | Chirality | Structure | Amine part | Carboxylic part | Observed MS | Retention time (min) |
|---|---|---|---|---|---|---|---|
| 109 | 2-propionamido-N-(1-(4-(trifluoromethoxy)phenyl)ethyl)isonicotinamide | single enantiomer | 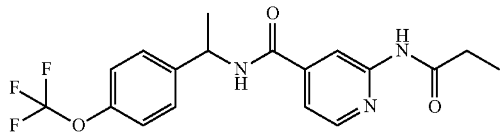 | Amine-10 | | 380.3 | 1.66 |
| 110 | 2-methyl-N-(1-(6-(2,2,2-trifluoroethoxy)pyridin-3-yl)ethyl)-1H-benzo[d]imidazole-4-carboxamide | single enantiomer | 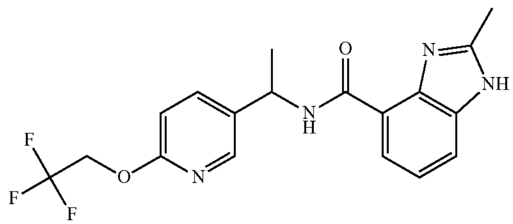 [SMILES: Cc1nc2c(C(=O)NC(C)c3ccc(OCC(F)(F)F)nc3)cccc2[nH]1] | Amine-1 | | 377.3 | 1.64 |
| 111 | N-(1-(5-chloro-6-(2,2,2-trifluoroethoxy)pyridin-3-yl)ethyl)-2-methyl-1H-benzo[d]imidazole-4-carboxamide | single enantiomer | 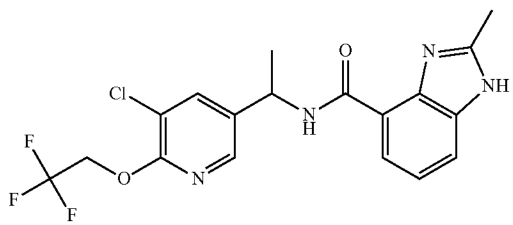 [SMILES: Cc1nc2c(C(=O)NC(C)c3cnc(OCC(F)(F)F)c(Cl)c3)cccc2[nH]1] | Amine-5 | | 411.2 | 1.75 |
| 112 | N-(1-(5-chloro-6-(2,2,2-trifluoroethoxy)pyridin-3-yl)ethyl)-2-(cyclopropanecarboxamido)oxazole-5-carboxamide | single enantiomer | 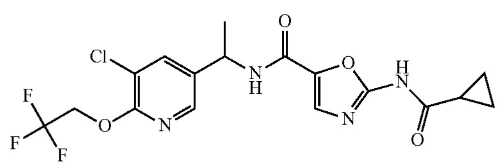 | | alternative route | 431.2 | 1.59 |

TABLE 1-continued

| Example | Name | Chirality | Structure | Amine part | Carboxylic part | Observed MS | Retention time (min) |
|---|---|---|---|---|---|---|---|
| 113 | N-(1-(5-chloro-6-(2,2,2-trifluoroethoxy)pyridin-3-yl)ethyl)-2-(cyclopropanecarboxamido)-4-methyloxazole-5-carboxamide | single enantiomer | 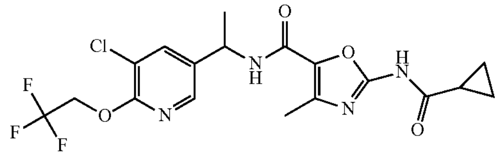 [SMILES: Cc1nc(NC(=O)C2CC2)oc1C(=O)NC(C)c1cnc(OCC(F)(F)F)c(Cl)c1] | alternative route | | 445.2 | 1.65 |
| 114 | 2-acetamido-N-(1-(6-(3,3,3-trifluoropropoxy)pyridin-3-yl)ethyl)isonicotinamide | single enantiomer | 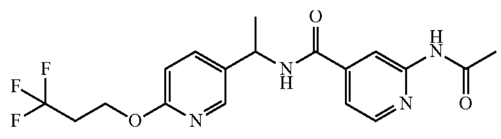 [SMILES: CC(=O)Nc1cc(C(=O)NC(C)c2ccc(OCCC(F)(F)F)nc2)ccn1] | Amine-21 | | 395.2 | 1.47 |
| 115 | 2-propionamido-N-(1-(6-(3,3,3-trifluoropropoxy)pyridin-3-yl)ethyl)isonicotinamide | single enantiomer | 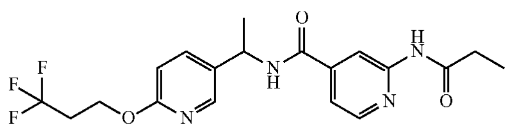 [SMILES: CCC(=O)Nc1cc(C(=O)NC(C)c2ccc(OCCC(F)(F)F)nc2)ccn1] | Amine-21 | | 409.2 | 1.56 |
| 116 | 2-(cyclopropanecarboxamido)-N-(1-(6-(3,3,3-trifluoropropoxy)pyridin-3-yl)ethyl)isonicotinamide | single enantiomer | 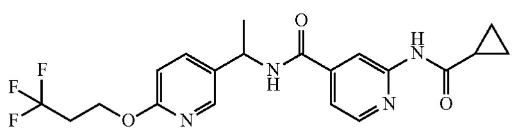 [SMILES: CC(NC(=O)c1ccnc(NC(=O)C2CC2)c1)c1ccc(OCCC(F)(F)F)nc1] | Amine-21 | | 421.2 | 1.6 |
| 117 | 6-propionamido-N-(1-(6-(2,2,2-trifluoroethoxy)pyridin-3-yl)pyrimidine-4-carboxamide | single enantiomer | 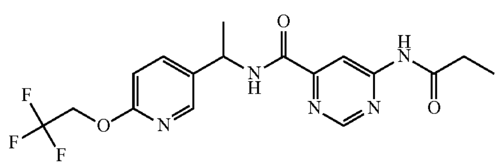 [SMILES: CCC(=O)Nc1cc(C(=O)NC(C)c2ccc(OCC(F)(F)F)nc2)ncn1] | alternative route | | 396.2 | 1.64 |

TABLE 1-continued

| Example | Name | Chirality | Structure | Amine part | Carboxylic part | Observed MS | Retention time (min) |
|---|---|---|---|---|---|---|---|
| 118 | 6-(cyclopropanecarboxamido)-N-(1-(6-(2,2,2-trifluoroethoxy)pyridin-3-yl)ethyl)pyrimidine-4-carboxamide | single enantiomer | 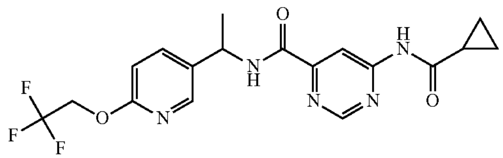 | | alternative route | 408.2 | 1.67 |
| 119 | N-(1-(5-chloro-6-(2,2,2-trifluoroethoxy)pyridin-3-yl)ethyl)-6-propionamidopyrimidine-4-carboxamide | single enantiomer | 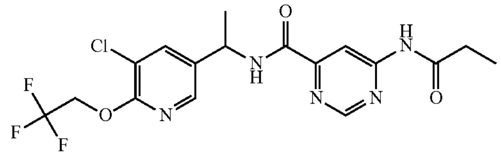 [SMILES: CCC(=O)Nc1cc(C(=O)NC(C)c2cnc(OCC(F)(F)F)c(Cl)c2)ncn1] | | alternative route | 430.1 | 1.74 |
| 120 | 6-methyl-2-propionamido-N-(1-(6-(2,2,2-trifluoroethoxy)pyridin-3-yl)ethyl)pyrimidine-4-carboxamide | single enantiomer | 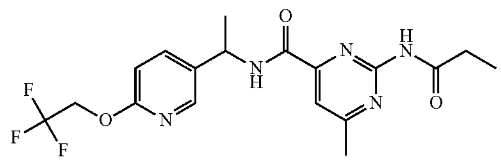 [SMILES: CCC(=O)Nc1nc(C)cc(C(=O)NC(C)c2ccc(OCC(F)(F)F)nc2)n1] | Amine-1 | | 410.2 | 1.61 |
| 121 | 2-(cyclopropanecarboxamido)-6-methyl-N-(1-(6-(2,2,2-trifluoroethoxy)pyridin-3-yl)ethyl)pyrimidine-4-carboxamide | single enantiomer | 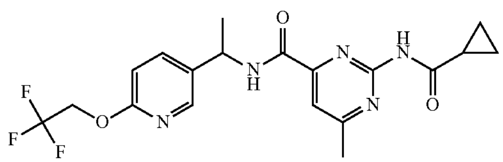 [SMILES: Cc1cc(C(=O)NC(C)c2ccc(OCC(F)(F)F)nc2)nc(NC(=O)C2CC2)n1] | Amine-1 | | 422.2 | 1.63 |
| 122 | 2-acetamido-N-(4-((trifluoromethyl)thio)benzyl)isonicotinamide | | 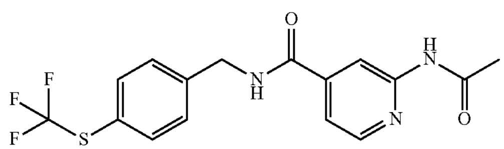 [SMILES: CC(=O)Nc1cc(C(=O)NCc2ccc(SC(F)(F)F)cc2)ccn1] | | | 368.0 | 1.59 |

| Example | Chirality | Name | Structure | Amine part | Carboxylic part | Observed MS | Retention time (min) |
|---|---|---|---|---|---|---|---|
| 123 | | 2-propionamido-N-(4-((trifluoromethyl)thio)benzyl)isonicotinamide | 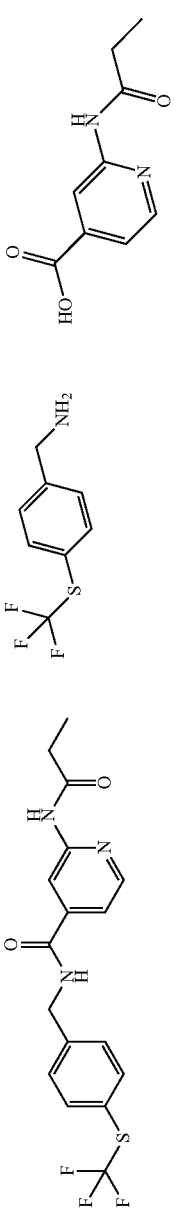 | 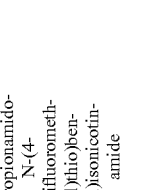 | 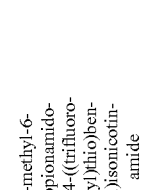 | 382.0 | 1.68 |
| 124 | | 2-(cyclopropanecarboxamido)-N-(4-((trifluoromethyl)thio)benzyl)isonicotinamide | 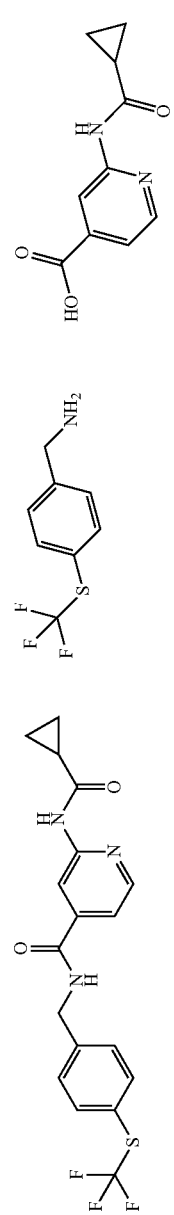 | 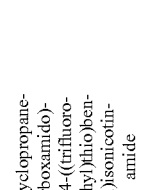 | 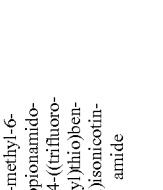 | 394.0 | 1.72 |
| 125 | | 2-methyl-6-propionamido-N-(4-((trifluoromethyl)thio)benzyl)isonicotinamide | 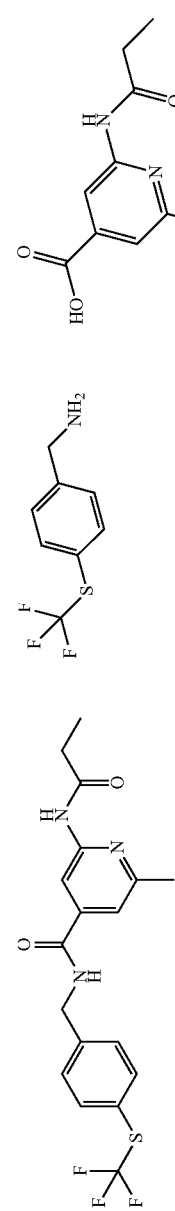 | 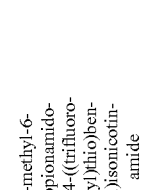 | 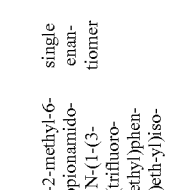 | 396.0 | 1.74 |
| 126 | single enantiomer | (R)-2-methyl-6-propionamido-N-(1-(3-(trifluoromethyl)phenyl)ethyl)isonicotinamide | 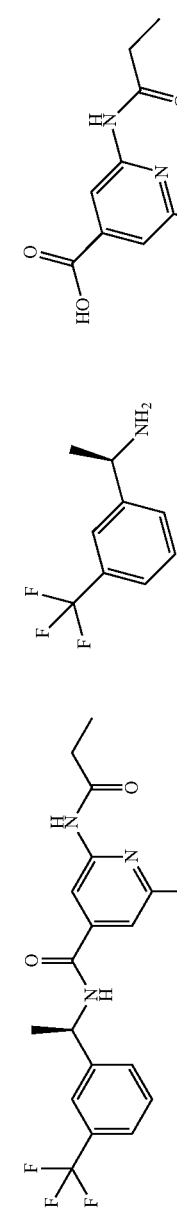 | 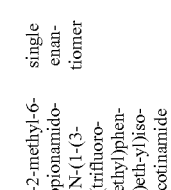 | 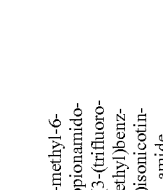 | 378.1 | 1.68 |
| 127 | | 2-methyl-6-propionamido-N-(3-(trifluoromethyl)benzyl)isonicotinamide | 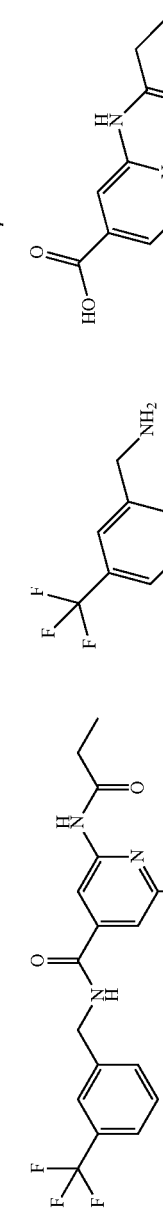 | 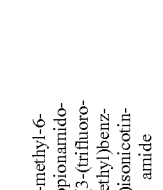 |  | 364.1 | 1.62 |

TABLE 1-continued

| Example | Name | Chirality | Structure | Amine part | Carboxylic part | Observed MS | Retention time (min) |
|---|---|---|---|---|---|---|---|
| 128 | N-(2-fluoro-5-(trifluoromethyl)benzyl)-2-methyl-6-propionamidoisonicotinamide | | 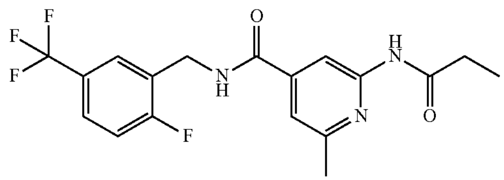 [SMILES: CCC(=O)Nc1cc(C(=O)NCc2cc(C(F)(F)F)ccc2F)cc(C)n1] | | | 382.1 | 1.63 |
| 129 | N-(3-(difluoromethoxy)benzyl)-2-methyl-6-propionamidoisonicotinamide | | 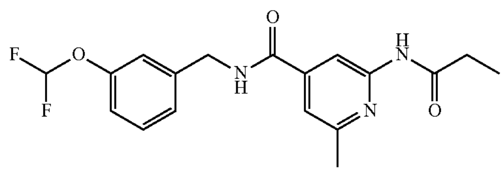 [SMILES: CCC(=O)Nc1cc(C(=O)NCc2cccc(OC(F)F)c2)cc(C)n1] | | | 362.1 | 1.53 |
| 130 | N-(1-(5-chloro-6-(2,2,2-trifluoroethoxy)pyridin-3-yl)ethyl)-2-methyl-6-propionamidoisonicotinamide | single enantiomer | 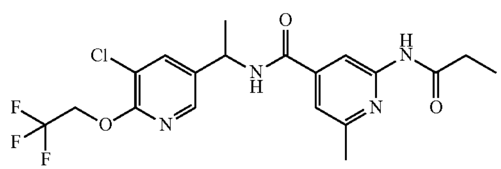 | Amine-5 | | 443.0 | 1.74 |
| 131 | N-(1-(5-fluoro-6-(2,2,2-trifluoroethoxy)pyridin-3-yl)ethyl)-2-methyl-6-propionamidoisonicotinamide | single enantiomer | 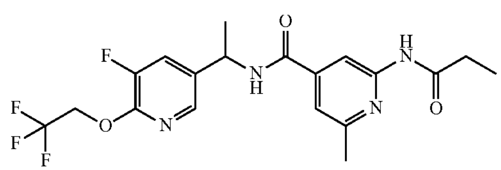 [SMILES: CCC(=O)Nc1cc(C(=O)NC(C)c2cnc(OCC(F)(F)F)c(F)c2)cc(C)n1] | Amine-12 | | 427.0 | 1.67 |

TABLE 1-continued

| Example | Name | Chirality | Structure | Amine part | Carboxylic part | Observed MS | Retention time (min) |
|---|---|---|---|---|---|---|---|
| 132 | 2-methyl-6-propionamido-N-(1-(5-methyl-6-(2,2,2-trifluoroethoxy)pyridin-3-yl)ethyl)-6-propionamidoisonicotinamide | single enantiomer | 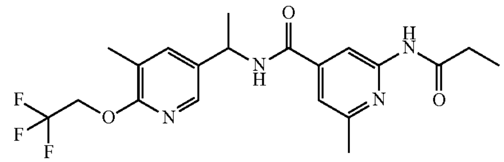 | Amine-17 | | 423.1 | 1.72 |
| 133 | 2-methyl-6-propionamido-N-(1-(6-(2,2,2-trifluoroethoxy)pyridin-3-yl)propyl)isonicotinamide | single enantiomer | 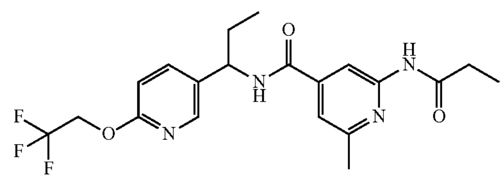 [SMILES: CCC(=O)Nc1cc(C(=O)NC(CC)c2ccc(OCC(F)(F)F)nc2)cc(C)n1] | Amine-6 | | 423.1 | 1.7 |
| 134 | 2-methyl-6-propionamido-N-(1-(3-(trifluoromethoxy)phenyl)ethyl)isonicotinamide | single enantiomer | 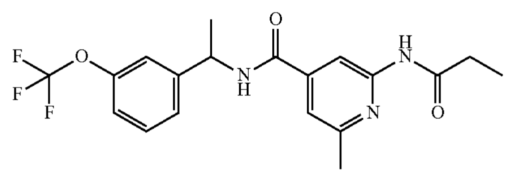 [SMILES: CCC(=O)Nc1cc(C(=O)NC(C)c2cccc(OC(F)(F)F)c2)cc(C)n1] | Amine-9 | | 394.1 | 1.71 |
| 135 | 2-methyl-6-propionamido-N-(1-(4-(trifluoromethoxy)phenyl)ethyl)isonicotinamide | single enantiomer | 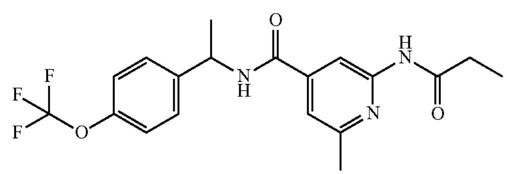 [SMILES: CCC(=O)Nc1cc(C(=O)NC(C)c2ccc(OC(F)(F)F)cc2)cc(C)n1] | Amine-10 | | 394.1 | 1.72 |

TABLE 1-continued

| Example | Name | Chirality | Structure | Amine part | Carboxylic part | Observed MS | Retention time (min) |
|---|---|---|---|---|---|---|---|
| 136 | 2-methyl-6-propionamido-N-(1-(4-(2,2,2-trifluoroethoxy)phenyl)ethyl)isonicotinamide | single enantiomer | 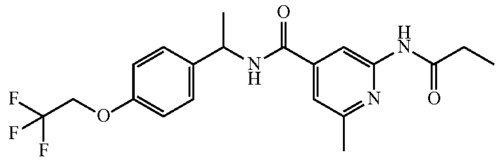 [SMILES: CCC(=O)Nc1cc(C(=O)NC(C)c2ccc(OCC(F)(F)F)cc2)cc(C)n1] | Amine-18 | | 408.1 | 1.65 |
| 137 | 2-methyl-6-propionamido-N-((2-(2,2,2-trifluoroethoxy)pyridin-4-yl)methyl)isonicotinamide | | 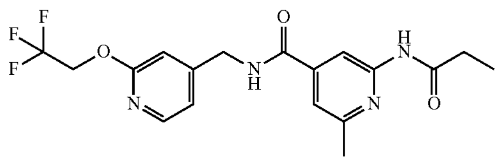 [SMILES: CCC(=O)Nc1cc(C(=O)NCc2ccnc(OCC(F)(F)F)c2)cc(C)n1] | | | 395.1 | 1.57 |
| 138 | N,2-dimethyl-6-propionamido-N-(1-(6-(2,2,2-trifluoroethoxy)pyridin-3-yl)ethyl)isonicotinamide | single enantiomer | 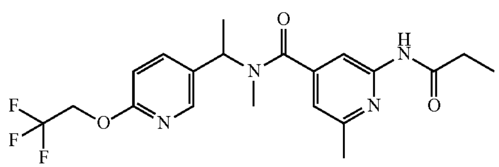 [SMILES: CCC(=O)Nc1cc(C(=O)N(C)C(C)c2ccc(OCC(F)(F)F)nc2)cc(C)n1] | Amine-3 | | 423.1 | 1.67 |
| 139 | 2-methyl-6-propionamido-N-(1-(6-(2,2,2-trifluoroethoxy)pyridin-2-yl)ethyl)isonicotinamide | single enantiomer | 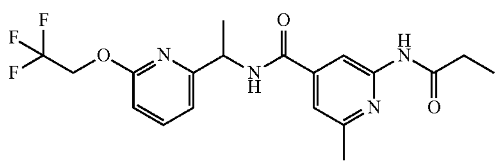 [SMILES: CCC(=O)Nc1cc(C(=O)NC(C)c2cccc(OCC(F)(F)F)n2)cc(C)n1] | Amine-7 | | 409.1 | 1.7 |

TABLE 1-continued

| Example | Name | Chirality | Structure | Amine part | Carboxylic part | Observed MS | Retention time (min) |
|---|---|---|---|---|---|---|---|
| 140 | 2-methyl-6-propionamido-N-(1-(6-(3,3,3-trifluoropropoxy)pyridin-3-yl)isonicotinamide | single enantiomer | 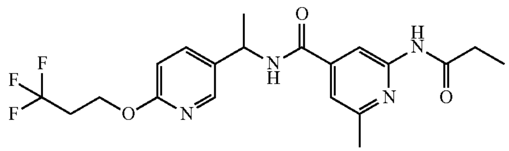 [SMILES: CCC(=O)Nc1cc(C(=O)NC(C)c2ccc(OCCC(F)(F)F)nc2)cc(C)n1] | Amine-21 | | 423.1 | 1.62 |
| 141 | 2-acetamido-N-(1-(5-methoxy-6-(2,2,2-trifluoroethoxy)pyridin-3-yl)ethyl)isonicotinamide | single enantiomer | 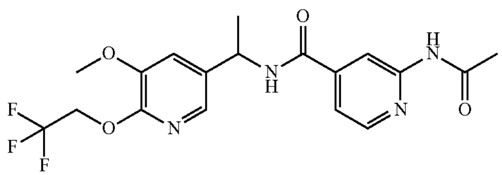 [SMILES: COc1cc(C(C)NC(=O)c2ccnc(NC(C)=O)c2)cnc1OCC(F)(F)F] | Amine-22 | | 411.1 | 1.47 |
| 142 | N-(1-(5-methoxy-6-2,2,2-trifluoroethoxy)pyridin-3-yl)ethyl)-2-propionamidosonicotinamide | single enantiomer | 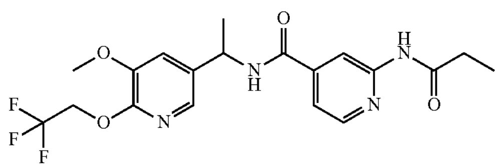 | Amine-22 | | 425.1 | 1.55 |
| 143 | 2-(cyclopropanecarboxamido)-N-(1-(5-methoxy-6-(2,2,2-trifluoroethoxy)pyridin-3-yl)ethyl)isonicotinamide | single enantiomer | 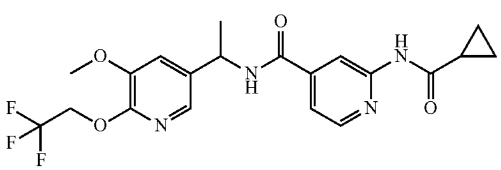 [SMILES: COc1cc(C(C)NC(=O)c2ccnc(NC(=O)C3CC3)c2)cnc1OCC(F)(F)F] | Amine-22 | | 437.1 | 1.59 |
| 144 | N-(1-(5-methoxy-6-(2,2,2-trifluoroethoxy)pyridin-3-yl)ethyl)-2-methyl-6-propionamido-isonicotinamide | single enantiomer | 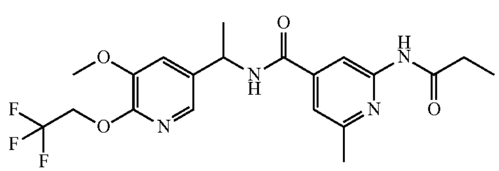 [SMILES: CCC(=O)Nc1cc(C(=O)NC(C)c2cnc(OCC(F)(F)F)c(OC)c2)cc(C)n1] | Amine-22 | | 439.1 | 1.61 |

TABLE 1-continued

| Example | Name | Chirality | Structure | Amine part | Carboxylic part | Observed MS | Retention time (min) |
|---|---|---|---|---|---|---|---|
| 145 | 2-propionamido-N-(1-(6-((2,2,2-trifluoroethyl)thio)pyridin-3-yl)ethyl)isonicotinamide | single enantiomer | 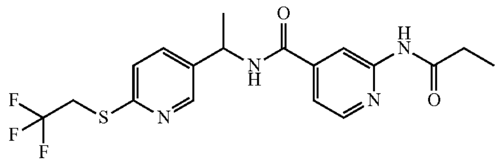 | Amine-23 | | 411.1 | 1.6 |
| 146 | 2-methyl-6-propionamido-N-(1-(6-((2,2,2-trifluoroethyl)thio)pyridin-3-yl)ethyl)isonicotinamide | single enantiomer | 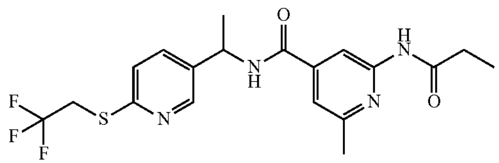 | Amine-23 | | 425.1 | 1.66 |
| 147 | 2-(cyclopropanecarboxamido)-N-((2-methoxy-6-(2,2,2-trifluoroethoxy)pyridin-3-yl)methyl)isonicotinamide | | 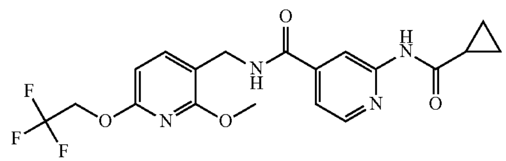 [SMILES: COc1nc(OCC(F)(F)F)ccc1CNC(=O)c1ccnc(NC(=O)C2CC2)c1] | Amine-24 | | 423.2 | 1.67 |
| 148 | 2-acetamido-N-((2-methoxy-6-(2,2,2-trifluoroethoxy)pyridin-3-yl)methyl)isonicotinamide | | 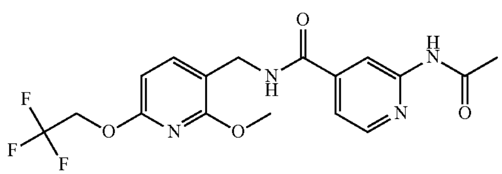 [SMILES: COc1nc(OCC(F)(F)F)ccc1CNC(=O)c1ccnc(NC(C)=O)c1] | Amine-24 | | 397.2 | 1.55 |
| 149 | N-((2-methoxy-6-(2,2,2-trifluoroethoxy)pyridin-3-yl)methyl)-2-propionamido-isonicotinamide | | 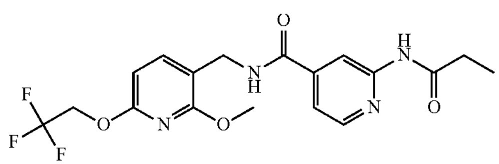 [SMILES: CCC(=O)Nc1cc(C(=O)NCc2ccc(OCC(F)(F)F)nc2OC)ccn1] | Amine-24 | | 411.2 | 1.63 |

TABLE 1-continued

| Example | Chirality | Name | Structure | Amine part | Carboxylic part | Observed MS | Retention time (min) |
|---|---|---|---|---|---|---|---|
| 150 | | N-((2-methoxy-6-(2,2,2-trifluoroethoxy)pyridin-3-yl)methyl)-2-methyl-6-propionamido-isonicotinamide | 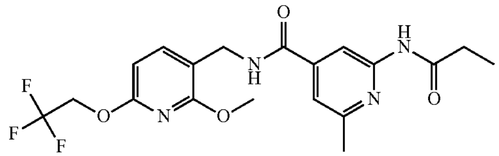 [SMILES: CCC(=O)Nc1cc(C(=O)NCc2ccc(OCC(F)(F)F)nc2OC)cc(C)n1] | Amine-24 | | 425.2 | 1.69 |
| 151 | | 2-propionamido-N-((6-(2,2,2-trifluoroethoxy)pyridin-3-yl)methyl)iso-nicotinamide | 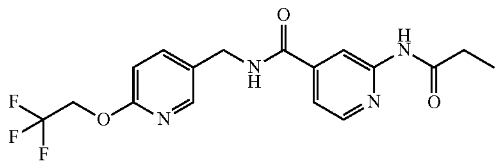 [SMILES: CCC(=O)Nc1cc(C(=O)NCc2ccc(OCC(F)(F)F)nc2)ccn1] | | | 381.2 | 1.51 |
| 152 | | 2-(cyclopropane-carboxamido)-N-((6-(2,2,2-trifluoroethoxy)pyridin-3-yl)methyl)iso-nicotinamide | 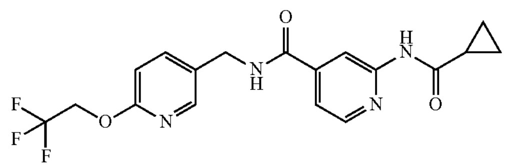 | | | 393.2 | 1.55 |
| 153 | | 2-methyl-6-propionamido-N-((6-(2,2,2-trifluoroethoxy)pyridin-3-yl)methyl)iso-nicotinamide | 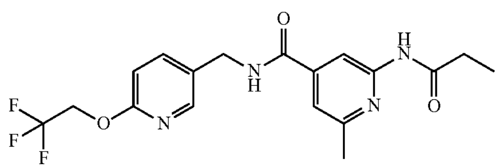 | | | 395.2 | 1.58 |

TABLE 1-continued

| Example | Name | Chirality | Structure | Amine part | Carboxylic part | Observed MS | Retention time (min) |
|---|---|---|---|---|---|---|---|
| 154 | 2-ethyl-6-propionamido-N-(1-(6-(2,2,2-trifluoroethoxy)pyridin-3-yl)ethyl)isonicotinamide | single enantiomer | 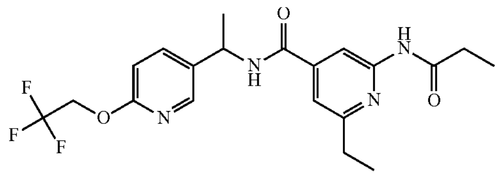 [SMILES: CCC(=O)Nc1cc(C(=O)NC(C)c2ccc(OCC(F)(F)F)nc2)cc(CC)n1] | Amine-1 | | 423.2 | 1.72 |
| 155 | 2-(cyclopropanecarboxamido)-N-methyl-N-(1-(6-(2,2,2-trifluoroethoxy)pyridin-3-yl)ethyl)isonicotinamide | single enantiomer | 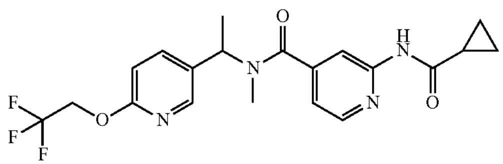 [SMILES: CC(c1ccc(OCC(F)(F)F)nc1)N(C)C(=O)c1ccnc(NC(=O)C2CC2)c1] | Amine-3 | | 421.2 | 1.64 |
| 156 | (R)-2-methyl-6-propionamido-N-(1-(5-(2,2,2-trifluoroethoxy)pyridin-2-yl)ethyl)isonicotinamide | single enantiomer | 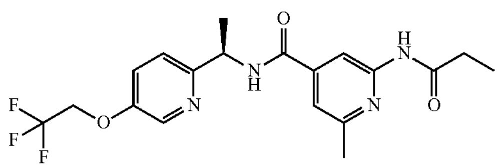 [SMILES: CCC(=O)Nc1cc(C(=O)N[C@H](C)c2ccc(OCC(F)(F)F)cn2)cc(C)n1] | | | 409.2 | 1.51 |
| 157 | 2-(cyclopropanecarboxamido)-N-(1-(6-((2,2,2-trifluoroethyl)amino)pyridin-3-yl)ethyl)isonicotinamide | single enantiomer | 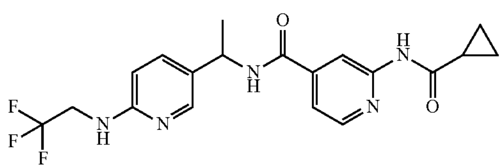 [SMILES: CC(NC(=O)c1ccnc(NC(=O)C2CC2)c1)c1ccc(NCC(F)(F)F)nc1] | Amine-25 | | 406.2 | 1.42 |

| Example | Name | Chirality | Structure | Amine part | Carboxylic part | Observed MS | Retention time (min) |
|---|---|---|---|---|---|---|---|
| 158 | 2-methyl-6-propionamido-N-(1-(6-((2,2,2-trifluoroethyl)amino)pyridin-3-yl)ethyl)isonicotinamide | single enantiomer | 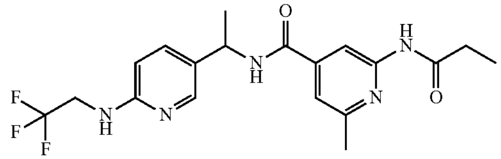 [SMILES: CCC(=O)Nc1cc(C(=O)NC(C)c2ccc(NCC(F)(F)F)nc2)cc(C)n1] | Amine-25 | | 408.2 | 1.44 |
| 159 | N-ethyl-2-methyl-6-propionamido-N-(1-(6-(2,2,2-trifluoroethoxy)pyridin-3-yl)ethyl)isonicotinamide | single enantiomer | 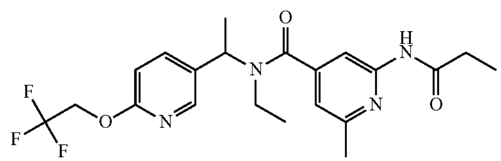 [SMILES: CCC(=O)Nc1cc(C(=O)N(CC)C(C)c2ccc(OCC(F)(F)F)nc2)cc(C)n1] | Amine-26 | | 437.2 | 1.72 |
| 160 | N4-(1-(5-chloro-6-(2,2,2-trifluoroethoxy)pyridin-3-yl)ethyl)-N2-ethylpyridine-2,4-dicarboxamide | single enantiomer | 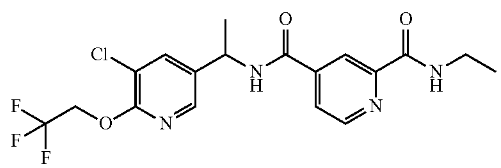 [SMILES: CCNC(=O)c1cc(C(=O)NC(C)c2cnc(OCC(F)(F)F)c(Cl)c2)ccn1] | Amine-5 | | 429.2 | 1.7 |
| 161 | 2-propionamido-N-((2-(2,2,2-trifluoroethoxy)pyridin-4-yl)methyl)isonicotinamide | | 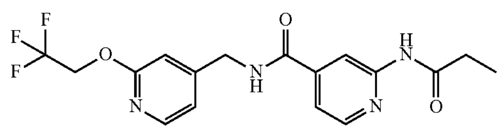 [SMILES: CCC(=O)Nc1cc(C(=O)NCc2ccnc(OCC(F)(F)F)c2)ccn1] | | | 381.2 | 1.5 |
| 162 | 2-(cyclopropanecarboxamido)-N-((2-(2,2,2-trifluoroethoxy)pyridin-4-yl)methyl)isonicotinamide | | 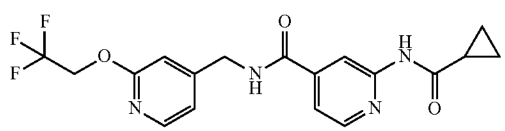 | | | 393.3 | 1.54 |

TABLE 1-continued

| Example | Name | Chirality | Structure | Amine part | Carboxylic part | Observed MS | Retention time (min) |
|---|---|---|---|---|---|---|---|
| 163 | 2-methyl-6-propionamido-N-(1-(2-(2,2,2-trifluoroethoxy)pyridin-4-yl)ethyl)isonicotinamide | single enantiomer | 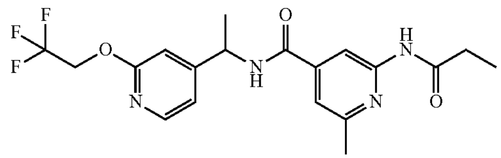 [SMILES: CCC(=O)Nc1cc(C(=O)NC(C)c2ccnc(OCC(F)(F)F)c2)cc(C)n1] | Amine-11 | | 409.3 | 1.63 |
| 164 | 2-methyl-6-propionamido-N-((4-(2,2,2-trifluoroethoxy)pyridin-2-yl)methyl)isonicotinamide | | 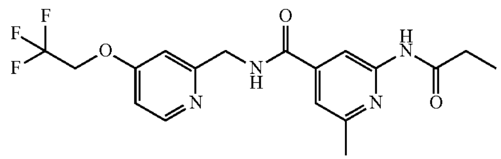 [SMILES: CCC(=O)Nc1cc(C(=O)NCc2cc(OCC(F)(F)F)ccn2)cc(C)n1] | Amine-2 | | 395.2 | 1.41 |
| 165 | 2-acetamido-N-((2-methyl-6-(2,2,2-trifluoroethoxy)pyridin-3-yl)methyl)isonicotinamide | | 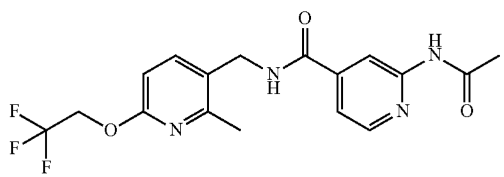 [SMILES: CC(=O)Nc1cc(C(=O)NCc2ccc(OCC(F)(F)F)nc2C)ccn1] | Amine-27 | | 381.3 | 1.52 |
| 166 | N-((2-methyl-6-(2,2,2-trifluoroethoxy)pyridin-3-yl)methyl)-2-propionamidoisonicotinamide | | 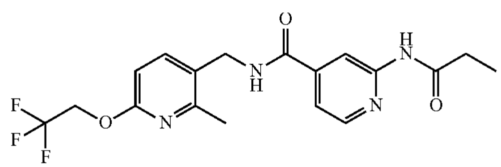 [SMILES: CCC(=O)Nc1cc(C(=O)NCc2ccc(OCC(F)(F)F)nc2C)ccn1] | Amine-27 | | 395.2 | 1.61 |
| 167 | 2-(cyclopropanecarboxamido)-N-((2-methyl-6-(2,2,2-trifluoroethoxy)pyridin-3-yl)methyl)isonicotinamide | | 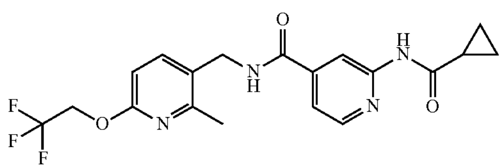 | Amine-27 | | 407.2 | 1.65 |

| Example | Name | Chirality | Structure | Amine part | Carboxylic part | Observed MS | Retention time (min) |
|---|---|---|---|---|---|---|---|
| 168 | 2-methyl-N-((2-methyl-6-(2,2,2-trifluoroethoxy)pyridin-3-yl)methyl)-6-propionamido-isonicotinamide | | 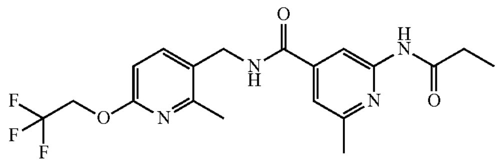 [SMILES: CCC(=O)Nc1cc(C(=O)NCc2ccc(OCC(F)(F)F)nc2C)cc(C)n1] | Amine-27 | | 409.3 | 1.67 |
| 169 | 2-isobutyramido-N-((6-(2,2,2-trifluoroethoxy)pyridin-3-yl)methyl)isonicotinamide | | 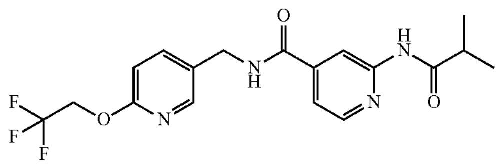 [SMILES: CC(C)C(=O)Nc1cc(C(=O)NCc2ccc(OCC(F)(F)F)nc2)ccn1] | | | 395.2 | 1.59 |
| 170 | 2-isobutyramido-N-((2-(2,2,2-trifluoroethoxy)pyridin-4-yl)methyl)isonicotinamide | | 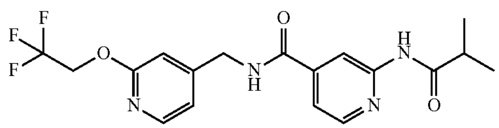 [SMILES: CC(C)C(=O)Nc1cc(C(=O)NCc2ccnc(OCC(F)(F)F)c2)ccn1] | | | 395.2 | 1.58 |
| 171 | 2-isobutyramido-N-((2-methoxy-6-(2,2,2-trifluoroethoxy)pyridin-3-yl)methyl)isonicotinamide | | 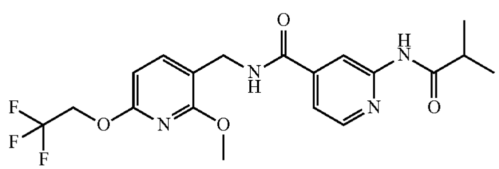 [SMILES: COc1nc(OCC(F)(F)F)ccc1CNC(=O)c1ccnc(NC(=O)C(C)C)c1] | Amine-24 | | 425.2 | 1.71 |
| 172 | N-((5-fluoro-6-(2,2,2-trifluoroethoxy)pyridin-3-yl)methyl)-2-propionamido-isonicotinamide | | 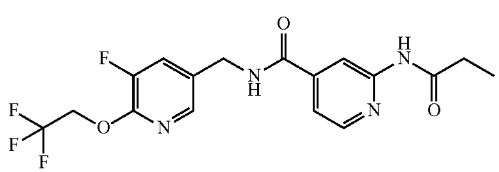 [SMILES: CCC(=O)Nc1cc(C(=O)NCc2cnc(OCC(F)(F)F)c(F)c2)ccn1] | Amine-28 | | 399.3 | 1.55 |

TABLE 1-continued

| Example | Chirality | Name | Structure | Amine part | Carboxylic part | Observed MS | Retention time (min) |
|---|---|---|---|---|---|---|---|
| 173 | | 2-(cyclopropanecarboxamido)-N-((5-fluoro-6-(2,2,2-trifluoroethoxy)pyridin-3-yl)methyl)isonicotinamide | 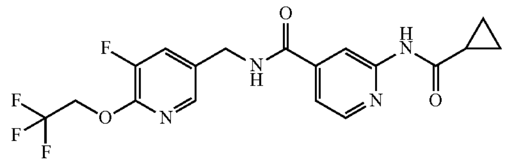 [SMILES: O=C(NCc1cnc(OCC(F)(F)F)c(F)c1)c1ccnc(NC(=O)C2CC2)c1] | Amine-28 | | 411.2 | 1.59 |
| 174 | | N-((5-fluoro-6-(2,2,2-trifluoroethoxy)pyridin-3-yl)methyl)-2-isobutyramidoisonicotinamide | 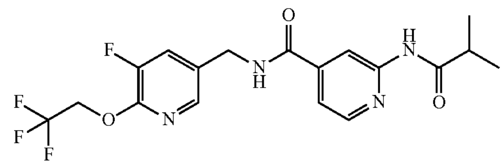 | Amine-28 | | 413.3 | 1.63 |
| 175 | | N-((5-fluoro-6-(2,2,2-trifluoroethoxy)pyridin-3-yl)methyl)-6-methyl-2-propionamidoisonicotinamide | 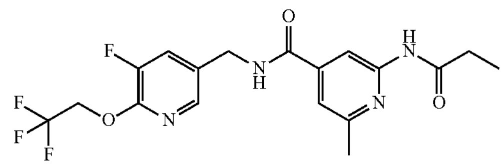 | Amine-28 | | 413.3 | 1.61 |
| 176 | | N-((4-methyl-6-(2,2,2-trifluoroethoxy)pyridin-3-yl)methyl)-2-propionamidoisonicotinamide | 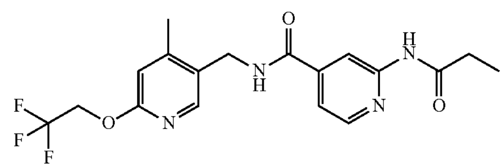 [SMILES: CCC(=O)Nc1cc(C(=O)NCc2cnc(OCC(F)(F)F)cc2C)ccn1] | Amine-29 | | 395.3 | 1.56 |
| 177 | | 2-(cyclopropanecarboxamido)-N-((4-methyl-6-(2,2,2-trifluoroethoxy)pyridin-3-yl)methyl)isonicotinamide | 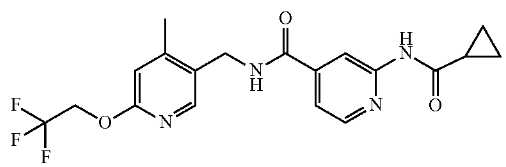 [SMILES: Cc1cc(OCC(F)(F)F)ncc1CNC(=O)c1ccnc(NC(=O)C2CC2)c1] | Amine-29 | | 407.3 | 1.6 |

TABLE 1-continued

| Example | Name | Chirality | Structure | Amine part | Carboxylic part | Observed MS | Retention time (min) |
|---|---|---|---|---|---|---|---|
| 178 | 2-isobutyramido-N-((4-methyl-6-(2,2,2-trifluoroethoxy)pyridin-3-yl)methyl)isonicotinamide | | 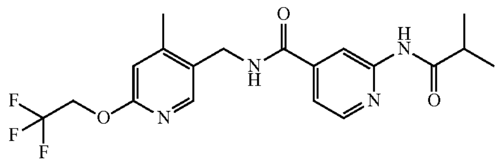 [SMILES: Cc1cc(OCC(F)(F)F)ncc1CNC(=O)c1ccnc(NC(=O)C(C)C)c1] | Amine-29 | | 409.3 | 1.64 |
| 179 | 2-methyl-N-((4-methyl-6-(2,2,2-trifluoroethoxy)pyridin-3-yl)methyl)-6-propionamidoisonicotinamide | | 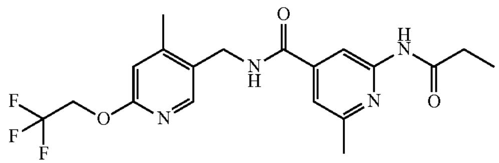 [SMILES: CCC(=O)Nc1cc(C(=O)NCc2cnc(OCC(F)(F)F)cc2C)cc(C)n1] | Amine-29 | | 409.3 | 1.63 |
| 180 | N-((2-methoxy-6-(2,2,2-trifluoroethoxy)pyridin-3-yl)methyl)-6-methyl-2-propionamidopyrimidine-4-carboxamide | | 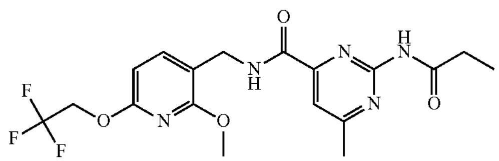 | Amine-24 | | 426.2 | 1.68 |
| 181 | 2-(cyclopropanecarboxamido)-N-((2-methoxy-6-(2,2,2-trifluoroethoxy)pyridin-3-yl)methyl)-6-methylpyrimidine-4-carboxamide | | 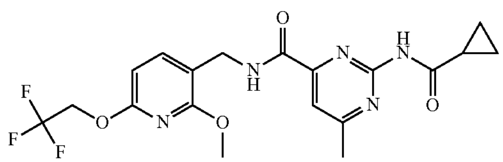 [SMILES: COc1nc(OCC(F)(F)F)ccc1CNC(=O)c1cc(C)nc(NC(=O)C2CC2)n1] | Amine-24 | | 438.2 | 1.7 |

TABLE 1-continued

| Example | Name | Chirality | Structure | Amine part | Carboxylic part | Observed MS | Retention time (min) |
|---|---|---|---|---|---|---|---|
| 182 | 2-(cyclopropanecarboxamido)-6-methyl-N-(1-(6-(3,3,3-trifluoropropoxy)pyridin-3-yl)ethyl)pyrimidine-4-carboxamide | single enantiomer | 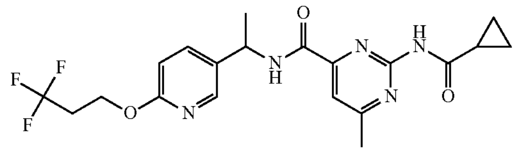 | Amine-21 | | 436.3 | 1.62 |
| 183 | 2-propionamido-N-(1-(6-(3,3,3-trifluoropropoxy)pyridin-3-yl)ethyl)pyrimidine-4-carboxamide | single enantiomer | 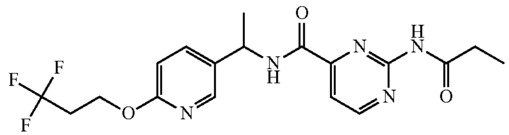 [SMILES: CCC(=O)Nc1nccc(C(=O)NC(C)c2ccc(OCCC(F)(F)F)nc2)n1] | alternative route | | 410.3 | 1.53 |
| 184 | 2-(cyclopropanecarboxamido)-N-(1-(6-(3,3,3-trifluoropropoxy)pyridin-3-yl)ethyl)pyrimidine-4-carboxamide | single enantiomer | 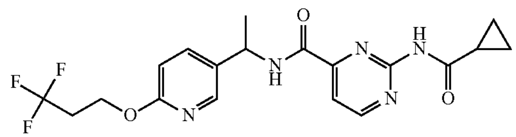 [SMILES: CC(NC(=O)c1ccnc(NC(=O)C2CC2)n1)c1ccc(OCCC(F)(F)F)nc1] | Amine-21 | | 422.3 | 1.56 |
| 185 | 2-propionamido-N-(1-(6-(2,2,2-trifluoroethoxy)pyridin-3-yl)propyl)isonicotinamide | single enantiomer | 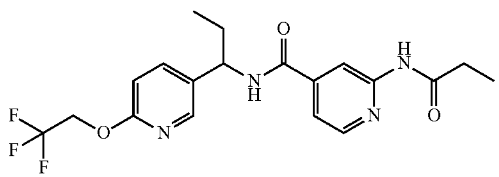 [SMILES: CCC(=O)Nc1cc(C(=O)NC(CC)c2ccc(OCC(F)(F)F)nc2)ccn1] | Amine-6 | | 409.3 | 1.64 |
| 186 | 2-isobutyramido-N-(1-(6-(3,3,3-trifluoropropoxy)pyridin-3-yl)ethyl)isonicotinamide | single enantiomer | 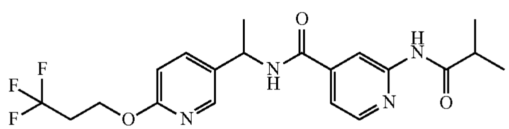 [SMILES: CC(C)C(=O)Nc1cc(C(=O)NC(C)c2ccc(OCCC(F)(F)F)nc2)ccn1] | Amine-21 | | 423.3 | 1.63 |

TABLE 1-continued

| Example | Name | Chirality | Structure | Amine part | Carboxylic part | Observed MS | Retention time (min) |
|---|---|---|---|---|---|---|---|
| 187 | 2-isobutyramido-N-((2-methyl-6-(2,2,2-trifluoroethoxy)pyridin-3-yl)methyl)isonicotinamide | single enantiomer | 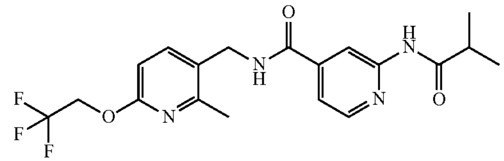 [SMILES: Cc1nc(OCC(F)(F)F)ccc1CNC(=O)c1ccnc(NC(=O)C(C)C)c1] | Amine-27 | | 409.3 | 1.68 |
| 188 | 2-isobutyramido-N-(1-(2-(2,2,2-trifluoroethoxy)pyridin-4-yl)ethyl)isonicotinamide | single enantiomer | 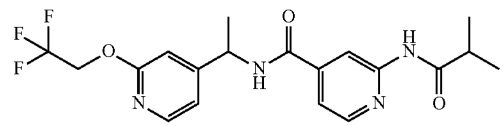 | Amine-11 | | 409.3 | 1.64 |
| 189 | 2-isobutyramido-N-(1-(6-(2,2,2-trifluoroethoxy)pyridin-2-yl)ethyl)isonicotinamide | single enantiomer | 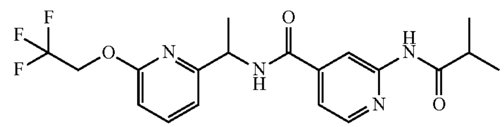 [SMILES: CC(C)C(=O)Nc1cc(C(=O)NC(C)c2cccc(OCC(F)(F)F)n2)ccn1] | Amine-7 | | 409.3 | 1.72 |
| 190 | 2-propionamido-N-((6-(3,3,3-trifluoropropoxy)pyridin-3-yl)methyl)isonicotinamide | | 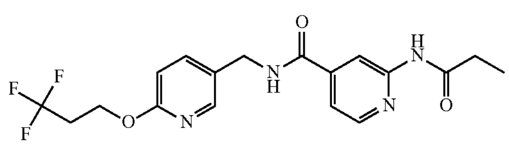 [SMILES: CCC(=O)Nc1cc(C(=O)NCc2ccc(OCCC(F)(F)F)nc2)ccn1] | Amine-30 | | 395.3 | 1.5 |
| 191 | 2-(cyclopropanecarboxamido)-N-((6-(3,3,3-trifluoropropoxy)pyridin-3-yl)methyl)isonicotinamide | | 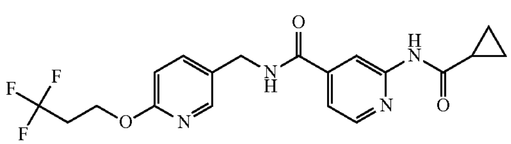 | Amine-30 | | 407.3 | 1.54 |

TABLE 1-continued

| Example | Name | Chirality | Structure | Amine part | Carboxylic part | Observed MS | Retention time (min) |
|---|---|---|---|---|---|---|---|
| 192 | 2-methyl-6-propionamido-N-((6-(3,3,3-trifluoropropoxy)pyridin-3-yl)methyl)isonicotinamide | | 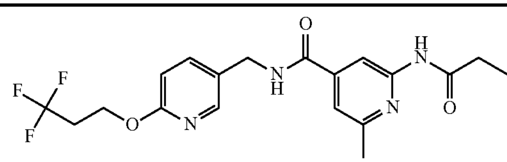 | Amine-30 | | 409.3 | 1.56 |
| 193 | N-(1-(5-methoxy-6-(2,2,2-trifluoroethoxy)pyridin-3-yl)ethyl)-6-methyl-2-propionamidopyrimidine-4-carboxamide | single enantiomer | 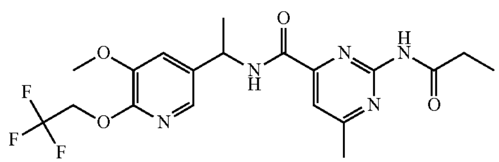 | Amine-22 | | 440.3 | 1.6 |
| 194 | 2-(cyclopropanecarboxamido)-N-(1-(5-methoxy-6-(2,2,2-trifluoroethoxy)pyridin-3-yl)ethyl)-6-methylpyrimidine-4-carboxamide | single enantiomer | 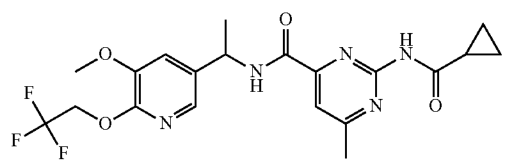 [SMILES: COc1cc(C(C)NC(=O)c2cc(C)nc(NC(=O)C3CC3)n2)cnc1OCC(F)(F)F] | Amine-22 | | 452.3 | 1.62 |
| 195 | 2-(cyclopropanecarboxamido)-N-(1-(6-(2-(2,2,2-trifluoroethoxy)ethoxy)pyridin-3-yl)ethyl)isonicotinamide | single enantiomer | 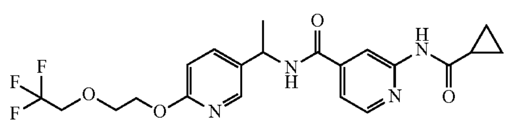 [SMILES: CC(NC(=O)c1ccnc(NC(=O)C2CC2)c1)c1ccc(OCCOCC(F)(F)F)nc1] | Amine-31 | | 451.3 | 1.56 |

| Example | Name | Chirality | Structure | Amine part | Carboxylic part | Observed MS | Retention time (min) |
|---|---|---|---|---|---|---|---|
| 196 | 2-isobutyramido-N-(1-(6-(2-(2,2,2-trifluoroethoxy)ethoxy)pyridin-3-yl)ethyl)isonicotinamide | single enantiomer | 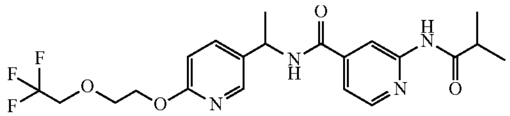 [SMILES: CC(C)C(=O)Nc1cc(C(=O)NC(C)c2ccc(OCCOCC(F)(F)F)nc2)ccn1] | Amine-31 | | 453.3 | 1.6 |
| 197 | 2-acetamido-N-((4-methyl-6-(2,2,2-trifluoroethoxy)pyridin-3-yl)methyl)isonicotinamide | | 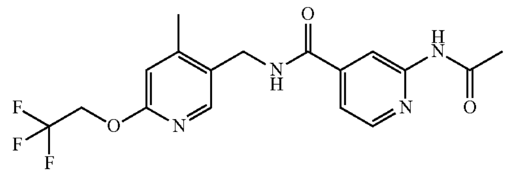 [SMILES: CC(=O)Nc1cc(C(=O)NCc2cnc(OCC(F)(F)F)cc2C)ccn1] | Amine-29 | | 381.3 | 1.48 |
| 198 | 2-acetamido-6-methyl-N-(1-(6-(3,3,3-trifluoropropoxy)pyridin-3-yl)ethyl)pyrimidine-4-carboxamide | single enantiomer | 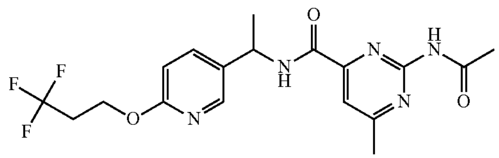 [SMILES: CC(=O)Nc1nc(C)cc(C(=O)NC(C)c2ccc(OCCC(F)(F)F)nc2)n1] | Amine-21 | | 410.3 | 1.51 |
| 199 | 2-isobutyramido-N-(1-(6-(3,3,3-trifluoropropoxy)pyridin-3-yl)ethyl)pyrimidine-4-carboxamide | single enantiomer | 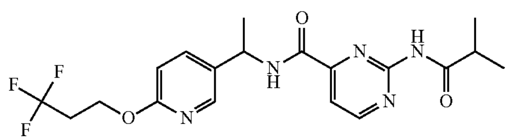 [SMILES: CC(C)C(=O)Nc1nccc(C(=O)NC(C)c2ccc(OCCC(F)(F)F)nc2)n1] | | alternative route | 424.3 | 1.6 |
| 200 | 2-(cyclopropanecarboxamido)-N-(1-(6-(2,2-difluoroethoxy)pyridin-3-yl)ethyl)isonicotinamide | single enantiomer | 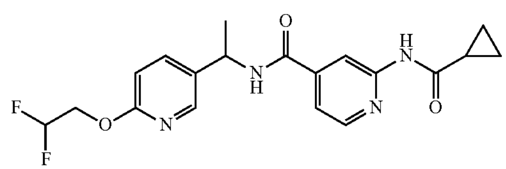 [SMILES: CC(NC(=O)c1ccnc(NC(=O)C2CC2)c1)c1ccc(OCC(F)F)nc1] | Amine-32 | | 389.3 | 1.49 |

TABLE 1-continued

| Example | Name | Chirality | Structure | Amine part | Carboxylic part | Observed MS | Retention time (min) |
|---|---|---|---|---|---|---|---|
| 201 | N-(1-(6-(2,2-difluoroethoxy)pyridin-3-yl)ethyl)-2-methyl-6-propionamidoisonicotinamide | single enantiomer | 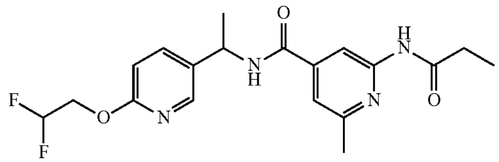 [SMILES: CCC(=O)Nc1cc(C(=O)NC(C)c2ccc(OCC(F)F)nc2)cc(C)n1] | Amine-32 | | 391.3 | 1.51 |
| 202 | 2-acetamido-N-((6-(3,3,3-trifluoropropoxy)pyridin-3-yl)methyl)isonicotinamide | | 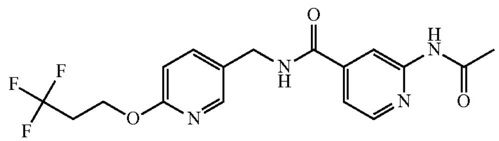 [SMILES: CC(=O)Nc1cc(C(=O)NCc2ccc(OCCC(F)(F)F)nc2)ccn1] | Amine-30 | | 381.3 | 1.41 |
| 203 | N-((5-fluoro-6-(2,2,2-trifluoroethoxy)pyridin-3-yl)methyl)-6-methyl-2-propionamidopyrimidine-4-carboxamide | | 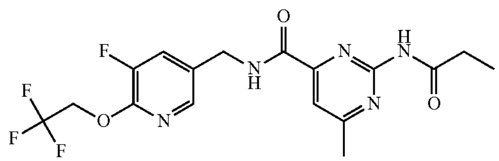 [SMILES: CCC(=O)Nc1nc(C)cc(C(=O)NCc2cnc(OCC(F)(F)F)c(F)c2)n1] | Amine-28 | | 414.3 | 1.58 |
| 204 | 2-(cyclopropanecarboxamido)-N-((5-fluoro-6-(2,2,2-trifluoroethoxy)pyridin-3-yl)methyl)-6-methylpyrimidine-4-carboxamide | | 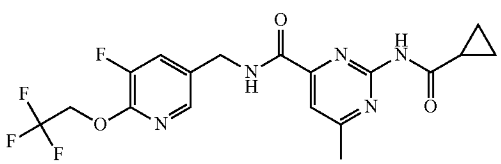 | Amine-28 | | 426.2 | 1.6 |

TABLE 1-continued

| Example | Name | Chirality | Structure | Amine part | Carboxylic part | Observed MS | Retention time (min) |
|---|---|---|---|---|---|---|---|
| 205 | 2-isobutyramido-6-methyl-N-(1-(6-(2,2,2-trifluoroethoxy)pyridin-3-yl)ethyl)pyrimidine-4-carboxamide | single enantiomer | 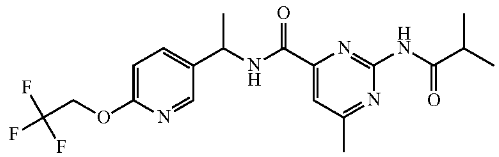 | Amine-1 | | 424.3 | 1.67 |
| 206 | 2-(cyclopropanecarboxamido)-N-(1-(5-fluoro-6-(2,2,2-trifluoroethoxy)pyridin-3-yl)ethyl)pyrimidine-4-carboxamide | single enantiomer | 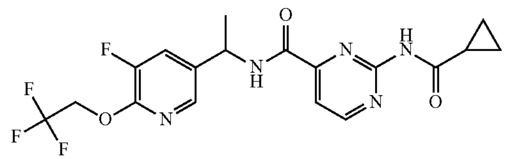 | Amine-12 | | 426.3 | 1.61 |
| 207 | 2-(cyclopropanecarboxamido)-N-(1-(5-fluoro-6-(2,2,2-trifluoroethoxy)pyridin-3-yl)ethyl)-6-methylpyrimidine-4-carboxamide | single enantiomer | 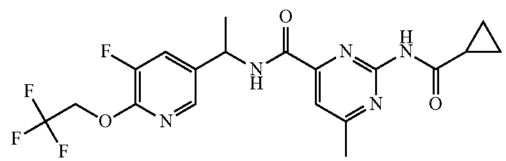 [SMILES: Cc1cc(C(=O)NCc2cnc(OCC(F)(F)F)c(F)c2)nc(NC(=O)C2CC2)n1] | Amine-12 | | 440.3 | 1.66 |
| 208 | 2-(cyclobutanecarboxamido)-N-(1-(5-fluoro-6-(2,2,2-trifluoroethoxy)pyridin-3-yl)ethyl)-6-methylpyrimidine-4-carboxamide | single enantiomer | 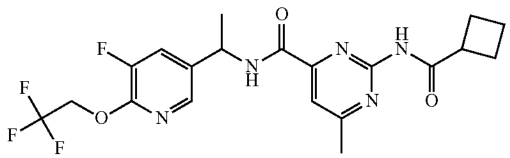 [SMILES: Cc1cc(C(=O)NC(C)c2cnc(OCC(F)(F)F)c(F)c2)nc(NC(=O)C2CCC2)n1] | alternative route | | 454.3 | 1.76 |

| Example | Name | Structure | Chirality | Amine part | Carboxylic part | Observed MS | Retention time (min) |
|---|---|---|---|---|---|---|---|
| 209 | N-(1-(5-fluoro-6-(2,2,2-trifluoroethoxy)pyridin-3-yl)ethyl)-2-isobutyramidopyrimidine-4-carboxamide | 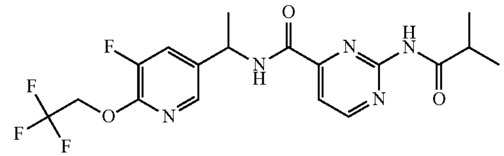 [SMILES: CC(C)C(=O)Nc1nccc(C(=O)NC(C)c2cnc(OCC(F)(F)F)c(F)c2)n1] | single enantiomer | alternative route | | 428.3 | 1.64 |
| 210 | N-(1-(5-chloro-6-(2,2,2-trifluoroethoxy)pyridin-3-yl)ethyl)-2-propionamidopyrimidine-4-carboxamide | 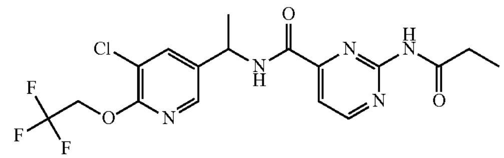 [SMILES: CCC(=O)Nc1nccc(C(=O)NC(C)c2cnc(OCC(F)(F)F)c(Cl)c2)n1] | single enantiomer | alternative route | | 430.2 | 1.65 |
| 211 | N-(1-(5-chloro-6-(2,2,2-trifluoroethoxy)pyridin-3-yl)ethyl)-2-(cyclopropanecarboxamido)pyrimidine-4-carboxamide | 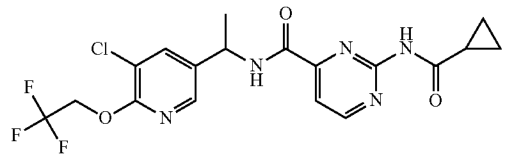 | single enantiomer | Amine-5 | | 442.2 | 1.67 |
| 212 | N-(1-(5-chloro-6-(2,2,2-trifluoroethoxy)pyridin-3-yl)ethyl)-2-isobutyramidopyrimidine-4-carboxamide | 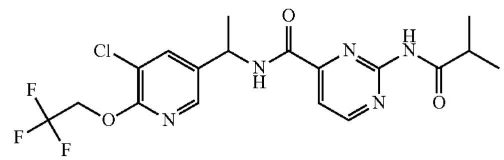 [SMILES: CC(C)C(=O)Nc1nccc(C(=O)NC(C)c2cnc(OCC(F)(F)F)c(Cl)c2)n1] | single enantiomer | alternative route | | 444.2 | 1.71 |
| 213 | N-(1-(5-chloro-6-(2,2,2-trifluoroethoxy)pyridin-3-yl)ethyl)-2-(cyclobutanecarboxamido)pyrimidine-4-carboxamide | 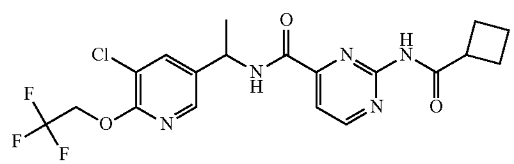 [SMILES: CC(NC(=O)c1ccnc(NC(=O)C2CCC2)n1)c1cnc(OCC(F)(F)F)c(Cl)c1] | single enantiomer | alternative route | | 456.2 | 1.76 |

TABLE 1-continued

| Example | Name | Chirality | Structure | Amine part | Carboxylic part | Observed MS | Retention time (min) |
|---|---|---|---|---|---|---|---|
| 214 | N-(1-(5-chloro-6-(2,2,2-trifluoroethoxy)pyridin-3-yl)ethyl)-6-methyl-2-propionamido-pyrimidine-4-carboxamide | single enantiomer | 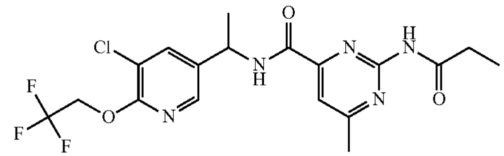 | Amine-5 | | 444.2 | 1.71 |
| 215 | N-(1-(5-chloro-6-(2,2,2-trifluoroethoxy)pyridin-3-yl)ethyl)-2-(cyclopropane-carboxamido)-6-methylpyrimidine-4-carboxamide | single enantiomer | 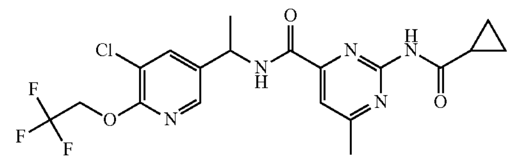 | Amine-5 | | 456.2 | 1.73 |
| 216 | N-(1-(5-chloro-6-(2,2,2-trifluoroethoxy)pyridin-3-yl)ethyl)-2-isobutyramido-6-methylpyrimidine-4-carboxamide | single enantiomer | 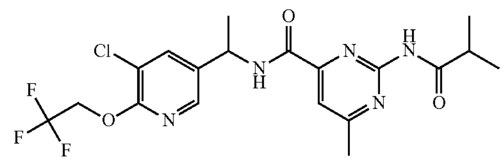 [SMILES: Cc1cc(C(=O)NC(C)c2cnc(OCC(F)(F)F)c(Cl)c2)nc(NC(=O)C(C)C)n1] | Amine-5 | | 458.2 | 1.77 |
| 217 | N-(1-(5-chloro-6-(2,2,2-trifluoroethoxy)pyridin-3-yl)ethyl)-2-(cyclobutane-carboxamido)-6-methylpyrimidine-4-carboxamide | single enantiomer | 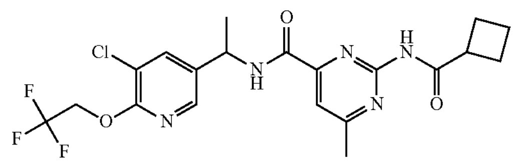 | | alternative route | 470.2 | 1.82 |

TABLE 1-continued

| Example | Name | Chirality | Structure | Amine part | Carboxylic part | Observed MS | Retention time (min) |
|---|---|---|---|---|---|---|---|
| 218 | 2-isobutyramido-N-(1-(5-methoxy-6-(2,2,2-trifluoroethoxy)pyridin-3-yl)ethyl)-6-methylpyrimidine-4-carboxamide | single enantiomer | 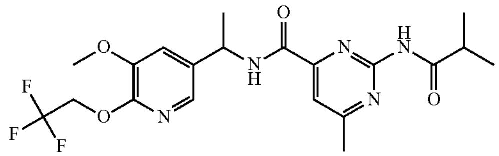 [SMILES: COc1cc(C(C)NC(=O)c2cc(C)nc(NC(=O)C(C)C)n2)cnc1OCC(F)(F)F] | Amine-22 | | 454.3 | 1.66 |
| 219 | 2-isobutyramido-N-(1-(6-(2,2,2-trifluoroethoxy)pyridin-3-yl)propyl)isonicotinamide | single enantiomer | 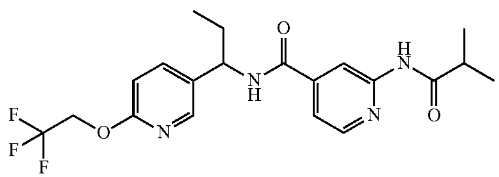 [SMILES: CCC(NC(=O)c1ccnc(NC(=O)C(C)C)c1)c1ccc(OCC(F)(F)F)nc1] | Amine-6 | | 423.3 | 1.71 |
| 220 | N-(1-(5-fluoro-6-(2,2,2-trifluoroethoxy)pyridin-3-yl)ethyl)-2-isobutyramidoisonicotinamide | single enantiomer | 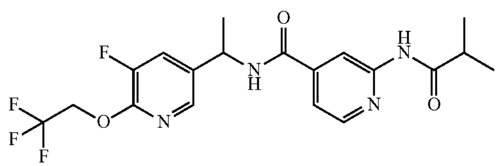 [SMILES: CC(C)C(=O)Nc1cc(C(=O)NC(C)c2cnc(OCC(F)(F)F)c(F)c2)ccn1] | Amine-12 | | 427.3 | 1.68 |
| 221 | 2-isobutyramido-N-(1-(5-methoxy-6-(2,2,2-trifluoroethoxy)pyridin-3-yl)ethyl)isonicotinamide | single enantiomer | 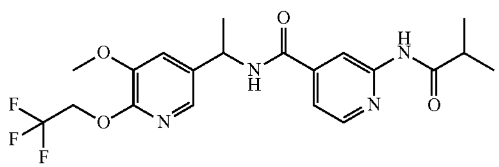 [SMILES: COc1cc(C(C)NC(=O)c2ccnc(NC(=O)C(C)C)c2)cnc1OCC(F)(F)F] | Amine-22 | | 439.3 | 1.63 |
| 222 | 2-isobutyramido-N-((6-(3,3,3-trifluoropropoxy)pyridin-3-yl)methyl)isonicotinamide | | 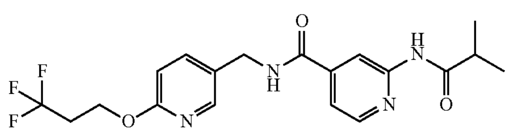 [SMILES: CC(C)C(=O)Nc1cc(C(=O)NCc2ccc(OCCC(F)(F)F)nc2)ccn1] | Amine-30 | | 409.3 | 1.58 |

TABLE 1-continued

| Example | Name | Chirality | Structure | Amine part | Carboxylic part | Observed MS | Retention time (min) |
|---|---|---|---|---|---|---|---|
| 223 | N-(1-(5-methyl-6-(2,2,2-trifluoroethoxy)pyridin-3-yl)ethyl)-2-propionamidopyrimidine-4-carboxamide | single enantiomer | 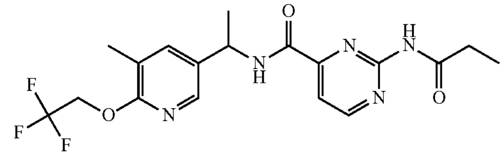 [SMILES: CCC(=O)Nc1nccc(C(=O)NC(C)c2cnc(OCC(F)(F)F)c(C)c2)n1] | alternative route | | 410.3 | 1.64 |
| 224 | 2-(cyclopropanecarboxamido)-N-(1-(5-methyl-6-(2,2,2-trifluoroethoxy)pyridin-3-yl)ethyl)pyrimidine-4-carboxamide | single enantiomer | 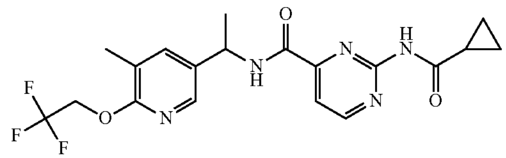 [SMILES: Cc1cc(C(C)NC(=O)c2ccnc(NC(=O)C3CC3)n2)cnc1OCC(F)(F)F] | Amine-17 | | 422.3 | 1.66 |
| 225 | 2-isobutyramido-N-(1-(5-methyl-6-(2,2,2-trifluoroethoxy)pyridin-3-yl)ethyl)pyrimidine-4-carboxamide | single enantiomer | 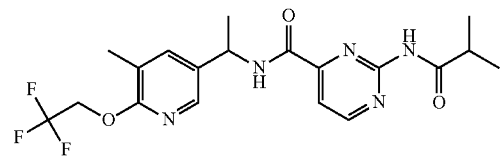 [SMILES: Cc1cc(C(C)NC(=O)c2ccnc(NC(=O)C(C)C)n2)cnc1OCC(F)(F)F] | alternative route | | 424.3 | 1.71 |
| 226 | 2-(cyclobutanecarboxamido)-N-(1-(5-methyl-6-(2,2,2-trifluoroethoxy)pyridin-3-yl)ethyl)pyrimidine-4-carboxamide | single enantiomer | 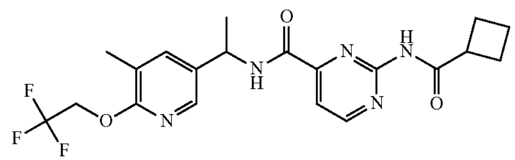 [SMILES: Cc1cc(C(C)NC(=O)c2ccnc(NC(=O)C3CCC3)n2)cnc1OCC(F)(F)F] | alternative route | | 436.3 | 1.75 |
| 227 | 6-methyl-N-(1-(5-methyl-6-(2,2,2-trifluoroethoxy)pyridin-3-yl)ethyl)-2-propionamidopyrimidine-4-carboxamide | single enantiomer | 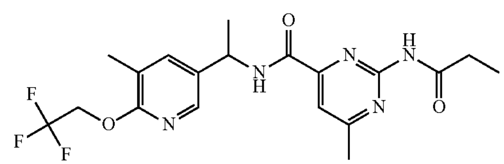 [SMILES: CCC(=O)Nc1nc(C)cc(C(=O)NC(C)c2cnc(OCC(F)(F)F)c(C)c2)n1] | Amine-17 | | 424.3 | 1.71 |

TABLE 1-continued

| Example | Name | Chirality | Structure | Amine part | Carboxylic part | Observed MS | Retention time (min) |
|---|---|---|---|---|---|---|---|
| 228 | 2-(cyclopropanecarboxamido)-6-methyl-N-(1-(5-methyl-6-(2,2,2-trifluoroethoxy)pyridin-3-yl)ethyl)pyrimidine-4-carboxamide | single enantiomer | 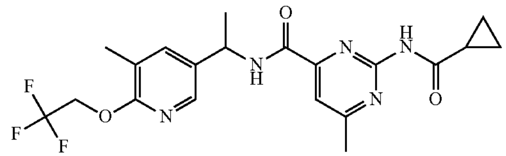 [SMILES: Cc1cc(C(=O)NC(C)c2cnc(OCC(F)(F)F)c(C)c2)nc(NC(=O)C2CC2)n1] | Amine-17 | | 436.3 | 1.73 |
| 229 | 2-isobutyramido-6-methyl-N-(1-(5-methyl-6-(2,2,2-trifluoroethoxy)pyridin-3-yl)ethyl)pyrimidine-4-carboxamide | single enantiomer | 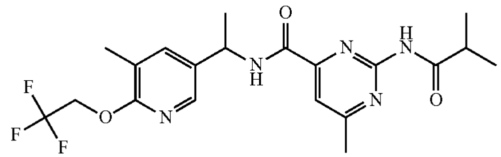 | Amine-17 | | 438.3 | 1.77 |
| 230 | 2-(cyclobutanecarboxamido)-6-methyl-N-(1-(5-methyl-6-(2,2,2-trifluoroethoxy)pyridin-3-yl)ethyl)pyrimidine-4-carboxamide | single enantiomer | 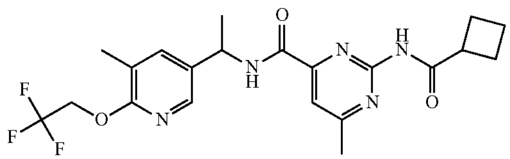 | alternative route | | 450.3 | 1.82 |
| 231 | 3-isobutyramido-N-(1-(6-(2,2,2-trifluoroethoxy)pyridin-3-yl)ethyl)picolinamide | single enantiomer | 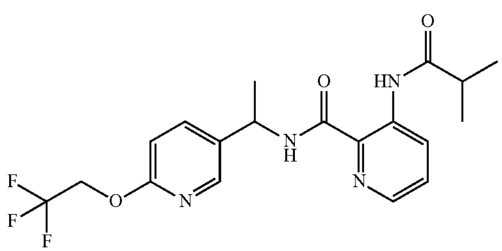 [SMILES: CC(C)C(=O)Nc1cccnc1C(=O)NC(C)c1ccc(OCC(F)(F)F)nc1] | alternative route | | 409.2 | 1.99 |

| Example | Name | Chirality | Structure | Amine part | Carboxylic part | Observed MS | Retention time (min) |
|---|---|---|---|---|---|---|---|
| 232 | 2-acetamido-N-(1-(5-chloro-6-(2,2,2-trifluoroethoxy)pyridin-3-yl)ethyl)pyrimidine-4-carboxamide | single enantiomer | 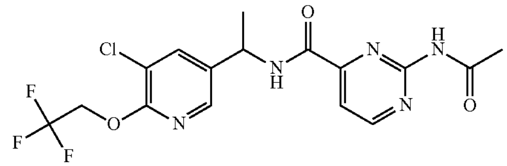 [SMILES: CC(=O)Nc1nccc(C(=O)NC(C)c2cnc(OCC(F)(F)F)c(Cl)c2)n1] | | alternative route | 416.2 | 1.57 |
| 233 | 2-acetamido-N-(1-(5-chloro-6-(2,2,2-trifluoroethoxy)pyridin-3-yl)ethyl)-6-methylpyrimidine-4-carboxamide | single enantiomer | 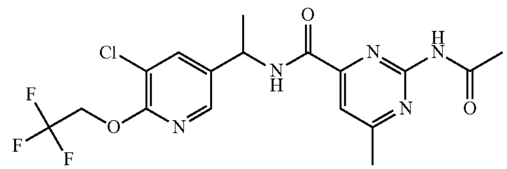 | Amine-5 | | 430.2 | 1.63 |
| 234 | 2-acetamido-N-(1-(5-methyl-6-(2,2,2-trifluoroethoxy)pyridin-3-yl)ethyl)pyrimidine-4-carboxamide | single enantiomer | 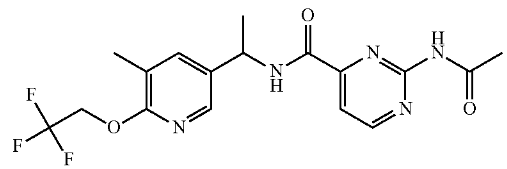 | | alternative route | 396.3 | 1.56 |
| 235 | 2-acetamido-6-methyl-N-(1-(5-methyl-6-(2,2,2-trifluoroethoxy)pyridin-3-yl)ethyl)pyrimidine-4-carboxamide | single enantiomer | 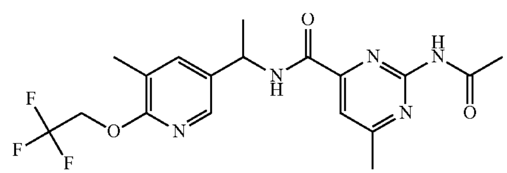 | Amine-17 | | 410.3 | 1.62 |

TABLE 1-continued

| Example | Name | Chirality | Structure | Amine part | Carboxylic part | Observed MS | Retention time (min) |
|---|---|---|---|---|---|---|---|
| 236 | 2-acetamido-6-methyl-N-(1-(6-(2,2,2-trifluoroethoxy)pyridin-3-yl)propyl)isonicotinamide | single enantiomer | 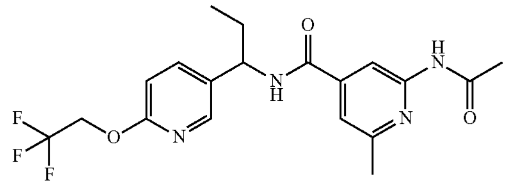 [SMILES: CCC(NC(=O)c1cc(C)nc(NC(C)=O)c1)c1ccc(OCC(F)(F)F)nc1] | Amine-6 | | 409.3 | 1.61 |
| 237 | 2-acetamido-6-methyl-N-((6-(2,2,2-trifluoroethoxy)pyridin-3-yl)methyl)isonicotinamide | | 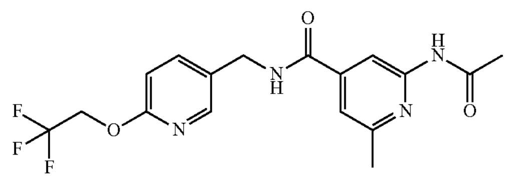 [SMILES: CC(=O)Nc1cc(C(=O)NCc2ccc(OCC(F)(F)F)nc2)cc(C)n1] | | | 381.3 | 1.48 |
| 238 | 2-acetamido-N,6-dimethyl-N-((6-(2,2,2-trifluoroethoxy)pyridin-3-yl)methyl)isonicotinamide | | 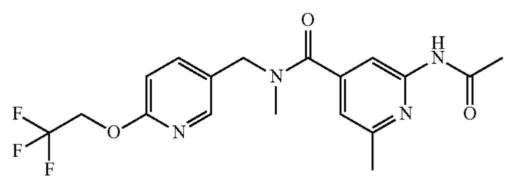 [SMILES: CC(=O)Nc1cc(C(=O)N(C)Cc2ccc(OCC(F)(F)F)nc2)cc(C)n1] | | | 395.2 | 1.52 |
| 239 | 2-acetamido-N-(1-(5-fluoro-6-(2,2,2-trifluoroethoxy)pyridin-3-yl)ethyl)-6-methylisonicotinamide | single enantiomer | 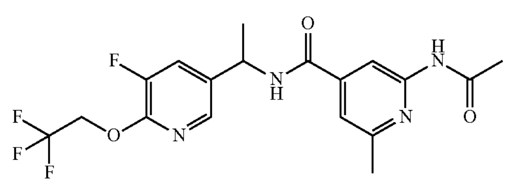 [SMILES: CC(=O)Nc1cc(C(=O)NC(C)c2cnc(OCC(F)(F)F)c(F)c2)cc(C)n1] | Amine-12 | | 413.2 | 1.58 |

TABLE 1-continued

| Example | Name | Chirality | Structure | Amine part | Carboxylic part | Observed MS | Retention time (min) |
|---|---|---|---|---|---|---|---|
| 240 | 2-acetamido-N-((5-fluoro-6-(2,2,2-trifluoroethoxy)pyridin-3-yl)methyl)-6-methylisonicotinamide | | 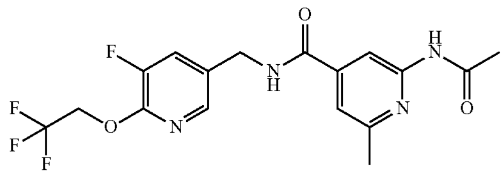 [SMILES: CC(=O)Nc1cc(C(=O)NCc2cnc(OCC(F)(F)F)c(F)c2)cc(C)n1] | Amine-28 | | 399.2 | 1.53 |
| 241 | 2-acetamido-N-((2-methoxy-6-(2,2,2-trifluoroethoxy)pyridin-3-yl)methyl)-6-methylisonicotinamide | | 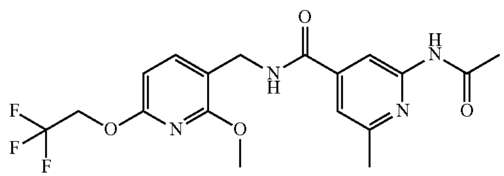 [SMILES: COc1nc(OCC(F)(F)F)ccc1CNC(=O)c1cc(C)nc(NC(C)=O)c1] | Amine-24 | | 411.3 | 1.61 |
| 242 | 2-acetamido-6-methyl-N-((2-methyl-6-(2,2,2-trifluoroethoxy)pyridin-3-yl)methyl)isonicotinamide | | 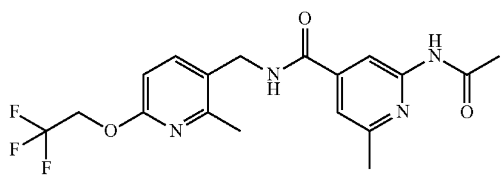 [SMILES: CC(=O)Nc1cc(C(=O)NCc2ccc(OCC(F)(F)F)nc2C)cc(C)n1] | Amine-27 | | 395.3 | 1.58 |
| 243 | 2-acetamido-6-methyl-N-((4-methyl-6-(2,2,2-trifluoroethoxy)pyridin-3-yl)methyl)isonicotinamide | | 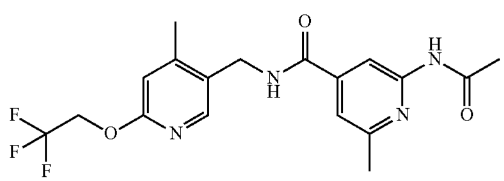 | Amine-29 | | 395.3 | 1.54 |

TABLE 1-continued

| Example | Chirality | Name | Structure | Amine part | Carboxylic part | Observed MS | Retention time (min) |
|---|---|---|---|---|---|---|---|
| 244 | single enantiomer | 2-acetamido-6-methyl-N-(1-(6-(3,3,3-trifluoropropoxy)pyridin-3-yl)ethyl)isonicotinamide | 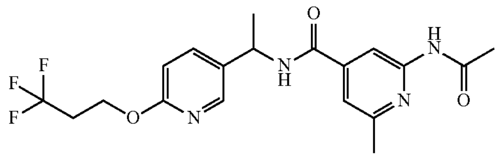 [SMILES: CC(=O)Nc1cc(C(=O)NC(C)c2ccc(OCCC(F)(F)F)nc2)cc(C)n1] | Amine-21 | | 409.3 | 1.53 |
| 245 | | 2-acetamido-6-methyl-N-((6-(3,3,3-trifluoropropoxy)pyridin-3-yl)methyl)isonicotinamide | 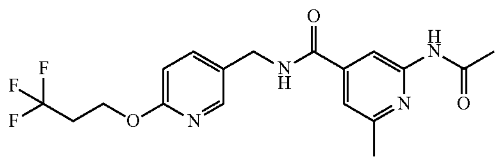 [SMILES: CC(=O)Nc1cc(C(=O)NCc2ccc(OCCC(F)(F)F)nc2)cc(C)n1] | Amine-30 | | 395.3 | 1.48 |
| 246 | | 2-acetamido-6-methyl-N-((2-(2,2,2-trifluoroethoxy)pyridin-4-yl)methyl)isonicotinamide | 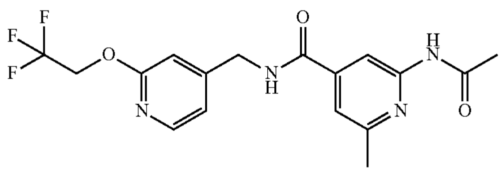 [SMILES: CC(=O)Nc1cc(C(=O)NCc2ccnc(OCC(F)(F)F)c2)cc(C)n1] | | | 381.3 | 1.47 |
| 247 | single enantiomer | 2-acetamido-6-methyl-N-(1-(6-(2,2,2-trifluoroethoxy)pyridin-2-yl)ethyl)isonicotinamide | 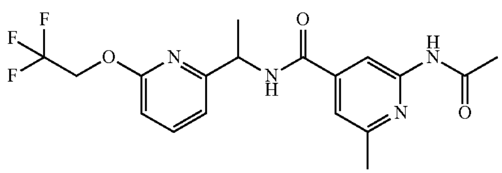 [SMILES: CC(=O)Nc1cc(C(=O)NC(C)c2cccc(OCC(F)(F)F)n2)cc(C)n1] | Amine-7 | | 395.3 | 1.6 |

TABLE 1-continued

| Example | Name | Chirality | Structure | Amine part | Carboxylic part | Observed MS | Retention time (min) |
|---|---|---|---|---|---|---|---|
| 248 | 6-methyl-2-propionamido-N-((6-(2,2,2-trifluoroethoxy)pyridin-3-yl)methyl)pyrimidine-4-carboxamide | | 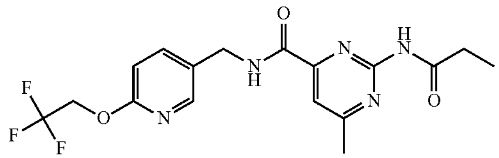 [SMILES: CCC(=O)Nc1nc(C)cc(C(=O)NCc2ccc(OCC(F)(F)F)nc2)n1] | | | 396.3 | 1.54 |
| 249 | 2-(cyclopropanecarboxamido)-6-methyl-N-((6-(2,2,2-trifluoroethoxy)pyridin-3-yl)methyl)pyrimidine-4-carboxamide | | 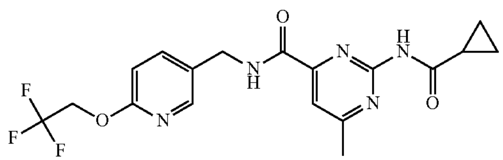 [SMILES: Cc1cc(C(=O)NCc2ccc(OCC(F)(F)F)nc2)nc(NC(=O)C2CC2)n1] | | | 408.2 | 1.56 |
| 250 | 2-isobutyramido-N-(1-(6-(2,2,2-trifluoroethoxy)pyridin-3-yl)ethyl)pyrimidine-4-carboxamide | single enantiomer | 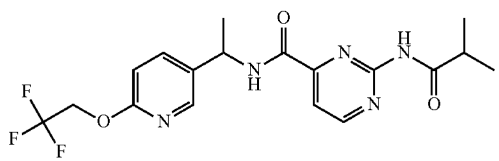 [SMILES: CC(C)C(=O)Nc1nccc(C(=O)NC(C)c2ccc(OCC(F)(F)F)nc2)n1] | alternative route | | 410.3 | 1.61 |
| 251 | 2-acetamido-N-(1-(5-fluoro-6-(2,2,2-trifluoroethoxy)pyridin-3-yl)ethyl)-N,6-dimethylisonicotinamide | single enantiomer | 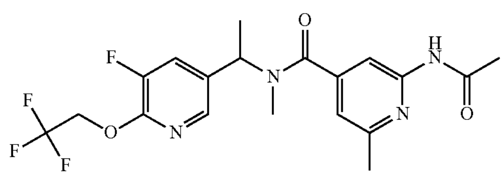 [SMILES: CC(=O)Nc1cc(C(=O)N(C)C(C)c2cnc(OCC(F)(F)F)c(F)c2)cc(C)n1] | Amine-33 | | 427.3 | 1.61 |

TABLE 1-continued

| Example | Name | Chirality | Structure | Amine part | Carboxylic part | Observed MS | Retention time (min) |
|---|---|---|---|---|---|---|---|
| 252 | N-(1-(5-fluoro-6-(2,2,2-trifluoroethoxy)pyridin-3-yl)ethyl)-N,2-dimethyl-6-propionamido-isonicotinamide | single enantiomer | 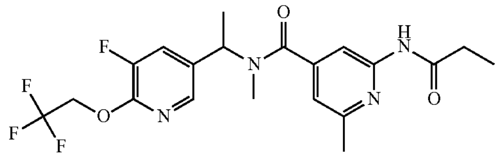 [SMILES: CCC(=O)Nc1cc(C(=O)N(C)C(C)c2cnc(OCC(F)(F)F)c(F)c2)cc(C)n1] | Amine-33 | | 441.2 | 1.67 |
| 253 | 6-propionamido-N-(1-(6-(2,2,2-trifluoroethoxy)pyridin-3-yl)ethyl)picolinamide | single enantiomer | 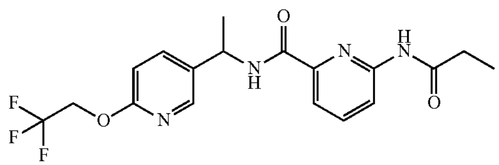 [SMILES: CCC(=O)Nc1cccc(C(=O)NC(C)c2ccc(OCC(F)(F)F)nc2)n1] | alternative route | | 395.2 | 1.68 |
| 254 | 6-(cyclopropanecarboxamido)-N-(1-(6-(2,2,2-trifluoroethoxy)pyridin-3-yl)ethyl)picolinamide | single enantiomer | 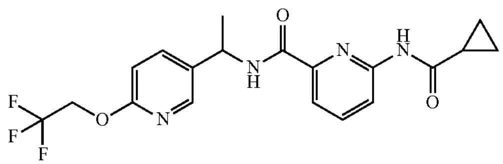 [SMILES: CC(NC(=O)c1cccc(NC(=O)C2CC2)n1)c1ccc(OCC(F)(F)F)nc1] | alternative route | | 407.2 | 1.72 |
| 255 | 6-isobutyramido-N-(1-(6-(2,2,2-trifluoroethoxy)pyridin-3-yl)ethyl)picolinamide | single enantiomer | 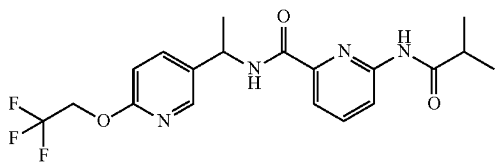 [SMILES: CC(C)C(=O)Nc1cccc(C(=O)NC(C)c2ccc(OCC(F)(F)F)nc2)n1] | alternative route | | 409.3 | 1.76 |
| 256 | N-(2-methoxy-1-(6-(2,2,2-trifluoroethoxy)pyridin-3-yl)ethyl)-2-propionamido-isonicotinamide | single enantiomer | 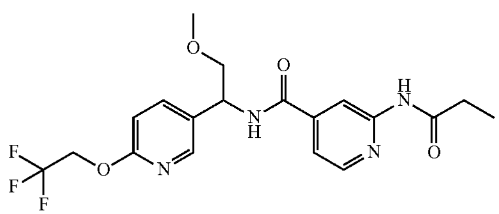 [SMILES: CCC(=O)Nc1cc(C(=O)NC(COC)c2ccc(OCC(F)(F)F)nc2)ccn1] | Amine-34 | | 425.2 | 1.55 |

TABLE 1-continued

| Example | Name | Chirality | Structure | Amine part | Carboxylic part | Observed MS | Retention time (min) |
|---|---|---|---|---|---|---|---|
| 257 | 2-(cyclopropanecarboxamido)-N-(2-methoxy-1-(6-(2,2,2-trifluoroethoxy)pyridin-3-yl)ethyl)isonicotinamide | single enantiomer | 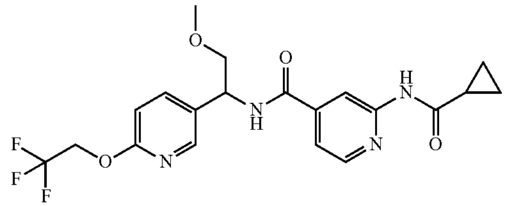 [SMILES: COCC(NC(=O)c1ccnc(NC(=O)C2CC2)c1)c1ccc(OCC(F)(F)F)nc1] | Amine-34 | | 437.2 | 1.59 |
| 258 | 2-acetamido-N-(2-methoxy-1-(6-(2,2,2-trifluoroethoxy)pyridin-3-yl)ethyl)-6-methylisonicotinamide | single enantiomer | 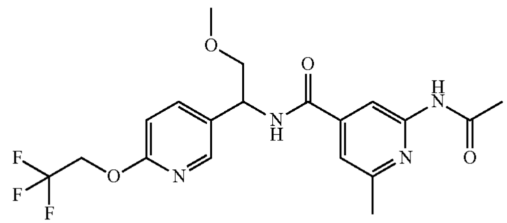 [SMILES: COCC(NC(=O)c1cc(C)nc(NC(C)=O)c1)c1ccc(OCC(F)(F)F)nc1] | Amine-34 | | 425.2 | 1.53 |
| 259 | 2-acetamido-N-((5-ethoxy-6-(2,2,2-trifluoroethoxy)pyridin-3-yl)methyl)isonicotinamide | | 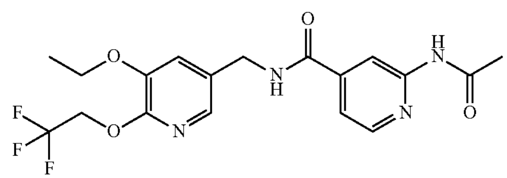 [SMILES: CCOc1cc(CNC(=O)c2ccnc(NC(C)=O)c2)cnc1OCC(F)(F)F] | Amine-35 | | 411.2 | 1.49 |
| 260 | N-((5-ethoxy-6-(2,2,2-trifluoroethoxy)pyridin-3-yl)methyl)-2-propionamidoisonicotinamide | | 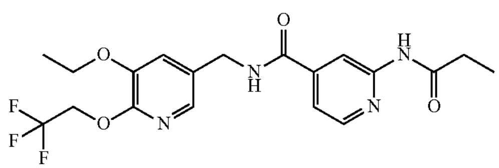 [SMILES: CCOc1cc(CNC(=O)c2ccnc(NC(=O)CC)c2)cnc1OCC(F)(F)F] | Amine-35 | | 425.2 | 1.58 |

TABLE 1-continued

| Example | Name | Chirality | Structure | Amine part | Carboxylic part | Observed MS | Retention time (min) |
|---|---|---|---|---|---|---|---|
| 261 | 2-(cyclopropane-carboxamido)-N-((5-ethoxy-6-(2,2,2-trifluoroethoxy)pyridin-3-yl)methyl)iso-nicotinamide | | 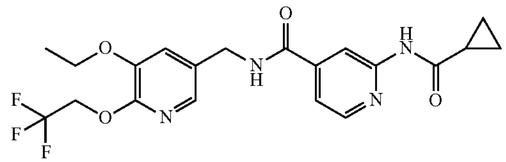 [SMILES: CCOc1cc(CNC(=O)c2ccnc(NC(=O)C3CC3)c2)cnc1OCC(F)(F)F] | Amine-35 | | 437.2 | 1.61 |
| 262 | N-((5-ethoxy-6-(2,2,2-trifluoroethoxy)pyridin-3-yl)methyl)-2-methyl-6-propionamido-isonicotinamide | | 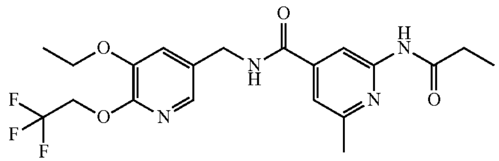 [SMILES: CCOc1cc(CNC(=O)c2cc(C)nc(NC(=O)CC)c2)cnc1OCC(F)(F)F] | Amine-35 | | 439.3 | 1.63 |
| 263 | N-((5-ethoxy-6-(2,2,2-trifluoroethoxy)pyridin-3-yl)methyl)-2-isobutyramido-isonicotinamide | | 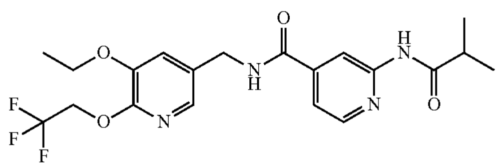 | Amine-35 | | 439.3 | 1.65 |
| 264 | 2-acetamido-N-((5-ethoxy-6-(2,2,2-trifluoroethoxy)pyridin-3-yl)methyl)-6-methylisonico-tinamide | | 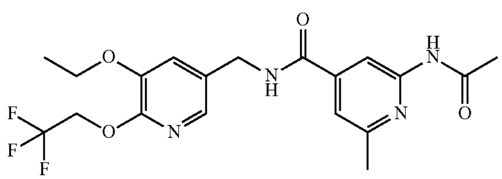 [SMILES: CCOc1cc(CNC(=O)c2cc(C)nc(NC(C)=O)c2)cnc1OCC(F)(F)F] | Amine-35 | | 425.2 | 1.55 |
| 265 | 2-butyramido-N-((6-(2,2,2-trifluoroethoxy)pyridin-3-yl)methyl)iso-nicotinamide | | 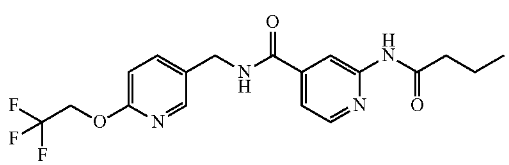 [SMILES: CCCC(=O)Nc1cc(C(=O)NCc2ccc(OCC(F)(F)F)nc2)ccn1] | | | 395.2 | 1.59 |

TABLE 1-continued

| Example | Name | Chirality | Structure | Amine part | Carboxylic part | Observed MS | Retention time (min) |
|---|---|---|---|---|---|---|---|
| 266 | 2-butyramido-N-(1-(5-fluoro-6-(2,2,2-trifluoroethoxy)pyridin-3-yl)ethyl)isonicotinamide | single enantiomer | 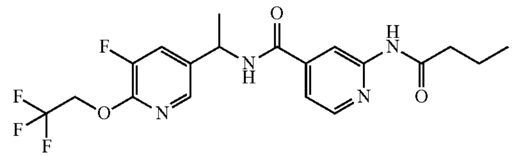 | Amine-12 | | 427.2 | 1.68 |
| 267 | 2-butyramido-N-((5-fluoro-6-(2,2,2-trifluoroethoxy)pyridin-3-yl)methyl)isonicotinamide | | 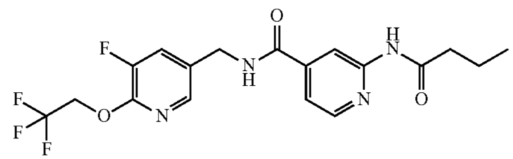 [SMILES: CCCC(=O)Nc1cc(C(=O)NCc2cnc(OCC(F)(F)F)c(F)c2)ccn1] | Amine-28 | | 413.1 | 1.63 |
| 268 | 2-butyramido-N-(1-(6-(3,3,3-trifluoropropoxy)pyridin-3-yl)ethyl)isonicotinamide | single enantiomer | 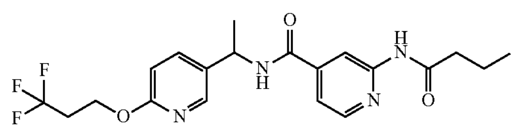 [SMILES: CCCC(=O)Nc1cc(C(=O)NC(C)c2ccc(OCCC(F)(F)F)nc2)ccn1] | Amine-21 | | 423.2 | 1.63 |
| 269 | 2-acetamido-N-((5-methoxy-6-(2,2,2-trifluoroethoxy)pyridin-3-yl)methyl)isonicotinamide | | 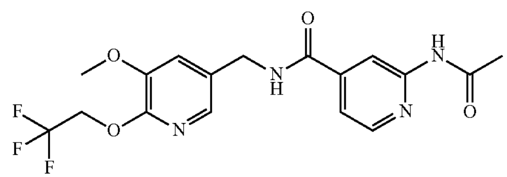 [SMILES: COc1cc(CNC(=O)c2ccnc(NC(C)=O)c2)cnc1OCC(F)(F)F] | Amine-36 | | 397.2 | 1.41 |
| 270 | N-((5-methoxy-6-2,2,2-trifluoroethoxy)pyridin-3-yl)methyl)-2-methyl-6-propionamido-isonicotinamide | | 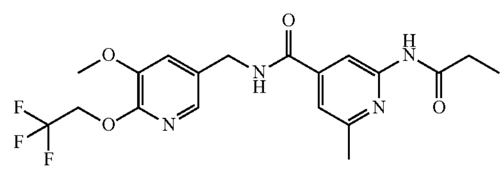 [SMILES: CCC(=O)Nc1cc(C(=O)NCc2cnc(OCC(F)(F)F)c(OC)c2)cc(C)n1] | Amine-36 | | 425.2 | 1.56 |

| Example | Chirality | Name | Structure | Amine part | Carboxylic part | Observed MS | Retention time (min) |
|---|---|---|---|---|---|---|---|
| 271 | | 2-isobutyramido-N-((5-methoxy-6-(2,2,2-trifluoroethoxy)pyridin-3-yl)methyl)iso-nicotinamide | 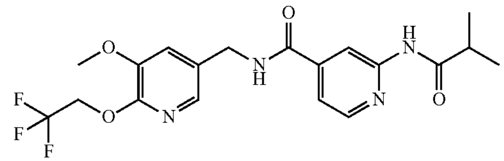 | Amine-36 | | 425.2 | 1.57 |
| 272 | | 2-acetamido-N-((5-methoxy-6-(2,2,2-trifluoroethoxy)pyridin-3-yl)methyl)-6-methylisonicotinamide | 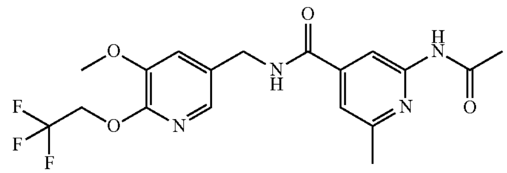 [SMILES: COc1cc(CNC(=O)c2cc(C)nc(NC(C)=O)c2)cnc1OCC(F)(F)F] | Amine-36 | | 411.2 | 1.47 |
| 273 | | 2-butyramido-N-((5-methoxy-6-(2,2,2-trifluoroethoxy)pyridin-3-yl)methyl)iso-nicotinamide | 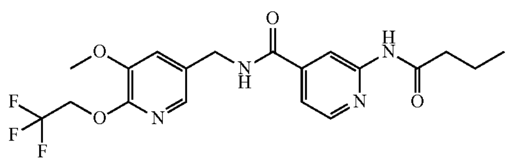 [SMILES: CCCC(=O)Nc1cc(C(=O)NCc2cnc(OCC(F)(F)F)c(OC)c2)ccn1] | Amine-36 | | 425.2 | 1.57 |
| 274 | single enantiomer | (R)-2-propionamido-N-(1-(3-(trifluoromethyl)phenyl)ethyl)pyrimidine-4-carboxamide | 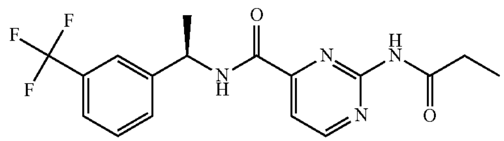 [SMILES: CCC(=O)Nc1nccc(C(=O)N[C@H](C)c2cccc(C(F)(F)F)c2)n1] | alternative route | | 365.2 | 1.59 |
| 275 | single enantiomer | (R)-2-isobutyramido-N-(1-(3-(trifluoromethyl)phenyl)ethyl)pyrimidine-4-carboxamide | 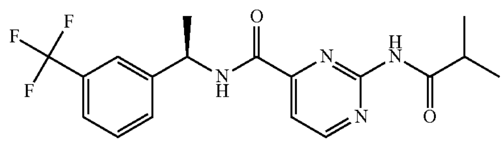 [SMILES: CC(C)C(=O)Nc1nccc(C(=O)N[C@H](C)c2cccc(C(F)(F)F)c2)n1] | alternative route | | 379.2 | 1.66 |

TABLE 1-continued

| Example | Name | Chirality | Structure | Amine part | Carboxylic part | Observed MS | Retention time (min) |
|---|---|---|---|---|---|---|---|
| 276 | (R)-2-(cyclobutanecarboxamido)-N-(1-(3-(trifluoromethyl)phenyl)ethyl)pyrimidine-4-carboxamide | single enantiomer | 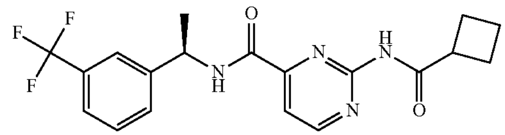 [SMILES: C[C@@H](NC(=O)c1ccnc(NC(=O)C2CCC2)n1)c1cccc(C(F)(F)F)c1] | | alternative route | 391.2 | 1.71 |
| 277 | 2-acetamido-N-(3-(trifluoromethoxy)benzyl)pyrimidine-4-carboxamide | | 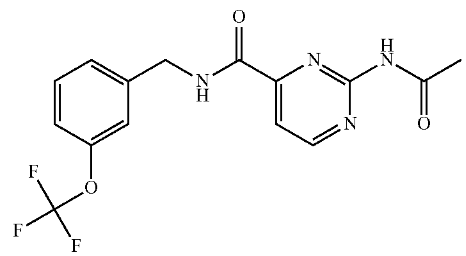 [SMILES: CC(=O)Nc1nccc(C(=O)NCc2cccc(OC(F)(F)F)c2)n1] | | alternative route | 353.2 | 1.47 |
| 278 | 2-propionamido-N-(3-(trifluoromethoxy)benzyl)pyrimidine-4-carboxamide | | 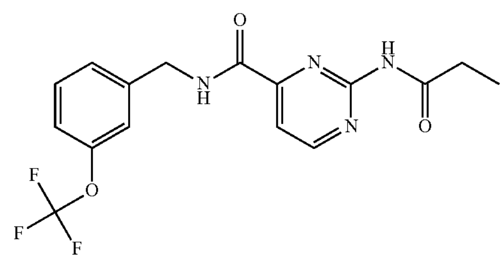 [SMILES: CCC(=O)Nc1nccc(C(=O)NCc2cccc(OC(F)(F)F)c2)n1] | | alternative route | 367.1 | 1.56 |
| 279 | 2-isobutyramido-N-(3-(trifluoromethoxy)benzyl)pyrimidine-4-carboxamide | | 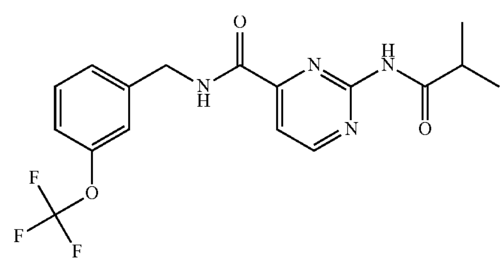 [SMILES: CC(C)C(=O)Nc1nccc(C(=O)NCc2cccc(OC(F)(F)F)c2)n1] | | alternative route | 381.2 | 1.63 |

| Example | Name | Chirality | Structure | Amine part | Carboxylic part | Observed MS | Retention time (min) |
|---|---|---|---|---|---|---|---|
| 280 | 2-(cyclobutanecarboxamido)-N-(3-(trifluoromethoxy)benzyl)pyrimidine-4-carboxamide | | 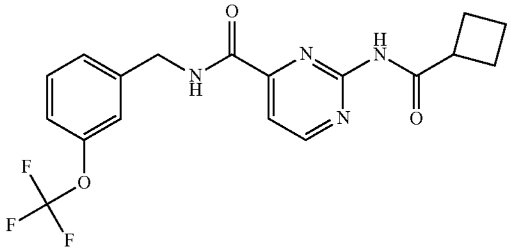 [SMILES: O=C(NCc1cccc(OC(F)(F)F)c1)c1ccnc(NC(=O)C2CCC2)n1] | alternative route | | 393.2 | 1.68 |
| 281 | 2-acetamido-N-((2-morpholino-6-(2,2,2-trifluoroethoxy)pyridin-3-yl)methyl)isonicotinamide | | 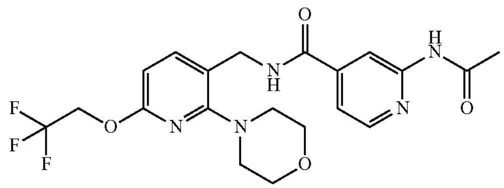 [SMILES: CC(=O)Nc1cc(C(=O)NCc2ccc(OCC(F)(F)F)nc2N2CCOCC2)ccn1] | Amine-37 | | 452.2 | 1.53 |
| 282 | 2-isobutyramido-N-((2-morpholino-6-(2,2,2-trifluoroethoxy)pyridin-3-yl)methyl)isonicotinamide | | 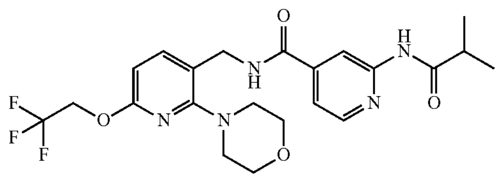 [SMILES: CC(C)C(=O)Nc1cc(C(=O)NCc2ccc(OCC(F)(F)F)nc2N2CCOCC2)ccn1] | Amine-37 | | 480.2 | 1.68 |
| 283 | 2-acetamido-6-methyl-N-((2-morpholino-6-(2,2,2-trifluoroethoxy)pyridin-3-yl)methyl)isonicotinamide | | 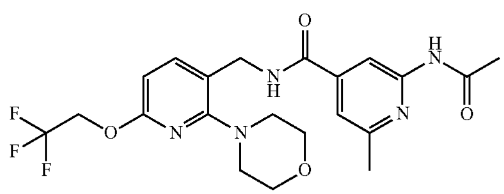 [SMILES: CC(=O)Nc1cc(C(=O)NCc2ccc(OCC(F)(F)F)nc2N2CCOCC2)cc(C)n1] | Amine-37 | | 466.2 | 1.59 |

TABLE 1-continued

| Example | Name | Chirality | Structure | Amine part | Carboxylic part | Observed MS | Retention time (min) |
|---|---|---|---|---|---|---|---|
| 284 | 2-methyl-N-((2-morpholino-6-(2,2,2-trifluoroethoxy)pyridin-3-yl)methyl)-6-propionamido-isonicotinamide | | 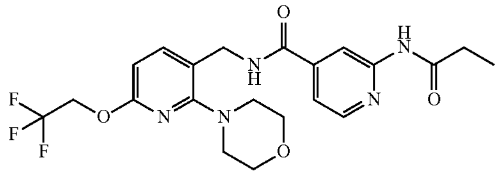 [SMILES: CCC(=O)Nc1cc(C(=O)NCc2ccc(OCC(F)(F)F)nc2N2CCOCC2)ccn1] | Amine-37 | | 480.2 | 1.67 |
| 285 | N-(1-(5-ethoxy-6-(2,2,2-trifluoroethoxy)pyridin-3-yl)ethyl)-2-methyl-6-propionamido-isonicotinamide | single enantiomer | 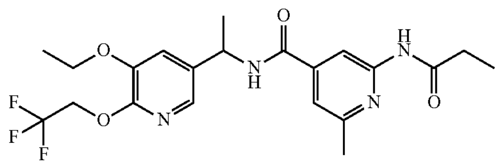 | Amine-38 | | 453.2 | 1.68 |
| 286 | 2-acetamido-N-(1-(5-ethoxy-6-(2,2,2-trifluoroethoxy)pyridin-3-yl)ethyl)-6-methylisonicotinamide | single enantiomer | 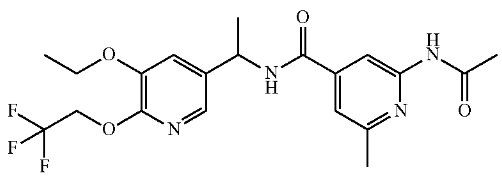 [SMILES: CCOc1cc(C(C)NC(=O)c2cc(C)nc(NC(C)=O)c2)cnc1OCC(F)(F)F] | Amine-38 | | 439.2 | 1.61 |
| 287 | 2-acetamido-N-((2-methoxy-6-(2,2,2-trifluoroethoxy)pyridin-3-yl)methyl)-N-methylisonicotinamide | | 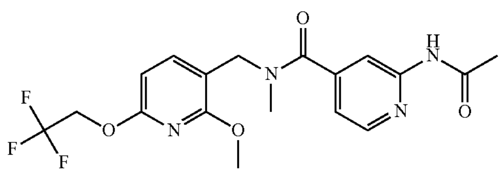 [SMILES: COc1nc(OCC(F)(F)F)ccc1CN(C)C(=O)c1ccnc(NC(C)=O)c1] | Amine-39 | | 411.2 | 1.58 |

TABLE 1-continued

| Example | Chirality | Name | Structure | Amine part | Carboxylic part | Observed MS | Retention time (min) |
|---|---|---|---|---|---|---|---|
| 288 | | N-((2-methoxy-6-(2,2,2-trifluoroethoxy)pyridin-3-yl)methyl)-N-methyl-2-propionamidoisonicotinamide | 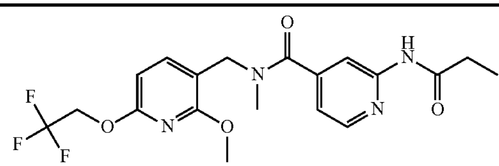 | Amine-39 | | 425.2 | 1.66 |
| 289 | | 2-(cyclopropanecarboxamido)-N-((2-methoxy-6-(2,2,2-trifluoroethoxy)pyridin-3-yl)methyl)-N-methylisonicotinamide | 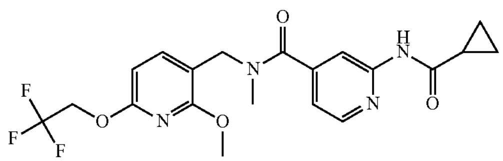 [SMILES: COc1nc(OCC(F)(F)F)ccc1CN(C)C(=O)c1ccnc(NC(=O)C2CC2)c1] | Amine-39 | | 437.2 | 1.7 |
| 290 | | 2-acetamido-N-((2-methoxy-6-(2,2,2-trifluoroethoxy)pyridin-3-yl)methyl)-N,6-dimethylisonicotinamide | 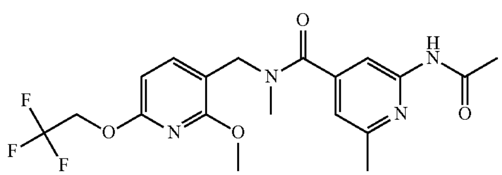 [SMILES: COc1nc(OCC(F)(F)F)ccc1CN(C)C(=O)c1cc(C)nc(NC(C)=O)c1] | Amine-39 | | 425.2 | 1.64 |
| 291 | | N-((2-methoxy-6-(2,2,2-trifluoroethoxy)pyridin-3-yl)methyl)-N,2-dimethyl-6-propionamidoisonicotinamide | 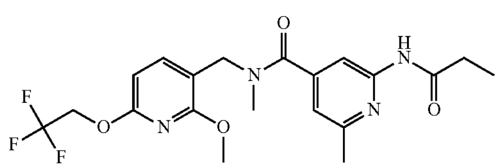 [SMILES: CCC(=O)Nc1cc(C(=O)N(C)Cc2ccc(OCC(F)(F)F)nc2OC)cc(C)n1] | Amine-39 | | 439.2 | 1.72 |

TABLE 1-continued

| Example | Name | Chirality | Structure | Amine part | Carboxylic part | Observed MS | Retention time (min) |
|---|---|---|---|---|---|---|---|
| 292 | N-((2-(4-methylpiperazin-1-yl)-6-(2,2,2-trifluoroethoxy)pyridin-3-yl)methyl)-2-propionamido-isonicotinamide | | 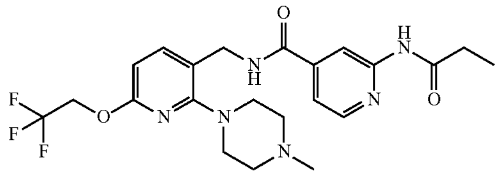 [SMILES: CCC(=O)Nc1cc(C(=O)NCc2ccc(OCC(F)(F)F)nc2N2CCN(C)CC2)ccn1] | Amine-40 | | 479.2 | 1.42 |
| 293 | 2-(cyclopropane-carboxamido)-N-((2-(4-methylpiperazin-1-yl)-6-(2,2,2-trifluoroethoxy)pyridin-3-yl)methyl)iso-nicotinamide | | 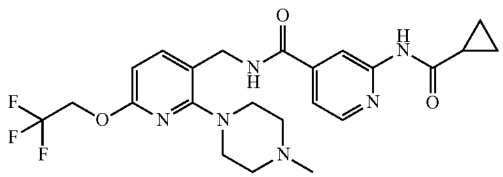 [SMILES: CN1CCN(c2nc(OCC(F)(F)F)ccc2CNC(=O)c2ccnc(NC(=O)C3CC3)c2)CC1] | Amine-40 | | 491.2 | 1.46 |
| 294 | 2-isobutyramido-N-((2-(4-methylpiperazin-1-yl)-6-(2,2,2-trifluoroethoxy)pyridin-3-yl)methyl)iso-nicotinamide | | 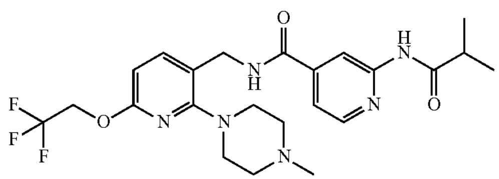 [SMILES: CC(C)C(=O)Nc1cc(C(=O)NCc2ccc(OCC(F)(F)F)nc2N2CCN(C)CC2)ccn1] | Amine-40 | | 493.3 | 1.51 |
| 295 | 2-methyl-N-((2-(4-methylpiperazin-1-yl)-6-(2,2,2-trifluoroethoxy)pyridin-3-yl)methyl)-6-propionamido-isonicotinamide | | 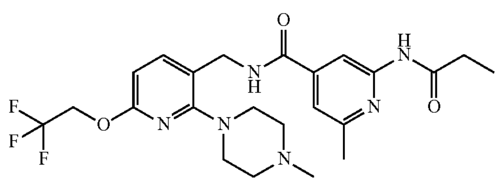 [SMILES: CCC(=O)Nc1cc(C(=O)NCc2ccc(OCC(F)(F)F)nc2N2CCN(C)CC2)cc(C)n1] | Amine-40 | | 493.3 | 1.49 |

| Example | Name | Chirality | Structure | Amine part | Carboxylic part | Observed MS | Retention time (min) |
|---|---|---|---|---|---|---|---|
| 296 | 2-isobutyramido-N-((2-methoxy-6-(2,2,2-trifluoroethoxy)pyridin-3-yl)methyl)-N-methylisonicotinamide | | 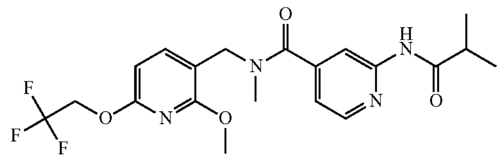 [SMILES: COc1nc(OCC(F)(F)F)ccc1CN(C)C(=O)c1ccnc(NC(=O)C(C)C)c1] | Amine-39 | | 439.2 | 1.74 |
| 297 | 2-acetamido-N-(1-(3-(trifluoromethoxy)phenyl)ethyl)pyrimidine-4-carboxamide | single enantiomer | 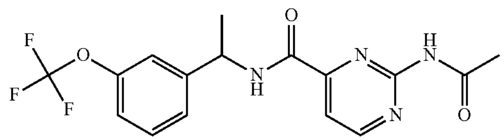 [SMILES: CC(=O)Nc1nccc(C(=O)NC(C)c2cccc(OC(F)(F)F)c2)n1] | alternative route | | 367.2 | 1.54 |
| 298 | 2-propionamido-N-(1-(3-(trifluoromethoxy)phenyl)ethyl)pyrimidine-4-carboxamide | single enantiomer | 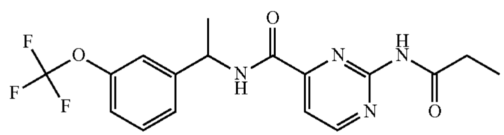 [SMILES: CCC(=O)Nc1nccc(C(=O)NC(C)c2cccc(OC(F)(F)F)c2)n1] | alternative route | | 381.2 | 1.63 |
| 299 | 2-(cyclopropanecarboxamido)-N-(1-(3-(trifluoromethoxy)phenyl)ethyl)pyrimidine-4-carboxamide | single enantiomer | 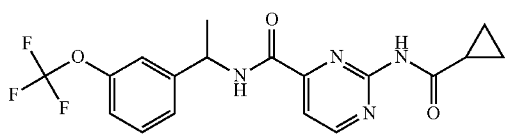 [SMILES: CC(NC(=O)c1ccnc(NC(=O)C2CC2)n1)c1cccc(OC(F)(F)F)c1] | Amine-9 | | 393.2 | 1.65 |
| 300 | 2-isobutyramido-N-(1-(3-(trifluoromethoxy)phenyl)ethyl)pyrimidine-4-carboxamide | single enantiomer | 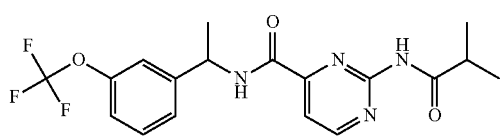 [SMILES: CC(C)C(=O)Nc1nccc(C(=O)NC(C)c2cccc(OC(F)(F)F)c2)n1] | alternative route | | 395.2 | 1.7 |
| 301 | 2-(cyclobutanecarboxamido)-N-(1-(3-(trifluoromethoxy)phenyl)ethyl)pyrimidine-4-carboxamide | single enantiomer | 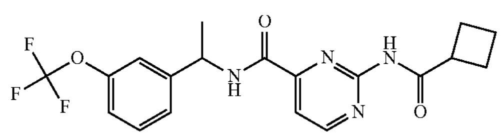 [SMILES: CC(NC(=O)c1ccnc(NC(=O)C2CCC2)n1)c1cccc(OC(F)(F)F)c1] | alternative route | | 407.2 | 1.75 |

TABLE 1-continued

| Example | Chirality | Name | Structure | Amine part | Carboxylic part | Observed MS | Retention time (min) |
|---|---|---|---|---|---|---|---|
| 302 | | 2-acetamido-N-((2-(piperidin-1-yl)-6-(2,2,2-trifluoroethoxy)pyridin-3-yl)methyl)iso-nicotinamide | 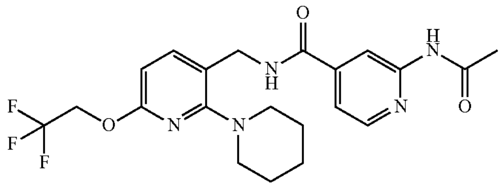 | Amine-41 | | 450.2 | 1.82 |
| 303 | | N-((2-(piperidin-1-yl)-6-(2,2,2-trifluoroethoxy)pyridin-3-yl)methyl)-2-propionamidoisonicotinamide | 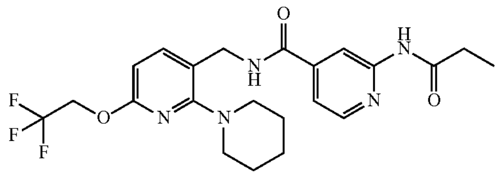 | Amine-41 | | 464.3 | 1.89 |
| 304 | | 2-(cyclopropane-carboxamido)-N-((2-(piperidin-1-yl)-6-(2,2,2-trifluoroethoxy)pyridin-3-yl)methyl)iso-nicotinamide | 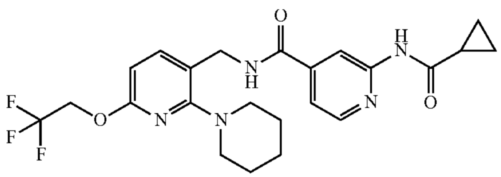 [SMILES: O=C(NCc1ccc(OCC(F)(F)F)nc1N1CCCCC1)c1ccnc(NC(=O)C2CC2)c1] | Amine-41 | | 476.3 | 1.92 |
| 305 | | 2-isobutyramido-N-((2-(piperidin-1-yl)-6-(2,2,2-trifluoroethoxy)pyridin-3-yl)methyl)iso-nicotinamide | 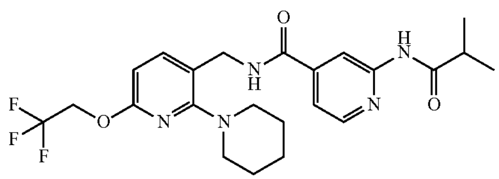 [SMILES: CC(C)C(=O)Nc1cc(C(=O)NCc2ccc(OCC(F)(F)F)nc2N2CCCCC2)ccn1] | Amine-41 | | 478.3 | 1.96 |
| 306 | | 2-methyl-N-((2-(piperidin-1-yl)-6-(2,2,2-trifluoroethoxy)pyridin-3-yl)methyl)-6-propionamidoisonicotinamide | 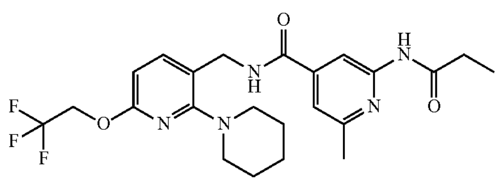 [SMILES: CCC(=O)Nc1cc(C(=O)NCc2ccc(OCC(F)(F)F)nc2N2CCCCC2)cc(C)n1] | Amine-41 | | 478.3 | 1.95 |

TABLE 1-continued

| Example | Name | Chirality | Structure | Amine part | Carboxylic part | Observed MS | Retention time (min) |
|---|---|---|---|---|---|---|---|
| 307 | 2-acetamido-6-methyl-N-((2-(piperidin-1-yl)-6-(2,2,2-trifluoroethoxy)pyridin-3-yl)methyl)isonicotinamide | | 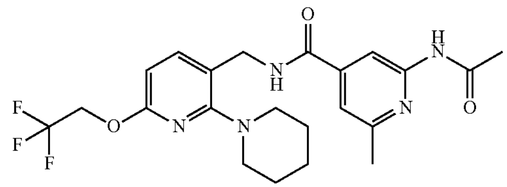 | Amine-41 | | 464.3 | 1.87 |
| 308 | 2-butyramido-N-((2-(piperidin-1-yl)-6-(2,2,2-trifluoroethoxy)pyridin-3-yl)methyl)isonicotinamide | | 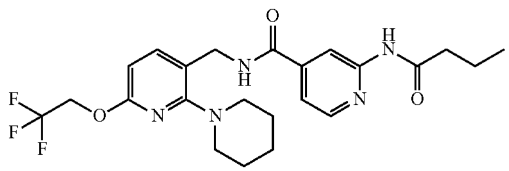 [SMILES: CCCC(=O)Nc1cc(C(=O)NCc2ccc(OCC(F)(F)F)nc2N2CCCCC2)ccn1] | Amine-41 | | 478.3 | 1.96 |
| 309 | 2-acetamido-N-((5-fluoro-2-methyl-6-(2,2,2-trifluoroethoxy)pyridin-3-yl)methyl)isonicotinamide | | 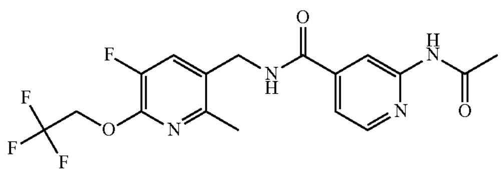 [SMILES: CC(=O)Nc1cc(C(=O)NCc2cc(F)c(OCC(F)(F)F)nc2C)ccn1] | Amine-42 | | 399.2 | 1.56 |
| 310 | N-((5-fluoro-2-methyl-6-(2,2,2-trifluoroethoxy)pyridin-3-yl)methyl)-2-propionamido-isonicotinamide | | 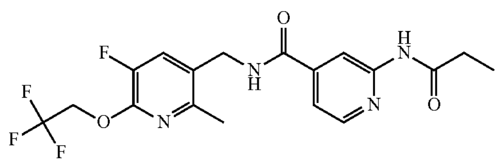 | Amine-42 | | 413.2 | 1.64 |
| 311 | 2-(cyclopropanecarboxamido)-N-((5-fluoro-2-methyl-6-(2,2,2-trifluoroethoxy)pyridin-3-yl)methyl)isonicotinamide | | 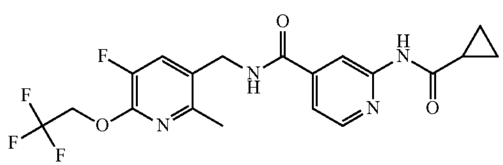 | Amine-42 | | 425.2 | 1.67 |

TABLE 1-continued

| Example | Name | Chirality | Structure | Amine part | Carboxylic part | Observed MS | Retention time (min) |
|---|---|---|---|---|---|---|---|
| 312 | 2-acetamido-N-((5-fluoro-2-methyl-6-(2,2,2-trifluoroethoxy)pyridin-3-yl)methyl)-6-methylisonicotinamide | | 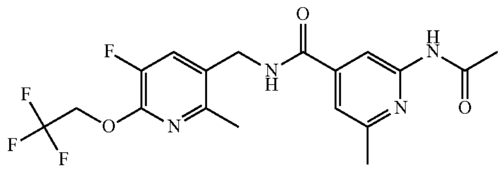 [SMILES: CC(=O)Nc1cc(C(=O)NCc2cc(F)c(OCC(F)(F)F)nc2C)cc(C)n1] | Amine-42 | | 413.2 | 1.62 |
| 313 | N-((5-fluoro-2-methyl-6-(2,2,2-trifluoroethoxy)pyridin-3-yl)methyl)-2-methyl-6-propionamidoisonicotinamide | | 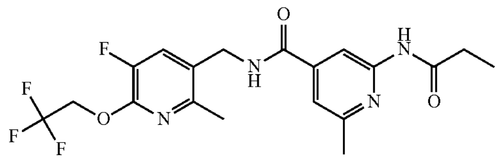 [SMILES: CCC(=O)Nc1cc(C(=O)NCc2cc(F)c(OCC(F)(F)F)nc2C)cc(C)n1] | Amine-42 | | 427.2 | 1.7 |
| 314 | N-((5-fluoro-2-methyl-6-(2,2,2-trifluoroethoxy)pyridin-3-yl)methyl)-2-isobutyramidoisonicotinamide | | 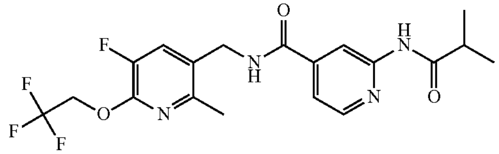 [SMILES: Cc1nc(OCC(F)(F)F)c(F)cc1CNC(=O)c1ccnc(NC(=O)C(C)C)c1] | Amine-42 | | 427.3 | 1.71 |
| 315 | (R)-2-acetamido-N-((6-((1,1,1-trifluoropropan-2-yl)oxy)pyridin-3-yl)methyl)isonicotinamide | single enantiomer | 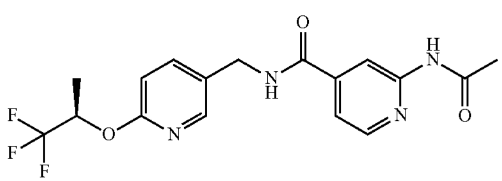 | Amine-43 | | 381.2 | 1.51 |
| 316 | (R)-2-propionamido-N-((6-((1,1,1-trifluoropropan-2-yl)oxy)pyridin-3-yl)methyl)isonicotinamide | single enantiomer | 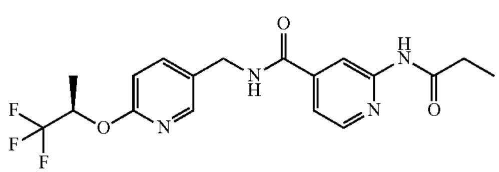 | Amine-43 | | 395.2 | 1.6 |

TABLE 1-continued

| Example | Name | Chirality | Structure | Amine part | Carboxylic part | Observed MS | Retention time (min) |
|---|---|---|---|---|---|---|---|
| 317 | (R)-2-(cyclopropanecarboxamido)-N-((6-((1,1,1-trifluoropropan-2-yl)oxy)pyridin-3-yl)methyl)isonicotinamide | single enantiomer | 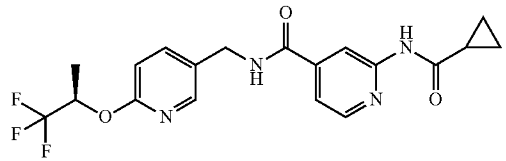 [SMILES: C[C@@H](Oc1ccc(CNC(=O)c2ccnc(NC(=O)C3CC3)c2)cn1)C(F)(F)F] | Amine-43 | | 407.2 | 1.64 |
| 318 | (R)-2-methyl-6-propionamido-N-((6-((1,1,1-trifluoropropan-2-yl)oxy)pyridin-3-yl)methyl)isonicotinamide | single enantiomer | 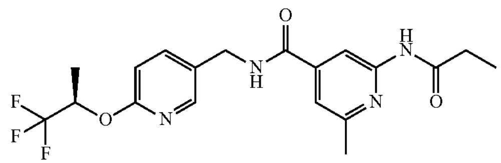 | Amine-43 | | 409.3 | 1.66 |
| 319 | (R)-2-isobutyramido-N-((6-((1,1,1-trifluoropropan-2-yl)oxy)pyridin-3-yl)methyl)isonicotinamide | single enantiomer | 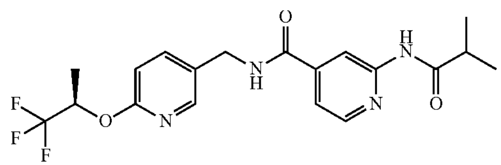 [SMILES: CC(C)C(=O)Nc1cc(C(=O)NCc2ccc(O[C@H](C)C(F)(F)F)nc2)ccn1] | Amine-43 | | 409.3 | 1.68 |
| 320 | (R)-2-acetamido-6-methyl-N-((6-((1,1,1-trifluoropropan-2-yl)oxy)pyridin-3-yl)methyl)isonicotinamide | single enantiomer | 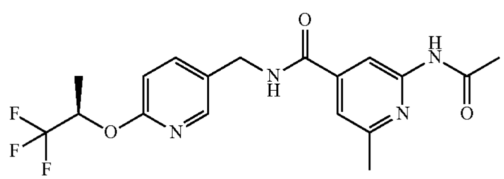 [SMILES: CC(=O)Nc1cc(C(=O)NCc2ccc(O[C@H](C)C(F)(F)F)nc2)cc(C)n1] | Amine-43 | | 395.2 | 1.58 |
| 321 | (R)-2-butyramido-N-((6-((1,1,1-trifluoropropan-2-yl)oxy)pyridin-3-yl)methyl)isonicotinamide | single enantiomer | 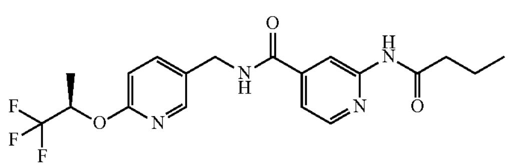 [SMILES: CCCC(=O)Nc1cc(C(=O)NCc2ccc(O[C@H](C)C(F)(F)F)nc2)ccn1] | Amine-43 | | 409.3 | 1.68 |

TABLE 1-continued

| Example | Name | Chirality | Structure | Amine part | Carboxylic part | Observed MS | Retention time (min) |
|---|---|---|---|---|---|---|---|
| 322 | 2-(2-hydroxy-2-methylpropanamido)-N-(2-methoxy-6-(2,2,2-trifluoroethoxy)pyridin-3-yl)methyl)-6-methylisonicotinamide | | 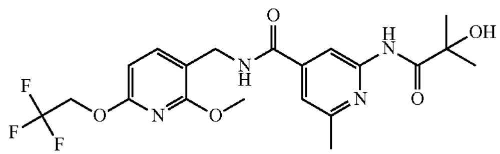 [SMILES: COc1nc(OCC(F)(F)F)ccc1CNC(=O)c1cc(C)nc(NC(=O)C(C)(C)O)c1] | Amine-24 | | 455.2 | 1.66 |
| 323 | 2-(2-hydroxy-2-methylpropanamido)-6-methyl-N-(1-(5-methyl-6-(2,2,2-trifluoroethoxy)pyridin-3-yl)ethyl)isonicotinamide | single enantiomer | 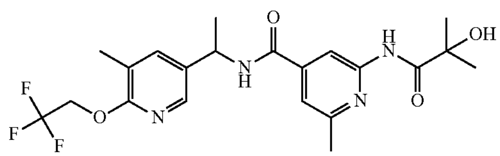 [SMILES: Cc1cc(C(=O)NC(C)c2cnc(OCC(F)(F)F)c(C)c2)cc(NC(=O)C(C)(C)O)n1] | Amine-17 | | 453.3 | 1.69 |
| 324 | N-(1-(5-chloro-6-(2,2,2-trifluoroethoxy)pyridin-3-yl)ethyl)-2-(2-hydroxy-2-methylpropanamido)-6-methylisonicotinamide | single enantiomer | 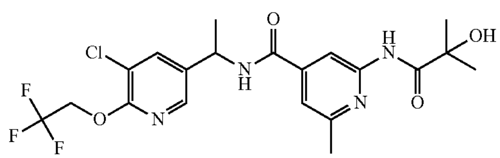 | Amine-5 | | 473.2 | 1.7 |
| 325 | 2-(2-hydroxy-2-methylpropanamido)-6-methyl-N-((2-methyl-6-(2,2,2-trifluoroethoxy)pyridin-3-yl)methyl)isonicotinamide | | 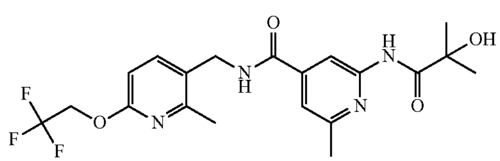 [SMILES: Cc1cc(C(=O)NCc2ccc(OCC(F)(F)F)nc2C)cc(NC(=O)C(C)(C)O)n1] | Amine-27 | | 439.3 | 1.64 |

TABLE 1-continued

| Example | Name | Chirality | Structure | Amine part | Carboxylic part | Observed MS | Retention time (min) |
|---|---|---|---|---|---|---|---|
| 326 | 2-(2-hydroxy-2-methylpropanamido)-6-methyl-N-((6-(3,3,3-trifluoropropoxy)pyridin-3-yl)methyl)isonicotinamide | | 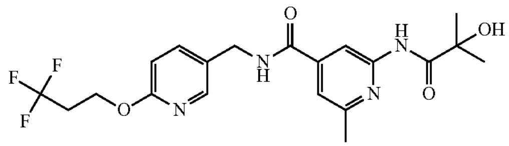 [SMILES: Cc1cc(C(=O)NCc2ccc(OCCC(F)(F)F)nc2)cc(NC(=O)C(C)(C)O)n1] | Amine-30 | | 439.3 | 1.53 |
| 327 | N-((5-fluoro-2-methoxy-6-(2,2,2-trifluoroethoxy)pyridin-3-yl)methyl)-2-propionamidoisonicotinamide | | 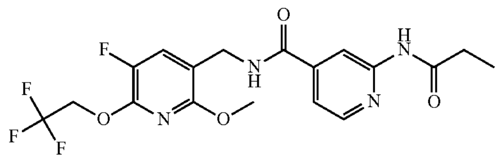 [SMILES: CCC(=O)Nc1cc(C(=O)NCc2cc(F)c(OCC(F)(F)F)nc2OC)ccn1] | Amine-44 | | 429.2 | 1.63 |
| 328 | N-((5-fluoro-2-methoxy-6-(2,2,2-trifluoroethoxy)pyridin-3-yl)methyl)-6-methyl-2-propionamidoisonicotinamide | | 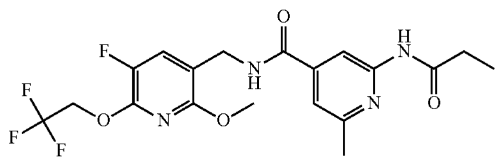 [SMILES: CCC(=O)Nc1cc(C(=O)NCc2cc(F)c(OCC(F)(F)F)nc2OC)cc(C)n1] | Amine-44 | | 443.2 | 1.69 |
| 329 | N-((5-fluoro-2-methoxy-6-(2,2,2-trifluoroethoxy)pyridin-3-yl)methyl)-2-isobutyramidoisonicotinamide | | 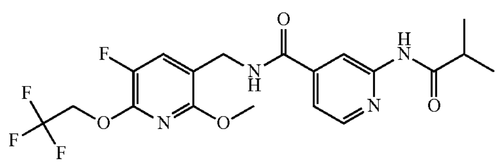 | Amine-44 | | 443.3 | 1.7 |
| 330 | 2-acetamido-N-(1-(5-methoxy-6-(2,2,2-trifluoroethoxy)pyridin-3-yl)ethyl)-6-methylisonicotinamide | single enantiomer | 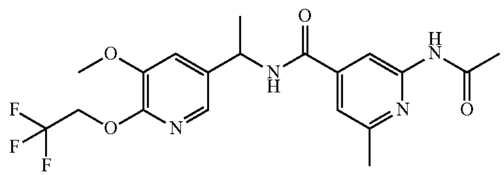 [SMILES: COc1cc(C(C)NC(=O)c2cc(C)nc(NC(C)=O)c2)cnc1OCC(F)(F)F] | Amine-22 | | 425.2 | 1.53 |

TABLE 1-continued

| Example | Name | Chirality | Structure | Amine part | Carboxylic part | Observed MS | Retention time (min) |
|---|---|---|---|---|---|---|---|
| 331 | 2-butyramido-N-(1-(5-methoxy-6-(2,2,2-trifluoroethoxy)pyridin-3-yl)ethyl)isonicotinamide | single enantiomer | 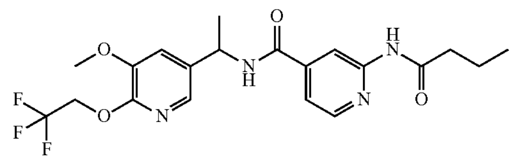 [SMILES: CCCC(=O)Nc1cc(C(=O)NC(C)c2cnc(OCC(F)(F)F)c(OC)c2)ccn1] | Amine-22 | | 439.3 | 1.63 |
| 332 | 2-acetamido-N-((2-ethoxy-6-(2,2,2-trifluoroethoxy)pyridin-3-yl)methyl)isonicotinamide | | 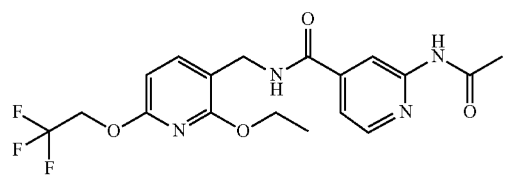 [SMILES: CCOc1nc(OCC(F)(F)F)ccc1CNC(=O)c1ccnc(NC(C)=O)c1] | Amine-45 | | 411.2 | 1.63 |
| 333 | N-((2-ethoxy-6-(2,2,2-trifluoroethoxy)pyridin-3-yl)methyl)-2-propionamidoisonicotinamide | | 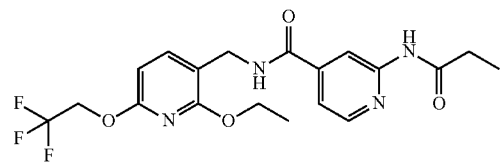 [SMILES: CCOc1nc(OCC(F)(F)F)ccc1CNC(=O)c1ccnc(NC(=O)CC)c1] | Amine-45 | | 425.2 | 1.71 |
| 334 | N-((2-ethoxy-6-(2,2,2-trifluoroethoxy)pyridin-3-yl)methyl)-2-methyl-6-propionamidoisonicotinamide | | 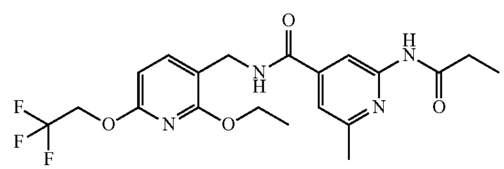 [SMILES: CCOc1nc(OCC(F)(F)F)ccc1CNC(=O)c1cc(C)nc(NC(=O)CC)c1] | Amine-45 | | 439.3 | 1.77 |
| 335 | N-(2-ethoxy-6-(2,2,2-trifluoroethoxy)pyridin-3-yl)methyl)-2-isobutyramidoisonicotinamide | | 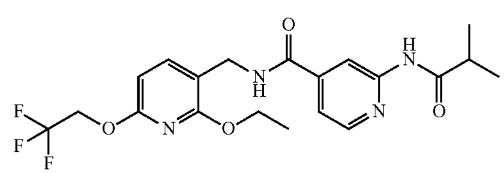 [SMILES: CCOc1nc(OCC(F)(F)F)ccc1CNC(=O)c1ccnc(NC(=O)C(C)C)c1] | Amine-45 | | 439.3 | 1.78 |

TABLE 1-continued

| Example | Chirality | Name | Structure | Amine part | Carboxylic part | Observed MS | Retention time (min) |
|---|---|---|---|---|---|---|---|
| 336 | | 2-acetamido-N-((2-ethoxy-6-(2,2,2-trifluoroethoxy)pyridin-3-yl)methyl)-6-methylisonicotinamide | 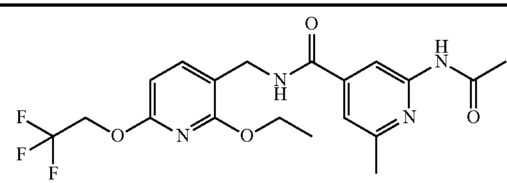 | Amine-45 | | 425.3 | 1.69 |
| 337 | | 2-butyramido-N-((2-ethoxy-6-(2,2,2-trifluoroethoxy)pyridin-3-yl)methyl)isonicotinamide | 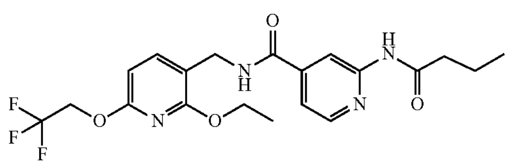 [SMILES: CCCC(=O)Nc1cc(C(=O)NCc2ccc(OCC(F)(F)F)nc2OCC)ccn1] | Amine-45 | | 439.3 | 1.78 |
| 338 | | 2-acetamido-N-((2-ethoxy-6-(2,2,2-trifluoroethoxy)pyridin-3-yl)methyl)-6-methylpyrimidine-4-carboxamide | 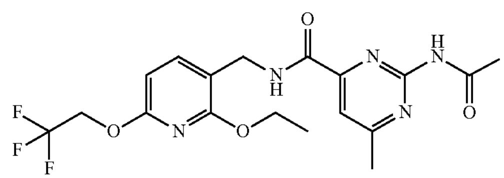 [SMILES: CCOc1nc(OCC(F)(F)F)ccc1CNC(=O)c1cc(C)nc(NC(C)=O)n1] | Amine-45 | | 426.3 | 1.68 |
| 339 | single enantiomer | 6-methyl-2-propionamido-N-(1-(6-(2,2,2-trifluoroethoxy)pyridin-3-yl)propyl)pyrimidine-4-carboxamide | 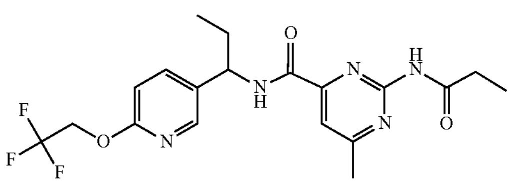 [SMILES: CCC(=O)Nc1nc(C)cc(C(=O)NC(CC)c2ccc(OCC(F)(F)F)nc2)n1] | Amine-6 | | 424.3 | 1.69 |

TABLE 1-continued

| Example | Name | Chirality | Structure | Amine part | Carboxylic part | Observed MS | Retention time (min) |
|---|---|---|---|---|---|---|---|
| 340 | 2-(cyclopropane-carboxamido)-6-methyl-N-(1-(6-(2,2,2-trifluoro-ethoxy)pyridin-3-yl)propyl)py-rimidine-4-carboxamide | single enantiomer | 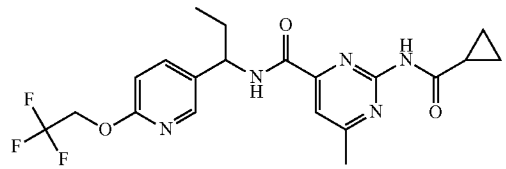 [SMILES: CCC(NC(=O)c1cc(C)nc(NC(=O)C2CC2)n1)c1ccc(OCC(F)(F)F)nc1] | Amine-6 | | 436.3 | 1.7 |
| 341 | 2-isobutyramido-6-methyl-N-((6-(2,2,2-trifluoro-ethoxy)pyridin-3-yl)methyl)py-rimidine-4-carboxamide | | 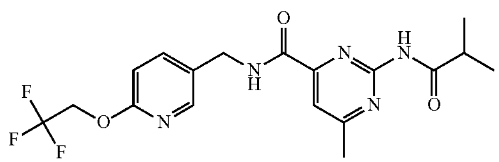 [SMILES: Cc1cc(C(=O)NCc2ccc(OCC(F)(F)F)nc2)nc(NC(=O)C(C)C)n1] | | | 410.3 | 1.6 |
| 342 | 2-acetamido-6-methyl-N-((2-methyl-6-(2,2,2-trifluoroethox-y)pyridin-3-yl)methyl)py-rimidine-4-carboxamide | | 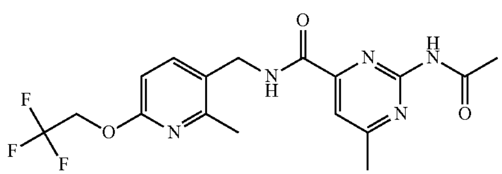 [SMILES: CC(=O)Nc1nc(C)cc(C(=O)NCc2ccc(OCC(F)(F)F)nc2C)n1] | Amine-27 | | 396.2 | 1.56 |
| 343 | 6-methyl-N-((2-methyl-6-(2,2,2-trifluoro-ethoxy)pyridin-3-yl)methyl)-2-propionamido-pyrimidine-4-carboxamide | | 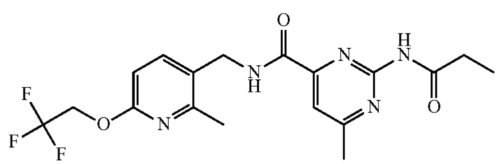 [SMILES: CCC(=O)Nc1nc(C)cc(C(=O)NCc2ccc(OCC(F)(F)F)nc2C)n1] | Amine-27 | | 410.3 | 1.64 |

TABLE 1-continued

| Example | Name | Chirality | Structure | Amine part | Carboxylic part | Observed MS | Retention time (min) |
|---|---|---|---|---|---|---|---|
| 344 | 2-(cyclopropanecarboxamido)-6-methyl-N-((2-methyl-6-(2,2,2-trifluoroethoxy)pyridin-3-yl)methyl)pyrimidine-4-carboxamide | | 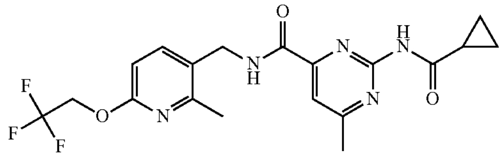 | Amine-27 | | 422.3 | 1.66 |
| 345 | 2-isobutyramido-6-methyl-N-((2-methyl-6-(2,2,2-trifluoroethoxy)pyridin-3-yl)methyl)pyrimidine-4-carboxamide | | 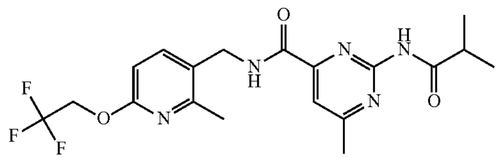 [SMILES: Cc1cc(C(=O)NCc2ccc(OCC(F)(F)F)nc2C)nc(NC(=O)C(C)C)n1] | Amine-27 | | 424.3 | 1.71 |
| 346 | 6-methyl-2-propionamido-N-(3-(trifluoromethoxy)benzyl)pyrimidine-4-carboxamide | | 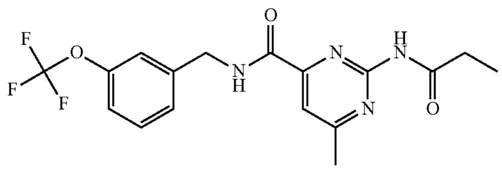 [SMILES: CCC(=O)Nc1nc(C)cc(C(=O)NCc2cccc(OC(F)(F)F)c2)n1] | | | 381.3 | 1.63 |
| 347 | 2-(cyclopropanecarboxamido)-6-methyl-N-(3-(trifluoromethoxy)benzyl)pyrimidine-4-carboxamide | | 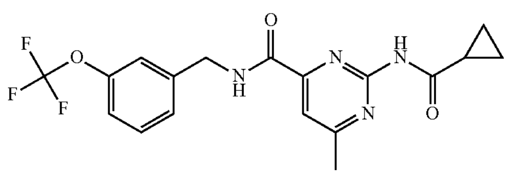 [SMILES: Cc1cc(C(=O)NCc2cccc(OC(F)(F)F)c2)nc(NC(=O)C2CC2)n1] | | | 393.3 | 1.65 |

TABLE 1-continued

| Example | Name | Chirality | Structure | Amine part | Carboxylic part | Observed MS | Retention time (min) |
|---|---|---|---|---|---|---|---|
| 348 | 2-isobutyramido-6-methyl-N-(3-(trifluoromethoxy)benzyl)pyrimidine-4-carboxamide | | 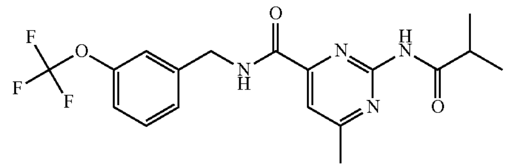 [SMILES: Cc1cc(C(=O)NCc2cccc(OC(F)(F)F)c2)nc(NC(=O)C(C)C)n1] | | | 395.3 | 1.69 |
| 349 | (R)-2-(cyclopropanecarboxamido)-6-methyl-N-(1-(3-(trifluoromethyl)phenyl)ethyl)pyrimidine-4-carboxamide | single enantiomer | 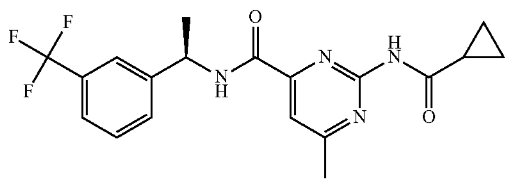 [SMILES: Cc1cc(C(=O)N[C@H](C)c2cccc(C(F)(F)F)c2)nc(NC(=O)C2CC2)n1] | | | 391.3 | 1.69 |
| 350 | 2-acetamido-6-methyl-N-((4-methyl-6-(2,2,2-trifluoroethoxy)pyridin-3-yl)methyl)pyrimidine-4-carboxamide | | 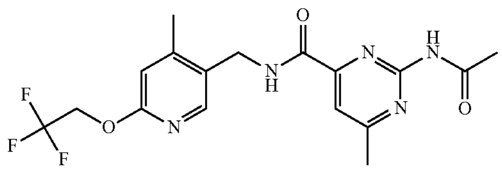 | Amine-29 | | 396.3 | 1.51 |
| 351 | 6-methyl-N-((4-methyl-6-(2,2,2-trifluoroethoxy)pyridin-3-yl)methyl)-2-propionamidopyrimidine-4-carboxamide | | 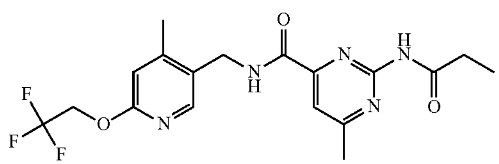 [SMILES: CCC(=O)Nc1nc(C)cc(C(=O)NCc2cnc(OCC(F)(F)F)cc2C)n1] | Amine-29 | | 410.3 | 1.6 |

TABLE 1-continued

| Example | Chirality | Name | Structure | Amine part | Carboxylic part | Observed MS | Retention time (min) |
|---|---|---|---|---|---|---|---|
| 352 | | 2-(cyclopropane-carboxamido)-6-methyl-N-((4-methyl-6-(2,2,2-trifluoroethoxy)pyridin-3-yl)methyl)pyrimidine-4-carboxamide | 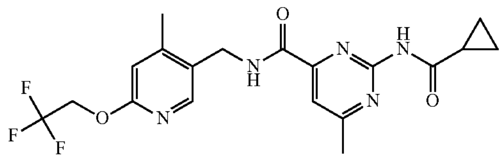 [SMILES: Cc1cc(C(=O)NCc2cnc(OCC(F)(F)F)cc2C)nc(NC(=O)C2CC2)n1] | Amine-29 | | 422.3 | 1.62 |
| 353 | | 2-isobutyramido-6-methyl-N-((4-methyl-6-(2,2,2-trifluoroethoxy)pyridin-3-yl)methyl)pyrimidine-4-carboxamide | 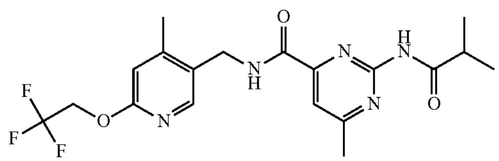 [SMILES: Cc1cc(C(=O)NCc2cnc(OCC(F)(F)F)cc2C)nc(NC(=O)C(C)C)n1] | Amine-29 | | 424.3 | 1.67 |
| 354 | | 2-(cyclopropane-carboxamido)-6-methyl-N-(3-(trifluoromethyl)benzyl)pyrimidine-4-carboxamide | 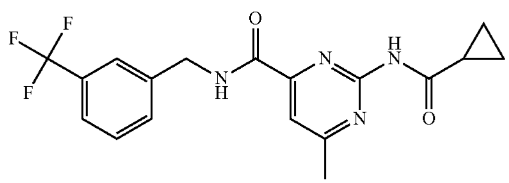 [SMILES: Cc1cc(C(=O)NCc2cccc(C(F)(F)F)c2)nc(NC(=O)C2CC2)n1] | | | 377.3 | 1.61 |
| 355 | | 2-isobutyramido-6-methyl-N-(3-(trifluoromethyl)benzyl)pyrimidine-4-carboxamide | 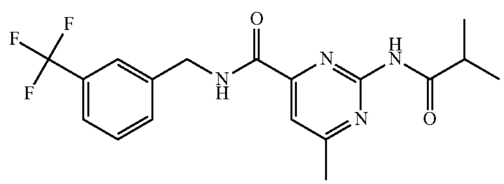 [SMILES: Cc1cc(C(=O)NCc2cccc(C(F)(F)F)c2)nc(NC(=O)C(C)C)n1] | | | 379.3 | 1.66 |

TABLE 1-continued

| Example | Name | Chirality | Structure | Amine part | Carboxylic part | Observed MS | Retention time (min) |
|---|---|---|---|---|---|---|---|
| 356 | 6-methyl-2-propionamido-N-(1-(4-(2,2,2-trifluoroethoxy)phenyl)ethyl)pyrimidine-4-carboxamide | single enantiomer | 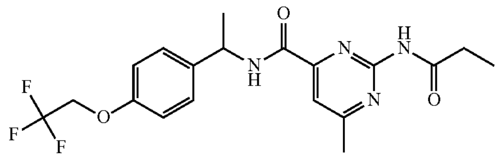 [SMILES: CCC(=O)Nc1nc(C)cc(C(=O)NC(C)c2ccc(OCC(F)(F)F)cc2)n1] | Amine-18 | | 409.3 | 1.64 |
| 357 | 2-(cyclopropanecarboxamido)-6-methyl-N-(1-(4-(2,2,2-trifluoroethoxy)phenyl)ethyl)pyrimidine-4-carboxamide | single enantiomer | 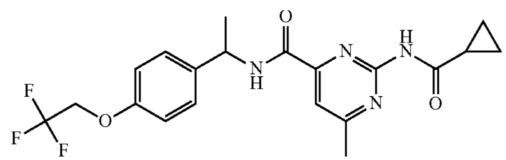 [SMILES: Cc1cc(C(=O)NC(C)c2ccc(OCC(F)(F)F)cc2)nc(NC(=O)C2CC2)n1] | Amine-18 | | 421.3 | 1.66 |
| 358 | 2-isobutyramido-6-methyl-N-(1-(4-(2,2,2-trifluoroethoxy)phenyl)ethyl)pyrimidine-4-carboxamide | single enantiomer | 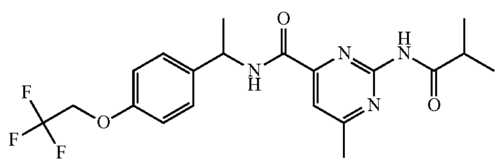 [SMILES: Cc1cc(C(=O)NC(C)c2ccc(OCC(F)(F)F)cc2)nc(NC(=O)C(C)C)n1] | Amine-18 | | 423.3 | 1.7 |
| 359 | N-((2-ethoxy-6-(2,2,2-trifluoroethoxy)pyridin-3-yl)methyl)-6-methyl-2-propionamido-pyrimidine-4-carboxamide | | 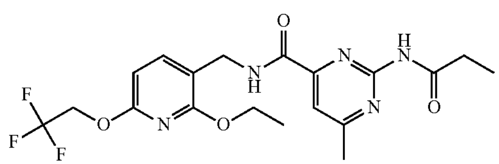 [SMILES: CCOc1nc(OCC(F)(F)F)ccc1CNC(=O)c1cc(C)nc(NC(=O)CC)n1] | Amine-45 | | 440.3 | 1.76 |

TABLE 1-continued

| Example | Name | Chirality | Structure | Amine part | Carboxylic part | Observed MS | Retention time (min) |
|---|---|---|---|---|---|---|---|
| 360 | N-((2-ethoxy-6-(2,2,2-trifluoroethoxy)pyridin-3-yl)methyl)-2-isobutyramido-6-methylpyrimidine-4-carboxamide | | 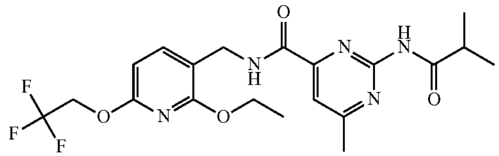 [SMILES: CCOc1nc(OCC(F)(F)F)ccc1CNC(=O)c1cc(C)nc(NC(=O)C(C)C)n1] | Amine-45 | | 454.3 | 1.83 |
| 361 | 2-(cyclopropanecarboxamido)-N-((2-ethoxy-6-(2,2,2-trifluoroethoxy)pyridin-3-yl)methyl)-6-methylpyrimidine-4-carboxamide | | 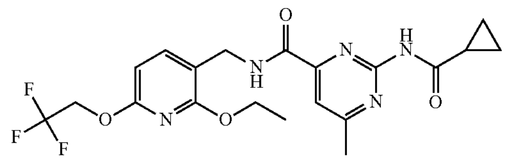 [SMILES: CCOc1nc(OCC(F)(F)F)ccc1CNC(=O)c1cc(C)nc(NC(=O)C2CC2)n1] | Amine-45 | | 452.3 | 1.78 |
| 362 | N-(1-(5-(hydroxymethyl)-6-(2,2,2-trifluoroethoxy)pyridin-3-yl)ethyl)-2-methyl-6-propionamidoisonicotinamide | single enantiomer | 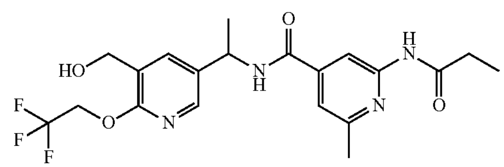 [SMILES: CCC(=O)Nc1cc(C(=O)NC(C)c2cnc(OCC(F)(F)F)c(CO)c2)cc(C)n1] | Amine-46 | | 439.3 | 1.47 |
| 363 | 2-acetamido-6-methyl-N-((5-methyl-6-(2,2,2-trifluoroethoxy)pyridin-3-yl)methyl)pyrimidine-4-carboxamide | | 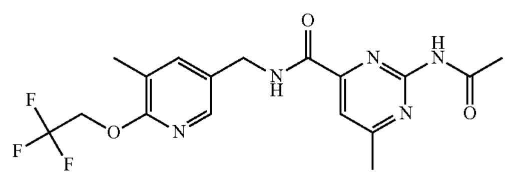 [SMILES: CC(=O)Nc1nc(C)cc(C(=O)NCc2cnc(OCC(F)(F)F)c(C)c2)n1] | Amine-47 | | 396.3 | 1.55 |

TABLE 1-continued

| Example | Chirality | Name | Structure | Amine part | Carboxylic part | Observed MS | Retention time (min) |
|---|---|---|---|---|---|---|---|
| 364 | | 6-methyl-N-((5-methyl-6-(2,2,2-trifluoroethoxy)pyridin-3-yl)methyl)-2-propionamido-pyrimidine-4-carboxamide | 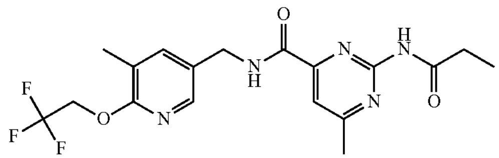 | Amine-47 | | 410.3 | 1.64 |
| 365 | | 2-(cyclopropanecarboxamido)-6-methyl-N-((5-methyl-6-(2,2,2-trifluoroethoxy)pyridin-3-yl)methyl)pyrimidine-4-carboxamide | 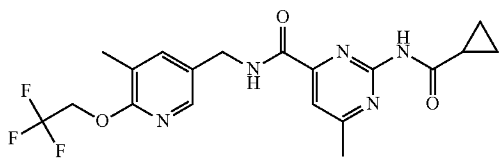 [SMILES: Cc1cc(C(=O)NCc2cnc(OCC(F)(F)F)c(C)c2)nc(NC(=O)C2CC2)n1] | Amine-47 | | 422.3 | 1.66 |
| 366 | | 2-isobutyramido-6-methyl-N-((5-methyl-6-(2,2,2-trifluoroethoxy)pyridin-3-yl)methyl)pyrimidine-4-carboxamide | 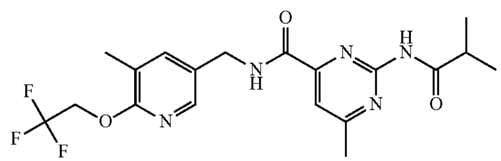 [SMILES: Cc1cc(C(=O)NCc2cnc(OCC(F)(F)F)c(C)c2)nc(NC(=O)C(C)C)n1] | Amine-47 | | 424.3 | 1.7 |
| 367 | | 2-acetamido-N-((5-methyl-6-(2,2,2-trifluoroethoxy)pyridin-3-yl)methyl)isonicotinamide | 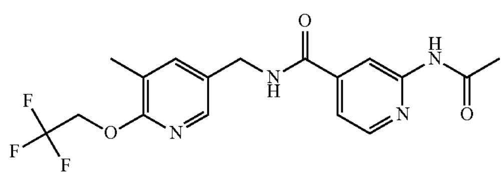 [SMILES: CC(=O)Nc1cc(C(=O)NCc2cnc(OCC(F)(F)F)c(C)c2)ccn1] | Amine-47 | | 381.3 | 1.52 |

TABLE 1-continued

| Example | Name | Chirality | Structure | Amine part | Carboxylic part | Observed MS | Retention time (min) |
|---|---|---|---|---|---|---|---|
| 368 | N-((5-methyl-6-(2,2,2-trifluoroethoxy)pyridin-3-yl)methyl)-2-propionamidoisonicotinamide | | 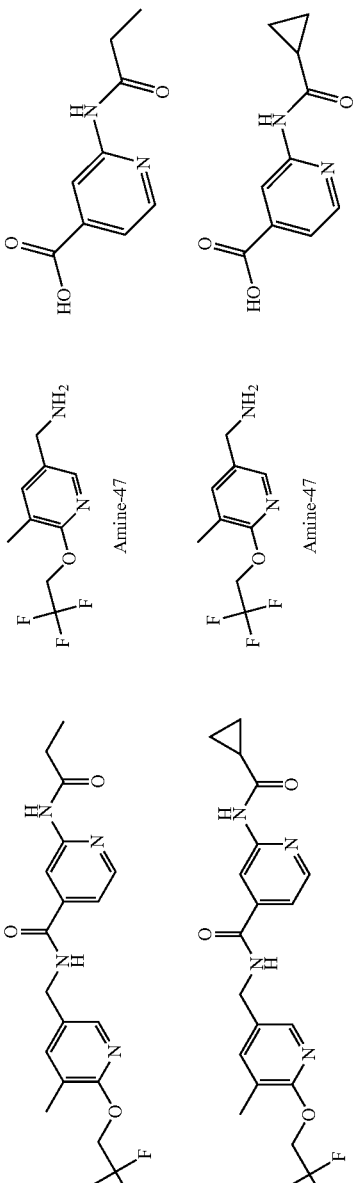 | 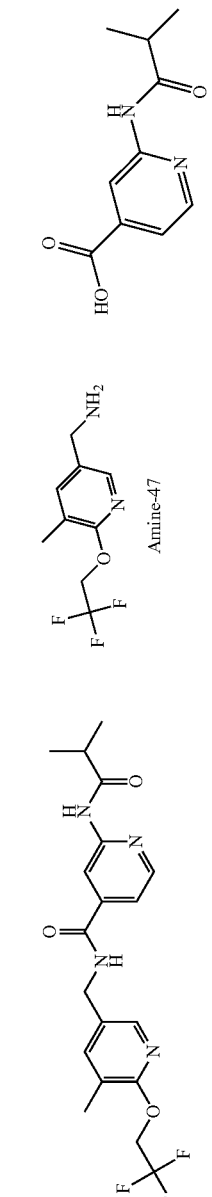 Amine-47 | 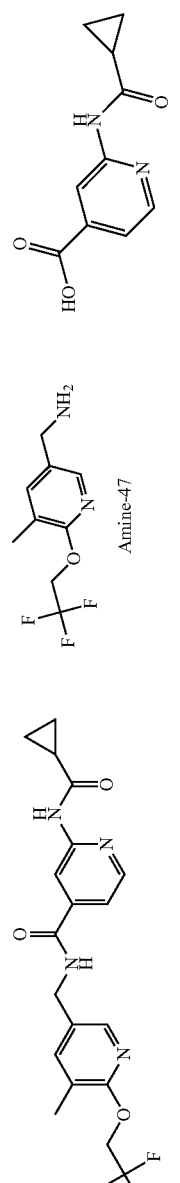 | 395.3 | 1.6 |
| 369 | 2-(cyclopropanecarboxamido)-N-((5-methyl-6-(2,2,2-trifluoroethoxy)pyridin-3-yl)methyl)isonicotinamide | | 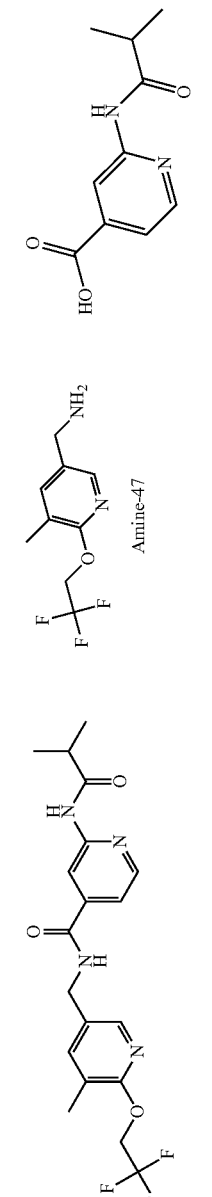 | 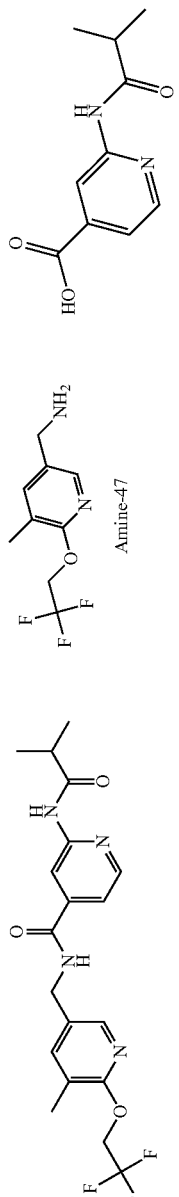 Amine-47 | 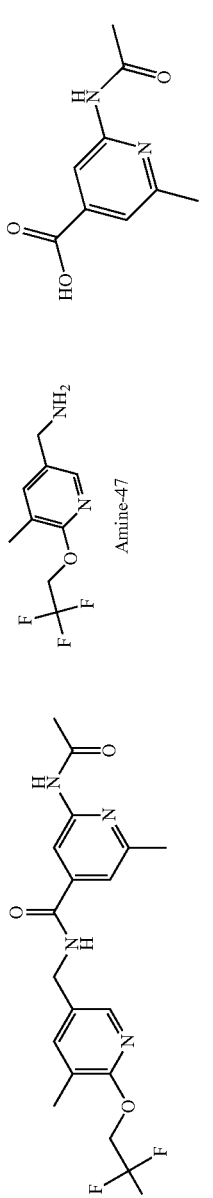 | 407.3 | 1.64 |
| 370 | 2-isobutyramido-N-((5-methyl-6-(2,2,2-trifluoroethoxy)pyridin-3-yl)methyl)isonicotinamide | | 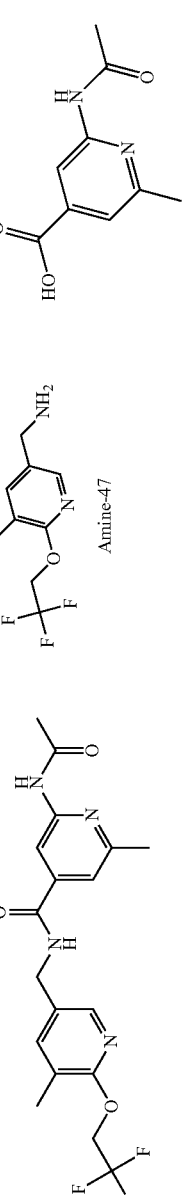 | 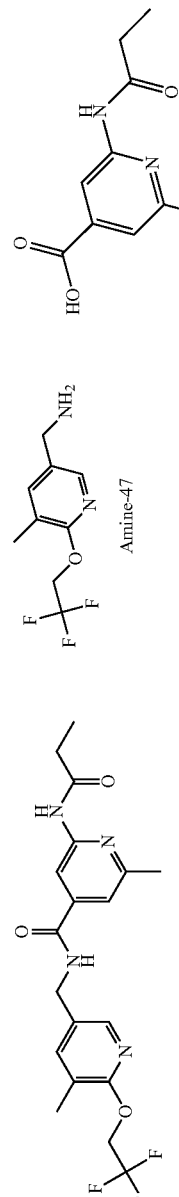 Amine-47 | 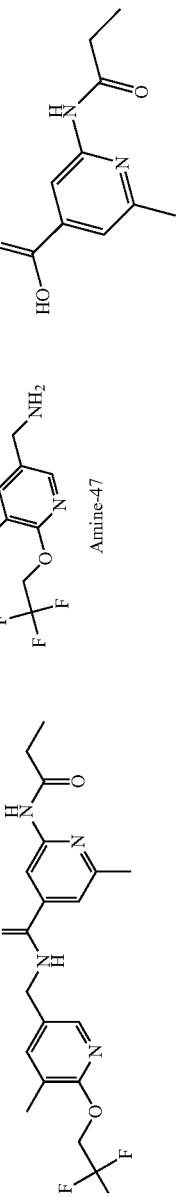 | 409.3 | 1.68 |
| 371 | 2-acetamido-6-methyl-N-((5-methyl-6-(2,2,2-trifluoroethoxy)pyridin-3-yl)methyl)isonicotinamide | | 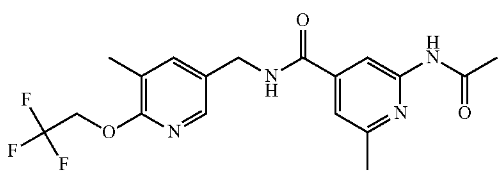 | Amine-47 | | 395.3 | 1.58 |
| 372 | 2-methyl-N-((5-methyl-6-(2,2,2-trifluoroethoxy)pyridin-3-yl)methyl)-6-propionamidoisonicotinamide | | 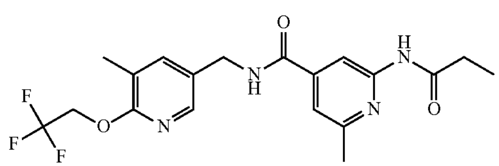 | Amine-47 | | 409.3 | 1.66 |

TABLE 1-continued

| Example | Name | Chirality | Structure | Amine part | Carboxylic part | Observed MS | Retention time (min) |
|---|---|---|---|---|---|---|---|
| 373 | 2-acetamido-N-((2-methoxy-6-(2,2,2-trifluoroethoxy)pyridin-3-yl)methyl)-6-methylpyrimidine-4-carboxamide | | 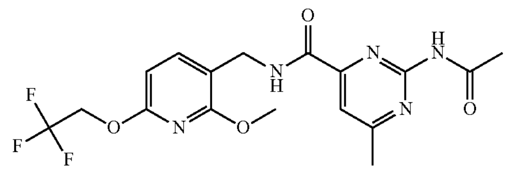 [SMILES: COc1nc(OCC(F)(F)F)ccc1CNC(=O)c1cc(C)nc(NC(C)=O)n1] | Amine-24 | | 412.3 | 1.59 |
| 374 | 2-isobutyramido-N-((2-methoxy-6-(2,2,2-trifluoroethoxy)pyridin-3-yl)methyl)-6-methylpyrimidine-4-carboxamide | | 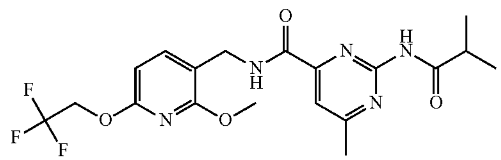 [SMILES: COc1nc(OCC(F)(F)F)ccc1CNC(=O)c1cc(C)nc(NC(=O)C(C)C)n1] | Amine-24 | | 440.3 | 1.74 |
| 375 | 6-methyl-2-propionamido-N-(1-(3-(2,2,2-trifluoroethoxy)phenyl)ethyl)pyrimidine-4-carboxamide | single enantiomer | 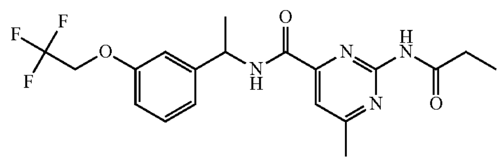 [SMILES: CCC(=O)Nc1nc(C)cc(C(=O)NC(C)c2cccc(OCC(F)(F)F)c2)n1] | Amine-16 | | 409.3 | 1.66 |
| 376 | 2-(cyclopropanecarboxamido)-6-methyl-N-(1-(3-(2,2,2-trifluoroethoxy)phenyl)ethyl)pyrimidine-4-carboxamide | single enantiomer | 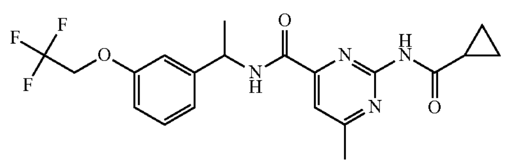 [SMILES: Cc1cc(C(=O)NC(C)c2cccc(OCC(F)(F)F)c2)nc(NC(=O)C2CC2)n1] | Amine-16 | | 421.3 | 1.67 |

TABLE 1-continued

| Example | Name | Chirality | Structure | Amine part | Carboxylic part | Observed MS | Retention time (min) |
|---|---|---|---|---|---|---|---|
| 377 | 2-isobutyramido-6-methyl-N-(1-(3-(2,2,2-trifluoroethoxy)phenyl)ethyl)pyrimidine-4-carboxamide | single enantiomer | 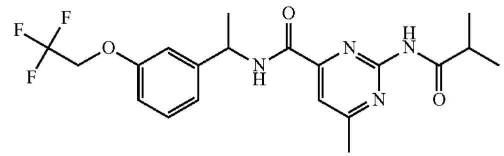 [SMILES: Cc1cc(C(=O)NC(C)c2cccc(OCC(F)(F)F)c2)nc(NC(=O)C(C)C)n1] | Amine-16 | | 423.3 | 1.72 |
| 378 | 2-isobutyramido-N-(1-(5-methyl-6-(2,2,2-trifluoroethoxy)pyridin-3-yl)ethyl)isonicotinamide | single enantiomer | 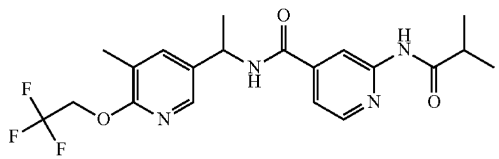 [SMILES: Cc1cc(C(C)NC(=O)c2ccnc(NC(=O)C(C)C)c2)cnc1OCC(F)(F)F] | Amine-17 | | 423.3 | 1.73 |
| 379 | 2-acetamido-6-methyl-N-(1-(5-methyl-6-(2,2,2-trifluoroethoxy)pyridin-3-yl)ethyl)isonicotinamide | single enantiomer | 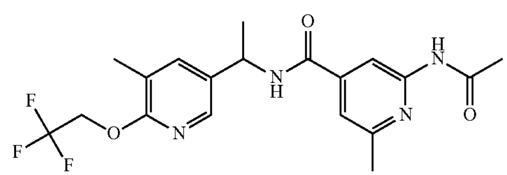 [SMILES: CC(=O)Nc1cc(C(=O)NC(C)c2cnc(OCC(F)(F)F)c(C)c2)cc(C)n1] | Amine-17 | | 409.3 | 1.63 |
| 380 | 2-(cyclopropanecarboxamido)-N-(2-fluoro-5-(trifluoromethyl)benzyl)pyrimidine-4-carboxamide | | 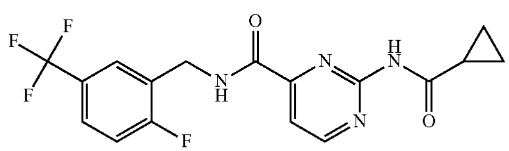 [SMILES: O=C(NCc1cc(C(F)(F)F)ccc1F)c1ccnc(NC(=O)C2CC2)n1] | | | 381.2 | 1.55 |
| 381 | 2-acetamido-N-(1-(3-(2,2,2-trifluoroethoxy)phenyl)ethyl)pyrimidine-4-carboxamide | single enantiomer | 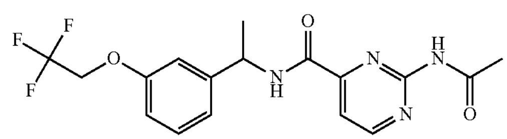 [SMILES: CC(=O)Nc1nccc(C(=O)NC(C)c2cccc(OCC(F)(F)F)c2)n1] | alternative route | | 381.2 | 1.51 |

TABLE 1-continued

| Example | Name | Chirality | Structure | Amine part | Carboxylic part | Observed MS | Retention time (min) |
|---|---|---|---|---|---|---|---|
| 382 | 2-propionamido-N-(1-(3-(2,2,2-trifluoroethoxy)phenyl)ethyl)pyrimidine-4-carboxamide | single enantiomer | 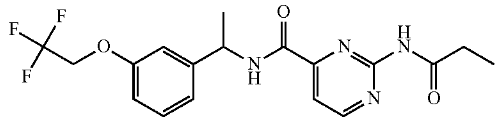 [SMILES: CCC(=O)Nc1nccc(C(=O)NC(C)c2cccc(OCC(F)(F)F)c2)n1] | | alternative route | 395.2 | 1.6 |
| 383 | 2-isobutyramido-N-(1-(3-(2,2,2-trifluoroethoxy)phenyl)ethyl)pyrimidine-4-carboxamide | single enantiomer | 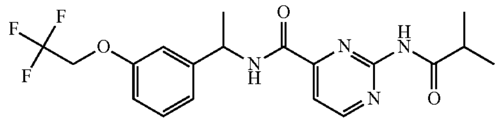 [SMILES: CC(C)C(=O)Nc1nccc(C(=O)NC(C)c2cccc(OCC(F)(F)F)c2)n1] | | alternative route | 409.3 | 1.66 |
| 384 | N-((5-chloro-6-(2,2,2-trifluoroethoxy)pyridin-3-yl)methyl)-6-methyl-2-propionamidopyrimidine-4-carboxamide | | 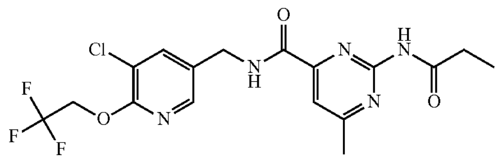 | Amine-19 | | 430.2 | 1.65 |
| 385 | N-((5-chloro-6-(2,2,2-trifluoroethoxy)pyridin-3-yl)methyl)-2-isobutyramido-6-methylpyrimidine-4-carboxamide | | 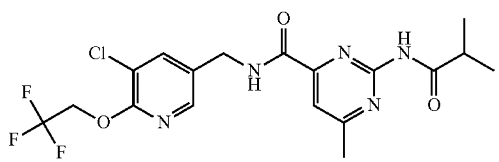 [SMILES: Cc1cc(C(=O)NCc2cnc(OCC(F)(F)F)c(Cl)c2)nc(NC(=O)C(C)C)n1] | Amine-19 | | 444.2 | 1.71 |
| 386 | N-((5-fluoro-2-methyl-6-(2,2,2-trifluoroethoxy)pyridin-3-yl)methyl)-2-isobutyramido-6-methylpyrimidine-4-carboxamide | | 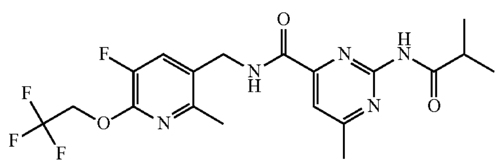 [SMILES: Cc1cc(C(=O)NCc2cc(F)c(OCC(F)(F)F)nc2C)nc(NC(=O)C(C)C)n1] | Amine-42 | | 442.2 | 1.73 |

TABLE 1-continued

| Example | Name | Chirality | Structure | Amine part | Carboxylic part | Observed MS | Retention time (min) |
|---|---|---|---|---|---|---|---|
| 387 | 2-(cyclopropanecarboxamido)-6-methyl-N-(1-(6-(2,2,2-trifluoroethoxy)pyridin-2-yl)ethyl)pyrimidine-4-carboxamide | single enantiomer | 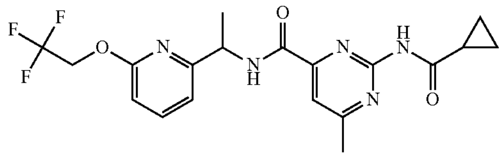 [SMILES: Cc1cc(C(=O)NC(C)c2cccc(OCC(F)(F)F)n2)nc(NC(=O)C2CC2)n1] | Amine-7 | | 422.3 | 1.73 |
| 388 | 2-isobutyramido-6-methyl-N-(1-(6-(2,2,2-trifluoroethoxy)pyridin-2-yl)ethyl)pyrimidine-4-carboxamide | single enantiomer | 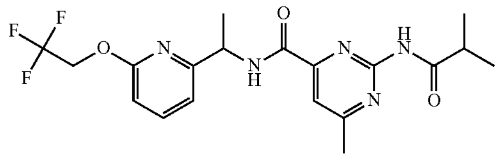 [SMILES: Cc1cc(C(=O)NC(C)c2cccc(OCC(F)(F)F)n2)nc(NC(=O)C(C)C)n1] | Amine-7 | | 424.3 | 1.79 |
| 389 | N-((5-fluoro-2-methyl-6-(2,2,2-trifluoroethoxy)pyridin-3-yl)methyl)-2-(2-hydroxypropan-2-amido)-6-methylisonicotinamide | | 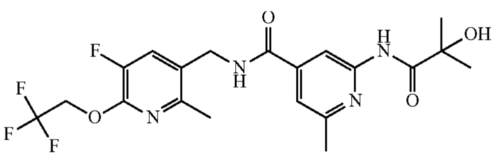 [SMILES: Cc1cc(C(=O)NCc2cc(F)c(OCC(F)(F)F)nc2C)cc(NC(=O)C(C)(C)O)n1] | Amine-42 | | 457.3 | 1.67 |
| 390 | 2-(cyclopropanecarboxamido)-N-((5-fluoro-2-methyl-6-(2,2,2-trifluoroethoxy)pyridin-3-yl)methyl)-6-methylpyrimidine-4-carboxamide | | 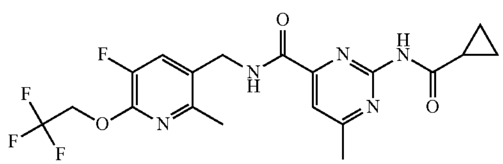 [SMILES: Cc1cc(C(=O)NCc2cc(F)c(OCC(F)(F)F)nc2C)nc(NC(=O)C2CC2)n1] | Amine-42 | | 440.3 | 1.69 |

| Example | Name | Chirality | Structure | Amine part | Carboxylic part | Observed MS | Retention time (min) |
|---|---|---|---|---|---|---|---|
| 391 | 2-acetamido-N,6-dimethyl-N-(1-(5-methyl-6-(2,2,2-trifluoroethoxy)pyridin-3-yl)ethyl)isonicotinamide | single enantiomer | 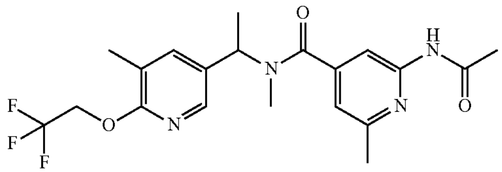 [SMILES: CC(=O)Nc1cc(C(=O)N(C)C(C)c2cnc(OCC(F)(F)F)c(C)c2)cc(C)n1] | Amine-48 | | 423.3 | 1.68 |
| 392 | 2-acetamido-N-methyl-N-(1-(5-methyl-6-(2,2,2-trifluoroethoxy)pyridin-3-yl)ethyl)isonicotinamide | single enantiomer | 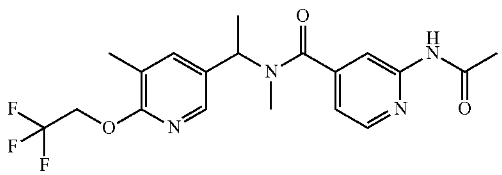 [SMILES: CC(=O)Nc1cc(C(=O)N(C)C(C)c2cnc(OCC(F)(F)F)c(C)c2)ccn1] | Amine-48 | | 409.3 | 1.62 |
| 393 | N-methyl-N-(1-(5-methyl-6-(2,2,2-trifluoroethoxy)pyridin-3-yl)ethyl)-2-propionamidoisonicotinamide | single enantiomer | 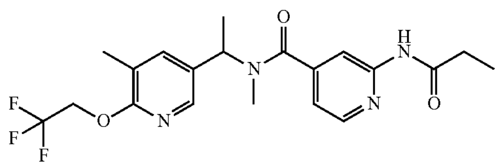 | Amine-48 | | 423.3 | 1.7 |
| 394 | 2-acetamido-N,6-dimethyl-N-((5-methyl-6-(2,2,2-trifluoroethoxy)pyridin-3-yl)methyl)isonicotinamide | | 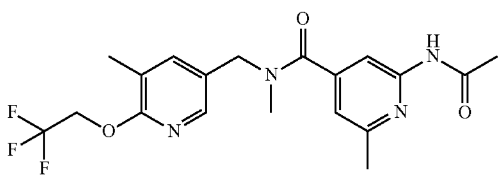 [SMILES: CC(=O)Nc1cc(C(=O)N(C)Cc2cnc(OCC(F)(F)F)c(C)c2)cc(C)n1] | Amine-49 | | 409.3 | 1.62 |
| 395 | 2-acetamido-N-methyl-N-((5-methyl-6-(2,2,2-trifluoroethoxy)pyridin-3-yl)methyl)isonicotinamide | | 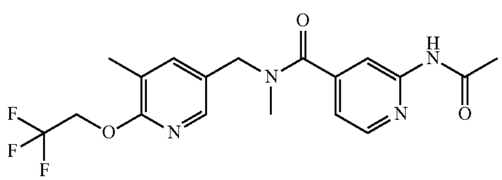 [SMILES: CC(=O)Nc1cc(C(=O)N(C)Cc2cnc(OCC(F)(F)F)c(C)c2)ccn1] | Amine-49 | | 395.3 | 1.56 |

TABLE 1-continued

| Example | Name | Chirality | Structure | Amine part | Carboxylic part | Observed MS | Retention time (min) |
|---|---|---|---|---|---|---|---|
| 396 | N-methyl-N-((5-methyl-6-(2,2,2-trifluoroethoxy)pyridin-3-yl)methyl)-2-propionamidoisonicotinamide | | 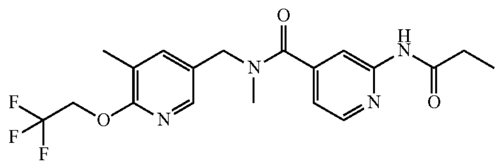 [SMILES: CCC(=O)Nc1cc(C(=O)N(C)Cc2cnc(OCC(F)(F)F)c(C)c2)ccn1] | Amine-49 | | 409.3 | 1.65 |
| 397 | 2-(cyclopropanecarboxamido)-N-((6-(2,2,2-trifluoroethoxy)pyridin-3-yl)methyl)pyrimidine-4-carboxamide | | 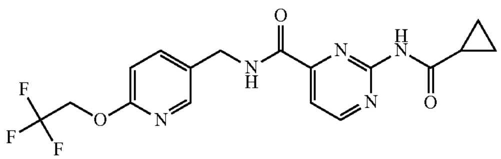 [SMILES: O=C(NCc1ccc(OCC(F)(F)F)nc1)c1ccnc(NC(=O)C2CC2)n1] | | | 394.3 | 1.5 |
| 398 | 2-isobutyramido-N-((6-(2,2,2-trifluoroethoxy)pyridin-3-yl)methyl)pyrimidine-4-carboxamide | | 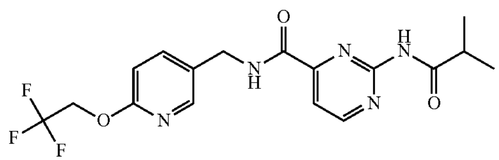 [SMILES: CC(C)C(=O)Nc1nccc(C(=O)NCc2ccc(OCC(F)(F)F)nc2)n1] | alternative route | | 396.3 | 1.54 |
| 399 | 2-acetamido-N-(1-(5-methoxy-6-(2,2,2-trifluoroethoxy)pyridin-3-yl)ethyl)pyrimidine-4-carboxamide | single enantiomer | 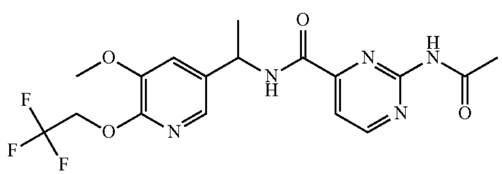 [SMILES: COc1cc(C(C)NC(=O)c2ccnc(NC(C)=O)n2)cnc1OCC(F)(F)F] | alternative route | | 412.3 | 1.45 |
| 400 | 2-(cyclopropanecarboxamido)-N-(1-(5-methoxy-6-(2,2,2-trifluoroethoxy)pyridin-3-yl)ethyl)pyrimidine-4-carboxamide | single enantiomer | 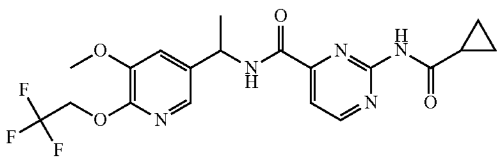 [SMILES: COc1cc(C(C)NC(=O)c2ccnc(NC(=O)C3CC3)n2)cnc1OCC(F)(F)F] | Amine-22 | | 438.3 | 1.56 |

TABLE 1-continued

| Example | Name | Chirality | Structure | Amine part | Carboxylic part | Observed MS | Retention time (min) |
|---|---|---|---|---|---|---|---|
| 401 | 2-isobutyramido-N-(1-(5-methoxy-6-(2,2,2-trifluoroethoxy)pyridin-3-yl)ethyl)pyrimidine-4-carboxamide | single enantiomer | 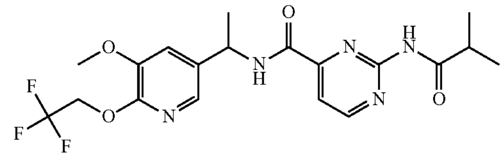 [SMILES: COc1cc(C(C)NC(=O)c2ccnc(NC(=O)C(C)C)n2)cnc1OCC(F)(F)F] | | alternative route | 440.3 | 1.6 |
| 402 | 2-(cyclopropanecarboxamido)-N-((5-fluoro-6-(2,2,2-trifluoroethoxy)pyridin-3-yl)methyl)pyrimidine-4-carboxamide | | 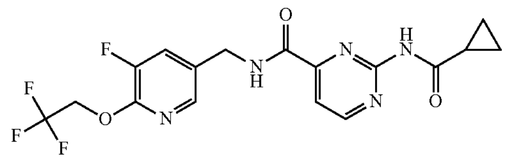 [SMILES: O=C(NCc1cnc(OCC(F)(F)F)c(F)c1)c1ccnc(NC(=O)C2CC2)n1] | Amine-28 | | 412.3 | 1.54 |
| 403 | 2-(cyclopropanecarboxamido)-N-((4-methyl-6-(2,2,2-trifluoroethoxy)pyridin-3-yl)methyl)pyrimidine-4-carboxamide | | 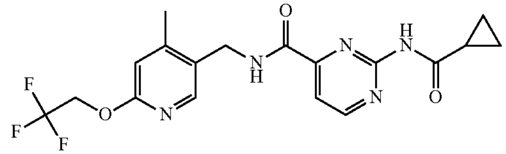 | Amine-29 | | 408.3 | 1.56 |
| 404 | 2-(cyclopropanecarboxamido)-N-(3-(trifluoromethyl)benzyl)pyrimidine-4-carboxamide | | 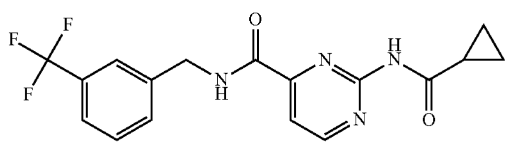 [SMILES: O=C(NCc1cccc(C(F)(F)F)c1)c1ccnc(NC(=O)C2CC2)n1] | | | 363.3 | 1.54 |
| 405 | 2-(cyclopropanecarboxamido)-N-(1-(4-(2,2,2-trifluoroethoxy)phenyl)ethyl)pyrimidine-4-carboxamide | single enantiomer | 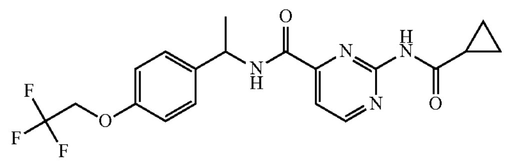 [SMILES: CC(NC(=O)c1ccnc(NC(=O)C2CC2)n1)c1ccc(OCC(F)(F)F)cc1] | Amine-18 | | 407.3 | 1.6 |

TABLE 1-continued

| Example | Name | Chirality | Structure | Amine part | Carboxylic part | Observed MS | Retention time (min) |
|---|---|---|---|---|---|---|---|
| 406 | 2-isobutyramido-N-(1-(4-(2,2,2-trifluoroethoxy)phenyl)ethyl)pyrimidine-4-carboxamide | single enantiomer | 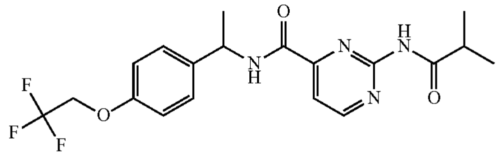 [SMILES: CC(C)C(=O)Nc1nccc(C(=O)NC(C)c2ccc(OCC(F)(F)F)cc2)n1] | alternative route | | 409.3 | 1.64 |
| 407 | 2-(cyclopropanecarboxamido)-N-((2-methyl-6-(2,2,2-trifluoroethoxy)pyridin-3-yl)methyl)pyrimidine-4-carboxamide | | 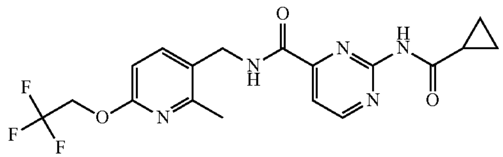 [SMILES: Cc1nc(OCC(F)(F)F)ccc1CNC(=O)c1ccnc(NC(=O)C2CC2)n1] | Amine-27 | | 408.3 | 1.6 |
| 408 | N-((5-chloro-6-(2,2,2-trifluoroethoxy)pyridin-3-yl)methyl)-2-(2-hydroxy-2-methylpropanamido)-6-methylisonicotinamide | | 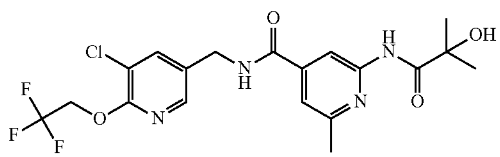 | Amine-19 | | 459.2 | 1.65 |
| 409 | 2-acetamido-N-((5-chloro-6-(2,2,2-trifluoroethoxy)pyridin-3-yl)methyl)pyrimidine-4-carboxamide | | 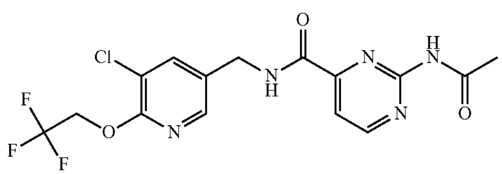 [SMILES: CC(=O)Nc1nccc(C(=O)NCc2cnc(OCC(F)(F)F)c(Cl)c2)n1] | | alternative route | 402.2 | 1.51 |
| 410 | N-((5-chloro-6-(2,2,2-trifluoroethoxy)pyridin-3-yl)methyl)-2-propionamidopyrimidine-4-carboxamide | | 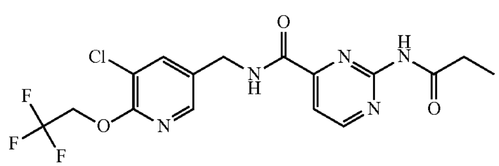 [SMILES: CCC(=O)Nc1nccc(C(=O)NCc2cnc(OCC(F)(F)F)c(Cl)c2)n1] | | alternative route | 416.2 | 1.58 |

TABLE 1-continued

| Example | Name | Chirality | Structure | Amine part | Carboxylic part | Observed MS | Retention time (min) |
|---|---|---|---|---|---|---|---|
| 411 | N-((5-chloro-6-(2,2,2-trifluoroethoxy)pyridin-3-yl)methyl)-2-(cyclopropanecarboxamido)pyrimidine-4-carboxamide | | 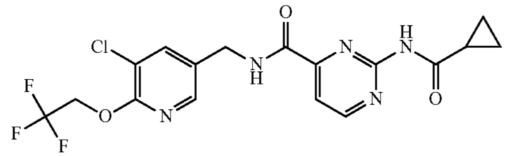 | Amine-19 | | 428.2 | 1.61 |
| 412 | N-((5-chloro-6-(2,2,2-trifluoroethoxy)pyridin-3-yl)methyl)-2-isobutyramidopyrimidine-4-carboxamide | | 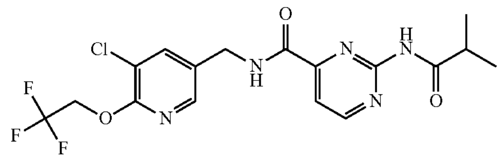 [SMILES: CC(C)C(=O)Nc1nccc(C(=O)NCc2cnc(OCC(F)(F)F)c(Cl)c2)n1] | | alternative route | 430.2 | 1.64 |
| 413 | 2-(cyclopropanecarboxamido)-N-(1-(6-(2,2,2-trifluoroethoxy)pyridin-3-yl)propyl)pyrimidine-4-carboxamide | single enantiomer | 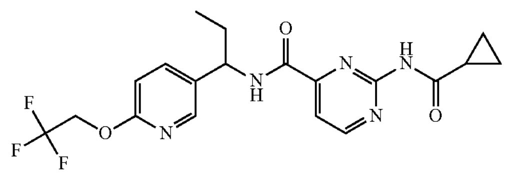 [SMILES: CCC(NC(=O)c1ccnc(NC(=O)C2CC2)n1)c1ccc(OCC(F)(F)F)nc1] | Amine-6 | | 422.3 | 1.65 |
| 414 | N-((4-methyl-6-(2,2,2-trifluoroethoxy)pyridin-3-yl)methyl)-2-pivalamidoisonicotinamide | | 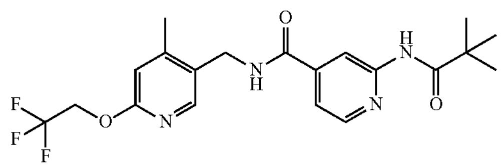 [SMILES: Cc1cc(OCC(F)(F)F)ncc1CNC(=O)c1ccnc(NC(=O)C(C)(C)C)c1] | Amine-29 | | 423.3 | 1.73 |
| 415 | 6-methyl-2-propionamido-N-(1-(3-(trifluoromethoxy)phenyl)ethyl)pyrimidine-4-carboxamide | single enantiomer | 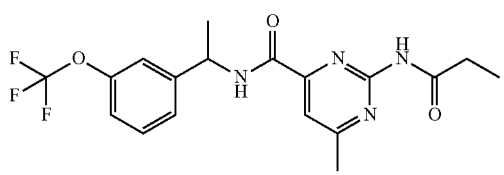 [SMILES: CCC(=O)Nc1nc(C)cc(C(=O)NC(C)c2cccc(OC(F)(F)F)c2)n1] | Amine-9 | | 395.3 | 1.7 |

TABLE 1-continued

| Example | Name | Chirality | Structure | Amine part | Carboxylic part | Observed MS | Retention time (min) |
|---|---|---|---|---|---|---|---|
| 416 | 2-(cyclopropanecarboxamido)-6-methyl-N-(1-(3-(trifluoromethoxy)phenyl)ethyl)pyrimidine-4-carboxamide | single enantiomer | 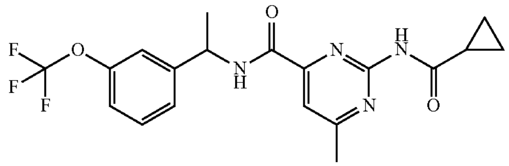 [SMILES: Cc1cc(C(=O)NC(C)c2cccc(OC(F)(F)F)c2)nc(NC(=O)C2CC2)n1] | Amine-9 | | 407.2 | 1.72 |
| 417 | 2-isobutyramido-6-methyl-N-(1-(3-(trifluoromethoxy)phenyl)ethyl)pyrimidine-4-carboxamide | single enantiomer | 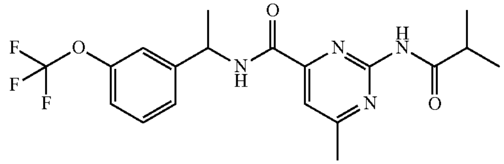 [SMILES: Cc1cc(C(=O)NC(C)c2cccc(OC(F)(F)F)c2)nc(NC(=O)C(C)C)n1] | Amine-9 | | 409.3 | 1.76 |
| 418 | 2-isobutyramido-N-(1-(3-(trifluoromethoxy)phenyl)ethyl)isonicotinamide | single enantiomer | 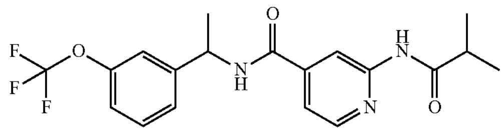 [SMILES: CC(C)C(=O)Nc1cc(C(=O)NC(C)c2cccc(OC(F)(F)F)c2)ccn1] | Amine-9 | | 394.3 | 1.72 |
| 419 | 2-butyramido-N-(1-(3-(trifluoromethoxy)phenyl)ethyl)isonicotinamide | single enantiomer | 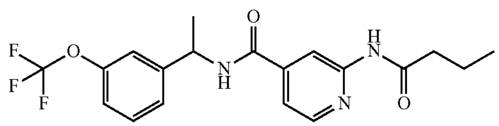 [SMILES: CCCC(=O)Nc1cc(C(=O)NC(C)c2cccc(OC(F)(F)F)c2)ccn1] | Amine-9 | | 394.3 | 1.72 |
| 420 | 2-acetamido-6-methyl-N-(1-(3-(trifluoromethoxy)phenyl)ethyl)isonicotinamide | single enantiomer | 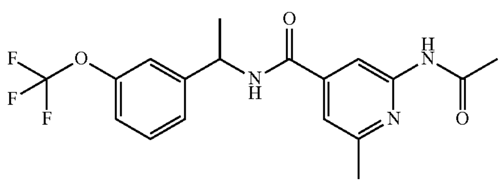 [SMILES: CC(=O)Nc1cc(C(=O)NC(C)c2cccc(OC(F)(F)F)c2)cc(C)n1] | Amine-9 | | 380.3 | 1.6 |

TABLE 1-continued

| Example | Name | Chirality | Structure | Amine part | Carboxylic part | Observed MS | Retention time (min) |
|---|---|---|---|---|---|---|---|
| 421 | 2-(2-hydroxy-2-methylpropanamido)-6-methyl-N-(1-(3-(trifluoromethoxy)phenyl)ethyl)isonicotinamide | single enantiomer | 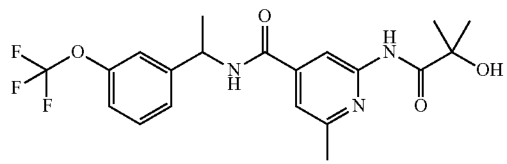 [SMILES: Cc1cc(C(=O)NC(C)c2cccc(OC(F)(F)F)c2)cc(NC(=O)C(C)(C)O)n1] | Amine-9 | | 424.2 | 1.68 |
| 422 | N-((2-ethoxy-6-(2,2,2-trifluoroethoxy)pyridin-3-yl)methyl)-2-(2-hydroxy-2-methylpropanamido)-6-methylisonicotinamide | | 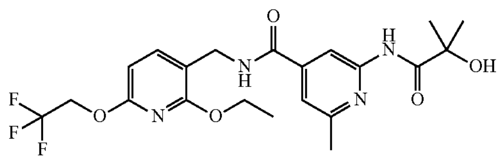 [SMILES: CCOc1nc(OCC(F)(F)F)ccc1CNC(=O)c1cc(C)nc(NC(=O)C(C)(C)O)c1] | Amine-45 | | 469.3 | 1.74 |
| 423 | 2-(cyclopropanecarboxamido)-6-methyl-N-((6-(3,3,3-trifluoropropoxy)pyridin-3-yl)methyl)pyrimidine-4-carboxamide | | 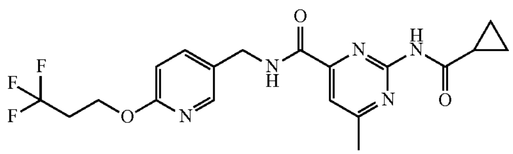 | Amine-30 | | 422.3 | 1.55 |
| 424 | 2-isobutyramido-6-methyl-N-((6-(3,3,3-trifluoropropoxy)pyridin-3-yl)methyl)pyrimidine-4-carboxamide | | 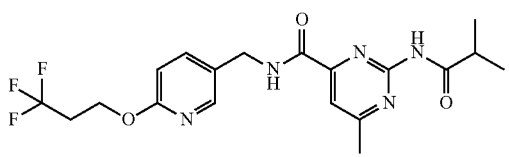 [SMILES: Cc1cc(C(=O)NCc2ccc(OCCC(F)(F)F)nc2)nc(NC(=O)C(C)C)n1] | Amine-30 | | 424.3 | 1.6 |

| Example | Name | Chirality | Structure | Amine part | Carboxylic part | Observed MS | Retention time (min) |
|---|---|---|---|---|---|---|---|
| 425 | 2-acetamido-6-methyl-N-(1-(3-(trifluoromethoxy)phenyl)ethyl)pyrimidine-4-carboxamide | single enantiomer | 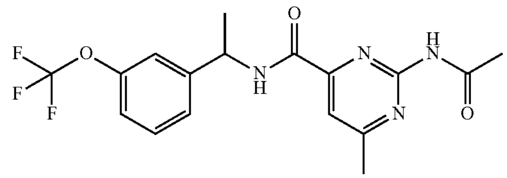 [SMILES: CC(=O)Nc1nc(C)cc(C(=O)NC(C)c2cccc(OC(F)(F)F)c2)n1] | Amine-9 | | 381.3 | 1.61 |
| 426 | N-(1-(5-methyl-6-(2,2,2-trifluoroethoxy)pyridin-3-yl)ethyl)-2-(methylamino)isonicotinamide | single enantiomer | 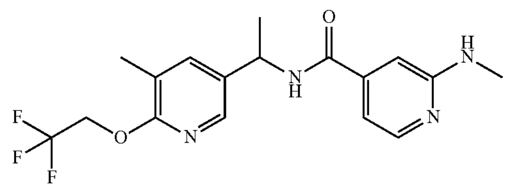 [SMILES: CNc1cc(C(=O)NC(C)c2cnc(OCC(F)(F)F)c(C)c2)ccn1] | Amine-17 | | 367.3 | 1.61 |
| 427 | 2-methoxy-N-(1-(5-methyl-6-(2,2,2-trifluoroethoxy)pyridin-3-yl)ethyl)isonicotinamide | single enantiomer | 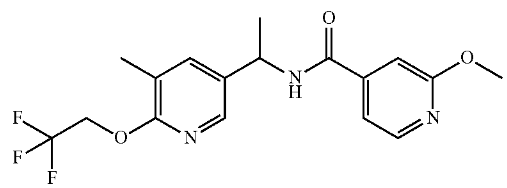 [SMILES: COc1cc(C(=O)NC(C)c2cnc(OCC(F)(F)F)c(C)c2)ccn1] | Amine-17 | | 368.3 | 1.75 |
| 428 | 6-acetamido-N-(1-(5-methyl-6-(2,2,2-trifluoroethoxy)pyridin-3-yl)ethyl)picolinamide | single enantiomer | 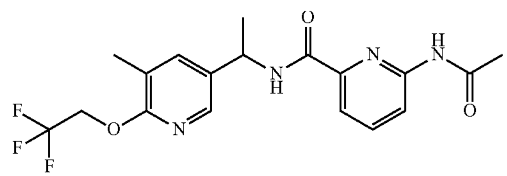 [SMILES: CC(=O)Nc1cccc(C(=O)NC(C)c2cnc(OCC(F)(F)F)c(C)c2)n1] | Amine-17 | | 395.3 | 1.68 |
| 429 | N-(1-(5-methyl-6-(2,2,2-trifluoroethoxy)pyridin-3-yl)ethyl)-3-(2-oxopyrrolidin-1-yl)benzamide | single enantiomer | 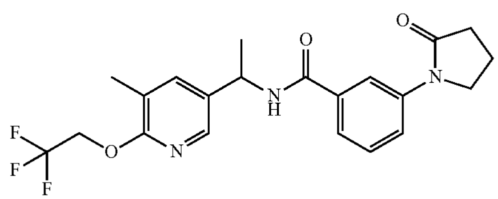 [SMILES: Cc1cc(C(C)NC(=O)c2cccc(N3CCCC3=O)c2)cnc1OCC(F)(F)F] | Amine-17 | | 420.3 | 1.68 |

TABLE 1-continued

| Example | Name | Chirality | Structure | Amine part | Carboxylic part | Observed MS | Retention time (min) |
|---|---|---|---|---|---|---|---|
| 430 | N-(1-(5-methyl-6-(2,2,2-trifluoroethoxy)pyridin-3-yl)ethyl)quinoline-6-carboxamide | single enantiomer | 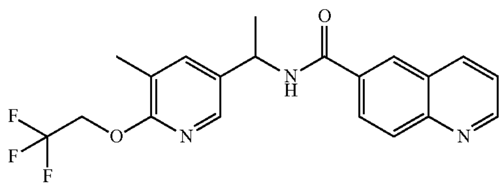 [SMILES: Cc1cc(C(C)NC(=O)c2ccc3ncccc3c2)cnc1OCC(F)(F)F] | Amine-17 | | 388.3 | 1.69 |
| 431 | N-(1-(5-methyl-6-(2,2,2-trifluoroethoxy)pyridin-3-yl)ethyl)quinoline-8-carboxamide | single enantiomer | 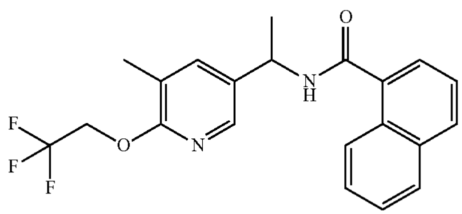 [SMILES: Cc1cc(C(C)NC(=O)c2cccc3ccccc23)cnc1OCC(F)(F)F] | Amine-17 | | 390.0 | 1.96 |
| 432 | N-(1-(5-methyl-6-(2,2,2-trifluoroethoxy)pyridin-3-yl)ethyl)quinoxaline-2-carboxamide | single enantiomer | 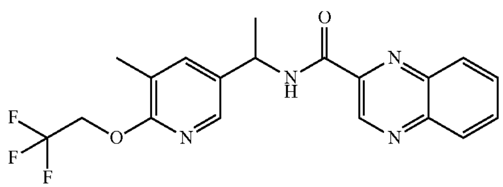 [SMILES: Cc1cc(C(C)NC(=O)c2cnc3ccccc3n2)cnc1OCC(F)(F)F] | Amine-17 | | 389.3 | 1.89 |
| 433 | N-(1-(5-methyl-6-(2,2,2-trifluoroethoxy)pyridin-3-yl)ethyl)quinoline-3-carboxamide | single enantiomer | 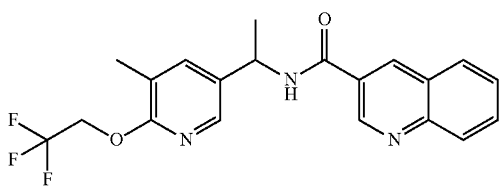 [SMILES: Cc1cc(C(C)NC(=O)c2cnc3ccccc3c2)cnc1OCC(F)(F)F] | Amine-17 | | 388.3 | 1.74 |

TABLE 1-continued

| Example | Name | Chirality | Structure | Amine part | Carboxylic part | Observed MS | Retention time (min) |
|---|---|---|---|---|---|---|---|
| 434 | N-(1-(5-methyl-6-(2,2,2-trifluoroethoxy)pyridin-3-yl)ethyl)imidazo[1,2-a]pyridine-2-carboxamide | single enantiomer | 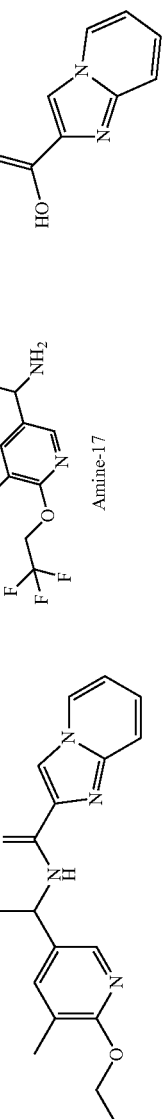 |  Amine-17 |  | 377.3 | 1.68 |
| 435 | 1-methyl-N-(1-(5-methyl-6-(2,2,2-trifluoroethoxy)pyridin-3-yl)ethyl)-1H-pyrazolo[3,4-b]pyridine-3-carboxamide | single enantiomer | 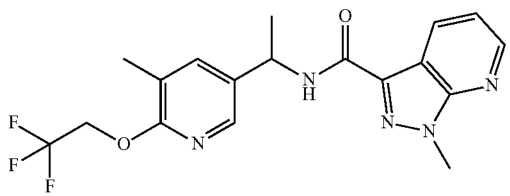 [SMILES: Cc1cc(C(C)NC(=O)c2nn(C)c3ncccc23)cnc1OCC(F)(F)F] |  Amine-17 |  | 392.3 | 1.8 |
| 436 | N-(1-(5-methyl-6-(2,2,2-trifluoroethoxy)pyridin-3-yl)ethyl)-1H-benzo[d]imidazole-4-carboxamide | single enantiomer | 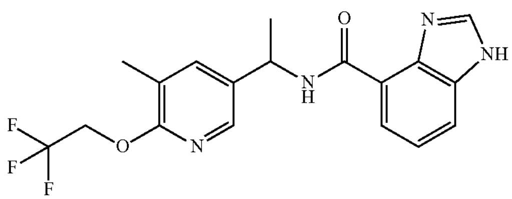 [SMILES: Cc1cc(C(C)NC(=O)c2cccc3[nH]cnc23)cnc1OCC(F)(F)F] | 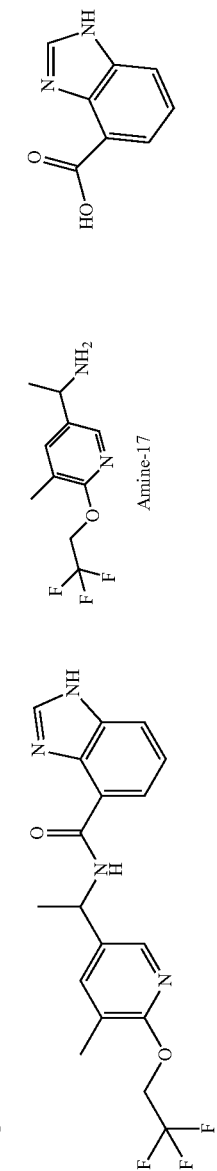 Amine-17 |  | 377.3 | 1.68 |
| 437 | (R)-6-methyl-2-propionamido-N-((6-((1,1,1-trifluoropropan-2-yl)oxy)pyridin-3-yl)methyl)pyrimidine-4-carboxamide | single enantiomer | 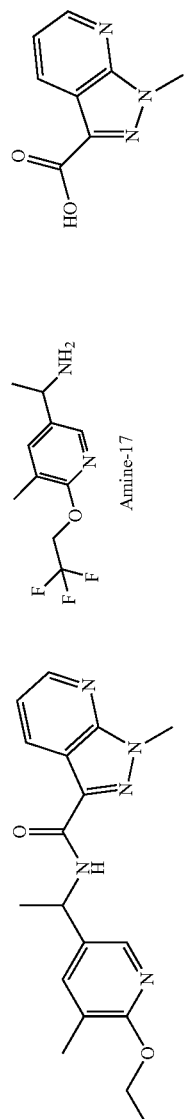 |  Amine-43 |  | 410.3 | 1.63 |

| Example | Name | Chirality | Structure | Amine part | Carboxylic part | Observed MS | Retention time (min) |
|---|---|---|---|---|---|---|---|
| 438 | (R)-2-(cyclopropanecarboxamido)-6-methyl-N-((6-((1,1,1-trifluoropropan-2-yl)oxy)pyridin-3-yl)methyl)pyrimidine-4-carboxamide | single enantiomer | 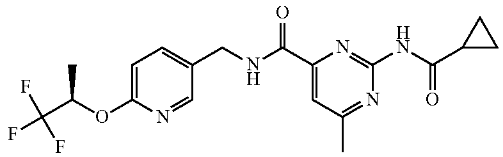 [SMILES: Cc1cc(C(=O)NCc2ccc(O[C@H](C)C(F)(F)F)nc2)nc(NC(=O)C2CC2)n1] | Amine-43 | | 422.3 | 1.65 |
| 439 | (R)-2-isobutyramido-6-methyl-N-((6-((1,1,1-trifluoropropan-2-yl)oxy)pyridin-3-yl)methyl)pyrimidine-4-carboxamide | single enantiomer | 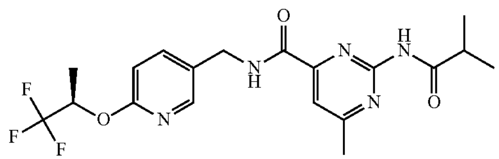 [SMILES: Cc1cc(C(=O)NCc2ccc(O[C@H](C)C(F)(F)F)nc2)nc(NC(=O)C(C)C)n1] | Amine-43 | | 424.3 | 1.7 |
| 440 | (R)-2-(cyclopropanecarboxamido)-N-((6-((1,1,1-trifluoropropan-2-yl)oxy)pyridin-3-yl)methyl)pyrimidine-4-carboxamide | single enantiomer | 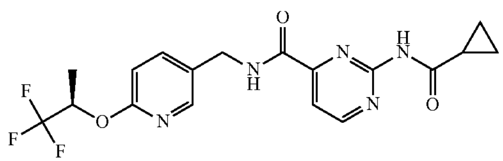 [SMILES: C[C@@H](Oc1ccc(CNC(=O)c2ccnc(NC(=O)C3CC3)n2)cn1)C(F)(F)F] | Amine-43 | | 408.2 | 1.59 |
| 441 | 2-acetamido-N-((5-methoxy-6-(2,2,2-trifluoroethoxy)pyridin-3-yl)methyl)-6-methylpyrimidine-4-carboxamide | | 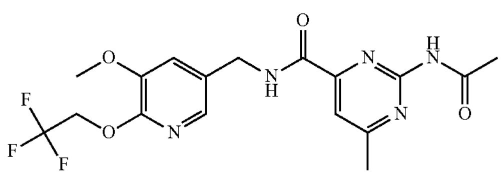 [SMILES: COc1cc(CNC(=O)c2cc(C)nc(NC(C)=O)n2)cnc1OCC(F)(F)F] | Amine-36 | | 412.3 | 1.44 |

TABLE 1-continued

| Example | Name | Chirality | Structure | Amine part | Carboxylic part | Observed MS | Retention time (min) |
|---|---|---|---|---|---|---|---|
| 442 | 2-(cyclopropanecarboxamido)-N-((5-methoxy-6-(2,2,2-trifluoroethoxy)pyridin-3-yl)methyl)-6-methylpyrimidine-4-carboxamide | | 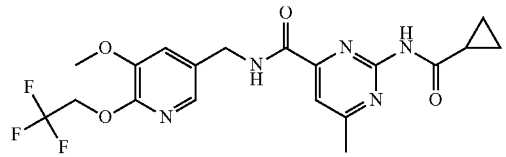 [SMILES: COc1cc(CNC(=O)c2cc(C)nc(NC(=O)C3CC3)n2)cnc1OCC(F)(F)F] | Amine-36 | | 438.3 | 1.54 |
| 443 | 2-isobutyramido-N-((5-methoxy-6-(2,2,2-trifluoroethoxy)pyridin-3-yl)methyl)-6-methylpyrimidine-4-carboxamide | | 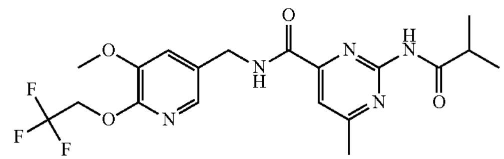 | Amine-36 | | 440.3 | 1.59 |
| 444 | 2-(cyclopropanecarboxamido)-N-((5-methoxy-6-(2,2,2-trifluoroethoxy)pyridin-3-yl)methyl)pyrimidine-4-carboxamide | | 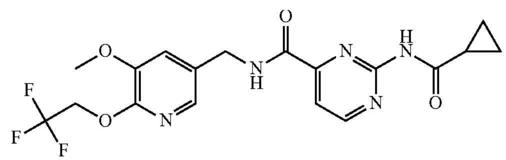 [SMILES: COc1cc(CNC(=O)c2ccnc(NC(=O)C3CC3)n2)cnc1OCC(F)(F)F] | Amine-36 | | 424.3 | 1.48 |
| 445 | 2-(hydroxymethyl)-N-(1-(5-methyl-6-(2,2,2-trifluoroethoxy)pyridin-3-yl)ethyl)-6-propionamidoisonicotinamide | single enantiomer | 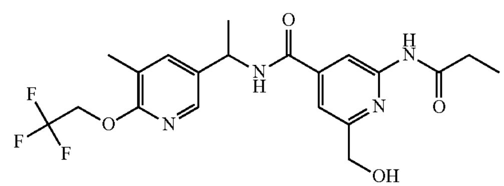 [SMILES: CCC(=O)Nc1cc(C(=O)NC(C)c2cnc(OCC(F)(F)F)c(C)c2)cc(CO)n1] | | alternative route | 439.3 | 1.57 |

| Example | Name | Chirality | Structure | Amine part | Carboxylic part | Observed MS | Retention time (min) |
|---|---|---|---|---|---|---|---|
| 446 | 2-(cyclopropane-carboxamido)-6-(hydroxymethyl)-N-(1-(5-methyl-6-(2,2,2-trifluoroethoxy)pyridin-3-yl)ethyl)isonicotinamide | single enantiomer | 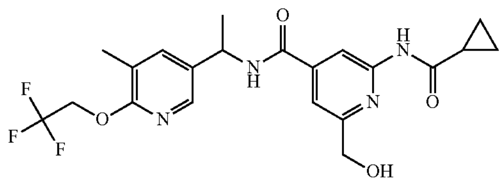 [SMILES: Cc1cc(C(C)NC(=O)c2cc(CO)nc(NC(=O)C3CC3)c2)cnc1OCC(F)(F)F] | alternative route | | 451.3 | 1.61 |
| 447 | 2-(hydroxymethyl)-6-isobutyramido-N-(1-(5-methyl-6-(2,2,2-trifluoroethoxy)pyridin-3-yl)ethyl)isonicotinamide | single enantiomer | 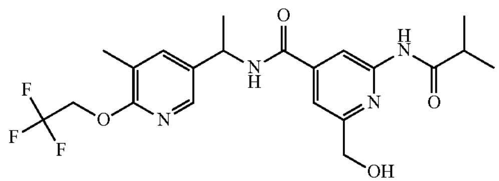 [SMILES: Cc1cc(C(C)NC(=O)c2cc(CO)nc(NC(=O)C(C)C)c2)cnc1OCC(F)(F)F] | alternative route | | 453.3 | 1.64 |
| 448 | N-(1-(4-(2,2-difluoroethoxy)-2-methylphenyl)ethyl)-2-isobutyramidoisonicotinamide | single enantiomer | 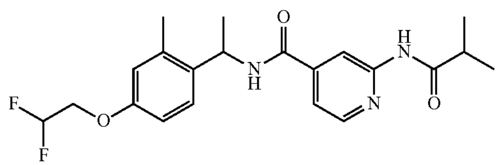 [SMILES: Cc1cc(OCC(F)F)ccc1C(C)NC(=O)c1ccnc(NC(=O)C(C)C)c1] | Amine-83 | | 404.3 | 1.66 |
| 449 | 2-(cyclopropane-carboxamido)-N-methyl-N-(1-(5-methyl-6-(2,2,2-trifluoroethoxy)pyridin-3-yl)ethyl)pyrimidine-4-carboxamide | single enantiomer | 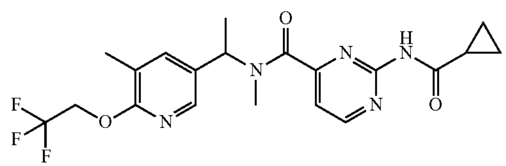 [SMILES: Cc1cc(C(C)N(C)C(=O)c2ccnc(NC(=O)C3CC3)n2)cnc1OCC(F)(F)F] | Amine-48 | | 436.2 | 1.64 |

TABLE 1-continued

| Example | Chirality | Name | Structure | Amine part | Carboxylic part | Observed MS | Retention time (min) |
|---|---|---|---|---|---|---|---|
| 450 | | 2-(cyclopropanecarboxamido)-N-methyl-N-((5-methyl-6-(2,2,2-trifluoroethoxy)pyridin-3-yl)methyl)pyrimidine-4-carboxamide | 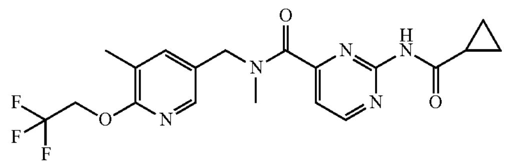 [SMILES: Cc1cc(CN(C)C(=O)c2ccnc(NC(=O)C3CC3)n2)cnc1OCC(F)(F)F] | Amine-49 | | 422.1 | 1.58 |
| 451 | | 2-(cyclopropanecarboxamido)-N,6-dimethyl-N-((5-methyl-6-(2,2,2-trifluoroethoxy)pyridin-3-yl)methyl)pyrimidine-4-carboxamide | 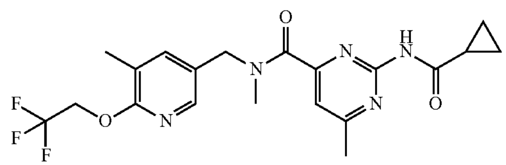 [SMILES: Cc1cc(C(=O)N(C)Cc2cnc(OCC(F)(F)F)c(C)c2)nc(NC(=O)C2CC2)n1] | Amine-49 | | 436.2 | 1.64 |
| 452 | single enantiomer | 2-(cyclobutanecarboxamido)-6-methyl-N-(1-(6-(2,2,2-trifluoroethoxy)pyridin-3-yl)ethyl)isonicotinamide | 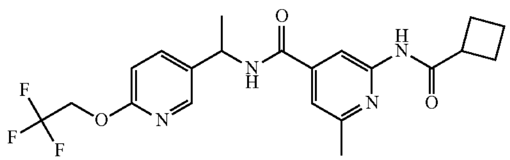 [SMILES: Cc1cc(C(=O)NC(C)c2ccc(OCC(F)(F)F)nc2)cc(NC(=O)C2CCC2)n1] | | alternative route | 435.1 | 1.74 |
| 453 | | 2-(cyclopropanecarboxamido)-N-(3-(trifluoromethoxy)benzyl)pyrimidine-4-carboxamide | 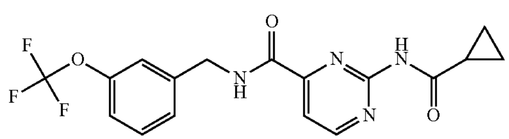 [SMILES: O=C(NCc1cccc(OC(F)(F)F)c1)c1ccnc(NC(=O)C2CC2)n1] | | | 379.1 | 1.58 |

TABLE 1-continued

| Example | Name | Chirality | Structure | Amine part | Carboxylic part | Observed MS | Retention time (min) |
|---|---|---|---|---|---|---|---|
| 454 | 2-(cyclopropanecarboxamido)-N-(1-(5-ethoxy-6-(2,2,2-trifluoroethoxy)pyridin-3-yl)ethyl)pyrimidine-4-carboxamide | single enantiomer | 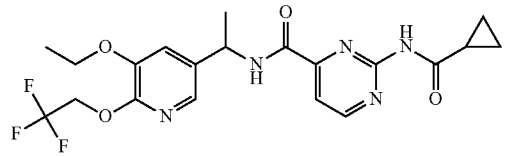 | Amine-38 | | 452.1 | 1.63 |
| 455 | 2-(cyclopropanecarboxamido)-N-((6-(3,3,3-trifluoropropoxy)pyridin-3-yl)methyl)pyrimidine-4-carboxamide | | 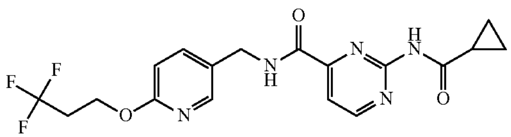 [SMILES: O=C(NCc1ccc(OCCC(F)(F)F)nc1)c1ccnc(NC(=O)C2CC2)n1] | Amine-30 | | 408.1 | 1.49 |
| 456 | 6-methyl-N-(1-(5-(2,2,2-trifluoroethoxy)pyridin-3-yl)ethyl)-2-(oxazol-2-ylamino)pyrimidine-4-carboxamide | single enantiomer | 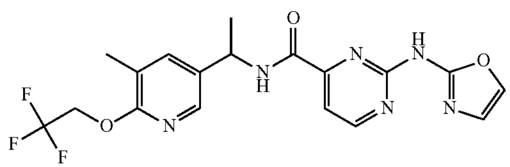 [SMILES: Cc1cc(C(C)NC(=O)c2ccnc(Nc3ncco3)n2)cnc1OCC(F)(F)F] | | alternative route | 435.1 | 1.68 |
| 457 | N-(1-(5-chloro-6-(2,2,2-trifluoroethoxy)pyridin-3-yl)ethyl)-2-methyl-6-(oxazol-2-ylamino)isonicotinamide | single enantiomer | 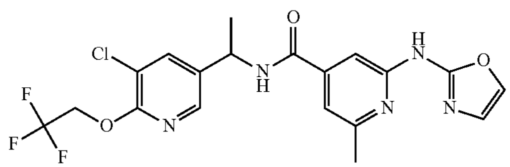 [SMILES: Cc1cc(C(=O)NC(C)c2cnc(OCC(F)(F)F)c(Cl)c2)cc(Nc2ncco2)n1] | | alternative route | 454.0 | 1.72 |
| 458 | 2-ethoxy-6-methyl-N-(1-(5-methyl-6-(2,2,2-trifluoroethoxy)pyridin-3-yl)ethyl)pyrimidine-4-carboxamide | single enantiomer | 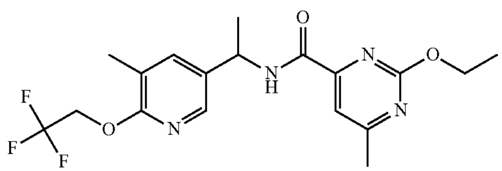 [SMILES: CCOc1nc(C)cc(C(=O)NC(C)c2cnc(OCC(F)(F)F)c(C)c2)n1] | | alternative route | 397.2 | 1.92 |

TABLE 1-continued

| Example | Name | Chirality | Structure | Amine part | Carboxylic part | Observed MS | Retention time (min) |
|---|---|---|---|---|---|---|---|
| 459 | 2-(cyclopentanecarboxamido)-6-methyl-N-(1-(6-(2,2,2-trifluoroethoxy)pyridin-3-yl)ethyl)isonicotinamide | single enantiomer | 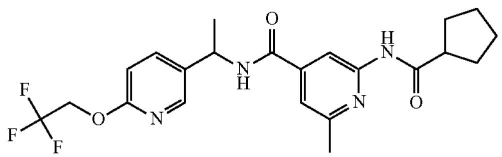 [SMILES: Cc1cc(C(=O)NC(C)c2ccc(OCC(F)(F)F)nc2)cc(NC(=O)C2CCCC2)n1] | | alternative route | 449.0 | 1.81 |
| 460 | 2-propionamido-N-((6-(trifluoromethyl)pyridin-2-yl)methyl)isonicotinamide | | 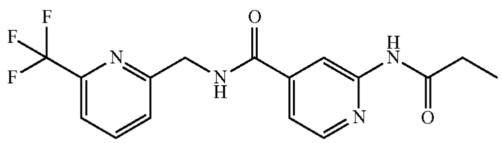 [SMILES: CCC(=O)Nc1cc(C(=O)NCc2cccc(C(F)(F)F)n2)ccn1] | | | 351.2 | 1.39 |
| 461 | 2-methyl-6-propionamido-N-((6-(trifluoromethyl)pyridin-2-yl)methyl)isonicotinamide | | 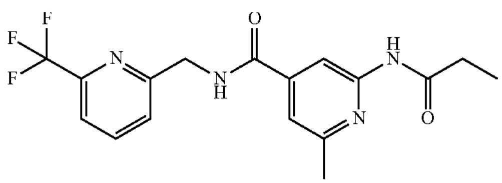 [SMILES: CCC(=O)Nc1cc(C(=O)NCc2cccc(C(F)(F)F)n2)cc(C)n1] | | | 365.1 | 1.47 |
| 462 | 2-isobutyramido-N-((6-(trifluoromethyl)pyridin-2-yl)methyl)isonicotinamide | | 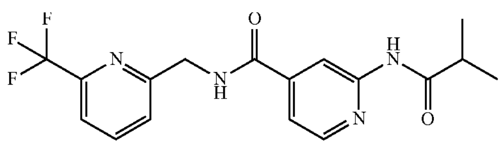 | | | 365.1 | 1.49 |

TABLE 1-continued

| Example | Chirality | Name | Structure | Amine part | Carboxylic part | Observed MS | Retention time (min) |
|---|---|---|---|---|---|---|---|
| 463 | | 2-amino-6-methyl-N-((5-methyl-6-(2,2,2-trifluoroethoxy)pyridin-3-yl)methyl)pyrimidine-4-carboxamide | 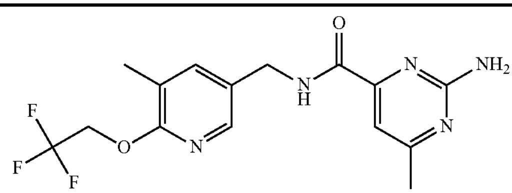 | Amine-47 | | 354.2 | 1.56 |
| 464 | | 2-propionamido-N-((6-(2,2,2-trifluoroethoxy)pyridin-2-yl)methyl)isonicotinamide | 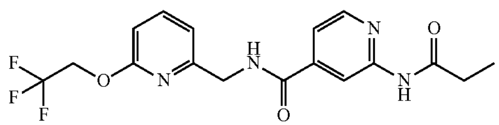 [SMILES: CCC(=O)Nc1cc(C(=O)NCc2cccc(OCC(F)(F)F)n2)ccn1] | Amine-4 | | 381.2 | 1.54 |
| 465 | | 2-(cyclopropanecarboxamido)-N-((6-(2,2,2-trifluoroethoxy)pyridin-2-yl)methyl)isonicotinamide | 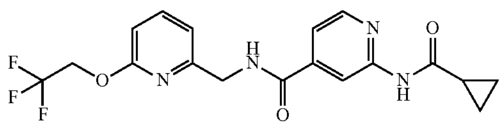 [SMILES: O=C(NCc1cccc(OCC(F)(F)F)n1)c1ccnc(NC(=O)C2CC2)c1] | Amine-4 | | 393.2 | 1.58 |
| 466 | | 2-acetamido-6-methyl-N-((6-(2,2,2-trifluoroethoxy)pyridin-2-yl)methyl)isonicotinamide | 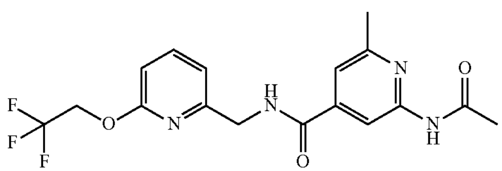 [SMILES: CC(=O)Nc1cc(C(=O)NCc2cccc(OCC(F)(F)F)n2)cc(C)n1] | Amine-4 | | 381.2 | 1.51 |

TABLE 1-continued

| Example | Name | Chirality | Structure | Amine part | Carboxylic part | Observed MS | Retention time (min) |
|---|---|---|---|---|---|---|---|
| 467 | 2-methyl-6-propionamido-N-((6-(2,2,2-trifluoroethoxy)pyridin-2-yl)methyl)isonicotinamide | | 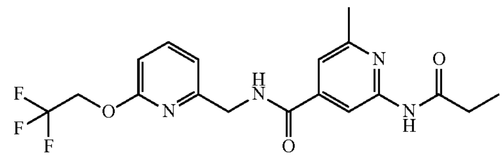 [SMILES: CCC(=O)Nc1cc(C(=O)NCc2cccc(OCC(F)(F)F)n2)cc(C)n1] | Amine-4 | | 395.2 | 1.61 |
| 468 | 2-isobutyramido-N-((6-(2,2,2-trifluoroethoxy)pyridin-2-yl)methyl)isonicotinamide | | 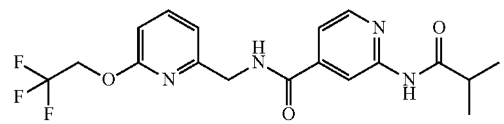 [SMILES: CC(C)C(=O)Nc1cc(C(=O)NCc2cccc(OCC(F)(F)F)n2)ccn1] | Amine-4 | | 395.2 | 1.63 |
| 469 | 2-butyramido-N-((6-(2,2,2-trifluoroethoxy)pyridin-2-yl)methyl)isonicotinamide | | 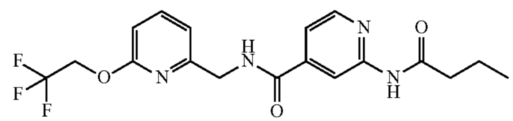 [SMILES: CCCC(=O)Nc1cc(C(=O)NCc2cccc(OCC(F)(F)F)n2)ccn1] | Amine-4 | | 395.2 | 1.62 |
| 470 | 2-(cyclopropanecarboxamido)-6-methyl-N-(((6-(2,2,2-trifluoroethoxy)pyridin-2-yl)methyl)pyrimidine-4-carboxamide | | 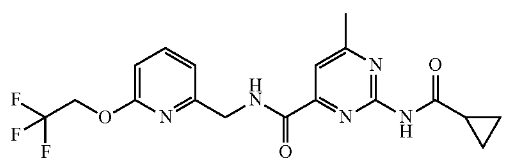 [SMILES: Cc1cc(C(=O)NCc2cccc(OCC(F)(F)F)n2)nc(NC(=O)C2CC2)n1] | Amine-4 | | 408.2 | 1.62 |

| Example | Name | Chirality | Structure | Amine part | Carboxylic part | Observed MS | Retention time (min) |
|---|---|---|---|---|---|---|---|
| 471 | 2-pivalamido-N-((6-(2,2,2-trifluoroethoxy)pyridin-2-yl)methyl)isonicotinamide | | 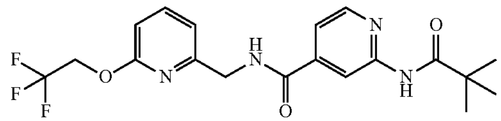 [SMILES: CC(C)(C)C(=O)Nc1cc(C(=O)NCc2cccc(OCC(F)(F)F)n2)ccn1] | Amine-4 | | 409.2 | 1.72 |
| 472 | 6-methyl-N-(1-(5-methyl-6-(2,2,2-trifluoroethoxy)pyridin-3-yl)ethyl)-2-(methylamino)pyrimidine-4-carboxamide | single enantiomer | 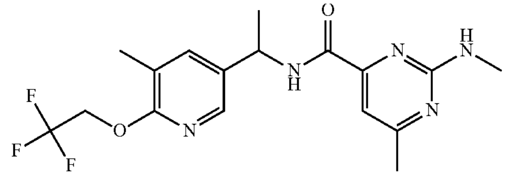 [SMILES: CNc1nc(C)cc(C(=O)NC(C)c2cnc(OCC(F)(F)F)c(C)c2)n1] | alternative route | | 282.3 | 1.78 |
| 473 | 2-(dimethylamino)-6-methyl-N-(1-(5-methyl-6-(2,2,2-trifluoroethoxy)pyridin-3-yl)ethyl)pyrimidine-4-carboxamide | single enantiomer | 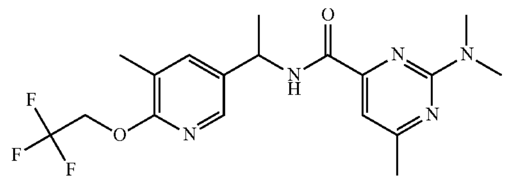 | alternative route | | 396.2 | 2.01 |
| 474 | 6-methyl-N-(1-(5-methyl-6-(2,2,2-trifluoroethoxy)pyridin-3-yl)ethyl)-2-(pyrrolidin-1-yl)pyrimidine-4-carboxamide | single enantiomer | 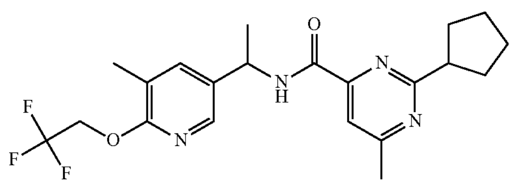 [SMILES: Cc1cc(C(=O)NC(C)c2cnc(OCC(F)(F)F)c(C)c2)nc(C2CCCC2)n1] | alternative route | | 422.3 | 2.09 |

TABLE 1-continued

| Example | Name | Chirality | Structure | Amine part | Carboxylic part | Observed MS | Retention time (min) |
|---|---|---|---|---|---|---|---|
| 475 | 2-((2-methoxyethyl)amino)-6-methyl-N-(1-(5-methyl-6-(2,2,2-trifluoroethoxy)pyridin-3-yl)ethyl)pyrimidine-4-carboxamide | single enantiomer | 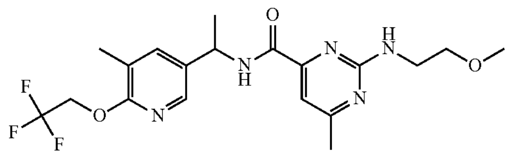 [SMILES: COCCNc1nc(C)cc(C(=O)NC(C)c2cnc(OCC(F)(F)F)c(C)c2)n1] | | alternative route | 426.2 | 1.81 |
| 476 | N4-(1-(5-chloro-6-(2,2,2-trifluoroethoxy)pyridin-3-yl)ethyl)-N2-ethyl-6-methyl-pyridine-2,4-dicarboxamide | single enantiomer | 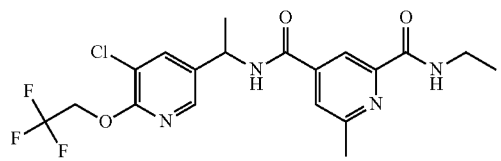 [SMILES: CCNC(=O)c1cc(C(=O)NC(C)c2cnc(OCC(F)(F)F)c(Cl)c2)cc(C)n1] | | alternative route | 443.1 | 1.77 |
| 477 | N2,6-dimethyl-N4-(1-(5-methyl-6-(2,2,2-trifluoroethoxy)pyridin-3-yl)ethyl)pyridine-2,4-dicarboxamide | single enantiomer | 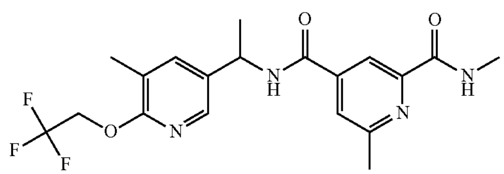 [SMILES: CNC(=O)c1cc(C(=O)NC(C)c2cnc(OCC(F)(F)F)c(C)c2)cc(C)n1] | | alternative route | 409.2 | 1.68 |
| 478 | N2-ethyl-6-methyl-N4-(1-(5-methyl-6-(2,2,2-trifluoroethoxy)pyridin-3-yl)ethyl)pyridine-2,4-dicarboxamide | single enantiomer | 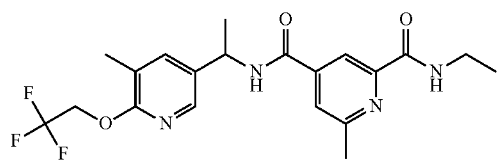 [SMILES: CCNC(=O)c1cc(C(=O)NC(C)c2cnc(OCC(F)(F)F)c(C)c2)cc(C)n1] | | alternative route | 423.2 | 1.75 |

TABLE 1-continued

| Example | Name | Chirality | Structure | Amine part | Carboxylic part | Observed MS | Retention time (min) |
|---|---|---|---|---|---|---|---|
| 479 | 2,6-dimethoxy-N-(1-(5-methyl-6-(2,2,2-trifluoroethoxy)pyridin-3-yl)ethyl)isonicotinamide | single enantiomer | 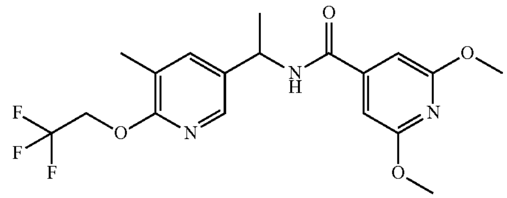 [SMILES: COc1cc(C(=O)NC(C)c2cnc(OCC(F)(F)F)c(C)c2)cc(OC)n1] | Amine-17 | | 398.1 | 1.87 |
| 480 | 2-methyl-6-pivalamido-N-((6-(2,2,2-trifluoroethoxy)pyridin-3-yl)methyl)isonicotinamide | | 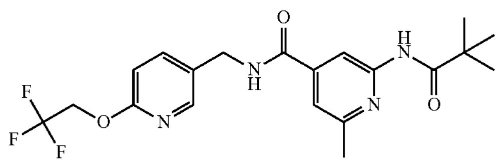 [SMILES: Cc1cc(C(=O)NCc2ccc(OCC(F)(F)F)nc2)cc(NC(=O)C(C)(C)C)n1] | alternative route | | 423.2 | 1.74 |
| 481 | N2-ethyl-N4-((2-methoxy-6-(2,2,2-trifluoroethoxy)pyridin-3-yl)methyl)pyridine-2,4-dicarboxamide | | 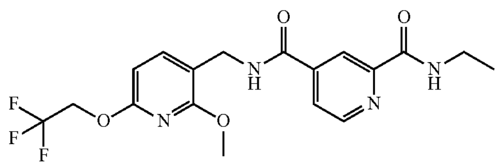 [SMILES: CCNC(=O)c1cc(C(=O)NCc2ccc(OCC(F)(F)F)nc2OC)ccn1] | Amine-24 | | 411.2 | 1.67 |
| 482 | 2-acrylamido-6-methyl-N-((6-(2,2,2-trifluoroethoxy)pyridin-3-yl)methyl)isonicotinamide | single enantiomer | 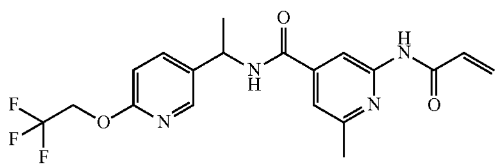 [SMILES: C=CC(=O)Nc1cc(C(=O)NC(C)c2ccc(OCC(F)(F)F)nc2)cc(C)n1] | alternative route | | 407.2 | 1.64 |
| 483 | 2-isobutyramido-6-methyl-N-((6-(2,2,2-trifluoroethoxy)pyridin-3-yl)methyl)isonicotinamide | | 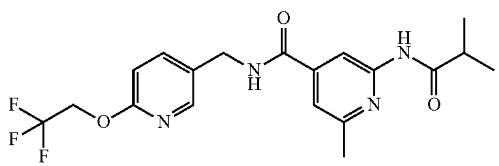 [SMILES: Cc1cc(C(=O)NCc2ccc(OCC(F)(F)F)nc2)cc(NC(=O)C(C)C)n1] | | | 409.2 | 1.67 |

TABLE 1-continued

| Example | Name | Chirality | Structure | Amine part | Carboxylic part | Observed MS | Retention time (min) |
|---|---|---|---|---|---|---|---|
| 484 | 2-isobutyramido-6-methyl-N-(1-(6-(2,2,2-trifluoroethoxy)pyridin-3-yl)propyl)isonicotinamide | single enantiomer | 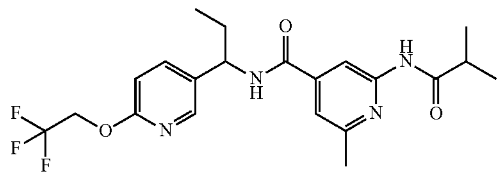 [SMILES: CCC(NC(=O)c1cc(C)nc(NC(=O)C(C)C)c1)c1ccc(OCC(F)(F)F)nc1] | Amine-6 | | 437.2 | 1.79 |
| 485 | N-(1-(6-(2,2-difluoroethoxy)pyridin-3-yl)ethyl)-2-isobutyramido-6-methylisonicotinamide | single enantiomer | 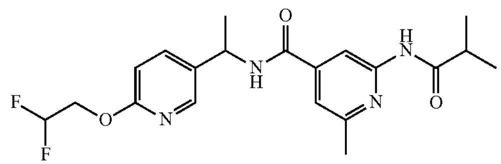 [SMILES: Cc1cc(C(=O)NC(C)c2ccc(OCC(F)F)nc2)cc(NC(=O)C(C)C)n1] | Amine-32 | | 405.3 | 1.62 |
| 486 | N-(1-(5-fluoro-6-(2,2,2-trifluoroethoxy)pyridin-3-yl)ethyl)-2-isobutyramido-6-methylisonicotinamide | single enantiomer | 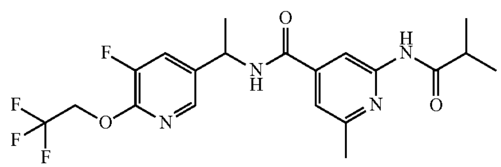 [SMILES: Cc1cc(C(=O)NC(C)c2cnc(OCC(F)(F)F)c(F)c2)cc(NC(=O)C(C)C)n1] | Amine-12 | | 441.2 | 1.76 |
| 487 | 2-isobutyramido-N-(1-(5-methoxy-6-(2,2,2-trifluoroethoxy)pyridin-3-yl)ethyl)-6-methylisonicotinamide | single enantiomer | 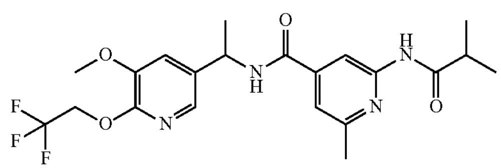 | Amine-22 | | 453.2 | 1.71 |

TABLE 1-continued

| Example | Name | Chirality | Structure | Amine part | Carboxylic part | Observed MS | Retention time (min) |
|---|---|---|---|---|---|---|---|
| 488 | 2-isobutyramido-6-methyl-N-(1-(6-(2-(2,2,2-trifluoroethoxy)ethoxy)pyridin-3-yl)ethyl)isonicotinamide | single enantiomer | 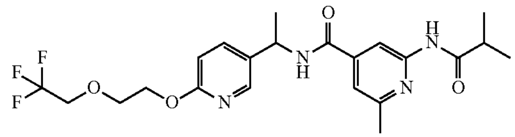 [SMILES: Cc1cc(C(=O)NC(C)c2ccc(OCCOCC(F)(F)F)nc2)cc(NC(=O)C(C)C)n1] | Amine-31 | | 467.3 | 1.67 |
| 489 | 2-isobutyramido-6-methyl-N-(1-(6-(3,3,3-trifluoropropoxy)pyridin-3-yl)ethyl)isonicotinamide | single enantiomer | 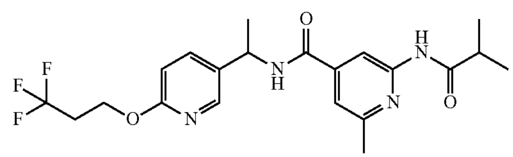 [SMILES: Cc1cc(C(=O)NC(C)c2ccc(OCCC(F)(F)F)nc2)cc(NC(=O)C(C)C)n1] | Amine-21 | | 437.2 | 1.71 |
| 490 | 2-isobutyramido-6-methyl-N-((6-(3,3,3-trifluoropropoxy)pyridin-3-yl)methyl)isonicotinamide | | 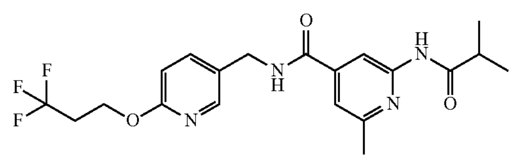 | Amine-30 | | 423.2 | 1.66 |
| 491 | N-((5-fluoro-6-(2,2,2-trifluoroethoxy)pyridin-3-yl)methyl)-2-isobutyramido-6-methylisonicotinamide | | 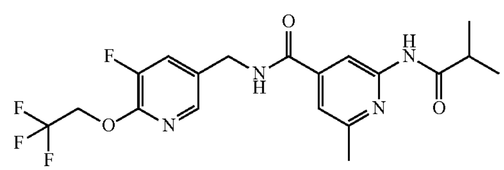 [SMILES: Cc1cc(C(=O)NCc2cnc(OCC(F)(F)F)c(F)c2)cc(NC(=O)C(C)C)n1] | Amine-28 | | 427.2 | 1.71 |

TABLE 1-continued

| Example | Chirality | Name | Structure | Amine part | Carboxylic part | Observed MS | Retention time (min) |
|---|---|---|---|---|---|---|---|
| 492 | | 2-isobutyramido-N-((5-methoxy-6-(2,2,2-trifluoroethoxy)pyridin-3-yl)methyl)-6-methylisonicotinamide | 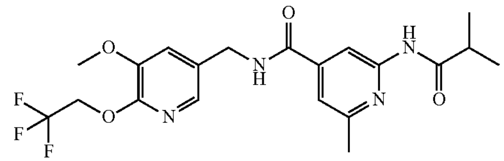 [SMILES: COc1cc(CNC(=O)c2cc(C)nc(NC(=O)C(C)C)c2)cnc1OCC(F)(F)F] | Amine-36 | | 439.2 | 1.65 |
| 493 | | 2-isobutyramido-6-methyl-N-((2-methyl-6-(2,2,2-trifluoroethoxy)pyridin-3-yl)methyl)isonicotinamide | 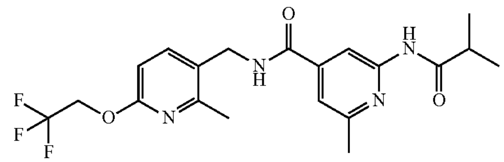 [SMILES: Cc1cc(C(=O)NCc2ccc(OCC(F)(F)F)nc2C)cc(NC(=O)C(C)C)n1] | Amine-27 | | 423.2 | 1.76 |
| 494 | | 2-isobutyramido-N-((2-methoxy-6-(2,2,2-trifluoroethoxy)pyridin-3-yl)methyl)-6-methylisonicotinamide | 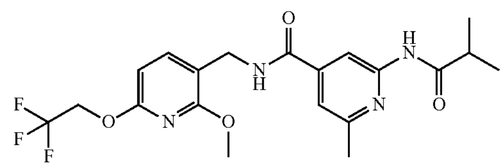 [SMILES: COc1nc(OCC(F)(F)F)ccc1CNC(=O)c1cc(C)nc(NC(=O)C(C)C)c1] | Amine-24 | | 439.2 | 1.78 |
| 495 | single enantiomer | (R)-2-isobutyramido-6-methyl-N-((6-((1,1,1-trifluoropropan-2-yl)oxy)pyridin-3-yl)methyl)isonicotinamide | 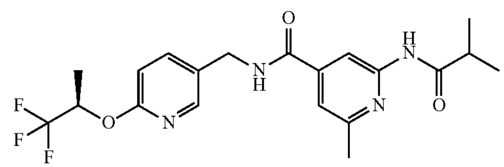 [SMILES: Cc1cc(C(=O)NCc2ccc(O[C@H](C)C(F)(F)F)nc2)cc(NC(=O)C(C)C)n1] | Amine-43 | | 423.2 | 1.76 |

TABLE 1-continued

| Example | Name | Chirality | Structure | Amine part | Carboxylic part | Observed MS | Retention time (min) |
|---|---|---|---|---|---|---|---|
| 496 | 2-isobutyramido-6-methyl-N-((6-(2,2,2-trifluoroethoxy)pyridin-2-yl)methyl)isonicotinamide | | 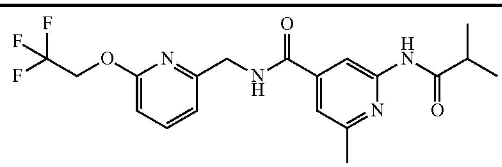 | Amine-4 | | 409.2 | 1.71 |
| 497 | 2-isobutyramido-6-methyl-N-(1-(2-(2,2,2-trifluoroethoxy)pyridin-4-yl)ethyl)isonicotinamide | single enantiomer | 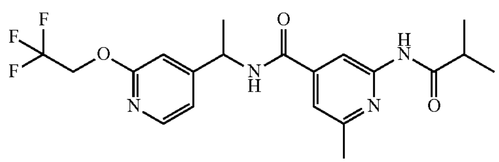 [SMILES: Cc1cc(C(=O)NC(C)c2ccnc(OCC(F)(F)F)c2)cc(NC(=O)C(C)C)n1] | Amine-11 | | 423.2 | 1.72 |
| 498 | 2-isobutyramido-6-methyl-N-((2-(2,2,2-trifluoroethoxy)pyridin-4-yl)methyl)isonicotinamide | | 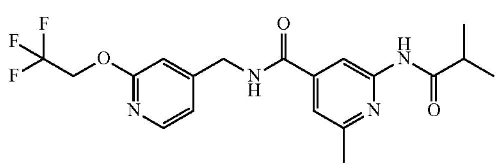 [SMILES: Cc1cc(C(=O)NCc2ccnc(OCC(F)(F)F)c2)cc(NC(=O)C(C)C)n1] | | | 409.3 | 1.66 |
| 499 | 2-isobutyramido-6-methyl-N-(1-(3-(trifluoromethoxy)phenyl)ethyl)isonicotinamide | single enantiomer | 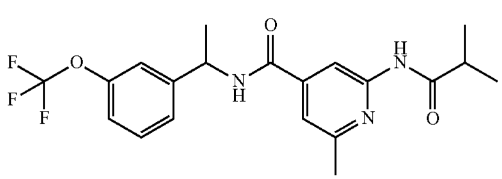 | Amine-9 | | 408.3 | 1.81 |

TABLE 1-continued

| Example | Name | Chirality | Structure | Amine part | Carboxylic part | Observed MS | Retention time (min) |
|---|---|---|---|---|---|---|---|
| 500 | 2-isobutyramido-6-methyl-N-((6-(trifluoromethyl)pyridin-2-yl)methyl)isonicotinamide | | 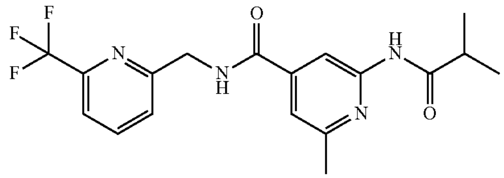 [SMILES: Cc1cc(C(=O)NCc2cccc(C(F)(F)F)n2)cc(NC(=O)C(C)C)n1] | | | 379.3 | 1.58 |
| 501 | N4-ethyl-N2-(1-(5-methyl-6-(2,2,2-trifluoroethoxy)pyridin-3-yl)ethyl)pyridine-2,4-dicarboxamide | single enantiomer | 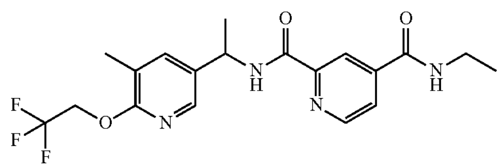 [SMILES: CCNC(=O)c1ccnc(C(=O)NC(C)c2cnc(OCC(F)(F)F)c(C)c2)c1] | Amine-17 | | 409.3 | 1.71 |
| 502 | N2-(1-(5-chloro-6-(2,2,2-trifluoroethoxy)pyridin-3-yl)ethyl)-N4-ethylpyridine-2,4-dicarboxamide | single enantiomer | 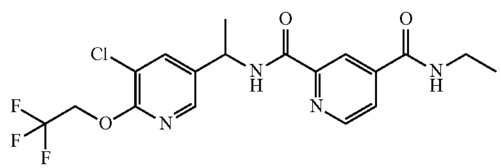 [SMILES: CCNC(=O)c1ccnc(C(=O)NC(C)c2cnc(OCC(F)(F)F)c(Cl)c2)c1] | Amine-5 | | 429.2 | 1.72 |
| 503 | 2-(2-hydroxy-2-methylpropanamido)-6-methyl-N-((5-methyl-6-(2,2,2-trifluoroethoxy)pyridin-3-yl)methyl)isonicotinamide | | 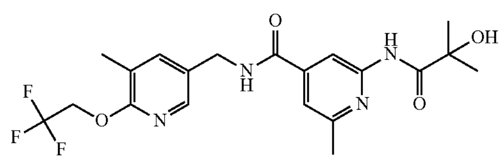 | Amine-47 | | 439.2 | 1.66 |

TABLE 1-continued

| Example | Name | Chirality | Structure | Amine part | Carboxylic part | Observed MS | Retention time (min) |
|---|---|---|---|---|---|---|---|
| 504 | 2-methoxy-6-methyl-N-(1-(5-methyl-6-(2,2,2-trifluoroethoxy)pyridin-3-yl)ethyl)pyrimidine-4-carboxamide | single enantiomer | 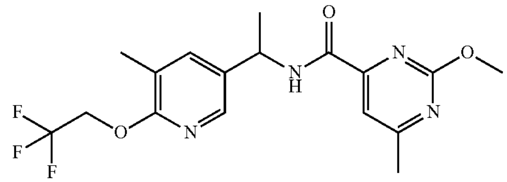 [SMILES: COc1nc(C)cc(C(=O)NC(C)c2cnc(OCC(F)(F)F)c(C)c2)n1] | Amine-17 | | 383.2 | 1.86 |
| 505 | N2-ethyl-6-methyl-N4-(1-(5-methyl-6-(2,2,2-trifluoroethoxy)pyridin-3-yl)ethyl)pyrimidine-2,4-dicarboxamide | single enantiomer | 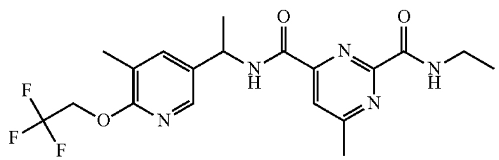 [SMILES: CCNC(=O)c1nc(C)cc(C(=O)NC(C)c2cnc(OCC(F)(F)F)c(C)c2)n1] | alternative route | | 424.2 | 1.7 |
| 506 | N2-isopropyl-6-methyl-N4-(1-(5-methyl-6-(2,2,2-trifluoroethoxy)pyridin-3-yl)ethyl)pyrimidine-2,4- | single enantiomer | 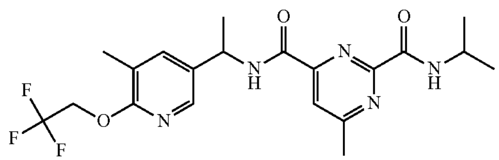 | alternative route | | 438.2 | 1.78 |
| 507 | 6-methyl-2-(oxazol-2-ylamino)-N-((6-(2,2,2-trifluoroethoxy)pyridin-3-yl)methyl)pyrimidine-4-carboxamide | | 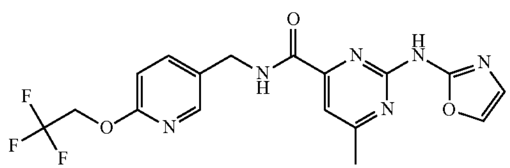 [SMILES: Cc1cc(C(=O)NCc2ccc(OCC(F)(F)F)nc2)nc(Nc2ncco2)n1] | alternative route | | 407.2 | 1.54 |

| Example | Name | Chirality | Structure | Amine part | Carboxylic part | Observed MS | Retention time (min) |
|---|---|---|---|---|---|---|---|
| 508 | N2-ethyl-N4-((2-methoxy-6-(2,2,2-trifluoroethoxy)pyridin-3-yl)methyl)-6-methylpyridine-2,4-dicarboxamide | | 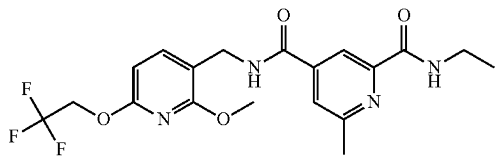 [SMILES: CCNC(=O)c1cc(C(=O)NCc2ccc(OCC(F)(F)F)nc2OC)cc(C)n1] | | alternative route | 425.2 | 1.75 |
| 509 | N2-cyclopropyl-N4-((2-methoxy-6-(2,2,2-trifluoroethoxy)pyridin-3-yl)methyl)-6-methylpyridine-2,4-dicarboxamide | | 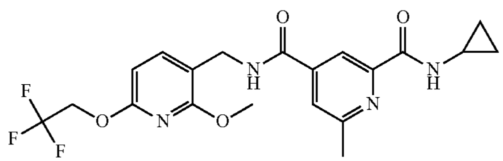 [SMILES: COc1nc(OCC(F)(F)F)ccc1CNC(=O)c1cc(C)nc(C(=O)NC2CC2)c1] | | alternative route | 437.2 | 1.75 |
| 510 | N2-isopropyl-N4-((2-methoxy-6-(2,2,2-trifluoroethoxy)pyridin-3-yl)methyl)-6-methylpyridine-2,4-dicarboxamide | | 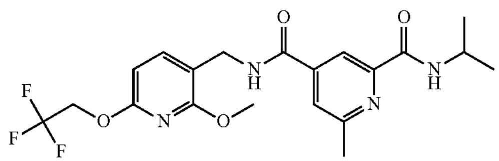 | | alternative route | 439.2 | 1.83 |
| 511 | N2,6-dimethyl-N4-(1-(3-(trifluoromethoxy)phenyl)ethyl)pyridine-2,4-dicarboxamide | single enantiomer | 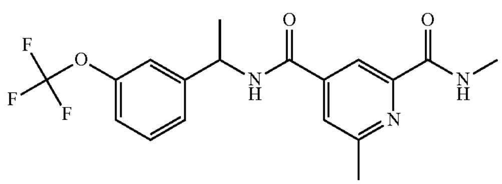 [SMILES: CNC(=O)c1cc(C(=O)NC(C)c2cccc(OC(F)(F)F)c2)cc(C)n1] | | alternative route | 380.2 | 1.69 |

TABLE 1-continued

| Example | Name | Chirality | Structure | Amine part | Carboxylic part | Observed MS | Retention time (min) |
|---|---|---|---|---|---|---|---|
| 512 | N2-ethyl-6-methyl-N4-(1-(3-(trifluoromethoxy)phenyl)ethyl)pyridine-2,4-dicarboxamide | single enantiomer | 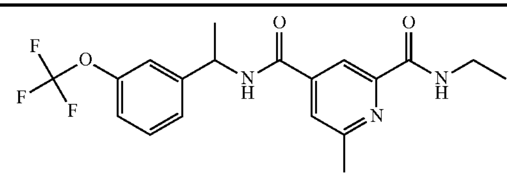 | | alternative route | 394.2 | 1.77 |
| 513 | N2-isopropyl-6-methyl-N4-(1-(3-(trifluoromethoxy)phenyl)ethyl)pyridine-2,4-dicarboxamide | single enantiomer | 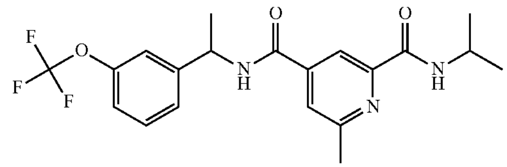 [SMILES: Cc1cc(C(=O)NC(C)c2cccc(OC(F)(F)F)c2)cc(C(=O)NC(C)C)n1] | | alternative route | 408.2 | 1.85 |
| 514 | 6-methyl-N4-(1-(3-(trifluoromethoxy)phenyl)ethyl)pyridine-2,4-dicarboxamide | single enantiomer | 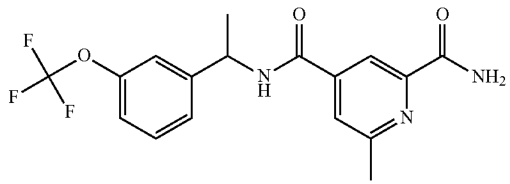 [SMILES: Cc1cc(C(=O)NC(C)c2cccc(OC(F)(F)F)c2)cc(C(N)=O)n1] | | alternative route | 366.2 | 1.62 |
| 515 | N-(1-(5-ethoxy-6-(2,2,2-trifluoroethoxy)pyridin-3-yl)ethyl)-2-isobutyramido-6-methylisonicotinamide | single enantiomer | 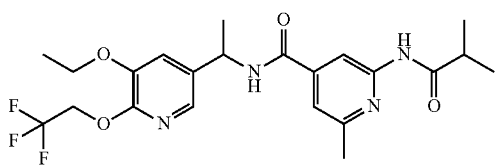 [SMILES: CCOc1cc(C(C)NC(=O)c2cc(C)nc(NC(=O)C(C)C)c2)cnc1OCC(F)(F)F] | Amine-38 | | 467.3 | 1.78 |
| 516 | 2-isobutyramido-6-methyl-N-((4-methyl-6-(2,2,2-trifluoroethoxy)pyridin-3-yl)methyl)isonicotinamide | | 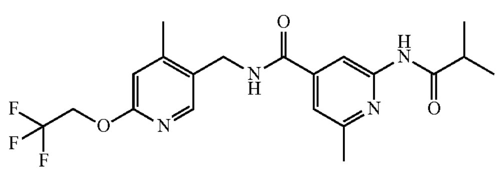 [SMILES: Cc1cc(C(=O)NCc2cnc(OCC(F)(F)F)cc2C)cc(NC(=O)C(C)C)n1] | Amine-29 | | 423.2 | 1.72 |

TABLE 1-continued

| Example | Name | Chirality | Structure | Amine part | Carboxylic part | Observed MS | Retention time (min) |
|---|---|---|---|---|---|---|---|
| 517 | 2-isobutyramido-6-methyl-N-(1-(6-((2,2,2-trifluoroethyl)amino)pyridin-3-yl)ethyl)isonicotinamide | single enantiomer | 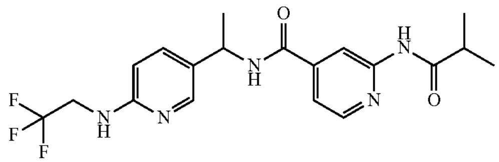 [SMILES: CC(C)C(=O)Nc1cc(C(=O)NC(C)c2ccc(NCC(F)(F)F)nc2)ccn1] | Amine-25 | | 422.3 | 1.54 |
| 518 | 3-acetamido-4-fluoro-N-(1-(5-methyl-6-(2,2,2-trifluoroethoxy)pyridin-3-yl)ethyl)benzamide | single enantiomer | 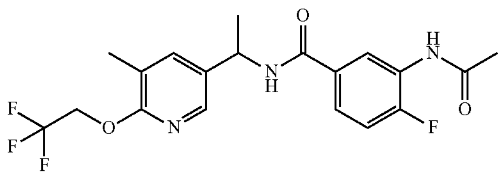 [SMILES: CC(=O)Nc1cc(C(=O)NC(C)c2cnc(OCC(F)(F)F)c(C)c2)ccc1F] | Amine-17 | | 412.2 | 1.64 |
| 519 | N2-ethyl-N4-((4-methyl-6-(2,2,2-trifluoroethoxy)pyridin-3-yl)methyl)pyridine-2,4-dicarboxamide | | 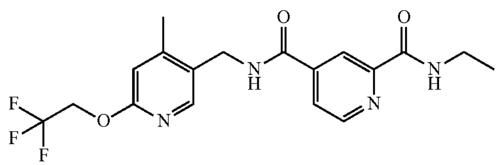 [SMILES: CCNC(=O)c1cc(C(=O)NCc2cnc(OCC(F)(F)F)cc2C)ccn1] | Amine-29 | | 395.2 | 1.61 |
| 520 | 2-isobutyramido-6-methyl-N-(1-(5-methyl-6-(2,2,2-trifluoroethoxy)pyridin-3-yl)ethyl)isonicotinamide | single enantiomer | 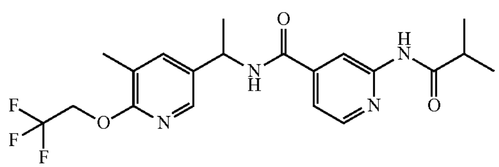 | Amine-17 | | 437.3 | 1.81 |

TABLE 1-continued

| Example | Name | Chirality | Structure | Amine part | Carboxylic part | Observed MS | Retention time (min) |
|---|---|---|---|---|---|---|---|
| 521 | N-(1-(5-chloro-6-(2,2,2-trifluoroethoxy)pyridin-3-yl)ethyl)-2-isobutyramido-6-methylisonicotinamide | single enantiomer | 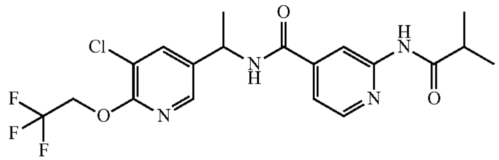 [SMILES: CC(C)C(=O)Nc1cc(C(=O)NC(C)c2cnc(OCC(F)(F)F)c(Cl)c2)ccn1] | Amine-5 | | 457.2 | 1.83 |
| 522 | N-(1-(5-chloro-6-(2,2,2-trifluoroethoxy)pyridin-3-yl)ethyl)-2-isobutyramidoisonicotinamide | single enantiomer | 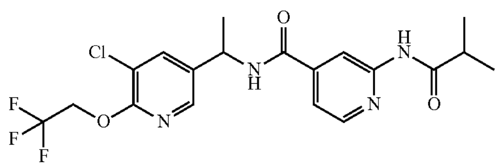 [SMILES: CC(C)C(=O)Nc1cc(C(=O)NC(C)c2cnc(OCC(F)(F)F)c(Cl)c2)ccn1] | Amine-5 | | 443.2 | 1.77 |
| 523 | 2-propionamido-N-(3-(trifluoromethoxy)benzyl)isonicotinamide | | 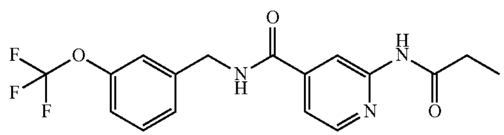 [SMILES: CCC(=O)Nc1cc(C(=O)NCc2cccc(OC(F)(F)F)c2)ccn1] | | | 366.3 | 1.61 |
| 524 | 2-(cyclopropanecarboxamido)-N-(3-(trifluoromethoxy)benzyl)isonicotinamide | | 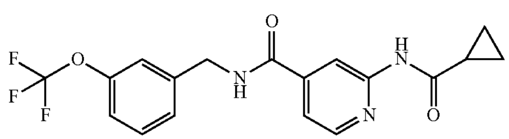 | | | 378.3 | 1.65 |
| 525 | 2-acetamido-6-methyl-N-(3-(trifluoromethoxy)benzyl)isonicotinamide | | 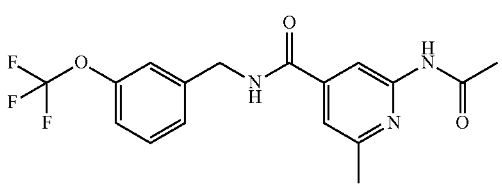 [SMILES: CC(=O)Nc1cc(C(=O)NCc2cccc(OC(F)(F)F)c2)cc(C)n1] | | | 366.3 | 1.58 |

TABLE 1-continued

| Example | Name | Chirality | Structure | Amine part | Carboxylic part | Observed MS | Retention time (min) |
|---|---|---|---|---|---|---|---|
| 526 | 2-methyl-6-propionamido-N-(3-(trifluoromethoxy)benzyl)isonicotinamide | | 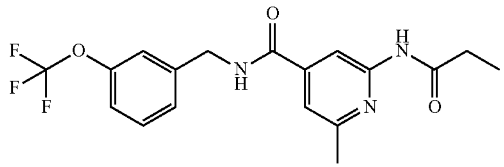 [SMILES: CCC(=O)Nc1cc(C(=O)NCc2cccc(OC(F)(F)F)c2)cc(C)n1] | | | 380.2 | 1.67 |
| 527 | 2-isobutyramido-N-(3-(trifluoromethoxy)benzyl)isonicotinamide | | 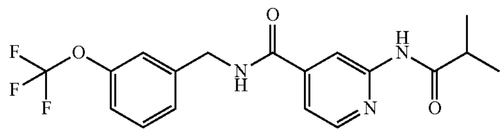 [SMILES: CC(C)C(=O)Nc1cc(C(=O)NCc2cccc(OC(F)(F)F)c2)ccn1] | | | 380.2 | 1.69 |
| 528 | 2-isobutyramido-6-methyl-N-(3-(trifluoromethoxy)benzyl)isonicotinamide | | 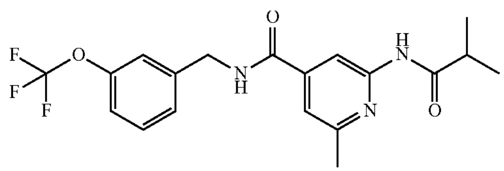 [SMILES: Cc1cc(C(=O)NCc2cccc(OC(F)(F)F)c2)cc(NC(=O)C(C)C)n1] | | | 394.3 | 1.75 |
| 529 | (R)-2-acetamido-6-methyl-N-(1-(3-(trifluoromethyl)phenyl)ethyl)isonicotinamide | single enantiomer | 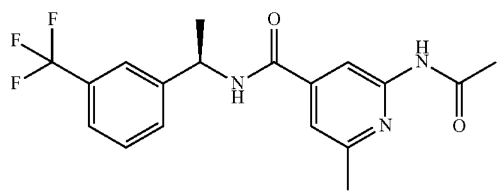 [SMILES: CC(=O)Nc1cc(C(=O)N[C@H](C)c2cccc(C(F)(F)F)c2)cc(C)n1] | | | 364.2 | 1.6 |

TABLE 1-continued

| Example | Name | Chirality | Structure | Amine part | Carboxylic part | Observed MS | Retention time (min) |
|---|---|---|---|---|---|---|---|
| 530 | (R)-2-isobutyramido-N-(1-(3-(trifluoromethyl)phenyl)ethyl)isonicotinamide | single enantiomer | 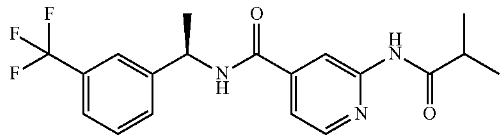 [SMILES: CC(C)C(=O)Nc1cc(C(=O)N[C@H](C)c2cccc(C(F)(F)F)c2)ccn1] | | | 378.3 | 1.71 |
| 531 | (R)-2-isobutyramido-6-methyl-N-(1-(3-(trifluoromethyl)phenyl)ethyl)isonicotinamide | single enantiomer | 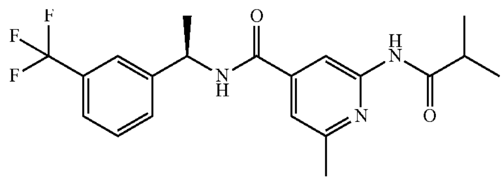 [SMILES: Cc1cc(C(=O)N[C@H](C)c2cccc(C(F)(F)F)c2)cc(NC(=O)C(C)C)n1] | | | 392.3 | 1.77 |
| 532 | 2-acetamido-6-methyl-N-(3-(trifluoromethyl)benzyl)isonicotinamide | | 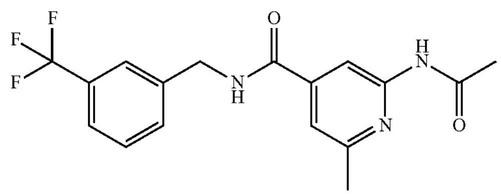 [SMILES: CC(=O)Nc1cc(C(=O)NCc2cccc(C(F)(F)F)c2)cc(C)n1] | | | 350.3 | 1.55 |
| 533 | 2-isobutyramido-N-(3-(trifluoromethyl)benzyl)isonicotinamide | | 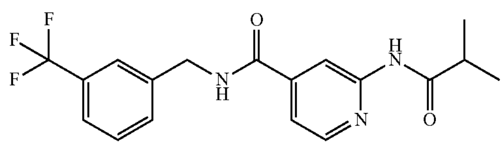 [SMILES: CC(C)C(=O)Nc1cc(C(=O)NCc2cccc(C(F)(F)F)c2)ccn1] | | | 364.2 | 1.65 |

TABLE 1-continued

| Example | Chirality | Name | Structure | Amine part | Carboxylic part | Observed MS | Retention time (min) |
|---|---|---|---|---|---|---|---|
| 534 | | 2-isobutyramido-6-methyl-N-(3-(trifluoromethyl)benzyl)isonicotinamide | 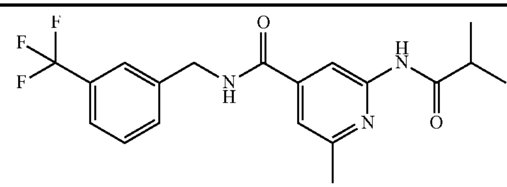 | | | 378.3 | 1.72 |
| 535 | single enantiomer | 8-hydroxy-N-(1-(5-methyl-6-(2,2,2-trifluoroethoxy)pyridin-3-yl)ethyl)quinoline-2-carboxamide | 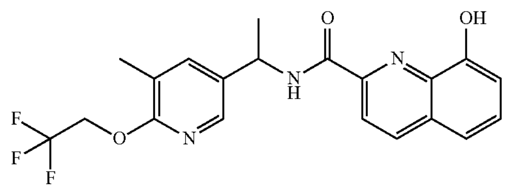 [SMILES: Cc1cc(C(C)NC(=O)c2ccc3cccc(O)c3n2)cnc1OCC(F)(F)F] | Amine-17 | | 404.2 | 1.9 |
| 536 | single enantiomer | 2-((3,4-dimethylisoxazol-5-yl)amino)-6-methyl-N-(1-(6-(2,2,2-trifluoroethoxy)pyridin-3-yl)ethyl)pyrimidine-4-carboxamide | 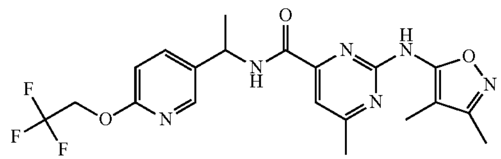 [SMILES: Cc1cc(C(=O)NC(C)c2ccc(OCC(F)(F)F)nc2)nc(Nc2onc(C)c2C)n1] | alternative route | | 449.2 | 1.76 |
| 537 | single enantiomer | 6-methyl-2-((1-methyl-1H-pyrazol-3-yl)amino)-N-(1-(6-(2,2,2-trifluoroethoxy)pyridin-3-yl)ethyl)pyrimidine-4-carboxamide | 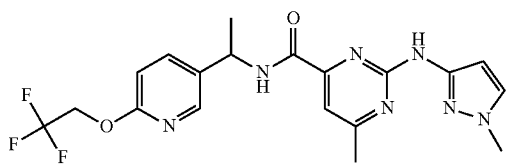 [SMILES: Cc1cc(C(=O)NC(C)c2ccc(OCC(F)(F)F)nc2)nc(Nc2ccn(C)n2)n1] | alternative route | | 434.3 | 1.68 |

| Example | Name | Chirality | Structure | Amine part | Carboxylic part | Observed MS | Retention time (min) |
|---|---|---|---|---|---|---|---|
| 538 | 2-((1,3-dimethyl-1H-pyrazol-5-yl)amino)-6-methyl-N-(1-(6-(2,2,2-trifluoroethoxy)pyridin-3-yl)ethyl)pyrimidine-4-carboxamide | single enantiomer | 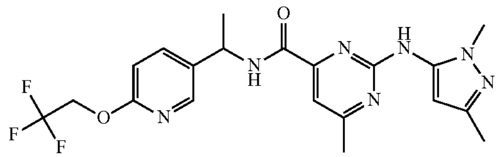 [SMILES: Cc1cc(C(=O)NC(C)c2ccc(OCC(F)(F)F)nc2)nc(Nc2cc(C)nn2C)n1] | | alternative route | 448.3 | 1.67 |
| 539 | 6-methyl-N-(1-(6-(2,2,2-trifluoroethoxy)pyridin-3-yl)ethyl)-2-((5-(trifluoromethyl)-4H-1,2,4-triazol-3-yl)amino)pyrimidine-4-carboxamide | single enantiomer | 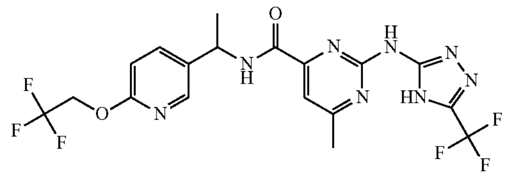 [SMILES: Cc1cc(C(=O)NC(C)c2ccc(OCC(F)(F)F)nc2)nc(Nc2nnc(C(F)(F)F)[nH]2)n1] | | alternative route | 489.2 | 1.77 |
| 540 | 6-methyl-2-((3-methyl-isothiazol-5-yl)amino)-N-(1-(6-(2,2,2-trifluoroethoxy)pyridin-3-yl)ethyl)pyrimidine-4-carboxamide | single enantiomer | 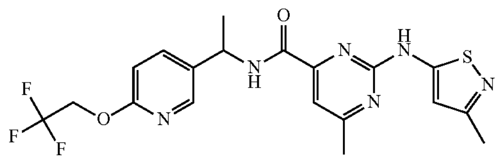 [SMILES: Cc1cc(Nc2nc(C)cc(C(=O)NC(C)c3ccc(OCC(F)(F)F)nc3)n2)sn1] | | alternative route | 451.2 | 1.76 |
| 541 | 6-methyl-N-(1-(6-(2,2,2-trifluoroethoxy)pyridin-3-yl)ethyl)-2-((4-(trifluoromethyl)oxazol-2-yl)amino)pyrimidine-4-carboxamide | single enantiomer | 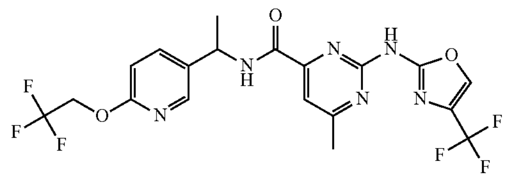 [SMILES: Cc1cc(C(=O)NC(C)c2ccc(OCC(F)(F)F)nc2)nc(Nc2nc(C(F)(F)F)co2)n1] | | alternative route | 489.2 | 1.84 |

TABLE 1-continued

| Example | Name | Chirality | Structure | Amine part | Carboxylic part | Observed MS | Retention time (min) |
|---|---|---|---|---|---|---|---|
| 542 | N-(4-fluoro-3-(trifluoromethyl)benzyl)-2-isobutyramido-isonicotinamide | | 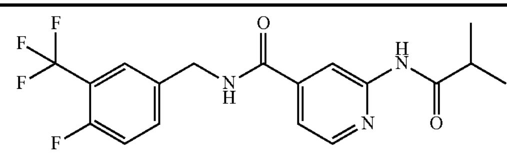 | | | 382.3 | 1.67 |
| 543 | N-(3,5-bis(trifluoromethyl)benzyl)-2-isobutyramido-isonicotinamide | | 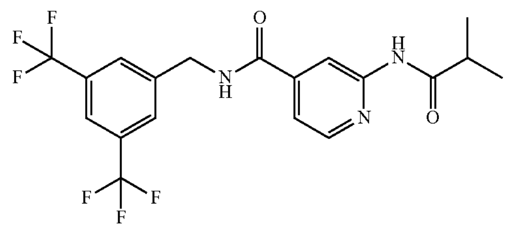 [SMILES: CC(C)C(=O)Nc1cc(C(=O)NCc2cc(C(F)(F)F)cc(C(F)(F)F)c2)ccn1] | | | 432.2 | 1.82 |
| 544 | N-(3-fluoro-4-(trifluoromethyl)benzyl)-2-isobutyramido-isonicotinamide | | 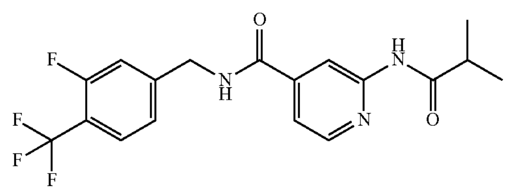 [SMILES: CC(C)C(=O)Nc1cc(C(=O)NCc2ccc(C(F)(F)F)c(F)c2)ccn1] | | | 382.3 | 1.68 |
| 545 | N-(3-fluoro-5-(trifluoromethyl)benzyl)-2-isobutyramido-isonicotinamide | | 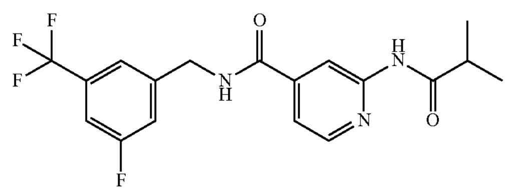 [SMILES: CC(C)C(=O)Nc1cc(C(=O)NCc2cc(F)cc(C(F)(F)F)c2)ccn1] | | | 382.3 | 1.7 |

TABLE 1-continued

| Example | Name | Chirality | Structure | Amine part | Carboxylic part | Observed MS | Retention time (min) |
|---|---|---|---|---|---|---|---|
| 546 | N-(2-chloro-5-(trifluoromethyl)benzyl)-2-isobutyramidoisonicotinamide | | 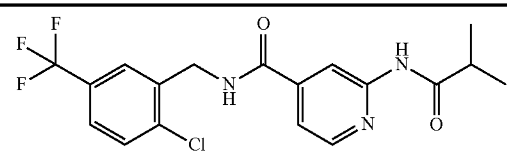 | | | 398.3 | 1.74 |
| 547 | N-(4-chloro-3-(trifluoromethyl)benzyl)-2-isobutyramidoisonicotinamide | | 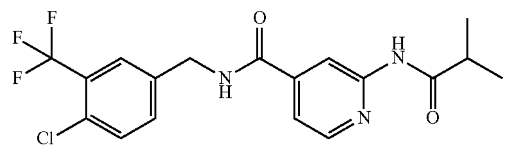 | | | 398.2 | 1.75 |
| 548 | (R)-N-(1-(3,5-bis(trifluoromethyl)phenyl)ethyl)-2-isobutyramidoisonicotinamide | single enantiomer | 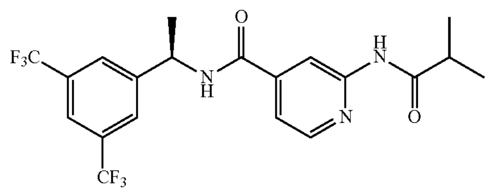 [SMILES: CC(C)C(=O)Nc1cc(C(=O)N[C@H](C)c2cc(C(F)(F)F)cc(C(F)(F)F)c2)ccn1] | | | 446.2 | 1.87 |
| 549 | 2-(2-hydroxy-2-methylpropanamido)-6-methyl-N-((6-(2,2,2-trifluoroethoxy)pyridin-2-yl)methyl)isonicotinamide | | 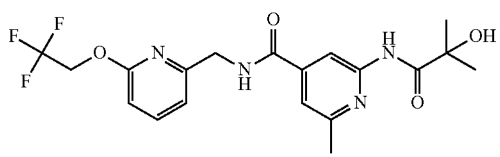 [SMILES: Cc1cc(C(=O)NCc2cccc(OCC(F)(F)F)n2)cc(NC(=O)C(C)(C)O)n1] | Amine-4 | | 425.3 | 1.59 |
| 550 | 2-(2-hydroxy-2-methylpropanamido)-6-methyl-N-(1-(3-(2,2,2-trifluoroethoxy)phenyl)ethyl)isonicotinamide | single enantiomer | 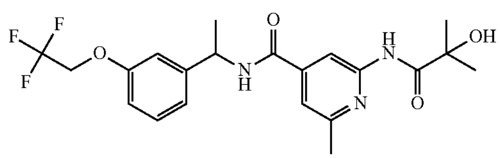 [SMILES: Cc1cc(C(=O)NC(C)c2cccc(OCC(F)(F)F)c2)cc(NC(=O)C(C)(C)O)n1] | Amine-16 | | 438.3 | 1.65 |

TABLE 1-continued

| Example | Name | Chirality | Structure | Amine part | Carboxylic part | Observed MS | Retention time (min) |
|---|---|---|---|---|---|---|---|
| 551 | 2-acetamido-N-(1-(6-(2,2-difluoroethoxy)-5-methylpyridin-3-yl)ethyl)isonicotinamide | single enantiomer | 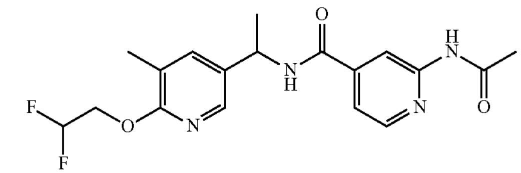 | Amine-14 | | 377.2 | 1.48 |
| 552 | N-(1-(6-(2,2-difluoroethoxy)-5-methylpyridin-3-yl)ethyl)-2-propionamidoisonicotinamide | single enantiomer | 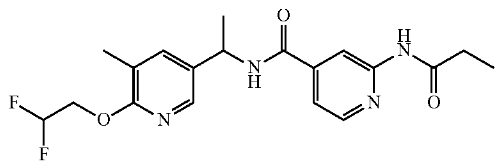 [SMILES: CCC(=O)Nc1cc(C(=O)NC(C)c2cnc(OCC(F)F)c(C)c2)ccn1] | Amine-14 | | 391.3 | 1.57 |
| 553 | 2-(cyclopropanecarboxamido)-N-(1-(6-(2,2-difluoroethoxy)-5-methylpyridin-3-yl)ethyl)isonicotinamide | single enantiomer | 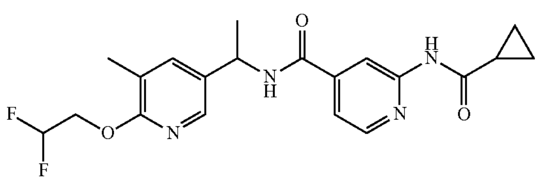 | Amine-14 | | 403.2 | 1.6 |
| 554 | N-(1-(6-(2,2-difluoroethoxy)-5-methylpyridin-3-yl)ethyl)-2-methyl-6-propionamidoisonicotinamide | single enantiomer | 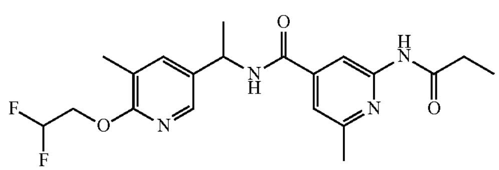 | Amine-14 | | 405.3 | 1.63 |
| 555 | N-(1-(6-(2,2-difluoroethoxy)-5-methylpyridin-3-yl)ethyl)-2-isobutyramidoisonicotinamide | single enantiomer | 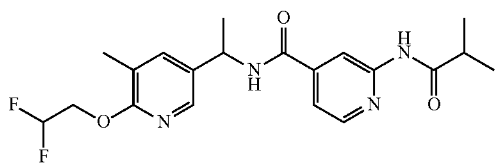 [SMILES: Cc1cc(C(C)NC(=O)c2ccnc(NC(=O)C(C)C)c2)cnc1OCC(F)F] | Amine-14 | | 405.3 | 1.65 |

| Example | Name | Chirality | Structure | Amine part | Carboxylic part | Observed MS | Retention time (min) |
|---|---|---|---|---|---|---|---|
| 556 | 2-acetamido-N-(1-(6-(2,2-difluoroethoxy)-5-methylpyridin-3-yl)ethyl)-6-methylisonicotinamide | single enantiomer | 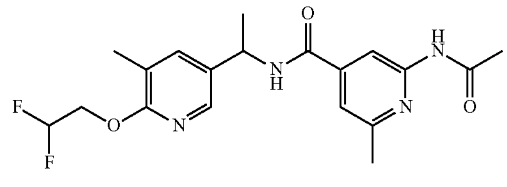 [SMILES: CC(=O)Nc1cc(C(=O)NC(C)c2cnc(OCC(F)F)c(C)c2)cc(C)n1] | Amine-14 | | 391.3 | 1.54 |
| 557 | N-(1-(6-(2,2-difluoroethoxy)-5-methylpyridin-3-yl)ethyl)-2-isobutyramido-6-methylisonicotinamide | single enantiomer | 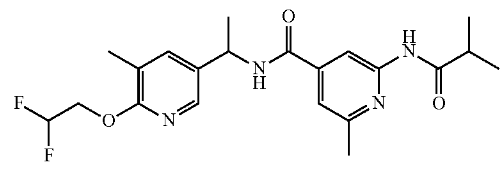 [SMILES: Cc1cc(C(=O)NC(C)c2cnc(OCC(F)F)c(C)c2)cc(NC(=O)C(C)C)n1] | Amine-14 | | 419.3 | 1.71 |
| 558 | 2-(cyclopropanecarboxamido)-N-(1-(6-(2,2-difluoroethoxy)-5-methylpyridin-3-yl)ethyl)pyrimidine-4-carboxamide | single enantiomer | 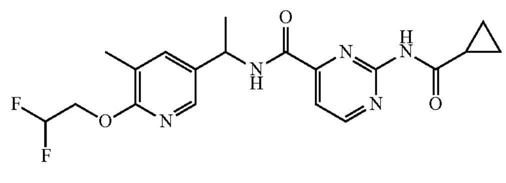 [SMILES: Cc1cc(C(C)NC(=O)c2ccnc(NC(=O)C3CC3)n2)cnc1OCC(F)F] | Amine-14 | | 404.3 | 1.57 |
| 559 | 2-(cyclopropanecarboxamido)-N-(1-(6-(2,2-difluoroethoxy)-5-methylpyridin-3-yl)ethyl)6-methylpyrimidine-4-carboxamide | single enantiomer | 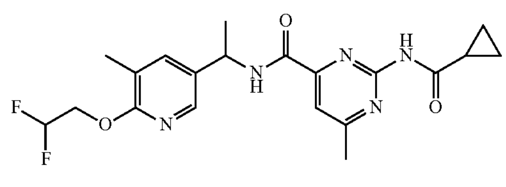 | Amine-14 | | 418.3 | 1.63 |

TABLE 1-continued

| Example | Name | Chirality | Structure | Amine part | Carboxylic part | Observed MS | Retention time (min) |
|---|---|---|---|---|---|---|---|
| 560 | N-(2-fluoro-5-(trifluoromethyl)benzyl)-2-isobutyramidoisonicotinamide | | 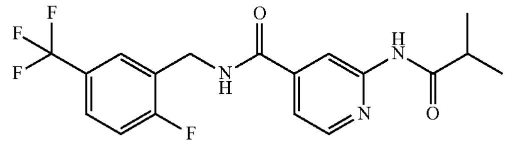 | | | 382.3 | 1.66 |
| 561 | 2-isobutyramido-N-(1-(3-(2,2,2-trifluoroethoxy)phenyl)ethyl)isonicotinamide | single enantiomer | 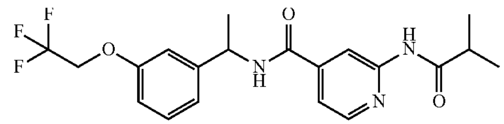 [SMILES: CC(C)C(=O)Nc1cc(C(=O)NC(C)c2cccc(OCC(F)(F)F)c2)ccn1] | Amine-16 | | 408.3 | 1.7 |
| 562 | 2-isobutyramido-N-(1-(4-(2,2,2-trifluoroethoxy)phenyl)ethyl)isonicotinamide | single enantiomer | 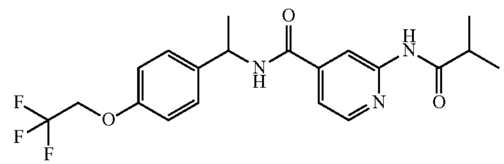 [SMILES: CC(C)C(=O)Nc1cc(C(=O)NC(C)c2ccc(OCC(F)(F)F)cc2)ccn1] | Amine-18 | | 408.3 | 1.68 |
| 563 | 2-(cyclopropanecarboxamido)-N-((2-methoxy-6-(2,2,2-trifluoroethoxy)pyridin-3-yl)methyl)pyrimidine-4-carboxamide | | 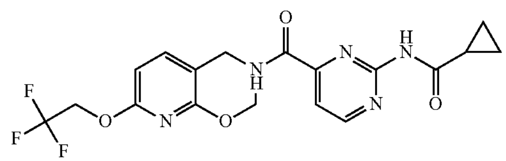 [SMILES: O=C(Nc1nccc(C(=O)N2COc3nc(OCC(F)(F)F)ccc3C2)n1)C1CC1] | Amine-24 | | 424.2 | 1.66 |
| 564 | 2-(cyclopropanecarboxamido)-N-((5-methyl-6-(2,2,2-trifluoroethoxy)pyridin-3-yl)methyl)pyrimidine-4-carboxamide | | 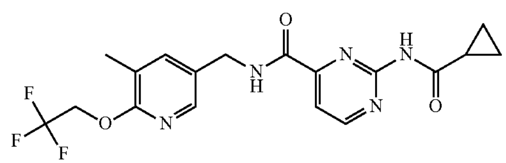 [SMILES: Cc1cc(CNC(=O)c2ccnc(NC(=O)C3CC3)n2)cnc1OCC(F)(F)F] | Amine-47 | | 408.3 | 1.61 |

TABLE 1-continued

| Example | Name | Chirality | Structure | Amine part | Carboxylic part | Observed MS | Retention time (min) |
|---|---|---|---|---|---|---|---|
| 565 | 2-acetamido-N-(1-(4-(2,2-difluoroethoxy)-2-methylphenyl)ethyl)-6-methylisonicotinamide | single enantiomer | 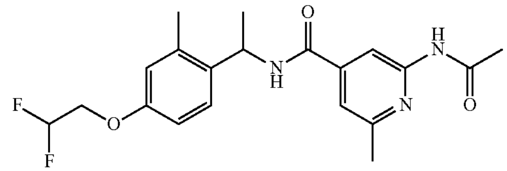 [SMILES: CC(=O)Nc1cc(C(=O)NC(C)c2ccc(OCC(F)F)cc2C)cc(C)n1] | Amine-83 | | 390.3 | 1.56 |
| 566 | 2-isobutyramido-N-((3-methyl-6-(2,2,2-trifluoroethoxy)pyridin-2-yl)methyl)isonicotinamide | | 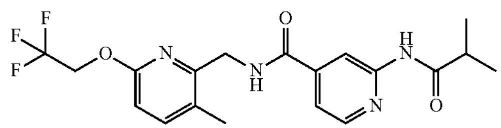 [SMILES: Cc1ccc(OCC(F)(F)F)nc1CNC(=O)c1ccnc(NC(=O)C(C)C)c1] | Amine-50 | | 409.3 | 1.73 |
| 567 | 2-isobutyramido-6-methyl-N-((3-methyl-6-(2,2,2-trifluoroethoxy)pyridin-2-yl)methyl)isonicotinamide | | 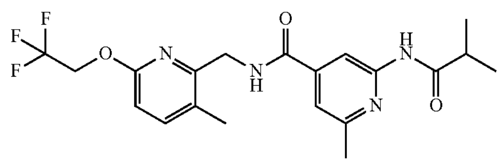 [SMILES: Cc1cc(C(=O)NCc2nc(OCC(F)(F)F)ccc2C)cc(NC(=O)C(C)C)n1] | Amine-50 | | 423.3 | 1.8 |
| 568 | 2-(cyclopropanecarboxamido)-N-((3-methyl-6-(2,2,2-trifluoroethoxy)pyridin-2-yl)methyl)isonicotinamide | | 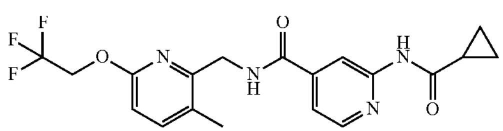 [SMILES: Cc1ccc(OCC(F)(F)F)nc1CNC(=O)c1ccnc(NC(=O)C2CC2)c1] | Amine-50 | | 407.2 | 1.69 |

TABLE 1-continued

| Example | Name | Chirality | Structure | Amine part | Carboxylic part | Observed MS | Retention time (min) |
|---|---|---|---|---|---|---|---|
| 569 | 2-methyl-6-(thiazol-2-yl)-N-(1-(6-(2,2,2-trifluoroethoxy)pyridin-3-yl)ethyl)isonicotinamide | single enantiomer | 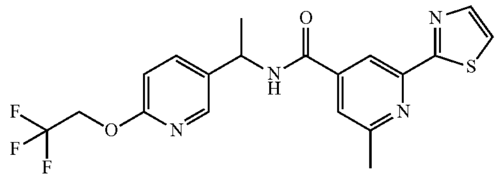 [SMILES: Cc1cc(C(=O)NC(C)c2ccc(OCC(F)(F)F)nc2)cc(-c2nccs2)n1] | alternative route | | 421.3 | 1.83 |
| 570 | N-(1-(5-methyl-6-(2,2,2-trifluoroethoxy)pyridin-3-yl)ethyl)-3-(1H-pyrazol-1-yl)benzamide | single enantiomer | 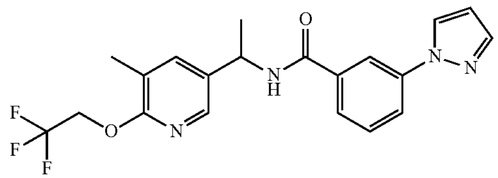 [SMILES: Cc1cc(C(C)NC(=O)c2cccc(-n3cccn3)c2)cnc1OCC(F)(F)F] | Amine-17 | | 403.3 | 1.82 |
| 571 | 2-methacrylamido-6-methyl-N-(1-(6-(2,2,2-trifluoroethoxy)pyridin-3-yl)ethyl)isonicotinamide | single enantiomer | 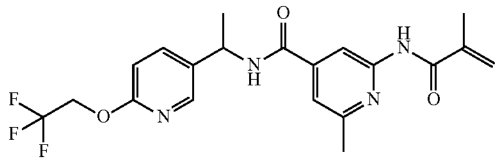 [SMILES: C=C(C)C(=O)Nc1cc(C(=O)NC(C)c2ccc(OCC(F)(F)F)nc2)cc(C)n1] | alternative route | | 421.3 | 1.72 |
| 572 | N-(2-fluoro-5-(trifluoromethyl)benzyl)-2-propionamido-isonicotinamide | | 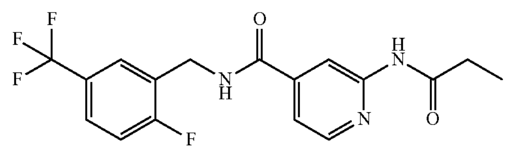 [SMILES: CCC(=O)Nc1cc(C(=O)NCc2cc(C(F)(F)F)ccc2F)ccn1] | | | 368.3 | 1.58 |
| 573 | 2-(cyclopropanecarboxamido)-N-(2-fluoro-5-(trifluoromethyl)benzyl)isonicotinamide | | 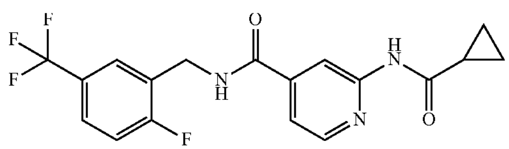 [SMILES: O=C(NCc1cc(C(F)(F)F)ccc1F)c1ccnc(NC(=O)C2CC2)c1] | | | 380.3 | 1.62 |

TABLE 1-continued

| Example | Name | Chirality | Structure | Amine part | Carboxylic part | Observed MS | Retention time (min) |
|---|---|---|---|---|---|---|---|
| 574 | 2-acetamido-N-(2-fluoro-5-(trifluoromethyl)benzyl)-6-methylisonicotinamide | | 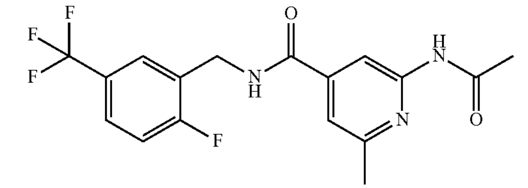 | | | 368.3 | 1.55 |
| 575 | N-(2-fluoro-5-(trifluoromethyl)benzyl)-2-isobutyramido-6-methylisonicotinamide | | 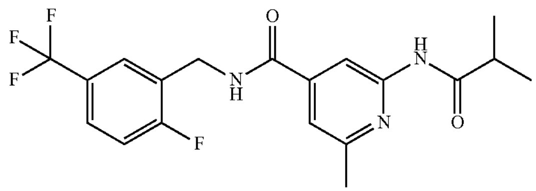 [SMILES: Cc1cc(C(=O)NCc2cc(C(F)(F)F)ccc2F)cc(NC(=O)C(C)C)n1] | | | 396.3 | 1.73 |
| 576 | 2-isobutyramido-N-((4-methyl-6-(2,2,2-trifluoroethoxy)pyridin-2-yl)methyl)isonicotinamide | | 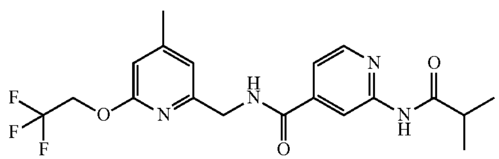 [SMILES: Cc1cc(CNC(=O)c2ccnc(NC(=O)C(C)C)c2)nc(OCC(F)(F)F)c1] | | Amine-51 | 409.3 | 1.73 |
| 577 | 2-isobutyramido-6-methyl-N-((4-methyl-6-(2,2,2-trifluoroethoxy)pyridin-2-yl)methyl)isonicotinamide | | 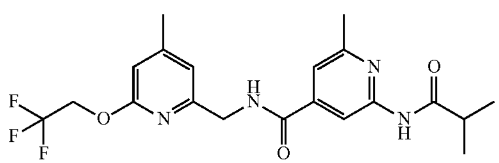 | | Amine-51 | 423.4 | 1.79 |

TABLE 1-continued

| Example | Chirality | Name | Structure | Amine part | Carboxylic part | Observed MS | Retention time (min) |
|---|---|---|---|---|---|---|---|
| 578 | | 2-(cyclopropane-carboxamido)-N-((4-methyl-6-(2,2,2-trifluoroethoxy)pyridin-2-yl)methyl)iso-nicotinamide | 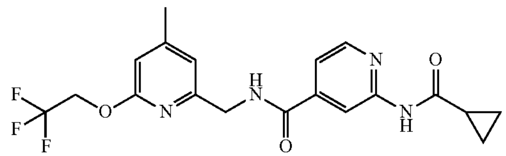 [SMILES: Cc1cc(CNC(=O)c2ccnc(NC(=O)C3CC3)c2)nc(OCC(F)(F)F)c1] | Amine-51 | | 407.3 | 1.69 |
| 579 | single enantiomer | N-(1-(5-chloro-6-(2,2,2-trifluoroethoxy)pyridin-3-yl)ethyl)-2,5-dimethyl-benzo[d]ox-azole-7-carboxamide | 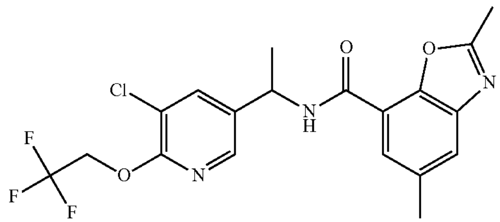 [SMILES: Cc1cc(C(=O)NC(C)c2cnc(OCC(F)(F)F)c(Cl)c2)c2oc(C)nc2c1] | Amine-5 | | 426.3 | 1.86 |
| 580 | | 5-dimethyl-N-((4-methyl-6-(2,2,2-trifluoroethoxy)pyridin-3-yl)meth-yl)benzo[d]ox-azole-7-carboxamide | 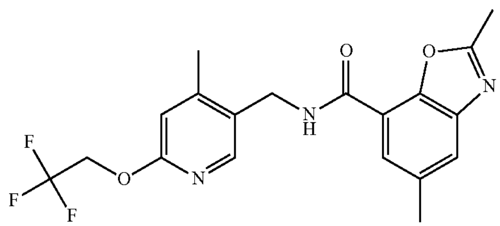 [SMILES: Cc1cc(C(=O)NCc2cnc(OCC(F)(F)F)cc2C)c2oc(C)nc2c1] | Amine-29 | | 392.3 | 1.75 |
| 581 | single enantiomer | N-(1-(6-(2,2-difluoroethoxy)-5-methylpyridin-3-yl)ethyl)-2,5-dimethyl-benzo[d]ox-azole-7-carboxamide | 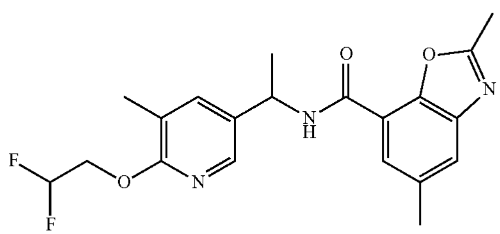 [SMILES: Cc1cc(C(=O)NC(C)c2cnc(OCC(F)F)c(C)c2)c2oc(C)nc2c1] | Amine-14 | | 388.3 | 1.75 |

TABLE 1-continued

| Example | Name | Chirality | Structure | Amine part | Carboxylic part | Observed MS | Retention time (min) |
|---|---|---|---|---|---|---|---|
| 582 | 2,5-dimethyl-N-((2-(2,2,2-trifluoroethoxy)pyridin-4-yl)methyl)benzo[d]oxazole-7-carboxamide | | 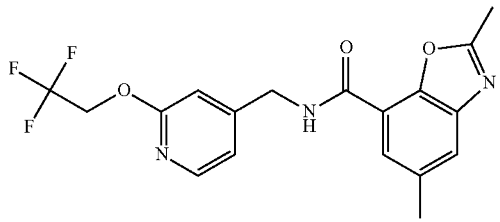 [SMILES: Cc1cc(C(=O)NCc2ccnc(OCC(F)(F)F)c2)c2oc(C)nc2c1] | | | 378.3 | 1.69 |
| 583 | 2,5-dimethyl-N-(1-(2-(2,2,2-trifluoroethoxy)pyridin-4-yl)ethyl)benzo[d]oxazole-7-carboxamide | single enantiomer | 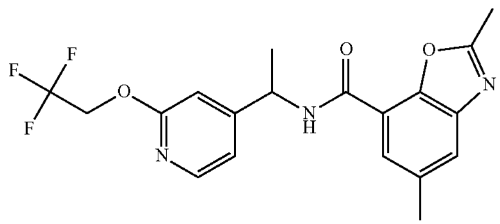 [SMILES: Cc1cc(C(=O)NC(C)c2ccnc(OCC(F)(F)F)c2)c2oc(C)nc2c1] | Amine-11 | | 392.3 | 1.76 |
| 584 | 2,5-dimethyl-N-((6-(2,2,2-trifluoroethoxy)pyridin-3-yl)methyl)benzo[d]oxazole-7-carboxamide | | 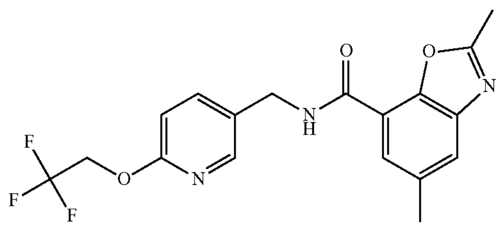 [SMILES: Cc1cc(C(=O)NCc2ccc(OCC(F)(F)F)nc2)c2oc(C)nc2c1] | | | 378.3 | 1.7 |
| 585 | 2,5-dimethyl-N-(1-(6-(2,2,2-trifluoroethoxy)pyridin-3-yl)ethyl)benzo[d]oxazole-7-carboxamide | single enantiomer | 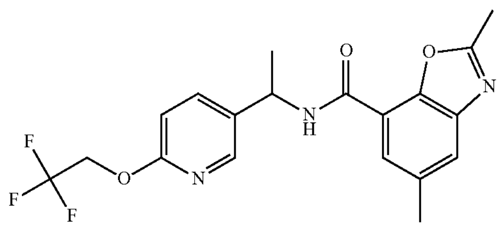 [SMILES: Cc1cc(C(=O)NC(C)c2ccc(OCC(F)(F)F)nc2)c2oc(C)nc2c1] | Amine-1 | | 392.3 | 1.76 |

TABLE 1-continued

| Example | Name | Chirality | Structure | Amine part | Carboxylic part | Observed MS | Retention time (min) |
|---|---|---|---|---|---|---|---|
| 586 | 6-methyl-N-(1-(6-(2,2,2-trifluoroethoxy)pyridin-3-yl)ethyl)-2-((2,2,2-trifluoroethyl)amino)pyrimidine-4 | single enantiomer | 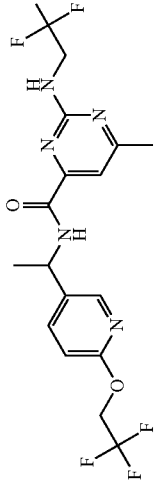 | alternative route | | 436.3 | 1.84 |
| 587 | 2-isobutyramido-6-methyl-N-(1-(4-(2,2,2-trifluoroethoxy)phenyl)ethyl)isonicotinamide | single enantiomer | 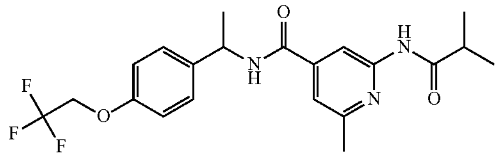 [SMILES: Cc1cc(C(=O)NC(C)c2ccc(OCC(F)(F)F)cc2)cc(NC(=O)C(C)C)n1] | 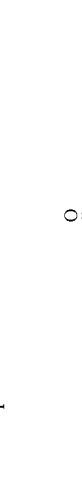 Amine-18 | 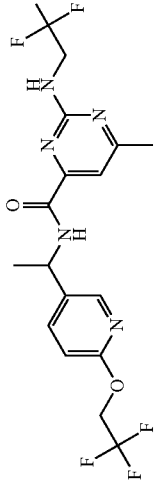 | 422.4 | 1.74 |
| 588 | 2-acetamido-N-(4-fluoro-3-(trifluoromethoxy)benzyl)isonicotinamide | | 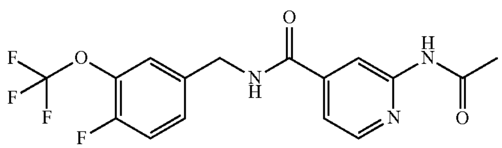 [SMILES: CC(=O)Nc1cc(C(=O)NCc2ccc(F)c(OC(F)(F)F)c2)ccn1] | 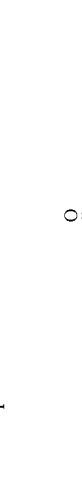 | 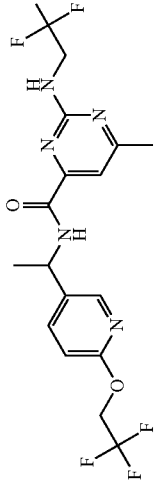 | 370.3 | 1.55 |
| 589 | N-(4-fluoro-3-(trifluoromethoxy)benzyl)-2-propionamidoisonicotinamide | | 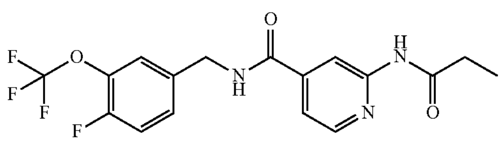 | 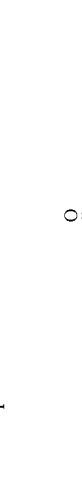 | 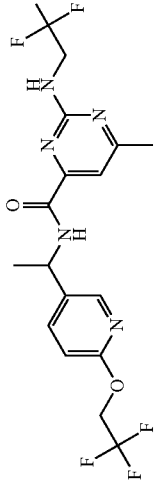 | 384.3 | 1.63 |
| 590 | 2-(cyclopropanecarboxamido)-N-(4-fluoro-3-(trifluoromethoxy)benzyl)isonicotinamide | | 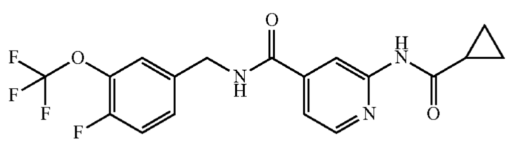 [SMILES: O=C(NCc1ccc(F)c(OC(F)(F)F)c1)c1ccnc(NC(=O)C2CC2)c1] | 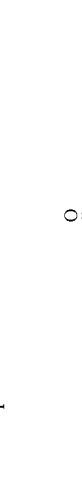 | 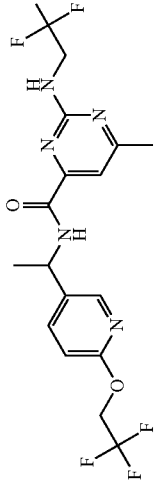 | 396.3 | 1.67 |

TABLE 1-continued

| Example | Chirality | Name | Structure | Amine part | Carboxylic part | Observed MS | Retention time (min) |
|---|---|---|---|---|---|---|---|
| 591 | | N-(4-fluoro-3-(trifluoromethoxy)benzyl)-2-methyl-6-propionamidoisonicotinamide | 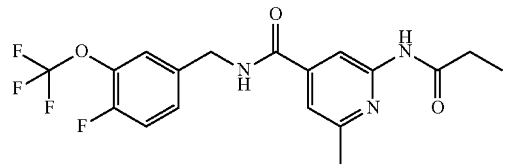 [SMILES: CCC(=O)Nc1cc(C(=O)NCc2ccc(F)c(OC(F)(F)F)c2)cc(C)n1] | | | 398.3 | 1.7 |
| 592 | | N-(4-fluoro-3-(trifluoromethoxy)benzyl)-2-isobutyramidoisonicotinamide | 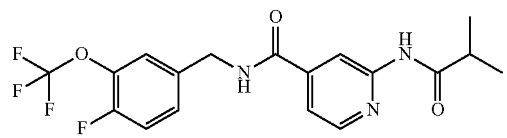 [SMILES: CC(C)C(=O)Nc1cc(C(=O)NCc2ccc(F)c(OC(F)(F)F)c2)ccn1] | | | 398.3 | 1.71 |
| 593 | | 2-acetamido-N-(4-fluoro-3-(trifluoromethoxy)benzyl)-6-methylisonicotinamide | 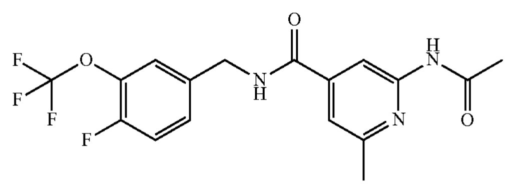 [SMILES: CC(=O)Nc1cc(C(=O)NCc2ccc(F)c(OC(F)(F)F)c2)cc(C)n1] | | | 384.3 | 1.61 |
| 594 | | N-(4-fluoro-3-(trifluoromethoxy)benzyl)-2-isobutyramido-6-methylisonicotinamide | 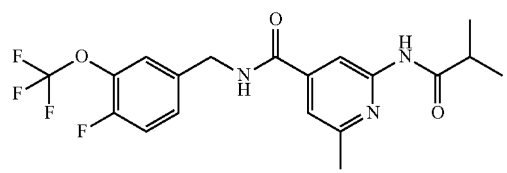 | | | 412.3 | 1.77 |
| 595 | | 2-(cyclopropanecarboxamido)-N-(4-fluoro-3-(trifluoromethoxy)benzyl)pyrimidine-4-carboxamide | 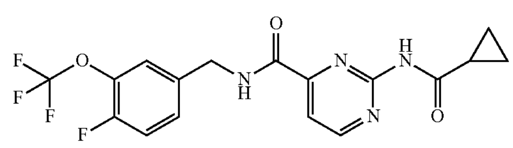 | | | 397.3 | 1.62 |

| Example | Chirality | Name | Structure | Amine part | Carboxylic part | Observed MS | Retention time (min) |
|---|---|---|---|---|---|---|---|
| 596 | | 2-(cyclopropane-carboxamido)-N-(4-fluoro-3-(trifluorometh-oxy)benzyl)-6-methylpyrimi-dine-4-carboxamide | 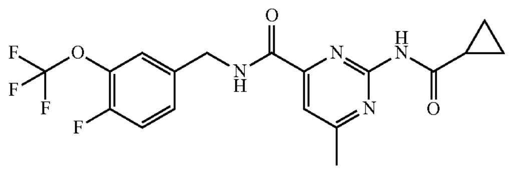 [SMILES: Cc1cc(C(=O)NCc2ccc(F)c(OC(F)(F)F)c2)nc(NC(=O)C2CC2)n1] | | | 411.3 | 1.69 |
| 597 | | 2-acetamido-N-(3-methyl-5-(trifluorometh-oxy)benzyl)isonicotinamide | 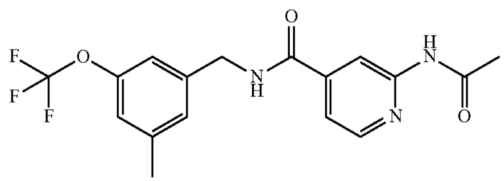 [SMILES: CC(=O)Nc1cc(C(=O)NCc2cc(C)cc(OC(F)(F)F)c2)ccn1] | | | 366.3 | 1.61 |
| 598 | | N-(3-methyl-5-(trifluorometh-oxy)benzyl)-2-propionamido-isonicotinamide | 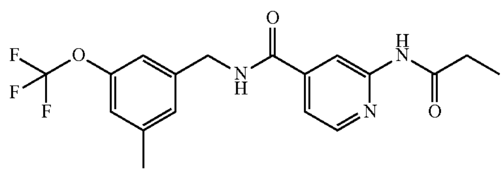 [SMILES: CCC(=O)Nc1cc(C(=O)NCc2cc(C)cc(OC(F)(F)F)c2)ccn1] | | | 380.3 | 1.69 |
| 599 | | 2-(cyclopropane-carboxamido)-N-(3-methyl-5-(trifluorometh-oxy)benzyl)iso-nicotinamide | 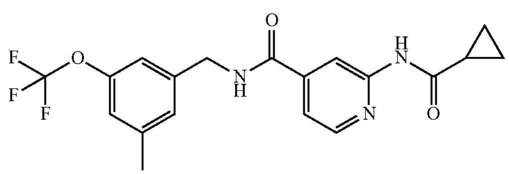 [SMILES: Cc1cc(CNC(=O)c2ccnc(NC(=O)C3CC3)c2)cc(OC(F)(F)F)c1] | | | 392.3 | 1.73 |
| 600 | | 2-methyl-N-(3-methyl-5-(trifluorometh-oxy)benzyl)-6-propionamido-isonicotinamide | 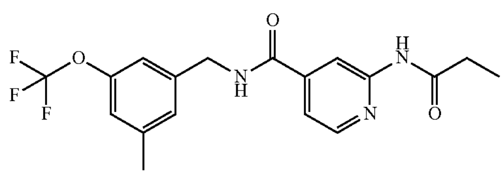 [SMILES: CCC(=O)Nc1cc(C(=O)NCc2cc(C)cc(OC(F)(F)F)c2)ccn1] | | | 394.4 | 1.76 |

TABLE 1-continued

| Example | Chirality | Name | Structure | Amine part | Carboxylic part | Observed MS | Retention time (min) |
|---|---|---|---|---|---|---|---|
| 601 | | 2-isobutyramido-N-(3-methyl-5-(trifluoromethoxy)benzyl)isonicotinamide | 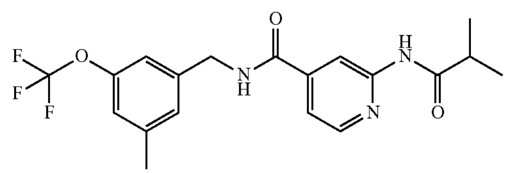 [SMILES: Cc1cc(CNC(=O)c2ccnc(NC(=O)C(C)C)c2)cc(OC(F)(F)F)c1] | | | 394.4 | 1.77 |
| 602 | | 2-acetamido-6-methyl-N-(3-methyl-5-(trifluoromethoxy)benzyl)isonicotinamide | 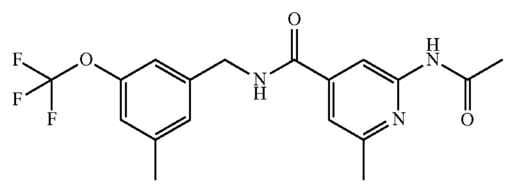 [SMILES: CC(=O)Nc1cc(C(=O)NCc2cc(C)cc(OC(F)(F)F)c2)cc(C)n1] | | | 380.4 | 1.67 |
| 603 | | 2-isobutyramido-6-methyl-N-(3-methyl-5-(trifluoromethoxy)benzyl)isonicotinamide | 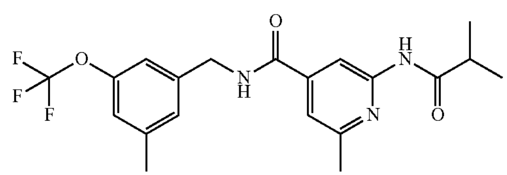 [SMILES: Cc1cc(CNC(=O)c2cc(C)nc(NC(=O)C(C)C)c2)cc(OC(F)(F)F)c1] | | | 408.4 | 1.83 |
| 604 | | 2-(cyclopropanecarboxamido)-N-(3-methyl-5-(trifluoromethoxy)benzyl)pyrimidine-4-carboxamide | 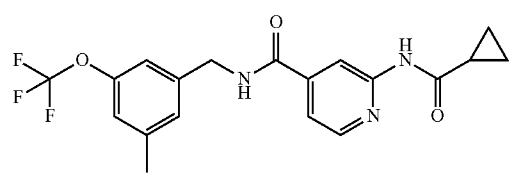 [SMILES: Cc1cc(CNC(=O)c2ccnc(NC(=O)C3CC3)c2)cc(OC(F)(F)F)c1] | | | 393.3 | 1.69 |

TABLE 1-continued

| Example | Chirality | Name | Structure | Amine part | Carboxylic part | Observed MS | Retention time (min) |
|---|---|---|---|---|---|---|---|
| 605 | | 2-(cyclopropane-carboxamido)-6-methyl-N-(3-(trifluoromethoxy)benzyl)pyrimidine-4-carboxamide | 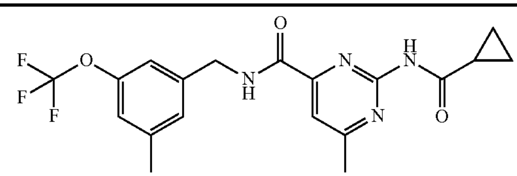 | | | 407.3 | 1.76 |
| 606 | | 2-acetamido-N-(2-fluoro-5-(trifluoromethoxy)benzyl)isonicotinamide | 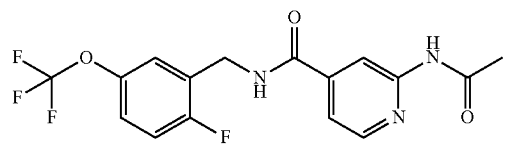 [SMILES: CC(=O)Nc1cc(C(=O)NCc2cc(OC(F)(F)F)ccc2F)ccn1] | | | 370.3 | 1.53 |
| 607 | | N-(2-fluoro-5-(trifluoromethoxy)benzyl)-2-propionamido-isonicotinamide | 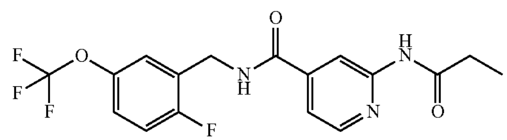 [SMILES: CCC(=O)Nc1cc(C(=O)NCc2cc(OC(F)(F)F)ccc2F)ccn1] | | | 384.3 | 1.62 |
| 608 | | 2-cyclopropane-carboxamido)-N-(2-fluoro-5-(trifluoromethoxy)benzyl)isonicotinamide | 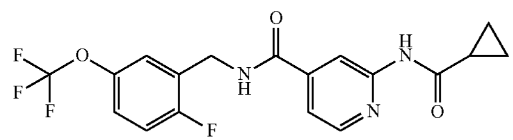 [SMILES: O=C(NCc1cc(OC(F)(F)F)ccc1F)c1ccnc(NC(=O)C2CC2)c1] | | | 396.3 | 1.66 |
| 609 | | N-(2-fluoro-5-(trifluoromethoxy)benzyl)-2-methyl-6-propionamido-isonicotinamide | 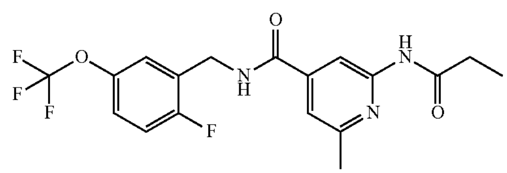 [SMILES: CCC(=O)Nc1cc(C(=O)NCc2cc(OC(F)(F)F)ccc2F)cc(C)n1] | | | 398.3 | 1.68 |

TABLE 1-continued

| Example | Chirality | Name | Structure | Amine part | Carboxylic part | Observed MS | Retention time (min) |
|---|---|---|---|---|---|---|---|
| 610 | | N-(2-fluoro-5-(trifluoromethoxy)benzyl)-2-isobutyramido-isonicotinamide | 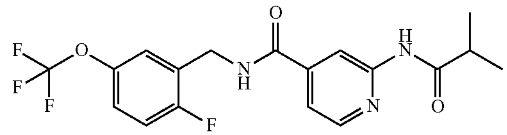 [SMILES: CC(C)C(=O)Nc1cc(C(=O)NCc2cc(OC(F)(F)F)ccc2F)ccn1] | | | 398.3 | 1.7 |
| 611 | | 2-acetamido-N-(2-fluoro-5-(trifluoromethoxy)benzyl)-6-methylisonicotinamide | 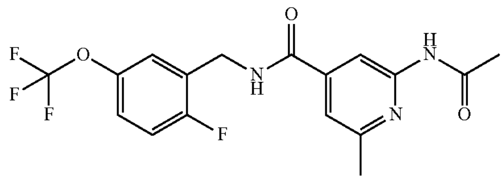 [SMILES: CC(=O)Nc1cc(C(=O)NCc2cc(OC(F)(F)F)ccc2F)cc(C)n1] | | | 384.3 | 1.59 |
| 612 | | N-(2-fluoro-5-(trifluoromethoxy)benzyl)-2-isobutyramido-6-methylisonicotinamide | 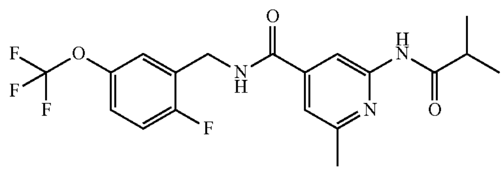 [SMILES: Cc1cc(C(=O)NCc2cc(OC(F)(F)F)ccc2F)cc(NC(=O)C(C)C)n1] | | | 412.3 | 1.76 |
| 613 | | 2-(cyclopropanecarboxamido)-N-(2-fluoro-5-(trifluoromethoxy)benzyl)pyrimidine-4-carboxamide | 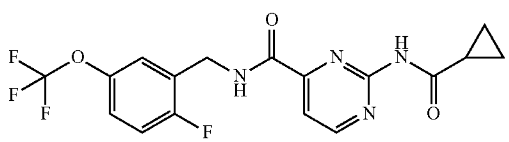 [SMILES: O=C(NCc1cc(OC(F)(F)F)ccc1F)c1ccnc(NC(=O)C2CC2)n1] | | | 397.3 | 1.61 |
| 614 | | 2-(cyclopropanecarboxamido)-N-(2-fluoro-5-(trifluoromethoxy)benzyl)-6-methylpyrimidine-4-carboxamide | 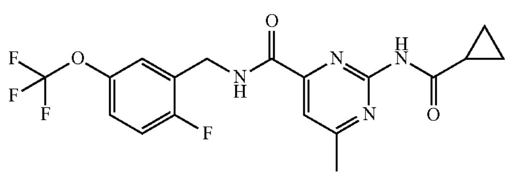 [SMILES: Cc1cc(C(=O)NCc2cc(OC(F)(F)F)ccc2F)nc(NC(=O)C2CC2)n1] | | | 411.3 | 1.68 |

TABLE 1-continued

| Example | Name | Chirality | Structure | Amine part | Carboxylic part | Observed MS | Retention time (min) |
|---|---|---|---|---|---|---|---|
| 615 | N-(3-(difluoromethoxy)benzyl)-2-isobutyramidoisonicotinamide | | 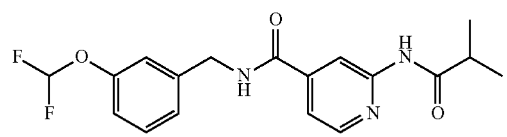 [SMILES: CC(C)C(=O)Nc1cc(C(=O)NCc2cccc(OC(F)F)c2)ccn1] | | | 362.3 | 1.56 |
| 616 | N-(3-(difluoromethoxy)benzyl)-2-isobutyramido-6-methylisonicotinamide | | 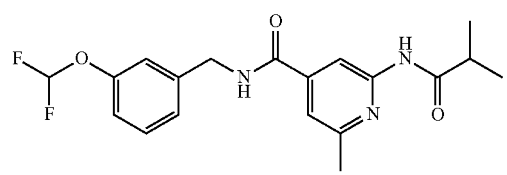 [SMILES: Cc1cc(C(=O)NCc2cccc(OC(F)F)c2)cc(NC(=O)C(C)C)n1] | | | 376.3 | 1.63 |
| 617 | N-((5-chloro-6-(2,2-difluoroethoxy)pyridin-3-yl)methyl)-2-propionamidoisonicotinamide | | 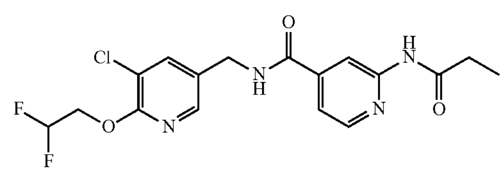 [SMILES: CCC(=O)Nc1cc(C(=O)NCc2cnc(OCC(F)F)c(Cl)c2)ccn1] | Amine-52 | | 397.3 | 1.54 |
| 618 | N-((5-chloro-6-(2,2-difluoroethoxy)pyridin-3-yl)methyl)-2-methyl-6-propionamidoisonicotinamide | | 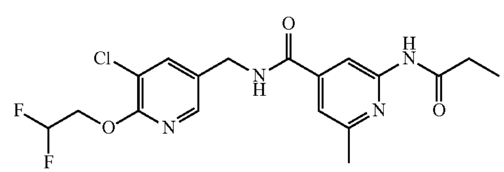 | Amine-52 | | 411.2 | 1.6 |

TABLE 1-continued

| Example | Name | Chirality | Structure | Amine part | Carboxylic part | Observed MS | Retention time (min) |
|---|---|---|---|---|---|---|---|
| 619 | N-((5-chloro-6-(2,2-difluoroethoxy)pyridin-3-yl)methyl)-2-isobutyramido-isonicotinamide | | 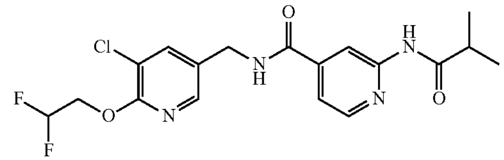 | Amine-52 | | 411.3 | 1.61 |
| 620 | N-((5-chloro-6-(2,2-difluoroethoxy)pyridin-3-yl)methyl)-2-isobutyramido-6-methylisonicotinamide | | 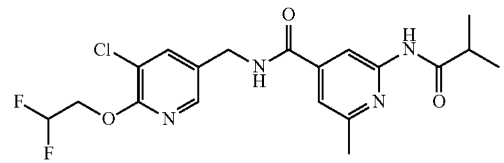 | Amine-52 | | 425.3 | 1.68 |
| 621 | 2-butyramido-N-((5-chloro-6-(2,2-difluoroethoxy)pyridin-3-yl)methyl)isonicotinamide | | 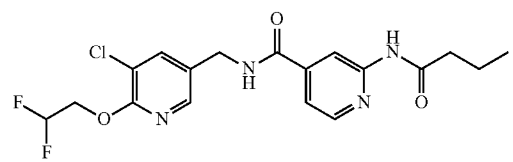 [SMILES: CCCC(=O)Nc1cc(C(=O)NCc2cnc(OCC(F)F)c(Cl)c2)ccn1] | Amine-52 | | 411.2 | 1.61 |
| 622 | N-((5-chloro-6-(2,2-difluoroethoxy)pyridin-3-yl)methyl)-2-(cyclopropanecarboxamido)-6-methylpyrimidine-4-carboxamide | | 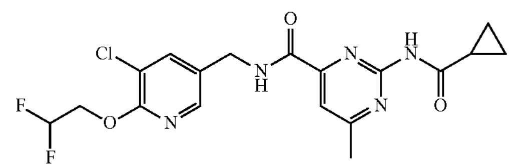 [SMILES: Cc1cc(C(=O)NCc2cnc(OCC(F)F)c(Cl)c2)nc(NC(=O)C2CC2)n1] | Amine-52 | | 424.3 | 1.59 |

TABLE 1-continued

| Example | Name | Chirality | Structure | Amine part | Carboxylic part | Observed MS | Retention time (min) |
|---|---|---|---|---|---|---|---|
| 623 | N-((5-chloro-6-(2,2-difluoroethoxy)pyridin-3-yl)methyl)-2-(2-hydroxy-2-methylpropanamido)-6-methylisonicotinamide | | 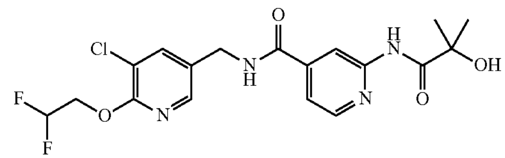 [SMILES: CC(C)(O)C(=O)Nc1cc(C(=O)NCc2cnc(OCC(F)F)c(Cl)c2)ccn1] | Amine-52 | | 441.2 | 1.57 |
| 624 | 2-acetamido-N-((5-chloro-6-(2,2-difluoroethoxy)pyridin-3-yl)ethyl)isonicotinamide | single enantiomer | 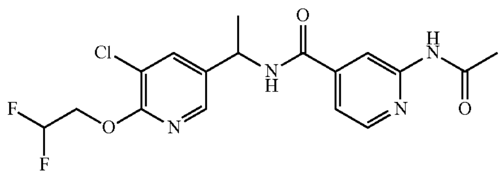 | Amine-53 | | 397.2 | 1.51 |
| 625 | N-(1-(5-chloro-6-(2,2-difluoroethoxy)pyridin-3-yl)ethyl)-2-propionamidoisonicotinamide | single enantiomer | 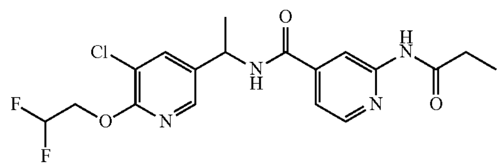 [SMILES: CCC(=O)Nc1cc(C(=O)NC(C)c2cnc(OCC(F)F)c(Cl)c2)ccn1] | Amine-53 | | 411.2 | 1.59 |
| 626 | N-(1-(5-chloro-6-(2,2-difluoroethoxy)pyridin-3-yl)ethyl)-2-(cyclopropanecarboxamido)isonicotinamide | single enantiomer | 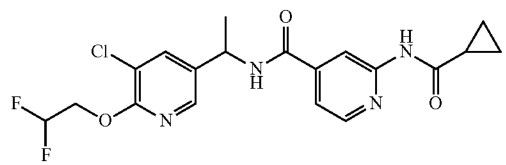 [SMILES: CC(NC(=O)c1ccnc(NC(=O)C2CC2)c1)c1cnc(OCC(F)F)c(Cl)c1] | Amine-53 | | 423.2 | 1.63 |

TABLE 1-continued

| Example | Name | Chirality | Structure | Amine part | Carboxylic part | Observed MS | Retention time (min) |
|---|---|---|---|---|---|---|---|
| 627 | 2-acetamido-N-(1-(5-chloro-6-(2,2-difluoroethoxy)pyridin-3-yl)ethyl)-6-methylisonicotinamide | single enantiomer | 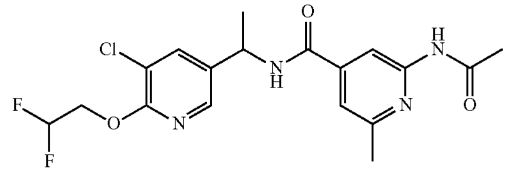 [SMILES: CC(=O)Nc1cc(C(=O)NC(C)c2cnc(OCC(F)F)c(Cl)c2)cc(C)n1] | Amine-53 | | 411.2 | 1.57 |
| 628 | N-(1-(5-chloro-6-(2,2-difluoroethoxy)pyridin-3-yl)ethyl)-2-methyl-6-propionamidoisonicotinamide | single enantiomer | 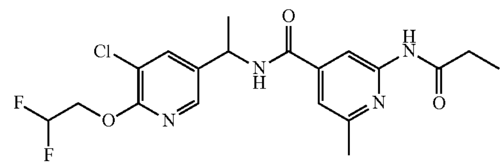 [SMILES: CCC(=O)Nc1cc(C(=O)NC(C)c2cnc(OCC(F)F)c(Cl)c2)cc(C)n1] | Amine-53 | | 425.3 | 1.65 |
| 629 | N-(1-(5-chloro-6-(2,2-difluoroethoxy)pyridin-3-yl)ethyl)-2-isobutyramidoisonicotinamide | single enantiomer | 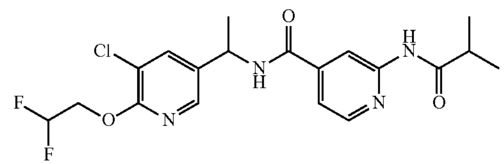 | Amine-53 | | 425.2 | 1.67 |
| 630 | N-(1-(5-chloro-6-(2,2-difluoroethoxy)pyridin-3-yl)ethyl)-2-isobutyramido-6-methylisonicotinamide | single enantiomer | 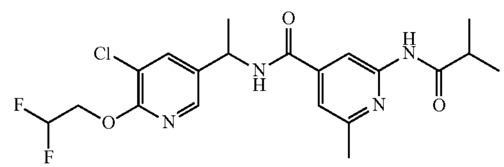 | Amine-53 | | 439.2 | 1.73 |
| 631 | 2-butyramido-N-(1-(5-chloro-6-(2,2-difluoroethoxy)pyridin-3-yl)ethyl)isonicotinamide | single enantiomer | 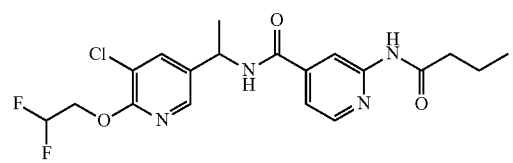 | Amine-53 | | 425.3 | 1.67 |

TABLE 1-continued

| Example | Name | Chirality | Structure | Amine part | Carboxylic part | Observed MS | Retention time (min) |
|---|---|---|---|---|---|---|---|
| 632 | N-(1-(5-chloro-6-(2,2-difluoroethoxy)pyridin-3-yl)ethyl)-2-(cyclopropane-carboxamido)pyrimidine-4-carboxamide | single enantiomer | 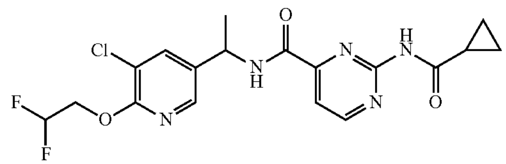 | Amine-53 | | 424.2 | 1.59 |
| 633 | 2-butyramido-N-(1-(6-(2,2-difluoroethoxy)-5-methylpyridin-3-yl)ethyl)isonicotinamide | single enantiomer | 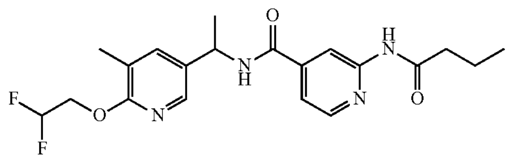 [SMILES: CCCC(=O)Nc1cc(C(=O)NC(C)c2cnc(OCC(F)F)c(C)c2)ccn1] | Amine-14 | | 405.3 | 1.64 |
| 634 | 2-propionamido-N-(6-(2,2,3,3-tetrafluoropropoxy)pyridin-3-yl)methyl)isonicotinamide | | 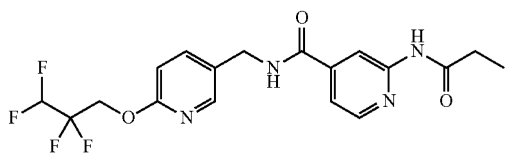 [SMILES: CCC(=O)Nc1cc(C(=O)NCc2ccc(OCC(F)(F)C(F)F)nc2)ccn1] | Amine-54 | | 413.3 | 1.54 |
| 635 | 2-(cyclopropanecarboxamido)-N-((6-(2,2,3,3-tetrafluoropropoxy)pyridin-3-yl)methyl)isonicotinamide | | 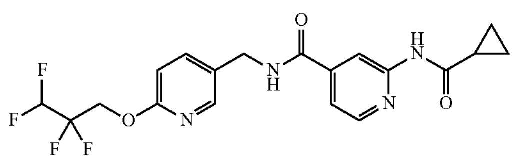 [SMILES: O=C(NCc1ccc(OCC(F)(F)C(F)F)nc1)c1ccnc(NC(=O)C2CC2)c1] | Amine-54 | | 425.2 | 1.57 |
| 636 | 2-isobutyramido-N-((6-(2,2,3,3-tetrafluoropropoxy)pyridin-3-yl)methyl)isonicotinamide | | 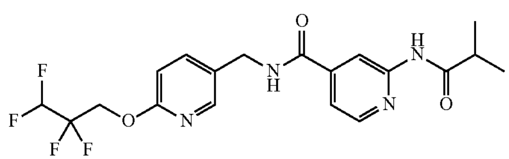 | Amine-54 | | 427.3 | 1.61 |

TABLE 1-continued

| Example | Chirality | Name | Structure | Amine part | Carboxylic part | Observed MS | Retention time (min) |
|---|---|---|---|---|---|---|---|
| 637 | | 2-isobutyramido-N-((4-methyl-5-(2,2,2-trifluoroethoxy)pyridin-2-yl)methyl)isonicotinamide | 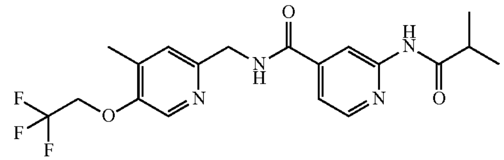 [SMILES: Cc1cc(CNC(=O)c2ccnc(NC(=O)C(C)C)c2)ncc1OCC(F)(F)F] | Amine-55 | | 409.3 | 1.55 |
| 638 | | 2-isobutyramido-6-methyl-N-((4-methyl-5-(2,2,2-trifluoroethoxy)pyridin-2-yl)methyl)isonicotinamide | 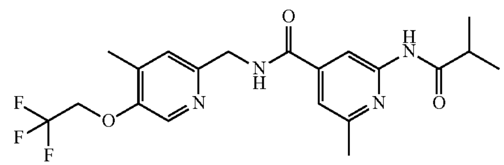 [SMILES: Cc1cc(C(=O)NCc2cc(C)c(OCC(F)(F)F)cn2)cc(NC(=O)C(C)C)n1] | Amine-55 | | 423.3 | 1.62 |
| 639 | | N-((6-(2,2,3,3,3-pentafluoropropoxy)pyridin-3-yl)methyl)-2-propionamidoisonicotinamide | 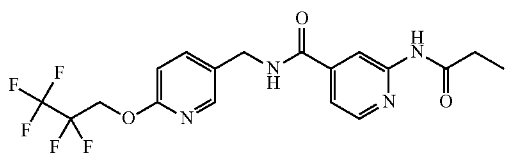 | Amine-56 | | 431.2 | 1.66 |
| 640 | | 2-(cyclopropanecarboxamido)-N-((6-(2,2,3,3,3-pentafluoropropoxy)pyridin-3-yl)methyl)isonicotinamide | 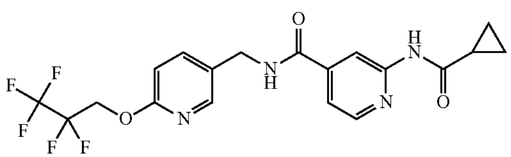 [SMILES: O=C(NCc1ccc(OCC(F)(F)C(F)(F)F)nc1)c1ccnc(NC(=O)C2CC2)c1] | Amine-56 | | 443.2 | 1.7 |
| 641 | | 2-isobutyramido-N-((6-(2,2,3,3,3-pentafluoropropoxy)pyridin-3-yl)methyl)isonicotinamide | 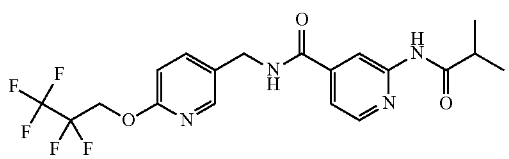 [SMILES: CC(C)C(=O)Nc1cc(C(=O)NCc2ccc(OCC(F)(F)C(F)(F)F)nc2)ccn1] | Amine-56 | | 445.3 | 1.74 |

TABLE 1-continued

| Example | Chirality | Name | Structure | Amine part | Carboxylic part | Observed MS | Retention time (min) |
|---|---|---|---|---|---|---|---|
| 642 | | 2-acetamido-6-methyl-N-((6-(2,2,3,3,3-pentafluoropropoxy)pyridin-3-yl)methyl)isonicotinamide | 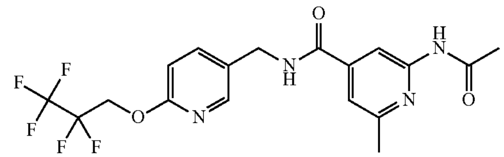 [SMILES: CC(=O)Nc1cc(C(=O)NCc2ccc(OCC(F)(F)C(F)(F)F)nc2)cc(C)n1] | Amine-56 | | 431.2 | 1.64 |
| 643 | | 2-methyl-N-((6-(2,2,3,3,3-pentafluoropropoxy)pyridin-3-yl)methyl)-6-propionamidoisonicotinamide | 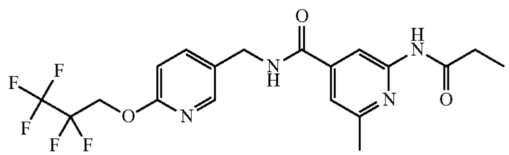 [SMILES: CCC(=O)Nc1cc(C(=O)NCc2ccc(OCC(F)(F)C(F)(F)F)nc2)cc(C)n1] | Amine-56 | | 445.2 | 1.72 |
| 644 | | 2-isobutyramido-6-methyl-N-((6-(2,2,3,3,3-pentafluoropropoxy)pyridin-3-yl)methyl)isonicotinamide | 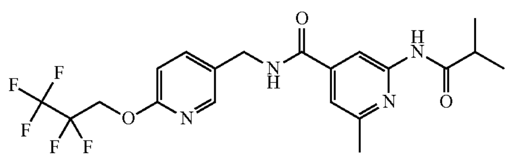 [SMILES: Cc1cc(C(=O)NCc2ccc(OCC(F)(F)C(F)(F)F)nc2)cc(NC(=O)C(C)C)n1] | Amine-56 | | 459.3 | 1.79 |
| 645 | | 2-acetamido-6-methyl-N-((6-(2,2,3,3-tetrafluoropropoxy)pyridin-3-yl)methyl)isonicotinamide | 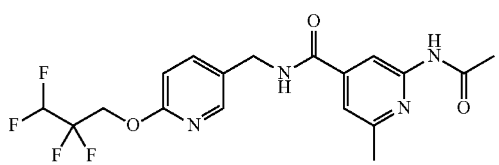 [SMILES: CC(=O)Nc1cc(C(=O)NCc2ccc(OCC(F)(F)C(F)F)nc2)cc(C)n1] | Amine-54 | | 413.3 | 1.51 |

TABLE 1-continued

| Example | Chirality | Name | Structure | Amine part | Carboxylic part | Observed MS | Retention time (min) |
|---|---|---|---|---|---|---|---|
| 646 | | 2-methyl-6-propionamido-N-((6-(2,2,3,3-tetrafluoropropoxy)pyridin-3-yl)methyl)isonicotinamide | 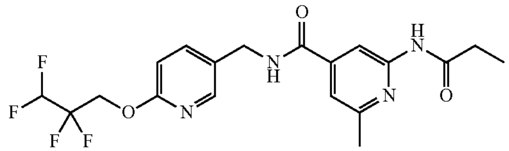 [SMILES: CCC(=O)Nc1cc(C(=O)NCc2ccc(OCC(F)(F)C(F)F)nc2)cc(C)n1] | Amine-54 | | 427.3 | 1.6 |
| 647 | | 2-isobutyramido-6-methyl-N-((6-(2,2,3,3-tetrafluoropropoxy)pyridin-3-yl)methyl)isonicotinamide | 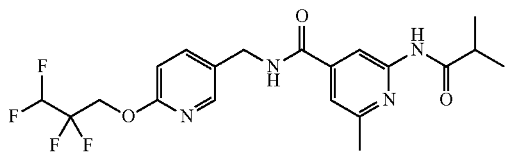 [SMILES: Cc1cc(C(=O)NCc2ccc(OCC(F)(F)C(F)F)nc2)cc(NC(=O)C(C)C)n1] | Amine-54 | | 441.3 | 1.67 |
| 648 | | N-((6-(2,2,3,3,3-pentafluoropropoxy)pyridin-3-yl)methyl)-2-pivalamidoisonicotinamide | 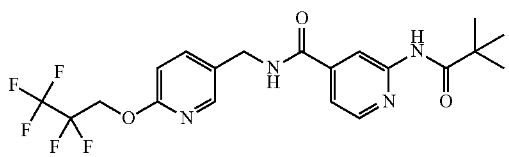 [SMILES: CC(C)(C)C(=O)Nc1cc(C(=O)NCc2ccc(OCC(F)(F)C(F)(F)F)nc2)ccn1] | Amine-56 | | 459.3 | 1.82 |
| 649 | | 2-(cyclopropanecarboxamido)-N-((6-(2,2,3,3,3-pentafluoropropoxy)pyridin-3-yl)methyl)pyrimidine-4-carboxamide | 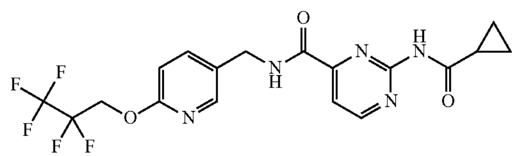 [SMILES: O=C(NCc1ccc(OCC(F)(F)C(F)(F)F)nc1)c1ccnc(NC(=O)C2CC2)n1] | Amine-56 | | 444.2 | 1.65 |
| 650 | | 2-(cyclopropanecarboxamido)-6-methyl-N-((6-(2,2,3,3,3-pentafluoropropoxy)pyridin-3-yl)methyl)pyrimidine-4-carboxamide | 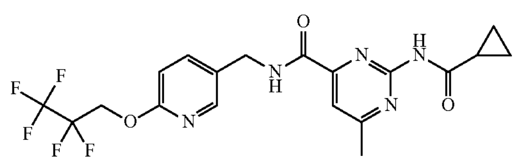 [SMILES: Cc1cc(C(=O)NCc2ccc(OCC(F)(F)C(F)(F)F)nc2)nc(NC(=O)C2CC2)n1] | Amine-56 | | 458.3 | 1.71 |

TABLE 1-continued

| Example | Name | Chirality | Structure | Amine part | Carboxylic part | Observed MS | Retention time (min) |
|---|---|---|---|---|---|---|---|
| 651 | 2-(cyclopropanecarboxamido)-N-((6-(2,2,3,3-tetrafluoropropoxy)pyridin-3-yl)methyl)pyrimidine-4-carboxamide | | 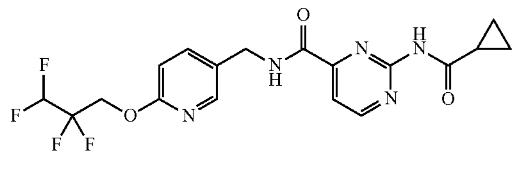 [SMILES: O=C(NCc1ccc(OCC(F)(F)C(F)F)nc1)c1ccnc(NC(=O)C2CC2)n1] | Amine-54 | | 426.2 | 1.52 |
| 652 | 2-(cyclopropanecarboxamido)-6-methyl-N-((6-(2,2,3,3-tetrafluoropropoxy)pyridin-3-yl)methyl)pyrimidine-4-carboxamide | | 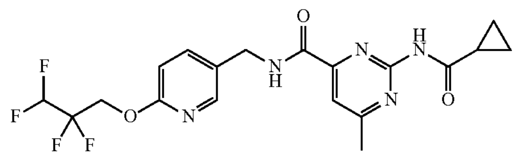 [SMILES: Cc1cc(C(=O)NCc2ccc(OCC(F)(F)C(F)F)nc2)nc(NC(=O)C2CC2)n1] | Amine-54 | | 440.2 | 1.59 |
| 653 | 2-propionamido-N-(1-(6-(2,2,3,3-tetrafluoropropoxy)pyridin-3-yl)ethyl)isonicotinamide | single enantiomer | 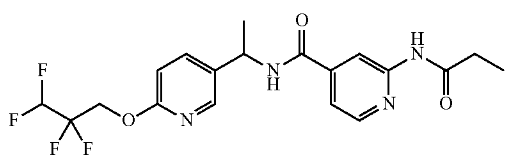 [SMILES: CCC(=O)Nc1cc(C(=O)NC(C)c2ccc(OCC(F)(F)C(F)F)nc2)ccn1] | Amine-57 | | 427.3 | 1.59 |
| 654 | 2-isobutyramido-N-(1-(6-(2,2,3,3-tetrafluoropropoxy)pyridin-3-yl)ethyl)isonicotinamide | single enantiomer | 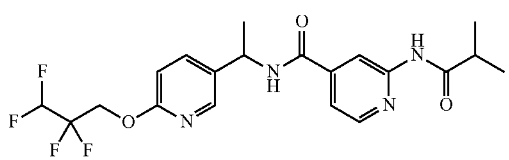 [SMILES: CC(C)C(=O)Nc1cc(C(=O)NC(C)c2ccc(OCC(F)(F)C(F)F)nc2)ccn1] | Amine-57 | | 441.3 | 1.66 |
| 655 | 2-acetamido-6-methyl-N-(1-(6-(2,2,3,3-tetrafluoropropoxy)pyridin-3-yl)ethyl)isonicotinamide | single enantiomer | 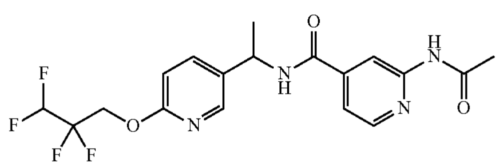 [SMILES: CC(=O)Nc1cc(C(=O)NC(C)c2ccc(OCC(F)(F)C(F)F)nc2)ccn1] | Amine-57 | | 427.3 | 1.57 |

TABLE 1-continued

| Example | Name | Chirality | Structure | Amine part | Carboxylic part | Observed MS | Retention time (min) |
|---|---|---|---|---|---|---|---|
| 656 | 2-methyl-6-propionamido-N-(1-(6-(2,2,3,3-tetrafluoropropoxy)pyridin-3-yl)ethyl)isonicotinamide | single enantiomer | 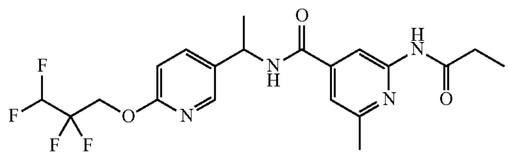 [SMILES: CCC(=O)Nc1cc(C(=O)NC(C)c2ccc(OCC(F)(F)C(F)F)nc2)cc(C)n1] | Amine-57 | | 441.3 | 1.65 |
| 657 | 2-isobutyramido-6-methyl-N-(1-(6-(2,2,3,3-tetrafluoropropoxy)pyridin-3-yl)ethyl)isonicotinamide | single enantiomer | 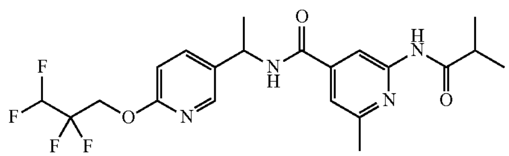 | Amine-57 | | 455.3 | 1.72 |
| 658 | 2-(cyclopropanecarboxamido)-N-(1-(6-(2,2,3,3-tetrafluoropropoxy)pyridin-3-yl)ethyl)pyrimidine-4-carboxamide | single enantiomer | 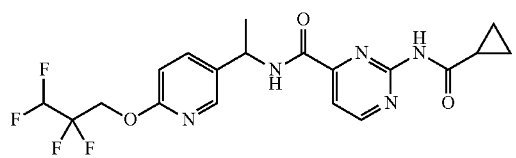 | Amine-57 | | 440.2 | 1.59 |
| 659 | 5-(4-chlorophenyl)-N-((5-methyl-6-(2,2,2-trifluoroethoxy)pyridin-3-yl)methyl)furan-2-carboxamide | | 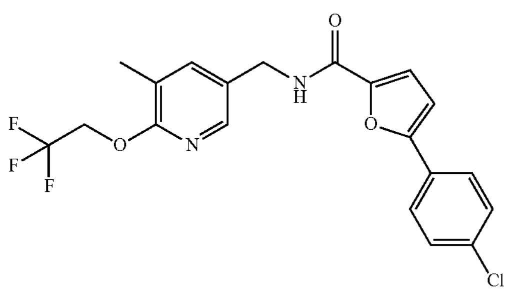 [SMILES: Cc1cc(CNC(=O)c2ccc(-c3ccc(Cl)cc3)o2)cnc1OCC(F)(F)F] | Amine-47 | | 423.2 | 2.02 |

TABLE 1-continued

| Example | Name | Chirality | Structure | Amine part | Carboxylic part | Observed MS | Retention time (min) |
|---|---|---|---|---|---|---|---|
| 660 | 5-(4-chlorophenyl)-N-((6-(2,2,2-trifluoroethoxy)pyridin-3-yl)methyl)furan-2-carboxamide | | 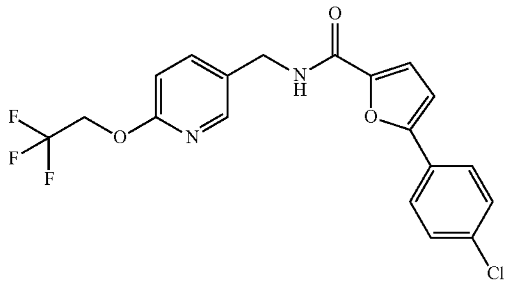 [SMILES: O=C(NCc1ccc(OCC(F)(F)F)nc1)c1ccc(-c2ccc(Cl)cc2)o1] | | | 409.2 | 1.94 |
| 661 | 5-(4-chlorophenyl)-N-(1-(6-(2,2,2-trifluoroethoxy)pyridin-3-yl)ethyl)furan-2-carboxamide | single enantiomer | 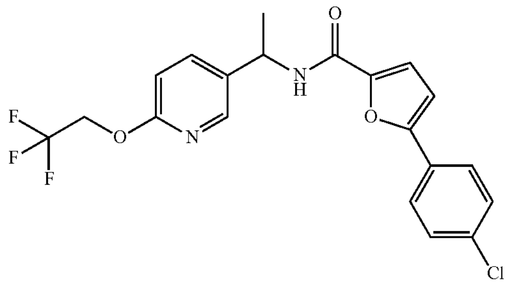 [SMILES: CC(NC(=O)c1ccc(-c2ccc(Cl)cc2)o1)c1ccc(OCC(F)(F)F)nc1] | Amine-1 | | 423.2 | 1.99 |
| 662 | 2-(3-methylbutanamido)-N-(1-(6-(2,2,2-trifluoroethoxy)pyridin-3-yl)ethyl)isonicotinamide | single enantiomer | 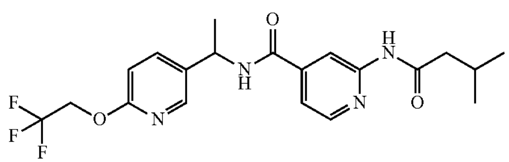 [SMILES: CC(C)CC(=O)Nc1cc(C(=O)NC(C)c2ccc(OCC(F)(F)F)nc2)ccn1] | alternative route | | 423.3 | 1.73 |
| 663 | 2-(3-methylbutanamido)-N-((6-(2,2,2-trifluoroethoxy)pyridin-3-yl)methyl)isonicotinamide | | 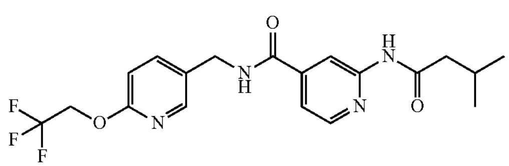 [SMILES: CC(C)CC(=O)Nc1cc(C(=O)NCc2ccc(OCC(F)(F)F)nc2)ccn1] | alternative route | | 409.3 | 1.68 |

TABLE 1-continued

| Example | Chirality | Name | Structure | Amine part | Carboxylic part | Observed MS | Retention time (min) |
|---|---|---|---|---|---|---|---|
| 664 | | 2-propionamido-N-(4-((2,2,2-trifluoroethoxy)methyl)benzyl)isonicotinamide | 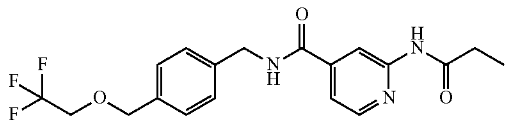 [SMILES: CCC(=O)Nc1cc(C(=O)NCc2ccc(COCC(F)(F)F)cc2)ccn1] | | | 394.3 | 1.57 |
| 665 | | 2-(cyclopropanecarboxamido)-N-(4-((2,2,2-trifluoroethoxy)methyl)benzyl)isonicotinamide | 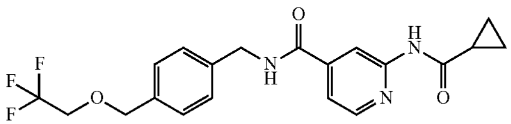 [SMILES: O=C(NCc1ccc(COCC(F)(F)F)cc1)c1ccnc(NC(=O)C2CC2)c1] | | | 406.3 | 1.6 |
| 666 | | 2-methyl-6-propionamido-N-(4-((2,2,2-trifluoroethoxy)methyl)benzyl)isonicotinamide | 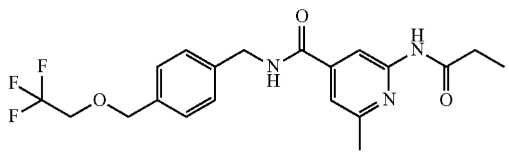 [SMILES: CCC(=O)Nc1cc(C(=O)NCc2ccc(COCC(F)(F)F)cc2)cc(C)n1] | | | 408.3 | 1.63 |
| 667 | | 2-isobutyramido-N-(4-((2,2,2-trifluoroethoxy)methyl)benzyl)isonicotinamide | 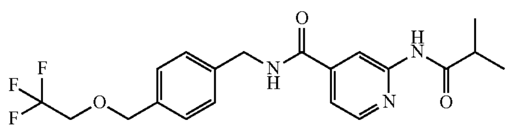 [SMILES: CC(C)C(=O)Nc1cc(C(=O)NCc2ccc(COCC(F)(F)F)cc2)ccn1] | | | 408.3 | 1.64 |
| 668 | | 2-acetamido-6-methyl-N-(4-((2,2,2-trifluoroethoxy)methyl)benzyl)isonicotinamide | 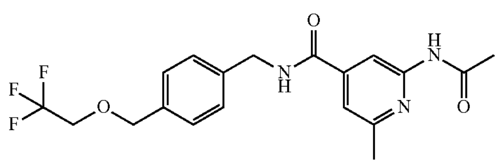 [SMILES: CC(=O)Nc1cc(C(=O)NCc2ccc(COCC(F)(F)F)cc2)cc(C)n1] | | | 394.3 | 1.54 |

TABLE 1-continued

| Example | Name | Chirality | Structure | Amine part | Carboxylic part | Observed MS | Retention time (min) |
|---|---|---|---|---|---|---|---|
| 669 | 2-isobutyramido-6-methyl-N-(4-((2,2,2-trifluoroethoxy)methyl)benzyl)isonicotinamide | | 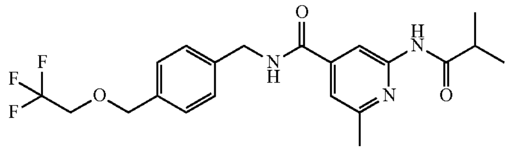 [SMILES: Cc1cc(C(=O)NCc2ccc(COCC(F)(F)F)cc2)cc(NC(=O)C(C)C)n1] | | | 422.3 | 1.7 |
| 670 | 2-(cyclopropanecarboxamido)-N-(4-((2,2,2-trifluoroethoxy)methyl)benzyl)pyrimidine-4-carboxamide | | 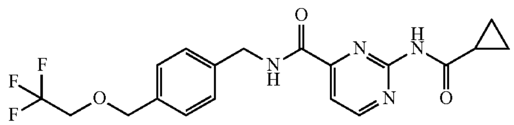 [SMILES: O=C(NCc1ccc(COCC(F)(F)F)cc1)c1ccnc(NC(=O)C2CC2)n1] | | | 407.3 | 1.56 |
| 671 | 2-(cyclopropanecarboxamido)-6-methyl-N-(4-((2,2,2-trifluoroethoxy)methyl)benzyl)pyrimidine-4-carboxamide | | 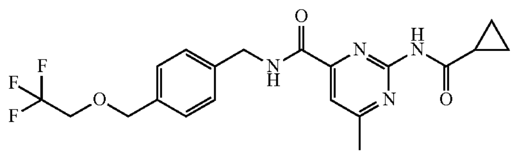 [SMILES: Cc1cc(C(=O)NCc2ccc(COCC(F)(F)F)cc2)nc(NC(=O)C2CC2)n1] | | | 421.3 | 1.62 |
| 672 | 2-acetamido-N-(1-(3-chloro-4-(2,2,2-trifluoroethoxy)phenyl)ethyl)isonicotinamide | single enantiomer | 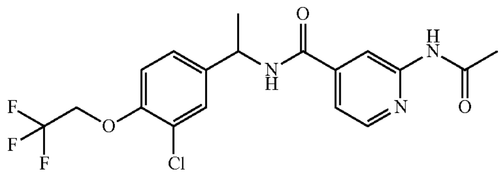 | Amine-58 | | 414.2 | 1.61 |
| 673 | N-(1-(3-chloro-4-(2,2,2-trifluoroethoxy)phenyl)ethyl)-2-propionamidoisonicotinamide | single enantiomer | 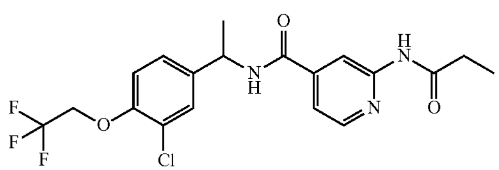 [SMILES: CCC(=O)Nc1cc(C(=O)NC(C)c2ccc(OCC(F)(F)F)c(Cl)c2)ccn1] | Amine-58 | | 428.2 | 1.68 |

TABLE 1-continued

| Example | Name | Chirality | Structure | Amine part | Carboxylic part | Observed MS | Retention time (min) |
|---|---|---|---|---|---|---|---|
| 674 | N-(1-(3-chloro-4-(2,2,2-trifluoroethoxy)phenyl)ethyl)-2-isobutyramidoisonicotinamide | single enantiomer | 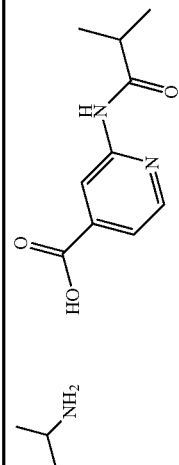 | 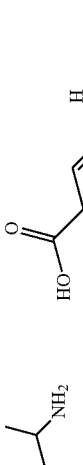 Amine-58 | 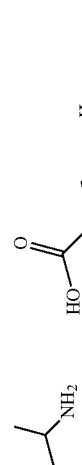 | 442.3 | 1.75 |
| 675 | N-(1-(3-chloro-4-(2,2,2-trifluoroethoxy)phenyl)ethyl)-2-(cyclopropanecarboxamido)isonicotinamide | single enantiomer | 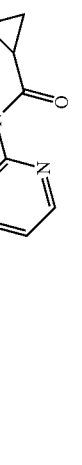 | 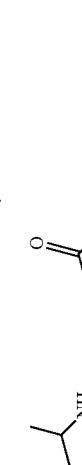 Amine-58 | 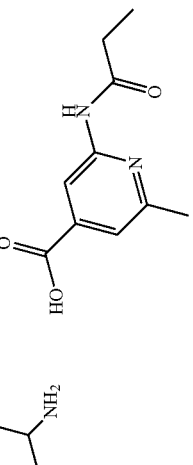 | 440.3 | 1.71 |
| 676 | 2-acetamido-N-(1-(3-chloro-4-(2,2,2-trifluoroethoxy)phenyl)ethyl)-6-methylisonicotinamide | single enantiomer | 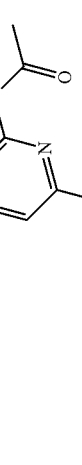 | 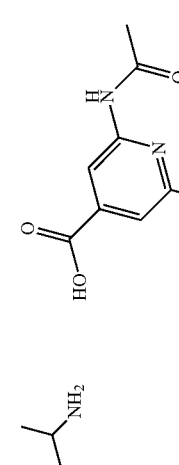 Amine-58 | 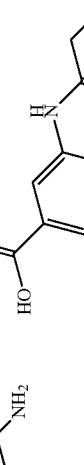 | 428.2 | 1.66 |
| 677 | N-(1-(3-chloro-4-(2,2,2-trifluoroethoxy)phenyl)ethyl)-2-methyl-6-propionamidoisonicotinamide | single enantiomer | 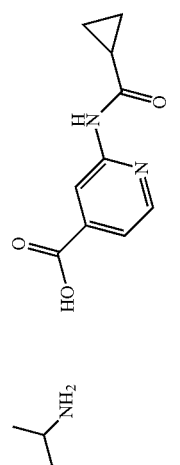 | 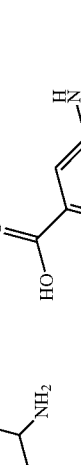 Amine-58 |  | 442.3 | 1.74 |

| Example | Name | Chirality | Structure | Amine part | Carboxylic part | Observed MS | Retention time (min) |
|---|---|---|---|---|---|---|---|
| 678 | N-(1-(3-chloro-4-(2,2,2-trifluoroethoxy)phenyl)ethyl)-2-isobutyramido-6-methylisonicotinamide | single enantiomer | 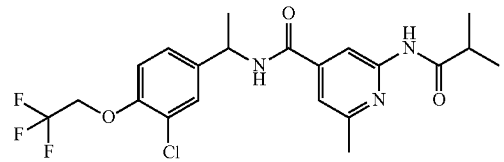 [SMILES: Cc1cc(C(=O)NC(C)c2ccc(OCC(F)(F)F)c(Cl)c2)cc(NC(=O)C(C)C)n1] | Amine-58 | | 456.3 | 1.81 |
| 679 | N-(1-(3-chloro-4-(2,2,2-trifluoroethoxy)phenyl)ethyl)-2-(cyclopropanecarboxamido)-6-methylpyrimidine-4-carboxamide | single enantiomer | 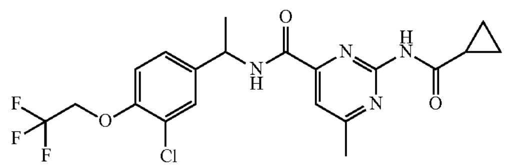 [SMILES: Cc1cc(C(=O)NC(C)c2ccc(OCC(F)(F)F)c(Cl)c2)nc(NC(=O)C2CC2)n1] | Amine-58 | | 455.3 | 1.74 |
| 680 | N-(1-(3-chloro-4-(2,2,2-trifluoroethoxy)phenyl)ethyl)-2-(cyclopropanecarboxamido)pyrimidine-4-carboxamide | single enantiomer | 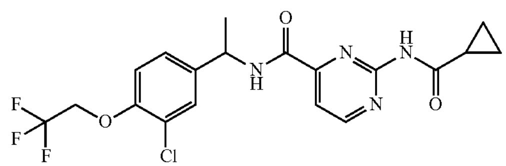 [SMILES: CC(NC(=O)c1ccnc(NC(=O)C2CC2)n1)c1ccc(OCC(F)(F)F)c(Cl)c1] | Amine-58 | | 441.2 | 1.69 |
| 681 | 2-acetamido-N-(4-fluoro-3-(trifluoromethyl)benzyl)isonicotinamide | | 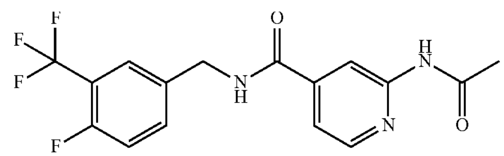 [SMILES: CC(=O)Nc1cc(C(=O)NCc2ccc(F)c(C(F)(F)F)c2)ccn1] | | | 354.3 | 1.51 |

TABLE 1-continued

| Example | Name | Chirality | Structure | Amine part | Carboxylic part | Observed MS | Retention time (min) |
|---|---|---|---|---|---|---|---|
| 682 | 2-acetamido-N-(4-chloro-3-(trifluoromethyl)benzyl)isonicotinamide | | 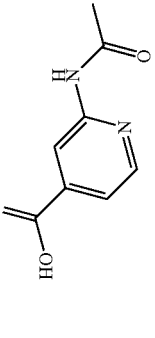 | 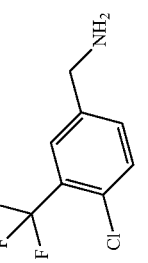 | 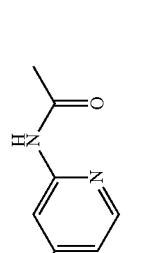 | 370.2 | 1.58 |
| 683 | 2-acetamido-N-(3,5-bis(trifluoromethyl)benzyl)isonicotinamide | | 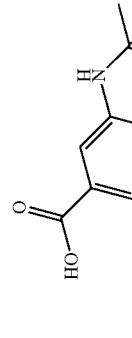 | 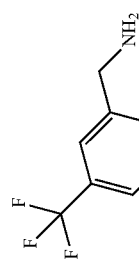 | 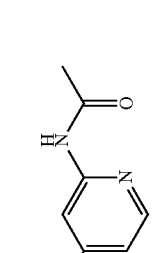 | 404.2 | 1.66 |
| 684 | (R)-2-(cyclopropanecarboxamido)-N-(1-(3-(trifluoromethyl)phenyl)ethyl)pyrimidine-4-carboxamide | single enantiomer | 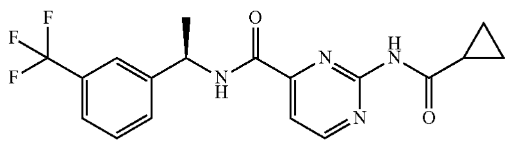 [SMILES: C[C@@H](NC(=O)c1ccnc(NC(=O)C2CC2)n1)c1cccc(C(F)(F)F)c1] | 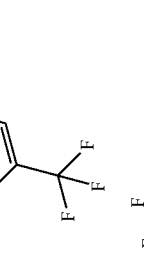 |  | 377.3 | 1.63 |
| 685 | 2-(cyclopropanecarboxamido)-N-((6-(3,3,3-trifluoropropyl)pyridin-3-yl)methyl)isonicotinamide | | 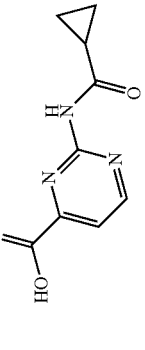 | 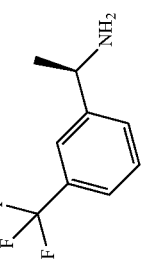
Amine-59 | 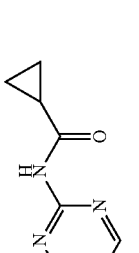 | 391.3 | 1.46 |

TABLE 1-continued

| Example | Chirality | Name | Structure | Amine part | Carboxylic part | Observed MS | Retention time (min) |
|---|---|---|---|---|---|---|---|
| 686 | | 2-methyl-6-propionamido-N-((6-(3,3,3-trifluoropropyl)pyridin-3-yl)methyl)isonicotinamide | 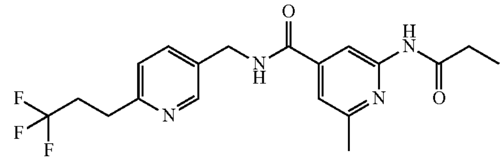 [SMILES: CCC(=O)Nc1cc(C(=O)NCc2ccc(CCC(F)(F)F)nc2)cc(C)n1] | Amine-59 | | 393.4 | 1.48 |
| 687 | | 2-isobutyramido-N-((6-(3,3,3-trifluoropropyl)pyridin-3-yl)methyl)isonicotinamide | 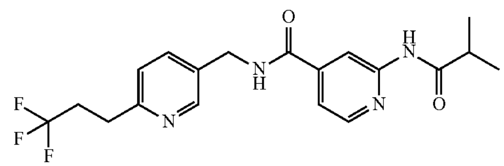 | Amine-59 | | 393.3 | 1.5 |
| 688 | | 2-isobutyramido-6-methyl-N-((6-(3,3,3-trifluoropropyl)pyridin-3-yl)methyl)isonicotinamide | 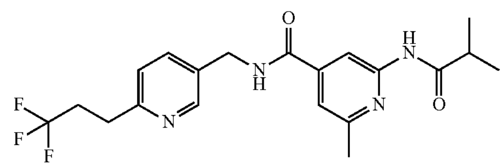 [SMILES: Cc1cc(C(=O)NCc2ccc(CCC(F)(F)F)nc2)cc(NC(=O)C(C)C)n1] | Amine-59 | | 407.4 | 1.56 |
| 689 | single enantiomer | 2-(cyclopropanecarboxamido)-N-(1-(6-(2,2,3,3,3-pentafluoropropoxy)pyridin-3-yl)ethyl)isonicotinamide | 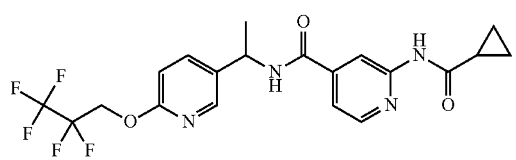 | Amine-60 | | 457.2 | 1.75 |
| 690 | single enantiomer | 2-isobutyramido-N-(1-(6-(2,2,3,3,3-pentafluoropropoxy)pyridin-3-yl)ethyl)isonicotinamide | 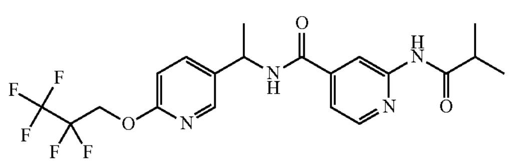 | Amine-60 | | 459.3 | 1.79 |

| Example | Name | Chirality | Structure | Amine part | Carboxylic part | Observed MS | Retention time (min) |
|---|---|---|---|---|---|---|---|
| 691 | 2-acetamido-6-methyl-N-(1-(6-(2,2,3,3,3-pentafluoropropoxy)pyridin-3-yl)ethyl)isonicotinamide | single enantiomer | 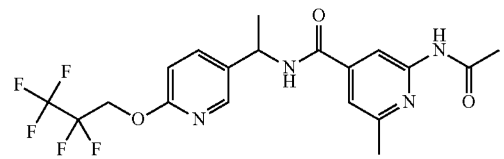 [SMILES: CC(=O)Nc1cc(C(=O)NC(C)c2ccc(OCC(F)(F)C(F)(F)F)nc2)cc(C)n1] | Amine-60 | | 445.3 | 1.69 |
| 692 | 2-methyl-N-(1-(6-(2,2,3,3,3-pentafluoropropoxy)pyridin-3-yl)ethyl)-6-propionamidoisonicotinamide | single enantiomer | 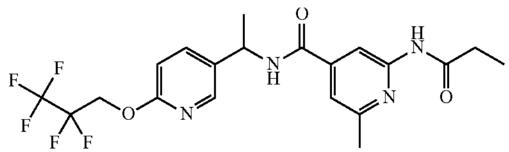 [SMILES: CCC(=O)Nc1cc(C(=O)NC(C)c2ccc(OCC(F)(F)C(F)(F)F)nc2)cc(C)n1] | Amine-60 | | 459.3 | 1.77 |
| 693 | 2-isobutyramido-6-methyl-N-(1-(6-(2,2,3,3,3-pentafluoropropoxy)pyridin-3-yl)ethyl)isonicotinamide | single enantiomer | 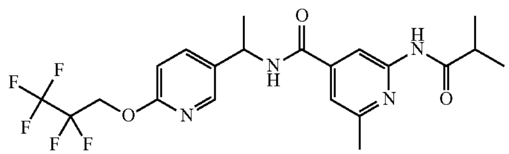 | Amine-60 | | 473.3 | 1.84 |
| 694 | 2-(cyclopropanecarboxamido)-N-(1-(6-(2,2,3,3,3-pentafluoropropoxy)pyridin-3-yl)ethyl)pyrimidine-4-carboxamide | single enantiomer | 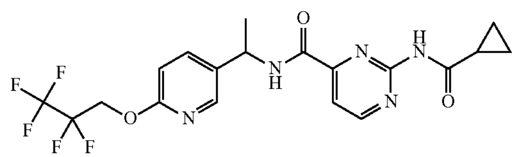 | Amine-60 | | 458.3 | 1.72 |

TABLE 1-continued

| Example | Name | Chirality | Structure | Amine part | Carboxylic part | Observed MS | Retention time (min) |
|---|---|---|---|---|---|---|---|
| 695 | 2-(cyclopropane-carboxamido)-6-pentafluoropropoxy)pyridin-3-yl)ethyl)pyrimidine-4-carboxamide | single enantiomer | 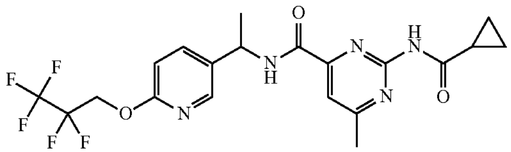 | Amine-60 | | 472.3 | 1.78 |
| 696 | 2-acetamido-N-(4-chloro-3-(trifluoromethyl)benzyl)-6-methylisonicotinamide | | 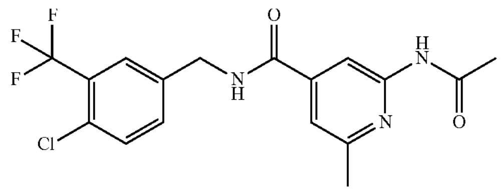 [SMILES: CC(=O)Nc1cc(C(=O)NCc2ccc(Cl)c(C(F)(F)F)c2)cc(C)n1] | | | 384.2 | 1.64 |
| 697 | 2-acetamido-N-(3,5-bis(trifluoromethyl)benzyl)-6-methylisonicotinamide | | 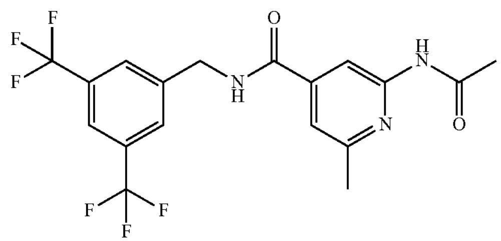 | | | 418.3 | 1.72 |
| 698 | 2-isobutyramido-6-methyl-N-(4-(2,2,2-trifluoroethoxy)benzyl)isonicotinamide | | 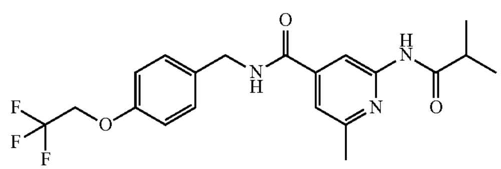 [SMILES: Cc1cc(C(=O)NCc2ccc(OCC(F)(F)F)cc2)cc(NC(=O)C(C)C)n1] | | | 408.3 | 1.69 |

TABLE 1-continued

| Example | Name | Chirality | Structure | Amine part | Carboxylic part | Observed MS | Retention time (min) |
|---|---|---|---|---|---|---|---|
| 699 | N-(1-(3-chloro-4-(2,2-difluoroethoxy)phenyl)-2-(cyclopropanecarboxamido)-6-methylisonicotinamide | single enantiomer | 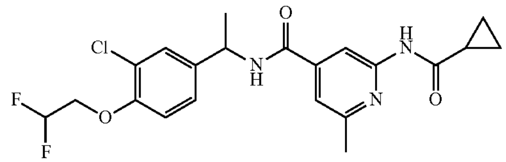 | Amine-82 | | 436.3 | 1.69 |
| 700 | N-(2-chloro-4-difluoroethoxybenzyl)-2-(cyclopropanecarboxamido)pyrimidine-4-carboxamide | | 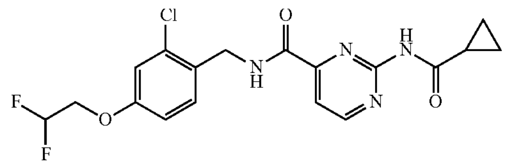 [SMILES: O=C(NCc1ccc(OCC(F)F)cc1Cl)c1ccnc(NC(=O)C2CC2)n1] | Amine-91 | | 409.3 | 1.56 |
| 701 | N-(3-(difluoromethoxy)benzyl)-2-propionamidoisonicotinamide | | 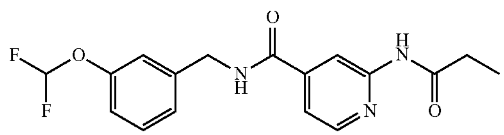 [SMILES: CCC(=O)Nc1cc(C(=O)NCc2cccc(OC(F)F)c2)ccn1] | | | 348.3 | 1.48 |
| 702 | 2-(cyclopropanecarboxamido)-N-(3-(difluoromethoxy)benzyl)isonicotinamide | | 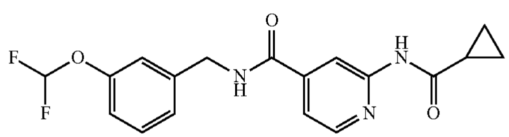 [SMILES: O=C(NCc1cccc(OC(F)F)c1)c1ccnc(NC(=O)C2CC2)c1] | | | 360.3 | 1.52 |
| 703 | 2-acetamido-N-(3-(difluoromethoxy)benzyl)-6-methylisonicotinamide | | 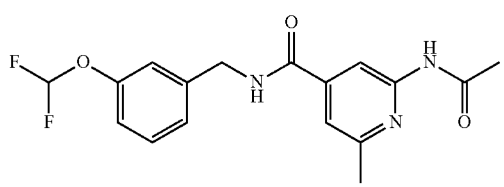 [SMILES: CC(=O)Nc1cc(C(=O)NCc2cccc(OC(F)F)c2)cc(C)n1] | | | 348.3 | 1.46 |

TABLE 1-continued

| Example | Name | Chirality | Structure | Amine part | Carboxylic part | Observed MS | Retention time (min) |
|---|---|---|---|---|---|---|---|
| 704 | 2-acetamido-N-((5-chloro-6-(2,2-difluoroethoxy)pyridin-3-yl)methyl)isonicotinamide | | 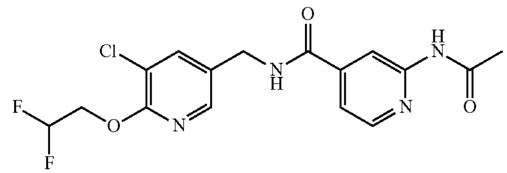 | Amine-52 | | 383.3 | 1.45 |
| 705 | N-((5-chloro-6-(2,2-difluoroethoxy)pyridin-3-yl)methyl)-2-(cyclopropanecarboxamido)isonicotinamide | | 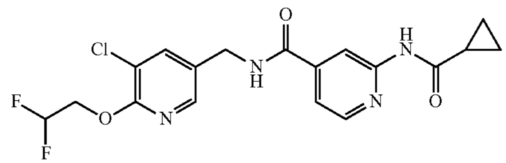 | Amine-52 | | 409.2 | 1.57 |
| 706 | 2-acetamido-N-((5-chloro-6-(2,2-difluoroethoxy)pyridin-3-yl)methyl)-6-methylisonicotinamide | | 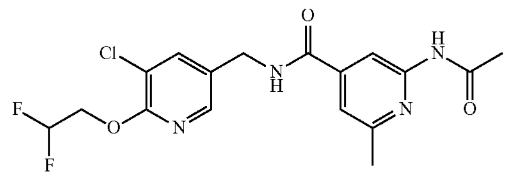 | Amine-52 | | 397.3 | 1.51 |
| 707 | N-((5-chloro-6-(2,2-difluoroethoxy)pyridin-3-yl)methyl)-2-(cyclopropanecarboxamido)pyrimidine-4-carboxamide | | 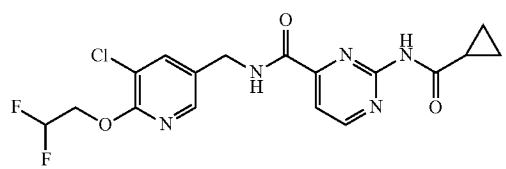 | Amine-52 | | 410.2 | 1.52 |
| 708 | 2-acetamido-N-(2-chloro-5-(trifluoromethyl)benzyl)-6-methylisonicotinamide | | 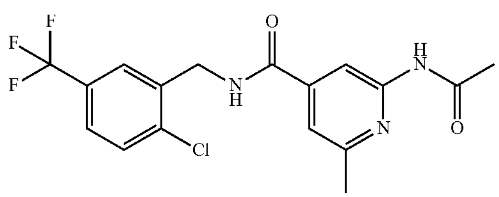 [SMILES: CC(=O)Nc1cc(C(=O)NCc2cc(C(F)(F)F)ccc2Cl)cc(C)n1] | | | 384.3 | 1.63 |

TABLE 1-continued

| Example | Name | Chirality | Structure | Amine part | Carboxylic part | Observed MS | Retention time (min) |
|---|---|---|---|---|---|---|---|
| 709 | 2-acetamido-N-((5-ethyl-6-(2,2,2-trifluoroethoxy)pyridin-3-yl)methyl)isonicotinamide | | 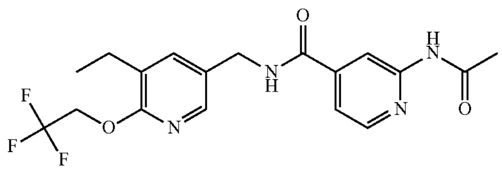 | Amine-61 | | 395.3 | 1.62 |
| 710 | N-((5-ethyl-6-(2,2,2-trifluoroethoxy)pyridin-3-yl)methyl)-2-propionamidoisonicotinamide | | 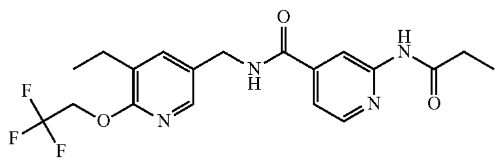 [SMILES: CCC(=O)Nc1cc(C(=O)NCc2cnc(OCC(F)(F)F)c(CC)c2)ccn1] | Amine-61 | | 409.3 | 1.7 |
| 711 | 2-(cyclopropanecarboxamido)-N-((5-ethyl-6-(2,2,2-trifluoroethoxy)pyridin-3-yl)methyl)isonicotinamide | | 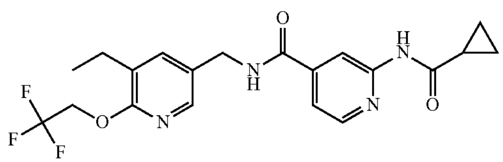 [SMILES: CCc1cc(CNC(=O)c2ccnc(NC(=O)C3CC3)c2)cnc1OCC(F)(F)F] | Amine-61 | | 421.3 | 1.74 |
| 712 | N-((5-ethyl-6-(2,2,2-trifluoroethoxy)pyridin-3-yl)methyl)-2-isobutyramidoisonicotinamide | | 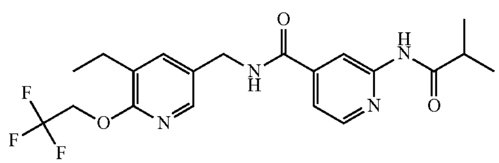 | Amine-61 | | 423.3 | 1.78 |
| 713 | 2-acetamido-N-((5-ethyl-6-(2,2,2-trifluoroethoxy)pyridin-3-yl)methyl)-6-methylisonicotinamide | | 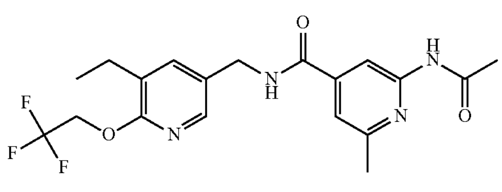 [SMILES: CCc1cc(CNC(=O)c2cc(C)nc(NC(C)=O)c2)cnc1OCC(F)(F)F] | Amine-61 | | 409.3 | 1.68 |

TABLE 1-continued

| Example | Name | Chirality | Structure | Amine part | Carboxylic part | Observed MS | Retention time (min) |
|---|---|---|---|---|---|---|---|
| 714 | N-((5-ethyl-6-(2,2,2-trifluoroethoxy)pyridin-3-yl)methyl)-2-methyl-6-propionamidoisonicotinamide | | 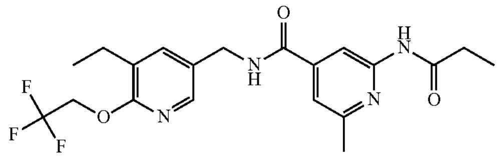 [SMILES: CCC(=O)Nc1cc(C(=O)NCc2cnc(OCC(F)(F)F)c(CC)c2)cc(C)n1] | Amine-61 | | 423.4 | 1.76 |
| 715 | N-((5-ethyl-6-(2,2,2-trifluoroethoxy)pyridin-3-yl)methyl)-2-isobutyramido-6-methylisonicotinamide | | 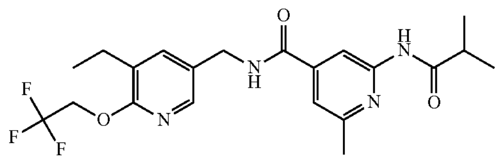 [SMILES: CCc1cc(CNC(=O)c2cc(C)nc(NC(=O)C(C)C)c2)cnc1OCC(F)(F)F] | Amine-61 | | 437.3 | 1.84 |
| 716 | N-((5-ethyl-6-(2,2,2-trifluoroethoxy)pyridin-3-yl)methyl)-2-(2-hydroxy-2-methylpropanamido)-6-methylisonicotinamide | | 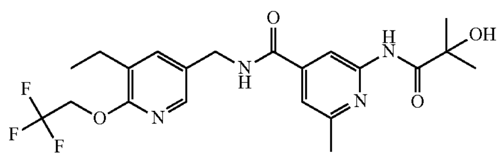 [SMILES: CCc1cc(CNC(=O)c2cc(C)nc(NC(=O)C(C)(C)O)c2)cnc1OCC(F)(F)F] | Amine-61 | | 453.3 | 1.73 |
| 717 | 2-(cyclopropanecarboxamido)-N-((5-ethyl-6-(2,2,2-trifluoroethoxy)pyridin-3-yl)methyl)pyrimidine-4-carboxamide | | 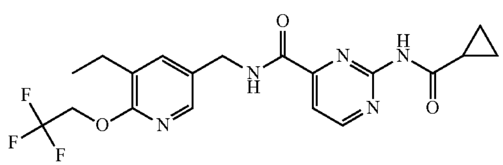 [SMILES: CCc1cc(CNC(=O)c2ccnc(NC(=O)C3CC3)n2)cnc1OCC(F)(F)F] | Amine-61 | | 422.3 | 1.7 |

TABLE 1-continued

| Example | Chirality | Name | Structure | Amine part | Carboxylic part | Observed MS | Retention time (min) |
|---|---|---|---|---|---|---|---|
| 718 | | 2-(cyclopropane-carboxamido)-N-((5-ethyl-6-(2,2,2-trifluoroethoxy)pyridin-3-yl)methyl)-6-methylpyrimidine-4-carboxamide | 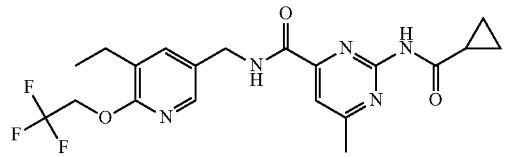 | Amine-61 | | 436.3 | 1.76 |
| 719 | | N-((6-(2,2-difluoropropoxy)pyridin-3-yl)methyl)-2-propionamidoisonicotinamide | 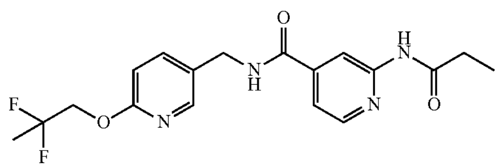 [SMILES: CCC(=O)Nc1cc(C(=O)NCc2ccc(OCC(C)(F)F)nc2)ccn1] | Amine-62 | | 377.3 | 1.47 |
| 720 | | 2-acetamido-N-(((6-(2,2-difluoropropoxy)pyridin-3-yl)methyl)-6-methylisonicotinamide | 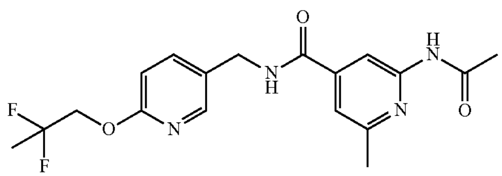 [SMILES: CC(=O)Nc1cc(C(=O)NCc2ccc(OCC(C)(F)F)nc2)cc(C)n1] | Amine-62 | | 377.3 | 1.45 |
| 721 | | N-((6-(2,2-difluoropropoxy)pyridin-3-yl)methyl)-2-methyl-6-propionamidoisonicotinamide | 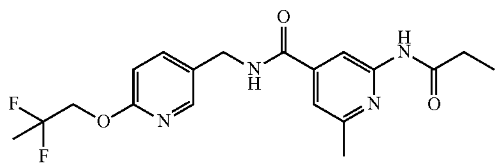 [SMILES: CCC(=O)Nc1cc(C(=O)NCc2ccc(OCC(C)(F)F)nc2)cc(C)n1] | Amine-62 | | 391.3 | 1.54 |

TABLE 1-continued

| Example | Name | Chirality | Structure | Amine part | Carboxylic part | Observed MS | Retention time (min) |
|---|---|---|---|---|---|---|---|
| 722 | N-((6-(2,2-difluoropropoxy)pyridin-3-yl)methyl)-2-isobutyramidoisonicotinamide | | 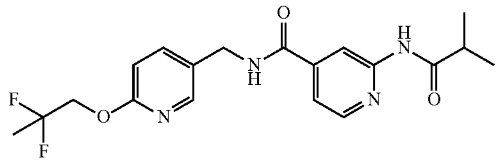 [SMILES: CC(C)C(=O)Nc1cc(C(=O)NCc2ccc(OCC(C)(F)F)nc2)ccn1] | Amine-62 | | 391.4 | 1.56 |
| 723 | N-((6-(2,2-difluoropropoxy)pyridin-3-yl)methyl)-2-isobutyramido-6-methylisonicotinamide | | 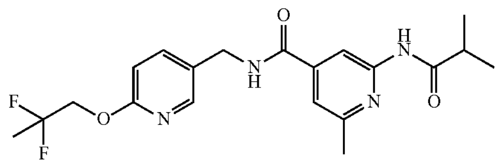 | Amine-62 | | 405.3 | 1.62 |
| 724 | 2-butyramido-N-((6-(2,2-difluoropropoxy)pyridin-3-yl)methyl)isonicotinamide | | 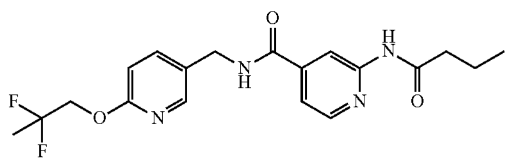 | Amine-62 | | 391.3 | 1.55 |
| 725 | 2-acetamido-N-((6-(2,2,2-trifluoroethoxy)-5-(trifluoromethyl)pyridin-3-yl)methyl)isonicotinamide | | 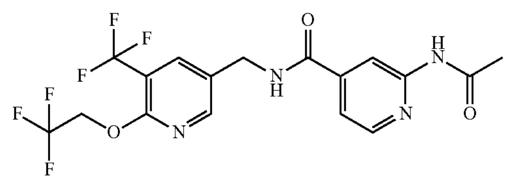 [SMILES: CC(=O)Nc1cc(C(=O)NCc2cnc(OCC(F)(F)F)c(C(F)(F)F)c2)ccn1] | Amine-63 | | 435.2 | 1.62 |
| 726 | 2-propionamido-N-((6-(2,2,2-trifluoroethoxy)-5-(trifluoromethyl)pyridin-3-yl)methyl)isonicotinamide | | 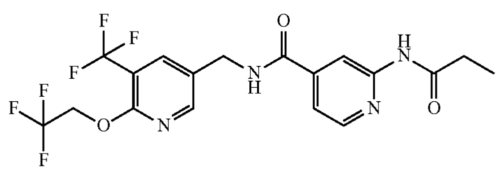 [SMILES: CCC(=O)Nc1cc(C(=O)NCc2cnc(OCC(F)(F)F)c(C(F)(F)F)c2)ccn1] | Amine-63 | | 449.3 | 1.69 |

TABLE 1-continued

| Example | Chirality | Name | Structure | Amine part | Carboxylic part | Observed MS | Retention time (min) |
|---|---|---|---|---|---|---|---|
| 727 | | 2-acetamido-6-methyl-N-((6-(2,2,2-trifluoroethoxy)-5-(trifluoromethyl)pyridin-3-yl)methyl)isonicotinamide | 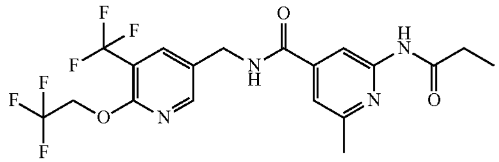 | Amine-63 | | 449.2 | 1.67 |
| 728 | | 2-acetamido-N-(2-fluoro-3-(trifluoromethyl)benzyl)isonicotinamide | 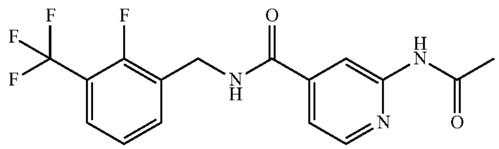 [SMILES: CC(=O)Nc1cc(C(=O)NCc2cccc(C(F)(F)F)c2F)ccn1] | | | 354.2 | 1.51 |
| 729 | | 2-acetamido-N-(2-fluoro-3-(trifluoromethyl)benzyl)-6-methylisonicotinamide | 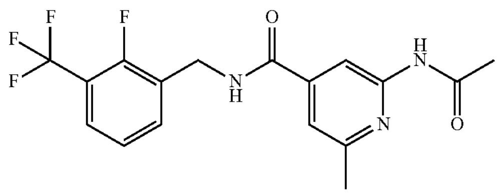 [SMILES: CC(=O)Nc1cc(C(=O)NCc2cccc(C(F)(F)F)c2F)cc(C)n1] | | | 368.2 | 1.57 |
| 730 | | N-(2-fluoro-3-(trifluoromethyl)benzyl)-2-isobutyramidoisonicotinamide | 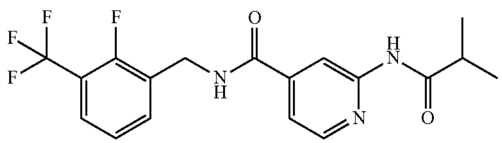 | | | 382.2 | 1.67 |
| 731 | | 2-(cyclopropanecarboxamido)-N-(2-fluoro-3-(trifluoromethyl)benzyl)pyrimidine-4-carboxamide | 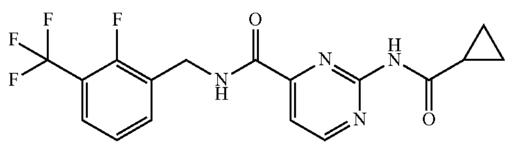 | | | 381.2 | 1.58 |

TABLE 1-continued

| Example | Name | Chirality | Structure | Amine part | Carboxylic part | Observed MS | Retention time (min) |
|---|---|---|---|---|---|---|---|
| 732 | 2-(cyclopropanecarboxamido)-N-(4-fluoro-3-(trifluoromethyl)benzyl)pyrimidine-4-carboxamide | | 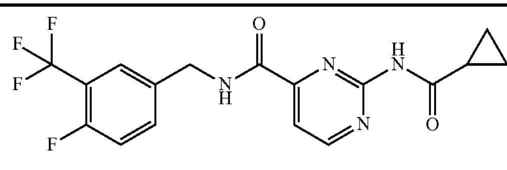 | | | 381.2 | 1.58 |
| 733 | 2-(cyclopropanecarboxamido)-N-(3-fluoro-5-(trifluoromethyl)benzyl)pyrimidine-4-carboxamide | | 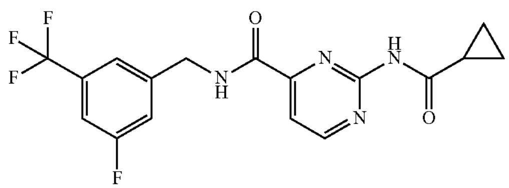 | | | 381.2 | 1.6 |
| 734 | N-(4-chloro-3-(trifluoromethyl)benzyl)-2-(cyclopropanecarboxamido)pyrimidine-4-carboxamide | | 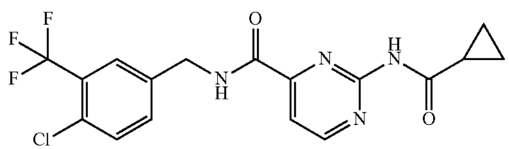 [SMILES: O=C(NCc1ccc(F)c(C(F)(F)F)c1)c1ccnc(NC(=O)C2CC2)n1] | | | 397.2 | 1.65 |
| 735 | N-(2-chloro-5-(trifluoromethyl)benzyl)-2-(cyclopropanecarboxamido)pyrimidine-4-carboxamide | | 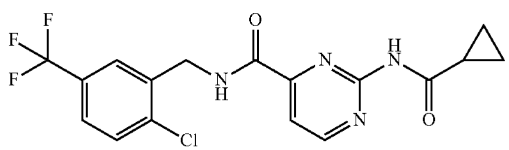 [SMILES: O=C(NCc1cc(C(F)(F)F)ccc1Cl)c1ccnc(NC(=O)C2CC2)n1] | | | 397.2 | 1.64 |

TABLE 1-continued

| Example | Name | Chirality | Structure | Amine part | Carboxylic part | Observed MS | Retention time (min) |
|---|---|---|---|---|---|---|---|
| 736 | N-(3,5-bis(trifluoromethyl)benzyl)-2-(cyclopropanecarboxamido)pyrimidine-4-carboxamide | | 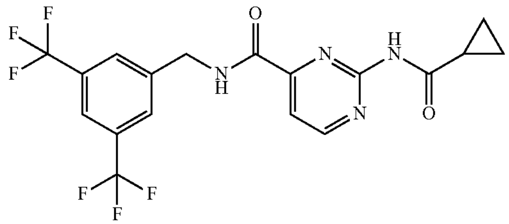 | | | 431.2 | 1.73 |
| 737 | 2-acetamido-N-((6-(2,2-difluoroethoxy)-5-methylpyridin-3-yl)methyl)isonicotinamide | | 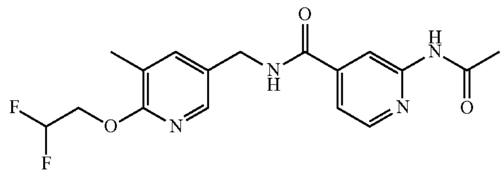 | Amine-64 | | 363.3 | 1.42 |
| 738 | N-((6-(2,2-difluoroethoxy)-5-methylpyridin-3-yl)methyl)-2-propionamidoisonicotinamide | | 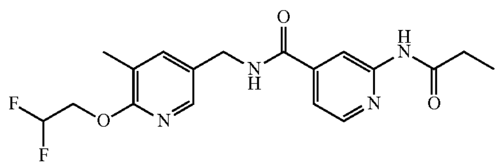 | Amine-64 | | 377.3 | 1.51 |
| 739 | 2-(cyclopropanecarboxamido)-N-((6-(2,2-difluoroethoxy)-5-methylpyridin-3-yl)methyl)isonicotinamide | | 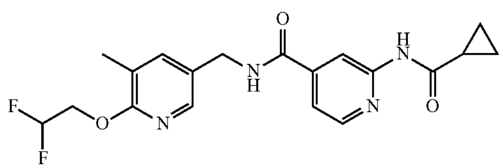 [SMILES: Cc1cc(CNC(=O)c2ccnc(NC(=O)C3CC3)c2)cnc1OCC(F)F] | Amine-64 | | 389.3 | 1.55 |

TABLE 1-continued

| Example | Name | Chirality | Structure | Amine part | Carboxylic part | Observed MS | Retention time (min) |
|---|---|---|---|---|---|---|---|
| 740 | N-((6-(2,2-difluoroethoxy)-5-methylpyridin-3-yl)methyl)-2-methyl-6-propionamidoisonicotinamide | | 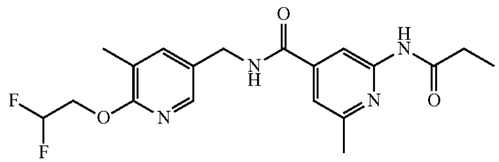 [SMILES: CCC(=O)Nc1cc(C(=O)NCc2cnc(OCC(F)F)c(C)c2)cc(C)n1] | Amine-64 | | 391.3 | 1.57 |
| 741 | N-((6-(2,2-difluoroethoxy)-5-methylpyridin-3-yl)methyl)-2-isobutyramidoisonicotinamide | | 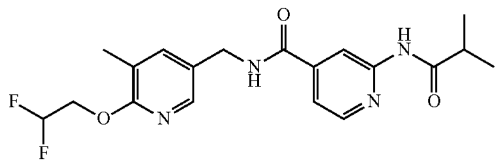 | Amine-64 | | 391.3 | 1.59 |
| 742 | 2-acetamido-N-((6-(2,2-difluoroethoxy)-5-methylpyridin-3-yl)methyl)-6-methylisonicotinamide | | 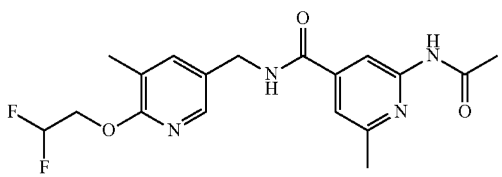 | Amine-64 | | 377.3 | 1.48 |
| 743 | N-((6-(2,2-difluoroethoxy)-5-methylpyridin-3-yl)methyl)-2-isobutyramido-6-methylisonicotinamide | | 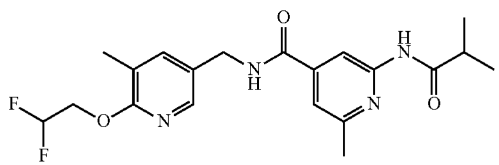 [SMILES: Cc1cc(C(=O)NCc2cnc(OCC(F)F)c(C)c2)cc(NC(=O)C(C)C)n1] | Amine-64 | | 405.3 | 1.65 |

TABLE 1-continued

| Example | Name | Chirality | Structure | Amine part | Carboxylic part | Observed MS | Retention time (min) |
|---|---|---|---|---|---|---|---|
| 744 | 2-(cyclopropanecarboxamido)-N-((6-(2,2-difluoroethoxy)-5-methylpyridin-3-yl)methyl)pyrimidine-4-carboxamide | | 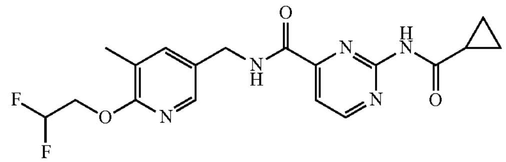 | Amine-64 | | 390.3 | 1.5 |
| 745 | 2-(cyclopropanecarboxamido)-N-((6-(2,2-difluoroethoxy)-5-methylpyridin-3-yl)methyl)-6-methylpyrimidine-4-carboxamide | | 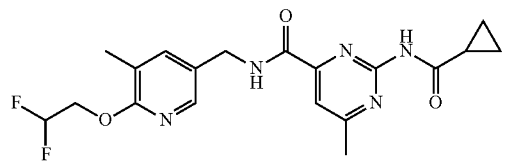 [SMILES: Cc1cc(C(=O)NCc2cnc(OCC(F)F)c(C)c2)nc(NC(=O)C2CC2)n1] | Amine-64 | | 404.3 | 1.56 |
| 746 | 2-acetamido-N-(2-fluoro-3-(trifluoromethoxy)benzyl)isonicotinamide | | 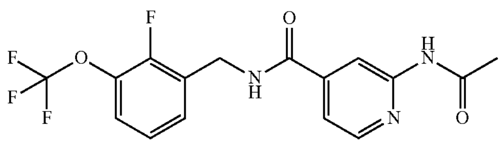 [SMILES: CC(=O)Nc1cc(C(=O)NCc2cccc(OC(F)(F)F)c2F)ccn1] | Amine-65 | | 370.3 | 1.54 |
| 747 | N-(2-fluoro-3-(trifluoromethoxy)benzyl)-2-propionamidoisonicotinamide | | 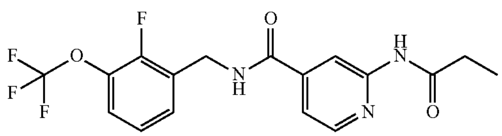 [SMILES: CCC(=O)Nc1cc(C(=O)NCc2cccc(OC(F)(F)F)c2F)ccn1] | Amine-65 | | 384.3 | 1.63 |
| 748 | 2-(cyclopropanecarboxamido)-N-(2-fluoro-3-(trifluoromethoxy)benzyl)isonicotinamide | | 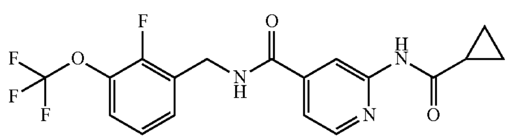 [SMILES: O=C(NCc1cccc(OC(F)(F)F)c1F)c1ccnc(NC(=O)C2CC2)c1] | Amine-65 | | 396.3 | 1.67 |

TABLE 1-continued

| Example | Name | Chirality | Structure | Amine part | Carboxylic part | Observed MS | Retention time (min) |
|---|---|---|---|---|---|---|---|
| 749 | N-(2-fluoro-3-(trifluoromethoxy)benzyl)-2-methyl-6-propionamidoisonicotinamide | | 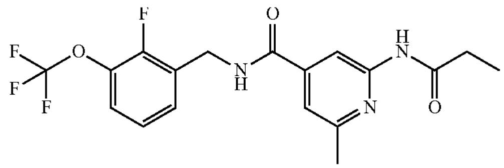 | Amine-65 | | 398.3 | 1.69 |
| 750 | N-(2-fluoro-3-(trifluoromethoxy)benzyl)-2-isobutyramidoisonicotinamide | | 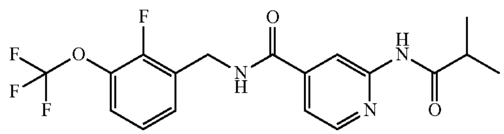 [SMILES: CC(C)C(=O)Nc1cc(C(=O)NCc2cccc(OC(F)(F)F)c2F)ccn1] | Amine-65 | | 398.3 | 1.71 |
| 751 | 2-acetamido-N-(2-fluoro-3-(trifluoromethoxy)benzyl)-6-methylisonicotinamide | | 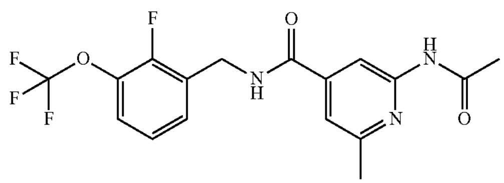 [SMILES: CC(=O)Nc1cc(C(=O)NCc2cccc(OC(F)(F)F)c2F)cc(C)n1] | Amine-65 | | 384.2 | 1.61 |
| 752 | N-(2-fluoro-3-(trifluoromethoxy)benzyl)-2-isobutyramido-6-methylisonicotinamide | | 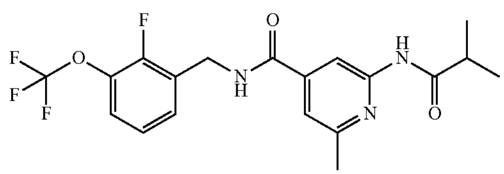 [SMILES: Cc1cc(C(=O)NCc2cccc(OC(F)(F)F)c2F)cc(NC(=O)C(C)C)n1] | Amine-65 | | 412.3 | 1.77 |

TABLE 1-continued

| Example | Chirality | Name | Structure | Amine part | Carboxylic part | Observed MS | Retention time (min) |
|---|---|---|---|---|---|---|---|
| 753 | | 2-(cyclopropanecarboxamido)-N-(2-fluoro-3-(trifluoromethoxy)benzyl)pyrimidine-4-carboxamide | 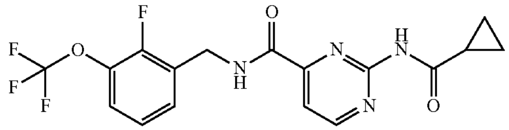 [SMILES: O=C(NCc1cccc(OC(F)(F)F)c1F)c1ccnc(NC(=O)C2CC2)n1] | Amine-65 | | 397.2 | 1.62 |
| 754 | | 2-(cyclopropanecarboxamido)-N-(2-fluoro-3-(trifluoromethoxy)benzyl)-6-methylpyrimidine-4-carboxamide | 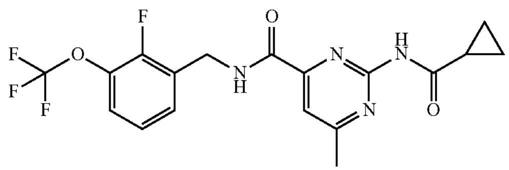 [SMILES: Cc1cc(C(=O)NCc2cccc(OC(F)(F)F)c2F)nc(NC(=O)C2CC2)n1] | Amine-65 | | 411.2 | 1.69 |
| 755 | | N-(2-fluoro-3-(trifluoromethoxy)benzyl)-2-(2-hydroxy-2-methylpropanamido)-6-methylisonicotinamide | 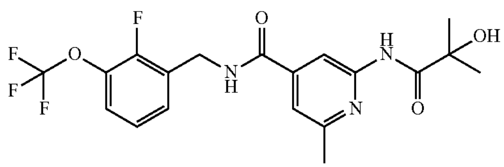 [SMILES: Cc1cc(C(=O)NCc2cccc(OC(F)(F)F)c2F)cc(NC(=O)C(C)(C)O)n1] | Amine-65 | | 428.2 | 1.66 |
| 756 | | 2-acetamido-N-(4-methoxy-3-(trifluoromethoxy)benzyl)-6-methylisonicotinamide | 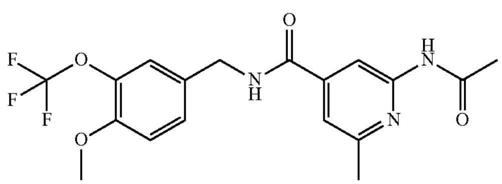 [SMILES: COc1ccc(CNC(=O)c2cc(C)nc(NC(C)=O)c2)cc1OC(F)(F)F] | Amine-66 | | 396.3 | 1.56 |
| 757 | | 2-butyramido-N-((6-(2,2-difluoroethoxy)-5-methylpyridin-3-yl)methyl)isonicotinamide | 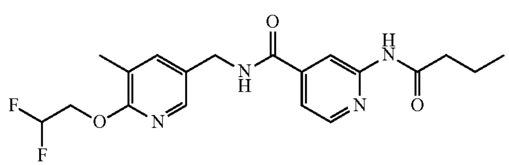 [SMILES: CCCC(=O)Nc1cc(C(=O)NCc2cnc(OCC(F)F)c(C)c2)ccn1] | Amine-64 | | 391.3 | 1.59 |

TABLE 1-continued

| Example | Name | Chirality | Structure | Amine part | Carboxylic part | Observed MS | Retention time (min) |
|---|---|---|---|---|---|---|---|
| 758 | 2-acetamido-N-(2-chloro-3-(trifluoromethyl)benzyl)isonicotinamide | | 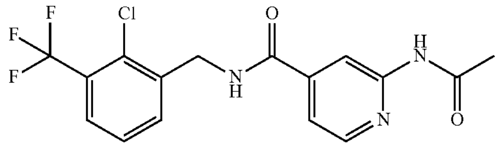 [SMILES: CC(=O)Nc1cc(C(=O)NCc2cccc(C(F)(F)F)c2Cl)ccn1] | | | 370.2 | 1.56 |
| 759 | 2-acetamido-N-(2-chloro-3-(trifluoromethyl)benzyl)-6-methylisonicotinamide | | 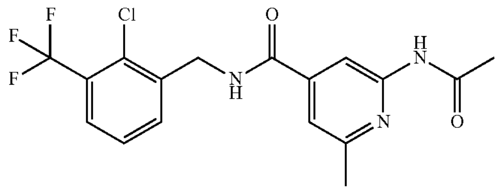 [SMILES: CC(=O)Nc1cc(C(=O)NCc2cccc(C(F)(F)F)c2Cl)cc(C)n1] | | | 384.2 | 1.62 |
| 760 | N-(2-chloro-3-(trifluoromethyl)benzyl)-2-isobutyramidoisonicotinamide | | 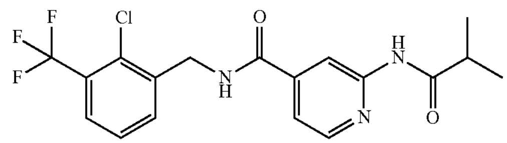 [SMILES: CC(C)C(=O)Nc1cc(C(=O)NCc2cccc(C(F)(F)F)c2Cl)ccn1] | | | 398.2 | 1.73 |
| 761 | 2-acetamido-N-(4-methyl-3-(trifluoromethyl)benzyl)isonicotinamide | | 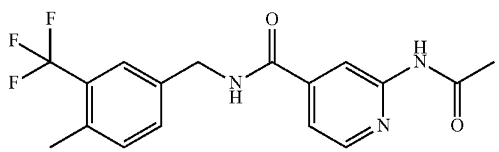 [SMILES: CC(=O)Nc1cc(C(=O)NCc2ccc(C)c(C(F)(F)F)c2)ccn1] | | | 350.3 | 1.56 |
| 762 | 2-acetamido-N-((5-bromo-6-(2,2,2-trifluoroethoxy)pyridin-3-yl)methyl)isonicotinamide | | 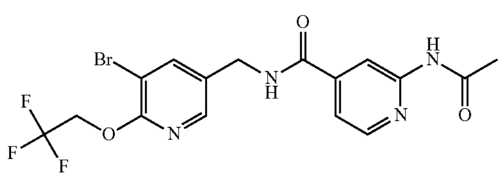 | | Amine-67 | 445.1 | 1.57 |

TABLE 1-continued

| Example | Name | Chirality | Structure | Amine part | Carboxylic part | Observed MS | Retention time (min) |
|---|---|---|---|---|---|---|---|
| 763 | 2-acetamido-N-((5-phenyl-6-(2,2,2-trifluoroethoxy)pyridin-3-yl)methyl)isonicotinamide | | 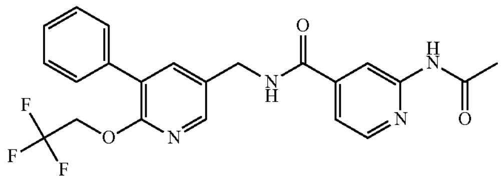 | | alternative route | 443.3 | 1.69 |
| 764 | 2-acetamido-N-((5-(2-fluorophenyl)-6-(2,2,2-trifluoroethoxy)pyridin-3-yl)methyl)isonicotinamide | | 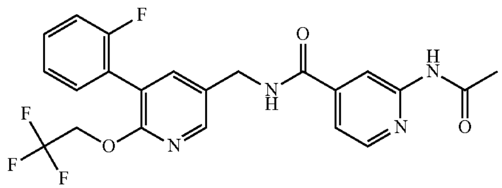 [SMILES: CC(=O)Nc1cc(C(=O)NCc2cnc(OCC(F)(F)F)c(-c3ccccc3F)c2)ccn1] | | alternative route | 461.2 | 1.66 |
| 765 | 2-acetamido-N-((5-(o-tolyl)-6-(2,2,2-trifluoroethoxy)pyridin-3-yl)methyl)isonicotinamide | | 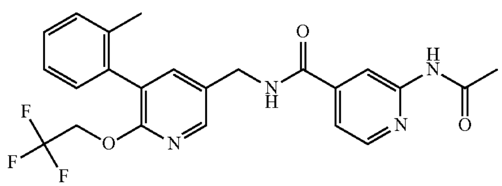 [SMILES: CC(=O)Nc1cc(C(=O)NCc2cnc(OCC(F)(F)F)c(-c3ccccc3C)c2)ccn1] | | alternative route | 457.3 | 1.72 |
| 766 | 2-acetamido-N-((5-(3-fluorophenyl)-6-(2,2,2-trifluoroethoxy)pyridin-3-yl)methyl)isonicotinamide | | 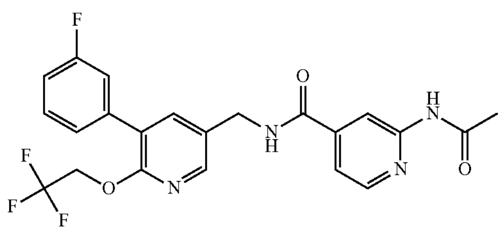 [SMILES: CC(=O)Nc1cc(C(=O)NCc2cnc(OCC(F)(F)F)c(-c3cccc(F)c3)c2)ccn1] | | alternative route | 461.2 | 1.7 |

TABLE 1-continued

| Example | Chirality | Name | Structure | Amine part | Carboxylic part | Observed MS | Retention time (min) |
|---|---|---|---|---|---|---|---|
| 767 | | 2-acetamido-N-((5-(m-tolyl)-6-(2,2,2-trifluoroethoxy)pyridin-3-yl)methyl)isonicotinamide | 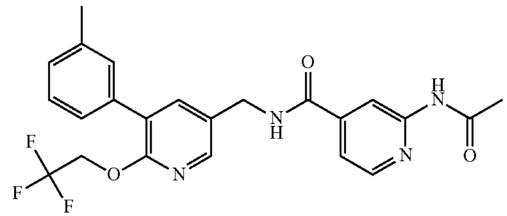 [SMILES: CC(=O)Nc1cc(C(=O)NCc2cnc(OCC(F)(F)F)c(-c3cccc(C)c3)c2)ccn1] | alternative route | | 457.3 | 1.76 |
| 768 | | 2-acetamido-N-((5-(4-fluorophenyl)-6-(2,2,2-trifluoroethoxy)pyridin-3-yl)methyl)isonicotinamide | 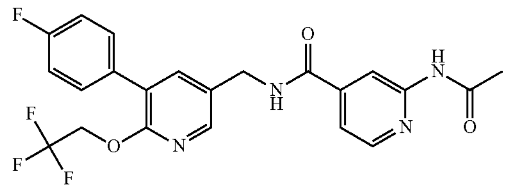 [SMILES: CC(=O)Nc1cc(C(=O)NCc2cnc(OCC(F)(F)F)c(-c3ccc(F)cc3)c2)ccn1] | alternative route | | 461.2 | 1.71 |
| 769 | | 2-acetamido-N-((5-(thiophen-3-yl)-6-(2,2,2-trifluoroethoxy)pyridin-3-yl)methyl)isonicotinamide | 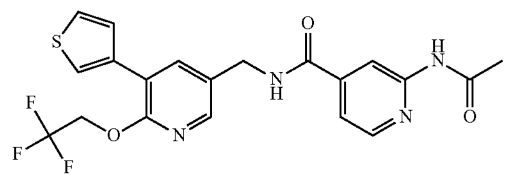 [SMILES: CC(=O)Nc1cc(C(=O)NCc2cnc(OCC(F)(F)F)c(-c3ccsc3)c2)ccn1] | alternative route | | 449.2 | 1.68 |
| 770 | | 2-acetamido-N-((5-(furan-2-yl)-6-(2,2,2-trifluoroethoxy)pyridin-3-yl)methyl)isonicotinamide | 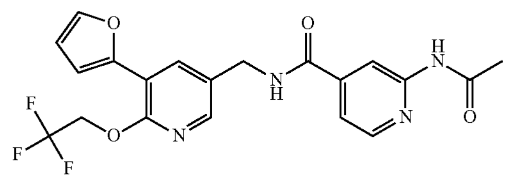 [SMILES: CC(=O)Nc1cc(C(=O)NCc2cnc(OCC(F)(F)F)c(-c3ccco3)c2)ccn1] | alternative route | | 433.2 | 1.65 |
| 771 | | 2-isobutyramido-N-(4-(2,2,2-trifluoroethyl)benzyl)isonicotinamide | 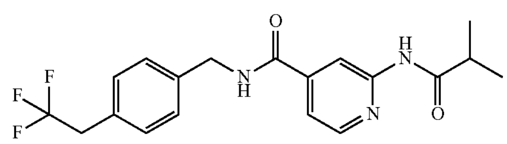 [SMILES: CC(C)C(=O)Nc1cc(C(=O)NCc2ccc(CC(F)(F)F)cc2)ccn1] | | | 378.3 | 1.63 |

TABLE 1-continued

| Example | Name | Chirality | Structure | Amine part | Carboxylic part | Observed MS | Retention time (min) |
|---|---|---|---|---|---|---|---|
| 772 | 2-propionamido-N-(4-(trifluoromethoxy)benzyl)isonicotinamide | | 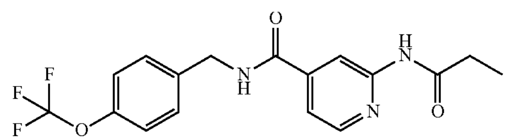 [SMILES: CCC(=O)Nc1cc(C(=O)NCc2ccc(OC(F)(F)F)cc2)ccn1] | | | 366.3 | 1.61 |
| 773 | 2-isobutyramido-N-(4-(trifluoromethoxy)benzyl)isonicotinamide | | 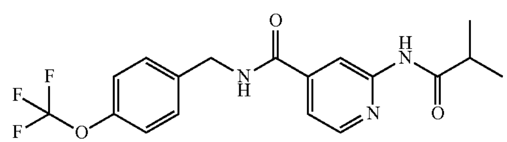 [SMILES: CC(C)C(=O)Nc1cc(C(=O)NCc2ccc(OC(F)(F)F)cc2)ccn1] | | | 380.3 | 1.69 |
| 774 | 2-isobutyramido-6-methyl-N-(4-(trifluoromethoxy)benzyl)isonicotinamide | | 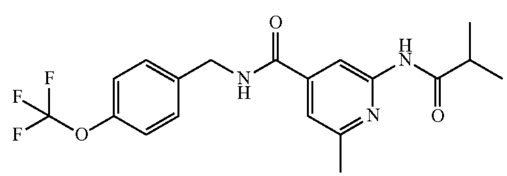 | | | 394.3 | 1.76 |
| 775 | 2-(cyclopropanecarboxamido)-6-methyl-N-(4-(trifluoromethoxy)benzyl)pyrimidine-4-carboxamide | | 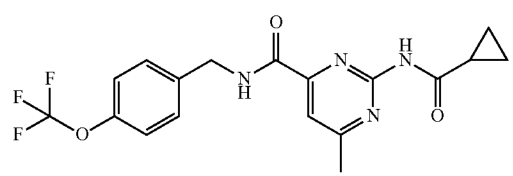 [SMILES: Cc1cc(C(=O)NCc2ccc(OC(F)(F)F)cc2)nc(NC(=O)C2CC2)n1] | | | 393.3 | 1.67 |

| Example | Name | Chirality | Structure | Amine part | Carboxylic part | Observed MS | Retention time (min) |
|---|---|---|---|---|---|---|---|
| 776 | 2-isobutyramido-6-methyl-N-(1-(4-(trifluoromethoxy)phenyl)ethyl)isonicotinamide | single enantiomer | 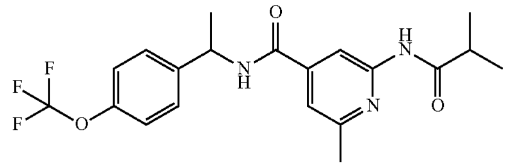 [SMILES: Cc1cc(C(=O)NC(C)c2ccc(OC(F)(F)F)cc2)cc(NC(=O)C(C)C)n1] | Amine-10 | | 408.3 | 1.8 |
| 777 | N-((6-(2,2-difluoroethoxy)-4-methylpyridin-3-yl)methyl)-2-propionamidoisonicotinamide | | 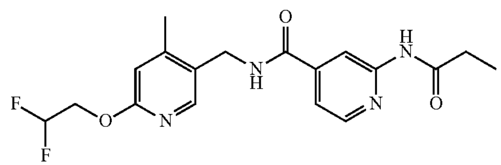 | Amine-69 | | 377.4 | 1.46 |
| 778 | 2-acetamido-N-((6-(2,2-difluoroethoxy)-4-methylpyridin-3-yl)methyl)-6-methylisonicotinamide | | 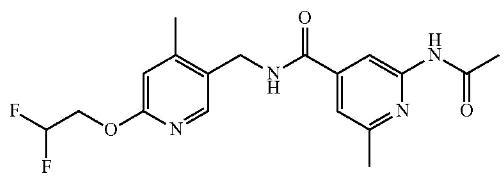 [SMILES: CC(=O)Nc1cc(C(=O)NCc2cnc(OCC(F)F)cc2C)cc(C)n1] | Amine-69 | | 377.4 | 1.44 |
| 779 | 2-(cyclopropanecarboxamido)-N-(3-methyl-4-(2,2,2-trifluoroethoxy)benzyl)pyrimidine-4-carboxamide | | 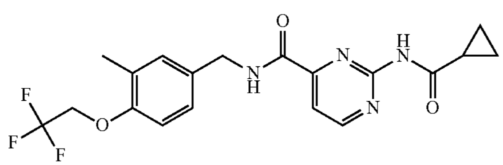 [SMILES: Cc1cc(CNC(=O)c2ccnc(NC(=O)C3CC3)n2)ccc1OCC(F)(F)F] | Amine-70 | | 407.2 | 1.64 |
| 780 | 2-(cyclopropanecarboxamido)-6-methyl-N-(3-methyl-4-(2,2,2-trifluoroethoxy)benzyl)pyrimidine-4-carboxamide | | 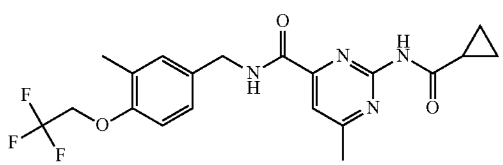 [SMILES: Cc1cc(C(=O)NCc2ccc(OCC(F)(F)F)c(C)c2)nc(NC(=O)C2CC2)n1] | Amine-70 | | 421.3 | 1.7 |

TABLE 1-continued

| Example | Name | Chirality | Structure | Amine part | Carboxylic part | Observed MS | Retention time (min) |
|---|---|---|---|---|---|---|---|
| 781 | N-(1-(6-(2,2-difluoropropoxy)pyridin-3-yl)ethyl)-2-propionamidoisonicotinamide | single enantiomer | 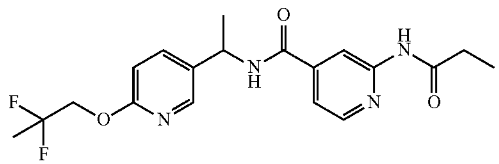 [SMILES: CCC(=O)Nc1cc(C(=O)NC(C)c2ccc(OCC(C)(F)F)nc2)ccn1] | Amine-71 | | 391.3 | 1.53 |
| 782 | 2-(cyclopropanecarboxamido)-N-(1-(6-(2,2-difluoropropoxy)pyridin-3-yl)ethyl)isonicotinamide | single enantiomer | 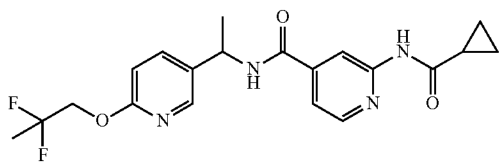 | Amine-71 | | 403.3 | 1.57 |
| 783 | 2-acetamido-N-(1-(6-(2,2-difluoropropoxy)pyridin-3-yl)ethyl)-6-methylisonicotinamide | single enantiomer | 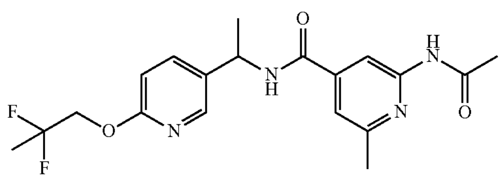 [SMILES: CC(=O)Nc1cc(C(=O)NC(C)c2ccc(OCC(C)(F)F)nc2)cc(C)n1] | Amine-71 | | 391.3 | 1.51 |
| 784 | N-(1-(6-(2,2-difluoropropoxy)pyridin-3-yl)ethyl)-2-methyl-6-propionamidoisonicotinamide | single enantiomer | 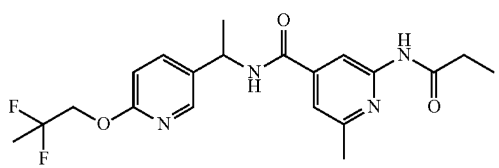 [SMILES: CCC(=O)Nc1cc(C(=O)NC(C)c2ccc(OCC(C)(F)F)nc2)cc(C)n1] | Amine-71 | | 405.3 | 1.59 |
| 785 | N-(1-(6-(2,2-difluoropropoxy)pyridin-3-yl)ethyl)-2-isobutyramidoisonicotinamide | single enantiomer | 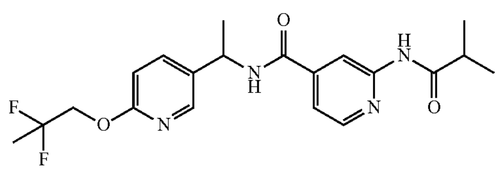 | Amine-71 | | 405.3 | 1.61 |

TABLE 1-continued

| Example | Name | Chirality | Structure | Amine part | Carboxylic part | Observed MS | Retention time (min) |
|---|---|---|---|---|---|---|---|
| 786 | N-(1-(6-(2,2-difluoropropoxy)pyridin-3-yl)ethyl)-2-isobutyramido-6-methylisonicotinamide | single enantiomer | 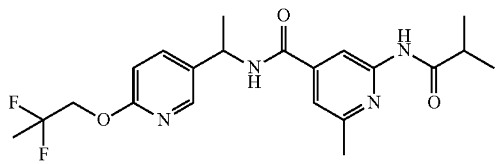 [SMILES: Cc1cc(C(=O)NC(C)c2ccc(OCC(C)(F)F)nc2)cc(NC(=O)C(C)C)n1] | Amine-71 | | 419.3 | 1.67 |
| 787 | 2-butyramido-N-(1-(6-(2,2-difluoropropoxy)pyridin-3-yl)ethyl)isonicotinamide | single enantiomer | 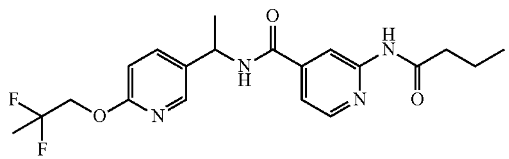 [SMILES: CCCC(=O)Nc1cc(C(=O)NC(C)c2ccc(OCC(C)(F)F)nc2)ccn1] | Amine-71 | | 405.3 | 1.61 |
| 788 | 2-acetamido-N-(3-methyl-4-(2,2,2-trifluoroethoxy)benzyl)isonicotinamide | | 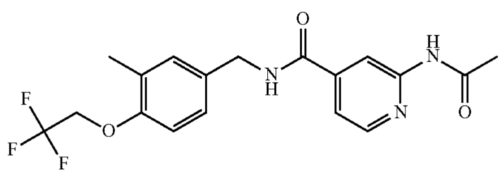 | Amine-70 | | 380.3 | 1.57 |
| 789 | N-(3-methyl-4-(2,2,2-trifluoroethoxy)benzyl)-2-propionamidoisonicotinamide | | 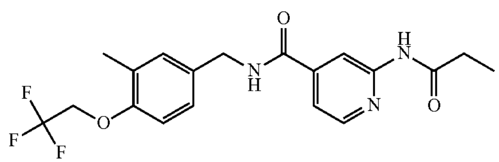 [SMILES: CCC(=O)Nc1cc(C(=O)NCc2ccc(OCC(F)(F)F)c(C)c2)ccn1] | Amine-70 | | 394.3 | 1.65 |
| 790 | 2-(cyclopropanecarboxamido)-N-(3-methyl-4-(2,2,2-trifluoroethoxy)benzyl)isonicotinamide | | 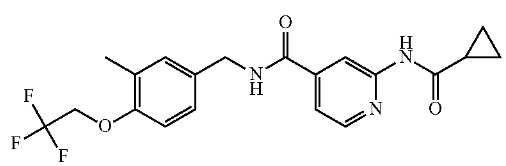 [SMILES: Cc1cc(CNC(=O)c2ccnc(NC(=O)C3CC3)c2)ccc1OCC(F)(F)F] | Amine-70 | | 406.3 | 1.68 |

TABLE 1-continued

| Example | Name | Chirality | Structure | Amine part | Carboxylic part | Observed MS | Retention time (min) |
|---|---|---|---|---|---|---|---|
| 791 | 2-isobutyramido-N-(3-methyl-4-(2,2,2-trifluoroethoxy)benzyl)isonicotinamide | | 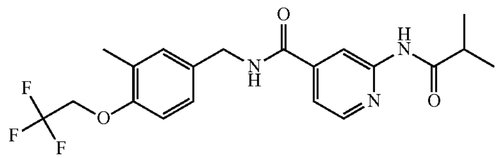 | Amine-70 | | 408.3 | 1.72 |
| 792 | 2-acetamido-6-methyl-N-(3-methyl-4-(2,2,2-trifluoroethoxy)benzyl)isonicotinamide | | 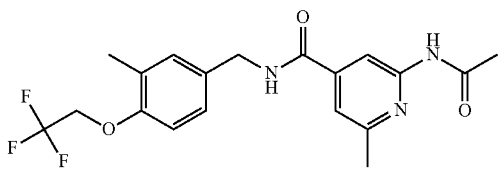 [SMILES: CC(=O)Nc1cc(C(=O)NCc2ccc(OCC(F)(F)F)c(C)c2)cc(C)n1] | Amine-70 | | 394.4 | 1.62 |
| 793 | 2-methyl-N-(3-methyl-4-(2,2,2-trifluoroethoxy)benzyl)-6-propionamidoisonicotinamide | | 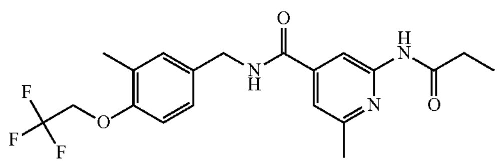 [SMILES: CCC(=O)Nc1cc(C(=O)NCc2ccc(OCC(F)(F)F)c(C)c2)cc(C)n1] | Amine-70 | | 408.3 | 1.7 |
| 794 | 2-isobutyramido-6-methyl-N-(3-methyl-4-(2,2,2-trifluoroethoxy)benzyl)isonicotinamide | | 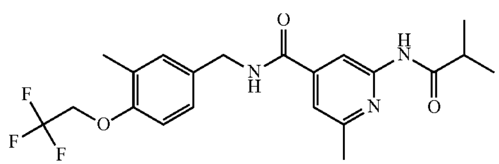 [SMILES: Cc1cc(C(=O)NCc2ccc(OCC(F)(F)F)c(C)c2)cc(NC(=O)C(C)C)n1] | Amine-70 | | 422.3 | 1.78 |

TABLE 1-continued

| Example | Name | Chirality | Structure | Amine part | Carboxylic part | Observed MS | Retention time (min) |
|---|---|---|---|---|---|---|---|
| 795 | 2-(2-hydropropanamido)-6-methyl-N-(3-methyl-4-(2,2,2-trifluoroethoxy)benzyl)isonicotinamide | | 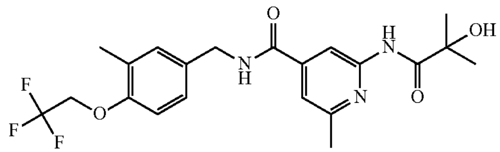 [SMILES: Cc1cc(C(=O)NCc2ccc(OCC(F)(F)F)c(C)c2)cc(NC(=O)C(C)(C)O)n1] | Amine-70 | | 438.3 | 1.67 |
| 796 | 2-acetamido-N-(1-(2-chloro-4-(2,2,2-trifluoroethoxy)phenyl)ethyl)isonicotinamide | single enantiomer | 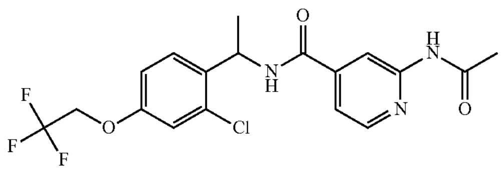 | Amine-72 | | 414.3 | 1.63 |
| 797 | N-(1-(2-chloro-4-(2,2,2-trifluoroethoxy)phenyl)ethyl)-2-propionamidoisonicotinamide | single enantiomer | 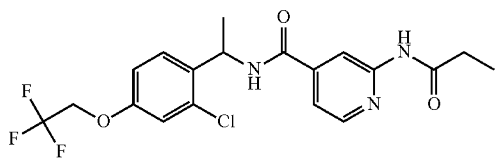 | Amine-72 | | 428.3 | 1.71 |
| 798 | N-(1-(2-chloro-4-(2,2,2-trifluoroethoxy)phenyl)ethyl)-2-(cyclopropanecarboxamido)isonicotinamide | single enantiomer | 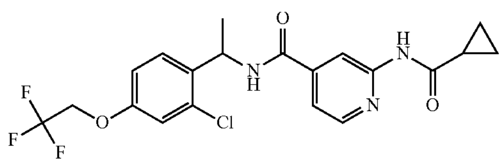 [SMILES: CC(NC(=O)c1ccnc(NC(=O)C2CC2)c1)c1ccc(OCC(F)(F)F)cc1Cl] | Amine-72 | | 440.2 | 1.74 |
| 799 | N-(1-(2-chloro-4-(2,2,2-trifluoroethoxy)phenyl)ethyl)-2-isobutyramidoisonicotinamide | single enantiomer | 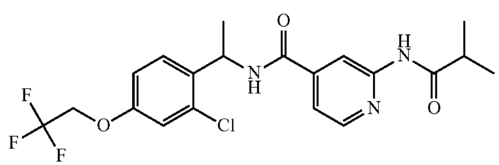 [SMILES: CC(C)C(=O)Nc1cc(C(=O)NC(C)c2ccc(OCC(F)(F)F)cc2Cl)ccn1] | Amine-72 | | 442.3 | 1.78 |

TABLE 1-continued

| Example | Name | Chirality | Structure | Amine part | Carboxylic part | Observed MS | Retention time (min) |
|---|---|---|---|---|---|---|---|
| 800 | 2-acetamido-N-(1-(2-chloro-4-(2,2,2-trifluoroethoxy)phenyl)ethyl)-6-methylisonicotinamide | single enantiomer | 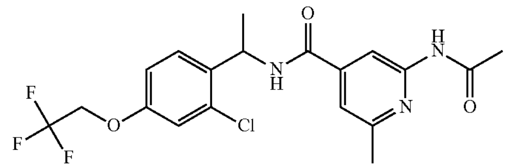 [SMILES: CC(=O)Nc1cc(C(=O)NC(C)c2ccc(OCC(F)(F)F)cc2Cl)cc(C)n1] | Amine-72 | | 428.3 | 1.69 |
| 801 | N-(1-(2-chloro-4-(2,2,2-trifluoroethoxy)phenyl)ethyl)-2-isobutyramido-6-methylisonicotinamide | single enantiomer | 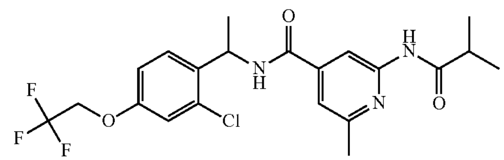 [SMILES: Cc1cc(C(=O)NC(C)c2ccc(OCC(F)(F)F)cc2Cl)cc(NC(=O)C(C)C)n1] | Amine-72 | | 456.3 | 1.83 |
| 802 | N-(1-(2-chloro-4-(2,2,2-trifluoroethoxy)phenyl)ethyl)-2-(cyclopropanecarboxamido)pyrimidine-4-carboxamide | single enantiomer | 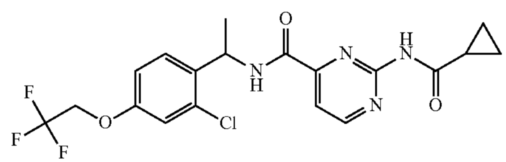 | Amine-72 | | 441.2 | 1.72 |
| 803 | N-(1-(2-chloro-4-(2,2,2-trifluoroethoxy)phenyl)ethyl)-2-(cyclopropanecarboxamido)-6-methylpyrimidine-4-carboxamide | single enantiomer | 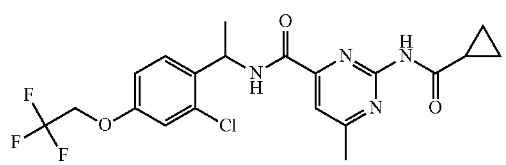 [SMILES: Cc1cc(C(=O)NC(C)c2ccc(OCC(F)(F)F)cc2Cl)nc(NC(=O)C2CC2)n1] | Amine-72 | | 455.3 | 1.78 |

TABLE 1-continued

| Example | Name | Chirality | Structure | Amine part | Carboxylic part | Observed MS | Retention time (min) |
|---|---|---|---|---|---|---|---|
| 804 | 2-acetamido-N-(3-methyl-4-(trifluoromethoxy)benzyl)isonicotinamide | | 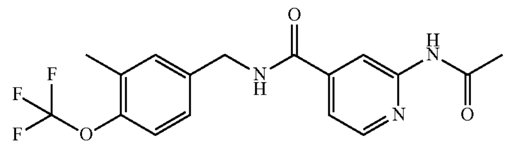 | Amine-73 | | 366.3 | 1.61 |
| 805 | N-(3-methyl-4-(trifluoromethoxy)benzyl)-2-propionamidoisonicotinamide | | 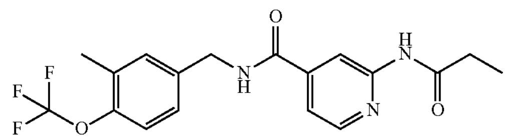 | Amine-73 | | 380.3 | 1.69 |
| 806 | 2-(cyclopropanecarboxamido)-N-(3-methyl-4-(trifluoromethoxy)benzyl)isonicotinamide | | 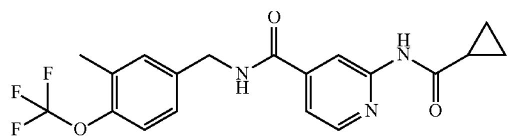 [SMILES: Cc1cc(CNC(=O)c2ccnc(NC(=O)C3CC3)c2)ccc1OC(F)(F)F] | Amine-73 | | 392.3 | 1.73 |
| 807 | 2-isobutyramido-N-(3-methyl-4-(trifluoromethoxy)benzyl)isonicotinamide | | 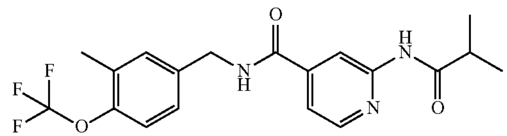 [SMILES: Cc1cc(CNC(=O)c2ccnc(NC(=O)C(C)C)c2)ccc1OC(F)(F)F] | Amine-73 | | 394.3 | 1.77 |
| 808 | 2-acetamido-6-methyl-N-(3-methyl-4-(trifluoromethoxy)benzyl)isonicotinamide | | 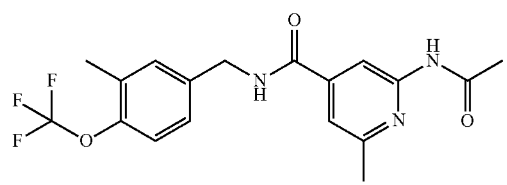 | Amine-73 | | 380.3 | 1.67 |

TABLE 1-continued

| Example | Chirality | Name | Structure | Amine part | Carboxylic part | Observed MS | Retention time (min) |
|---|---|---|---|---|---|---|---|
| 809 | | 2-isobutyramido-6-methyl-N-(3-methyl-4-(trifluoromethoxy)benzyl)isonicotinamide | 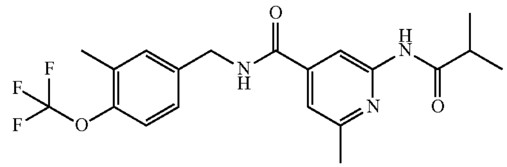 [SMILES: Cc1cc(C(=O)NCc2ccc(OC(F)(F)F)c(C)c2)cc(NC(=O)C(C)C)n1] | Amine-73 | | 408.3 | 1.83 |
| 810 | | 2-(cyclopropanecarboxamido)-N-(3-methyl-4-(trifluoromethoxy)benzyl)pyrimidine-4-carboxamide | 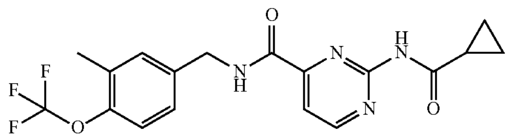 [SMILES: Cc1cc(CNC(=O)c2ccnc(NC(=O)C3CC3)n2)ccc1OC(F)(F)F] | Amine-73 | | 393.3 | 1.69 |
| 811 | | 2-(cyclopropanecarboxamido)-6-methyl-N-(3-methyl-4-(trifluoromethoxy)benzyl)pyrimidine-4-carboxamide | 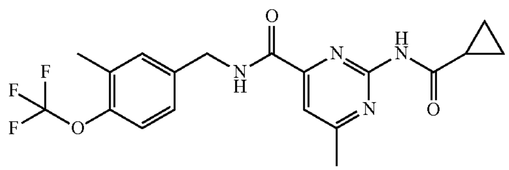 [SMILES: Cc1cc(C(=O)NCc2ccc(OC(F)(F)F)c(C)c2)nc(NC(=O)C2CC2)n1] | Amine-73 | | 407.3 | 1.75 |
| 812 | | 2-(2-hydroxy-2-methylpropanamido)-6-methyl-N-(3-methyl-4-(trifluoromethoxy)benzyl)isonicotinamide | 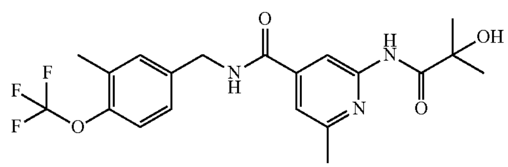 [SMILES: Cc1cc(C(=O)NCc2ccc(OC(F)(F)F)c(C)c2)cc(NC(=O)C(C)(C)O)n1] | Amine-73 | | 424.3 | 1.73 |
| 813 | | 2-acetamido-N-(4-methoxy-3-(trifluoromethyl)benzyl)-6-methylisonicotinamide | 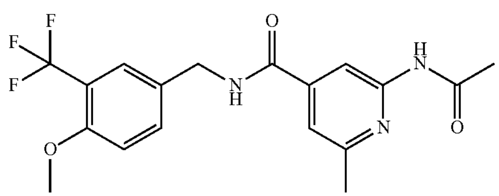 [SMILES: COc1ccc(CNC(=O)c2cc(C)nc(NC(C)=O)c2)cc1C(F)(F)F] | | | 380.3 | 1.53 |

TABLE 1-continued

| Example | Name | Chirality | Structure | Amine part | Carboxylic part | Observed MS | Retention time (min) |
|---|---|---|---|---|---|---|---|
| 814 | 2-acetamido-N-(2-methyl-3-(trifluoromethyl)benzyl)isonicotinamide | | 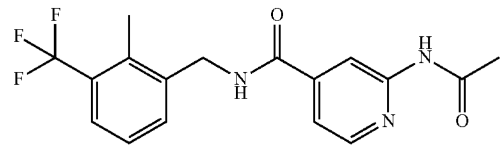 [SMILES: CC(=O)Nc1cc(C(=O)NCc2cccc(C(F)(F)F)c2C)ccn1] | | | 350.3 | 1.55 |
| 815 | 2-acetamido-6-methyl-N-(2-methyl-3-(trifluoromethyl)benzyl)isonicotinamide | | 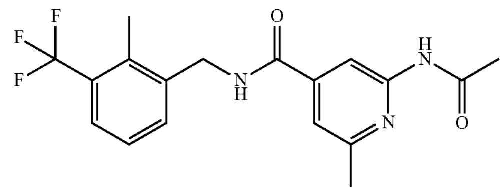 [SMILES: CC(=O)Nc1cc(C(=O)NCc2cccc(C(F)(F)F)c2C)cc(C)n1] | | | 364.2 | 1.62 |
| 816 | 2-isobutyramido-N-(2-methyl-3-(trifluoromethyl)benzyl)isonicotinamide | | 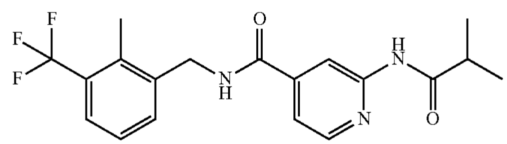 | | | 378.3 | 1.72 |
| 817 | 2-(cyclopropanecarboxamido)-N-(2-methyl-3-(trifluoromethyl)benzyl)pyrimidine-4-carboxamide | | 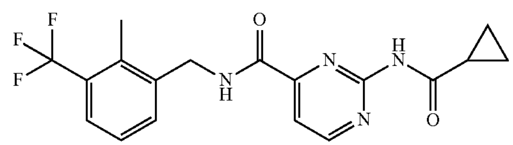 [SMILES: Cc1c(CNC(=O)c2ccnc(NC(=O)C3CC3)n2)cccc1C(F)(F)F] | | | 377.2 | 1.64 |
| 818 | 2-acetamido-N-(2-methoxy-3-(trifluoromethyl)benzyl)isonicotinamide | | 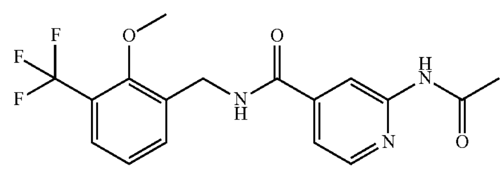 [SMILES: COc1c(CNC(=O)c2ccnc(NC(C)=O)c2)cccc1C(F)(F)F] | | | 366.3 | 1.51 |

TABLE 1-continued

| Example | Chirality | Structure | Name | Amine part | Carboxylic part | Observed MS | Retention time (min) |
|---|---|---|---|---|---|---|---|
| 819 | | 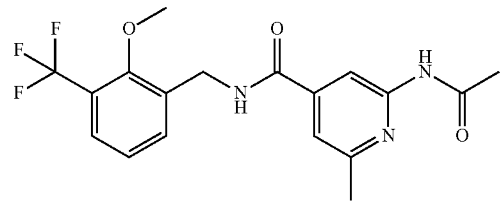 [SMILES: COc1c(CNC(=O)c2cc(C)nc(NC(C)=O)c2)cccc1C(F)(F)F] | 2-acetamido-N-(2-methoxy-3-(trifluoromethyl)benzyl)-6-methylisonicotinamide | | | 380.2 | 1.57 |
| 820 | | 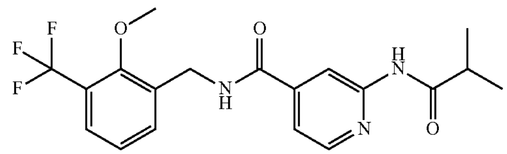 | 2-isobutyramido-N-(2-methoxy-3-(trifluoromethyl)benzyl)isonicotinamide | | | 394.3 | 1.68 |
| 821 | | 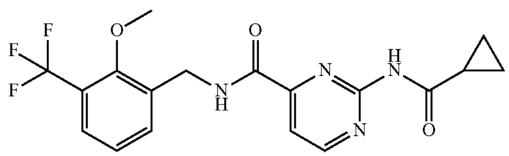 [SMILES: COc1c(CNC(=O)c2ccnc(NC(=O)C3CC3)n2)cccc1C(F)(F)F] | 2-(cyclopropanecarboxamido)-N-(2-methoxy-3-(trifluoromethyl)benzyl)pyrimidine-4-carboxamide | | | 393.3 | 1.59 |
| 822 | | 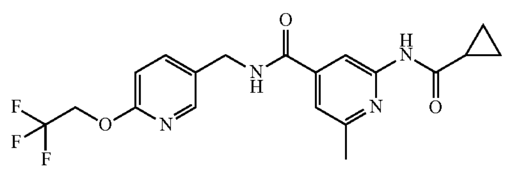 [SMILES: Cc1cc(C(=O)NCc2ccc(OCC(F)(F)F)nc2)cc(NC(=O)C2CC2)n1] | 2-(cyclopropanecarboxamido)-6-methyl-N-((6-(2,2,2-trifluoroethoxy)pyridin-3-yl)methyl)isonicotinamide | | | 407.2 | 1.63 |
| 823 | single enantiomer | 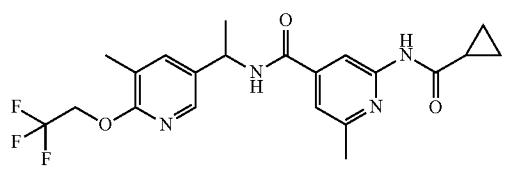 | 2-(cyclopropanecarboxamido)-6-methyl-N-(1-(5-methyl-6-(2,2,2-trifluoroethoxy)pyridin-3-yl)ethyl)isonicotinamide | Amine-17 | | 435.3 | 1.77 |

TABLE 1-continued

| Example | Chirality | Name | Structure | Amine part | Carboxylic part | Observed MS | Retention time (min) |
|---|---|---|---|---|---|---|---|
| 824 | | 2-(cyclopropane-carboxamido)-6-methyl-N-((5-methyl-6-(2,2,2-trifluoroethoxy)pyridin-3-yl)methyl)iso-nicotinamide | 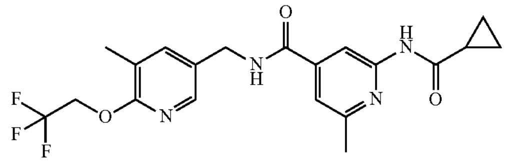 [SMILES: Cc1cc(C(=O)NCc2cnc(OCC(F)(F)F)c(C)c2)cc(NC(=O)C2CC2)n1] | Amine-47 | | 421.3 | 1.72 |
| 825 | | 2-(cyclopropane-carboxamido)-N-((5-ethyl-6-(2,2,2-trifluoroethoxy)pyridin-3-yl)methyl)-6-methylisonic-otinamide | 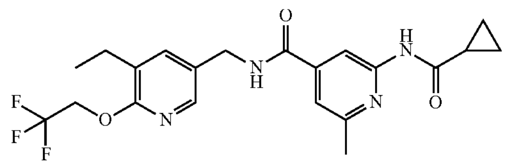 [SMILES: CCc1cc(CNC(=O)c2cc(C)nc(NC(=O)C3CC3)c2)cnc1OCC(F)(F)F] | Amine-61 | | 435.3 | 1.8 |
| 826 | | N-((5-chloro-6-(2,2-difluoroethoxy)pyridin-3-yl)methyl)-2-(cyclopropane-carboxamido)-6-methylisonic-otinamide | 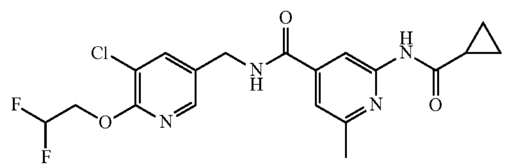 | Amine-52 | | 423.2 | 1.64 |
| 827 | | 2-(cyclopropane-carboxamido)-6-methyl-N-((6-(2,3,3,3-pentafluoropro-poxy)pyridin-3-yl)methyl)iso-nicotinamide | 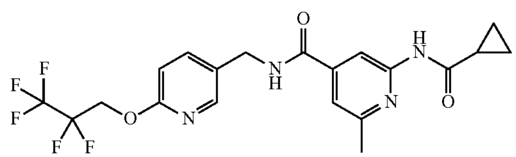 [SMILES: Cc1cc(C(=O)NCc2ccc(OCC(F)(F)C(F)(F)F)nc2)cc(NC(=O)C2CC2)n1] | Amine-56 | | 457.3 | 1.76 |

TABLE 1-continued

| Example | Name | Chirality | Structure | Amine part | Carboxylic part | Observed MS | Retention time (min) |
|---|---|---|---|---|---|---|---|
| 828 | 2-(cyclopropanecarboxamido)-6-tetrafluoropropoxypyridin-3-yl)ethyl)isonicotinamide | single enantiomer | 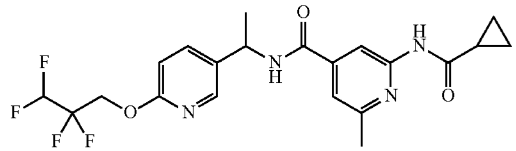 [SMILES: Cc1cc(C(=O)NC(C)c2ccc(OCC(F)(F)C(F)F)nc2)cc(NC(=O)C2CC2)n1] | Amine-57 | | 453.3 | 1.68 |
| 829 | 2-(cyclopropanecarboxamido)-N-((6-(2,2-difluoropropoxy)pyridin-3-yl)methyl)-6-methylisonicotinamide | | 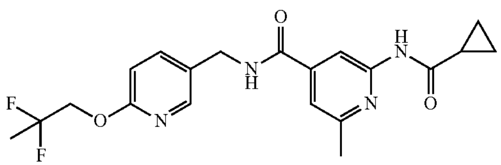 | Amine-62 | | 403.3 | 1.58 |
| 830 | 2-(cyclopropanecarboxamido)-6-methyl-N-((6-(2,2,3,3-tetrafluoropropoxy)pyridin-3-yl)methyl)isonicotinamide | | 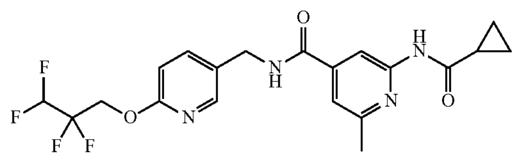 | Amine-54 | | 439.3 | 1.63 |
| 831 | 2-(cyclopropanecarboxamido)-6-methyl-N-(3-methyl-4-(2,2,2-trifluoroethoxy)benzyl)isonicotinamide | | 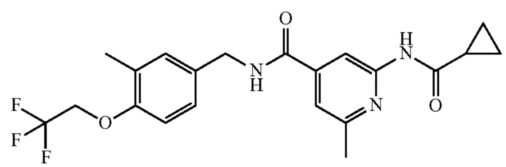 | Amine-70 | | 420.3 | 1.74 |

TABLE 1-continued

| Example | Name | Chirality | Structure | Amine part | Carboxylic part | Observed MS | Retention time (min) |
|---|---|---|---|---|---|---|---|
| 832 | N-(1-(5-chloro-6-(2,2,2-trifluoroethoxy)pyridin-3-yl)ethyl)-2-(cyclopropanecarboxamido)-6-methylisonicotinamide | single enantiomer | 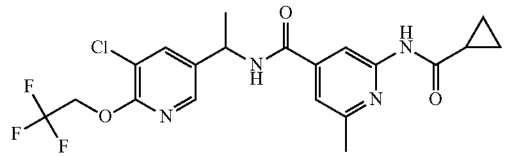 [SMILES: Cc1cc(C(=O)NC(C)c2cnc(OCC(F)(F)F)c(Cl)c2)cc(NC(=O)C2CC2)n1] | Amine-5 | | 455.3 | 1.79 |
| 833 | 2-(cyclopropanecarboxamido)-N-(1-(5-fluoro-6-(2,2,2-trifluoroethoxy)pyridin-3-yl)ethyl)-6-methylisonicotinamide | single enantiomer | 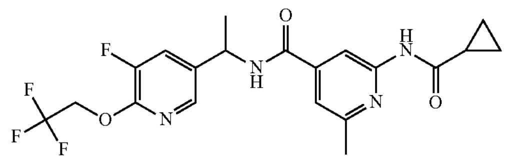 | Amine-12 | | 439.3 | 1.72 |
| 834 | 2-(cyclopropanecarboxamido)-N-(1-(5-methoxy-6-(2,2,2-trifluoroethoxy)pyridin-3-yl)ethyl)-6-methylisonicotinamide | single enantiomer | 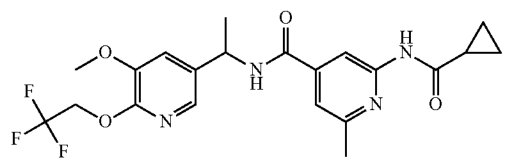 [SMILES: COc1cc(C(C)NC(=O)c2cc(C)nc(NC(=O)C3CC3)c2)cnc1OCC(F)(F)F] | Amine-22 | | 451.3 | 1.66 |
| 835 | 2-(cyclopropanecarboxamido)-6-methyl-N-((2-methyl-6-(2,2,2-trifluoroethoxy)pyridin-3-yl)methyl)isonicotinamide | | 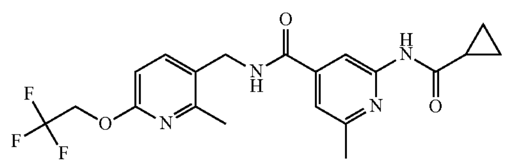 [SMILES: Cc1cc(C(=O)NCc2ccc(OCC(F)(F)F)nc2C)cc(NC(=O)C2CC2)n1] | Amine-27 | | 421.3 | 1.72 |

TABLE 1-continued

| Example | Name | Chirality | Structure | Amine part | Carboxylic part | Observed MS | Retention time (min) |
|---|---|---|---|---|---|---|---|
| 836 | 2-(cyclopropanecarboxamido)-6-methyl-N-(3-(trifluoromethoxy)benzyl)isonicotinamide | | 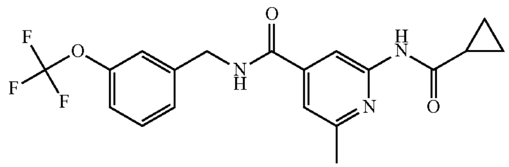 [SMILES: Cc1cc(C(=O)NCc2cccc(OC(F)(F)F)c2)cc(NC(=O)C2CC2)n1] | | | 392.3 | 1.71 |
| 837 | 2-(cyclopropanecarboxamido)-6-methyl-N-(1-(6-(2,2,3,3,3-pentafluoropropoxy)pyridin-3-yl)ethyl)isonicotinamide | single enantiomer | 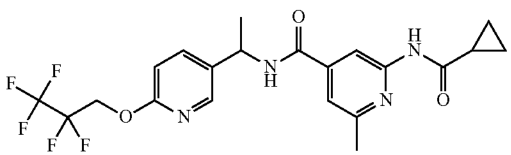 | Amine-60 | | 471.3 | 1.81 |
| 838 | (R)-2-(cyclopropanecarboxamido)-6-methyl-N-(1-(3-(trifluoromethyl)phenyl)ethyl)isonicotinamide | single enantiomer | 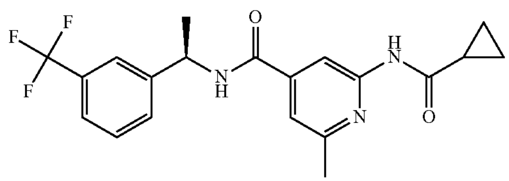 [SMILES: Cc1cc(C(=O)N[C@H](C)c2cccc(C(F)(F)F)c2)cc(NC(=O)C2CC2)n1] | | | 390.3 | 1.73 |
| 839 | 2-(cyclopropanecarboxamido)-6-methyl-N-(1-(3-(trifluoromethoxy)phenyl)ethyl)isonicotinamide | single enantiomer | 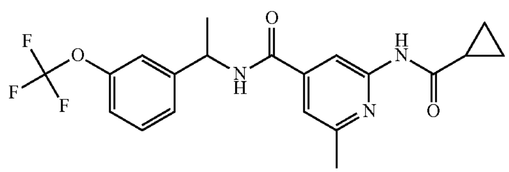 [SMILES: Cc1cc(C(=O)NC(C)c2cccc(OC(F)(F)F)c2)cc(NC(=O)C2CC2)n1] | Amine-9 | | 406.3 | 1.76 |
| 840 | N-(1-(5-ethoxy-6-(2,2,2-trifluoroethoxy)pyridin-3-yl)ethyl)-2-propionamidoisonicotinamide | single enantiomer | 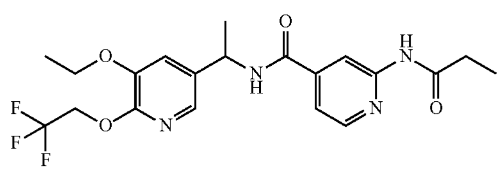 | Amine-38 | | 439.2 | 1.63 |

TABLE 1-continued

| Example | Name | Chirality | Structure | Amine part | Carboxylic part | Observed MS | Retention time (min) |
|---|---|---|---|---|---|---|---|
| 841 | N-(1-(5-ethoxy-6-(2,2,2-trifluoroethoxy)pyridin-3-yl)ethyl)-2-isobutyramido-isonicotinamide | single enantiomer | 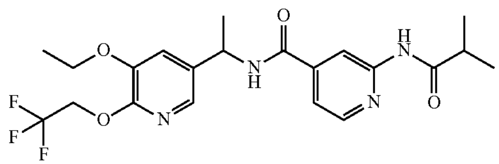 [SMILES: CCOc1cc(C(C)NC(=O)c2ccnc(NC(=O)C(C)C)c2)cnc1OCC(F)(F)F] | Amine-38 | | 453.2 | 1.7 |
| 842 | 2-acetamido-6-methyl-N-((6-(2,2,2-trifluoroethoxy)pyridin-3-yl)methyl)pyrimidine-4-carboxamide | | 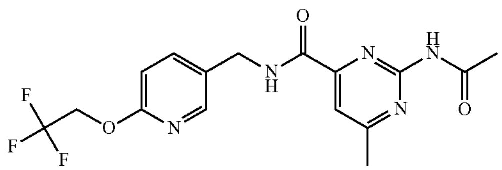 [SMILES: CC(=O)Nc1nc(C)cc(C(=O)NCc2ccc(OCC(F)(F)F)nc2)n1] | | | 382.3 | 1.45 |
| 843 | N-(2-fluoro-5-(trifluoromethyl)benzyl)-6-methyl-2-propionamido-pyrimidine-4-carboxamide | | 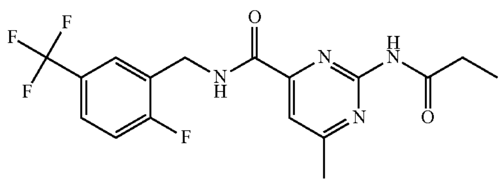 [SMILES: CCC(=O)Nc1nc(C)cc(C(=O)NCc2cc(C(F)(F)F)ccc2F)n1] | | | 383.2 | 1.6 |
| 844 | 2-acetamido-6-methyl-N-(3-(trifluoromethoxy)benzyl)pyrimidine-4-carboxamide | | 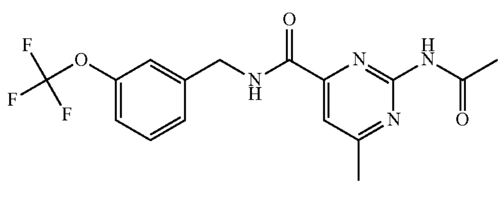 [SMILES: CC(=O)Nc1nc(C)cc(C(=O)NCc2cccc(OC(F)(F)F)c2)n1] | | | 367.3 | 1.54 |

TABLE 1-continued

| Example | Chirality | Name | Structure | Amine part | Carboxylic part | Observed MS | Retention time (min) |
|---|---|---|---|---|---|---|---|
| 845 | | 2-acetamido-6-methyl-N-(3-(trifluoromethyl)benzyl)pyrimidine-4-carboxamide | 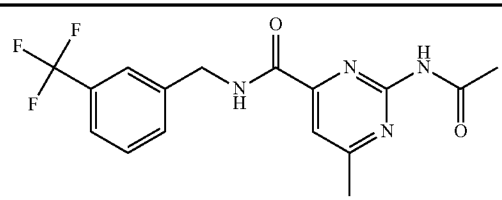 | | | 351.3 | 1.5 |
| 846 | single enantiomer | 2-acetamido-6-methyl-N-(1-(4-(2,2,2-trifluoroethoxy)phenyl)ethyl)pyrimidine-4-carboxamide | 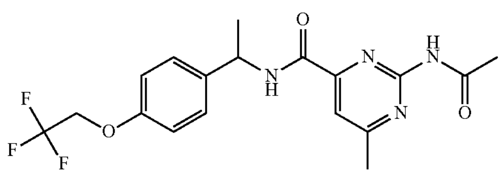 [SMILES: CC(=O)Nc1nc(C)cc(C(=O)NC(C)c2ccc(OCC(F)(F)F)cc2)n1] | Amine-18 | | 395.3 | 1.56 |
| 847 | single enantiomer | N-(1-(5-(hydroxymethyl)-6-(2,2,2-trifluoroethoxy)pyridin-3-yl)ethyl)-2-isobutyramido-isonicotinamide | 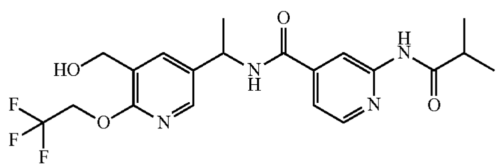 [SMILES: CC(C)C(=O)Nc1cc(C(=O)NC(C)c2cnc(OCC(F)(F)F)c(CO)c2)ccn1] | Amine-46 | | 439.3 | 1.49 |
| 848 | single enantiomer | 2-acetamido-6-methyl-N-(1-(3-(2,2,2-trifluoroethoxy)phenyl)ethyl)pyrimidine-4-carboxamide | 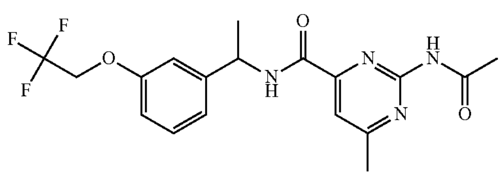 [SMILES: CC(=O)Nc1nc(C)cc(C(=O)NC(C)c2cccc(OCC(F)(F)F)c2)n1] | Amine-16 | | 395.3 | 1.57 |

TABLE 1-continued

| Example | Name | Chirality | Structure | Amine part | Carboxylic part | Observed MS | Retention time (min) |
|---|---|---|---|---|---|---|---|
| 849 | 2-(cyclopropanecarboxamido)-N-(1-(6-(2,2-difluoroethoxy)pyridin-3-yl)ethyl)pyrimidine-4-carboxamide | single enantiomer | 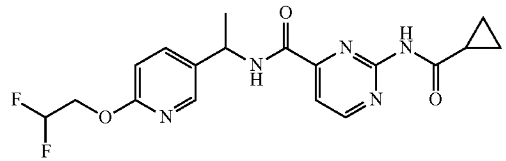 [SMILES: CC(NC(=O)c1ccnc(NC(=O)C2CC2)n1)c1ccc(OCC(F)F)nc1] | Amine-32 | | 390.3 | 1.47 |
| 850 | 2-(cyclopropanecarboxamido)-N-((5-fluoro-2-methoxy-6-(2,2,2-trifluoroethoxy)pyridin-3-yl)methyl)pyrimidine-4-carboxamide | | 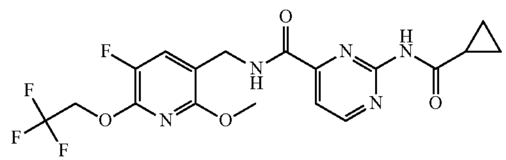 [SMILES: COc1nc(OCC(F)(F)F)c(F)cc1CNC(=O)c1ccnc(NC(=O)C2CC2)n1] | Amine-44 | | 442.2 | 1.65 |
| 851 | 2-(cyclopropanecarboxamido)-N-((6-(2,2-difluoroethoxy)-5-methylpyridin-3-yl)methyl)-6-methylisonicotinamide | | 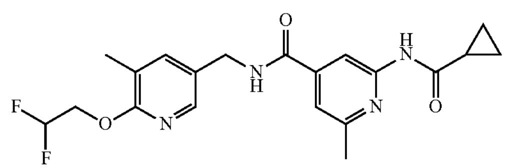 | Amine-64 | | 403.3 | 1.61 |
| 852 | 2-(cyclopropanecarboxamido)-6-methyl-N-(3-(trifluoromethyl)benzyl)isonicotinamide | | 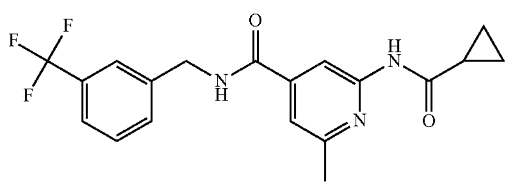 | | | 376.3 | 1.68 |
| 853 | 2-(1-methylcyclopropanecarboxamido)-N-((6-(2,2,2-trifluoroethoxy)pyridin-3-yl)methyl)isonicotinamide | | 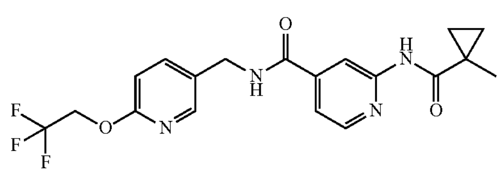 [SMILES: CC1(C(=O)Nc2cc(C(=O)NCc3ccc(OCC(F)(F)F)nc3)ccn2)CC1] | | | 407.3 | 1.65 |

TABLE 1-continued

| Example | Name | Chirality | Structure | Amine part | Carboxylic part | Observed MS | Retention time (min) |
|---|---|---|---|---|---|---|---|
| 854 | N-(1-(5-methyl-6-(2,2,2-trifluoroethoxy)pyridin-3-yl)ethyl)-2-(1-methylcyclopropanecarboxamido)iso | single enantiomer | 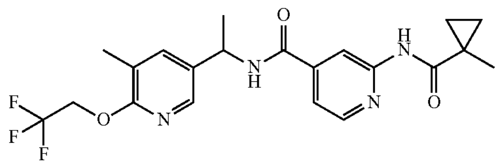 [SMILES: Cc1cc(C(C)NC(=O)c2ccnc(NC(=O)C3(C)CC3)c2)cnc1OCC(F)(F)F] | Amine-17 | | 435.3 | 1.79 |
| 855 | N-((5-methyl-6-(2,2,2-trifluoroethoxy)pyridin-3-yl)methyl)-2-(1-methylcyclopropanecarboxamido)iso | | 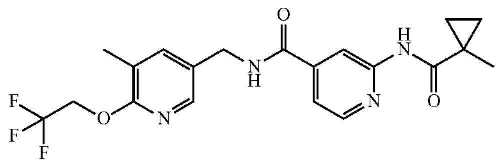 [SMILES: Cc1cc(CNC(=O)c2ccnc(NC(=O)C3(C)CC3)c2)cnc1OCC(F)(F)F] | Amine-47 | | 421.3 | 1.74 |
| 856 | N-(1-(5-chloro-6-(2,2,2-trifluoroethoxy)pyridin-3-yl)ethyl)-2-(1-methylcyclopropanecarboxamido)iso | single enantiomer | 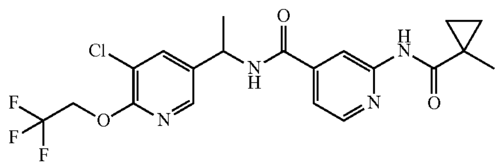 [SMILES: CC(NC(=O)c1ccnc(NC(=O)C2(C)CC2)c1)c1cnc(OCC(F)(F)F)c(Cl)c1] | Amine-5 | | 455.3 | 1.81 |
| 857 | N-((5-chloro-6-(2,2,2-trifluoroethoxy)pyridin-3-yl)methyl)-2-(1-methylcyclopropanecarboxamido)iso | | 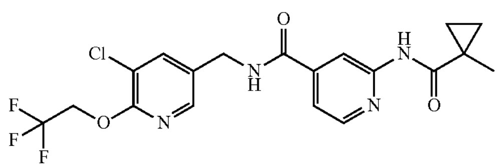 | Amine-19 | | 441.2 | 1.76 |
| 858 | 2-(1-methylcyclopropanecarboxamido)-N-(3-(trifluoromethoxy)benzyl)isonicotina | | 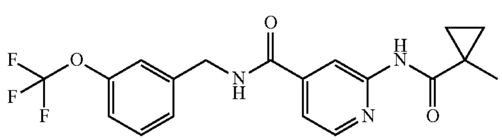 [SMILES: CC1(C(=O)Nc2cc(C(=O)NCc3cccc(OC(F)(F)F)c3)ccn2)CC1] | | | 392.3 | 1.74 |

TABLE 1-continued

| Example | Name | Chirality | Structure | Amine part | Carboxylic part | Observed MS | Retention time (min) |
|---|---|---|---|---|---|---|---|
| 859 | 2-acetamido-N-(1-(4-(2,2-difluoroethoxy)-3-methylphenyl)ethyl)isonicotinamide | single enantiomer | 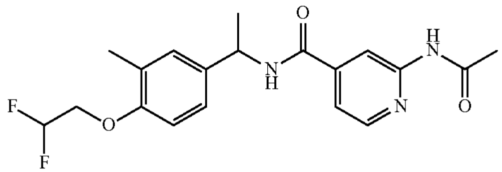 | Amine-68 | | 376.3 | 1.52 |
| 860 | N-(1-(4-(2,2-difluoroethoxy)-3-methylphenyl)ethyl)-2-propionamidoisonicotinamide | single enantiomer | 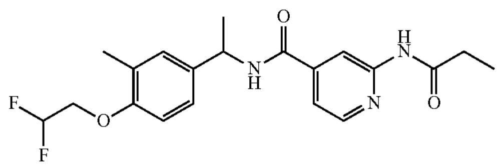 | Amine-68 | | 390.3 | 1.6 |
| 861 | 2-cyclopropanecarboxamido-N-(1-(4-(2,2-difluoroethoxy)-3-methylphenyl)ethyl)isonicotinamide | single enantiomer | 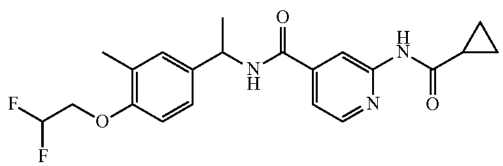 [SMILES: Cc1cc(C(C)NC(=O)c2ccnc(NC(=O)C3CC3)c2)ccc1OCC(F)F] | Amine-68 | | 402.4 | 1.64 |
| 862 | N-(1-(4-(2,2-difluoroethoxy)-3-methylphenyl)ethyl)-2-isobutyramidoisonicotinamide | single enantiomer | 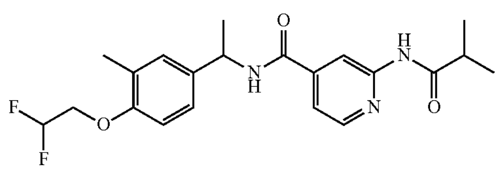 | Amine-68 | | 404.3 | 1.68 |
| 863 | 2-(cyclopropanecarboxamido)-N-(1-(4-(2,2-difluoroethoxy)-3-methylphenyl)ethyl)pyrimidine-4-carboxamide | single enantiomer | 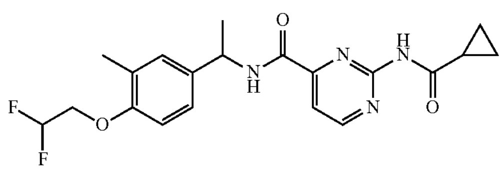 | Amine-68 | | 403.3 | 1.62 |

TABLE 1-continued

| Example | Name | Chirality | Structure | Amine part | Carboxylic part | Observed MS | Retention time (min) |
|---|---|---|---|---|---|---|---|
| 864 | 2-acetamido-N-(1-(4-(2,2-difluoroethoxy)-3-methylphenyl)ethyl)-6-methylisonicotinamide | single enantiomer | 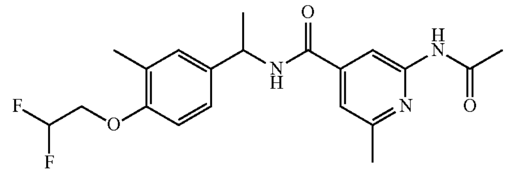 [SMILES: CC(=O)Nc1cc(C(=O)NC(C)c2ccc(OCC(F)F)c(C)c2)cc(C)n1] | Amine-68 | | 390.1 | 1.58 |
| 865 | N-(1-(4-(2,2-difluoroethoxy)-3-methylphenyl)ethyl)-2-isobutyramido-6-methylisonicotinamide | single enantiomer | 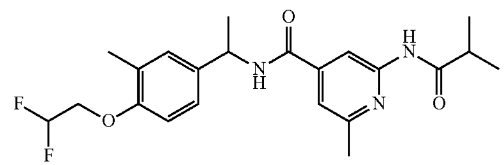 [SMILES: Cc1cc(C(=O)NC(C)c2ccc(OCC(F)F)c(C)c2)cc(NC(=O)C(C)C)n1] | Amine-68 | | 418.3 | 1.73 |
| 866 | 2-(cyclopropanecarboxamido)-N-(1-(4-(2,2-difluoroethoxy)-3-methylphenyl)ethyl)-6-methylisonicotinamide | single enantiomer | 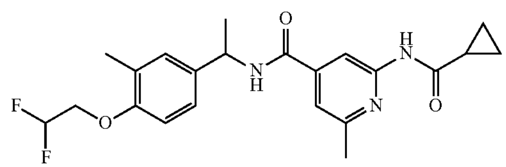 | Amine-68 | | 416.3 | 1.7 |
| 867 | N-(2-methoxy-4-(trifluoromethoxy)benzyl)-2-propionamidoisonicotinamide | | 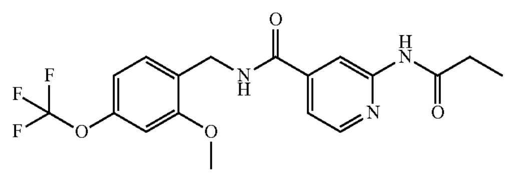 [SMILES: CCC(=O)Nc1cc(C(=O)NCc2ccc(OC(F)(F)F)cc2OC)ccn1] | | | 396.3 | 1.65 |
| 868 | 2-(cyclopropanecarboxamido)-N-(2-methoxy-4-(trifluoromethoxy)benzyl)isonicotinamide | | 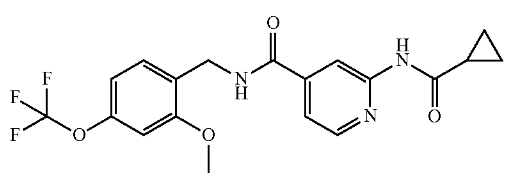 [SMILES: COc1cc(OC(F)(F)F)ccc1CNC(=O)c1ccnc(NC(=O)C2CC2)c1] | | | 408.3 | 1.69 |

TABLE 1-continued

| Example | Name | Chirality | Structure | Amine part | Carboxylic part | Observed MS | Retention time (min) |
|---|---|---|---|---|---|---|---|
| 869 | 2-isobutyramido-N-(2-methoxy-4-(trifluoromethoxy)benzyl)isonicotinamide | | 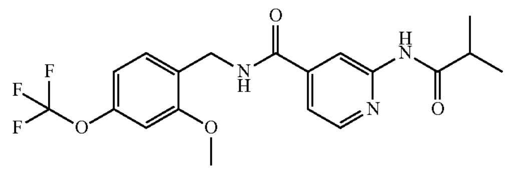 [SMILES: COc1cc(OC(F)(F)F)ccc1CNC(=O)c1ccnc(NC(=O)C(C)C)c1] | | | 410.3 | 1.73 |
| 870 | 2-acetamido-N-(2-methoxy-4-(trifluoromethoxy)benzyl)-6-methylisonicotinamide | | 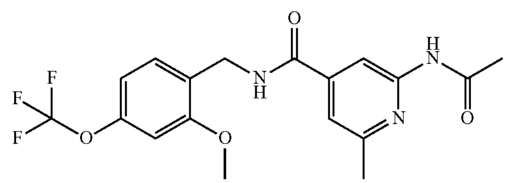 [SMILES: COc1cc(OC(F)(F)F)ccc1CNC(=O)c1cc(C)nc(NC(C)=O)c1] | | | 396.3 | 1.62 |
| 871 | 2-isobutyramido-N-(2-methoxy-4-(trifluoromethoxy)benzyl)-6-methylisonicotinamide | | 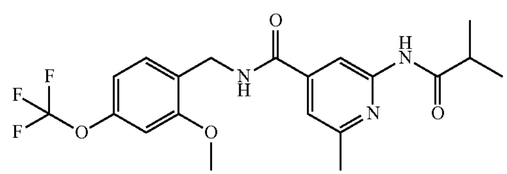 [SMILES: COc1cc(OC(F)(F)F)ccc1CNC(=O)c1cc(C)nc(NC(=O)C(C)C)c1] | | | 424.3 | 1.79 |
| 872 | 2-(cyclopropanecarboxamido)-N-(2-methoxy-4-(trifluoromethoxy)benzyl)pyrimidine-4-carboxamide | | 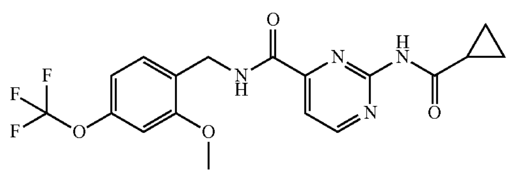 [SMILES: COc1cc(OC(F)(F)F)ccc1CNC(=O)c1ccnc(NC(=O)C2CC2)n1] | | | 409.3 | 1.66 |

TABLE 1-continued

| Example | Chirality | Name | Structure | Amine part | Carboxylic part | Observed MS | Retention time (min) |
|---|---|---|---|---|---|---|---|
| 873 | | 2-(cyclopropane-carboxamido)-N-(2-methoxy-4-(trifluoromethoxy)benzyl)-6-methylpyrimidine-4-carboxamide | 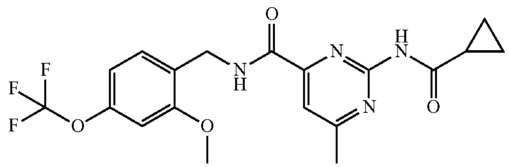 [SMILES: COc1cc(OC(F)(F)F)ccc1CNC(=O)c1cc(C)nc(NC(=O)C2CC2)n1] | | | 423.2 | 1.73 |
| 874 | | N-(4-fluoro-3-(trifluoromethyl)benzyl)-2-isobutyramido-6-methylisonicotinamide | 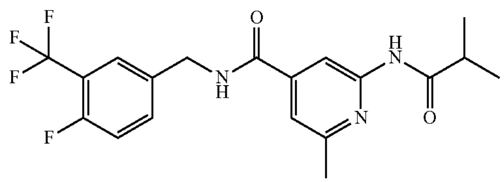 [SMILES: Cc1cc(C(=O)NCc2ccc(F)c(C(F)(F)F)c2)cc(NC(=O)C(C)C)n1] | | | 396.3 | 1.74 |
| 875 | | N-(3-fluoro-5-(trifluoromethyl)benzyl)-2-isobutyramido-6-methylisonicotinamide | 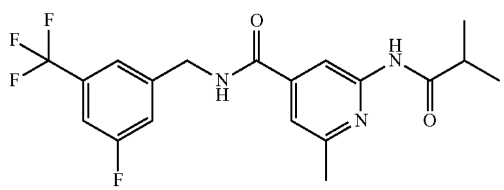 | | | 396.3 | 1.76 |
| 876 | | N-(2-fluoro-3-(trifluoromethyl)benzyl)-2-isobutyramido-6-methylisonicotinamide | 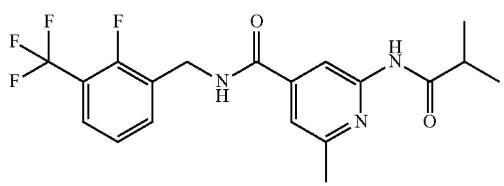 | | | 396.3 | 1.74 |

TABLE 1-continued

| Example | Name | Chirality | Structure | Amine part | Carboxylic part | Observed MS | Retention time (min) |
|---|---|---|---|---|---|---|---|
| 877 | N-(4-chloro-3-(trifluoromethyl)benzyl)-2-isobutyramido-6-methylisonicotinamide | | 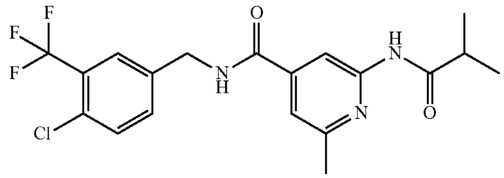 [SMILES: Cc1cc(C(=O)NCc2ccc(Cl)c(C(F)(F)F)c2)cc(NC(=O)C(C)C)n1] | | | 412.2 | 1.81 |
| 878 | N-(2-chloro-3-(trifluoromethyl)benzyl)-2-isobutyramido-6-methylisonicotinamide | | 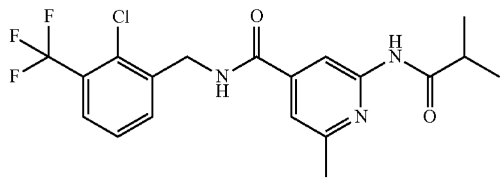 [SMILES: Cc1cc(C(=O)NCc2cccc(C(F)(F)F)c2Cl)cc(NC(=O)C(C)C)n1] | | | 412.3 | 1.79 |
| 879 | 2-isobutyramido-6-methyl-N-(2-methyl-3-(trifluoromethyl)benzyl)isonicotinamide | | 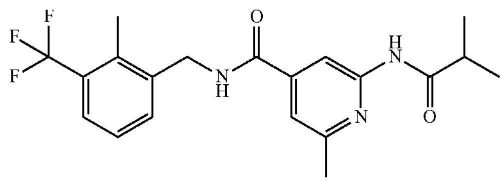 [SMILES: Cc1cc(C(=O)NCc2cccc(C(F)(F)F)c2C)cc(NC(=O)C(C)C)n1] | | | 392.3 | 1.78 |
| 880 | 2-isobutyramido-N-(2-methoxy-3-(trifluoromethyl)benzyl)-6-methylisonicotinamide | | 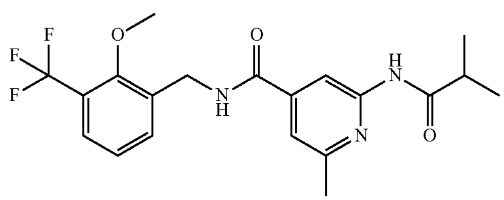 [SMILES: COc1c(CNC(=O)c2cc(C)nc(NC(=O)C(C)C)c2)cccc1C(F)(F)F] | | | 408.3 | 1.74 |

| Example | Name | Chirality | Structure | Amine part | Carboxylic part | Observed MS | Retention time (min) |
|---|---|---|---|---|---|---|---|
| 881 | 2-isobutyramido-6-methyl-N-(1-(3-(2,2,2-trifluoroethoxy)phenyl)ethyl)isonicotinamide | single enantiomer | 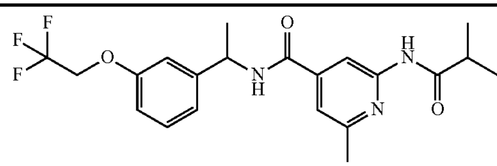 | Amine-16 | | 422.3 | 1.75 |
| 882 | N-(3-methoxy-4-(2,2,2-trifluoroethoxy)benzyl)-2-propionamido-isonicotinamide | | 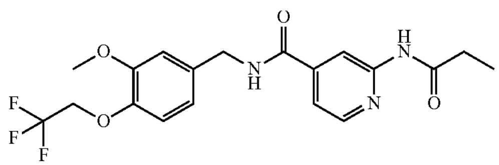 [SMILES: CCC(=O)Nc1cc(C(=O)NCc2ccc(OCC(F)(F)F)c(OC)c2)ccn1] | | | 410.3 | 1.54 |
| 883 | 2-isobutyramido-N-(3-methoxy-4-(2,2,2-trifluoroethoxy)benzyl)isonicotinamide | | 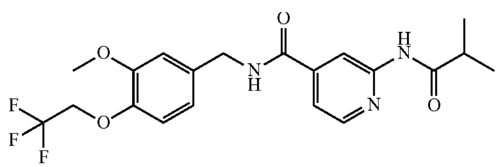 [SMILES: COc1cc(CNC(=O)c2ccnc(NC(=O)C(C)C)c2)ccc1OCC(F)(F)F] | | | 424.3 | 1.62 |
| 884 | 2-acetamido-N-(3-methoxy-4-(2,2,2-trifluoroethoxy)benzyl)-6-methylisonicotinamide | | 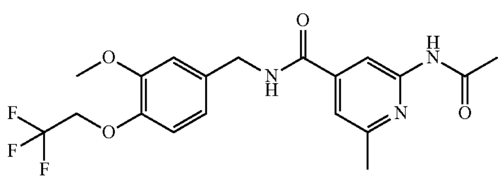 [SMILES: COc1cc(CNC(=O)c2cc(C)nc(NC(C)=O)c2)ccc1OCC(F)(F)F] | | | 410.2 | 1.51 |

TABLE 1-continued

| Example | Name | Chirality | Structure | Amine part | Carboxylic part | Observed MS | Retention time (min) |
|---|---|---|---|---|---|---|---|
| 885 | 2-isobutyramido-N-(3-methoxy-4-(2,2,2-trifluoroethoxy)benzyl)-6-methylisonicotinamide | | 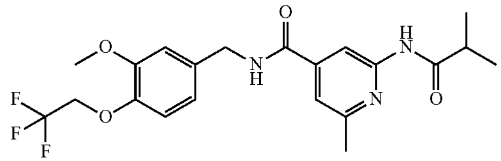 | | | 438.3 | 1.67 |
| 886 | 2-(cyclopropanecarboxamido)-N-(3-methoxy-4-(2,2,2-trifluoroethoxy)benzyl)-6-methylpyrimidine-4-carboxamide | | 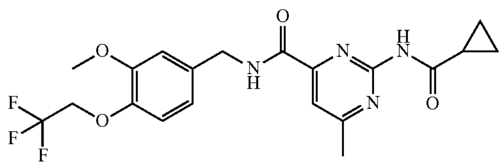 [SMILES: COc1cc(CNC(=O)c2cc(C)nc(NC(=O)C3CC3)n2)ccc1OCC(F)(F)F] | | | 437.2 | 1.6 |
| 887 | N-(1-(6-(2,2-difluoroethoxy)-5-ethylpyridin-3-yl)ethyl)-2-propionamidoisonicotinamide | single enantiomer | 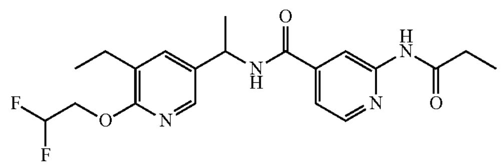 | Amine-74 | | 405.3 | 1.65 |
| 888 | 2-(cyclopropanecarboxamido)-N-(1-(6-(2,2-difluoroethoxy)-5-ethylpyridin-3-yl)ethyl)isonicotinamide | single enantiomer | 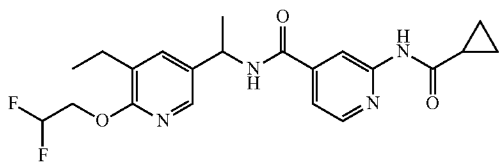 [SMILES: CCc1cc(C(C)NC(=O)c2ccnc(NC(=O)C3CC3)c2)cnc1OCC(F)F] | Amine-74 | | 417.3 | 1.68 |
| 889 | N-(1-(6-(2,2-difluoroethoxy)-5-ethylpyridin-3-yl)ethyl)-2-isobutyramidoisonicotinamide | single enantiomer | 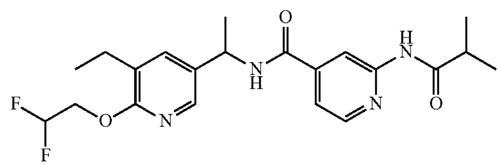 [SMILES: CCc1cc(C(C)NC(=O)c2ccnc(NC(=O)C(C)C)c2)cnc1OCC(F)F] | Amine-74 | | 419.3 | 1.72 |

TABLE 1-continued

| Example | Name | Chirality | Structure | Amine part | Carboxylic part | Observed MS | Retention time (min) |
|---|---|---|---|---|---|---|---|
| 890 | 2-(cyclopropanecarboxamido)-N-(1-(6-(2,2-difluoroethoxy)-5-ethylpyridin-3-yl)ethyl)pyrimidine-4-carboxamide | single enantiomer | 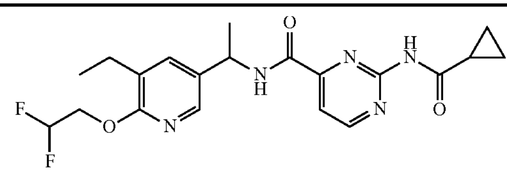 | Amine-74 | | 418.3 | 1.65 |
| 891 | 2-acetamido-N-(1-(6-(2,2-difluoroethoxy)-5-ethylpyridin-3-yl)ethyl)-6-methylisonicotinamide | single enantiomer | 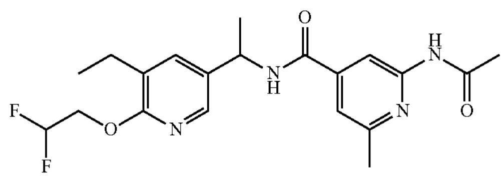 | Amine-74 | | 405.3 | 1.62 |
| 892 | 2-(cyclopropanecarboxamido)-N-(1-(6-(2,2-difluoroethoxy)-5-ethylpyridin-3-yl)ethyl)-6-methylisonicotinamide | single enantiomer | 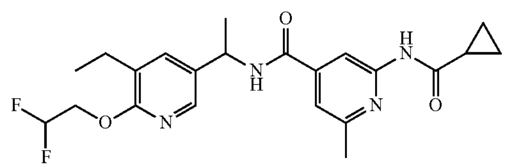 [SMILES: CCc1cc(C(C)NC(=O)c2cc(C)nc(NC(=O)C3CC3)c2)cnc1OCC(F)F] | Amine-74 | | 431.3 | 1.74 |
| 893 | N-(1-(6-(2,2-difluoroethoxy)-5-ethylpyridin-3-yl)ethyl)-2-isobutyramido-6-methylisonicotinamide | single enantiomer | 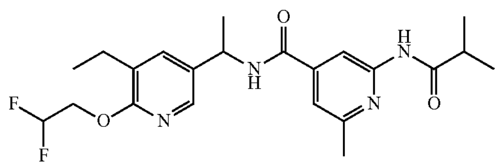 [SMILES: CCc1cc(C(C)NC(=O)c2cc(C)nc(NC(=O)C(C)C)c2)cnc1OCC(F)F] | Amine-74 | | 433.3 | 1.78 |

TABLE 1-continued

| Example | Name | Chirality | Structure | Amine part | Carboxylic part | Observed MS | Retention time (min) |
|---|---|---|---|---|---|---|---|
| 894 | 2-(cyclopropanecarboxamido)-N-(1-(6-(2,2-difluoroethoxy)-5-ethylpyridin-3-yl)ethyl)-6-methylpyrimidine-4-carboxamide | single enantiomer | 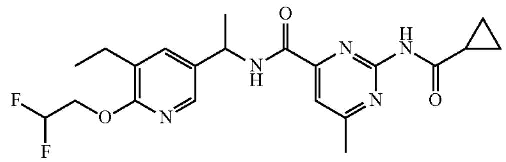 | Amine-74 | | 432.3 | 1.72 |
| 895 | N-((5-bromo-6-(2,2,2-trifluoroethoxy)pyridin-3-yl)methyl)-2-propionamidoisonicotinamide | | 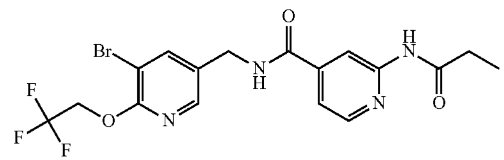 [SMILES: CCC(=O)Nc1cc(C(=O)NCc2cnc(OCC(F)(F)F)c(Br)c2)ccn1] | Amine-67 | | 459.1 | 1.65 |
| 896 | N-((5-bromo-6-(2,2,2-trifluoroethoxy)pyridin-3-yl)methyl)-2-(cyclopropanecarboxamido)isonicotinamide | | 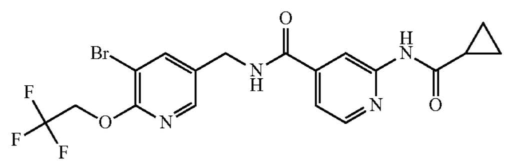 [SMILES: O=C(NCc1cnc(OCC(F)(F)F)c(Br)c1)c1ccnc(NC(=O)C2CC2)c1] | Amine-67 | | 471.1 | 1.69 |
| 897 | N-((5-bromo-6-(2,2,2-trifluoroethoxy)pyridin-3-yl)methyl)-2-isobutyramidoisonicotinamide | | 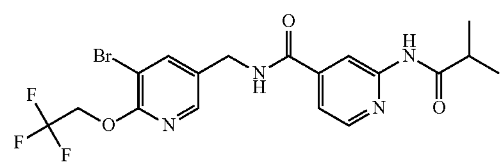 [SMILES: CC(C)C(=O)Nc1cc(C(=O)NCc2cnc(OCC(F)(F)F)c(Br)c2)ccn1] | Amine-67 | | 473.2 | 1.73 |

| Example | Name | Chirality | Structure | Amine part | Carboxylic part | Observed MS | Retention time (min) |
|---|---|---|---|---|---|---|---|
| 898 | N-((5-bromo-6-(2,2,2-trifluoroethoxy)pyridin-3-yl)methyl)-2-(cyclopropanecarboxamido)pyrimidine-4-carboxamide | | 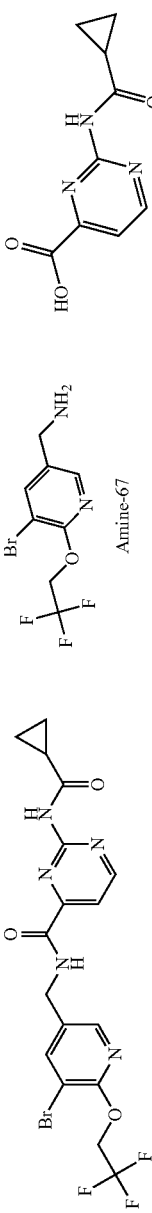 |  Amine-67 | 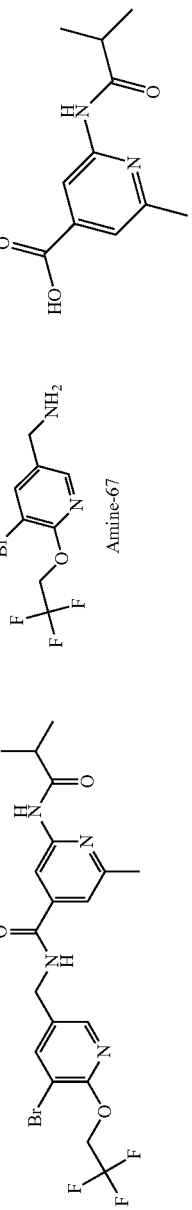 | 472.1 | 1.64 |
| 899 | 2-acetamido-N-((5-bromo-6-(2,2,2-trifluoroethoxy)pyridin-3-yl)methyl)-6-methylisonicotinamide | | 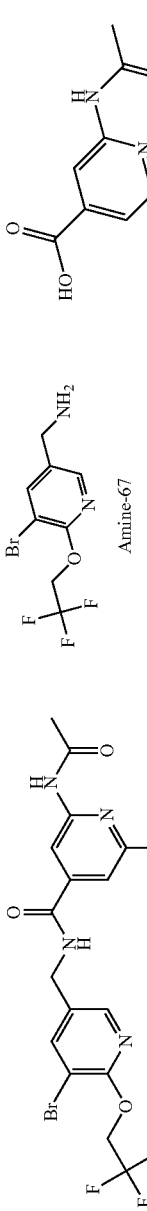 | 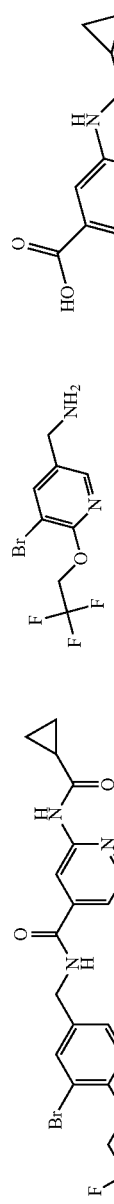 Amine-67 | 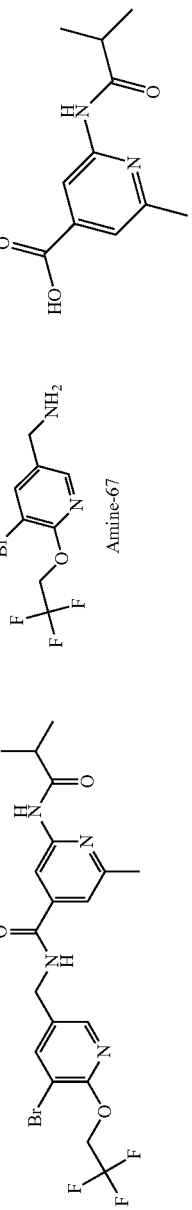 | 459.1 | 1.63 |
| 900 | N-((5-bromo-6-(2,2,2-trifluoroethoxy)pyridin-3-yl)methyl)-2-(cyclopropanecarboxamido)-6-methylisonicotinamide | | 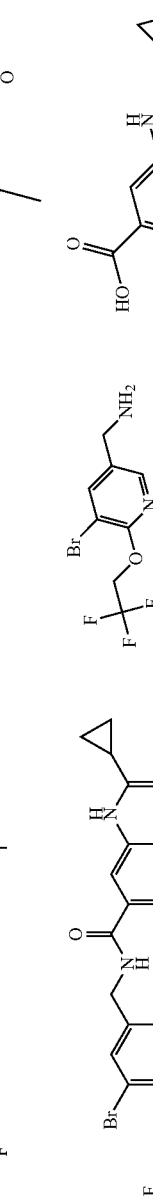 |  Amine-67 | 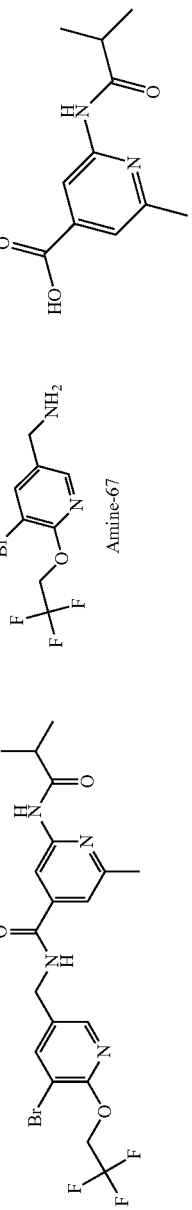 | 485.1 | 1.75 |
| 901 | N-((5-bromo-6-(2,2,2-trifluoroethoxy)pyridin-3-yl)methyl)-2-isobutyramido-6-methylisonicotinamide | | 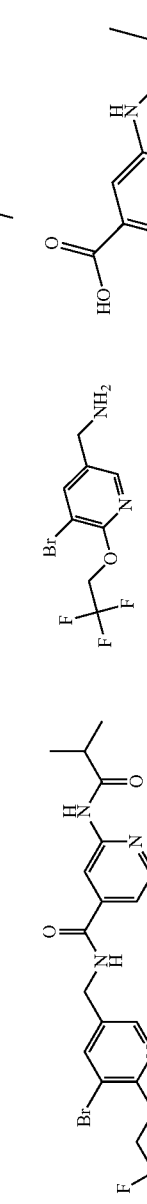 | 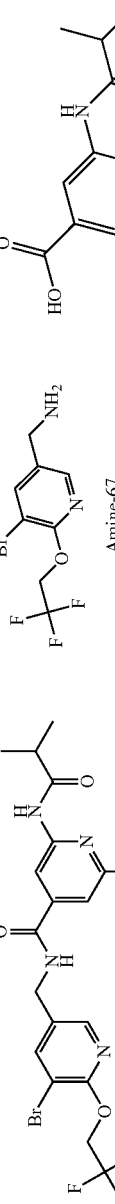 Amine-67 | 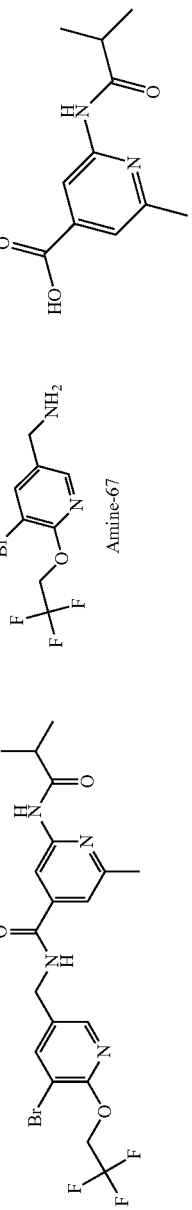 | 487.2 | 1.79 |

TABLE 1-continued

| Example | Name | Chirality | Structure | Amine part | Carboxylic part | Observed MS | Retention time (min) |
|---|---|---|---|---|---|---|---|
| 902 | N-((5-bromo-6-(2,2,2-trifluoroethoxy)pyridin-3-yl)methyl)-2-(cyclopropane-carboxamido)-6-methyl-pyrimidine-4-carboxamide | | 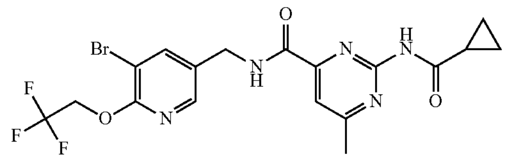 [SMILES: Cc1cc(C(=O)NCc2cnc(OCC(F)(F)F)c(Br)c2)nc(NC(=O)C2CC2)n1] | Amine-67 | | 486.2 | 1.71 |
| 903 | 2-acetamido-N-(1-(5-methyl-6-(2,2,3,3-tetrafluoropropoxy)pyridin-3-yl)ethyl)isonicotinamide | single enantiomer | 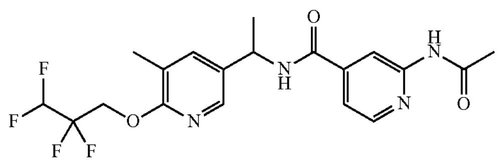 [SMILES: CC(=O)Nc1cc(C(=O)NC(C)c2cnc(OCC(F)(F)C(F)F)c(C)c2)ccn1] | Amine-75 | | 427.3 | 1.59 |
| 904 | 2-isobutyramido-N-(1-(5-methyl-6-(2,2,3,3-tetrafluoropropoxy)pyridin-3-yl)ethyl)isonicotinamide | single enantiomer | 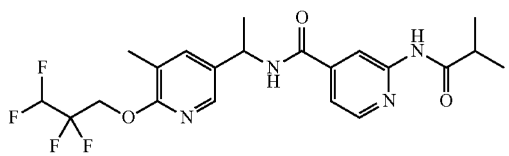 | Amine-75 | | 455.3 | 1.74 |
| 905 | 2-isobutyramido-6-methyl-N-(1-(5-methyl-6-(2,2,3,3-tetrafluoropropoxy)pyridin-3-yl)ethyl)isonicotinamide | single enantiomer | 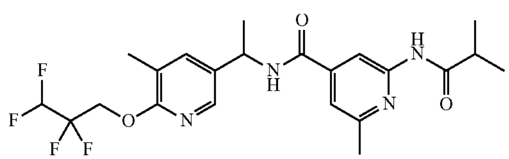 | Amine-75 | | 469.3 | 1.8 |

TABLE 1-continued

| Example | Name | Chirality | Structure | Amine part | Carboxylic part | Observed MS | Retention time (min) |
|---|---|---|---|---|---|---|---|
| 906 | 2-(cyclopropanecarboxamido)-N-(1-(5-methyl-6-(2,2,3,3-tetrafluoropropoxy)pyridin-3-yl)ethyl)pyrimidine-4-carboxamide | single enantiomer | 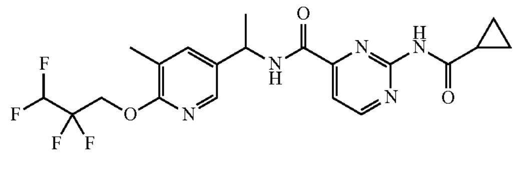 | Amine-75 | | 454.3 | 1.67 |
| 907 | 2-(cyclopropanecarboxamido)-6-methyl-N-(1-(5-methyl-6-(2,2,3,3-tetrafluoropropoxy)pyridin-3-yl)ethyl)pyrimidine-4-carboxamide | single enantiomer | 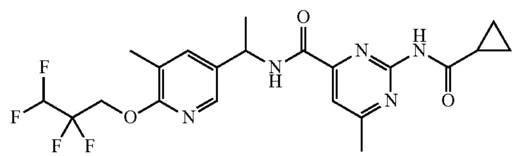 | Amine-75 | | 468.3 | 1.73 |
| 908 | 2-(2-hydroxy-2-methylpropanamido)-6-methyl-N-(1-(5-methyl-6-(2,2,3,3-tetrafluoropropoxy)pyridin-3-yl)isonicotinamide | single enantiomer | 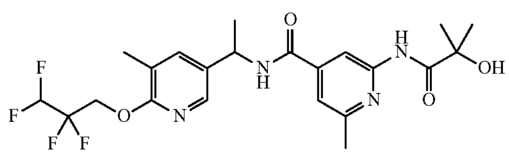 [SMILES: Cc1cc(C(=O)NC(C)c2cnc(OCC(F)(F)C(F)F)c(C)c2)cc(NC(=O)C(C)(C)O)n1] | Amine-75 | | 485.3 | 1.7 |
| 909 | 2-acetamido-N-((6-(2,2-difluoroethoxy)-5-ethylpyridin-3-yl)methyl)isonicotinamide | | 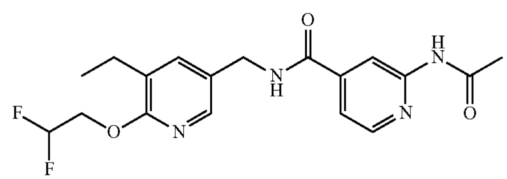 | Amine-76 | | 377.3 | 1.51 |

| Example | Name | Chirality | Structure | Amine part | Carboxylic part | Observed MS | Retention time (min) |
|---|---|---|---|---|---|---|---|
| 910 | N-((6-(2,2-difluoroethoxy)-5-ethylpyridin-3-yl)methyl)-2-isobutyramidoisonicotinamide | | 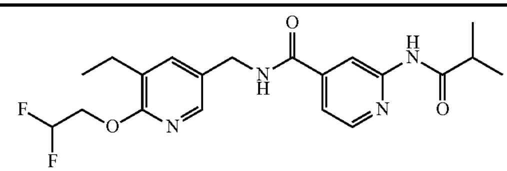 | Amine-76 | | 405.3 | 1.67 |
| 911 | N-((6-(2,2-difluoroethoxy)-5-ethylpyridin-3-yl)methyl)-2-isobutyramido-6-methylisonicotinamide | | 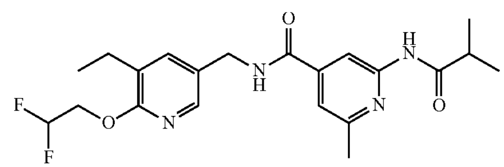 [SMILES: CCc1cc(CNC(=O)c2cc(C)nc(NC(=O)C(C)C)c2)cnc1OCC(F)F] | Amine-76 | | 419.4 | 1.73 |
| 912 | 2-(cyclopropanecarboxamido)-N-((6-(2,2-difluoroethoxy)-5-ethylpyridin-3-yl)methyl)pyrimidine-4-carboxamide | | 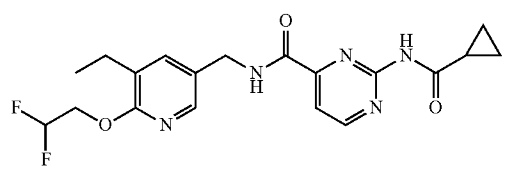 [SMILES: CCc1cc(CNC(=O)c2ccnc(NC(=O)C3CC3)n2)cnc1OCC(F)F] | Amine-76 | | 404.3 | 1.58 |
| 913 | 2-(cyclopropanecarboxamido)-N-((6-(2,2-difluoroethoxy)-5-ethylpyridin-3-yl)methyl)-6-methylpyrimidine-4-carboxamide | | 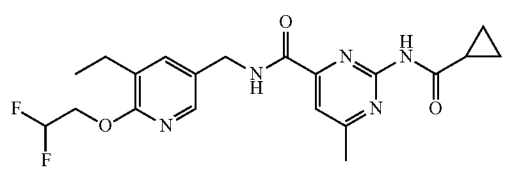 [SMILES: CCc1cc(CNC(=O)c2cc(C)nc(NC(=O)C3CC3)n2)cnc1OCC(F)F] | Amine-76 | | 418.3 | 1.65 |

TABLE 1-continued

| Example | Name | Chirality | Structure | Amine part | Carboxylic part | Observed MS | Retention time (min) |
|---|---|---|---|---|---|---|---|
| 914 | N-((6-(2,2-difluoroethoxy)-5-ethylpyridin-3-yl)methyl)-2-(2-hydroxy-2-methylpropanamido)-6-methylisonicotinamide | | 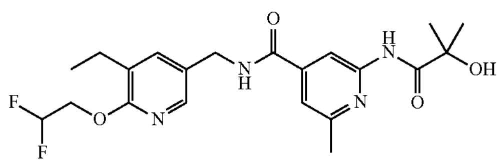 [SMILES: CCc1cc(CNC(=O)c2cc(C)nc(NC(=O)C(C)(C)O)c2)cnc1OCC(F)F] | Amine-76 | | 435.4 | 1.62 |
| 915 | 2-acetamido-N-((5-cyclopropyl-6-(2,2-difluoroethoxy)pyridin-3-yl)methyl)isonicotinamide | | 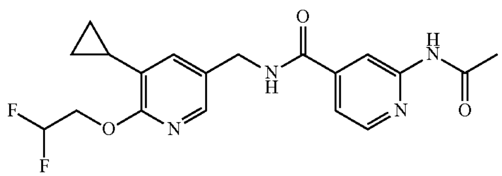 [SMILES: CC(=O)Nc1cc(C(=O)NCc2cnc(OCC(F)F)c(C3CC3)c2)ccn1] | Amine-77 | | 389.3 | 1.51 |
| 916 | N-((5-cyclopropyl-6-(2,2-difluoroethoxy)pyridin-3-yl)methyl)-2-isobutyramidoisonicotinamide | | 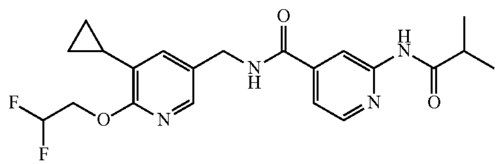 [SMILES: CC(C)C(=O)Nc1cc(C(=O)NCc2cnc(OCC(F)F)c(C3CC3)c2)ccn1] | Amine-77 | | 417.3 | 1.67 |
| 917 | N-((5-cyclopropyl-6-(2,2-difluoroethoxy)pyridin-3-yl)methyl)-2-isobutyramido-6-methylisonicotinamide | | 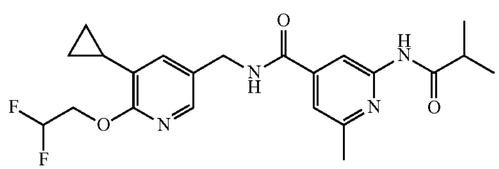 [SMILES: Cc1cc(C(=O)NCc2cnc(OCC(F)F)c(C3CC3)c2)cc(NC(=O)C(C)C)n1] | Amine-77 | | 431.3 | 1.73 |

| Example | Name | Chirality | Structure | Amine part | Carboxylic part | Observed MS | Retention time (min) |
|---|---|---|---|---|---|---|---|
| 918 | 2-(cyclopropane-carboxamido)-N-((5-cyclopropyl-6-(2,2-difluoroethoxy)pyridin-3-yl)methyl)pyrimidine-4-carboxamide | | 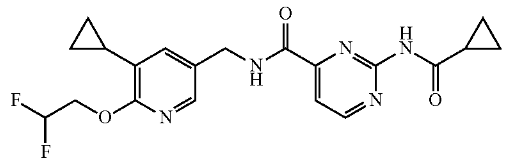 [SMILES: O=C(NCc1cnc(OCC(F)F)c(C2CC2)c1)c1ccnc(NC(=O)C2CC2)n1] | Amine-77 | | 416.3 | 1.59 |
| 919 | 5-chloro-2-propionamido-N-(1-(6-(2,2,2-trifluoroethoxy)pyridin-3-yl)ethyl)isonicotinamide | single enantiomer | 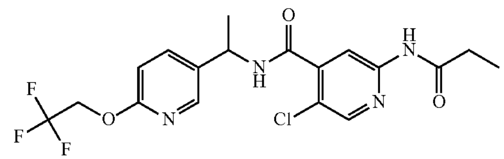 [SMILES: CCC(=O)Nc1cc(C(=O)NC(C)c2ccc(OCC(F)(F)F)nc2)c(Cl)cn1] | alternative route | | 429.2 | 1.64 |
| 920 | 5-chloro-2-(cyclopropane-carboxamido)-N-(1-(6-(2,2,2-trifluoroethoxy)pyridin-3-yl)ethyl)isonicotinamide | single enantiomer | 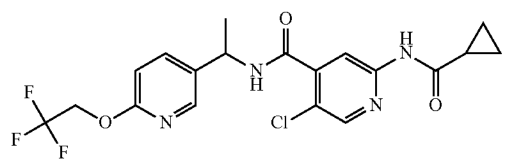 [SMILES: CC(NC(=O)c1cc(NC(=O)C2CC2)ncc1Cl)c1ccc(OCC(F)(F)F)nc1] | alternative route | | 441.2 | 1.68 |
| 921 | 2-acetamido-N-((6-(2,2,3,3,3-pentafluoropropoxy)pyridin-3-yl)methyl)isonicotinamide | | 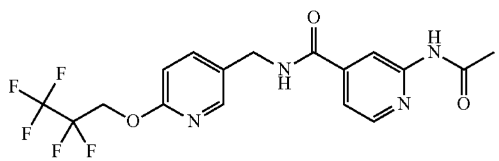 [SMILES: CC(=O)Nc1cc(C(=O)NCc2ccc(OCC(F)(F)C(F)(F)F)nc2)ccn1] | Amine-56 | | 417.2 | 1.58 |
| 922 | 2-(cyclopropane-carboxamido)-N-(1-(6-(2,2,3,3-tetrafluoropropoxy)pyridin-3-yl)ethyl)isonicotinamide | single enantiomer | 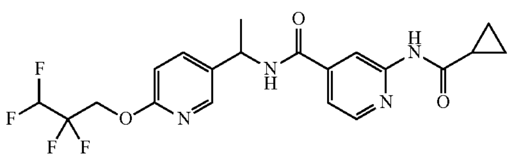 | Amine-57 | | 439.3 | 1.63 |

TABLE 1-continued

| Example | Chirality | Name | Structure | Amine part | Carboxylic part | Observed MS | Retention time (min) |
|---|---|---|---|---|---|---|---|
| 923 | | 2-propionamido-N-((6-(3,3,3-trifluoropropyl)pyridin-3-yl)methyl)isonicotinamide | 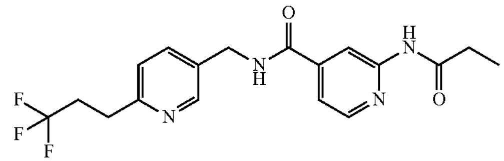 [SMILES: CCC(=O)Nc1cc(C(=O)NCc2ccc(CCC(F)(F)F)nc2)ccn1] | Amine-59 | | 379.3 | 1.41 |
| 924 | single enantiomer | 2-acetamido-N-(1-(6-(2,2,3,3,3-pentafluoropropoxy)pyridin-3-yl)ethyl)isonicotinamide | 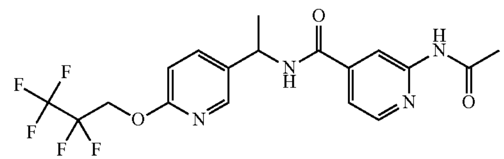 [SMILES: CC(=O)Nc1cc(C(=O)NC(C)c2ccc(OCC(F)(F)C(F)(F)F)nc2)ccn1] | Amine-60 | | 431.2 | 1.64 |
| 925 | single enantiomer | N-(1-(5-methyl-6-(2,2,3,3-tetrafluoropropoxy)pyridin-3-yl)ethyl)-2-propionamidoisonicotinamide | 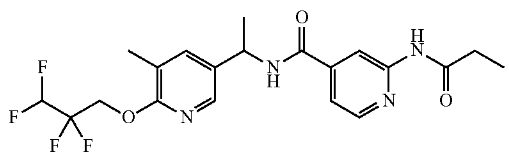 | Amine-75 | | 441.3 | 1.67 |
| 926 | single enantiomer | 2-(cyclopropanecarboxamido)-N-(1-(5-methyl-6-(2,2,3,3-tetrafluoropropoxy)pyridin-3-yl)ethyl)isonicotinamide | 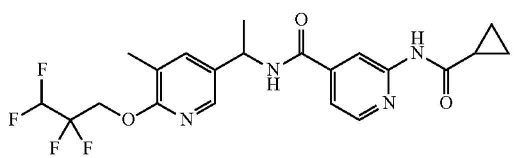 | Amine-75 | | 453.3 | 1.7 |
| 927 | single enantiomer | 2-acetamido-6-methyl-N-(1-(5-methyl-6-(2,2,3,3-tetrafluoropropoxy)pyridin-3-yl)ethyl)isonicotinamide | 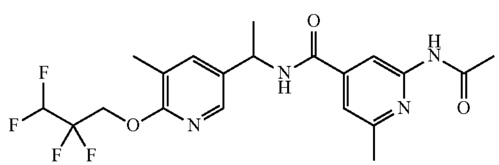 [SMILES: CC(=O)Nc1cc(C(=O)NC(C)c2cnc(OCC(F)(F)C(F)F)c(C)c2)cc(C)n1] | Amine-75 | | 441.3 | 1.65 |

TABLE 1-continued

| Example | Name | Chirality | Structure | Amine part | Carboxylic part | Observed MS | Retention time (min) |
|---|---|---|---|---|---|---|---|
| 928 | 2-butyramido-N-(1-(5-methyl-6-(2,2,3,3-tetrafluoropropoxy)pyridin-3-yl)ethyl)isonicotinamide | single enantiomer | 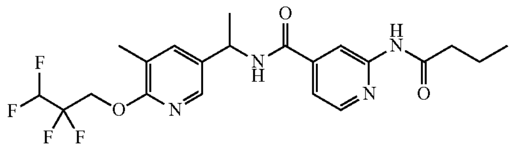 [SMILES: CCCC(=O)Nc1cc(C(=O)NC(C)c2cnc(OCC(F)(F)C(F)F)c(C)c2)ccn1] | Amine-75 | | 455.3 | 1.74 |
| 929 | N-(1-(5-methyl-6-(2,2,3,3-tetrafluoropropoxy)pyridin-3-yl)ethyl)-2-pivalamidoisonicotinamide | single enantiomer | 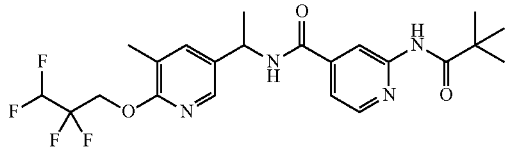 [SMILES: Cc1cc(C(C)NC(=O)c2ccnc(NC(=O)C(C)(C)C)c2)cnc1OCC(F)(F)C(F)F] | Amine-75 | | 469.4 | 1.82 |
| 930 | N-((6-(2,2-difluoroethoxy)-5-ethylpyridin-3-yl)methyl)-2-propionamidoisonicotinamide | | 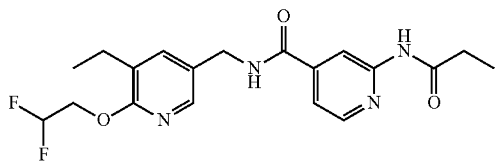 [SMILES: CCC(=O)Nc1cc(C(=O)NCc2cnc(OCC(F)F)c(CC)c2)ccn1] | Amine-76 | | 391.3 | 1.59 |
| 931 | 2-(cyclopropanecarboxamido)-N-((6-(2,2-difluoroethoxy)-5-ethylpyridin-3-yl)methyl)isonicotinamide | | 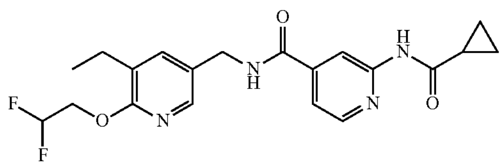 | Amine-76 | | 403.3 | 1.63 |
| 932 | 2-acetamido-N-((6-(2,2-difluoroethoxy)-5-ethylpyridin-3-yl)methyl)-6-methylisonicotinamide | | 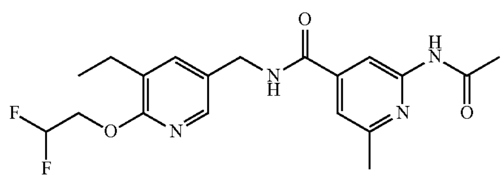 [SMILES: CCc1cc(CNC(=O)c2cc(C)nc(NC(C)=O)c2)cnc1OCC(F)F] | Amine-76 | | 391.3 | 1.57 |

TABLE 1-continued

| Example | Chirality | Name | Structure | Amine part | Carboxylic part | Observed MS | Retention time (min) |
|---|---|---|---|---|---|---|---|
| 933 | | 2-butyramido-N-((6-(2,2-difluoroethoxy)-5-ethylpyridin-3-yl)methyl)isonicotinamide | 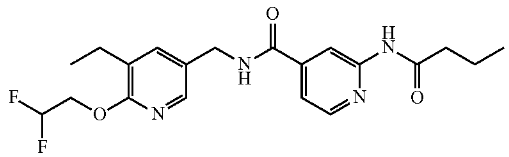 [SMILES: CCCC(=O)Nc1cc(C(=O)NCc2cnc(OCC(F)F)c(CC)c2)ccn1] | Amine-76 | | 405.3 | 1.67 |
| 934 | single enantiomer | N-(1-(5-cyclopropyl-6-(2,2-difluoroethoxy)pyridin-3-yl)ethyl)-2-isobutyramido-6-methylisonicotinamide | 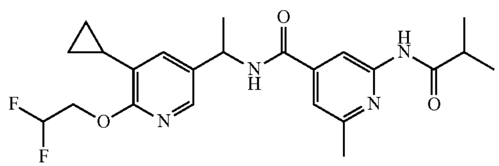 [SMILES: Cc1cc(C(=O)NC(C)c2cnc(OCC(F)F)c(C3CC3)c2)cc(NC(=O)C(C)C)n1] | Amine-78 | | 445.4 | 1.78 |
| 935 | single enantiomer | 2-(cyclopropanecarboxamido)-N-(1-(5-cyclopropyl-6-(2,2-difluoroethoxy)pyridin-3-yl)ethyl)pyrimidine-4-carboxamide | 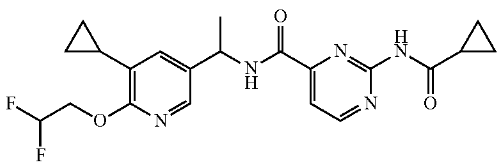 [SMILES: CC(NC(=O)c1ccnc(NC(=O)C2CC2)n1)c1cnc(OCC(F)F)c(C2CC2)c1] | Amine-78 | | 430.3 | 1.66 |
| 936 | single enantiomer | 2-acetamido-N-(1-(6-(2,2-difluoroethoxy)-5-methylpyridin-3-yl)ethyl)-N,6-dimethylisonicotinamide | 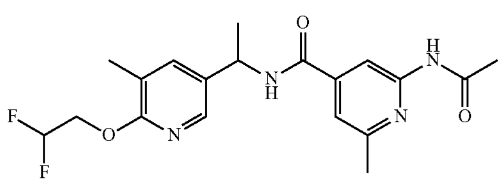 [SMILES: CC(=O)Nc1cc(C(=O)NC(C)c2cnc(OCC(F)F)c(C)c2)cc(C)n1] | Amine-79 | | 405.3 | 1.58 |

TABLE 1-continued

| Example | Name | Chirality | Structure | Amine part | Carboxylic part | Observed MS | Retention time (min) |
|---|---|---|---|---|---|---|---|
| 937 | N-(1-(6-(2,2-difluoroethoxy)-5-methylpyridin-3-yl)ethyl)-2-isobutyramido-N,6-dimethylisonicotinamide | single enantiomer | 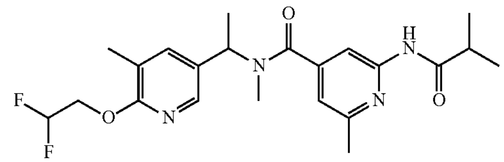 [SMILES: Cc1cc(C(=O)N(C)C(C)c2cnc(OCC(F)F)c(C)c2)cc(NC(=O)C(C)C)n1] | Amine-79 | | 433.4 | 1.75 |
| 938 | 2-(cyclopropanecarboxamido)-N-(1-(6-(2,2-difluoroethoxy)-5-methylpyridin-3-yl)ethyl)-6-methylisonicotinamide | single enantiomer | 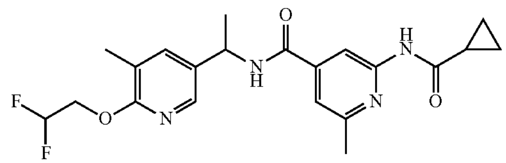 [SMILES: Cc1cc(C(=O)NC(C)c2cnc(OCC(F)F)c(C)c2)cc(NC(=O)C2CC2)n1] | Amine-14 | | 417.3 | 1.66 |
| 939 | 2-acetamido-N-((5-methyl-6-(2,2,3,3-tetrafluoropropoxy)pyridin-3-yl)methyl)isonicotinamide | | 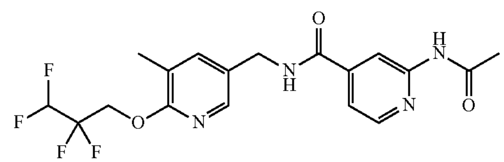 [SMILES: CC(=O)Nc1cc(C(=O)NCc2cnc(OCC(F)(F)C(F)F)c(C)c2)ccn1] | Amine-80 | | 413.3 | 1.54 |
| 940 | N-((5-methyl-6-(2,2,3,3-tetrafluoropropoxy)pyridin-3-yl)methyl)-2-propionamidoisonicotinamide | | 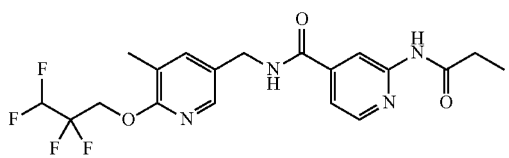 [SMILES: CCC(=O)Nc1cc(C(=O)NCc2cnc(OCC(F)(F)C(F)F)c(C)c2)ccn1] | Amine-80 | | 427.4 | 1.62 |
| 941 | 2-isobutyramido-N-((5-methyl-6-(2,2,3,3-tetrafluoropropoxy)pyridin-3-yl)methyl)isonicotinamide | | 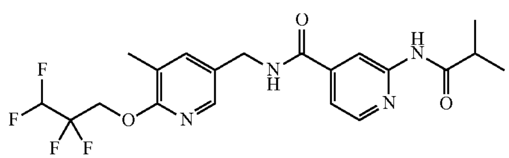 | Amine-80 | | 441.3 | 1.69 |

TABLE 1-continued

| Example | Chirality | Name | Structure | Amine part | Carboxylic part | Observed MS | Retention time (min) |
|---|---|---|---|---|---|---|---|
| 942 | | 2-(cyclopropanecarboxamido)-N-((5-methyl-6-(2,2,3,3-tetrafluoropropoxy)pyridin-3-yl)methyl)isonicotinamide | 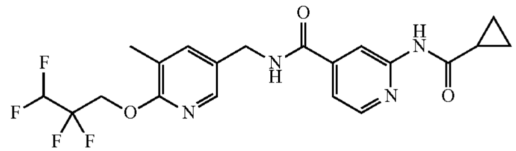 [SMILES: Cc1cc(CNC(=O)c2ccnc(NC(=O)C3CC3)c2)cnc1OCC(F)(F)C(F)F] | Amine-80 | | 439.3 | 1.65 |
| 943 | | 2-(cyclopropanecarboxamido)-N-((5-methyl-6-(2,2,3,3-tetrafluoropropoxy)pyridin-3-yl)methyl)pyrimidine-4-carboxamide | 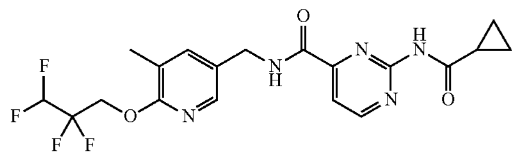 [SMILES: Cc1cc(CNC(=O)c2ccnc(NC(=O)C3CC3)n2)cnc1OCC(F)(F)C(F)F] | Amine-80 | | 440.3 | 1.61 |
| 944 | | 2-acetamido-6-methyl-N-((5-methyl-6-(2,2,3,3-tetrafluoropropoxy)pyridin-3-yl)methyl)isonicotinamide | 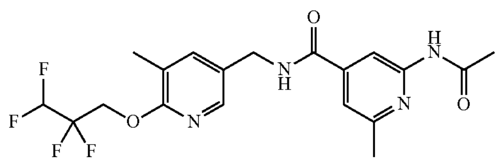 | Amine-80 | | 427.3 | 1.6 |
| 945 | | 2-isobutyramido-6-methyl-N-((5-methyl-6-(2,2,3,3-tetrafluoropropoxy)pyridin-3-yl)methyl)isonicotinamide | 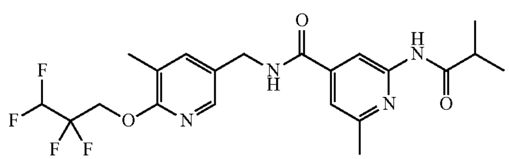 | Amine-80 | | 455.3 | 1.75 |

| Example | Name | Chirality | Structure | Amine part | Carboxylic part | Observed MS | Retention time (min) |
|---|---|---|---|---|---|---|---|
| 946 | 2-(cyclopropanecarboxamido)-6-methyl-N-((5-methyl-6-(2,2,3,3-tetrafluoropropoxy)pyridin-3-yl)methyl)isonicotinamide | | 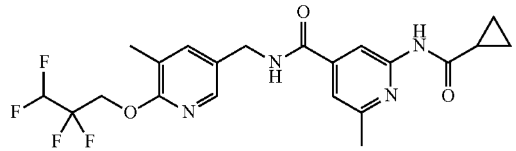 [SMILES: Cc1cc(C(=O)NCc2cnc(OCC(F)(F)C(F)F)c(C)c2)cc(NC(=O)C2CC2)n1] | Amine-80 | | 453.3 | 1.71 |
| 947 | 2-(cyclopropanecarboxamido)-6-methyl-N-((5-methyl-6-(2,2,3,3-tetrafluoropropoxy)pyridin-3-yl)methyl)pyrimidine-4-carboxamide | | 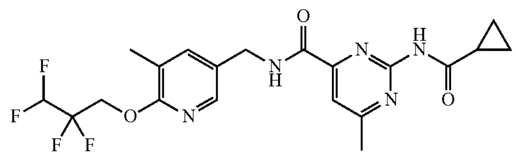 [SMILES: Cc1cc(C(=O)NCc2cnc(OCC(F)(F)C(F)F)c(C)c2)nc(NC(=O)C2CC2)n1] | Amine-80 | | 454.3 | 1.67 |
| 948 | 2-(2-cyclopropylacetamido)-6-methyl-N-(1-(6-(2,2,2-trifluoroethoxy)pyridin-3-yl)ethyl)isonicotinamide | single enantiomer | 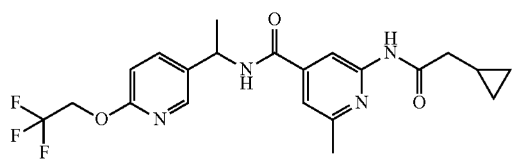 [SMILES: Cc1cc(C(=O)NC(C)c2ccc(OCC(F)(F)F)nc2)cc(NC(=O)CC2CC2)n1] | Amine-1 | | 435.3 | 1.73 |
| 949 | 2-(2-cyclopropylacetamido)-6-methyl-N-((6-(2,2,2-trifluoroethoxy)pyridin-3-yl)methyl)isonicotinamide | | 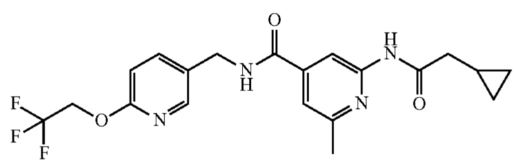 | | | 421.3 | 1.68 |
| 950 | 2-(2-cyclopropylacetamido)-N-(1-(6-(2,2-difluoroethoxy)-5-methylpyridin-3-yl)ethyl)-6-methylisonicotinamide | single enantiomer | 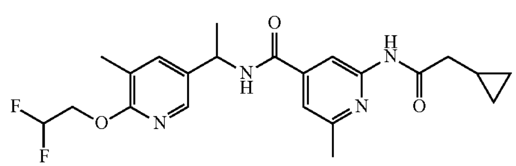 [SMILES: Cc1cc(C(=O)NC(C)c2cnc(OCC(F)F)c(C)c2)cc(NC(=O)CC2CC2)n1] | Amine-14 | | 431.4 | 1.71 |

TABLE 1-continued

| Example | Name | Chirality | Structure | Amine part | Carboxylic part | Observed MS | Retention time (min) |
|---|---|---|---|---|---|---|---|
| 951 | 2-(2-cyclopropylacetamido)-N-((6-(2,2-difluoroethoxy)-5-methylpyridin-3-yl)methyl)-6-methylisonicotinamide | | 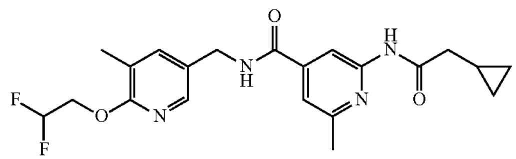 | Amine-64 | | 417.3 | 1.66 |
| 952 | N-(1-(5-chloro-6-(2,2-difluoroethoxy)pyridin-3-yl)ethyl)-2-(2-cyclopropylacetamido)-6-methylisonicotinamide | single enantiomer | 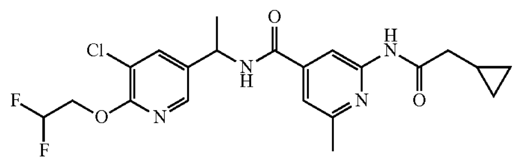 [SMILES: Cc1cc(C(=O)NC(C)c2cnc(OCC(F)F)c(Cl)c2)cc(NC(=O)CC2CC2)n1] | Amine-53 | | 451.3 | 1.74 |
| 953 | 2-(2-cyclopropylacetamido)-6-methyl-N-(1-(5-methyl-6-(2,2,2-trifluoroethoxy)pyridin-3-yl)ethyl)isonicotinamide | single enantiomer | 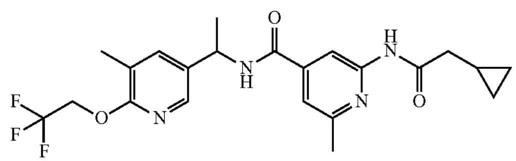 [SMILES: Cc1cc(C(=O)NC(C)c2cnc(OCC(F)(F)F)c(C)c2)cc(NC(=O)CC2CC2)n1] | Amine-17 | | 449.4 | 1.81 |
| 954 | 2-(2-cyclopropylacetamido)-6-methyl-N-((5-methyl-6-(2,2,2-trifluoroethoxy)pyridin-3-yl)methyl)isonicotinamide | | 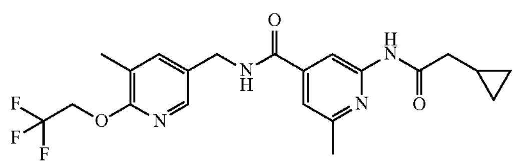 | Amine-47 | | 435.4 | 1.77 |

TABLE 1-continued

| Example | Name | Chirality | Structure | Amine part | Carboxylic part | Observed MS | Retention time (min) |
|---|---|---|---|---|---|---|---|
| 955 | N-(1-(5-chloro-6-(2,2,2-trifluoroethoxy)pyridin-3-yl)ethyl)-2-(2-cyclopropylacetamido)-6-methylisonicotinamide | single enantiomer | 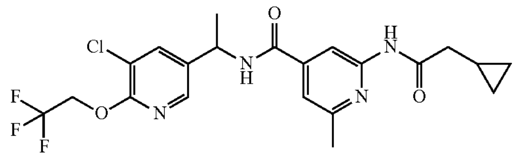 [SMILES: Cc1cc(C(=O)NC(C)c2cnc(OCC(F)(F)F)c(Cl)c2)cc(NC(=O)CC2CC2)n1] | Amine-5 | | 469.3 | 1.83 |
| 956 | N-((5-chloro-6-(2,2,2-trifluoroethoxy)pyridin-3-yl)methyl)-2-(2-cyclopropylacetamido)-6-methylisonicotinamide | | 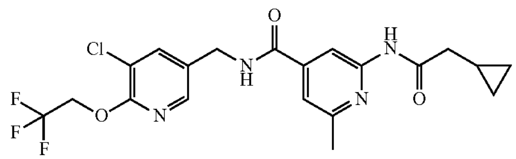 [SMILES: Cc1cc(C(=O)NCc2cnc(OCC(F)(F)F)c(Cl)c2)cc(NC(=O)CC2CC2)n1] | Amine-19 | | 455.3 | 1.78 |
| 957 | 2-(2-cyclopropylacetamido)-N-(1-(5-fluoro-6-(2,2,2-trifluoroethoxy)pyridin-3-yl)ethyl)-6-methylisonicotinamide | single enantiomer | 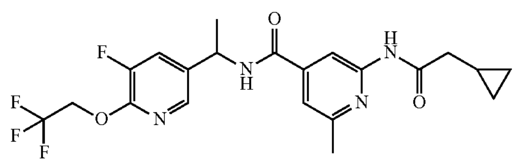 [SMILES: Cc1cc(C(=O)NC(C)c2cnc(OCC(F)(F)F)c(F)c2)cc(NC(=O)CC2CC2)n1] | Amine-12 | | 453.3 | 1.76 |
| 958 | 2-(2-cyclopropylacetamido)-6-methyl-N-((4-methyl-6-(2,2,2-trifluoroethoxy)pyridin-3-yl)methyl)isonicotinamide | | 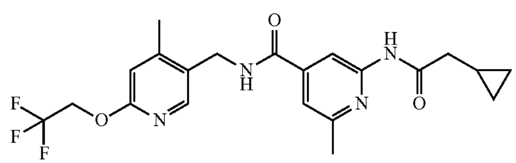 [SMILES: Cc1cc(C(=O)NCc2cnc(OCC(F)(F)F)cc2C)cc(NC(=O)CC2CC2)n1] | Amine-29 | | 435.3 | 1.73 |
| 959 | 2-(2-cyclopropylacetamido)-6-methyl-N-(1-(6-(3,3,3-trifluoropropoxy)pyridin-3-yl)ethyl)isonicotinamide | single enantiomer | 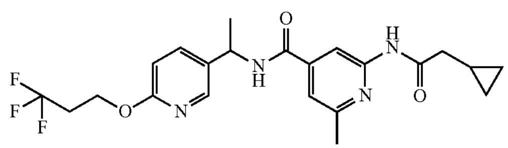 [SMILES: Cc1cc(C(=O)NC(C)c2ccc(OCCC(F)(F)F)nc2)cc(NC(=O)CC2CC2)n1] | Amine-21 | | 449.3 | 1.72 |

TABLE 1-continued

| Example | Chirality | Name | Structure | Amine part | Carboxylic part | Observed MS | Retention time (min) |
|---|---|---|---|---|---|---|---|
| 960 | | 2-(2-cyclopropylacetamido)-N-((2-methoxy-6-(2,2,2-trifluoroethoxy)pyridin-3-yl)methyl)-6-methylisonicotinamide | 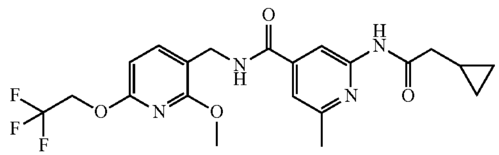 [SMILES: COc1nc(OCC(F)(F)F)ccc1CNC(=O)c1cc(C)nc(NC(=O)CC2CC2)c1] | Amine-24 | | 451.3 | 1.79 |
| 961 | | 2-(2-cyclopropylacetamido)-6-methyl-N-(3-(trifluoromethyl)benzyl)isonicotinamide | 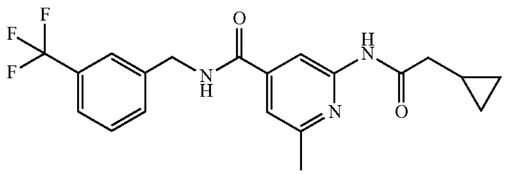 [SMILES: Cc1cc(C(=O)NCc2cccc(C(F)(F)F)c2)cc(NC(=O)CC2CC2)n1] | | | 390.3 | 1.73 |
| 962 | | 2-(2-cyclopropylacetamido)-6-methyl-N-(3-(trifluoromethoxy)benzyl)isonicotinamide | 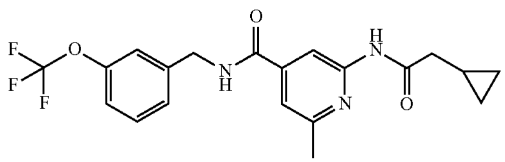 [SMILES: Cc1cc(C(=O)NCc2cccc(OC(F)(F)F)c2)cc(NC(=O)CC2CC2)n1] | | | 406.3 | 1.76 |
| 963 | | N-(3-fluoro-4-(trifluoromethoxy)benzyl)-2-propionamido-isonicotinamide | 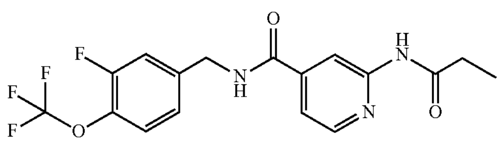 [SMILES: CCC(=O)Nc1cc(C(=O)NCc2ccc(OC(F)(F)F)c(F)c2)ccn1] | | | 384.3 | 1.64 |
| 964 | | N-(3-fluoro-4-(trifluoromethoxy)benzyl)-2-isobutyramido-isonicotinamide | 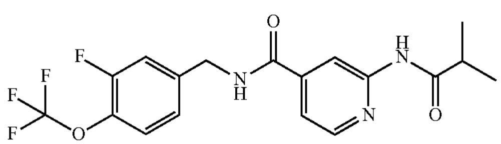 | | | 398.3 | 1.72 |

TABLE 1-continued

| Example | Name | Chirality | Structure | Amine part | Carboxylic part | Observed MS | Retention time (min) |
|---|---|---|---|---|---|---|---|
| 965 | N-(3-fluoro-4-(trifluoromethoxy)benzyl)-2-isobutyramido-6-methyl-isonicotinamide | | 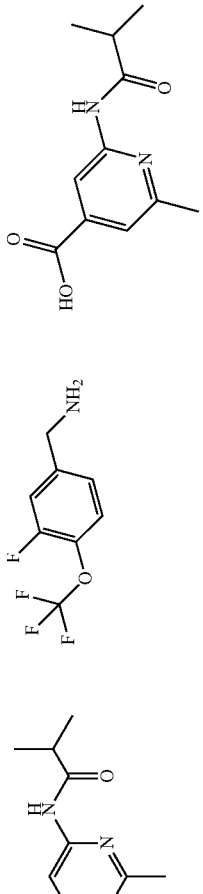 | 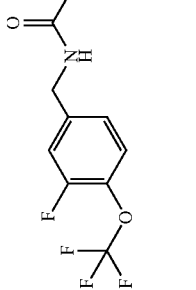 | 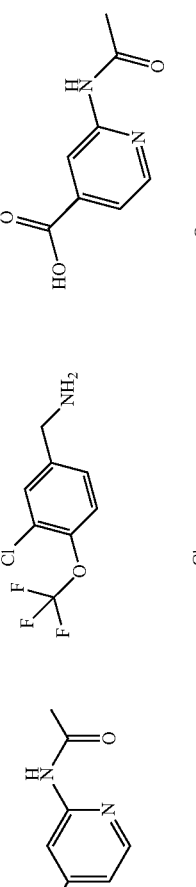 | 412.3 | 1.78 |
| 966 | 2-(cyclopropanecarboxamido)-N-(3-fluoro-4-(trifluoromethoxy)benzyl)pyrimidine-4-carboxamide | | 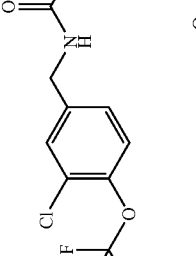 | 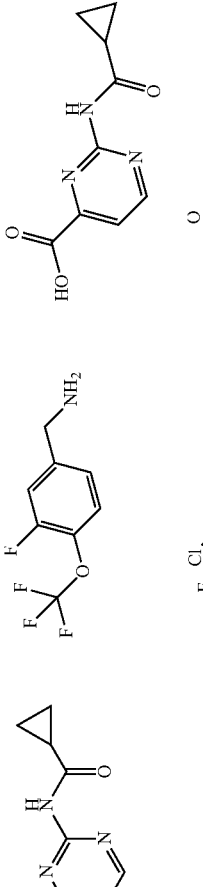 | 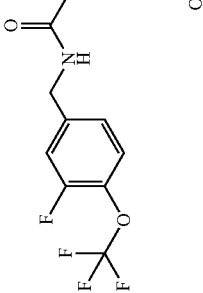 | 397.2 | 1.63 |
| 967 | 2-acetamido-N-(3-chloro-4-(trifluoromethoxy)benzyl)isonicotinamide | | 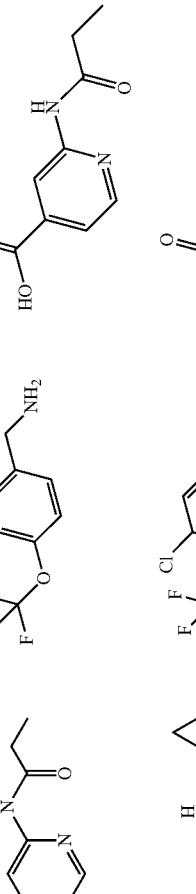 | 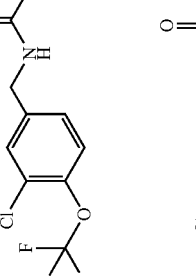 | 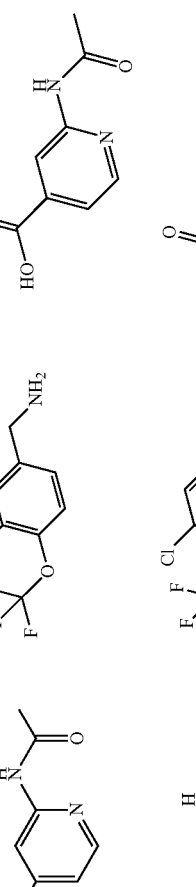 | 386.2 | 1.62 |
| 968 | N-(3-chloro-4-(trifluoromethoxy)benzyl)-2-propionamidoisonicotinamide | | 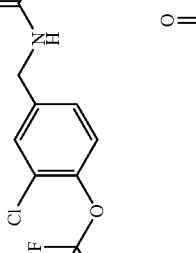 | 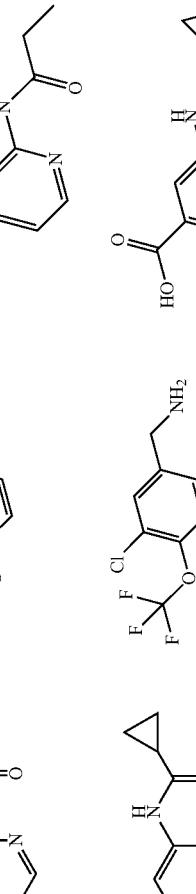 | 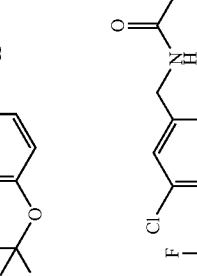 | 400.2 | 1.71 |
| 969 | N-(3-chloro-4-(trifluoromethoxy)benzyl)-2-(cyclopropanecarboxamido)isonicotinamide | | 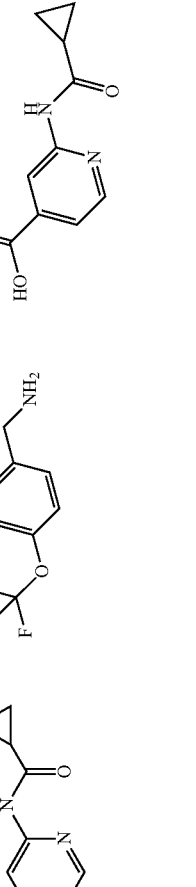 | 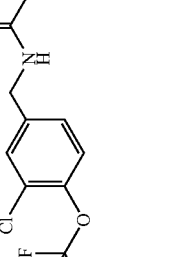 |  | 412.2 | 1.74 |

TABLE 1-continued

| Example | Name | Chirality | Structure | Amine part | Carboxylic part | Observed MS | Retention time (min) |
|---|---|---|---|---|---|---|---|
| 970 | N-(3-chloro-4-(trifluoromethoxy)benzyl)-2-isobutyramido-isonicotinamide | | 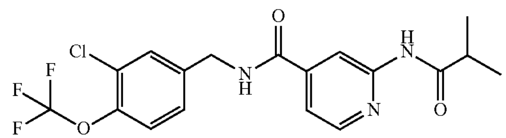 [SMILES: CC(C)C(=O)Nc1cc(C(=O)NCc2ccc(OC(F)(F)F)c(Cl)c2)ccn1] | | | 414.2 | 1.78 |
| 971 | 2-acetamido-N-(3-chloro-4-(trifluoromethoxy)benzyl)-6-methylisonicotinamide | | 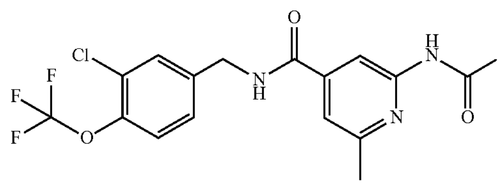 [SMILES: CC(=O)Nc1cc(C(=O)NCc2ccc(OC(F)(F)F)c(Cl)c2)cc(C)n1] | | | 400.2 | 1.68 |
| 972 | N-(3-chloro-4-(trifluoromethoxy)benzyl)-2-isobutyramido-6-methylisonicotinamide | | 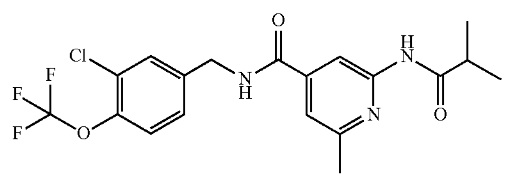 [SMILES: Cc1cc(C(=O)NCc2ccc(OC(F)(F)F)c(Cl)c2)cc(NC(=O)C(C)C)n1] | | | 428.2 | 1.85 |
| 973 | N-(3-chloro-4-(trifluoromethoxy)benzyl)-2-(cyclopropanecarboxamido)pyrimidine-4-carboxamide | | 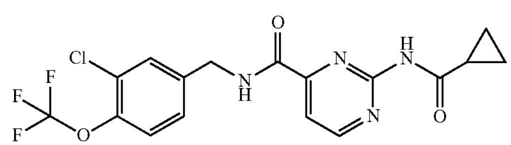 [SMILES: O=C(NCc1ccc(OC(F)(F)F)c(Cl)c1)c1ccnc(NC(=O)C2CC2)n1] | | | 413.2 | 1.7 |
| 974 | N-(3-chloro-4-(trifluoromethoxy)benzyl)-2-(cyclopropanecarboxamido)-6-methylpyrimidine-4-carboxamide | | 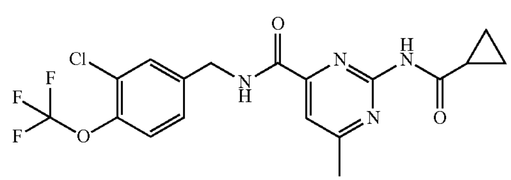 [SMILES: Cc1cc(C(=O)NCc2ccc(OC(F)(F)F)c(Cl)c2)nc(NC(=O)C2CC2)n1] | | | 427.2 | 1.76 |

TABLE 1-continued

| Example | Name | Chirality | Structure | Amine part | Carboxylic part | Observed MS | Retention time (min) |
|---|---|---|---|---|---|---|---|
| 975 | 2-(cyclopropanecarboxamido)-N-(2-fluoro-5-(trifluoromethyl)benzyl)-6-methylisonicotinamide | | 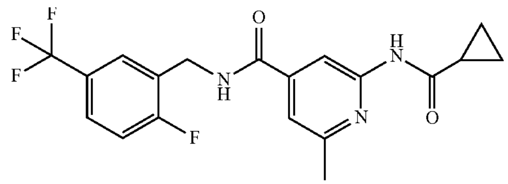 [SMILES: Cc1cc(C(=O)NCc2cc(C(F)(F)F)ccc2F)cc(NC(=O)C2CC2)n1] | | | 394.3 | 1.69 |
| 976 | 2-(cyclopropanecarboxamido)-N-(3-fluoro-5-(trifluoromethyl)benzyl)-6-methylisonicotinamide | | 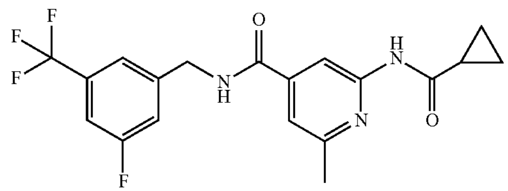 [SMILES: Cc1cc(C(=O)NCc2cc(F)cc(C(F)(F)F)c2)cc(NC(=O)C2CC2)n1] | | | 394.3 | 1.72 |
| 977 | 2-(cyclopropanecarboxamido)-N-(2-fluoro-3-(trifluoromethyl)benzyl)-6-methylisonicotinamide | | 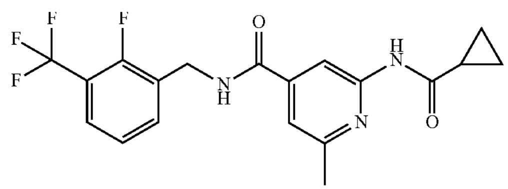 [SMILES: Cc1cc(C(=O)NCc2cccc(C(F)(F)F)c2F)cc(NC(=O)C2CC2)n1] | | | 394.3 | 1.7 |
| 978 | 2-(cyclopropanecarboxamido)-N-(4-fluoro-3-(trifluoromethyl)benzyl)isonicotinamide | | 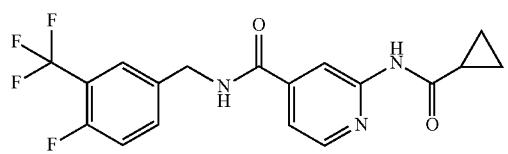 [SMILES: O=C(NCc1ccc(F)c(C(F)(F)F)c1)c1ccnc(NC(=O)C2CC2)c1] | | | 380.3 | 1.63 |
| 979 | 2-(cyclopropanecarboxamido)-N-(2-fluoro-3-(trifluoromethyl)benzyl)isonicotinamide | | 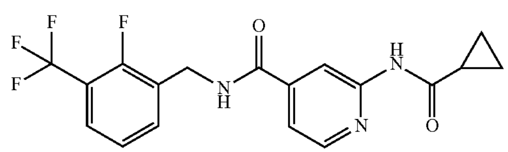 [SMILES: O=C(NCc1cccc(C(F)(F)F)c1F)c1ccnc(NC(=O)C2CC2)c1] | | | 380.3 | 1.63 |

TABLE 1-continued

| Example | Name | Chirality | Structure | Amine part | Carboxylic part | Observed MS | Retention time (min) |
|---|---|---|---|---|---|---|---|
| 980 | N-(1-(2-fluoro-5-(trifluoromethyl)phenyl)-2-isobutyramido-6-methyl-isonicotinamide | single enantiomer | 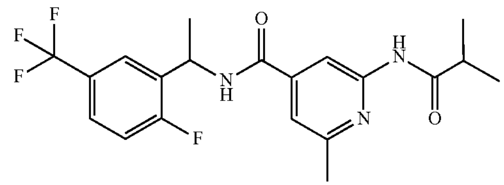 [SMILES: Cc1cc(C(=O)NC(C)c2cc(C(F)(F)F)ccc2F)cc(NC(=O)C(C)C)n1] | Amine-81 | | 410.4 | 1.79 |
| 981 | 2-acetamido-N-(1-(2-fluoro-5-(trifluoromethyl)phenyl)ethyl)-6-methyl-isonicotinamide | single enantiomer | 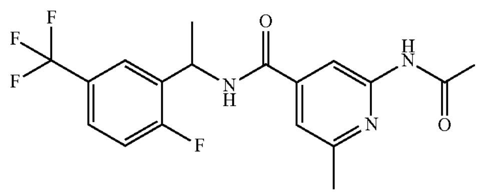 [SMILES: CC(=O)Nc1cc(C(=O)NC(C)c2cc(C(F)(F)F)ccc2F)cc(C)n1] | Amine-81 | | 384.1 | 1.62 |
| 982 | N-(1-(3-chloro-4-(2,2-difluoroethoxy)phenyl)ethyl)-2-propionamidoisonicotinamide | single enantiomer | 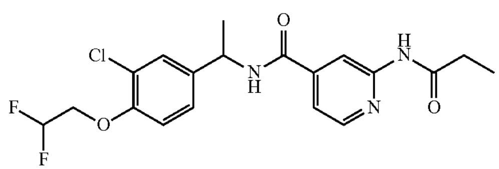 | Amine-82 | | 410.3 | 1.6 |
| 983 | N-(1-(3-chloro-4-(2,2-difluoroethoxy)phenyl)ethyl)-2-(cyclopropanecarboxamido)pyrimidine-4-carboxamide | single enantiomer | 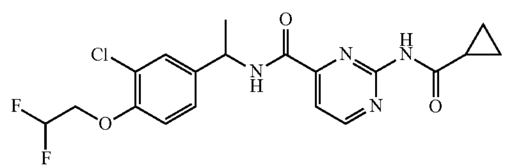 | Amine-82 | | 423.3 | 1.6 |

TABLE 1-continued

| Example | Name | Chirality | Structure | Amine part | Carboxylic part | Observed MS | Retention time (min) |
|---|---|---|---|---|---|---|---|
| 984 | N-(1-(3-chloro-4-(2,2-difluoroethoxy)phenyl)ethyl)-2-(cyclopropanecarboxamido)-6-methylpyrimidine-4-carboxamide | single enantiomer | 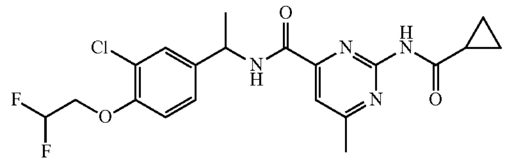 [SMILES: Cc1cc(C(=O)NC(C)c2ccc(OCC(F)F)c(Cl)c2)nc(NC(=O)C2CC2)n1] | Amine-82 | | 437.3 | 1.66 |
| 985 | (R)-2-(2-cyclopropyl-acetamido)-6-methyl-N-(1-(3-(trifluoromethyl)phenyl)ethyl)isonicotinamide | single enantiomer | 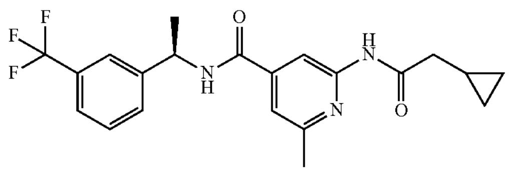 [SMILES: Cc1cc(C(=O)N[C@H](C)c2cccc(C(F)(F)F)c2)cc(NC(=O)CC2CC2)n1] | | | 404.3 | 1.78 |
| 986 | N-(2-chloro-3-(trifluoromethyl)benzyl)-2-(cyclopropanecarboxamido)pyrimidine-4-carboxamide | | 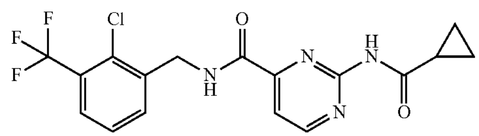 [SMILES: O=C(NCc1cccc(C(F)(F)F)c1Cl)c1ccnc(NC(=O)C2CC2)n1] | | | 397.2 | 1.64 |
| 987 | 2-acetamido-6-methyl-N-(4-methyl-3-(trifluoromethyl)benzyl)isonicotinamide | | 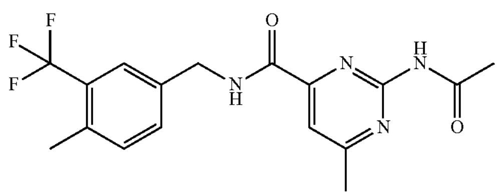 [SMILES: CC(=O)Nc1nc(C)cc(C(=O)NCc2ccc(C)c(C(F)(F)F)c2)n1] | | | 364.3 | 1.63 |
| 988 | 2-acetamido-N-(4-(2,2-difluoroethoxy)-3-methylbenzyl)isonicotinamide | | 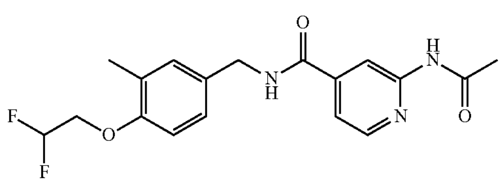 [SMILES: CC(=O)Nc1cc(C(=O)NCc2ccc(OCC(F)F)c(C)c2)ccn1] | Amine-84 | | 362.3 | 1.47 |

TABLE 1-continued

| Example | Name | Chirality | Structure | Amine part | Carboxylic part | Observed MS | Retention time (min) |
|---|---|---|---|---|---|---|---|
| 989 | N-(4-(2,2-difluoroethoxy)-3-methylbenzyl)-2-propionamidoisonicotinamide | | 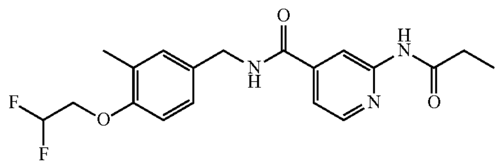 [SMILES: CCC(=O)Nc1cc(C(=O)NCc2ccc(OCC(F)F)c(C)c2)ccn1] | Amine-84 | | 376.3 | 1.55 |
| 990 | 2-(cyclopropanecarboxamido)-N-(4-(2,2-difluoroethoxy)-3-methylbenzyl)isonicotinamide | | 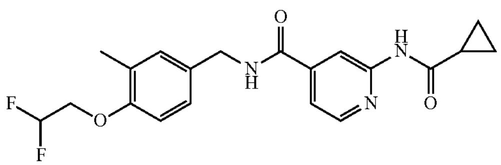 [SMILES: Cc1cc(CNC(=O)c2ccnc(NC(=O)C3CC3)c2)ccc1OCC(F)F] | Amine-84 | | 388.3 | 1.59 |
| 991 | N-(4-(2,2-difluoroethoxy)-3-methylbenzyl)-2-isobutyramidoisonicotinamide | | 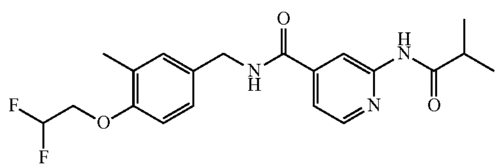 | Amine-84 | | 390.3 | 1.63 |
| 992 | 2-(cyclopropanecarboxamido)-N-(4-(2,2-difluoroethoxy)-3-methylbenzyl)pyrimidine-4-carboxamide | | 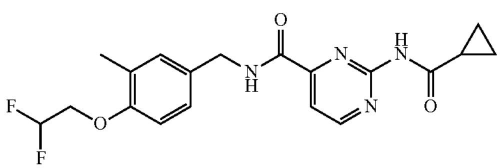 [SMILES: Cc1cc(CNC(=O)c2ccnc(NC(=O)C3CC3)n2)ccc1OCC(F)F] | Amine-84 | | 389.3 | 1.55 |
| 993 | 2-acetamido-N-(4-(2,2-difluoroethoxy)-3-methylbenzyl)-6-methylisonicotinamide | | 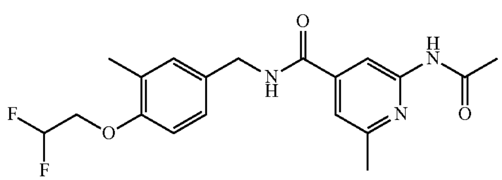 [SMILES: CC(=O)Nc1cc(C(=O)NCc2ccc(OCC(F)F)c(C)c2)cc(C)n1] | Amine-84 | | 376.3 | 1.53 |

TABLE 1-continued

| Example | Chirality | Name | Structure | Amine part | Carboxylic part | Observed MS | Retention time (min) |
|---|---|---|---|---|---|---|---|
| 994 | | N-(4-(2,2-difluoroethoxy)-3-methylbenzyl)-2-isobutyramido-6-methylisonicotinamide | 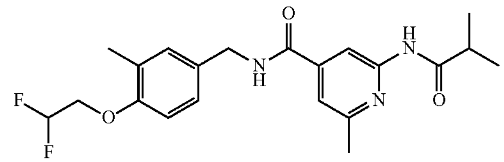 | Amine-84 | | 404.3 | 1.69 |
| 995 | | N-(4-(2,2-difluoroethoxy)-3-methylbenzyl)-2-(2-hydroxy-2-methylpropanamido)-6-methylisonicotinamide | 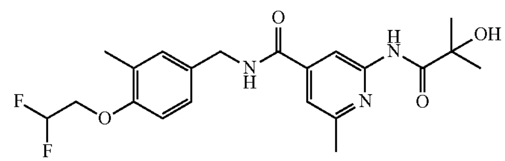 | Amine-84 | | 420.3 | 1.58 |
| 996 | | 2-(cyclopropanecarboxamido)-N-(4-(2,2-difluoroethoxy)-3-methylbenzyl)-6-methylpyrimidine-4-carboxamide | 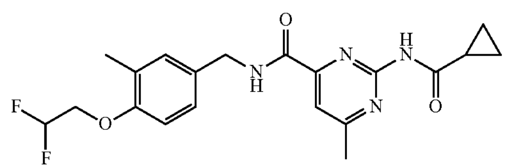 [SMILES: Cc1cc(C(=O)NCc2ccc(OCC(F)F)c(C)c2)nc(NC(=O)C2CC2)n1] | Amine-84 | | 403.3 | 1.61 |
| 997 | | 2-acetamido-N-(3-chloro-4-(2,2-difluoroethoxy)benzyl)isonicotinamide | 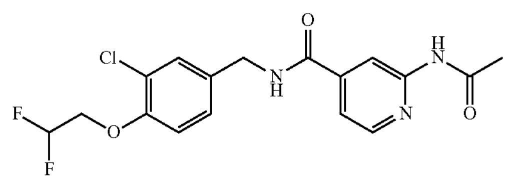 | Amine-85 | | 382.2 | 1.47 |
| 998 | | N-(3-chloro-4-(2,2-difluoroethoxy)benzyl)-2-propionamidoisonicotinamide | 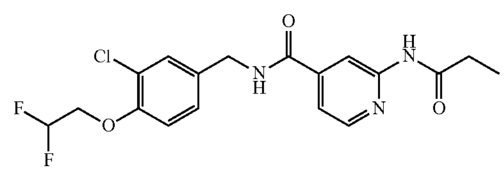 | Amine-85 | | 396.3 | 1.54 |

TABLE 1-continued

| Example | Name | Chirality | Structure | Amine part | Carboxylic part | Observed MS | Retention time (min) |
|---|---|---|---|---|---|---|---|
| 999 | N-(3-chloro-4-(2,2-difluoroethoxy)benzyl)-2-(cyclopropanecarboxamido)isonicotinamide | | 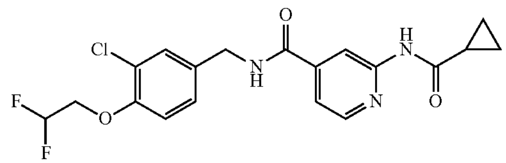 | Amine-85 | | 408.3 | 1.58 |
| 1000 | N-(3-chloro-4-(2,2-difluoroethoxy)benzyl)-2-isobutyramidoisonicotinamide | | 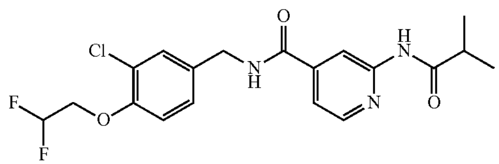 | Amine-85 | | 410.2 | 1.62 |
| 1001 | N-(3-chloro-4-(2,2-difluoroethoxy)benzyl)-2-(cyclopropanecarboxamido)pyrimidine-4-carboxamide | | 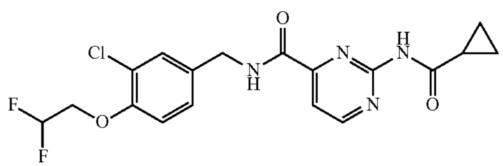 [SMILES: O=C(NCc1ccc(OCC(F)F)c(Cl)c1)c1ccnc(NC(=O)C2CC2)n1] | Amine-85 | | 409.2 | 1.53 |
| 1002 | 2-acetamido-N-(3-chloro-4-(2,2-difluoroethoxy)benzyl)-6-methylisonicotinamide | | 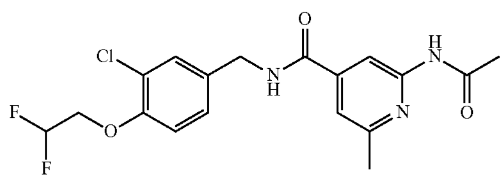 | Amine-85 | | 396.3 | 1.52 |

TABLE 1-continued

| Example | Name | Chirality | Structure | Amine part | Carboxylic part | Observed MS | Retention time (min) |
|---|---|---|---|---|---|---|---|
| 1003 | N-(3-chloro-4-(2,2-difluoroethoxy)benzyl)-2-isobutyramido-6-methylisonicotinamide | | 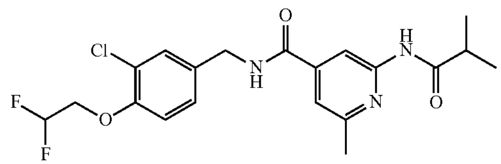 | Amine-85 | | 424.2 | 1.68 |
| 1004 | N-(3-chloro-4-(2,2-difluoroethoxy)benzyl)-2-(cyclopropanecarboxamido)-6-methylpyrimidine-4-carboxamide | | 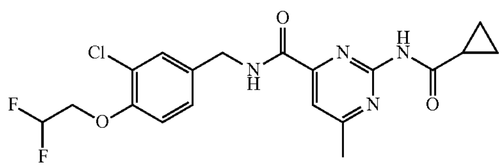 | Amine-85 | | 423.3 | 1.6 |
| 1005 | 2-(cyclopropanecarboxamido)-N-(4-(2,2-difluoroethoxy)-2-methylbenzyl)isonicotinamide | | 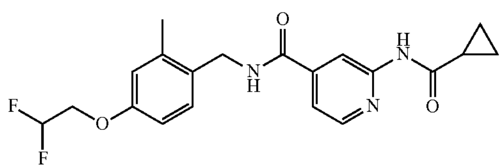 | Amine-86 | | 388.3 | 1.56 |
| 1006 | N-(4-(2,2-difluoroethoxy)-2-methylbenzyl)-2-isobutyramido-isonicotinamide | | 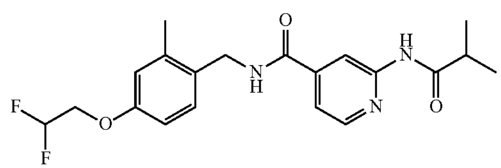 | Amine-86 | | 390.3 | 1.6 |
| 1007 | 2-acetamido-N-(4-(2,2-difluoroethoxy)-2-methylbenzyl)-6-methyl-isonicotinamide | | 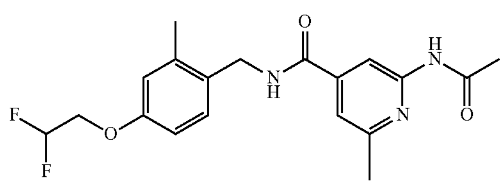 [SMILES: CC(=O)Nc1cc(C(=O)NCc2ccc(OCC(F)F)cc2C)cc(C)n1] | Amine-86 | | 376.4 | 1.5 |

| Example | Chirality | Structure | Name | Amine part | Carboxylic part | Observed MS | Retention time (min) |
|---|---|---|---|---|---|---|---|
| 1008 | | 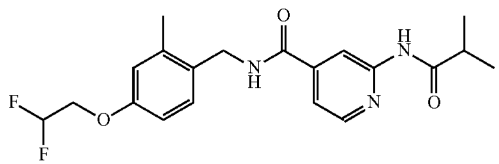 [SMILES: Cc1cc(OCC(F)F)ccc1CNC(=O)c1ccnc(NC(=O)C(C)C)c1] | N-(4-(2,2-difluoroethoxy)-2-methylbenzyl)-2-isobutyramido-6-methylisonicotinamide | Amine-86 | | 404.3 | 1.66 |
| 1009 | single enantiomer | 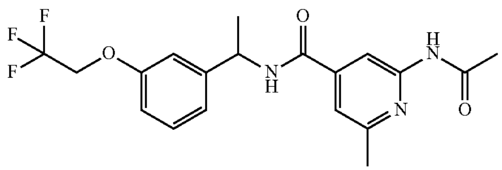 [SMILES: CC(=O)Nc1cc(C(=O)NC(C)c2cccc(OCC(F)(F)F)c2)cc(C)n1] | 2-acetamido-6-methyl-N-(1-(3-(2,2,2-trifluoroethoxy)phenyl)ethyl)isonicotinamide | Amine-16 | | 394.3 | 1.6 |
| 1010 | | 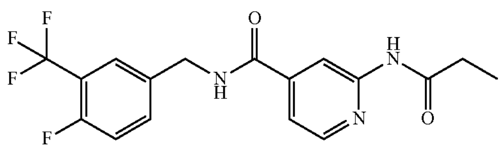 [SMILES: CCC(=O)Nc1cc(C(=O)NCc2ccc(F)c(C(F)(F)F)c2)ccn1] | N-(4-fluoro-3-(trifluoromethyl)benzyl)-2-propionamido-isonicotinamide | | | 368.2 | 1.59 |
| 1011 | | 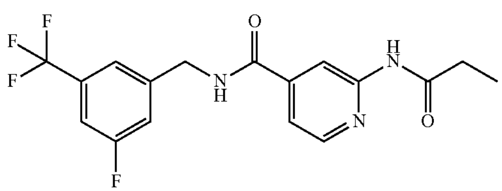 [SMILES: CCC(=O)Nc1cc(C(=O)NCc2cc(F)cc(C(F)(F)F)c2)ccn1] | N-(3-fluoro-5-(trifluoromethyl)benzyl)-2-propionamidoisonicotinamide | | | 368.3 | 1.62 |

TABLE 1-continued

| Example | Name | Chirality | Structure | Amine part | Carboxylic part | Observed MS | Retention time (min) |
|---|---|---|---|---|---|---|---|
| 1012 | N-(2-fluoro-3-(trifluoromethyl)benzyl)-2-propionamido-isonicotinamide | | 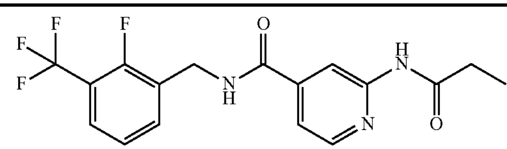 | | | 368.3 | 1.59 |
| 1013 | N-(4-chloro-3-(trifluoromethyl)benzyl)-2-propionamido-isonicotinamide | | 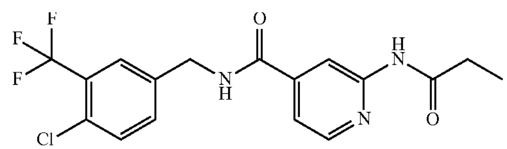 | | | 384.2 | 1.67 |
| 1014 | N-(2-chloro-3-(trifluoromethyl)benzyl)-2-propionamido-isonicotinamide | | 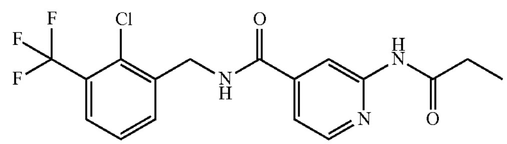 [SMILES: CCC(=O)Nc1cc(C(=O)NCc2cccc(C(F)(F)F)c2F)ccn1] | | | 384.2 | 1.65 |
| 1015 | N-(3,5-bis(trifluoromethyl)benzyl)-2-propionamido-isonicotinamide | | 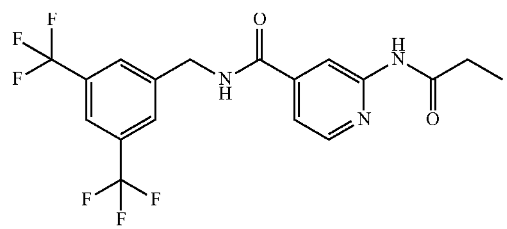 [SMILES: CCC(=O)Nc1cc(C(=O)NCc2cc(C(F)(F)F)cc(C(F)(F)F)c2)ccn1] | | | 418.2 | 1.74 |

| Example | Chirality | Name | Structure | Amine part | Carboxylic part | Observed MS | Retention time (min) |
|---|---|---|---|---|---|---|---|
| 1016 | | N-(2-methyl-3-(trifluoromethyl)benzyl)-2-propionamido-isonicotinamide | 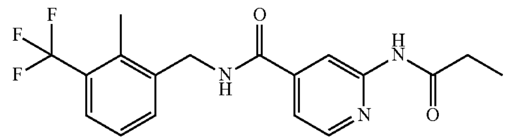 [SMILES: CCC(=O)Nc1cc(C(=O)NCc2cccc(C(F)(F)F)c2C)ccn1] | | | 364.3 | 1.64 |
| 1017 | | N-(2-methoxy-3-(trifluoromethyl)benzyl)-2-propionamido-isonicotinamide | 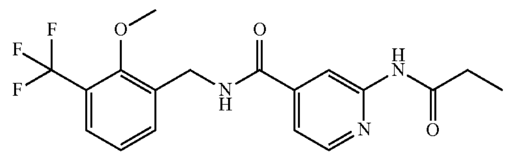 [SMILES: CCC(=O)Nc1cc(C(=O)NCc2cccc(C(F)(F)F)c2OC)ccn1] | | | 380.3 | 1.6 |
| 1018 | | N-(4-methyl-3-(trifluoromethyl)benzyl)-2-propionamido-isonicotinamide | 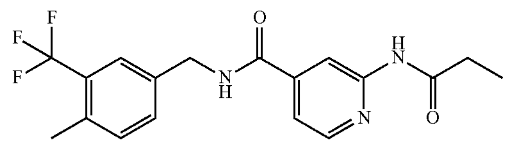 [SMILES: CCC(=O)Nc1cc(C(=O)NCc2ccc(C)c(C(F)(F)F)c2)ccn1] | | | 364.3 | 1.65 |
| 1019 | | 2-(cyclopropane-carboxamido)-N-(4-fluoro-3-(trifluoromethyl)benzyl)-6-methylpyrimidine-4-carboxamide | 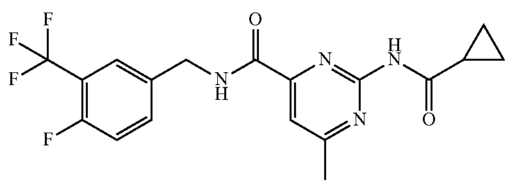 | | | 395.3 | 1.65 |
| 1020 | | 2-(cyclopropane-carboxamido)-N-(3-fluoro-5-(trifluoromethyl)benzyl)-6-methylpyrimidine-4-carboxamide | 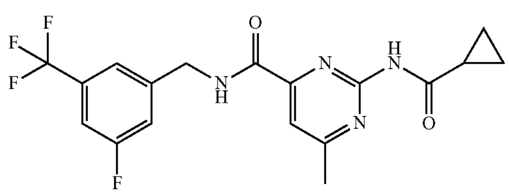 | | | 395.3 | 1.67 |

TABLE 1-continued

| Example | Chirality | Name | Structure | Amine part | Carboxylic part | Observed MS | Retention time (min) |
|---|---|---|---|---|---|---|---|
| 1021 | | 2-(cyclopropanecarboxamido)-N-(2-fluoro-3-(trifluoromethyl)benzyl)-6-methylpyrimidine-4-carboxamide | 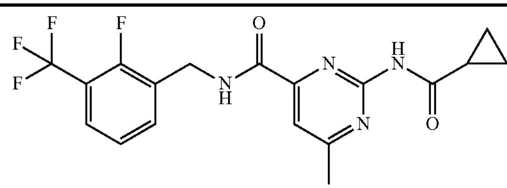 | | | 395.3 | 1.65 |
| 1022 | | N-(4-chloro-3-(trifluoromethyl)benzyl)-2-(cyclopropanecarboxamido)-6-methylpyrimidine-4-carboxamide | 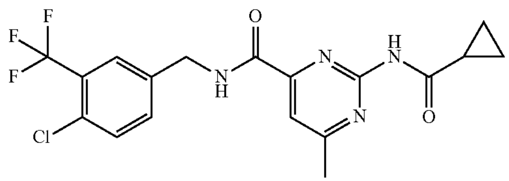 [SMILES: Cc1cc(C(=O)NCc2ccc(Cl)c(C(F)(F)F)c2)nc(NC(=O)C2CC2)n1] | | | 411.2 | 1.72 |
| 1023 | | N-(2-chloro-3-(trifluoromethyl)benzyl)-2-(cyclopropanecarboxamido)-6-methylpyrimidine-4-carboxamide | 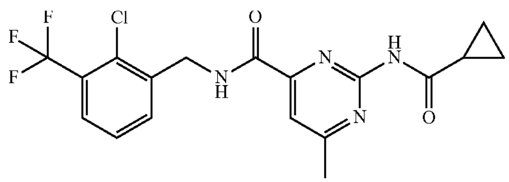 [SMILES: Cc1cc(C(=O)NCc2cccc(C(F)(F)F)c2Cl)nc(NC(=O)C2CC2)n1] | | | 411.2 | 1.71 |
| 1024 | | N-(3,5-bis(trifluoromethyl)benzyl)-2-(cyclopropanecarboxamido)-6-methylpyrimidine-4-carboxamide | 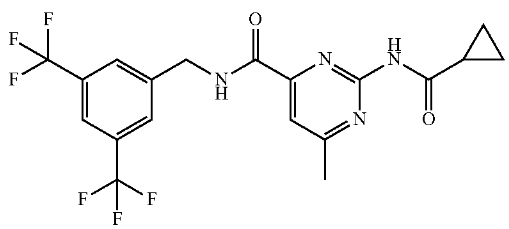 [SMILES: Cc1cc(C(=O)NCc2cc(C(F)(F)F)cc(C(F)(F)F)c2)nc(NC(=O)C2CC2)n1] | | | 445.2 | 1.79 |

TABLE 1-continued

| Example | Name | Chirality | Structure | Amine part | Carboxylic part | Observed MS | Retention time (min) |
|---|---|---|---|---|---|---|---|
| 1025 | 2-(cyclopropanecarboxamido)-6-methyl-N-(2-methyl-3-(trifluoromethyl)benzyl)pyrimidine-4-carboxamide | | 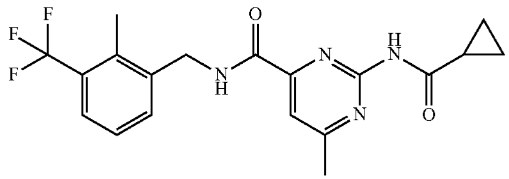 [SMILES: Cc1cc(C(=O)NCc2cccc(C(F)(F)F)c2C)nc(NC(=O)C2CC2)n1] | | | 391.3 | 1.71 |
| 1026 | 2-(cyclopropanecarboxamido)-N-(2-methoxy-3-(trifluoromethyl)benzyl)-6-methylpyrimidine-4-carboxamide | | 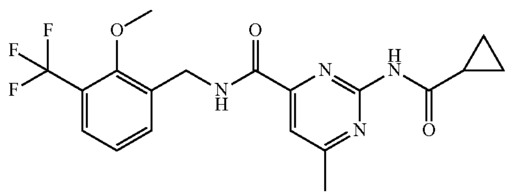 [SMILES: COc1c(CNC(=O)c2cc(C)nc(NC(=O)C3CC3)n2)cccc1C(F)(F)F] | | | 407.2 | 1.66 |
| 1027 | 2-(cyclopropanecarboxamido)-6-methyl-N-(4-methyl-3-(trifluoromethyl)benzyl)pyrimidine-4-carboxamide | | 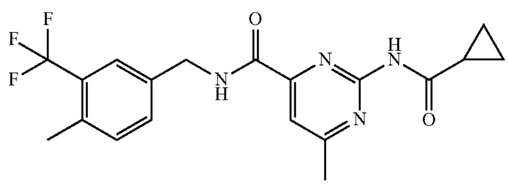 [SMILES: Cc1cc(C(=O)NCc2ccc(C)c(C(F)(F)F)c2)nc(NC(=O)C2CC2)n1] | | | 391.3 | 1.71 |
| 1028 | 2-(cyclopropanecarboxamido)-N-(4-methoxy-3-(trifluoromethyl)benzyl)-6-methylpyrimidine-4-carboxamide | | 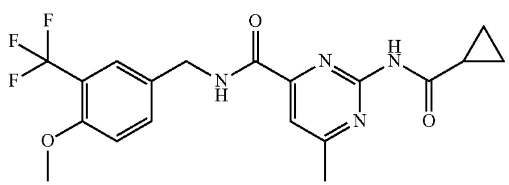 | | | 407.2 | 1.61 |

TABLE 1-continued

| Example | Name | Chirality | Structure | Amine part | Carboxylic part | Observed MS | Retention time (min) |
|---|---|---|---|---|---|---|---|
| 1029 | 2-acetamido-N-(1-(3-((trifluoromethyl)thio)phenyl)ethyl)isonicotinamide | single enantiomer | 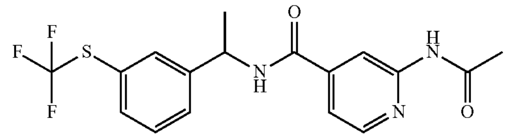 [SMILES: CC(=O)Nc1cc(C(=O)NC(C)c2cccc(SC(F)(F)F)c2)ccn1] | Amine-88 | | 382.2 | 1.65 |
| 1030 | 2-isobutyramido-N-(1-(3-((trifluoromethyl)thio)phenyl)ethyl)isonicotinamide | single enantiomer | 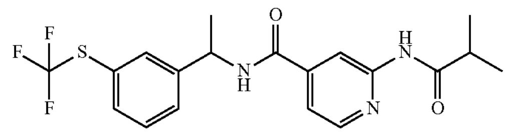 [SMILES: CC(C)C(=O)Nc1cc(C(=O)NC(C)c2cccc(SC(F)(F)F)c2)ccn1] | Amine-88 | | 410.3 | 1.81 |
| 1031 | 2-acetamido-6-methyl-N-(1-(3-((trifluoromethyl)thio)phenyl)ethyl)isonicotinamide | single enantiomer | 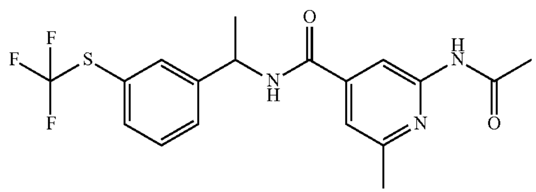 [SMILES: CC(=O)Nc1cc(C(=O)NC(C)c2cccc(SC(F)(F)F)c2)cc(C)n1] | Amine-88 | | 396.3 | 1.71 |
| 1032 | 2-isobutyramido-6-methyl-N-(1-(3-((trifluoromethyl)thio)phenyl)ethyl)isonicotinamide | single enantiomer | 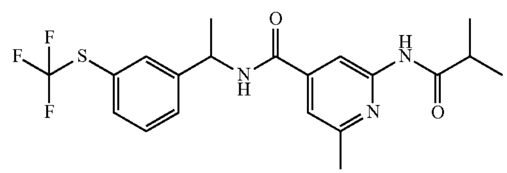 [SMILES: Cc1cc(C(=O)NC(C)c2cccc(SC(F)(F)F)c2)cc(NC(=O)C(C)C)n1] | Amine-88 | | 424.2 | 1.87 |

TABLE 1-continued

| Example | Name | Chirality | Structure | Amine part | Carboxylic part | Observed MS | Retention time (min) |
|---|---|---|---|---|---|---|---|
| 1033 | 2-(cyclopropanecarboxamido)-N-(1-(3-((trifluoromethyl)thiophenyl)ethyl)pyrimidine-4-carboxamide | single enantiomer | 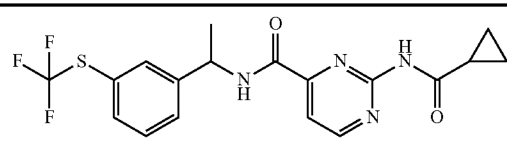 | Amine-88 | | 409.3 | 1.74 |
| 1034 | N-(4-(2,2-difluoroethoxy)-3-fluorobenzyl)-2-propionamidoisonicotinamide | | 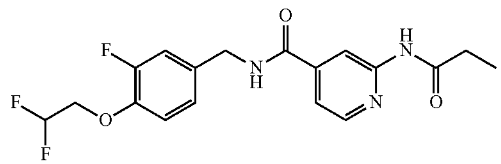 | Amine-92 | | 380.3 | 1.48 |
| 1035 | 2-(cyclopropanecarboxamido)-N-(4-(2,2-difluoroethoxy)-3-fluorobenzyl)isonicotinamide | | 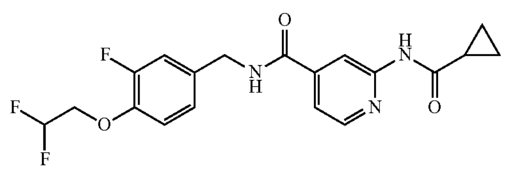 [SMILES: O=C(NCc1ccc(OCC(F)F)c(F)c1)c1ccnc(NC(=O)C2CC2)c1] | Amine-92 | | 392.3 | 1.52 |
| 1036 | N-(4-(2,2-difluoroethoxy)-3-fluorobenzyl)-2-isobutyramido-6-methylisonicotinamide | | 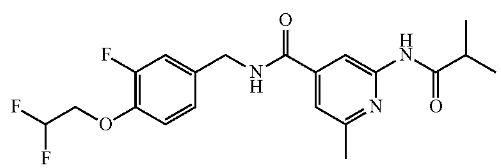 [SMILES: Cc1cc(C(=O)NCc2ccc(OCC(F)F)c(F)c2)cc(NC(=O)C(C)C)n1] | Amine-92 | | 408.3 | 1.62 |
| 1037 | 2-butyramido-N-(4-(2,2-difluoroethoxy)-3-fluorobenzyl)isonicotinamide | | 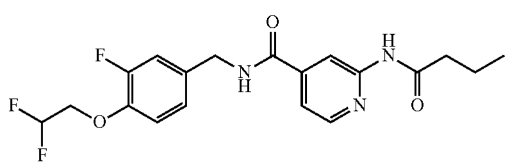 | Amine-92 | | 394.3 | 1.56 |

| Example | Chirality | Name | Structure | Amine part | Carboxylic part | Observed MS | Retention time (min) |
|---|---|---|---|---|---|---|---|
| 1038 | | 2-(cyclopropane-carboxamido)-N-(4-(2,2-difluoroethoxy)-3-fluorobenzyl)-6-methyl-pyrimidine-4-carboxamide | 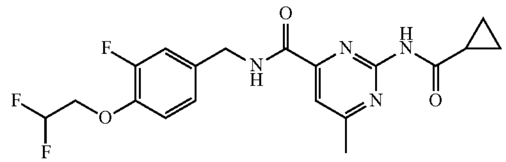 [SMILES: Cc1cc(C(=O)NCc2ccc(OCC(F)F)c(F)c2)nc(NC(=O)C2CC2)n1] | Amine-92 | | 407.3 | 1.53 |
| 1039 | single enantiomer | 2-acetamido-N-(1-(3-chloro-5-(trifluoromethoxy)phenyl)ethyl)isonicotinamide | 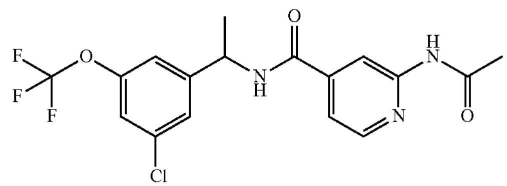 [SMILES: CC(=O)Nc1cc(C(=O)NC(C)c2cc(Cl)cc(OC(F)(F)F)c2)ccn1] | | | 400.2 | 1.71 |
| 1040 | single enantiomer | N-(1-(3-chloro-5-(trifluoromethoxy)phenyl)ethyl)-2-isobutyramido-isonicotinamide | 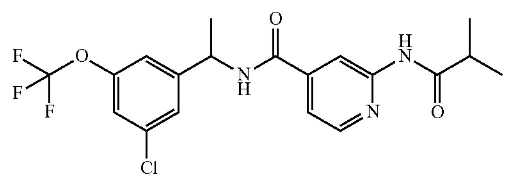 [SMILES: CC(C)C(=O)Nc1cc(C(=O)NC(C)c2cc(Cl)cc(OC(F)(F)F)c2)ccn1] | Amine-90 | | 428.2 | 1.87 |
| 1041 | single enantiomer | N-(1-(3-chloro-5-(trifluoromethoxy)phenyl)ethyl)-2-isobutyramido-6-methyliso-nicotinamide | 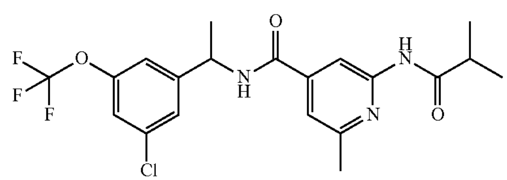 [SMILES: Cc1cc(C(=O)NC(C)c2cc(Cl)cc(OC(F)(F)F)c2)cc(NC(=O)C(C)C)n1] | Amine-90 | | 442.3 | 1.93 |

| Example | Name | Chirality | Structure | Amine part | Carboxylic part | Observed MS | Retention time (min) |
|---|---|---|---|---|---|---|---|
| 1042 | 2-acetamido-N-(1-(3-chloro-5-(trifluoromethoxyphenyl)ethyl)-6-methylisonicotinamide | single enantiomer | 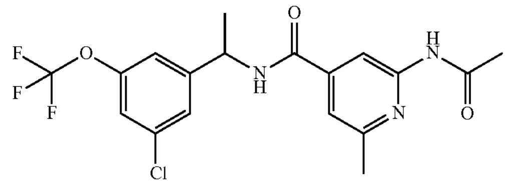 [SMILES: CC(=O)Nc1cc(C(=O)NC(C)c2cc(Cl)cc(OC(F)(F)F)c2)cc(C)n1] | Amine-90 | | 414.2 | 1.77 |
| 1043 | N-(1-(3-chloro-5-(trifluoromethoxyphenyl)ethyl)-2-(cyclopropanecarboxamido)pyrimidine-4-carboxamide | single enantiomer | 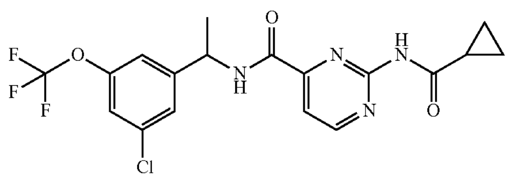 [SMILES: CC(NC(=O)c1ccnc(NC(=O)C2CC2)n1)c1cc(Cl)cc(OC(F)(F)F)c1] | Amine-90 | | 427.2 | 1.8 |
| 1044 | 2-(cyclopropanecarboxamido)-N-(1-(4-fluoro-3-(2,2,2-trifluoroethoxy)phenyl)ethyl)-6-methylpyrimidine-4-carboxamide | single enantiomer | 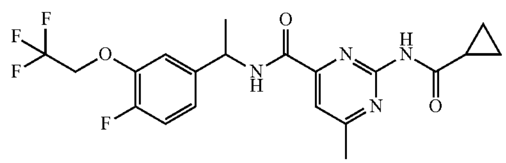 [SMILES: Cc1cc(C(=O)NC(C)c2ccc(F)c(OCC(F)(F)F)c2)nc(NC(=O)C2CC2)n1] | Amine-20 | | 439.3 | 1.71 |
| 1045 | N-(2-chloro-4-(2,2-difluoroethoxy)benzyl)-2-propionamidoisonicotinamide | | 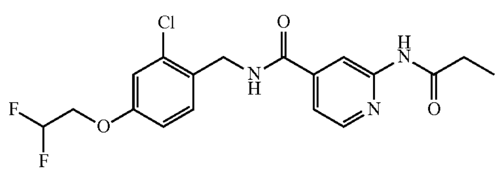 [SMILES: CCC(=O)Nc1cc(C(=O)NCc2ccc(OCC(F)F)cc2Cl)ccn1] | Amine-91 | | 396.3 | 1.56 |

TABLE 1-continued

| Example | Chirality | Name | Structure | Amine part | Carboxylic part | Observed MS | Retention time (min) |
|---|---|---|---|---|---|---|---|
| 1046 | | N-(2-chloro-4-(2,2-difluoroethoxy)benzyl)-2-(cyclopropanecarboxamido)isonicotinamide | 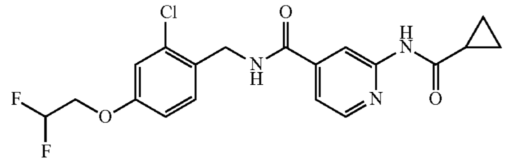 [SMILES: O=C(NCc1ccc(OCC(F)F)cc1Cl)c1ccnc(NC(=O)C2CC2)c1] | Amine-91 | | 408.3 | 1.6 |
| 1047 | | N-(2-chloro-4-(2,2-difluoroethoxy)benzyl)-2-isobutyramidoisonicotinamide | 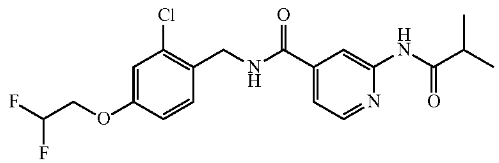 [SMILES: CC(C)C(=O)Nc1cc(C(=O)NCc2ccc(OCC(F)F)cc2Cl)ccn1] | Amine-91 | | 410.3 | 1.64 |
| 1048 | | 2-acetamido-N-(2-chloro-4-(2,2-difluoroethoxy)benzyl)-6-methylisonicotinamide | 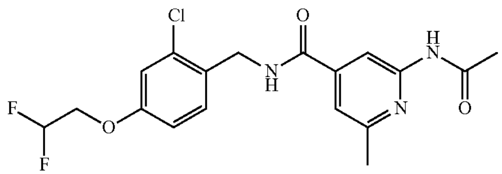 [SMILES: CC(=O)Nc1cc(C(=O)NCc2ccc(OCC(F)F)cc2Cl)cc(C)n1] | Amine-91 | | 396.3 | 1.54 |
| 1049 | | N-(2-chloro-4-(2,2-difluoroethoxy)benzyl)-2-isobutyramido-6-methylisonicotinamide | 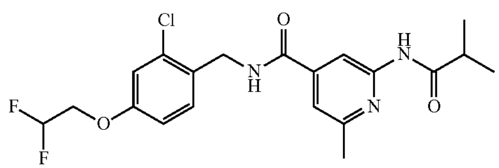 [SMILES: Cc1cc(C(=O)NCc2ccc(OCC(F)F)cc2Cl)cc(NC(=O)C(C)C)n1] | Amine-91 | | 424.3 | 1.7 |
| 1050 | | N-(2-chloro-4-(2,2-difluoroethoxy)benzyl)-2-(cyclopropanecarboxamido)-6-methylpyrimidine-4-carboxamide | 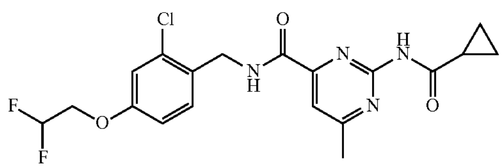 [SMILES: Cc1cc(C(=O)NCc2ccc(OCC(F)F)cc2Cl)nc(NC(=O)C2CC2)n1] | Amine-91 | | 423.2 | 1.62 |

TABLE 1-continued

| Example | Name | Chirality | Structure | Amine part | Carboxylic part | Observed MS | Retention time (min) |
|---|---|---|---|---|---|---|---|
| 1051 | N-(1-(4-(2,2-difluoroethoxy)-3-fluorophenyl)ethyl)-2-isobutyramido-6-methylisonicotinamide | single enantiomer | 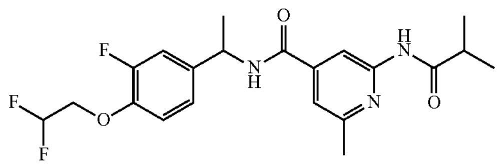 [SMILES: Cc1cc(C(=O)NC(C)c2ccc(OCC(F)F)c(F)c2)cc(NC(=O)C(C)C)n1] | Amine-89 | | 422.3 | 1.67 |
| 1052 | N-(1-(2-fluoro-3-(trifluoromethyl)phenyl)ethyl)-2-isobutyramido-6-methylisonicotinamide | single enantiomer | 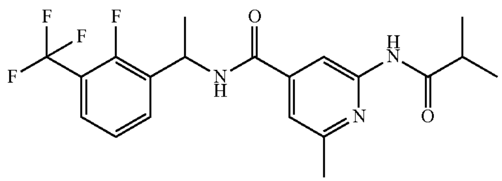 [SMILES: Cc1cc(C(=O)NC(C)c2cccc(C(F)(F)F)c2F)cc(NC(=O)C(C)C)n1] | Amine-93 | | 410.3 | 1.79 |
| 1053 | 2-(cyclopropanecarboxamido)-N-(4-(trifluoromethoxy)benzyl)isonicotinamide | | 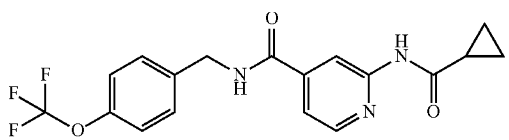 | | | 378.3 | 1.65 |
| 1054 | 2-methyl-6-propionamido-N-(4-(trifluoromethoxy)benzyl)isonicotinamide | | 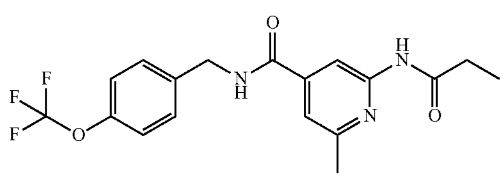 | | | 380.3 | 1.68 |

TABLE 1-continued

| Example | Name | Chirality | Structure | Amine part | Carboxylic part | Observed MS | Retention time (min) |
|---|---|---|---|---|---|---|---|
| 1055 | 2-acetamido-6-methyl-N-(4-(trifluoromethoxy)benzyl)isonicotinamide | | 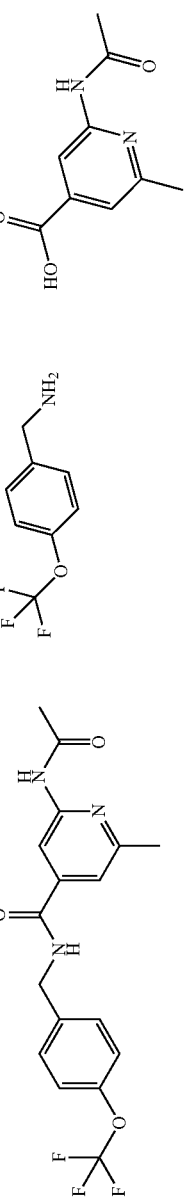 | 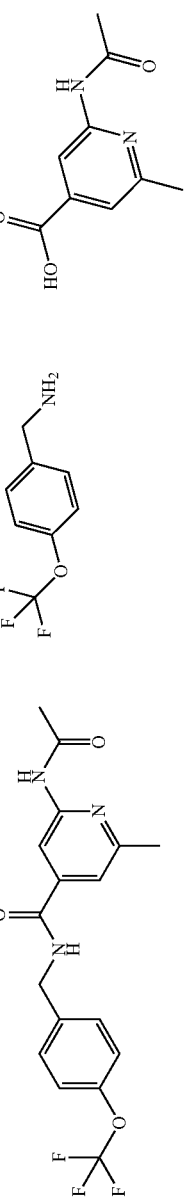 | 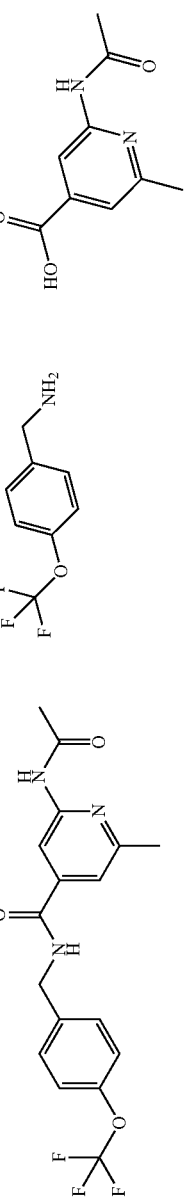 | 366.3 | 1.59 |
| 1056 | (R)-2-acetamido-6-methyl-N-(1-(4-(trifluoromethoxy)phenyl)ethyl)isonicotinamide | single enantiomer | 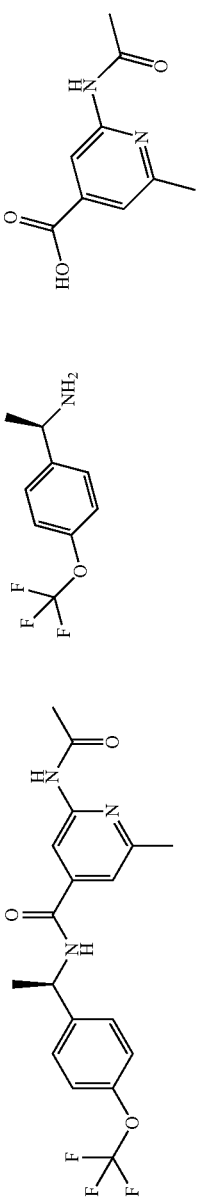 | 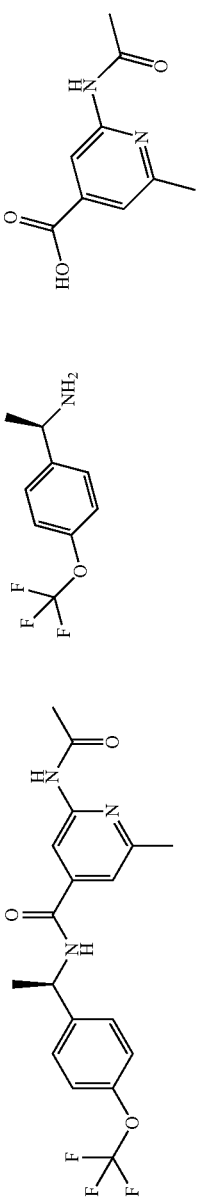 | 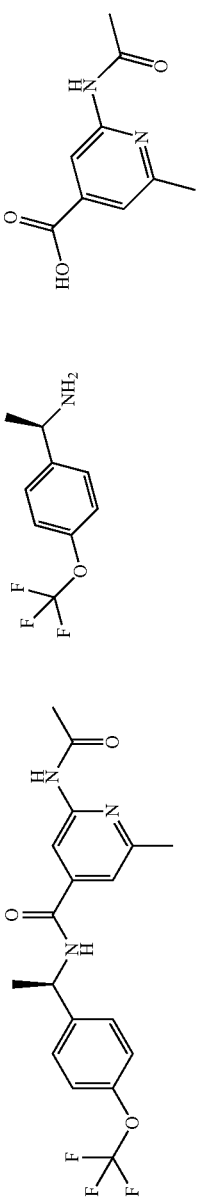 | 380.3 | 1.64 |
| 1057 | (R)-2-(cyclopropanecarboxamido)-N-(1-(4-(trifluoromethoxy)phenyl)ethyl)pyrimidine-4-carboxamide | single enantiomer | 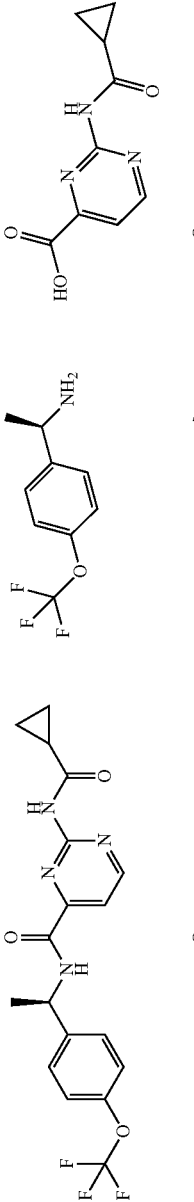 | 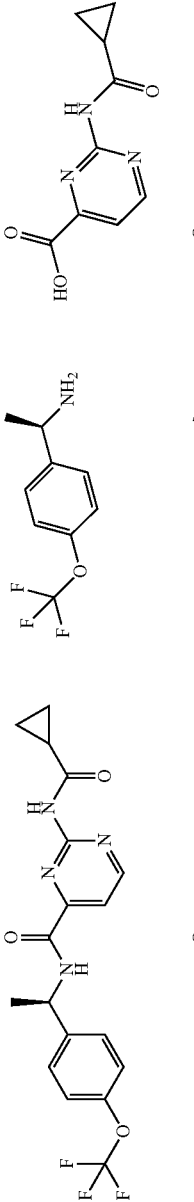 | 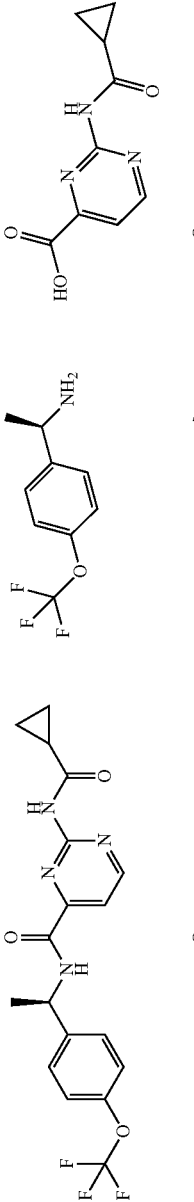 | 393.3 | 1.68 |
| 1058 | (R)-2-(cyclopropanecarboxamido)-6-methyl-N-(1-(4-(trifluoromethoxy)phenyl)ethyl)pyrimidine-4-carboxamide | single enantiomer | 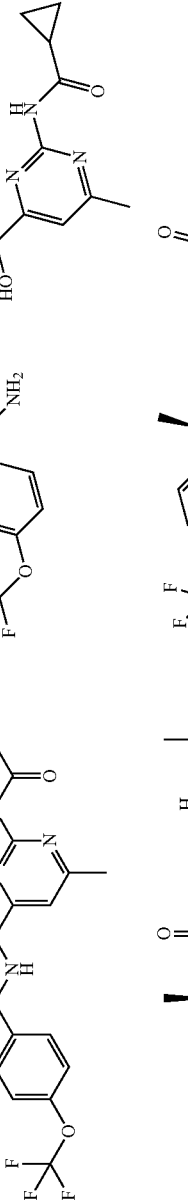 | 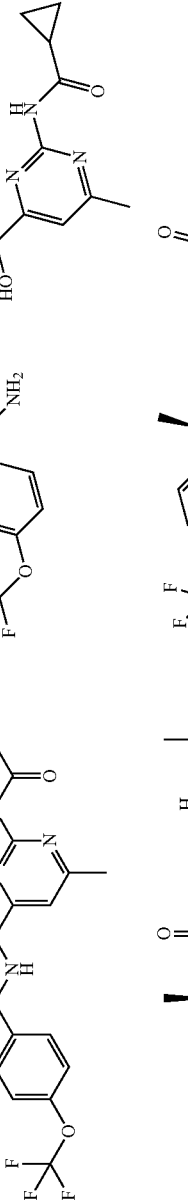 | 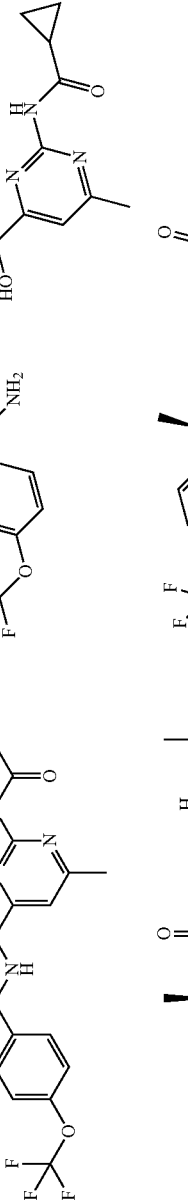 | 407.3 | 1.74 |
| 1059 | (R)-2-isobutyramido-N-(1-(4-(trifluoromethoxy)phenyl)ethyl)isonicotinamide | single enantiomer | 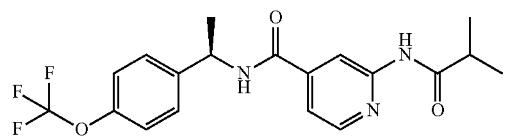 [SMILES: CC(C)C(=O)Nc1cc(C(=O)N[C@H](C)c2ccc(OC(F)(F)F)cc2)ccn1] |  |  | 394.3 | 1.75 |

TABLE 1-continued

| Example | Name | Chirality | Structure | Amine part | Carboxylic part | Observed MS | Retention time (min) |
|---|---|---|---|---|---|---|---|
| 1060 | N-((6-(2,2-difluoroethoxy)-4-methylpyridin-3-yl)methyl)-2-isobutyramido-isonicotinamide | | 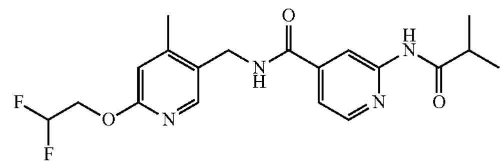 [SMILES: Cc1cc(OCC(F)F)ncc1CNC(=O)c1ccnc(NC(=O)C(C)C)c1] | Amine-69 | | 391.3 | 1.54 |
| 1061 | 2-(cyclopropanecarboxamido)-N-(1-(6-(2,2-difluoropropoxy)pyridin-3-yl)ethyl)pyrimidine-4-carboxamide | single enantiomer | 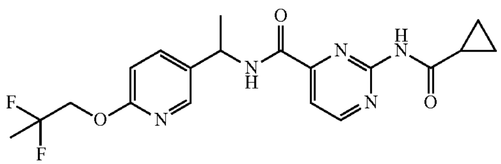 [SMILES: CC(NC(=O)c1ccnc(NC(=O)C2CC2)n1)c1ccc(OCC(C)(F)F)nc1] | Amine-71 | | 404.3 | 1.53 |
| 1062 | 2-(cyclopropanecarboxamido)-N-(4-methoxy-3-(trifluoromethyl)benzyl)pyrimidine-4-carboxamide | | 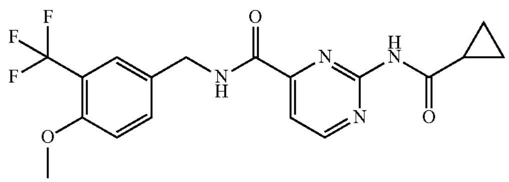 [SMILES: COc1ccc(CNC(=O)c2ccnc(NC(=O)C3CC3)n2)cc1C(F)(F)F] | | | 393.3 | 1.55 |
| 1063 | N-(1-(5-chloro-6-(2,2-difluoroethoxy)pyridin-3-yl)ethyl)-2-(cyclopropanecarboxamido)-6-methyl-isonicotinamide | single enantiomer | 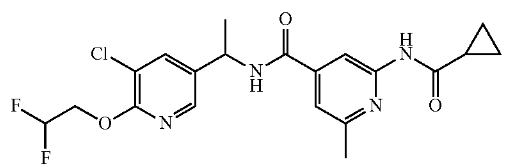 | Amine-53 | | 437.2 | 1.69 |
| 1064 | 2-cyclopropanecarboxamido)-N-(1-(6-(2,2-difluoropropoxy)pyridin-3-yl)ethyl)-6-methylisonicotinamide | single enantiomer | 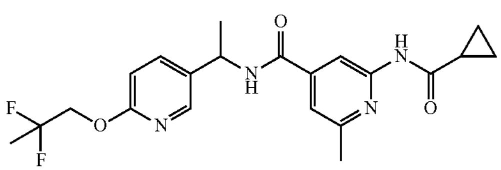 [SMILES: Cc1cc(C(=O)NC(C)c2ccc(OCC(C)(F)F)nc2)cc(NC(=O)C2CC2)n1] | Amine-71 | | 417.3 | 1.63 |

TABLE 1-continued

| Example | Name | Chirality | Structure | Amine part | Carboxylic part | Observed MS | Retention time (min) |
|---|---|---|---|---|---|---|---|
| 1065 | 2-(cyclopropanecarboxamido)-N-((5-fluoro-6-(2,2,2-trifluoroethoxy)pyridin-3-yl)methyl)-6-methylisonicotinamide | | 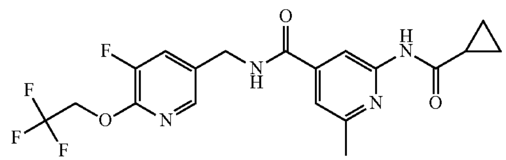 [SMILES: Cc1cc(C(=O)NCc2cnc(OCC(F)(F)F)c(F)c2)cc(NC(=O)C2CC2)n1] | Amine-28 | | 425.3 | 1.67 |
| 1066 | 2-(cyclopropanecarboxamido)-6-methyl-N-((6-(3,3,3-trifluoropropyl)pyridin-3-yl)methyl)isonicotinamide | | 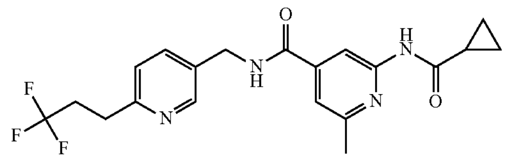 [SMILES: Cc1cc(C(=O)NCc2ccc(CCC(F)(F)F)nc2)cc(NC(=O)C2CC2)n1] | Amine-59 | | 405.3 | 1.52 |
| 1067 | 2-(cyclopropanecarboxamido)-6-methyl-N-(1-(6-(3,3,3-trifluoropropoxy)pyridin-3-yl)ethyl)isonicotinamide | single enantiomer | 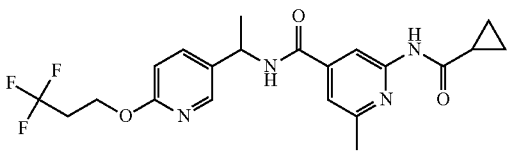 [SMILES: Cc1cc(C(=O)NC(C)c2ccc(OCCC(F)(F)F)nc2)cc(NC(=O)C2CC2)n1] | Amine-21 | | 435.3 | 1.67 |
| 1068 | 2-(1-methylcyclopropanecarboxamido)-N-(1-(6-(2,2,2-trifluoroethoxy)pyridin-3-yl)ethyl)isonicotinamide | single enantiomer | 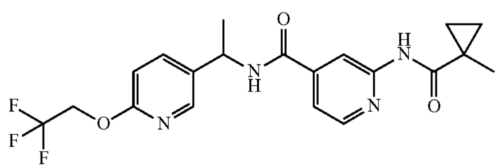 | Amine-1 | | 421.3 | 1.71 |

TABLE 1-continued

| Example | Name | Chirality | Structure | Amine part | Carboxylic part | Observed MS | Retention time (min) |
|---|---|---|---|---|---|---|---|
| 1069 | N-((6-(2,2-difluoroethoxy)-5-methylpyridin-3-yl)methyl)-2-(1-methylcyclopropane-carboxamido)isonicotinamide | | 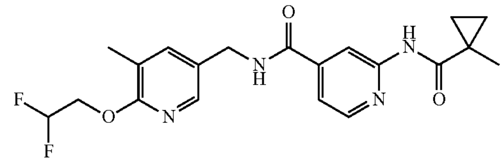 [SMILES: Cc1cc(CNC(=O)c2ccnc(NC(=O)C3(C)CC3)c2)cnc1OCC(F)F] | Amine-64 | | 403.3 | 1.63 |
| 1070 | 2-(1-methylcyclopropane-carboxamido)-N-(1-(6-(3,3,3-trifluoropropoxy)pyridin-3-yl)ethyl)isonicotinamide | single enantiomer | 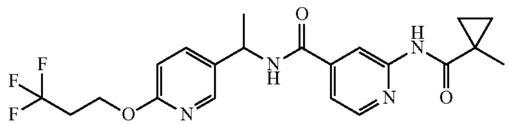 [SMILES: CC(NC(=O)c1ccnc(NC(=O)C2(C)CC2)c1)c1ccc(OCCC(F)(F)F)nc1] | Amine-21 | | 435.3 | 1.69 |
| 1071 | 2-(1-methylcyclopropanecarboxamido)-N-((6-(3,3,3-trifluoropropoxy)pyridin-3-yl)methyl)isonicotinamide | | 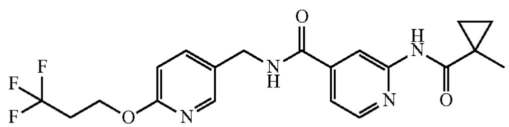 | Amine-30 | | 421.3 | 1.64 |
| 1072 | N-((4-methyl-6-(2,2,2-trifluoroethoxy)pyridin-3-yl)methyl)-2-(1-methylcyclopropanecarboxamido)isonicotinamide | | 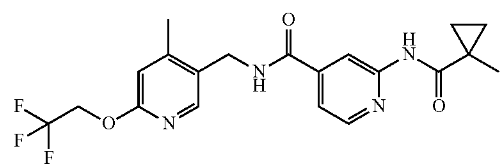 [SMILES: Cc1cc(OCC(F)(F)F)ncc1CNC(=O)c1ccnc(NC(=O)C2(C)CC2)c1] | Amine-29 | | 421.3 | 1.7 |
| 1073 | N-((2-methoxy-6-(2,2,2-trifluoroethoxy)pyridin-3-yl)methyl)-2-(1-methylcyclopropanecarboxamido)isonicotinamide | | 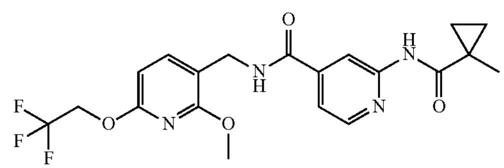 [SMILES: COc1nc(OCC(F)(F)F)ccc1CNC(=O)c1ccnc(NC(=O)C2(C)CC2)c1] | Amine-24 | | 437.3 | 1.77 |

TABLE 1-continued

| Example | Chirality | Structure | Name | Amine part | Carboxylic part | Observed MS | Retention time (min) |
|---|---|---|---|---|---|---|---|
| 1074 | | 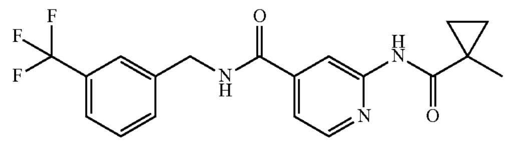 [SMILES: CC1(C(=O)Nc2cc(C(=O)NCc3cccc(C(F)(F)F)c3)ccn2)CC1] | 2-(1-methylcyclopropanecarboxamido)-N-(3-(trifluoromethyl)benzyl)isonicotinami | | | 376.3 | 1.7 |
| 1075 | single enantiomer | 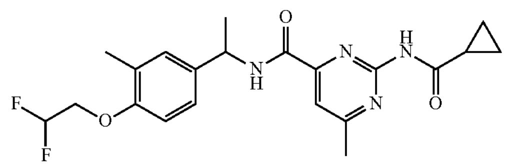 | 2-(cyclopropanecarboxamido)-N-(1-(4-(2,2-difluoroethoxy)-3-methylphenyl)ethyl)-6-methylpyrimidine-4-carboxamide | Amine-68 | | 417.3 | 1.67 |
| 1076 | | 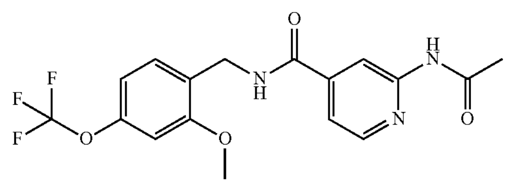 [SMILES: COc1cc(OC(F)(F)F)ccc1CNC(=O)c1ccnc(NC(C)=O)c1] | 2-acetamido-N-(2-methoxy-4-(trifluoromethoxy)benzyl)isonicotinamide | | | 382.3 | 1.56 |
| 1077 | | 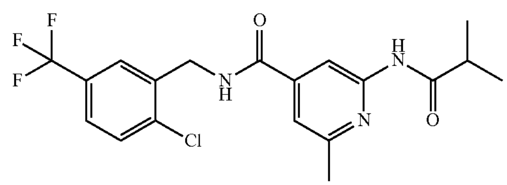 [SMILES: Cc1cc(C(=O)NCc2cc(C(F)(F)F)ccc2Cl)cc(NC(=O)C(C)C)n1] | N-(2-chloro-5-(trifluoromethyl)benzyl)-2-isobutyramido-6-methylisonicotinamide | | | 412.3 | 1.8 |
| 1078 | | 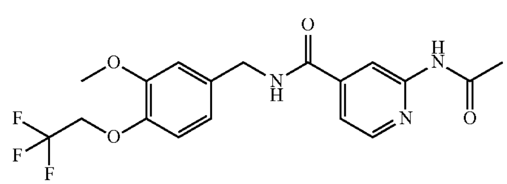 [SMILES: COc1cc(CNC(=O)c2ccnc(NC(C)=O)c2)ccc1OCC(F)(F)F] | 2-acetamido-N-(3-methoxy-4-(2,2,2-trifluoroethoxy)benzyl)isonicotinamide | | | 396.3 | 1.46 |

TABLE 1-continued

| Example | Name | Chirality | Structure | Amine part | Carboxylic part | Observed MS | Retention time (min) |
|---|---|---|---|---|---|---|---|
| 1079 | 2-(cyclopropanecarboxamido)-N-((5-cyclopropyl-6-(2,2-difluoroethoxy)pyridin-3-yl)methyl)-6-methylpyrimidine-4-carboxamide | | 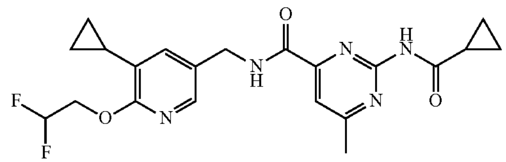 | Amine-77 | | 430.3 | 1.65 |
| 1080 | N-((5-cyclopropyl-6-(2,2-difluoroethoxy)pyridin-3-yl)methyl)-2-(2-hydroxy-2-methylpropanamido)-6-methylisonicotinamide | | 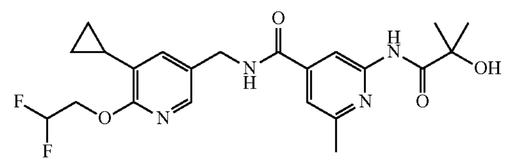 [SMILES: Cc1cc(C(=O)NCc2cnc(OCC(F)F)c(C3CC3)c2)cc(NC(=O)C(C)(C)O)n1] | Amine-77 | | 447.3 | 1.62 |
| 1081 | N-((5-cyclopropyl-6-(2,2-difluoroethoxy)pyridin-3-yl)methyl)-2-propionamidoisonicotinamide | | 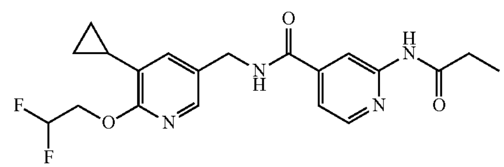 [SMILES: CCC(=O)Nc1cc(C(=O)NCc2cnc(OCC(F)F)c(C3CC3)c2)ccn1] | Amine-77 | | 403.3 | 1.59 |
| 1082 | 2-acetamido-N-((5-cyclopropyl-6-(2,2-difluoroethoxy)pyridin-3-yl)methyl)-6-methylisonicotinamide | | 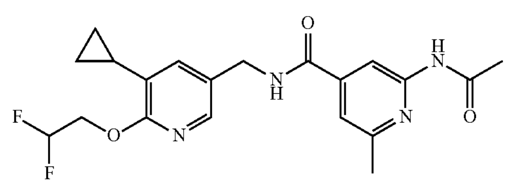 | Amine-77 | | 403.3 | 1.57 |

TABLE 1-continued

| Example | Name | Chirality | Structure | Amine part | Carboxylic part | Observed MS | Retention time (min) |
|---|---|---|---|---|---|---|---|
| 1083 | 2-acetamido-N-(1-(5-cyclopropyl-6-(2,2-difluoroethoxy)pyridin-3-yl)ethyl)-6-methylisonicotinamide | single enantiomer | 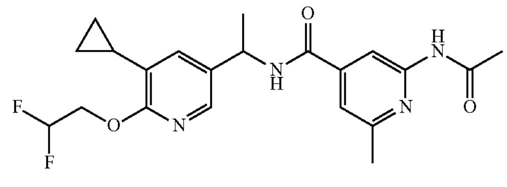 | Amine-78 | | 417.3 | 1.63 |
| 1084 | N-(1-(5-cyclopropyl-6-(2,2-difluoroethoxy)pyridin-3-yl)ethyl)-2-isobutyramidoisonicotinamide | single enantiomer | 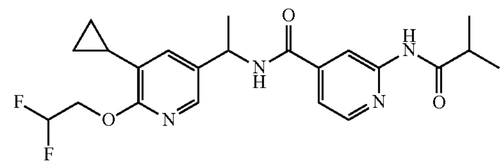 [SMILES: CC(C)C(=O)Nc1cc(C(=O)NC(C)c2cnc(OCC(F)F)c(C3CC3)c2)ccn1] | Amine-78 | | 431.4 | 1.72 |
| 1085 | 2-(cyclopropanecarboxamido)-N-(1-(5-cyclopropyl-6-(2,2-difluoroethoxy)pyridin-3-yl)ethyl)-6-methylpyrimidine-4-carboxamide | single enantiomer | 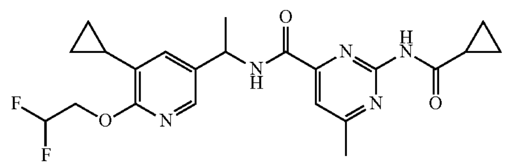 | Amine-78 | | 444.4 | 1.72 |
| 1086 | N-((6-(2,2-difluoroethoxy)-5-isopropylpyridin-3-yl)methyl)-2-isobutyramidoisonicotinamide | | 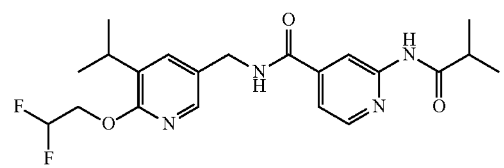 [SMILES: CC(C)C(=O)Nc1cc(C(=O)NCc2cnc(OCC(F)F)c(C(C)C)c2)ccn1] | Amine-87 | | 419.4 | 1.74 |

TABLE 1-continued

| Example | Name | Chirality | Structure | Amine part | Carboxylic part | Observed MS | Retention time (min) |
|---|---|---|---|---|---|---|---|
| 1087 | N-((6-(2,2-difluoroethoxy)-5-isopropylpyridin-3-yl)methyl)-2-isobutyramido-6-methylisonicotinamide | | 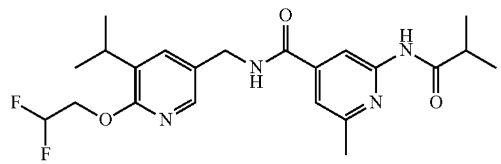 [SMILES: Cc1cc(C(=O)NCc2cnc(OCC(F)F)c(C(C)C)c2)cc(NC(=O)C(C)C)n1] | Amine-87 | | 433.3 | 1.8 |
| 1088 | 2-(cyclopropanecarboxamido)-N-((6-(2,2-difluoroethoxy)-5-isopropylpyridin-3-yl)methyl)pyrimidine-4-carboxamide | | 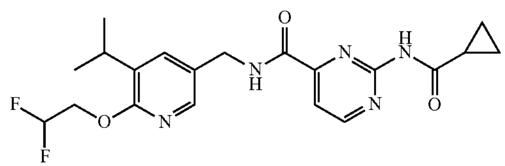 | Amine-87 | | 418.3 | 1.66 |
| 1089 | 2-(cyclopropanecarboxamido)-N-((6-(2,2-difluoroethoxy)-5-isopropylpyridin-3-yl)methyl)-6-methylpyrimidine-4-carboxamide | | 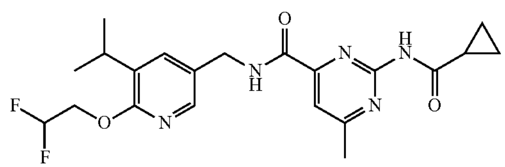 [SMILES: Cc1cc(C(=O)NCc2cnc(OCC(F)F)c(C(C)C)c2)nc(NC(=O)C2CC2)n1] | Amine-87 | | 432.4 | 1.72 |
| 1090 | 2-(cyclopropanecarboxamido)-N-(1-((6-(2,2-difluoroethoxy)-5-methylpyridin-3-yl)ethyl)-N,6-dimethylpyrimidine-4-carboxamide | single enantiomer | 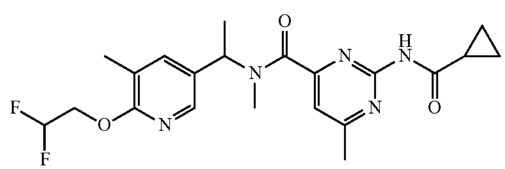 [SMILES: Cc1cc(C(=O)N(C)C(C)c2cnc(OCC(F)F)c(C)c2)nc(NC(=O)C2CC2)n1] | Amine-79 | | 432.4 | 1.6 |

TABLE 1-continued

| Example | Chirality | Name | Structure | Amine part | Carboxylic part | Observed MS | Retention time (min) |
|---|---|---|---|---|---|---|---|
| 1091 | | N-((5-chloro-6-(2,2-difluoroethoxy)pyridin-3-yl)methyl)-2-(2-cyclopropyl-acetamido)-6-methylisonicotinamide | 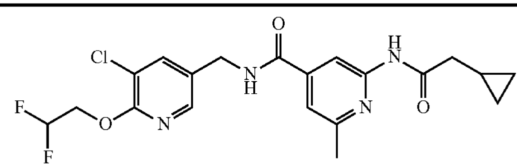 | Amine-52 | | 437.3 | 1.68 |
| 1092 | | 2-(2-cyclopropyl-acetamido)-6-methyl-N-((6-(3,3,3-trifluoropropoxy)pyridin-3-yl)methyl)isonicotinamide | 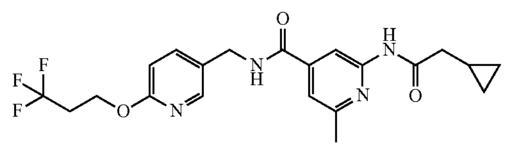 [SMILES: Cc1cc(C(=O)NCc2ccc(OCCC(F)(F)F)nc2)cc(NC(=O)CC2CC2)n1] | Amine-30 | | 435.4 | 1.67 |
| 1093 | | 2-(cyclopropanecarboxamido)-N-(3-fluoro-4-(trifluoromethoxy)benzyl)isonicotinamide | 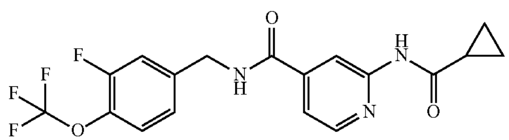 | | | 396.3 | 1.68 |
| 1094 | | 2-acetamido-N-(3-fluoro-4-(trifluoromethoxy)benzyl)-6-methylisonicotinamide | 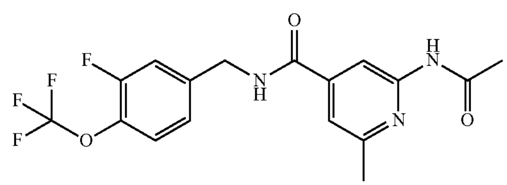 [SMILES: CC(=O)Nc1cc(C(=O)NCc2ccc(OC(F)(F)F)c(F)c2)cc(C)n1] | | | 384.3 | 1.62 |

TABLE 1-continued

| Example | Name | Chirality | Structure | Amine part | Carboxylic part | Observed MS | Retention time (min) |
|---|---|---|---|---|---|---|---|
| 1095 | 2-(cyclopropanecarboxamido)-N-(3-fluoro-4-(trifluoromethoxy)benzyl)-6-methylpyrimidine-4-carboxamide | | 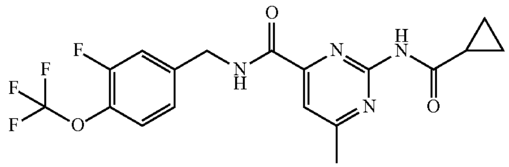 [SMILES: Cc1cc(C(=O)NCc2ccc(OC(F)(F)F)c(F)c2)nc(NC(=O)C2CC2)n1] | | | 411.2 | 1.7 |
| 1096 | 2-acetamido-N-(1-(2-fluoro-5-(trifluoromethyl)phenyl)ethyl)isonicotinamide | single enantiomer | 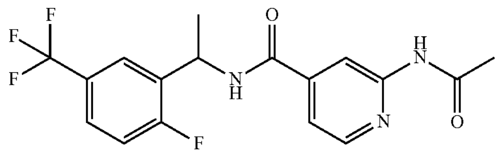 [SMILES: CC(=O)Nc1cc(C(=O)NC(C)c2cc(C(F)(F)F)ccc2F)ccn1] | Amine-81 | | 370.1 | 1.55 |
| 1097 | N-(1-(2-fluoro-5-(trifluoromethyl)phenyl)ethyl)-2-isobutyramidoisonicotinamide | single enantiomer | 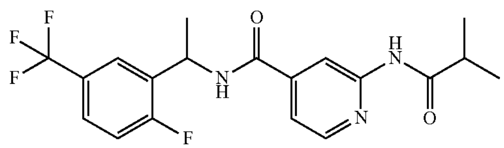 [SMILES: CC(C)C(=O)Nc1cc(C(=O)NC(C)c2cc(C(F)(F)F)ccc2F)ccn1] | Amine-81 | | 396.3 | 1.72 |
| 1098 | 2-acetamido-N-(1-(3-chloro-4-(2,2-difluoroethoxy)phenyl)ethyl)isonicotinamide | single enantiomer | 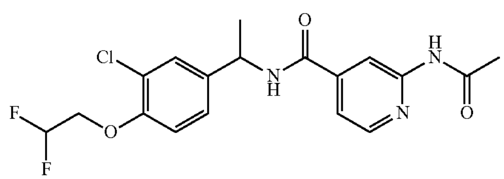 | Amine-82 | | 396.2 | 1.51 |

TABLE 1-continued

| Example | Name | Chirality | Structure | Amine part | Carboxylic part | Observed MS | Retention time (min) |
|---|---|---|---|---|---|---|---|
| 1099 | N-(1-(3-chloro-4-(2,2-difluoroethoxy)phenyl)ethyl)-2-isobutyramidoisonicotinamide | single enantiomer | 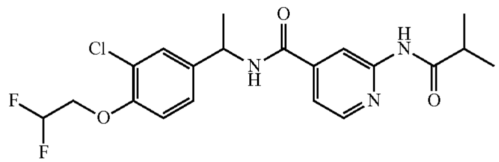 [SMILES: CC(C)C(=O)Nc1cc(C(=O)NC(C)c2ccc(OCC(F)F)c(Cl)c2)ccn1] | Amine-82 | | 424.3 | 1.67 |
| 1100 | 2-acetamido-N-(1-(3-chloro-4-(2,2-difluoroethoxy)phenyl)ethyl)-6-methylisonicotinamide | single enantiomer | 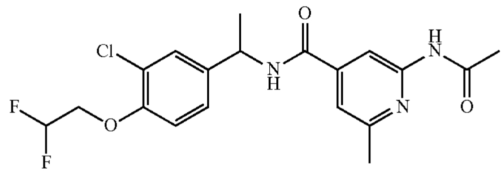 | Amine-82 | | 410.3 | 1.57 |
| 1101 | N-(1-(3-chloro-4-(2,2-difluoroethoxy)phenyl)ethyl)-2-isobutyramido-6-methylisonicotinamide | single enantiomer | 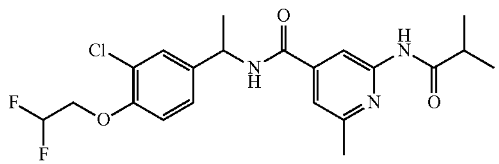 | Amine-82 | | 438.3 | 1.73 |
| 1102 | 2-(cyclopropanecarboxamido)-N-(3-methoxy-4-(2,2,2-trifluoroethoxy)benzyl)isonicotinamide | | 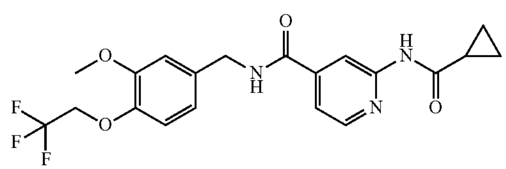 [SMILES: COc1cc(CNC(=O)c2ccnc(NC(=O)C3CC3)c2)ccc1OCC(F)(F)F] | | | 424.1 | 1.58 |
| 1103 | 2-(cyclopropanecarboxamido)-N-(1-(4-(2,2-difluoroethoxy)-2-methylphenyl)ethyl)pyrimidine-4-carboxamide | single enantiomer | 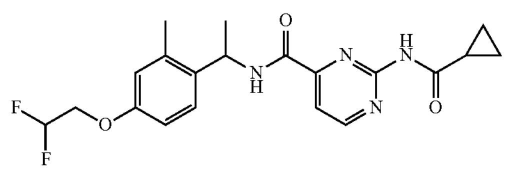 [SMILES: Cc1cc(OCC(F)F)ccc1C(C)NC(=O)c1ccnc(NC(=O)C2CC2)n1] | Amine-83 | | 403.3 | 1.59 |

TABLE 1-continued

| Example | Name | Chirality | Structure | Amine part | Carboxylic part | Observed MS | Retention time (min) |
|---|---|---|---|---|---|---|---|
| 1104 | N-(1-(4-(2,2-difluoroethoxy)-2-methylphenyl)ethyl)-2-isobutyramido-6-methylisonicotinamide | single enantiomer | 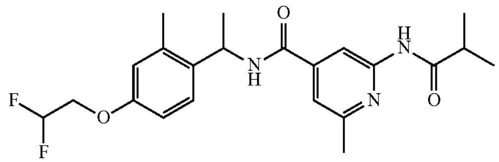 | Amine-83 | | 418.3 | 1.72 |
| 1105 | 2-isobutyramido-N,6-dimethyl-N-(1-(6-(2,2,2-trifluoroethoxy)pyridin-3-yl)ethyl)isonicotinamide | single enantiomer | 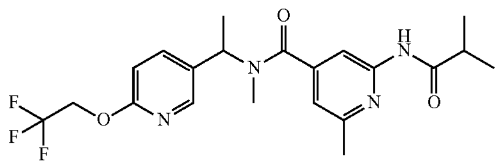 | Amine-3 | | 437.3 | 1.76 |
| 1106 | N-(4-(2,2-difluoroethoxy)-3-methoxybenzyl)-2-propionamidoisonicotinamide | | 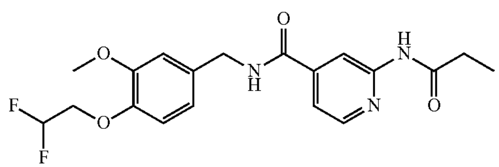 [SMILES: CCC(=O)Nc1cc(C(=O)NCc2ccc(OCC(F)F)c(OC)c2)ccn1] | Amine-106 | | 392.3 | 1.43 |
| 1107 | N-(4-(2,2-difluoroethoxy)-3-methoxybenzyl)-2-isobutyramido-6-methylisonicotinamide | | 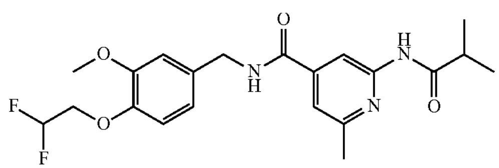 [SMILES: COc1cc(CNC(=O)c2cc(C)nc(NC(=O)C(C)C)c2)ccc1OCC(F)F] | Amine-106 | | 420.4 | 1.57 |

| Example | Name | Chirality | Structure | Amine part | Carboxylic part | Observed MS | Retention time (min) |
|---|---|---|---|---|---|---|---|
| 1108 | 2-(cyclopropanecarboxamido)-N-(1-(6-(2,2-difluoroethoxy)-5-methoxypyridin-3-yl)ethyl)isonicotinamide | single enantiomer | 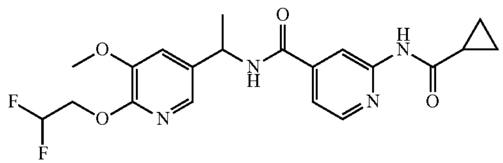 [SMILES: COc1cc(C(C)NC(=O)c2ccnc(NC(=O)C3CC3)c2)cnc1OCC(F)F] | Amine-94 | | 419.4 | 1.5 |
| 1109 | 2-acetamido-N-(1-(6-(2,2-difluoroethoxy)-5-methoxypyridin-3-yl)ethyl)-6-methylisonicotinamide | single enantiomer | 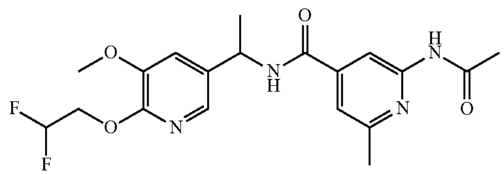 | Amine-94 | | 407.3 | 1.43 |
| 1110 | N-(1-(6-(2,2-difluoroethoxy)-5-methoxypyridin-3-yl)ethyl)-2-isobutyramido-6-methylisonicotinamide | single enantiomer | 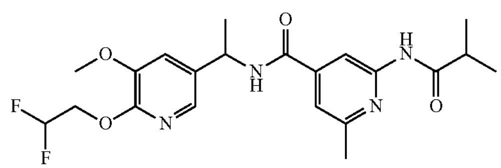 [SMILES: COc1cc(C(C)NC(=O)c2cc(C)nc(NC(=O)C(C)C)c2)cnc1OCC(F)F] | Amine-94 | | 435.3 | 1.6 |
| 1111 | 2-acetamido-N-(1-(4-(2,2-difluoroethoxy)-3-methoxyphenyl)ethyl)-6-methylisonicotinamide | single enantiomer | 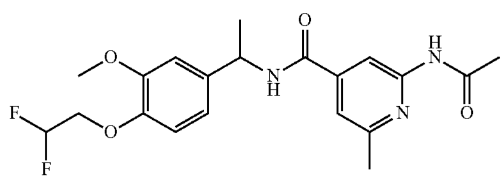 [SMILES: COc1cc(C(C)NC(=O)c2cc(C)nc(NC(C)=O)c2)ccc1OCC(F)F] | Amine-102 | | 406.3 | 1.46 |

TABLE 1-continued

| Example | Name | Chirality | Structure | Amine part | Carboxylic part | Observed MS | Retention time (min) |
|---|---|---|---|---|---|---|---|
| 1112 | N-(1-(4-(2,2-difluoroethoxy)-3-methoxyphenyl)ethyl)-2-isobutyramidoisonicotinamide | single enantiomer | 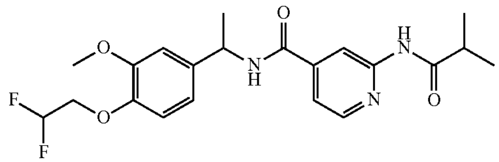 [SMILES: COc1cc(C(C)NC(=O)c2ccnc(NC(=O)C(C)C)c2)ccc1OCC(F)F] | Amine-102 | | 420.3 | 1.57 |
| 1113 | N-(1-(4-(2,2-difluoroethoxy)-3-methoxyphenyl)ethyl)-2-isobutyramido-6-methylisonicotinamide | single enantiomer | 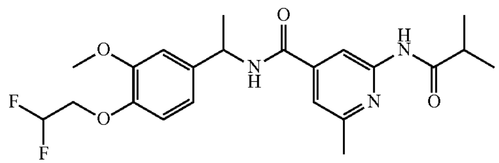 [SMILES: COc1cc(C(C)NC(=O)c2cc(C)nc(NC(=O)C(C)C)c2)ccc1OCC(F)F] | Amine-102 | | 434.4 | 1.63 |
| 1114 | 2-(cyclopropanecarboxamido)-N-(1-(2-fluoro-4-(trifluoromethyl)phenyl)ethyl)pyrimidine-4-carboxamide | single enantiomer | 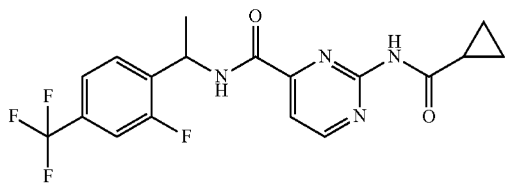 [SMILES: CC(NC(=O)c1ccnc(NC(=O)C2CC2)n1)c1ccc(C(F)(F)F)cc1F] | Amine-104 | | 395.3 | 1.68 |
| 1115 | 2-acetamido-N-(1-(2-chloro-4-(2,2-difluoroethoxy)phenyl)ethyl)isonicotinamide | single enantiomer | 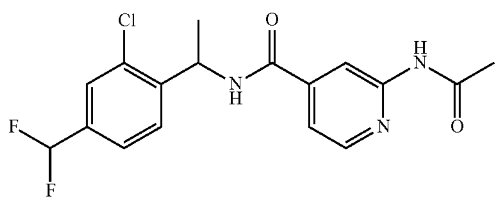 [SMILES: CC(=O)Nc1cc(C(=O)NC(C)c2ccc(C(F)F)cc2Cl)ccn1] | Amine-95 | | 396.2 | 1.54 |
| 1116 | N-(1-(2-chloro-4-(2,2-difluoroethoxy)phenyl)ethyl)-2-propionamidoisonicotinamide | single enantiomer | 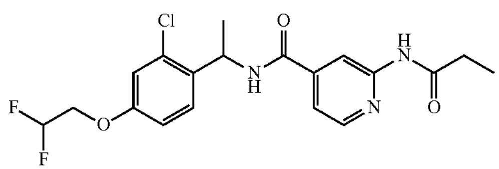 | Amine-95 | | 410.2 | 1.62 |

TABLE 1-continued

| Example | Name | Chirality | Structure | Amine part | Carboxylic part | Observed MS | Retention time (min) |
|---|---|---|---|---|---|---|---|
| 1117 | N-(1-(2-chloro-4-(2,2-difluoroethoxy)phenyl)ethyl)-2-(cyclopropanecarboxamido)isonicotinamide | single enantiomer | 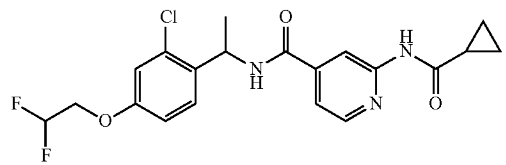 [SMILES: CC(NC(=O)c1ccnc(NC(=O)C2CC2)c1)c1ccc(OCC(F)F)cc1Cl] | Amine-95 | | 422.2 | 1.65 |
| 1118 | N-(1-(2-chloro-4-(2,2-difluoroethoxy)phenyl)ethyl)-2-isobutyramidoisonicotinamide | single enantiomer | 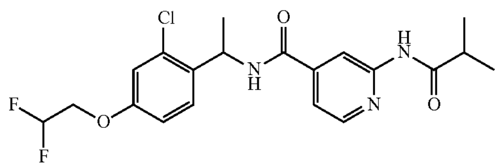 | Amine-95 | | 424.3 | 1.69 |
| 1119 | N-(1-(2-chloro-4-(2,2-difluoroethoxy)phenyl)ethyl)-2-(cyclopropanecarboxamido)pyrimidine-4-carboxamide | single enantiomer | 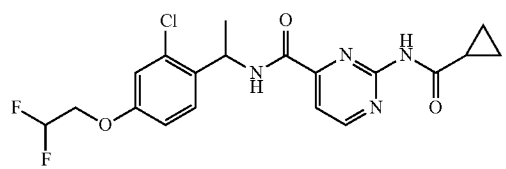 | Amine-95 | | 423.2 | 1.63 |
| 1120 | N-(1-(2-chloro-4-(2,2-difluoroethoxy)phenyl)ethyl)-2-isobutyramido-6-methylisonicotinamide | single enantiomer | 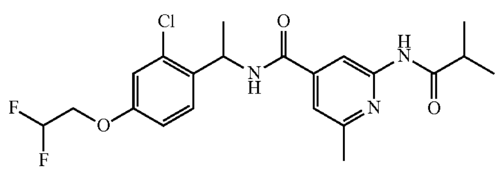 [SMILES: Cc1cc(C(=O)NC(C)c2ccc(OCC(F)F)cc2Cl)cc(NC(=O)C(C)C)n1] | Amine-95 | | 438.3 | 1.75 |

| Example | Name | Chirality | Structure | Amine part | Carboxylic part | Observed MS | Retention time (min) |
|---|---|---|---|---|---|---|---|
| 1121 | N-(1-(2-chloro-4-(2,2-difluoroethoxy)phenyl)ethyl)-2-(cyclopropanecarboxamido)-6-methylpyrimidine-4-carboxamide | single enantiomer | 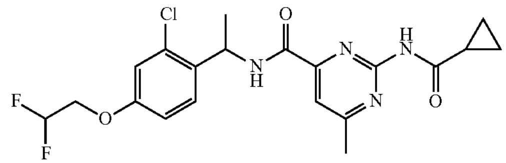 | Amine-95 | | 437.2 | 1.69 |
| 1122 | N-(1-(4-(2,2-difluoroethoxy)-3,5-difluorophenyl)ethyl)-2-propionamidoisonicotinamide | single enantiomer | 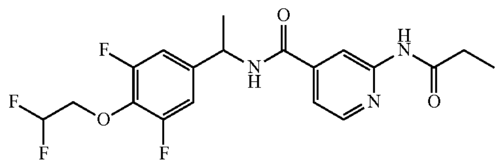 | Amine-96 | | 412.3 | 1.59 |
| 1123 | 2-(cyclopropanecarboxamido)-N-(1-(4-(2,2-difluoroethoxy)-3,5-difluorophenyl)ethyl)isonicotinamide | single enantiomer | 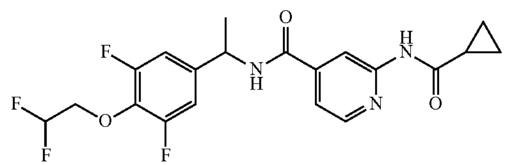 [SMILES: CC(NC(=O)c1ccnc(NC(=O)C2CC2)c1)c1cc(F)c(OCC(F)F)c(F)c1] | Amine-96 | | 424.2 | 1.62 |
| 1124 | N-(1-(4-(2,2-difluoroethoxy)-3,5-difluorophenyl)ethyl)-2-isobutyramido-6-methylisonicotinamide | single enantiomer | 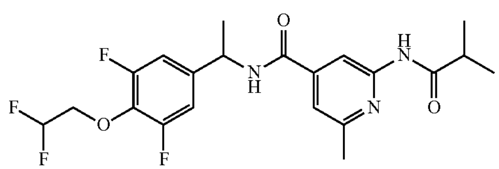 [SMILES: Cc1cc(C(=O)NC(C)c2cc(F)c(OCC(F)F)c(F)c2)cc(NC(=O)C(C)C)n1] | Amine-96 | | 440.3 | 1.72 |

TABLE 1-continued

| Example | Name | Chirality | Structure | Amine part | Carboxylic part | Observed MS | Retention time (min) |
|---|---|---|---|---|---|---|---|
| 1125 | 2-acetamido-N-(3-(2,2-difluoroethoxy)-2-methylbenzyl)isonicotinamide | | 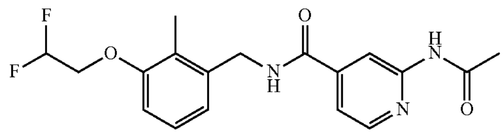 [SMILES: CC(=O)Nc1cc(C(=O)NCc2cccc(OCC(F)F)c2C)ccn1] | Amine-98 | | 362.3 | 1.45 |
| 1126 | N-(3-(2,2-difluoroethoxy)-2-methylbenzyl)-2-propionamidoisonicotinamide | | 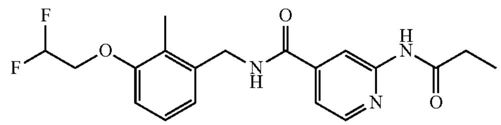 [SMILES: CCC(=O)Nc1cc(C(=O)NCc2cccc(OCC(F)F)c2C)ccn1] | Amine-98 | | 376.3 | 1.53 |
| 1127 | 2-(cyclopropanecarboxamido)-N-(3-(2,2-difluoroethoxy)-2-methylbenzyl)isonicotinamide | | 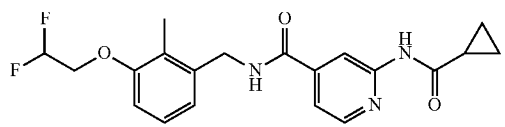 [SMILES: Cc1c(CNC(=O)c2ccnc(NC(=O)C3CC3)c2)cccc1OCC(F)F] | Amine-98 | | 388.3 | 1.57 |
| 1128 | N-(3-(2,2-difluoroethoxy)-2-methylbenzyl)-2-isobutyramidoisonicotinamide | | 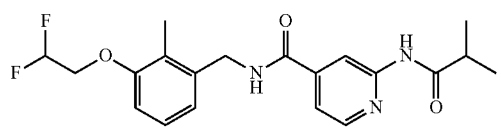 [SMILES: Cc1c(CNC(=O)c2ccnc(NC(=O)C(C)C)c2)cccc1OCC(F)F] | Amine-98 | | 390.3 | 1.61 |
| 1129 | 2-(cyclopropanecarboxamido)-N-(3-(2,2-difluoroethoxy)-2-methylbenzyl)pyrimidine-4-carboxamide | | 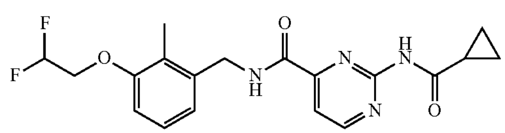 [SMILES: Cc1c(CNC(=O)c2ccnc(NC(=O)C3CC3)n2)cccc1OCC(F)F] | Amine-98 | | 389.3 | 1.54 |

| Example | Name | Chirality | Structure | Amine part | Carboxylic part | Observed MS | Retention time (min) |
|---|---|---|---|---|---|---|---|
| 1130 | 2-acetamido-N-(3-(2,2-difluoroethoxy)-2-methylbenzyl)-6-methylisonicotinamide | | 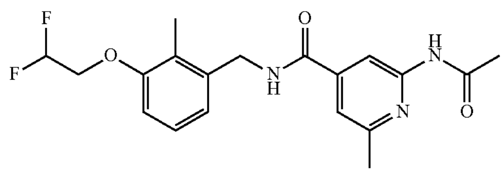 [SMILES: CC(=O)Nc1cc(C(=O)NCc2cccc(OCC(F)F)c2C)cc(C)n1] | Amine-98 | | 376.4 | 1.51 |
| 1131 | N-(3-(2,2-difluoroethoxy)-2-methylbenzyl)-2-isobutyramido-6-methylisonicotinamide | | 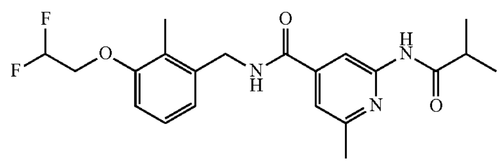 [SMILES: Cc1cc(C(=O)NCc2cccc(OCC(F)F)c2C)cc(NC(=O)C(C)C)n1] | Amine-98 | | 404.3 | 1.67 |
| 1132 | N-(3-(2,2-difluoroethoxy)-2-methylbenzyl)-2-(2-hydroxy-2-methylpropanamido)-6-methylisonicotinamide | | 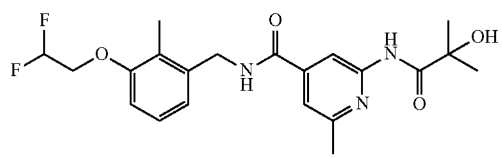 [SMILES: Cc1cc(C(=O)NCc2cccc(OCC(F)F)c2C)cc(NC(=O)C(C)(C)O)n1] | Amine-98 | | 420.3 | 1.57 |
| 1133 | 2-(cyclopropanecarboxamido)-N-(3-(2,2-difluoroethoxy)-2-methylbenzyl)-6-methylpyrimidine-4-carboxamide | | 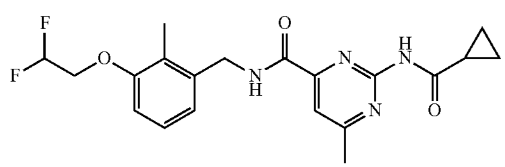 [SMILES: Cc1cc(C(=O)NCc2cccc(OCC(F)F)c2C)nc(NC(=O)C2CC2)n1] | Amine-98 | | 403.3 | 1.6 |

TABLE 1-continued

| Example | Name | Chirality | Structure | Amine part | Carboxylic part | Observed MS | Retention time (min) |
|---|---|---|---|---|---|---|---|
| 1134 | N-((6-(2,2-difluoroethoxy)-2-methylpyridin-3-yl)methyl)-2-propionamido-isonicotinamide | | 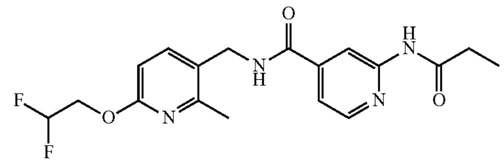 [SMILES: CCC(=O)Nc1cc(C(=O)NCc2ccc(OCC(F)F)nc2C)ccn1] | Amine-101 | | 377.3 | 1.5 |
| 1135 | 2-(cyclopropanecarboxamido)-N-((6-(2,2-difluoroethoxy)-2-methylpyridin-3-yl)methyl)isonicotinamide | | 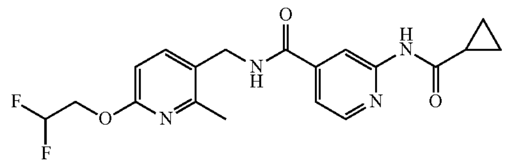 | Amine-101 | | 389.3 | 1.54 |
| 1136 | N-((6-(2,2-difluoroethoxy)-2-methylpyridin-3-yl)methyl)-2-isobutyramidoisonicotinamide | | 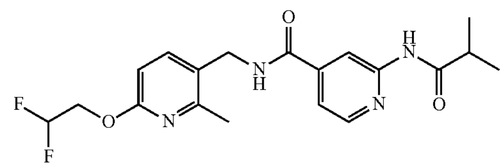 [SMILES: Cc1nc(OCC(F)F)ccc1CNC(=O)c1ccnc(NC(=O)C(C)C)c1] | Amine-101 | | 391.3 | 1.59 |
| 1137 | 2-acetamido-N-((6-(2,2-difluoroethoxy)-2-methylpyridin-3-yl)methyl)-6-methylisonicotinamide | | 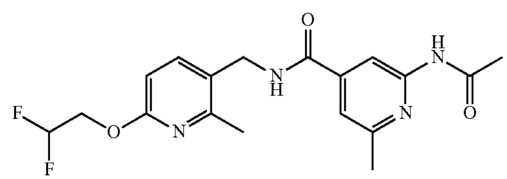 [SMILES: CC(=O)Nc1cc(C(=O)NCc2ccc(OCC(F)F)nc2C)cc(C)n1] | Amine-101 | | 377.3 | 1.48 |
| 1138 | 2-(cyclopropanecarboxamido)-N-((6-(2,2-difluoroethoxy)-2-methylpyridin-3-yl)methyl)-6-methylisonicotinamide | | 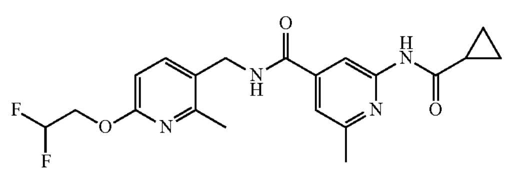 [SMILES: Cc1cc(C(=O)NCc2ccc(OCC(F)F)nc2C)cc(NC(=O)C2CC2)n1] | Amine-101 | | 403.3 | 1.61 |

TABLE 1-continued

| Example | Name | Chirality | Structure | Amine part | Carboxylic part | Observed MS | Retention time (min) |
|---|---|---|---|---|---|---|---|
| 1139 | N-((6-(2,2-difluoroethoxy)-2-methylpyridin-3-yl)methyl)-2-isobutyramido-6-methylisonicotinamide | | 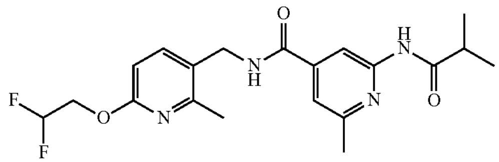 | Amine-101 | | 405.3 | 1.65 |
| 1140 | 2-(cyclopropanecarboxamido)-N-((6-(2,2-difluoroethoxy)-2-methylpyridin-3-yl)methyl)-6-methylpyrimidine-4-carboxamide | | 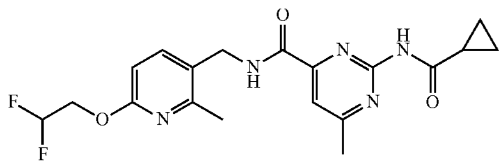 [SMILES: Cc1cc(C(=O)NCc2ccc(OCC(F)F)nc2C)nc(NC(=O)C2CC2)n1] | Amine-101 | | 404.3 | 1.56 |
| 1141 | 2-acetamido-N-(1-(5-(2,2-difluoroethoxy)-2-methylphenyl)ethyl)isonicotinamide | single enantiomer | 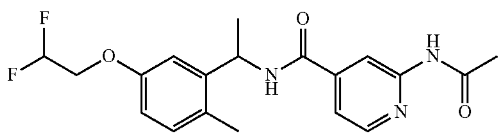 [SMILES: CC(=O)Nc1cc(C(=O)NC(C)c2cc(OCC(F)F)ccc2C)ccn1] | Amine-100 | | 376.3 | 1.53 |
| 1142 | 2-acetamido-N-(1-(5-(2,2-difluoroethoxy)-2-methylphenyl)ethyl)-6-methylisonicotinamide | single enantiomer | 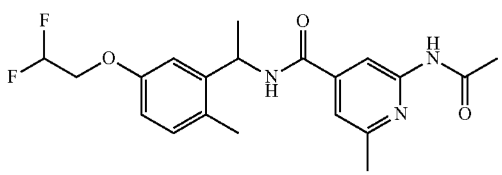 [SMILES: CC(=O)Nc1cc(C(=O)NC(C)c2cc(OCC(F)F)ccc2C)cc(C)n1] | Amine-100 | | 390.3 | 1.58 |

| Example | Name | Chirality | Structure | Amine part | Carboxylic part | Observed MS | Retention time (min) |
|---|---|---|---|---|---|---|---|
| 1143 | 2-(cyclopropanecarboxamido)-N-(1-(5-(2,2-difluoroethoxy)-2-methylphenyl)ethyl)pyrimidine-4-carboxamide | single enantiomer | 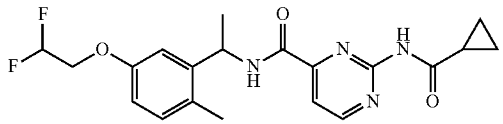 [SMILES: Cc1ccc(OCC(F)F)cc1C(C)NC(=O)c1ccnc(NC(=O)C2CC2)n1] | Amine-100 | | 403.3 | 1.62 |
| 1144 | 2-(cyclopropanecarboxamido)-N-(1-(5-(2,2-difluoroethoxy)-2-methylphenyl)ethyl)-6-methylpyrimidine-4-carboxamide | single enantiomer | 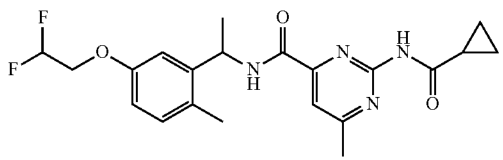 [SMILES: Cc1cc(C(=O)NC(C)c2cc(OCC(F)F)ccc2C)nc(NC(=O)C2CC2)n1] | Amine-100 | | 417.3 | 1.68 |
| 1145 | 2-(cyclopropanecarboxamido)-N-(1-(3-(2,2-difluoroethoxy)-4-methylphenyl)ethyl)pyrimidine-4-carboxamide | single enantiomer | 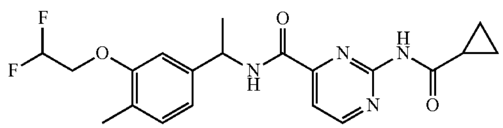 [SMILES: Cc1ccc(C(C)NC(=O)c2ccnc(NC(=O)C3CC3)n2)cc1OCC(F)F] | Amine-103 | | 405.1 | 1.66 |
| 1146 | 2-(cyclopropanecarboxamido)-N-(4-(2,2-difluoroethoxy)-3-methoxybenzyl)isonicotinamide | | 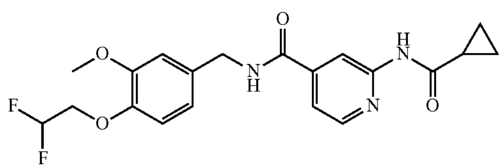 [SMILES: COc1cc(CNC(=O)c2ccnc(NC(=O)C3CC3)c2)ccc1OCC(F)F] | Amine-106 | | 406.1 | 1.47 |

TABLE 1-continued

| Example | Name | Chirality | Structure | Amine part | Carboxylic part | Observed MS | Retention time (min) |
|---|---|---|---|---|---|---|---|
| 1147 | N-((5-chloro-6-(2,2,2-trifluoroethoxy)pyridin-3-yl)methyl)-2-(cyclopropanecarboxamido)-6-methylpyrimidine-4-carboxamide | | 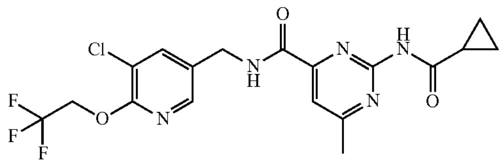 [SMILES: Cc1cc(C(=O)NCc2cnc(OCC(F)(F)F)c(Cl)c2)nc(NC(=O)C2CC2)n1] | Amine-19 | | 444.0 | 1.69 |
| 1148 | 2-(2-hydroxy-2-methylpropanamido)-N-(2-methoxy-3-(trifluoromethyl)benzyl)-6-methylisonicotinamide | | 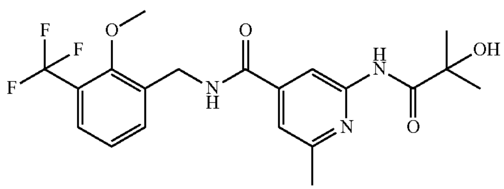 [SMILES: COc1c(CNC(=O)c2cc(C)nc(NC(=O)C(C)(C)O)c2)cccc1C(F)(F)F] | | | 426.1 | 1.63 |
| 1149 | 2-(2-hydroxy-2-methylpropanamido)-6-methyl-N-((5-methyl-6-(2,2,3,3-tetrafluoropropoxy)pyridin-3-yl)methyl)isonicotinamide | | 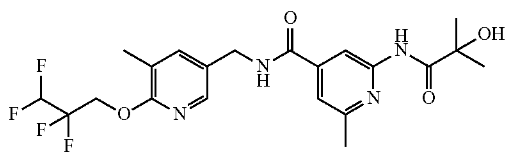 [SMILES: Cc1cc(C(=O)NCc2cnc(OCC(F)(F)C(F)F)c(C)c2)cc(NC(=O)C(C)(C)O)n1] | Amine-80 | | 473.2 | 1.65 |
| 1150 | 2-(cyclopropanecarboxamido)-N,6-dimethyl-N-((6-(2,2,2-trifluoroethoxy)pyridin-3-yl)methyl)isonicotinamide | | 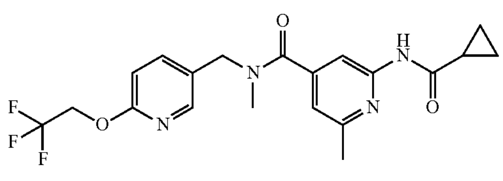 [SMILES: Cc1cc(C(=O)N(C)Cc2ccc(OCC(F)(F)F)nc2)cc(NC(=O)C2CC2)n1] | | | 423.1 | 1.66 |

TABLE 1-continued

| Example | Chirality | Name | Structure | Amine part | Carboxylic part | Observed MS | Retention time (min) |
|---|---|---|---|---|---|---|---|
| 1151 | | 2-acetamido-N-((6-(2,2-difluoroethoxy)-2-methoxy-pyridin-3-yl)methyl)iso-nicotinamide | 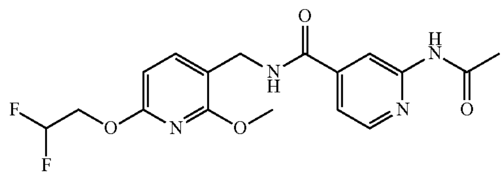 [SMILES: COc1nc(OCC(F)F)ccc1CNC(=O)c1ccnc(NC(C)=O)c1] | Amine-99 | | 379.3 | 1.46 |
| 1152 | | N-((6-(2,2-difluoroethoxy)-2-methoxy-pyridin-3-yl)methyl)-2-propionamido-isonicotinamide | 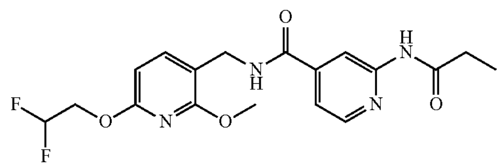 [SMILES: CCC(=O)Nc1cc(C(=O)NCc2ccc(OCC(F)F)nc2OC)ccn1] | Amine-99 | | 393.3 | 1.55 |
| 1153 | | 2-(cyclopropane-carboxamido)-N-((6-(2,2-difluoroethoxy)-2-methoxy-pyridin-3-yl)methyl)iso-nicotinamide | 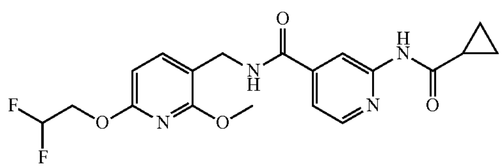 [SMILES: COc1nc(OCC(F)F)ccc1CNC(=O)c1ccnc(NC(=O)C2CC2)c1] | Amine-99 | | 405.3 | 1.59 |
| 1154 | | N-((6-(2,2-difluoroethoxy)-2-methoxy-pyridin-3-yl)methyl)-2-isobutyramido-isonicotinamide | 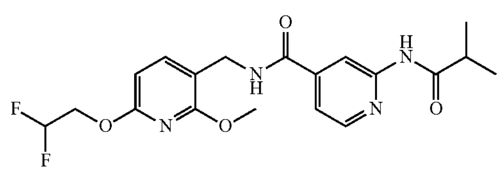 [SMILES: COc1nc(OCC(F)F)ccc1CNC(=O)c1ccnc(NC(=O)C(C)C)c1] | Amine-99 | | 407.3 | 1.63 |
| 1155 | | 2-(cyclopropane-carboxamido)-N-((6-(2,2-difluoroethoxy)-2-methoxy-pyridin-3-yl)methyl)-pyrimidine-4-carboxamide | 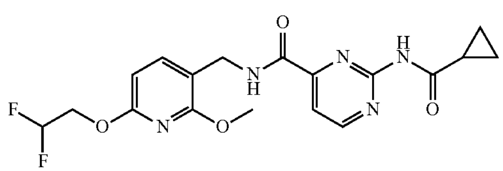 [SMILES: COc1nc(OCC(F)F)ccc1CNC(=O)c1ccnc(NC(=O)C2CC2)n1] | Amine-99 | | 406.3 | 1.56 |

| Example | Name | Chirality | Structure | Amine part | Carboxylic part | Observed MS | Retention time (min) |
|---|---|---|---|---|---|---|---|
| 1156 | 2-acetamido-N-((6-(2,2-difluoroethoxy)-2-methoxypyridin-3-yl)methyl)-6-methylisonicotinamide | | 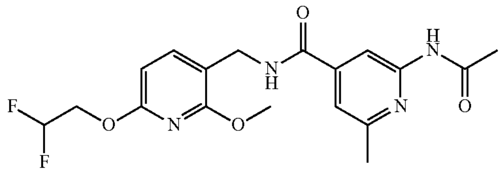 [SMILES: COc1nc(OCC(F)F)ccc1CNC(=O)c1cc(C)nc(NC(C)=O)c1] | Amine-99 | | 393.3 | 1.52 |
| 1157 | N-((6-(2,2-difluoroethoxy)-2-methoxypyridin-3-yl)methyl)-2-isobutyramido-6-methylisonicotinamide | | 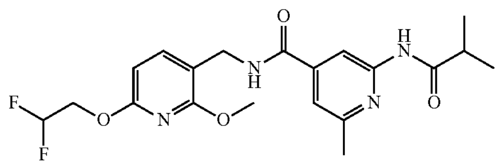 [SMILES: COc1nc(OCC(F)F)ccc1CNC(=O)c1cc(C)nc(NC(=O)C(C)C)c1] | Amine-99 | | 421.3 | 1.69 |
| 1158 | N-((6-(2,2-difluoroethoxy)-2-methoxypyridin-3-yl)methyl)-2-(2-hydroxy-2-methylpropanamido)-6-methylisonicotinamide | | 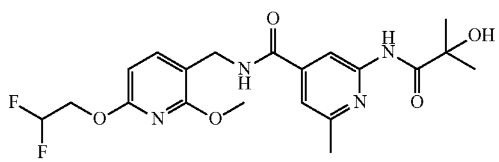 | Amine-99 | | 437.3 | 1.58 |
| 1159 | 2-(cyclopropanecarboxamido)-N-((6-(2,2-difluoroethoxy)-2-methoxypyridin-3-yl)methyl)-6-methylpyrimidine-4-carboxamide | | 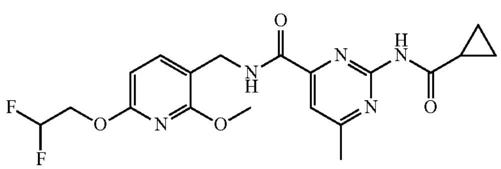 [SMILES: COc1nc(OCC(F)F)ccc1CNC(=O)c1cc(C)nc(NC(=O)C2CC2)n1] | Amine-99 | | 420.3 | 1.62 |

TABLE 1-continued

| Example | Name | Chirality | Structure | Amine part | Carboxylic part | Observed MS | Retention time (min) |
|---|---|---|---|---|---|---|---|
| 1160 | 2-acetamido-N-(1-(6-(2,2-difluoroethoxy)-2-methoxypyridin-3-yl)ethyl)isonicotinamide | single enantiomer | 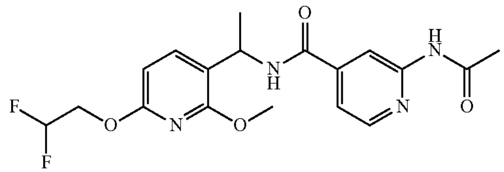 [SMILES: COc1nc(OCC(F)F)ccc1C(C)NC(=O)c1ccnc(NC(C)=O)c1] | Amine-97 | | 393.3 | 1.53 |
| 1161 | N-(1-(6-(2,2-difluoroethoxy)-2-methoxypyridin-3-yl)ethyl)-2-propionamidoisonicotinamide | single enantiomer | 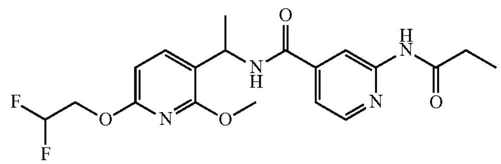 [SMILES: CCC(=O)Nc1cc(C(=O)NC(C)c2ccc(OCC(F)F)nc2OC)ccn1] | Amine-97 | | 407.4 | 1.62 |
| 1162 | 2-(cyclopropanecarboxamido)-N-(1-(6-(2,2-difluoroethoxy)-2-methoxypyridin-3-yl)ethyl)isonicotinamide | single enantiomer | 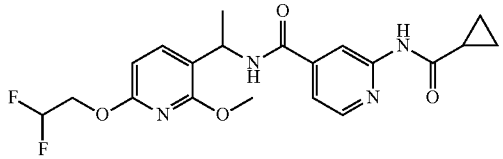 | Amine-97 | | 419.3 | 1.66 |
| 1163 | N-(1-(6-(2,2-difluoroethoxy)-2-methoxypyridin-3-yl)ethyl)-2-isobutyramidoisonicotinamide | single enantiomer | 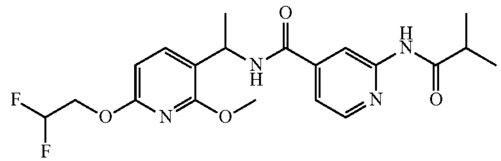 | Amine-97 | | 421.3 | 1.70 |
| 1164 | 2-(cyclopropanecarboxamido)-N-(1-(6-(2,2-difluoroethoxy)-2-methoxypyridin-3-yl)ethyl)pyrimidine-4-carboxamide | single enantiomer | 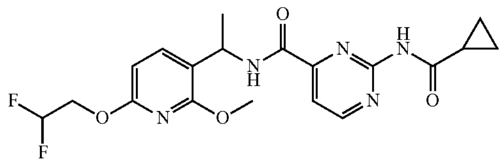 | Amine-97 | | 420.3 | 1.64 |

TABLE 1-continued

| Example | Name | Chirality | Structure | Amine part | Carboxylic part | Observed MS | Retention time (min) |
|---|---|---|---|---|---|---|---|
| 1165 | 2-acetamido-N-(1-(6-(2,2-difluoroethoxy)-2-methoxy-pyridin-3-yl)ethyl)-6-methylisonicotinamide | single enantiomer | 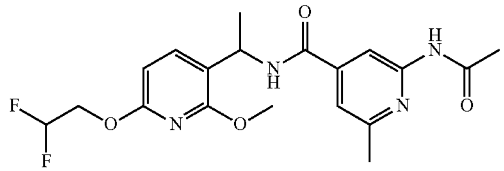 [SMILES: COc1nc(OCC(F)F)ccc1C(C)NC(=O)c1cc(C)nc(NC(C)=O)c1] | Amine-97 | | 407.3 | 1.59 |
| 1166 | N-(1-(6-(2,2-difluoroethoxy)-2-methoxy-pyridin-3-yl)ethyl)-2-isobutyramido-6-methylisonicotinamide | single enantiomer | 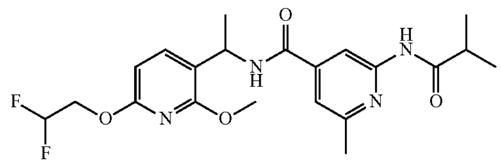 [SMILES: COc1nc(OCC(F)F)ccc1C(C)NC(=O)c1cc(C)nc(NC(=O)C(C)C)c1] | Amine-97 | | 435.4 | 1.76 |
| 1167 | N-(1-(6-(2,2-difluoroethoxy)-2-methoxy-pyridin-3-yl)ethyl)-2-(2-hydroxy-2-methylpropanamido)-6-methylisonicotinamide | single enantiomer | 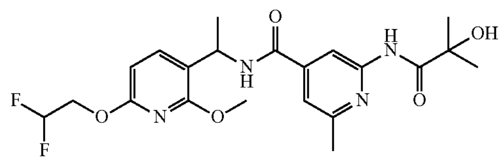 [SMILES: COc1nc(OCC(F)F)ccc1C(C)NC(=O)c1cc(C)nc(NC(=O)C(C)(C)O)c1] | Amine-97 | | 451.3 | 1.65 |
| 1168 | 2-(cyclopropanecarboxamido)-N-(1-(6-(2,2-difluoroethoxy)-2-methoxy-pyridin-3-yl)ethyl)-6-methylpyrimidine-4-carboxamide | single enantiomer | 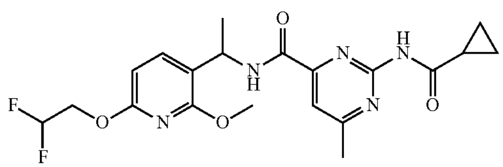 | Amine-97 | | 434.3 | 1.70 |

| Example | Name | Chirality | Structure | Amine part | Carboxylic part | Observed MS | Retention time (min) |
|---|---|---|---|---|---|---|---|
| 1169 | N-(1-(6-(2,2,3,3,3-pentafluoropropoxy)pyridin-3-yl)ethyl)-2-propionamidoisonicotinamide | single enantiomer | 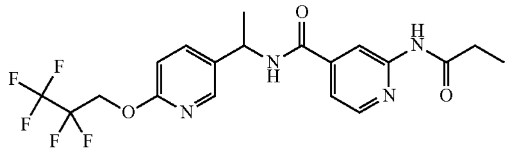 [SMILES: CCC(=O)Nc1cc(C(=O)NC(C)c2ccc(OCC(F)(F)C(F)(F)F)nc2)ccn1] | Amine-60 | | 445.3 | 1.72 |
| 1170 | 2-(cyclopropanecarboxamido)-N-((6-(2,2-difluoropropoxy)pyridin-3-yl)methyl)isonicotinamide | | 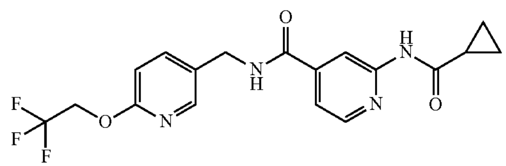 | Amine-62 | | 389.4 | 1.51 |
| 1171 | 2-(cyclopropanecarboxamido)-N-((6-(2,2-difluoropropoxy)pyridin-3-yl)methyl)pyrimidine-4-carboxamide | | 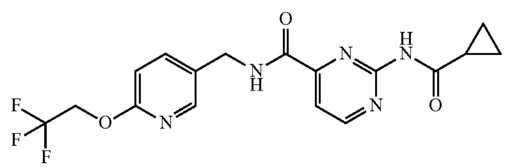 [SMILES: O=C(NCc1ccc(OCC(F)(F)F)nc1)c1ccnc(NC(=O)C2CC2)n1] | Amine-62 | | 390.3 | 1.46 |
| 1172 | N-((6-(2,2-difluoroethoxy)-5-ethylpyridin-3-yl)methyl)-2-pivalamidoisonicotinamide | | 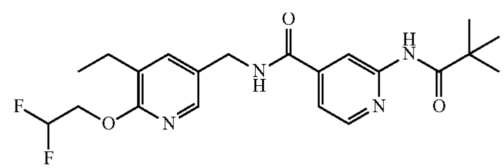 [SMILES: CCc1cc(CNC(=O)c2ccnc(NC(=O)C(C)(C)C)c2)cnc1OCC(F)F] | Amine-76 | | 419.0 | 1.76 |
| 1173 | N-(1-(5-cyclopropyl-6-(2,2-difluoroethoxy)pyridin-3-yl)ethyl)-2-propionamidoisonicotinamide | single enantiomer | 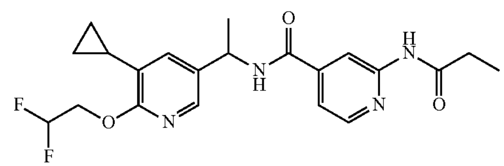 [SMILES: CCC(=O)Nc1cc(C(=O)NC(C)c2cnc(OCC(F)F)c(C3CC3)c2)ccn1] | Amine-78 | | 417.3 | 1.65 |

TABLE 1-continued

| Example | Name | Chirality | Structure | Amine part | Carboxylic part | Observed MS | Retention time (min) |
|---|---|---|---|---|---|---|---|
| 1174 | 2-(cyclopropanecarboxamido)-N-(1-(5-cyclopropyl-6-(2,2-difluoroethoxy)pyridin-3-yl)ethyl)isonicotinamide | single enantiomer | 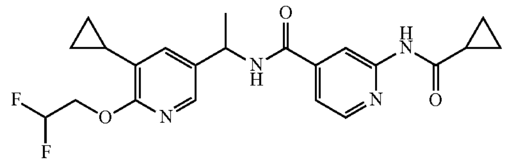 | Amine-78 | | 429.3 | 1.68 |
| 1175 | N-(1-(3-chloro-4-(2,2-difluoroethoxy)phenyl)ethyl)-2-(cyclopropanecarboxamido)isonicotinamide | single enantiomer | 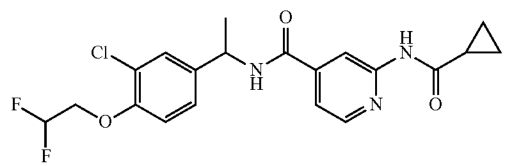 | Amine-82 | | 422.3 | 1.63 |
| 1176 | N-(1-(4-(2,2-difluoroethoxy)-2-methylphenyl)ethyl)-2-propionamidoisonicotinamide | single enantiomer | 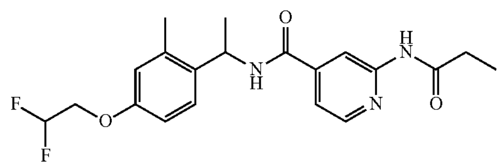 [SMILES: CCC(=O)Nc1cc(C(=O)NC(C)c2ccc(OCC(F)F)cc2C)ccn1] | Amine-83 | | 390.3 | 1.58 |
| 1177 | 2-(cyclopropanecarboxamido)-N-(1-(4-(2,2-difluoroethoxy)-2-methylphenyl)ethyl)isonicotinamide | single enantiomer | 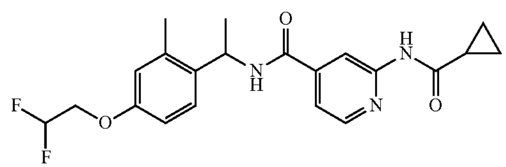 [SMILES: Cc1cc(OCC(F)F)ccc1C(C)NC(=O)c1ccnc(NC(=O)C2CC2)c1] | Amine-83 | | 402.3 | 1.62 |
| 1178 | 2-(cyclopropanecarboxamido)-N-(4-(2,2-difluoroethoxy)-2-methylbenzyl)-6-methylpyrimidine-4-carboxamide | | 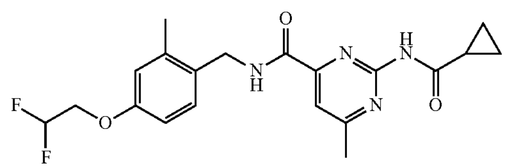 | Amine-86 | | 403.3 | 1.59 |

TABLE 1-continued

| Example | Name | Chirality | Structure | Amine part | Carboxylic part | Observed MS | Retention time (min) |
|---|---|---|---|---|---|---|---|
| 1179 | 2-acetamido-6-methyl-N-(1-(4-(2,2,2-trifluoroethoxy)phenyl)ethyl)isonicotinamide | single enantiomer | 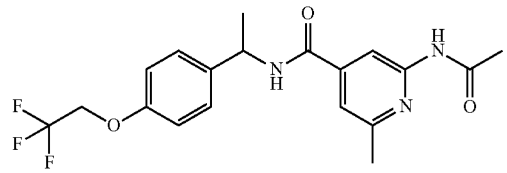 [SMILES: CC(=O)Nc1cc(C(=O)NC(C)c2ccc(OCC(F)(F)F)cc2)cc(C)n1] | Amine-18 | | 394.3 | 1.59 |
| 1180 | N-(4-methoxy-3-(trifluoromethyl)benzyl)-2-propionamidoisonicotinamide | | 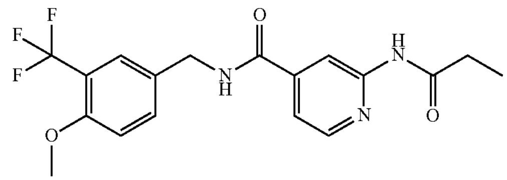 [SMILES: CCC(=O)Nc1cc(C(=O)NCc2ccc(OC)c(C(F)(F)F)c2)ccn1] | | | 380.3 | 1.56 |
| 1181 | 2-acetamido-N-((6-(2-(trifluoromethoxy)ethoxy)pyridin-3-yl)methyl)isonicotinamide | | 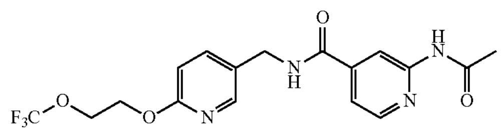 [SMILES: CC(=O)Nc1cc(C(=O)NCc2ccc(OCCOC(F)(F)F)nc2)ccn1] | Amine-105 | | 399.1 | 1.47 |
| 1182 | 2-propionamido-N-((6-(2-(trifluoromethoxy)ethoxy)pyridin-3-yl)methyl)isonicotinamide | | 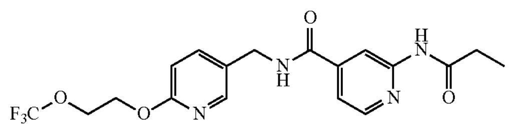 | Amine-105 | | 413.1 | 1.55 |
| 1183 | 2-(cyclopropanecarboxamido)-N-((6-(2-(trifluoromethoxy)ethoxy)pyridin-3-yl)methyl)isonicotinamide | | 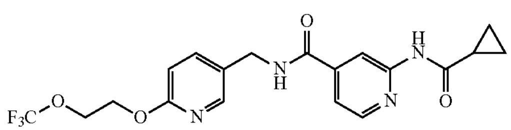 [SMILES: O=C(NCc1ccc(OCCOC(F)(F)F)nc1)c1ccnc(NC(=O)C2CC2)c1] | Amine-105 | | 425.1 | 1.58 |

TABLE 1-continued

| Example | Chirality | Name | Structure | Amine part | Carboxylic part | Observed MS | Retention time (min) |
|---|---|---|---|---|---|---|---|
| 1184 | | 2-isobutyramido-N-((6-(2-(trifluoromethoxy)ethoxy)pyridin-3-yl)methyl)isonicotinamide | 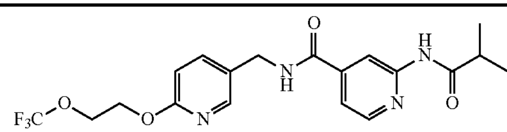 | Amine-105 | | 427.1 | 1.62 |
| 1185 | | 2-acetamido-6-methyl-N-((6-(2-(trifluoromethoxy)ethoxy)pyridin-3-yl)methyl)isonicotinamide | 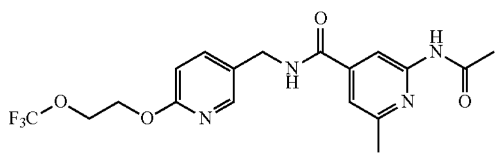 [SMILES: CC(=O)Nc1cc(C(=O)NCc2ccc(OCCOC(F)(F)F)nc2)cc(C)n1] | Amine-105 | | 413.1 | 1.52 |
| 1186 | | 2-isobutyramido-6-methyl-N-((6-(2-(trifluoromethoxy)ethoxy)pyridin-3-yl)methyl)isonicotinamide | 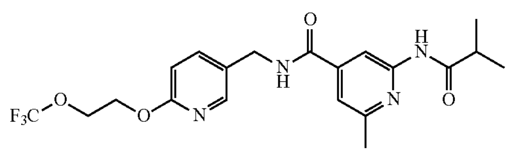 [SMILES: Cc1cc(C(=O)NCc2ccc(OCCOC(F)(F)F)nc2)cc(NC(=O)C(C)C)n1] | Amine-105 | | 441.1 | 1.68 |
| 1187 | | 2-(2-hydroxy-2-methylpropanamido)-6-methyl-N-((6-(2-(trifluoromethoxy)ethoxy)pyridin-3-yl)methyl)isonicotinamide | 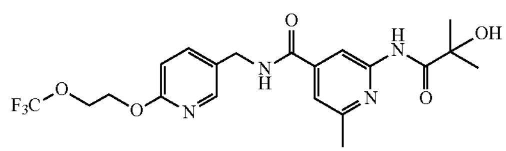 [SMILES: Cc1cc(C(=O)NCc2ccc(OCCOC(F)(F)F)nc2)cc(NC(=O)C(C)(C)O)n1] | Amine-105 | | 457.1 | 1.58 |

TABLE 1-continued

| Example | Name | Chirality | Structure | Amine part | Carboxylic part | Observed MS | Retention time (min) |
|---|---|---|---|---|---|---|---|
| 1188 | 2-cyclopropanecarboxamido-N-((6-(2-(trifluoromethoxy)ethoxy)pyridin-3-yl)methyl)pyrimidine-4-carboxamide | | 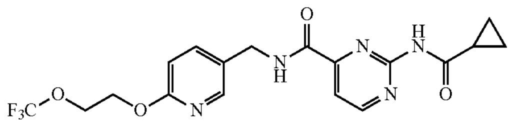 | Amine-105 | | 426.1 | 1.54 |
| 1189 | 2-acetamido-N-(1-(3-(2,2-difluoroethoxy)-5-methylphenyl)ethyl)isonicotinamide | single enantiomer | 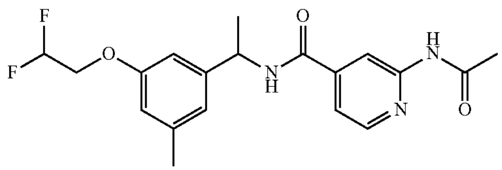 | Amine-107 | | 378.1 | 1.53 |
| 1190 | N-(1-(3-(2,2-difluoroethoxy)-5-methylphenyl)ethyl)-2-propionamidoisonicotinamide | single enantiomer | 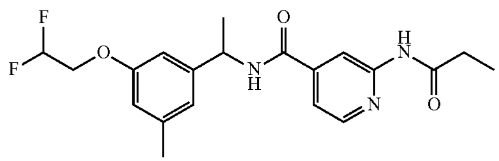 [SMILES: CCC(=O)Nc1cc(C(=O)NC(C)c2cc(C)cc(OCC(F)F)c2)ccn1] | Amine-107 | | 392.1 | 1.61 |
| 1191 | 2-(cyclopropanecarboxamido)-N-(1-(3-(2,2-difluoroethoxy)-5-methylphenyl)ethyl)isonicotinamide | single enantiomer | 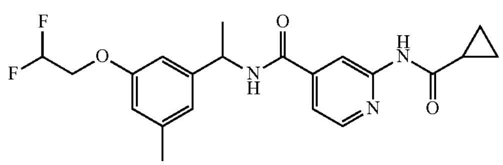 [SMILES: Cc1cc(OCC(F)F)cc(C(C)NC(=O)c2ccnc(NC(=O)C3CC3)c2)c1] | Amine-107 | | 404.1 | 1.65 |

| Example | Name | Chirality | Structure | Amine part | Carboxylic part | Observed MS | Retention time (min) |
|---|---|---|---|---|---|---|---|
| 1192 | N-(1-(3-(2,2-difluoroethoxy)-5-methylphenyl)ethyl)-2-isobutyramidoisonicotinamide | single enantiomer | 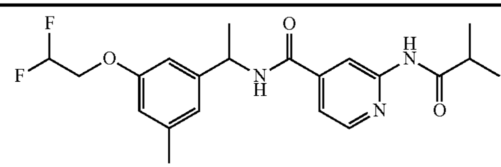 | Amine-107 | | 406.2 | 1.68 |
| 1193 | 2-acetamido-N-(1-(3-(2,2-difluoroethoxy)-5-methylphenyl)ethyl)-6-methylisonicotinamide | single enantiomer | 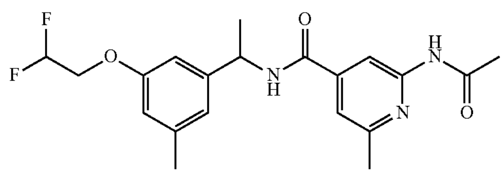 [SMILES: CC(=O)Nc1cc(C(=O)NC(C)c2cc(C)cc(OCC(F)F)c2)cc(C)n1] | Amine-107 | | 392.1 | 1.59 |
| 1194 | N-(1-(3-(2,2-difluoroethoxy)-5-methylphenyl)ethyl)-2-isobutyramido-6-methylisonicotinamide | single enantiomer | 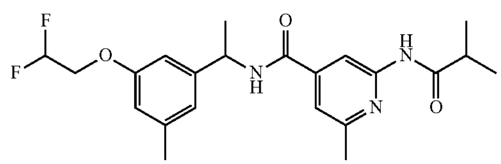 [SMILES: Cc1cc(OCC(F)F)cc(C(C)NC(=O)c2cc(C)nc(NC(=O)C(C)C)c2)c1] | Amine-107 | | 420.2 | 1.74 |
| 1195 | N-(1-(3-(2,2-difluoroethoxy)-5-methylphenyl)ethyl)-2-(2-hydroxy-2-methylpropanamido)-6-methylisonicotinamide | single enantiomer | 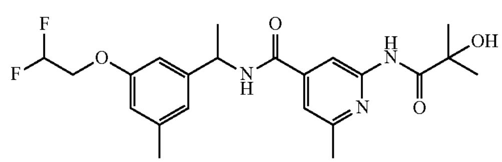 [SMILES: Cc1cc(OCC(F)F)cc(C(C)NC(=O)c2cc(C)nc(NC(=O)C(C)(C)O)c2)c1] | Amine-107 | | 436 | 1.64 |

TABLE 1-continued

| Example | Name | Chirality | Structure | Amine part | Carboxylic part | Observed MS | Retention time (min) |
|---|---|---|---|---|---|---|---|
| 1196 | 2-(cyclopropanecarboxamido)-N-(1-(3-(2,2-difluoroethoxy)-5-methylphenyl)ethyl)pyrimidine-4-carboxamide | single enantiomer | 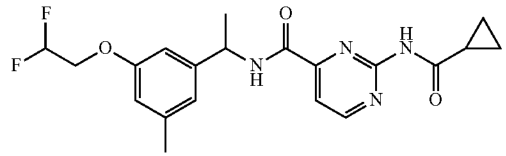 [SMILES: Cc1cc(OCC(F)F)cc(C(C)NC(=O)c2ccnc(NC(=O)C3CC3)n2)c1] | Amine-107 | | 405.1 | 1.63 |
| 1197 | 2-(cyclopropanecarboxamido)-N-(1-(3-(2,2-difluoroethoxy)-5-methylphenyl)ethyl)-6-methylpyrimidine-4-carboxamide | single enantiomer | 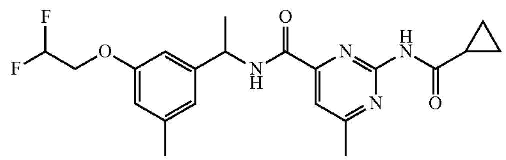 [SMILES: Cc1cc(OCC(F)F)cc(C(C)NC(=O)c2cc(C)nc(NC(=O)C3CC3)n2)c1] | Amine-107 | | 419.1 | 1.68 |
| 1198 | 2-acetamido-N-(3-(2,2-difluoroethoxy)-5-methylbenzyl)isonicotinamide | | 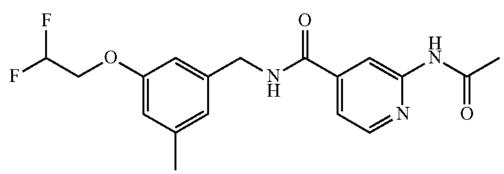 [SMILES: CC(=O)Nc1cc(C(=O)NCc2cc(C)cc(OCC(F)F)c2)ccn1] | Amine-108 | | 364.1 | 1.47 |
| 1199 | N-(3-(2,2-difluoroethoxy)-5-methylbenzyl)-2-propionamidoisonicotinamide | | 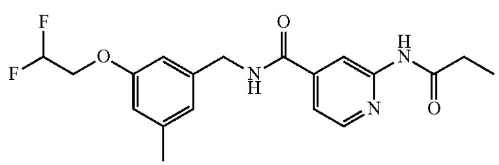 [SMILES: CCC(=O)Nc1cc(C(=O)NCc2cc(C)cc(OCC(F)F)c2)ccn1] | Amine-108 | | 378.1 | 1.56 |

TABLE 1-continued

| Example | Name | Chirality | Structure | Amine part | Carboxylic part | Observed MS | Retention time (min) |
|---|---|---|---|---|---|---|---|
| 1200 | 2-(cyclopropane-carboxamido)-N-(3-(2,2-difluoroethoxy)-5-methylbenzyl)isonicotinamide | | 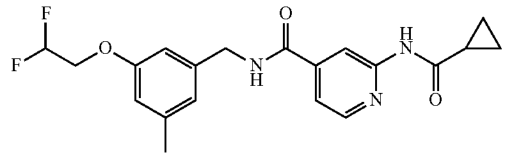 [SMILES: Cc1cc(CNC(=O)c2ccnc(NC(=O)C3CC3)c2)cc(OCC(F)F)c1] | Amine-108 | | 390 | 1.59 |
| 1201 | N-(3-(2,2-difluoroethoxy)-5-methylbenzyl)-2-isobutyramidoisonicotinamide | | 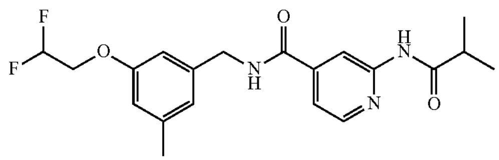 [SMILES: Cc1cc(CNC(=O)c2ccnc(NC(=O)C(C)C)c2)cc(OCC(F)F)c1] | Amine-108 | | 392.1 | 1.63 |
| 1202 | 2-acetamido-N-(3-(2,2-difluoroethoxy)-5-methylbenzyl)-6-methylisonicotinamide | | 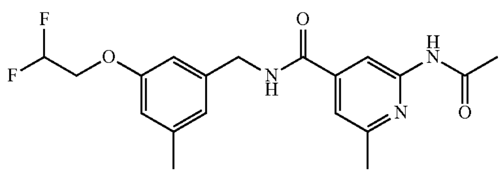 | Amine-108 | | 378.1 | 1.53 |
| 1203 | N-(3-(2,2-difluoroethoxy)-5-methylbenzyl)-2-isobutyramido-6-methylisonicotinamide | | 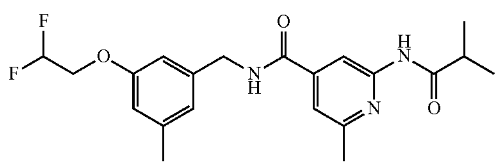 [SMILES: Cc1cc(CNC(=O)c2cc(C)nc(NC(=O)C(C)C)c2)cc(OCC(F)F)c1] | Amine-108 | | 406.2 | 1.69 |

TABLE 1-continued

| Example | Chirality | Name | Structure | Amine part | Carboxylic part | Observed MS | Retention time (min) |
|---|---|---|---|---|---|---|---|
| 1204 | | N-(3-(2,2-difluoroethoxy)-5-methylbenzyl)-2-(2-hydroxy-2-methylpropanamido)-6-methylisonicotinamide | 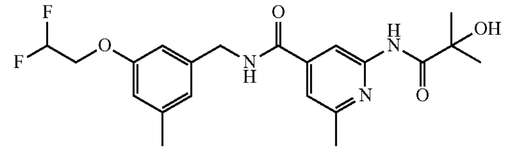 [SMILES: Cc1cc(CNC(=O)c2cc(C)nc(NC(=O)C(C)(C)O)c2)cc(OCC(F)F)c1] | Amine-108 | | 422 | 1.58 |
| 1205 | | 2-(cyclopropanecarboxamido)-N-(3-(2,2-difluoroethoxy)-5-methylbenzyl)pyrimidine-4-carboxamide | 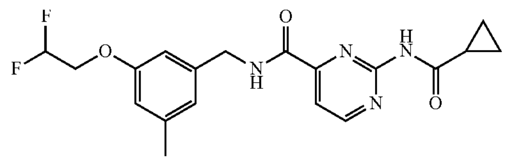 [SMILES: Cc1cc(CNC(=O)c2ccnc(NC(=O)C3CC3)n2)cc(OCC(F)F)c1] | Amine-108 | | 391.1 | 1.55 |
| 1206 | | 2-(cyclopropanecarboxamido)-N-(3-(2,2-difluoroethoxy)-5-methylbenzyl)-6-methylpyrimidine-4-carboxamide | 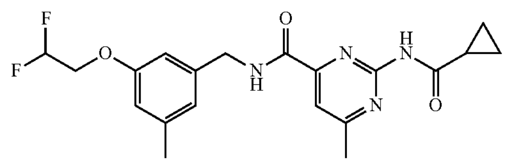 [SMILES: Cc1cc(CNC(=O)c2cc(C)nc(NC(=O)C3CC3)n2)cc(OCC(F)F)c1] | Amine-108 | | 405.1 | 1.62 |
| 1207 | single enantiomer | 2-acetamido-N-(1-(3-chloro-4-(2,2-difluoroethoxy)-5-methylphenyl)ethyl)isonicotinamide | 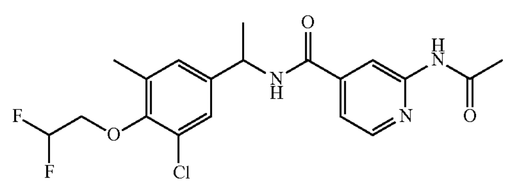 | Amine-109 | | 412 | 1.6 |

TABLE 1-continued

| Example | Name | Chirality | Structure | Amine part | Carboxylic part | Observed MS | Retention time (min) |
|---|---|---|---|---|---|---|---|
| 1208 | N-(1-(3-chloro-4-(2,2-difluoroethoxy)-5-methylphenyl)ethyl)-2-propionamidoisonicotinamide | single enantiomer | 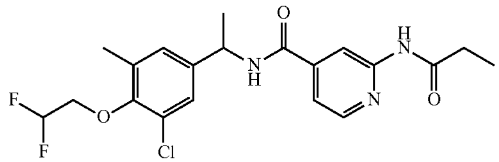 [SMILES: CCC(=O)Nc1cc(C(=O)NC(C)c2cc(C)c(OCC(F)F)c(Cl)c2)ccn1] | Amine-109 | | 426 | 1.68 |
| 1209 | N-(1-(3-chloro-4-(2,2-difluoroethoxy)-5-methylphenyl)ethyl)-2-(cyclopropanecarboxamido)isonicotinamide | single enantiomer | 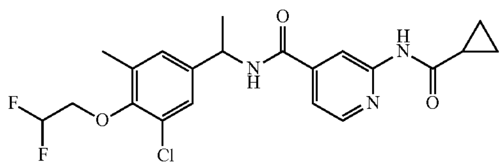 [SMILES: Cc1cc(C(C)NC(=O)c2ccnc(NC(=O)C3CC3)c2)cc(Cl)c1OCC(F)F] | Amine-109 | | 438 | 1.71 |
| 1210 | N-(1-(3-chloro-4-(2,2-difluoroethoxy)-5-methylphenyl)ethyl)-2-isobutyramidoisonicotinamide | single enantiomer | 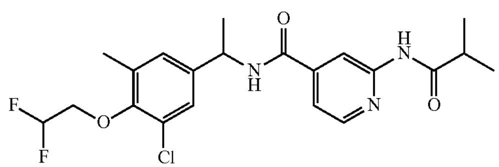 [SMILES: Cc1cc(C(C)NC(=O)c2ccnc(NC(=O)C(C)C)c2)cc(Cl)c1OCC(F)F] | Amine-109 | | 440.1 | 1.75 |
| 1211 | 2-acetamido-N-(1-(3-chloro-4-(2,2-difluoroethoxy)-5-methylphenyl)ethyl)-6-methylisonicotinamide | single enantiomer | 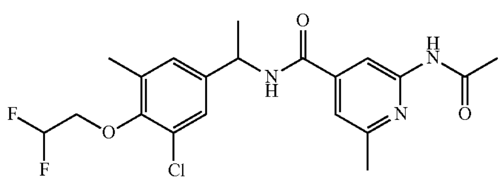 [SMILES: CC(=O)Nc1cc(C(=O)NC(C)c2cc(C)c(OCC(F)F)c(Cl)c2)cc(C)n1] | Amine-109 | | 426.1 | 1.65 |

TABLE 1-continued

| Example | Name | Chirality | Structure | Amine part | Carboxylic part | Observed MS | Retention time (min) |
|---|---|---|---|---|---|---|---|
| 1212 | N-(1-(3-chloro-4-(2,2-difluoroethoxy)-5-methylphenyl)ethyl)-2-isobutyramido-6-methylisonicotinamide | single enantiomer | 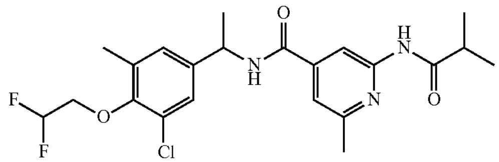 [SMILES: Cc1cc(C(=O)NC(C)c2cc(C)c(OCC(F)F)c(Cl)c2)cc(NC(=O)C(C)C)n1] | Amine-109 | | 454.1 | 1.81 |
| 1213 | N-(1-(3-chloro-4-(2,2-difluoroethoxy)-5-methylphenyl)ethyl)-2-(2-hydroxy-2-methylpropanamido)-6-methylisonicotinamide | single enantiomer | 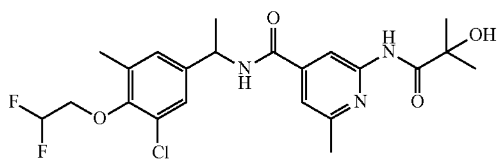 [SMILES: Cc1cc(C(=O)NC(C)c2cc(C)c(OCC(F)F)c(Cl)c2)cc(NC(=O)C(C)(C)O)n1] | Amine-109 | | 470 | 1.71 |
| 1214 | N-(1-(3-chloro-4-(2,2-difluoroethoxy)-5-methylphenyl)ethyl)-2-(cyclopropanecarboxamido)pyrimidine-4-carboxamide | single enantiomer | 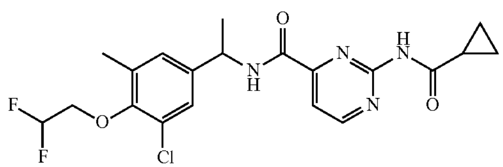 [SMILES: Cc1cc(C(C)NC(=O)c2ccnc(NC(=O)C3CC3)n2)cc(Cl)c1OCC(F)F] | Amine-109 | | 439.1 | 1.68 |
| 1215 | N-(1-(3-chloro-4-(2,2-difluoroethoxy)-5-methylphenyl)ethyl)-2-(cyclopropanecarboxamido)-6-methylpyrimidine-4-carboxamide | single enantiomer | 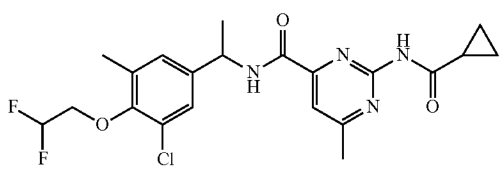 | Amine-109 | | 453 | 1.75 |

TABLE 1-continued

| Example | Name | Chirality | Structure | Amine part | Carboxylic part | Observed MS | Retention time (min) |
|---|---|---|---|---|---|---|---|
| 1216 | 2-acetamido-N-(1-(4-(2,2-difluoroethoxy)-3,5-dimethylphenyl)ethyl)isonicotinamide | single enantiomer | 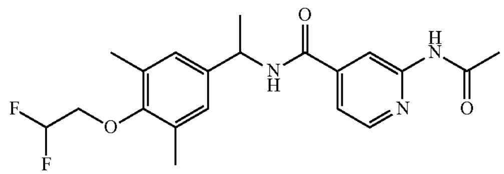 | Amine-110 | | 392 | 1.56 |
| 1217 | N-(1-(4-(2,2-difluoroethoxy)-3,5-dimethylphenyl)ethyl)-2-propionamidoisonicotinamide | single enantiomer | 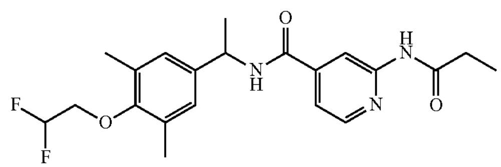 [SMILES: CCC(=O)Nc1cc(C(=O)NC(C)c2cc(C)c(OCC(F)F)c(C)c2)ccn1] | Amine-110 | | 406.2 | 1.64 |
| 1218 | 2-(cyclopropanecarboxamido)-N-(1-(4-(2,2-difluoroethoxy)-3,5-dimethylphenyl)ethyl)isonicotinamide | single enantiomer | 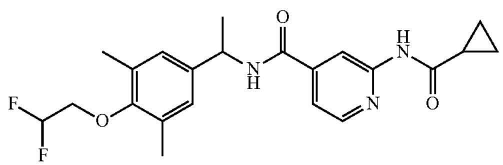 [SMILES: Cc1cc(C(C)NC(=O)c2ccnc(NC(=O)C3CC3)c2)cc(C)c1OCC(F)F] | Amine-110 | | 418 | 1.68 |
| 1219 | N-(1-(4-(2,2-difluoroethoxy)-3,5-dimethylphenyl)ethyl)-2-isobutyramidoisonicotinamide | single enantiomer | 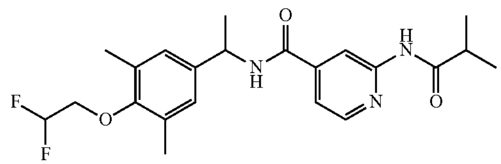 [SMILES: Cc1cc(C(C)NC(=O)c2ccnc(NC(=O)C(C)C)c2)cc(C)c1OCC(F)F] | Amine-110 | | 420.2 | 1.72 |
| 1220 | 2-acetamido-N-(1-(4-(2,2-difluoroethoxy)-3,5-dimethylphenyl)ethyl)-6-methylisonicotinamide | single enantiomer | 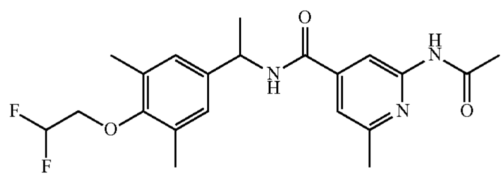 [SMILES: CC(=O)Nc1cc(C(=O)NC(C)c2cc(C)c(OCC(F)F)c(C)c2)cc(C)n1] | Amine-110 | | 406.1 | 1.62 |

TABLE 1-continued

| Example | Name | Chirality | Structure | Amine part | Carboxylic part | Observed MS | Retention time (min) |
|---|---|---|---|---|---|---|---|
| 1221 | N-(1-(4-(2,2-difluoroethoxy)-3,5-dimethylphenyl)ethyl)-2-isobutyramido-6-methylisonicotinamide | single enantiomer | 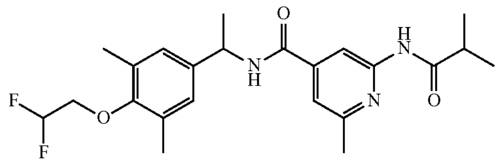 [SMILES: Cc1cc(C(=O)NC(C)c2cc(C)c(OCC(F)F)c(C)c2)cc(NC(=O)C(C)C)n1] | Amine-110 | | 434.2 | 1.77 |
| 1222 | N-(1-(4-(2,2-difluoroethoxy)-3,5-dimethylphenyl)ethyl)-2-(2-hydroxy-2-methylpropanamido)-6-methylisonicotinamide | single enantiomer | 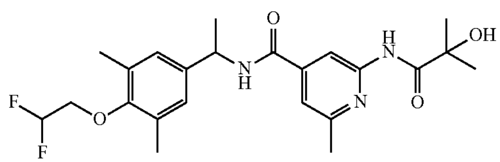 [SMILES: Cc1cc(C(=O)NC(C)c2cc(C)c(OCC(F)F)c(C)c2)cc(NC(=O)C(C)(C)O)n1] | Amine-110 | | 450.2 | 1.67 |
| 1223 | 2-(cyclopropanecarboxamido)-N-(1-(4-(2,2-difluoroethoxy)-3,5-dimethylphenyl)ethyl)pyrimidine-4-carboxamide | single enantiomer | 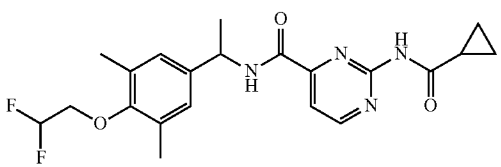 [SMILES: Cc1cc(C(C)NC(=O)c2ccnc(NC(=O)C3CC3)n2)cc(C)c1OCC(F)F] | Amine-110 | | 419.2 | 1.66 |
| 1224 | 2-(cyclopropanecarboxamido)-N-(1-(4-(2,2-difluoroethoxy)-3,5-dimethylphenyl)ethyl)-6-methylpyrimidine-4-carboxamide | single enantiomer | 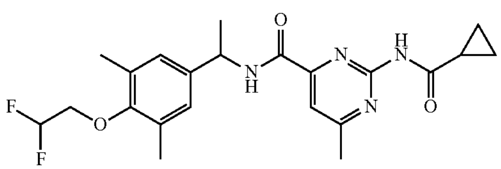 [SMILES: Cc1cc(C(=O)NC(C)c2cc(C)c(OCC(F)F)c(C)c2)nc(NC(=O)C2CC2)n1] | Amine-110 | | 433.2 | 1.72 |

TABLE 1-continued

| Example | Name | Chirality | Structure | Amine part | Carboxylic part | Observed MS | Retention time (min) |
|---|---|---|---|---|---|---|---|
| 1225 | 2-acetamido-N-(4-(2,2-difluoroethoxy)-3,5-dimethylbenzyl)isonicotinamide | | 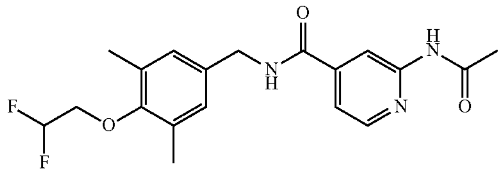 | Amine-111 | | 376.3 | 1.51 |
| 1226 | N-(4-(2,2-difluoroethoxy)-3,5-dimethylbenzyl)-2-propionamidoisonicotinamide | | 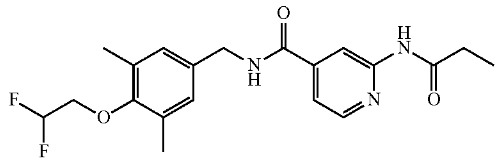 | Amine-111 | | 390.3 | 1.59 |
| 1227 | 2-(cyclopropanecarboxamido)-N-(4-(2,2-difluoroethoxy)-3,5-dimethylbenzyl)isonicotinamide | | 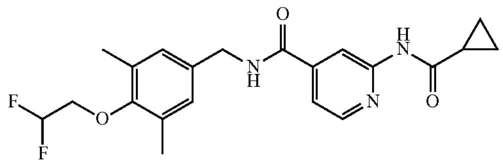 | Amine-111 | | 404.1 | 1.63 |
| 1228 | N-(4-(2,2-difluoroethoxy)-3,5-dimethylbenzyl)-2-isobutyramidoisonicotinamide | | 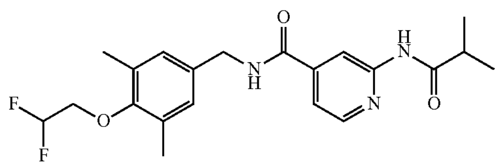 [SMILES: Cc1cc(CNC(=O)c2ccnc(NC(=O)C(C)C)c2)cc(C)c1OCC(F)F] | Amine-111 | | 404.3 | 1.66 |
| 1229 | 2-acetamido-N-(4-(2,2-difluoroethoxy)-3,5-dimethylbenzyl)-6-methylisonicotinamide | | 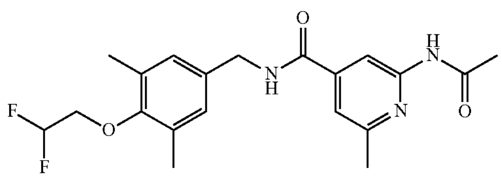 [SMILES: CC(=O)Nc1cc(C(=O)NCc2cc(C)c(OCC(F)F)c(C)c2)cc(C)n1] | Amine-111 | | 390.3 | 1.57 |

TABLE 1-continued

| Example | Name | Chirality | Structure | Amine part | Carboxylic part | Observed MS | Retention time (min) |
|---|---|---|---|---|---|---|---|
| 1230 | N-(4-(2,2-difluoroethoxy)-3,5-dimethylbenzyl)-2-isobutyramido-6-methylisonicotinamide | | 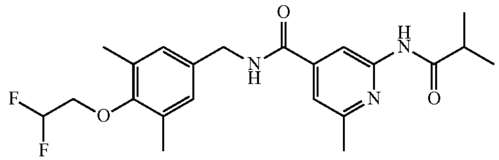 | Amine-111 | | 418.4 | 1.72 |
| 1231 | N-(4-(2,2-difluoroethoxy)-3,5-dimethylbenzyl)-2-(2-hydroxy-2-methylpropanamido)-6-methylisonicotinamide | | 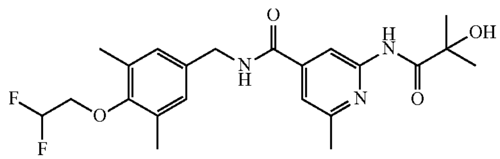 [SMILES: Cc1cc(C(=O)NCc2cc(C)c(OCC(F)F)c(C)c2)cc(NC(=O)C(C)(C)O)n1] | Amine-111 | | 436 | 1.62 |
| 1232 | 2-(cyclopropanecarboxamido)-N-(4-(2,2-difluoroethoxy)-3,5-dimethylbenzyl)pyrimidine-4-carboxamide | | 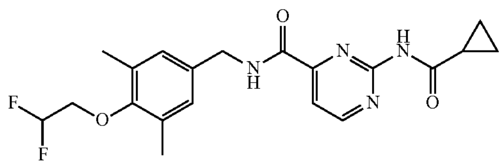 [SMILES: Cc1cc(CNC(=O)c2ccnc(NC(=O)C3CC3)n2)cc(C)c1OCC(F)F] | Amine-111 | | 403.3 | 1.59 |
| 1233 | 2-(cyclopropanecarboxamido)-N-(4-(2,2-difluoroethoxy)-3,5-dimethylbenzyl)-6-methylpyrimidine-4-carboxamide | | 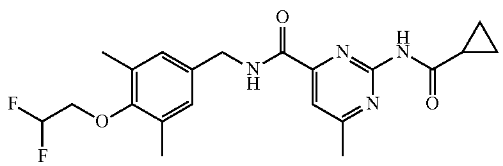 [SMILES: Cc1cc(C(=O)NCc2cc(C)c(OCC(F)F)c(C)c2)nc(NC(=O)C2CC2)n1] | Amine-111 | | 417.3 | 1.65 |
| 1234 | 2-acetamido-N-(1-(4-(1,1,2,2-tetrafluoroethoxy)phenyl)ethyl)isonicotinamide | single enantiomer | 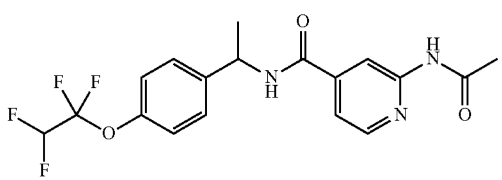 [SMILES: CC(=O)Nc1cc(C(=O)NC(C)c2ccc(OC(F)(F)C(F)F)cc2)ccn1] | Amine-112 | | 400.1 | 1.5 |

TABLE 1-continued

| Example | Name | Chirality | Structure | Amine part | Carboxylic part | Observed MS | Retention time (min) |
|---|---|---|---|---|---|---|---|
| 1235 | 2-propionamido-N-(1-(4-(1,1,2,2-tetrafluoroethoxy)phenyl)ethyl)isonicotinamide | single enantiomer | 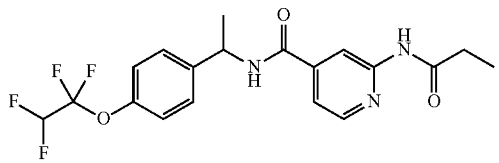 [SMILES: CCC(=O)Nc1cc(C(=O)NC(C)c2ccc(OC(F)(F)C(F)F)cc2)ccn1] | Amine-112 | | 414 | 1.63 |
| 1236 | 2-(cyclopropanecarboxamido)-N-(1-(4-(1,1,2,2-tetrafluoroethoxy)phenyl)ethyl)isonicotinamide | single enantiomer | 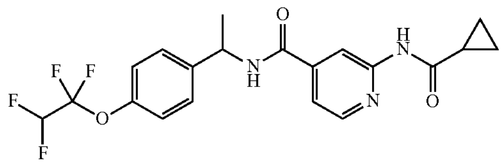 [SMILES: CC(NC(=O)c1ccnc(NC(=O)C2CC2)c1)c1ccc(OC(F)(F)C(F)F)cc1] | Amine-112 | | 426.1 | 1.66 |
| 1237 | 2-isobutyramido-N-(1-(4-(1,1,2,2-tetrafluoroethoxy)phenyl)ethyl)isonicotinamide | single enantiomer | 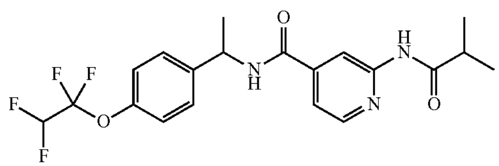 [SMILES: CC(C)C(=O)Nc1cc(C(=O)NC(C)c2ccc(OC(F)(F)C(F)F)cc2)ccn1] | Amine-112 | | 428.1 | 1.7 |
| 1238 | 2-acetamido-6-methyl-N-(1-(4-(1,1,2,2-tetrafluoroethoxy)phenyl)ethyl)isonicotinamide | single enantiomer | 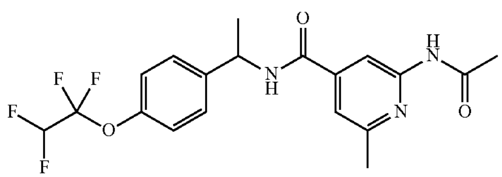 [SMILES: CC(=O)Nc1cc(C(=O)NC(C)c2ccc(OC(F)(F)C(F)F)cc2)cc(C)n1] | Amine-112 | | 414 | 1.61 |

TABLE 1-continued

| Example | Name | Chirality | Structure | Amine part | Carboxylic part | Observed MS | Retention time (min) |
|---|---|---|---|---|---|---|---|
| 1239 | 2-isobutyramido-6-methyl-N-(1-(4-(1,1,2,2-tetrafluoroethoxy)phenyl)ethyl)isonicotinamide | single enantiomer | 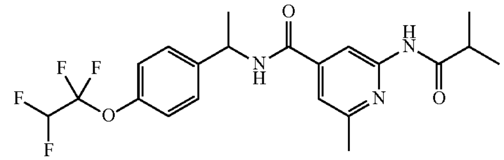 | Amine-112 | | 442.1 | 1.75 |
| 1240 | 2-(2-hydroxy-2-methylpropanamido)-6-methyl-N-(1-(4-(1,1,2,2-tetrafluoroethoxy)phenyl)ethyl)isonicotinamide | single enantiomer | 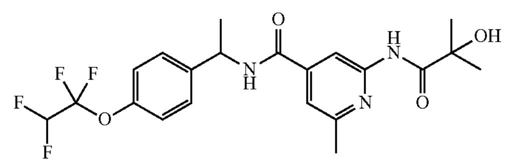 [SMILES: Cc1cc(C(=O)NC(C)c2ccc(OC(F)(F)C(F)F)cc2)cc(NC(=O)C(C)(C)O)n1] | Amine-112 | | 458.1 | 1.66 |
| 1241 | 2-(cyclopropanecarboxamido)-N-(1-(4-(1,1,2,2-tetrafluoroethoxy)phenyl)ethyl)pyrimidine-4-carboxamide | single enantiomer | 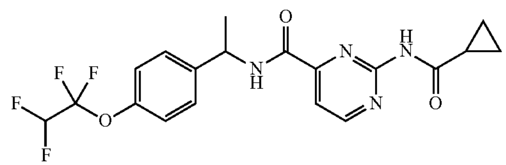 [SMILES: CC(NC(=O)c1ccnc(NC(=O)C2CC2)n1)c1ccc(OC(F)(F)C(F)F)cc1] | Amine-112 | | 427.1 | 1.63 |
| 1242 | 2-cyclopropanecarboxamido)-6-methyl-N-(1-(4-(1,1,2,2-tetrafluoroethoxy)phenyl)ethyl)pyrimidine-4-carboxamide | single enantiomer | 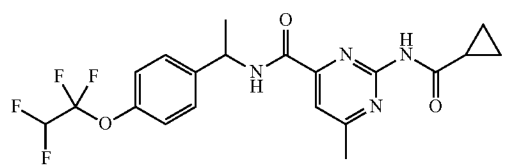 [SMILES: Cc1cc(C(=O)NC(C)c2ccc(OC(F)(F)C(F)F)cc2)nc(NC(=O)C2CC2)n1] | Amine-112 | | 441 | 1.69 |

TABLE 1-continued

| Example | Name | Chirality | Structure | Amine part | Carboxylic part | Observed MS | Retention time (min) |
|---|---|---|---|---|---|---|---|
| 1243 | 2-acetamido-N-(1-(3-(1,1,2,2-tetrafluoroethoxyphenyl)ethyl)isonicotinamide | single enantiomer | 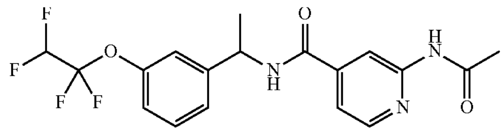 [SMILES: CC(=O)Nc1cc(C(=O)NC(C)c2cccc(OC(F)(F)C(F)F)c2)ccn1] | Amine-113 | | 400.1 | 1.56 |
| 1244 | 2-propionamido-N-(1-(3-1,1,2,2-tetrafluoroethoxyphenyl)ethyl)isonicotinamide | single enantiomer | 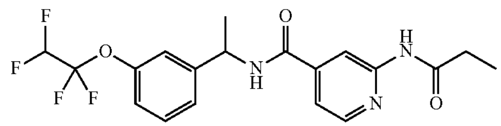 [SMILES: CCC(=O)Nc1cc(C(=O)NC(C)c2cccc(OC(F)(F)C(F)F)c2)ccn1] | Amine-113 | | 414.1 | 1.63 |
| 1245 | 2-(cyclopropanecarboxamido)-N-(1-(3-(1,1,2,2-tetrafluoroethoxyphenyl)ethyl)isonicotinamide | single enantiomer | 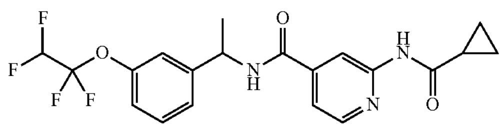 [SMILES: CC(NC(=O)c1ccnc(NC(=O)C2CC2)c1)c1cccc(OC(F)(F)C(F)F)c1] | Amine-113 | | 426.2 | 1.67 |
| 1246 | 2-isobutyramido-N-(1-(3-(1,1,2,2-tetrafluoroethoxyphenyl)ethyl)isonicotinamide | single enantiomer | 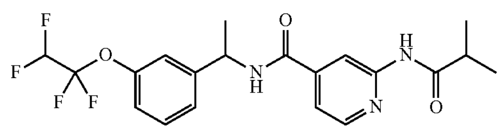 [SMILES: CC(C)C(=O)Nc1cc(C(=O)NC(C)c2cccc(OC(F)(F)C(F)F)c2)ccn1] | Amine-113 | | 428.2 | 1.7 |
| 1247 | 2-acetamido-6-methyl-N-(1-(3-(1,1,2,2-tetrafluoroethoxyphenyl)ethyl)isonicotinamide | single enantiomer | 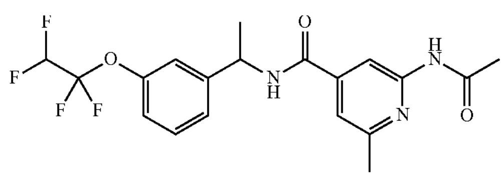 [SMILES: CC(=O)Nc1cc(C(=O)NC(C)c2cccc(OC(F)(F)C(F)F)c2)cc(C)n1] | Amine-113 | | 414.1 | 1.62 |

| Example | Name | Chirality | Structure | Amine part | Carboxylic part | Observed MS | Retention time (min) |
|---|---|---|---|---|---|---|---|
| 1248 | 2-isobutyramido-6-methyl-N-(1-(3-(1,1,2,2-tetrafluoroethoxy)phenyl)ethyl)isonicotinamide | single enantiomer | 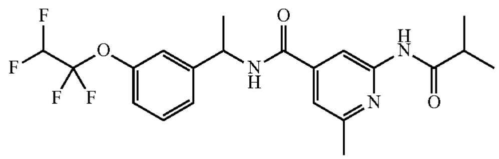 [SMILES: Cc1cc(C(=O)NC(C)c2cccc(OC(F)(F)C(F)F)c2)cc(NC(=O)C(C)C)n1] | Amine-113 | | 442.2 | 1.75 |
| 1249 | 2-(2-hydroxy-2-methylpropan-amido)-6-methyl-N-(1-(3-(1,1,2,2-tetrafluoroethoxy)phenyl)ethyl)isonicotinamide | single enantiomer | 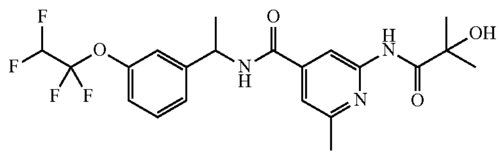 [SMILES: Cc1cc(C(=O)NC(C)c2cccc(OC(F)(F)C(F)F)c2)cc(NC(=O)C(C)(C)O)n1] | Amine-113 | | 458.2 | 1.67 |
| 1250 | 2-(cyclopropanecarboxamido)-N-(1-(3-(1,1,2,2-tetrafluoroethoxy)phenyl)ethyl)pyrimidine-4-carboxamide | single enantiomer | 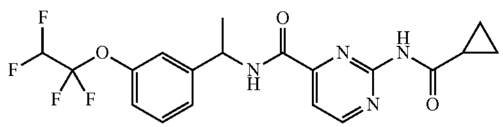 [SMILES: CC(NC(=O)c1ccnc(NC(=O)C2CC2)n1)c1cccc(OC(F)(F)C(F)F)c1] | Amine-113 | | 427.1 | 1.63 |
| 1251 | 2-(cyclopropanecarboxamido)-6-methyl-N-(1-(3-(1,1,2,2-tetrafluoroethoxy)phenyl)ethyl)pyrimidine-4-carboxamide | single enantiomer | 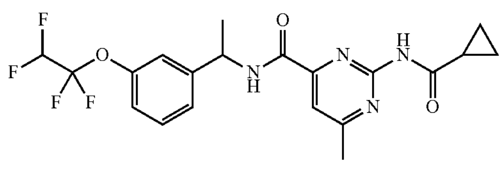 [SMILES: Cc1cc(C(=O)NC(C)c2cccc(OC(F)(F)C(F)F)c2)nc(NC(=O)C2CC2)n1] | Amine-113 | | 441.2 | 1.7 |

TABLE 1-continued

| Example | Name | Chirality | Structure | Amine part | Carboxylic part | Observed MS | Retention time (min) |
|---|---|---|---|---|---|---|---|
| 1252 | 2-acetamido-N-(1-(3-(difluoromethyl)phenyl)ethyl)isonicotinamide | single enantiomer | 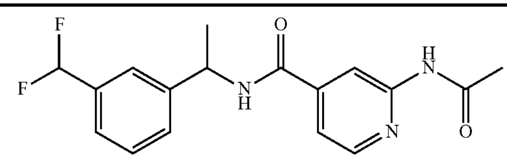 | Amine-114 | | 334 | 1.42 |
| 1253 | N-(1-(3-(difluoromethyl)phenyl)ethyl)-2-propionamidoisonicotinamide | single enantiomer | 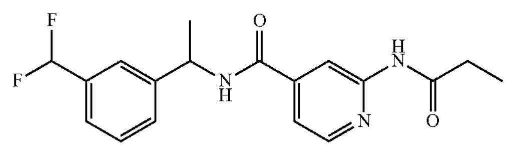 [SMILES: CCC(=O)Nc1cc(C(=O)NC(C)c2cccc(C(F)F)c2)ccn1] | Amine-114 | | 348 | 1.51 |
| 1254 | 2-(cyclopropanecarboxamido)-N-(1-(3-(difluoromethyl)phenyl)ethyl)isonicotinamide | single enantiomer | 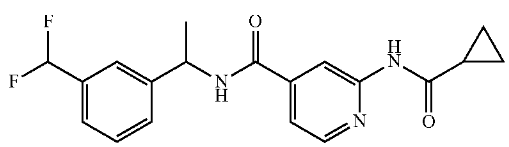 [SMILES: CC(NC(=O)c1ccnc(NC(=O)C2CC2)c1)c1cccc(C(F)F)c1] | Amine-114 | | 360 | 1.55 |
| 1255 | N-(1-(3-(difluoromethyl)phenyl)ethyl)-2-isobutyramidoisonicotinamide | single enantiomer | 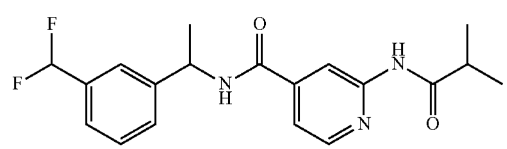 [SMILES: CC(C)C(=O)Nc1cc(C(=O)NC(C)c2cccc(C(F)F)c2)ccn1] | Amine-114 | | 360.4 | 1.59 |

TABLE 1-continued

| Example | Name | Chirality | Structure | Amine part | Carboxylic part | Observed MS | Retention time (min) |
|---|---|---|---|---|---|---|---|
| 1256 | 2-acetamido-N-(1-(3-(difluoromethyl)phenyl)ethyl)-6-methylisonicotinamide | single enantiomer | 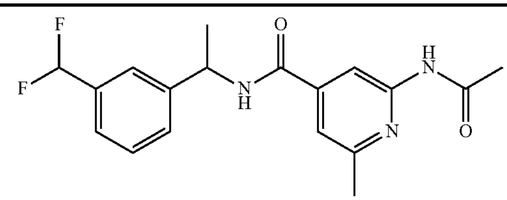 | Amine-114 | | 346.4 | 1.48 |
| 1257 | N-(1-(3-difluoromethyl)phenyl)ethyl)-2-isobutyramido-6-methylisonicotinamide | single enantiomer | 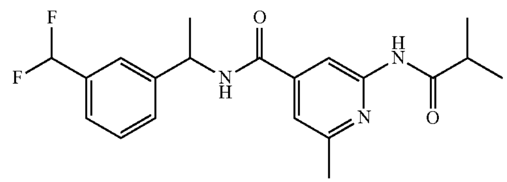 [SMILES: Cc1cc(C(=O)NC(C)c2cccc(C(F)F)c2)cc(NC(=O)C(C)C)n1] | Amine-114 | | 374.4 | 1.66 |
| 1258 | N-(1-(3-(difluoromethyl)phenyl)ethyl)-2-(2-hydroxy-2-methylpropanamido)-6-methylisonicotinamide | single enantiomer | 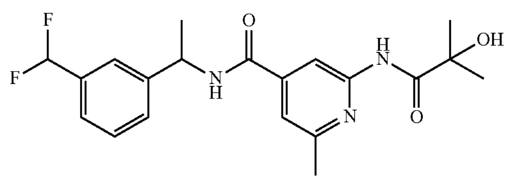 [SMILES: Cc1cc(C(=O)NC(C)c2cccc(C(F)F)c2)cc(NC(=O)C(C)(C)O)n1] | Amine-114 | | 392 | 1.55 |
| 1259 | 2-(cyclopropanecarboxamido)-N-(1-(3-(difluoromethyl)phenyl)ethyl)pyrimidine-4-carboxamide | single enantiomer | 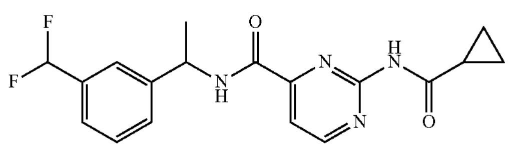 [SMILES: CC(NC(=O)c1ccnc(NC(=O)C2CC2)n1)c1cccc(C(F)F)c1] | Amine-114 | | 359.3 | 1.51 |

TABLE 1-continued

| Example | Chirality | Name | Structure | Amine part | Carboxylic part | Observed MS | Retention time (min) |
|---|---|---|---|---|---|---|---|
| 1260 | single enantiomer | 2-(cyclopropanecarboxamido)-N-(1-(3-(difluoromethyl)phenyl)ethyl)-6-methylpyrimidine-4-carboxamide | 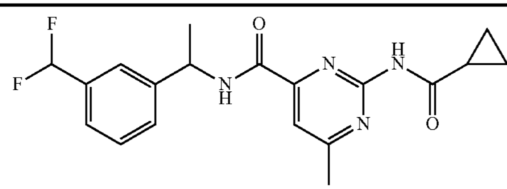 | Amine-114 | | 375 | 1.58 |
| 1261 | single enantiomer | 2-acetamido-N-(1-(4-(perfluoroethoxy)phenyl)ethyl)isonicotinamide | 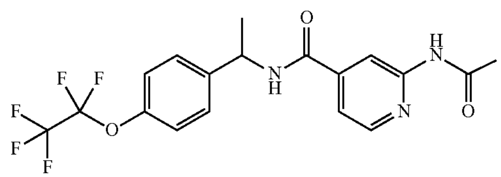 [SMILES: CC(=O)Nc1cc(C(=O)NC(C)c2ccc(OC(F)(F)C(F)(F)F)cc2)ccn1] | Amine-115 | | 418.1 | 1.63 |
| 1262 | single enantiomer | N-(1-(4-(perfluoroethoxy)phenyl)ethyl)-2-propionamidoisonicotinamide | 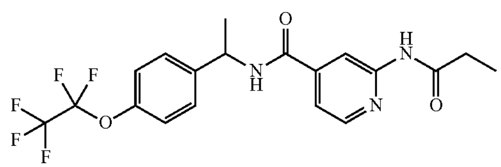 [SMILES: CCC(=O)Nc1cc(C(=O)NC(C)c2ccc(OC(F)(F)C(F)(F)F)cc2)ccn1] | Amine-115 | | 432.1 | 1.72 |
| 1263 | single enantiomer | 2-cyclopropanecarboxamido)-N-(1-(4-(perfluoroethoxy)phenyl)ethyl)isonicotinamide | 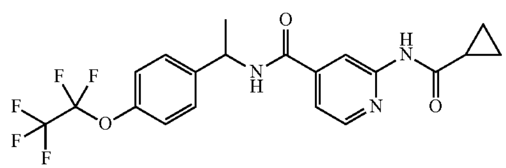 [SMILES: CC(NC(=O)c1ccnc(NC(=O)C2CC2)c1)c1ccc(OC(F)(F)C(F)(F)F)cc1] | Amine-115 | | 444.2 | 1.74 |
| 1264 | single enantiomer | 2-obutyramido-N-(1-(4-(perfluoroethoxy)phenyl)ethyl)isonicotinamide | 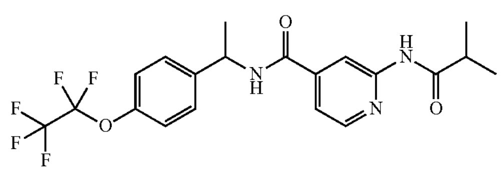 [SMILES: CC(C)C(=O)Nc1cc(C(=O)NC(C)c2ccc(OC(F)(F)C(F)(F)F)cc2)ccn1] | Amine-115 | | 446.2 | 1.8 |

TABLE 1-continued

| Example | Name | Chirality | Structure | Amine part | Carboxylic part | Observed MS | Retention time (min) |
|---|---|---|---|---|---|---|---|
| 1265 | 2-acetamido-6-methyl-N-(1-(4-(perfluoroethoxy)phenyl)ethyl)isonicotinamide | single enantiomer | 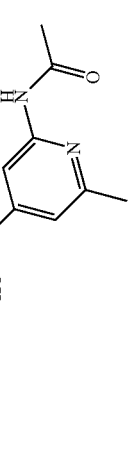 | 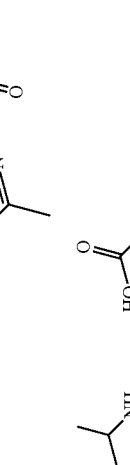 Amine-115 | 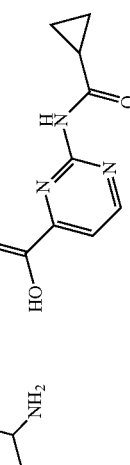 | 432.2 | 1.7 |
| 1266 | 2-isobutyramido-6-methyl-N-(1-(4-(perfluoroethoxy)phenyl)ethyl)isonicotinamide | single enantiomer | 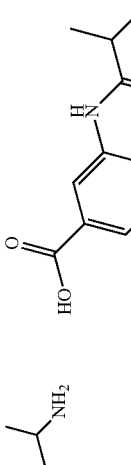 | 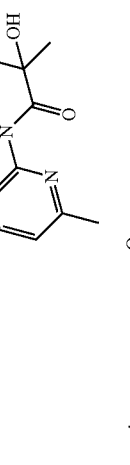 Amine-115 | 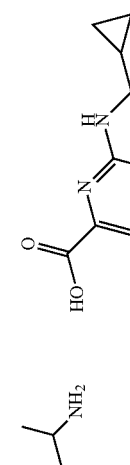 | 460.2 | 1.86 |
| 1267 | 2-(2-hydroxy-2-methylpropanamido)-6-methyl-N-(1-(4-(perfluoroethoxy)phenyl)ethyl)isonicotinamide | single enantiomer | 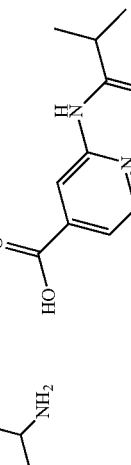 | 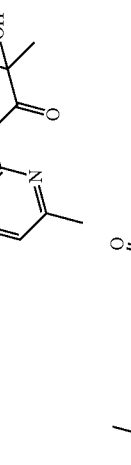 Amine-115 | 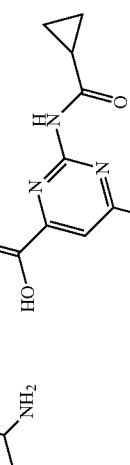 | 474.1 | 1.75 |
| 1268 | 2-(cyclopropanecarboxamido)-N-(1-(4-(perfluoroethoxy)phenyl)ethyl)pyrimidine-4-carboxamide | single enantiomer | 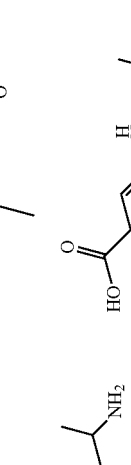 | 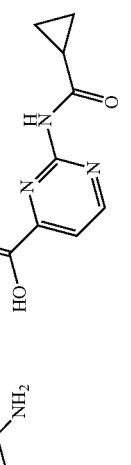 Amine-115 | 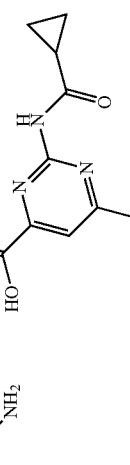 | 445.2 | 1.72 |
| 1269 | 2-(cyclopropanecarboxamido)-6-methyl-N-(1-(4-(perfluoroethoxy)phenyl)pyrimidine-4-carboxamide | single enantiomer | 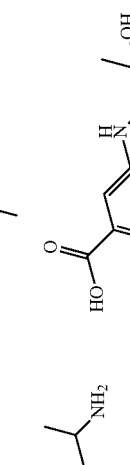 | 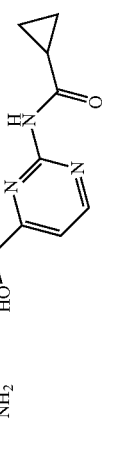 Amine-115 | 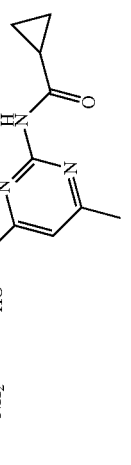 | 459.2 | 1.77 |

TABLE 1-continued

| Example | Name | Chirality | Structure | Amine part | Carboxylic part | Observed MS | Retention time (min) |
|---|---|---|---|---|---|---|---|
| 1270 | (R)-2-acetamido-N-(1-(3-(perfluoroethoxyphenyl)ethyl)isonicotinamide | single enantiomer | 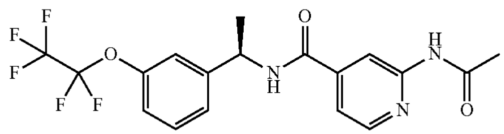 [SMILES: CC(=O)Nc1cc(C(=O)N[C@H](C)c2cccc(OC(F)(F)C(F)(F)F)c2)ccn1] | | | 418.2 | 1.64 |
| 1271 | (R)-N-(1-(3-(perfluoroethoxyphenyl)ethyl)-2-propionamidoisonicotinamide | single enantiomer | 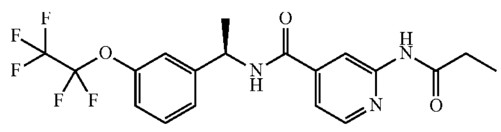 [SMILES: CCC(=O)Nc1cc(C(=O)N[C@H](C)c2cccc(OC(F)(F)C(F)(F)F)c2)ccn1] | | | 432.2 | 1.72 |
| 1272 | (R)-2-(cyclopropanecarboxamido)-N-(1-(3-(perfluoroethoxyphenyl)ethyl)isonicotinamide | single enantiomer | 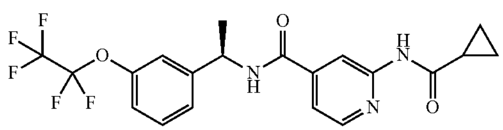 [SMILES: C[C@@H](NC(=O)c1ccnc(NC(=O)C2CC2)c1)c1cccc(OC(F)(F)C(F)(F)F)c1] | | | 444.2 | 1.74 |
| 1273 | (R)-2-isobutyramido-N-(1-(3-(perfluoroethoxyphenyl)ethyl)isonicotinamide | single enantiomer | 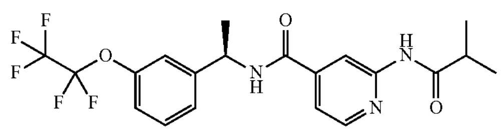 [SMILES: CC(C)C(=O)Nc1cc(C(=O)N[C@H](C)c2cccc(OC(F)(F)C(F)(F)F)c2)ccn1] | | | 446.2 | 1.81 |
| 1274 | (R)-2-acetamido-6-methyl-N-(1-(3-(perfluoroethoxyphenyl)ethyl)isonicotinamide | single enantiomer | 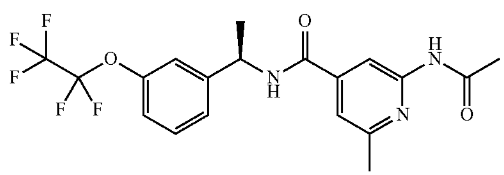 [SMILES: CC(=O)Nc1cc(C(=O)N[C@H](C)c2cccc(OC(F)(F)C(F)(F)F)c2)cc(C)n1] | | | 432.2 | 1.7 |

TABLE 1-continued

| Example | Name | Chirality | Structure | Amine part | Carboxylic part | Observed MS | Retention time (min) |
|---|---|---|---|---|---|---|---|
| 1275 | (R)-2-isobutyramido-6-methyl-N-(1-(3-(perfluoroethoxy)phenyl)ethyl)isonicotinamide | single enantiomer | 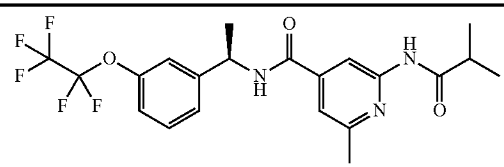 | | | 460.2 | 1.86 |
| 1276 | (R)-2-(2-hydroxy-2-methylpropanamido)-6-methyl-N-(1-(3-(perfluoroethoxy)phenyl)ethyl)isonicotinamide | single enantiomer | 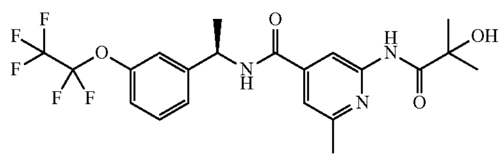 [SMILES: Cc1cc(C(=O)N[C@H](C)c2cccc(OC(F)(F)C(F)(F)F)c2)cc(NC(=O)C(C)(C)O)n1] | | | 476.2 | 1.75 |
| 1277 | (R)-2-(cyclopropanecarboxamido)-N-(1-(3-(perfluoroethoxy)phenyl)ethyl)pyrimidine-4-carboxamide | single enantiomer | 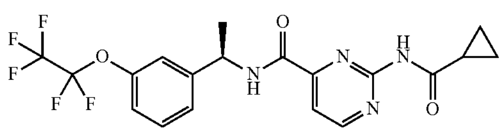 [SMILES: C[C@@H](NC(=O)c1ccnc(NC(=O)C2CC2)n1)c1cccc(OC(F)(F)C(F)(F)F)c1] | | | 443.1 | 1.73 |
| 1278 | (R)-2-(cyclopropanecarboxamido)-6-methyl-N-(1-(3-(perfluoroethoxy)phenyl)ethyl)pyrimidine-4-carboxamide | single enantiomer | 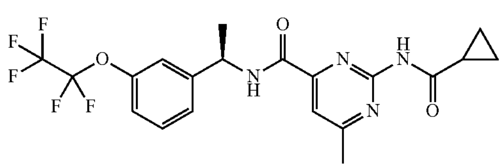 [SMILES: Cc1cc(C(=O)N[C@H](C)c2cccc(OC(F)(F)C(F)(F)F)c2)nc(NC(=O)C2CC2)n1] | | | 459.2 | 1.78 |

TABLE 1-continued

| Example | Name | Chirality | Structure | Amine part | Carboxylic part | Observed MS | Retention time (min) |
|---|---|---|---|---|---|---|---|
| 1279 | 2-butyramido-N-((5-cyclopropyl-6-(2,2-difluoroethoxy)pyridin-3-yl)methyl)isonicotinamide | | 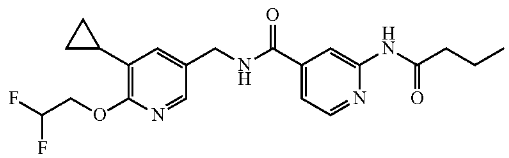 [SMILES: CCCC(=O)Nc1cc(C(=O)NCc2cnc(OCC(F)F)c(C3CC3)c2)ccn1] | | | 417.3 | 1.67 |
| 1280 | 2-acetamido-N-(3-fluoro-4-(trifluoromethoxy)benzyl)isonicotinamide | | 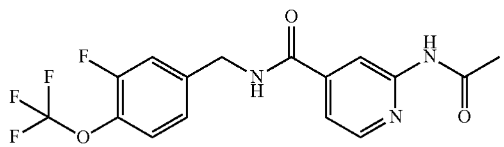 [SMILES: CC(=O)Nc1cc(C(=O)NCc2ccc(OC(F)(F)F)c(F)c2)ccn1] | Amine-77 | | 370.3 | 1.56 |
| 1281 | 2-(cyclopropanecarboxamido)-N-(4-fluoro-3-(trifluoromethyl)benzyl)-6-methylisonicotinamide | | 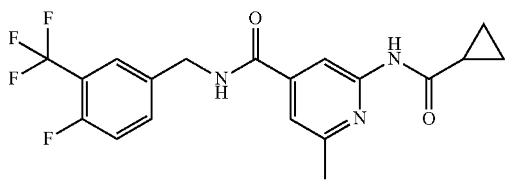 [SMILES: Cc1cc(C(=O)NCc2ccc(F)c(C(F)(F)F)c2)cc(NC(=O)C2CC2)n1] | | | 394.3 | 1.7 |

TABLE 2

| Example | ¹H-NMR data | salt | observed MS |
|---|---|---|---|
| Example 8 | (270 MHz, DMSO-$d_6$) δ 10.67 (1H, brs), 9.15 (1H, d, J = 7.9 Hz), 8.45-8.40 (1H, m), 8.41 (1H, s), 8.20 (1H, s), 7.84 (1H, d, J = 8.6 Hz), 7.46 (1H, d, J = 4.6 Hz), 6.97 (1H, d, J = 8.6 Hz), 5.16 (1H, quintet, J = 7.2 Hz), 4.97 (1H, q, J = 9.2 Hz), 2.77 (1H, septet, J = 6.6 Hz), 1.50 (3H, d, J = 7.2 Hz), 1.10 (6H, d, J = 6.6 Hz). | HCl salt | 411 |
| Example 9 | (300 MHz, CDCl$_3$) δ 8.40 (1H, s), 8.38 (1H, d, J = 5.1 Hz), 8.30 (1H, br), 8.17 (1H, d, J = 2.2 Hz), 7.66 (1H, dd, J = 8.1 , 2.2 Hz), 7.51 (1H, dd, J = 5.1, 1.4 Hz), 6.84 (1H, d, J = 8.8 Hz), 6.63 (1H, d, J = 8.1 Hz), 5.29 (1H, quintet, 7.3 Hz), 4.74 (2H, q, J = 8.8 Hz), 1.59 (3H, d, J = 7.3 Hz), 1.62-1.54 (1H, m), 1.15-1.08 (2H, m), 1.00-0.92 (2H, m). | free | 409 |
| Example 9 | (300 MHz, DMSO-$d_6$) δ 11.1 (1H, s), 9.17 (1H, d, J = 7.7 Hz), 8.43 (1H, d, J = 5.5 Hz), 8.38 (1H, s), 8.20 (1H, d, J = 1.8 Hz), 7.85 (1H, dd, J = 8.4, 1.8 Hz), 7.49 (1H, d, J = 5.5 Hz), 6.98 (1H, d, J = 8.4 Hz), 5.12 (1H, quintet, J = 7.3 Hz), 4.98 (2H, q, J = 9.2 Hz), 2.03 (1H, m), 1.49 (3H, d, J = 7.0 Hz), 1.04 (2H, dd, J = 5.7, 0.7 Hz), 0.85 (2H, d, J = 5.7 Hz). | HCl salt | 409 |
| Example 11 | (300 MHz, DMSO-$d_6$) δ 10.58 (1H, s), 9.09 (1H, d, 7.7 Hz), 8.48-8.35 (2H, m), 8.19 (1H, d, J = 2.6 Hz), 7.83 (1H, dd, J = 8.4, 2.2 Hz), 7.42 (1H, dd, J = 5.1 & 1.5 Hz), 6.96 (1H, d, J = 8.4 Hz), 5.15 (1H, quintet, J = 7.3 Hz), 4.96 (2H, q, J = 9.2 Hz), 2.31 (2H, q, J = 7.7 Hz), 1.48 (3H, d, J = 7.0 Hz), 1.06 (3H, t, J = 7.3 Hz). | free | 397 |
| Example 52 | (300 MHz, DMSO-$d_6$) δ 10.64 (1H, s), 9.08 (1H, d, J = 7.7 Hz), 8.40 (1H, d, J = 5.5 Hz), 8.38 (1H, s), 8.17 (1H, d, J = 1.8 Hz), 8.04 (1H, d, J = 2.2 Hz), 7.44 (1H, dd, J = 5.1, 1.5 Hz), 5.19 (1H, quintet, J = 7.3 Hz), 5.06 (2H, q, J = 8.8 Hz), 2.09 (3H, s), 1.48 (3H, d, J = 7.3 Hz). | free | 417 |
| Example 60 | (300 MHz, DMSO-$d_6$) δ 10.53 (1H, s), 9.04 (1H, d, J = 7.3 Hz), 8.23 (1H, s), 8.20 (1H, d, J = 2.9 Hz), 7.83 (1H, dd, J = 8.0, 5.9 Hz), 7.30 (1H, s), 6.97 (1H, d, J = 8.0 Hz), 5.15 (1H, quintet, 7.3 Hz), 4.98 (2H, q, J = 9.5 Hz), 2.45 (3H, s), 2.38 (2H, q, J = 8.0 Hz), 1.48 (3H, d, J = 7.3 Hz), 1.06 (3H, t, J = 8.0 Hz). | free | 411 |
| Example 62 | (300 MHz, DMSO-$d_6$) δ 10.54 (1H, d, J = 9.5 Hz), 9.09-9.02 (1H, m), 8.22 (1H, s), 8.19 (1H, d, J = 2.2 Hz), 7.82 (1H, dd, J = 8.8, 2.2 Hz), 7.30 (1H, d, J = 3.7 Hz), 6.98 (1H, d, J = 8.8 Hz), 5.14 (1H, quintet, J = 7.3 Hz), 4.96 (2H, q, J = 8.8 Hz), 2.74 (1H, septet, J = 6.6 Hz), 2.45 (3H, s), 1.47 (3H, d, J = 6.6 Hz), 1.06 (6H, d, J = 7.4 Hz). | HCl salt | 425 |
| Example 169 | (300 MHz, DMSO-$d_6$) δ 10.87 (1H, s), 9.41 (1H, t, J = 5.9 Hz), 8.51-8.42 (2H, m), 8.17 (1H, d, J = 2.2 Hz), 7.78 (1H, dd, J = 8.8, 2.2 Hz), 7.51 (1H, d, J = 6.6 Hz), 6.97 (1H, d, J = 8.0 Hz), 4.97 (2H, q, J = 9.5 Hz), 4.43 (2H, d, J = 5.9 Hz), 2.78 (1H, septet, J = 6.6 Hz), 1.10 (6H, d, J = 7.3 Hz). | HCl salt | 397 |
| Example 235 | (300 MHz, CDCl$_3$) δ 8.1-8.0 (1H, m), 8.00 (1H, s), 7.95 (1H, brs), 7.63 (1H, s), 7.46 (1H, s), 5.21 (1H, quintet, J = 7.3 Hz), 4.75 (2H, q, J = 8.1 Hz), 2.55 (3H, s), 2.48 (3H, s), 2.23 (3H, s), 1.61 (3H, d, J = 7.3 Hz). | free | 412 |
| Example 483 | (300 MHz, DMSO-$d_6$) δ 10.61 (1H, s), 9.27 (1H, t, J = 5.5 Hz), 8.26 (1H, s), 8.15 (1H, d, J = 2.2 Hz), 7.75 (1H, dd, J = 8.8, 2.2 Hz), 7.34 (1H, s), 6.95 (1H, d, J = 8.5 Hz), 4.97 (2H, q, J = 9.2 Hz), 4.40 (2H, d, J = 5.8 Hz), 2.74 (1H, septet, J = 6.6 Hz), 2.44 (3 H, s), 1.06 (6H, d, J = 7.0 Hz). | HCl salt | 411 |
| Example 499 | (300 MHz, DMSO-$d_6$) δ 10.5 (1H, s), 9.08 (1H, d, J = 7.7 Hz), 8.25 (1H, s), 7.49-7.21 (5H, m), 5.17 (1H, quintet, J = 7.0 Hz), 2.75 (1H, quintet, J = 7.0 Hz), 2.45 (3H, s), 1.47 (3H, d, J = 7.0 Hz), 1.06 (6H, d, J = 7.0 Hz). | free | 410 |
| Example 531 | (300 MHz, CDCl$_3$) δ 8.28 (1H, s), 7.94 (1H, br), 7.63-7.43 (4H, m), 7.40 (1H, s), 6.64 (1H, d, J = 7.3 Hz), 5.36 (1H, quintet, J = 7.3 Hz), 2.56 (1H, septet, J = 7.3 Hz), 2.49 (3H, s), 1.62 (3H, d, J = 7.3 Hz), 1.27 (6H, d, J = 6.6 Hz). | free | 394 |
| Example 555 | (300 MHz, DMSO-$d_6$) δ 10.69 (1H, d, J = 10.3 Hz), 9.12-9.08 (1H, m), 8.44-8.38 (2H, m), 8.01 (1H, d, J = 2.2 Hz), 7.66 (1H, s), 7.50-7.44 (1H, m), 6.39 (1H, tt, J = 55, 3.7 Hz), 5.12 (1H, quintet, J = 7.3 Hz), 4.56 (2H, td, J = 14.6, 3.7 Hz), 2.77 (1H, septet, J = 6.6 Hz), 2.17 (3H, s), 1.48 (3H, d, J = 6.6 Hz), 1.09 (6H, d, J = 7.3 Hz). | HCl salt | 407 |
| Example 557 | (300 MHz, DMSO-$d_6$) δ 10.51 (1H, s), 9.01 (1H, d, J = 7.4 Hz), 8.24 (1H, s), 8.01 (1H, s), 7.64 (1H, s), 7.30 (1H, s), 6.38 (1H, tt, J = 55, 3.7 Hz), 5.11 (1H, quintet, J = 7.3 Hz), 4.56 (2H, td, J = 15.4, 3.7 Hz), 2.75 (1H, septet, J = 6.6 Hz), 2.45 (3H, s), 2.17 (3H, s), 1.47 (3H, d, J = 7.3 Hz), 1.08 (6H, d, J = 6.6 Hz). | free | 421 |
| Example 558 | (300 MHz, CDCl$_3$) δ 8.78 (1H, d, J = 5.1 Hz), 8.33 (1H, s), 8.12 (1H, d, J = 8.1 Hz), 7.99 (1H, d, J = 2.9 Hz), 7.76 (1H, d, J = 5.1 Hz), 7.45 (1H, d, J = 2.2 Hz), 6.13 (1H, tt, J = 56, 4.4 Hz), 5.21 (1H, quintet, J = 7.3 Hz), 4.53 (2H, td, J = 13.2, 4.4 Hz), 2.21 (3H, s), 2.15-2.03 (1H, m), 1.61 (3H, d, J = 7.3 Hz), 1.25-1.15 (2H, m), 1.00-0.92 (2H, m). | free | 406 |

Pharmacological Assays

In Vitro Human Voltage Gated Sodium Channels Activity

The inhibitory activities of compounds against voltage gated sodium channels are determined by methodology well known in the art.

The ability of the aryl substituted carboxamide derivatives of the formula (I) to inhibit the $Na_{v1.3}$, $Na_{v1.7}$ and $Na_{v1.5}$ channels is measured by Fluorescence Resonance Energy Transfer (FRET) assay and electrophysiology assay described below.

FRET Assay

This screen is used to determine the effects of compounds on human $Na_{v1.3}$, human $Na_{v1.7}$, and human $Na_{v1.5}$ channels, utilising electrical field stimulation (EFS) system in 96-well plate format on FDSS (Hamamatsu Photonics) platform. The change of membrane potential is monitored with FRET dye pair, oxonol (DiSBAC2(3)) and coumarin (CC2-DMPE).

Cell Maintenance:

Each HEK293 cells expressing human $Na_{v1.3}$ channels and HEK293 cells expressing human $Na_{v1.5}$ channels are grown in T225 flasks, in a 5% $CO_2$ humidified incubator to about 80% confluence. Media composition consists of Dulbecco's Modified Eagle Medium (high glucose), 10% FCS, 100 units/mL Penicillin, 100 microgram/mL Streptomycin and 500 microgram/mL Geneticine.

CHO cells expressing human $Na_{v1.7}$ channels are grown in T225 flasks, in a 5% $CO_2$ humidified incubator to about 80% confluence. Media composition consists of HAM/F12 with Glutamax 1.10% FCS, 100 units/mL Penicillin and 100 microgram/mL Hygromycin.

Protocol:

Seed each cell lines (1×10⁵ cells/well) into poly-D-lysine coated 96-well plates prior to experimentation.

Incubate at 37° C. in 5% $CO_2$ for 24 hours.

Wash each well with assay buffer (140 mM NaCl, 4.5 mM KCl, 10 mM D-Glucose, 2 mM $CaCl_2$, 1 mM $MgCl_2$, 10 mM HEPES, pH 7.4 adjusted with NaOH) twice.

Add 1st loading solution containing 10 microM CC2-DMPE and 0.06% Pluronic F-127 in assay buffer.

Incubate the plate at room temperature in dark for 1 hour.

Remove 1st loading solution and added 2nd loading solution containing 15 microM DiSBAC2(3), 0.555 mM VABSC-1 and 0.004% Pluronic F-127 in assay buffer.

Place the plate under the dark at room temperature for 25 minutes.
Add compound solutions into the assay plate.
Set the assay plate in FDSS and placed an EFS device on the plate.
Measure EFS-induced fluorescent response by FDSS.

The data are analyzed and reported as normalized ratios of intensities measured at 440 nm. The process of calculating these ratios is performed as follows:

[Math. 1]

$$FIR = \text{Fluorescence Integration Ratio} =$$
the integral of the ratio normalized by baseline (before EFS)

$$\% \text{ inhibition} = \left\{1 - \frac{(FIR \text{ of each well} - \text{median } FIR \text{ in } 100\% \text{ Inh.})}{(\text{median } FIR \text{ in } 0\% \text{ Inh.} - \text{median } FIR \text{ in } 100\% \text{ Inh.})}\right\} \times 100$$

This analysis is performed using a computerized specific program designed for FDSS generated data. Fluorescence ratio values are plotted using XLfit to determine an $IC_{50}$ value for each compound.

All tested compounds show less than about 5 microM of $IC_{50}$ against $Na_{v1.3}$ and/or $Na_{v1.7}$ in the above assays. Preferable compounds show less than about 3 microM of $IC_{50}$ against $Na_{v1.3}$ and/or $Na_{v1.7}$ in the above assays.

Compounds with $IC_{50}$ against $Na_{v1.3}$<1 microM are:
Examples 8, 62, 69, 85, 87, 89, 93, 94, 95, 126, 127, 128, 129, 130, 132, 134, 136, 139, 147, 148, 149, 150, 151, 152, 153, 169, 171, 180, 223, 224, 225, 226, 227, 228, 229, 235, 241, 359, 360, 363, 364, 368, 369, 371, 372, 410, 411, 443, 456, 464, 465, 466, 467, 468, 469, 475, 483, 492, 494, 496, 499, 508, 516, 520, 523, 524, 525, 526, 527, 528, 533, 534, 535, 554, 555, 557, 558, 564, 566, 568, 571, 572, 573, 574, 575, 576, 577, 578, 591, 597, 598, 599, 600, 602, 604, 607, 608, 609, 639, 641, 643, 665, 677, 680, 682, 690, 692, 694, 707, 709, 710, 711, 712, 713, 714, 715, 717, 718, 719, 721, 727, 729, 730, 736, 738, 739, 740, 742, 743, 746, 747, 748, 749, 750, 751, 752, 757, 762, 779, 780, 788, 789, 790, 791, 792, 793, 794, 804, 805, 806, 807, 808, 809, 810, 811, 815, 816, 823, 824, 825, 831, 832, 836, 880, 895, 896, 898, 899, 902, 904, 905, 906, 911, 918, 925, 926, 927, 930, 939, 940, 941, 942, 943, 944, 945, 946, 947, 953, 954, 956, 958, 960, 961, 962, 967, 968, 975, and 984.

Compounds with $IC_{50}$ against $Na_{v1.7}$<1 microM are:
Examples 1, 7, 8, 9, 11, 22, 24, 40, 52, 57, 60, 61, 62, 69, 73, 74, 79, 84, 85, 87, 89, 94, 115, 116, 126, 127, 128, 129, 130, 131, 132, 133, 134, 135, 136, 137, 139, 140, 142, 143, 144, 147, 148, 149, 150, 152, 153, 168, 169, 171, 178, 179, 180, 181, 186, 194, 210, 211, 212, 213, 214, 216, 220, 223, 224, 225, 226, 227, 228, 229, 234, 235, 237, 241, 243, 264, 270, 272, 281, 282, 283, 284, 290, 291, 302, 303, 304, 305, 306, 307, 308, 312, 313, 314, 316, 318, 319, 320, 328, 330, 331, 332, 333, 334, 335, 336, 337, 338, 353, 359, 360, 363, 364, 365, 366, 367, 368, 369, 370, 371, 372, 374, 378, 379, 385, 391, 392, 394, 397, 400, 403, 404, 405, 407, 410, 411, 412, 418, 420, 421, 442, 443, 444, 456, 467, 482, 483, 486, 487, 490, 492, 493, 494, 499, 520, 521, 522, 523, 524, 525, 526, 527, 528, 529, 530, 531, 532, 533, 534, 551, 552, 553, 554, 555, 556, 557, 558, 559, 561, 562, 564, 597, 600, 602, 618, 620, 633, 635, 643, 651, 653, 654, 657, 673, 675, 676, 677, 678, 679, 680, 689, 693, 705, 706, 707, 751, 757, 762, 770, 778, 780, 781, 782, 783, 785, 787, 788, 789, 790, 791, 792, 793, 794, 796, 797, 798, 799, 800, 801, 802, 803, 804, 805, 806, 807, 808, 809, 810, 811, 815, 816, 819, 820, 822, 823, 824, 825, 826, 827, 828, 831, 832, 836, 837, 838, 839, 851, 852, 862, 863, 865, 866, 869, 870, 871, 876, 878, 879, 880, 881, 882, 884, 885, 890, 893, 895, 896, 897, 898, 899, 900, 901, 902, 903, 904, 905, 906, 907, 910, 911, 912, 922, 924, 925, 926, 927, 928, 930, 931, 932, 933, 938, 939, 940, 941, 942, 943, 944, 945, 946, 947, 953, 954, 962, 975, 980, 981, 988, 989, 990, 991, 992, 993, 994, 996, 998, 1003, 1007, 1008, 1009, 1012, 1017, 1030, 1031, 1032, 1049, 1063, 1064, 1075, 1078, 1082, 1096, 1100, 1101, 1102, 1104, 1116, 1131, 1147, 1152, 1153, 1154, 1156, 1157, 1160, 1161, 1162, 1163, 1166, 1169, 1210, and 1212.

Regarding all tested compounds, the ratio of activities against $Na_{v1.5}$ vs. $Na_{v1.3}$ or $Na_{v1.7}$ is more than three times. For example, the activities of example 1 against $Na_{v1.5}$, $Na_{v1.3}$ and $Na_{v1.7}$ are more than 30 microM, 2.8 microM, and 0.94 microM, respectively.

Electrophysiology Assay for Navs

Whole cell patch clamp recording is used to assess the efficacy or selectivity of Na channel blocker on human $Na_{v1.3}$ (hSCN3A) expressing HEK293 cells or human $Na_{v1.7}$ (hSCN9A) expressing CHO cells. Human $Na_{v1.3}$ expressing HEK293 cells are grown in growth media which comprised: DMEM, 10% heat-inactivated FBS (Hyclone Laboratories Inc), 100 microgram/mL Penicillin/100 U/mL Streptomycin, 150 microgram/mL Zeocin, 3 microgram/mL Geneticin. Human $Na_{v1.7}$ expressing CHO cells are grown in growth media which comprised: HAM/F-12, 9% heat-inactivated FBS (Hyclone Laboratories Inc), 100 microgram/mL Penicillin/100 U/mL Streptomycin, 100 microgram/mL Hygromycin.

Na channel expressing cells are dissociated by 0.05% Trypsine-EDTA, and then seeded on cover glass for 24-48 hr.

Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier (Axon Instruments or HEKA elektronik). The extracellular recording solution consists of (mM): 140 NaCl, 5 KCl, 2 $CaCl_2$, 1 $MgCl_2$, 10 HEPES, 10 Glucose, pH 7.4 adjusted with NaOH. The internal solution consists of (mM): 120 CsF, 15 NaCl, 10 EGTA, 10 HEPES, pH 7.2 adjusted with CsOH; Upon insertion of the pipette tip into the bath, the pipette resistance is noted (acceptable range is between 1-3 megaohm). The junction potential between the pipette and bath solutions is zeroed on the amplifier. After establishing the whole-cell configuration, approximately 10 minutes are allowed for the pipette solution to equilibrate within the cell before beginning recording. Currents are low-pass filtered between 2-5 kHz and digitally sampled at 10 kHz.

The normalized steady-state inactivation curve is constructed using 2 sec (for vehicle) or 60 sec (for drugs) conditioning pulse to different potentials followed immediately by the test pulse to −10 mV. Peak currents are plotted as fraction of the maximum current at the conditioning potentials ranging from −120 mV to −40 mV for $Na_{v1.3}$ and from −130 mV to −60 mV for $Na_{v1.7}$. V1/2 or k values are estimated from Boltzmann fits. The affinity of drugs to resting state of Na channels ($K_{resting}$ or $K_r$) is assessed by 30 msec test pulse from a negative holding potential of −120 or −130 mV, where virtually all channels are in the resting state. $K_r$ value is calculated by a conventional 1:1 binding model:

$$K_{resting}(K_r) = \{[\text{drug}]I_{max},\text{drug}/(I_{max},\text{control} - I_{max},\text{drug})\}$$

where $K_{resting}$ (=$K_r$) is a dissociation constant for the resting state and [drug] is compound concentration. $I_{max}$, control and $I_{max}$, drug are peak currents in the absence and presence of compound, respectively.

The affinity of drug to inactivated state of Na channels ($K_{inact}$ or $K_i$) is estimated from the shift of the availability curve by compound. Interaction of the compound with the channel on inactivated state is evaluated by the following equation:

$$K_{inact}(K_i) = \{[\text{drug}]/((1+[\text{drug}]/K_r)^* \exp(-\Delta V/k)-1)\} \quad [\text{Math.2}]$$

where $K_{inact}$ (=$K_i$) is a dissociation constant for the inactivated state. $\Delta V$ is the compound-induced voltage shift of half maximal voltage of Boltzmann curve and k is the slop factor on presense of compound.

All tested compounds of the invention show potent activities in this model. For example, the activities ($K_i$) of example 1 against $Na_{v1.3}$ and $Na_{v1.7}$ are 1.5 microM and 1.2 microM, respectively.

In Vivo Assay

Chronic Constriction Injury (CCU-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. CCI-induced static allodynia is assessed by von Frey hair (VFH) test. Surgery is performed according to the method of Bennett G J and Xie Y K (Pain 1988, 33: 87-107). The animals are anesthetized with intraperitoneal injection of pentobarbital sodium. The left common sciatic nerve is exposed at the level of the middle of the thigh, freed of adhering tissue, and four ligatures are loosely tided around it by using 4-0 silk thread. The incision is sutured, and the rats are allowed to recover in their cages with soft bedding. Sham operation is performed in the same manner except of sciatic nerve ligation. The animals are individually placed in a Plexiglas test chamber on an elevated grid to acclimate for 1 hour before the day of testing. On postoperative day (POD) 14-28, evaluation is performed using a series of calibrated VFH (Semmes-Winstein monofilaments) with 0.4, 0.6, 1, 2, 4, 6, 8 and 15 g force. VFH starting with the 2 g force is applied in an ascending or descending fashion according to a modified Dixon up-down method described by Chaplan S R et al. (J Neurosci Methods 1994, 53: 55-63). Each VFH is presented to the plantar surface of the operated hind paw with steady upward pressure until bent for approximately 6 seconds. In the absence of a paw withdrawal, a stronger stimulus is presented. In the event of a paw withdrawal, the next weaker stimulus is chosen. After the initial change from positive to negative or vice verse, 4 more stimulations are applied. The 6-score pattern of positive and negative responses is converted into a 50% paw withdrawal threshold (PWT) using the following formula:

$$50\% \text{ PWT}(g) = (10^{[Xf+\kappa\delta]})/10,000 \quad [\text{Math.3}]$$

where Xf is the value (in log units) of the final VFH used, K is the tabular value for the pattern of positive/negative responses and S is the mean difference between stimuli in log units (here, 0.224).

In the cases where continuous positive or negative responses are observed all the way out to the end of the stimulus spectrum, values of 0.25 and 15 g are assigned, respectively. The animals showing static allodynia (<3 g of 50% PWT) by CCI surgery are selected for evaluation and randomized to be nearly equal mean 50% PWT across all groups. The compounds of the invention or their vehicles are administered systemically. The rats are habituated to the chamber for at least 20 minutes before each measurement. The 50% PWT is measured at the appropriated time after compound administration.

All tested compounds of the invention show potent activities in this model. For example, example 1 shows potent activity at 100 mg/kg per os.

Complete Freund's Adjuvant (CFA)-Induced Thermal Hyperalgesia in Rats

Male Sprague-Dawley rats at 6 weeks old are purchased from Charles River Japan Inc., and housed in groups of two per cage under a 12-h light/dark cycle (lights on at 07:00) with access to food and water ad libitum. CFA-induced thermal hyperalgesia is assessed using the plantar test apparatus (Ugo Basile) as described by Hargreaves K et al. (Pain 1988, 32: 77-88). The animals are placed in an apparatus consisting of individual testing box on an elevated glass table and allowed to acclimate for at least 10 minutes. Following the habituation, a mobile radiant heat source is located under the table and heat stimulation is applied to the plantar surface of the right hind paw. The latency to remove its hind paw is defined as paw withdrawal latency (PWL) in sec. The cut-off point is set at 30 seconds to prevent tissue damage. CFA is prepared at a concentration of 2-3 mg/mL of *Mycobacterium tuberculosis* H37 RA in liquid paraffin. After disinfections with 70% ethanol, the rats are injected intraplantarly with 100 microL of CFA (200-300 microgram) into the right hind paw. Two days after CFA injection, PWL is measured in the same manner as mentioned above. The animals showing decrease of the PWL (hyperalgesia) by CFA injection are selected for evaluation and randomized to be nearly equal mean PWL across all groups. The compounds of the invention or their vehicles are administered systemically. The rats are habituated to the apparatus for at least 10 minutes before each measurement. The PWL is measured at the appropriated time after compound administration. All tested compounds of the invention show potent activities in this model. For example, example 1 shows significant activity at 30 mg/kg per os.

CFA-Induced Weight Bearing Deficit in Rats

Male Sprague-Dawley rats at 7 weeks old are purchased from Charles River Japan Inc., and housed in groups of two per cage under a 12-h light/dark cycle (lights on at 07:00) with access to food and water ad libitum. CFA-induced weight bearing (WB) deficit is assessed using Incapacitance tester (Linton Instrumentation). The animals are habituated to a plastic case that comes with Incapacitance tester before the day of CFA injection. On the day of CFA injection, the weight distribution of each hind paw is measured 3 times per rat using the tester, and the difference of weight distribution, weight on the right (injected) paw minus weight on left (non-injected) paw, is defined as WB deficit value in g. The duration of the each measurement is adjusted to 3 seconds. CFA is prepared at a concentration of 2-3 mg/mL of *Mycobacterium tuberculosis* H37 RA in liquid paraffin. After disinfections with 70% ethanol, the rats are injected intraplantarly with 100 microL of CFA (200-300 microgram) into the right hind paw. Two days after CFA injection, the weight distribution of each hind paw is measured and the WB deficit value is calculated in the same manner as mentioned above. The animals showing decrease of the WB deficit (>30%) by CFA injection are selected for evaluation and randomized to be nearly equal across all groups. The compounds of the invention or their vehicles are administered systemically. The weight distribution of each hind paw is measured at the appropriated time after compound administration, and the WB deficit value is calculated as previously explained.

All tested compounds of the invention show potent activities in this model. For example, example 1 shows significant activity at 10 mg/kg per os.

Paw Incision-Induced Static Allodynia in Rats

Male Sprague-Dawley rats at 7 weeks old are purchased from Charles River Japan Inc., and housed in groups of two per cage under a 12-h light/dark cycle (lights on at 07:00) with access to food and water ad libitum. Paw incision-induced static allodynia is assessed by VFH test. Surgery is performed according to the procedure described by Brennan et al. (Pain 1996, 64: 493-501). The animals are initially anesthetized with 3-4% isoflurane/$O_2$ mixture in an anesthetic chamber and maintained with 2-3% delivered through a nose cone. The plantar surface of the right hind paw is sterilized with 7.5% povidone-iodine solution. A 1-cm longitudinal incision is made with a number 11 blade, through skin and fascia of the plantar aspect of the paw, starting 0.5 cm from the proximal edge of the heel and extending toward the toes. The plantaris muscle is elevated using forceps and retracted. The muscle origin and insertion remain intact. After hemostasis with gentle pressure, the skin is apposed with 2 sutures of 5-0 nylon. The wound site is covered with Terramycin ointment, and the rats are allowed to recover in their cages with soft bedding. The animals are individually placed in a Plexiglas test chamber on an elevated grid to acclimate for 1 hour before the day of surgery. On POD1, evaluation is performed using a series of calibrated VFH (0.008, 0.02, 0.04, 0.07, 0.16, 0.4, 0.6, 1, 1.4, 2, 4, 6, 8, 10, 15 and 26 g). Starting with the 0.16 g force in an ascending or descending fashion, each VFH is presented to the proximal end of the wound near the lateral heel with steady upward pressure until bent for approximately 6 seconds. In the absence of a paw withdrawal (negative response), a stronger stimulus is presented. In the event of a paw withdrawal (positive response), the next weaker stimulus is chosen. The lowest amount of force required to elicit two positive responses is defined as paw withdrawal threshold (PWT) in g. In the cases where continuous positive or negative responses are observed all the way out to the end of the stimulus spectrum, values of 0.008 and 26 g are assigned, respectively. The animals showing <1.4 g of PWT by incisional surgery are selected for evaluation and randomized to be nearly equal median PWT across all groups. The compounds of the invention or their vehicles are administered systemically. The rats are habituated to the chamber for at least 20 minutes before each measurement. The PWT is measured at the appropriated time after compound administration.

All tested compounds of the invention show potent activities in this model. For example, example 1 shows significant activity at 30 mg/kg per os.

Human Dofetilide Binding Assay

Human HERG transfected HEK293S cells are prepared and grown in-house. The collected cells are suspended in 50 mM Tris-HCl (pH 7.4 at 4° C.) and homogenized using a hand held Polytron PT 1200 disruptor set at full power for 20 sec on ice. The homogenates are centri-fuged at 48,000×g at 4° C. for 20 min. The pellets are then resuspended, homogenized, and centrifuged once more in the same manner. The final pellets are resuspended in an appropri-ate volume of 50 mM Tris-HCl, 10 mM KCl, 1 mM $MgCl_2$ (pH 7.4 at 4° C.), homogenized, ali-quoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microgram protein) for 120 minutes at room temperature. Nonspecific binding is determined by 10 microM E4031 at the final concentration.

All tested compounds of the invention show higher $IC_{50}$ values in human dofetilide binding than $IC_{50}$ values in $Na_{V1.3}$ or $Na_{V1.7}$ FRET Assay. The high $IC_{50}$ values in human dofetilide binding activities lead to reducing the risk of cardiovascular adverse events.

Metabolic Stability Assay:

Half-Life in Human Liver Microsomes (HLM)

Test compounds (1 microM) are incubated with 3.3 mM $MgCl_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. (NADPH generation system is also used instead of NADPH.) An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yield the rate of metabolism (k). This is converted to a half-life value using following equations: Half-life=ln 2/k The compounds of this invention show preferable stability, which show the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam (ULTRAFINE UC-429) 2 microM) at 3 microM of the each compound.

More specifically, the assay is carried out as follows. The compounds (60 microM, 10 microL) are pre-incubated in 170 microL of mixture including 0.1 mg protein/mL human liver microsomes, 100 mM potassium phosphate buffer (pH 7.4), 1 mM $MgCl_2$ and probes as substrate for 5 min. Reaction is started by adding a 20 microL of 10 mM NADPH (20 microL of NADPH generating system, which consist of 10 mM $NADP^+$, 50 mM DL-lsocitric acid and 10 U/mL Isocitric Dehydrogenase, is also used). The assay plate is incubated at 37° C. Acetonitrile is added to the incubate solution at appropriate time (e.g. 8 min).

The metabolites' concentration in the supernatant is measured by LC/MS/MS system.

The degree of drug interaction is interpreted based on generation % of metabolites in the presence or absence of test compound.

The compounds of this invention show preferable results, which show the above-mentioned practical use.

Plasma Protein Binding Assay

Plasma protein binding of the test compound (1 microM) is measured by the method of equilibrium dialysis using 96-well plate type equipment.

HTD96a (registered trademark), regenerated cellulose membranes (molecular weight cut-off 12,000-14,000, 22 mm×120 mm) are soaked for over night in distilled water, then for 15 minutes in 30% ethanol, and finally for 20 minutes in dialysis buffer (Dulbecco's phosphate buffered saline, pH7.4). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 r.p.m, aliquots of plasma and buffer are sampled. The compound in plasma and buffer are extracted with 300 microL of acetonitrile containing internal standard compounds for analysis. The concentration of the compound is determined with LC/MS/MS analysis.

The fraction of the compound unbound is calculated by the following equation (A) or (B):

$$(A) fu = 1 - \{([plasma]_{eq} - [buffer]_{eq})/([plasma]_{eq})\}$$

wherein $[plasma]_{eq}$ and $[buffer]_{eq}$ are the concentrations of the compound in plasma and buffer, respectively.

[Math. 4]

$$fu(\%) = \frac{Cb/Cis, b \times 4}{Cp/Cis, p \times \frac{4}{3}} \times 100 \quad (B)$$

wherein Cp is the peak area of the compound in plasma sample;

Cis,p is the peak area of the internal standard in plasma sample;

Cb is the peak area of the compound in buffer sample;

Cis,b is the peak area of the internal standard in buffer sample;

4 and 4/3 is the reciprocal of the dilution rate in plasma and buffer, respectively.

The compounds of this invention show preferable plasma protein binding, which show the above-mentioned practical use.

Equilibrium Aqueous Solubility Study

The DMSO solution (2 microL, 30 mM) of each compound is dispensed into each well of a 96-well glass bottom plate. Potassium phosphate buffer solution (50 mM, 198 microL, pH 6.5) is added to each well, and the mixture is incubated at 37° C. with rotate shaking for 24 hours. After centrifugation at 2000 g for 5 minutes, the supernatant is filtered through the polycarbonate iso-pore membrane. The concentration of samples is determined by a general gradient HPLC method (J. Pharm. Sci. 2006, 95, 2115-2122).

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

INDUSTRIAL APPLICABILITY

The Arylamide derivatives of the present invention are useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

The invention claimed is:

1. A compound of the following formula (II)

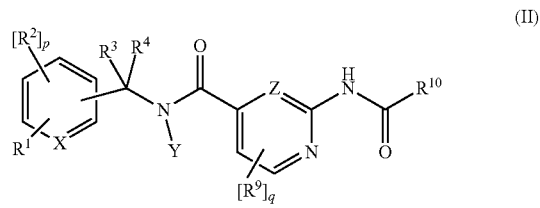

wherein:

$R^1$ is independently selected from the group consisting of —$CF_3$, —$CHF_2$, —$OCF_3$, —$OCHF_2$, —$OCH_2CHF_2$, —$OCH_2CF_3$, —$OCF_2CHF_2$, —$OCF_2CF_3$, —$OCH_2CH_2CF_3$, —$OCH(CH_3)CF_3$, —$OCH_2C(CH_3)F_2$, —$OCH_2CF_2CHF_2$, —$OCH_2CF_2CF_3$, —$OCH_2CH_2OCH_2CF_3$, —$NHCH_2CF_3$, —$SCF_3$, —$SCH_2CF_3$, —$CH_2CF_3$, —$CH_2CH_2CF_3$, —$CH_2OCH_2CF_3$, and —$OCH_2CH_2OCF_3$;

$R^2$ is independently selected from the group consisting of: (1) hydrogen, (2) halogen, (3) hydroxyl, (4) —$O_n$—$C_{1-6}$ alkyl, where the alkyl is unsubstituted or substituted with one or more substituents independently selected from $R^5$, (5) —$O_n$—$C_{3-6}$ cycloalkyl, where the cycloalkyl is unsubstituted or substituted with one or more substituents independently selected from $R^5$, (6) —$O_n$—$C_{2-4}$ alkenyl, where the alkenyl is unsubstituted or substituted with one or more substituents independently selected from $R^5$, (7) —$O_n$-phenyl or —$O_n$-naphthyl, where the phenyl or naphthyl is unsubstituted or substituted with one or more substituents independently selected from $R^5$, (8) —$O_n$-heterocyclic group, where the heterocyclic group is unsubstituted or substituted with one or more substituents independently selected from $R^5$, (9) —(C=O)—$NR^7R^8$, (10) —$NR^7R^8$, (11) —$S(O)_2$—$NR^7R^8$, (12) —$NR^7$—$S(O)_2R^8$, (13) —$S(O)_t$—$R^7$, where t is 0, 1 or 2, (14) —$NR^7(C=O)R^8$, (15) —CN, and (16) —$NO_2$;

wherein n is 0 or 1, when n is 0, a chemical bond is present in the place of —$O_n$—;

p is 1, 2, 3, or 4; when p is two or more than two, $R^2$ may be the same or different;

$R^3$ and $R^4$ are independently hydrogen or $C_{1-6}$ alkyl which is unsubstituted or substituted with one or more substituents independently selected from the group consisting of halogen, hydroxyl, and —O—$C_{1-6}$ alkyl, wherein both $R^3$ and $R^4$ are not $C_{1-6}$ alkyl at the same time;

$R^5$ is selected from the group consisting of:

(1) hydrogen, (2) halogen, (3) hydroxyl, (4) —(C=O)$_m$—$O_f$—$C_{1-6}$ alkyl, where the alkyl is unsubstituted or substituted with one or more substituents independently selected from $R^6$, (5) —$O_f$—($C_{1-3}$)perfluoroalkyl, (6) —(C=O)$_m$—$O_f$—$C_{3-6}$ cycloalkyl, where the cycloalkyl is unsubstituted or substituted with one or more substituents independently selected from $R^6$, (7) —(C=O)$_m$—$O_f$—$C_{2-4}$alkenyl, where the alkenyl is unsubstituted or substituted with one or more substituents independently selected from $R^6$, (8) —(C=O)$_m$—$O_f$-phenyl or —(C=O)$_m$—$O_f$-naphthyl, where the phenyl or naphthyl is unsubstituted or substituted with one or more substituents independently selected from $R^6$, (9) —$(C=O)_m$—$O_l$-heterocyclic group, where the heterocyclic group is unsubstituted or substituted with one or more substituents independently selected from $R^6$, (10) —(C=O)—$NR^7R^8$, (11) —$N R^7R^8$, (12) —$S(O)_2$—$NR^7R^8$, (13) —$S(O)_t$—$R^7$, where t is 0, 1 or 2, (14) —$CO_2H$, (15) —CN, and (16) —$NO_2$;

wherein l is 0 or 1 and m is 0 or 1; when l is 0 or m is 0, a chemical bond is present in the place of —$O_l$— or —$(C=O)_m$—, and when l is 0 and m is 0, a chemical bond is present in the place of —$(C=O)_m$—$O_l$—;

$R^6$ is independently selected from the group consisting of: (1) hydrogen, (2) hydroxyl, (3) halogen, (4) —$C_{1-6}$ alkyl, (5) —$C_{3-6}$ cycloalkyl, (6) —O—$C_{1-6}$ alkyl, (7) —O(C=O)—$C_{1-6}$ alkyl, (8) —NH—$C_{1-6}$ alkyl, (9) phenyl, (10) heterocyclic group, and (11) —CN;

$R^7$ and $R^8$ are independently hydrogen, $C_{1-6}$ alkyl, $C_{2-6}$ alkenyl, $C_{3-7}$ cycloalkyl, or aryl, which is unsubstituted or substituted with one or more substituents independently selected from the group consisting of halogen, hydroxyl, $C_{1-6}$ alkyl, and —O—$C_{1-6}$ alkyl; or $R^7$ forms a 4 to 7 membered ring with $R^8$ which may contain a nitrogen atom, an oxygen atom, a sulfur atom or a double bond, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^6$, (5) $C_{3-6}$ cycloalkyl, which is unsubstituted or substituted with one or more substituents independently selected from $R^6$, (6) —O—$C_{1-6}$ alkyl, which is unsubstituted or substituted with one or more substituents independently selected from $R^6$, and (7) —O—$C_{3-6}$ cycloalkyl, which is unsubstituted or substituted with one or more substituents independently selected from $R^6$;

X is a nitrogen atom or a carbon atom;
Z is a nitrogen atom or a carbon atom;
Y is hydrogen, or $C_{1-6}$ alkyl;
$R^9$ is independently selected from the group consisting of:
(1) hydrogen, (2) halogen, (3) —$O_n$—$C_{1-6}$ alkyl, where the alkyl is unsubstituted or substituted with one or more substituents independently selected from $R^5$, (4) —$O_n$—$C_{3-6}$ cycloalkyl, where the cycloalkyl is unsubstituted or substituted with one or more substituents independently selected from $R^5$, and (5) —$O_n$—$C_{2-4}$ alkenyl, where the alkenyl is unsubstituted or substituted with one or more substituents independently selected from $R^5$;

wherein n is 0 or 1, when n is 0, a chemical bond is present in the place of —$O_n$—;

q is 1, 2 or 3; when q is two or more than two, $R^9$ may be the same or different;

$R^{10}$ is independently hydrogen, $C_{1-6}$ alkyl, $C_{2-6}$ alkenyl, or $C_{3-7}$ cycloalkyl, which is unsubstituted or substituted with one or more substituents independently selected from the group consisting of halogen, hydroxyl, $C_{1-6}$ alkyl, —O—$C_{1-6}$ alkyl, —$C_{3-7}$ cycloalkyl, and —O—$C_{3-7}$ cycloalkyl;

or a pharmaceutically acceptable salt thereof.

2. The compound according to claim 1, wherein:
$R^1$ is selected from the group consisting of —$CF_3$, —$OCF_3$, —$OCH_2CHF_2$, —$OCF_2CHF_2$, —$OCF_2CF_3$, —$OCH_2CF_2CF_3$, —$OCH_2CF_2CHF_2$ and —$OCH_2CF_3$;
$R^2$ is independently selected from the group consisting of:
(1) hydrogen, (2) halogen, (3) methyl, and (4) methoxy;
p is 1;
$R^3$ is hydrogen;
$R^4$ is hydrogen or methyl;
Y is hydrogen;

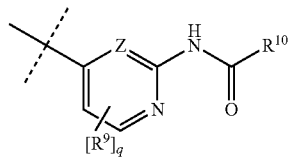

is selected from the group consisting of:

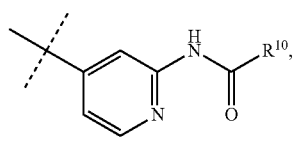

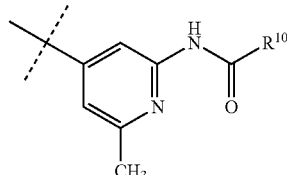

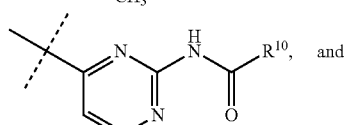 and

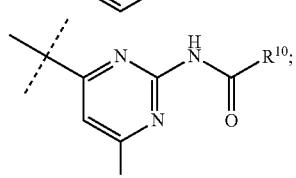

and $R^{10}$ is selected from the group consisting of methyl, ethyl, isopropyl, and cyclopropyl;

or a pharmaceutically acceptable salt thereof.

3. The compound according to claim 1, wherein:
$R^1$ is selected from the group consisting of —$CF_3$, —$OCF_3$, —$OCH_2CHF_2$, —$OCF_2CHF_2$, —$OCF_2CF_3$, —$OCH_2CF_2CF_3$, —$OCH_2CF_2CHF_2$ and —$OCH_2CF_3$;
$R^2$ is independently selected from the group consisting of:
(1) hydrogen, (2) halogen, (3) methyl, and (4) methoxy;
p is 1;
$R^3$ is hydrogen;
$R^4$ is methyl;
Y is hydrogen;

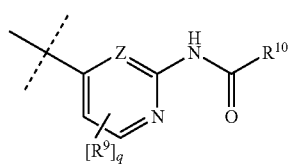

is selected from the group consisting of:

and $R^{10}$ is selected from the group consisting of methyl, ethyl, isopropyl, and cyclopropyl;
or a pharmaceutically acceptable salt thereof.

4. The compound according to claim 1, wherein:
$R^1$ is selected from the group consisting of —$CF_3$, —$OCF_3$, —$OCH_2CHF_2$, —$OCF_2CHF_2$, —$OCF_2CF_3$, —$OCH_2CF_2CF_3$, —$OCH_2CF_2CHF_2$ and —$OCH_2CF_3$;
$R^2$ is independently selected from the group consisting of: (1) hydrogen, (2) halogen, (3) methyl, and (4) methoxy;
p is 1;
$R^3$ and $R^4$ are both hydrogen;
X is a nitrogen atom;
Y is hydrogen;

is selected from the group consisting of:

and $R^{10}$ is selected from the group consisting of methyl, ethyl, isopropyl, and cyclopropyl;
or a pharmaceutically acceptable salt thereof.

5. A compound selected from the group consisting of:
2-acetamido-N-(1-(6-(2,2,2-trifluoroethoxy)pyridin-3-yl)ethyl)isonicotinamide;
2-acetamido-N-((4-(2,2,2-trifluoroethoxy)pyridin-2-yl)methyl)isonicotinamide;
N-((5-acetamido-6-(2,2,2-trifluoroethoxy)pyridin-3-yl)methyl)-3-(trifluoromethoxy)benzamide;
2-oxo-N-(1-(6-(2,2,2-trifluoroethoxy)pyridin-3-yl)ethyl)-2,3-dihydro-1H-benzo[d]imidazole-4-carboxamide;
2-methyl-N-(1-(6-(2,2,2-trifluoroethoxy)pyridin-3-yl)ethyl)-2H-indazole-3-carboxamide;
(R)-2-acetamido-N-(1-(4-(trifluoromethyl)phenyl)ethyl)isonicotinamide;
(R)-2-acetamido-N-(1-(3-(trifluoromethyl)phenyl)ethyl)isonicotinamide;
2-isobutyramido-N-(1-(6-(2,2,2-trifluoroethoxy)pyridin-3-yl)ethyl)isonicotinamide;
2-(cyclopropanecarboxamido)-N-(1-(6-(2,2,2-trifluoroethoxy)pyridin-3-yl)ethyl)isonicotinamide;
2-benzamido-N-(1-(6-(2,2,2-trifluoroethoxy)pyridin-3-yl)ethyl)isonicotinamide;
2-propionamido-N-(1-(6-(2,2,2-trifluoroethoxy)pyridin-3-yl)ethyl)isonicotinamide;
2-(methylsulfonamido)-N-(1-(6-(2,2,2-trifluoroethoxy)pyridin-3-yl)ethyl)benzamide;
3-(1H-imidazol-1-yl)-N-(1-(6-(2,2,2-trifluoroethoxy)pyridin-3-yl)ethyl)benzamide;
2-acetamido-N-((6-(2,2,2-trifluoroethoxy)pyridin-3-yl)methyl)isonicotinamide;
N-(1-(6-(2,2,2-trifluoroethoxy)pyridin-3-yl)ethyl)quinoline-8-carboxamide;
N-(1-(6-(2,2,2-trifluoroethoxy)pyridin-3-yl)ethyl)quinoline-2-carboxamide;
2-acetamido-N-((2-(2,2,2-trifluoroethoxy)pyridin-4-yl)methyl)isonicotinamide;
2-acetamido-N-(4-(trifluoromethoxy)benzyl)isonicotinamide;
3-acetamido-N-(1-(6-(2,2,2-trifluoroethoxy)pyridin-3-yl)ethyl)picolinamide;
2-(1H-imidazol-1-yl)-N-(1-(6-(2,2,2-trifluoroethoxy)pyridin-3-yl)ethyl)isonicotinamide;
2-acetamido-N-methyl-N-(1-(6-(2,2,2-trifluoroethoxy)pyridin-3-yl)ethyl)isonicotinamide;
2-acetamido-N-((6-(2,2,2-trifluoroethoxy)pyridin-2-yl)methyl)isonicotinamide;
6-acetamido-N-((6-(2,2,2-trifluoroethoxy)pyridin-2-yl)methyl)picolinamide;
2-acetamido-N-(3-(trifluoromethoxy)benzyl)isonicotinamide;

N-(1-(6-(2,2,2-trifluoroethoxy)pyridin-3-yl)ethyl)-1,6-naphthyridine-2-carboxamide;
N-(1-(6-(2,2,2-trifluoroethoxy)pyridin-3-yl)ethyl)quinoline-3-carboxamide;
N-(1-(6-(2,2,2-trifluoroethoxy)pyridin-3-yl)ethyl)isoquinoline-3-carboxamide;
N-(1-(6-(2,2,2-trifluoroethoxy)pyridin-3-yl)ethyl)quinoxaline-2-carboxamide;
N-(1-(6-(2,2,2-trifluoroethoxy)pyridin-3-yl)ethyl)isoquinoline-6-carboxamide;
6-(tert-butyl)-N-(1-(6-(2,2,2-trifluoroethoxy)pyridin-3-yl)ethyl)nicotinamide;
1-methyl-N-(1-(6-(2,2,2-trifluoroethoxy)pyridin-3-yl)ethyl)-1H-indazole-3-carboxamide;
N-(1-(6-(2,2,2-trifluoroethoxy)pyridin-3-yl)ethyl)benzo[c]isoxazole-3-carboxamide;
1-methyl-N-(1-(6-(2,2,2-trifluoroethoxy)pyridin-3-yl)ethyl)-1H-pyrazolo[3,4-b]pyridine-3-carboxamide;
N-(1-(6-(2,2,2-trifluoroethoxy)pyridin-3-yl)ethyl)imidazo[1,2-a]pyridine-2-carboxamide;
1-methyl-N-(1-(6-(2,2,2-trifluoroethoxy)pyridin-3-yl)ethyl)-3-(trifluoromethyl)-1H-pyrazole-5-carboxamide;
5-methyl-1-phenyl-N-(1-(6-(2,2,2-trifluoroethoxy)pyridin-3-yl)ethyl)-1H-1,2,3-triazole-4-carboxamide;
4-methyl-2-phenyl-N-(1-(6-(2,2,2-trifluoroethoxy)pyridin-3-yl)ethyl)thiazole-5-carboxamide;
1-methyl-5-phenyl-N-(1-(6-(2,2,2-trifluoroethoxy)pyridin-3-yl)ethyl)-1H-pyrazole-3-carboxamide;
2-acetamido-N-(2-fluoro-5-(trifluoromethyl)benzyl)isonicotinamide;
2-butyramido-N-(1-(6-(2,2,2-trifluoroethoxy)pyridin-3-yl)ethyl)isonicotinamide;
2-(2-methoxyacetamido)-N-(1-(6-(2,2,2-trifluoroethoxy)pyridin-3-yl)ethyl)isonicotinamide;
2-(cyclobutanecarboxamido)-N-(1-(6-(2,2,2-trifluoroethoxy)pyridin-3-yl)ethyl)isonicotinamide;
2-acetamido-N-(3-(difluoromethoxy)benzyl)isonicotinamide;
4-methoxy-N-(1-(6-(2,2,2-trifluoroethoxy)pyridin-3-yl)ethyl)quinoline-2-carboxamide;
8-hydroxy-N-(1-(6-(2,2,2-trifluoroethoxy)pyridin-3-yl)ethyl)quinoline-2-carboxamide;
3-isopropyl-N-(1-(6-(2,2,2-trifluoroethoxy)pyridin-3-yl)ethyl)-1H-pyrazole-5-carboxamide;
3-(tert-butyl)-1-methyl-N-(1-(6-(2,2,2-trifluoroethoxy)pyridin-3-yl)ethyl)-1H-pyrazole-5-carboxamide;
6-(piperidin-1-yl)-N-(1-(6-(2,2,2-trifluoroethoxy)pyridin-3-yl)ethyl)nicotinamide;
N-(1-(6-(2,2,2-trifluoroethoxy)pyridin-3-yl)ethyl)-1H-benzo[d]imidazole-2-carboxamide;
N-(1-(6-(2,2,2-trifluoroethoxy)pyridin-3-yl)ethyl)pyrazolo[1,5-a]pyridine-2-carboxamide;
N-(1-(6-(2,2,2-trifluoroethoxy)pyridin-3-yl)ethyl)benzo[d]isoxazole-3-carboxamide;
2-acetamido-N-(1-(5-chloro-6-(2,2,2-trifluoroethoxy)pyridin-3-yl)ethyl)isonicotinamide;
2-acetamido-N-(3-(trifluoromethyl)benzyl)isonicotinamide;
N-((6-(2,2,2-trifluoroethoxy)pyridin-2-yl)methyl)quinoline-8-carboxamide;
2-methyl-N-((6-(2,2,2-trifluoroethoxy)pyridin-2-yl)methyl)-2H-indazole-3-carboxamide;
6-(tert-butyl)-N-((6-(2,2,2-trifluoroethoxy)pyridin-2-yl)methyl)nicotinamide;
2-oxo-N-((6-(2,2,2-trifluoroethoxy)pyridin-2-yl)methyl)-2,3-dihydro-1H-benzo[d]imidazole-4-carboxamide;
2-acetamido-N-(1-(6-(2,2,2-trifluoroethoxy)pyridin-3-yl)propyl)isonicotinamide;
2-acetamido-6-methyl-N-(1-(6-(2,2,2-trifluoroethoxy)pyridin-3-yl)ethyl)isonicotinamide;
2-methyl-6-propionamido-N-(1-(6-(2,2,2-trifluoroethoxy)pyridin-3-yl)ethyl)isonicotinamide;
2-(cyclopropanecarboxamido)-6-methyl-N-(1-(6-(2,2,2-trifluoroethoxy)pyridin-3-yl)ethyl)isonicotinamide;
2-isobutyramido-6-methyl-N-(1-(6-(2,2,2-trifluoroethoxy)pyridin-3-yl)ethyl)isonicotinamide;
2-acetamido-N-(1-(6-(2,2,2-trifluoroethoxy)pyridin-2-yl)ethyl)isonicotinamide;
N-(1-(6-(2,2,2-trifluoroethoxy)pyridin-2-yl)ethyl)benzo[c]isoxazole-3-carboxamide;
1-methyl-N-(1-(6-(2,2,2-trifluoroethoxy)pyridin-2-yl)ethyl)-1H-indazole-3-carboxamide;
2-acetamido-N-(1-(4-(2,2,2-trifluoroethoxy)pyridin-2-yl)ethyl)isonicotinamide;
2-acetamido-N-(1-(3-(trifluoromethoxy)phenyl)ethyl)isonicotinamide;
2-acetamido-N-(1-(4-(trifluoromethoxy)phenyl)ethyl)isonicotinamide;
N-(1-(5-chloro-6-(2,2,2-trifluoroethoxy)pyridin-3-yl)ethyl)-2-propionamidoisonicotinamide;
2-propionamido-N-(1-(6-(2,2,2-trifluoroethoxy)pyridin-2-yl)ethyl)isonicotinamide;
2-propionamido-N-(1-(2-(2,2,2-trifluoroethoxy)pyridin-4-yl)ethyl)isonicotinamide;
2-acetamido-N-(1-(5-fluoro-6-(2,2,2-trifluoroethoxy)pyridin-3-yl)ethyl)isonicotinamide;
2-acetamido-N-(1-(2-methyl-6-(2,2,2-trifluoroethoxy)pyridin-4-yl)ethyl)isonicotinamide;
N-(1-(5-fluoro-6-(2,2,2-trifluoroethoxy)pyridin-3-yl)ethyl)-2-propionamidoisonicotinamide;
N-(1-(2-methyl-6-(2,2,2-trifluoroethoxy)pyridin-4-yl)ethyl)-2-propionamidoisonicotinamide;
2-(cyclopropanecarboxamido)-N-(1-(6-(2,2,2-trifluoroethoxy)pyridin-2-yl)ethyl)isonicotinamide;
2-(cyclopropanecarboxamido)-N-(1-(6-(2,2,2-trifluoroethoxy)pyridin-3-yl)propyl)isonicotinamide;
2-(cyclopropanecarboxamido)-N-(1-(3-(trifluoromethoxy)phenyl)ethyl)isonicotinamide;
N-(1-(5-chloro-6-(2,2,2-trifluoroethoxy)pyridin-3-yl)ethyl)-2-(cyclopropanecarboxamido)isonicotinamide;
2-(cyclopropanecarboxamido)-N-(1-(5-fluoro-6-(2,2,2-trifluoroethoxy)pyridin-3-yl)ethyl)isonicotinamide;
2-methoxy-6-propionamido-N-(1-(6-(2,2,2-trifluoroethoxy)pyridin-3-yl)ethyl)isonicotinamide;
2-(cyclopropanecarboxamido)-6-methoxy-N-(1-(6-(2,2,2-trifluoroethoxy)pyridin-3-yl)ethyl)isonicotinamide;
2-isobutyramido-6-methoxy-N-(1-(6-(2,2,2-trifluoroethoxy)pyridin-3-yl)ethyl)isonicotinamide;
2-acetamido-N-(1-(3-(2,2,2-trifluoroethoxy)phenyl)ethyl)isonicotinamide;
2-acetamido-N-(1-(5-methyl-6-(2,2,2-trifluoroethoxy)pyridin-3-yl)ethyl)isonicotinamide;
2-propionamido-N-(1-(3-(2,2,2-trifluoroethoxy)phenyl)ethyl)isonicotinamide;
N-(1-(5-methyl-6-(2,2,2-trifluoroethoxy)pyridin-3-yl)ethyl)-2-propionamidoisonicotinamide;
2-(cyclopropanecarboxamido)-N-(1-(3-(2,2,2-trifluoroethoxy)phenyl)ethyl)isonicotinamide;
2-(cyclopropanecarboxamido)-N-(1-(5-methyl-6-(2,2,2-trifluoroethoxy)pyridin-3-yl)ethyl)isonicotinamide;
2-acetamido-N-(1-(4-(2,2,2-trifluoroethoxy)phenyl)ethyl)isonicotinamide;

2-propionamido-N-(1-(4-(2,2,2-trifluoroethoxy)phenyl)ethyl)isonicotinamide;
2-(cyclopropanecarboxamido)-N-(1-(4-(2,2,2-trifluoroethoxy)phenyl)ethyl)isonicotinamide;
2-acetamido-N-((5-chloro-6-(2,2,2-trifluoroethoxy)pyridin-3-yl)methyl)isonicotinamide;
N-((5-chloro-6-(2,2,2-trifluoroethoxy)pyridin-3-yl)methyl)-2-propionamidoisonicotinamide;
N-((5-chloro-6-(2,2,2-trifluoroethoxy)pyridin-3-yl)methyl)-2-(cyclopropanecarboxamido)isonicotinamide;
2-(cyclopropanecarboxamido)-N-(1-(6-(2,2,2-trifluoroethoxy)pyridin-3-yl)ethyl)pyrimidine-4-carboxamide;
2-propionamido-N-(1-(6-(2,2,2-trifluoroethoxy)pyridin-3-yl)ethyl)pyrimidine-4-carboxamide;
2-acetamido-N-(1-(4-fluoro-3-(2,2,2-trifluoroethoxy)phenyl)ethyl)isonicotinamide;
N-(1-(4-fluoro-3-(2,2,2-trifluoroethoxy)phenyl)ethyl)-2-propionamidoisonicotinamide;
2-acetamido-N-(3-fluoro-5-(trifluoromethyl)benzyl)isonicotinamide;
2-(cyclopropanecarboxamido)-N-(3-fluoro-5-(trifluoromethyl)benzyl)isonicotinamide;
2-(cyclopropanecarboxamido)-5-fluoro-N-(1-(6-(2,2,2-trifluoroethoxy)pyridin-3-yl)ethyl)isonicotinamide;
2-(cyclopropanecarboxamido)-N-(3-(trifluoromethyl)benzyl)isonicotinamide;
(R)-2-(cyclopropanecarboxamido)-N-(1-(3-(trifluoromethyl)phenyl)ethyl)isonicotinamide;
2-(cyclopropanecarboxamido)-N-(1-(4-(trifluoromethoxy)phenyl)ethyl)isonicotinamide;
2-propionamido-N-(3-(trifluoromethyl)benzyl)isonicotinamide;
(R)-2-propionamido-N-(1-(3-(trifluoromethyl)phenyl)ethyl)isonicotinamide;
2-propionamido-N-(1-(3-(trifluoromethoxy)phenyl)ethyl)isonicotinamide;
2-propionamido-N-(1-(4-(trifluoromethoxy)phenyl)ethyl)isonicotinamide;
2-methyl-N-(1-(6-(2,2,2-trifluoroethoxy)pyridin-3-yl)ethyl)-1H-benzo[d]imidazole-4-carboxamide;
N-(1-(5-chloro-6-(2,2,2-trifluoroethoxy)pyridin-3-yl)ethyl)-2-methyl-1H-benzo[d]imidazole-4-carboxamide;
N-(1-(5-chloro-6-(2,2,2-trifluoroethoxy)pyridin-3-yl)ethyl)-2-(cyclopropanecarboxamido)oxazole-5-carboxamide;
N-(1-(5-chloro-6-(2,2,2-trifluoroethoxy)pyridin-3-yl)ethyl)-2-(cyclopropanecarboxamido)-4-methyloxazole-5-carboxamide;
2-acetamido-N-(1-(6-(3,3,3-trifluoropropoxy)pyridin-3-yl)ethyl)isonicotinamide;
2-propionamido-N-(1-(6-(3,3,3-trifluoropropoxy)pyridin-3-yl)ethyl)isonicotinamide;
2-(cyclopropanecarboxamido)-N-(1-(6-(3,3,3-trifluoropropoxy)pyridin-3-yl)ethyl)isonicotinamide;
6-propionamido-N-(1-(6-(2,2,2-trifluoroethoxy)pyridin-3-yl)ethyl)pyrimidine-4-carboxamide;
6-(cyclopropanecarboxamido)-N-(1-(6-(2,2,2-trifluoroethoxy)pyridin-3-yl)ethyl)pyrimidine-4-carboxamide;
N-(1-(5-chloro-6-(2,2,2-trifluoroethoxy)pyridin-3-yl)ethyl)-6-propionamidopyrimidine-4-carboxamide;
6-methyl-2-propionamido-N-(1-(6-(2,2,2-trifluoroethoxy)pyridin-3-yl)ethyl)pyrimidine-4-carboxamide;
2-(cyclopropanecarboxamido)-6-methyl-N-(1-(6-(2,2,2-trifluoroethoxy)pyridin-3-yl)ethyl)pyrimidine-4-carboxamide;
2-acetamido-N-(4-((trifluoromethyl)thio)benzyl)isonicotinamide;
2-propionamido-N-(4-((trifluoromethyl)thio)benzyl)isonicotinamide;
2-(cyclopropanecarboxamido)-N-(4-((trifluoromethyl)thio)benzyl)isonicotinamide;
2-methyl-6-propionamido-N-(4-((trifluoromethyl)thio)benzyl)isonicotinamide;
(R)-2-methyl-6-propionamido-N-(1-(3-(trifluoromethyl)phenyl)ethyl)isonicotinamide;
2-methyl-6-propionamido-N-(3-(trifluoromethyl)benzyl)isonicotinamide;
N-(2-fluoro-5-(trifluoromethyl)benzyl)-2-methyl-6-propionamidoisonicotinamide;
N-(3-(difluoromethoxy)benzyl)-2-methyl-6-propionamidoisonicotinamide;
N-(1-(5-chloro-6-(2,2,2-trifluoroethoxy)pyridin-3-yl)ethyl)-2-methyl-6-propionamidoisonicotinamide;
N-(1-(5-fluoro-6-(2,2,2-trifluoroethoxy)pyridin-3-yl)ethyl)-2-methyl-6-propionamidoisonicotinamide;
2-methyl-N-(1-(5-methyl-6-(2,2,2-trifluoroethoxy)pyridin-3-yl)ethyl)-6-propionamidoisonicotinamide;
2-methyl-6-propionamido-N-(1-(6-(2,2,2-trifluoroethoxy)pyridin-3-yl)propyl)isonicotinamide;
2-methyl-6-propionamido-N-(1-(3-(trifluoromethoxy)phenyl)ethyl)isonicotinamide;
2-methyl-6-propionamido-N-(1-(4-(trifluoromethoxy)phenyl)ethyl)isonicotinamide;
2-methyl-6-propionamido-N-(1-(4-(2,2,2-trifluoroethoxy)phenyl)ethyl)isonicotinamide;
2-methyl-6-propionamido-N-((2-(2,2,2-trifluoroethoxy)pyridin-4-yl)methyl)isonicotinamide;
N,2-dimethyl-6-propionamido-N-(1-(6-(2,2,2-trifluoroethoxy)pyridin-3-yl)ethyl)isonicotinamide;
2-methyl-6-propionamido-N-(1-(6-(2,2,2-trifluoroethoxy)pyridin-2-yl)ethyl)isonicotinamide;
2-methyl-6-propionamido-N-(1-(6-(3,3,3-trifluoropropoxy)pyridin-3-yl)ethyl)isonicotinamide;
2-acetamido-N-(1-(5-methoxy-6-(2,2,2-trifluoroethoxy)pyridin-3-yl)ethyl)isonicotinamide;
N-(1-(5-methoxy-6-(2,2,2-trifluoroethoxy)pyridin-3-yl)ethyl)-2-propionamidoisonicotinamide;
2-(cyclopropanecarboxamido)-N-(1-(5-methoxy-6-(2,2,2-trifluoroethoxy)pyridin-3-yl)ethyl)isonicotinamide;
N-(1-(5-methoxy-6-(2,2,2-trifluoroethoxy)pyridin-3-yl)ethyl)-2-methyl-6-propionamidoisonicotinamide;
2-propionamido-N-(1-(6-((2,2,2-trifluoroethyl)thio)pyridin-3-yl)ethyl)isonicotinamide;
2-methyl-6-propionamido-N-(1-(6-((2,2,2-trifluoroethyl)thio)pyridin-3-yl)ethyl)isonicotinamide;
2-(cyclopropanecarboxamido)-N-((2-methoxy-6-(2,2,2-trifluoroethoxy)pyridin-3-yl)methyl)isonicotinamide;
2-acetamido-N-((2-methoxy-6-(2,2,2-trifluoroethoxy)pyridin-3-yl)methyl)isonicotinamide;
N-((2-methoxy-6-(2,2,2-trifluoroethoxy)pyridin-3-yl)methyl)-2-propionamidoisonicotinamide;
N-((2-methoxy-6-(2,2,2-trifluoroethoxy)pyridin-3-yl)methyl)-2-methyl-6-propionamidoisonicotinamide;
2-propionamido-N-((6-(2,2,2-trifluoroethoxy)pyridin-3-yl)methyl)isonicotinamide;
2-(cyclopropanecarboxamido)-N-((6-(2,2,2-trifluoroethoxy)pyridin-3-yl)methyl)isonicotinamide;
2-methyl-6-propionamido-N-((6-(2,2,2-trifluoroethoxy)pyridin-3-yl)methyl)isonicotinamide;
2-ethyl-6-propionamido-N-(1-(6-(2,2,2-trifluoroethoxy)pyridin-3-yl)ethyl)isonicotinamide;

2-(cyclopropanecarboxamido)-N-methyl-N-(1-(6-(2,2,2-trifluoroethoxy)pyridin-3-yl)ethyl)isonicotinamide;
(R)-2-methyl-6-propionamido-N-(1-(5-(2,2,2-trifluoroethoxy)pyridin-2-yl)ethyl)isonicotinamide;
2-(cyclopropanecarboxamido)-N-(1-(6-((2,2,2-trifluoroethyl)amino)pyridin-3-yl)ethyl)isonicotinamide;
2-methyl-6-propionamido-N-(1-(6-((2,2,2-trifluoroethyl)amino)pyridin-3-yl)ethyl)isonicotinamide;
N-ethyl-2-methyl-6-propionamido-N-(1-(6-(2,2,2-trifluoroethoxy)pyridin-3-yl)ethyl)isonicotinamide;
N4-(1-(5-chloro-6-(2,2,2-trifluoroethoxy)pyridin-3-yl)ethyl)-N2-ethylpyridine-2,4-dicarboxamide;
2-propionamido-N-((2-(2,2,2-trifluoroethoxy)pyridin-4-yl)methyl)isonicotinamide;
2-(cyclopropanecarboxamido)-N-((2-(2,2,2-trifluoroethoxy)pyridin-4-yl)methyl)isonicotinamide;
2-methyl-6-propionamido-N-(1-(2-(2,2,2-trifluoroethoxy)pyridin-4-yl)ethyl)isonicotinamide;
2-methyl-6-propionamido-N-((4-(2,2,2-trifluoroethoxy)pyridin-2-yl)methyl)isonicotinamide;
2-acetamido-N-((2-methyl-6-(2,2,2-trifluoroethoxy)pyridin-3-yl)methyl)isonicotinamide;
N-((2-methyl-6-(2,2,2-trifluoroethoxy)pyridin-3-yl)methyl)-2-propionamidoisonicotinamide;
2-(cyclopropanecarboxamido)-N-((2-methyl-6-(2,2,2-trifluoroethoxy)pyridin-3-yl)methyl)isonicotinamide;
2-methyl-N-((2-methyl-6-(2,2,2-trifluoroethoxy)pyridin-3-yl)methyl)-6-propionamidoisonicotinamide;
2-isobutyramido-N-((6-(2,2,2-trifluoroethoxy)pyridin-3-yl)methyl)isonicotinamide;
2-isobutyramido-N-((2-(2,2,2-trifluoroethoxy)pyridin-4-yl)methyl)isonicotinamide;
2-isobutyramido-N-((2-methoxy-6-(2,2,2-trifluoroethoxy)pyridin-3-yl)methyl)isonicotinamide;
N-((5-fluoro-6-(2,2,2-trifluoroethoxy)pyridin-3-yl)methyl)-2-propionamidoisonicotinamide;
2-(cyclopropanecarboxamido)-N-((5-fluoro-6-(2,2,2-trifluoroethoxy)pyridin-3-yl)methyl)isonicotinamide;
N-((5-fluoro-6-(2,2,2-trifluoroethoxy)pyridin-3-yl)methyl)-2-isobutyramidoisonicotinamide;
N-((5-fluoro-6-(2,2,2-trifluoroethoxy)pyridin-3-yl)methyl)-2-methyl-6-propionamidoisonicotinamide;
N-((4-methyl-6-(2,2,2-trifluoroethoxy)pyridin-3-yl)methyl)-2-propionamidoisonicotinamide;
2-(cyclopropanecarboxamido)-N-((4-methyl-6-(2,2,2-trifluoroethoxy)pyridin-3-yl)methyl)isonicotinamide;
2-isobutyramido-N-((4-methyl-6-(2,2,2-trifluoroethoxy)pyridin-3-yl)methyl)isonicotinamide;
2-methyl-N-((4-methyl-6-(2,2,2-trifluoroethoxy)pyridin-3-yl)methyl)-6-propionamidoisonicotinamide;
N-((2-methoxy-6-(2,2,2-trifluoroethoxy)pyridin-3-yl)methyl)-6-methyl-2-propionamidopyrimidine-4-carboxamide;
2-(cyclopropanecarboxamido)-N-((2-methoxy-6-(2,2,2-trifluoroethoxy)pyridin-3-yl)methyl)-6-methylpyrimidine-4-carboxamide;
2-(cyclopropanecarboxamido)-6-methyl-N-(1-(6-(3,3,3-trifluoropropoxy)pyridin-3-yl)ethyl)pyrimidine-4-carboxamide;
2-propionamido-N-(1-(6-(3,3,3-trifluoropropoxy)pyridin-3-yl)ethyl)pyrimidine-4-carboxamide;
2-(cyclopropanecarboxamido)-N-(1-(6-(3,3,3-trifluoropropoxy)pyridin-3-yl)ethyl)pyrimidine-4-carboxamide;
2-propionamido-N-(1-(6-(2,2,2-trifluoroethoxy)pyridin-3-yl)propyl)isonicotinamide;
2-isobutyramido-N-(1-(6-(3,3,3-trifluoropropoxy)pyridin-3-yl)ethyl)isonicotinamide;
2-isobutyramido-N-((2-methyl-6-(2,2,2-trifluoroethoxy)pyridin-3-yl)methyl)isonicotinamide;
2-isobutyramido-N-(1-(2-(2,2,2-trifluoroethoxy)pyridin-4-yl)ethyl)isonicotinamide;
2-isobutyramido-N-(1-(6-(2,2,2-trifluoroethoxy)pyridin-2-yl)ethyl)isonicotinamide;
2-propionamido-N-((6-(3,3,3-trifluoropropoxy)pyridin-3-yl)methyl)isonicotinamide;
2-(cyclopropanecarboxamido)-N-((6-(3,3,3-trifluoropropoxy)pyridin-3-yl)methyl)isonicotinamide;
2-methyl-6-propionamido-N-((6-(3,3,3-trifluoropropoxy)pyridin-3-yl)methyl)isonicotinamide;
N-(1-(5-methoxy-6-(2,2,2-trifluoroethoxy)pyridin-3-yl)ethyl)-6-methyl-2-propionamidopyrimidine-4-carboxamide;
2-(cyclopropanecarboxamido)-N-(1-(5-methoxy-6-(2,2,2-trifluoroethoxy)pyridin-3-yl)ethyl)-6-methylpyrimidine-4-carboxamide;
2-(cyclopropanecarboxamido)-N-(1-(6-(2-(2,2,2-trifluoroethoxy)ethoxy)pyridin-3-yl)ethyl)isonicotinamide;
2-isobutyramido-N-(1-(6-(2-(2,2,2-trifluoroethoxy)ethoxy)pyridin-3-yl)ethyl)isonicotinamide;
2-acetamido-N-((4-methyl-6-(2,2,2-trifluoroethoxy)pyridin-3-yl)methyl)isonicotinamide;
2-acetamido-6-methyl-N-(1-(6-(3,3,3-trifluoropropoxy)pyridin-3-yl)ethyl)pyrimidine-4-carboxamide;
2-isobutyramido-N-(1-(6-(3,3,3-trifluoropropoxy)pyridin-3-yl)ethyl)pyrimidine-4-carboxamide;
2-(cyclopropanecarboxamido)-N-(1-(6-(2,2-difluoroethoxy)pyridin-3-yl)ethyl)isonicotinamide;
N-(1-(6-(2,2-difluoroethoxy)pyridin-3-yl)ethyl)-2-methyl-6-propionamidoisonicotinamide;
2-acetamido-N-((6-(3,3,3-trifluoropropoxy)pyridin-3-yl)methyl)isonicotinamide;
N-((5-fluoro-6-(2,2,2-trifluoroethoxy)pyridin-3-yl)methyl)-6-methyl-2-propionamidopyrimidine-4-carboxamide;
2-(cyclopropanecarboxamido)-N-((5-fluoro-6-(2,2,2-trifluoroethoxy)pyridin-3-yl)methyl)-6-methylpyrimidine-4-carboxamide;
2-isobutyramido-6-methyl-N-(1-(6-(2,2,2-trifluoroethoxy)pyridin-3-yl)ethyl)pyrimidine-4-carboxamide;
2-(cyclopropanecarboxamido)-N-(1-(5-fluoro-6-(2,2,2-trifluoroethoxy)pyridin-3-yl)ethyl)pyrimidine-4-carboxamide;
2-(cyclopropanecarboxamido)-N-(1-(5-fluoro-6-(2,2,2-trifluoroethoxy)pyridin-3-yl)ethyl)-6-methylpyrimidine-4-carboxamide;
2-(cyclobutanecarboxamido)-N-(1-(5-fluoro-6-(2,2,2-trifluoroethoxy)pyridin-3-yl)ethyl)-6-methylpyrimidine-4-carboxamide;
N-(1-(5-fluoro-6-(2,2,2-trifluoroethoxy)pyridin-3-yl)ethyl)-2-isobutyramidopyrimidine-4-carboxamide;
N-(1-(5-chloro-6-(2,2,2-trifluoroethoxy)pyridin-3-yl)ethyl)-2-propionamidopyrimidine-4-carboxamide;
N-(1-(5-chloro-6-(2,2,2-trifluoroethoxy)pyridin-3-yl)ethyl)-2-(cyclopropanecarboxamido)pyrimidine-4-carboxamide;
N-(1-(5-chloro-6-(2,2,2-trifluoroethoxy)pyridin-3-yl)ethyl)-2-isobutyramidopyrimidine-4-carboxamide;
N-(1-(5-chloro-6-(2,2,2-trifluoroethoxy)pyridin-3-yl)ethyl)-2-(cyclobutanecarboxamido)pyrimidine-4-carboxamide;

N-(1-(5-chloro-6-(2,2,2-trifluoroethoxy)pyridin-3-yl)ethyl)-6-methyl-2-propionamidopyrimidine-4-carboxamide;
N-(1-(5-chloro-6-(2,2,2-trifluoroethoxy)pyridin-3-yl)ethyl)-2-(cyclopropanecarboxamido)-6-methylpyrimidine-4-carboxamide;
N-(1-(5-chloro-6-(2,2,2-trifluoroethoxy)pyridin-3-yl)ethyl)-2-isobutyramido-6-methylpyrimidine-4-carboxamide;
N-(1-(5-chloro-6-(2,2,2-trifluoroethoxy)pyridin-3-yl)ethyl)-2-(cyclobutanecarboxamido)-6-methylpyrimidine-4-carboxamide;
2-isobutyramido-N-(1-(5-methoxy-6-(2,2,2-trifluoroethoxy)pyridin-3-yl)ethyl)-6-methylpyrimidine-4-carboxamide;
2-isobutyramido-N-(1-(6-(2,2,2-trifluoroethoxy)pyridin-3-yl)propyl)isonicotinamide;
N-(1-(5-fluoro-6-(2,2,2-trifluoroethoxy)pyridin-3-yl)ethyl)-2-isobutyramidoisonicotinamide;
2-isobutyramido-N-(1-(5-methoxy-6-(2,2,2-trifluoroethoxy)pyridin-3-yl)ethyl)isonicotinamide;
2-isobutyramido-N-((6-(3,3,3-trifluoropropoxy)pyridin-3-yl)methyl)isonicotinamide;
N-(1-(5-methyl-6-(2,2,2-trifluoroethoxy)pyridin-3-yl)ethyl)-2-propionamidopyrimidine-4-carboxamide;
2-(cyclopropanecarboxamido)-N-(1-(5-methyl-6-(2,2,2-trifluoroethoxy)pyridin-3-yl)ethyl)pyrimidine-4-carboxamide;
2-isobutyramido-N-(1-(5-methyl-6-(2,2,2-trifluoroethoxy)pyridin-3-yl)ethyl)pyrimidine-4-carboxamide;
2-(cyclobutanecarboxamido)-N-(1-(5-methyl-6-(2,2,2-trifluoroethoxy)pyridin-3-yl)ethyl)pyrimidine-4-carboxamide;
6-methyl-N-(1-(5-methyl-6-(2,2,2-trifluoroethoxy)pyridin-3-yl)ethyl)-2-propionamidopyrimidine-4-carboxamide;
2-(cyclopropanecarboxamido)-6-methyl-N-(1-(5-methyl-6-(2,2,2-trifluoroethoxy)pyridin-3-yl)ethyl)pyrimidine-4-carboxamide;
2-isobutyramido-6-methyl-N-(1-(5-methyl-6-(2,2,2-trifluoroethoxy)pyridin-3-yl)ethyl)pyrimidine-4-carboxamide;
2-(cyclobutanecarboxamido)-6-methyl-N-(1-(5-methyl-6-(2,2,2-trifluoroethoxy)pyridin-3-yl)ethyl)pyrimidine-4-carboxamide;
3-isobutyramido-N-(1-(6-(2,2,2-trifluoroethoxy)pyridin-3-yl)ethyl)picolinamide;
2-acetamido-N-(1-(5-chloro-6-(2,2,2-trifluoroethoxy)pyridin-3-yl)ethyl)pyrimidine-4-carboxamide;
2-acetamido-N-(1-(5-chloro-6-(2,2,2-trifluoroethoxy)pyridin-3-yl)ethyl)-6-methylpyrimidine-4-carboxamide;
2-acetamido-N-(1-(5-methyl-6-(2,2,2-trifluoroethoxy)pyridin-3-yl)ethyl)pyrimidine-4-carboxamide;
2-acetamido-6-methyl-N-(1-(5-methyl-6-(2,2,2-trifluoroethoxy)pyridin-3-yl)ethyl)pyrimidine-4-carboxamide;
2-acetamido-6-methyl-N-(1-(6-(2,2,2-trifluoroethoxy)pyridin-3-yl)propyl)isonicotinamide;
2-acetamido-6-methyl-N-((6-(2,2,2-trifluoroethoxy)pyridin-3-yl)methyl)isonicotinamide;
2-acetamido-N,6-dimethyl-N-((6-(2,2,2-trifluoroethoxy)pyridin-3-yl)methyl)isonicotinamide;
2-acetamido-N-(1-(5-fluoro-6-(2,2,2-trifluoroethoxy)pyridin-3-yl)ethyl)-6-methylisonicotinamide;
2-acetamido-N-((5-fluoro-6-(2,2,2-trifluoroethoxy)pyridin-3-yl)methyl)-6-methylisonicotinamide;
2-acetamido-N-((2-methoxy-6-(2,2,2-trifluoroethoxy)pyridin-3-yl)methyl)-6-methylisonicotinamide;
2-acetamido-6-methyl-N-((2-methyl-6-(2,2,2-trifluoroethoxy)pyridin-3-yl)methyl)isonicotinamide;
2-acetamido-6-methyl-N-((4-methyl-6-(2,2,2-trifluoroethoxy)pyridin-3-yl)methyl)isonicotinamide;
2-acetamido-6-methyl-N-(1-(6-(3,3,3-trifluoropropoxy)pyridin-3-yl)ethyl)isonicotinamide;
2-acetamido-6-methyl-N-((6-(3,3,3-trifluoropropoxy)pyridin-3-yl)methyl)isonicotinamide;
2-acetamido-6-methyl-N-((2-(2,2,2-trifluoroethoxy)pyridin-4-yl)methyl)isonicotinamide;
2-acetamido-6-methyl-N-(1-(6-(2,2,2-trifluoroethoxy)pyridin-2-yl)ethyl)isonicotinamide;
6-methyl-2-propionamido-N-((6-(2,2,2-trifluoroethoxy)pyridin-3-yl)methyl)pyrimidine-4-carboxamide;
2-(cyclopropanecarboxamido)-6-methyl-N-((6-(2,2,2-trifluoroethoxy)pyridin-3-yl)methyl)pyrimidine-4-carboxamide;
2-isobutyramido-N-(1-(6-(2,2,2-trifluoroethoxy)pyridin-3-yl)ethyl)pyrimidine-4-carboxamide;
2-acetamido-N-(1-(5-fluoro-6-(2,2,2-trifluoroethoxy)pyridin-3-yl)ethyl)-N,6-dimethylisonicotinamide;
N-(1-(5-fluoro-6-(2,2,2-trifluoroethoxy)pyridin-3-yl)ethyl)-N,2-dimethyl-6-propionamidoisonicotinamide;
6-propionamido-N-(1-(6-(2,2,2-trifluoroethoxy)pyridin-3-yl)ethyl)picolinamide;
6-(cyclopropanecarboxamido)-N-(1-(6-(2,2,2-trifluoroethoxy)pyridin-3-yl)ethyl)picolinamide;
6-isobutyramido-N-(1-(6-(2,2,2-trifluoroethoxy)pyridin-3-yl)ethyl)picolinamide;
N-(2-methoxy-1-(6-(2,2,2-trifluoroethoxy)pyridin-3-yl)ethyl)-2-propionamidoisonicotinamide;
2-(cyclopropanecarboxamido)-N-(2-methoxy-1-(6-(2,2,2-trifluoroethoxy)pyridin-3-yl)ethyl)isonicotinamide;
2-acetamido-N-(2-methoxy-1-(6-(2,2,2-trifluoroethoxy)pyridin-3-yl)ethyl)-6-methylisonicotinamide;
2-acetamido-N-((5-ethoxy-6-(2,2,2-trifluoroethoxy)pyridin-3-yl)methyl)isonicotinamide;
N-((5-ethoxy-6-(2,2,2-trifluoroethoxy)pyridin-3-yl)methyl)-2-propionamidoisonicotinamide;
2-(cyclopropanecarboxamido)-N-((5-ethoxy-6-(2,2,2-trifluoroethoxy)pyridin-3-yl)methyl)isonicotinamide;
N-((5-ethoxy-6-(2,2,2-trifluoroethoxy)pyridin-3-yl)methyl)-2-methyl-6-propionamidoisonicotinamide;
N-((5-ethoxy-6-(2,2,2-trifluoroethoxy)pyridin-3-yl)methyl)-2-isobutyramidoisonicotinamide;
2-acetamido-N-((5-ethoxy-6-(2,2,2-trifluoroethoxy)pyridin-3-yl)methyl)-6-methylisonicotinamide;
2-butyramido-N-((6-(2,2,2-trifluoroethoxy)pyridin-3-yl)methyl)isonicotinamide;
2-butyramido-N-(1-(5-fluoro-6-(2,2,2-trifluoroethoxy)pyridin-3-yl)ethyl)isonicotinamide;
2-butyramido-N-((5-fluoro-6-(2,2,2-trifluoroethoxy)pyridin-3-yl)methyl)isonicotinamide;
2-butyramido-N-(1-(6-(3,3,3-trifluoropropoxy)pyridin-3-yl)ethyl)isonicotinamide;
2-acetamido-N-((5-methoxy-6-(2,2,2-trifluoroethoxy)pyridin-3-yl)methyl)isonicotinamide;
N-((5-methoxy-6-(2,2,2-trifluoroethoxy)pyridin-3-yl)methyl)-2-methyl-6-propionamidoisonicotinamide;
2-isobutyramido-N-((5-methoxy-6-(2,2,2-trifluoroethoxy)pyridin-3-yl)methyl)isonicotinamide;
2-acetamido-N-((5-methoxy-6-(2,2,2-trifluoroethoxy)pyridin-3-yl)methyl)-6-methylisonicotinamide;
2-butyramido-N-((5-methoxy-6-(2,2,2-trifluoroethoxy)pyridin-3-yl)methyl)isonicotinamide;
(R)-2-propionamido-N-(1-(3-(trifluoromethyl)phenyl)ethyl)pyrimidine-4-carboxamide;

(R)-2-isobutyramido-N-(1-(3-(trifluoromethyl)phenyl)ethyl)pyrimidine-4-carboxamide;
(R)-2-(cyclobutanecarboxamido)-N-(1-(3-(trifluoromethyl)phenyl)ethyl)pyrimidine-4-carboxamide;
2-acetamido-N-(3-(trifluoromethoxy)benzyl)pyrimidine-4-carboxamide;
2-propionamido-N-(3-(trifluoromethoxy)benzyl)pyrimidine-4-carboxamide;
2-isobutyramido-N-(3-(trifluoromethoxy)benzyl)pyrimidine-4-carboxamide;
2-(cyclobutanecarboxamido)-N-(3-(trifluoromethoxy)benzyl)pyrimidine-4-carboxamide;
2-acetamido-N-((2-morpholino-6-(2,2,2-trifluoroethoxy)pyridin-3-yl)methyl)isonicotinamide;
2-isobutyramido-N-((2-morpholino-6-(2,2,2-trifluoroethoxy)pyridin-3-yl)methyl)isonicotinamide;
2-acetamido-6-methyl-N-((2-morpholino-6-(2,2,2-trifluoroethoxy)pyridin-3-yl)methyl)isonicotinamide;
2-methyl-N-((2-morpholino-6-(2,2,2-trifluoroethoxy)pyridin-3-yl)methyl)-6-propionamidoisonicotinamide;
N-(1-(5-ethoxy-6-(2,2,2-trifluoroethoxy)pyridin-3-yl)ethyl)-2-methyl-6-propionamidoisonicotinamide;
2-acetamido-N-((1-(5-ethoxy-6-(2,2,2-trifluoroethoxy)pyridin-3-yl)ethyl)-6-methylisonicotinamide;
2-acetamido-N-((2-methoxy-6-(2,2,2-trifluoroethoxy)pyridin-3-yl)methyl)-N-methylisonicotinamide;
N-((2-methoxy-6-(2,2,2-trifluoroethoxy)pyridin-3-yl)methyl)-N-methyl-2-propionamidoisonicotinamide;
2-(cyclopropanecarboxamido)-N-((2-methoxy-6-(2,2,2-trifluoroethoxy)pyridin-3-yl)methyl)-N-methylisonicotinamide;
2-acetamido-N-((2-methoxy-6-(2,2,2-trifluoroethoxy)pyridin-3-yl)methyl)-N,6-dimethylisonicotinamide;
N-((2-methoxy-6-(2,2,2-trifluoroethoxy)pyridin-3-yl)methyl)-N,2-dimethyl-6-propionamidoisonicotinamide;
N-((2-(4-methylpiperazin-1-yl)-6-(2,2,2-trifluoroethoxy)pyridin-3-yl)methyl)-2-propionamidoisonicotinamide;
2-(cyclopropanecarboxamido)-N-((2-(4-methylpiperazin-1-yl)-6-(2,2,2-trifluoroethoxy)pyridin-3-yl)methyl)isonicotinamide;
2-isobutyramido-N-((2-(4-methylpiperazin-1-yl)-6-(2,2,2-trifluoroethoxy)pyridin-3-yl)methyl)isonicotinamide;
2-methyl-N-((2-(4-methylpiperazin-1-yl)-6-(2,2,2-trifluoroethoxy)pyridin-3-yl)methyl)-6-propionamidoisonicotinamide;
2-isobutyramido-N-((2-methoxy-6-(2,2,2-trifluoroethoxy)pyridin-3-yl)methyl)-N-methylisonicotinamide;
2-acetamido-N-(1-(3-(trifluoromethoxy)phenyl)ethyl)pyrimidine-4-carboxamide;
2-propionamido-N-(1-(3-(trifluoromethoxy)phenyl)ethyl)pyrimidine-4-carboxamide;
2-(cyclopropanecarboxamido)-N-(1-(3-(trifluoromethoxy)phenyl)ethyl)pyrimidine-4-carboxamide;
2-isobutyramido-N-(1-(3-(trifluoromethoxy)phenyl)ethyl)pyrimidine-4-carboxamide;
2-(cyclobutanecarboxamido)-N-(1-(3-(trifluoromethoxy)phenyl)ethyl)pyrimidine-4-carboxamide;
2-acetamido-N-((2-(piperidin-1-yl)-6-(2,2,2-trifluoroethoxy)pyridin-3-yl)methyl)isonicotinamide;
N-((2-(piperidin-1-yl)-6-(2,2,2-trifluoroethoxy)pyridin-3-yl)methyl)-2-propionamidoisonicotinamide;
2-(cyclopropanecarboxamido)-N-((2-(piperidin-1-yl)-6-(2,2,2-trifluoroethoxy)pyridin-3-yl)methyl)isonicotinamide;
2-isobutyramido-N-((2-(piperidin-1-yl)-6-(2,2,2-trifluoroethoxy)pyridin-3-yl)methyl)isonicotinamide;
2-methyl-N-((2-(piperidin-1-yl)-6-(2,2,2-trifluoroethoxy)pyridin-3-yl)methyl)-6-propionamidoisonicotinamide;
2-acetamido-6-methyl-N-((2-(piperidin-1-yl)-6-(2,2,2-trifluoroethoxy)pyridin-3-yl)methyl)isonicotinamide;
2-butyramido-N-((2-(piperidin-1-yl)-6-(2,2,2-trifluoroethoxy)pyridin-3-yl)methyl)isonicotinamide;
2-acetamido-N-((5-fluoro-2-methyl-6-(2,2,2-trifluoroethoxy)pyridin-3-yl)methyl)isonicotinamide;
N-((5-fluoro-2-methyl-6-(2,2,2-trifluoroethoxy)pyridin-3-yl)methyl)-2-propionamidoisonicotinamide;
2-(cyclopropanecarboxamido)-N-((5-fluoro-2-methyl-6-(2,2,2-trifluoroethoxy)pyridin-3-yl)methyl)isonicotinamide;
2-acetamido-N-((5-fluoro-2-methyl-6-(2,2,2-trifluoroethoxy)pyridin-3-yl)methyl)-6-methylisonicotinamide;
N-((5-fluoro-2-methyl-6-(2,2,2-trifluoroethoxy)pyridin-3-yl)methyl)-2-methyl-6-propionamidoisonicotinamide;
N-((5-fluoro-2-methyl-6-(2,2,2-trifluoroethoxy)pyridin-3-yl)methyl)-2-isobutyramidoisonicotinamide;
(R)-2-acetamido-N-((6-((1,1,1-trifluoropropan-2-yl)oxy)pyridin-3-yl)methyl)isonicotinamide;
(R)-2-propionamido-N-((6-((1,1,1-trifluoropropan-2-yl)oxy)pyridin-3-yl)methyl)isonicotinamide;
(R)-2-(cyclopropanecarboxamido)-N-((6-((1,1,1-trifluoropropan-2-yl)oxy)pyridin-3-yl)methyl)isonicotinamide;
(R)-2-methyl-6-propionamido-N-((6-((1,1,1-trifluoropropan-2-yl)oxy)pyridin-3-yl)methyl)isonicotinamide;
(R)-2-isobutyramido-N-((6-((1,1,1-trifluoropropan-2-yl)oxy)pyridin-3-yl)methyl)isonicotinamide;
(R)-2-acetamido-6-methyl-N-((6-((1,1,1-trifluoropropan-2-yl)oxy)pyridin-3-yl)methyl)isonicotinamide;
(R)-2-butyramido-N-((6-((1,1,1-trifluoropropan-2-yl)oxy)pyridin-3-yl)methyl)isonicotinamide;
2-(2-hydroxy-2-methylpropanamido)-N-((2-methoxy-6-(2,2,2-trifluoroethoxy)pyridin-3-yl)methyl)-6-methylisonicotinamide;
2-(2-hydroxy-2-methylpropanamido)-6-methyl-N-(1-(5-methyl-6-(2,2,2-trifluoroethoxy)pyridin-3-yl)ethyl)isonicotinamide;
N-(1-(5-chloro-6-(2,2,2-trifluoroethoxy)pyridin-3-yl)ethyl)-2-(2-hydroxy-2-methylpropanamido)-6-methylisonicotinamide;
2-(2-hydroxy-2-methylpropanamido)-6-methyl-N-((2-methyl-6-(2,2,2-trifluoroethoxy)pyridin-3-yl)methyl)isonicotinamide;
2-(2-hydroxy-2-methylpropanamido)-6-methyl-N-((6-(3,3,3-trifluoropropoxy)pyridin-3-yl)methyl)isonicotinamide;
N-((5-fluoro-2-methoxy-6-(2,2,2-trifluoroethoxy)pyridin-3-yl)methyl)-2-propionamidoisonicotinamide;
N-((5-fluoro-2-methoxy-6-(2,2,2-trifluoroethoxy)pyridin-3-yl)methyl)-2-methyl-6-propionamidoisonicotinamide;
N-((5-fluoro-2-methoxy-6-(2,2,2-trifluoroethoxy)pyridin-3-yl)methyl)-2-isobutyramidoisonicotinamide;
2-acetamido-N-(1-(5-methoxy-6-(2,2,2-trifluoroethoxy)pyridin-3-yl)ethyl)-6-methylisonicotinamide;
2-butyramido-N-(1-(5-methoxy-6-(2,2,2-trifluoroethoxy)pyridin-3-yl)ethyl)isonicotinamide;
2-acetamido-N-((2-ethoxy-6-(2,2,2-trifluoroethoxy)pyridin-3-yl)methyl)isonicotinamide;
N-((2-ethoxy-6-(2,2,2-trifluoroethoxy)pyridin-3-yl)methyl)-2-propionamidoisonicotinamide;
N-((2-ethoxy-6-(2,2,2-trifluoroethoxy)pyridin-3-yl)methyl)-2-methyl-6-propionamidoisonicotinamide;

N-((2-ethoxy-6-(2,2,2-trifluoroethoxy)pyridin-3-yl)methyl)-2-isobutyramidoisonicotinamide;
2-acetamido-N-((2-ethoxy-6-(2,2,2-trifluoroethoxy)pyridin-3-yl)methyl)-6-methylisonicotinamide;
2-butyramido-N-((2-ethoxy-6-(2,2,2-trifluoroethoxy)pyridin-3-yl)methyl)isonicotinamide;
2-acetamido-N-((2-ethoxy-6-(2,2,2-trifluoroethoxy)pyridin-3-yl)methyl)-6-methylpyrimidine-4-carboxamide;
6-methyl-2-propionamido-N-(1-(6-(2,2,2-trifluoroethoxy)pyridin-3-yl)propyl)pyrimidine-4-carboxamide;
2-(cyclopropanecarboxamido)-6-methyl-N-(1-(6-(2,2,2-trifluoroethoxy)pyridin-3-yl)propyl)pyrimidine-4-carboxamide;
2-isobutyramido-6-methyl-N-((6-(2,2,2-trifluoroethoxy)pyridin-3-yl)methyl)pyrimidine-4-carboxamide;
2-acetamido-6-methyl-N-((2-methyl-6-(2,2,2-trifluoroethoxy)pyridin-3-yl)methyl)pyrimidine-4-carboxamide;
6-methyl-N-((2-methyl-6-(2,2,2-trifluoroethoxy)pyridin-3-yl)methyl)-2-propionamidopyrimidine-4-carboxamide;
2-(cyclopropanecarboxamido)-6-methyl-N-((2-methyl-6-(2,2,2-trifluoroethoxy)pyridin-3-yl)methyl)pyrimidine-4-carboxamide;
2-isobutyramido-6-methyl-N-((2-methyl-6-(2,2,2-trifluoroethoxy)pyridin-3-yl)methyl)pyrimidine-4-carboxamide;
6-methyl-2-propionamido-N-(3-(trifluoromethoxy)benzyl)pyrimidine-4-carboxamide;
2-(cyclopropanecarboxamido)-6-methyl-N-(3-(trifluoromethoxy)benzyl)pyrimidine-4-carboxamide;
2-isobutyramido-6-methyl-N-(3-(trifluoromethoxy)benzyl)pyrimidine-4-carboxamide;
(R)-2-(cyclopropanecarboxamido)-6-methyl-N-(1-(3-(trifluoromethyl)phenyl)ethyl)pyrimidine-4-carboxamide;
2-acetamido-6-methyl-N-((4-methyl-6-(2,2,2-trifluoroethoxy)pyridin-3-yl)methyl)pyrimidine-4-carboxamide;
6-methyl-N-((4-methyl-6-(2,2,2-trifluoroethoxy)pyridin-3-yl)methyl)-2-propionamidopyrimidine-4-carboxamide;
2-(cyclopropanecarboxamido)-6-methyl-N-((4-methyl-6-(2,2,2-trifluoroethoxy)pyridin-3-yl)methyl)pyrimidine-4-carboxamide;
2-isobutyramido-6-methyl-N-((4-methyl-6-(2,2,2-trifluoroethoxy)pyridin-3-yl)methyl)pyrimidine-4-carboxamide;
2-(cyclopropanecarboxamido)-6-methyl-N-(3-(trifluoromethyl)benzyl)pyrimidine-4-carboxamide;
2-isobutyramido-6-methyl-N-(3-(trifluoromethyl)benzyl)pyrimidine-4-carboxamide;
6-methyl-2-propionamido-N-(1-(4-(2,2,2-trifluoroethoxy)phenyl)ethyl)pyrimidine-4-carboxamide;
2-(cyclopropanecarboxamido)-6-methyl-N-(1-(4-(2,2,2-trifluoroethoxy)phenyl)ethyl)pyrimidine-4-carboxamide;
2-isobutyramido-6-methyl-N-(1-(4-(2,2,2-trifluoroethoxy)phenyl)ethyl)pyrimidine-4-carboxamide;
N-((2-ethoxy-6-(2,2,2-trifluoroethoxy)pyridin-3-yl)methyl)-6-methyl-2-propionamidopyrimidine-4-carboxamide;
N-((2-ethoxy-6-(2,2,2-trifluoroethoxy)pyridin-3-yl)methyl)-2-isobutyramido-6-methylpyrimidine-4-carboxamide;
2-(cyclopropanecarboxamido)-N-((2-ethoxy-6-(2,2,2-trifluoroethoxy)pyridin-3-yl)methyl)-6-methylpyrimidine-4-carboxamide;
N-(1-(5-(hydroxymethyl)-6-(2,2,2-trifluoroethoxy)pyridin-3-yl)ethyl)-2-methyl-6-propionamidoisonicotinamide;
2-acetamido-6-methyl-N-((5-methyl-6-(2,2,2-trifluoroethoxy)pyridin-3-yl)methyl)pyrimidine-4-carboxamide;
6-methyl-N-((5-methyl-6-(2,2,2-trifluoroethoxy)pyridin-3-yl)methyl)-2-propionamidopyrimidine-4-carboxamide;
2-(cyclopropanecarboxamido)-6-methyl-N-((5-methyl-6-(2,2,2-trifluoroethoxy)pyridin-3-yl)methyl)pyrimidine-4-carboxamide;
2-isobutyramido-6-methyl-N-((5-methyl-6-(2,2,2-trifluoroethoxy)pyridin-3-yl)methyl)pyrimidine-4-carboxamide;
2-acetamido-N-((5-methyl-6-(2,2,2-trifluoroethoxy)pyridin-3-yl)methyl)isonicotinamide;
N-((5-methyl-6-(2,2,2-trifluoroethoxy)pyridin-3-yl)methyl)-2-propionamidoisonicotinamide;
2-(cyclopropanecarboxamido)-N-((5-methyl-6-(2,2,2-trifluoroethoxy)pyridin-3-yl)methyl)isonicotinamide;
2-isobutyramido-N-((5-methyl-6-(2,2,2-trifluoroethoxy)pyridin-3-yl)methyl)isonicotinamide;
2-acetamido-6-methyl-N-((5-methyl-6-(2,2,2-trifluoroethoxy)pyridin-3-yl)methyl)isonicotinamide;
2-methyl-N-((5-methyl-6-(2,2,2-trifluoroethoxy)pyridin-3-yl)methyl)-6-propionamidoisonicotinamide;
2-acetamido-N-((2-methoxy-6-(2,2,2-trifluoroethoxy)pyridin-3-yl)methyl)-6-methylpyrimidine-4-carboxamide;
2-isobutyramido-N-((2-methoxy-6-(2,2,2-trifluoroethoxy)pyridin-3-yl)methyl)-6-methylpyrimidine-4-carboxamide;
6-methyl-2-propionamido-N-(1-(3-(2,2,2-trifluoroethoxy)phenyl)ethyl)pyrimidine-4-carboxamide;
2-(cyclopropanecarboxamido)-6-methyl-N-(1-(3-(2,2,2-trifluoroethoxy)phenyl)ethyl)pyrimidine-4-carboxamide;
2-isobutyramido-6-methyl-N-(1-(3-(2,2,2-trifluoroethoxy)phenyl)ethyl)pyrimidine-4-carboxamide;
2-isobutyramido-N-(1-(5-methyl-6-(2,2,2-trifluoroethoxy)pyridin-3-yl)ethyl)isonicotinamide;
2-acetamido-6-methyl-N-(1-(5-methyl-6-(2,2,2-trifluoroethoxy)pyridin-3-yl)ethyl)isonicotinamide;
2-(cyclopropanecarboxamido)-N-(2-fluoro-5-(trifluoromethyl)benzyl)pyrimidine-4-carboxamide;
2-acetamido-N-(1-(3-(2,2,2-trifluoroethoxy)phenyl)ethyl)pyrimidine-4-carboxamide;
2-propionamido-N-(1-(3-(2,2,2-trifluoroethoxy)phenyl)ethyl)pyrimidine-4-carboxamide;
2-isobutyramido-N-(1-(3-(2,2,2-trifluoroethoxy)phenyl)ethyl)pyrimidine-4-carboxamide;
N-((5-chloro-6-(2,2,2-trifluoroethoxy)pyridin-3-yl)methyl)-6-methyl-2-propionamidopyrimidine-4-carboxamide;
N-((5-chloro-6-(2,2,2-trifluoroethoxy)pyridin-3-yl)methyl)-2-isobutyramido-6-methylpyrimidine-4-carboxamide;
N-((5-fluoro-2-methyl-6-(2,2,2-trifluoroethoxy)pyridin-3-yl)methyl)-2-isobutyramido-6-methylpyrimidine-4-carboxamide;
2-(cyclopropanecarboxamido)-6-methyl-N-(1-(6-(2,2,2-trifluoroethoxy)pyridin-2-yl)ethyl)pyrimidine-4-carboxamide;
2-isobutyramido-6-methyl-N-(1-(6-(2,2,2-trifluoroethoxy)pyridin-2-yl)ethyl)pyrimidine-4-carboxamide;

N-((5-fluoro-2-methyl-6-(2,2,2-trifluoroethoxy)pyridin-3-yl)methyl)-2-(2-hydroxy-2-methylpropanamido)-6-methylisonicotinamide;
2-(cyclopropanecarboxamido)-N-((5-fluoro-2-methyl-6-(2,2,2-trifluoroethoxy)pyridin-3-yl)methyl)-6-methylpyrimidine-4-carboxamide;
2-acetamido-N,6-dimethyl-N-(1-(5-methyl-6-(2,2,2-trifluoroethoxy)pyridin-3-yl)ethyl)isonicotinamide;
2-acetamido-N-methyl-N-(1-(5-methyl-6-(2,2,2-trifluoroethoxy)pyridin-3-yl)ethyl)isonicotinamide;
N-methyl-N-(1-(5-methyl-6-(2,2,2-trifluoroethoxy)pyridin-3-yl)ethyl)-2-propionamidoisonicotinamide;
2-acetamido-N,6-dimethyl-N-((5-methyl-6-(2,2,2-trifluoroethoxy)pyridin-3-yl)methyl)isonicotinamide;
2-acetamido-N-methyl-N-((5-methyl-6-(2,2,2-trifluoroethoxy)pyridin-3-yl)methyl)isonicotinamide;
N-methyl-N-((5-methyl-6-(2,2,2-trifluoroethoxy)pyridin-3-yl)methyl)-2-propionamidoisonicotinamide;
2-(cyclopropanecarboxamido)-N-((6-(2,2,2-trifluoroethoxy)pyridin-3-yl)methyl)pyrimidine-4-carboxamide;
2-isobutyramido-N-((6-(2,2,2-trifluoroethoxy)pyridin-3-yl)methyl)pyrimidine-4-carboxamide;
2-acetamido-N-(1-(5-methoxy-6-(2,2,2-trifluoroethoxy)pyridin-3-yl)ethyl)pyrimidine-4-carboxamide;
2-(cyclopropanecarboxamido)-N-(1-(5-methoxy-6-(2,2,2-trifluoroethoxy)pyridin-3-yl)ethyl)pyrimidine-4-carboxamide;
2-isobutyramido-N-(1-(5-methoxy-6-(2,2,2-trifluoroethoxy)pyridin-3-yl)ethyl)pyrimidine-4-carboxamide;
2-(cyclopropanecarboxamido)-N-((5-fluoro-6-(2,2,2-trifluoroethoxy)pyridin-3-yl)methyl)pyrimidine-4-carboxamide;
2-(cyclopropanecarboxamido)-N-((4-methyl-6-(2,2,2-trifluoroethoxy)pyridin-3-yl)methyl)pyrimidine-4-carboxamide;
2-(cyclopropanecarboxamido)-N-(3-(trifluoromethyl)benzyl)pyrimidine-4-carboxamide;
2-(cyclopropanecarboxamido)-N-(1-(4-(2,2,2-trifluoroethoxy)phenyl)ethyl)pyrimidine-4-carboxamide;
2-isobutyramido-N-(1-(4-(2,2,2-trifluoroethoxy)phenyl)ethyl)pyrimidine-4-carboxamide;
2-(cyclopropanecarboxamido)-N-((2-methyl-6-(2,2,2-trifluoroethoxy)pyridin-3-yl)methyl)pyrimidine-4-carboxamide;
N-((5-chloro-6-(2,2,2-trifluoroethoxy)pyridin-3-yl)methyl)-2-(2-hydroxy-2-methylpropanamido)-6-methylisonicotinamide;
2-acetamido-N-((5-chloro-6-(2,2,2-trifluoroethoxy)pyridin-3-yl)methyl)pyrimidine-4-carboxamide;
N-((5-chloro-6-(2,2,2-trifluoroethoxy)pyridin-3-yl)methyl)-2-propionamidopyrimidine-4-carboxamide;
N-((5-chloro-6-(2,2,2-trifluoroethoxy)pyridin-3-yl)methyl)-2-(cyclopropanecarboxamido)pyrimidine-4-carboxamide;
N-((5-chloro-6-(2,2,2-trifluoroethoxy)pyridin-3-yl)methyl)-2-isobutyramidopyrimidine-4-carboxamide;
2-(cyclopropanecarboxamido)-N-(1-(6-(2,2,2-trifluoroethoxy)pyridin-3-yl)propyl)pyrimidine-4-carboxamide;
N-((4-methyl-6-(2,2,2-trifluoroethoxy)pyridin-3-yl)methyl)-2-pivalamidoisonicotinamide;
6-methyl-2-propionamido-N-(1-(3-(trifluoromethoxy)phenyl)ethyl)pyrimidine-4-carboxamide;
2-(cyclopropanecarboxamido)-6-methyl-N-(1-(3-(trifluoromethoxy)phenyl)ethyl)pyrimidine-4-carboxamide;
2-isobutyramido-6-methyl-N-(1-(3-(trifluoromethoxy)phenyl)ethyl)pyrimidine-4-carboxamide;
2-isobutyramido-N-(1-(3-(trifluoromethoxy)phenyl)ethyl)isonicotinamide;
2-butyramido-N-(1-(3-(trifluoromethoxy)phenyl)ethyl)isonicotinamide;
2-acetamido-6-methyl-N-(1-(3-(trifluoromethoxy)phenyl)ethyl)isonicotinamide;
2-(2-hydroxy-2-methylpropanamido)-6-methyl-N-(1-(3-(trifluoromethoxy)phenyl)ethyl)isonicotinamide;
N-((2-ethoxy-6-(2,2,2-trifluoroethoxy)pyridin-3-yl)methyl)-2-(2-hydroxy-2-methylpropanamido)-6-methylisonicotinamide;
2-(cyclopropanecarboxamido)-6-methyl-N-((6-(3,3,3-trifluoropropoxy)pyridin-3-yl)methyl)pyrimidine-4-carboxamide;
2-isobutyramido-6-methyl-N-((6-(3,3,3-trifluoropropoxy)pyridin-3-yl)methyl)pyrimidine-4-carboxamide;
2-acetamido-6-methyl-N-(1-(3-(trifluoromethoxy)phenyl)ethyl)pyrimidine-4-carboxamide;
N-(1-(5-methyl-6-(2,2,2-trifluoroethoxy)pyridin-3-yl)ethyl)-2-(methylamino)isonicotinamide;
2-methoxy-N-(1-(5-methyl-6-(2,2,2-trifluoroethoxy)pyridin-3-yl)ethyl)isonicotinamide;
6-acetamido-N-(1-(5-methyl-6-(2,2,2-trifluoroethoxy)pyridin-3-yl)ethyl)picolinamide;
N-(1-(5-methyl-6-(2,2,2-trifluoroethoxy)pyridin-3-yl)ethyl)-3-(2-oxopyrrolidin-1-yl)benzamide;
N-(1-(5-methyl-6-(2,2,2-trifluoroethoxy)pyridin-3-yl)ethyl)quinoline-6-carboxamide;
N-(1-(5-methyl-6-(2,2,2-trifluoroethoxy)pyridin-3-yl)ethyl)quinoline-8-carboxamide;
N-(1-(5-methyl-6-(2,2,2-trifluoroethoxy)pyridin-3-yl)ethyl)quinoxaline-2-carboxamide;
N-(1-(5-methyl-6-(2,2,2-trifluoroethoxy)pyridin-3-yl)ethyl)quinoline-3-carboxamide;
N-(1-(5-methyl-6-(2,2,2-trifluoroethoxy)pyridin-3-yl)ethyl)imidazo[1,2-a]pyridine-2-carboxamide;
1-methyl-N-(1-(5-methyl-6-(2,2,2-trifluoroethoxy)pyridin-3-yl)ethyl)-1H-pyrazolo[3,4-b]pyridine-3-carboxamide;
N-(1-(5-methyl-6-(2,2,2-trifluoroethoxy)pyridin-3-yl)ethyl)-1H-benzo[d]imidazole-4-carboxamide;
(R)-6-methyl-2-propionamido-N-((6-((1,1,1-trifluoropropan-2-yl)oxy)pyridin-3-yl)methyl)pyrimidine-4-carboxamide;
(R)-2-(cyclopropanecarboxamido)-6-methyl-N-((6-((1,1,1-trifluoropropan-2-yl)oxy)pyridin-3-yl)methyl)pyrimidine-4-carboxamide;
(R)-2-isobutyramido-6-methyl-N-((6-((1,1,1-trifluoropropan-2-yl)oxy)pyridin-3-yl)methyl)pyrimidine-4-carboxamide;
(R)-2-(cyclopropanecarboxamido)-N-((6-((1,1,1-trifluoropropan-2-yl)oxy)pyridin-3-yl)methyl)pyrimidine-4-carboxamide;
2-acetamido-N-((5-methoxy-6-(2,2,2-trifluoroethoxy)pyridin-3-yl)methyl)-6-methylpyrimidine-4-carboxamide;
2-(cyclopropanecarboxamido)-N-((5-methoxy-6-(2,2,2-trifluoroethoxy)pyridin-3-yl)methyl)-6-methylpyrimidine-4-carboxamide;
2-isobutyramido-N-((5-methoxy-6-(2,2,2-trifluoroethoxy)pyridin-3-yl)methyl)-6-methylpyrimidine-4-carboxamide;
2-(cyclopropanecarboxamido)-N-((5-methoxy-6-(2,2,2-trifluoroethoxy)pyridin-3-yl)methyl)pyrimidine-4-carboxamide;

2-(hydroxymethyl)-N-(1-(5-methyl-6-(2,2,2-trifluoroethoxy)pyridin-3-yl)ethyl)-6-propionamidoisonicotinamide;
2-(cyclopropanecarboxamido)-6-(hydroxymethyl)-N-(1-(5-methyl-6-(2,2,2-trifluoroethoxy)pyridin-3-yl)ethyl)isonicotinamide;
2-(hydroxymethyl)-6-isobutyramido-N-(1-(5-methyl-6-(2,2,2-trifluoroethoxy)pyridin-3-yl)ethyl)isonicotinamide;
N-(1-(4-(2,2-difluoroethoxy)-2-methylphenyl)ethyl)-2-isobutyramidoisonicotinamide;
2-(cyclopropanecarboxamido)-N-methyl-N-(1-(5-methyl-6-(2,2,2-trifluoroethoxy)pyridin-3-yl)ethyl)pyrimidine-4-carboxamide;
2-(cyclopropanecarboxamido)-N-methyl-N-((5-methyl-6-(2,2,2-trifluoroethoxy)pyridin-3-yl)methyl)pyrimidine-4-carboxamide;
2-(cyclopropanecarboxamido)-N,6-dimethyl-N-((5-methyl-6-(2,2,2-trifluoroethoxy)pyridin-3-yl)methyl)pyrimidine-4-carboxamide;
2-(cyclobutanecarboxamido)-6-methyl-N-(1-(6-(2,2,2-trifluoroethoxy)pyridin-3-yl)ethyl)isonicotinamide;
2-(cyclopropanecarboxamido)-N-(3-(trifluoromethoxy)benzyl)pyrimidine-4-carboxamide;
2-(cyclopropanecarboxamido)-N-(1-(5-ethoxy-6-(2,2,2-trifluoroethoxy)pyridin-3-yl)ethyl)pyrimidine-4-carboxamide;
2-(cyclopropanecarboxamido)-N-((6-(3,3,3-trifluoropropoxy)pyridin-3-yl)methyl)pyrimidine-4-carboxamide;
6-methyl-N-(1-(5-methyl-6-(2,2,2-trifluoroethoxy)pyridin-3-yl)ethyl)-2-(oxazol-2-ylamino)pyrimidine-4-carboxamide;
N-(1-(5-chloro-6-(2,2,2-trifluoroethoxy)pyridin-3-yl)ethyl)-2-methyl-6-(oxazol-2-ylamino)isonicotinamide;
2-ethoxy-6-methyl-N-(1-(5-methyl-6-(2,2,2-trifluoroethoxy)pyridin-3-yl)ethyl)pyrimidine-4-carboxamide;
2-(cyclopentanecarboxamido)-6-methyl-N-(1-(6-(2,2,2-trifluoroethoxy)pyridin-3-yl)ethyl)isonicotinamide;
2-propionamido-N-((6-(trifluoromethyl)pyridin-2-yl)methyl)isonicotinamide;
2-methyl-6-propionamido-N-((6-(trifluoromethyl)pyridin-2-yl)methyl)isonicotinamide;
2-isobutyramido-N-((6-(trifluoromethyl)pyridin-2-yl)methyl)isonicotinamide;
2-amino-6-methyl-N-((5-methyl-6-(2,2,2-trifluoroethoxy)pyridin-3-yl)methyl)pyrimidine-4-carboxamide;
2-propionamido-N-((6-(2,2,2-trifluoroethoxy)pyridin-2-yl)methyl)isonicotinamide;
2-(cyclopropanecarboxamido)-N-((6-(2,2,2-trifluoroethoxy)pyridin-2-yl)methyl)isonicotinamide;
2-acetamido-6-methyl-N-((6-(2,2,2-trifluoroethoxy)pyridin-2-yl)methyl)isonicotinamide;
2-methyl-6-propionamido-N-((6-(2,2,2-trifluoroethoxy)pyridin-2-yl)methyl)isonicotinamide;
2-isobutyramido-N-((6-(2,2,2-trifluoroethoxy)pyridin-2-yl)methyl)isonicotinamide;
2-butyramido-N-((6-(2,2,2-trifluoroethoxy)pyridin-2-yl)methyl)isonicotinamide;
2-(cyclopropanecarboxamido)-6-methyl-N-((6-(2,2,2-trifluoroethoxy)pyridin-2-yl)methyl)pyrimidine-4-carboxamide;
2-pivalamido-N-((6-(2,2,2-trifluoroethoxy)pyridin-2-yl)methyl)isonicotinamide;
6-methyl-N-(1-(5-methyl-6-(2,2,2-trifluoroethoxy)pyridin-3-yl)ethyl)-2-(methylamino)pyrimidine-4-carboxamide;
2-(dimethylamino)-6-methyl-N-(1-(5-methyl-6-(2,2,2-trifluoroethoxy)pyridin-3-yl)ethyl)pyrimidine-4-carboxamide;
6-methyl-N-(1-(5-methyl-6-(2,2,2-trifluoroethoxy)pyridin-3-yl)ethyl)-2-(pyrrolidin-1-yl)pyrimidine-4-carboxamide;
2-((2-methoxyethyl)amino)-6-methyl-N-(1-(5-methyl-6-(2,2,2-trifluoroethoxy)pyridin-3-yl)ethyl)pyrimidine-4-carboxamide;
N4-(1-(5-chloro-6-(2,2,2-trifluoroethoxy)pyridin-3-yl)ethyl)-N2-ethyl-6-methylpyridine-2,4-dicarboxamide;
N2,6-dimethyl-N4-(1-(5-methyl-6-(2,2,2-trifluoroethoxy)pyridin-3-yl)ethyl)pyridine-2,4-dicarboxamide;
N2-ethyl-6-methyl-N4-(1-(5-methyl-6-(2,2,2-trifluoroethoxy)pyridin-3-yl)ethyl)pyridine-2,4-dicarboxamide;
2,6-dimethoxy-N-(1-(5-methyl-6-(2,2,2-trifluoroethoxy)pyridin-3-yl)ethyl)isonicotinamide;
2-methyl-6-pivalamido-N-((6-(2,2,2-trifluoroethoxy)pyridin-3-yl)methyl)isonicotinamide;
N2-ethyl-N4-((2-methoxy-6-(2,2,2-trifluoroethoxy)pyridin-3-yl)methyl)pyridine-2,4-dicarboxamide;
2-acrylamido-6-methyl-N-(1-(6-(2,2,2-trifluoroethoxy)pyridin-3-yl)ethyl)isonicotinamide;
2-isobutyramido-6-methyl-N-((6-(2,2,2-trifluoroethoxy)pyridin-3-yl)methyl)isonicotinamide;
2-isobutyramido-6-methyl-N-(1-(6-(2,2,2-trifluoroethoxy)pyridin-3-yl)propyl)isonicotinamide;
N-(1-(6-(2,2-difluoroethoxy)pyridin-3-yl)ethyl)-2-isobutyramido-6-methylisonicotinamide;
N-(1-(5-fluoro-6-(2,2,2-trifluoroethoxy)pyridin-3-yl)ethyl)-2-isobutyramido-6-methylisonicotinamide;
2-isobutyramido-N-(1-(5-methoxy-6-(2,2,2-trifluoroethoxy)pyridin-3-yl)ethyl)-6-methylisonicotinamide;
2-isobutyramido-6-methyl-N-(1-(6-(2-(2,2,2-trifluoroethoxy)ethoxy)pyridin-3-yl)ethyl)isonicotinamide;
2-isobutyramido-6-methyl-N-(1-(6-(3,3,3-trifluoropropoxy)pyridin-3-yl)ethyl)isonicotinamide;
2-isobutyramido-6-methyl-N-((6-(3,3,3-trifluoropropoxy)pyridin-3-yl)methyl)isonicotinamide;
N-((5-fluoro-6-(2,2,2-trifluoroethoxy)pyridin-3-yl)methyl)-2-isobutyramido-6-methylisonicotinamide;
2-isobutyramido-N-((5-methoxy-6-(2,2,2-trifluoroethoxy)pyridin-3-yl)methyl)-6-methylisonicotinamide;
2-isobutyramido-6-methyl-N-((2-methyl-6-(2,2,2-trifluoroethoxy)pyridin-3-yl)methyl)isonicotinamide;
2-isobutyramido-N-((2-methoxy-6-(2,2,2-trifluoroethoxy)pyridin-3-yl)methyl)-6-methylisonicotinamide;
(R)-2-isobutyramido-6-methyl-N-((6-(((1,1,1-trifluoropropan-2-yl)oxy)pyridin-3-yl)methyl)isonicotinamide;
2-isobutyramido-6-methyl-N-((6-(2,2,2-trifluoroethoxy)pyridin-2-yl)methyl)isonicotinamide;
2-isobutyramido-6-methyl-N-(1-(2-(2,2,2-trifluoroethoxy)pyridin-4-yl)ethyl)isonicotinamide;
2-isobutyramido-6-methyl-N-((2-(2,2,2-trifluoroethoxy)pyridin-4-yl)methyl)isonicotinamide;
2-isobutyramido-6-methyl-N-(1-(3-(trifluoromethoxy)phenyl)ethyl)isonicotinamide;
2-isobutyramido-6-methyl-N-((6-(trifluoromethyl)pyridin-2-yl)methyl)isonicotinamide;
N4-ethyl-N2-(1-(5-methyl-6-(2,2,2-trifluoroethoxy)pyridin-3-yl)ethyl)pyridine-2,4-dicarboxamide;
N2-(1-(5-chloro-6-(2,2,2-trifluoroethoxy)pyridin-3-yl)ethyl)-N4-ethylpyridine-2,4-dicarboxamide;
2-(2-hydroxy-2-methylpropanamido)-6-methyl-N-((5-methyl-6-(2,2,2-trifluoroethoxy)pyridin-3-yl)methyl)isonicotinamide;

2-methoxy-6-methyl-N-(1-(5-methyl-6-(2,2,2-trifluoroethoxy)pyridin-3-yl)ethyl)pyrimidine-4-carboxamide;
N2-ethyl-6-methyl-N4-(1-(5-methyl-6-(2,2,2-trifluoroethoxy)pyridin-3-yl)ethyl)pyrimidine-2,4-dicarboxamide;
N2-isopropyl-6-methyl-N4-(1-(5-methyl-6-(2,2,2-trifluoroethoxy)pyridin-3-yl)ethyl)pyrimidine-2,4-dicarboxamide;
6-methyl-2-(oxazol-2-ylamino)-N-((6-(2,2,2-trifluoroethoxy)pyridin-3-yl)methyl)pyrimidine-4-carboxamide;
N2-ethyl-N4-((2-methoxy-6-(2,2,2-trifluoroethoxy)pyridin-3-yl)methyl)-6-methylpyridine-2,4-dicarboxamide;
N2-cyclopropyl-N4-((2-methoxy-6-(2,2,2-trifluoroethoxy)pyridin-3-yl)methyl)-6-methylpyridine-2,4-dicarboxamide;
N2-isopropyl-N4-((2-methoxy-6-(2,2,2-trifluoroethoxy)pyridin-3-yl)methyl)-6-methylpyridine-2,4-dicarboxamide;
N2,6-dimethyl-N4-(1-(3-(trifluoromethoxy)phenyl)ethyl)pyridine-2,4-dicarboxamide;
N2-ethyl-6-methyl-N4-(1-(3-(trifluoromethoxy)phenyl)ethyl)pyridine-2,4-dicarboxamide;
N2-isopropyl-6-methyl-N4-(1-(3-(trifluoromethoxy)phenyl)ethyl)pyridine-2,4-dicarboxamide;
6-methyl-N4-(1-(3-(trifluoromethoxy)phenyl)ethyl)pyridine-2,4-dicarboxamide;
N-(1-(5-ethoxy-6-(2,2,2-trifluoroethoxy)pyridin-3-yl)ethyl)-2-isobutyramido-6-methylisonicotinamide;
2-isobutyramido-6-methyl-N-((4-methyl-6-(2,2,2-trifluoroethoxy)pyridin-3-yl)methyl)isonicotinamide;
2-isobutyramido-6-methyl-N-(1-(6-((2,2,2-trifluoroethyl)amino)pyridin-3-yl)ethyl)isonicotinamide;
3-acetamido-4-fluoro-N-(1-(5-methyl-6-(2,2,2-trifluoroethoxy)pyridin-3-yl)ethyl)benzamide;
N2-ethyl-N4-((4-methyl-6-(2,2,2-trifluoroethoxy)pyridin-3-yl)methyl)pyridine-2,4-dicarboxamide;
2-isobutyramido-6-methyl-N-(1-(5-methyl-6-(2,2,2-trifluoroethoxy)pyridin-3-yl)ethyl)isonicotinamide;
N-(1-(5-chloro-6-(2,2,2-trifluoroethoxy)pyridin-3-yl)ethyl)-2-isobutyramido-6-methylisonicotinamide;
N-(1-(5-chloro-6-(2,2,2-trifluoroethoxy)pyridin-3-yl)ethyl)-2-isobutyramidoisonicotinamide;
2-propionamido-N-(3-(trifluoromethoxy)benzyl)isonicotinamide;
2-(cyclopropanecarboxamido)-N-(3-(trifluoromethoxy)benzyl)isonicotinamide;
2-acetamido-6-methyl-N-(3-(trifluoromethoxy)benzyl)isonicotinamide;
2-methyl-6-propionamido-N-(3-(trifluoromethoxy)benzyl)isonicotinamide;
2-isobutyramido-N-(3-(trifluoromethoxy)benzyl)isonicotinamide;
2-isobutyramido-6-methyl-N-(3-(trifluoromethoxy)benzyl)isonicotinamide;
(R)-2-acetamido-6-methyl-N-(1-(3-(trifluoromethyl)phenyl)ethyl)isonicotinamide;
(R)-2-isobutyramido-N-(1-(3-(trifluoromethyl)phenyl)ethyl)isonicotinamide;
(R)-2-isobutyramido-6-methyl-N-(1-(3-(trifluoromethyl)phenyl)ethyl)isonicotinamide;
2-acetamido-6-methyl-N-(3-(trifluoromethyl)benzyl)isonicotinamide;
2-isobutyramido-N-(3-(trifluoromethyl)benzyl)isonicotinamide;
2-isobutyramido-6-methyl-N-(3-(trifluoromethyl)benzyl)isonicotinamide;
8-hydroxy-N-(1-(5-methyl-6-(2,2,2-trifluoroethoxy)pyridin-3-yl)ethyl)quinoline-2-carboxamide;
2-((3,4-dimethylisoxazol-5-yl)amino)-6-methyl-N-(1-(6-(2,2,2-trifluoroethoxy)pyridin-3-yl)ethyl)pyrimidine-4-carboxamide;
6-methyl-2-((1-methyl-1H-pyrazol-3-yl)amino)-N-(1-(6-(2,2,2-trifluoroethoxy)pyridin-3-yl)ethyl)pyrimidine-4-carboxamide;
2-((1,3-dimethyl-1H-pyrazol-5-yl)amino)-6-methyl-N-(1-(6-(2,2,2-trifluoroethoxy)pyridin-3-yl)ethyl)pyrimidine-4-carboxamide;
6-methyl-N-(1-(6-(2,2,2-trifluoroethoxy)pyridin-3-yl)ethyl)-2-((5-(trifluoromethyl)-4H-1,2,4-triazol-3-yl)amino)pyrimidine-4-carboxamide;
6-methyl-2-((3-methylisothiazol-5-yl)amino)-N-(1-(6-(2,2,2-trifluoroethoxy)pyridin-3-yl)ethyl)pyrimidine-4-carboxamide;
6-methyl-N-(1-(6-(2,2,2-trifluoroethoxy)pyridin-3-yl)ethyl)-2-((4-(trifluoromethyl)oxazol-2-yl)amino)pyrimidine-4-carboxamide;
N-(4-fluoro-3-(trifluoromethyl)benzyl)-2-isobutyramidoisonicotinamide;
N-(3,5-bis(trifluoromethyl)benzyl)-2-isobutyramidoisonicotinamide;
N-(3-fluoro-4-(trifluoromethyl)benzyl)-2-isobutyramidoisonicotinamide;
N-(3-fluoro-5-(trifluoromethyl)benzyl)-2-isobutyramidoisonicotinamide;
N-(2-chloro-5-(trifluoromethyl)benzyl)-2-isobutyramidoisonicotinamide;
N-(4-chloro-3-(trifluoromethyl)benzyl)-2-isobutyramidoisonicotinamide;
(R)—N-(1-(3,5-bis(trifluoromethyl)phenyl)ethyl)-2-isobutyramidoisonicotinamide;
2-(2-hydroxy-2-methylpropanamido)-6-methyl-N-((6-(2,2,2-trifluoroethoxy)pyridin-2-yl)methyl)isonicotinamide;
2-(2-hydroxy-2-methylpropanamido)-6-methyl-N-(1-(3-(2,2,2-trifluoroethoxy)phenyl)ethyl)isonicotinamide;
2-acetamido-N-(1-(6-(2,2-difluoroethoxy)-5-methylpyridin-3-yl)ethyl)isonicotinamide;
N-(1-(6-(2,2-difluoroethoxy)-5-methylpyridin-3-yl)ethyl)-2-propionamidoisonicotinamide;
2-(cyclopropanecarboxamido)-N-(1-(6-(2,2-difluoroethoxy)-5-methylpyridin-3-yl)ethyl)isonicotinamide;
N-(1-(6-(2,2-difluoroethoxy)-5-methylpyridin-3-yl)ethyl)-2-methyl-6-propionamidoisonicotinamide;
N-(1-(6-(2,2-difluoroethoxy)-5-methylpyridin-3-yl)ethyl)-2-isobutyramidoisonicotinamide;
2-acetamido-N-(1-(6-(2,2-difluoroethoxy)-5-methylpyridin-3-yl)ethyl)-6-methylisonicotinamide;
N-(1-(6-(2,2-difluoroethoxy)-5-methylpyridin-3-yl)ethyl)-2-isobutyramido-6-methylisonicotinamide;
2-(cyclopropanecarboxamido)-N-(1-(6-(2,2-difluoroethoxy)-5-methylpyridin-3-yl)ethyl)pyrimidine-4-carboxamide;
2-(cyclopropanecarboxamido)-N-(1-(6-(2,2-difluoroethoxy)-5-methylpyridin-3-yl)ethyl)-6-methylpyrimidine-4-carboxamide;
N-(2-fluoro-5-(trifluoromethyl)benzyl)-2-isobutyramidoisonicotinamide;
2-isobutyramido-N-(1-(3-(2,2,2-trifluoroethoxy)phenyl)ethyl)isonicotinamide;
2-isobutyramido-N-(1-(4-(2,2,2-trifluoroethoxy)phenyl)ethyl)isonicotinamide;

2-(cyclopropanecarboxamido)-N-((2-methoxy-6-(2,2,2-trifluoroethoxy)pyridin-3-yl)methyl)pyrimidine-4-carboxamide;
2-(cyclopropanecarboxamido)-N-((5-methyl-6-(2,2,2-trifluoroethoxy)pyridin-3-yl)methyl)pyrimidine-4-carboxamide;
2-acetamido-N-(1-(4-(2,2-difluoroethoxy)-2-methylphenyl)ethyl)-6-methylisonicotinamide;
2-isobutyramido-N-((3-methyl-6-(2,2,2-trifluoroethoxy)pyridin-2-yl)methyl)isonicotinamide;
2-isobutyramido-6-methyl-N-((3-methyl-6-(2,2,2-trifluoroethoxy)pyridin-2-yl)methyl)isonicotinamide;
2-(cyclopropanecarboxamido)-N-((3-methyl-6-(2,2,2-trifluoroethoxy)pyridin-2-yl)methyl)isonicotinamide;
2-methyl-6-(thiazol-2-yl)-N-(1-(6-(2,2,2-trifluoroethoxy)pyridin-3-yl)ethyl)isonicotinamide;
N-(1-(5-methyl-6-(2,2,2-trifluoroethoxy)pyridin-3-yl)ethyl)-3-(1H-pyrazol-1-yl)benzamide;
2-methacrylamido-6-methyl-N-(1-(6-(2,2,2-trifluoroethoxy)pyridin-3-yl)ethyl)isonicotinamide;
N-(2-fluoro-5-(trifluoromethyl)benzyl)-2-propionamidoisonicotinamide;
2-(cyclopropanecarboxamido)-N-(2-fluoro-5-(trifluoromethyl)benzyl)isonicotinamide;
2-acetamido-N-(2-fluoro-5-(trifluoromethyl)benzyl)-6-methylisonicotinamide;
N-(2-fluoro-5-(trifluoromethyl)benzyl)-2-isobutyramido-6-methylisonicotinamide;
2-isobutyramido-N-((4-methyl-6-(2,2,2-trifluoroethoxy)pyridin-2-yl)methyl)isonicotinamide;
2-isobutyramido-6-methyl-N-((4-methyl-6-(2,2,2-trifluoroethoxy)pyridin-2-yl)methyl)isonicotinamide;
2-(cyclopropanecarboxamido)-N-((4-methyl-6-(2,2,2-trifluoroethoxy)pyridin-2-yl)methyl)isonicotinamide;
N-(1-(5-chloro-6-(2,2,2-trifluoroethoxy)pyridin-3-yl)ethyl)-2,5-dimethylbenzo[d]oxazole-7-carboxamide;
2,5-dimethyl-N-((4-methyl-6-(2,2,2-trifluoroethoxy)pyridin-3-yl)methyl)benzo[d]oxazole-7-carboxamide;
N-(1-(6-(2,2-difluoroethoxy)-5-methylpyridin-3-yl)ethyl)-2,5-dimethylbenzo[d]oxazole-7-carboxamide;
2,5-dimethyl-N-((2-(2,2,2-trifluoroethoxy)pyridin-4-yl)methyl)benzo[d]oxazole-7-carboxamide;
2,5-dimethyl-N-(1-(2-(2,2,2-trifluoroethoxy)pyridin-4-yl)ethyl)benzo[d]oxazole-7-carboxamide;
2,5-dimethyl-N-((6-(2,2,2-trifluoroethoxy)pyridin-3-yl)methyl)benzo[d]oxazole-7-carboxamide;
2,5-dimethyl-N-(1-(6-(2,2,2-trifluoroethoxy)pyridin-3-yl)ethyl)benzo[d]oxazole-7-carboxamide;
6-methyl-N-(1-(6-(2,2,2-trifluoroethoxy)pyridin-3-yl)ethyl)-2-((2,2,2-trifluoroethyl)amino)pyrimidine-4-carboxamide;
2-isobutyramido-6-methyl-N-(1-(4-(2,2,2-trifluoroethoxy)phenyl)ethyl)isonicotinamide;
2-acetamido-N-(4-fluoro-3-(trifluoromethoxy)benzyl)isonicotinamide;
N-(4-fluoro-3-(trifluoromethoxy)benzyl)-2-propionamidoisonicotinamide;
2-(cyclopropanecarboxamido)-N-(4-fluoro-3-(trifluoromethoxy)benzyl)isonicotinamide;
N-(4-fluoro-3-(trifluoromethoxy)benzyl)-2-methyl-6-propionamidoisonicotinamide;
N-(4-fluoro-3-(trifluoromethoxy)benzyl)-2-isobutyramidoisonicotinamide;
2-acetamido-N-(4-fluoro-3-(trifluoromethoxy)benzyl)-6-methylisonicotinamide;
N-(4-fluoro-3-(trifluoromethoxy)benzyl)-2-isobutyramido-6-methylisonicotinamide;
2-(cyclopropanecarboxamido)-N-(4-fluoro-3-(trifluoromethoxy)benzyl)pyrimidine-4-carboxamide;
2-(cyclopropanecarboxamido)-N-(4-fluoro-3-(trifluoromethoxy)benzyl)-6-methylpyrimidine-4-carboxamide;
2-acetamido-N-(3-methyl-5-(trifluoromethoxy)benzyl)isonicotinamide;
N-(3-methyl-5-(trifluoromethoxy)benzyl)-2-propionamidoisonicotinamide;
2-(cyclopropanecarboxamido)-N-(3-methyl-5-(trifluoromethoxy)benzyl)isonicotinamide;
2-methyl-N-(3-methyl-5-(trifluoromethoxy)benzyl)-6-propionamidoisonicotinamide;
2-isobutyramido-N-(3-methyl-5-(trifluoromethoxy)benzyl)isonicotinamide;
2-acetamido-6-methyl-N-(3-methyl-5-(trifluoromethoxy)benzyl)isonicotinamide;
2-isobutyramido-6-methyl-N-(3-methyl-5-(trifluoromethoxy)benzyl)isonicotinamide;
2-(cyclopropanecarboxamido)-N-(3-methyl-5-(trifluoromethoxy)benzyl)pyrimidine-4-carboxamide;
2-(cyclopropanecarboxamido)-6-methyl-N-(3-methyl-5-(trifluoromethoxy)benzyl)pyrimidine-4-carboxamide;
2-acetamido-N-(2-fluoro-5-(trifluoromethoxy)benzyl)isonicotinamide;
N-(2-fluoro-5-(trifluoromethoxy)benzyl)-2-propionamidoisonicotinamide;
2-(cyclopropanecarboxamido)-N-(2-fluoro-5-(trifluoromethoxy)benzyl)isonicotinamide;
N-(2-fluoro-5-(trifluoromethoxy)benzyl)-2-methyl-6-propionamidoisonicotinamide;
N-(2-fluoro-5-(trifluoromethoxy)benzyl)-2-isobutyramidoisonicotinamide;
2-acetamido-N-(2-fluoro-5-(trifluoromethoxy)benzyl)-6-methylisonicotinamide;
N-(2-fluoro-5-(trifluoromethoxy)benzyl)-2-isobutyramido-6-methylisonicotinamide;
2-(cyclopropanecarboxamido)-N-(2-fluoro-5-(trifluoromethoxy)benzyl)pyrimidine-4-carboxamide;
2-(cyclopropanecarboxamido)-N-(2-fluoro-5-(trifluoromethoxy)benzyl)-6-methylpyrimidine-4-carboxamide;
N-(3-(difluoromethoxy)benzyl)-2-isobutyramidoisonicotinamide;
N-(3-(difluoromethoxy)benzyl)-2-isobutyramido-6-methylisonicotinamide;
N-((5-chloro-6-(2,2-difluoroethoxy)pyridin-3-yl)methyl)-2-propionamidoisonicotinamide;
N-((5-chloro-6-(2,2-difluoroethoxy)pyridin-3-yl)methyl)-2-methyl-6-propionamidoisonicotinamide;
N-((5-chloro-6-(2,2-difluoroethoxy)pyridin-3-yl)methyl)-2-isobutyramidoisonicotinamide;
N-((5-chloro-6-(2,2-difluoroethoxy)pyridin-3-yl)methyl)-2-isobutyramido-6-methylisonicotinamide;
2-butyramido-N-((5-chloro-6-(2,2-difluoroethoxy)pyridin-3-yl)methyl)isonicotinamide;
N-((5-chloro-6-(2,2-difluoroethoxy)pyridin-3-yl)methyl)-2-(cyclopropanecarboxamido)-6-methylpyrimidine-4-carboxamide;
N-((5-chloro-6-(2,2-difluoroethoxy)pyridin-3-yl)methyl)-2-(2-hydroxy-2-methylpropanamido)-6-methylisonicotinamide;
2-acetamido-N-(1-(5-chloro-6-(2,2-difluoroethoxy)pyridin-3-yl)ethyl)isonicotinamide;
N-(1-(5-chloro-6-(2,2-difluoroethoxy)pyridin-3-yl)ethyl)-2-propionamidoisonicotinamide;

N-(1-(5-chloro-6-(2,2-difluoroethoxy)pyridin-3-yl)ethyl)-2-(cyclopropanecarboxamido)isonicotinamide;
2-acetamido-N-(1-(5-chloro-6-(2,2-difluoroethoxy)pyridin-3-yl)ethyl)-6-methylisonicotinamide;
N-(1-(5-chloro-6-(2,2-difluoroethoxy)pyridin-3-yl)ethyl)-2-methyl-6-propionamidoisonicotinamide;
N-(1-(5-chloro-6-(2,2-difluoroethoxy)pyridin-3-yl)ethyl)-2-isobutyramidoisonicotinamide;
N-(1-(5-chloro-6-(2,2-difluoroethoxy)pyridin-3-yl)ethyl)-2-isobutyramido-6-methylisonicotinamide;
2-butyramido-N-(1-(5-chloro-6-(2,2-difluoroethoxy)pyridin-3-yl)ethyl)isonicotinamide;
N-(1-(5-chloro-6-(2,2-difluoroethoxy)pyridin-3-yl)ethyl)-2-(cyclopropanecarboxamido)pyrimidine-4-carboxamide;
2-butyramido-N-(1-(6-(2,2-difluoroethoxy)-5-methylpyridin-3-yl)ethyl)isonicotinamide;
2-propionamido-N-((6-(2,2,3,3-tetrafluoropropoxy)pyridin-3-yl)methyl)isonicotinamide;
2-(cyclopropanecarboxamido)-N-((6-(2,2,3,3-tetrafluoropropoxy)pyridin-3-yl)methyl)isonicotinamide;
2-isobutyramido-N-((6-(2,2,3,3-tetrafluoropropoxy)pyridin-3-yl)methyl)isonicotinamide;
2-isobutyramido-N-((4-methyl-5-(2,2,2-trifluoroethoxy)pyridin-2-yl)methyl)isonicotinamide;
2-isobutyramido-6-methyl-N-((4-methyl-5-(2,2,2-trifluoroethoxy)pyridin-2-yl)methyl)isonicotinamide;
N-((6-(2,2,3,3,3-pentafluoropropoxy)pyridin-3-yl)methyl)-2-propionamidoisonicotinamide;
2-(cyclopropanecarboxamido)-N-((6-(2,2,3,3,3-pentafluoropropoxy)pyridin-3-yl)methyl)isonicotinamide;
2-isobutyramido-N-((6-(2,2,3,3,3-pentafluoropropoxy)pyridin-3-yl)methyl)isonicotinamide;
2-acetamido-6-methyl-N-((6-(2,2,3,3,3-pentafluoropropoxy)pyridin-3-yl)methyl)isonicotinamide;
2-methyl-N-((6-(2,2,3,3,3-pentafluoropropoxy)pyridin-3-yl)methyl)-6-propionamidoisonicotinamide;
2-isobutyramido-6-methyl-N-((6-(2,2,3,3,3-pentafluoropropoxy)pyridin-3-yl)methyl)isonicotinamide;
2-acetamido-6-methyl-N-((6-(2,2,3,3-tetrafluoropropoxy)pyridin-3-yl)methyl)isonicotinamide;
2-methyl-6-propionamido-N-((6-(2,2,3,3-tetrafluoropropoxy)pyridin-3-yl)methyl)isonicotinamide;
2-isobutyramido-6-methyl-N-((6-(2,2,3,3-tetrafluoropropoxy)pyridin-3-yl)methyl)isonicotinamide;
N-((6-(2,2,3,3,3-pentafluoropropoxy)pyridin-3-yl)methyl)-2-pivalamidoisonicotinamide;
2-(cyclopropanecarboxamido)-N-((6-(2,2,3,3,3-pentafluoropropoxy)pyridin-3-yl)methyl)pyrimidine-4-carboxamide;
2-(cyclopropanecarboxamido)-6-methyl-N-((6-(2,2,3,3,3-pentafluoropropoxy)pyridin-3-yl)methyl)pyrimidine-4-carboxamide;
2-(cyclopropanecarboxamido)-N-((6-(2,2,3,3-tetrafluoropropoxy)pyridin-3-yl)methyl)pyrimidine-4-carboxamide;
2-(cyclopropanecarboxamido)-6-methyl-N-((6-(2,2,3,3-tetrafluoropropoxy)pyridin-3-yl)methyl)pyrimidine-4-carboxamide;
2-propionamido-N-(1-(6-(2,2,3,3-tetrafluoropropoxy)pyridin-3-yl)ethyl)isonicotinamide;
2-isobutyramido-N-(1-(6-(2,2,3,3-tetrafluoropropoxy)pyridin-3-yl)ethyl)isonicotinamide;
2-acetamido-6-methyl-N-(1-(6-(2,2,3,3-tetrafluoropropoxy)pyridin-3-yl)ethyl)isonicotinamide;
2-methyl-6-propionamido-N-(1-(6-(2,2,3,3-tetrafluoropropoxy)pyridin-3-yl)ethyl)isonicotinamide;
2-isobutyramido-6-methyl-N-(1-(6-(2,2,3,3-tetrafluoropropoxy)pyridin-3-yl)ethyl)isonicotinamide;
2-(cyclopropanecarboxamido)-N-(1-(6-(2,2,3,3-tetrafluoropropoxy)pyridin-3-yl)ethyl)pyrimidine-4-carboxamide;
5-(4-chlorophenyl)-N-((5-methyl-6-(2,2,2-trifluoroethoxy)pyridin-3-yl)methyl)furan-2-carboxamide;
5-(4-chlorophenyl)-N-((6-(2,2,2-trifluoroethoxy)pyridin-3-yl)methyl)furan-2-carboxamide;
5-(4-chlorophenyl)-N-(1-(6-(2,2,2-trifluoroethoxy)pyridin-3-yl)ethyl)furan-2-carboxamide;
2-(3-methylbutanamido)-N-(1-(6-(2,2,2-trifluoroethoxy)pyridin-3-yl)ethyl)isonicotinamide;
2-(3-methylbutanamido)-N-((6-(2,2,2-trifluoroethoxy)pyridin-3-yl)methyl)isonicotinamide;
2-propionamido-N-(4-((2,2,2-trifluoroethoxy)methyl)benzyl)isonicotinamide;
2-(cyclopropanecarboxamido)-N-(4-((2,2,2-trifluoroethoxy)methyl)benzyl)isonicotinamide;
2-methyl-6-propionamido-N-(4-((2,2,2-trifluoroethoxy)methyl)benzyl)isonicotinamide;
2-isobutyramido-N-(4-((2,2,2-trifluoroethoxy)methyl)benzyl)isonicotinamide;
2-acetamido-6-methyl-N-(4-((2,2,2-trifluoroethoxy)methyl)benzyl)isonicotinamide;
2-isobutyramido-6-methyl-N-(4-((2,2,2-trifluoroethoxy)methyl)benzyl)isonicotinamide;
2-(cyclopropanecarboxamido)-N-(4-((2,2,2-trifluoroethoxy)methyl)benzyl)pyrimidine-4-carboxamide;
2-(cyclopropanecarboxamido)-6-methyl-N-(4-((2,2,2-trifluoroethoxy)methyl)benzyl)pyrimidine-4-carboxamide;
2-acetamido-N-(1-(3-chloro-4-(2,2,2-trifluoroethoxy)phenyl)ethyl)isonicotinamide;
N-(1-(3-chloro-4-(2,2,2-trifluoroethoxy)phenyl)ethyl)-2-propionamidoisonicotinamide;
N-(1-(3-chloro-4-(2,2,2-trifluoroethoxy)phenyl)ethyl)-2-isobutyramidoisonicotinamide;
N-(1-(3-chloro-4-(2,2,2-trifluoroethoxy)phenyl)ethyl)-2-(cyclopropanecarboxamido)isonicotinamide;
2-acetamido-N-(1-(3-chloro-4-(2,2,2-trifluoroethoxy)phenyl)ethyl)-6-methylisonicotinamide;
N-(1-(3-chloro-4-(2,2,2-trifluoroethoxy)phenyl)ethyl)-2-methyl-6-propionamidoisonicotinamide;
N-(1-(3-chloro-4-(2,2,2-trifluoroethoxy)phenyl)ethyl)-2-isobutyramido-6-methylisonicotinamide;
N-(1-(3-chloro-4-(2,2,2-trifluoroethoxy)phenyl)ethyl)-2-(cyclopropanecarboxamido)-6-methylpyrimidine-4-carboxamide;
N-(1-(3-chloro-4-(2,2,2-trifluoroethoxy)phenyl)ethyl)-2-(cyclopropanecarboxamido)pyrimidine-4-carboxamide;
2-acetamido-N-(4-fluoro-3-(trifluoromethyl)benzyl)isonicotinamide;
2-acetamido-N-(4-chloro-3-(trifluoromethyl)benzyl)isonicotinamide;
2-acetamido-N-(3,5-bis(trifluoromethyl)benzyl)isonicotinamide;
(R)-2-(cyclopropanecarboxamido)-N-(1-(3-(trifluoromethyl)phenyl)ethyl)pyrimidine-4-carboxamide;
2-(cyclopropanecarboxamido)-N-((6-(3,3,3-trifluoropropyl)pyridin-3-yl)methyl)isonicotinamide;
2-methyl-6-propionamido-N-((6-(3,3,3-trifluoropropyl)pyridin-3-yl)methyl)isonicotinamide;
2-isobutyramido-N-((6-(3,3,3-trifluoropropyl)pyridin-3-yl)methyl)isonicotinamide;

2-isobutyramido-6-methyl-N-((6-(3,3,3-trifluoropropyl)pyridin-3-yl)methyl)isonicotinamide;
2-(cyclopropanecarboxamido)-N-(1-(6-(2,2,3,3,3-pentafluoropropoxy)pyridin-3-yl)ethyl)isonicotinamide;
2-isobutyramido-N-(1-(6-(2,2,3,3,3-pentafluoropropoxy)pyridin-3-yl)ethyl)isonicotinamide;
2-acetamido-6-methyl-N-(1-(6-(2,2,3,3,3-pentafluoropropoxy)pyridin-3-yl)ethyl)isonicotinamide;
2-methyl-N-(1-(6-(2,2,3,3,3-pentafluoropropoxy)pyridin-3-yl)ethyl)-6-propionamidoisonicotinamide;
2-isobutyramido-6-methyl-N-(1-(6-(2,2,3,3,3-pentafluoropropoxy)pyridin-3-yl)ethyl)isonicotinamide;
2-(cyclopropanecarboxamido)-N-(1-(6-(2,2,3,3,3-pentafluoropropoxy)pyridin-3-yl)ethyl)pyrimidine-4-carboxamide;
2-(cyclopropanecarboxamido)-6-methyl-N-(1-(6-(2,2,3,3,3-pentafluoropropoxy)pyridin-3-yl)ethyl)pyrimidine-4-carboxamide;
2-acetamido-N-(4-chloro-3-(trifluoromethyl)benzyl)-6-methylisonicotinamide;
2-acetamido-N-(3,5-bis(trifluoromethyl)benzyl)-6-methylisonicotinamide;
2-isobutyramido-6-methyl-N-(4-((2,2,2-trifluoroethoxy)benzyl)isonicotinamide;
N-(1-(3-chloro-4-(2,2-difluoroethoxy)phenyl)ethyl)-2-(cyclopropanecarboxamido)-6-methylisonicotinamide;
N-(2-chloro-4-(2,2-difluoroethoxy)benzyl)-2-(cyclopropanecarboxamido)pyrimidine-4-carboxamide;
N-(3-(difluoromethoxy)benzyl)-2-propionamidoisonicotinamide;
2-(cyclopropanecarboxamido)-N-(3-(difluoromethoxy)benzyl)isonicotinamide;
2-acetamido-N-(3-(difluoromethoxy)benzyl)-6-methylisonicotinamide;
2-acetamido-N-((5-chloro-6-(2,2-difluoroethoxy)pyridin-3-yl)methyl)isonicotinamide;
N-((5-chloro-6-(2,2-difluoroethoxy)pyridin-3-yl)methyl)-2-(cyclopropanecarboxamido)isonicotinamide;
2-acetamido-N-((5-chloro-6-(2,2-difluoroethoxy)pyridin-3-yl)methyl)-6-methylisonicotinamide;
N-((5-chloro-6-(2,2-difluoroethoxy)pyridin-3-yl)methyl)-2-(cyclopropanecarboxamido)pyrimidine-4-carboxamide;
2-acetamido-N-(2-chloro-5-(trifluoromethyl)benzyl)-6-methylisonicotinamide;
2-acetamido-N-((5-ethyl-6-(2,2,2-trifluoroethoxy)pyridin-3-yl)methyl)isonicotinamide;
N-((5-ethyl-6-(2,2,2-trifluoroethoxy)pyridin-3-yl)methyl)-2-propionamidoisonicotinamide;
2-(cyclopropanecarboxamido)-N-((5-ethyl-6-(2,2,2-trifluoroethoxy)pyridin-3-yl)methyl)isonicotinamide;
N-((5-ethyl-6-(2,2,2-trifluoroethoxy)pyridin-3-yl)methyl)-2-isobutyramidoisonicotinamide;
2-acetamido-N-((5-ethyl-6-(2,2,2-trifluoroethoxy)pyridin-3-yl)methyl)-6-methylisonicotinamide;
N-((5-ethyl-6-(2,2,2-trifluoroethoxy)pyridin-3-yl)methyl)-2-methyl-6-propionamidoisonicotinamide;
N-((5-ethyl-6-(2,2,2-trifluoroethoxy)pyridin-3-yl)methyl)-2-isobutyramido-6-methylisonicotinamide;
N-((5-ethyl-6-(2,2,2-trifluoroethoxy)pyridin-3-yl)methyl)-2-(2-hydroxy-2-methylpropanamido)-6-methylisonicotinamide;
2-(cyclopropanecarboxamido)-N-((5-ethyl-6-(2,2,2-trifluoroethoxy)pyridin-3-yl)methyl)pyrimidine-4-carboxamide;
2-(cyclopropanecarboxamido)-N-((5-ethyl-6-(2,2,2-trifluoroethoxy)pyridin-3-yl)methyl)-6-methylpyrimidine-4-carboxamide;
N-((6-(2,2-difluoropropoxy)pyridin-3-yl)methyl)-2-propionamidoisonicotinamide;
2-acetamido-N-((6-(2,2-difluoropropoxy)pyridin-3-yl)methyl)-6-methylisonicotinamide;
N-((6-(2,2-difluoropropoxy)pyridin-3-yl)methyl)-2-methyl-6-propionamidoisonicotinamide;
N-((6-(2,2-difluoropropoxy)pyridin-3-yl)methyl)-2-isobutyramidoisonicotinamide;
N-((6-(2,2-difluoropropoxy)pyridin-3-yl)methyl)-2-isobutyramido-6-methylisonicotinamide;
2-butyramido-N-((6-(2,2-difluoropropoxy)pyridin-3-yl)methyl)isonicotinamide;
2-acetamido-N-((6-(2,2,2-trifluoroethoxy)-5-(trifluoromethyl)pyridin-3-yl)methyl)isonicotinamide;
2-propionamido-N-((6-(2,2,2-trifluoroethoxy)-5-(trifluoromethyl)pyridin-3-yl)methyl)isonicotinamide;
2-acetamido-6-methyl-N-((6-(2,2,2-trifluoroethoxy)-5-(trifluoromethyl)pyridin-3-yl)methyl)isonicotinamide;
2-acetamido-N-(2-fluoro-3-(trifluoromethyl)benzyl)isonicotinamide;
2-acetamido-N-(2-fluoro-3-(trifluoromethyl)benzyl)-6-methylisonicotinamide;
N-(2-fluoro-3-(trifluoromethyl)benzyl)-2-isobutyramidoisonicotinamide;
2-(cyclopropanecarboxamido)-N-(2-fluoro-3-(trifluoromethyl)benzyl)pyrimidine-4-carboxamide;
2-(cyclopropanecarboxamido)-N-(4-fluoro-3-(trifluoromethyl)benzyl)pyrimidine-4-carboxamide;
2-(cyclopropanecarboxamido)-N-(3-fluoro-5-(trifluoromethyl)benzyl)pyrimidine-4-carboxamide;
N-(4-chloro-3-(trifluoromethyl)benzyl)-2-(cyclopropanecarboxamido)pyrimidine-4-carboxamide;
N-(2-chloro-5-(trifluoromethyl)benzyl)-2-(cyclopropanecarboxamido)pyrimidine-4-carboxamide;
N-(3,5-bis(trifluoromethyl)benzyl)-2-(cyclopropanecarboxamido)pyrimidine-4-carboxamide;
2-acetamido-N-((6-(2,2-difluoroethoxy)-5-methylpyridin-3-yl)methyl)isonicotinamide;
N-((6-(2,2-difluoroethoxy)-5-methylpyridin-3-yl)methyl)-2-propionamidoisonicotinamide;
2-(cyclopropanecarboxamido)-N-((6-(2,2-difluoroethoxy)-5-methylpyridin-3-yl)methyl)isonicotinamide;
N-((6-(2,2-difluoroethoxy)-5-methylpyridin-3-yl)methyl)-2-methyl-6-propionamidoisonicotinamide;
N-((6-(2,2-difluoroethoxy)-5-methylpyridin-3-yl)methyl)-2-isobutyramidoisonicotinamide;
2-acetamido-N-((6-(2,2-difluoroethoxy)-5-methylpyridin-3-yl)methyl)-6-methylisonicotinamide;
N-((6-(2,2-difluoroethoxy)-5-methylpyridin-3-yl)methyl)-2-isobutyramido-6-methylisonicotinamide;
2-(cyclopropanecarboxamido)-N-((6-(2,2-difluoroethoxy)-5-methylpyridin-3-yl)methyl)pyrimidine-4-carboxamide;
2-(cyclopropanecarboxamido)-N-((6-(2,2-difluoroethoxy)-5-methylpyridin-3-yl)methyl)-6-methylpyrimidine-4-carboxamide;
2-acetamido-N-(2-fluoro-3-(trifluoromethoxy)benzyl)isonicotinamide;
N-(2-fluoro-3-(trifluoromethoxy)benzyl)-2-propionamidoisonicotinamide;
2-(cyclopropanecarboxamido)-N-(2-fluoro-3-(trifluoromethoxy)benzyl)isonicotinamide;
N-(2-fluoro-3-(trifluoromethoxy)benzyl)-2-methyl-6-propionamidoisonicotinamide;

N-(2-fluoro-3-(trifluoromethoxy)benzyl)-2-isobutyramidoisonicotinamide;
2-acetamido-N-(2-fluoro-3-(trifluoromethoxy)benzyl)-6-methylisonicotinamide;
N-(2-fluoro-3-(trifluoromethoxy)benzyl)-2-isobutyramido-6-methylisonicotinamide;
2-(cyclopropanecarboxamido)-N-(2-fluoro-3-(trifluoromethoxy)benzyl)pyrimidine-4-carboxamide;
2-(cyclopropanecarboxamido)-N-(2-fluoro-3-(trifluoromethoxy)benzyl)-6-methylpyrimidine-4-carboxamide;
N-(2-fluoro-3-(trifluoromethoxy)benzyl)-2-(2-hydroxy-2-methylpropanamido)-6-methylisonicotinamide;
2-acetamido-N-(4-methoxy-3-(trifluoromethoxy)benzyl)-6-methylisonicotinamide;
2-butyramido-N-((6-(2,2-difluoroethoxy)-5-methylpyridin-3-yl)methyl)isonicotinamide;
2-acetamido-N-(2-chloro-3-(trifluoromethyl)benzyl)isonicotinamide;
2-acetamido-N-(2-chloro-3-(trifluoromethyl)benzyl)-6-methylisonicotinamide;
N-(2-chloro-3-(trifluoromethyl)benzyl)-2-isobutyramidoisonicotinamide;
2-acetamido-N-(4-methyl-3-(trifluoromethyl)benzyl)isonicotinamide;
2-acetamido-N-((5-bromo-6-(2,2,2-trifluoroethoxy)pyridin-3-yl)methyl)isonicotinamide;
2-acetamido-N-((5-phenyl-6-(2,2,2-trifluoroethoxy)pyridin-3-yl)methyl)isonicotinamide;
2-acetamido-N-((5-(2-fluorophenyl)-6-(2,2,2-trifluoroethoxy)pyridin-3-yl)methyl)isonicotinamide;
2-acetamido-N-((5-(o-tolyl)-6-(2,2,2-trifluoroethoxy)pyridin-3-yl)methyl)isonicotinamide;
2-acetamido-N-((5-(3-fluorophenyl)-6-(2,2,2-trifluoroethoxy)pyridin-3-yl)methyl)isonicotinamide;
2-acetamido-N-((5-(m-tolyl)-6-(2,2,2-trifluoroethoxy)pyridin-3-yl)methyl)isonicotinamide;
2-acetamido-N-((5-(4-fluorophenyl)-6-(2,2,2-trifluoroethoxy)pyridin-3-yl)methyl)isonicotinamide;
2-acetamido-N-((5-(thiophen-3-yl)-6-(2,2,2-trifluoroethoxy)pyridin-3-yl)methyl)isonicotinamide;
2-acetamido-N-((5-(furan-2-yl)-6-(2,2,2-trifluoroethoxy)pyridin-3-yl)methyl)isonicotinamide;
2-isobutyramido-N-(4-((2,2,2-trifluoroethyl)benzyl)isonicotinamide;
2-propionamido-N-(4-(trifluoromethoxy)benzyl)isonicotinamide;
2-isobutyramido-N-(4-(trifluoromethoxy)benzyl)isonicotinamide;
2-isobutyramido-6-methyl-N-(4-(trifluoromethoxy)benzyl)isonicotinamide;
2-(cyclopropanecarboxamido)-6-methyl-N-(4-(trifluoromethoxy)benzyl)pyrimidine-4-carboxamide;
2-isobutyramido-6-methyl-N-(1-(4-(trifluoromethoxy)phenyl)ethyl)isonicotinamide;
N-((6-(2,2-difluoroethoxy)-4-methylpyridin-3-yl)methyl)-2-propionamidoisonicotinamide;
2-acetamido-N-((6-(2,2-difluoroethoxy)-4-methylpyridin-3-yl)methyl)-6-methylisonicotinamide;
2-(cyclopropanecarboxamido)-N-(3-methyl-4-(2,2,2-trifluoroethoxy)benzyl)pyrimidine-4-carboxamide;
2-(cyclopropanecarboxamido)-6-methyl-N-(3-methyl-4-(2,2,2-trifluoroethoxy)benzyl)pyrimidine-4-carboxamide;
N-(1-(6-(2,2-difluoropropoxy)pyridin-3-yl)ethyl)-2-propionamidoisonicotinamide;
2-(cyclopropanecarboxamido)-N-(1-(6-(2,2-difluoropropoxy)pyridin-3-yl)ethyl)isonicotinamide;
2-acetamido-N-(1-(6-(2,2-difluoropropoxy)pyridin-3-yl)ethyl)-6-methylisonicotinamide;
N-(1-(6-(2,2-difluoropropoxy)pyridin-3-yl)ethyl)-2-methyl-6-propionamidoisonicotinamide;
N-(1-(6-(2,2-difluoropropoxy)pyridin-3-yl)ethyl)-2-isobutyramidoisonicotinamide;
N-(1-(6-(2,2-difluoropropoxy)pyridin-3-yl)ethyl)-2-isobutyramido-6-methylisonicotinamide;
2-butyramido-N-(1-(6-(2,2-difluoropropoxy)pyridin-3-yl)ethyl)isonicotinamide;
2-acetamido-N-(3-methyl-4-(2,2,2-trifluoroethoxy)benzyl)isonicotinamide;
N-(3-methyl-4-(2,2,2-trifluoroethoxy)benzyl)-2-propionamidoisonicotinamide;
2-(cyclopropanecarboxamido)-N-(3-methyl-4-(2,2,2-trifluoroethoxy)benzyl)isonicotinamide;
2-isobutyramido-N-(3-methyl-4-(2,2,2-trifluoroethoxy)benzyl)isonicotinamide;
2-acetamido-6-methyl-N-(3-methyl-4-(2,2,2-trifluoroethoxy)benzyl)isonicotinamide;
2-methyl-N-(3-methyl-4-(2,2,2-trifluoroethoxy)benzyl)-6-propionamidoisonicotinamide;
2-isobutyramido-6-methyl-N-(3-methyl-4-(2,2,2-trifluoroethoxy)benzyl)isonicotinamide;
2-(2-hydroxy-2-methylpropanamido)-6-methyl-N-(3-methyl-4-(2,2,2-trifluoroethoxy)benzyl)isonicotinamide;
2-acetamido-N-(1-(2-chloro-4-(2,2,2-trifluoroethoxy)phenyl)ethyl)isonicotinamide;
N-(1-(2-chloro-4-(2,2,2-trifluoroethoxy)phenyl)ethyl)-2-propionamidoisonicotinamide;
N-(1-(2-chloro-4-(2,2,2-trifluoroethoxy)phenyl)ethyl)-2-(cyclopropanecarboxamido)isonicotinamide;
N-(1-(2-chloro-4-(2,2,2-trifluoroethoxy)phenyl)ethyl)-2-isobutyramidoisonicotinamide;
2-acetamido-N-(1-(2-chloro-4-(2,2,2-trifluoroethoxy)phenyl)ethyl)-6-methylisonicotinamide;
N-(1-(2-chloro-4-(2,2,2-trifluoroethoxy)phenyl)ethyl)-2-isobutyramido-6-methylisonicotinamide;
N-(1-(2-chloro-4-(2,2,2-trifluoroethoxy)phenyl)ethyl)-2-(cyclopropanecarboxamido)pyrimidine-4-carboxamide;
N-(1-(2-chloro-4-(2,2,2-trifluoroethoxy)phenyl)ethyl)-2-(cyclopropanecarboxamido)-6-methylpyrimidine-4-carboxamide;
2-acetamido-N-(3-methyl-4-(trifluoromethoxy)benzyl)isonicotinamide;
N-(3-methyl-4-(trifluoromethoxy)benzyl)-2-propionamidoisonicotinamide;
2-(cyclopropanecarboxamido)-N-(3-methyl-4-(trifluoromethoxy)benzyl)isonicotinamide;
2-isobutyramido-N-(3-methyl-4-(trifluoromethoxy)benzyl)isonicotinamide;
2-acetamido-6-methyl-N-(3-methyl-4-(trifluoromethoxy)benzyl)isonicotinamide;
2-isobutyramido-6-methyl-N-(3-methyl-4-(trifluoromethoxy)benzyl)isonicotinamide;
2-(cyclopropanecarboxamido)-N-(3-methyl-4-(trifluoromethoxy)benzyl)pyrimidine-4-carboxamide;
2-(cyclopropanecarboxamido)-6-methyl-N-(3-methyl-4-(trifluoromethoxy)benzyl)pyrimidine-4-carboxamide;
2-(2-hydroxy-2-methylpropanamido)-6-methyl-N-(3-methyl-4-(trifluoromethoxy)benzyl)isonicotinamide;
2-acetamido-N-(4-methoxy-3-(trifluoromethyl)benzyl)-6-methylisonicotinamide;

2-acetamido-N-(2-methyl-3-(trifluoromethyl)benzyl)
isonicotinamide;
2-acetamido-6-methyl-N-(2-methyl-3-(trifluoromethyl)
benzyl)isonicotinamide;
2-isobutyramido-N-(2-methyl-3-(trifluoromethyl)benzyl)
isonicotinamide;
2-(cyclopropanecarboxamido)-N-(2-methyl-3-(trifluoromethyl)benzyl)pyrimidine-4-carboxamide;
2-acetamido-N-(2-methoxy-3-(trifluoromethyl)benzyl)
isonicotinamide;
2-acetamido-N-(2-methoxy-3-(trifluoromethyl)benzyl)-6-methylisonicotinamide;
2-isobutyramido-N-(2-methoxy-3-(trifluoromethyl)benzyl)isonicotinamide;
2-(cyclopropanecarboxamido)-N-(2-methoxy-3-(trifluoromethyl)benzyl)pyrimidine-4-carboxamide;
2-(cyclopropanecarboxamido)-6-methyl-N-((6-(2,2,2-trifluoroethoxy)pyridin-3-yl)methyl)isonicotinamide;
2-(cyclopropanecarboxamido)-6-methyl-N-(1-(5-methyl-6-(2,2,2-trifluoroethoxy)pyridin-3-yl)ethyl)isonicotinamide;
2-(cyclopropanecarboxamido)-6-methyl-N-((5-methyl-6-(2,2,2-trifluoroethoxy)pyridin-3-yl)methyl)isonicotinamide;
2-(cyclopropanecarboxamido)-N-((5-ethyl-6-(2,2,2-trifluoroethoxy)pyridin-3-yl)methyl)-6-methylisonicotinamide;
N-((5-chloro-6-(2,2-difluoroethoxy)pyridin-3-yl)methyl)-2-(cyclopropanecarboxamido)-6-methylisonicotinamide;
2-(cyclopropanecarboxamido)-6-methyl-N-((6-(2,2,3,3,3-pentafluoropropoxy)pyridin-3-yl)methyl)isonicotinamide;
2-(cyclopropanecarboxamido)-6-methyl-N-(1-(6-(2,2,3,3-tetrafluoropropoxy)pyridin-3-yl)ethyl)isonicotinamide;
2-(cyclopropanecarboxamido)-N-((6-(2,2-difluoropropoxy)pyridin-3-yl)methyl)-6-methylisonicotinamide;
2-(cyclopropanecarboxamido)-6-methyl-N-((6-(2,2,3,3-tetrafluoropropoxy)pyridin-3-yl)methyl)isonicotinamide;
2-(cyclopropanecarboxamido)-6-methyl-N-(3-methyl-4-(2,2,2-trifluoroethoxy)benzyl)isonicotinamide;
N-(1-(5-chloro-6-(2,2,2-trifluoroethoxy)pyridin-3-yl)ethyl)-2-(cyclopropanecarboxamido)-6-methylisonicotinamide;
2-(cyclopropanecarboxamido)-N-(1-(5-fluoro-6-(2,2,2-trifluoroethoxy)pyridin-3-yl)ethyl)-6-methylisonicotinamide;
2-(cyclopropanecarboxamido)-N-(1-(5-methoxy-6-(2,2,2-trifluoroethoxy)pyridin-3-yl)ethyl)-6-methylisonicotinamide;
2-(cyclopropanecarboxamido)-6-methyl-N-((2-methyl-6-(2,2,2-trifluoroethoxy)pyridin-3-yl)methyl)isonicotinamide;
2-(cyclopropanecarboxamido)-6-methyl-N-(3-(trifluoromethoxy)benzyl)isonicotinamide;
2-(cyclopropanecarboxamido)-6-methyl-N-(1-(6-(2,2,3,3,3-pentafluoropropoxy)pyridin-3-yl)ethyl)isonicotinamide;
(R)-2-(cyclopropanecarboxamido)-6-methyl-N-(1-(3-(trifluoromethyl)phenyl)ethyl)isonicotinamide;
2-(cyclopropanecarboxamido)-6-methyl-N-(1-(3-(trifluoromethoxy)phenyl)ethyl)isonicotinamide;
N-(1-(5-ethoxy-6-(2,2,2-trifluoroethoxy)pyridin-3-yl)ethyl)-2-propionamidoisonicotinamide;
N-(1-(5-ethoxy-6-(2,2,2-trifluoroethoxy)pyridin-3-yl)ethyl)-2-isobutyramidoisonicotinamide;
2-acetamido-6-methyl-N-((6-(2,2,2-trifluoroethoxy)pyridin-3-yl)methyl)pyrimidine-4-carboxamide;
N-(2-fluoro-5-(trifluoromethyl)benzyl)-6-methyl-2-propionamidopyrimidine-4-carboxamide;
2-acetamido-6-methyl-N-(3-(trifluoromethoxy)benzyl)
pyrimidine-4-carboxamide;
2-acetamido-6-methyl-N-(3-(trifluoromethyl)benzyl)pyrimidine-4-carboxamide;
2-acetamido-6-methyl-N-(1-(4-(2,2,2-trifluoroethoxy)phenyl)ethyl)pyrimidine-4-carboxamide;
N-(1-(5-(hydroxymethyl)-6-(2,2,2-trifluoroethoxy)pyridin-3-yl)ethyl)-2-isobutyramidoisonicotinamide;
2-acetamido-6-methyl-N-(1-(3-(2,2,2-trifluoroethoxy)phenyl)ethyl)pyrimidine-4-carboxamide;
2-(cyclopropanecarboxamido)-N-(1-(6-(2,2-difluoroethoxy)pyridin-3-yl)ethyl)pyrimidine-4-carboxamide;
2-(cyclopropanecarboxamido)-N-((5-fluoro-2-methoxy-6-(2,2,2-trifluoroethoxy)pyridin-3-yl)methyl)pyrimidine-4-carboxamide;
2-(cyclopropanecarboxamido)-N-((6-(2,2-difluoroethoxy)-5-methylpyridin-3-yl)methyl)-6-methylisonicotinamide;
2-(cyclopropanecarboxamido)-6-methyl-N-(3-(trifluoromethyl)benzyl)isonicotinamide;
2-(1-methylcyclopropanecarboxamido)-N-((6-(2,2,2-trifluoroethoxy)pyridin-3-yl)methyl)isonicotinamide;
N-(1-(5-methyl-6-(2,2,2-trifluoroethoxy)pyridin-3-yl)ethyl)-2-(1-methylcyclopropanecarboxamido)isonicotinamide;
N-((5-methyl-6-(2,2,2-trifluoroethoxy)pyridin-3-yl)methyl)-2-(1-methylcyclopropanecarboxamido)isonicotinamide;
N-(1-(5-chloro-6-(2,2,2-trifluoroethoxy)pyridin-3-yl)ethyl)-2-(1-methylcyclopropanecarboxamido)isonicotinamide;
N-((5-chloro-6-(2,2,2-trifluoroethoxy)pyridin-3-yl)methyl)-2-(1-methylcyclopropanecarboxamido)isonicotinamide;
2-(1-methylcyclopropanecarboxamido)-N-(3-(trifluoromethoxy)benzyl)isonicotinamide;
2-acetamido-N-(1-(4-(2,2-difluoroethoxy)-3-methylphenyl)ethyl)isonicotinamide;
N-(1-(4-(2,2-difluoroethoxy)-3-methylphenyl)ethyl)-2-propionamidoisonicotinamide;
2-(cyclopropanecarboxamido)-N-(1-(4-(2,2-difluoroethoxy)-3-methylphenyl)ethyl)isonicotinamide;
N-(1-(4-(2,2-difluoroethoxy)-3-methylphenyl)ethyl)-2-isobutyramidoisonicotinamide;
2-(cyclopropanecarboxamido)-N-(1-(4-(2,2-difluoroethoxy)-3-methylphenyl)ethyl)pyrimidine-4-carboxamide;
2-acetamido-N-(1-(4-(2,2-difluoroethoxy)-3-methylphenyl)ethyl)-6-methylisonicotinamide;
N-(1-(4-(2,2-difluoroethoxy)-3-methylphenyl)ethyl)-2-isobutyramido-6-methylisonicotinamide;
2-(cyclopropanecarboxamido)-N-(1-(4-(2,2-difluoroethoxy)-3-methylphenyl)ethyl)-6-methylisonicotinamide;
N-(2-methoxy-4-(trifluoromethoxy)benzyl)-2-propionamidoisonicotinamide;
2-(cyclopropanecarboxamido)-N-(2-methoxy-4-(trifluoromethoxy)benzyl)isonicotinamide;
2-isobutyramido-N-(2-methoxy-4-(trifluoromethoxy)benzyl)isonicotinamide;

2-acetamido-N-(2-methoxy-4-(trifluoromethoxy)benzyl)-6-methylisonicotinamide;
2-isobutyramido-N-(2-methoxy-4-(trifluoromethoxy)benzyl)-6-methylisonicotinamide;
2-(cyclopropanecarboxamido)-N-(2-methoxy-4-(trifluoromethoxy)benzyl)pyrimidine-4-carboxamide;
2-(cyclopropanecarboxamido)-N-(2-methoxy-4-(trifluoromethoxy)benzyl)-6-methylpyrimidine-4-carboxamide;
N-(4-fluoro-3-(trifluoromethyl)benzyl)-2-isobutyramido-6-methylisonicotinamide;
N-(3-fluoro-5-(trifluoromethyl)benzyl)-2-isobutyramido-6-methylisonicotinamide;
N-(2-fluoro-3-(trifluoromethyl)benzyl)-2-isobutyramido-6-methylisonicotinamide;
N-(4-chloro-3-(trifluoromethyl)benzyl)-2-isobutyramido-6-methylisonicotinamide;
N-(2-chloro-3-(trifluoromethyl)benzyl)-2-isobutyramido-6-methylisonicotinamide;
2-isobutyramido-6-methyl-N-(2-methyl-3-(trifluoromethyl)benzyl)isonicotinamide;
2-isobutyramido-N-(2-methoxy-3-(trifluoromethyl)benzyl)-6-methylisonicotinamide;
2-isobutyramido-6-methyl-N-(1-(3-(2,2,2-trifluoroethoxy)phenyl)ethyl)isonicotinamide;
N-(3-methoxy-4-(2,2,2-trifluoroethoxy)benzyl)-2-propionamidoisonicotinamide;
2-isobutyramido-N-(3-methoxy-4-(2,2,2-trifluoroethoxy)benzyl)isonicotinamide;
2-acetamido-N-(3-methoxy-4-(2,2,2-trifluoroethoxy)benzyl)-6-methylisonicotinamide;
2-isobutyramido-N-(3-methoxy-4-(2,2,2-trifluoroethoxy)benzyl)-6-methylisonicotinamide;
2-(cyclopropanecarboxamido)-N-(3-methoxy-4-(2,2,2-trifluoroethoxy)benzyl)-6-methylpyrimidine-4-carboxamide;
N-(1-(6-(2,2-difluoroethoxy)-5-ethylpyridin-3-yl)ethyl)-2-propionamidoisonicotinamide;
2-(cyclopropanecarboxamido)-N-(1-(6-(2,2-difluoroethoxy)-5-ethylpyridin-3-yl)ethyl)isonicotinamide;
N-(1-(6-(2,2-difluoroethoxy)-5-ethylpyridin-3-yl)ethyl)-2-isobutyramidoisonicotinamide;
2-(cyclopropanecarboxamido)-N-(1-(6-(2,2-difluoroethoxy)-5-ethylpyridin-3-yl)ethyl)pyrimidine-4-carboxamide;
2-acetamido-N-(1-(6-(2,2-difluoroethoxy)-5-ethylpyridin-3-yl)ethyl)-6-methylisonicotinamide;
2-(cyclopropanecarboxamido)-N-(1-(6-(2,2-difluoroethoxy)-5-ethylpyridin-3-yl)ethyl)-6-methylisonicotinamide;
N-(1-(6-(2,2-difluoroethoxy)-5-ethylpyridin-3-yl)ethyl)-2-isobutyramido-6-methylisonicotinamide;
2-(cyclopropanecarboxamido)-N-(1-(6-(2,2-difluoroethoxy)-5-ethylpyridin-3-yl)ethyl)-6-methylpyrimidine-4-carboxamide;
N-((5-bromo-6-(2,2,2-trifluoroethoxy)pyridin-3-yl)methyl)-2-propionamidoisonicotinamide;
N-((5-bromo-6-(2,2,2-trifluoroethoxy)pyridin-3-yl)methyl)-2-(cyclopropanecarboxamido)isonicotinamide;
N-((5-bromo-6-(2,2,2-trifluoroethoxy)pyridin-3-yl)methyl)-2-isobutyramidoisonicotinamide;
N-((5-bromo-6-(2,2,2-trifluoroethoxy)pyridin-3-yl)methyl)-2-(cyclopropanecarboxamido)pyrimidine-4-carboxamide;
2-acetamido-N-((5-bromo-6-(2,2,2-trifluoroethoxy)pyridin-3-yl)methyl)-6-methylisonicotinamide;
N-((5-bromo-6-(2,2,2-trifluoroethoxy)pyridin-3-yl)methyl)-2-(cyclopropanecarboxamido)-6-methylisonicotinamide;
N-((5-bromo-6-(2,2,2-trifluoroethoxy)pyridin-3-yl)methyl)-2-isobutyramido-6-methylisonicotinamide;
N-((5-bromo-6-(2,2,2-trifluoroethoxy)pyridin-3-yl)methyl)-2-(cyclopropanecarboxamido)-6-methylpyrimidine-4-carboxamide;
2-acetamido-N-(1-(5-methyl-6-(2,2,3,3-tetrafluoropropoxy)pyridin-3-yl)ethyl)isonicotinamide;
2-isobutyramido-N-(1-(5-methyl-6-(2,2,3,3-tetrafluoropropoxy)pyridin-3-yl)ethyl)isonicotinamide;
2-isobutyramido-6-methyl-N-(1-(5-methyl-6-(2,2,3,3-tetrafluoropropoxy)pyridin-3-yl)ethyl)isonicotinamide;
2-(cyclopropanecarboxamido)-N-(1-(5-methyl-6-(2,2,3,3-tetrafluoropropoxy)pyridin-3-yl)ethyl)pyrimidine-4-carboxamide;
2-(cyclopropanecarboxamido)-6-methyl-N-(1-(5-methyl-6-(2,2,3,3-tetrafluoropropoxy)pyridin-3-yl)ethyl)pyrimidine-4-carboxamide;
2-(2-hydroxy-2-methylpropanamido)-6-methyl-N-(1-(5-methyl-6-(2,2,3,3-tetrafluoropropoxy)pyridin-3-yl)ethyl)isonicotinamide;
2-acetamido-N-((6-(2,2-difluoroethoxy)-5-ethylpyridin-3-yl)methyl)isonicotinamide;
N-((6-(2,2-difluoroethoxy)-5-ethylpyridin-3-yl)methyl)-2-isobutyramidoisonicotinamide;
N-((6-(2,2-difluoroethoxy)-5-ethylpyridin-3-yl)methyl)-2-isobutyramido-6-methylisonicotinamide;
2-(cyclopropanecarboxamido)-N-((6-(2,2-difluoroethoxy)-5-ethylpyridin-3-yl)methyl)pyrimidine-4-carboxamide;
2-(cyclopropanecarboxamido)-N-((6-(2,2-difluoroethoxy)-5-ethylpyridin-3-yl)methyl)-6-methylpyrimidine-4-carboxamide;
N-((6-(2,2-difluoroethoxy)-5-ethylpyridin-3-yl)methyl)-2-(2-hydroxy-2-methylpropanamido)-6-methylisonicotinamide;
2-acetamido-N-((5-cyclopropyl-6-(2,2-difluoroethoxy)pyridin-3-yl)methyl)isonicotinamide;
N-((5-cyclopropyl-6-(2,2-difluoroethoxy)pyridin-3-yl)methyl)-2-isobutyramidoisonicotinamide;
N-((5-cyclopropyl-6-(2,2-difluoroethoxy)pyridin-3-yl)methyl)-2-isobutyramido-6-methylisonicotinamide;
2-(cyclopropanecarboxamido)-N-((5-cyclopropyl-6-(2,2-difluoroethoxy)pyridin-3-yl)methyl)pyrimidine-4-carboxamide;
5-chloro-2-propionamido-N-(1-(6-(2,2,2-trifluoroethoxy)pyridin-3-yl)ethyl)isonicotinamide;
5-chloro-2-(cyclopropanecarboxamido)-N-(1-(6-(2,2,2-trifluoroethoxy)pyridin-3-yl)ethyl)isonicotinamide;
2-acetamido-N-((6-(2,2,3,3,3-pentafluoropropoxy)pyridin-3-yl)methyl)isonicotinamide;
2-(cyclopropanecarboxamido)-N-(1-(6-(2,2,3,3-tetrafluoropropoxy)pyridin-3-yl)ethyl)isonicotinamide;
2-propionamido-N-((6-(3,3,3-trifluoropropyl)pyridin-3-yl)methyl)isonicotinamide;
2-acetamido-N-(1-(6-(2,2,3,3,3-pentafluoropropoxy)pyridin-3-yl)ethyl)isonicotinamide;
N-(1-(5-methyl-6-(2,2,3,3-tetrafluoropropoxy)pyridin-3-yl)ethyl)-2-propionamidoisonicotinamide;
2-(cyclopropanecarboxamido)-N-(1-(5-methyl-6-(2,2,3,3-tetrafluoropropoxy)pyridin-3-yl)ethyl)isonicotinamide;
2-acetamido-6-methyl-N-(1-(5-methyl-6-(2,2,3,3-tetrafluoropropoxy)pyridin-3-yl)ethyl)isonicotinamide;

2-butyramido-N-(1-(5-methyl-6-(2,2,3,3-tetrafluoropropoxy)pyridin-3-yl)ethyl)isonicotinamide;

N-(1-(5-methyl-6-(2,2,3,3-tetrafluoropropoxy)pyridin-3-yl)ethyl)-2-pivalamidoisonicotinamide;

N-((6-(2,2-difluoroethoxy)-5-ethylpyridin-3-yl)methyl)-2-propionamidoisonicotinamide;

2-(cyclopropanecarboxamido)-N-((6-(2,2-difluoroethoxy)-5-ethylpyridin-3-yl)methyl)isonicotinamide;

2-acetamido-N-((6-(2,2-difluoroethoxy)-5-ethylpyridin-3-yl)methyl)-6-methylisonicotinamide;

2-butyramido-N-((6-(2,2-difluoroethoxy)-5-ethylpyridin-3-yl)methyl)isonicotinamide;

N-(1-(5-cyclopropyl-6-(2,2-difluoroethoxy)pyridin-3-yl)ethyl)-2-isobutyramido-6-methylisonicotinamide;

2-(cyclopropanecarboxamido)-N-(1-(5-cyclopropyl-6-(2,2-difluoroethoxy)pyridin-3-yl)ethyl)pyrimidine-4-carboxamide;

2-acetamido-N-(1-(6-(2,2-difluoroethoxy)-5-methylpyridin-3-yl)ethyl)-N,6-dimethylisonicotinamide;

N-(1-(6-(2,2-difluoroethoxy)-5-methylpyridin-3-yl)ethyl)-2-isobutyramido-N,6-dimethylisonicotinamide;

2-(cyclopropanecarboxamido)-N-(1-(6-(2,2-difluoroethoxy)-5-methylpyridin-3-yl)ethyl)-6-methylisonicotinamide;

2-acetamido-N-((5-methyl-6-(2,2,3,3-tetrafluoropropoxy)pyridin-3-yl)methyl)isonicotinamide;

N-((5-methyl-6-(2,2,3,3-tetrafluoropropoxy)pyridin-3-yl)methyl)-2-propionamidoisonicotinamide;

2-isobutyramido-N-((5-methyl-6-(2,2,3,3-tetrafluoropropoxy)pyridin-3-yl)methyl)isonicotinamide;

2-(cyclopropanecarboxamido)-N-((5-methyl-6-(2,2,3,3-tetrafluoropropoxy)pyridin-3-yl)methyl)isonicotinamide;

2-(cyclopropanecarboxamido)-N-((5-methyl-6-(2,2,3,3-tetrafluoropropoxy)pyridin-3-yl)methyl)pyrimidine-4-carboxamide;

2-acetamido-6-methyl-N-((5-methyl-6-(2,2,3,3-tetrafluoropropoxy)pyridin-3-yl)methyl)isonicotinamide;

2-isobutyramido-6-methyl-N-((5-methyl-6-(2,2,3,3-tetrafluoropropoxy)pyridin-3-yl)methyl)isonicotinamide;

2-(cyclopropanecarboxamido)-6-methyl-N-((5-methyl-6-(2,2,3,3-tetrafluoropropoxy)pyridin-3-yl)methyl)isonicotinamide;

2-(cyclopropanecarboxamido)-6-methyl-N-((5-methyl-6-(2,2,3,3-tetrafluoropropoxy)pyridin-3-yl)methyl)pyrimidine-4-carboxamide;

2-(2-cyclopropylacetamido)-6-methyl-N-(1-(6-(2,2,2-trifluoroethoxy)pyridin-3-yl)ethyl)isonicotinamide;

2-(2-cyclopropylacetamido)-6-methyl-N-((6-(2,2,2-trifluoroethoxy)pyridin-3-yl)methyl)isonicotinamide;

2-(2-cyclopropylacetamido)-N-(1-(6-(2,2-difluoroethoxy)-5-methylpyridin-3-yl)ethyl)-6-methylisonicotinamide;

2-(2-cyclopropylacetamido)-N-((6-(2,2-difluoroethoxy)-5-methylpyridin-3-yl)methyl)-6-methylisonicotinamide;

N-(1-(5-chloro-6-(2,2-difluoroethoxy)pyridin-3-yl)ethyl)-2-(2-cyclopropylacetamido)-6-methylisonicotinamide;

2-(2-cyclopropylacetamido)-6-methyl-N-(1-(5-methyl-6-(2,2,2-trifluoroethoxy)pyridin-3-yl)ethyl)isonicotinamide;

2-(2-cyclopropylacetamido)-6-methyl-N-((5-methyl-6-(2,2,2-trifluoroethoxy)pyridin-3-yl)methyl)isonicotinamide;

N-(1-(5-chloro-6-(2,2,2-trifluoroethoxy)pyridin-3-yl)ethyl)-2-(2-cyclopropylacetamido)-6-methylisonicotinamide;

N-((5-chloro-6-(2,2,2-trifluoroethoxy)pyridin-3-yl)methyl)-2-(2-cyclopropylacetamido)-6-methylisonicotinamide;

2-(2-cyclopropylacetamido)-N-(1-(5-fluoro-6-(2,2,2-trifluoroethoxy)pyridin-3-yl)ethyl)-6-methylisonicotinamide;

2-(2-cyclopropylacetamido)-6-methyl-N-((4-methyl-6-(2,2,2-trifluoroethoxy)pyridin-3-yl)methyl)isonicotinamide;

2-(2-cyclopropylacetamido)-6-methyl-N-(1-(6-(3,3,3-trifluoropropoxy)pyridin-3-yl)ethyl)isonicotinamide;

2-(2-cyclopropylacetamido)-N-((2-methoxy-6-(2,2,2-trifluoroethoxy)pyridin-3-yl)methyl)-6-methylisonicotinamide;

2-(2-cyclopropylacetamido)-6-methyl-N-(3-(trifluoromethyl)benzyl)isonicotinamide;

2-(2-cyclopropylacetamido)-6-methyl-N-(3-(trifluoromethoxy)benzyl)isonicotinamide;

N-(3-fluoro-4-(trifluoromethoxy)benzyl)-2-propionamidoisonicotinamide;

N-(3-fluoro-4-(trifluoromethoxy)benzyl)-2-isobutyramidoisonicotinamide;

N-(3-fluoro-4-(trifluoromethoxy)benzyl)-2-isobutyramido-6-methylisonicotinamide;

2-(cyclopropanecarboxamido)-N-(3-fluoro-4-(trifluoromethoxy)benzyl)pyrimidine-4-carboxamide;

2-acetamido-N-(3-chloro-4-(trifluoromethoxy)benzyl)isonicotinamide;

N-(3-chloro-4-(trifluoromethoxy)benzyl)-2-propionamidoisonicotinamide;

N-(3-chloro-4-(trifluoromethoxy)benzyl)-2-(cyclopropanecarboxamido)isonicotinamide;

N-(3-chloro-4-(trifluoromethoxy)benzyl)-2-isobutyramidoisonicotinamide;

2-acetamido-N-(3-chloro-4-(trifluoromethoxy)benzyl)-6-methylisonicotinamide;

N-(3-chloro-4-(trifluoromethoxy)benzyl)-2-isobutyramido-6-methylisonicotinamide;

N-(3-chloro-4-(trifluoromethoxy)benzyl)-2-(cyclopropanecarboxamido)pyrimidine-4-carboxamide;

N-(3-chloro-4-(trifluoromethoxy)benzyl)-2-(cyclopropanecarboxamido)-6-methylpyrimidine-4-carboxamide;

2-(cyclopropanecarboxamido)-N-(2-fluoro-5-(trifluoromethyl)benzyl)-6-methylisonicotinamide;

2-(cyclopropanecarboxamido)-N-(3-fluoro-5-(trifluoromethyl)benzyl)-6-methylisonicotinamide;

2-(cyclopropanecarboxamido)-N-(2-fluoro-3-(trifluoromethyl)benzyl)-6-methylisonicotinamide;

2-(cyclopropanecarboxamido)-N-(4-fluoro-3-(trifluoromethyl)benzyl)isonicotinamide;

2-(cyclopropanecarboxamido)-N-(2-fluoro-3-(trifluoromethyl)benzyl)isonicotinamide;

N-(1-(2-fluoro-5-(trifluoromethyl)phenyl)ethyl)-2-isobutyramido-6-methylisonicotinamide;

2-acetamido-N-(1-(2-fluoro-5-(trifluoromethyl)phenyl)ethyl)-6-methylisonicotinamide;

N-(1-(3-chloro-4-(2,2-difluoroethoxy)phenyl)ethyl)-2-propionamidoisonicotinamide;

N-(1-(3-chloro-4-(2,2-difluoroethoxy)phenyl)ethyl)-2-(cyclopropanecarboxamido)pyrimidine-4-carboxamide;

N-(1-(3-chloro-4-(2,2-difluoroethoxy)phenyl)ethyl)-2-(cyclopropanecarboxamido)-6-methylpyrimidine-4-carboxamide;
(R)-2-(2-cyclopropylacetamido)-6-methyl-N-(1-(3-(trifluoromethyl)phenyl)ethyl)isonicotinamide;
N-(2-chloro-3-(trifluoromethyl)benzyl)-2-(cyclopropanecarboxamido)pyrimidine-4-carboxamide;
2-acetamido-6-methyl-N-(4-methyl-3-(trifluoromethyl)benzyl)isonicotinamide;
2-acetamido-N-(4-(2,2-difluoroethoxy)-3-methylbenzyl)isonicotinamide;
N-(4-(2,2-difluoroethoxy)-3-methylbenzyl)-2-propionamidoisonicotinamide;
2-(cyclopropanecarboxamido)-N-(4-(2,2-difluoroethoxy)-3-methylbenzyl)isonicotinamide;
N-(4-(2,2-difluoroethoxy)-3-methylbenzyl)-2-isobutyramidoisonicotinamide;
2-(cyclopropanecarboxamido)-N-(4-(2,2-difluoroethoxy)-3-methylbenzyl)pyrimidine-4-carboxamide;
2-acetamido-N-(4-(2,2-difluoroethoxy)-3-methylbenzyl)-6-methylisonicotinamide;
N-(4-(2,2-difluoroethoxy)-3-methylbenzyl)-2-isobutyramido-6-methylisonicotinamide;
N-(4-(2,2-difluoroethoxy)-3-methylbenzyl)-2-(2-hydroxy-2-methylpropanamido)-6-methylisonicotinamide;
2-(cyclopropanecarboxamido)-N-(4-(2,2-difluoroethoxy)-3-methylbenzyl)-6-methylpyrimidine-4-carboxamide;
2-acetamido-N-(3-chloro-4-(2,2-difluoroethoxy)benzyl)isonicotinamide;
N-(3-chloro-4-(2,2-difluoroethoxy)benzyl)-2-propionamidoisonicotinamide;
N-(3-chloro-4-(2,2-difluoroethoxy)benzyl)-2-(cyclopropanecarboxamido)isonicotinamide;
N-(3-chloro-4-(2,2-difluoroethoxy)benzyl)-2-isobutyramidoisonicotinamide;
N-(3-chloro-4-(2,2-difluoroethoxy)benzyl)-2-(cyclopropanecarboxamido)pyrimidine-4-carboxamide;
2-acetamido-N-(3-chloro-4-(2,2-difluoroethoxy)benzyl)-6-methylisonicotinamide;
N-(3-chloro-4-(2,2-difluoroethoxy)benzyl)-2-isobutyramido-6-methylisonicotinamide;
N-(3-chloro-4-(2,2-difluoroethoxy)benzyl)-2-(cyclopropanecarboxamido)-6-methylpyrimidine-4-carboxamide;
2-(cyclopropanecarboxamido)-N-(4-(2,2-difluoroethoxy)-2-methylbenzyl)isonicotinamide;
N-(4-(2,2-difluoroethoxy)-2-methylbenzyl)-2-isobutyramidoisonicotinamide;
2-acetamido-N-(4-(2,2-difluoroethoxy)-2-methylbenzyl)-6-methylisonicotinamide;
N-(4-(2,2-difluoroethoxy)-2-methylbenzyl)-2-isobutyramido-6-methylisonicotinamide;
2-acetamido-6-methyl-N-(1-(3-(2,2,2-trifluoroethoxy)phenyl)ethyl)isonicotinamide;
N-(4-fluoro-3-(trifluoromethyl)benzyl)-2-propionamidoisonicotinamide;
N-(3-fluoro-5-(trifluoromethyl)benzyl)-2-propionamidoisonicotinamide;
N-(2-fluoro-3-(trifluoromethyl)benzyl)-2-propionamidoisonicotinamide;
N-(4-chloro-3-(trifluoromethyl)benzyl)-2-propionamidoisonicotinamide;
N-(2-chloro-3-(trifluoromethyl)benzyl)-2-propionamidoisonicotinamide;
N-(3,5-bis(trifluoromethyl)benzyl)-2-propionamidoisonicotinamide;
N-(2-methyl-3-(trifluoromethyl)benzyl)-2-propionamidoisonicotinamide;
N-(2-methoxy-3-(trifluoromethyl)benzyl)-2-propionamidoisonicotinamide;
N-(4-methyl-3-(trifluoromethyl)benzyl)-2-propionamidoisonicotinamide;
2-(cyclopropanecarboxamido)-N-(4-fluoro-3-(trifluoromethyl)benzyl)-6-methylpyrimidine-4-carboxamide;
2-(cyclopropanecarboxamido)-N-(3-fluoro-5-(trifluoromethyl)benzyl)-6-methylpyrimidine-4-carboxamide;
2-(cyclopropanecarboxamido)-N-(2-fluoro-3-(trifluoromethyl)benzyl)-6-methylpyrimidine-4-carboxamide;
N-(4-chloro-3-(trifluoromethyl)benzyl)-2-(cyclopropanecarboxamido)-6-methylpyrimidine-4-carboxamide;
N-(2-chloro-3-(trifluoromethyl)benzyl)-2-(cyclopropanecarboxamido)-6-methylpyrimidine-4-carboxamide;
N-(3,5-bis(trifluoromethyl)benzyl)-2-(cyclopropanecarboxamido)-6-methylpyrimidine-4-carboxamide;
2-(cyclopropanecarboxamido)-6-methyl-N-(2-methyl-3-(trifluoromethyl)benzyl)pyrimidine-4-carboxamide;
2-(cyclopropanecarboxamido)-N-(2-methoxy-3-(trifluoromethyl)benzyl)-6-methylpyrimidine-4-carboxamide;
2-(cyclopropanecarboxamido)-6-methyl-N-(4-methyl-3-(trifluoromethyl)benzyl)pyrimidine-4-carboxamide;
2-(cyclopropanecarboxamido)-N-(4-methoxy-3-(trifluoromethyl)benzyl)-6-methylpyrimidine-4-carboxamide;
2-acetamido-N-(1-(3-((trifluoromethyl)thio)phenyl)ethyl)isonicotinamide;
2-isobutyramido-N-(1-(3-((trifluoromethyl)thio)phenyl)ethyl)isonicotinamide;
2-acetamido-6-methyl-N-(1-(3-((trifluoromethyl)thio)phenyl)ethyl)isonicotinamide;
2-isobutyramido-6-methyl-N-(1-(3-((trifluoromethyl)thio)phenyl)ethyl)isonicotinamide;
2-(cyclopropanecarboxamido)-N-(1-(3-((trifluoromethyl)thio)phenyl)ethyl)pyrimidine-4-carboxamide;
N-(4-(2,2-difluoroethoxy)-3-fluorobenzyl)-2-propionamidoisonicotinamide;
2-(cyclopropanecarboxamido)-N-(4-(2,2-difluoroethoxy)-3-fluorobenzyl)isonicotinamide;
N-(4-(2,2-difluoroethoxy)-3-fluorobenzyl)-2-isobutyramido-6-methylisonicotinamide;
2-butyramido-N-(4-(2,2-difluoroethoxy)-3-fluorobenzyl)isonicotinamide;
2-(cyclopropanecarboxamido)-N-(4-(2,2-difluoroethoxy)-3-fluorobenzyl)-6-methylpyrimidine-4-carboxamide;
2-acetamido-N-(1-(3-chloro-5-(trifluoromethoxy)phenyl)ethyl)isonicotinamide;
N-(1-(3-chloro-5-(trifluoromethoxy)phenyl)ethyl)-2-isobutyramidoisonicotinamide;
N-(1-(3-chloro-5-(trifluoromethoxy)phenyl)ethyl)-2-isobutyramido-6-methylisonicotinamide;
2-acetamido-N-(1-(3-chloro-5-(trifluoromethoxy)phenyl)ethyl)-6-methylisonicotinamide;
N-(1-(3-chloro-5-(trifluoromethoxy)phenyl)ethyl)-2-(cyclopropanecarboxamido)pyrimidine-4-carboxamide;
2-(cyclopropanecarboxamido)-N-(1-(4-fluoro-3-(2,2,2-trifluoroethoxy)phenyl)ethyl)-6-methylpyrimidine-4-carboxamide;
N-(2-chloro-4-(2,2-difluoroethoxy)benzyl)-2-propionamidoisonicotinamide;
N-(2-chloro-4-(2,2-difluoroethoxy)benzyl)-2-(cyclopropanecarboxamido)isonicotinamide;

N-(2-chloro-4-(2,2-difluoroethoxy)benzyl)-2-isobutyramidoisonicotinamide;
2-acetamido-N-(2-chloro-4-(2,2-difluoroethoxy)benzyl)-6-methylisonicotinamide;
N-(2-chloro-4-(2,2-difluoroethoxy)benzyl)-2-isobutyramido-6-methylisonicotinamide;
N-(2-chloro-4-(2,2-difluoroethoxy)benzyl)-2-(cyclopropanecarboxamido)-6-methylpyrimidine-4-carboxamide;
N-(1-(4-(2,2-difluoroethoxy)-3-fluorophenyl)ethyl)-2-isobutyramido-6-methylisonicotinamide;
N-(1-(2-fluoro-3-(trifluoromethyl)phenyl)ethyl)-2-isobutyramido-6-methylisonicotinamide;
2-(cyclopropanecarboxamido)-N-(4-(trifluoromethoxy)benzyl)isonicotinamide;
2-methyl-6-propionamido-N-(4-(trifluoromethoxy)benzyl)isonicotinamide;
2-acetamido-6-methyl-N-(4-(trifluoromethoxy)benzyl)isonicotinamide;
(R)-2-acetamido-6-methyl-N-(1-(4-(trifluoromethoxy)phenyl)ethyl)isonicotinamide;
(R)-2-(cyclopropanecarboxamido)-N-(1-(4-(trifluoromethoxy)phenyl)ethyl)pyrimidine-4-carboxamide;
(R)-2-(cyclopropanecarboxamido)-6-methyl-N-(1-(4-(trifluoromethoxy)phenyl)ethyl)pyrimidine-4-carboxamide;
(R)-2-isobutyramido-N-(1-(4-(trifluoromethoxy)phenyl)ethyl)isonicotinamide;
N-((6-(2,2-difluoroethoxy)-4-methylpyridin-3-yl)methyl)-2-isobutyramidoisonicotinamide;
2-(cyclopropanecarboxamido)-N-(1-(6-(2,2-difluoropropoxy)pyridin-3-yl)ethyl)pyrimidine-4-carboxamide;
2-(cyclopropanecarboxamido)-N-(4-methoxy-3-(trifluoromethyl)benzyl)pyrimidine-4-carboxamide;
N-(1-(5-chloro-6-(2,2-difluoroethoxy)pyridin-3-yl)ethyl)-2-(cyclopropanecarboxamido)-6-methylisonicotinamide;
2-(cyclopropanecarboxamido)-N-(1-(6-(2,2-difluoropropoxy)pyridin-3-yl)ethyl)-6-methylisonicotinamide;
2-(cyclopropanecarboxamido)-N-((5-fluoro-6-(2,2,2-trifluoroethoxy)pyridin-3-yl)methyl)-6-methylisonicotinamide;
2-(cyclopropanecarboxamido)-6-methyl-N-((6-(3,3,3-trifluoropropyl)pyridin-3-yl)methyl)isonicotinamide;
2-(cyclopropanecarboxamido)-6-methyl-N-(1-(6-(3,3,3-trifluoropropoxy)pyridin-3-yl)ethyl)isonicotinamide;
2-(1-methylcyclopropanecarboxamido)-N-(1-(6-(2,2,2-trifluoroethoxy)pyridin-3-yl)ethyl)isonicotinamide;
N-((6-(2,2-difluoroethoxy)-5-methylpyridin-3-yl)methyl)-2-(1-methylcyclopropanecarboxamido)isonicotinamide;
2-(1-methylcyclopropanecarboxamido)-N-(1-(6-(3,3,3-trifluoropropoxy)pyridin-3-yl)ethyl)isonicotinamide;
2-(1-methylcyclopropanecarboxamido)-N-((6-(3,3,3-trifluoropropoxy)pyridin-3-yl)methyl)isonicotinamide;
N-((4-methyl-6-(2,2,2-trifluoroethoxy)pyridin-3-yl)methyl)-2-(1-methylcyclopropanecarboxamido)isonicotinamide;
N-((2-methoxy-6-(2,2,2-trifluoroethoxy)pyridin-3-yl)methyl)-2-(1-methylcyclopropanecarboxamido)isonicotinamide;
2-(1-methylcyclopropanecarboxamido)-N-(3-(trifluoromethyl)benzyl)isonicotinamide;
2-(cyclopropanecarboxamido)-N-(1-(4-(2,2-difluoroethoxy)-3-methylphenyl)ethyl)-6-methylpyrimidine-4-carboxamide;
2-acetamido-N-(2-methoxy-4-(trifluoromethoxy)benzyl)isonicotinamide;
N-(2-chloro-5-(trifluoromethyl)benzyl)-2-isobutyramido-6-methylisonicotinamide;
2-acetamido-N-(3-methoxy-4-(2,2,2-trifluoroethoxy)benzyl)isonicotinamide;
2-(cyclopropanecarboxamido)-N-((5-cyclopropyl-6-(2,2-difluoroethoxy)pyridin-3-yl)methyl)-6-methylpyrimidine-4-carboxamide;
N-((5-cyclopropyl-6-(2,2-difluoroethoxy)pyridin-3-yl)methyl)-2-(2-hydroxy-2-methylpropanamido)-6-methylisonicotinamide;
N-((5-cyclopropyl-6-(2,2-difluoroethoxy)pyridin-3-yl)methyl)-2-propionamidoisonicotinamide;
2-acetamido-N-((5-cyclopropyl-6-(2,2-difluoroethoxy)pyridin-3-yl)methyl)-6-methylisonicotinamide;
2-acetamido-N-(1-(5-cyclopropyl-6-(2,2-difluoroethoxy)pyridin-3-yl)ethyl)-6-methylisonicotinamide;
N-(1-(5-cyclopropyl-6-(2,2-difluoroethoxy)pyridin-3-yl)ethyl)-2-isobutyramidoisonicotinamide;
2-(cyclopropanecarboxamido)-N-(1-(5-cyclopropyl-6-(2,2-difluoroethoxy)pyridin-3-yl)ethyl)-6-methylpyrimidine-4-carboxamide;
N-((6-(2,2-difluoroethoxy)-5-isopropylpyridin-3-yl)methyl)-2-isobutyramidoisonicotinamide;
N-((6-(2,2-difluoroethoxy)-5-isopropylpyridin-3-yl)methyl)-2-isobutyramido-6-methylisonicotinamide;
2-(cyclopropanecarboxamido)-N-((6-(2,2-difluoroethoxy)-5-isopropylpyridin-3-yl)methyl)pyrimidine-4-carboxamide;
2-(cyclopropanecarboxamido)-N-((6-(2,2-difluoroethoxy)-5-isopropylpyridin-3-yl)methyl)-6-methylpyrimidine-4-carboxamide;
2-(cyclopropanecarboxamido)-N-(1-(6-(2,2-difluoroethoxy)-5-methylpyridin-3-yl)ethyl)-N,6-dimethylpyrimidine-4-carboxamide;
N-((5-chloro-6-(2,2-difluoroethoxy)pyridin-3-yl)methyl)-2-(2-cyclopropylacetamido)-6-methylisonicotinamide;
2-(2-cyclopropylacetamido)-6-methyl-N-((6-(3,3,3-trifluoropropoxy)pyridin-3-yl)methyl)isonicotinamide;
2-(cyclopropanecarboxamido)-N-(3-fluoro-4-(trifluoromethoxy)benzyl)isonicotinamide;
2-acetamido-N-(3-fluoro-4-(trifluoromethoxy)benzyl)-6-methylisonicotinamide;
2-(cyclopropanecarboxamido)-N-(3-fluoro-4-(trifluoromethoxy)benzyl)-6-methylpyrimidine-4-carboxamide;
2-acetamido-N-(1-(2-fluoro-5-(trifluoromethyl)phenyl)ethyl)isonicotinamide;
N-(1-(2-fluoro-5-(trifluoromethyl)phenyl)ethyl)-2-isobutyramidoisonicotinamide;
2-acetamido-N-(1-(3-chloro-4-(2,2-difluoroethoxy)phenyl)ethyl)isonicotinamide;
N-(1-(3-chloro-4-(2,2-difluoroethoxy)phenyl)ethyl)-2-isobutyramidoisonicotinamide;
2-acetamido-N-(1-(3-chloro-4-(2,2-difluoroethoxy)phenyl)ethyl)-6-methylisonicotinamide;
N-(1-(3-chloro-4-(2,2-difluoroethoxy)phenyl)ethyl)-2-isobutyramido-6-methylisonicotinamide;
2-(cyclopropanecarboxamido)-N-(3-methoxy-4-(2,2,2-trifluoroethoxy)benzyl)isonicotinamide;
2-(cyclopropanecarboxamido)-N-(1-(4-(2,2-difluoroethoxy)-2-methylphenyl)ethyl)pyrimidine-4-carboxamide;
N-(1-(4-(2,2-difluoroethoxy)-2-methylphenyl)ethyl)-2-isobutyramido-6-methylisonicotinamide;

2-isobutyramido-N,6-dimethyl-N-(1-(6-(2,2,2-trifluoro-ethoxy)pyridin-3-yl)ethyl)isonicotinamide;
N-(4-(2,2-difluoroethoxy)-3-methoxybenzyl)-2-propionamidoisonicotinamide;
N-(4-(2,2-difluoroethoxy)-3-methoxybenzyl)-2-isobutyramido-6-methylisonicotinamide;
2-(cyclopropanecarboxamido)-N-(1-(6-(2,2-difluoroethoxy)-5-methoxypyridin-3-yl)ethyl)isonicotinamide;
2-acetamido-N-(1-(6-(2,2-difluoroethoxy)-5-methoxypyridin-3-yl)ethyl)-6-methylisonicotinamide;
N-(1-(6-(2,2-difluoroethoxy)-5-methoxypyridin-3-yl)ethyl)-2-isobutyramido-6-methylisonicotinamide;
2-acetamido-N-(1-(4-(2,2-difluoroethoxy)-3-methoxyphenyl)ethyl)-6-methylisonicotinamide;
N-(1-(4-(2,2-difluoroethoxy)-3-methoxyphenyl)ethyl)-2-isobutyramidoisonicotinamide;
N-(1-(4-(2,2-difluoroethoxy)-3-methoxyphenyl)ethyl)-2-isobutyramido-6-methylisonicotinamide;
2-(cyclopropanecarboxamido)-N-(1-(2-fluoro-4-(trifluoromethyl)phenyl)ethyl)pyrimidine-4-carboxamide;
2-acetamido-N-(1-(2-chloro-4-(2,2-difluoroethoxy)phenyl)ethyl)isonicotinamide;
N-(1-(2-chloro-4-(2,2-difluoroethoxy)phenyl)ethyl)-2-propionamidoisonicotinamide;
N-(1-(2-chloro-4-(2,2-difluoroethoxy)phenyl)ethyl)-2-(cyclopropanecarboxamido)isonicotinamide;
N-(1-(2-chloro-4-(2,2-difluoroethoxy)phenyl)ethyl)-2-isobutyramidoisonicotinamide;
N-(1-(2-chloro-4-(2,2-difluoroethoxy)phenyl)ethyl)-2-(cyclopropanecarboxamido)pyrimidine-4-carboxamide;
N-(1-(2-chloro-4-(2,2-difluoroethoxy)phenyl)ethyl)-2-isobutyramido-6-methylisonicotinamide;
N-(1-(2-chloro-4-(2,2-difluoroethoxy)phenyl)ethyl)-2-(cyclopropanecarboxamido)-6-methylpyrimidine-4-carboxamide;
N-(1-(4-(2,2-difluoroethoxy)-3,5-difluorophenyl)ethyl)-2-propionamidoisonicotinamide;
2-(cyclopropanecarboxamido)-N-(1-(4-(2,2-difluoroethoxy)-3,5-difluorophenyl)ethyl)isonicotinamide;
N-(1-(4-(2,2-difluoroethoxy)-3,5-difluorophenyl)ethyl)-2-isobutyramido-6-methylisonicotinamide;
2-acetamido-N-(3-(2,2-difluoroethoxy)-2-methylbenzyl)isonicotinamide;
N-(3-(2,2-difluoroethoxy)-2-methylbenzyl)-2-propionamidoisonicotinamide;
2-(cyclopropanecarboxamido)-N-(3-(2,2-difluoroethoxy)-2-methylbenzyl)isonicotinamide;
N-(3-(2,2-difluoroethoxy)-2-methylbenzyl)-2-isobutyramidoisonicotinamide;
2-(cyclopropanecarboxamido)-N-(3-(2,2-difluoroethoxy)-2-methylbenzyl)pyrimidine-4-carboxamide;
2-acetamido-N-(3-(2,2-difluoroethoxy)-2-methylbenzyl)-6-methylisonicotinamide;
N-(3-(2,2-difluoroethoxy)-2-methylbenzyl)-2-isobutyramido-6-methylisonicotinamide;
N-(3-(2,2-difluoroethoxy)-2-methylbenzyl)-2-(2-hydroxy-2-methylpropanamido)-6-methylisonicotinamide;
2-(cyclopropanecarboxamido)-N-(3-(2,2-difluoroethoxy)-2-methylbenzyl)-6-methylpyrimidine-4-carboxamide;
N-((6-(2,2-difluoroethoxy)-2-methylpyridin-3-yl)methyl)-2-propionamidoisonicotinamide;
2-(cyclopropanecarboxamido)-N-((6-(2,2-difluoroethoxy)-2-methylpyridin-3-yl)methyl)isonicotinamide;
N-((6-(2,2-difluoroethoxy)-2-methylpyridin-3-yl)methyl)-2-isobutyramidoisonicotinamide;
2-acetamido-N-((6-(2,2-difluoroethoxy)-2-methylpyridin-3-yl)methyl)-6-methylisonicotinamide;
2-(cyclopropanecarboxamido)-N-((6-(2,2-difluoroethoxy)-2-methylpyridin-3-yl)methyl)-6-methylisonicotinamide;
N-((6-(2,2-difluoroethoxy)-2-methylpyridin-3-yl)methyl)-2-isobutyramido-6-methylisonicotinamide;
2-(cyclopropanecarboxamido)-N-((6-(2,2-difluoroethoxy)-2-methylpyridin-3-yl)methyl)-6-methylpyrimidine-4-carboxamide;
2-acetamido-N-(1-(5-(2,2-difluoroethoxy)-2-methylphenyl)ethyl)isonicotinamide;
2-acetamido-N-(1-(5-(2,2-difluoroethoxy)-2-methylphenyl)ethyl)-6-methylisonicotinamide;
2-(cyclopropanecarboxamido)-N-(1-(5-(2,2-difluoroethoxy)-2-methylphenyl)ethyl)pyrimidine-4-carboxamide;
2-(cyclopropanecarboxamido)-N-(1-(5-(2,2-difluoroethoxy)-2-methylphenyl)ethyl)-6-methylpyrimidine-4-carboxamide;
2-(cyclopropanecarboxamido)-N-(1-(3-(2,2-difluoroethoxy)-4-methylphenyl)ethyl)pyrimidine-4-carboxamide;
2-(cyclopropanecarboxamido)-N-(4-(2,2-difluoroethoxy)-3-methoxybenzyl)isonicotinamide;
N-((5-chloro-6-(2,2,2-trifluoroethoxy)pyridin-3-yl)methyl)-2-(cyclopropanecarboxamido)-6-methylpyrimidine-4-carboxamide;
2-(2-hydroxy-2-methylpropanamido)-N-(2-methoxy-3-(trifluoromethyl)benzyl)-6-methylisonicotinamide;
2-(2-hydroxy-2-methylpropanamido)-6-methyl-N-((5-methyl-6-(2,2,3,3-tetrafluoropropoxy)pyridin-3-yl)methyl)isonicotinamide;
2-(cyclopropanecarboxamido)-N,6-dimethyl-N-((6-(2,2,2-trifluoroethoxy)pyridin-3-yl)methyl)isonicotinamide;
2-acetamido-N-((6-(2,2-difluoroethoxy)-2-methoxypyridin-3-yl)methyl)isonicotinamide;
N-((6-(2,2-difluoroethoxy)-2-methoxypyridin-3-yl)methyl)-2-propionamidoisonicotinamide;
2-(cyclopropanecarboxamido)-N-((6-(2,2-difluoroethoxy)-2-methoxypyridin-3-yl)methyl)isonicotinamide;
N-((6-(2,2-difluoroethoxy)-2-methoxypyridin-3-yl)methyl)-2-isobutyramidoisonicotinamide;
2-(cyclopropanecarboxamido)-N-((6-(2,2-difluoroethoxy)-2-methoxypyridin-3-yl)methyl)pyrimidine-4-carboxamide;
2-acetamido-N-((6-(2,2-difluoroethoxy)-2-methoxypyridin-3-yl)methyl)-6-methylisonicotinamide;
N-((6-(2,2-difluoroethoxy)-2-methoxypyridin-3-yl)methyl)-2-isobutyramido-6-methylisonicotinamide;
N-((6-(2,2-difluoroethoxy)-2-methoxypyridin-3-yl)methyl)-2-(2-hydroxy-2-methylpropanamido)-6-methylisonicotinamide;
2-(cyclopropanecarboxamido)-N-((6-(2,2-difluoroethoxy)-2-methoxypyridin-3-yl)methyl)-6-methylpyrimidine-4-carboxamide;
2-acetamido-N-(1-(6-(2,2-difluoroethoxy)-2-methoxypyridin-3-yl)ethyl)isonicotinamide;
N-(1-(6-(2,2-difluoroethoxy)-2-methoxypyridin-3-yl)ethyl)-2-propionamidoisonicotinamide;
2-(cyclopropanecarboxamido)-N-(1-(6-(2,2-difluoroethoxy)-2-methoxypyridin-3-yl)ethyl)isonicotinamide;
N-(1-(6-(2,2-difluoroethoxy)-2-methoxypyridin-3-yl)ethyl)-2-isobutyramidoisonicotinamide;

2-(cyclopropanecarboxamido)-N-(1-(6-(2,2-difluoroethoxy)-2-methoxypyridin-3-yl)ethyl)pyrimidine-4-carboxamide;
2-acetamido-N-(1-(6-(2,2-difluoroethoxy)-2-methoxypyridin-3-yl)ethyl)-6-methylisonicotinamide;
N-(1-(6-(2,2-difluoroethoxy)-2-methoxypyridin-3-yl)ethyl)-2-isobutyramido-6-methylisonicotinamide;
N-(1-(6-(2,2-difluoroethoxy)-2-methoxypyridin-3-yl)ethyl)-2-(2-hydroxy-2-methylpropanamido)-6-methylisonicotinamide;
2-(cyclopropanecarboxamido)-N-(1-(6-(2,2-difluoroethoxy)-2-methoxypyridin-3-yl)ethyl)-6-methylpyrimidine-4-carboxamide;
N-(1-(6-(2,2,3,3,3-pentafluoropropoxy)pyridin-3-yl)ethyl)-2-propionamidoisonicotinamide;
2-(cyclopropanecarboxamido)-N-((6-(2,2-difluoropropoxy)pyridin-3-yl)methyl)isonicotinamide;
2-(cyclopropanecarboxamido)-N-((6-(2,2-difluoropropoxy)pyridin-3-yl)methyl)pyrimidine-4-carboxamide;
N-((6-(2,2-difluoroethoxy)-5-ethylpyridin-3-yl)methyl)-2-pivalamidoisonicotinamide;
N-(1-(5-cyclopropyl-6-(2,2-difluoroethoxy)pyridin-3-yl)ethyl)-2-propionamidoisonicotinamide;
2-(cyclopropanecarboxamido)-N-(1-(5-cyclopropyl-6-(2,2-difluoroethoxy)pyridin-3-yl)ethyl)isonicotinamide;
N-(1-(3-chloro-4-(2,2-difluoroethoxy)phenyl)ethyl)-2-(cyclopropanecarboxamido)isonicotinamide;
N-(1-(4-(2,2-difluoroethoxy)-2-methylphenyl)ethyl)-2-propionamidoisonicotinamide;
2-(cyclopropanecarboxamido)-N-(1-(4-(2,2-difluoroethoxy)-2-methylphenyl)ethyl)isonicotinamide;
2-(cyclopropanecarboxamido)-N-(4-(2,2-difluoroethoxy)-2-methylbenzyl)-6-methylpyrimidine-4-carboxamide;
2-acetamido-6-methyl-N-(1-(4-(2,2,2-trifluoroethoxy)phenyl)ethyl)isonicotinamide;
N-(4-methoxy-3-(trifluoromethyl)benzyl)-2-propionamidoisonicotinamide;
2-acetamido-N-((6-(2-(trifluoromethoxy)ethoxy)pyridin-3-yl)methyl)isonicotinamide;
2-propionamido-N-((6-(2-(trifluoromethoxy)ethoxy)pyridin-3-yl)methyl)isonicotinamide;
2-(cyclopropanecarboxamido)-N-((6-(2-(trifluoromethoxy)ethoxy)pyridin-3-yl)methyl)isonicotinamide;
2-isobutyramido-N-((6-(2-(trifluoromethoxy)ethoxy)pyridin-3-yl)methyl)isonicotinamide;
2-acetamido-6-methyl-N-((6-(2-(trifluoromethoxy)ethoxy)pyridin-3-yl)methyl)isonicotinamide;
2-isobutyramido-6-methyl-N-((6-(2-(trifluoromethoxy)ethoxy)pyridin-3-yl)methyl)isonicotinamide;
2-(2-hydroxy-2-methylpropanamido)-6-methyl-N-((6-(2-(trifluoromethoxy)ethoxy)pyridin-3-yl)methyl)isonicotinamide;
2-(cyclopropanecarboxamido)-N-((6-(2-(trifluoromethoxy)ethoxy)pyridin-3-yl)methyl)pyrimidine-4-carboxamide;
2-acetamido-N-(1-(3-(2,2-difluoroethoxy)-5-methylphenyl)ethyl)isonicotinamide;
N-(1-(3-(2,2-difluoroethoxy)-5-methylphenyl)ethyl)-2-propionamidoisonicotinamide;
2-(cyclopropanecarboxamido)-N-(1-(3-(2,2-difluoroethoxy)-5-methylphenyl)ethyl)isonicotinamide;
N-(1-(3-(2,2-difluoroethoxy)-5-methylphenyl)ethyl)-2-isobutyramidoisonicotinamide;
2-acetamido-N-(1-(3-(2,2-difluoroethoxy)-5-methylphenyl)ethyl)-6-methylisonicotinamide;
N-(1-(3-(2,2-difluoroethoxy)-5-methylphenyl)ethyl)-2-isobutyramido-6-methylisonicotinamide;
N-(1-(3-(2,2-difluoroethoxy)-5-methylphenyl)ethyl)-2-(2-hydroxy-2-methylpropanamido)-6-methylisonicotinamide;
2-(cyclopropanecarboxamido)-N-(1-(3-(2,2-difluoroethoxy)-5-methylphenyl)ethyl)pyrimidine-4-carboxamide;
2-(cyclopropanecarboxamido)-N-(1-(3-(2,2-difluoroethoxy)-5-methylphenyl)ethyl)-6-methylpyrimidine-4-carboxamide;
2-acetamido-N-(3-(2,2-difluoroethoxy)-5-methylbenzyl)isonicotinamide;
N-(3-(2,2-difluoroethoxy)-5-methylbenzyl)-2-propionamidoisonicotinamide;
2-(cyclopropanecarboxamido)-N-(3-(2,2-difluoroethoxy)-5-methylbenzyl)isonicotinamide;
N-(3-(2,2-difluoroethoxy)-5-methylbenzyl)-2-isobutyramidoisonicotinamide;
2-acetamido-N-(3-(2,2-difluoroethoxy)-5-methylbenzyl)-6-methylisonicotinamide;
N-(3-(2,2-difluoroethoxy)-5-methylbenzyl)-2-isobutyramido-6-methylisonicotinamide;
N-(3-(2,2-difluoroethoxy)-5-methylbenzyl)-2-(2-hydroxy-2-methylpropanamido)-6-methylisonicotinamide;
2-(cyclopropanecarboxamido)-N-(3-(2,2-difluoroethoxy)-5-methylbenzyl)pyrimidine-4-carboxamide;
2-(cyclopropanecarboxamido)-N-(3-(2,2-difluoroethoxy)-5-methylbenzyl)-6-methylpyrimidine-4-carboxamide;
2-acetamido-N-(1-(3-chloro-4-(2,2-difluoroethoxy)-5-methylphenyl)ethyl)isonicotinamide;
N-(1-(3-chloro-4-(2,2-difluoroethoxy)-5-methylphenyl)ethyl)-2-propionamidoisonicotinamide;
N-(1-(3-chloro-4-(2,2-difluoroethoxy)-5-methylphenyl)ethyl)-2-(cyclopropanecarboxamido)isonicotinamide;
N-(1-(3-chloro-4-(2,2-difluoroethoxy)-5-methylphenyl)ethyl)-2-isobutyramidoisonicotinamide;
2-acetamido-N-(1-(3-chloro-4-(2,2-difluoroethoxy)-5-methylphenyl)ethyl)-6-methylisonicotinamide;
N-(1-(3-chloro-4-(2,2-difluoroethoxy)-5-methylphenyl)ethyl)-2-isobutyramido-6-methylisonicotinamide;
N-(1-(3-chloro-4-(2,2-difluoroethoxy)-5-methylphenyl)ethyl)-2-(2-hydroxy-2-methylpropanamido)-6-methylisonicotinamide;
N-(1-(3-chloro-4-(2,2-difluoroethoxy)-5-methylphenyl)ethyl)-2-(cyclopropanecarboxamido)pyrimidine-4-carboxamide;
N-(1-(3-chloro-4-(2,2-difluoroethoxy)-5-methylphenyl)ethyl)-2-(cyclopropanecarboxamido)-6-methylpyrimidine-4-carboxamide;
2-acetamido-N-(1-(4-(2,2-difluoroethoxy)-3,5-dimethylphenyl)ethyl)isonicotinamide;
N-(1-(4-(2,2-difluoroethoxy)-3,5-dimethylphenyl)ethyl)-2-propionamidoisonicotinamide;
2-(cyclopropanecarboxamido)-N-(1-(4-(2,2-difluoroethoxy)-3,5-dimethylphenyl)ethyl)isonicotinamide;
N-(1-(4-(2,2-difluoroethoxy)-3,5-dimethylphenyl)ethyl)-2-isobutyramidoisonicotinamide;
2-acetamido-N-(1-(4-(2,2-difluoroethoxy)-3,5-dimethylphenyl)ethyl)-6-methylisonicotinamide;
N-(1-(4-(2,2-difluoroethoxy)-3,5-dimethylphenyl)ethyl)-2-isobutyramido-6-methylisonicotinamide;
N-(1-(4-(2,2-difluoroethoxy)-3,5-dimethylphenyl)ethyl)-2-(2-hydroxy-2-methylpropanamido)-6-methylisonicotinamide;

2-(cyclopropanecarboxamido)-N-(1-(4-(2,2-difluoroethoxy)-3,5-dimethylphenyl)ethyl)pyrimidine-4-carboxamide;

2-(cyclopropanecarboxamido)-N-(1-(4-(2,2-difluoroethoxy)-3,5-dimethylphenyl)ethyl)-6-methylpyrimidine-4-carboxamide;

2-acetamido-N-(4-(2,2-difluoroethoxy)-3,5-dimethylbenzyl)isonicotinamide;

N-(4-(2,2-difluoroethoxy)-3,5-dimethylbenzyl)-2-propionamidoisonicotinamide;

2-(cyclopropanecarboxamido)-N-(4-(2,2-difluoroethoxy)-3,5-dimethylbenzyl)isonicotinamide;

N-(4-(2,2-difluoroethoxy)-3,5-dimethylbenzyl)-2-isobutyramidoisonicotinamide;

2-acetamido-N-(4-(2,2-difluoroethoxy)-3,5-dimethylbenzyl)-6-methylisonicotinamide;

N-(4-(2,2-difluoroethoxy)-3,5-dimethylbenzyl)-2-isobutyramido-6-methylisonicotinamide;

N-(4-(2,2-difluoroethoxy)-3,5-dimethylbenzyl)-2-(2-hydroxy-2-methylpropanamido)-6-methylisonicotinamide;

2-(cyclopropanecarboxamido)-N-(4-(2,2-difluoroethoxy)-3,5-dimethylbenzyl)pyrimidine-4-carboxamide;

2-(cyclopropanecarboxamido)-N-(4-(2,2-difluoroethoxy)-3,5-dimethylbenzyl)-6-methylpyrimidine-4-carboxamide;

2-acetamido-N-(1-(4-(1,1,2,2-tetrafluoroethoxy)phenyl)ethyl)isonicotinamide;

2-propionamido-N-(1-(4-(1,1,2,2-tetrafluoroethoxy)phenyl)ethyl)isonicotinamide;

2-(cyclopropanecarboxamido)-N-(1-(4-(1,1,2,2-tetrafluoroethoxy)phenyl)ethyl)isonicotinamide;

2-isobutyramido-N-(1-(4-(1,1,2,2-tetrafluoroethoxy)phenyl)ethyl)isonicotinamide;

2-acetamido-6-methyl-N-(1-(4-(1,1,2,2-tetrafluoroethoxy)phenyl)ethyl)isonicotinamide;

2-isobutyramido-6-methyl-N-(1-(4-(1,1,2,2-tetrafluoroethoxy)phenyl)ethyl)isonicotinamide;

2-(2-hydroxy-2-methylpropanamido)-6-methyl-N-(1-(4-(1,1,2,2-tetrafluoroethoxy)phenyl)ethyl)isonicotinamide;

2-(cyclopropanecarboxamido)-N-(1-(4-(1,1,2,2-tetrafluoroethoxy)phenyl)ethyl)pyrimidine-4-carboxamide;

2-(cyclopropanecarboxamido)-6-methyl-N-(1-(4-(1,1,2,2-tetrafluoroethoxy)phenyl)ethyl)pyrimidine-4-carboxamide;

2-acetamido-N-(1-(3-(1,1,2,2-tetrafluoroethoxy)phenyl)ethyl)isonicotinamide;

2-propionamido-N-(1-(3-(1,1,2,2-tetrafluoroethoxy)phenyl)ethyl)isonicotinamide;

2-(cyclopropanecarboxamido)-N-(1-(3-(1,1,2,2-tetrafluoroethoxy)phenyl)ethyl)isonicotinamide;

2-isobutyramido-N-(1-(3-(1,1,2,2-tetrafluoroethoxy)phenyl)ethyl)isonicotinamide;

2-acetamido-6-methyl-N-(1-(3-(1,1,2,2-tetrafluoroethoxy)phenyl)ethyl)isonicotinamide;

2-isobutyramido-6-methyl-N-(1-(3-(1,1,2,2-tetrafluoroethoxy)phenyl)ethyl)isonicotinamide;

2-(2-hydroxy-2-methylpropanamido)-6-methyl-N-(1-(3-(1,1,2,2-tetrafluoroethoxy)phenyl)ethyl)isonicotinamide;

2-(cyclopropanecarboxamido)-N-(1-(3-(1,1,2,2-tetrafluoroethoxy)phenyl)ethyl)pyrimidine-4-carboxamide;

2-(cyclopropanecarboxamido)-6-methyl-N-(1-(3-(1,1,2,2-tetrafluoroethoxy)phenyl)ethyl)pyrimidine-4-carboxamide;

2-acetamido-N-(1-(3-(difluoromethyl)phenyl)ethyl)isonicotinamide;

N-(1-(3-(difluoromethyl)phenyl)ethyl)-2-propionamidoisonicotinamide;

2-(cyclopropanecarboxamido)-N-(1-(3-(difluoromethyl)phenyl)ethyl)isonicotinamide;

N-(1-(3-(difluoromethyl)phenyl)ethyl)-2-isobutyramidoisonicotinamide;

2-acetamido-N-(1-(3-(difluoromethyl)phenyl)ethyl)-6-methylisonicotinamide;

N-(1-(3-(difluoromethyl)phenyl)ethyl)-2-isobutyramido-6-methylisonicotinamide;

N-(1-(3-(difluoromethyl)phenyl)ethyl)-2-(2-hydroxy-2-methylpropanamido)-6-methylisonicotinamide;

2-(cyclopropanecarboxamido)-N-(1-(3-(difluoromethyl)phenyl)ethyl)pyrimidine-4-carboxamide;

2-(cyclopropanecarboxamido)-N-(1-(3-(difluoromethyl)phenyl)ethyl)-6-methylpyrimidine-4-carboxamide;

2-acetamido-N-(1-(4-(perfluoroethoxy)phenyl)ethyl)isonicotinamide;

N-(1-(4-(perfluoroethoxy)phenyl)ethyl)-2-propionamidoisonicotinamide;

2-(cyclopropanecarboxamido)-N-(1-(4-(perfluoroethoxy)phenyl)ethyl)isonicotinamide;

2-isobutyramido-N-(1-(4-(perfluoroethoxy)phenyl)ethyl)isonicotinamide;

2-acetamido-6-methyl-N-(1-(4-(perfluoroethoxy)phenyl)ethyl)isonicotinamide;

2-isobutyramido-6-methyl-N-(1-(4-(perfluoroethoxy)phenyl)ethyl)isonicotinamide;

2-(2-hydroxy-2-methylpropanamido)-6-methyl-N-(1-(4-(perfluoroethoxy)phenyl)ethyl)isonicotinamide;

2-(cyclopropanecarboxamido)-N-(1-(4-(perfluoroethoxy)phenyl)ethyl)pyrimidine-4-carboxamide;

2-(cyclopropanecarboxamido)-6-methyl-N-(1-(4-(perfluoroethoxy)phenyl)ethyl)pyrimidine-4-carboxamide;

(R)-2-acetamido-N-(1-(3-(perfluoroethoxy)phenyl)ethyl)isonicotinamide;

(R)—N-(1-(3-(perfluoroethoxy)phenyl)ethyl)-2-propionamidoisonicotinamide;

(R)-2-(cyclopropanecarboxamido)-N-(1-(3-(perfluoroethoxy)phenyl)ethyl)isonicotinamide;

(R)-2-isobutyramido-N-(1-(3-(perfluoroethoxy)phenyl)ethyl)isonicotinamide;

(R)-2-acetamido-6-methyl-N-(1-(3-(perfluoroethoxy)phenyl)ethyl)isonicotinamide;

(R)-2-isobutyramido-6-methyl-N-(1-(3-(perfluoroethoxy)phenyl)ethyl)isonicotinamide;

(R)-2-(2-hydroxy-2-methylpropanamido)-6-methyl-N-(1-(3-(perfluoroethoxy)phenyl)ethyl)isonicotinamide;

(R)-2-(cyclopropanecarboxamido)-N-(1-(3-(perfluoroethoxy)phenyl)ethyl)pyrimidine-4-carboxamide;

(R)-2-(cyclopropanecarboxamido)-6-methyl-N-(1-(3-(perfluoroethoxy)phenyl)ethyl)pyrimidine-4-carboxamide;

2-butyramido-N-((5-cyclopropyl-6-(2,2-difluoroethoxy)pyridin-3-yl)methyl)isonicotinamide;

2-acetamido-N-(3-fluoro-4-(trifluoromethoxy)benzyl)isonicotinamide; and 2-(cyclopropanecarboxamido)-N-(4-fluoro-3-(trifluoromethyl)benzyl)-6-methylisonicotinamide;

or a pharmaceutically acceptable salt thereof.

6. A compound selected from the group consisting of:

2-acetamido-N-(1-(6-(2,2,2-trifluoroethoxy)pyridin-3-yl)ethyl)isonicotinamide;

2-isobutyramido-N-(1-(6-(2,2,2-trifluoroethoxy)pyridin-3-yl)ethyl)isonicotinamide;

2-(cyclopropanecarboxamido)-N-(1-(6-(2,2,2-trifluoroethoxy)pyridin-3-yl)ethyl)isonicotinamide;
2-propionamido-N-(1-(6-(2,2,2-trifluoroethoxy)pyridin-3-yl)ethyl)isonicotinamide;
2-acetamido-6-methyl-N-(1-(6-(2,2,2-trifluoroethoxy)pyridin-3-yl)ethyl)isonicotinamide;
2-methyl-6-propionamido-N-(1-(6-(2,2,2-trifluoroethoxy)pyridin-3-yl)ethyl)isonicotinamide;
2-isobutyramido-6-methyl-N-(1-(6-(2,2,2-trifluoroethoxy)pyridin-3-yl)ethyl)isonicotinamide;
2-acetamido-N-(1-(3-(trifluoromethoxy)phenyl)ethyl)isonicotinamide;
N-(1-(5-fluoro-6-(2,2,2-trifluoroethoxy)pyridin-3-yl)ethyl)-2-methyl-6-propionamidoisonicotinamide;
2-methyl-6-propionamido-N-(1-(6-(3,3,3-trifluoropropoxy)pyridin-3-yl)ethyl)isonicotinamide;
2-isobutyramido-N-((6-(2,2,2-trifluoroethoxy)pyridin-3-yl)methyl)isonicotinamide;
2-isobutyramido-N-((4-methyl-6-(2,2,2-trifluoroethoxy)pyridin-3-yl)methyl)isonicotinamide;
2-isobutyramido-N-(1-(6-(3,3,3-trifluoropropoxy)pyridin-3-yl)ethyl)isonicotinamide;
N-(1-(5-fluoro-6-(2,2,2-trifluoroethoxy)pyridin-3-yl)ethyl)-2-isobutyramidoisonicotinamide;
2-acetamido-6-methyl-N-((4-methyl-6-(2,2,2-trifluoroethoxy)pyridin-3-yl)methyl)isonicotinamide;
2-acetamido-N-methyl-N-(1-(5-methyl-6-(2,2,2-trifluoroethoxy)pyridin-3-yl)ethyl)isonicotinamide;
2-isobutyramido-N-(1-(3-(trifluoromethoxy)phenyl)ethyl)isonicotinamide;
2-isobutyramido-6-methyl-N-((6-(2,2,2-trifluoroethoxy)pyridin-3-yl)methyl)isonicotinamide;
N-(1-(5-fluoro-6-(2,2,2-trifluoroethoxy)pyridin-3-yl)ethyl)-2-isobutyramido-6-methylisonicotinamide;
2-isobutyramido-6-methyl-N-(1-(6-(3,3,3-trifluoropropoxy)pyridin-3-yl)ethyl)isonicotinamide;
2-isobutyramido-6-methyl-N-(1-(3-(trifluoromethoxy)phenyl)ethyl)isonicotinamide;
2-isobutyramido-6-methyl-N-((4-methyl-6-(2,2,2-trifluoroethoxy)pyridin-3-yl)methyl)isonicotinamide;
(R)-2-isobutyramido-N-(1-(3-(trifluoromethyl)phenyl)ethyl)isonicotinamide;
(R)-2-isobutyramido-6-methyl-N-(1-(3-(trifluoromethyl)phenyl)ethyl)isonicotinamide;
2-acetamido-N-(1-(6-(2,2-difluoroethoxy)-5-methylpyridin-3-yl)ethyl)isonicotinamide;
N-(1-(6-(2,2-difluoroethoxy)-5-methylpyridin-3-yl)ethyl)-2-isobutyramidoisonicotinamide;
2-acetamido-N-(1-(6-(2,2-difluoroethoxy)-5-methylpyridin-3-yl)ethyl)-6-methylisonicotinamide;
N-(1-(6-(2,2-difluoroethoxy)-5-methylpyridin-3-yl)ethyl)-2-isobutyramido-6-methylisonicotinamide;
2-(cyclopropanecarboxamido)-N-(1-(6-(2,2-difluoroethoxy)-5-methylpyridin-3-yl)ethyl)pyrimidine-4-carboxamide;
2-(cyclopropanecarboxamido)-N-(1-(6-(2,2-difluoroethoxy)-5-methylpyridin-3-yl)ethyl)-6-methylpyrimidine-4-carboxamide;
2-isobutyramido-N-(1-(3-(2,2,2-trifluoroethoxy)phenyl)ethyl)isonicotinamide;
2-isobutyramido-N-(1-(4-(2,2,2-trifluoroethoxy)phenyl)ethyl)isonicotinamide;
2-isobutyramido-6-methyl-N-(1-(4-(2,2,2-trifluoroethoxy)phenyl)ethyl)isonicotinamide;
2-isobutyramido-6-methyl-N-(1-(6-(2,2,3,3,3-pentafluoropropoxy)pyridin-3-yl)ethyl)isonicotinamide;
N-((5-chloro-6-(2,2-difluoroethoxy)pyridin-3-yl)methyl)-2-(cyclopropanecarboxamido)pyrimidine-4-carboxamide;
N-((6-(2,2-difluoroethoxy)-5-methylpyridin-3-yl)methyl)-2-isobutyramidoisonicotinamide;
2-acetamido-N-((6-(2,2-difluoroethoxy)-4-methylpyridin-3-yl)methyl)-6-methylisonicotinamide;
N-(1-(6-(2,2-difluoropropoxy)pyridin-3-yl)ethyl)-2-isobutyramido-6-methylisonicotinamide;
2-acetamido-N-(3-methyl-4-(trifluoromethoxy)benzyl)isonicotinamide;
2-isobutyramido-N-(2-methoxy-3-(trifluoromethyl)benzyl)isonicotinamide;
2-isobutyramido-N-(2-methoxy-4-(trifluoromethoxy)benzyl)isonicotinamide;
2-acetamido-N-(2-methoxy-4-(trifluoromethoxy)benzyl)-6-methylisonicotinamide;
2-isobutyramido-6-methyl-N-(1-(3-(2,2,2-trifluoroethoxy)phenyl)ethyl)isonicotinamide;
2-acetamido-N-(1-(5-methyl-6-(2,2,3,3-tetrafluoropropoxy)pyridin-3-yl)ethyl)isonicotinamide;
2-isobutyramido-N-(1-(5-methyl-6-(2,2,3,3-tetrafluoropropoxy)pyridin-3-yl)ethyl)isonicotinamide;
2-isobutyramido-6-methyl-N-(1-(5-methyl-6-(2,2,3,3-tetrafluoropropoxy)pyridin-3-yl)ethyl)isonicotinamide;
2-(cyclopropanecarboxamido)-N-(1-(5-methyl-6-(2,2,3,3-tetrafluoropropoxy)pyridin-3-yl)ethyl)pyrimidine-4-carboxamide;
2-(cyclopropanecarboxamido)-6-methyl-N-(1-(5-methyl-6-(2,2,3,3-tetrafluoropropoxy)pyridin-3-yl)ethyl)pyrimidine-4-carboxamide;
2-acetamido-6-methyl-N-(1-(5-methyl-6-(2,2,3,3-tetrafluoropropoxy)pyridin-3-yl)ethyl)isonicotinamide;
2-acetamido-N-((5-methyl-6-(2,2,3,3-tetrafluoropropoxy)pyridin-3-yl)methyl)isonicotinamide;
2-isobutyramido-N-((5-methyl-6-(2,2,3,3-tetrafluoropropoxy)pyridin-3-yl)methyl)isonicotinamide;
2-(cyclopropanecarboxamido)-N-((5-methyl-6-(2,2,3,3-tetrafluoropropoxy)pyridin-3-yl)methyl)pyrimidine-4-carboxamide;
2-acetamido-6-methyl-N-(1-(3-(2,2,2-trifluoroethoxy)phenyl)ethyl)isonicotinamide;
N-((6-(2,2-difluoroethoxy)-2-methoxypyridin-3-yl)methyl)-2-isobutyramidoisonicotinamide;
2-(cyclopropanecarboxamido)-N-(1-(6-(2,2-difluoroethoxy)-2-methoxypyridin-3-yl)ethyl)isonicotinamide; and
N-(1-(6-(2,2-difluoroethoxy)-2-methoxypyridin-3-yl)ethyl)-2-isobutyramidoisonicotinamide;
or a pharmaceutically acceptable salt thereof.

* * * * *